US011806346B2

(12) United States Patent
Dominguez et al.

(10) Patent No.: US 11,806,346 B2
(45) Date of Patent: Nov. 7, 2023

(54) HTT MODULATORS FOR TREATING HUNTINGTON'S DISEASE

(71) Applicant: CHDI Foundation, Inc., New York, NY (US)

(72) Inventors: Celia Dominguez, Los Angeles, CA (US); Elizabeth M. Doherty, Thousand Oaks, CA (US); Longbin Liu, Thousand Oaks, CA (US); Matthew Lee, San Diego, CA (US); Mark Stuart Chambers, Saffron Walden (GB); Karine Fabienne Malagu, Saffron Walden (GB); Perla Breccia, Cambridge (GB); Alan F. Haughan, Saffron Walden (GB); Huw D. Vater, Saffron Walden (GB); Andrew J. Stott, Saffron Walden (GB); William R. K. Esmieu, Cambridge (GB); Stephen John Webster, Saffron Walden (GB); Amanda J. Van De Poël, Saffron Walden (GB)

(73) Assignee: CHDI Foundation, Inc., New York, NY (US)

(*) Notice: Subject to any disclaimer, the term of this patent is extended or adjusted under 35 U.S.C. 154(b) by 0 days.

(21) Appl. No.: 17/318,693

(22) Filed: May 12, 2021

(65) Prior Publication Data
US 2022/0409615 A1 Dec. 29, 2022

Related U.S. Application Data

(60) Provisional application No. 63/024,052, filed on May 13, 2020.

(51) Int. Cl.
A61K 31/497 (2006.01)
A61P 25/28 (2006.01)
A61K 31/4985 (2006.01)
A61K 31/501 (2006.01)
A61K 31/506 (2006.01)
C07D 403/14 (2006.01)
C07D 413/14 (2006.01)
C07D 471/04 (2006.01)
C07D 487/04 (2006.01)
C07D 519/00 (2006.01)

(52) U.S. Cl.
CPC ........ A61K 31/497 (2013.01); A61K 31/4985 (2013.01); A61K 31/501 (2013.01); A61K 31/506 (2013.01); A61P 25/28 (2018.01); C07D 403/14 (2013.01); C07D 413/14 (2013.01); C07D 471/04 (2013.01); C07D 487/04 (2013.01); C07D 519/00 (2013.01)

(58) Field of Classification Search
None
See application file for complete search history.

(56) References Cited

U.S. PATENT DOCUMENTS

| 7,504,412 B2* | 3/2009 | Kishino ............... A61P 15/00 546/121 |
| 8,168,630 B2* | 5/2012 | Tamura ............... C07D 279/06 544/55 |
| 9,604,957 B2* | 3/2017 | Chang .................. A61P 25/14 |
| 9,975,900 B2 | 5/2018 | Pinard et al. |
| 10,501,482 B2 | 12/2019 | Dakka et al. |
| 10,874,672 B2 | 12/2020 | Babu et al. |
| 10,881,658 B2 | 1/2021 | Babu et al. |
| 2019/0330159 A1 | 10/2019 | Kitano et al. |

FOREIGN PATENT DOCUMENTS

| EP | 3386511 B1 | 5/2021 |
| WO | WO2004/078163 A2 | 9/2004 |
| WO | WO2007/041634 A1 | 4/2007 |
| WO | WO2014/028459 A1 | 2/2014 |
| WO | WO2014/209841 A2 | 12/2014 |
| WO | WO2015/197503 A1 | 12/2015 |
| WO | WO2016/187544 A1 | 11/2016 |
| WO | WO2017/100726 A1 | 6/2017 |
| WO | WO2018/098446 A1 | 5/2018 |
| WO | WO2018/226622 A1 | 12/2018 |
| WO | WO2018/232039 A1 | 12/2018 |
| WO | WO2019/005980 A1 | 1/2019 |
| WO | WO2019/005993 A1 | 1/2019 |
| WO | WO2019/028440 A1 | 2/2019 |
| WO | WO2019/191092 A1 | 10/2019 |
| WO | WO2019/191229 A1 | 10/2019 |
| WO | WO2020/005873 A1 | 1/2020 |
| WO | WO2020/005877 A1 | 1/2020 |
| WO | WO2020/005882 A1 | 1/2020 |
| WO | WO2020/163248 A1 | 8/2020 |
| WO | WO2020/163323 A1 | 8/2020 |
| WO | WO2020/163375 A1 | 8/2020 |
| WO | WO2020/163382 A1 | 8/2020 |
| WO | WO2020/163401 A1 | 8/2020 |
| WO | WO2020/163405 A1 | 8/2020 |

(Continued)

OTHER PUBLICATIONS

Wu et al., Toxicology, vol. 236, pp. 1-6 (Year: 2007).*
International Search Report and Writtem Opinion for PCT/US2021/031988, dated Jul. 20, 2021, 14 pages.
Database Registry [Online] Chemical Abstracts Service, Columbus, Ohio, Mar. 25, 2010, Asinex, "5-Pyrimidinecarboxamide, N-(2-methyl-6-benzothiazolyl)-2-(4-methyll-piperidinyl)-", retrieved from STN Database accession No. 1214424-22-2 abstract, XP055821964.
Database Registry [Online] Chemical Abstracts Service, Columbus, Ohio, Jul. 29, 2015, Enamine LLC, "3-Pyridazinecarboxamide, N-(5-methyl-IH-indazol-6-yl)-6-(1-pyrrolidinyl)-", retrieved from STN Database accession No. 1808451-86-6 abstract, XP055821949.
Database Registry [Online] Chemical Abstracts Service, Columbus, Ohio, US; Sep. 27, 2012, Life Chemical et al.,"3-Pyridazinecarboxamide,N-IH-indazol-6-yl-6-(4-morpholinyl)-", retrieved from STN Database accession No. 1396882-20-4 abstract, XP055821536.

(Continued)

Primary Examiner — Zinna Northington Davis
(74) Attorney, Agent, or Firm — SHEPPARD MULLIN RICHTER & HAMPTON LLP

(57) ABSTRACT

Provided herein are certain compounds useful as HTT modulators. Such compound are useful in the treatment of Huntington's disease.

37 Claims, No Drawings

(56) References Cited

FOREIGN PATENT DOCUMENTS

| WO | WO2020/163406 A1 | 8/2020 |
| WO | WO2020/163409 A1 | 8/2020 |
| WO | WO2020/163541 A1 | 8/2020 |
| WO | WO2020/163544 A1 | 8/2020 |
| WO | WO2020/163647 A1 | 8/2020 |
| WO | WO2020/167624 A1 | 8/2020 |
| WO | WO2020/167628 A1 | 8/2020 |
| WO | WO2020/231977 A1 | 11/2020 |
| WO | WO2021/007378 A1 | 1/2021 |
| WO | WO2021/084495 A1 | 5/2021 |
| WO | WO2021/174163 A1 | 9/2021 |
| WO | WO2021/174164 A1 | 9/2021 |
| WO | WO2021/174165 A1 | 9/2021 |
| WO | WO2021/174167 A1 | 9/2021 |
| WO | WO2021/174170 A1 | 9/2021 |
| WO | WO2021/174174 A1 | 9/2021 |
| WO | WO2021/174176 A1 | 9/2021 |
| WO | WO2021/207453 A1 | 10/2021 |
| WO | WO2021/207530 A1 | 10/2021 |
| WO | WO2021/207532 A1 | 10/2021 |
| WO | WO2021/207550 A1 | 10/2021 |
| WO | WO2021/207554 A1 | 10/2021 |

OTHER PUBLICATIONS

Hintermann et al., "Synthesis and Biological Evaluation of New Triazolo- and Imidazolaoyridine ROR [gamma] t Inverse Agonists", CHEMMEDCHEM Communication, Dec. 16, 2016, vol. 11, No. 24, pp. 2640-2468.

Kargbo, "Modulation of RNA Splicing for the Treatment of Cancer", ACS Medicinal Chemistry Letters, 2020, vol. 11, No. 1, pp. 7-8.

Cheung et al., Discovery of Small Molecule Splicing Modulators of Survival Motor Neuron-2 (SMN2) for the Treatment of Spinal Muscular Atrophy (SMA), Journal of Medicinal Chemistry, 2018, vol. 61, pp. 11021-11036.

* cited by examiner

HTT MODULATORS FOR TREATING HUNTINGTON'S DISEASE

CROSS-REFERENCE TO RELATED PATENT APPLICATIONS

This application claims the benefit under 35 U.S.C. § 119(e) of U.S. Provisional Application No. 63/024,052 filed May 13, 2020, which is hereby incorporated by reference in its entirety.

FIELD

The present disclosure relates to methods of preventing and/or treating a neurodegenerative disease or condition.

BACKGROUND

Huntington's disease (HD) is a dominant inherited progressive neurodegenerative disorder, characterized by motor, cognitive, and psychiatric deficits as well as neurodegeneration and brain atrophy beginning in the striatum and the cortex and extending to other subcortical brain regions. HD has a prevalence of 5-10 cases per 100,000 worldwide, which makes it the most common inherited monogenetic neurodegenerative disease.

Neurodegenerative diseases and conditions, such as Huntington's disease, have a profound negative impact on the lives of those effected. Current treatments for Huntington's disease are palliative, aimed at lessening the severity of symptoms. There is no disease modifying treatment available.

Huntington's disease is caused by the expansion of a CAG repeat domain in Exon 1 of the huntingtin gene (HTT), which is expressed as mutant huntingtin protein (mHTT), containing an expanded polyglutamine tract in the amino terminal domain of the protein. The molecular route of pathogenesis is not entirely understood even though HD is monogenic and autosomal dominant. Therefore, mHTT lowering is a clear therapeutic strategy targeting the gene products of the causative gene. In fact, several therapeutic strategies targeting mHTT lowering via antisense oligonucleotide (ASO) or AAV-miR mediated HTT RNA degradation are advancing through clinical trials in HD and have demonstrated lowering of mHTT levels in the CSF of treated patients.

While these modalities show great promise, they are invasive (involving repeated intrathecal injections); their distribution throughout the brain to all affected regions is not certain; and they do not address any peripheral dysfunction the ubiquitously distributed mHTT may be responsible for. Therefore small molecule HTT lowering agents that can be delivered systemically and non-invasively would be an attractive HTT lowering therapy to pursue. Thus, there is a need for small molecule modulators of HTT protein. Such molecules may find use in treating the symptoms and/or delaying the disease progression of Huntington's disease.

SUMMARY

The present disclosure relates generally to small molecule modulators of HTT, and use thereof as therapeutic agents, for example, in treating diseases such as Huntington's disease.

Thus, provided herein are compounds, or an isotopically enriched analog, pharmaceutically acceptable salt, prodrug, tautomer, stereoisomer, or a mixture of stereoisomers of the compounds, that are useful in treating Huntington's disease.

In certain embodiments, provided are compounds that modulate a protein or a protein fragment implicated in neurodegenerative disease, for example, HTT protein.

In certain embodiments, provided is a pharmaceutical composition comprising a compound described herein, or an isotopically enriched analog, pharmaceutically acceptable salt, prodrug, tautomer, stereoisomer, or a mixture of stereoisomers thereof, and a pharmaceutically acceptable excipient.

The disclosure also provides compositions, including pharmaceutical compositions, kits that include the compounds, and methods of using (or administering) and making the compounds. The disclosure further provides compounds or compositions thereof for use in a method of treating a disease or condition that is mediated, at least in part, by a protein, or a protein fragment, implicated in neurodegenerative disease. Moreover, the disclosure provides uses of the compounds or compositions thereof in the manufacture of a medicament for the treatment of a disease or condition that is mediated, at least in part, by a protein, or a protein fragment, implicated in neurodegenerative disease.

DETAILED DESCRIPTION

The following description sets forth exemplary embodiments of the present technology. It should be recognized, however, that such description is not intended as a limitation on the scope of the present disclosure but is instead provided as a description of exemplary embodiments.

Definitions

As used in the present specification, the following words, phrases and symbols are generally intended to have the meanings as set forth below, except to the extent that the context in which they are used indicates otherwise.

A compound described herein refers to a compound, or an isotopically labeled analog, pharmaceutically acceptable salt, solvate, prodrug, stereoisomer, or mixture of stereoisomers thereof, of any formula described herein, including those of Formula I, Formula Ia, Formula Ib, Formula Ic, Formula IIa, Formula IIb, Formula IIc, Formula IId, Formula IIIa, Formula IIIb, Formula IIIc, Formula IIId, Formula IIIe, Formula IIIf, or a compound described any wherein herein including the Examples, or a compound of Table 1 or Table 1A.

A dash ("-") that is not between two letters or symbols is used to indicate a point of attachment to a parent structure for a substituent. For example, —C(O)NH$_2$ is attached to a parent structure through the carbon atom. A dash at the front or end of a chemical group is a matter of convenience; chemical groups may be depicted with or without one or more dashes without losing their ordinary meaning. A wavy line or a dashed line drawn through a bond in a structure indicates a specified point of attachment. Unless chemically or structurally required, no directionality or stereochemistry is indicated or implied by the order in which a chemical group is written or named.

The prefix "$C_{u-v}$" indicates that the following group has from u to v carbon atoms, exclusive of further substitution. For example, "$C_{1-6}$ alkyl" indicates an alkyl group having from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 9 carbon atoms (i.e., $C_{1-9}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., $-(CH_2)_3CH_3$), sec-butyl (i.e., $-CH(CH_3)CH_2CH_3$), isobutyl (i.e., $-CH_2CH(CH_3)_2$) and tert-butyl (i.e., $-C(CH_3)_3$); and "propyl" includes n-propyl (i.e., $-(CH_2)_2CH_3$) and isopropyl (i.e., $-CH(CH_3)_2$).

Alternative chemical names known to those of skill in the art may be used in lieu of the terms provided herein. For example, a divalent group such as a divalent "alkyl" group or a divalent "aryl" group, etc., may also be referred to as an "alkylene" or an "arylene" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl), and isoprenyl.

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to a group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkylamino" refers to a group "alkyl-NH—". Examples of alkylamino groups include, e.g., methylamino, ethylamino, iso-propylamino, tert-butylamino, and n-hexylamino. "Dialkylamino" refers to a group "(alkyl)$_2$N—". Examples of dialkylamino groups include, e.g., dimethylamino, diethylamino, (iso-propyl)(methyl)amino, (n-pentyl)(tert-butyl)amino, and di-n-hexylamino.

"Alkylthio" refers to a group "alkyl-S—". "Alkylsulfinyl" refers to a group "alkyl-S(O)—". "Alkylsulfonyl" refers to a group "alkyl-S(O)$_2$—".

"Acyl" refers to a group $-C(O)R^y$, wherein $R^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethylcarbonyl and benzoyl.

"Amido" refers to both a "C-amido" group which refers to a group $-C(O)NR^yR^z$ and an "N-amido" group which refers to a group $-NR^yC(O)R^z$, wherein $R^y$ and $R^z$ are independently hydrogen, alkyl, alkenyl, alkynyl, haloalkyl, cycloalkyl, heterocyclyl, aryl, heteroalkyl or heteroaryl; each of which may be optionally substituted, as defined herein, or $R^y$ and $R^z$ are taken together to form a cycloalkyl or heterocyclyl; each of which may be optionally substituted, as defined herein.

"Amino" refers to a group $-NR^yR^z$ wherein $R^y$ and $R^z$ are independently hydrogen, alkyl, alkenyl, alkynyl, haloalkyl, cycloalkyl, heterocyclyl, aryl, heteroalkyl or heteroaryl; each of which may be optionally substituted, as defined herein. In some embodiments, "amino" refers to a group $NH_2$.

"Amidino" refers to a group $-C(NR^y)(NR^z{}_2)$, wherein $R^y$ and $R^z$ are independently hydrogen, alkyl, alkenyl, alkynyl, haloalkyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl) or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to a group "aryl-alkyl-".

"Carbamoyl" refers to both an "O-carbamoyl" group which refers to a group $-O-C(O)NR^yR^z$ and an "N-carbamoyl" group which refers to a group $-NR^yC(O)OR^z$, wherein $R^y$ and $R^z$ are independently hydrogen, alkyl, alkenyl, alkynyl, haloalkyl, cycloalkyl, heterocyclyl, aryl, heteroalkyl or heteroaryl; each of which may be optionally substituted, as defined herein.

"Carboxyl ester" or "ester" refer to both $-OC(O)R^x$ and $-C(O)OR^x$, wherein $R^x$ is alkyl, alkenyl, alkynyl, haloalkyl, cycloalkyl, heterocyclyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one sp$^3$ ring carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cyclohexenyl, cycloheptyl and cyclooctyl. Polycyclic groups include, for example, bicyclo[2.2.1]heptanyl, bicyclo[2.2.2]octanyl, adamantyl, norbornyl, norbornenyl, decalinyl, 7,7-dimethyl-bicyclo[2.2.1]heptanyl and the like. Further, the term cycloalkyl is intended to encompass any non-aromatic ring system which may include a fused aryl ring, regardless of the attachment to the remainder of the molecule. Still further, cycloalkyl also includes "spirocycloalkyl," for example spiro[2.5]octanyl, spiro[4.5]decanyl, or spiro[5.5]undecanyl. When there are two positions for substitution on a carbon atom in a parent structure, cycloalkyl as a substituent group may include spirocycloalkyl. A cycloalkyl may be substituted at its carbon atom of attachment to a parent structure.

"Cycloalkoxy" refers to a group "—O-cycloalkyl."

"Cycloalkylalkyl" refers to a group "cycloalkyl-alkyl-".

"Guanidino" refers to —NR$^y$C(=NR$^z$)(NR$^y$R$^z$), wherein each R$^y$ and R$^z$ are independently hydrogen, alkyl, alkenyl, alkynyl, haloalkyl, cycloalkyl, heterocyclyl, aryl, heteroalkyl or heteroaryl; each of which may be optionally substituted, as defined herein.

"Imino" refers to a group —C(NR$^y$)R$^z$, wherein R$^y$ and R$^z$ are each independently hydrogen, alkyl, alkenyl, alkynyl, haloalkyl, cycloalkyl, heterocyclyl, aryl, heteroalkyl or heteroaryl; each of which may be optionally substituted, as defined herein.

"Imido" refers to a group —C(O)NR$^y$C(O)R$^z$, wherein R$^y$ and R$^z$ are each independently hydrogen, alkyl, alkenyl, alkynyl, haloalkyl, cycloalkyl, heterocyclyl, aryl, heteroalkyl or heteroaryl; each of which may be optionally substituted, as defined herein.

"Halogen" or "halo" refers to a substituent atom of group VIIA of the periodic table, such as fluoro, chloro, bromo or iodo.

"Haloalkyl" refers to an unbranched or branched alkyl group as defined above, wherein one or more (e.g., 1 to 6 or 1 to 3) hydrogen atoms, up to and including all hydrogen atoms, are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. A perhaloalkyl group is a haloalkyl group in which every hydrogen substituent is replaced by halo. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6 or 1 to 3) hydrogen atoms, up to and including all hydrogen atoms, are replaced by a halogen.

"Hydroxyalkyl" refers to an alkyl group as defined above, wherein one or more (e.g., 1 to 6 or 1 to 3) hydrogen atoms are replaced by a hydroxy group.

"Heteroalkyl" refers to an alkyl group in which one or more of the carbon atoms of the alkyl chain (and any associated hydrogen atoms) are each independently replaced with the same or different heteroatomic group, provided the point of attachment to the remainder of the molecule is through a carbon atom. The term "heteroalkyl" includes unbranched or branched saturated chains having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R is hydrogen, alkyl, alkenyl, alkynyl, haloalkyl, cycloalkyl, heterocyclyl, aryl, heteroalkyl or heteroaryl; each of which may be optionally substituted, as defined herein. Examples of heteroalkyl groups include, e.g., ethers (e.g., —CH$_2$OCH$_3$, —CH(CH$_3$)OCH$_3$, —CH$_2$CH$_2$OCH$_3$, —CH$_2$CH$_2$OCH$_2$CH$_2$OCH$_3$, etc.), thioethers (e.g., —CH$_2$SCH$_3$, —CH(CH$_3$)SCH$_3$, —CH$_2$CH$_2$SCH$_3$, —CH$_2$CH$_2$SCH$_2$CH$_2$SCH$_3$, etc.), sulfones (e.g., —CH$_2$S(O)$_2$CH$_3$, —CH(CH$_3$)S(O)$_2$CH$_3$, —CH$_2$CH$_2$S(O)$_2$CH$_3$, —CH$_2$CH$_2$S(O)$_2$CH$_2$CH$_2$OCH$_3$, etc.) and aminoalkyls (e.g., —CH$_2$NR$^y$CH$_3$, —CH(CH$_3$)NR$^y$CH$_3$, —CH$_2$CH$_2$NR$^y$CH$_3$, —CH$_2$CH$_2$NR$^y$CH$_2$CH$_2$NR$^y$CH$_3$, etc., where R$^y$ is hydrogen, alkyl, alkenyl, alkynyl, haloalkyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring or multiple fused rings, with one or more ring heteroatoms independently selected from nitrogen, oxygen, and sulfur, and may comprise one or more (e.g., 1 to 3)N-oxide (—O—) moieties. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring system, having a single or multiple fused rings containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to a group "heteroaryl-alkyl-".

"Heterocyclyl" refers to a saturated or partially unsaturated cyclic alkyl group, with one or more ring heteroatoms independently selected from nitrogen, oxygen and sulfur, wherein the nitrogen or sulfur atoms are optionally oxidized to form an N-oxide, a sulfinyl (—S(O)—), or a sulfoxide (—S(O)$_2$—). The term "heterocyclyl" includes heterocycloalkenyl groups (i.e., a heterocyclyl group having at least one endocyclic or exocyclic double bond), bridged-heterocyclyl groups, fused-heterocyclyl groups, oxo-heterocyclyl (i.e., a heterocyclyl including at least one oxo) and spiro-heterocyclyl groups. A heterocyclyl may be a single ring or multiple rings wherein the multiple rings may be fused, bridged or spiro. Regardless of substituent groups listed, a heterocyclyl may comprise one or more (e.g., 1 to 3) oxo (=O) or N-oxide (—O⁻) moieties unless stated otherwise. A heterocyclyl can be bound through a carbon atom or a heteroatom as valency permits. Further, the term heterocyclyl encompasses any ring system including a non-aromatic ring containing at least one heteroatom, which ring may be fused to an aryl or heteroaryl ring, regardless of the attachment to the remainder of the molecule. A heterocyclyl may have a charged resonance structure that is aromatic (e.g., pyridin-2(1H)-on-1-yl). As used herein, a heterocyclyl may include 3 to 14 ring atoms, 3 to 10 ring atoms, 3 to 6 ring atoms, or 5 to 6 ring atoms, and/or 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl.". Examples of the spiroheterocyclyl rings include, e.g., bicyclic and tricyclic ring systems, such as 2-oxa-7-azaspiro[3.5] nonanyl, 2-oxa-6-azaspiro[3.4]octanyl and 6-oxa-1-azaspiro [3.3]heptanyl. Examples of bridged-heterocyclyl rings include, but are not limited to, 2,5-diazabicyclo[2.2.1]heptane, 2-oxa-5-azabicyclo[2.2.1]heptanyl. When there are two positions for substitution on a carbon atom in a parent structure, heterocyclyl as a substituent group may include spiroheterocyclyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to a group "heterocyclylalkyl-."

"Oxime" refers to a group —CR$^y$(=NOH) wherein R$^y$ is hydrogen, alkyl, alkenyl, alkynyl, haloalkyl, cycloalkyl, heterocyclyl, aryl, heteroalkyl or heteroaryl; each of which may be optionally substituted, as defined herein.

"Sulfonyl" refers to a group —S(O)$_2$R$^y$, where R$^y$ is hydrogen, alkyl, alkenyl, alkynyl, haloalkyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to a group —S(O)R$^y$, where R$^y$ is hydrogen, alkyl, alkenyl, alkynyl, haloalkyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —SO$_2$NR$^y$R$^z$ and —NR$^y$SO$_2$R$^z$, where R$^y$ and R$^z$ are each independently hydrogen, alkyl, alkenyl, alkynyl, haloalkyl, cycloalkyl, heterocyclyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to a group which is unsubstituted or substituted.

The term "substituted" used herein refers to a group in which any one or more (e.g., 1 to 5 or 1 to 3) hydrogen atoms is replaced by a non-hydrogen group such as, but not limited to alkyl, alkenyl, alkynyl, alkoxy, alkylthio, acyl, amido, amino, amidino, aryl, arylalkyl, azido, carbamoyl, carboxyl, carboxyl ester, cyano, cycloalkyl, cycloalkoxy, cycloalkylalkyl, guanidino, halo, haloalkyl, haloalkoxy, hydroxyalkyl, heteroalkyl, heteroaryl, heteroarylalkyl, heterocyclyl, heterocyclylalkyl, —NHNH$_2$, =NNH$_2$, imino, imido, hydroxy, oxo, oxime, nitro, sulfonyl, sulfinyl, alkylsulfonyl, alkylsulfinyl, thiocyanate, —S(O)OH, —S(O)$_2$OH, sulfonamido, thiol, thioxo, N-oxide or —Si(R$^y$)$_3$, wherein each R$^y$ is independently hydrogen, alkyl, alkenyl, alkynyl, haloalkyl, heteroalkyl, cycloalkyl, aryl, heteroaryl, or heterocyclyl.

In certain embodiments, "substituted" refers to a group in which one or more (e.g., 1 to 5 or 1 to 3) hydrogen atoms are independently replaced with deuterium, halo, cyano, hydroxyl, imino, nitro, azido, oxo, thioxo, alkyl, alkenyl, alkynyl, haloalkyl, alkoxy, thioalkyl, haloalkoxy, cycloalkyl, heterocyclyl, N-heterocyclyl, heterocyclylalkyl, aryl, arylalkyl, heteroaryl, heteroarylalkyl, —NR$^g$R$^h$, —NR$^g$C(=O) R$^h$, —NR$^g$C(=O)NR$^g$R$^h$, —NR$^g$C(=O)OR$^h$, —NR$^g$S (=O)$_{1-2}$R$^h$, —C(=O)R$^g$, —C(=O)OR$^g$, —OC(=O)OR$^g$, —OC(=O)R$^g$, —C(=O)NR$^g$R$^h$, —OC(=O)NR$^g$R$^h$, —OR$^g$, —SR$^g$, —S(=O)R$^g$, —S(=O)$_2$R$^g$, —OS(=O)$_{1-2}$ R$^g$, —S(=O)$_{1-2}$OR$^g$, —NR$^g$S(=O)$_{1-2}$NR$^g$R$^h$, =NSO$_2$R$^g$, =NOR$^g$, —S(=O)$_{1-2}$NR$^g$R$^h$, —SF$_5$, or —SCF$_3$. In certain embodiments, "substituted" also means a group in which one or more (e.g., 1 to 5 or 1 to 3) hydrogen atoms are replaced with —C(=O)R$^g$, —C(=O)OR$^g$, —C(=O)NR$^g$R$^h$, —CH$_2$SO$_2$R$^g$, or —CH$_2$SO$_2$NR$^g$R$^h$. In the foregoing, R$^g$ and R$^h$ are the same or different and independently hydrogen, alkyl, alkenyl, alkynyl, alkoxy, thioalkyl, aryl, arylalkyl, cycloalkyl, cycloalkylalkyl, haloalkyl, heterocyclyl, heterocyclylalkyl, heteroaryl, and/or heteroarylalkyl, or two of R$^g$ and R$^h$ and R$^i$ are taken together with the atoms to which they are attached to form a heterocyclyl ring optionally substituted with oxo, halo or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended to arise from the above definitions. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to encompass compounds having chemically unfeasable or unisolable substitution patterns (e.g., methyl substituted with 5 fluorines or heteroaryl groups having three consecutive oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein is intended to represent unlabeled forms as well as "isotopically enriched analogs" of the compounds. Isotopically enriched forms of compounds may also be referred to as "labeled." Isotopically enriched analogs have structures depicted herein, except that one or more atoms are enriched in an isotope having a selected atomic mass or mass number. Examples of isotopes that can be incorporated into the compounds described herein include isotopes of hydrogen, carbon, nitrogen, oxygen, phosphorous, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Generally, an isotopically enriched analog includes compounds having any isotopic enrichment above the natural abundance of the isotope (e.g., at Earth's surface). Various isotopically labeled compounds are included in the present disclosure, for example those into which radioactive isotopes such as $^{3}H$, $^{18}F$, $^{11}C$, $^{13}C$ and $^{14}C$ are incorporated. Compounds labeled with $^{18}F$, $^{3}H$, or $^{11}C$ may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds may exhibit increased resistance to metabolism and are thus may be useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Where a compound is described as a deuterated analog, the compound may be drawn with deuterium as a substituent.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen and its isotopes at their natural abundances.

In many cases, the compounds of this disclosure are capable of forming acid and/or base salts by virtue of the presence of amino and/or carboxyl groups or groups similar thereto.

Provided also are isotopically enriched analogs, pharmaceutically acceptable salts, prodrugs, tautomers, stereoisomers, and mixtures of stereoisomers of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a compound described herein refers to salts that retain the biological effectiveness and properties of the given compound and which are not biologically or otherwise undesirable. "Pharmaceutically acceptable salts" or "physiologically acceptable salts" of compounds described herein include, for example, acid addition salts obtained by interacting a compound with a basic functional group with an acid, and base addition salts obtained by interacting a compounds with an acidic functional group with a base. If the compound is obtained as an acid addition salt, the free base can be obtained by basifying a solution of the acid salt. Conversely, if the compound is a free base (e.g., of an amine), an addition salt may be produced by dissolving the free base in a suitable organic solvent and treating the solution with an acid. Those skilled in the art will recognize various synthetic methodologies that may be used to prepare nontoxic pharmaceutically acceptable addition salts. Pharmaceutically acceptable acid addition salts of compounds described herein may be prepared from inorganic and organic acids. Suitable inorganic acids include, e.g., hydrochloric acid, hydrobromic acid, sulfuric acid, nitric acid, phosphoric acid and the like. Suitable organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), cyclic amines (e.g., piperidine, piperazine, 1,4-diazabicyclo[2.2.2]octane), aromatic amines (e.g., pyridine, quinoline), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Some compounds described herein may exist as tautomers. For example, where a compound is drawn as including an amide, the compound may exist as an imidic acid tautomer, and where a compound is drawn as including a ketone, the compound may also exist as an enol tautomer. Regardless of which tautomer is shown and regardless of the nature of the equilibrium among tautomers, the compounds are understood by one of ordinary skill in the art to comprise both tautomers. Thus, for example, the amide containing compounds are understood to include their imidic acid tautomers, and the imidic acid containing compounds are understood to include their amide tautomers.

The compounds described herein may include an asymmetric center and may thus give rise to enantiomers, diastereomers, and other stereoisomeric forms that may be defined, in terms of absolute stereochemistry, as (R)- or (S)-, or as (D)- or (L)- for amino acids. Compounds described herein are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). When the compounds described herein contain double bonds or other centers of geometric asymmetry, and unless specified otherwise, it is intended that the compounds include both cis- and trans- or E- and Z-geometric isomers.

A "stereoisomer" refers to one of a set of compounds made up of the same atoms bonded by the same bonds but having different three-dimensional structures. Various stereoisomers and mixtures thereof are contemplated including "enantiomers," which refers to stereoisomeric compounds that are non-superimposable mirror images of one another.

A "diastereomer" is one of a set of stereoisomers that have at least two asymmetric atoms that are not mirror-images of each other.

A "prodrug" is any molecule which releases a putatively active parent drug according to a compound described herein in vivo when such prodrug is administered to a mammalian subject. A prodrug may be a form of a compound described herein modified in such a way that the modifications may be cleaved in vivo to release the parent compound. Prodrugs may be prepared by modifying functional groups present in the compound described herein in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As used herein the terms "group," "moiety," "radical," "substituent," and "fragment" are synonymous and are intended to indicate portions of molecules attachable to other portions of molecules, e.g., through an indicated attachment point or bond.

The term "active agent" is used to indicate a compound which has biological activity in the treatment, amelioration, or prevention of a disease or condition. In some embodiments, an "active agent" is a compound or an isotopically labeled analog, pharmaceutically acceptable salt, solvate, prodrug, stereoisomer, or mixture of stereoisomers thereof, having pharmaceutical utility. For example an active agent may be an anti-neurodegenerative therapeutic.

The term "effective amount" means an amount, for example, of a compound described herein, sufficient to bring about a desired response in an individual or patient. The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease described herein. The (therapeutically) effective amount may vary depending on the subject, and disease or condition being treated, the weight and age of the subject, the severity of the disease or condition, and the manner of administering, which can be determined by one of ordinary skill in the art.

The term "huntingtin protein" or "HTT protein" as used herein, refers to the protein encoded by the human huntingtin gene (HTT gene) located on the short (p) arm of chromosome 4 at position 16.3. More precisely, the $IT_{15}$ gene coding for the HTT protein is located from base pair 3,076,407 to base pair 3,245,686 on chromosome 4.

The term "protein aggregate," as used herein refers to an aggregation of protein which may be, for example, an insoluble fibrous amyloid comprising mis-folded HTT protein molecules ("HTT protein aggregate") or mis-folded β-amyloid protein molecules ("-amyloid aggregate"). A "protein implicated in neurodegenerative disease" may be a protein that is capable of forming such aggregates, in its wild type or in a mutated form, or may be a protein that participates in a pathological process related to a neurodegenerative disease.

In some embodiments, the term "neurodegenerative disease" refers to a disease or condition in which the function of a subject's nervous system becomes impaired. Examples of neurodegenerative diseases include those described herein.

"Treatment" or "treating" means any treatment of a disease state in a patient, including
a) inhibiting the disease (e.g., decreasing one or more symptoms resulting from the disease or condition, and/or diminishing the extent of the disease or condition);
b) slowing or arresting the development of clinical symptoms associated with the disease or condition (e.g., stabilizing the disease or condition, preventing or delaying the worsening or progression of the disease or condition, and/or preventing or delaying the spread (e.g., metastasis) of the disease or condition); and/or
c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival).

"Prevention" or "preventing" means any treatment of a disease or condition that causes the clinical symptoms of the disease or condition not to develop. Compounds may, in some embodiments, be administered to a subject (including a human) who is at risk (e.g., carries a genetic or epigenetic marker, has engaged in an activity, or has been exposed to an environmental condition, associated with the disease or condition) or has a family history of the disease or condition.

"Subject" or "patient" refers to an animal, such as a mammal, that has been or will be the object of treatment, observation or experiment. The methods described herein may be useful in both human therapy and veterinary applications. In some embodiments, the subject or patient is a mammal. In some embodiments the subject or patient is human.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination. All combinations of the embodiments pertaining to the chemical groups represented by the variables contained within Formula I are specifically embraced herein just as if each and every combination was individually and explicitly recited, to the extent that such combinations result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced herein just as if each and every subcombination of chemical groups and subcombination of uses and medical indications was individually and explicitly recited herein. In addition, some embodiments include every combination of one or more additional agents disclosed herein just as if each and every combination was individually and explicitly recited.

| List of Abbreviations and Acronyms | |
|---|---|
| δ | Chemical shift |
| Ac | Acetate |
| addn. | Addition |
| approx. | Approximately |
| aq | Aqueous |
| Ar | Aryl |
| BINAP | 2,2'-Bis(diphenylphosphino)-1,1'-binaphthyl |
| Boc | Tert-butyloxycarbonyl |
| br | Broad |
| BrettPhos | 2-(Dicyclohexylphosphino)3,6-dimethoxy-2',4',6'-triisopropyl-1,1'-biphenyl |
| CV | Column volumes |
| d | Doublet |
| dd | Doublet of doublets |
| dba | Dibenzylideneacetone |
| DCM | Dichloromethane |
| DME | Dimethoxyethane |
| DMEDA | N,N'-Dimethylethylenediamine |
| DMF | N,N-dimethylformamide |
| DMSO | Dimethyl sulfoxide |
| eq or equiv | Equivalent |
| ES+ | Electrospray positive ionization |
| Et | Ethyl |
| EtOAc | Ethyl acetate |
| h | Hour(s) |
| HATU | N-(Dimethylamino)-1H-1,2,3-triazolo-[4,5-b]pyridin-1-ylmethylene]-N-methylmethanaminium hexafluorophosphate N-oxide |
| HBTU | N,N,N',N'-Tetramethyl-O-(1H-benzotriazol-1-yl)uronium hexafluorophosphate |
| HPLC | High performance liquid chromatography |
| HTRF | Homogeneous time resolved fluorescence |
| LCMS | Liquid chromatography-mass spectrometry |
| J | Coupling constant |
| m | Multiplet |
| Me | Methyl |
| MeCN | Acetonitrile |
| MeOH | Methanol |
| min | Minute(s) |
| MS | Mass spectrometry |
| m/z | Mass to charge ratio |
| NMR | Nuclear magnetic resonance |
| p | Para |
| Ph | Phenyl |
| ppm | Part(s) per million |
| prep | Preparative |
| q | Quartet |
| R.M | Reaction mixture |
| RT | Retention time |
| rt | Room temperature |
| RuPhos Pd G2 | 2nd Generation RuPhos Precatalyst, Chloro(2-dicyclohexylphosphino-2',6'-diisopropoxy-1,1'-biphenyl)[2-(2'-amino-1,1'-biphenyl)]palladium(II) |
| s | Singlet |
| sat. | Saturated |
| SCX | Strong cation exchange |
| SFC | Supercritical fluid chromatography |
| $S_NAr$ | Nucleophilic substitution, aromatic |
| t | Triplet |
| t-Bu | tert-Butyl |
| TCFH | Chloro-N,N,N',N'-tetramethylformamidinium hexafluorophosphate |
| TFA | Trifluoroacetic acid |
| THF | Tetrahydrofuran |
| Ts | p-Toluenesulfonyl |
| UV | Ultraviolet |

Compounds

Provided herein are compounds for modulating HTT. In certain embodiments, provided is a compound of Formula I:

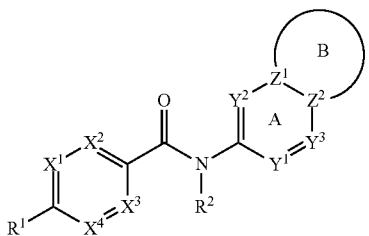

or an isotopically enriched analog, pharmaceutically acceptable salt, prodrug, tautomer, stereoisomer, or a mixture of stereoisomers thereof, wherein:

$X^1$, $X^2$, $X^3$, and $X^4$ are $CR^4$ or N, wherein at least two but no more than three of $X^1$, $X^2$, $X^3$, and $X^4$ are N;

each $R^4$ is independently hydrogen, halo, hydroxy, $C_{1-6}$alkyl, $C_{1-6}$haloalkyl, or $C_{1-6}$alkoxy;

$Y^1$ is $CR^5$ or N;

$R^5$ is hydrogen, cyano, halo, hydroxy, $C_{1-6}$alkyl, $C_{1-6}$haloalkyl, $C_{1-6}$alkylthio, $C_{1-6}$alkoxy, $C_{1-6}$haloalkoxy, heterocyclyl, —$NH_2$, —$NHR^{17}$, or —$N(R^{17})_2$, and optionally substituted on an available nitrogen atom with $C_{1-6}$alkyl or $C_{1-6}$haloalkyl;

$Y^2$ is absent, $CR^6$ or N;

$R^6$ is hydrogen, cyano, halo, hydroxy, $C_{1-6}$alkyl, $C_{1-6}$haloalkyl, $C_{1-6}$alkylthio, $C_{1-6}$alkoxy, $C_{1-6}$haloalkoxy, heterocyclyl, —$NH_2$, —$NHR^{17}$, or —$N(R^{17})_2$, and optionally substituted on an available nitrogen atom with $C_{1-6}$alkyl or $C_{1-6}$haloalkyl; and $Y^3$ is $CR^3$ or N;

$R^3$ is hydrogen, cyano, halo, hydroxy, $C_{1-6}$alkyl, $C_{1-6}$haloalkyl, $C_{1-6}$alkylthio, $C_{1-6}$alkoxy, $C_{1-6}$haloalkoxy, heterocyclyl, —$NH_2$, —$NHR^{17}$, or —$N(R^{17})_2$, and optionally substituted on an available nitrogen atom with $C_{1-6}$alkyl or $C_{1-6}$haloalkyl;

each $R^{17}$ is independently $C_{1-4}$alkyl, or two $R^{17}$ join, with any intervening atoms, to form a 3- to 6-membered heterocyclyl;

each of $Z^1$ and $Z^2$ is C or N;

Ring A and Ring B together form a 9- or 10-membered bicyclic heteroaryl containing 1 to 3 ring nitrogen atoms;

Ring B contains 1 to 3 heteroatoms selected from N, O, and S, and is optionally substituted on available carbon atom(s) with 1 to 3 substituents independently selected from halo, hydroxy, $C_{1-6}$alkyl, $C_{1-6}$haloalkyl, $C_{1-6}$alkoxy, and $C_{1-6}$haloalkoxy, and optionally substituted on an available nitrogen atom with $C_{1-6}$alkyl or $C_{1-6}$haloalkyl;

$R^1$ is -$L^1$-$R^{11}$, wherein $L^1$ is —O—, —S—, —S(O)—, —S(O)$_2$—, —N($R^{12}$)—, —$C_{1-3}$alkylene-, —O—$C_{1-3}$alkylene-, —N($R^{12}$)—$C_{1-3}$alkylene-, or absent, and $R^{11}$ is $C_{2-6}$alkynyl, $C_{3-10}$cycloalkyl, $C_{6-10}$aryl, heteroaryl, or heterocyclyl, wherein $R^{11}$ is optionally substituted with 1 to 4 $R^{13}$ groups;

$R^{12}$ is hydrogen or $C_{1-6}$alkyl;

each $R^{13}$ is independently selected from halo, cyano, hydroxy, $C_{1-6}$alkyl optionally substituted with $R^{16}$, $C_{1-6}$haloalkyl, $C_{1-6}$hydroxyalkyl, $C_{3-10}$cycloalkyl optionally substituted with $R^{16}$, $C_{3-10}$cycloalkyl-$C_{1-6}$alkyl optionally substituted with $R^{16}$, $C_{6-10}$aryl optionally substituted with $R^{16}$, $C_{6-10}$aryl-$C_{1-6}$alkyl optionally substituted with $R^{16}$, heteroaryl optionally substituted with $R^{16}$, heteroaryl-$C_{1-6}$alkyl optionally substituted with $R^{16}$, heterocyclyl optionally substituted with $R^{16}$, heterocyclyl-$C_{1-6}$alkyl optionally substituted with $R^{16}$, $OR^{14}$, —$NH_2$, —$NHR^{14}$, —$N(R^{14})_2$, —$C_{1-6}$ alkylene-$NH_2$, —$C_{1-6}$alkylene-$NHR^{14}$, —$C_{1-6}$alkylene-$N(R^{14})_2$, —$C(O)R^{15}$, —$C(O)OR^{15}$, —$C(O)NHR^{15}$, —$C(O)N(C_{1-4}$alkyl)$R^{15}$, —$S(O)_2R^{15}$, —$S(O)R^{15}$, —$NHC(O)R^{15}$, —$N(C_{1-4}$alkyl)$C(O)R^{15}$, —$NHS(O)R^{15}$, —$N(C_{1-4}$alkyl)$S(O)R^{15}$, —$NHS(O)_2R^{15}$, and —$N(C_{1-4}$alkyl)$S(O)_2R^{15}$;

each $R^{14}$ is independently selected from $C_{1-6}$alkyl, $C_{3-10}$cycloalkyl, $C_{6-10}$aryl, heteroaryl, and heterocyclyl; and each $R^{14}$ is optionally substituted with one to six halo, $C_{1-3}$alkyl, $C_{1-3}$ alkoxy, $C_{3-10}$cycloalkyl, or —$NHSO_2$-aryl-$N(CH_3)_2$;

each $R^{15}$ is independently hydrogen, —OH, $C_{1-6}$alkyl, $C_{1-6}$haloalkyl, $C_{3-10}$cycloalkyl, $C_{6-10}$aryl, heteroaryl, or heterocyclyl;

each $R^{16}$ is independently halo, cyano, hydroxy, —$NH_2$, —$NHR^{21}$, —$N(R^{21})_2$, $C_{1-6}$alkyl, $C_{1-6}$haloalkyl, $OR^{21}$, or $C_{3-10}$cycloalkyl;

each $R^{21}$ is independently selected from $C_{1-6}$alkyl, $C_{3-10}$cycloalkyl, $C_{6-10}$aryl, heteroaryl, and heterocyclyl, and each $R^{21}$ is optionally substituted with one to six halo or $C_{1-3}$alkoxy; and $R^2$ is hydrogen or $C_{1-6}$alkyl.

In certain embodiments, provided is a compound of Formula I:

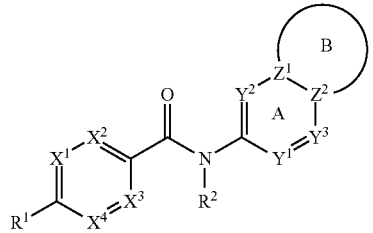

or an isotopically enriched analog, pharmaceutically acceptable salt, prodrug, tautomer, stereoisomer, or a mixture of stereoisomers thereof, wherein:

$X^1$, $X^2$, $X^3$, and $X^4$ are $CR^4$ or N, wherein at least two but no more than three of $X^1$, $X^2$, $X^3$, and $X^4$ are N;

$Y^1$ is $CR^5$ or N;

$Y^2$ is $CR^6$ or N;

$Y^3$ is $CR^3$ or N;

each of $Z^1$ and $Z^2$ is C or N;

Ring A and Ring B together form a 9- or 10-membered bicyclic heteroaryl containing 1 to 3 ring nitrogen atoms; and Ring B contains 1 to 3 nitrogen atoms and is optionally substituted on an available carbon atom with halo, hydroxy, $C_{1-6}$alkyl, $C_{1-6}$haloalkyl, or $C_{1-6}$alkoxy and optionally substituted on an available nitrogen atom with $C_{1-6}$alkyl or $C_{1-6}$haloalkyl;

$R^1$ is -$L^1$-$R^{11}$, wherein $L^1$ is —O—, —S—, —S(O)—, —S(O)$_2$—, —N($R^{12}$)—, or absent, and $R^{11}$ is $C_{3-10}$cycloalkyl, $C_{6-10}$aryl, heteroaryl, or heterocyclyl, wherein $R^{11}$ is optionally substituted with 1 to 4 $R^{13}$ groups;

$R^{12}$ is hydrogen or $C_{1-6}$alkyl;

each $R^{13}$ is independently selected from halo, cyano, hydroxy, $C_{1-6}$alkyl optionally substituted with $R^{16}$, $C_{1-6}$haloalkyl, $C_{1-6}$hydroxyalkyl, $C_{3-10}$cycloalkyl optionally substituted with $R^{16}$, $C_{3-10}$cycloalkyl-$C_{1-6}$ alkyl optionally substituted with $R^{16}$, $C_{6-10}$aryl optionally substituted with $R^{16}$, $C_{6-10}$aryl-$C_{1-6}$alkyl optionally substituted with $R^{16}$, heteroaryl optionally substituted with $R^{16}$, heteroaryl-$C_{1-6}$alkyl optionally substituted with $R^{16}$, heterocyclyl optionally substituted with $R^{16}$, heterocyclyl-$C_{1-6}$alkyl optionally substituted with $R^{16}$, $OR^{14}$, —$NH_2$, —$NHR^{14}$, —$N(R^{14})_2$, —$C_{1-6}$alkylene-$NH_2$, —$C_{1-6}$alkylene-$NHR^{14}$, —$C_{1-6}$alkylene-$N(R^{14})_2$, —$C(O)R^{15}$, —$C(O)OR^{15}$, —$C(O)NHR^{15}$, —$C(O)N(C_{1-4}$alkyl)$R^{15}$, —$S(O)_2R^{15}$, —$S(O)R^{15}$, —$NHC(O)R^{15}$, —$N(C_{1-4}$alkyl)$C(O)R^{15}$, —$NHS(O)R^{15}$, —$N(C_{1-4}$alkyl)$S(O)R^{15}$, —$NHS(O)_2R^{15}$, and —$N(C_{1-4}$alkyl)$S(O)_2R^{15}$;

each $R^{14}$ is independently selected from $C_{1-6}$alkyl, $C_{3-10}$cycloalkyl, $C_{6-10}$aryl, heteroaryl, and heterocyclyl, and each $R^{14}$ is optionally substituted with one to three halo;

each $R^{15}$ is independently hydrogen, —OH, $C_{1-6}$alkyl, $C_{1-6}$haloalkyl, $C_{3-10}$cycloalkyl, $C_{6-10}$aryl, heteroaryl, or heterocyclyl;

each $R^{16}$ is independently halo, cyano, hydroxy, amino, alkylamino, dialkylamino, or $C_{1-6}$alkyl;

$R^2$ is hydrogen or $C_{1-6}$alkyl;

$R^3$ is hydrogen, cyano, halo, hydroxy, $C_{1-6}$alkyl, $C_{1-6}$haloalkyl, $C_{1-6}$alkylthio, $C_{1-6}$alkoxy, heterocyclyl, —$NH_2$, —$NHR^{17}$, or —$N(R^7)_2$;

wherein each $R^{17}$ is independently $C_{1-4}$alkyl, or two $R^{17}$ join, with any intervening atoms, to form a 3- to 6-membered heterocyclyl;

each $R^4$ is independently hydrogen, halo, hydroxy, $C_{1-6}$alkyl, $C_{1-6}$haloalkyl, or $C_{1-6}$alkoxy;

$R^5$ is hydrogen, cyano, halo, hydroxy, $C_{1-6}$alkyl, $C_{1-6}$haloalkyl, $C_{1-6}$alkylthio, $C_{1-6}$alkoxy, heterocyclyl, —$NH_2$, —$NHR^{17}$, —$N(R^{17})_2$; and $R^6$ is hydrogen, halo, hydroxy, $C_{1-6}$alkyl, $C_{1-6}$haloalkyl, or $C_{1-6}$alkoxy.

In certain embodiments, Ring B is a 5-membered heteroaryl containing 1 to 3 nitrogen atoms.

In certain embodiments, Ring B is a 6-membered heteroaryl containing 1 to 3 nitrogen atoms.

In certain embodiments, Ring B is selected from

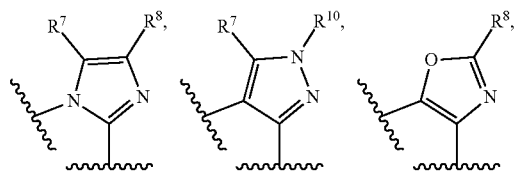

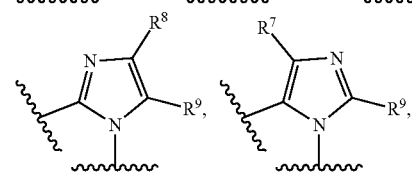

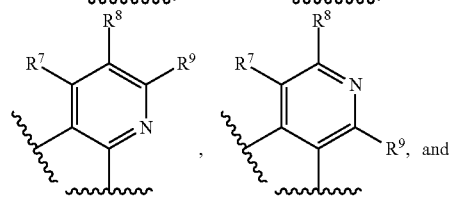

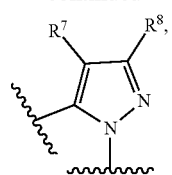

wherein each of $R^7$, $R^8$, and $R^9$ is independently hydrogen, halo, hydroxy, $C_{1-6}$alkyl, $C_{1-6}$haloalkyl, or $C_{1-6}$alkoxy; and $R^{10}$ is hydrogen, $C_{1-6}$alkyl, or $C_{1-6}$haloalkyl.

In certain embodiments, Ring B is selected from

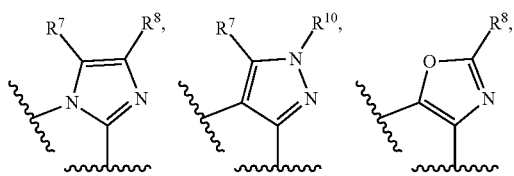

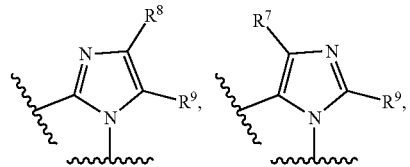

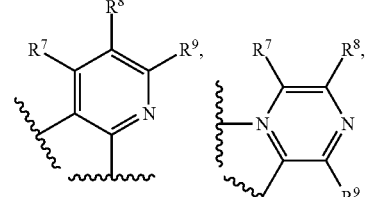

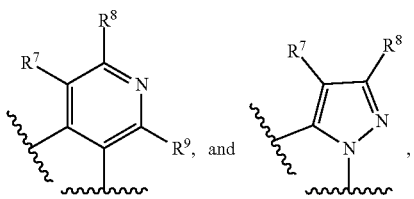

wherein each of $R^7$, $R^8$, and $R^9$ is independently hydrogen, halo, hydroxy, $C_{1-6}$alkyl, $C_{1-6}$haloalkyl, or $C_{1-6}$alkoxy; and $R^{10}$ is hydrogen, $C_{1-6}$alkyl, or $C_{1-6}$haloalkyl.

In certain embodiments, Ring B is selected from

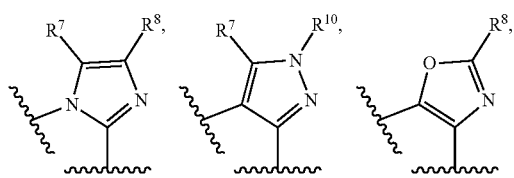

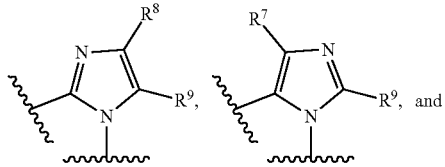

-continued

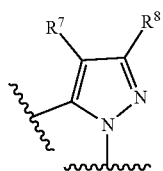

wherein each of $R^7$, $R^8$, and $R^9$ is hydrogen, halo, hydroxy, $C_{1-6}$alkyl, $C_{1-6}$haloalkyl, or $C_{1-6}$alkoxy; and $R^{10}$ is hydrogen, $C_{1-6}$alkyl, or $C_{1-6}$haloalkyl.

In certain embodiments, Ring B is selected from

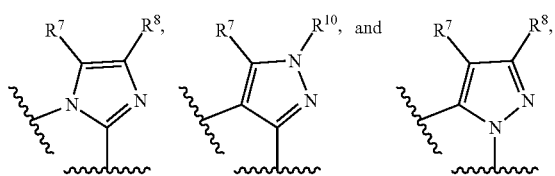

wherein each of $R^7$ and $R^8$ is hydrogen, halo, hydroxy, $C_{1-6}$alkyl, $C_{1-6}$haloalkyl, or $C_{1-6}$alkoxy; and $R^{10}$ is hydrogen, $C_{1-6}$alkyl, or $C_{1-6}$haloalkyl.

In certain embodiments, Ring B is selected from

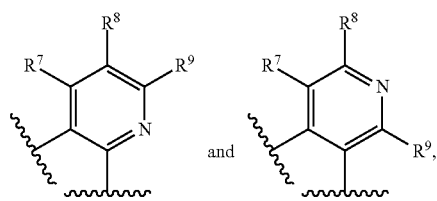

wherein each of $R^7$, $R^8$, and $R^9$ is hydrogen, halo, hydroxy, $C_{1-6}$alkyl, $C_{1-6}$haloalkyl, or $C_{1-6}$alkoxy.

In certain embodiments, provided is a compound of Formula Ia:

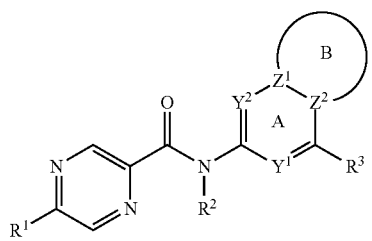

Ia or an isotopically enriched analog, pharmaceutically acceptable salt, prodrug, tautomer, stereoisomer, or a mixture of stereoisomers thereof, where Ring A, Ring B, $R^1$, $R^2$, $R^3$, $Y^1$, $Y^2$, $Z^1$ and $Z^2$ are as defined herein.

In certain embodiments, provided is a compound of Formula Ib:

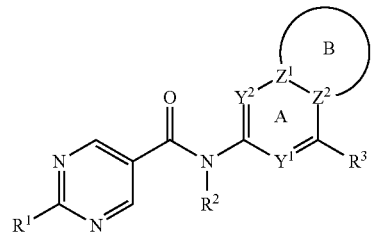

Ib or an isotopically enriched analog, pharmaceutically acceptable salt, prodrug, tautomer, stereoisomer, or a mixture of stereoisomers thereof, where Ring A, Ring B, $R^1$, $R^2$, $R^3$, $Y^1$, $Y^2$, $Z^1$ and $Z^2$ are as defined herein.

In certain embodiments, provided is a compound of Formula Ic:

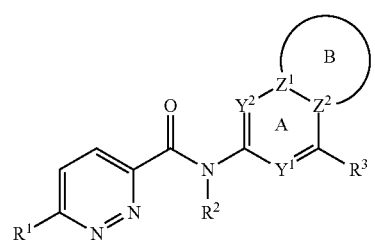

Ic or an isotopically enriched analog, pharmaceutically acceptable salt, prodrug, tautomer, stereoisomer, or a mixture of stereoisomers thereof, where Ring A, Ring B, $R^1$, $R^2$, $R^3$, $Y^1$, $Y^2$, $Z^1$ and $Z^2$ are as defined herein.

In certain embodiments, provided is a compound of Formula IIa:

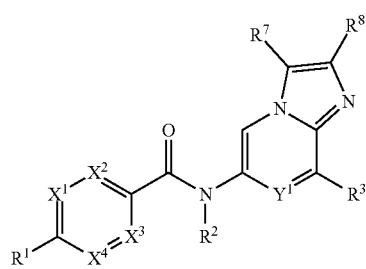

IIa or an isotopically enriched analog, pharmaceutically acceptable salt, prodrug, tautomer, stereoisomer, or a mixture of stereoisomers thereof, where $R^1$, $R^2$, $R^3$, $R^7$, $R^8$, $X^1$, $X^2$, $X^3$, $X^4$, and $Y^1$ are as defined herein.

In certain embodiments, provided is a compound of Formula IIb:

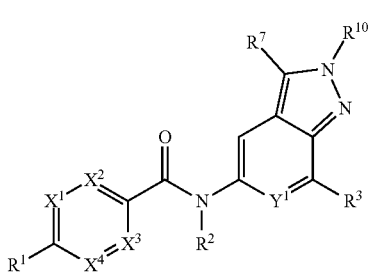

IIb or an isotopically enriched analog, pharmaceutically acceptable salt, prodrug, tautomer, stereoisomer, or a mixture of stereoisomers thereof, where $R^1$, $R^2$, $R^3$, $R^7$, $R^{10}$, $X^1$, $X^2$, $X^3$, $X^4$, and $Y^1$ are as defined herein.

In certain embodiments, provided is a compound of Formula IIc:

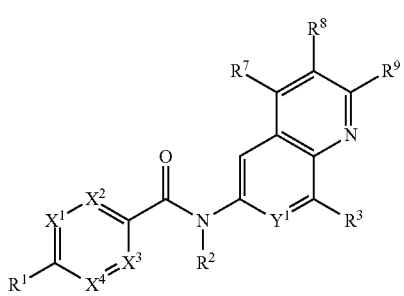

IIc or an isotopically enriched analog, pharmaceutically acceptable salt, prodrug, tautomer, stereoisomer, or a mixture of stereoisomers thereof, where $R^1$, $R^2$, $R^3$, $R^7$, $R^8$, $R^9$, $X^1$, $X^2$, $X^3$, $X^4$, and $Y^1$ are as defined herein.

In certain embodiments, provided is a compound of Formula IId:

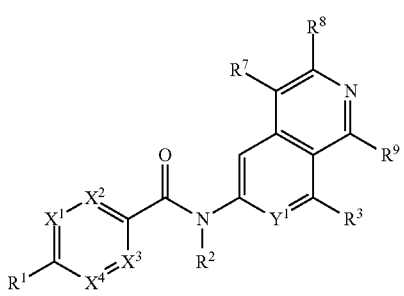

IId or an isotopically enriched analog, pharmaceutically acceptable salt, prodrug tautomer, stereoisomer, or a mixture of stereoisomers thereof, where $R^1$, $R^2$, $R^3$, $R^7$, $R^8$, $R^9$, $X^1$, $X^2$, $X^3$, $X^4$, and $Y^1$ are as defined herein.

In certain embodiments, provided is a compound of Formula IIIa:

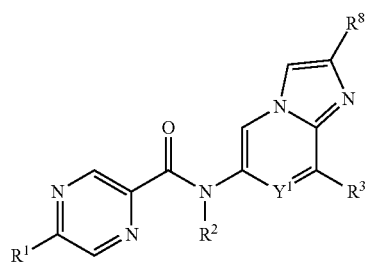

IIIa or an isotopically enriched analog, pharmaceutically acceptable salt, prodrug, tautomer, stereoisomer, or a mixture of stereoisomers thereof, where $R^1$, $R^2$, $R^3$, $R^8$, and $Y^1$ are as defined herein.

In certain embodiments, provided is a compound of Formula IIIb:

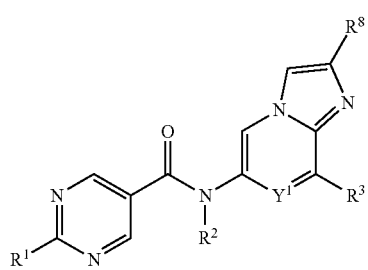

IIIb or an isotopically enriched analog, pharmaceutically acceptable salt, prodrug, tautomer, stereoisomer, or a mixture of stereoisomers thereof, where $R^1$, $R^2$, $R^3$, $R^8$, and $Y^1$ are as defined herein.

In certain embodiments, provided is a compound of Formula IIIc:

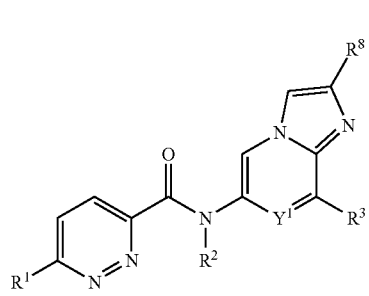

IIIc or an isotopically enriched analog, pharmaceutically acceptable salt, prodrug, tautomer, stereoisomer, or a mixture of stereoisomers thereof, where $R^1$, $R^2$, $R^3$, $R^8$, and $Y^1$ are as defined herein.

In certain embodiments, provided is a compound of Formula IIId:

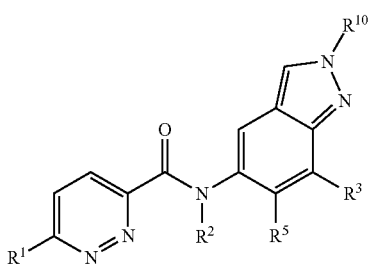

or an isotopically enriched analog, pharmaceutically acceptable salt, prodrug, tautomer, stereoisomer, or a mixture of stereoisomers thereof, where $R^1$, $R^2$, $R^3$, $R^5$, and $R^{10}$ are as defined herein.

In certain embodiments, provided is a compound of Formula IIIe:

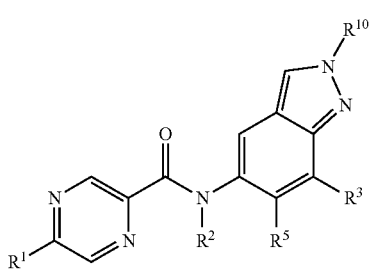

or an isotopically enriched analog, pharmaceutically acceptable salt, prodrug, tautomer, stereoisomer, or a mixture of stereoisomers thereof, where $R^1$, $R^2$, $R^3$, $R^5$, and $R^{10}$ are as defined herein.

In certain embodiments, provided is a compound of Formula IIIf:

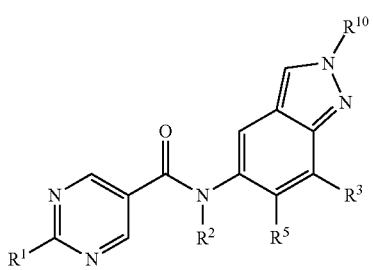

or an isotopically enriched analog, pharmaceutically acceptable salt, prodrug, tautomer, stereoisomer, or a mixture of stereoisomers thereof, where $R^1$, $R^2$, $R^3$, $R^5$, and $R^{10}$ are as defined herein.

In certain embodiments, $L^1$ is absent or —$N(R^{12})$—. In certain embodiments, $L^1$ is absent.

In certain embodiments, $R^{11}$ is heterocyclyl optionally substituted with 1 to 4 groups independently selected from halo, $C_{1-6}$alkyl, $C_{1-6}$haloalkyl, $C_{3-10}$cycloalkyl, heteroaryl, heterocyclyl, heterocyclyl-$C_{1-6}$alkyl, —$NH_2$, —$NHR^{14}$, —$N(R^{14})_2$, —$C_{1-6}$alkylene-$NH_2$, —$C_{1-6}$alkylene-$NHR^{14}$, —$C_{1-6}$alkylene-$N(R^{14})_2$, and —$C(O)OR^{15}$; wherein each $R^{14}$ is independently selected from $C_{1-6}$alkyl, $C_{3-10}$cycloalkyl, and heterocyclyl, and each $R^{14}$ is optionally substituted with one to three halo; and wherein $R^{15}$ is $C_{1-6}$alkyl.

In certain embodiments, $R^{11}$ is unsubstituted heterocyclyl. In certain embodiments, $R^{11}$ is heterocyclyl substituted by methyl.

In certain embodiments, $R^{11}$ is

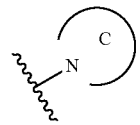

wherein Ring C is a 3- to 10-membered heterocyclyl containing 0, 1 or 2 additional ring nitrogen atoms optionally substituted with 1 to 4 $R^{13}$ groups. In certain embodiments, Ring C is

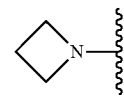

substituted with 1 to 4 $R^{13}$ groups. In certain embodiments, Ring C is

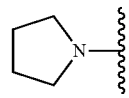

substituted with 1 to 4 $R^{13}$ groups. In certain embodiments, Ring C is

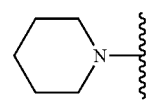 [SMILES: *N1CCCCC1]

substituted with 1 to 4 $R^{13}$ groups.

In certain embodiments, Ring C is a 5- to 10-membered bicyclic heterocyclyl containing one additional ring nitrogen atom optionally substituted with 1 to 4 $R^{13}$ groups.

In certain embodiments, Ring C is a 5- to 10-membered spirobicyclic heterocyclyl containing one additional ring nitrogen atom optionally substituted with 1 to 4 $R^{13}$ groups.

In certain embodiments, Ring C is a 5- to 10-membered fused bicyclic heterocyclyl containing one additional ring nitrogen atom optionally substituted with 1 to 4 $R^{13}$ groups.

In certain embodiments, $R^{11}$ is selected from

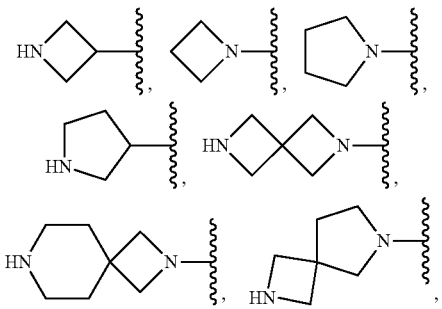

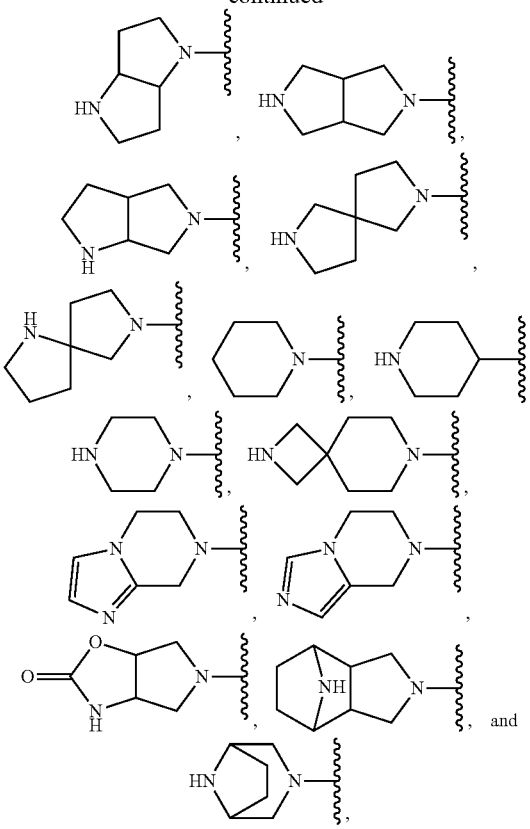

each of which is optionally substituted with 1 to 4 $R^{13}$ groups.

In certain embodiments, $R^{11}$ selected from

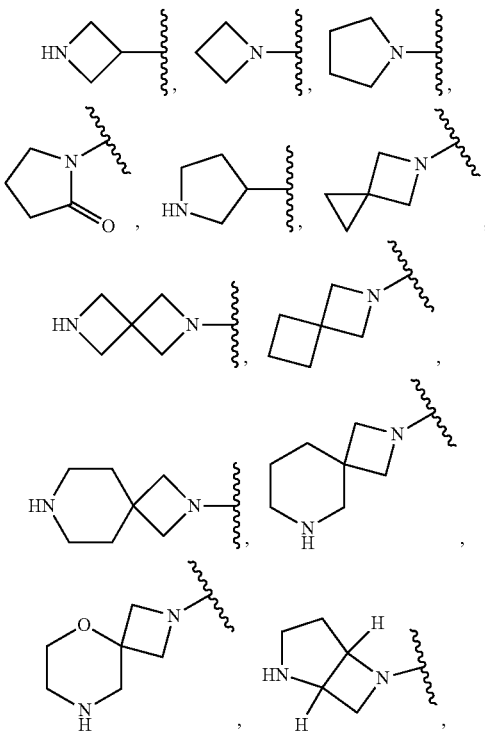

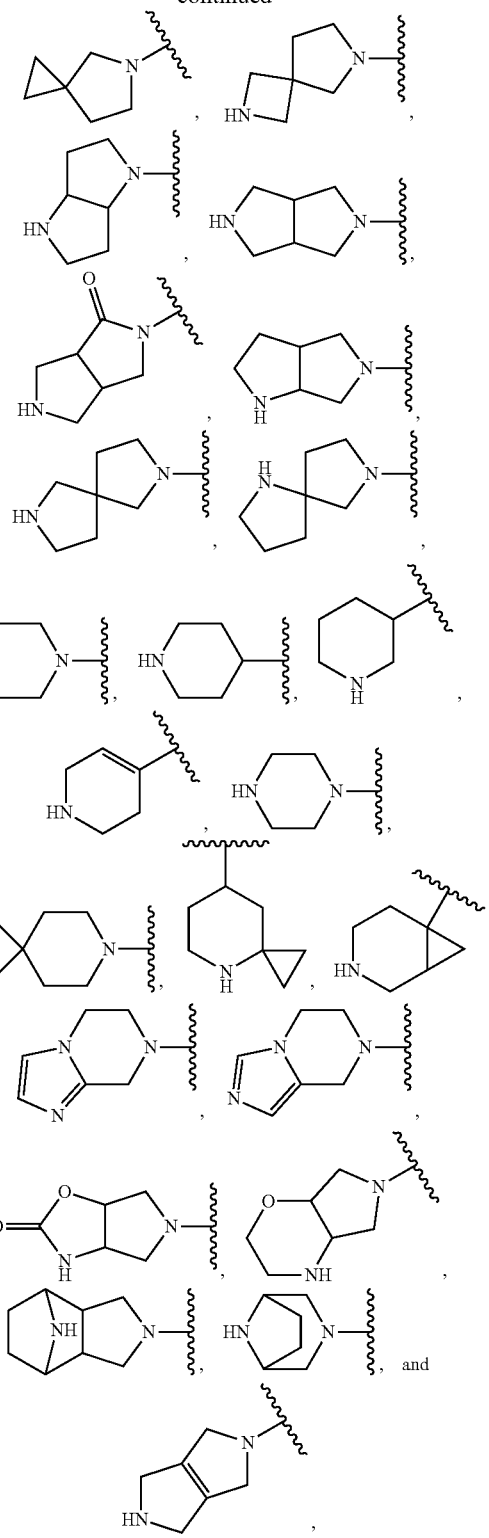

each of which is optionally substituted with 1 to 4 $R^{13}$ groups.

In certain embodiments, $R^{11}$ is optionally substituted with 1 to 4 groups independently selected from fluoro, methyl, ethyl, trifluoromethyl, cyclopropyl, 1-pyrrolyl, N-morpholinyl, N-pyrrolidinyl, N-pyrrolidinylmethyl, cyclopropylamino, amino, aminomethyl, methylamino, ethylamino, isopropylamino, tert-butylamino, n-butylamino, N-methylaminomethyl, N,N-dimethylaminomethyl, 3,3-difluorocyclobutylamino, tetrahydropyranylamino, oxetanylamino, and tert-butoxycarbonyl.

In certain embodiments, $R^{11}$ is optionally substituted with 1 to 4 groups independently selected from fluoro, methyl, ethyl, methoxyethoxy, trifluoromethyl, 2,2-difluoroethylaminomethyl, N-methyl-2,2-difluoroethylaminomethyl, (3,3,3-trifluoroprop-1-ylamino)methyl, cyclopropyl, 1-(cyclopropylamino)-1-cyclopropyl, 1-pyrrolyl, N-morpholinyl, N-pyrrolidinyl, N-pyrrolidinylmethyl, 2-pyrrolidinyl, 1-methyl-2-pyrrolidinyl, 1-methyl-2-piperdinyl, 1-cyclopropyl-2-piperdinyl, cyclopropylamino, N-cyclopropylaminomethyl, (1-methyl-1-cyclopropylamino)methyl, N-tert-butoxycarbonyl-N-cyclopropylaminomethyl, 1-(N-cyclopropylamino)ethyl, N,N-dicyclopropylaminomethyl, N-methoxyethyl-N-cyclopropylaminomethyl, N-cyclopropyl-N-methylamino, N-cyclopropyl-N-methylaminomethyl, amino, aminomethyl, methylamino, ethylamino, isopropylamino, isopropylaminomethyl, N-isopropyl-N-aminomethyl, tert-butylamino, n-butylamino, N-methylaminomethyl, N,N-dimethylaminomethyl, 3,3-difluorocyclobutylamino, tetrahydropyranylamino, oxetanylamino, (3-methoxy-1-azetidinyl)methyl, (3-methoxy-1-pyrrolidinyl)methyl, (3-fluoro-1-pyrrolidinyl)methyl, (3-fluoro-3-methyl-1-pyrrolidinyl)methyl, 4-morpholinylmethyl, and tert-butoxycarbonyl.

In certain embodiments, $R^{11}$ is optionally substituted with 1 to 4 groups independently selected from 2,2-difluoroethylaminomethyl, N-methyl-2,2-difluoroethylaminomethyl, (3,3,3-trifluoroprop-1-ylamino)methyl, N-cyclopropylaminomethyl, (1-methyl-1-cyclopropylamino)methyl, N-tert-butoxycarbonyl-N-cyclopropylaminomethyl, 1-(N-cyclopropylamino)ethyl, N,N-dicyclopropylaminomethyl, N-methoxyethyl-N-cyclopropylaminomethyl, N-cyclopropyl-N-methylamino, N-cyclopropyl-N-methylaminomethyl, isopropylaminomethyl, N-isopropyl-N-aminomethyl, N-methylaminomethyl, N,N-dimethylaminomethyl, (3-methoxy-1-azetidinyl)methyl, (3-methoxy-1-pyrrolidinyl)methyl, (3-fluoro-1-pyrrolidinyl)methyl, (3-fluoro-3-methyl-1-pyrrolidinyl)methyl, and 4-morpholinylmethyl.

In certain embodiments, $R^{11}$ is optionally substituted with 1 to 4 groups independently selected from amino, methylamino, ethylamino, isopropylamino, tert-butylamino, n-butylamino, cyclopropylamino, N-cyclopropyl-N-methylamino, 3,3-difluorocyclobutylamino, tetrahydropyranylamino, and oxetanylamino.

In certain embodiments, two of $X^1$, $X^2$, $X^3$, and $X^4$ are N. In certain embodiments, one of $X^1$, $X^2$, $X^3$, and $X^4$ are N.

In certain embodiments, $Y^2$ is absent, $CR^6$ or N.

In certain embodiments, $R^1$ is -$L^1$-$R^{11}$, wherein $L^1$ is —O—, —S—, —S(O)—, —S(O)$_2$—, —N($R^{12}$)—, —C$_{1-3}$alkylene-, —O—C$_{1-3}$alkylene-, —N($R^{12}$)—C$_{1-3}$alkylene-, or absent, and $R^{11}$ is C$_{2-6}$alkynyl, C$_{3-10}$cycloalkyl, C$_{6-10}$aryl, heteroaryl, or heterocyclyl, wherein $R^{11}$ is optionally substituted with 1 to 4 $R^{13}$ groups.

In some embodiments, each $R^{13}$ is independently selected from halo, cyano, hydroxy, C$_{1-6}$alkyl optionally substituted with $R^{16}$, C$_{1-6}$haloalkyl, C$_{1-6}$hydroxyalkyl, C$_{3-10}$cycloalkyl optionally substituted with $R^{16}$, C$_{3-10}$cycloalkyl-C$_{1-6}$alkyl optionally substituted with $R^{16}$, C$_{6-10}$aryl optionally substituted with $R^{16}$, C$_{6-10}$aryl-C$_{1-6}$alkyl optionally substituted with $R^{16}$, heteroaryl optionally substituted with $R^{16}$, heteroaryl-C$_{1-6}$alkyl optionally substituted with $R^{16}$, heterocyclyl optionally substituted with $R^{16}$, heterocyclyl-C$_{1-6}$alkyl optionally substituted with $R^{16}$, O$R^{14}$, —NH$_2$, —NH$R^{14}$, —N($R^{14}$)$_2$, —C$_{1-6}$alkylene-NH$_2$, —C$_{1-6}$alkylene-NH$R^{14}$, —C$_{1-6}$alkylene-N($R^{14}$)$_2$, —C(O)$R^{15}$, —C(O)O$R^5$, —C(O)NH$R^{15}$, —C(O)N(C$_{1-4}$alkyl)$R^{15}$, —S(O)$_2$$R^{15}$, —S(O)$R^{15}$, —NHC(O)$R^{15}$, —N(C$_{1-4}$alkyl)C(O)$R^{15}$, —NHS(O)$R^{15}$, —N(C$_{1-4}$alkyl)S(O)$R^{15}$, —NHS(O)$_2$$R^{15}$, and —N(C$_{1-4}$alkyl)S(O)$_2$$R^{15}$; each $R^{14}$ is independently selected from C$_{1-6}$alkyl, C$_{3-10}$cycloalkyl, C$_{6-10}$aryl, heteroaryl, and heterocyclyl; and each $R^{14}$ is optionally substituted with one to six halo, C$_{1-3}$alkyl, C$_{1-3}$alkoxy, C$_{3-10}$cycloalkyl, or —NHSO$_2$-aryl-N(CH$_3$)$_2$; each $R^{15}$ is independently hydrogen, —OH, C$_{1-6}$alkyl, C$_{1-6}$haloalkyl, C$_{3-10}$cycloalkyl, C$_{6-10}$aryl, heteroaryl, or heterocyclyl; each $R^{16}$ is independently halo, cyano, hydroxy, —NH$_2$, —NH$R^{21}$, —N($R^{21}$)$_2$, C$_{1-6}$alkyl, C$_{1-6}$haloalkyl, O$R^{21}$, or C$_{3-10}$cycloalkyl; and each $R^{21}$ is independently selected from C$_{1-6}$alkyl, C$_{3-10}$cycloalkyl, C$_{6-10}$aryl, heteroaryl, and heterocyclyl, and each $R^{21}$ is optionally substituted with one to six halo or C$_{1-3}$alkoxy.

In certain embodiments, $R^2$ is hydrogen.

In certain embodiments, $R^3$ is hydrogen. In certain embodiments, $R^3$ is halo. In certain embodiments, $R^3$ is fluoro. In certain embodiments, $R^3$ is C$_{1-6}$alkyl. In certain embodiments, $R^3$ is methyl. In certain embodiments, $R^3$ is C$_{1-6}$alkoxy. In certain embodiments, $R^3$ is methoxy.

In certain embodiments, each $R^4$ is hydrogen. In certain embodiments, one $R^4$ is halo and the rest are hydrogen.

In certain embodiments, $R^5$ is hydrogen. In certain embodiments, $R^5$ is C$_{1-6}$alkoxy. In certain embodiments, $R^5$ is methoxy.

In certain embodiments, $R^6$ is hydrogen.

In certain embodiments, $R^7$ is hydrogen.

In certain embodiments, $R^8$ is C$_{1-6}$alkyl. In certain embodiments, $R^8$ is methyl.

In certain embodiments, $R^9$ is C$_{1-6}$alkyl. In certain embodiments, $R^9$ is methyl.

In certain embodiments, $R^{10}$ is C$_{1-6}$alkyl. In certain embodiments, $R^{10}$ is methyl.

In certain embodiments, $L^1$ is absent.

In certain embodiments, $Y^1$ is $CR^5$. In certain embodiments, $Y^1$ is N. In certain embodiments, $Y^1$ is CH.

In certain embodiments, $Y^2$ is $CR^6$. In certain embodiments, $Y^2$ is N. In certain embodiments, $Y^2$ is CH.

In certain embodiments, $Y^3$ is $CR^3$. In certain embodiments, $Y^3$ is CH.

In certain embodiments, Ring B contains 1 to 3 heteroatoms independently selected from N, O, and S, and is optionally substituted on available carbon atom(s) with 1 to 3 substituents independently selected from halo, hydroxy, C$_{1-6}$alkyl, C$_{1-6}$haloalkyl, C$_{1-6}$alkoxy, and C$_{1-6}$haloalkoxy, and optionally substituted on an available nitrogen atom with C$_{1-6}$alkyl or C$_{1-6}$haloalkyl.

In certain embodiments, Ring B is

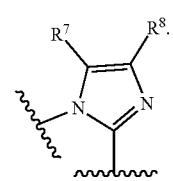

In certain embodiments, Ring B is

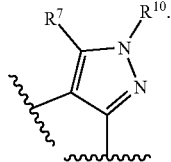

In certain embodiments, Ring B is

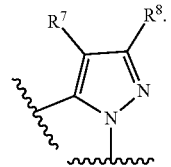

In certain embodiments, each $R^{13}$ is independently selected from halo, $C_{1-6}$alkyl, $C_{3-10}$cycloalkyl optionally substituted with $R^{16}$, heterocyclyl optionally substituted with $R^{16}$, —$NH_2$, —$NHR^{14}$, —$N(R^{14})_2$, —$C_{1-6}$ alkylene-$NH_2$, —$C_{1-6}$alkylene-$NHR^{14}$, —$C_{1-6}$alkylene-$N(R^{14})_2$, wherein $R^{16}$ and $R^{14}$ are as defined herein. In certain embodiments, each $R^{13}$ is independently selected from —$NH_2$, —$NHR^{14}$, —$N(R^{14})_2$, —$C_{1-6}$alkylene-$NH_2$, —$C_{1-6}$alkylene-$NHR^{14}$, and —$C_{1-6}$alkylene-$N(R^{14})_2$, wherein $R^{14}$ is as defined herein. In certain embodiments, each $R^{13}$ is independently selected from halo, $C_{1-6}$alkyl, —$NH_2$, —$NHR^{14}$, —$N(R^{14})_2$, —$C_{1-6}$ alkylene-$NH_2$, —$C_{1-6}$alkylene-$NHR^{14}$, and —$C_{1-6}$alkylene-$N(R^{14})_2$, wherein $R^{14}$ is as defined herein. In certain embodiments, the heterocyclyl of $R^{13}$ includes one ring nitrogen atom. In certain embodiments, $R^{13}$ is heterocyclyl optionally substituted with $R^{16}$, wherein the heterocyclyl includes one ring nitrogen atom.

In certain embodiments, $R^{13}$ is —$NH_2$, —$NHR^{14}$ or —$C_{1-6}$alkylene-$NHR^{14}$, and $R^{14}$ is as defined herein. In certain embodiments, $R^{13}$ is —$NHR^{14}$ or —$C_{1-6}$alkylene-$NHR^{14}$, and $R^{14}$ is as defined herein. In certain embodiments, $R^{13}$ is —$NHR^{14}$ or —$C_{1-6}$alkylene-$NHR^{14}$, and $R^{14}$ is $C_{3-10}$cycloalkyl. In certain embodiments, $R^{13}$ is —NH-cyclopropyl. In certain embodiments, $R^{13}$ is —NH-methyl. In certain embodiments, $R^{13}$ is —$CH_2$—NH-cyclopropyl. In certain embodiments, $R^{13}$ is —$CH_2$—NH-methyl. In certain embodiments, $R^{13}$ is —$CH_2$-heterocyclyl optionally substituted with $R^{16}$, where $R^{16}$ is as defined herein.

In certain embodiments, $R^{14}$ is $C_{1-6}$alkyl. In certain embodiments, $R^{14}$ is $C_{1-6}$alkyl substituted by one to six fluoro. In certain embodiments, $R^{14}$ is methyl. In certain embodiments, $R^{14}$ is $C_{3-10}$cycloalkyl. In certain embodiments, $R^{14}$ is cyclopropyl.

In certain embodiments, $R^{15}$ is hydrogen or $C_{1-6}$alkyl.

In certain embodiments, $R^{16}$ is amino, alkylamino, or dialkylamino. In certain embodiments, each $R^{16}$ is independently —$NH_2$, —$NHR^{21}$, or —$N(R^{21})_2$; and each $R^{21}$ is independently selected from $C_{1-6}$alkyl, $C_{1-6}$haloalkyl, or $C_{3-10}$cycloalkyl. In certain embodiments, each $R^{16}$ is independently halo, $C_{1-6}$alkyl, or $OR^{21}$, and $R^{21}$ is as defined herein.

In certain embodiments, provided is a compound of Formula I:

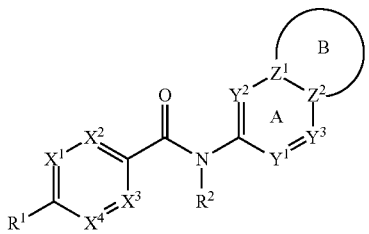

or an isotopically enriched analog, pharmaceutically acceptable salt, prodrug, tautomer, stereoisomer, or a mixture of stereoisomers thereof, wherein:
$X^1$, $X^2$, $X^3$, and $X^4$ are $CR^4$ or N, wherein at least two but no more than three of $X^1$, $X^2$, $X^3$, and $X^4$ are N;
$Y^1$ is $CR^5$ or N;
$Y^2$ is $CR^6$ or N;
$Y^3$ is $CR^3$ or N;
each of $Z^1$ and $Z^2$ is C or N;
Ring A and Ring B together form a 9-membered bicyclic heteroaryl containing 1 to 3 ring nitrogen atoms; and
Ring B is selected from

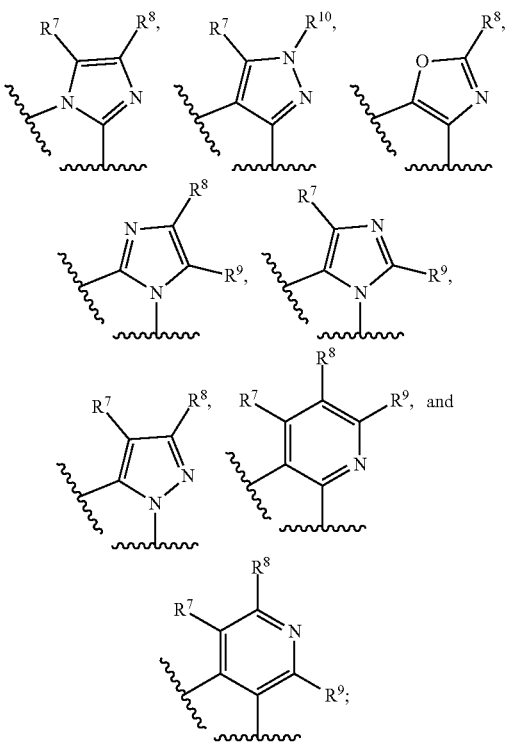

$R^1$ is -$L^1$-$R^{11}$, wherein $L^1$ is —O—, —S—, —S(O)—, —$S(O)_2$—, —$N(R^{12})$—, or absent, and $R^{11}$ is $C_{3-10}$cycloalkyl, $C_{6-10}$aryl, heteroaryl, or heterocyclyl, wherein $R^{11}$ is optionally substituted with 1 to 4 $R^{13}$ groups;
$R^{12}$ is hydrogen or $C_{1-6}$alkyl;
each $R^{13}$ is independently selected from halo, cyano, hydroxy, $C_{1-6}$alkyl optionally substituted with $R^{16}$, $C_{1-6}$haloalkyl, $C_{1-6}$hydroxyalkyl, $C_{3-10}$cycloalkyl optionally substituted with $R^{16}$, $C_{3-10}$cycloalkyl-$C_{1-6}$ alkyl optionally substituted with $R^{16}$, $C_{6-10}$aryl optionally substituted with $R^{16}$, $C_{6-10}$aryl-$C_{1-6}$alkyl optionally substituted with $R^{16}$, heteroaryl optionally substituted with R[16], heteroaryl-$C_{1-6}$alkyl optionally substituted with R[16], heterocyclyl optionally substituted with R[16], heterocyclyl-$C_{1-6}$alkyl optionally substituted with R[16], OR[14], —NH$_2$, —NHR[14], —N(R[14])$_2$, —$C_{1-6}$ alkylene-NH$_2$, —$C_{1-6}$alkylene-NHR[14], —$C_{1-6}$alkylene-N(R[14])$_2$, —C(O)R[15], —C(O)OR[5], —C(O)NHR[15], —C(O)N($C_{1-4}$alkyl)R[15], —S(O)$_2$R[15], —S(O)R[15], —NHC(O)R[15], —N($C_{1-4}$alkyl)C(O)R[15], —NHS(O)R[15], —N($C_{1-4}$alkyl)S(O)R[15], —NHS(O)$_2$R[15], and —N($C_{1-4}$alkyl)S(O)$_2$R[15];

each R[14] is independently selected from $C_{1-6}$alkyl, $C_{3-10}$cycloalkyl, $C_{6-10}$aryl, heteroaryl, and heterocyclyl, and each R[14] is optionally substituted with one to three halo;

each R[15] is independently hydrogen, —OH, $C_{1-6}$alkyl, $C_{1-6}$haloalkyl, $C_{3-10}$cycloalkyl, $C_{6-10}$aryl, heteroaryl, or heterocyclyl;

each R[16] is independently halo, cyano, hydroxy, amino, alkylamino, dialkylamino, or $C_{1-6}$alkyl;

R[2] is hydrogen or $C_{1-6}$alkyl;

R[3] is hydrogen, cyano, halo, hydroxy, $C_{1-6}$alkyl, $C_{1-6}$haloalkyl, $C_{1-6}$alkylthio, $C_{1-6}$alkoxy, heterocyclyl, —NH$_2$, —NHR[17], or —N(R[7])$_2$;

wherein each R[17] is independently $C_{1-4}$alkyl, or two R[17] join, with any intervening atoms, to form a 3- to 6-membered heterocyclyl;

each R[4] is independently hydrogen, halo, hydroxy, $C_{1-6}$alkyl, $C_{1-6}$haloalkyl, or $C_{1-6}$alkoxy;

R[5] is hydrogen, cyano, halo, hydroxy, $C_{1-6}$alkyl, $C_{1-6}$haloalkyl, $C_{1-6}$alkylthio, $C_{1-6}$alkoxy, heterocyclyl, —NH$_2$, —NHR[17], —N(R[17])$_2$;

R[6] is hydrogen, halo, hydroxy, $C_{1-6}$alkyl, $C_{1-6}$haloalkyl, or $C_{1-6}$alkoxy;

each of R[7], R[8], and R[9] is independently hydrogen, halo, hydroxy, $C_{1-6}$alkyl, $C_{1-6}$haloalkyl, or $C_{1-6}$alkoxy; and R[10] is hydrogen, $C_{1-6}$alkyl, or $C_{1-6}$haloalkyl.

In certain embodiments, provided is a pharmaceutical composition comprising a compound described herein, or an isotopically enriched analog, pharmaceutically acceptable salt, prodrug, tautomer, stereoisomer, or a mixture of stereoisomers thereof, and a pharmaceutically acceptable excipient.

In certain embodiments, provided is a method for treating Huntington's disease in a patient in need thereof, comprising administering to the patient a therapeutically effective amount of a compound or a pharmaceutical composition described herein.

In certain embodiments, provided is a method for treating Huntington's disease in a patient in need thereof, comprising administering to the patient a therapeutically effective amount of a compound or pharmaceutical composition described herein in combination with a second active agent.

Also is provided a compound, or an isotopically enriched analog, pharmaceutically acceptable salt, prodrug, tautomer, stereoisomer, or a mixture of stereoisomers thereof, selected from Table 1:

TABLE 1

| Ex. | Structure |
| --- | --- |
| 1 | 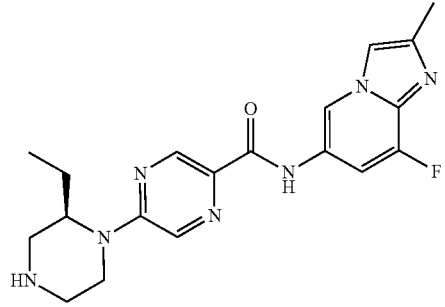 [SMILES: CC[C@@H]1CNCCN1c1cnc(C(=O)Nc2cc(F)c3nc(C)cn3c2)cn1] |
| 2 | 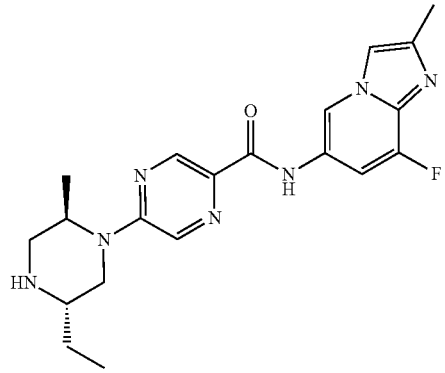 [SMILES: CC[C@H]1CN(c2cnc(C(=O)Nc3cc(F)c4nc(C)cn4c3)cn2)[C@H](C)CN1] |

TABLE 1-continued

| Ex. | Structure |
|---|---|
| 3 | 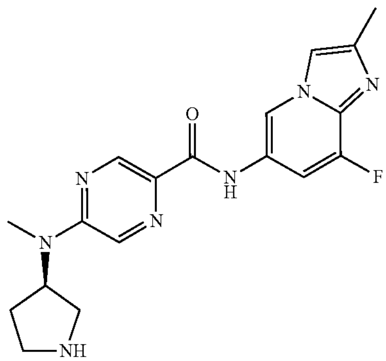 [SMILES: Cc1cn2cc(NC(=O)c3cnc(N(C)[C@@H]4CCNC4)cn3)cc(F)c2n1] |
| 4 | 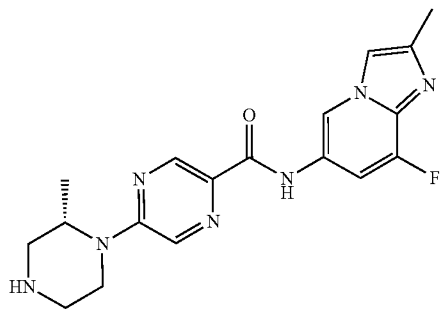 [SMILES: Cc1cn2cc(NC(=O)c3cnc(N4CCNC[C@@H]4C)cn3)cc(F)c2n1] |
| 5 | 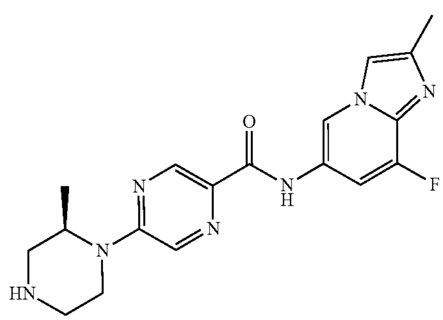 [SMILES: Cc1cn2cc(NC(=O)c3cnc(N4CCNC[C@H]4C)cn3)cc(F)c2n1] |
| 6 | 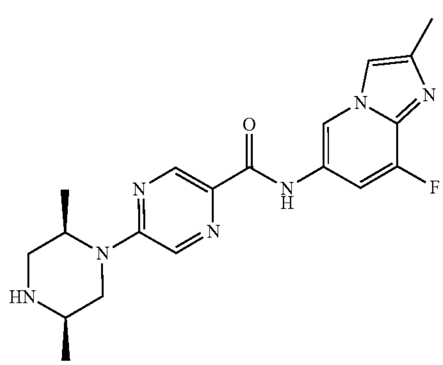 [SMILES: Cc1cn2cc(NC(=O)c3cnc(N4C[C@@H](C)NC[C@H]4C)cn3)cc(F)c2n1] |

TABLE 1-continued
| Ex. | Structure |
|---|---|
| 7 | 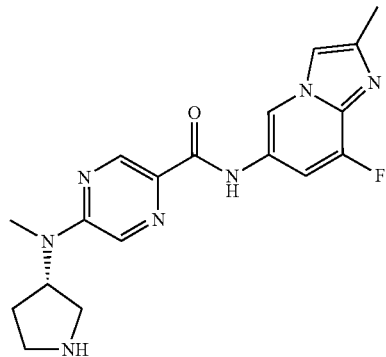 [SMILES: Cc1cn2cc(NC(=O)c3cnc(N(C)[C@H]4CCNC4)cn3)cc(F)c2n1] |
| 8 | 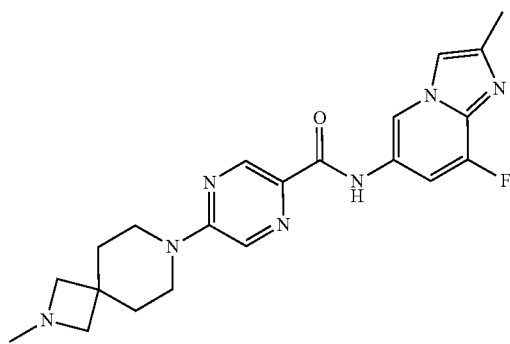 [SMILES: Cc1cn2cc(NC(=O)c3cnc(N4CCC5(CC4)CN(C)C5)cn3)cc(F)c2n1] |
| 9 | 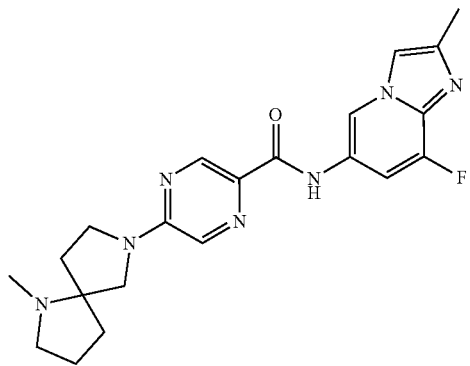<br>Enantiomer 1 + Enantiomer 2 |
| 10 | 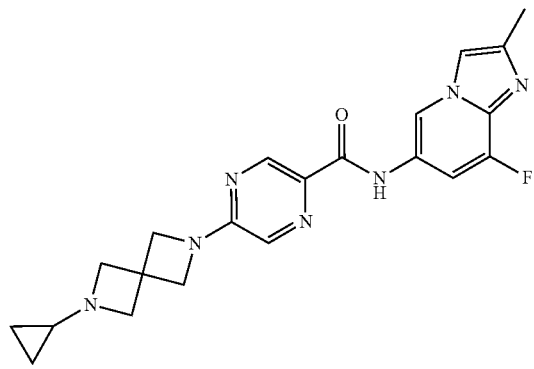 [SMILES: Cc1cn2cc(NC(=O)c3cnc(N4CC5(C4)CN(C4CC4)C5)cn3)cc(F)c2n1] |

TABLE 1-continued

| Ex. | Structure |
|---|---|
| 11 | *(structure: N-(8-fluoro-2-methylimidazo[1,2-a]pyridin-6-yl)-5-[(3R)-3-(ethylamino)pyrrolidin-1-yl]pyrazine-2-carboxamide)* |
| 12 | *(structure: 5-[3-((cyclopropylamino)methyl)pyrrolidin-1-yl]-N-(8-fluoro-2-methylimidazo[1,2-a]pyridin-6-yl)pyrazine-2-carboxamide)*<br>Enantiomer 1 + Enantiomer 2 |
| 13 | *(structure: pyrazine-2-carboxamide with 5,6,7,8-tetrahydroimidazo[1,5-a]pyrazin-7-yl substituent, N-(8-fluoro-2-methylimidazo[1,2-a]pyridin-6-yl))* |
| 14 | *(structure: 5-(7-methyl-2,7-diazaspiro[4.4]nonan-2-yl)-N-(8-fluoro-2-methylimidazo[1,2-a]pyridin-6-yl)pyrazine-2-carboxamide)*<br>Enantiomer 2 |

TABLE 1-continued
| Ex. | Structure |
|---|---|
| 15 | 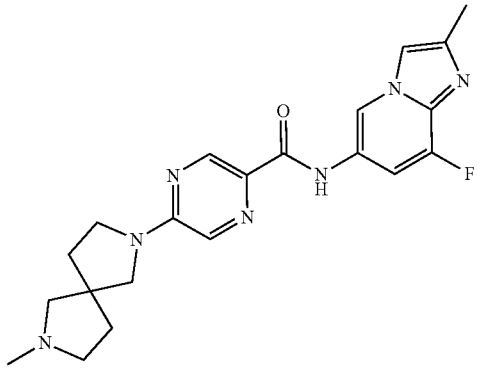<br>Enantiomer 1 |
| 16 | 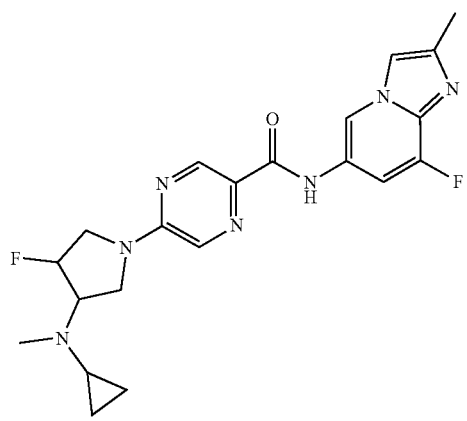<br>Cis Isomer, Enantiomer 1 |
| 17 | 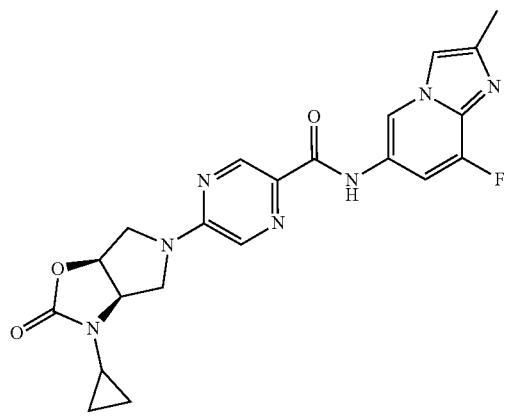 [SMILES: Cc1cn2cc(NC(=O)c3cnc(N4C[C@@H]5OC(=O)N(C6CC6)[C@@H]5C4)cn3)cc(F)c2n1] |

TABLE 1-continued
| Ex. | Structure |
|---|---|
| 18 | 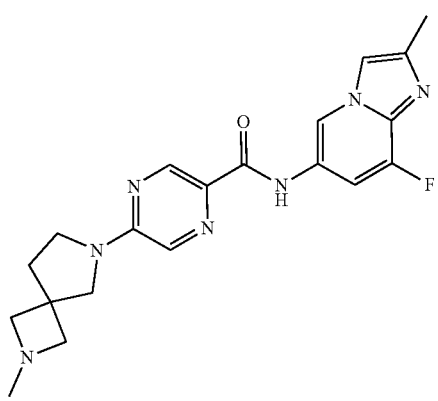 [SMILES: Cc1cn2cc(NC(=O)c3cnc(N4CCC5(CN(C)C5)C4)cn3)cc(F)c2n1] |
| 19 | 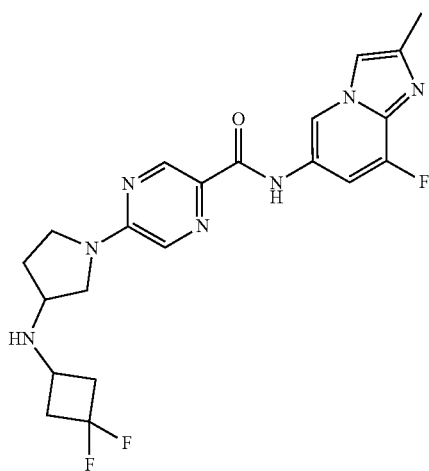  Enantiomer 1 |
| 20 | 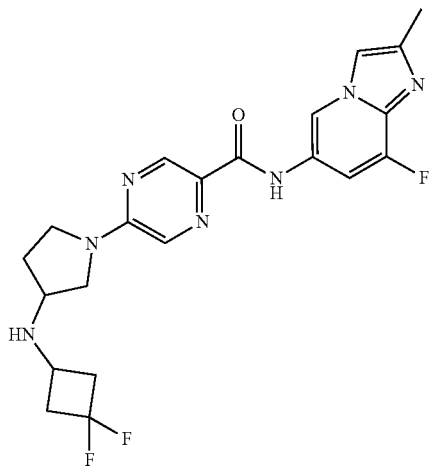  Enantiomer 2 |

TABLE 1-continued
| Ex. | Structure |
|---|---|
| 21 | 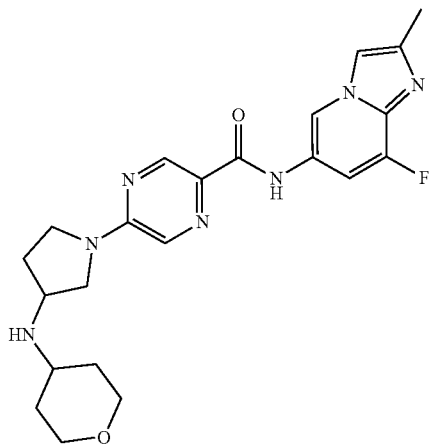<br>Enantiomer 2 |
| 22 | 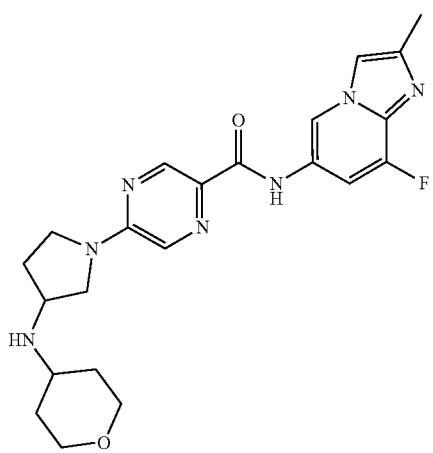<br>Enantiomer 1 |
| 23 | 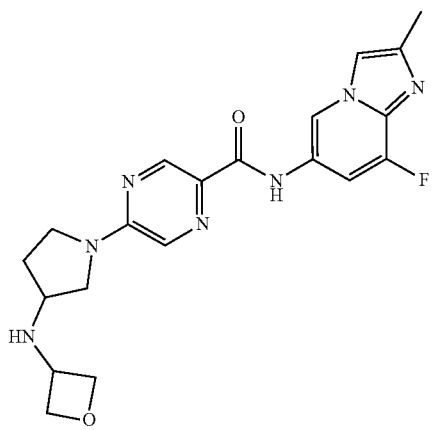<br>Enantiomer 1 + Enantiomer 2 |

TABLE 1-continued
| Ex. | Structure |
|---|---|
| 24 | 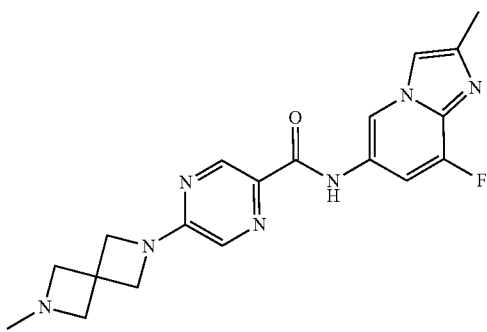 [SMILES: Cc1cn2cc(NC(=O)c3cnc(N4CC5(CN(C)C5)C4)cn3)cc(F)c2n1] |
| 25 | 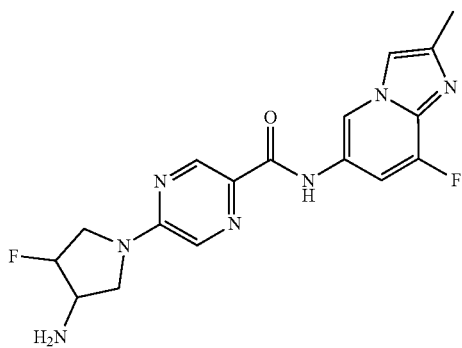
Cis Isomers, Enantiomer 1 + Enantiomer 2 |
| 26 | 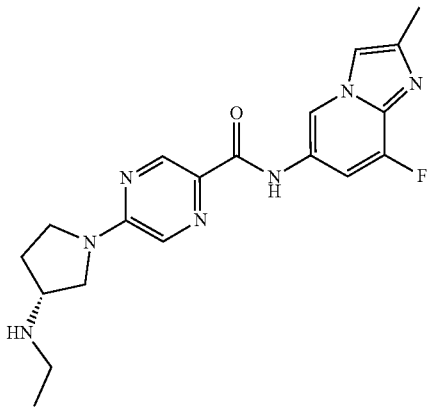 [SMILES: CCN[C@@H]1CCN(c2cnc(C(=O)Nc3cc(F)c4nc(C)cn4c3)cn2)C1] |
| 27 | 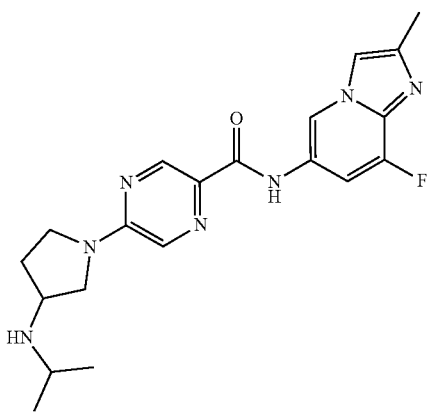
Enantiomer 1 |

TABLE 1-continued
| Ex. | Structure |
|---|---|
| 28 | 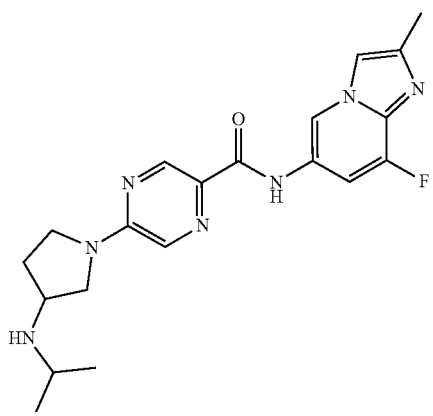<br>Enantiomer 2 |
| 29 | 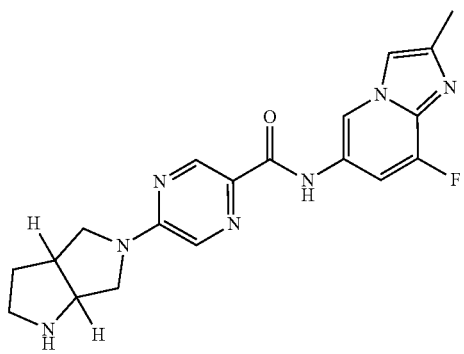<br>Cis Isomer, Enantiomer 1 |
| 30 | 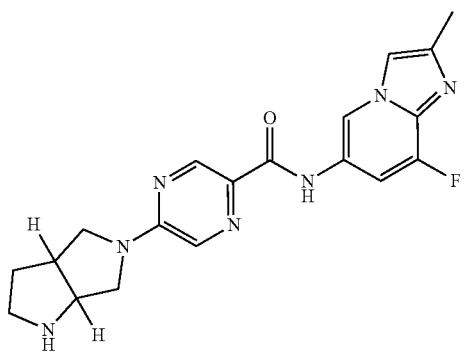<br>Cis Isomer, Enantiomer 2 |

TABLE 1-continued
| Ex. | Structure |
|---|---|
| 31 | 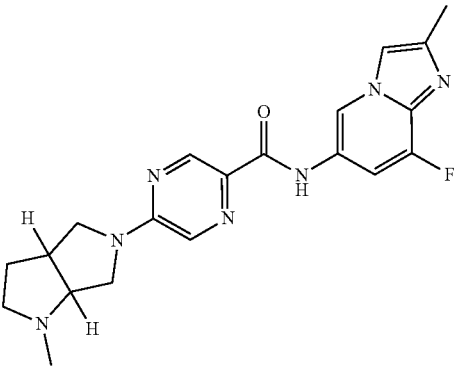<br>Cis isomer, Enantiomer 1 |
| 32 | 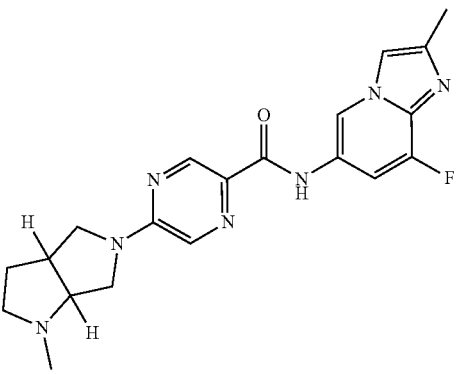<br>Cis Isomer, Enantiomer 2 |
| 33 | 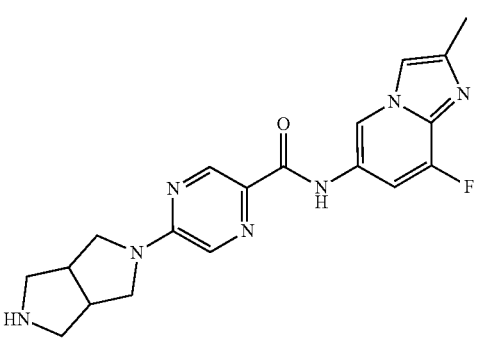 [SMILES: Cc1cn2cc(NC(=O)c3cnc(N4CC5CNCC5C4)cn3)cc(F)c2n1] |
| 34 | 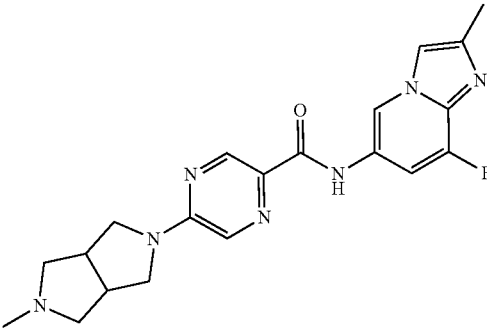 |

TABLE 1-continued
| Ex. | Structure |
|---|---|
| 35 | 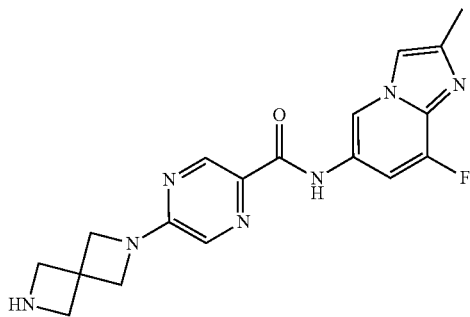 [SMILES: Cc1cn2cc(NC(=O)c3cnc(N4CC5(CNC5)C4)cn3)cc(F)c2n1] |
| 36 | 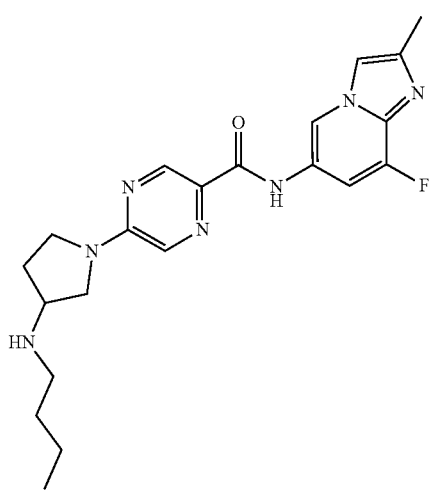
Enantiomer 1 + Enantiomer 2 |
| 37 | 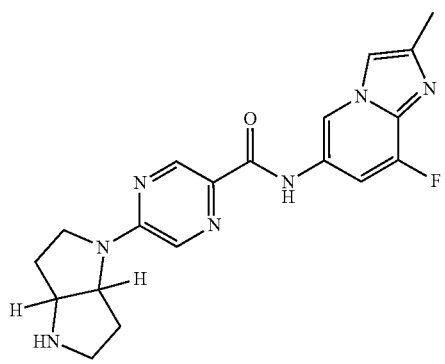
Cis Isomer, Enantiomer 2 |

TABLE 1-continued
| Ex. | Structure |
|---|---|
| 38 | 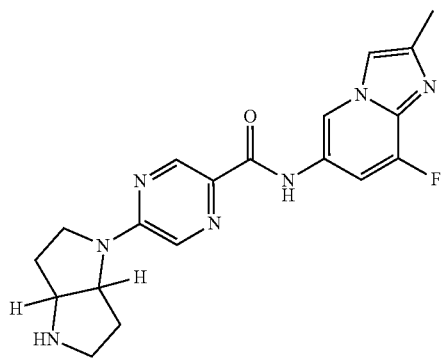<br>Cis Isomer, Enantiomer 1 |
| 39 | 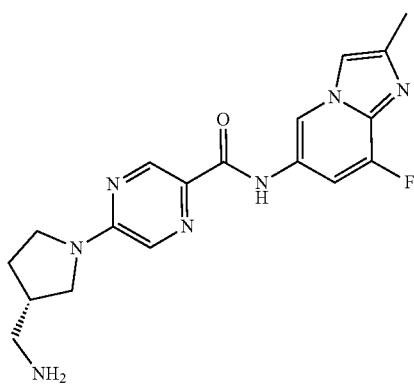 [SMILES: Cc1cn2cc(NC(=O)c3cnc(N4CC[C@@H](CN)C4)cn3)cc(F)c2n1] |
| 40 | 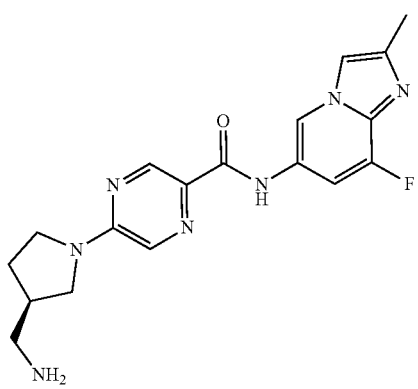 [SMILES: Cc1cn2cc(NC(=O)c3cnc(N4CC[C@H](CN)C4)cn3)cc(F)c2n1] |

TABLE 1-continued
| Ex. | Structure |
|---|---|
| 41 | 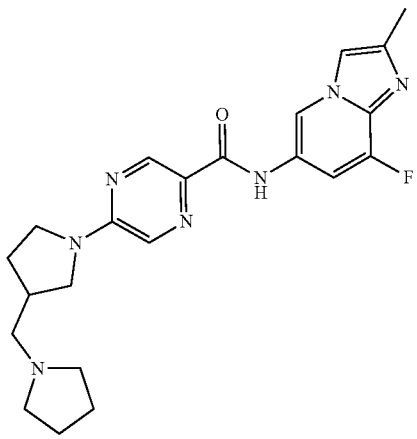<br>Enantiomer 1 + Enantiomer 2 |
| 42 | 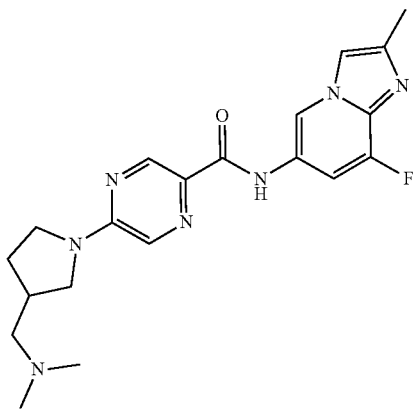<br>Enantiomer 1 + Enantiomer 2 |
| 43 | 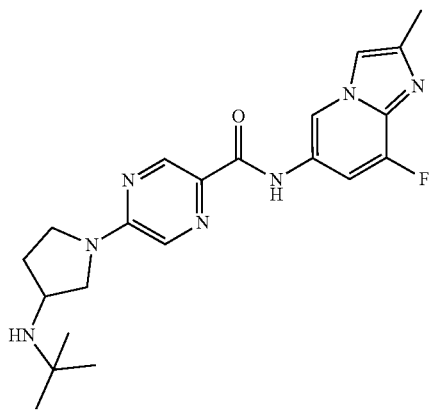<br>Enantiomer 1 + Enantiomer 2 |

TABLE 1-continued
| Ex. | Structure |
|---|---|
| 44 | 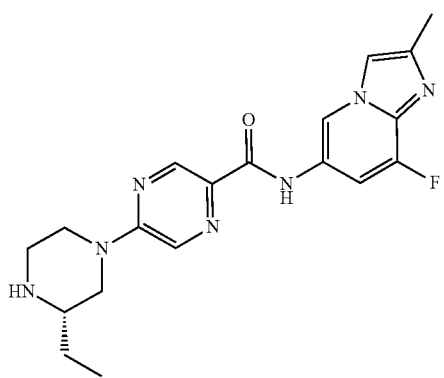 [SMILES: CC[C@H]1CN(c2cnc(C(=O)Nc3cc(F)c4nc(C)cn4c3)cn2)CCN1] |
| 45 | 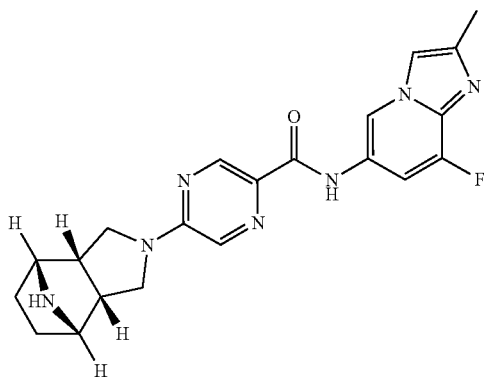 [SMILES: Cc1cn2cc(NC(=O)c3cnc(N4C[C@@H]5[C@H](C4)[C@@H]4CC[C@H]5N4)cn3)cc(F)c2n1] |
| 46 | 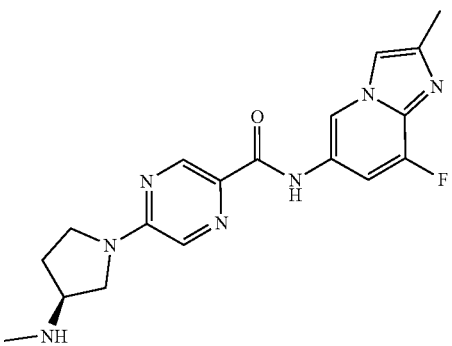 [SMILES: CN[C@H]1CCN(c2cnc(C(=O)Nc3cc(F)c4nc(C)cn4c3)cn2)C1] |
| 47 | 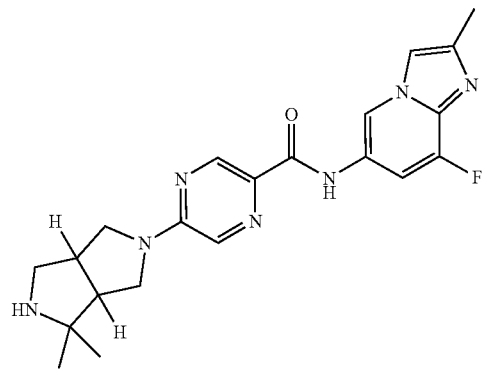<br>Cis Isomers, Enantiomer 1 + Enantiomer 2 |

TABLE 1-continued

| Ex. | Structure |
|---|---|
| 48 | 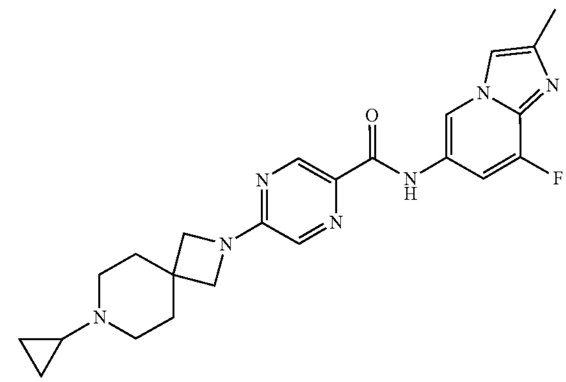 [SMILES: Cc1cn2cc(NC(=O)c3cnc(N4CC5(CCN(C6CC6)CC5)C4)cn3)cc(F)c2n1] |
| 49 | 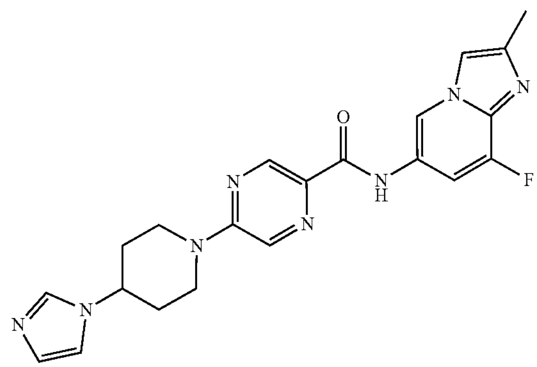 [SMILES: Cc1cn2cc(NC(=O)c3cnc(N4CCC(n5ccnc5)CC4)cn3)cc(F)c2n1] |
| 50 | 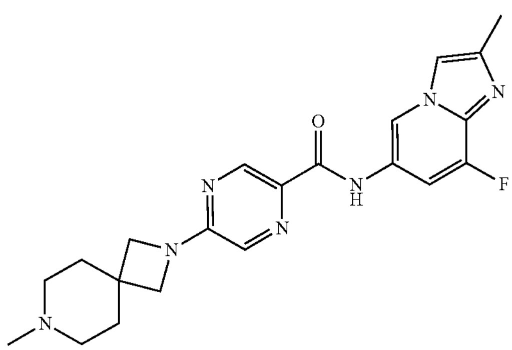 [SMILES: Cc1cn2cc(NC(=O)c3cnc(N4CC5(CCN(C)CC5)C4)cn3)cc(F)c2n1] |
| 51 | 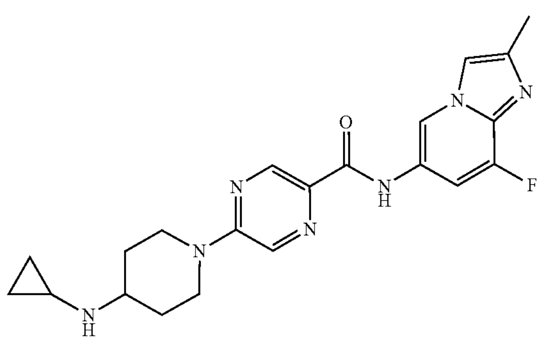 [SMILES: Cc1cn2cc(NC(=O)c3cnc(N4CCC(NC5CC5)CC4)cn3)cc(F)c2n1] |

TABLE 1-continued
| Ex. | Structure |
|---|---|
| 52 | 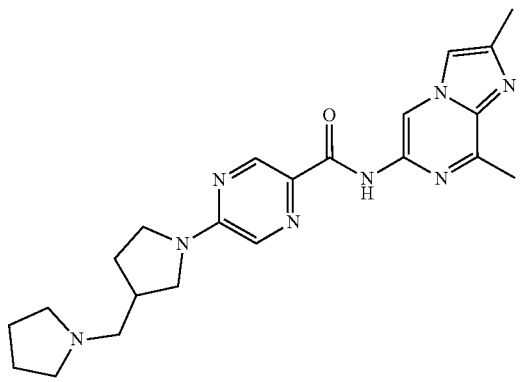<br>Enantiomer 1 + Enantiomer 2 |
| 53 | 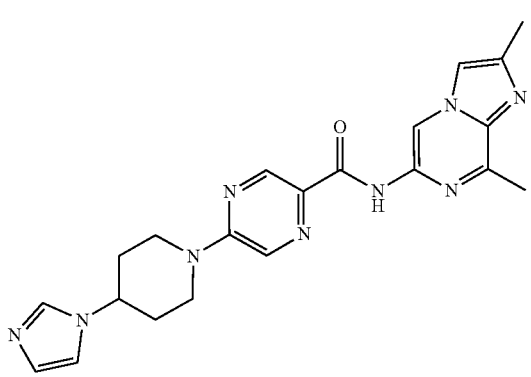 [SMILES: Cc1cn2cc(NC(=O)c3cnc(N4CCC(n5ccnc5)CC4)cn3)nc(C)c2n1] |
| 54 | 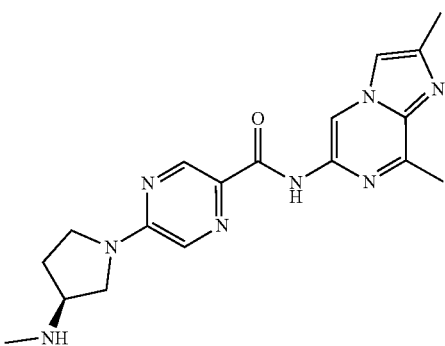 |
| 55 | 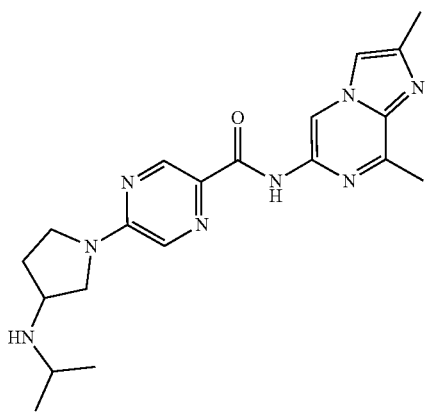<br>Enantiomer 1 |

TABLE 1-continued
| Ex. | Structure |
|---|---|
| 56 | 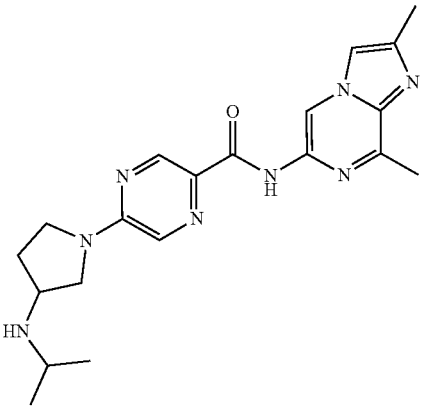<br>Enantiomer 2 |
| 57 | 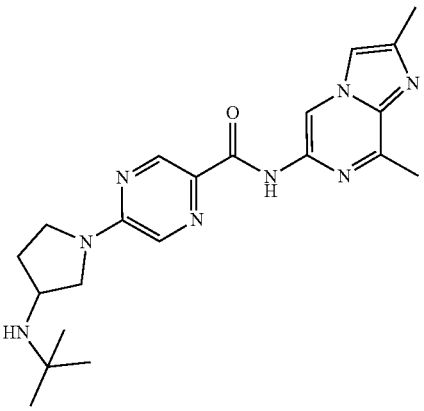<br>Enantiomer 1 + Enantiomer 2 |
| 58 | 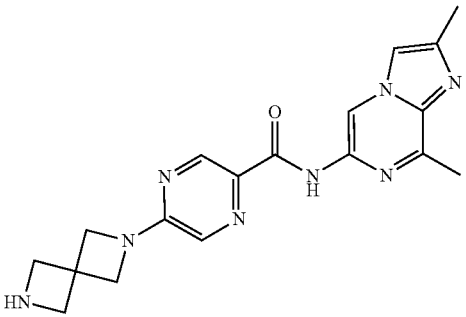 [SMILES: Cc1cn2cc(NC(=O)c3cnc(N4CC5(CNC5)C4)cn3)nc(C)c2n1] |
| 59 | 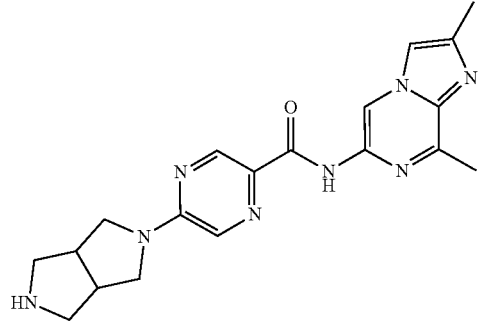 [SMILES: Cc1cn2cc(NC(=O)c3cnc(N4CC5CNCC5C4)cn3)nc(C)c2n1] |

TABLE 1-continued
| Ex. | Structure |
| --- | --- |
| 60 | 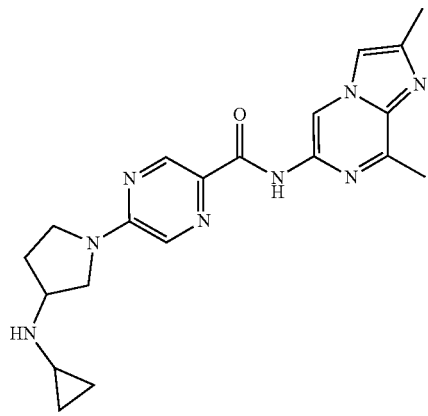
Enantiomer 2 |
| 61 | 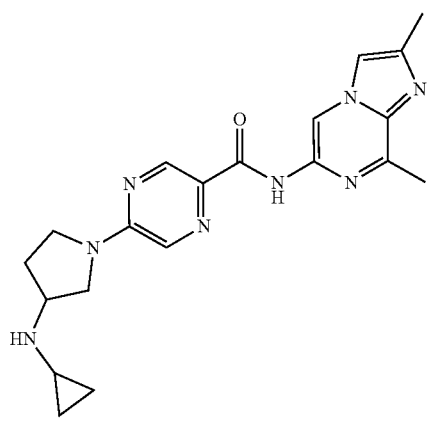
Enantiomer 1 |
| 62 | 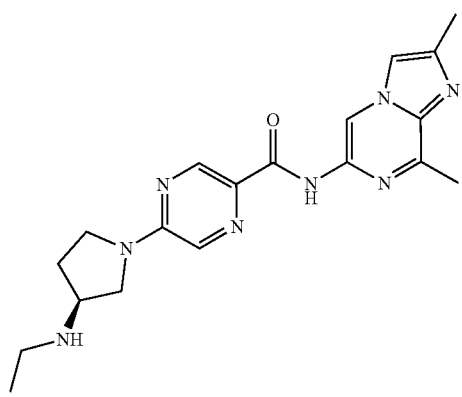 [SMILES: CCN[C@H]1CCN(c2cnc(C(=O)Nc3cn4cc(C)nc4c(C)n3)cn2)C1] |

TABLE 1-continued
| Ex. | Structure |
|---|---|
| 63 | 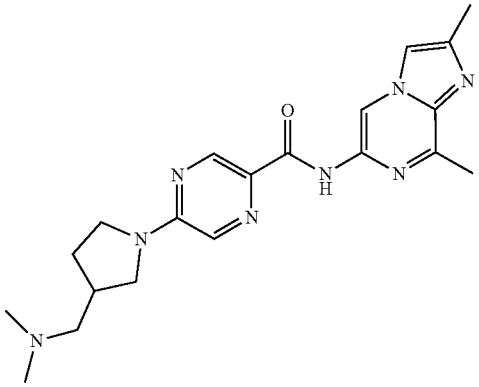<br>Enantiomer 1 + Enantiomer 2 |
| 64 | 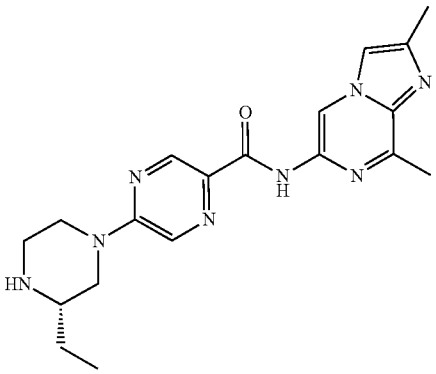 [SMILES: CC[C@H]1CN(c2cnc(C(=O)Nc3cn4cc(C)nc4c(C)n3)cn2)CCN1] |
| 65 | 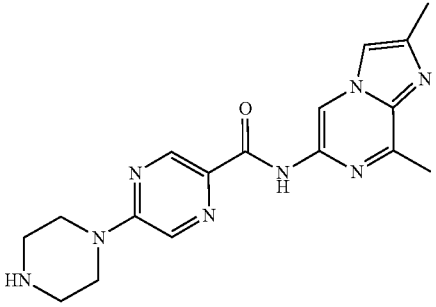 [SMILES: Cc1cn2cc(NC(=O)c3cnc(N4CCNCC4)cn3)nc(C)c2n1] |
| 66 | 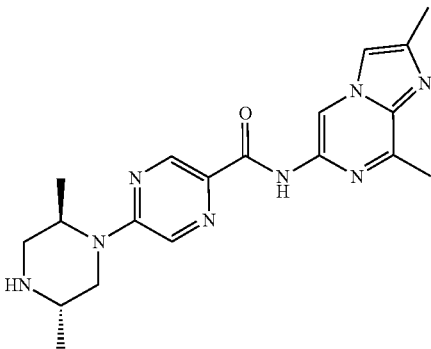 [SMILES: Cc1cn2cc(NC(=O)c3cnc(N4C[C@H](C)NC[C@H]4C)cn3)nc(C)c2n1] |

TABLE 1-continued

| Ex. | Structure |
|---|---|
| 67 | 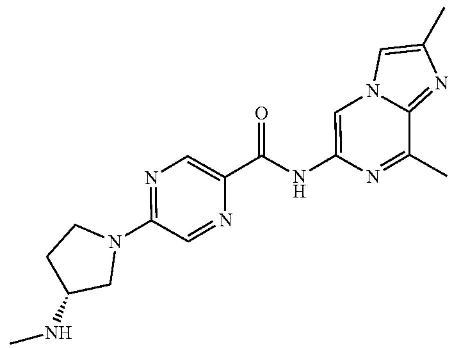 |
| 68 | 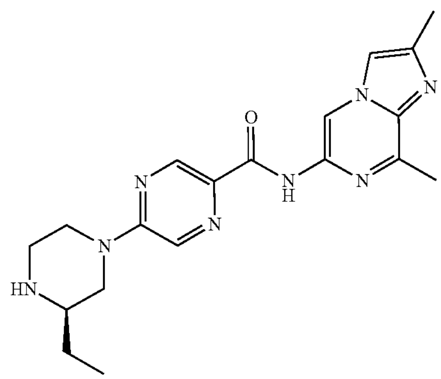 [SMILES: CC[C@@H]1CN(c2cnc(C(=O)Nc3cn4cc(C)nc4c(C)n3)cn2)CCN1] |
| 69 | 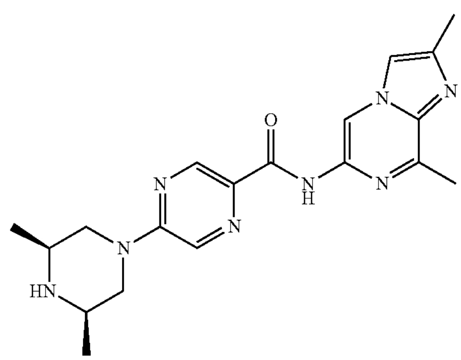 |
| 70 | 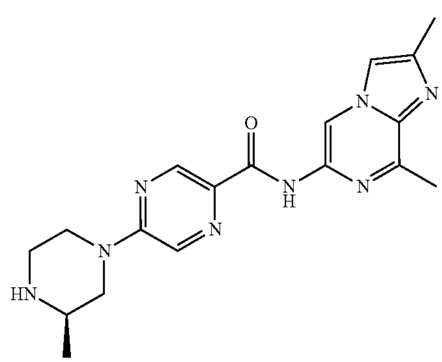 [SMILES: Cc1cn2cc(NC(=O)c3cnc(N4CCN[C@H](C)C4)cn3)nc(C)c2n1] |

TABLE 1-continued
| Ex. | Structure |
|---|---|
| 71 | 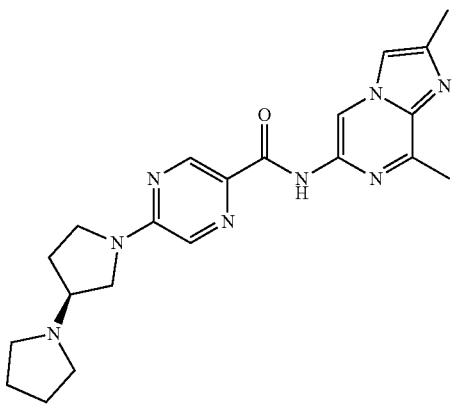 [SMILES: Cc1cn2cc(NC(=O)c3cnc(N4CC[C@H](N5CCCC5)C4)cn3)nc(C)c2n1] |
| 72 | 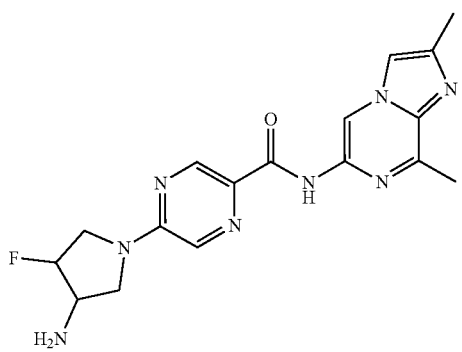<br>Trans Isomers, Enantiomer 1 + Enantiomer 2 |
| 73 | 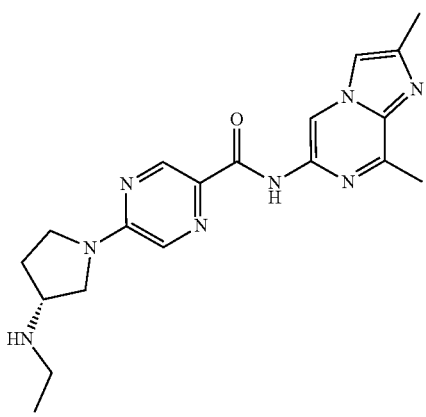 [SMILES: CCN[C@@H]1CCN(c2cnc(C(=O)Nc3cn4cc(C)nc4c(C)n3)cn2)C1] |
| 74 | 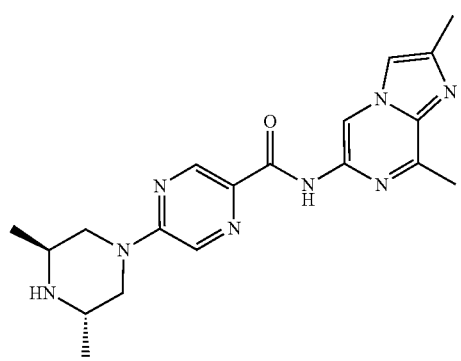 |

TABLE 1-continued
| Ex. | Structure |
|---|---|
| 75 | 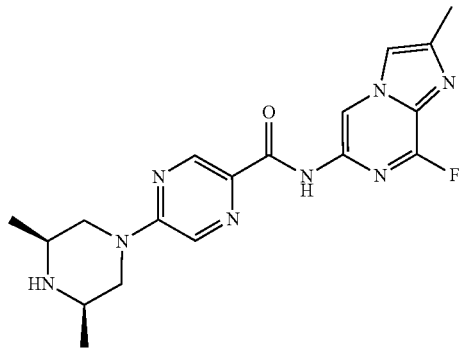 [SMILES: Cc1cn2cc(NC(=O)c3cnc(N4C[C@@H](C)N[C@@H](C)C4)cn3)nc(F)c2n1] |
| 76 | 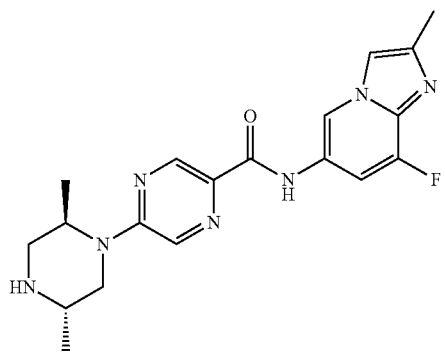 [SMILES: Cc1cn2cc(NC(=O)c3cnc(N4C[C@H](C)NC[C@H]4C)cn3)cc(F)c2n1] |
| 77 | 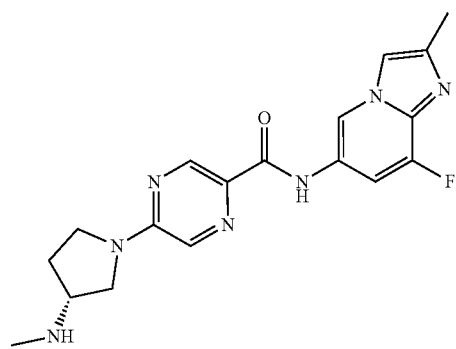 [SMILES: CN[C@@H]1CCN(c2cnc(C(=O)Nc3cc(F)c4nc(C)cn4c3)cn2)C1] |
| 78 | 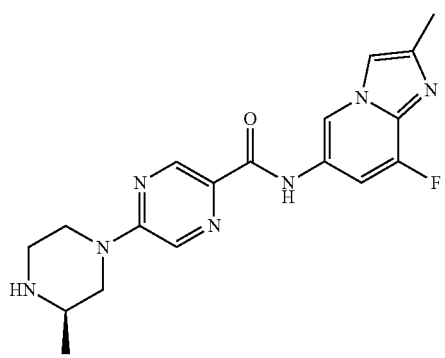 [SMILES: Cc1cn2cc(NC(=O)c3cnc(N4CCN[C@H](C)C4)cn3)cc(F)c2n1] |

TABLE 1-continued
| Ex. | Structure |
|---|---|
| 79 | 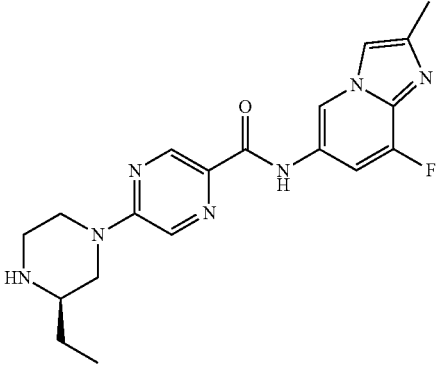 [SMILES: CC[C@@H]1CN(c2cnc(C(=O)Nc3cc(F)c4nc(C)cn4c3)cn2)CCN1] |
| 80 | 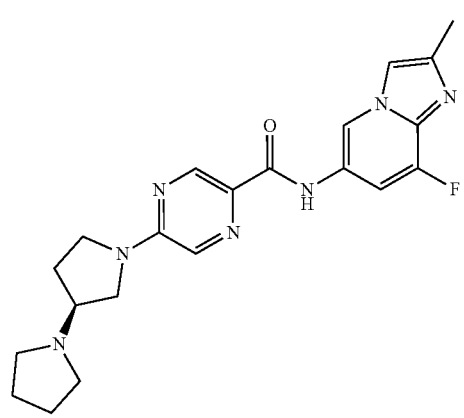 [SMILES: Cc1cn2cc(NC(=O)c3cnc(N4CC[C@H](N5CCCC5)C4)cn3)cc(F)c2n1] |
| 81 | 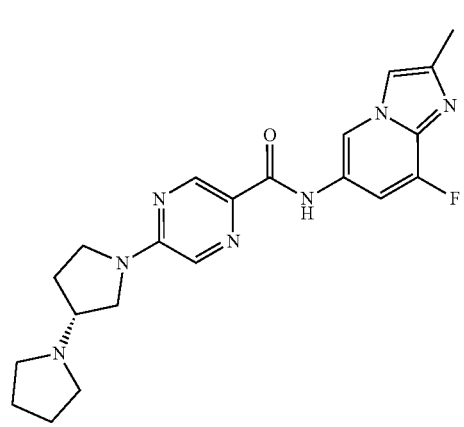 [SMILES: Cc1cn2cc(NC(=O)c3cnc(N4CC[C@@H](N5CCCC5)C4)cn3)cc(F)c2n1] |
| 82 | 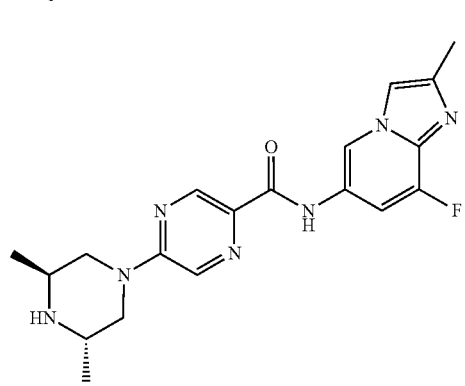 |

TABLE 1-continued
| Ex. | Structure |
|---|---|
| 83 | 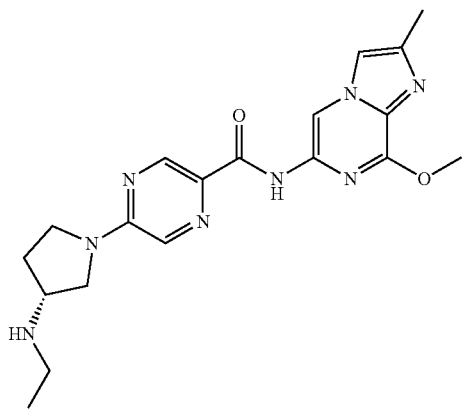 [SMILES: CCN[C@@H]1CCN(c2cnc(C(=O)Nc3cn4cc(C)nc4c(OC)n3)cn2)C1] |
| 84 | 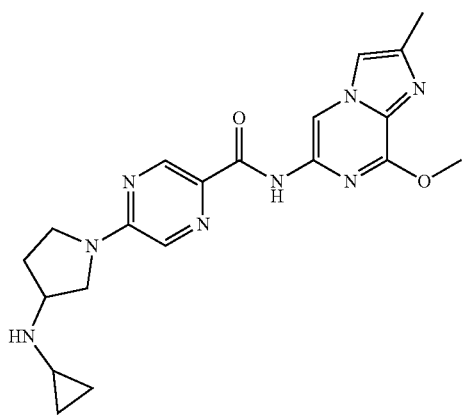
Enantiomer 1 |
| 85 | 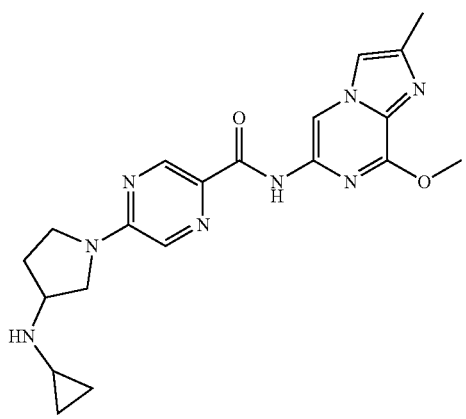
Enantiomer 2 |

TABLE 1-continued

| Ex. | Structure |
|---|---|
| 86 | (structure) |
| 87 | (structure)<br>Cis Isomer, Enantiomer 1 |
| 88 | (structure)<br>Cis Isomer, Enantiomer 2 |
| 89 | (structure)<br>Trans Isomers, Enantiomer 1 and Enantiomer 2 |

TABLE 1-continued

| Ex. | Structure |
|---|---|
| 90 | *Trans Isomers, Enantiomer 1 and Enantiomer 2* |
| 91 | *Cis Isomer, Enantiomer 1* |
| 92 | 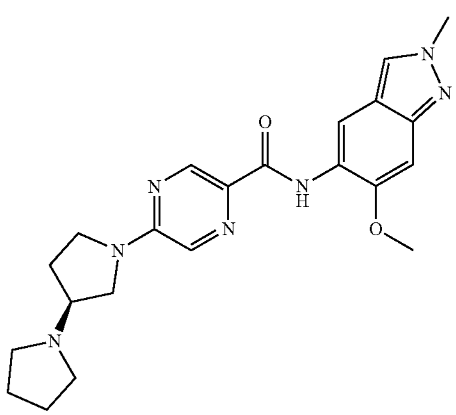 [SMILES: COc1cc2nn(C)cc2cc1NC(=O)c1cnc(N2CC[C@H](N3CCCC3)C2)cn1] |

TABLE 1-continued
| Ex. | Structure |
|---|---|
| 93 | 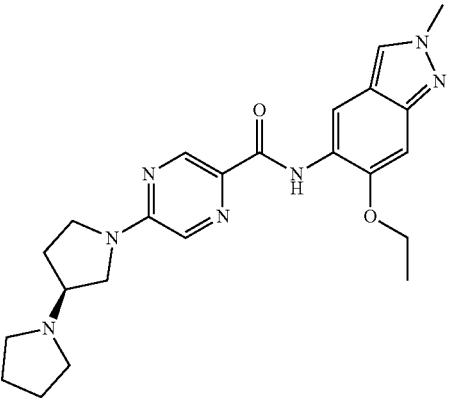 [SMILES: CCOc1cc2nn(C)cc2cc1NC(=O)c1cnc(N2CC[C@H](N3CCCC3)C2)cn1] |
| 94 | 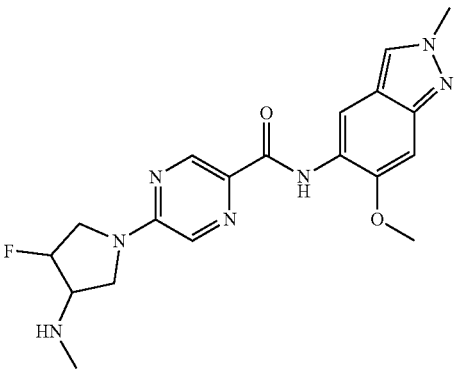<br>Cis Isomers, Enantiomer 1 + Enantiomer 2 |
| 95 | 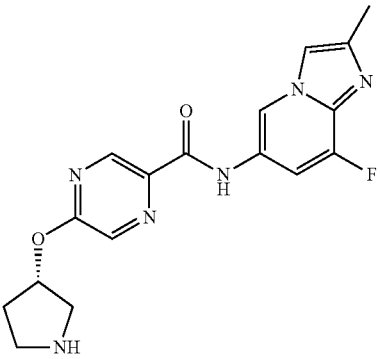 |
| 96 | 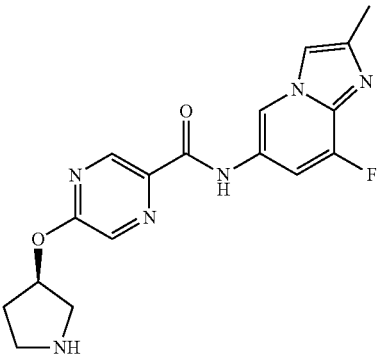 [SMILES: Cc1cn2cc(NC(=O)c3cnc(O[C@@H]4CCNC4)cn3)cc(F)c2n1] |

TABLE 1-continued

| Ex. | Structure |
|---|---|
| 97 | 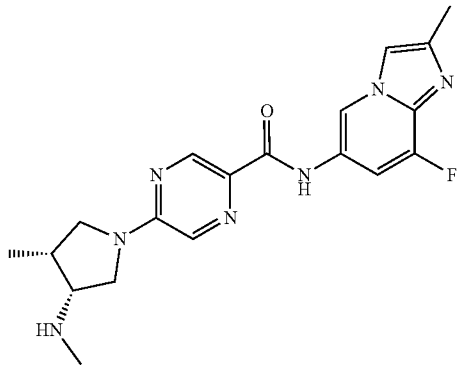 [SMILES: CN[C@H]1CN(c2cnc(C(=O)Nc3cc(F)c4nc(C)cn4c3)cn2)C[C@H]1C] |
| 98 | 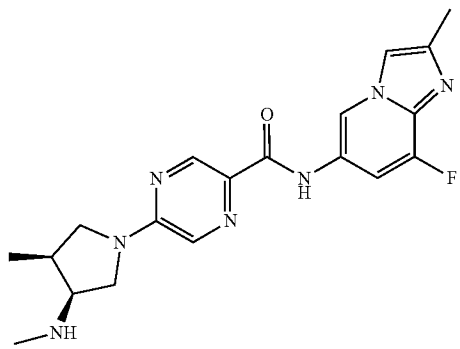 [SMILES: CN[C@@H]1CN(c2cnc(C(=O)Nc3cc(F)c4nc(C)cn4c3)cn2)C[C@@H]1C] |
| 99 | 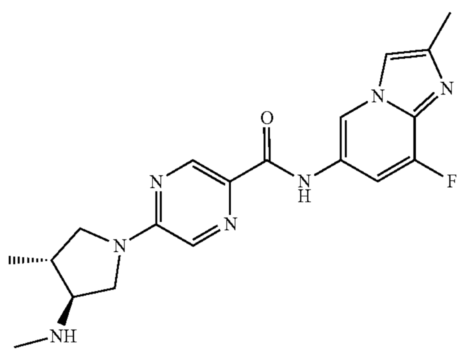 [SMILES: CN[C@@H]1CN(c2cnc(C(=O)Nc3cc(F)c4nc(C)cn4c3)cn2)C[C@H]1C] |
| 100 | 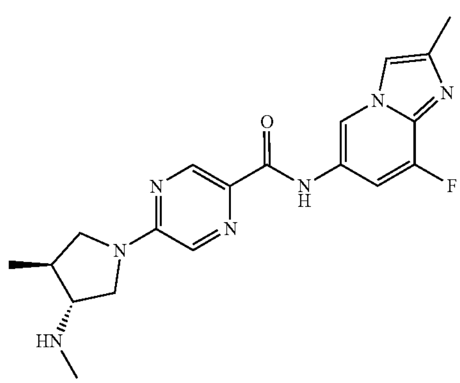 [SMILES: CN[C@H]1CN(c2cnc(C(=O)Nc3cc(F)c4nc(C)cn4c3)cn2)C[C@@H]1C] |

TABLE 1-continued
| Ex. | Structure |
| --- | --- |
| 101 | 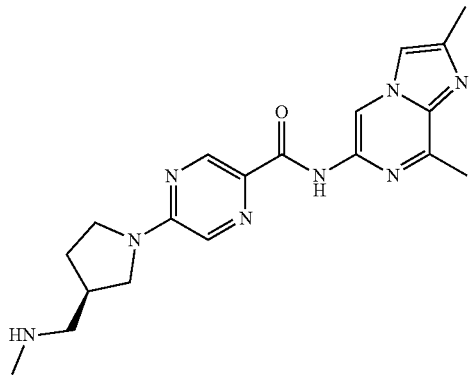 |
| 102 | 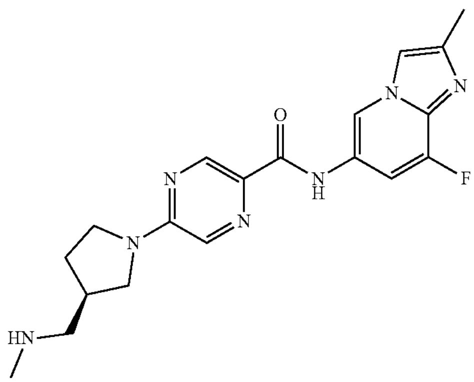 [SMILES: CNC[C@H]1CCN(c2cnc(C(=O)Nc3cc(F)c4nc(C)cn4c3)cn2)C1] |
| 103 | 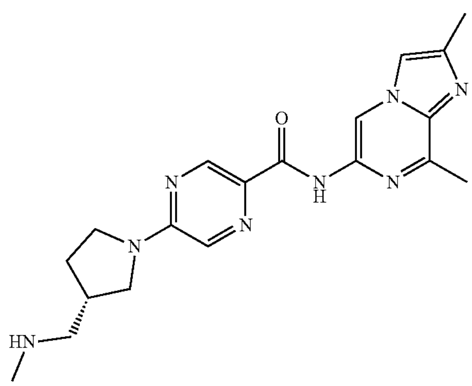 |
| 104 | 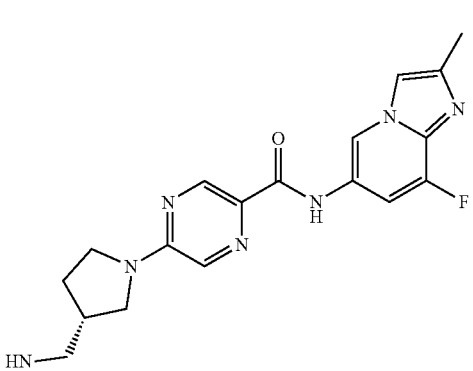 |

TABLE 1-continued
| Ex. | Structure |
|---|---|
| 105 | 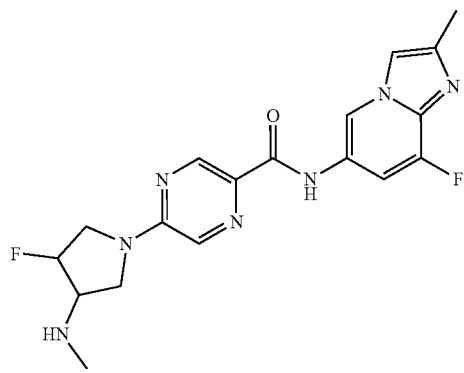
Cis Isomer, Enantiomer 1 + Enantiomer 2 |
| 106 | 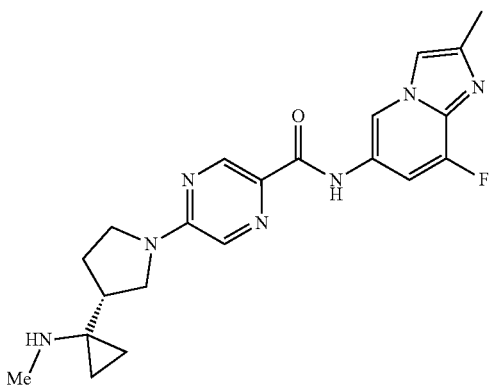 [SMILES: CNC1([C@@H]2CCN(c3cnc(C(=O)Nc4cc(F)c5nc(C)cn5c4)cn3)C2)CC1] |
| 107 | 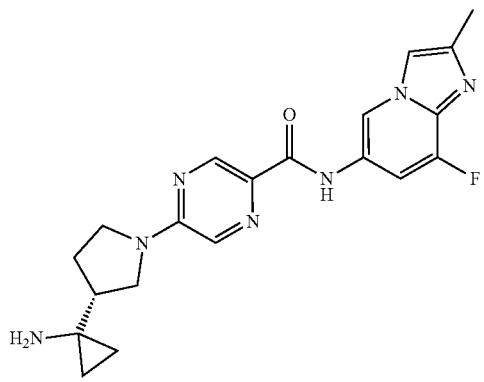 [SMILES: Cc1cn2cc(NC(=O)c3cnc(N4CC[C@@H](C5(N)CC5)C4)cn3)cc(F)c2n1] |
| 108 | 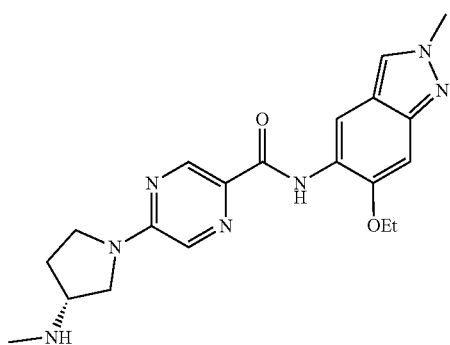 |

TABLE 1-continued

| Ex. | Structure |
|---|---|
| 109 | 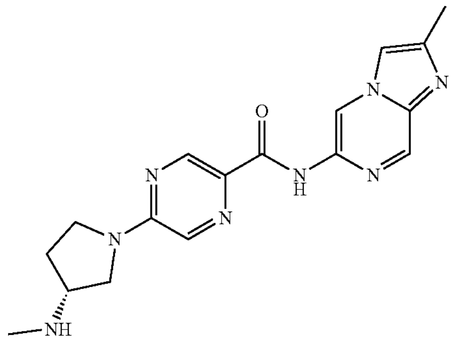 |
| 110 | 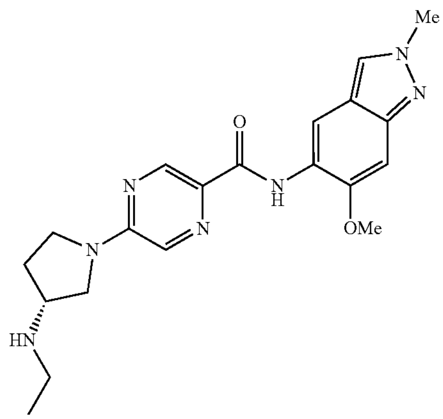 [SMILES: CCN[C@@H]1CCN(c2cnc(C(=O)Nc3cc4cn(C)nc4cc3OC)cn2)C1] |
| 111 | 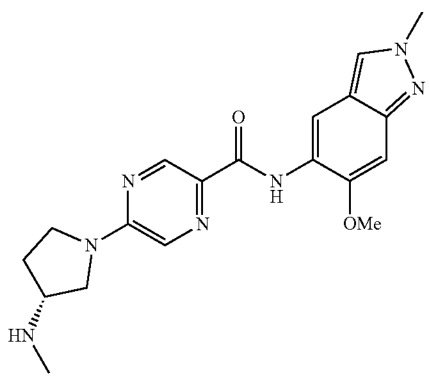 [SMILES: CN[C@@H]1CCN(c2cnc(C(=O)Nc3cc4cn(C)nc4cc3OC)cn2)C1] |
| 112 | 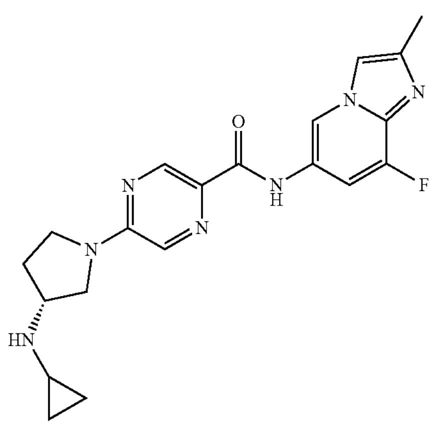 [SMILES: Cc1cn2cc(NC(=O)c3cnc(N4CC[C@@H](NC5CC5)C4)cn3)cc(F)c2n1] |

TABLE 1-continued
| Ex. | Structure |
|---|---|
| 113 | 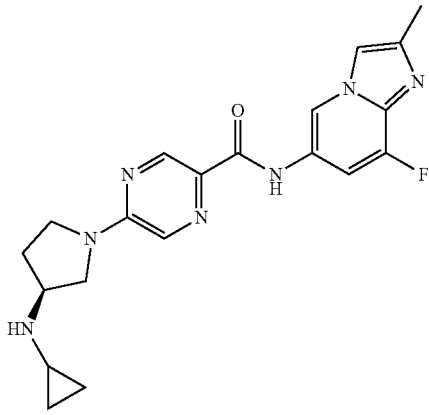 [SMILES: Cc1cn2cc(NC(=O)c3cnc(N4CC[C@H](NC5CC5)C4)cn3)cc(F)c2n1] |
| 114 | 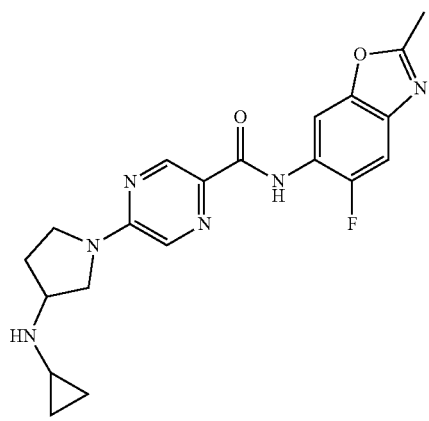
Enantiomer 1 + Enantiomer 2 |
| 115 | 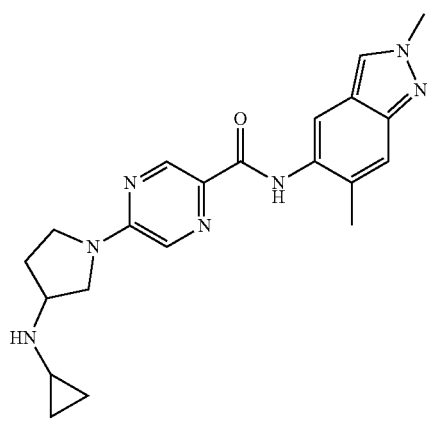
Enantiomer 1 + Enantiomer 2 |

TABLE 1-continued
| Ex. | Structure |
|---|---|
| 116 | 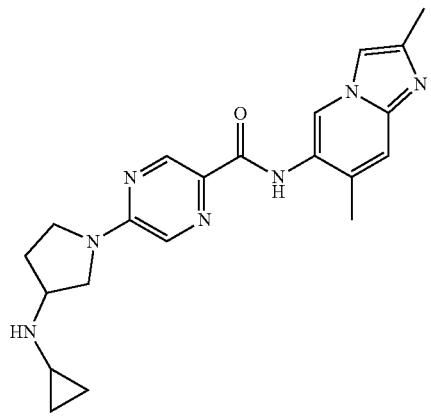<br>Enantiomer 1 + Enantiomer 2 |
| 117 | 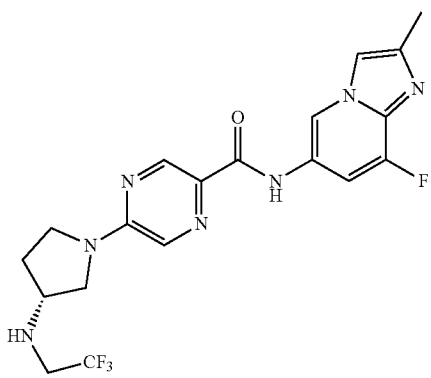 [SMILES: Cc1cn2cc(NC(=O)c3cnc(N4CC[C@@H](NCC(F)(F)F)C4)cn3)cc(F)c2n1] |
| 118 | 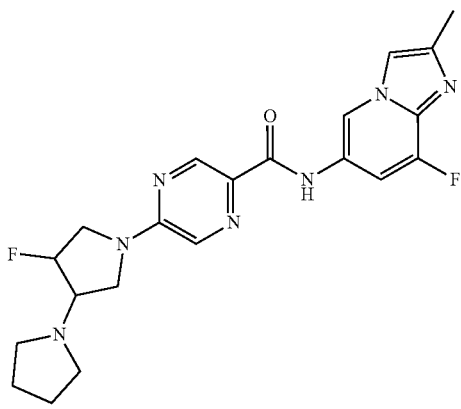<br>Cis Isomer, Enantiomer 1 |

TABLE 1-continued
| Ex. | Structure |
|---|---|
| 119 | 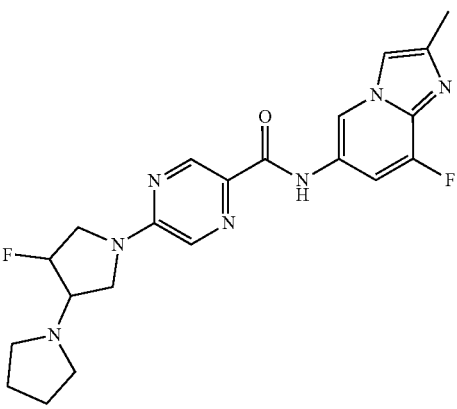<br>Cis Isomer, Enantiomer 2 |
| 120 | 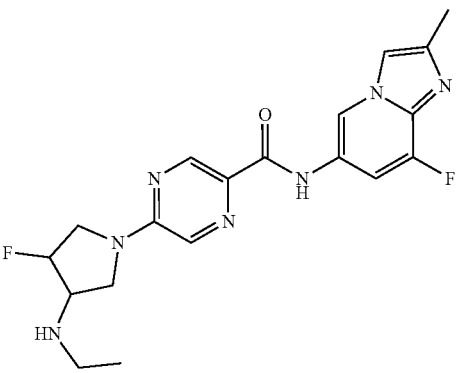<br>Cis Isomer, Enantiomer 1 |
| 121 | 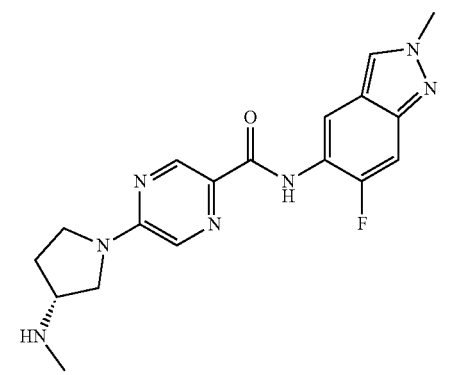 [SMILES: CN[C@@H]1CCN(c2cnc(C(=O)Nc3cc4cn(C)nc4cc3F)cn2)C1] |
| 122 | 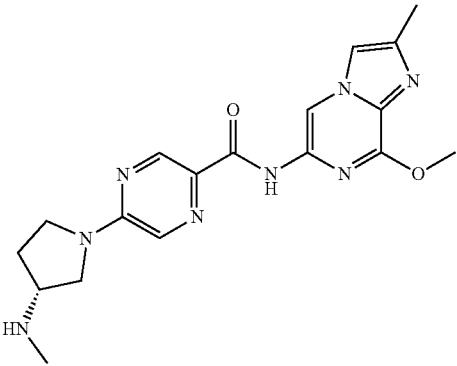 [SMILES: CN[C@@H]1CCN(c2cnc(C(=O)Nc3cn4cc(C)nc4c(OC)n3)cn2)C1] |

TABLE 1-continued
| Ex. | Structure |
|---|---|
| 123 | 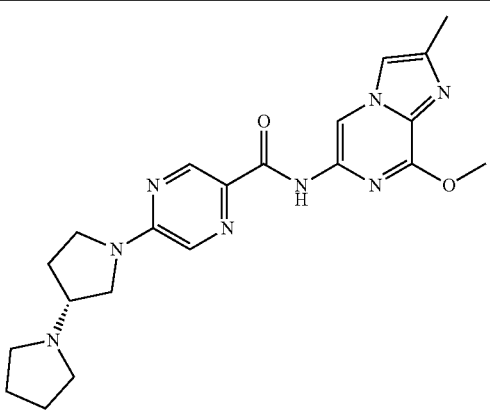 |
| 124 | 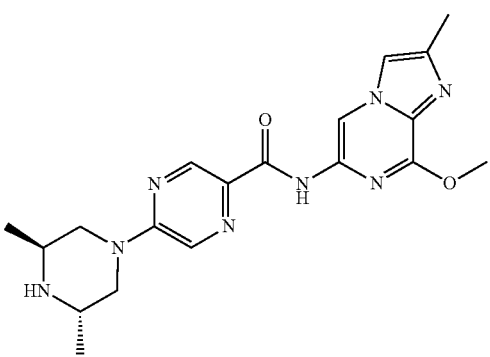 |
| 125 | 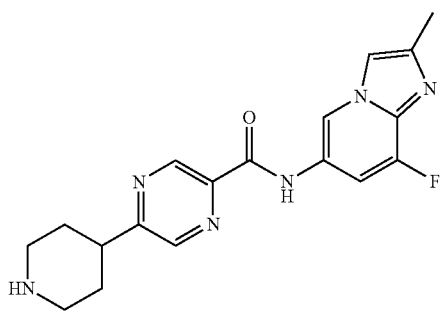 [SMILES: Cc1cn2cc(NC(=O)c3cnc(C4CCNCC4)cn3)cc(F)c2n1] |
| 126 | 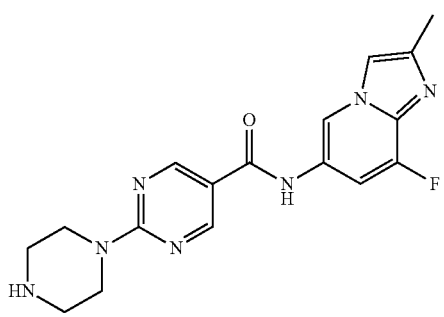 [SMILES: Cc1cn2cc(NC(=O)c3cnc(N4CCNCC4)nc3)cc(F)c2n1] |

TABLE 1-continued

| Ex. | Structure |
|-----|-----------|
| 127 | 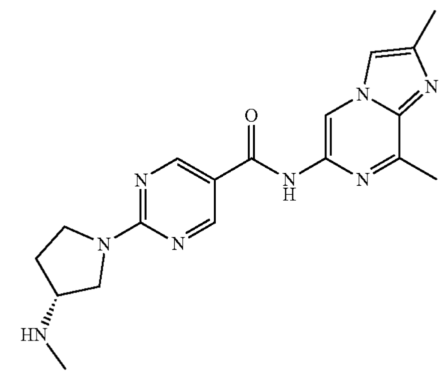 [SMILES: CN[C@@H]1CCN(c2ncc(C(=O)Nc3cn4cc(C)nc4c(C)n3)cn2)C1] |
| 128 | 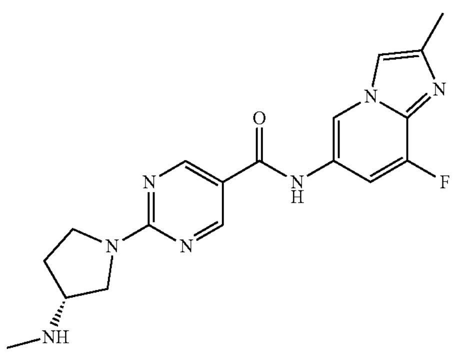 [SMILES: CN[C@@H]1CCN(c2ncc(C(=O)Nc3cc(F)c4nc(C)cn4c3)cn2)C1] |
| 129 | 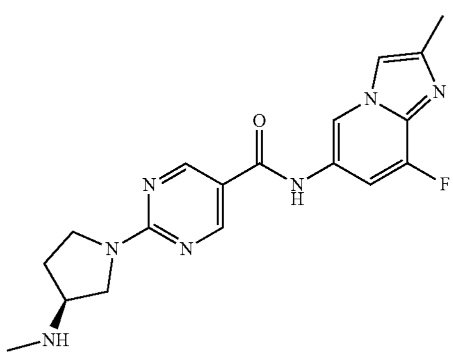 [SMILES: CN[C@H]1CCN(c2ncc(C(=O)Nc3cc(F)c4nc(C)cn4c3)cn2)C1] |
| 130 | 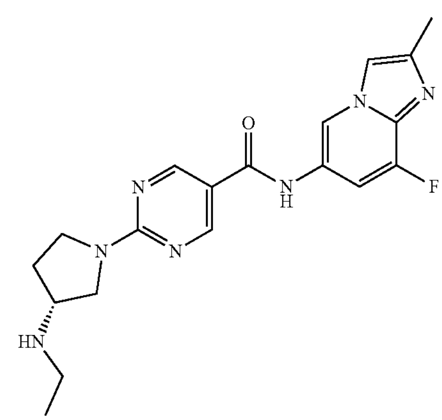 [SMILES: CCN[C@@H]1CCN(c2ncc(C(=O)Nc3cc(F)c4nc(C)cn4c3)cn2)C1] |

TABLE 1-continued
| Ex. | Structure |
|---|---|
| 131 | 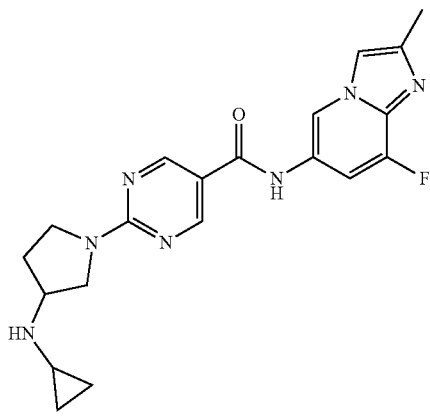<br>Enantiomer 1 + Enantiomer 2 |
| 132 | 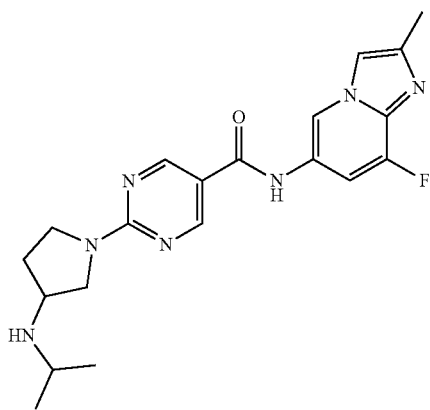<br>Enantiomer 1 + Enantiomer 2 |
| 133 | 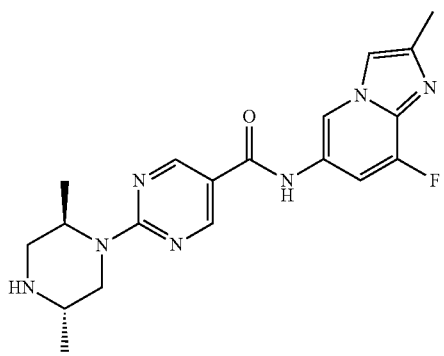 [SMILES: Cc1cn2cc(NC(=O)c3cnc(N4C[C@H](C)NC[C@H]4C)nc3)cc(F)c2n1] |

TABLE 1-continued
| Ex. | Structure |
|---|---|
| 134 | 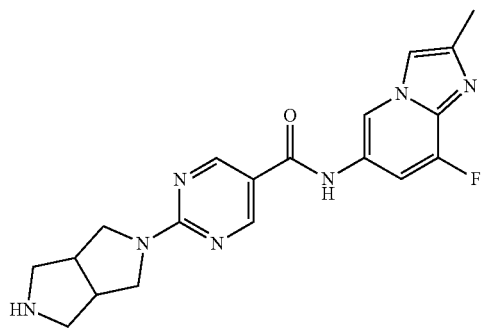<br>Cis Isomer |
| 135 | 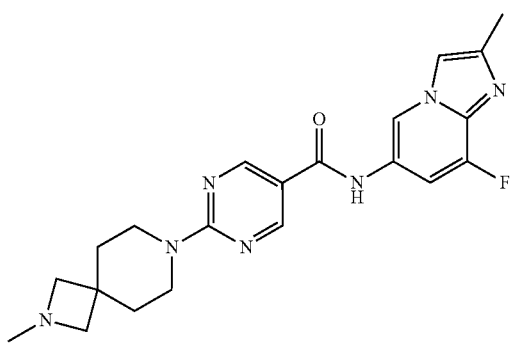 [SMILES: Cc1cn2cc(NC(=O)c3cnc(N4CCC5(CC4)CN(C)C5)nc3)cc(F)c2n1] |
| 136 | 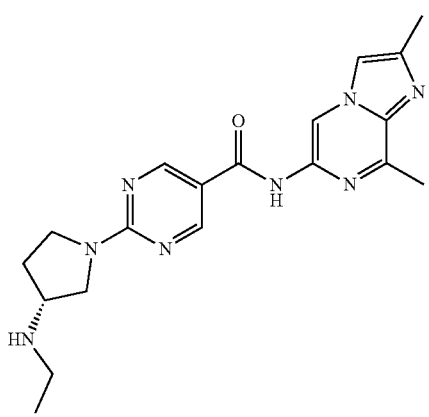 [SMILES: CCN[C@@H]1CCN(c2ncc(C(=O)Nc3cn4cc(C)nc4c(C)n3)cn2)C1] |
| 137 | 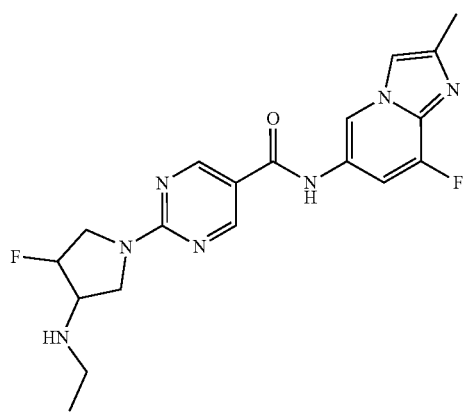<br>Cis Isomer, Enantiomer 1 |

TABLE 1-continued
| Ex. | Structure |
|---|---|
| 138 | 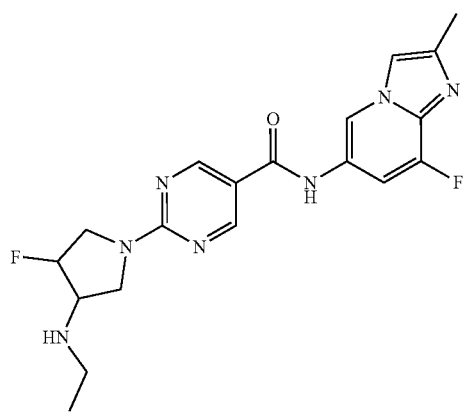<br>Cis Isomer, Enantiomer 2 |
| 139 | 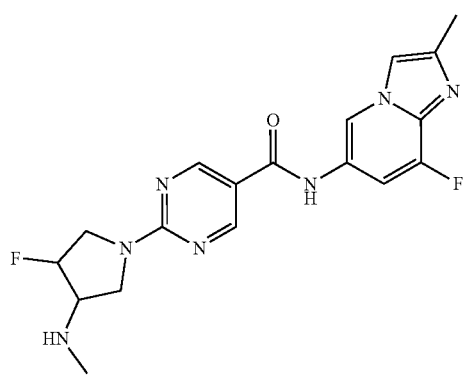<br>Cis Isomer, Enantiomer 1 |
| 140 | 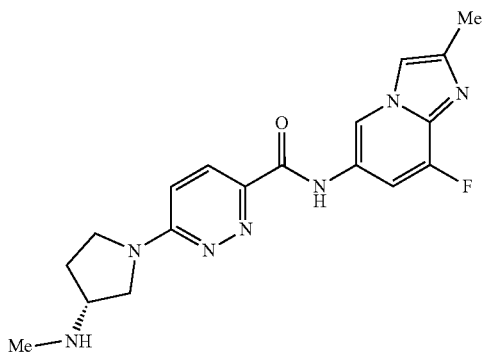 [SMILES: CN[C@@H]1CCN(c2ccc(C(=O)Nc3cc(F)c4nc(C)cn4c3)nn2)C1] |
| 141 | 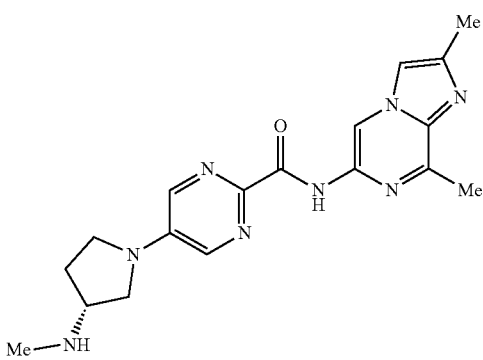 [SMILES: CN[C@@H]1CCN(c2cnc(C(=O)Nc3cn4cc(C)nc4c(C)n3)nc2)C1] |

TABLE 1-continued
| Ex. | Structure |
|---|---|
| 142 | 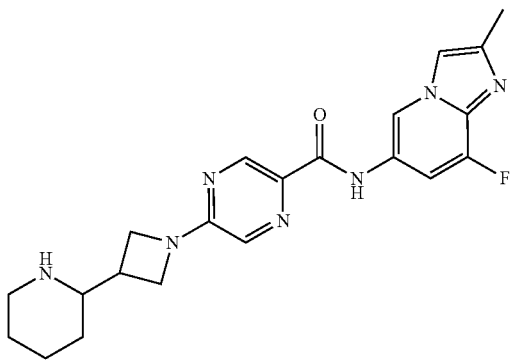
Enantiomer 1 |
| 143 | 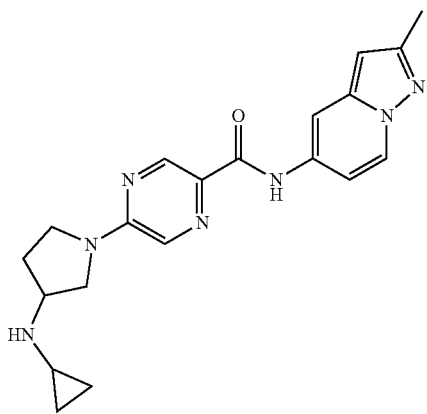
Enantiomer 1 + Enantiomer 2 |
| 144 | 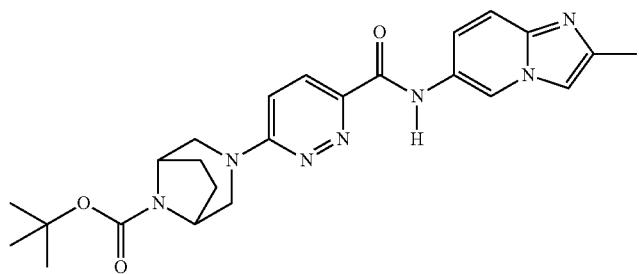 [SMILES: Cc1cn2cc(NC(=O)c3ccc(N4CC5CCC(C4)N5C(=O)OC(C)(C)C)nn3)ccc2n1] |
| 148 | 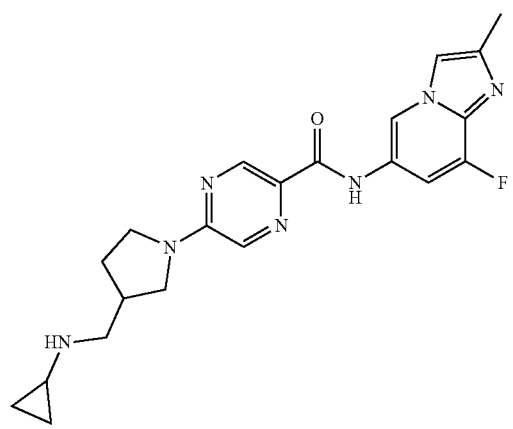
Enantiomer 1 |

TABLE 1-continued
| Ex. | Structure |
|---|---|
| 149 | 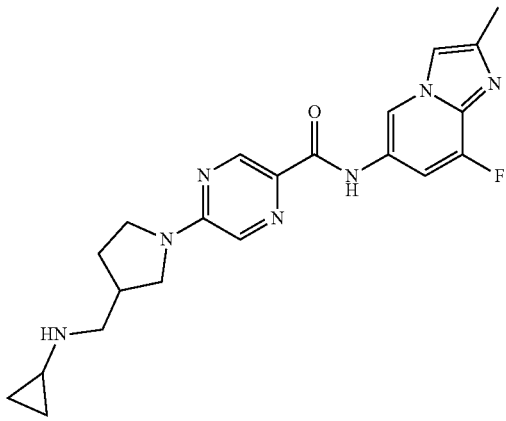<br>Enantiomer 2 |
| 150 | 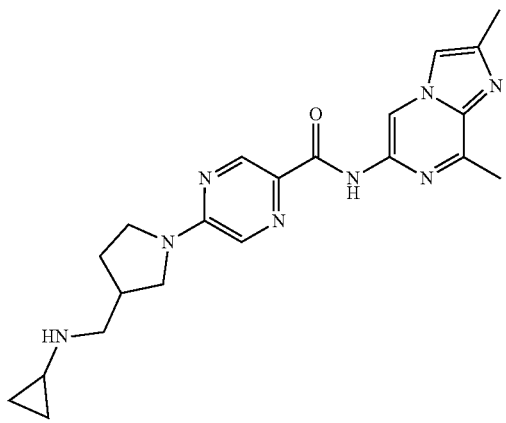 [SMILES: Cc1cn2cc(NC(=O)c3cnc(N4CCC(CNC5CC5)C4)cn3)nc(C)c2n1] |
| 151 | 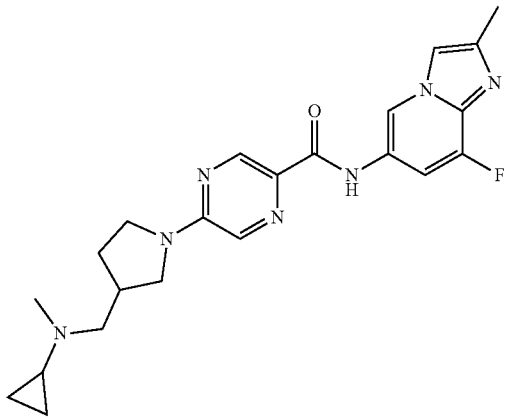<br>Enantiomer 1 |

TABLE 1-continued
| Ex. | Structure |
|---|---|
| 152 | 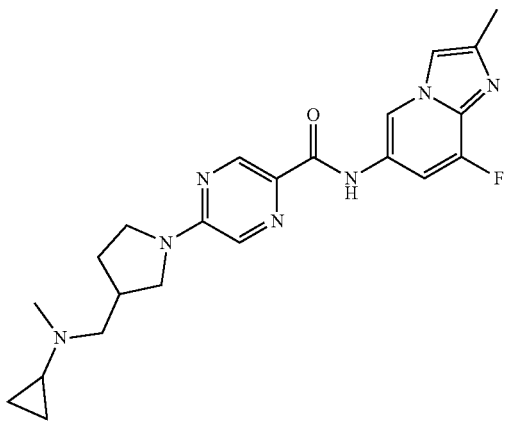<br>Enantiomer 2 |
| 153 | 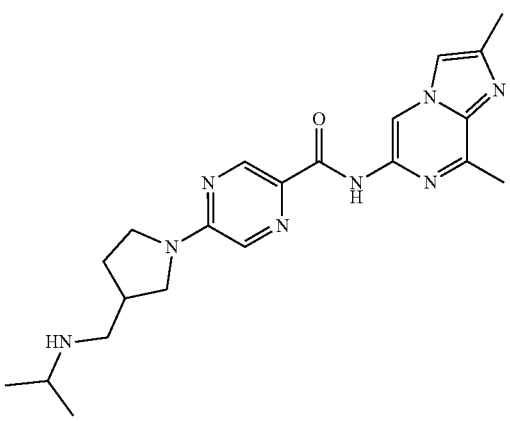<br>Enantiomer 1 |
| 154 | 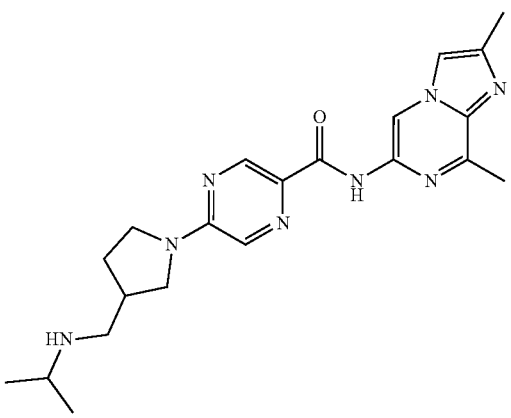<br>Enantiomer 2 |

TABLE 1-continued
| Ex. | Structure |
|---|---|
| 155 | 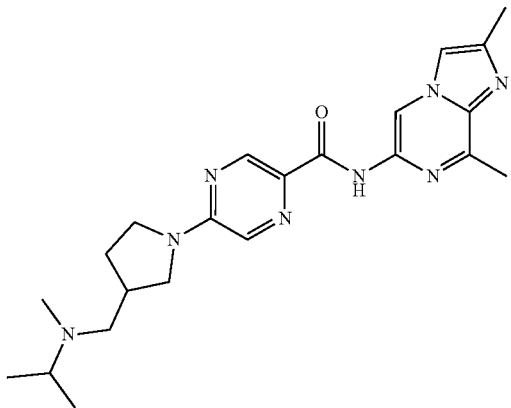<br>Enantiomer 1 |
| 156 | 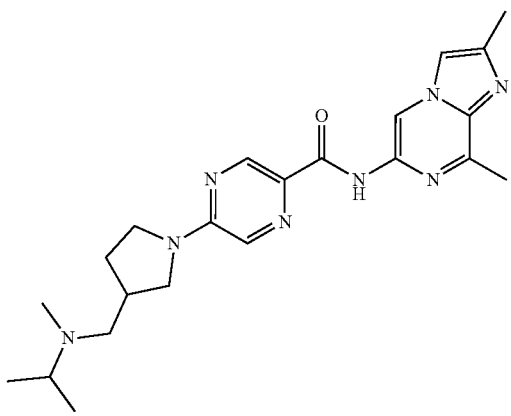<br>Enantiomer 2 |
| 157 | 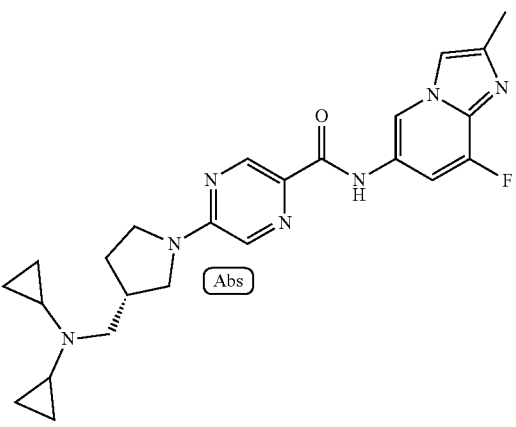 [SMILES: Cc1cn2cc(NC(=O)c3cnc(N4CC[C@@H](CN(C5CC5)C5CC5)C4)cn3)cc(F)c2n1] |

TABLE 1-continued

| Ex. | Structure |
|---|---|
| 158 | (structure) |
| 159 | (structure) Enantiomer 1 |
| 160 | (structure) Stereoisomer 1 |

TABLE 1-continued
| Ex. | Structure |
|---|---|
| 161 | 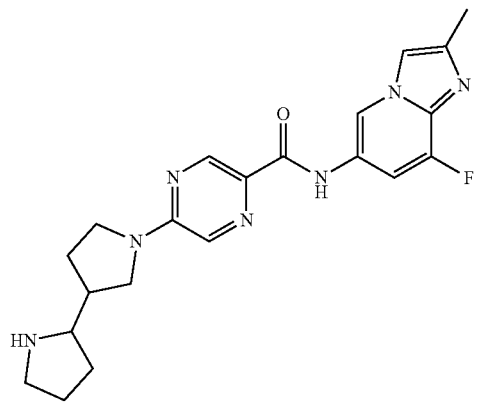<br>Stereoisomer 2 |
| 162 | 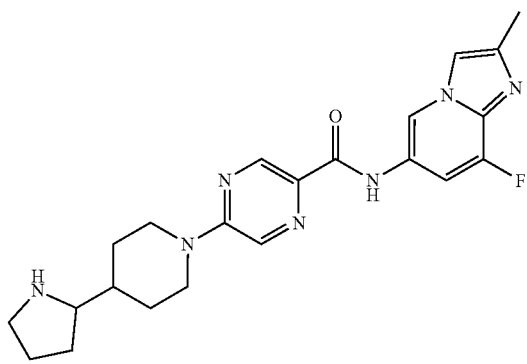<br>Enantiomer 2 |
| 163 | 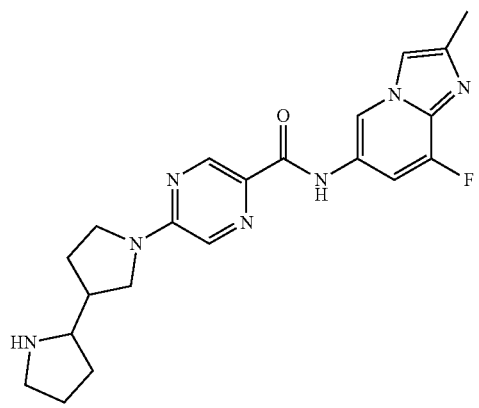<br>Stereoisomer 3 |

121
122
TABLE 1-continued
| Ex. | Structure |
|---|---|
| 164 | 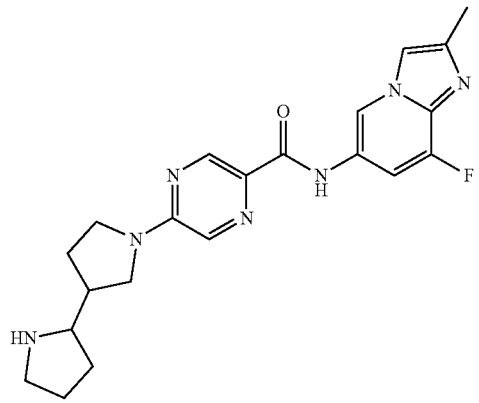
Stereoisomer 4 |
| 165 | 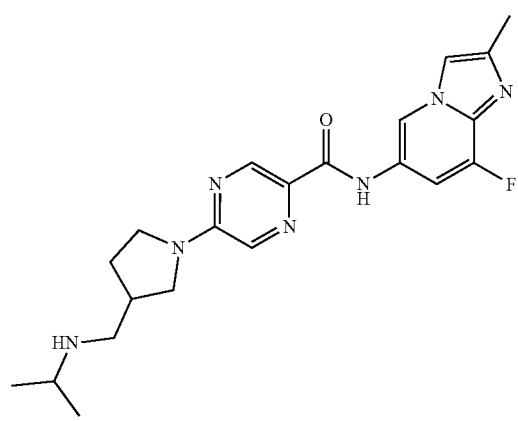
Enantiomer 1 |
| 166 | 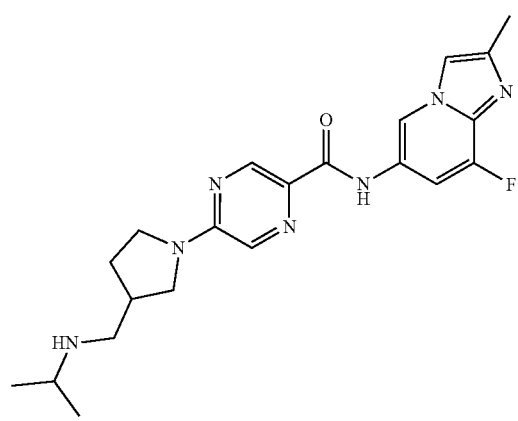
Enantiomer 2 |

TABLE 1-continued
| Ex. | Structure |
|---|---|
| 167 | 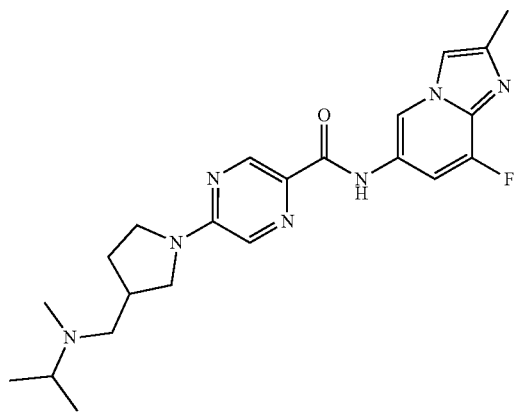<br>Enantiomer 1 |
| 168 | 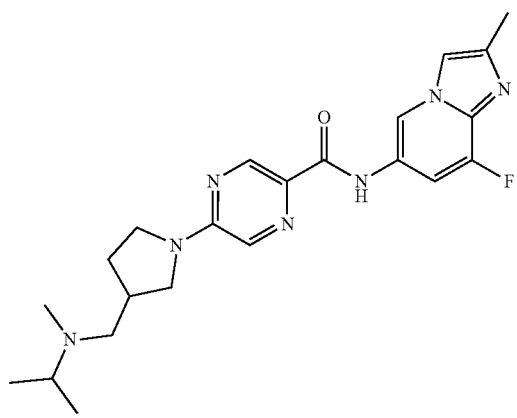<br>Enantiomer 2 |
| 169 | 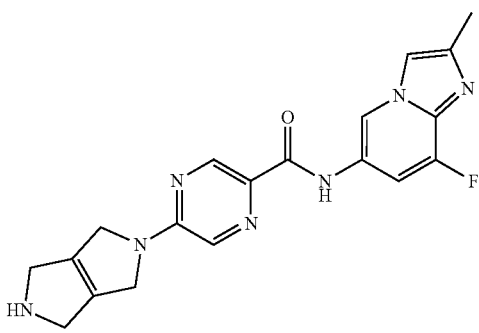 [SMILES: Cc1cn2cc(NC(=O)c3cnc(N4CC5=C(CNC5)C4)cn3)cc(F)c2n1] |
| 170 | 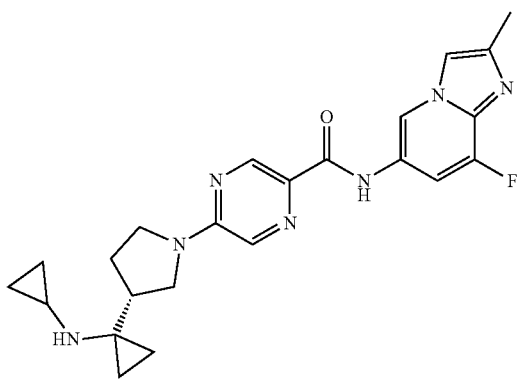 [SMILES: Cc1cn2cc(NC(=O)c3cnc(N4CC[C@@H](C5(NC6CC6)CC5)C4)cn3)cc(F)c2n1] |

TABLE 1-continued
| Ex. | Structure |
|---|---|
| 171 | 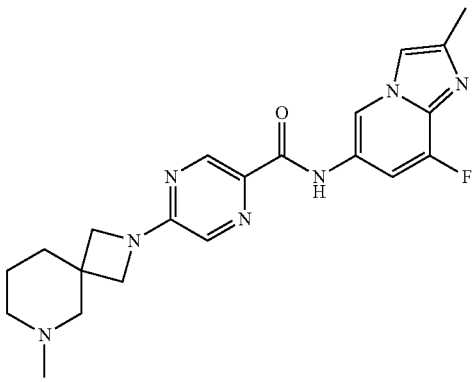 [SMILES: Cc1cn2cc(NC(=O)c3cnc(N4CC5(CCCN(C)C5)C4)cn3)cc(F)c2n1] |
| 172 | 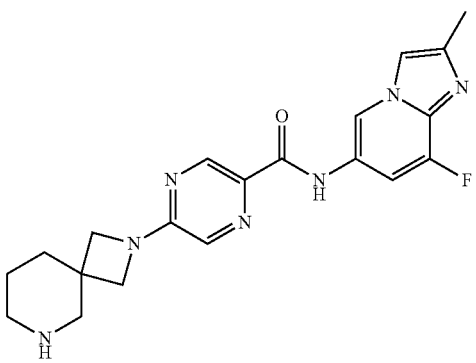 |
| 173 | 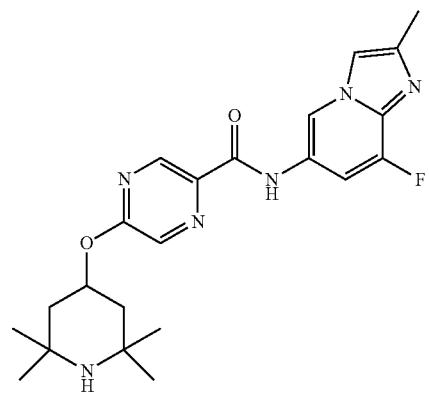 [SMILES: Cc1cn2cc(NC(=O)c3cnc(OC4CC(C)(C)NC(C)(C)C4)cn3)cc(F)c2n1] |
| 174 | 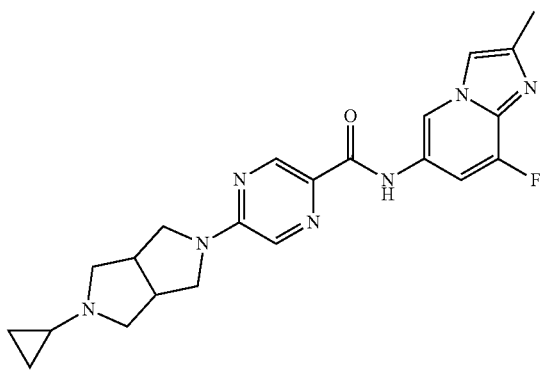 [SMILES: Cc1cn2cc(NC(=O)c3cnc(N4CC5CN(C6CC6)CC5C4)cn3)cc(F)c2n1] |

TABLE 1-continued
| Ex. | Structure |
|---|---|
| 175 | 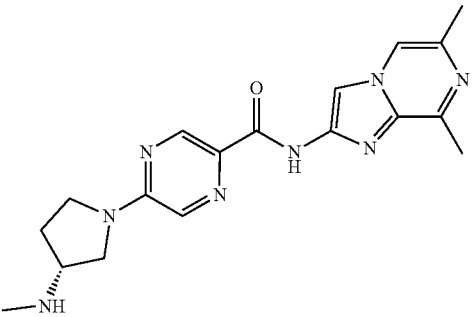 |
| 176 | 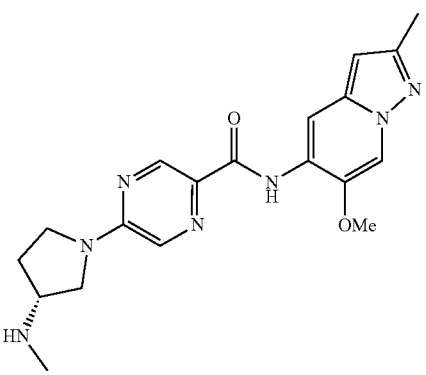 [SMILES: CN[C@@H]1CCN(c2cnc(C(=O)Nc3cc4cc(C)nn4cc3OC)cn2)C1] |
| 177 | 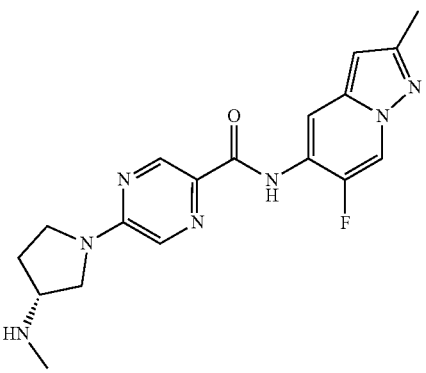 [SMILES: CN[C@@H]1CCN(c2cnc(C(=O)Nc3cc4cc(C)nn4cc3F)cn2)C1] |
| 178 | 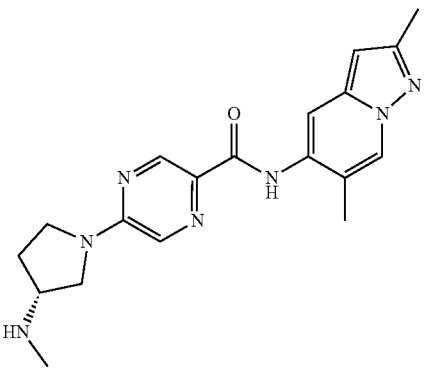 [SMILES: CN[C@@H]1CCN(c2cnc(C(=O)Nc3cc4cc(C)nn4cc3C)cn2)C1] |

TABLE 1-continued
| Ex. | Structure |
|---|---|
| 179 | 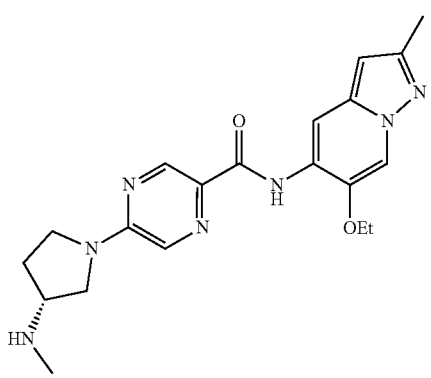 [SMILES: CCOc1cn2nc(C)cc2cc1NC(=O)c1cnc(N2CC[C@@H](NC)C2)cn1] |
| 180 | 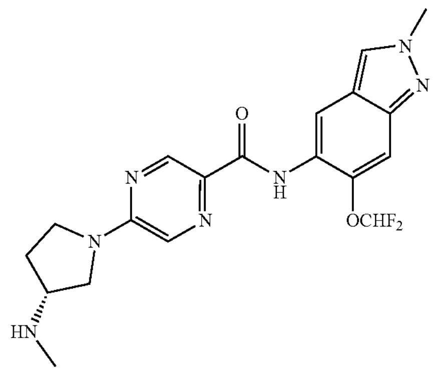 [SMILES: CN[C@@H]1CCN(c2cnc(C(=O)Nc3cc4cn(C)nc4cc3OC(F)F)cn2)C1] |
| 181 | 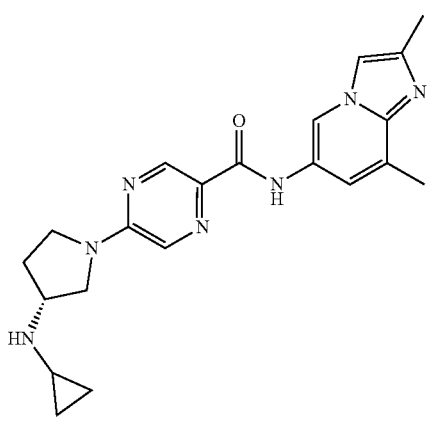 [SMILES: Cc1cn2cc(NC(=O)c3cnc(N4CC[C@@H](NC5CC5)C4)cn3)cc(C)c2n1] |
| 182 | 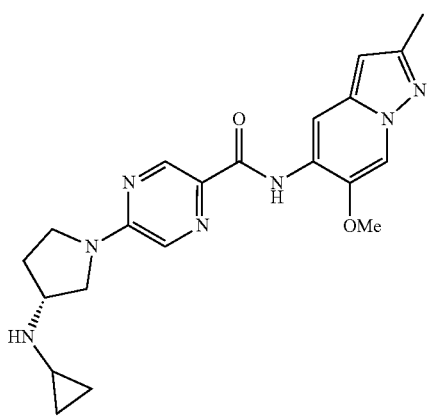 [SMILES: COc1cn2nc(C)cc2cc1NC(=O)c1cnc(N2CC[C@@H](NC3CC3)C2)cn1] |

TABLE 1-continued

| Ex. | Structure |
|-----|-----------|
| 183 | 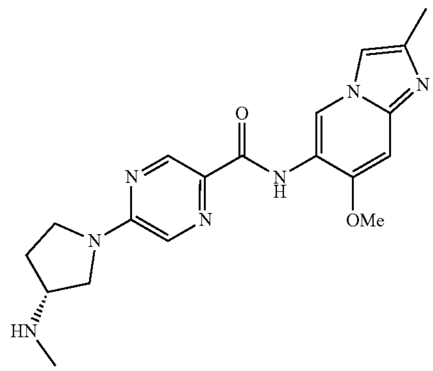 [SMILES: CN[C@@H]1CCN(c2cnc(C(=O)Nc3cn4cc(C)nc4cc3OC)cn2)C1] |
| 184 | 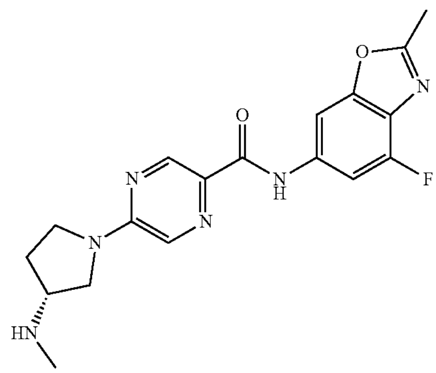 [SMILES: CN[C@@H]1CCN(c2cnc(C(=O)Nc3cc(F)c4nc(C)oc4c3)cn2)C1] |
| 185 | 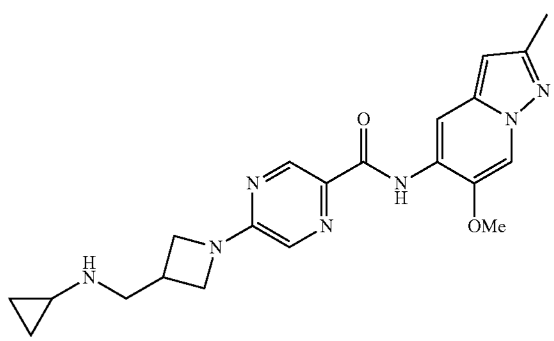 [SMILES: COc1cn2nc(C)cc2cc1NC(=O)c1cnc(N2CC(CNC3CC3)C2)cn1] |
| 186 | 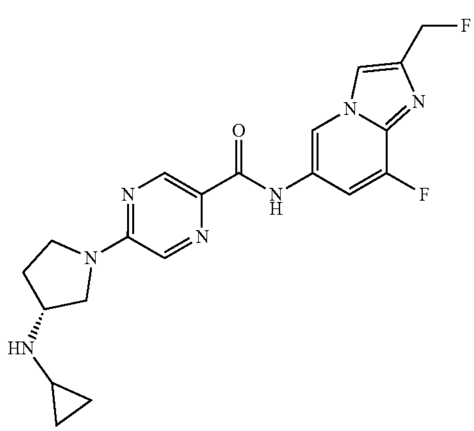 [SMILES: O=C(Nc1cc(F)c2nc(CF)cn2c1)c1cnc(N2CC[C@@H](NC3CC3)C2)cn1] |

TABLE 1-continued
| Ex. | Structure |
|---|---|
| 187 | 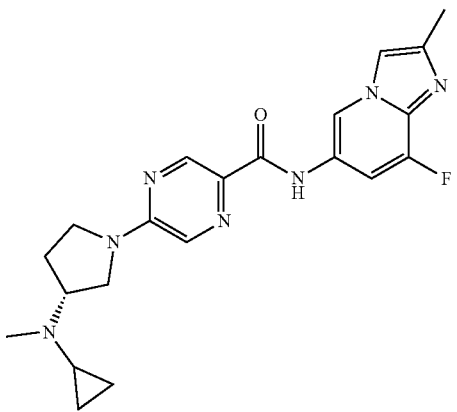 |
| 188 | 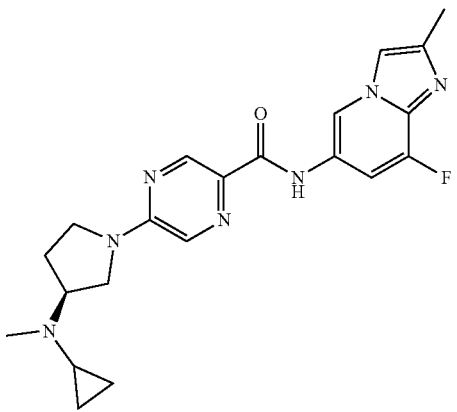 [SMILES: Cc1cn2cc(NC(=O)c3cnc(N4CC[C@H](N(C)C5CC5)C4)cn3)cc(F)c2n1] |
| 189 | 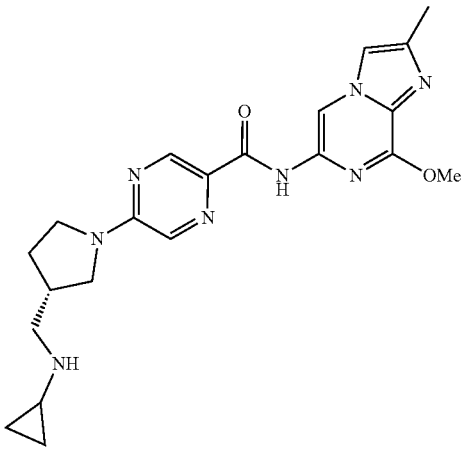 [SMILES: COc1nc(NC(=O)c2cnc(N3CC[C@@H](CNC4CC4)C3)cn2)cn2cc(C)nc12] |
| 190 | 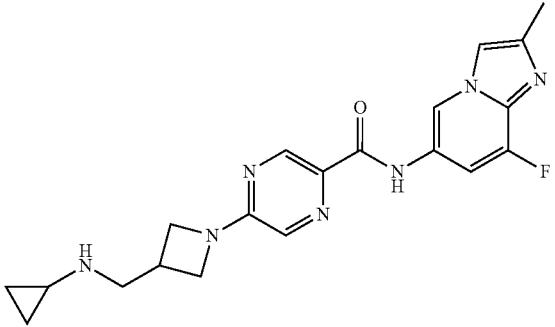 [SMILES: Cc1cn2cc(NC(=O)c3cnc(N4CC(CNC5CC5)C4)cn3)cc(F)c2n1] |

TABLE 1-continued
| Ex. | Structure |
|---|---|
| 191 | 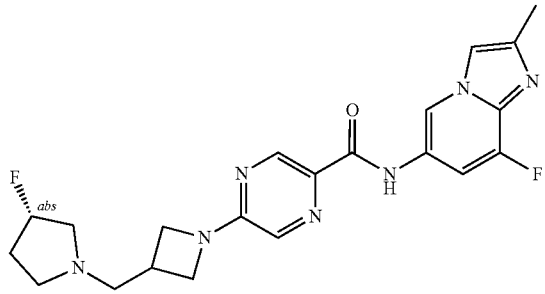 [SMILES: Cc1cn2cc(NC(=O)c3cnc(N4CC(CN5CC[C@H](F)C5)C4)cn3)cc(F)c2n1] |
| 192 | 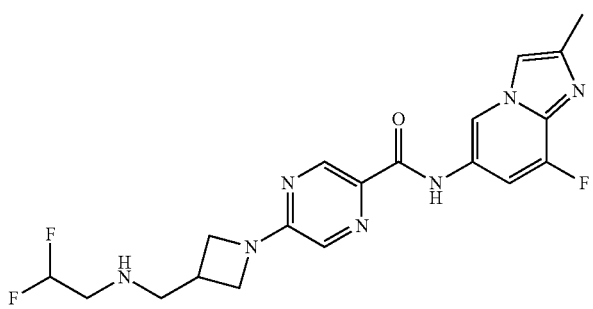 |
| 193 | 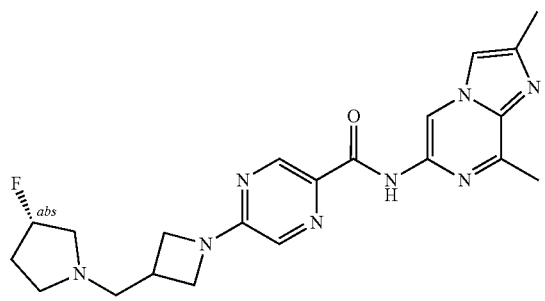 [SMILES: Cc1cn2cc(NC(=O)c3cnc(N4CC(CN5CC[C@H](F)C5)C4)cn3)nc(C)c2n1] |
| 194 | 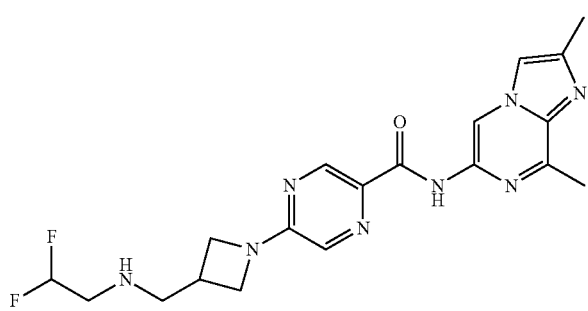 [SMILES: Cc1cn2cc(NC(=O)c3cnc(N4CC(CNCC(F)F)C4)cn3)nc(C)c2n1] |
| 195 | 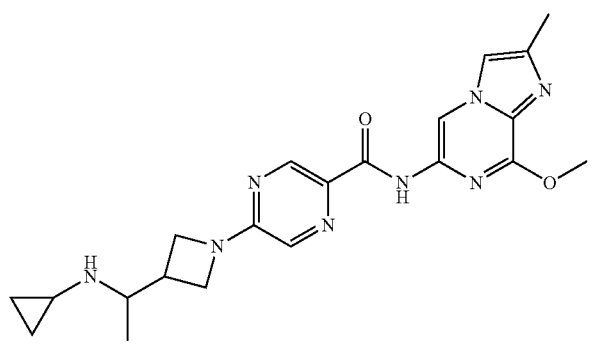<br>Enantiomer 1 |

TABLE 1-continued
| Ex. | Structure |
|---|---|
| 196 | 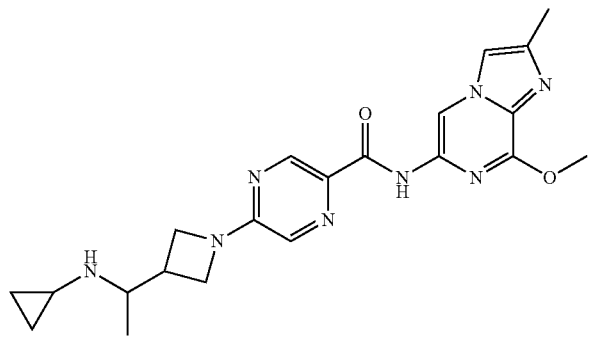<br>Enantiomer 2 |
| 197 | 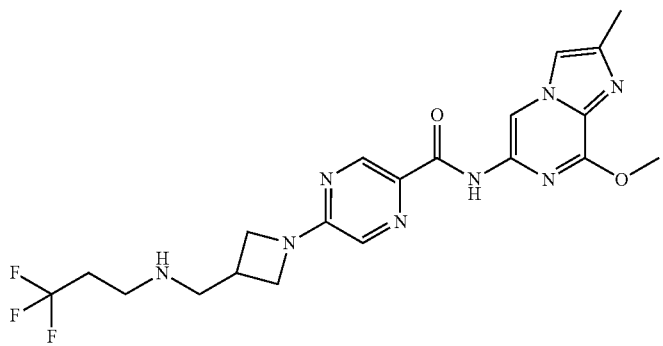 [SMILES: COc1nc(NC(=O)c2cnc(N3CC(CNCCC(F)(F)F)C3)cn2)cn2cc(C)nc12] |
| 198 | 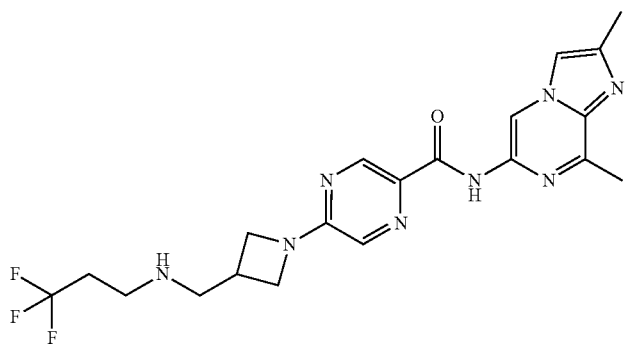 [SMILES: Cc1cn2cc(NC(=O)c3cnc(N4CC(CNCCC(F)(F)F)C4)cn3)nc(C)c2n1] |
| 199 | 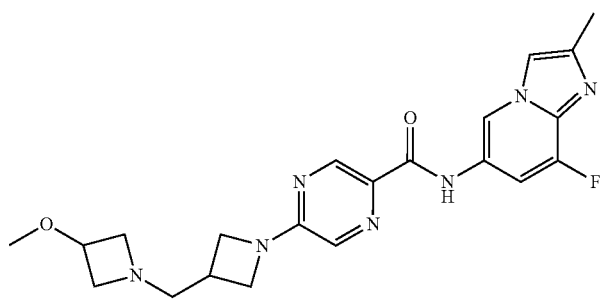 [SMILES: COC1CN(CC2CN(c3cnc(C(=O)Nc4cc(F)c5nc(C)cn5c4)cn3)C2)C1] |

TABLE 1-continued
| Ex. | Structure |
|---|---|
| 200 | 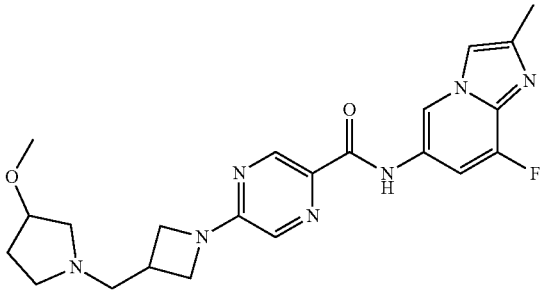 [SMILES: COC1CCN(CC2CN(c3cnc(C(=O)Nc4cc(F)c5nc(C)cn5c4)cn3)C2)C1] |
| 201 | 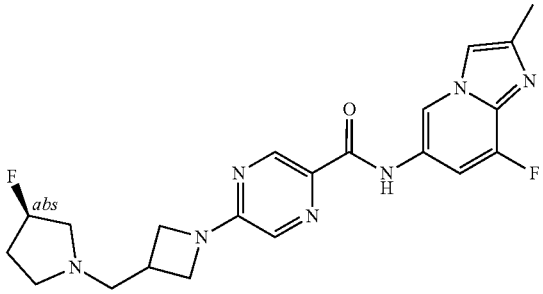 [SMILES: Cc1cn2cc(NC(=O)c3cnc(N4CC(CN5CC[C@@H](F)C5)C4)cn3)cc(F)c2n1] |
| 202 | 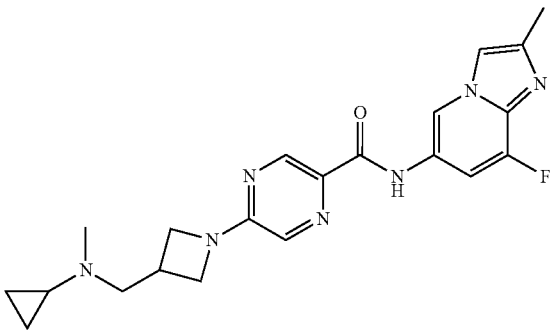 [SMILES: Cc1cn2cc(NC(=O)c3cnc(N4CC(CN(C)C5CC5)C4)cn3)cc(F)c2n1] |
| 203 | 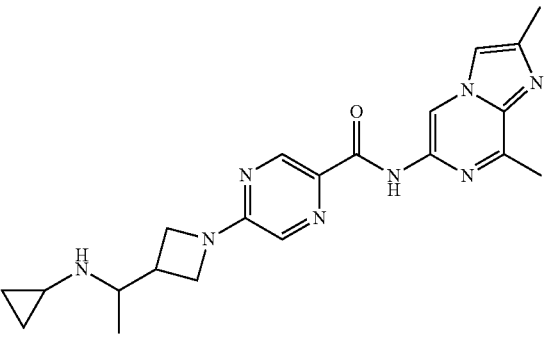<br>Enantiomer 1 |

TABLE 1-continued
| Ex. | Structure |
|---|---|
| 204 | 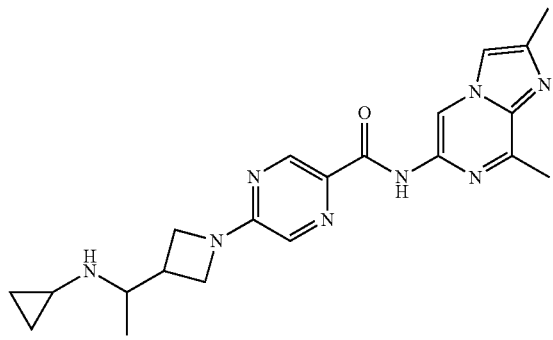<br>Enantiomer 2 |
| 205 | 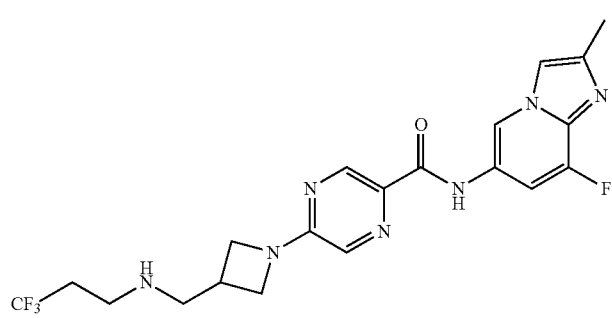 [SMILES: Cc1cn2cc(NC(=O)c3cnc(N4CC(CNCCC(F)(F)F)C4)cn3)cc(F)c2n1] |
| 206 | 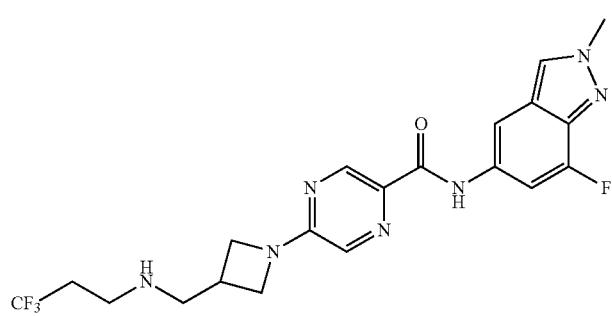 [SMILES: Cn1cc2cc(NC(=O)c3cnc(N4CC(CNCCC(F)(F)F)C4)cn3)cc(F)c2n1] |
| 207 | 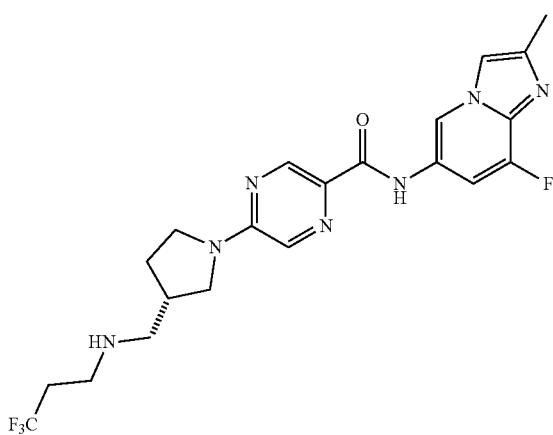 [SMILES: Cc1cn2cc(NC(=O)c3cnc(N4CC[C@@H](CNCCC(F)(F)F)C4)cn3)cc(F)c2n1] |

TABLE 1-continued
| Ex. | Structure |
|---|---|
| 208 | 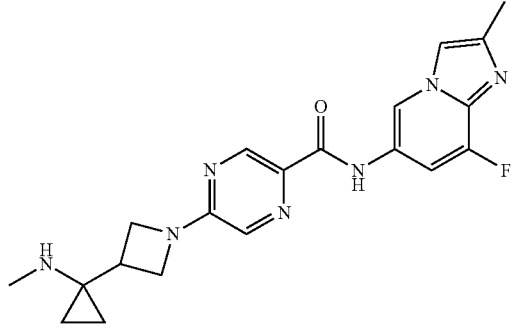 [SMILES: CNC1(C2CN(c3cnc(C(=O)Nc4cc(F)c5nc(C)cn5c4)cn3)C2)CC1] |
| 209 | 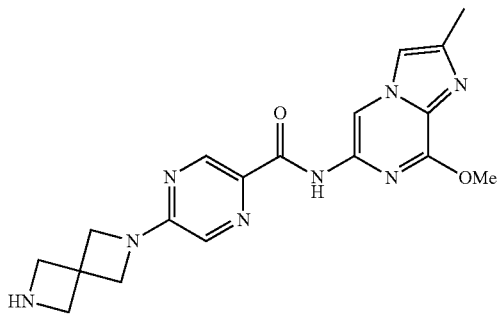 [SMILES: COc1nc(NC(=O)c2cnc(N3CC4(CNC4)C3)cn2)cn2cc(C)nc12] |
| 210 | 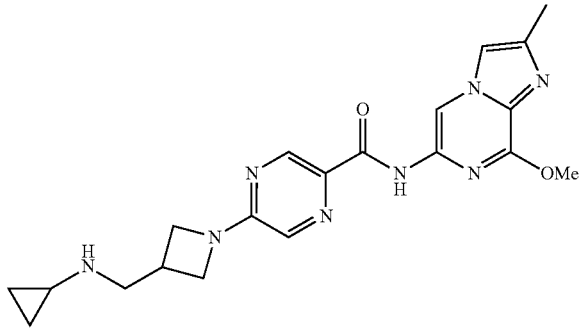 [SMILES: COc1nc(NC(=O)c2cnc(N3CC(CNC4CC4)C3)cn2)cn2cc(C)nc12] |
| 211 | 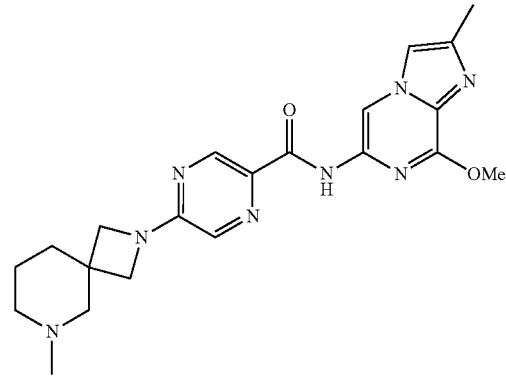 [SMILES: COc1nc(NC(=O)c2cnc(N3CC4(CCCN(C)C4)C3)cn2)cn2cc(C)nc12] |

TABLE 1-continued
| Ex. | Structure |
|---|---|
| 212 | 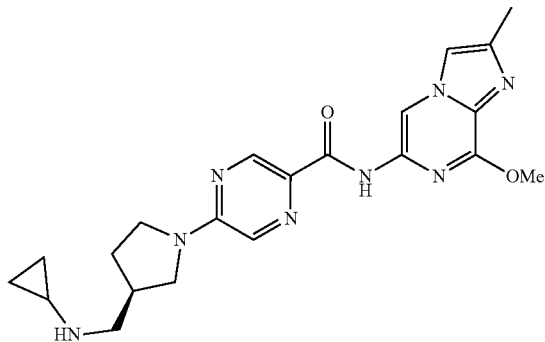 [SMILES: COc1nc(NC(=O)c2cnc(N3CC[C@H](CNC4CC4)C3)cn2)cn2cc(C)nc12] |
| 213 | 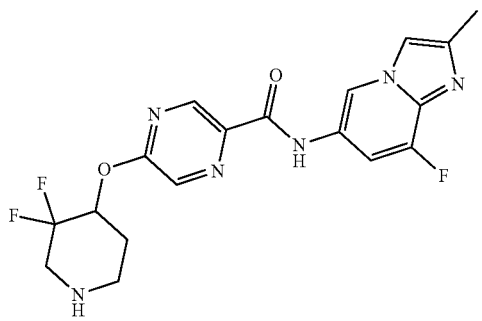 [SMILES: Cc1cn2cc(NC(=O)c3cnc(OC4CCNCC4(F)F)cn3)cc(F)c2n1] |
| 214 | 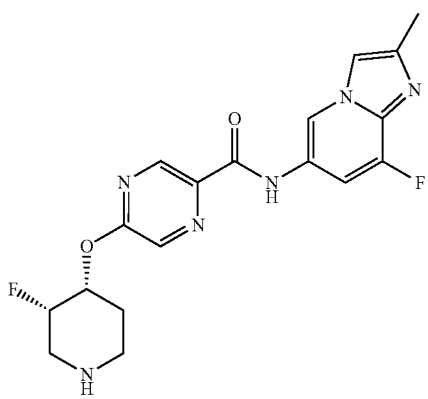 [SMILES: Cc1cn2cc(NC(=O)c3cnc(O[C@@H]4CCNC[C@@H]4F)cn3)cc(F)c2n1] |
| 215 | 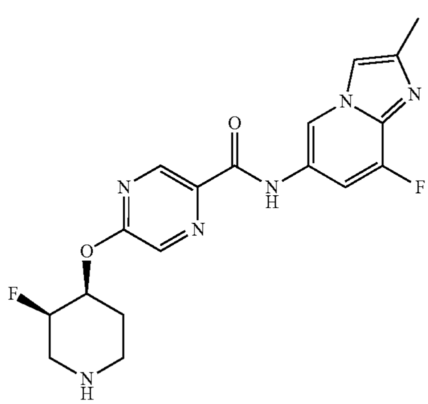 [SMILES: Cc1cn2cc(NC(=O)c3cnc(O[C@H]4CCNC[C@H]4F)cn3)cc(F)c2n1] |

TABLE 1-continued
| Ex. | Structure |
|---|---|
| 216 | 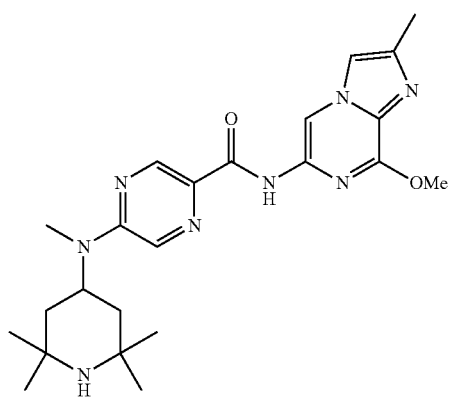 [SMILES: COc1nc(NC(=O)c2cnc(N(C)C3CC(C)(C)NC(C)(C)C3)cn2)cn2cc(C)nc12] |
| 217 | 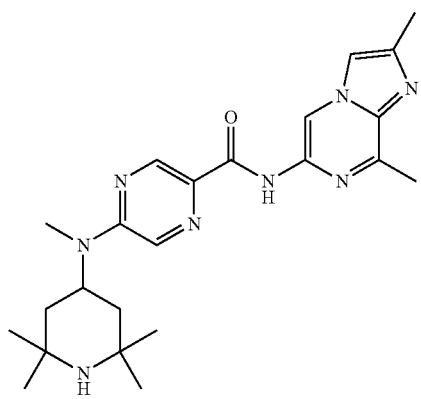 |
| 218 | 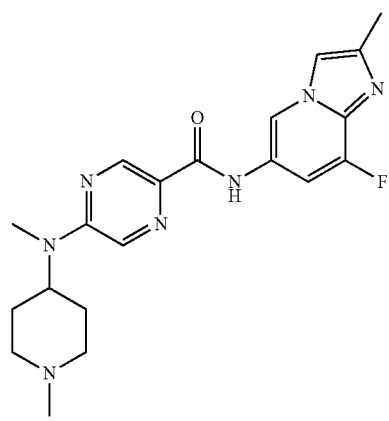 [SMILES: Cc1cn2cc(NC(=O)c3cnc(N(C)C4CCN(C)CC4)cn3)cc(F)c2n1] |
| 219 | 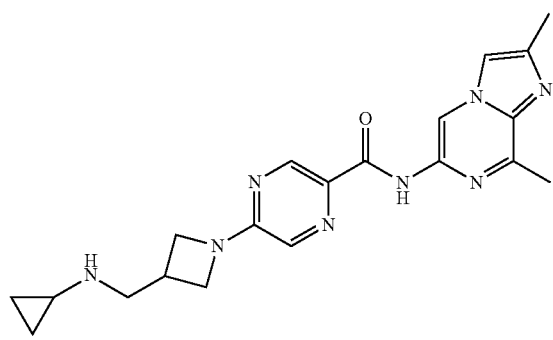 [SMILES: Cc1cn2cc(NC(=O)c3cnc(N4CC(CNC5CC5)C4)cn3)nc(C)c2n1] |

TABLE 1-continued
| Ex. | Structure |
|---|---|
| 220 | 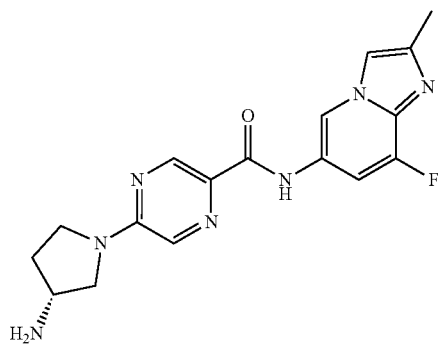 |
| 221 | 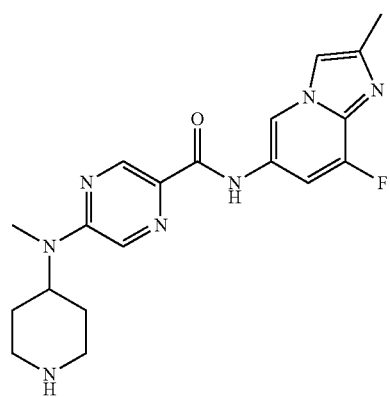 [SMILES: Cc1cn2cc(NC(=O)c3cnc(N(C)C4CCNCC4)cn3)cc(F)c2n1] |
| 222 | 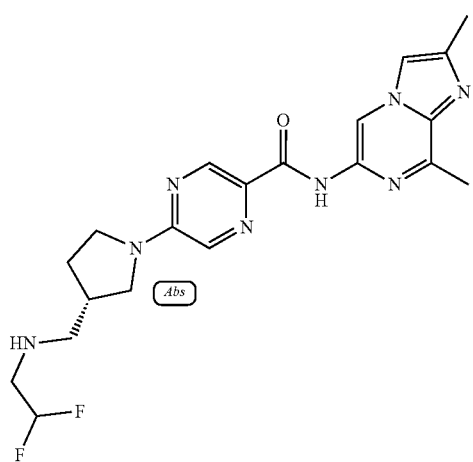 [SMILES: Cc1cn2cc(NC(=O)c3cnc(N4CC[C@@H](CNCC(F)F)C4)cn3)nc(C)c2n1] |

TABLE 1-continued
| Ex. | Structure |
|---|---|
| 223 | 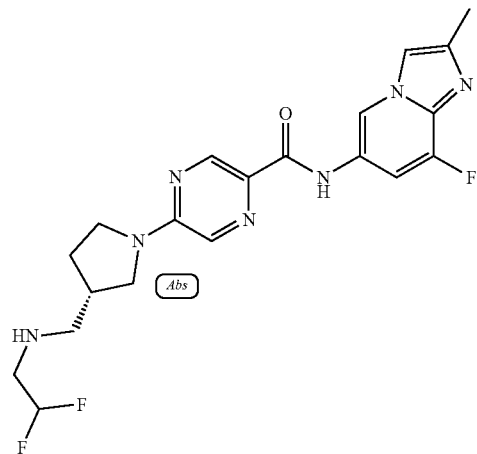 [SMILES: Cc1cn2cc(NC(=O)c3cnc(N4CC[C@@H](CNCC(F)F)C4)cn3)cc(F)c2n1] |
| 224 | 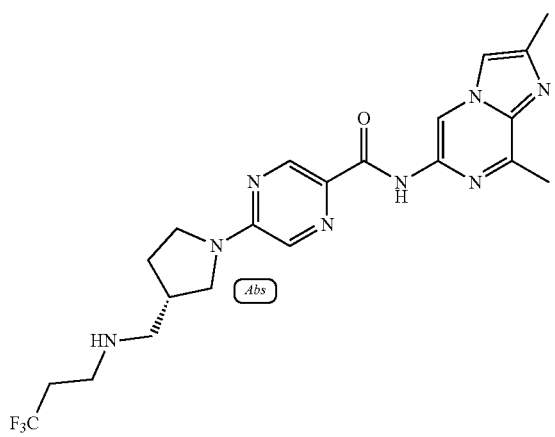 [SMILES: Cc1cn2cc(NC(=O)c3cnc(N4CC[C@@H](CNCCC(F)(F)F)C4)cn3)nc(C)c2n1] |
| 225 | 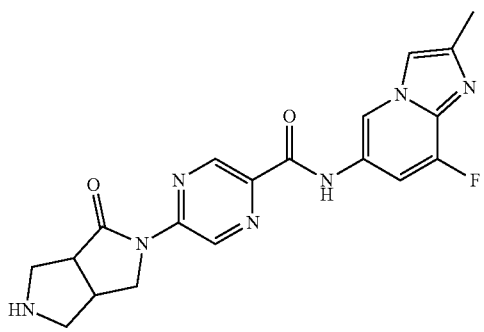 [SMILES: Cc1cn2cc(NC(=O)c3cnc(N4CC5CNCC5C4=O)cn3)cc(F)c2n1] |
| 226 | 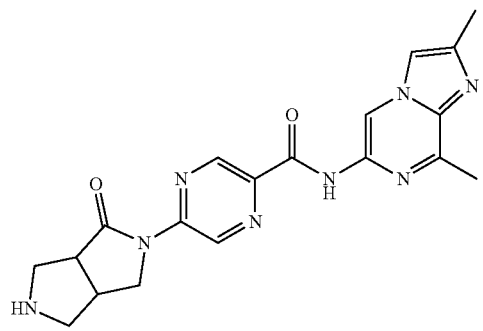 [SMILES: Cc1cn2cc(NC(=O)c3cnc(N4CC5CNCC5C4=O)cn3)nc(C)c2n1] |

| Ex. | Structure |
|---|---|
| 227 | 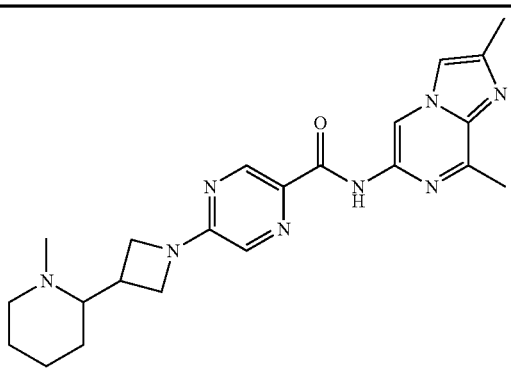<br>Enantiomer 1 |
| 228 | 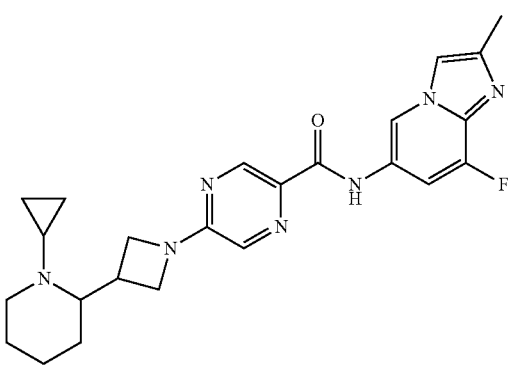<br>Enantiomer 1 |
| 229 | 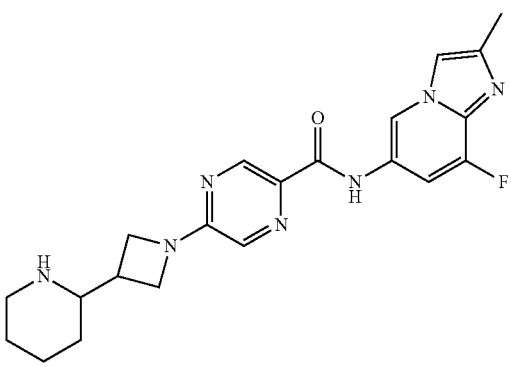<br>Enantiomer 1 |
| 230 | 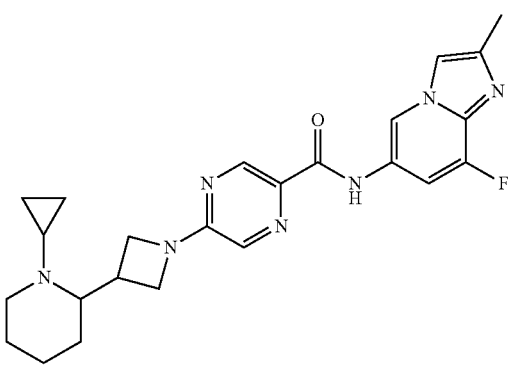<br>Enantiomer 2 |

TABLE 1-continued
| Ex. | Structure |
|---|---|
| 231 | 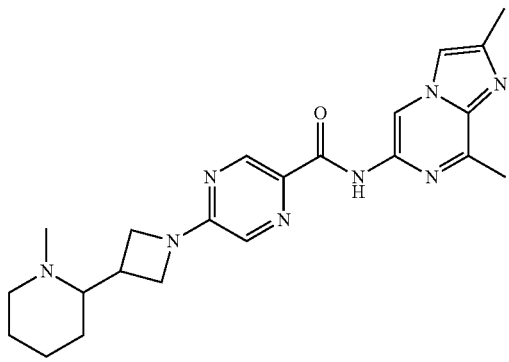
Enantiomer 2 |
| 232 | 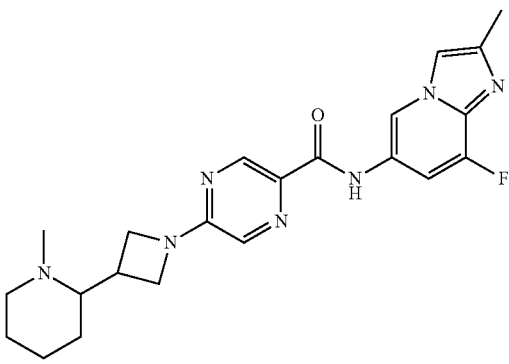
Enantiomer 1 |
| 233 | 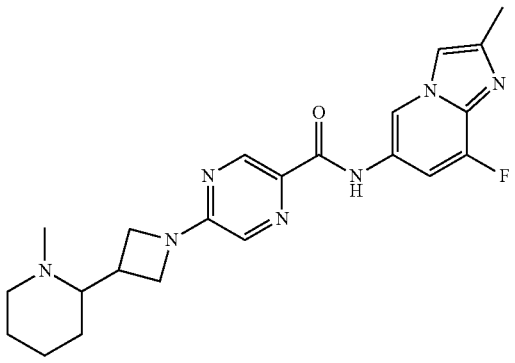
Enantiomer 2 |
| 234 | 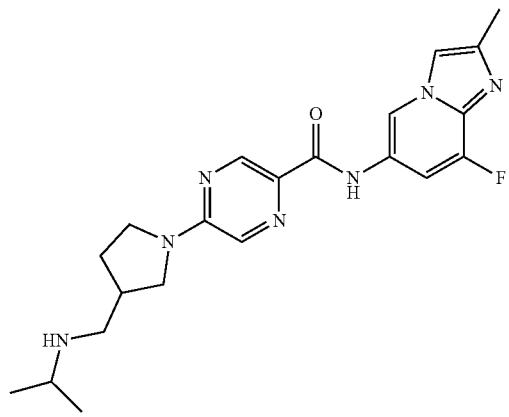 [SMILES: Cc1cn2cc(NC(=O)c3cnc(N4CCC(CNC(C)C)C4)cn3)cc(F)c2n1] |

TABLE 1-continued
| Ex. | Structure |
| --- | --- |
| 235 | 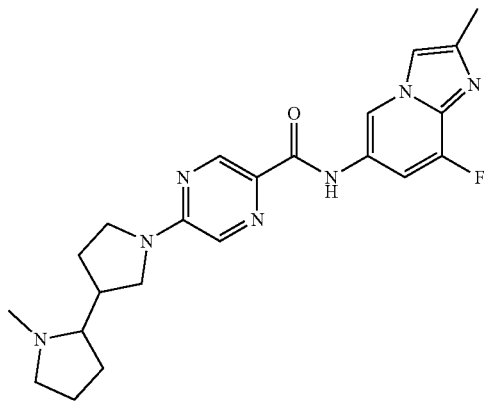<br>Stereoisomer 1 |
| 236 | 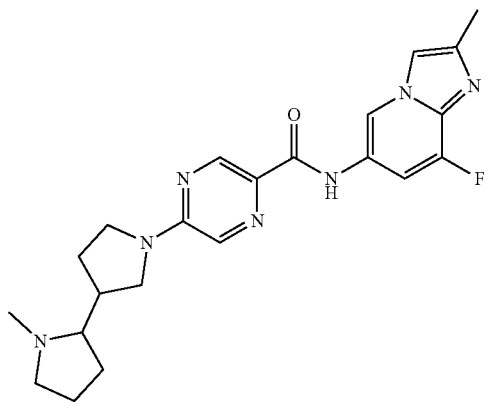<br>Stereoisomer 2 |
| 237 | 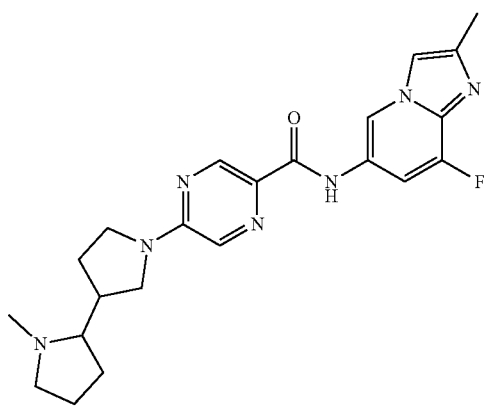<br>Stereoisomer 3 |

TABLE 1-continued
| Ex. | Structure |
|---|---|
| 238 | 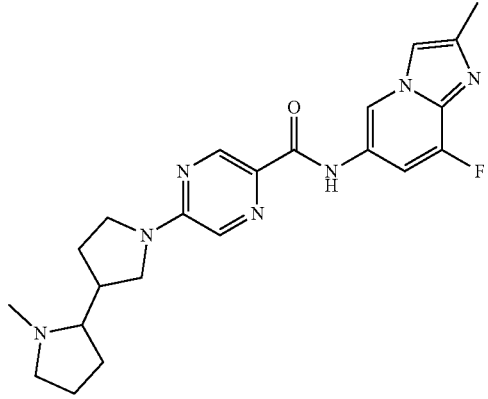<br>Stereoisomer 4 |
| 239 | 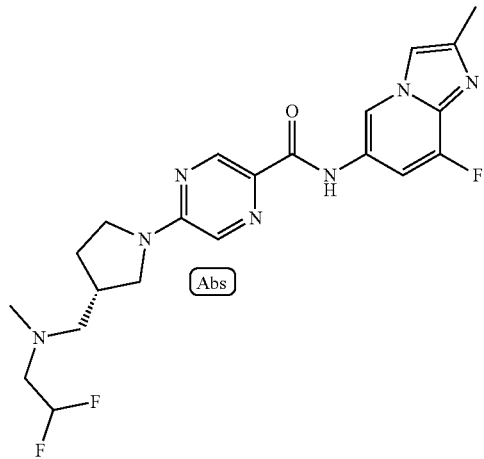 [SMILES: Cc1cn2cc(NC(=O)c3cnc(N4CC[C@@H](CN(C)CC(F)F)C4)cn3)cc(F)c2n1] |
| 240 | 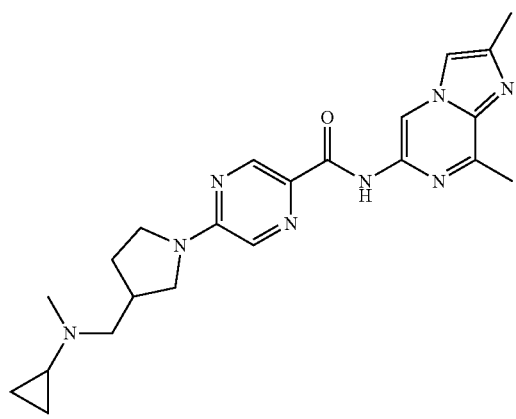<br>Enantiomer 1 |

161
TABLE 1-continued
| Ex. | Structure |
|---|---|
| 241 | 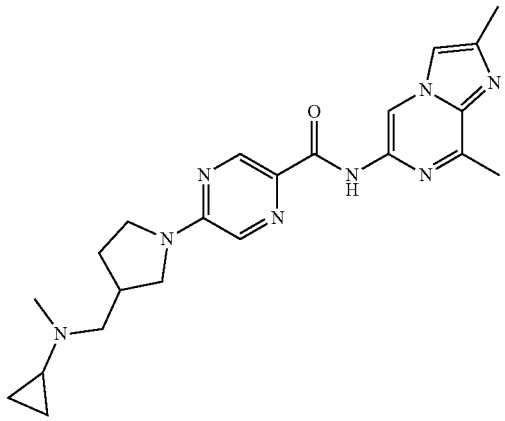
Enantiomer 2 |
| 242 | 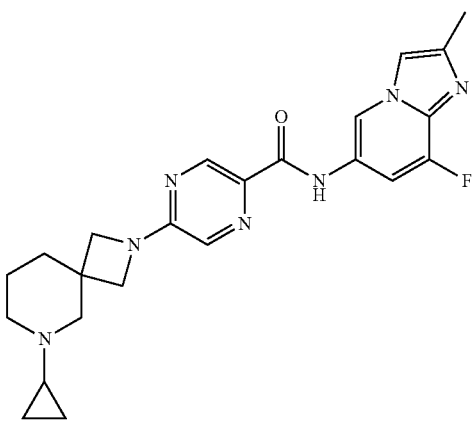 [SMILES: Cc1cn2cc(NC(=O)c3cnc(N4CC5(CCCN(C6CC6)C5)C4)cn3)cc(F)c2n1] |
| 243 | 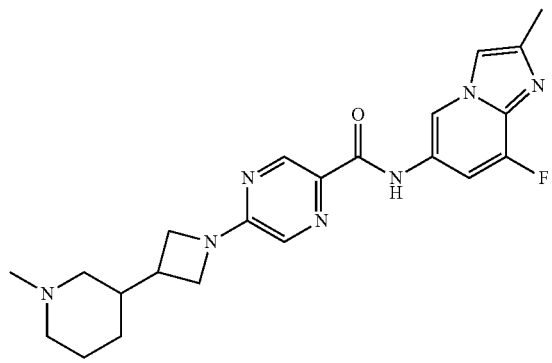
Enantiomer 1 + Enantiomer 2 |

TABLE 1-continued
| Ex. | Structure |
|---|---|
| 244 | 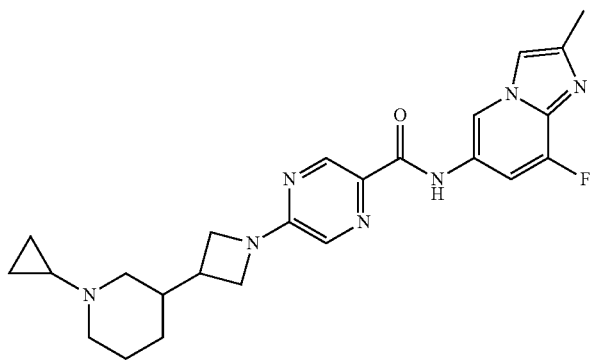<br>Enantiomer 1 + Enantiomer 2 |
| 245 | 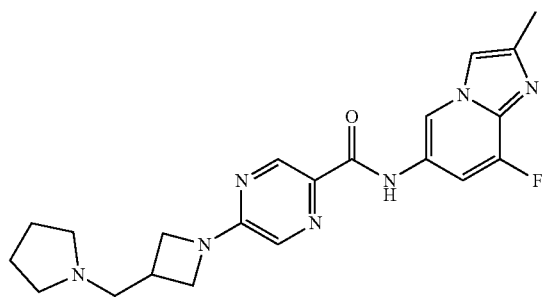 [SMILES: Cc1cn2cc(NC(=O)c3cnc(N4CC(CN5CCCC5)C4)cn3)cc(F)c2n1] |
| 246 | 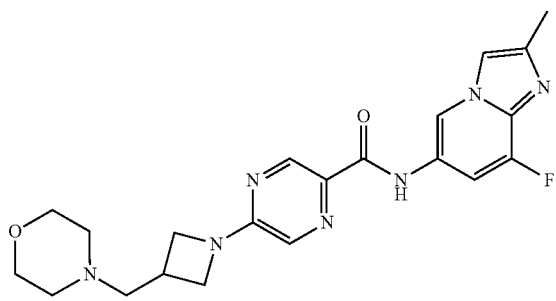 [SMILES: Cc1cn2cc(NC(=O)c3cnc(N4CC(CN5CCOCC5)C4)cn3)cc(F)c2n1] |
| 247 | 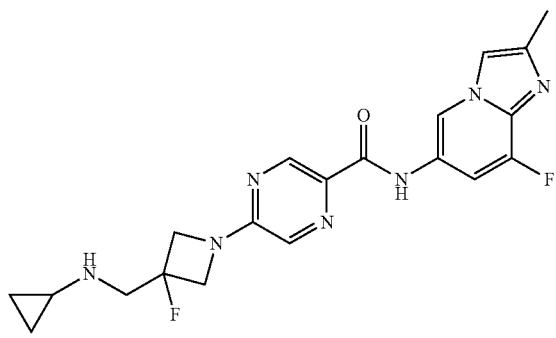 [SMILES: Cc1cn2cc(NC(=O)c3cnc(N4CC(F)(CNC5CC5)C4)cn3)cc(F)c2n1] |

TABLE 1-continued
| Ex. | Structure |
|---|---|
| 248 | 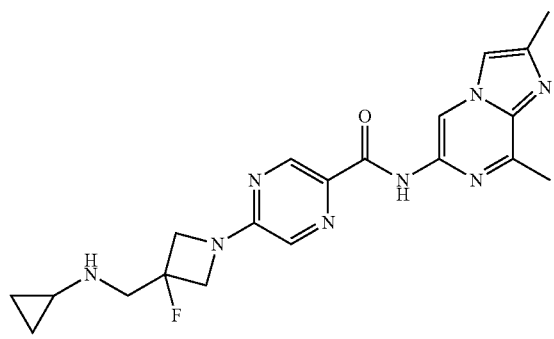 [SMILES: Cc1cn2cc(NC(=O)c3cnc(N4CC(F)(CNC5CC5)C4)cn3)nc(C)c2n1] |
| 249 | 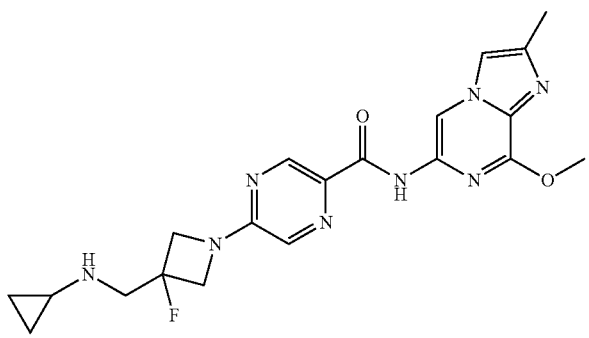 [SMILES: COc1nc(NC(=O)c2cnc(N3CC(F)(CNC4CC4)C3)cn2)cn2cc(C)nc12] |
| 250 | 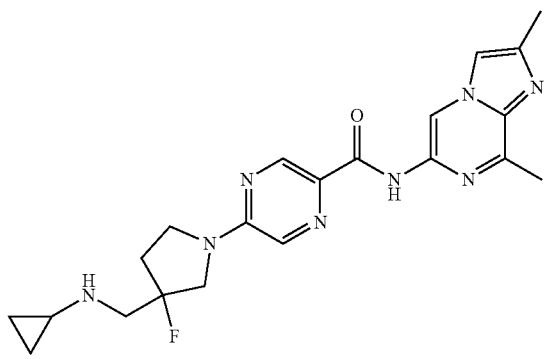
Enantiomer 1 + Enantiomer 2 |
| 251 | 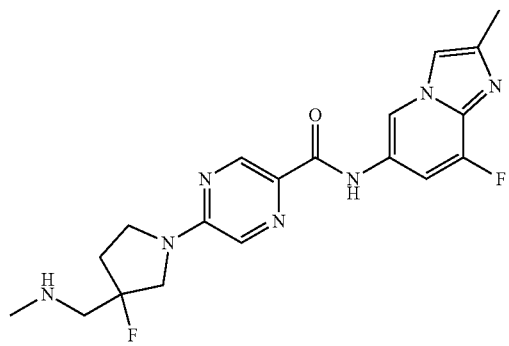
Enantiomer 1 + Enantiomer 2 |

US 11,806,346 B2
TABLE 1-continued
| Ex. | Structure |
|---|---|
| 252 | 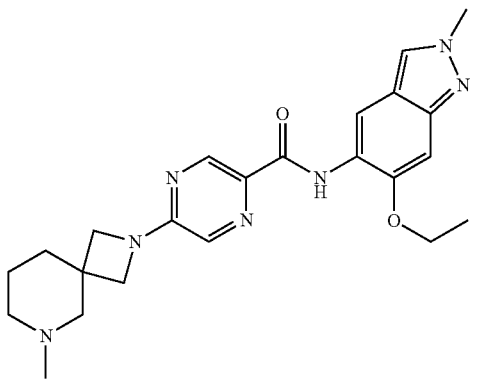 [SMILES: CCOc1cc2nn(C)cc2cc1NC(=O)c1cnc(N2CC3(CCCN(C)C3)C2)cn1] |
| 253 | 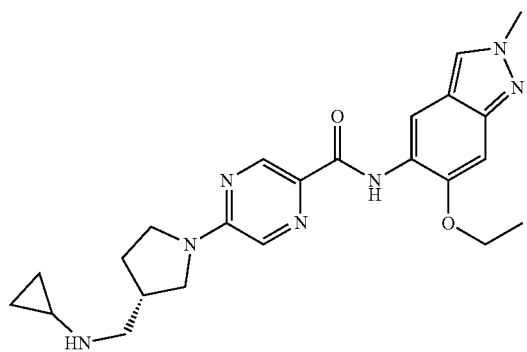 [SMILES: CCOc1cc2nn(C)cc2cc1NC(=O)c1cnc(N2CC[C@@H](CNC3CC3)C2)cn1] |
| 254 | 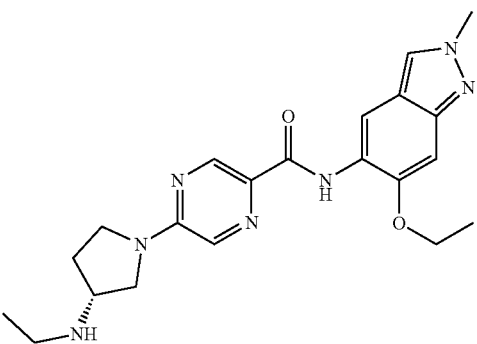 [SMILES: CCN[C@@H]1CCN(c2cnc(C(=O)Nc3cc4cn(C)nc4cc3OCC)cn2)C1] |
| 255 | 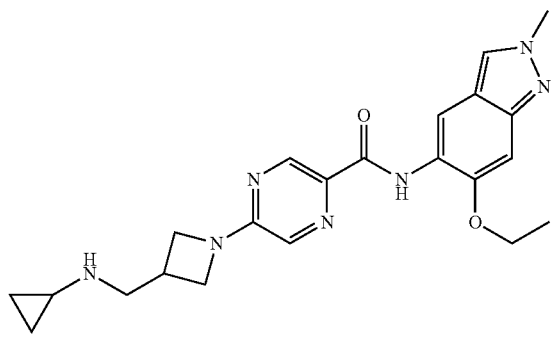 [SMILES: CCOc1cc2nn(C)cc2cc1NC(=O)c1cnc(N2CC(CNC3CC3)C2)cn1] |

TABLE 1-continued
| Ex. | Structure |
|---|---|
| 256 | 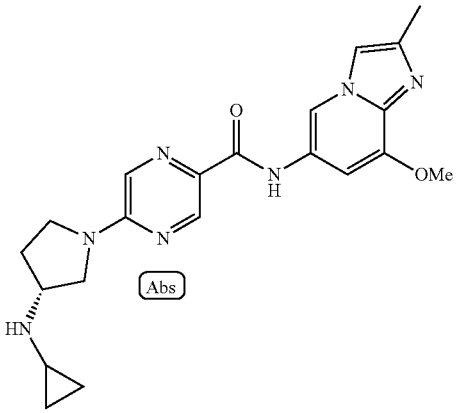 [SMILES: COc1cc(NC(=O)c2cnc(N3CC[C@@H](NC4CC4)C3)cn2)cn2cc(C)nc12] |
| 257 | 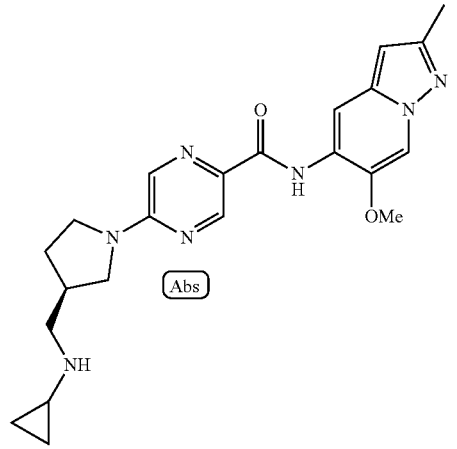 [SMILES: COc1cn2nc(C)cc2cc1NC(=O)c1cnc(N2CC[C@H](CNC3CC3)C2)cn1] |
| 258 | 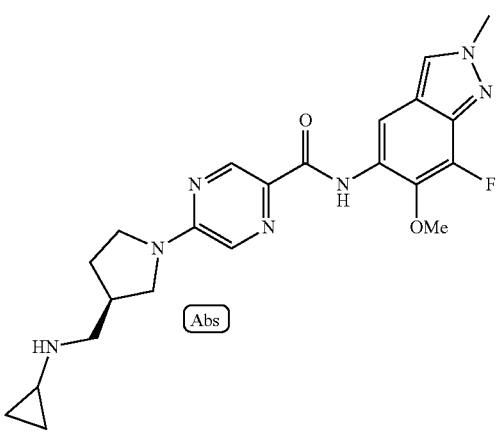 [SMILES: COc1c(NC(=O)c2cnc(N3CC[C@H](CNC4CC4)C3)cn2)cc2cn(C)nc2c1F] |

TABLE 1-continued
| Ex. | Structure |
|---|---|
| 259 | 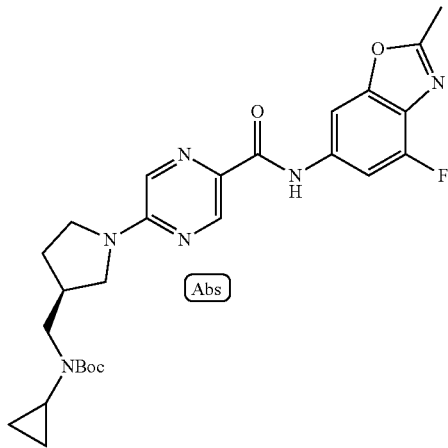 [SMILES: Cc1nc2c(F)cc(NC(=O)c3cnc(N4CC[C@H](CN(C(=O)OC(C)(C)C)C5CC5)C4)cn3)cc2o1] |
| 260 | 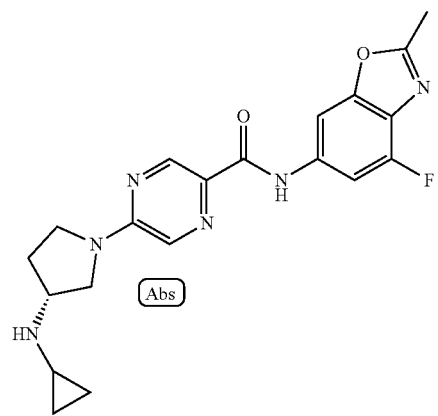 [SMILES: Cc1nc2c(F)cc(NC(=O)c3cnc(N4CC[C@@H](NC5CC5)C4)cn3)cc2o1] |
| 261 | 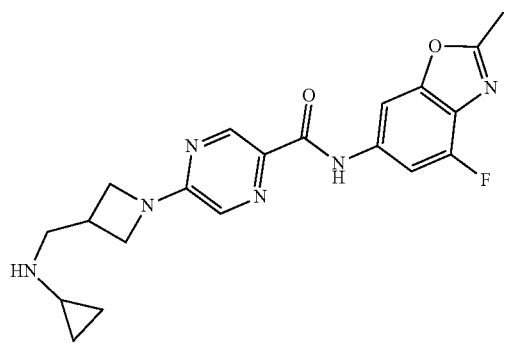 [SMILES: Cc1nc2c(F)cc(NC(=O)c3cnc(N4CC(CNC5CC5)C4)cn3)cc2o1] |

TABLE 1-continued
| Ex. | Structure |
|---|---|
| 262 | 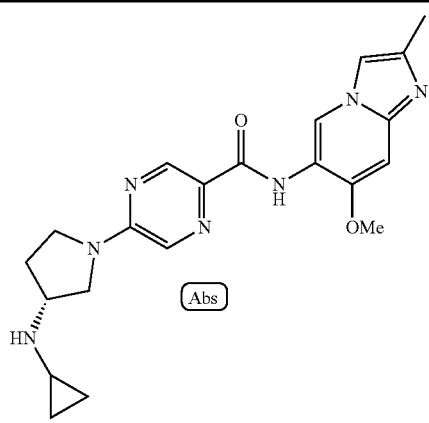 |
| 263 | 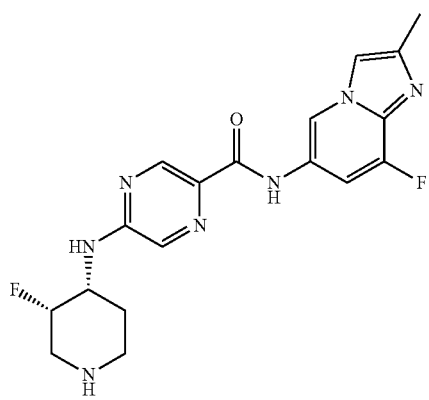 [SMILES: Cc1cn2cc(NC(=O)c3cnc(N[C@@H]4CCNC[C@@H]4F)cn3)cc(F)c2n1] |
| 264 | 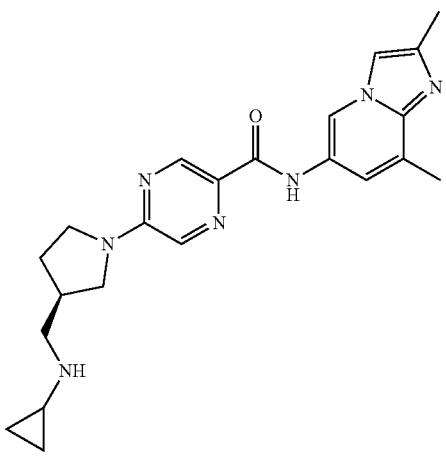 [SMILES: Cc1cn2cc(NC(=O)c3cnc(N4CC[C@H](CNC5CC5)C4)cn3)cc(C)c2n1] |
| 265 | 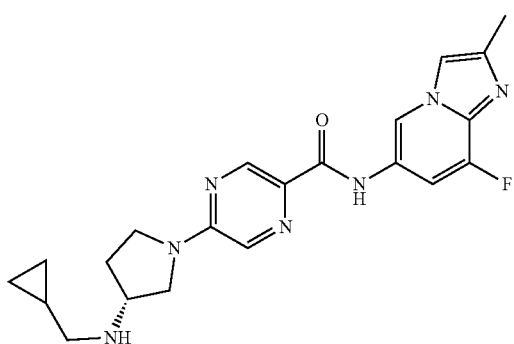 [SMILES: Cc1cn2cc(NC(=O)c3cnc(N4CC[C@@H](NCC5CC5)C4)cn3)cc(F)c2n1] |

TABLE 1-continued
| Ex. | Structure |
|---|---|
| 266 | 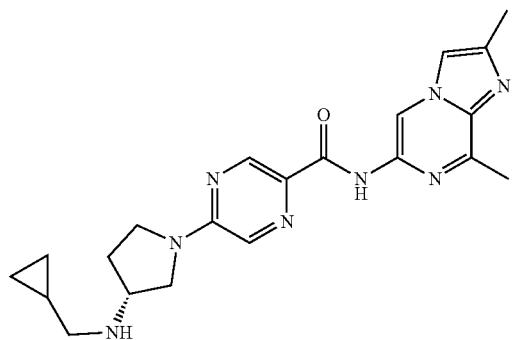 [SMILES: Cc1cn2cc(NC(=O)c3cnc(N4CC[C@@H](NCC5CC5)C4)cn3)nc(C)c2n1] |
| 267 | 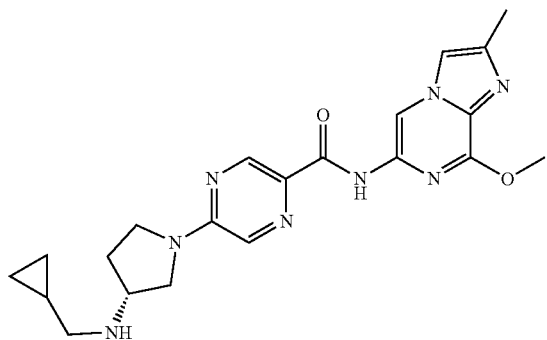 [SMILES: COc1nc(NC(=O)c2cnc(N3CC[C@@H](NCC4CC4)C3)cn2)cn2cc(C)nc12] |
| 268 | 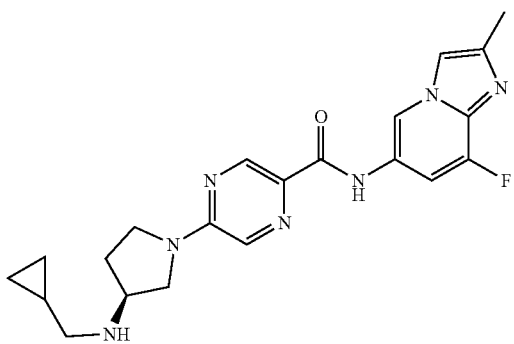 [SMILES: Cc1cn2cc(NC(=O)c3cnc(N4CC[C@H](NCC5CC5)C4)cn3)cc(F)c2n1] |
| 269 | 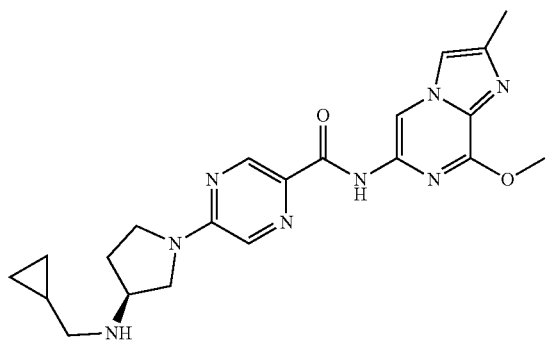 [SMILES: COc1nc(NC(=O)c2cnc(N3CC[C@H](NCC4CC4)C3)cn2)cn2cc(C)nc12] |

TABLE 1-continued

| Ex. | Structure |
|---|---|
| 270 | 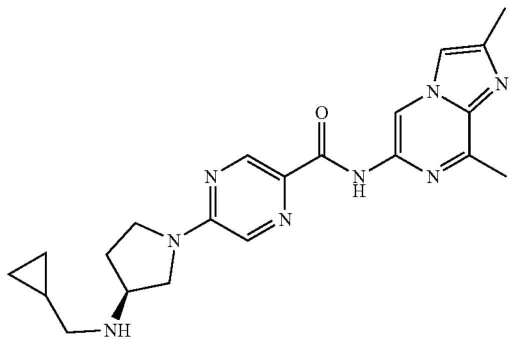 [SMILES: Cc1cn2cc(NC(=O)c3cnc(N4CC[C@H](NCC5CC5)C4)cn3)nc(C)c2n1] |
| 271 | 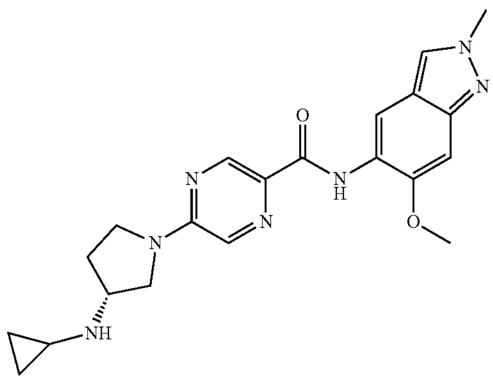 [SMILES: COc1cc2nn(C)cc2cc1NC(=O)c1cnc(N2CC[C@@H](NC3CC3)C2)cn1] |
| 272 | 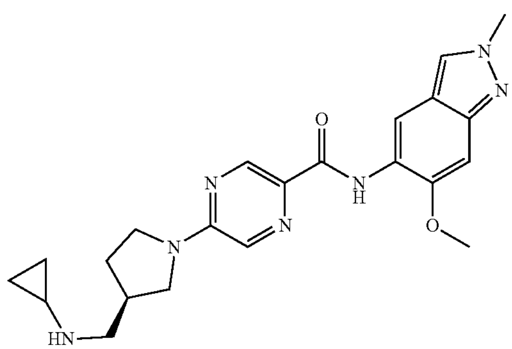 [SMILES: COc1cc2nn(C)cc2cc1NC(=O)c1cnc(N2CC[C@H](CNC3CC3)C2)cn1] |
| 273 | 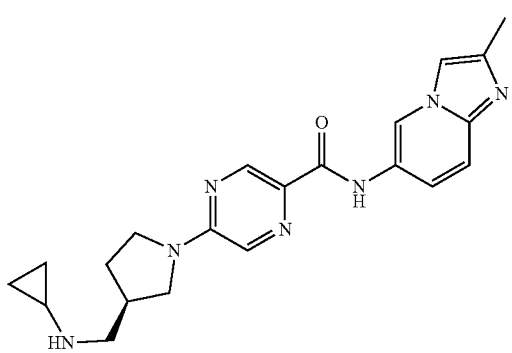 [SMILES: Cc1cn2cc(NC(=O)c3cnc(N4CC[C@H](CNC5CC5)C4)cn3)ccc2n1] |

TABLE 1-continued
| Ex. | Structure |
|---|---|
| 274 | 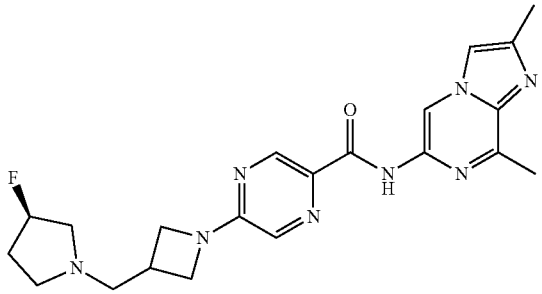 [SMILES: Cc1cn2cc(NC(=O)c3cnc(N4CC(CN5CC[C@@H](F)C5)C4)cn3)nc(C)c2n1] |
| 275 | 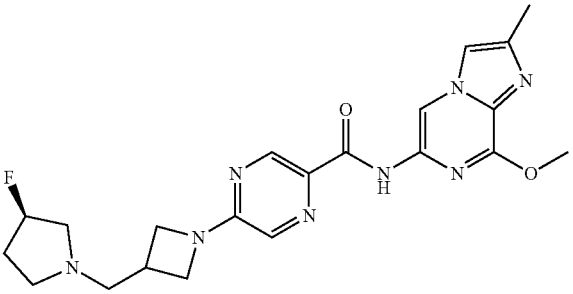 [SMILES: COc1nc(NC(=O)c2cnc(N3CC(CN4CC[C@@H](F)C4)C3)cn2)cn2cc(C)nc12] |
| 276 | 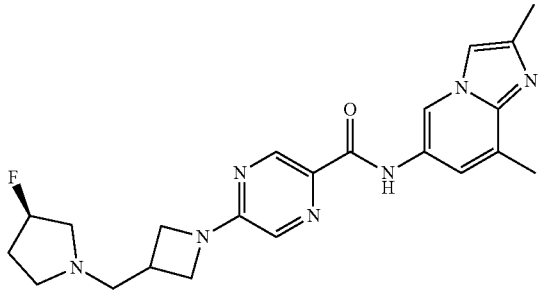 [SMILES: Cc1cn2cc(NC(=O)c3cnc(N4CC(CN5CC[C@@H](F)C5)C4)cn3)cc(C)c2n1] |
| 277 | 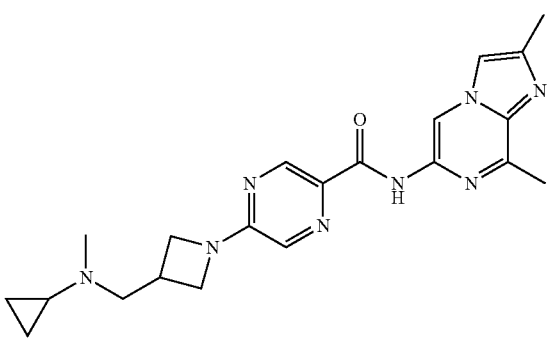 [SMILES: Cc1cn2cc(NC(=O)c3cnc(N4CC(CN(C)C5CC5)C4)cn3)nc(C)c2n1] |
| 278 | 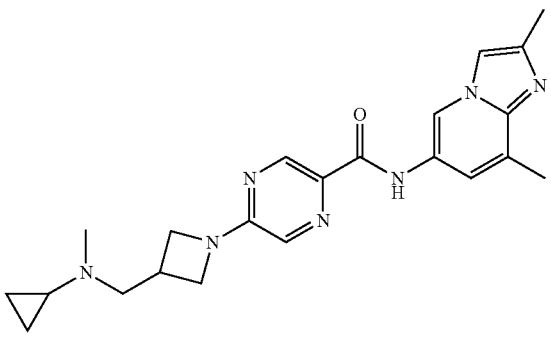 [SMILES: Cc1cn2cc(NC(=O)c3cnc(N4CC(CN(C)C5CC5)C4)cn3)cc(C)c2n1] |

TABLE 1-continued
| Ex. | Structure |
|---|---|
| 279 | 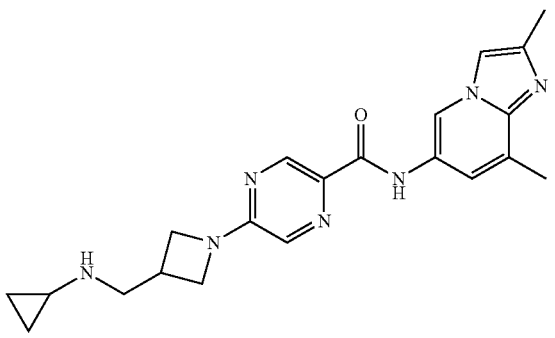 |
| 280 | 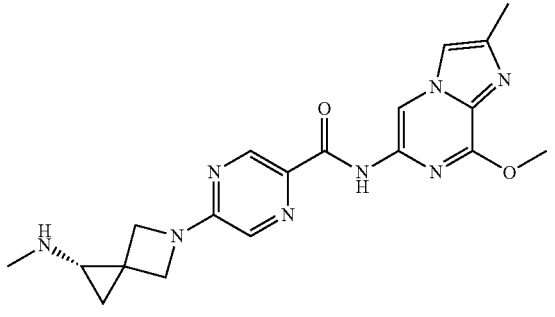 |
| 281 | 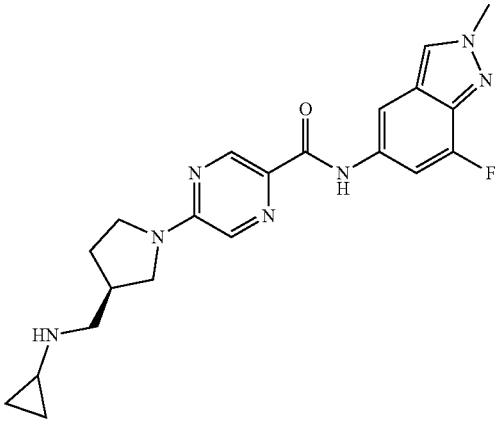 [SMILES: Cn1cc2cc(NC(=O)c3cnc(N4CC[C@H](CNC5CC5)C4)cn3)cc(F)c2n1] |
| 282 | 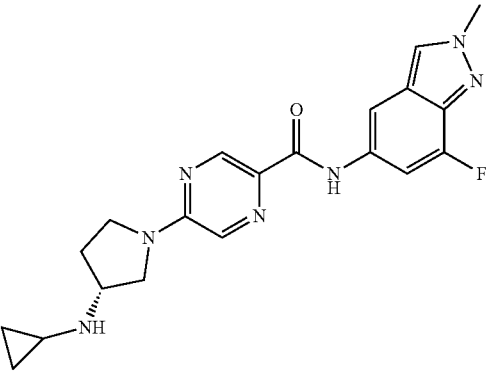 [SMILES: Cn1cc2cc(NC(=O)c3cnc(N4CC[C@@H](NC5CC5)C4)cn3)cc(F)c2n1] |

TABLE 1-continued
| Ex. | Structure |
|---|---|
| 283 | 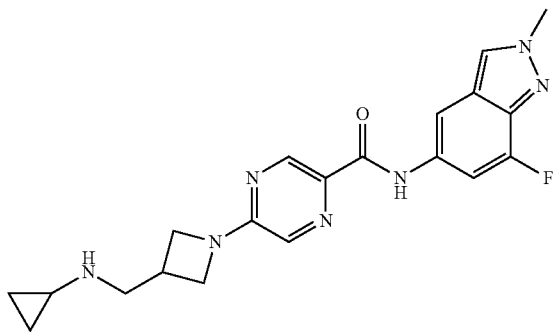 [SMILES: Cn1cc2cc(NC(=O)c3cnc(N4CC(CNC5CC5)C4)cn3)cc(F)c2n1] |
| 284 | 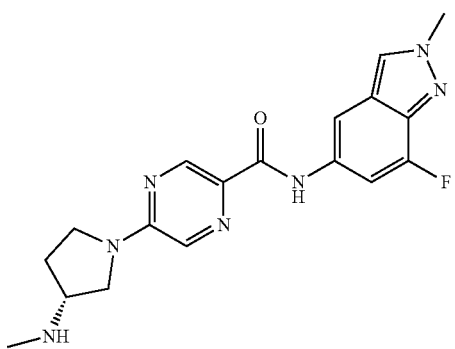 [SMILES: CN[C@@H]1CCN(c2cnc(C(=O)Nc3cc(F)c4nn(C)cc4c3)cn2)C1] |
| 285 | 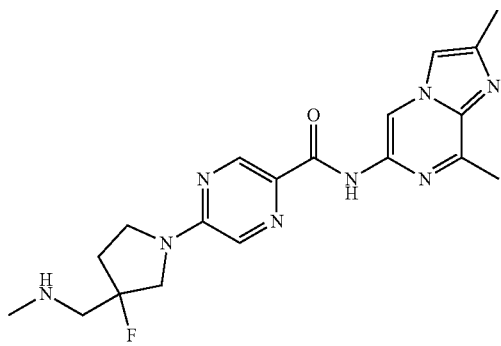
Enantiomer 1 + Enantiomer 2 |
| 286 | 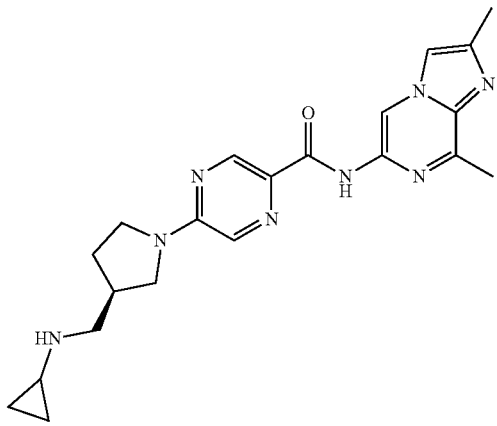 [SMILES: Cc1cn2cc(NC(=O)c3cnc(N4CC[C@H](CNC5CC5)C4)cn3)nc(C)c2n1] |

TABLE 1-continued
| Ex. | Structure |
|---|---|
| 287 | 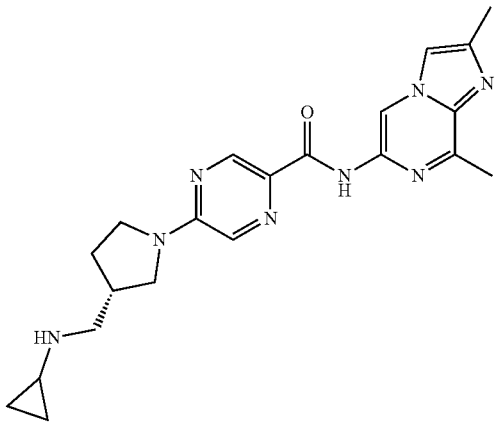 [SMILES: Cc1cn2cc(NC(=O)c3cnc(N4CC[C@@H](CNC5CC5)C4)cn3)nc(C)c2n1] |
| 288 | 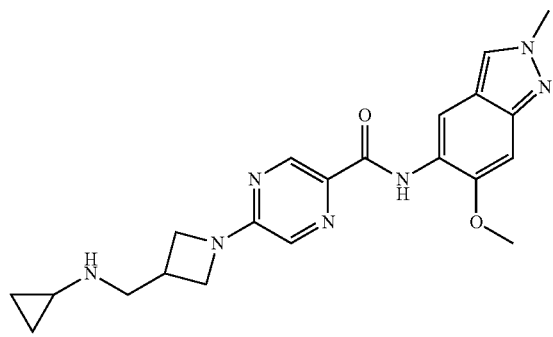 [SMILES: COc1cc2nn(C)cc2cc1NC(=O)c1cnc(N2CC(CNC3CC3)C2)cn1] |
| 289 | 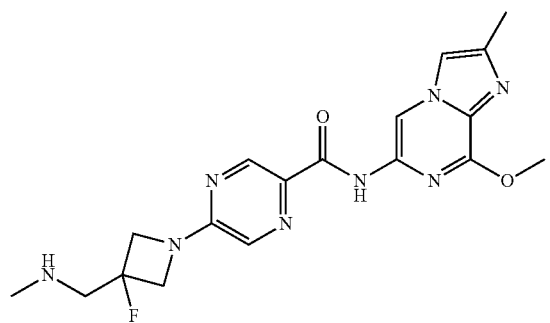 |
| 290 | 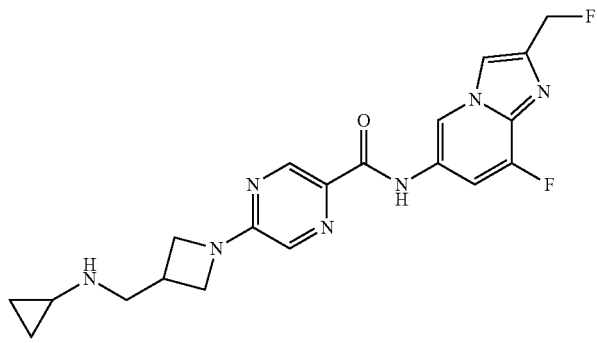 [SMILES: O=C(Nc1cc(F)c2nc(CF)cn2c1)c1cnc(N2CC(CNC3CC3)C2)cn1] |

TABLE 1-continued
| Ex. | Structure |
|---|---|
| 291 | 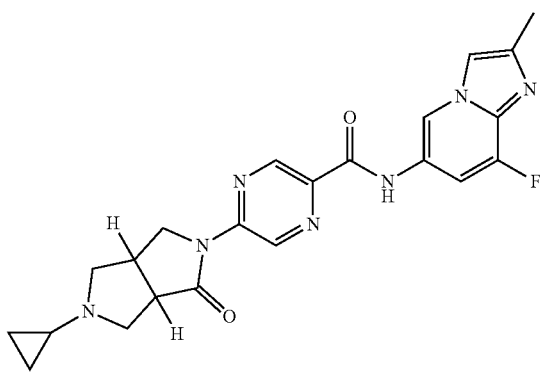<br>Cis Isomer, Enantiomer 1 |
| 292 | 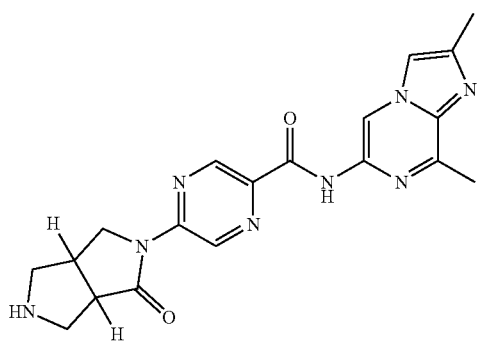<br>Cis Isomer, Enantiomer 1 |
| 293 | 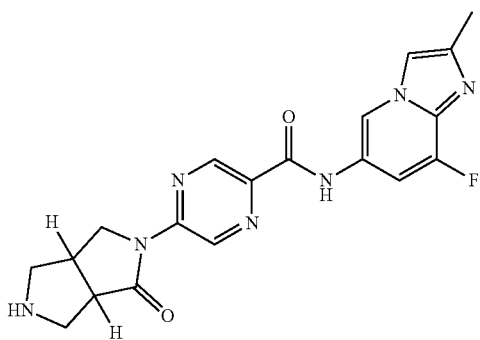<br>Cis Isomer, Enantiomer 1 |
| 294 | 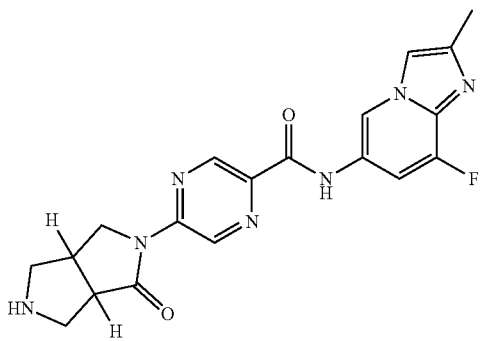<br>Cis Isomer, Enantiomer 2 |

TABLE 1-continued
| Ex. | Structure |
|---|---|
| 295 | 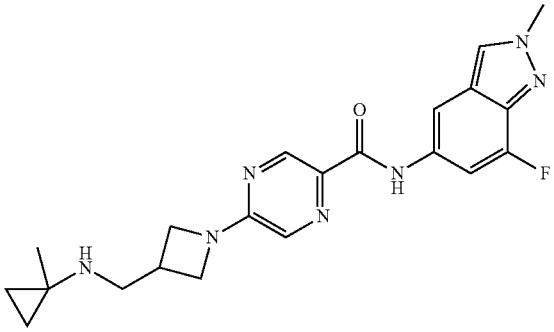 [SMILES: Cn1cc2cc(NC(=O)c3cnc(N4CC(CNC5(C)CC5)C4)cn3)cc(F)c2n1] |
| 296 | 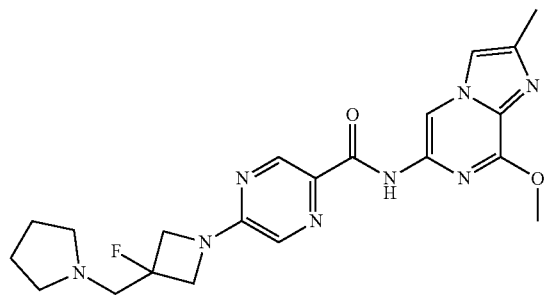 [SMILES: COc1nc(NC(=O)c2cnc(N3CC(F)(CN4CCCC4)C3)cn2)cn2cc(C)nc12] |
| 297 | 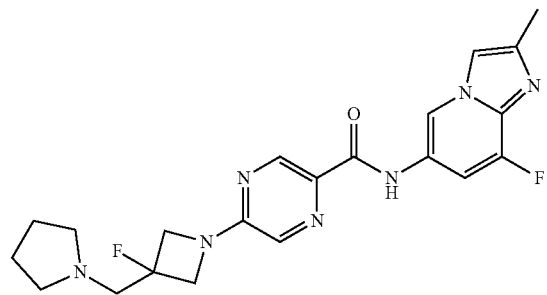 [SMILES: Cc1cn2cc(NC(=O)c3cnc(N4CC(F)(CN5CCCC5)C4)cn3)cc(F)c2n1] |
| 298 | 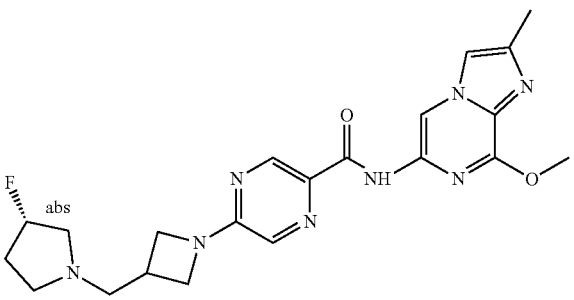 [SMILES: COc1nc(NC(=O)c2cnc(N3CC(CN4CC[C@H](F)C4)C3)cn2)cn2cc(C)nc12] |
| 299 | 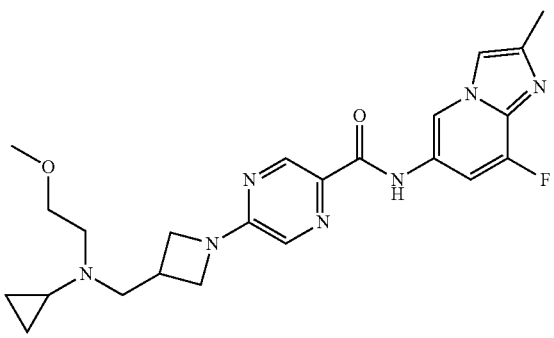 [SMILES: COCCN(CC1CN(c2cnc(C(=O)Nc3cc(F)c4nc(C)cn4c3)cn2)C1)C1CC1] |

TABLE 1-continued
| Ex. | Structure |
|---|---|
| 300 | 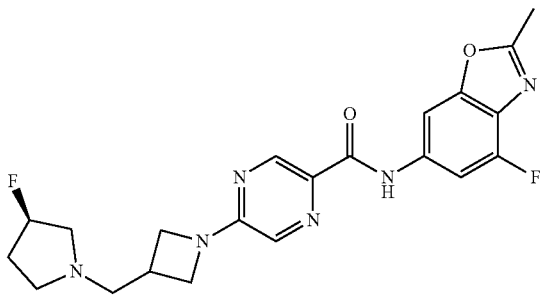 [SMILES: Cc1nc2c(F)cc(NC(=O)c3cnc(N4CC(CN5CC[C@@H](F)C5)C4)cn3)cc2o1] |
| 301 | 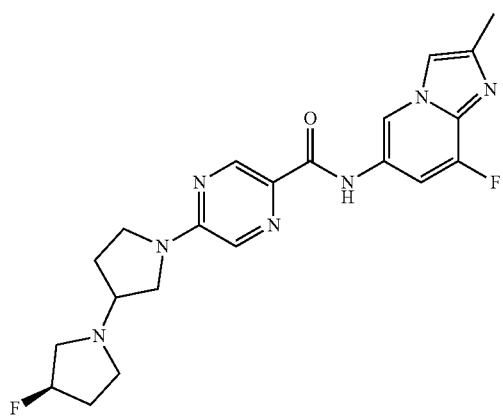
Diastereoisomer 1 |
| 302 | 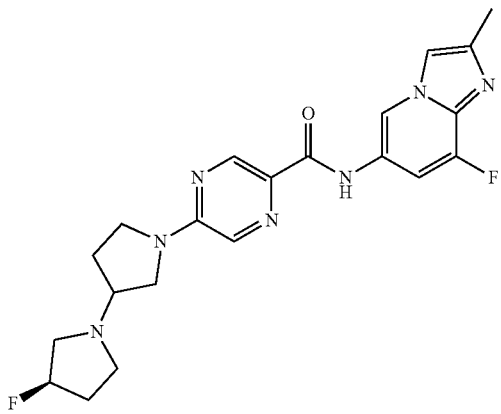
Diastereoisomer 2 |
| 303 | 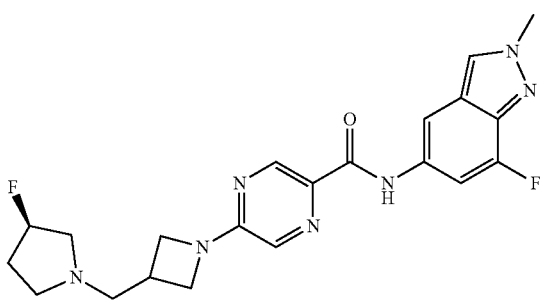 [SMILES: Cn1cc2cc(NC(=O)c3cnc(N4CC(CN5CC[C@@H](F)C5)C4)cn3)cc(F)c2n1] |

TABLE 1-continued

| Ex. | Structure |
|---|---|
| 304 | 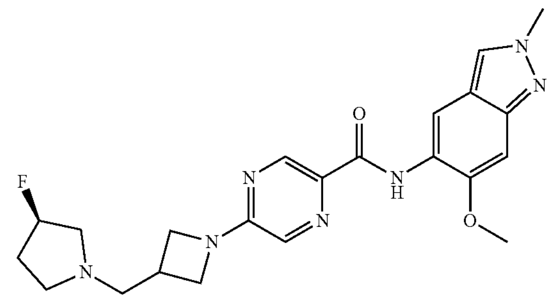 [SMILES: COc1cc2nn(C)cc2cc1NC(=O)c1cnc(N2CC(CN3CC[C@@H](F)C3)C2)cn1] |
| 305 | 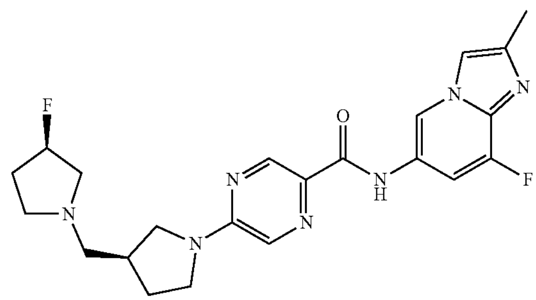 [SMILES: Cc1cn2cc(NC(=O)c3cnc(N4CC[C@@H](CN5CC[C@@H](F)C5)C4)cn3)cc(F)c2n1] |
| 306 | 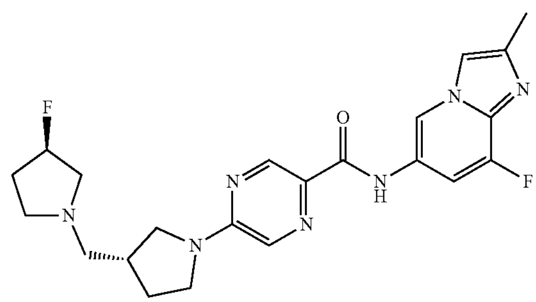 [SMILES: Cc1cn2cc(NC(=O)c3cnc(N4CC[C@H](CN5CC[C@@H](F)C5)C4)cn3)cc(F)c2n1] |
| 307 | 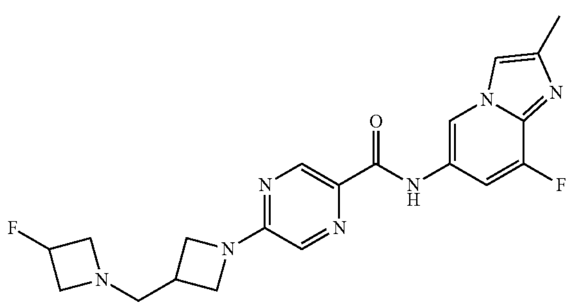 [SMILES: Cc1cn2cc(NC(=O)c3cnc(N4CC(CN5CC(F)C5)C4)cn3)cc(F)c2n1] |
| 308 | Enantiomer 1 + Enantiomer 2 |

TABLE 1-continued
| Ex. | Structure |
|---|---|
| 309 | 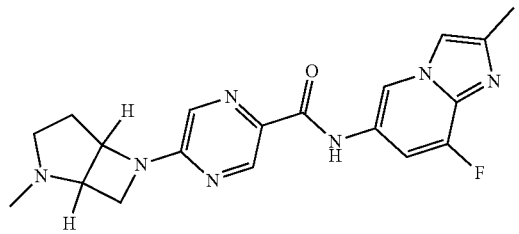 Enantiomer 1 |
| 310 | 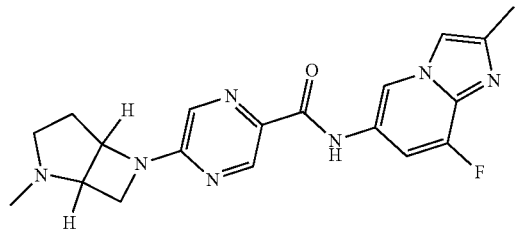 Enantiomer 2 |
| 311 | 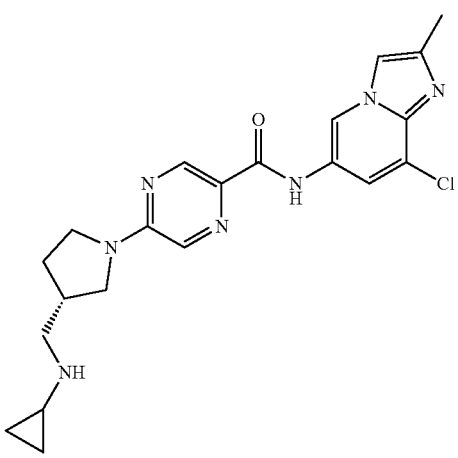 [SMILES: Cc1cn2cc(NC(=O)c3cnc(N4CC[C@@H](CNC5CC5)C4)cn3)cc(Cl)c2n1] |
| 312 | 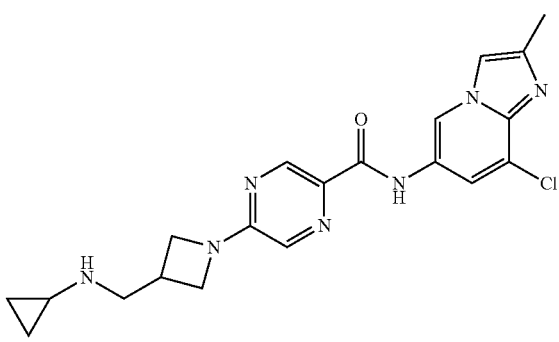 [SMILES: Cc1cn2cc(NC(=O)c3cnc(N4CC(CNC5CC5)C4)cn3)cc(Cl)c2n1] |

TABLE 1-continued

| Ex. | Structure |
|---|---|
| 313 | 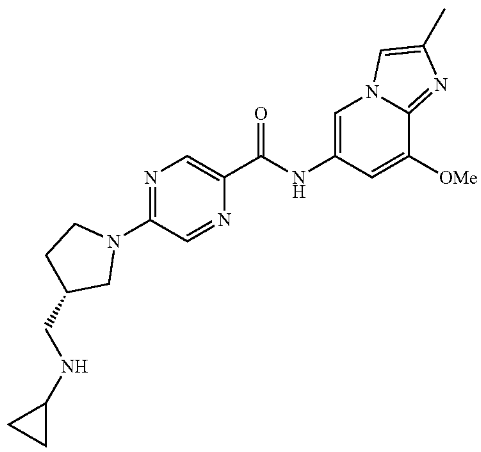 [SMILES: COc1cc(NC(=O)c2cnc(N3CC[C@@H](CNC4CC4)C3)cn2)cn2cc(C)nc12] |
| 314 | 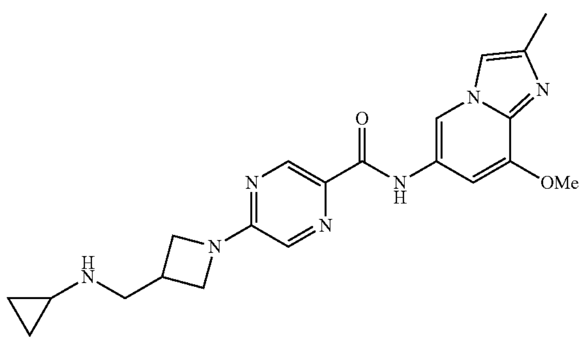 [SMILES: COc1cc(NC(=O)c2cnc(N3CC(CNC4CC4)C3)cn2)cn2cc(C)nc12] |
| 315 | 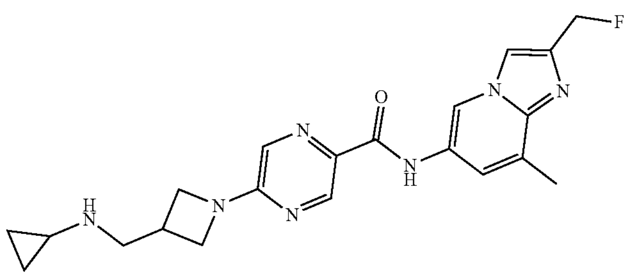 [SMILES: Cc1cc(NC(=O)c2cnc(N3CC(CNC4CC4)C3)cn2)cn2cc(CF)nc12] |
| 316 | Enantiomer 1 + Enantiomer 2 |

TABLE 1-continued
| Ex. | Structure |
|---|---|
| 317 | 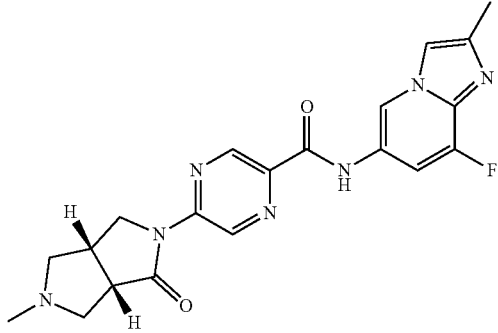 [SMILES: Cc1cn2cc(NC(=O)c3cnc(N4C[C@H]5CN(C)C[C@H]5C4=O)cn3)cc(F)c2n1] |
| 318 | 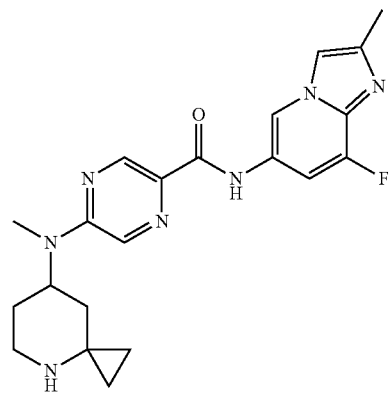
Enantiomer 1 |
| 319 | 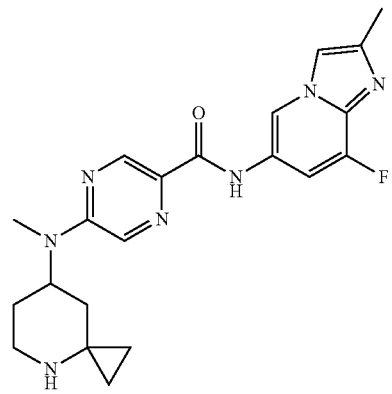
Enantiomer 2 |
| 320 | 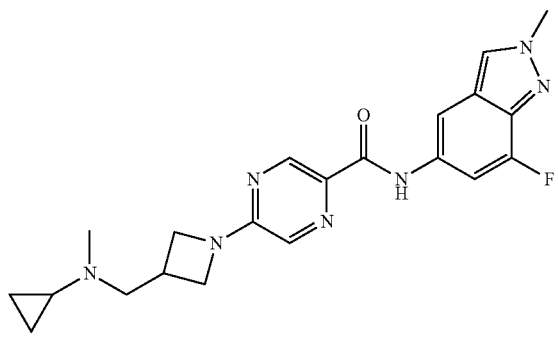 [SMILES: CN(CC1CN(c2cnc(C(=O)Nc3cc(F)c4nn(C)cc4c3)cn2)C1)C1CC1] |

TABLE 1-continued
| Ex. | Structure |
|---|---|
| 321 | 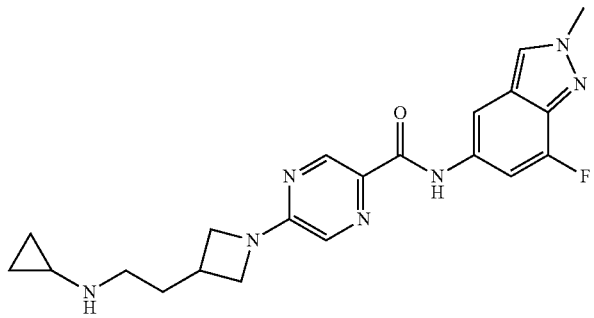 [SMILES: Cn1cc2cc(NC(=O)c3cnc(N4CC(CCNC5CC5)C4)cn3)cc(F)c2n1] |
| 322 | 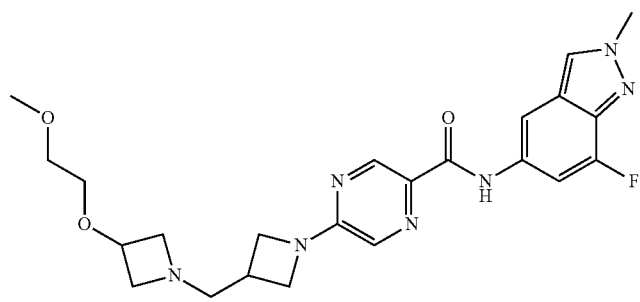 [SMILES: COCCOC1CN(CC2CN(c3cnc(C(=O)Nc4cc(F)c5nn(C)cc5c4)cn3)C2)C1] |
| 323 | 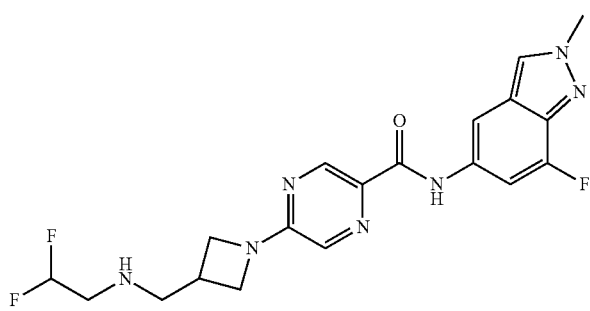 [SMILES: Cn1cc2cc(NC(=O)c3cnc(N4CC(CNCC(F)F)C4)cn3)cc(F)c2n1] |
| 324 | 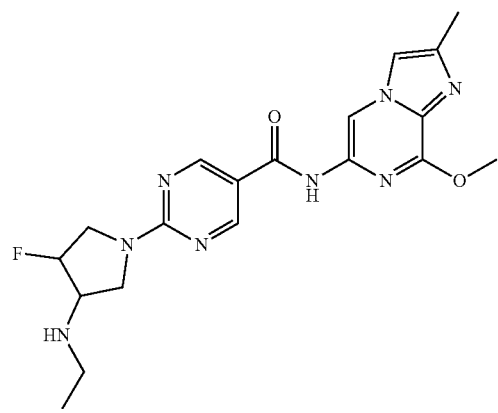<br>Cis Isomer<br>Enantiomer 1 |

TABLE 1-continued
| Ex. | Structure |
|-----|-----------|
| 325 | 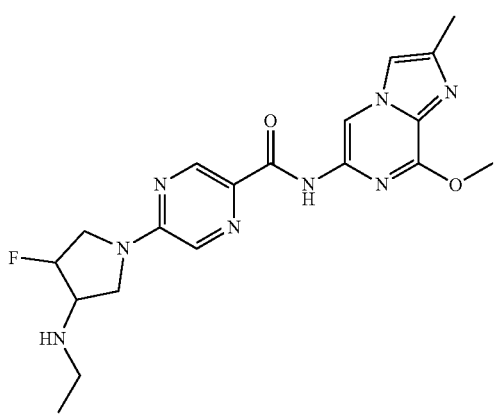
Cis Isomer
Enantiomer 2 |
| 326 | 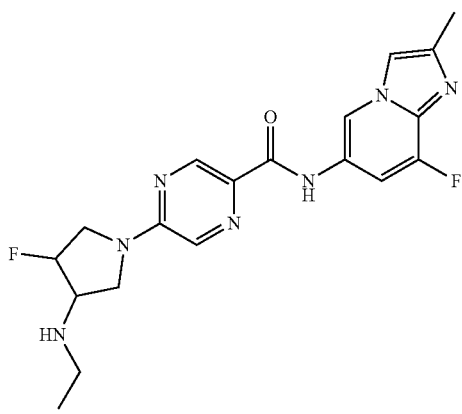
Cis Isomer, Enantiomer 1 |
| 327 | 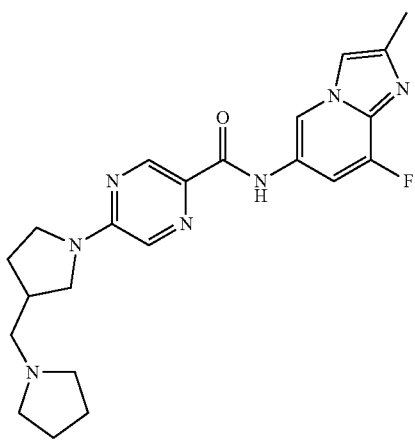 [SMILES: Cc1cn2cc(NC(=O)c3cnc(N4CCC(CN5CCCC5)C4)cn3)cc(F)c2n1] |

TABLE 1-continued
| Ex. | Structure |
|---|---|
| 328 | 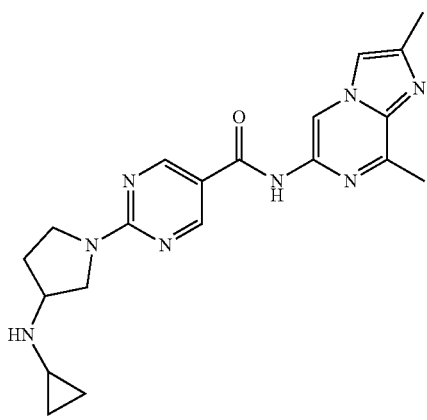<br>Enantiomer 1 |
| 329 | 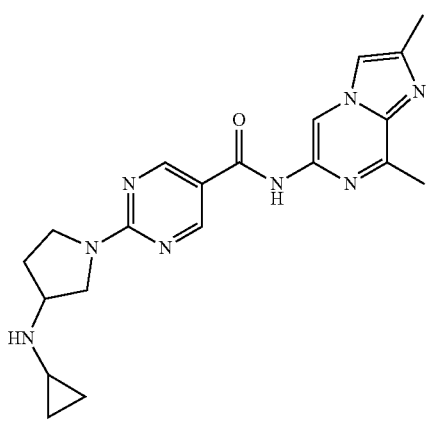<br>Enantiomer 2 |
| 330 | 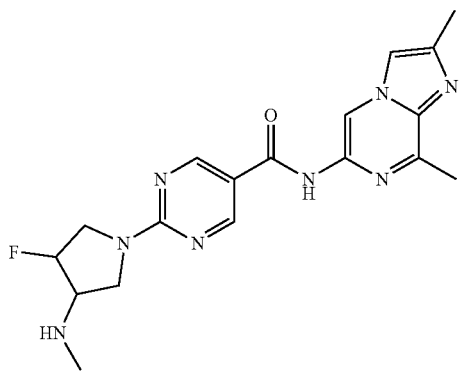<br>Cis Isomer, Enantiomer 1 |

TABLE 1-continued
| Ex. | Structure |
|---|---|
| 331 | 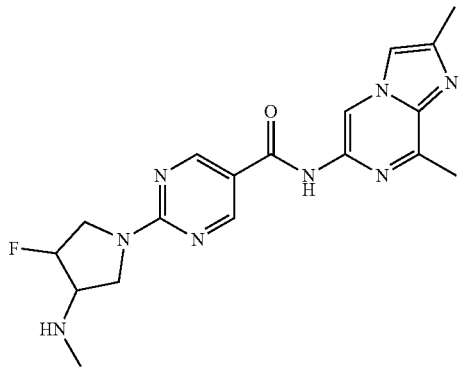<br>Cis Isomer, Enantiomer 2 |
| 332 | 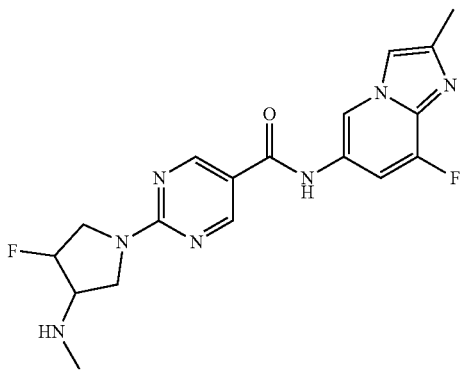<br>Cis Isomer, Enantiomer 1 |
| 333 | 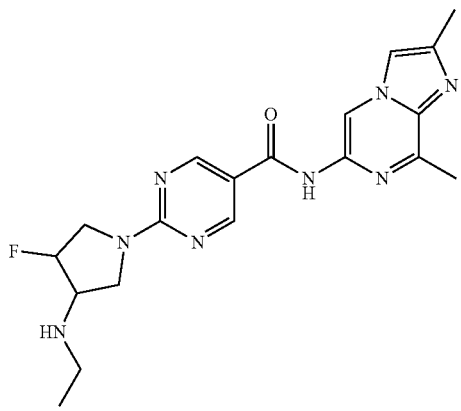<br>Cis Isomer, Enantiomer 1 |

TABLE 1-continued
| Ex. | Structure |
|---|---|
| 334 | 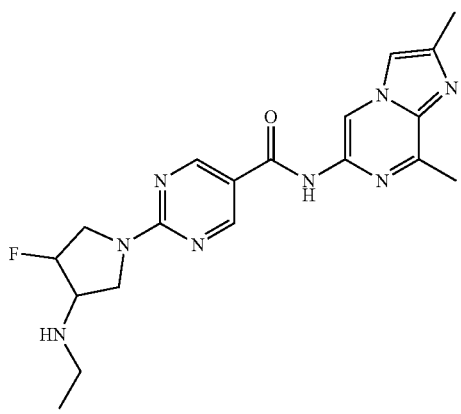<br>Cis Isomer, Enantiomer 2 |
| 335 | 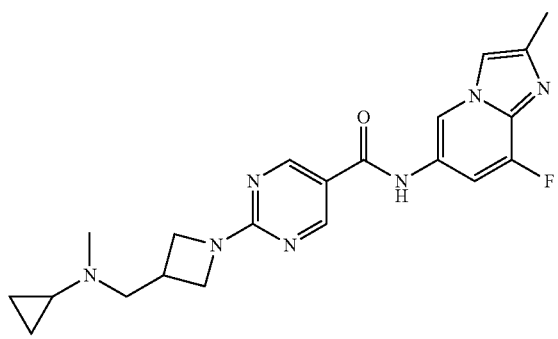 [SMILES: Cc1cn2cc(NC(=O)c3cnc(N4CC(CN(C)C5CC5)C4)nc3)cc(F)c2n1] |
| 336 | 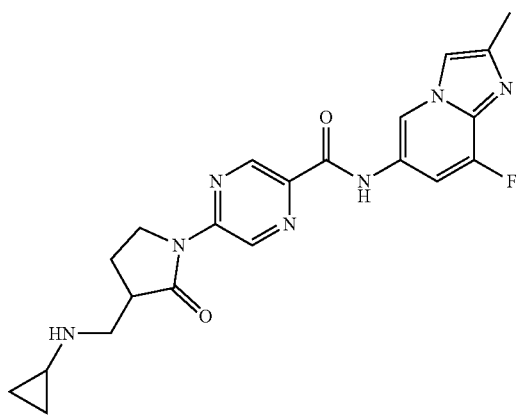<br>Enantiomer 1 |

TABLE 1-continued
| Ex. | Structure |
|---|---|
| 337 | 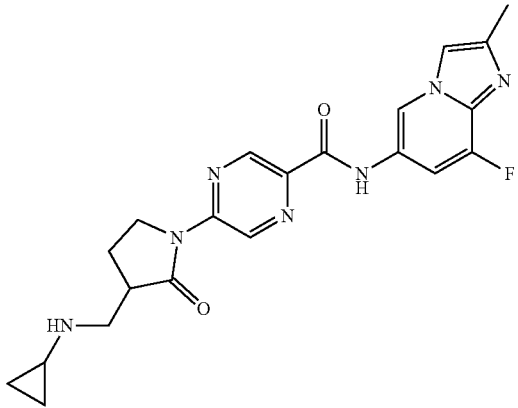
Enantiomer 2 |
| 338 | 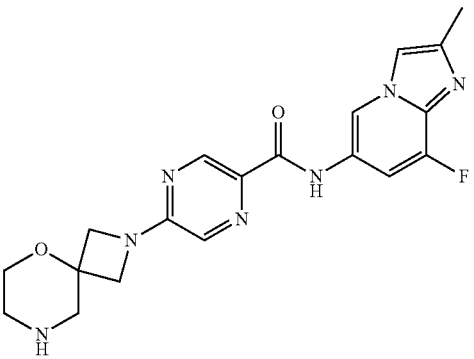 [SMILES: Cc1cn2cc(NC(=O)c3cnc(N4CC5(CNCCO5)C4)cn3)cc(F)c2n1] |
| 339 | 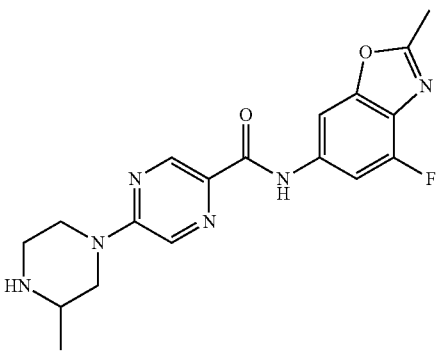 [SMILES: Cc1nc2c(F)cc(NC(=O)c3cnc(N4CCNC(C)C4)cn3)cc2o1] |
| 340 | 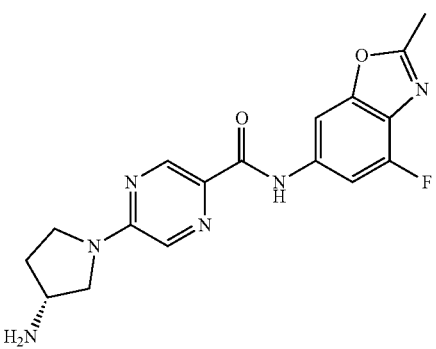 [SMILES: Cc1nc2c(F)cc(NC(=O)c3cnc(N4CC[C@@H](N)C4)cn3)cc2o1] |

TABLE 1-continued
| Ex. | Structure |
|---|---|
| 341 | 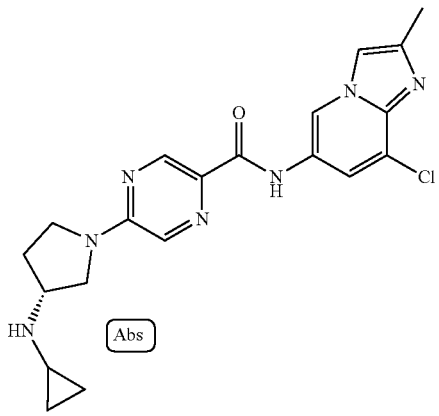 [SMILES: Cc1cn2cc(NC(=O)c3cnc(N4CC[C@@H](NC5CC5)C4)cn3)cc(Cl)c2n1] |
| 342 | 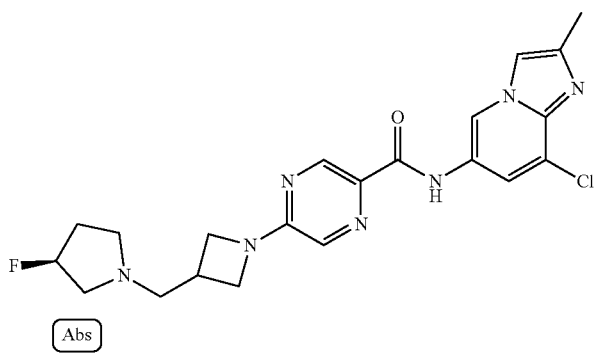 [SMILES: Cc1cn2cc(NC(=O)c3cnc(N4CC(CN5CC[C@H](F)C5)C4)cn3)cc(Cl)c2n1] |
| 343 | 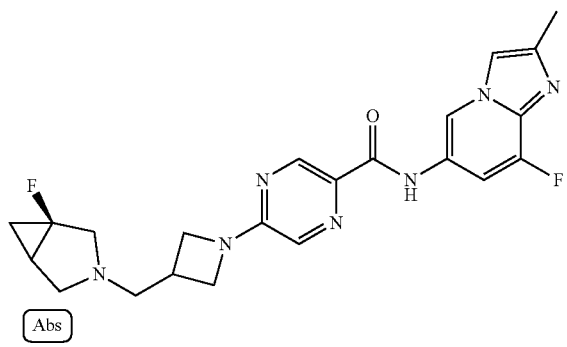 [SMILES: Cc1cn2cc(NC(=O)c3cnc(N4CC(CN5CC6C[C@]6(F)C5)C4)cn3)cc(F)c2n1] |
| 344 | 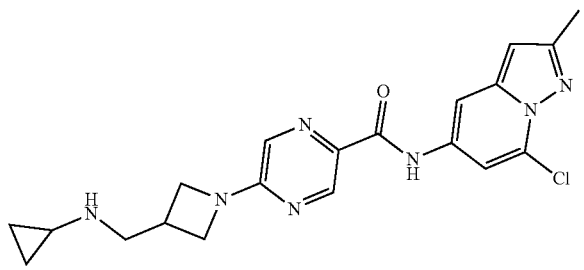 [SMILES: Cc1cc2cc(NC(=O)c3cnc(N4CC(CNC5CC5)C4)cn3)cc(Cl)n2n1] |

TABLE 1-continued
| Ex. | Structure |
|---|---|
| 345 | 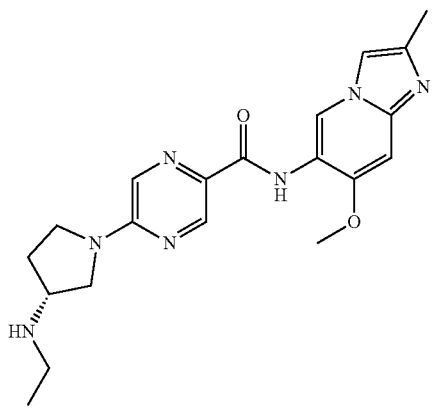 [SMILES: CCN[C@@H]1CCN(c2cnc(C(=O)Nc3cn4cc(C)nc4cc3OC)cn2)C1] |
| 346 | 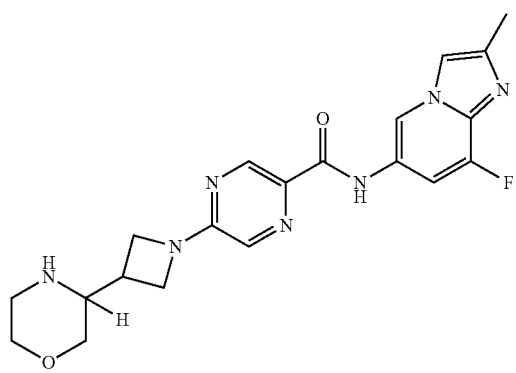
Enantiomer 1 |
| 347 | 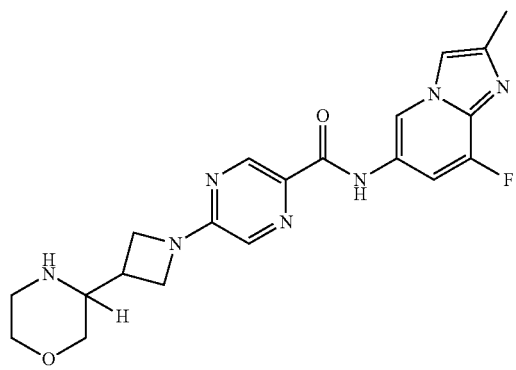
Enantiomer 2 |

TABLE 1-continued
| Ex. | Structure |
|---|---|
| 348 | 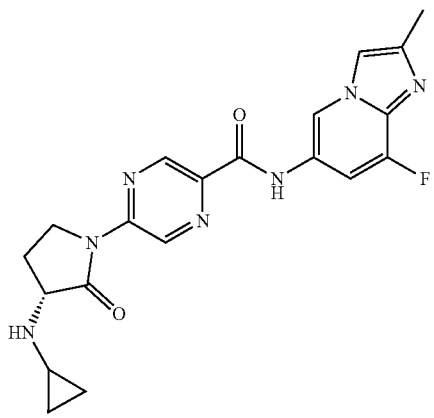 [SMILES: Cc1cn2cc(NC(=O)c3cnc(N4CC[C@@H](NC5CC5)C4=O)cn3)cc(F)c2n1] |
| 349 | 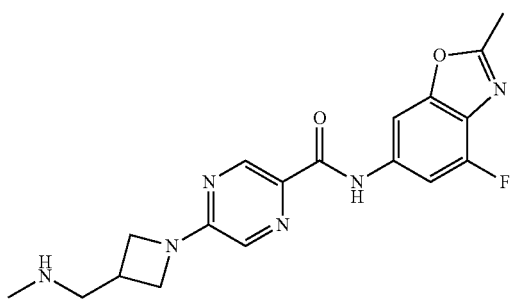 [SMILES: CNCC1CN(c2cnc(C(=O)Nc3cc(F)c4nc(C)oc4c3)cn2)C1] |
| 350 | 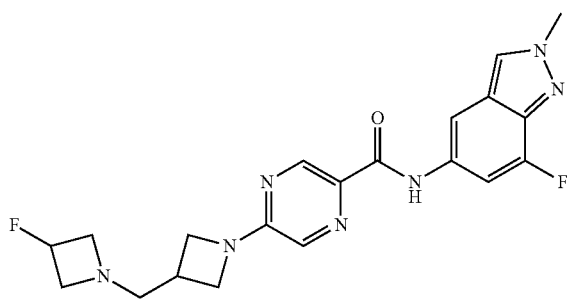 [SMILES: Cn1cc2cc(NC(=O)c3cnc(N4CC(CN5CC(F)C5)C4)cn3)cc(F)c2n1] |
| 351 | 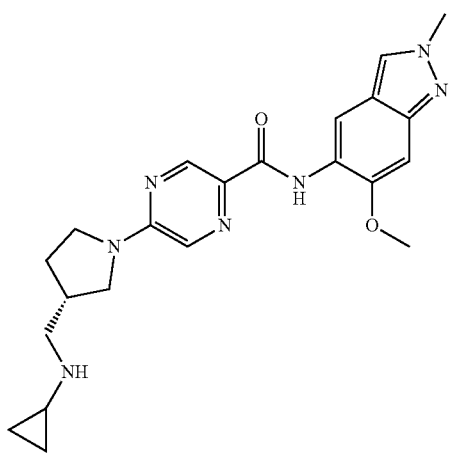 [SMILES: COc1cc2nn(C)cc2cc1NC(=O)c1cnc(N2CC[C@@H](CNC3CC3)C2)cn1] |

TABLE 1-continued
| Ex. | Structure |
|---|---|
| 352 | 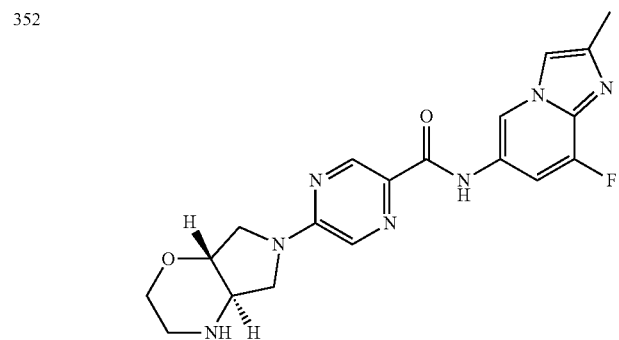 |
| 353 | 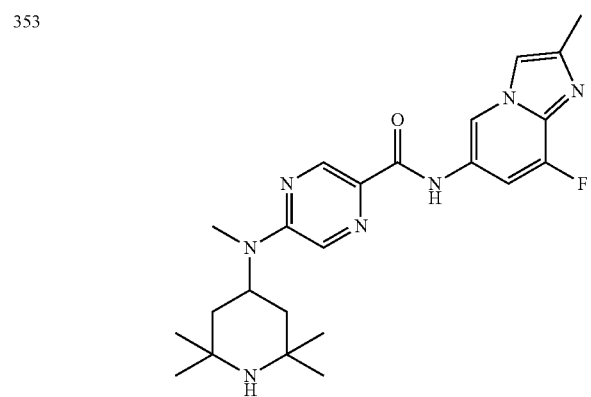 |
| 354 | 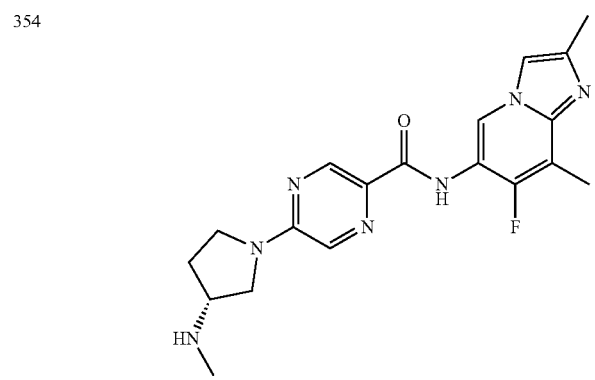 |
| 355 | 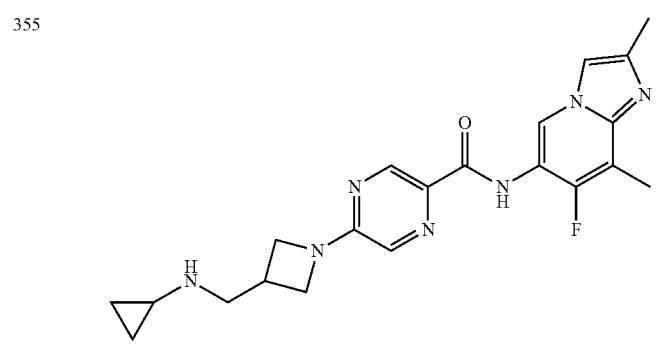 |

TABLE 1-continued

| Ex. | Structure |
|---|---|
| 356 | 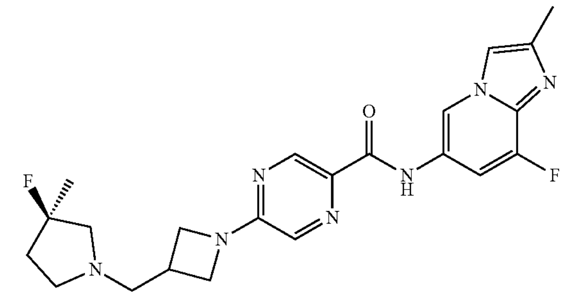 [SMILES: Cc1cn2cc(NC(=O)c3cnc(N4CC(CN5CC[C@@](C)(F)C5)C4)cn3)cc(F)c2n1] |
| 357 | 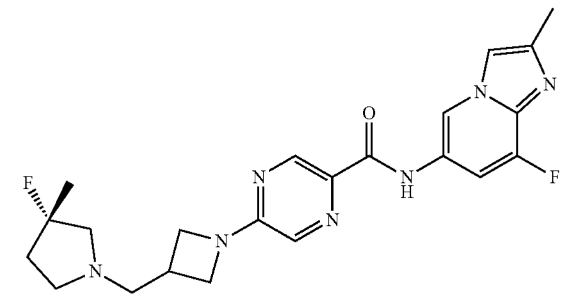 [SMILES: Cc1cn2cc(NC(=O)c3cnc(N4CC(CN5CC[C@](C)(F)C5)C4)cn3)cc(F)c2n1] |
| 358 | 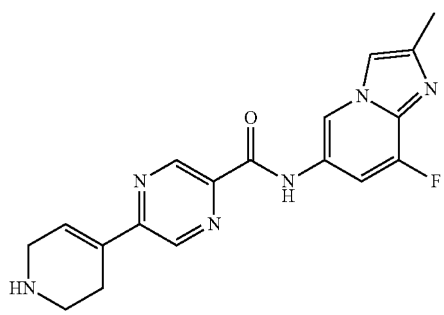 [SMILES: Cc1cn2cc(NC(=O)c3cnc(C4=CCNCC4)cn3)cc(F)c2n1] |
| 359 | 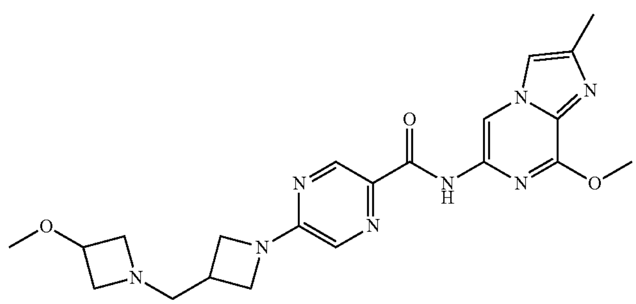 |
| 360 | 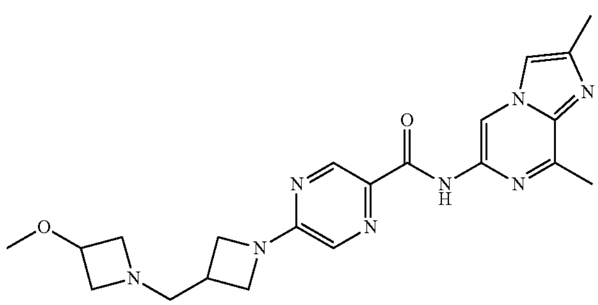 |

TABLE 1-continued
| Ex. | Structure |
|---|---|
| 361 | 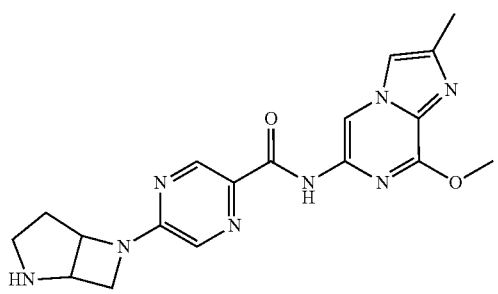
Enantiomer 1 + Enantiomer 2 |
| 362 | 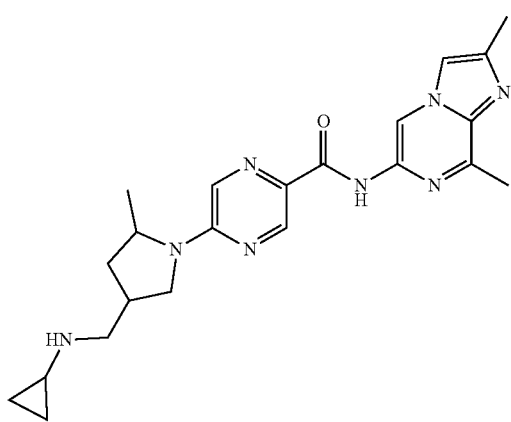 [SMILES: Cc1cn2cc(NC(=O)c3cnc(N4CC(CNC5CC5)CC4C)cn3)nc(C)c2n1] |
| 363 | 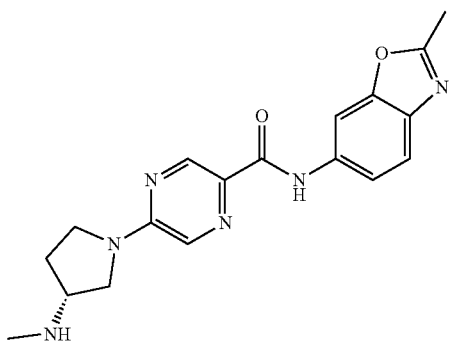 |
| 364 | 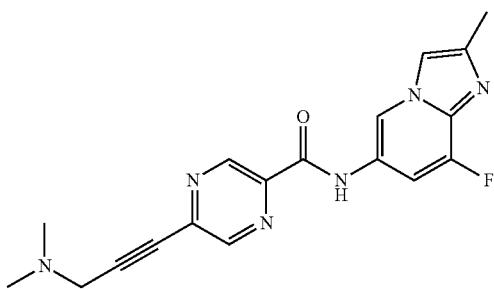 [SMILES: Cc1cn2cc(NC(=O)c3cnc(C#CCN(C)C)cn3)cc(F)c2n1] |

TABLE 1-continued
| Ex. | Structure |
|---|---|
| 365 | 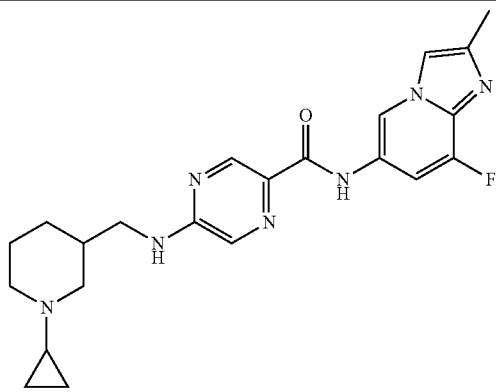
Enantiomer 1 + Enantiomer 2 |
| 366 | 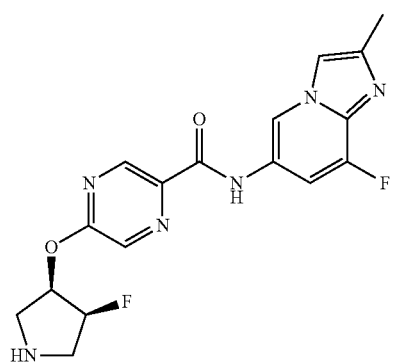 [SMILES: Cc1cn2cc(NC(=O)c3cnc(O[C@@H]4CNC[C@@H]4F)cn3)cc(F)c2n1] |
| 367 | 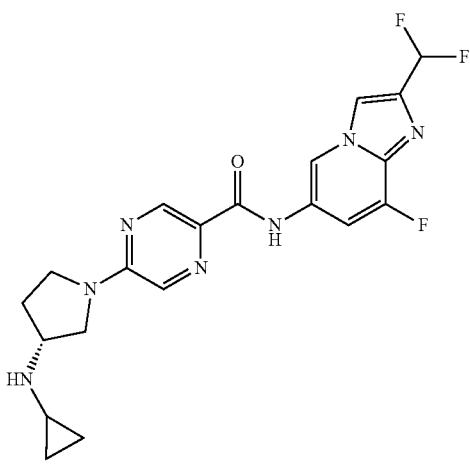 [SMILES: O=C(Nc1cc(F)c2nc(C(F)F)cn2c1)c1cnc(N2CC[C@@H](NC3CC3)C2)cn1] |
| 368 | 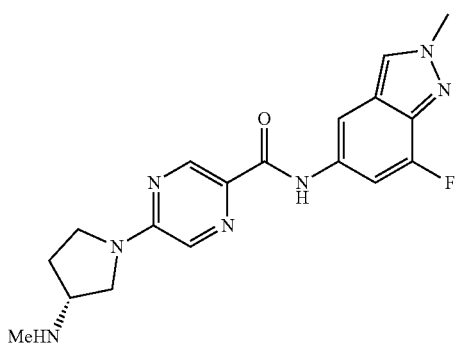 [SMILES: CN[C@@H]1CCN(c2cnc(C(=O)Nc3cc(F)c4nn(C)cc4c3)cn2)C1] |

TABLE 1-continued

| Ex. | Structure |
| --- | --- |
| 369 | 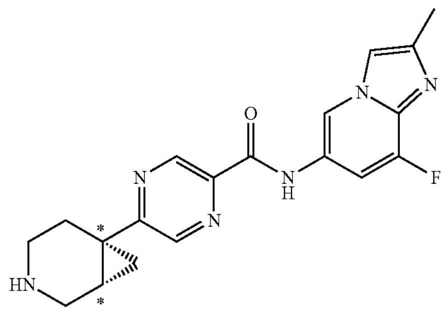 [SMILES: Cc1cn2cc(NC(=O)c3cnc([C@]45CCNC[C@H]4C5)cn3)cc(F)c2n1] |
| 370 | 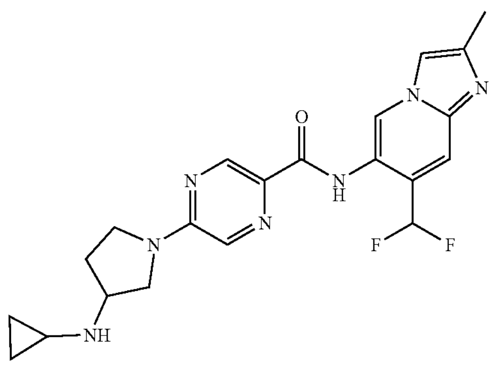 [SMILES: Cc1cn2cc(NC(=O)c3cnc(N4CCC(NC5CC5)C4)cn3)c(C(F)F)cc2n1] |
| 371 | 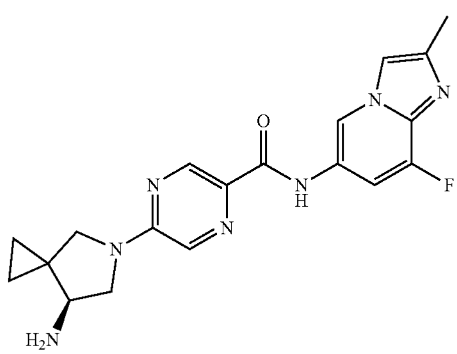 [SMILES: Cc1cn2cc(NC(=O)c3cnc(N4C[C@@H](N)C5(CC5)C4)cn3)cc(F)c2n1] |
| 372 | 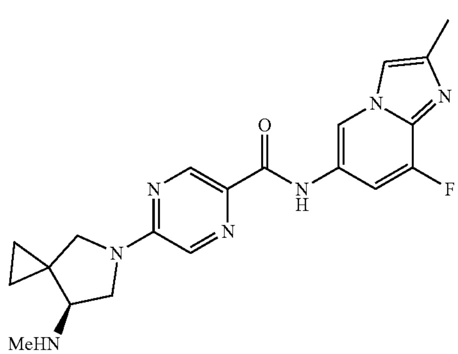 [SMILES: CN[C@@H]1CN(c2cnc(C(=O)Nc3cc(F)c4nc(C)cn4c3)cn2)CC12CC2] |

TABLE 1-continued
| Ex. | Structure |
|---|---|
| 373 | 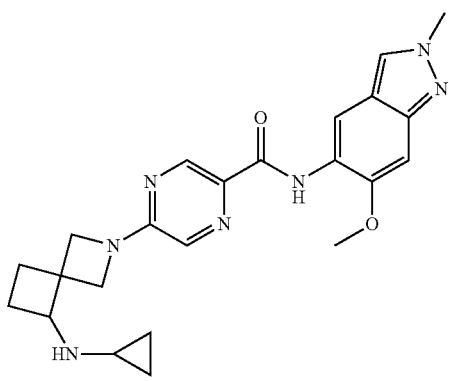 [SMILES: COc1cc2nn(C)cc2cc1NC(=O)c1cnc(N2CC3(CCC3NC3CC3)C2)cn1] |
| 374 | 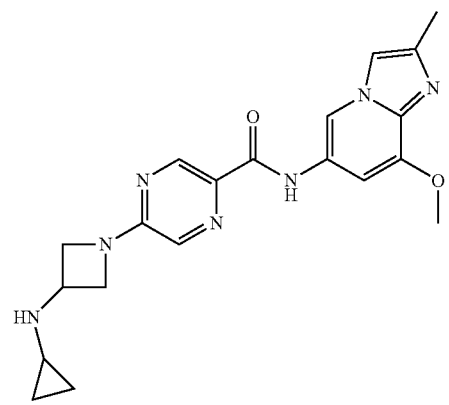 [SMILES: COc1cc(NC(=O)c2cnc(N3CC(NC4CC4)C3)cn2)cn2cc(C)nc12] |
| 375 | 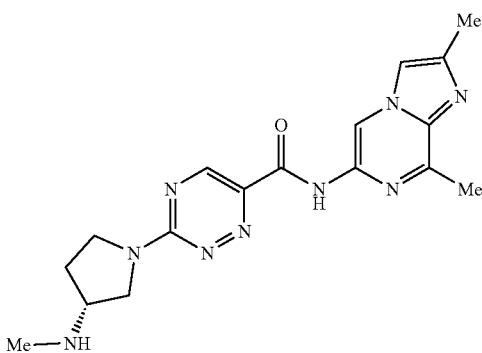 [SMILES: CN[C@@H]1CCN(c2ncc(C(=O)Nc3cn4cc(C)nc4c(C)n3)nn2)C1] |

Also is provided a compound, or an isotopically enriched analog, pharmaceutically acceptable salt, prodrug, tautomer, stereoisomer, or a mixture of stereoisomers thereof, selected from Table 1A:
TABLE 1A
Structure
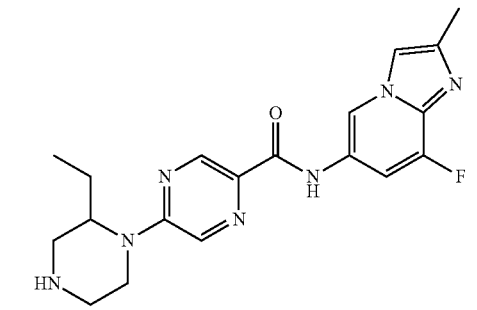 [SMILES: CCC1CNCCN1c1cnc(C(=O)Nc2cc(F)c3nc(C)cn3c2)cn1]
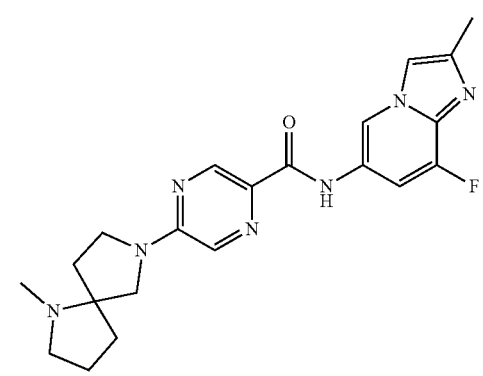 [SMILES: Cc1cn2cc(NC(=O)c3cnc(N4CCC5(CCCN5C)C4)cn3)cc(F)c2n1]
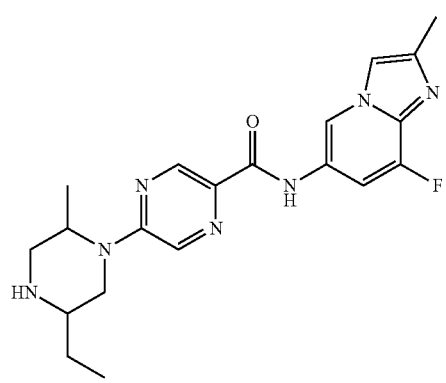 [SMILES: CCC1CN(c2cnc(C(=O)Nc3cc(F)c4nc(C)cn4c3)cn2)C(C)CN1]
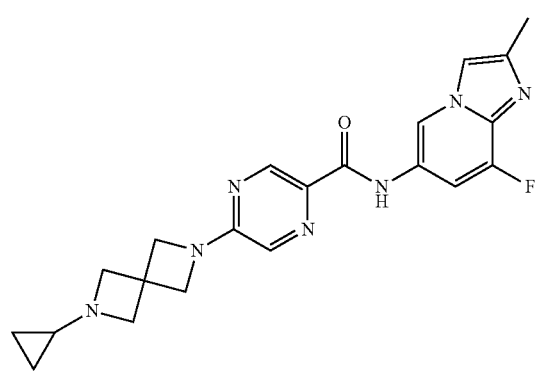 [SMILES: Cc1cn2cc(NC(=O)c3cnc(N4CC5(C4)CN(C4CC4)C5)cn3)cc(F)c2n1]
TABLE 1A-continued
Structure
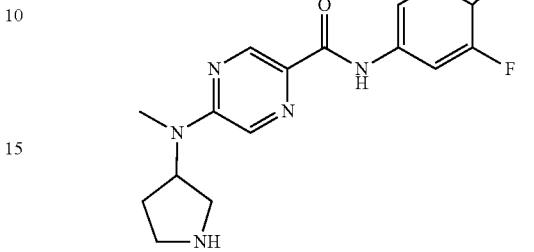
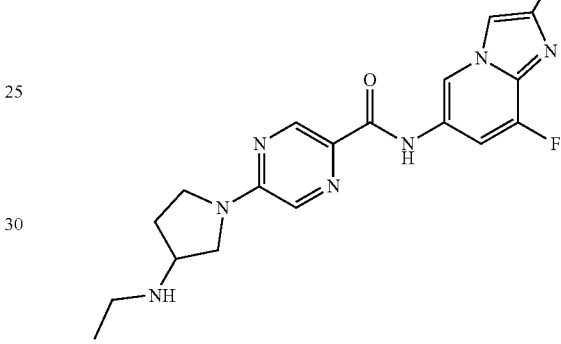
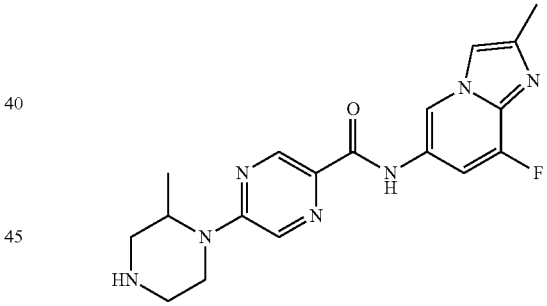
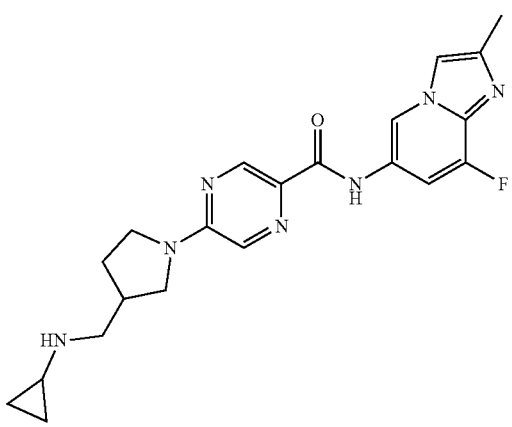 [SMILES: Cc1cn2cc(NC(=O)c3cnc(N4CCC(CNC5CC5)C4)cn3)cc(F)c2n1]

TABLE 1A-continued
Structure
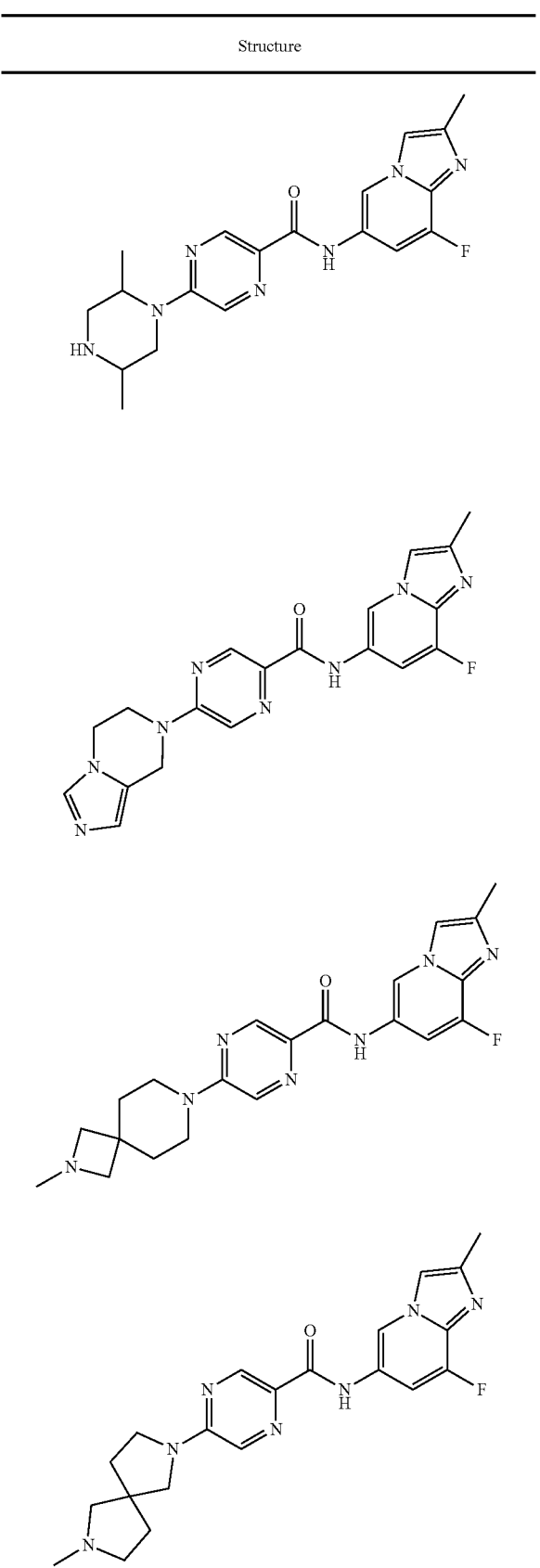
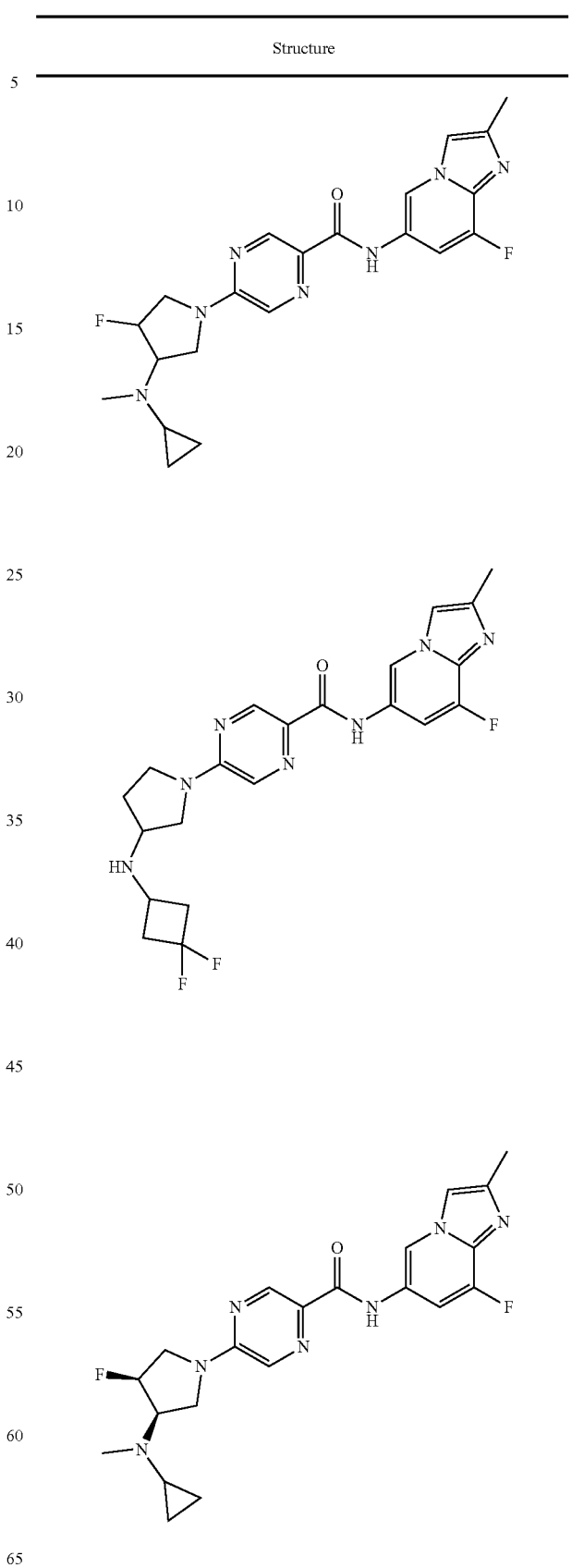

TABLE 1A-continued
| Structure |
|---|
| 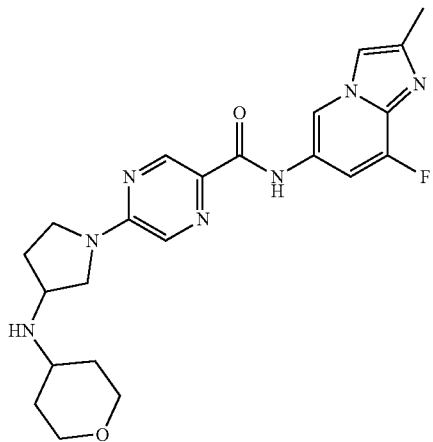 [SMILES: Cc1cn2cc(NC(=O)c3cnc(N4CCC(NC5CCOCC5)C4)cn3)cc(F)c2n1] |
| 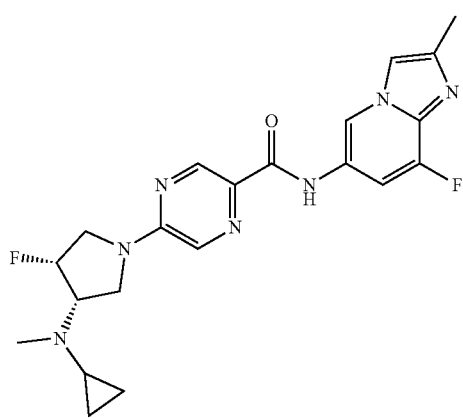 [SMILES: Cc1cn2cc(NC(=O)c3cnc(N4C[C@@H](F)[C@@H](N(C)C5CC5)C4)cn3)cc(F)c2n1] |
| 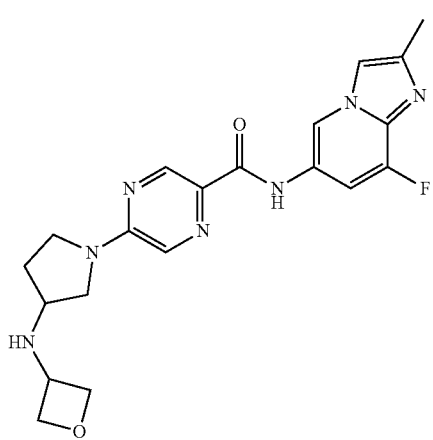 [SMILES: Cc1cn2cc(NC(=O)c3cnc(N4CCC(NC5COC5)C4)cn3)cc(F)c2n1] |
TABLE 1A-continued
| Structure |
|---|
| 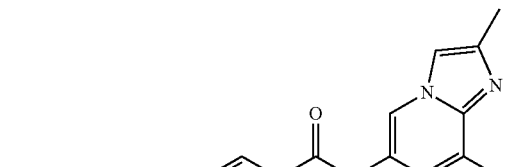 |
| 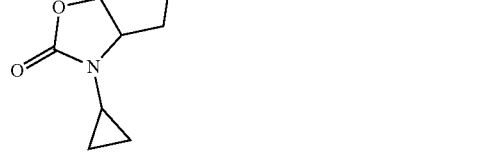 |
| 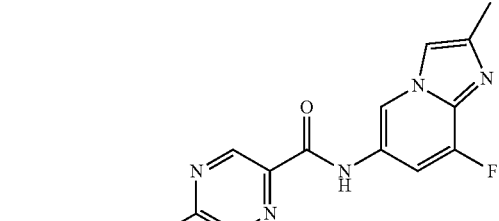 |
| 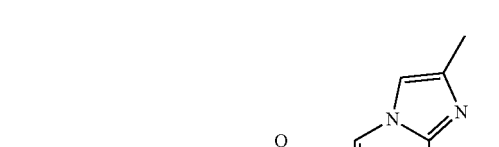 |
| 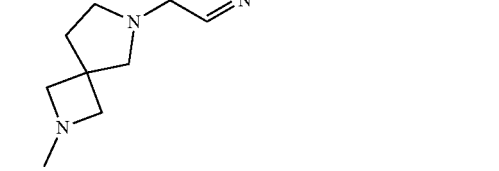 |
| 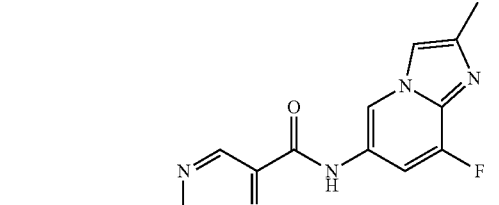 |
|  |

TABLE 1A-continued
Structure
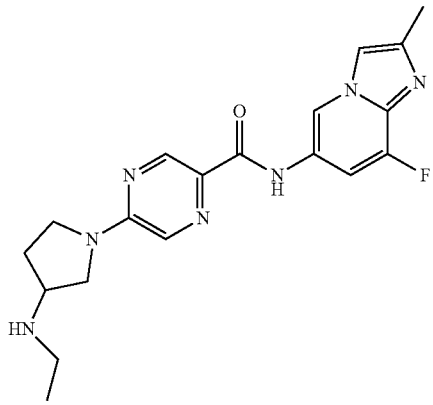 [SMILES: CCNC1CCN(c2cnc(C(=O)Nc3cc(F)c4nc(C)cn4c3)cn2)C1]
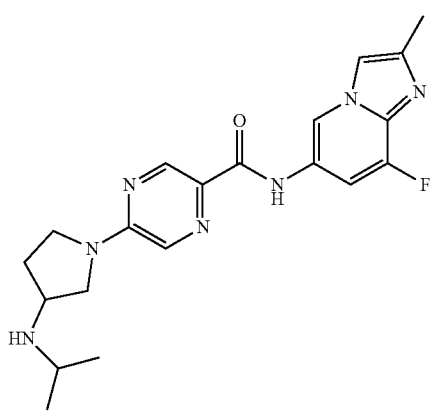 [SMILES: Cc1cn2cc(NC(=O)c3cnc(N4CCC(NC(C)C)C4)cn3)cc(F)c2n1]
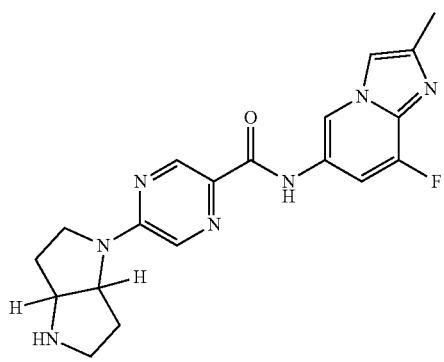 [SMILES: Cc1cn2cc(NC(=O)c3cnc(N4CCC5NCCC54)cn3)cc(F)c2n1]
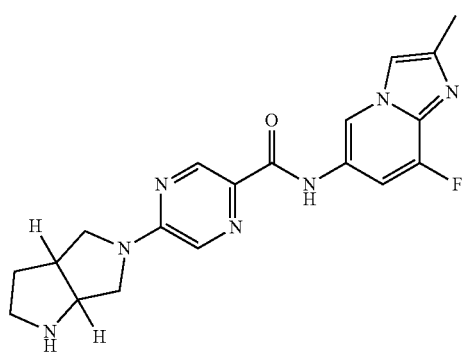 [SMILES: Cc1cn2cc(NC(=O)c3cnc(N4CC5CCNC5C4)cn3)cc(F)c2n1]
TABLE 1A-continued
Structure
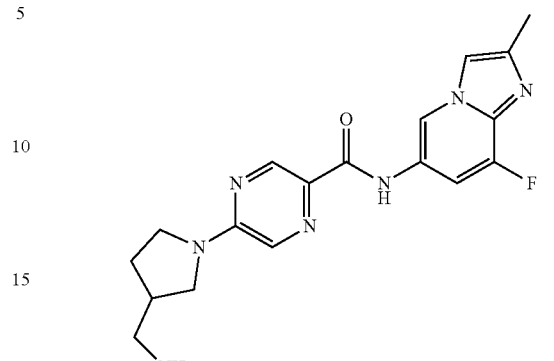
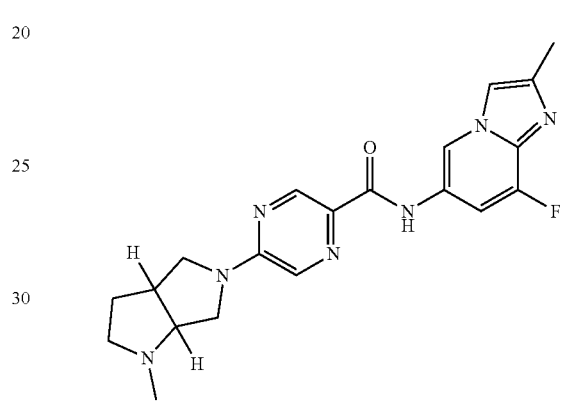
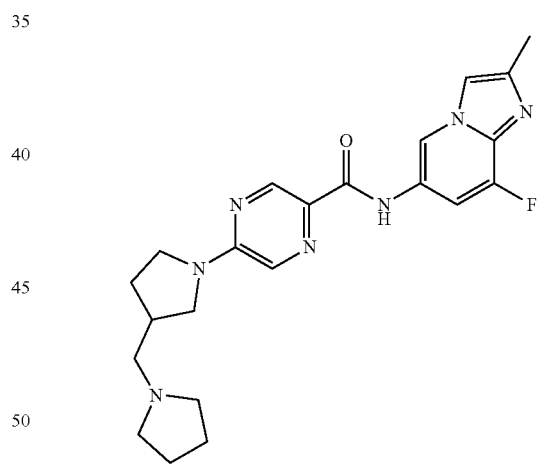
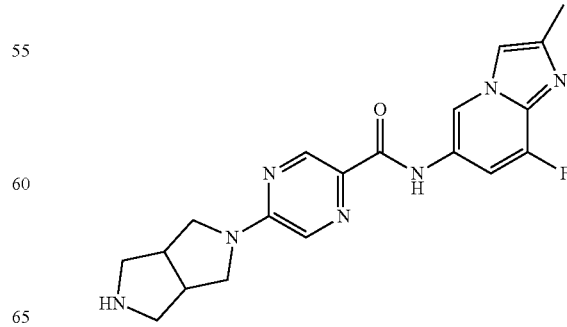

TABLE 1A-continued
Structure
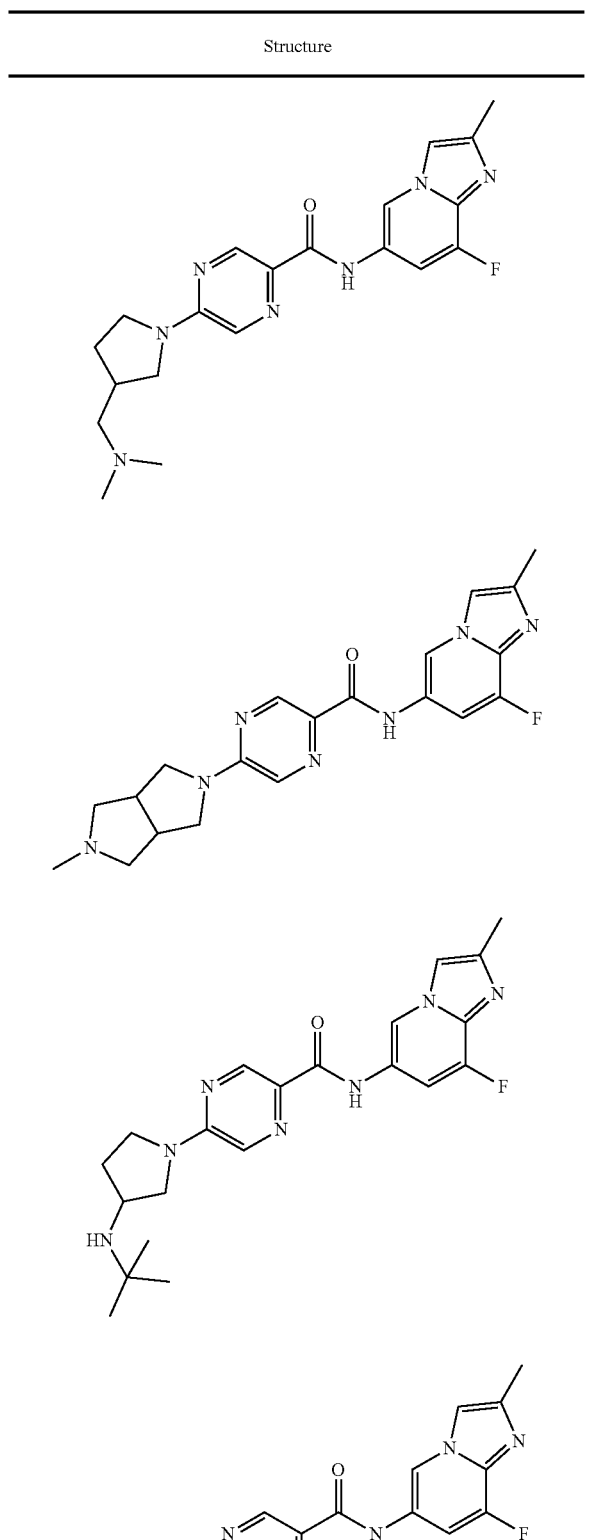
TABLE 1A-continued
Structure
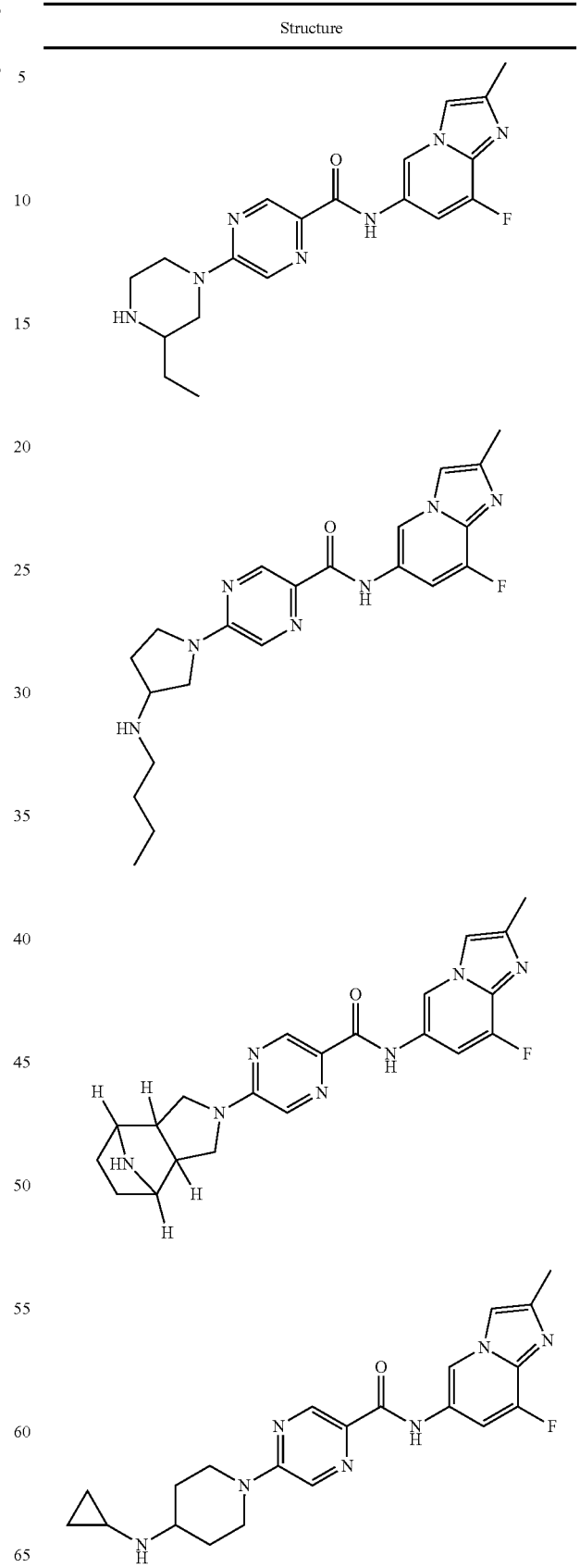

TABLE 1A-continued
Structure
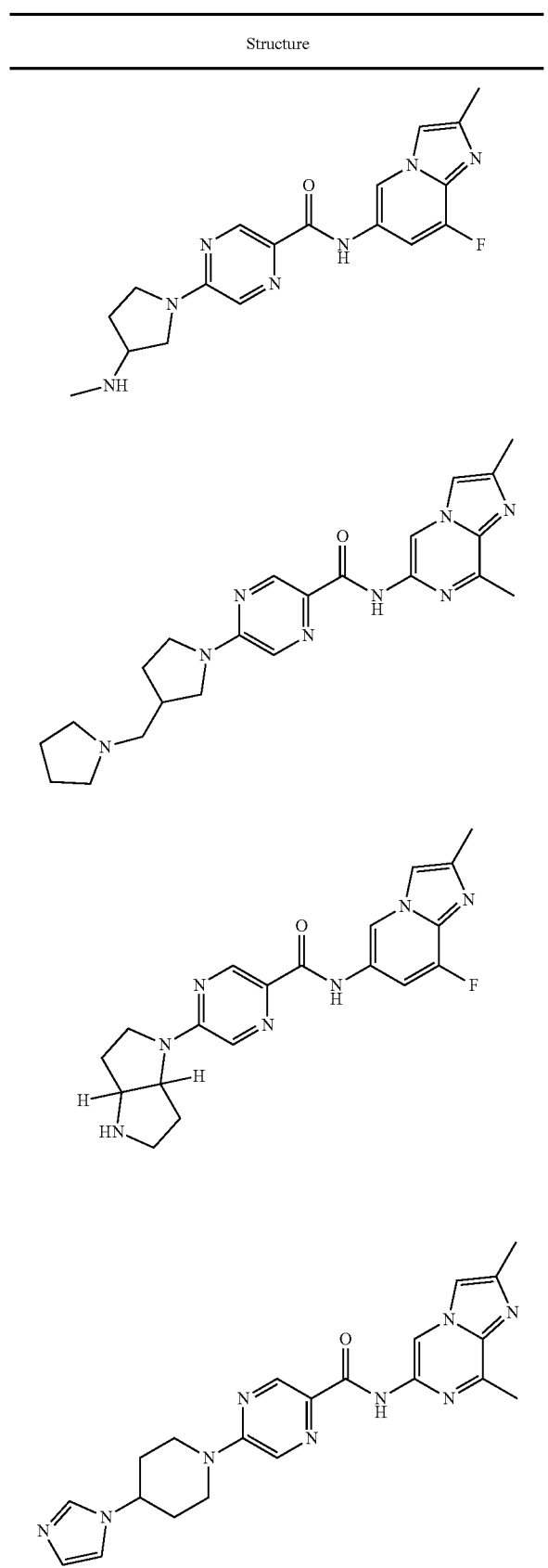
TABLE 1A-continued
Structure
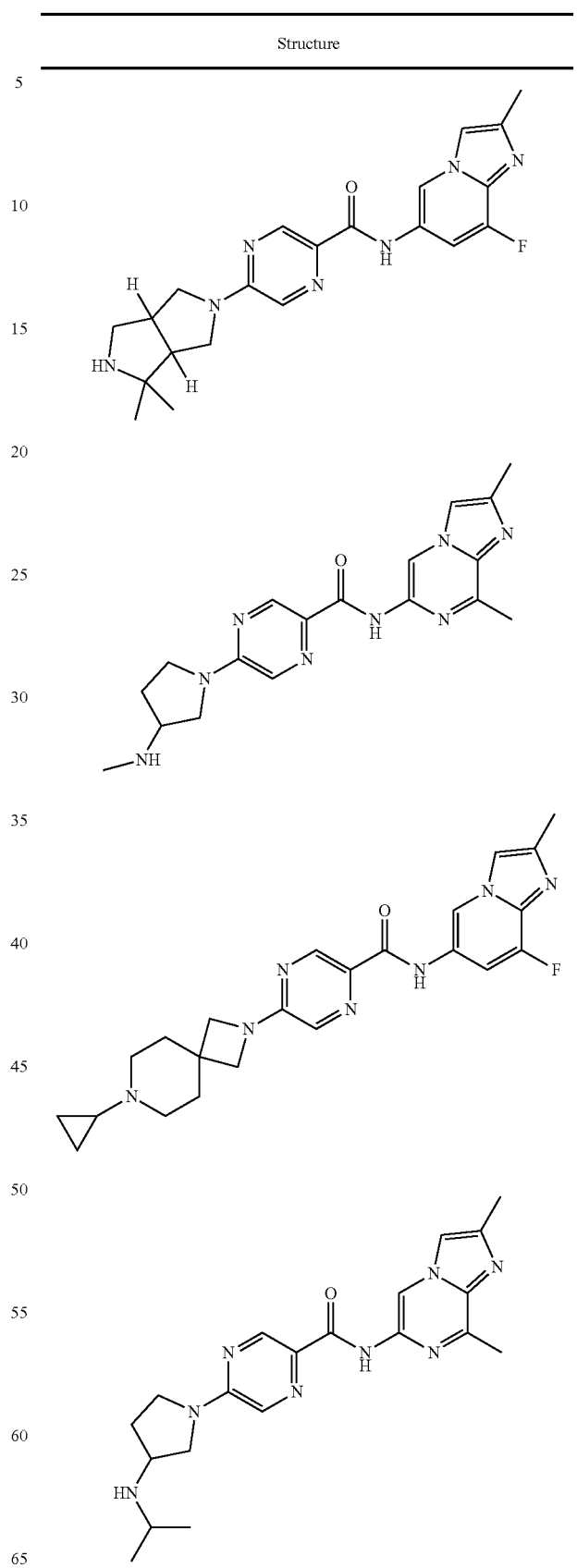

TABLE 1A-continued

| Structure |
| --- |

TABLE 1A-continued

| Structure |
|---|

TABLE 1A-continued

Structure

TABLE 1A-continued
Structure
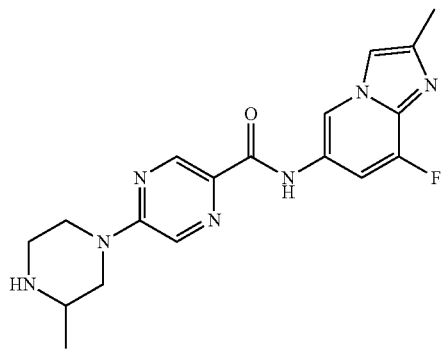 [SMILES: Cc1cn2cc(NC(=O)c3cnc(N4CCNC(C)C4)cn3)cc(F)c2n1]
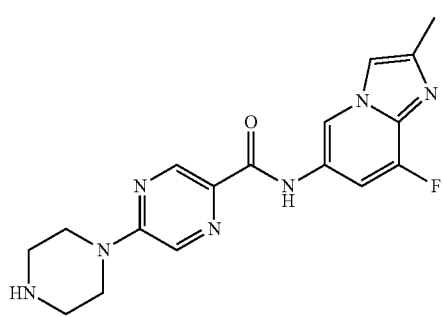
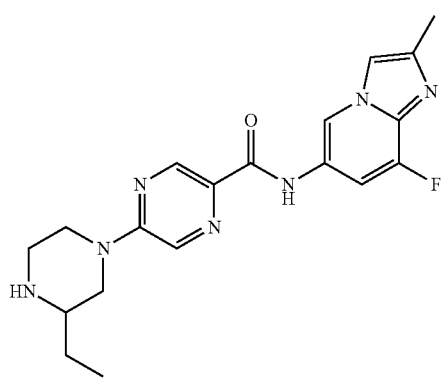
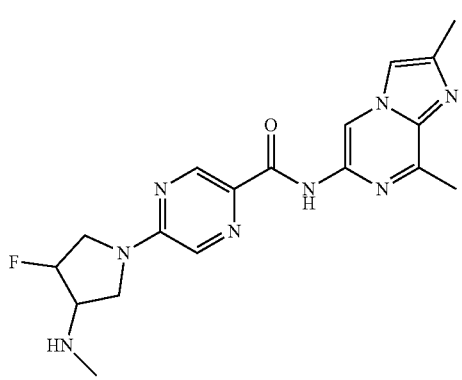 [SMILES: CNC1CN(c2cnc(C(=O)Nc3cn4cc(C)nc4c(C)n3)cn2)CC1F]
TABLE 1A-continued
Structure
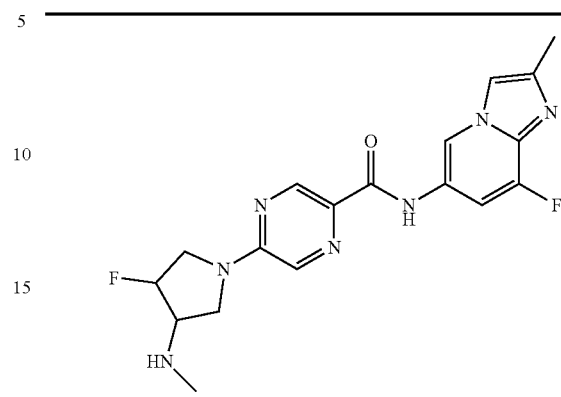
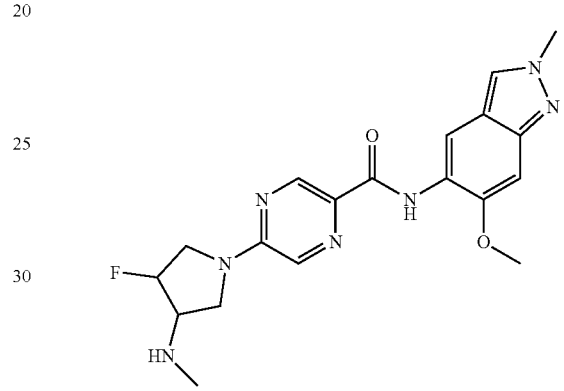
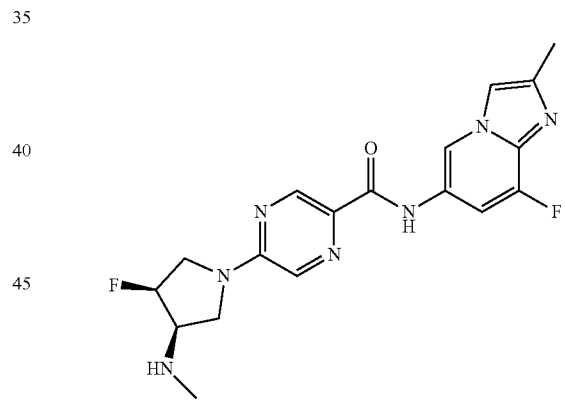
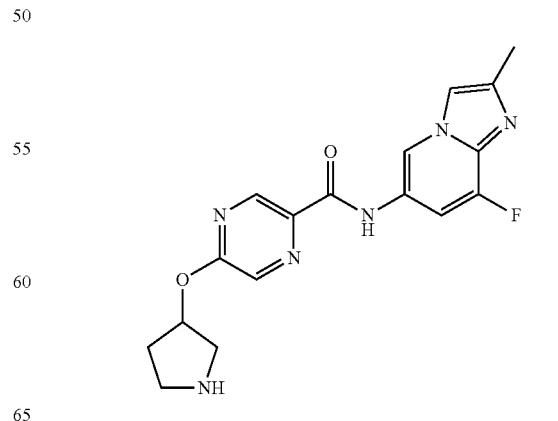

TABLE 1A-continued
Structure
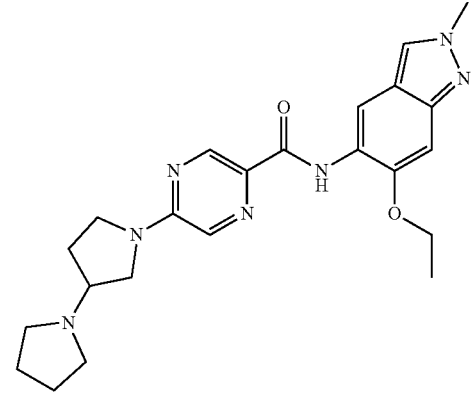 [SMILES: CCOc1cc2nn(C)cc2cc1NC(=O)c1cnc(N2CCC(N3CCCC3)C2)cn1]

TABLE 1A-continued
| Structure |
|---|
| 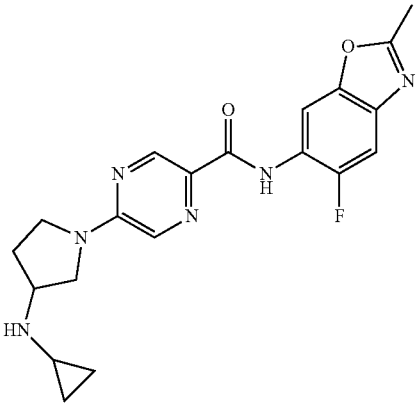 [SMILES: Cc1nc2cc(F)c(NC(=O)c3cnc(N4CCC(NC5CC5)C4)cn3)cc2o1] |
| 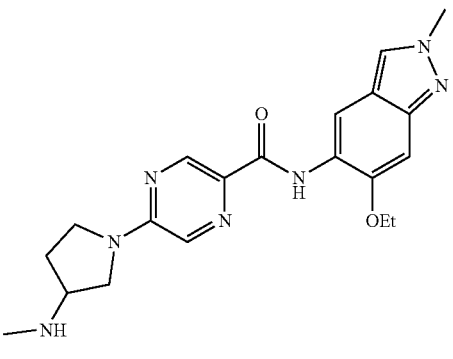 |
| 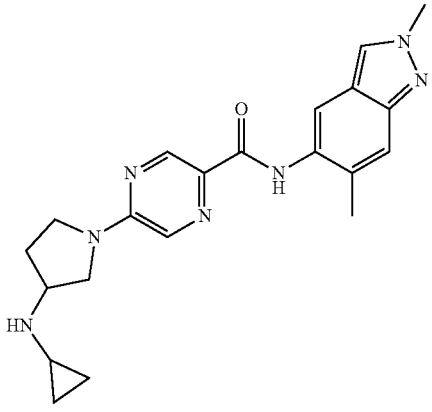 [SMILES: Cc1cc2nn(C)cc2cc1NC(=O)c1cnc(N2CCC(NC3CC3)C2)cn1] |
| 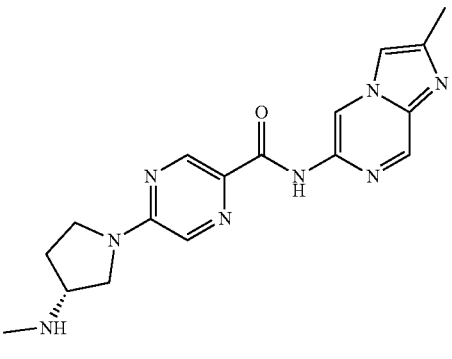 |
| 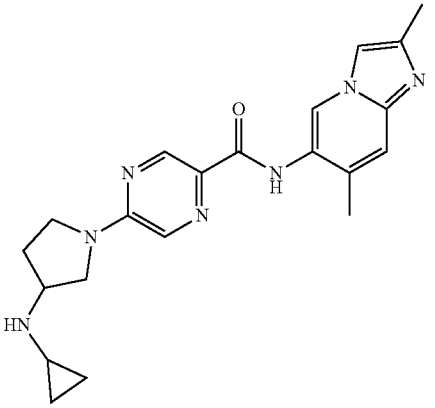 [SMILES: Cc1cn2cc(NC(=O)c3cnc(N4CCC(NC5CC5)C4)cn3)c(C)cc2n1] |
| 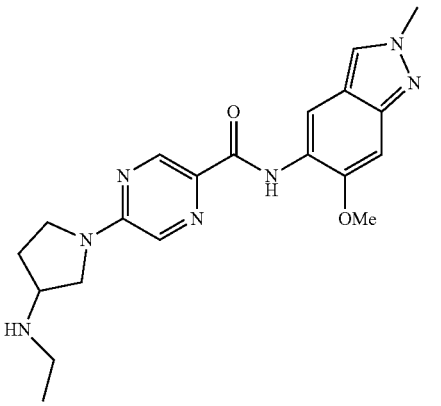 [SMILES: CCNC1CCN(c2cnc(C(=O)Nc3cc4cn(C)nc4cc3OC)cn2)C1] |
| 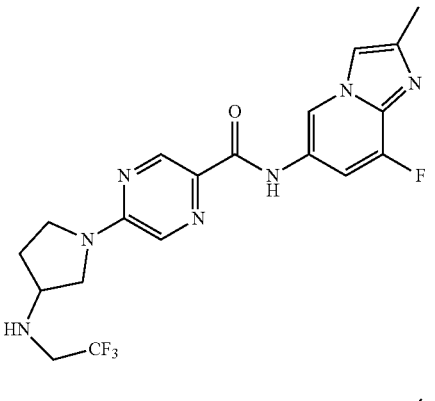 |
| 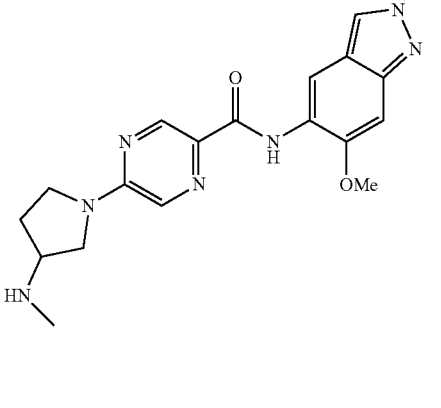 |

TABLE 1A-continued

Structure

TABLE 1A-continued
Structure
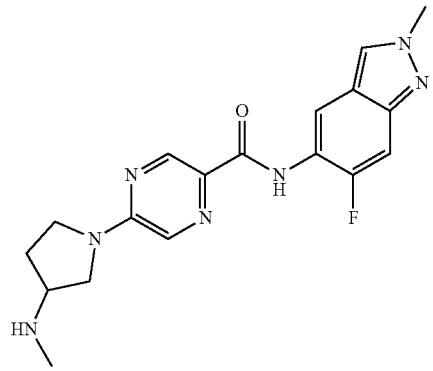 [SMILES: CNC1CCN(c2cnc(C(=O)Nc3cc4cn(C)nc4cc3F)cn2)C1]
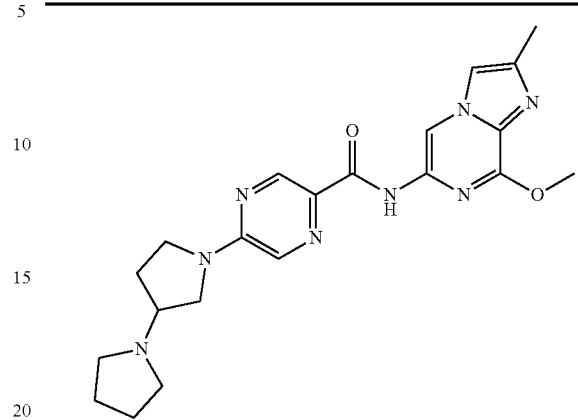
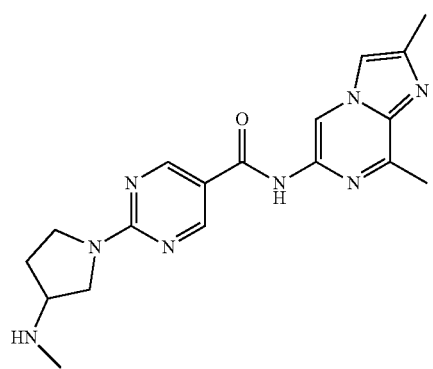 [SMILES: CNC1CCN(c2ncc(C(=O)Nc3cn4cc(C)nc4c(C)n3)cn2)C1]
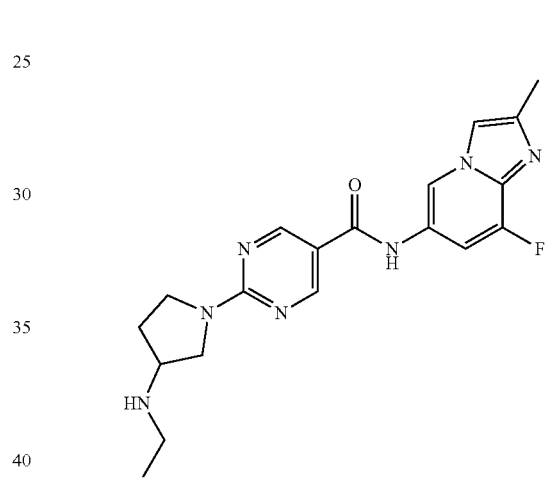
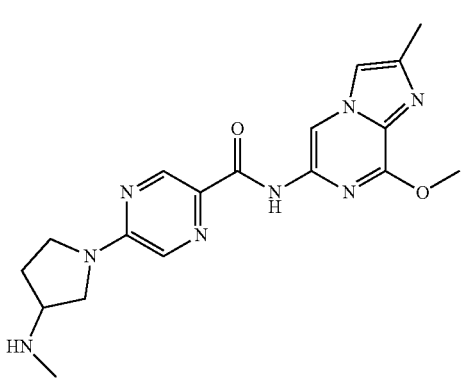 [SMILES: CNC1CCN(c2cnc(C(=O)Nc3cn4cc(C)nc4c(OC)n3)cn2)C1]
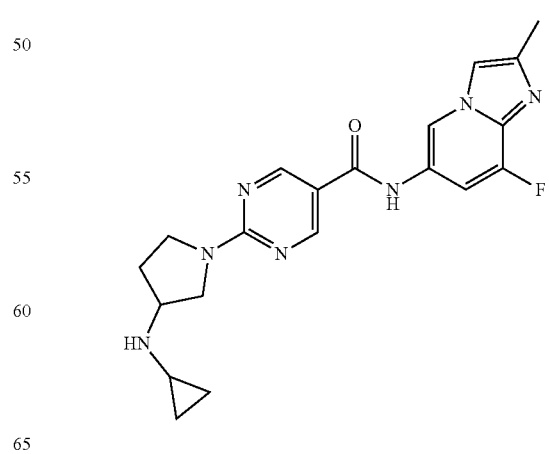

TABLE 1A-continued

TABLE 1A-continued
Structure
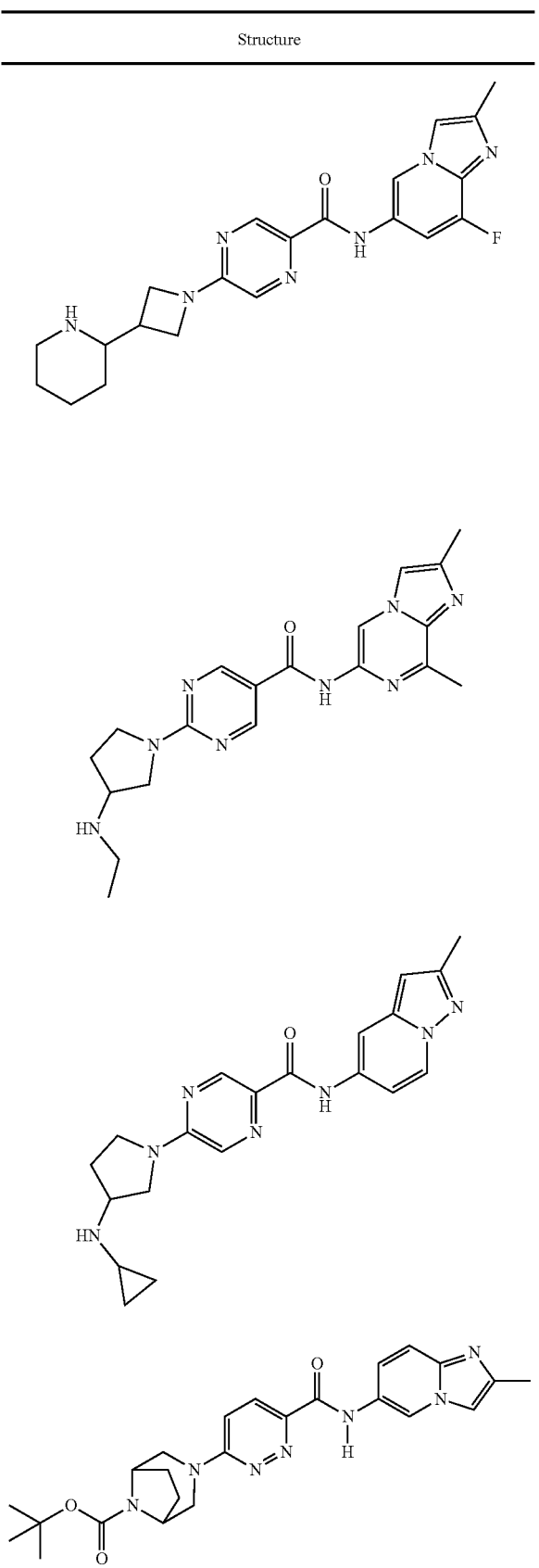
TABLE 1A-continued
Structure
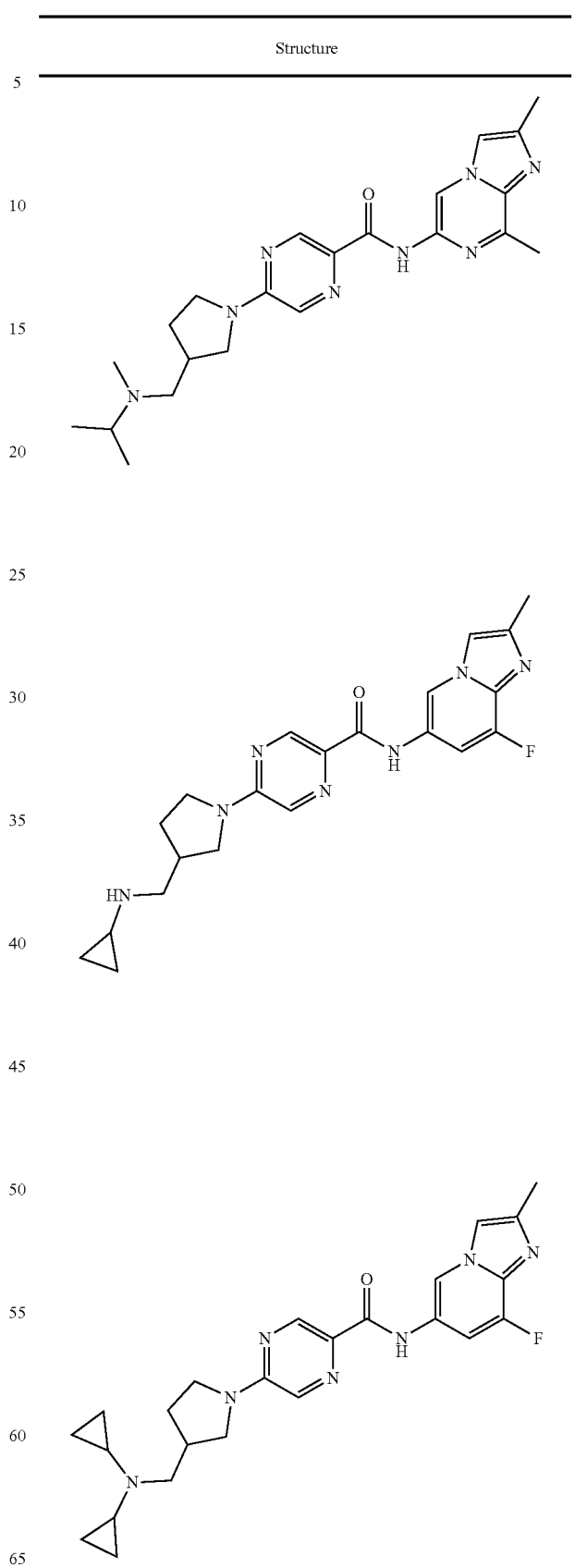

TABLE 1A-continued
Structure
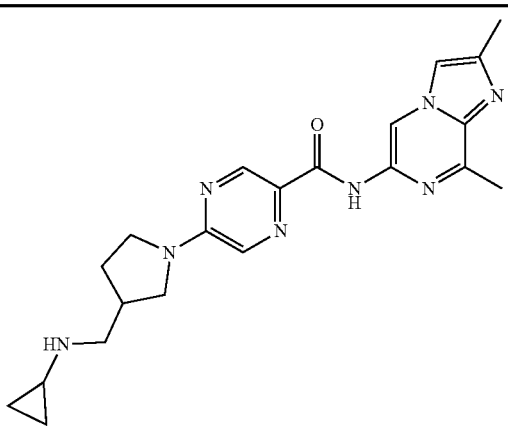
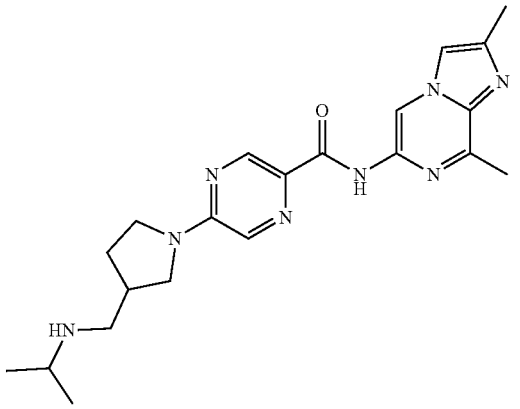
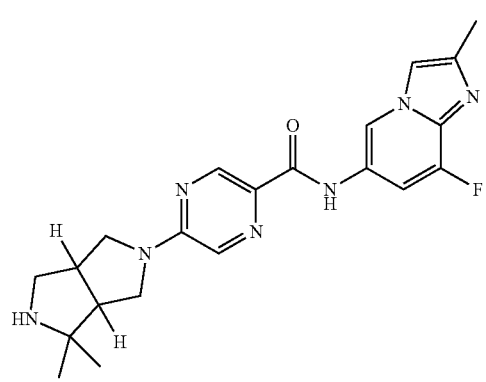 [SMILES: Cc1cn2cc(NC(=O)c3cnc(N4CC5CNC(C)(C)C5C4)cn3)cc(F)c2n1]
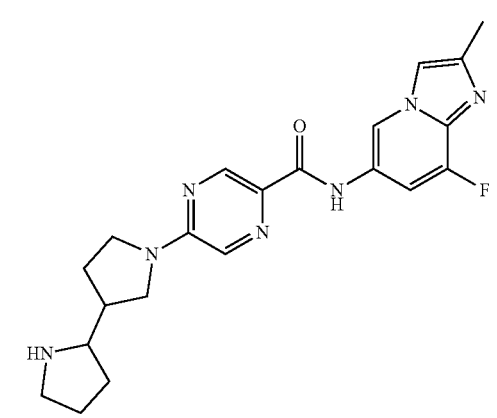
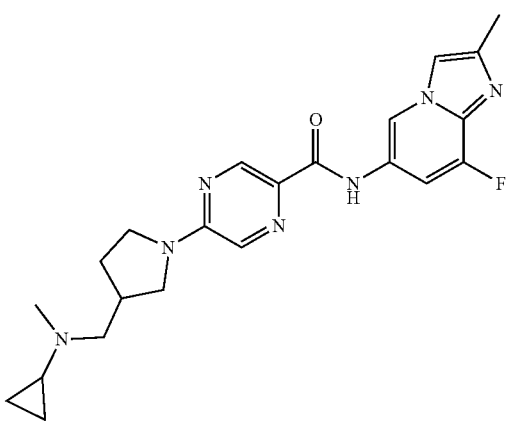 [SMILES: Cc1cn2cc(NC(=O)c3cnc(N4CCC(CN(C)C5CC5)C4)cn3)cc(F)c2n1]
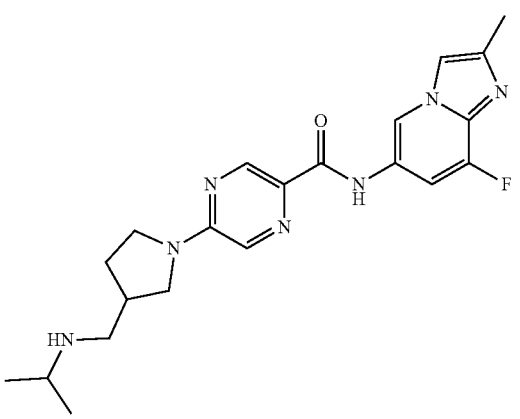
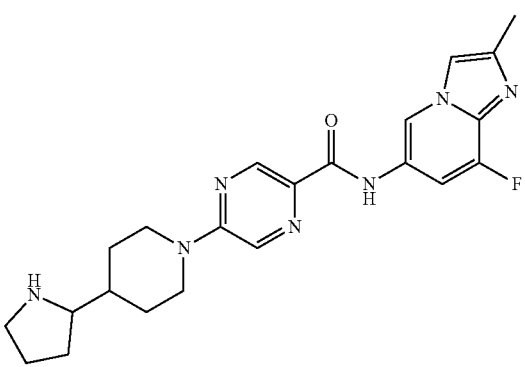 [SMILES: Cc1cn2cc(NC(=O)c3cnc(N4CCC(C5CCCN5)CC4)cn3)cc(F)c2n1]
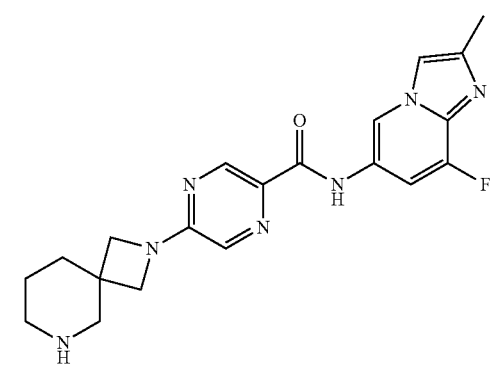 [SMILES: Cc1cn2cc(NC(=O)c3cnc(N4CC5(CCCNC5)C4)cn3)cc(F)c2n1]

TABLE 1A-continued

Structure

TABLE 1A-continued
Structure
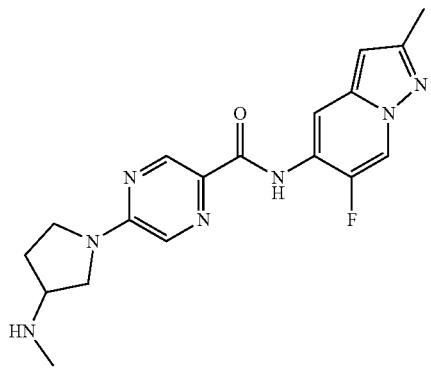
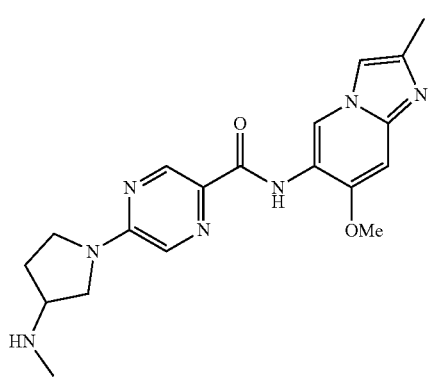
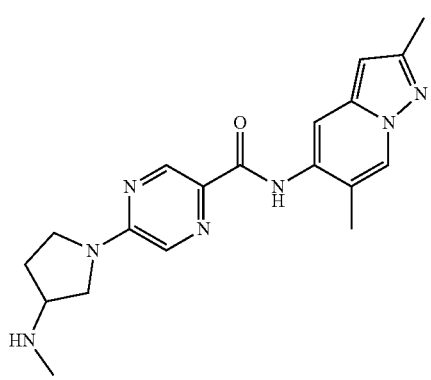
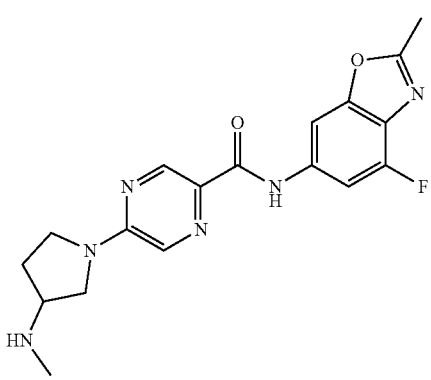 [SMILES: CNC1CCN(c2cnc(C(=O)Nc3cc(F)c4nc(C)oc4c3)cn2)C1]
TABLE 1A-continued
Structure
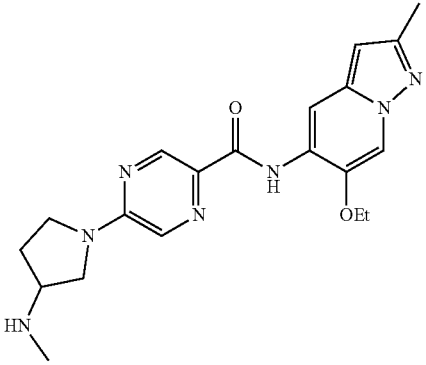
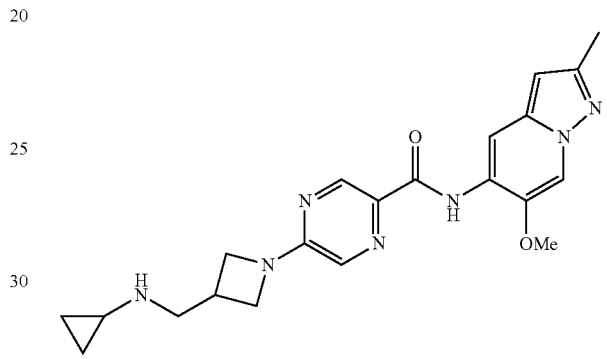
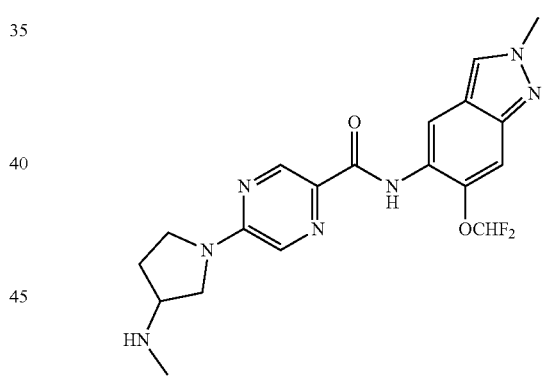
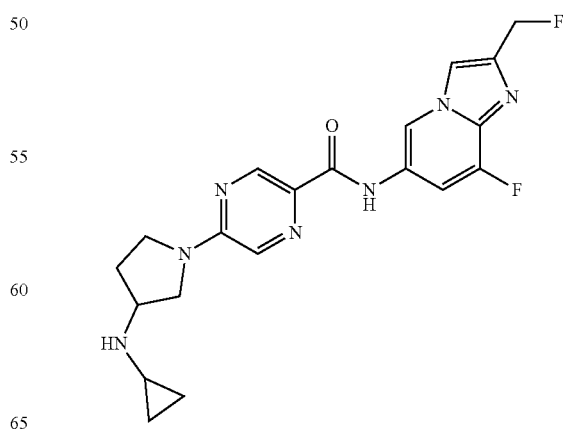

TABLE 1A-continued
Structure
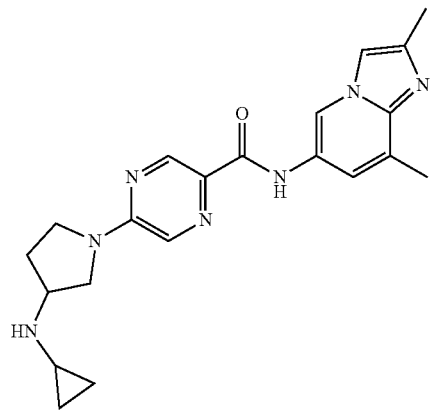
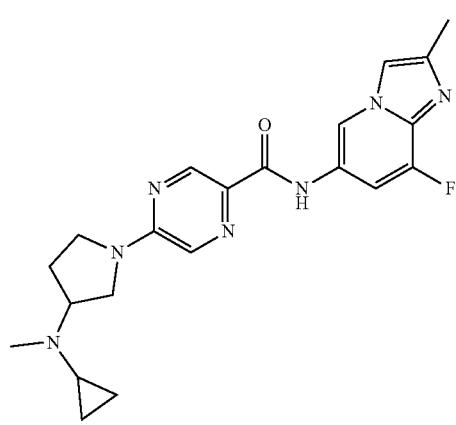 [SMILES: Cc1cn2cc(NC(=O)c3cnc(N4CCC(N(C)C5CC5)C4)cn3)cc(F)c2n1]
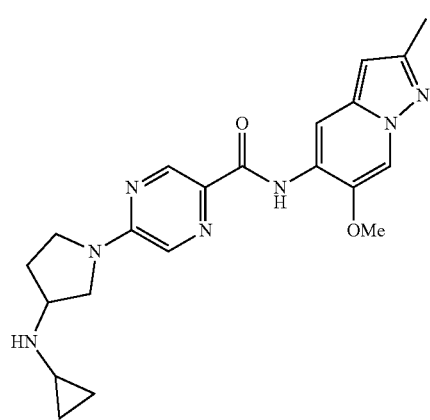
TABLE 1A-continued
Structure
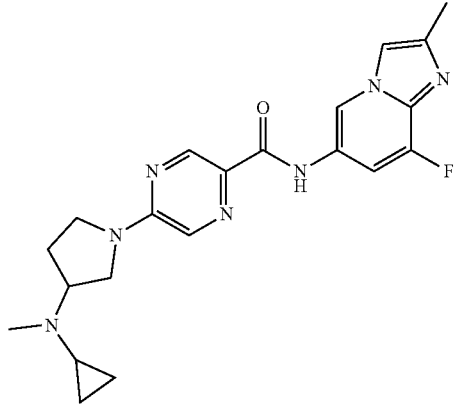 [SMILES: Cc1cn2cc(NC(=O)c3cnc(N4CCC(N(C)C5CC5)C4)cn3)cc(F)c2n1]
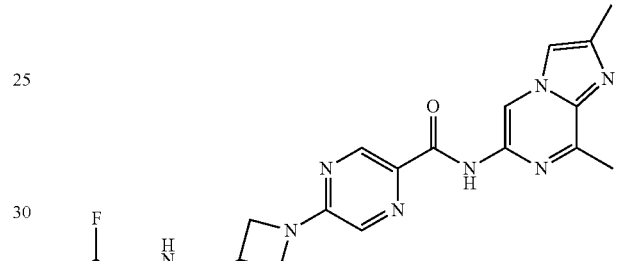
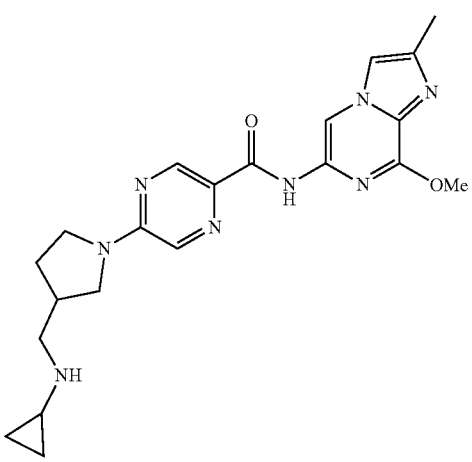 [SMILES: COc1nc(NC(=O)c2cnc(N3CCC(CNC4CC4)C3)cn2)cn2cc(C)nc12]
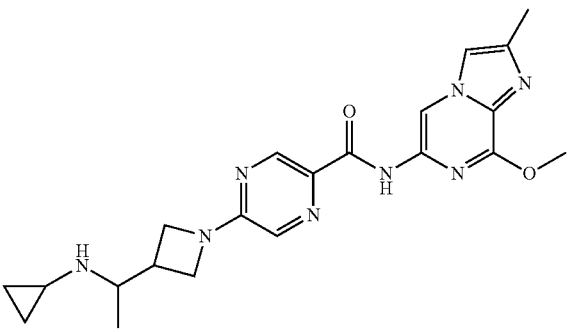 [SMILES: COc1nc(NC(=O)c2cnc(N3CC(C(C)NC4CC4)C3)cn2)cn2cc(C)nc12]

TABLE 1A-continued

Structure

TABLE 1A-continued
Structure
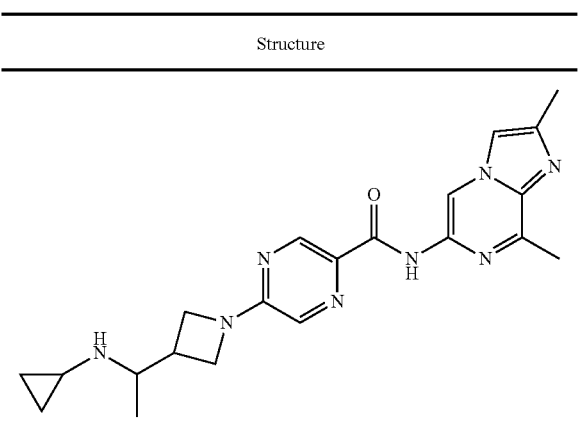
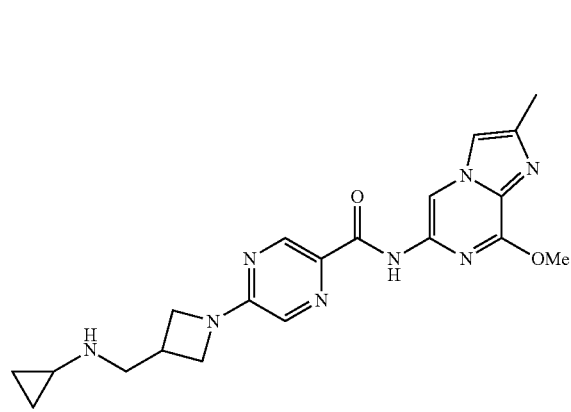 [SMILES: COc1nc(NC(=O)c2cnc(N3CC(CNC4CC4)C3)cn2)cn2cc(C)nc12]
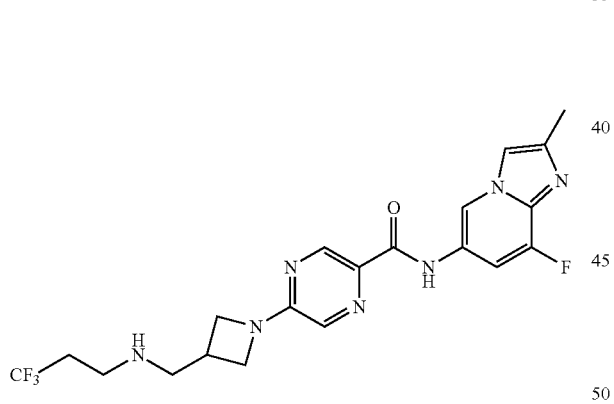
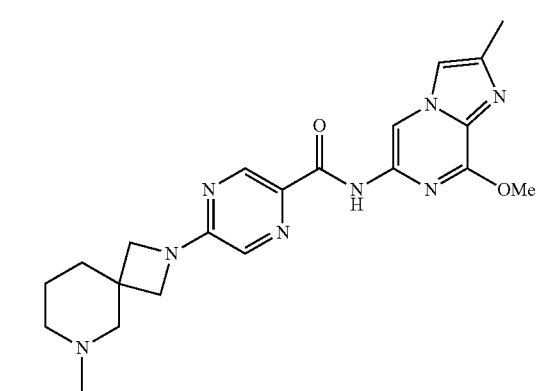 [SMILES: COc1nc(NC(=O)c2cnc(N3CC4(CCCN(C)C4)C3)cn2)cn2cc(C)nc12]
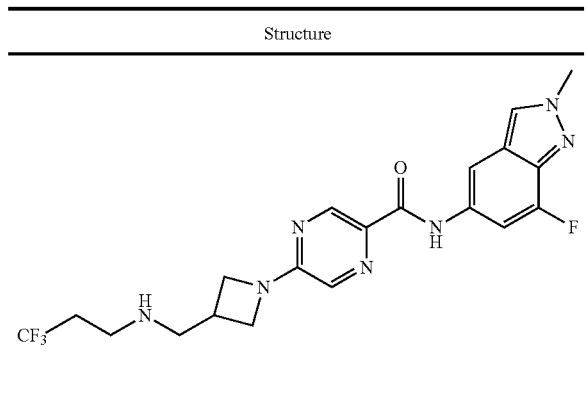
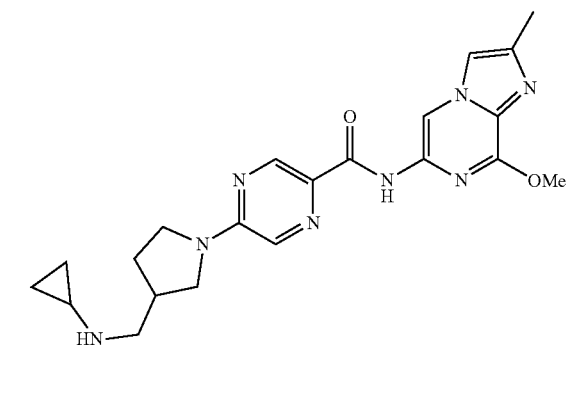 [SMILES: COc1nc(NC(=O)c2cnc(N3CCC(CNC4CC4)C3)cn2)cn2cc(C)nc12]
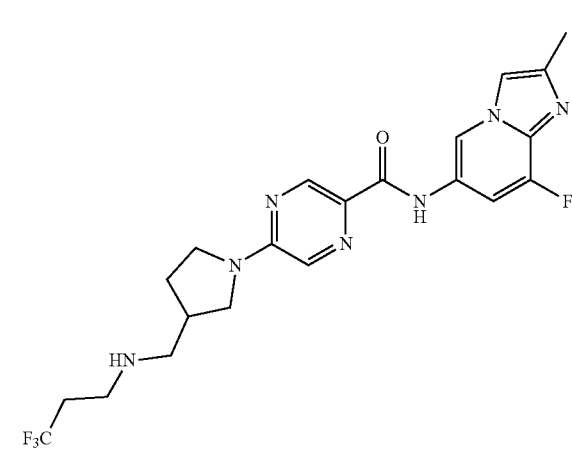 [SMILES: Cc1cn2cc(NC(=O)c3cnc(N4CCC(CNCCC(F)(F)F)C4)cn3)cc(F)c2n1]
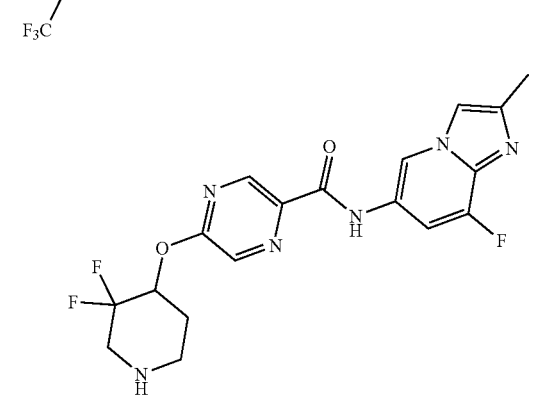

TABLE 1A-continued

Structure

TABLE 1A-continued
Structure
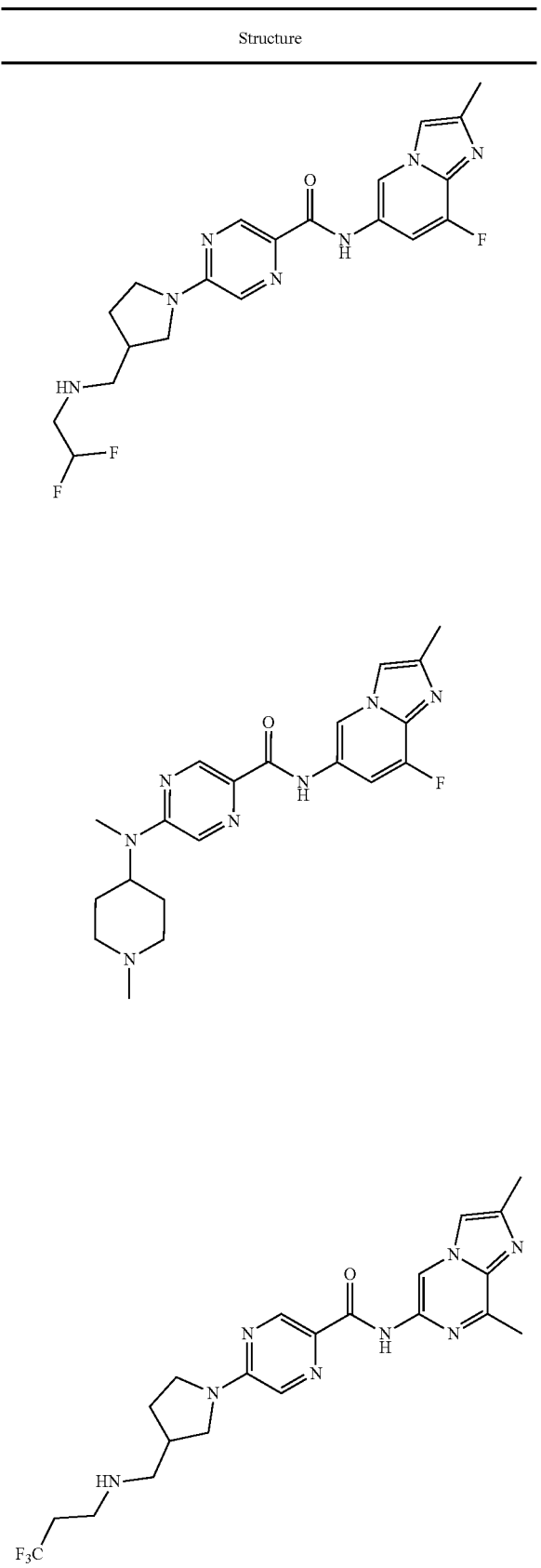
TABLE 1A-continued
Structure
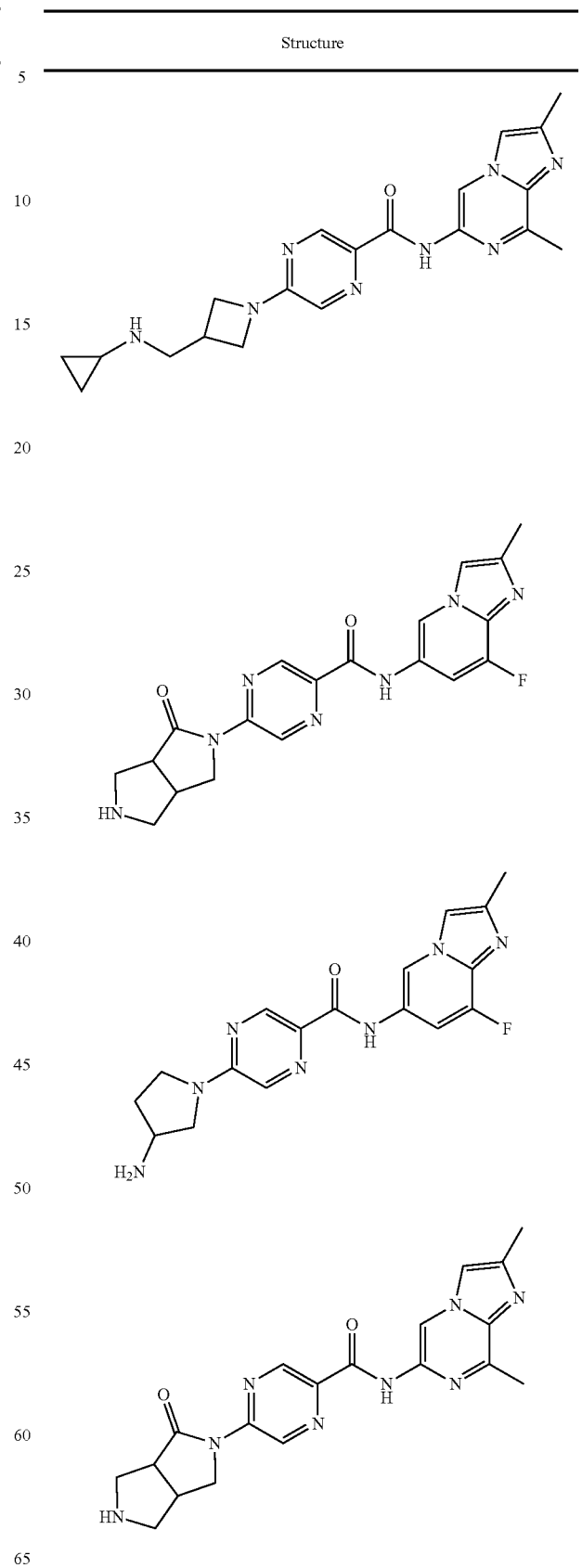

TABLE 1A-continued
Structure
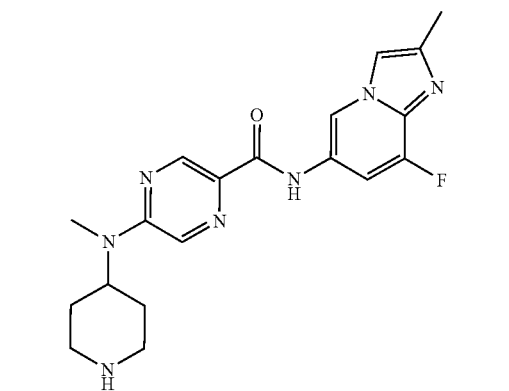 [SMILES: Cc1cn2cc(NC(=O)c3cnc(N(C)C4CCNCC4)cn3)cc(F)c2n1]
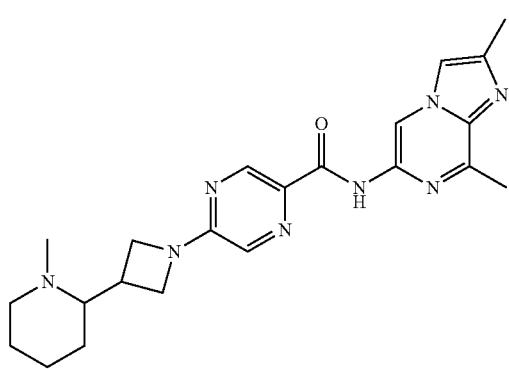 [SMILES: Cc1cn2cc(NC(=O)c3cnc(N4CC(C5CCCCN5C)C4)cn3)nc(C)c2n1]
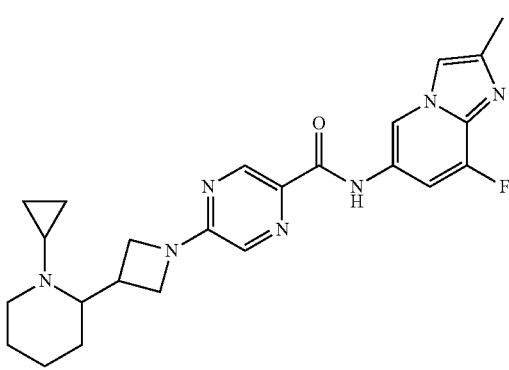 [SMILES: Cc1cn2cc(NC(=O)c3cnc(N4CC(C5CCCCN5C5CC5)C4)cn3)cc(F)c2n1]

TABLE 1A-continued
Structure
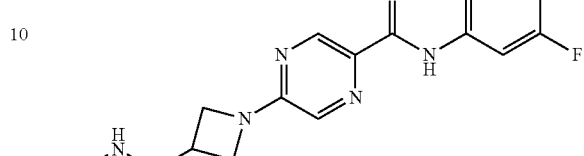
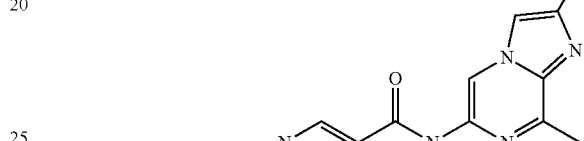
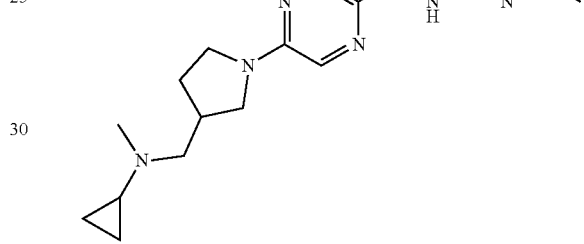
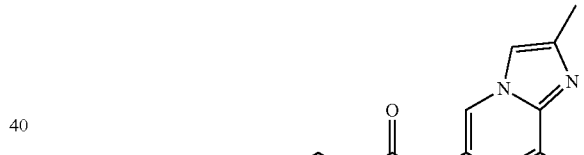

281
TABLE 1A-continued
Structure
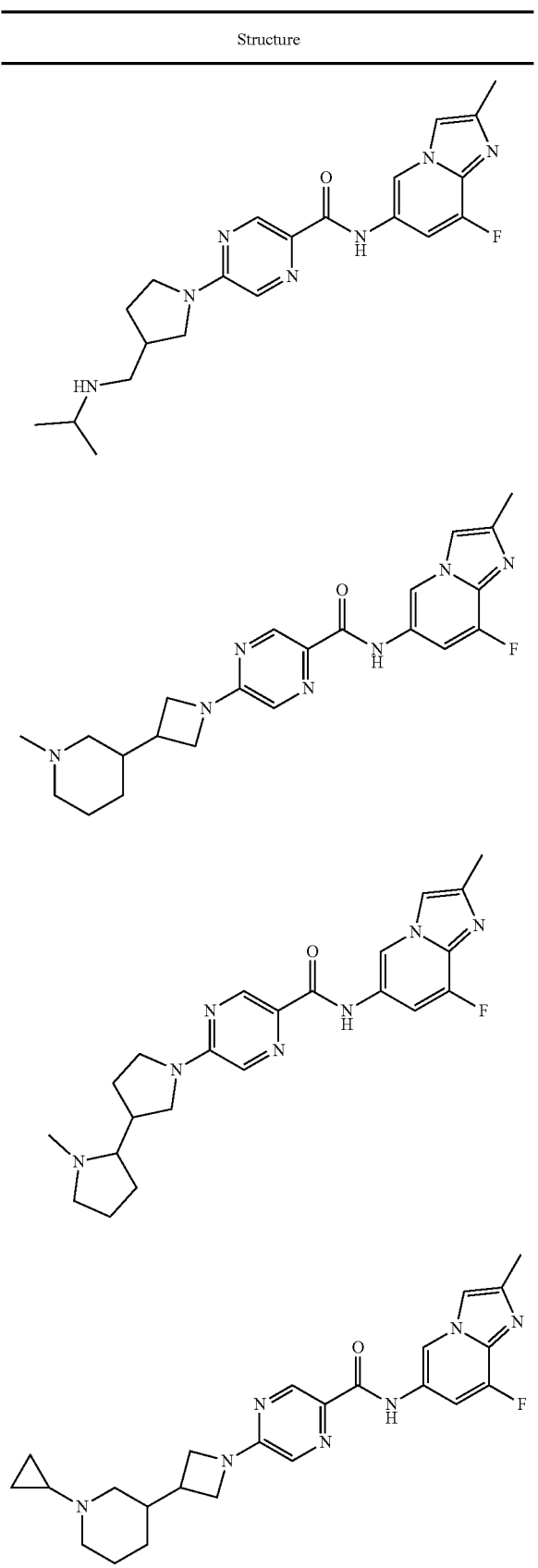
282
TABLE 1A-continued
Structure
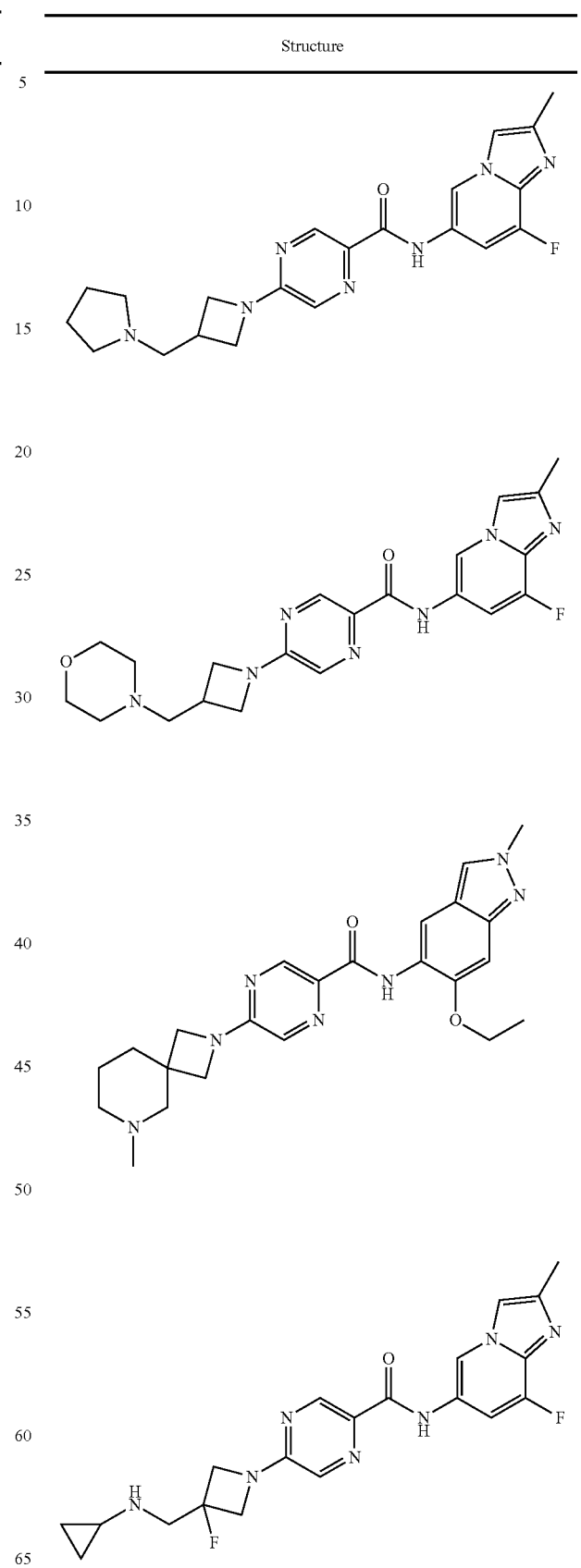

TABLE 1A-continued
Structure
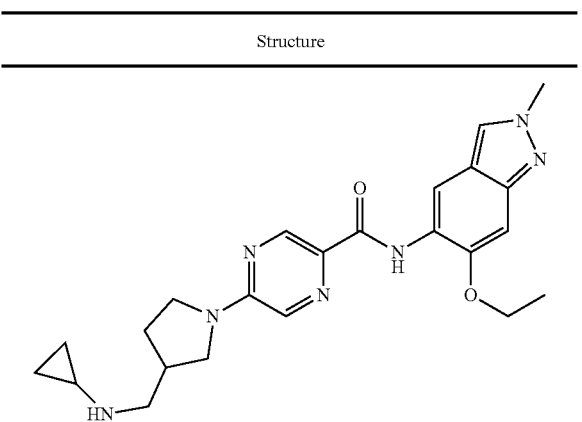
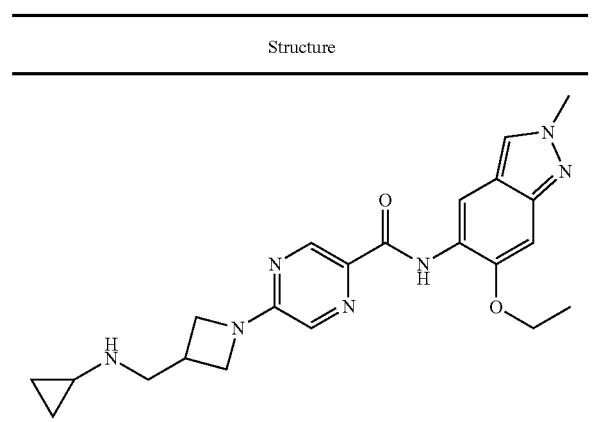
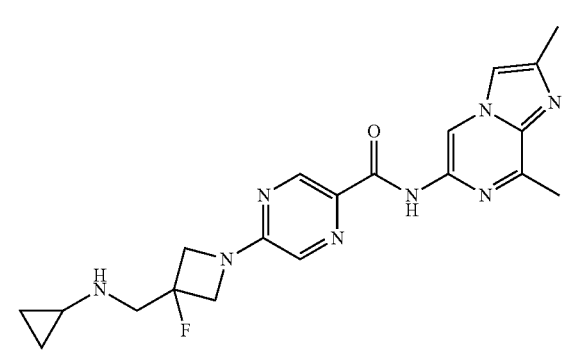 [SMILES: Cc1cn2cc(NC(=O)c3cnc(N4CC(F)(CNC5CC5)C4)cn3)nc(C)c2n1]
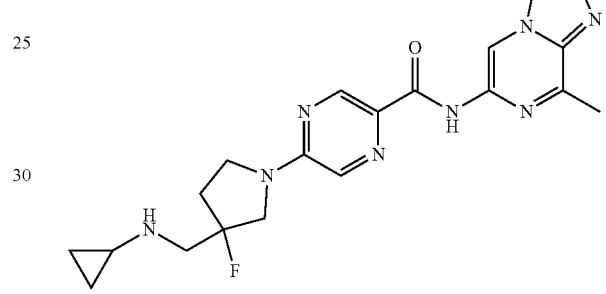
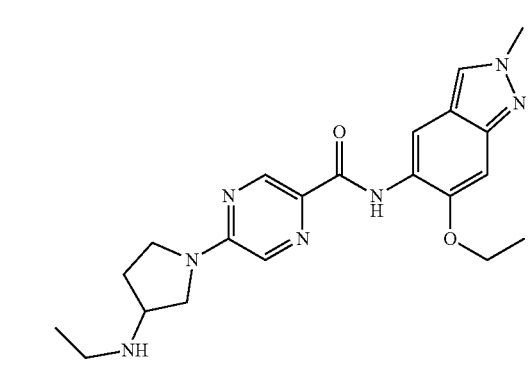 [SMILES: CCNC1CCN(c2cnc(C(=O)Nc3cc4cn(C)nc4cc3OCC)cn2)C1]
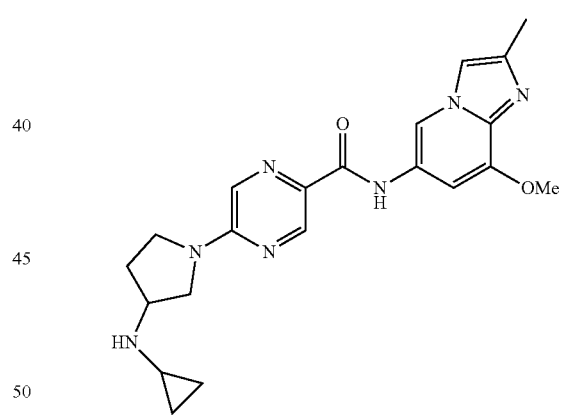
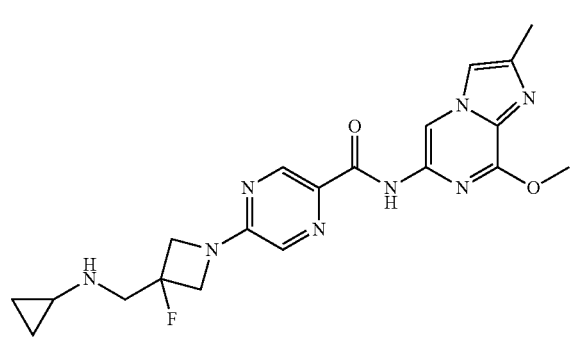 [SMILES: COc1nc(NC(=O)c2cnc(N3CC(F)(CNC4CC4)C3)cn2)cn2cc(C)nc12]
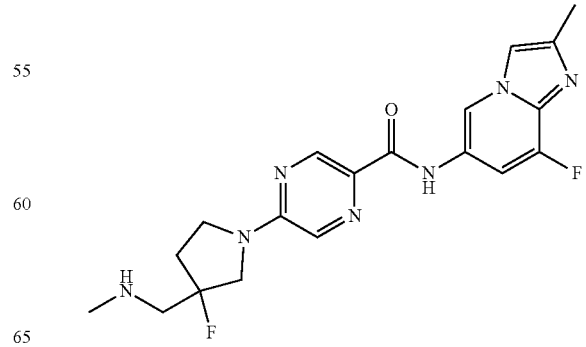

TABLE 1A-continued
Structure
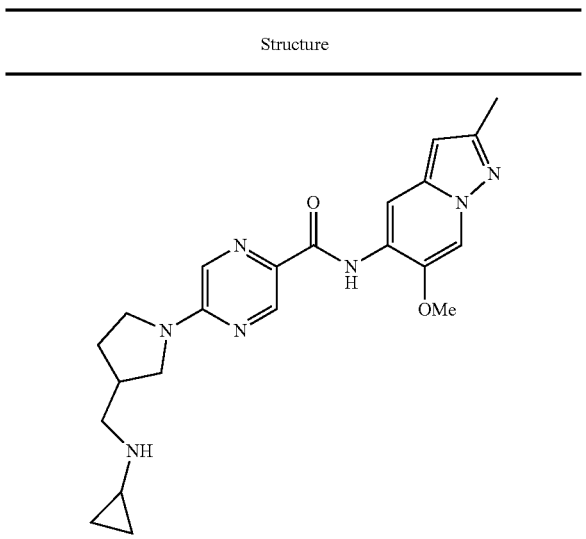
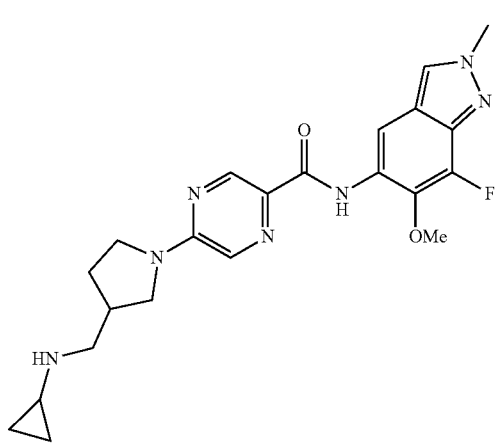 [SMILES: COc1c(NC(=O)c2cnc(N3CCC(CNC4CC4)C3)cn2)cc2cn(C)nc2c1F]
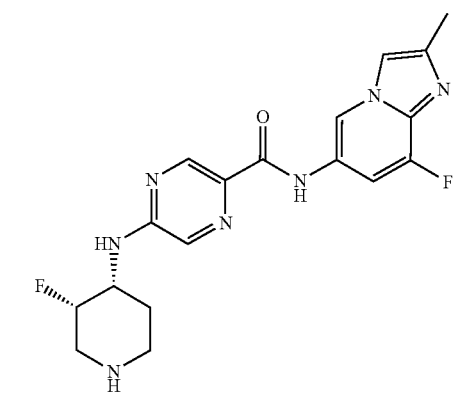 [SMILES: Cc1cn2cc(NC(=O)c3cnc(N[C@@H]4CCNC[C@@H]4F)cn3)cc(F)c2n1]
TABLE 1A-continued
Structure
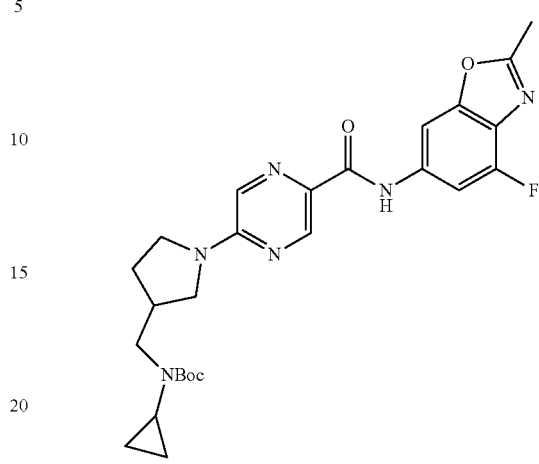
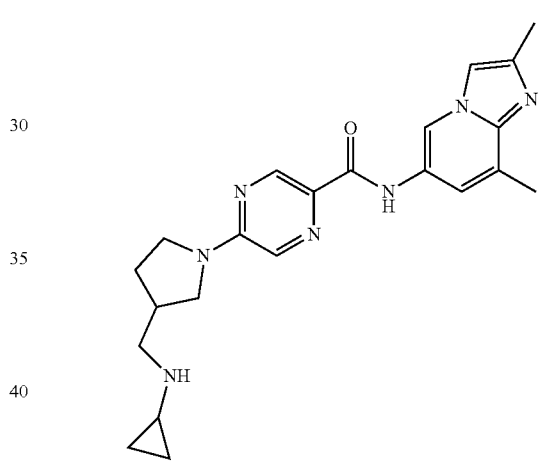
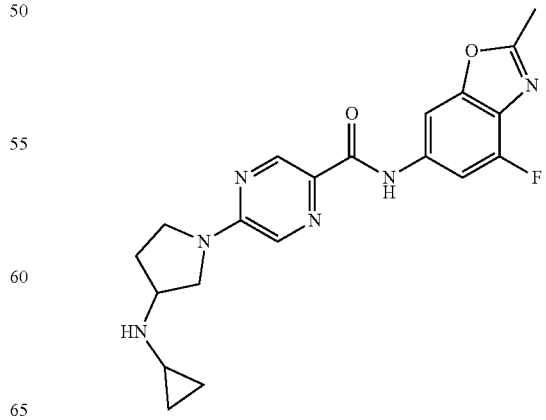

TABLE 1A-continued
Structure
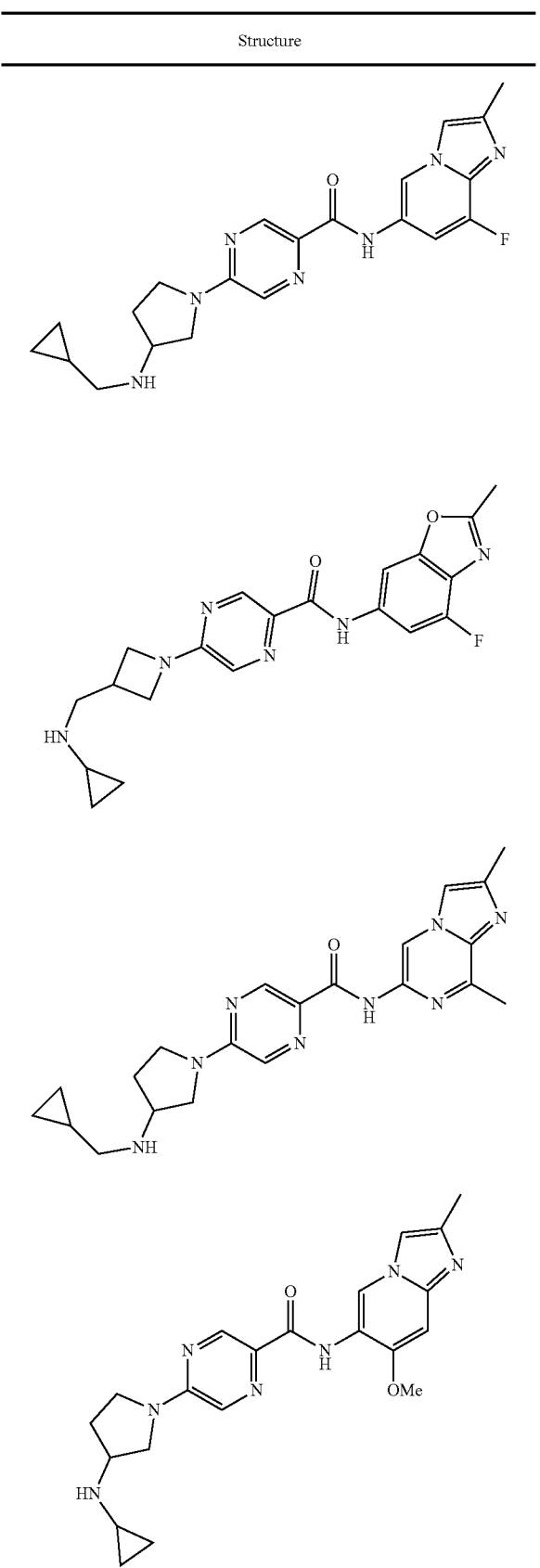
TABLE 1A-continued
Structure
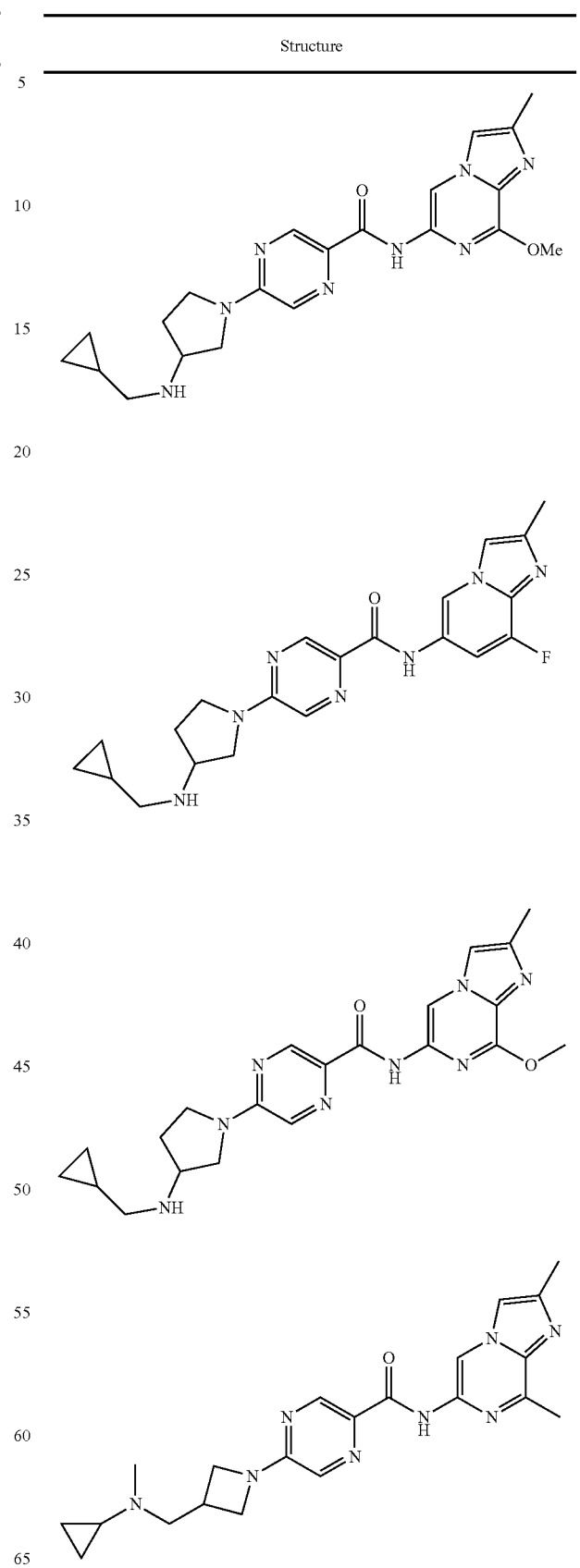

TABLE 1A-continued
Structure
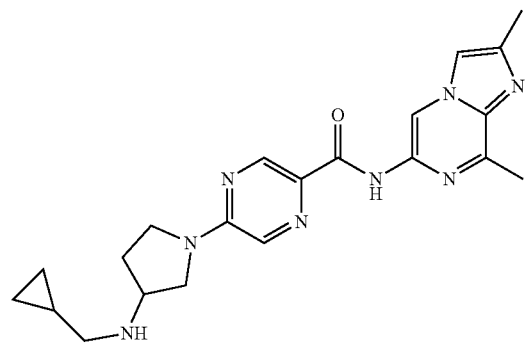 [SMILES: Cc1cn2cc(NC(=O)c3cnc(N4CCC(NCC5CC5)C4)cn3)nc(C)c2n1]
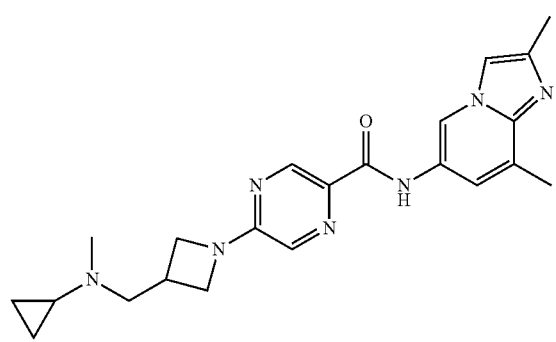 [SMILES: Cc1cn2cc(NC(=O)c3cnc(N4CC(CN(C)C5CC5)C4)cn3)cc(C)c2n1]
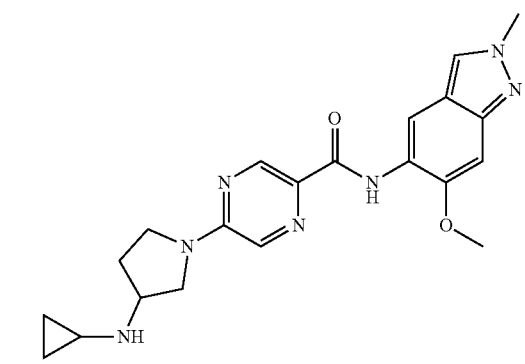 [SMILES: COc1cc2nn(C)cc2cc1NC(=O)c1cnc(N2CCC(NC3CC3)C2)cn1]
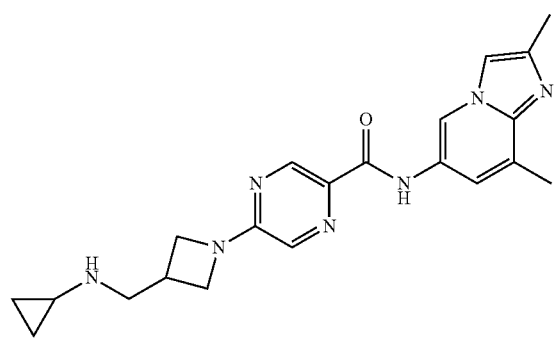 [SMILES: Cc1cn2cc(NC(=O)c3cnc(N4CC(CNC5CC5)C4)cn3)cc(C)c2n1]
TABLE 1A-continued
Structure
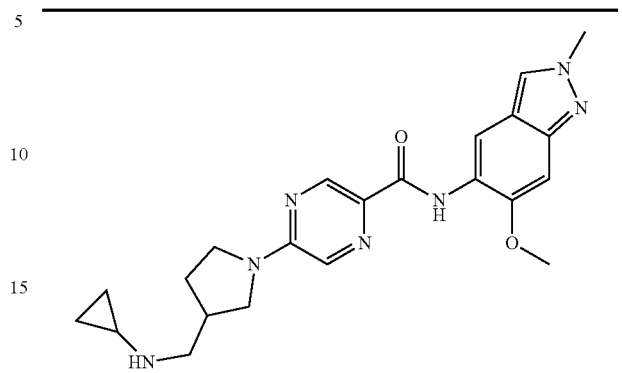
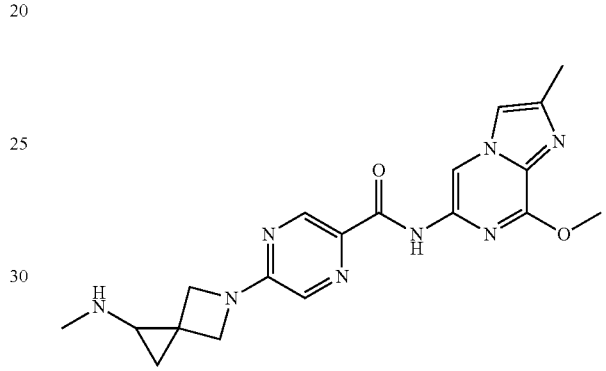
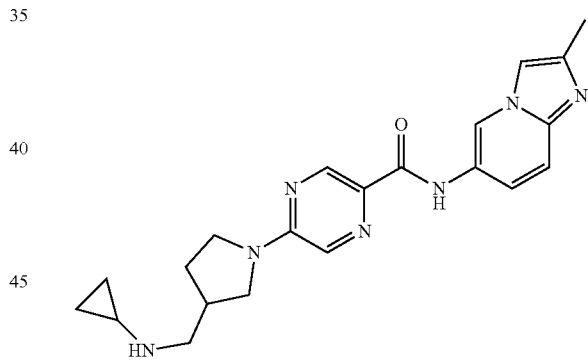
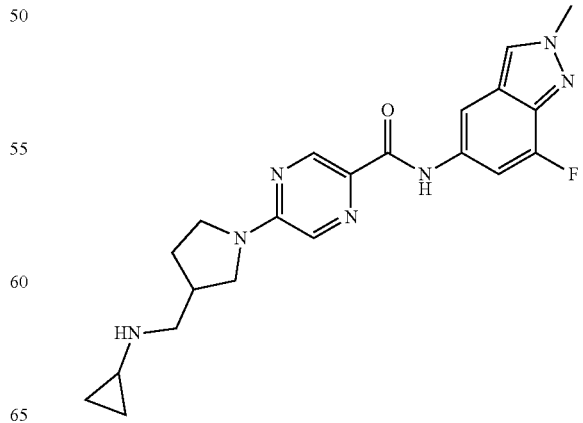

TABLE 1A-continued
Structure
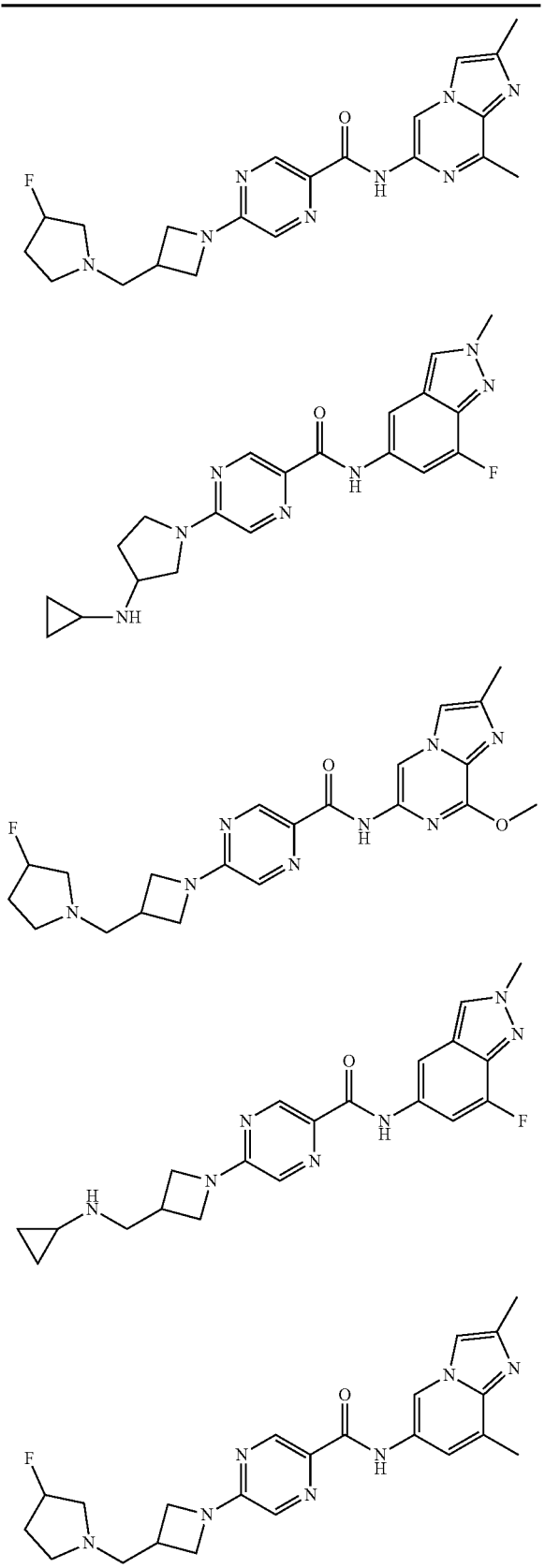
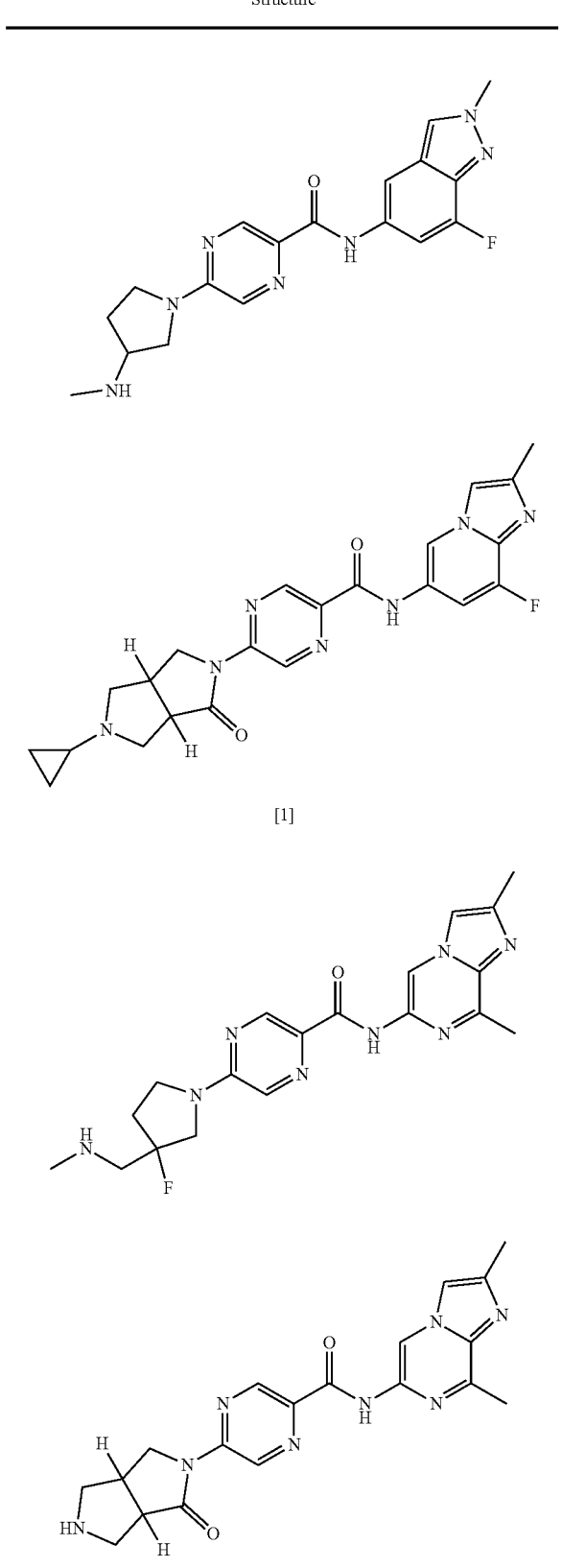
[1]

TABLE 1A-continued
Structure
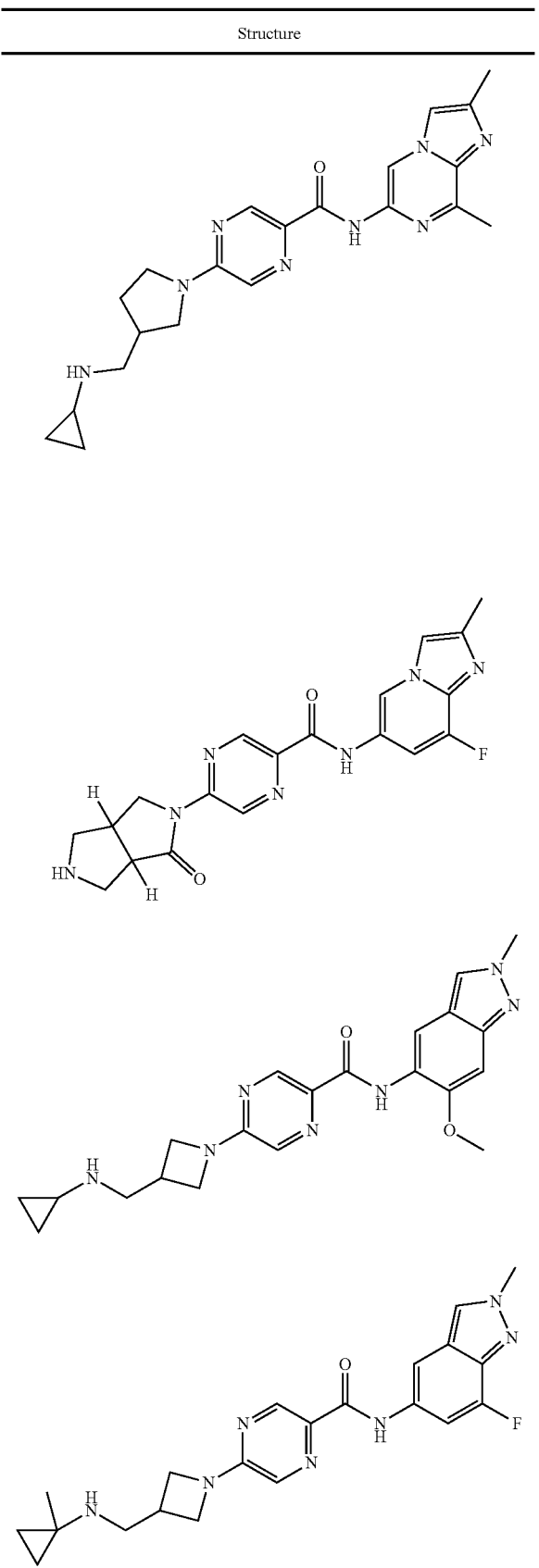
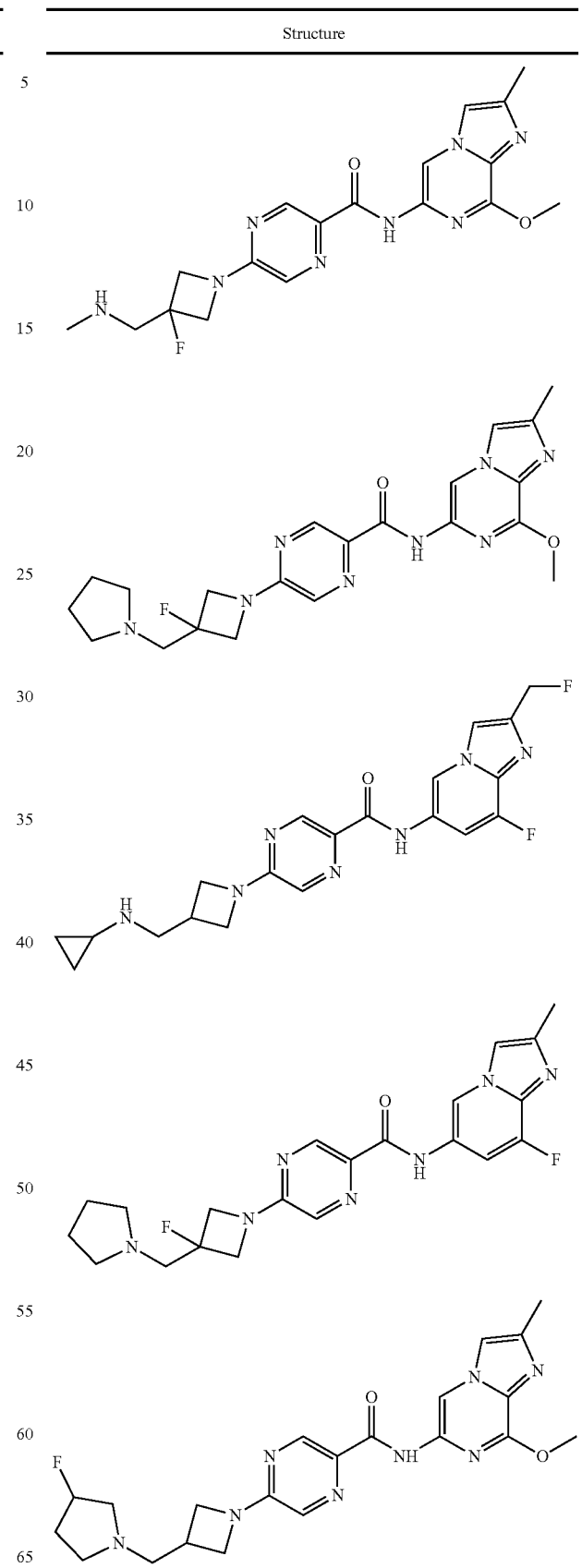

TABLE 1A-continued
Structure
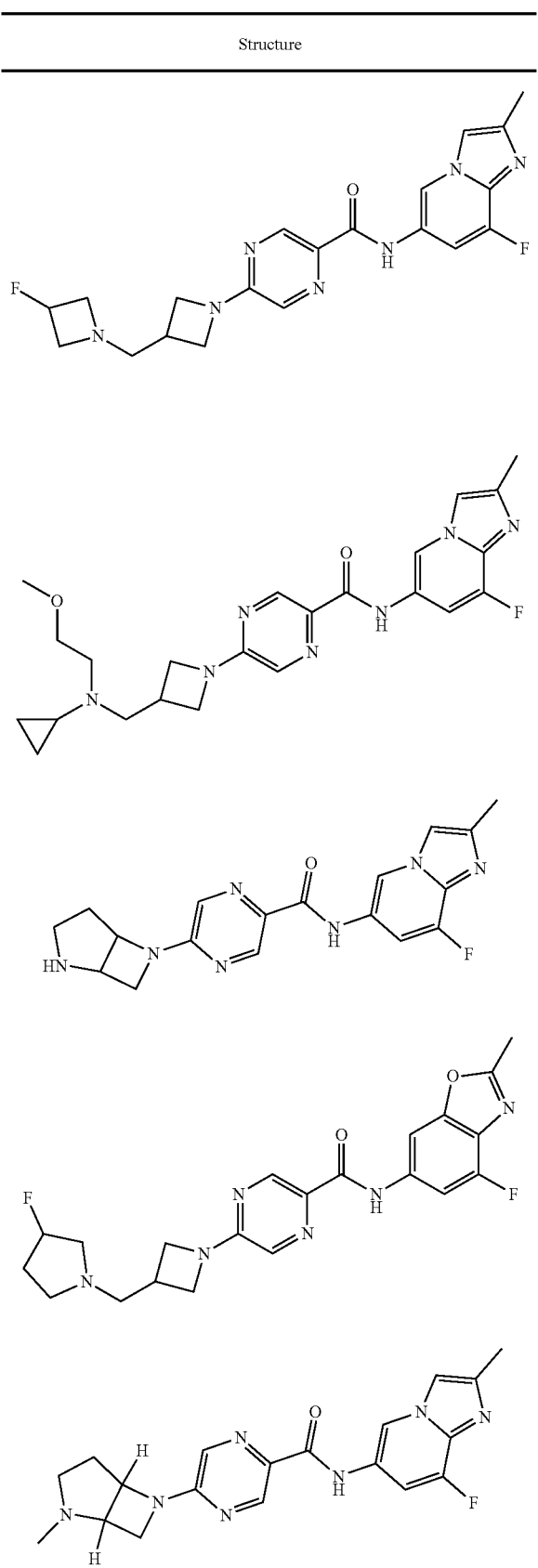
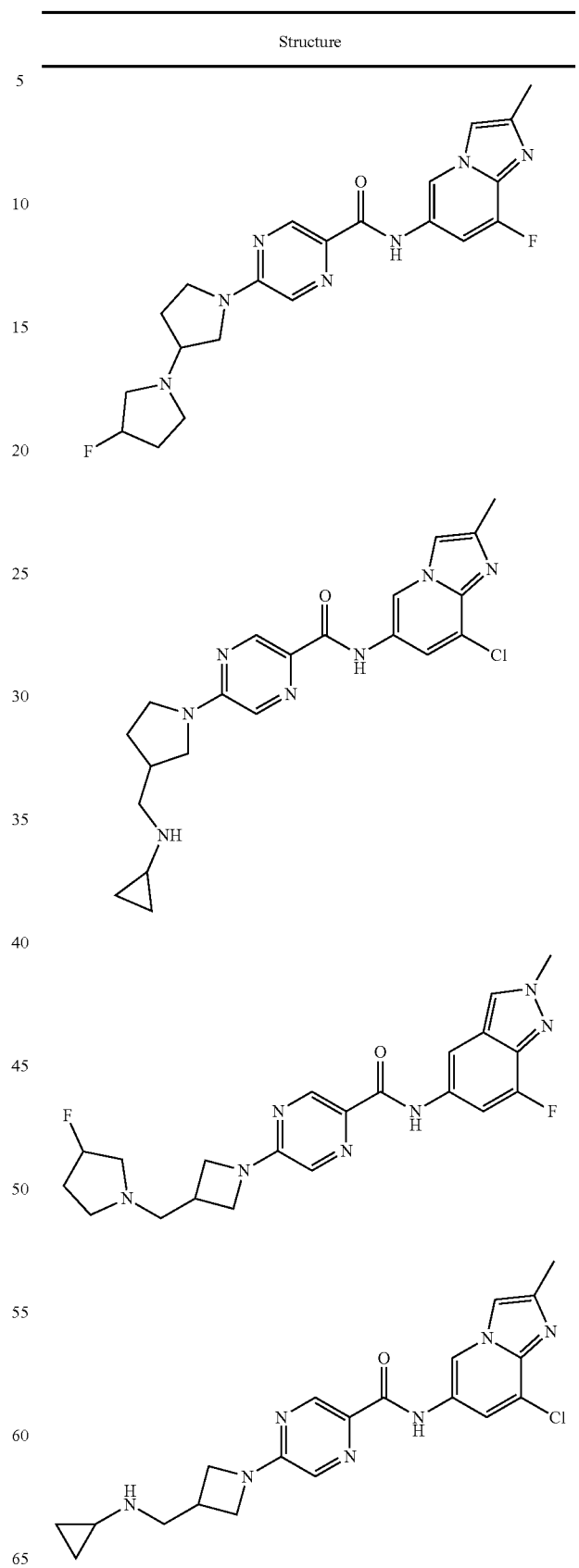

TABLE 1A-continued
Structure

TABLE 1A-continued
Structure
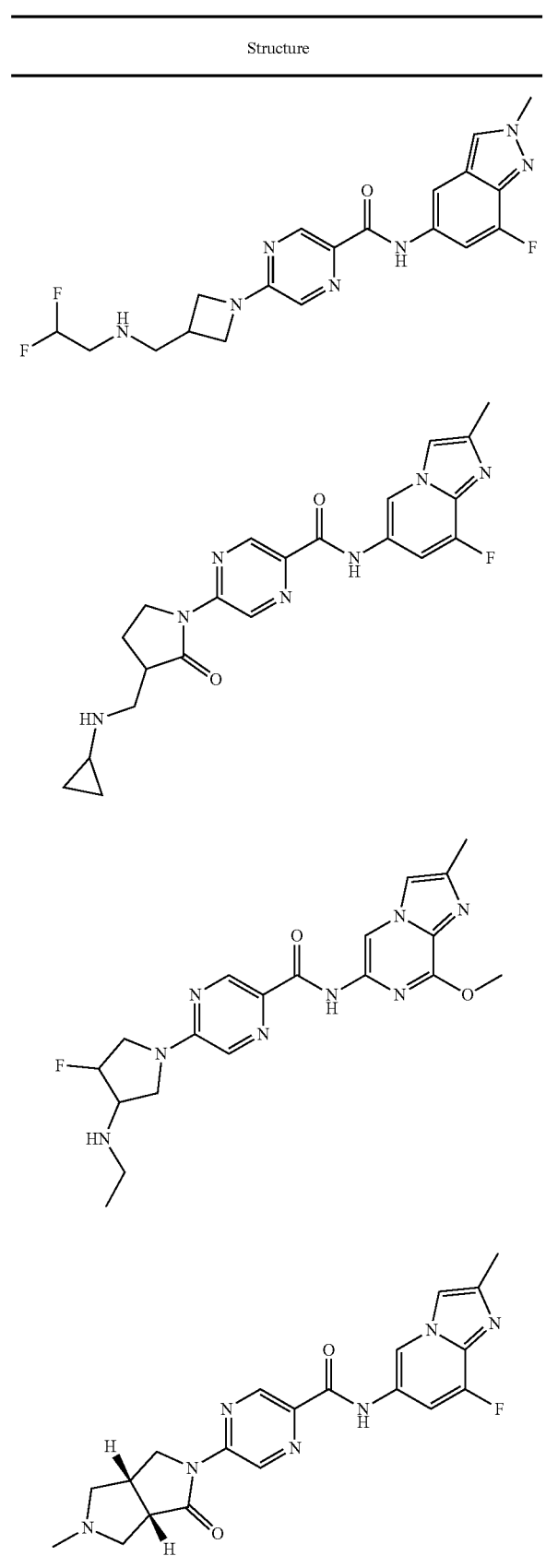

TABLE 1A-continued

Structure

TABLE 1A-continued

Structure

TABLE 1A-continued
| Structure |
|---|
| 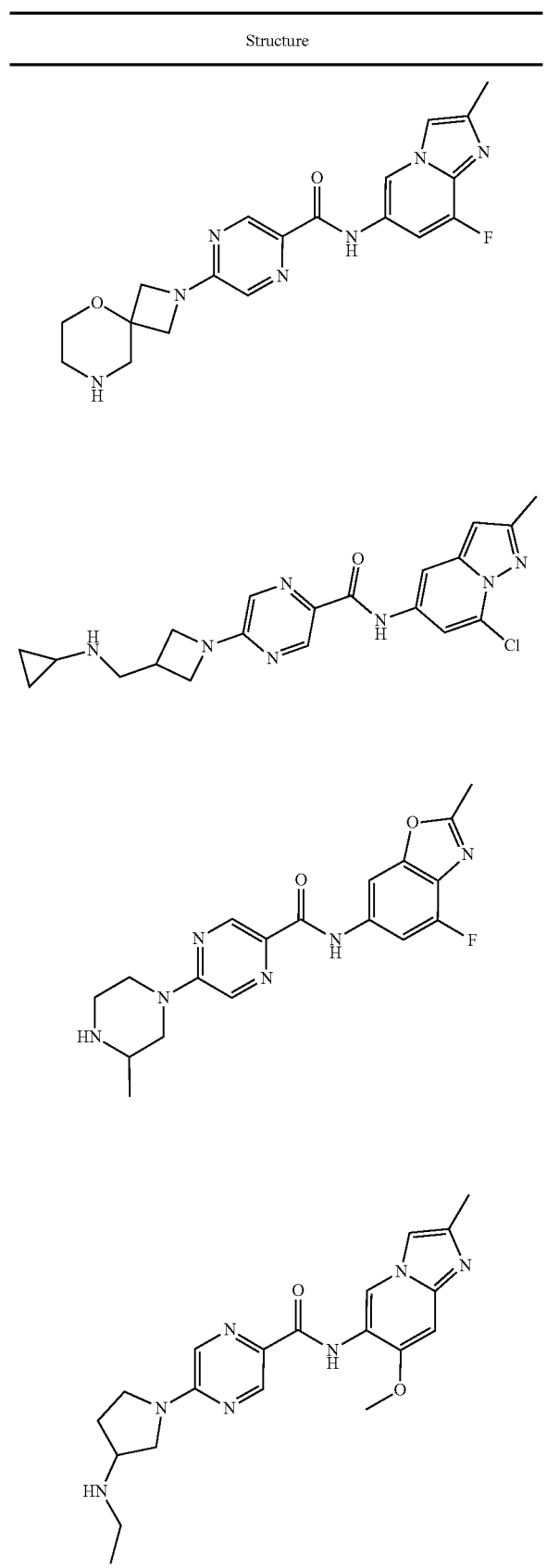 |
TABLE 1A-continued
| Structure |
|---|
| 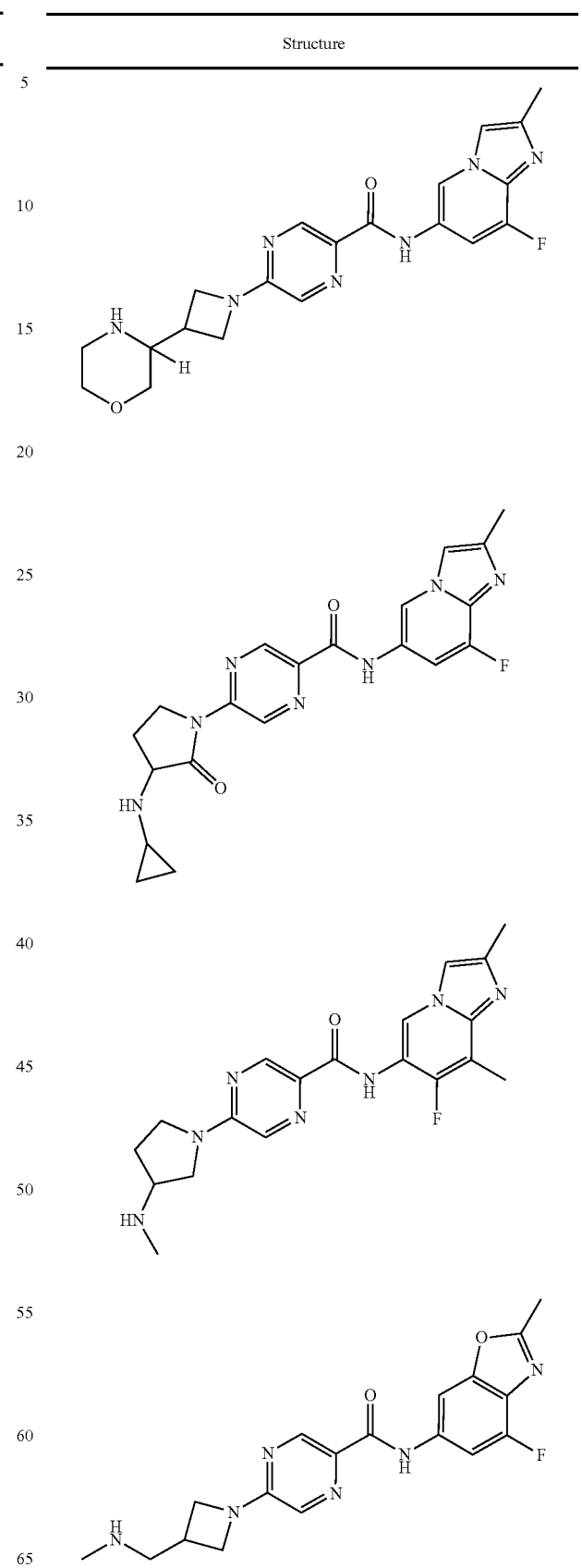 |

TABLE 1A-continued
Structure
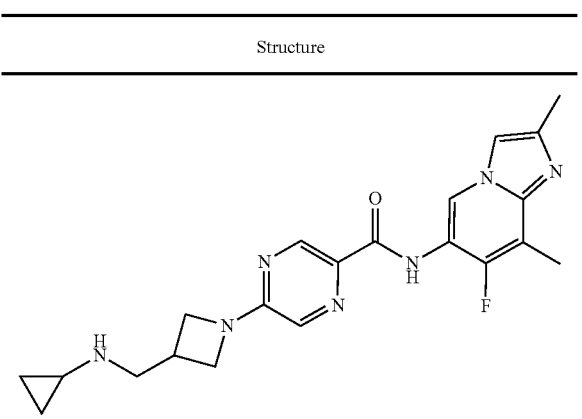
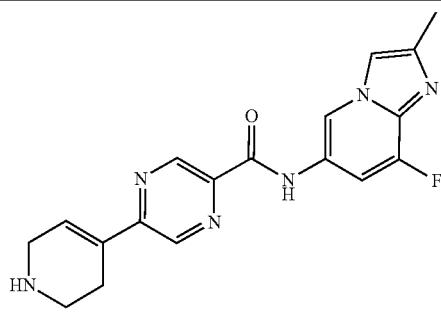
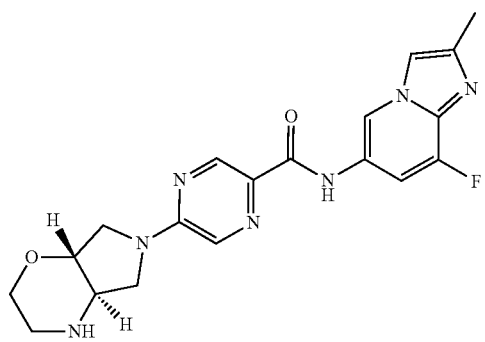
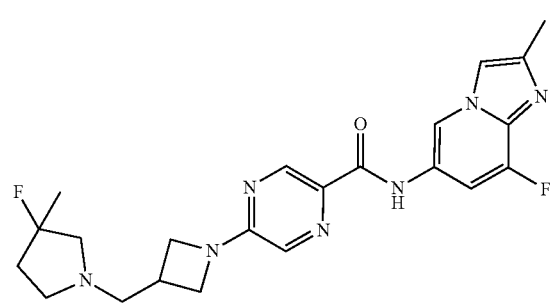 [SMILES: Cc1cn2cc(NC(=O)c3cnc(N4CC(CN5CCC(C)(F)C5)C4)cn3)cc(F)c2n1]
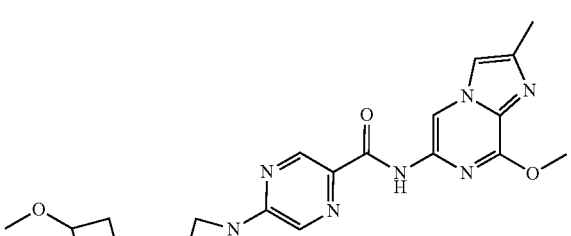
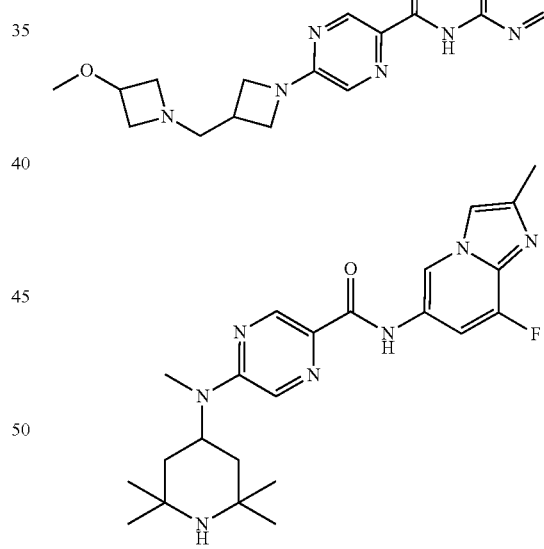
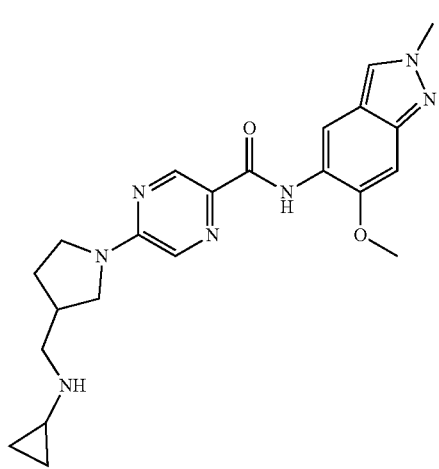 [SMILES: COc1cc2nn(C)cc2cc1NC(=O)c1cnc(N2CCC(CNC3CC3)C2)cn1]
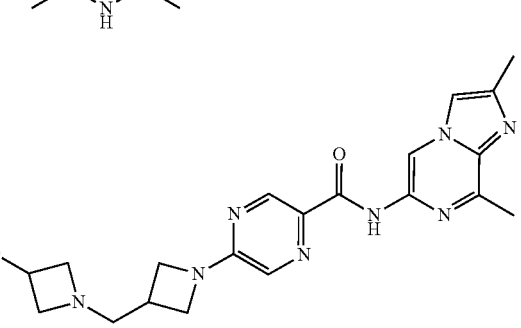

TABLE 1A-continued
| Structure |
|---|
| 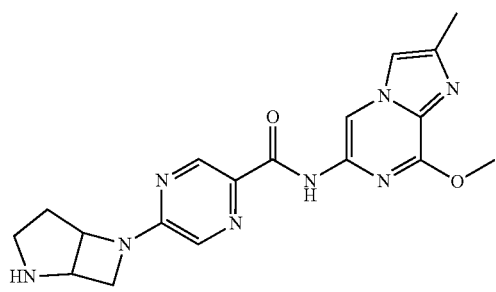 [SMILES: COc1nc(NC(=O)c2cnc(N3CC4NCCC43)cn2)cn2cc(C)nc12] |
| 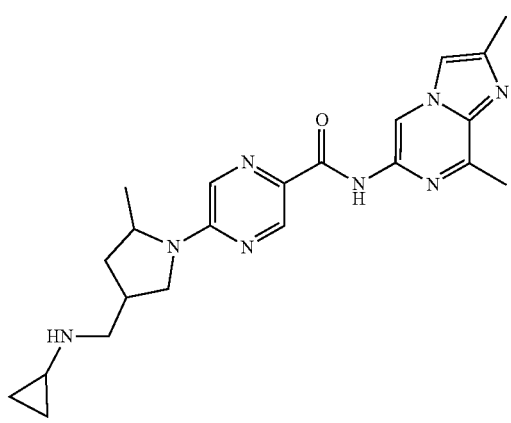 [SMILES: Cc1cn2cc(NC(=O)c3cnc(N4CC(CNC5CC5)CC4C)cn3)nc(C)c2n1] |
| 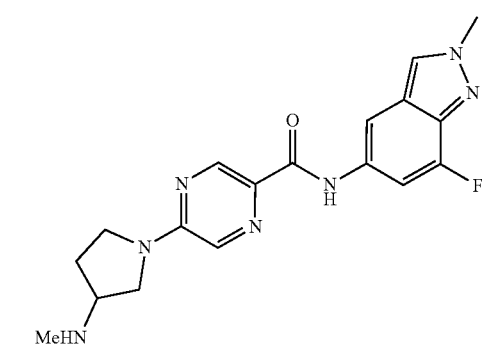 [SMILES: CNC1CCN(c2cnc(C(=O)Nc3cc(F)c4nn(C)cc4c3)cn2)C1] |
| 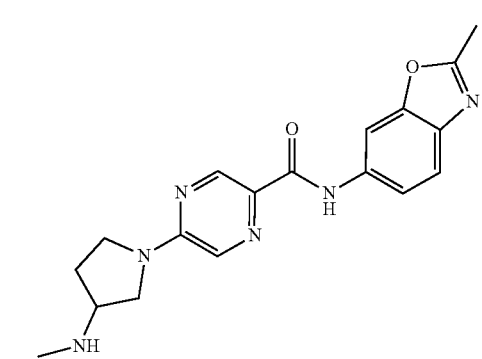 |
TABLE 1A-continued
| Structure |
|---|
| 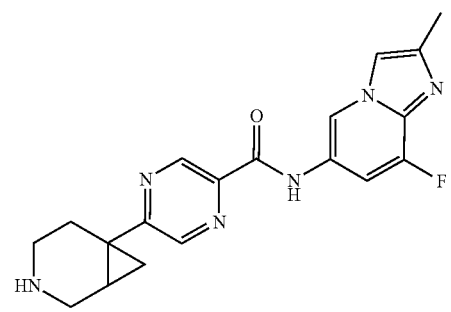 [SMILES: Cc1cn2cc(NC(=O)c3cnc(C45CCNCC4C5)cn3)cc(F)c2n1] |
| 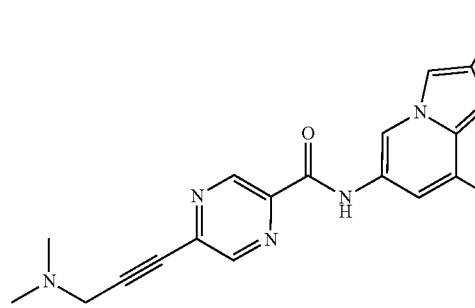 |
| 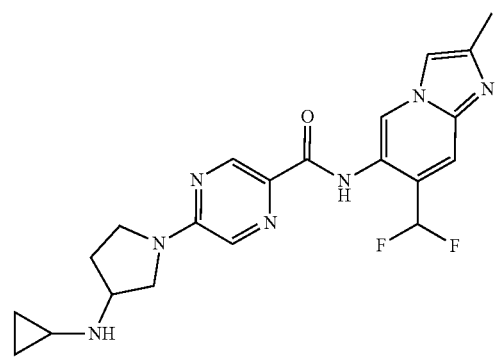 [SMILES: Cc1cn2cc(NC(=O)c3cnc(N4CCC(NC5CC5)C4)cn3)c(C(F)F)cc2n1] |
| 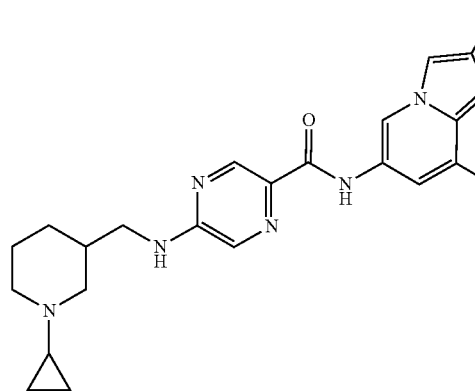 |

TABLE 1A-continued

Structure

[Chemical structures shown]

Indications and Treatment Methods

A compound described herein may be useful for treating a disease or condition mediated, at least in part, by a protein implicated in neurodegenerative disease. In some embodiments, a compound described herein is useful for detecting diseases or conditions mediated, at least in part, by HTT protein. In some embodiments, treatment of a disease or condition mediated, at least in part, by a protein implicated in neurodegenerative disease may comprise administration of a compound described herein. Treatment may include coadministration of a compound described herein and one or more other active agents and/or therapies.

In some embodiments, provided is a method of treating or preventing a disease or condition mediated, at least in part, by a protein implicated in neurodegenerative disease in a patient in need thereof, comprising administering to the patient a therapeutically effective amount of a compound described herein.

Exemplary diseases or conditions are as follows.

Huntington's Disease (HD)

Huntington's disease (HD) is an inherited progressive neurodegenerative condition, characterized by motor, cognitive, and psychiatric deficits as well as neurodegeneration and brain atrophy. Atrophy may begin in the striatum and cortex and extend to other subcortical brain regions. HD belongs to a family of neurodegenerative diseases in which an expanded CAG repeat tract results in long stretches of polyglutamine (polyQ) in an encoded protein. The family also includes dentatorubral-pallidoluysian atrophy (DRPLA), spinal and bulbar muscular atrophy (SBMA) and the spinocerebellar ataxias (SCAs). In HD, the selective neurodegeneration of the γ-aminobutyric acid-releasing spiny-projection neurons of the striatum had been observed, although neuron loss in many other brain regions has also been reported. Symptoms of HD include loss of motor control, psychiatric symptoms, memory and/or cognitive impairment.

Huntingtin protein (HTT protein) is a 348-kDa multidomain protein that contains a polymorphic glutamine/proline-rich domain at its amino-terminus. The number of CAG repeats in the $IT_{15}$ gene that encodes them varies from 6 to 35 in healthy individuals; repeats of 36 or more define an HD allele. The length of the CAG expansion has been inversely correlated with age of disease onset, with cases of juvenile onset characterized by expansions of more than 60 repeats. Reduced penetrance is seen between 36 and 39 repeats. See McColgan P, et al., Huntington's disease: a clinical review, Eur. J. Neurology, 2017, Vol. 25, 24-34, which is incorporated by reference herein in its entirety. The longer polyQ domain is believed to induce conformational changes in the HTT protein, which causes it to form intracellular aggregates that, in many, manifest as nuclear inclusions. However, aggregates can also form outside the nucleus. HTT protein is present in the nucleus, cell body, dendrites and nerve terminals of neurons, and is also associated with a number of organelles including the Golgi apparatus, endoplasmic reticulum and mitochondria.

A diagnosis of Huntington's disease is based on a confirmed family history or positive genetic test and the onset of motor disturbance as defined by the Unified HD Rating Scale (UHDRS) total motor score (TMS) diagnostic confidence score. This score ranges from 0 (no motor abnormalities suggestive of HD) to 4 (≥99% to be due to HD), with a score of 4 defining motor onset or 'manifest' HD. However, subtle motor, cognitive and psychiatric deficits can be identified up to 10-15 before the onset of manifest disease and this is referred to as the pre-manifest stage of the disease.

Huntington's disease (HD) stages are described in, e.g., Winder, J. Y. et al., Assessment Scales for Patients with Advanced Huntington's Disease: Comparison of the UHDRS and UHDRS-FAP, Mov Disord Clin Pract. 2018 September-October; 5(5): 527-533, which is incorporated by reference herein in its entirety. HD may be classified as early stage (stage 1 or 2 TFC score), mid stage (stage 3 TFC score), or late stage (stage 4 or 5 TFC score). See, e.g., Shoulson, I. et al., Huntington disease: Clinical care and evaluation, Neurology, 1979, Vol. 29(1), 1; Shoulson, I., Huntington disease: functional capacities in patients treated with neuroleptic and antidepressant drugs, Neurology, 1981, Vol. 31(10), 1333-35. The part of the brain most affected by HD, and thus believed to be most likely to contain HTT protein abnormalities, is a group of nerve cells at the base of the brain known collectively as the basal ganglia. The basal ganglia organize muscle-driven movements of the body, or "motor movement." The major components of the basal ganglia are the caudate and the putamen (together known as the striatum) and the globus pallidus (external and internal regions). The substantia nigra and the subthalamic nucleus are often included as part of the basal ganglia as well.

Basal ganglia are a group of subcortical nuclei responsible primarily for motor control, as well as other roles such as motor learning, executive functions and behaviors, and emotions. Disruption of the basal ganglia network are believed to contribute to several movement disorders. Normal function of the basal ganglia requires fine tuning of neuronal excitability within each nucleus to determine the degree of movement facilitation or inhibition at any given moment. This is mediated by the complex organization of the striatum, where the excitability of medium spiny neurons is controlled by several pre- and postsynaptic mechanisms as well as interneuron activity, and secured by several recurrent or internal basal ganglia circuits. The motor circuit of the basal ganglia has two entry points, the striatum and the subthalamic nucleus, and an output, the globus pallidus pars interna, which connects to the cortex via the motor thalamus.

A compound described herein, when administered to a subject, may inhibit neuron degeneration. In some embodiments, inhibiting neuron degeneration may include inhibiting axon or neuron degeneration in a neuron. Such inhibition with respect to the entire neuron or a portion thereof, such as the neuron cell body, axons and dendrites. This can be assessed, for example, by analysis of neurological function according to methods known in the art.

The administration of a compound described herein may result in a rescue, for example, at least a 10% reduction (e.g., at least 15%, 20%, 25%, 30%, 35%, 40%, 45%, 50%, 55%, 60%, 65%, 70%, 75%, 80%, 85%, 90% or 100%) in one or more symptoms of a disease or condition described herein. The disease or condition may be a disorder of the nervous system that is secondary to a disease, condition, or therapy having a primary effect outside of the nervous system; an injury to the nervous system caused by physical, mechanical or chemical trauma; autoimmune neural degeration; neurodegeneration secondary to infection; and/or ocular neurodegeneration. Symptoms of nerve degeneration include, e.g., tremors, slowness of movement, ataxia, loss of balance, depression, decreased cognitive function, short term memory loss, long term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity.

The administration of a compound described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or 100%) in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the compounds described herein.

Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment according to the disclosure include cerebellar granule neurons, dorsal root ganglion neurons, PNS neurons (e.g. sensory neurons), and cortical neurons. Other examples of cell types that may be subject to treatment according to the disclosure include astrocytes and microglia.

A neurodegenerative disease is a disease or condition in which the function of a subject's nervous system becomes impaired. Examples of neurodegenerative diseases include, e.g., Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion disease, Refsum's disease, Sandhoff disease, Schilder's disease, Subacute combined degeneration of spinal cord secondary to Pernicious Anaemia, Schizophrenia, Spinocerebellar ataxia, Spinal muscular atrophy, Steele-Richardson-Olszewski disease, insulin resistance or Tabes dorsalis.

In some embodiments, the disease or condition is selected from Huntington's disease (HD), dentatorubropallidoluysian atrophy, spinal and bulbar muscular atrophy, spinocerebellar ataxia, spinal cord and/or brain injury, chronic pulmonary hypertension, Parkinson's disease, amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, nephropathy (non-hypertensive), hypertensive nephropathy, hypertension (high blood pressure), optic nerve lesion, hepatic fibrosis, lupus, liver failure after transplant, encephalomyelitis, epilepsy, and glioblastoma.

Further, the compounds described herein can be used in the prevention or treatment of memory loss. Types of memory that can be affected by loss, and thus treated according to the disclosure, include episodic memory, semantic memory, short-term memory, and long-term memory.

In some embodiments, the disease or condition is a neurodegenerative disease selected from Alzheimer's disease, amyotrophic lateral sclerosis, Huntington's disease, Parkinson's disease, Prion disease and spinocerebellar ataxias. In some embodiments, the neurodegnerative disease is classified as a trinucleotide repeat disorder. In some embodiments, the trinucleotide repeat disorder is classified as belonging to Category I, Category II, or Category III.

In some embodiments, the neurodegenerative disease is Huntington's disease.

Also provided is use of a compound described herein for the manufacture of a medicament for use in diagnosis, prevention, or treatment of a disease or condition described herein. For example, the disease or condition may be Huntington's disease.

Pharmaceutical Compositions and Administration Thereof

Compounds provided herein may be administered in the form of a pharmaceutical composition. Thus, provided herein are also pharmaceutical compositions that contain a compound described herein and a pharmaceutically acceptable excipient.

Suitable pharmaceutically acceptable excipients may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical composition may be formulated for administration by various methods including, for example, oral, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

The pharmaceutical composition may be formulated for administration by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical excipients.

The pharmaceutical composition may be in the form of a sterile injectable aqueous or oleaginous suspension. This suspension may be formulated according to the known art using suitable dispersing or wetting agents and suspending agents. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables. Such solutions may be formulated as 0.01%-10% isotonic solutions, pH 5-7, with appropriate salts.

The compound described herein may be administered parenterally in a sterile medium. Parenteral administration includes subcutaneous injections, intravenous, intramuscular, intrathecal injection or infusion techniques. The compound described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

A pharmaceutical composition, for example, for injection, may comprise a cyclodextrin. The cyclodextrin may be, for example, a hydroxypropyl cyclodextrin or a sulfobutylether cyclodextrin. The cyclodextrin may be, for example, an α-cyclodextrin, a β-cyclodextrin, or a γ-cyclodextrin.

A compound described herein may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples can be found, e.g., in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

The pharmaceutical composition may be formulated for oral administration. The pharmaceutical composition may be in the form of, for example, a capsule or a tablet. The oral formulation may include an enteric coating. In making the pharmaceutical composition the compound described herein is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include, e.g., lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup and methyl cellulose. The pharmaceutical composition can additionally include lubricating agents such as talc, magnesium stearate and mineral oil; wetting agents; emulsifying and suspending agents; preserving agents such as methyl and propylhydroxy-benzoates; sweetening agents; and flavoring agents.

The pharmaceutical composition can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. Such patches may be constructed for continuous, pulsatile, or on demand delivery of pharmaceutical agents.

For preparing solid compositions such as tablets, the compound described herein may be mixed with a pharmaceutical excipient to form a solid preformulation composition containing a homogeneous mixture. When referring to these preformulation compositions as homogeneous, the compound may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the intestine, or to be delayed in release. A variety of materials can be used for such enteric layers or coatings, such materials including a number of polymeric acids and mixtures of polymeric acids with such materials as shellac, cetyl alcohol and cellulose acetate.

The compound described herein can be incorporated into oral liquid preparations such as aqueous or oily suspensions, solutions, emulsions, syrups, or elixirs, for example. Furthermore, pharmaceutical compositions containing the compound described herein can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monooleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

A compound described herein, or a pharmaceutical composition thereof, may be administered in an appropriate dose as determined by an informed medical practitioner. The compound or pharmaceutical composition may be administered in a single dosage or in multiple dosages, and in a single dosage form or in a plurality of dosage forms (e.g., two tablets or three capsules). For any particular subject, an appropriate dose will depend upon a variety of factors including the activity of the specific compound employed, the age, body weight, general health, sex, diet, time of administration, route of administration, rate of excretion, active agents used in combination, and the severity of the particular disease or condition, of the subject. For example, a dose may be expressed as a number of milligrams of a compound described herein per kilogram of the subject's body weight (mg/kg) per day. A dose of about 0.1 to about 150 mg/kg may be appropriate. In some embodiments, a dose of about 0.1 to about 100 mg/kg may be appropriate. In some embodiments, a dose of from about 0.0001 to about 100 mg per kg of body weight per day, from about 0.001 to about 50 mg of compound per kg of body weight, or from about 0.01 to about 10 mg of compound per kg of body weight may be appropriate. In some embodiments, a dose may be administered in multiple administrations per day, for example, in one administration per day, two administrations per day, or three administrations per day. In some embodiments, a dose may be administered once in two days, once in three days, once in four days, or once per week. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

Kits

Also provided herein are kits that include a compound described herein and suitable packaging. In certain embodiments, a kit further includes instructions for use. In one aspect, a kit includes a compound described herein, and a label and/or instructions for use of the compound in the treatment of a disease or condition described herein.

Also provided herein are articles of manufacture that include a compound described herein in a suitable container. The container may be a vial, jar, ampoule, preloaded syringe and/or intravenous bag.

Combination Therapy

In some embodiments, a compound described herein is administered in combination with one or more additional active agents.

The methods described herein include methods for detecting, treating or preventing a disease or condition described herein, for example, Huntington's disease, comprising administering to a subject, simultaneously or sequentially, a compound described herein and one or more additional active agents. In methods using simultaneous administration, the agents can be present in a combined composition or can be administered separately. When used in combination with one or more additional active agents, a compound described herein may be administered prior to, concurrently with, or following administration of the additional active agents. The administration can be by the some route or by different routes.

Also provided is a pharmaceutical composition comprising a compound described herein and one or more additional pharmaceutical agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. Similarly, also provided is a packaged pharmaceutical composition containing a pharmaceutical composition comprising a compound described herein, and another composition comprising one or more additional pharmaceutical agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. In some embodiments, the active agent is carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, or risperidone.

Also provided are methods for treating or preventing Alzheimer's disease, including treating memory and/or cognitive impairment associated with Alzheimer's disease, comprising administering to a subject, simultaneously or sequentially, a compound described herein and one or more additional agents. In some embodiments, the active agent is Reminyl®, Cognex®, Aricept®, Exelon®, Akatinol®, Neotropin™, Eldepryl®, Estrogen or Clioquinol.

In some embodiments, compounds described herein can be administered with an active agent for treating Parkinson's disease, for example, with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In some embodiments, compounds described herein can be administered with an active agent for treating Alzheimer's disease, for example, with acetylcholinesterase inhibitors (e.g., donepezil, galantamine, and rivastigmine) and/or NMDA receptor antagonists (e.g., memantine).

Synthesis of the Compounds

A compound described herein may be prepared using the methods disclosed herein and routine modifications thereof, which will be apparent given the disclosure herein and methods well known in the art. Conventional and well-known synthetic methods may be used in addition to the teachings herein. The synthesis of a typical compound described herein may be accomplished as described in the following examples. If available, reagents may be purchased commercially, e.g., from Sigma Aldrich or other chemical suppliers.

A compound described herein can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006), Greene's protective groups in organic synthesis. Hoboken, N.J., Wiley-Interscience, and references cited therein.

Furthermore, a compound described herein may contain one or more asymmetric ("chiral") centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, supercritical fluid chromatography, chiral resolving agents, and the like. When enantiomerically pure or enriched compounds are desired, chiral chromatography and/or enantiomerically pure or enriched starting materials may be employed as conventionally used in the art or as described in the Examples.

The starting materials for the following reactions are generally known compounds or can be prepared by known procedures or obvious modifications thereof. For example, many of the starting materials are available from commercial suppliers such as Sigma Aldrich, Alfa Aesar, and the like. Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" and "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Generally, the term inert, as used herein with respect to a solvent, refers to a material that does not undergo reaction to form the target compound of interest though carbon-carbon bond forming reactions. Unless specified to the contrary, the solvents used in the reactions of the present disclosure are inert organic solvents, and the reactions are carried out under an inert gas, preferably nitrogen or argon.

The term "q.s." means adding a quantity sufficient to achieve a stated function, e.g., to bring a solution to the desired volume (i.e., 100%).

It will also be appreciated that in each of the below schemes, the addition of any substituent may result in the production of a number of isomeric products (including, but not limited to, enantiomers or one or more diastereomers) any or all of which may be isolated and purified using conventional techniques.

Incorporation of an isotopical label, e.g., a deuterium atom, into a compound described herein may be conducted by reacting an appropriate starting material(s) with a reagent including a radioactive isotope. Methods typically follow the same principles as standard organic chemical reactions, and may be carried out by any method known to those of skill in the art, including those provided in the present disclosure.

Scheme 1 provides exemplary synthetic routes for the synthesis of compounds provided herein (e.g., compounds of Formula I). The compounds of Formula I, or other formulas or compounds disclosed herein, are typically prepared by first providing Formulas Va and Vb and then attaching the desired substituents using suitable conditions (e.g., amide bond formation, nucleophilic aromatic substitution, or cross coupling).

In some embodiments, synthesis of a compound of Formula I proceeds according to Scheme 1. Synthesis of a compound of Formula I may proceed by coupling Compound Va with Compound Vb to form Compound Vc, coupling Compound Vc with Compound Vd, and preparing a compound of Formula I by one or more subsequent steps.

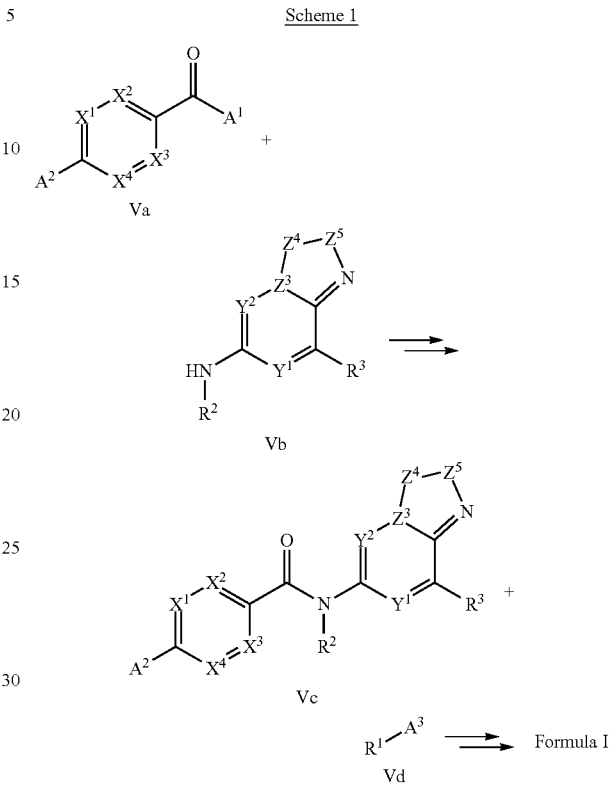

Scheme 1

In Scheme 1, $R^1$, $R^2$, $R^3$, $X^1$, $X^2$, $X^3$, $X^4$, $Y^1$, and $Y^2$ are as defined herein. $A^1$, $A^2$, and $A^3$ are as defined below, and $Z^3$—$Z^4$-$Z^5$ is N—$CR^7$=$CR^8$ or C=$CR^7$—$NR^{10}$.

In Scheme 1, Compound Va may be joined with Compound Vb by amide bond formation through a leaving group at $A^1$ and an amine in Compound Vb (as shown in Scheme 1). $A^1$ may be a suitable leaving group such as, for example, a halide, a pseudohalide, a carboxylic acid or carboylate. Compound Va may be activated at $A^1$ by an activating agent for activating a carboxylate group (e.g., chloro-N,N,N',N'-tetramethylformamidinium hexafluorophosphate, HATU, HBTU), optionally in the presence of a base (e.g., 1-methylimidazole, triethylamine, diisopropylethylamine), and in a suitable solvent (e.g., a polar aprotic solvent such as acetonitrile, DMF, or dichloromethane). Alternatively, a carboxylate at $A^1$ may be first activated by an activating agent (e.g., oxalyl chloride) and then combined with Compound Vb in the presence of a base (e.g., triethylamine, diisopropylethylamine). In such embodiments, an activated form of Compound Va (e.g., where $A^1$ is a halide such as a chloride) need not be isolated, and the reaction can be conducted in one pot.

In Scheme 1, a compound of Formula I may be prepared. Thus, Compound Vc may be joined with Compound Vd in a coupling reaction, e.g., by nucleophlic addition such as nucleophilic aromatic substitution to Compound Vc at $A^2$. In such embodiments, $A^2$ may be a suitable leaving group (e.g., a halide such as a chloride or a fluoride, or a pseudohalide such as a sulfonyl), and $A^3$ may be a hydrogen atom or, where $R^1$ is present as an anion, a cation (e.g., sodium ion, potassium ion). A nucleophilic aromatic substitution may be carried out heated (e.g., to a temperature of 50 to 200° C.)

in the presence of a base (e.g., triethylamine, cesium carbonate, NaH, potassium carbonate, pyridine), and in a suitable solvent (e.g., dioxane, DMF, acetonitrile, DMSO). Alternatively, Compound Vc may be joined with Compound Vd in a coupling reaction (e.g., a metal-catalyzed coupling reaction). In such embodiments, for example, $A^2$ may be a leaving group (e.g., a halide such as a chloride or a bromide, or a pseudohalide such as a sulfonyl), and $R^1$ may comprise a suitable coupling functionality (e.g., a carbon-carbon double bond) and $A^3$ may be a complimentary coupling partner to $A^2$ (e.g., a hydrogen atom or a tin- or boron-containing group). The reaction may be conducted with a catalyst (e.g., bis(triphenylphosphine)palladium(II) dichloride), and optionally in the presence of a base (e.g., sodium carbonate).

In some embodiments, $A^2$ may be $R^1$, and Compound Vc may be converted to a compound of Formula I directly (without reaction with Compound Vd).

In Compound Va, Vb, Vc, and/or Vd, any of $R^1$, $R^2$, $R^3$, $X^1$, $X^2$, $X^3$, $X^4$, $Y^1$, $Y^2$, $Z^4$, and $Z^5$ may be present in a protected form, for example at an amine or hydroxyl group. Amine protecting groups include those known in the art and described herein, including, for example, the tert-butoxycarbonyl group. In such embodiments, an additional step of deprotection may be needed. For example, where the protecting group is a tert-butoxycarbonyl group, an acidic deprotection step (e.g., using HCl in dioxane or TFA) may be needed to prepare the compound of Formula I.

A person of skill in the art will appreciate that any of Compound Va, Vb, Vc, or Vd may be available from a commercial supplier for a particular embodiment. Alternative synthesis of Compound Va, Vb, Vc, or Vd may be as described herein or as known to those of skill in the art.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Analytical Methods

Acidic QC Methods

| AcHSSC18-standard acidic UPLC-MS | | | |
|---|---|---|---|
| Instrumentation MassLynx Files | UPLC + Waters DAD + Waters SQD2, single quadrapole UPLC-MS | | |
| Column | Acquity UPLC HSS C18 1.8 um 100 × 2.1 mm. (Plus guard cartridge), maintained at temp | | |
| Mobile Phase A | Water (High purity via PureLab Option unit) with 0.1% formic acid | | |
| Mobile Phase B | Acetonitrile (Far UV grade) with 0.1% (V/V) formic acid | | |
| Flow | 0.4 mL/min | | |
| Gradient Program | Time (mins) | % A | % B |
| | 0.0 | 95 | 05 |
| | 0.4 | 95 | 05 |
| | 6.0 | 05 | 95 |
| | 6.8 | 05 | 95 |
| | 7.0 | 95 | 05 |
| | 8.0 | 95 | 05 |
| Sample | 0.5-2 uL (concentration~0.2-1 mg/mL). | | |
| Detectors | UV, diode array 210 nm-400 nm Resolution 1.2 nm Other wavelength traces are extracted from the DAD data MS, mass 100-700 (or ~1500 for HM method) in ES+ & ES− (300 μL/min split to MS) | | |

| 10 cm_Formic_AQ-standard acidic UPLC-MS | | | |
|---|---|---|---|
| Instrumentation MassLynx Files | UPLC + Waters DAD + Waters SQD2, single quadrapole UPLC-MS | | |
| Column | Acquity UPLC HSS C18 1.8 um 100 × 2.1 mm. (Plus guard cartridge), maintained at temp | | |
| Mobile Phase A | Water (High purity via PureLab Option unit) with 0.1% formic acid | | |
| Mobile Phase B | Acetonitrile (Far UV grade) with 0.1% (V/V) formic acid | | |
| Flow | 0.5 mL/min | | |
| Gradient Program | Time (mins) | % A | % B |
| | 0.0 | 95 | 05 |
| | 1.2 | 95 | 05 |
| | 3.5 | 0 | 100 |
| | 4.9 | 0 | 100 |
| | 5 | 95 | 05 |
| | 6 | 95 | 05 |

-continued

| 10 cm_Formic_AQ-standard acidic UPLC-MS | |
|---|---|
| Sample | 0.5-2 uL (concentration~0.2-1 mg/mL). |
| Detectors | UV, diode array 210 nm-400 nm Resolution 1.2 nm |
| | Other wavelength traces are extracted from the DAD data |
| | MS, mass 100-700 (or –1500 for HM method) in ES+ & ES– (300 μL/min split to MS) |

| Acidic 1-standard acidic UPLC-MS | | | |
|---|---|---|---|
| Instrumentation | UPLC + Shimadzu SQD2, single quadrapole UPLC-MS | | |
| Column | Phenomenex C18 Kinetex column, 5 μm (4.6 × 150 mm) (Plus guard cartridge), maintained at temp | | |
| Mobile Phase A | Water with 0.1% v/v trifluoroacetic acid | | |
| Mobile Phase B | Acetonitrile with 0.1% v/v trifluoroacetic acid | | |
| Flow | 2.0 mL/min | | |
| Gradient Program | Time (mins) | % A | % B |
| | 0.0 | 95 | 5 |
| | 10.0 | 0 | 100 |
| | 13.0 | 0 | 100 |
| | 14.0 | 95 | 5 |
| Sample | 0.5-2 uL (concentration~0.2-1 mg/mL). | | |
| Detectors | UV, 254 nm and 215 nm | | |
| | MS, mass 100-700 in ES+ & ES– (300 μL/min split to MS) | | |

Basic QC Methods

| BicarbBEHC18-standard basic UPLC-MS | | | |
|---|---|---|---|
| Instrumentation MassLynx Files | UPLC + Waters DAD + Waters SQD2, single quadrupole UPLC-MS | | |
| Column | Acquity UPLC BEH Shield RP18 1.7 um 100 × 2.1 mm. (Plus guard cartridge), maintained at temp | | |
| Mobile Phase A | Water (High purity via PureLab Option unit) with 10 mM ammonium bicarbonate (ammonium hydrogen carbonate) | | |
| Mobile Phase B | Acetonitrile (Far UV grade) | | |
| Flow | 0.4 mL/min | | |
| Gradient Program | Time (mins) | % A | % B |
| | 0.0 | 95 | 05 |
| | 0.4 | 95 | 05 |
| | 6.0 | 05 | 95 |
| | 6.8 | 05 | 95 |
| | 7.0 | 95 | 05 |
| | 8.0 | 95 | 05 |
| Sample | 0.5-2 uL (concentration~0.2 -1 mg/mL). | | |
| Detectors | UV, diode array 210 nm-400 nm Resolution 1.2 nm | | |
| | Other wavelength traces are extracted from the DAD data | | |
| | MS, mass 100-700 (or –1500 for HM method) in ES+ & ES- (300 μL/min split to MS) | | |

| 10 cm_Bicarb_AQ-standard-basic UPLC-MS | | | |
|---|---|---|---|
| Instrumentation MassLynx Files | UPLC + Waters DAD + Waters SQD2, single quadrupole UPLC-MS | | |
| Column | Acquity UPLC BEH Shield RP18 1.7 um 100 × 2.1 mm. (Plus guard cartridge), maintained at temp | | |
| Mobile Phase A | Water (High purity via PureLab Option unit) with 10 mM ammonium bicarbonate (ammonium hydrogen carbonate) | | |
| Mobile Phase B | Acetonitrile (Far UV grade) | | |
| Flow | 0.5 mL/min | | |
| Gradient Program | Time (mins) | % A | % B |
| | 0.0 | 95 | 05 |
| | 1.2 | 95 | 05 |
| | 3.5 | 0 | 100 |
| | 4.9 | 0 | 100 |
| | 5 | 95 | 05 |
| | 6 | 95 | 05 |
| Sample | 0.5-2 uL (concentration~0.2-1 mg/mL). | | |
| Detectors | UV, diode array 210 nm-400 nm Resolution 1.2 nm | | |
| | Other wavelength traces are extracted from the DAD data | | |
| | MS, mass 100-700 (or –1500 for HM method) in ES+ & ES- (300 μL/min split to MS) | | |

General Procedures

Compounds were named with the Chemdraw 18.1 structure naming tool. All reactions involving air- or moisture-sensitive reagents were performed under a nitrogen atmosphere using dried solvents and glassware.

Examples 1-140

Examples 1-140 were conducted in accordance with the following:

Method A Ester Hydrolysis

Ester, methanol (11 mL/mmol), water (1.08 mL/mmol) and LiOH·H$_2$O (1 eq.) were combined and stirred at room temperature for 17 hours, then at 50° C. for 3 days. The reaction mixture was evaporated to dryness to give the corresponding lithium carboxylate salt.

Method B HBTU Coupling

Lithium carboxylate salt, amine (1.0 eq), HBTU (1.0 eq), triethylamine (12 eq.) and DMF (7 mL/mmol) were combined and stirred at r.t. for 19 hours. The reaction mixture was filtered and purified by preparative HPLC.

Method C HCl Boc Deprotection

Boc protected amine, methanol (20 mL/mmol) and 4N HCl in dioxane (20 mL/mmol) were combined and stirred at r.t. for 2-17 hours. Reaction mixture was evaporated to dryness and purified by preparative HPLC.

Method D S$_N$Ar Displacement

Substituted aryl halides, amine (1 eq), cesium carbonate (1.1 eq) and DMF (5 mL/mmol) were combined in a sealed tube and heated to 100° C. for 1-5 days. The reaction mixture was cooled to room temperature. The cesium salts were removed by filtration and the filtrate evaporated to dryness to give crude product which was used directly in next step.

Method D2 S$_N$Ar Displacement

Substituted aryl halides, amine (1 eq), triethylamine (1.1 eq) and MeCN (5 mL/mmol) were combined in a sealed tube and heated to 60° C. for 1-5 days. The reaction mixture was evaporated to dryness to give crude product, which could be purified or used directly in the next step.

Method E TFA Boc Deprotection

Boc protected amine, dichloromethane (4 mL/mmol) and TFA (23 eq) were combined and stirred for 1 day. Reaction mixture was evaporated to dryness and purified by preparative HPLC.

Method F CuI Coupling Conditions

Benzamide, aryl halide (1.05 eq.), copper (I) iodide (0.10 eq.), potassium carbonate (1.5-2.5 eq.) and DMEDA (0.20 eq.) in toluene (2 mL/mmol) was degassed, sealed and heated at 100° C. for 20-114 hours. After this time the reaction mixture was filtered through celite and concentrated under reduced pressure.

Method G t-BuBrettPhos Conditions

Benzamide, aryl halide (1.05 eq.) tert-BuBrettPhos-Pd-G3 (0.10 eq.) and K$_3$PO$_4$ (1.4-2.4 eq.) were placed in a stem block tube. Toluene (3 mL/mmol) was added and the reaction degassed. The reaction mixture was heated at 110° C. for 18-114 hours. After this time the reaction mixture was filtered through celite and concentrated under reduced pressure.

Method H TCFH Coupling

TCFH (1.20 eq.) was added to acid (1.0 eq.), amine (1.30 eq.) and 1-methylimidazole (2.5-3.5 eq.) in MeCN (3 mL/mmol) at room temperature with stirring for 16 h.

Method I Tri-tert-butylphosphine Buchwald Conditions

Aryl bromide, amine (2 eq), Pd(PtBu$_3$)$_2$(0.2 eq) and Cs$_2$CO$_3$ (3 eq) were suspended in dioxane (3 mL/mmol) and the mixture purged with N$_2$ for 10 minutes. The tube was sealed and heated to 100° C. for 16 h. After cooling to room temperature, the mixture was filtered through Celite, washing with DCM, and the filtrate was concentrated to dryness.

Method J Pd$_2$(dba)$_3$ Buchwald Conditions

Aryl bromide, amine (1 eq), Pd$_2$(dba)$_3$ (0.1 eq), rac-BINAP (0.2 equiv) and Cs$_2$CO$_3$ (4 eq) were suspended in DMF (3 mL/mmol) and the mixture purged with N$_2$ for 10 minutes. The tube was sealed and heated to 100° C. for 16 h. After cooling to room temperature, the mixture was filtered through Celite, washing with MeOH, and the filtrate was concentrated to dryness.

Method K RuPhos Pd G2 Buchwald Conditions

Aryl bromide, amine (2 eq), RuPhos Pd G2 (0.1 eq), and Cs$_2$CO$_3$ (3 eq) were suspended in $^t$BuOH (20 mL/mmol) and the mixture purged with N$_2$ for 10 minutes. The tube was sealed and heated to 100° C. for 16 h. After cooling to room temperature, the mixture was filtered through Celite, washing with MeOH, and the filtrate was concentrated to dryness.

Method L Boc Protection

Aryl amine (1 eq), di-tert-butyl dicarbonate (1.3 eq) and EtOAc (0.298 M) were combined and the reaction mixture stirred at room temperature for 16 hours. The reaction mixture was diluted with water and the layers separated, The aq. layer was washed with EtOAc (×2), and the combined organics washed with brine, dried (phase separating filter paper) and concentrated in vacuo.

Method M Amino Pyridinium Salt Formation

Substituted pyridine (1 eq) was dissolved in DMF (0.13 M) and O-(2,4-dinitrophenyl)hydroxylamine (1.1 eq) was added. The reaction mixture was stirred at r.t. for 16 h.

Method N 1,3 Dipolar Addition

Amino pyridinium salt (1 eq), ethyl 2-butynoate (1.1 eq), K$_2$CO$_3$ (1.5 eq) were dissolved in DMF (0.088 M) and the reaction mixture was stirred at r.t. overnight.

Method O HBr Decarboxylation

Ester (1 eq) was dissolved in 48 wt. % in H$_2$O Hydrobromic acid (0.2 M) and the reaction mixture stirred at 100° C. for 4 h.

Method P Pd Catalyzed Amidation

Lactam (1 eq), heteroaryl chloride (1 eq) and Cs$_2$CO$_3$ (1.5 eq) were suspended in dioxane (0.2 M) and the mixture purged with N$_2$ for 10 minutes. Pd2(dba)$_3$ (0.2 eq), Xantphos (0.2 equiv) were then added, the tube was sealed and heated to 100° C. for 16 h. After cooling to RT the mixture was evaporated to dryness, loaded onto silica in DCM/MeOH and purified by silica gel chromatography.

Method Q Formaldehyde Reductive Amination

Amine (1 eq), formaldehyde (37% solution, 50 eq), methanol (1 mL), and sodium triacetoxyborohydride (2 eq) (1.5 eq) were combined and the resulting mixture was stirred at rt for 16 h. The mixture was partitioned between DCM and saturated sodium bicarbonate, dried and evaporated. The crude material was purified by achiral SFC or prep HPLC.

Intermediate 1: 5-Chloro-N-(8-fluoro-2-methylimidazo[1,2-a]pyridin-6-yl)pyrazine-2-carboxamide

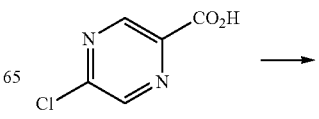

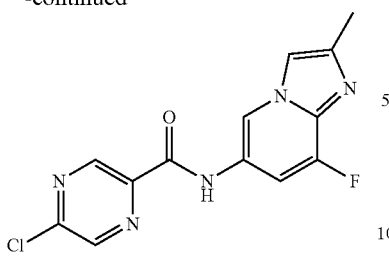

5-Chloro-2-pyrazinecarboxylic acid (960 mg, 6.05 mmol), 8-fluoro-2-methylimidazo[1,2-a]pyridin-6-amine (1000 mg, 6.05 mmol), Chloro-N,N,N,N-tetramethylformamidinium hexafluorophosphate (2038 mg, 7.25 mmol), 1-methylimidazole (1.49 mL, 18.16 mmol) and acetonitrile (25 mL) were combined and stirred at room temperature for 18 hours. Water (50 mL) was added and the reaction mixture was filtered and the solid dried in vacuo to give 5-chloro-N-(8-fluoro-2-methylimidazo[1,2-a]pyridin-6-yl)pyrazine-2-carboxamide, which was used crude in the next step. MS (ES+) 306 (M+H), $^1$H NMR (400 MHz, CDCl$_3$) 9.37 (1H, s), 9.26 (1H, d, J=1.4 Hz), 9.08 (1H, d, J=1.8 Hz), 8.60 (1H, d, J=1.4 Hz), 7.46 (1H, d, J=2.8 Hz), 6.87 (1H, dd, J=1.8, 10.8 Hz), 2.49 (3H, s).

Intermediate 2: 5-Chloro-N-(2,8-dimethylimidazo[1,2-a]pyrazin-6-yl)pyrazine-2-carboxamide

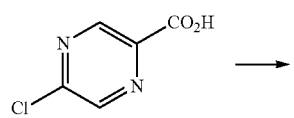

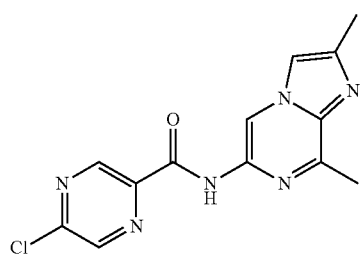

5-Chloro-2-pyrazinecarboxylic acid (1466 mg, 9.25 mmol), 2,8-dimethylimidazo[1,2-a]pyrazin-6-amine (1500 mg, 9.25 mmol), Chloro-N,N,N',N'-tetramethylformamidinium hexafluorophosphate (3114 mg, 11.10 mmol), 1-methylimidazole (2.20 mL, 27.74 mmol) and acetonitrile (25 mL) were combined and stirred at room temperature for 2 hours. Water (50 mL) was added and left to stir for 16 h, before the reaction mixture was filtered and the solid dried in vacuo to give 5-Chloro-N-(2,8-dimethylimidazo[1,2-a]pyrazin-6-yl)pyrazine-2-carboxamide, which was used crude in the next step. MS (ES+) 302 (M+H), $^1$H NMR (400 MHz, CDCl$_3$) 9.82 (s, 1H), 9.25 (d, J=1.4 Hz, 1H), 9.14 (s, 1H), 8.62 (d, J=1.4 Hz, 1H), 7.50 (s, 1H), 2.85 (s, 3H), 2.52 (s, 3H).

Intermediate 3:
6-Ethoxy-2-methyl-2H-indazol-5-amine

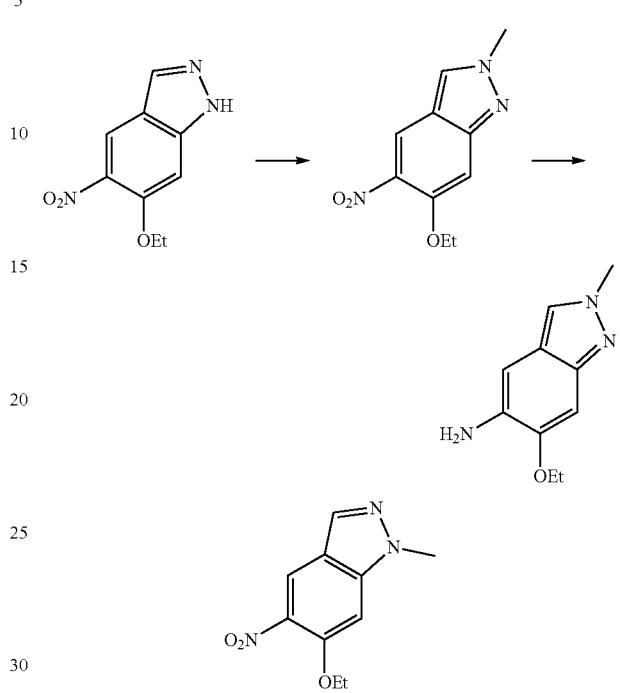

6-Ethoxy-5-nitro-1H-indazole (3.12 g, 15.07 mmol), DMF (30 mL), potassium carbonate (2.29 g, 16.58 mmol) and MeI (1.03 mL, 16.58 mmol) were combined and stirred at room temperature for 20 hours. The reaction was then diluted with EtOAc, washed with water (3×), brine (1×), evaporated to dryness onto silica and purified by flash chromatography, with the minor of the two main peaks being 6-ethoxy-2-methyl-5-nitro-2H-indazole, which was used directly in the next step.

6-Ethoxy-2-methyl-5-nitro-2H-indazole (117 mg, 0.53 mmol), EtOAc (15 mL) and methanol (15 mL) were combined and pumped through an H-cube with 10% Pd/C cartridge at 1 mL per minute flow rate, 40° C., 40 bar pressure. Evaporation of reaction mixture to dryness gave 6-ethoxy-2-methyl-2H-indazol-5-amine, which was used crude in the next step.

Intermediate 4:
6-Methoxy-2-methyl-2H-indazol-5-amine

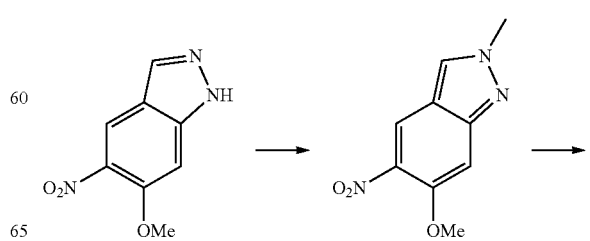

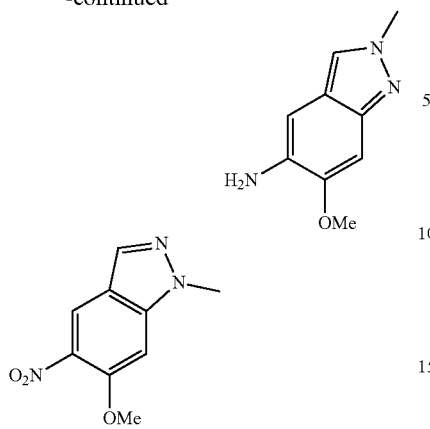

6-Methoxy-5-nitro-1H-indazole (1 g, 5.18 mmol), potassium carbonate (0.79 g, 5.7 mmol), DMF (10 mL) and MeI (0.35 mL, 5.7 mmol) were combined at room temperature under a nitrogen atmosphere and stirred for 3 days. The reaction mixture was then diluted with EtOAc, washed with water (×3), brine (×1), evaporated to dryness onto silica and purified by flash chromatography to give two regioisomeric products. The minor regioisomer corresponds to 6-methoxy-2-methyl-5-nitro-2H-indazole. MS (ES+) 208 (M+H). $^1$H NMR (400 MHz, DMSO) δ 8.56 (s, 1H), 8.42 (s, 1H), 7.25 (s, 1H), 4.18 (s, 3H), 3.92 (s, 3H).

6-Methoxy-2-methyl-5-nitro-2H-indazole (224 mg, 1.08 mmol), EtOAc (15 mL) and MeOH (15 mL) were combined and then pumped at 1 ml per min through an H-Cube with 10% Pd/C cartridge at 50 bar of hydrogen and 40° C. The reaction mixture was evaporated to dryness to give 6-methoxy-2-methyl-2H-indazol-5-amine, which was used crude in next reaction. MS (ES+) 178 (M+H).

Intermediate 5:
N-Isopropylpyrrolidin-3-amine-2HCl

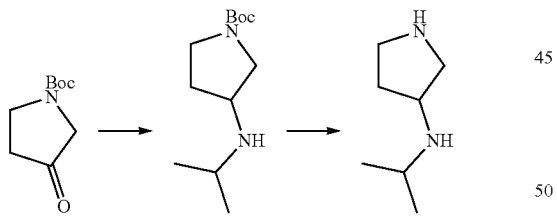

tert-butyl 3-oxopyrrolidine-1-carboxylate (1.31 g, 7.07 mmol), isopropylamine (0.67 mL, 7.78 mmol), dichloromethane (10 mL) and sodium triacetoxyborohydride (3.15 g, 14.85 mmol) were combined and stirred at room temperature for 3 days. The reaction mixture was then quenched with sat. aq. NaHCO$_3$, extracted with dichloromethane, dried (MgSO$_4$) and evaporated to dryness to give tert-butyl 3-(isopropylamino)pyrrolidine-1-carboxylate, which was used crude in next step.

tert-butyl 3-(isopropylamino)pyrrolidine-1-carboxylate (1.53 g, 6.7 mmol), MeOH (5 mL) and 4N HCl in dioxane (20 mL) were combined and stirred at room temperature for 16 hours. The reaction mixture was then evaporated to dryness to give the title compound, which was used crude in next step.

Intermediate 6:
N-(3,3-difluorocyclobutyl)pyrrolidin-3-amine-2HCl

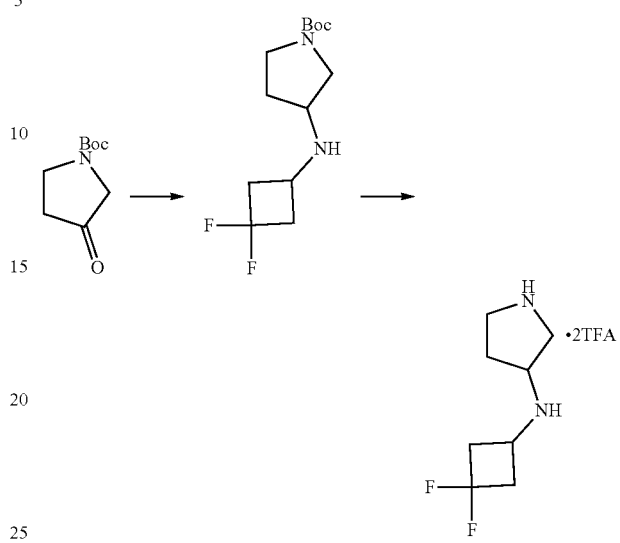

tert-butyl 3-oxopyrrolidine-1-carboxylate (1310 mg, 7.07 mmol, 1 equiv) was dissolved in DCM (80 mL) and 3,3-difluorocyclobutan-1-amine (1120 mg, 7.78 mmol, 1.10 equiv) and sodium triacetoxyborohydride (4650 mg, 21.9 mmol, 3.10 equiv) were added. The reaction mixture was stirred at room temperature for 16 h. The mixture was diluted with NaHCO$_3$ (aq) and extracted with DCM three times. The combined organics were dried (MgSO$_4$) and concentrated in vacuo to give crude tert-butyl 3-((3,3-difluorocyclobutyl)amino)pyrrolidine-1-carboxylate, which was used without further purification.

Crude tert-butyl tert-butyl 3-((3,3-difluorocyclobutyl)amino)pyrrolidine-1-carboxylate (1910 mg, 6.92 mmol, 1 equiv) was dissolved in methanol (5 mL) and 4M HCl in dioxane (20 mL) was added and the reaction mixture stirred at room temperature for 16 h. The solvent was removed in vacuo to give crude title compound, which was used without further purification.

Intermediate 7:
N-(oxetan-3-yl)pyrrolidin-3-amine-2TFA

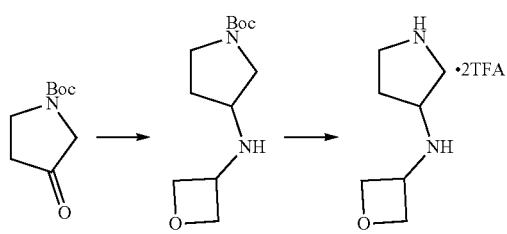 [SMILES: CC(C)(C)OC(=O)N1CCC(=O)C1 ; CC(C)(C)OC(=O)N1CCC(NC2COC2)C1 ; C1CC(NC2COC2)CN1]

tert-butyl 3-oxopyrrolidine-1-carboxylate (1310 mg, 7.70 mmol, 1 equiv) was dissolved in DCM (10 mL) and oxetan-3-amine (568 mg, 7.78 mmol, 1.10 equiv) and sodium triacetoxyborohydride (3140 mg, 14.84 mmol, 2.10 equiv) were added. The reaction mixture was stirred at room temperature for 16 h. The mixture was diluted with NaHCO$_3$ (aq) and washed with DCM three times. The combined organics were washed with saturated brine solution, dried (phase separating filter paper) and concentrated in vacuo to give crude tert-butyl 3-(oxetan-3-ylamino)pyrrolidine-1-carboxylate, which was used without further purification.

Crude tert-butyl 3-(oxetan-3-ylamino)pyrrolidine-1-carboxylate (1.69 g, 7 mmol, 1 equiv) was dissolved in dichloromethane (5 mL) and TFA (4 mL) was added and the reaction mixture stirred at room temperature for 16 h. The solvent was removed in vacuo to give crude title compound, which was used without further purification.

Intermediate 8: (3R*,4S*)—N-cyclopropyl-4-fluoro-N-methylpyrrolidin-3-amine-2HCl

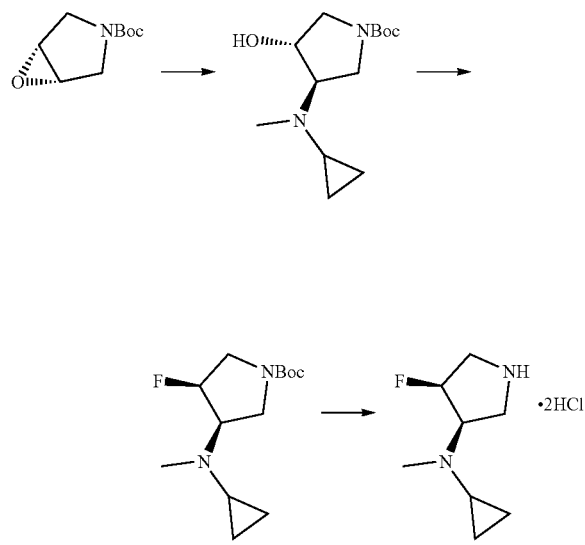 [SMILES: CC(C)(C)OC(=O)N1C[C@@H]2O[C@@H]2C1 ; CN(C1CC1)[C@@H]1CN(C(=O)OC(C)(C)C)C[C@H]1O ; CN(C1CC1)[C@@H]1CN(C(=O)OC(C)(C)C)C[C@@H]1F ; CN(C1CC1)[C@@H]1CNC[C@@H]1F]

tert-Butyl (1R*,5S*)-6-oxa-3-azabicyclo[3.1.0]hexane-3-carboxylate (896 mg, 4.69 mmol), N-methylcyclopropanamine (1 g, 14.08 mmol) and water (1 mL) were combined in a sealed tube and heated to 50° C. for 2 days. The reaction was cooled to room temperature, quenched with sat. aq. NaHCO₃, extracted with dichloromethane (2×), dried (MgSO₄) and evaporated to dryness to give tert-butyl (3R*,4R*)-3-(cyclopropyl(methyl)amino)-4-hydroxypyrrolidine-1-carboxylate, which was used crude in next step.

tert-Butyl (3R*,4R*)-3-(cyclopropyl(methyl)amino)-4-hydroxypyrrolidine-1-carboxylate (200 mg, 0.78 mmol) and dichloromethane (10 mL) were combined. Deoxo-Fluor® 50% in THF (0.32 mL, 0.86 mmol) was added dropwise at r.t. and the reaction stirred overnight. The reaction was quenched by addition of saturated sodium hydrogen carbonate and extracted with DCM (×2). The organic layer was dried (MgSO₄) and the solvent removed in vacuo to give tert-butyl (3R*,4S*)-3-(cyclopropyl(methyl)amino)-4-fluoropyrrolidine-1-carboxylate, which was used crude in next step.

tert-Butyl (3R*,4S*)-3-(cyclopropyl(methyl)amino)-4-fluoropyrrolidine-1-carboxylate, MeOH (3 mL) and 4N HCl in dioxane (3 mL) were combined and stirred at room temperature for 16 hours. The reaction mixture was then evaporated to dryness to give the title compound as a brown oil, which was used crude in next step.

Intermediate 9: (3aR*,6aS*)-3-cyclopropylhexahydro-2H-pyrrolo[3,4-d]oxazol-2-one hydrochloride

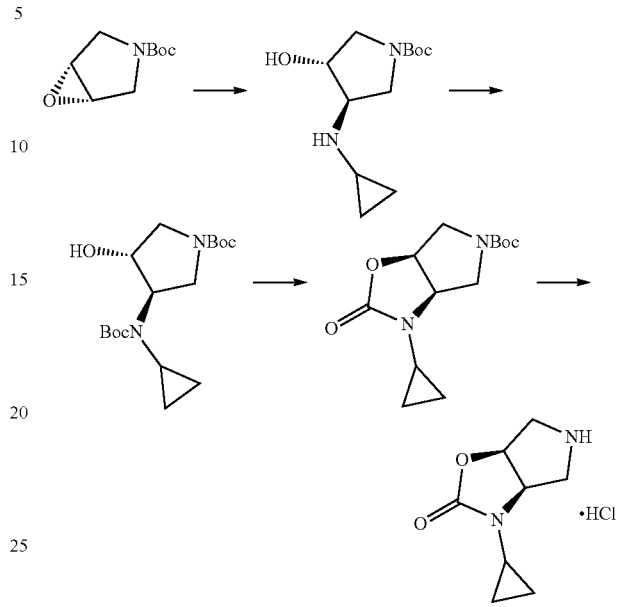

tert-Butyl (1R*,5S*)-6-oxa-3-azabicyclo[3.1.0]hexane-3-carboxylate (1.25 g, 6.75 mmol), cyclopropylamine (8.0 mL, 95.84 mmol) and water (12 mL) was added to a reaction tube. The reaction tube was sealed and heated to 50° C. for 48 h. The reaction was cooled to r.t. and quenched by addition of saturated sodium hydrogen carbonate. The aqueous layer was extracted with DCM (×2) and the organic layer dried (MgSO₄). The solvent was removed in vacuo to give crude tert-butyl (3R*,4R*)-3-(cyclopropylamino)-4-hydroxypyrrolidine-1-carboxylate, which was used in the next step without further purification.

Crude material from the previous step tert-butyl (3R*,4R*)-3-(cyclopropylamino)-4-hydroxypyrrolidine-1-carboxylate was dissolved in DCM (40 mL) and di-tert-butyl dicarbonate (1.62 g, 7.43 mmol) was added followed by triethylamine (2 mL, 14.35 mmol). The reaction was stirred overnight at r.t. The solvent was removed in vacuo to give crude tert-butyl (3R*,4R*)-3-((tert-butoxycarbonyl)(cyclopropyl)amino)-4-hydroxypyrrolidine-1-carboxylate, which was used in the next step without further purification.

Crude tert-butyl (3R*,4R*)-3-((tert-butoxycarbonyl)(cyclopropyl)amino)-4-hydroxypyrrolidine-1-carboxylate (342 mg, 1.00 mmol) was dissolved in DCM (10 mL). Deoxo-Fluor® 50% in THF (487 mg, 1.10 mmol) was added dropwise at r.t. and the reaction stirred overnight. The reaction was quenched by addition of saturated sodium hydrogen carbonate and extracted with DCM (×2). The organic layer was dried (MgSO₄) and the solvent removed in vacuo to give tert-butyl (3aR*,6aS*)-3-cyclopropyl-2-oxohexahydro-5H-pyrrolo[3,4-d]oxazole-5-carboxylate. The material was used without further purification.

Crude tert-butyl (3aR*,6aS*)-3-cyclopropyl-2-oxohexahydro-5H-pyrrolo[3,4-d]oxazole-5-carboxylate (239 mg, 0.69 mmol) was dissolved in methanol (3 mL) and 4 N HCl in dioxane (3 mL) was added dropwise. The reaction was stirred at r.t. overnight and the solvent removed in vacuo to give the title compound. The material was used in the next step without further purification.

Intermediate 10: 8-methoxy-2-methylimidazo[1,2-a]pyrazin-6-amine-2HCl

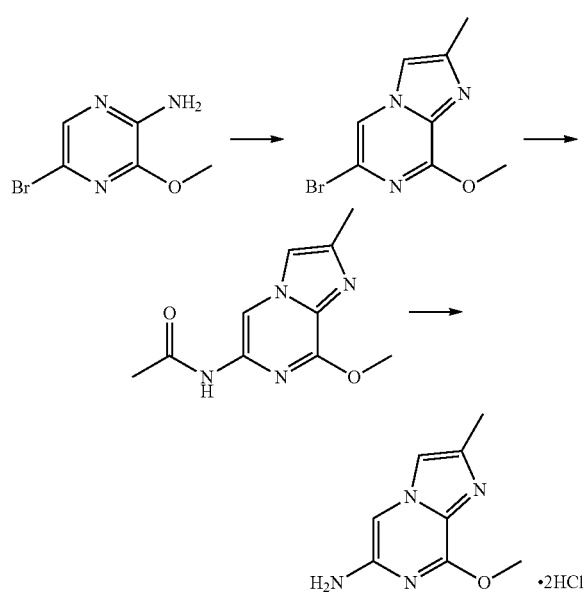

1-Bromo-2,2-dimethoxypropane (4.2 mL, 31.0 mmol) was added to 2-amino-5-bromo-3-methoxypyrazine (3.96 g, 19.4 mmol) and pyridinium p-toluenesulfonate (0.51 g, 1.94 mmol) in isopropanol (60 mL). The reaction mixture was heated at 65° C. for 66 hours. The reaction mixture was cooled to room temperature and diluted with DCM and saturated sodium bicarbonate solution. The layers were separated and the DCM layer dried (phase separator). The solvents were removed under reduced pressure and the crude material purified by silica gel column chromatography (gradient elution 0-100% ethyl acetate in cyclohexane) to afford the title compound. $^1$H NMR (400 MHz, CDCl$_3$) δ 7.82 (d, J=1.6 Hz, 1H), 6.49 (d, J=1.5 Hz, 1H), 3.99 (s, 3H), 2.43 (s, 3H). LCMS (ES+) 244 (M+H)+, RT 3.07 min (Analytical method AcHSSC18).

6-Bromo-8-methoxy-2-methylimidazo[1,2-a]pyrazine (1 g, 4.13 mmol), acetamide (240 mg, 4.13 mmol), CuI (79 mg, 0.413 mmol), K$_2$CO$_3$ (1.71 g, 12.39 mmol), N, N'-dimethylethylenediamine (73 mg, 0.826 mmol), and toluene (11 mL) were placed in a sealed tube, de-gassed by bubbling nitrogen through for 5 mins, then hot block heated to 100° C. for 42 hours. After cooling to room temperature, LCMS analysis indicated partial conversion. The reaction mixture was evaporated to dryness onto silica and purified by flash chromatography, eluting with 1-9% MeOH in EtOAc to give N-(8-methoxy-2-methylimidazo[1,2-a]pyrazin-6-yl)acetamide. MS (ES+) 221 (M+H). $^1$H NMR (400 MHz, d$_6$-DMSO) δ 10.20 (s, 1H), 8.79 (s, 1H), 7.88 (s, 1H), 4.04 (s, 3H), 2.32 (s, 3H), 2.10 (s, 3H).

HCl (4 M in dioxane, 4.3 mL, 17.25 mmol) was added to N-(8-methoxy-2-methylimidazo[1,2-a]pyrazin-6-yl)acetamide (380 mg, 1.73 mmol) in methanol (11 mL) at room temperature with stirring. After 18 hours the reaction mixture was concentrated under reduced pressure to afford the title compound.

Intermediate 11: N-(tert-butyl)pyrrolidin-3-amine-2HCl

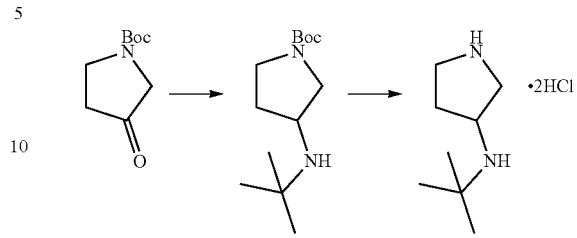

tert-butyl 3-oxopyrrolidine-1-carboxylate (1000 mg, 5.40 mmol, 1 equiv) was dissolved in DCM (10 mL) and tert-butylamine (0.62 mL, 5.94 mmol, 1.10 equiv) and sodium triacetoxyborohydride (2400 mg, 11.34 mmol, 2.10 equiv) were added. The reaction mixture was stirred at room temperature for 16 h. The mixture was diluted with NaHCO$_3$ (aq) and washed with DCM three times. The combined organics were washed with saturated brine solution, dried (phase separating filter paper) and concentrated in vacuo to give crude tert-butyl 3-(tert-butylamino)pyrrolidine-1-carboxylate, which was used without further purification.

Crude tert-butyl 3-(tert-butylamino)pyrrolidine-1-carboxylate (1310 mg, 5.41 mmol, 1 equiv) was dissolved in methanol (10 mL) and 4M HCl in dioxane (13.5 mL, 54.05 mmol, 10 equiv) was added and the reaction mixture stirred at room temperature for 16 h. The solvent was removed in vacuo to give crude N-(tert-butyl)pyrrolidin-3-amine-2HCl, which was used without further purification.

Intermediate 12: N-cyclopropylpyrrolidin-3-amine-2HCl

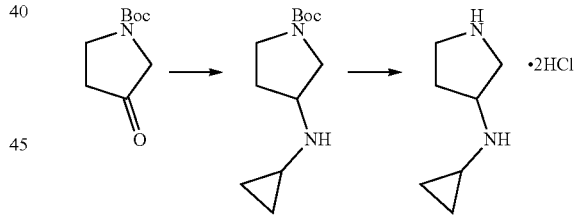

tert-butyl 3-oxopyrrolidine-1-carboxylate (1000 mg, 5.40 mmol, 1 equiv) was dissolved in DCM (10 mL) and cyclopropylamine (0.41 mL, 5.94 mmol, 1.10 equiv) and sodium triacetoxyborohydride (2400 g, 11.34 mmol, 2.10 equiv) were added. The reaction mixture was stirred at room temperature for 16 h. The mixture was diluted with NaHCO$_3$ (aq) and washed with DCM three times. The combined organics were washed with saturated brine solution, dried (phase separating filter paper) and concentrated in vacuo to give crude tert-butyl 3-(cyclopropylamino)pyrrolidine-1-carboxylate, which was used without further purification.

Crude tert-butyl 3-(cyclopropylamino)pyrrolidine-1-carboxylate (1220 mg, 5.39 mmol, 1 equiv) was dissolved in methanol (10 mL) and 4M HCl in dioxane (13.5 mL, 53.91 mmol, 10 equiv) was added and the reaction mixture stirred at room temperature for 16 h. The solvent was removed in vacuo to give crude N-cyclopropylpyrrolidin-3-amine-2HCl, which was used without further purification.

Intermediate 13: N-(cyclopropylmethyl)pyrrolidin-3-amine

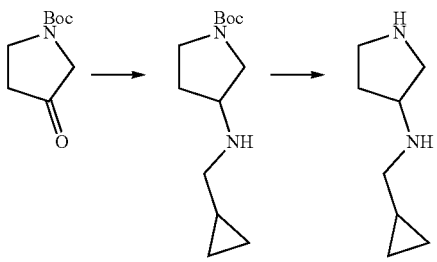 [SMILES: CC(C)(C)OC(=O)N1CCC(=O)C1 ; CC(C)(C)OC(=O)N1CCC(NCC2CC2)C1 ; C1CC(NCC2CC2)CN1]

tert-butyl 3-oxopyrrolidine-1-carboxylate (1000 mg, 5.40 mmol, 1 equiv) was dissolved in DCM (10 mL) and cyclopropanemethylamine (0.42 mL, 5.94 mmol, 1.10 equiv) and sodium triacetoxyborohydride (2400 mg, 11.34 mmol, 2.10 equiv) were added. The reaction mixture was stirred at room temperature for 16 h. The mixture was diluted with NaHCO$_3$ (aq) and extracted with DCM three times. The combined organics were washed with saturated brine solution, dried (phase separating filter paper) and concentrated in vacuo to give crude tert-butyl 3-((cyclopropylmethyl)amino)pyrrolidine-1-carboxylate, which was used without further purification.

Crude tert-butyl 3-((cyclopropylmethyl)amino)pyrrolidine-1-carboxylate (1340 mg, 5.58 mmol, 1 equiv) was dissolved in methanol (10 mL) and 4M HCl in dioxane (13.9 mL, 55.75 mmol, 10 equiv) was added and the reaction mixture stirred at room temperature for 16 h. The solvent was removed in vacuo and the residue loaded in MeOH onto a 10 g SCX cartridge (pre-conditioned with MeOH), eluting with MeOH (2 CV) then 2.3 M NH$_3$/MeOH (3 CV). The ammonia fraction was concentrated in vacuo to give crude N-(cyclopropylmethyl)pyrrolidin-3-amine, which was used without further purification.

Intermediate 14: 4-(pyrrolidin-3-yl)morpholine

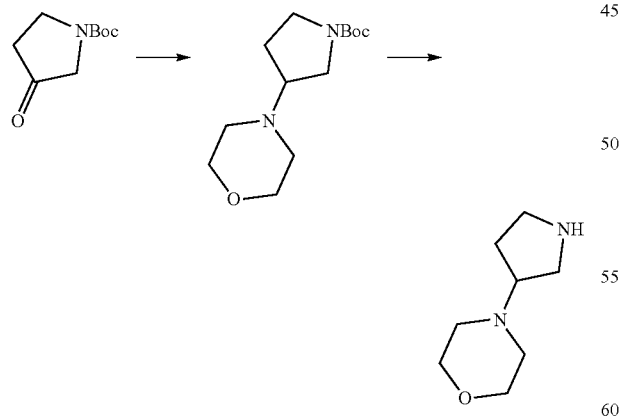

tert-Butyl 3-oxopyrrolidine-1-carboxylate (1 g, 5.4 mmol) and morpholine (0.52 mL, 5.94 mmol) were dissolved in DCM (10 mL). Sodium triacetoxyborohydride (2.4 g, 11.34 mmol) was added at r.t. and the reaction was stirred for 18 h. The reaction was diluted with DCM and washed with water and brine, separating the layers using a phase separator. The solvent was removed in vacuo to give the crude tert-butyl 3-morpholinopyrrolidine-1-carboxylate, which was used without further purification.

tert-Butyl 3-morpholinopyrrolidine-1-carboxylate (1.38 g, 5.40 mmol) was dissolved in methanol (10 mL) and 4M HCl in dioxane (13.5 mL, 53.99 mL) was added at r.t. The reaction was stirred for 18 h and the solvent removed in vacuo to give crude product, which was purified by SCX 10 g cartridge (pre-conditioned with MeOH), eluting with MeOH (2 CV) then 2.3 M NH$_3$/MeOH (3 CV). The ammonia fraction was concentrated in vacuo to give crude 4-(pyrrolidin-3-yl)morpholine, which was used without further purification.

Intermediate 15: N-butylpyrrolidin-3-amine-2HCl

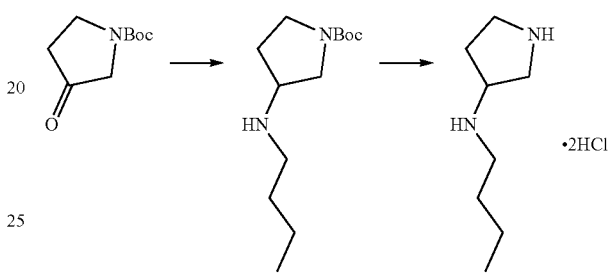

tert-Butyl 3-oxopyrrolidine-1-carboxylate (1 g, 5.4 mmol) and butylamine (0.59 mL, 5.94 mmol) were dissolved in DCM (10 mL). Sodium triacetoxyborohydride (2.4 g, 11.34 mmol) was added at r.t. and the reaction was stirred for 18 h. The reaction was diluted with DCM and washed with water and brine, separating the layers using a phase separator. The solvent was removed in vacuo to give crude tert-butyl 3-(butylamino)pyrrolidine-1-carboxylate, which was used without further purification.

tert-Butyl 3-(butylamino)pyrrolidine-1-carboxylate (1.31 g, 5.41 mmol) was dissolved in methanol (10 mL) and 4M HCl in dioxane (13.5 mL, 13.5 mL) was added at r.t. The reaction was stirred for 18 h and the solvent removed in vacuo to give crude N-butylpyrrolidin-3-amine, which was used without further purification.

Intermediate 16: N-(tetrahydro-2H-pyran-4-yl)pyrrolidin-3-amine-2HCl

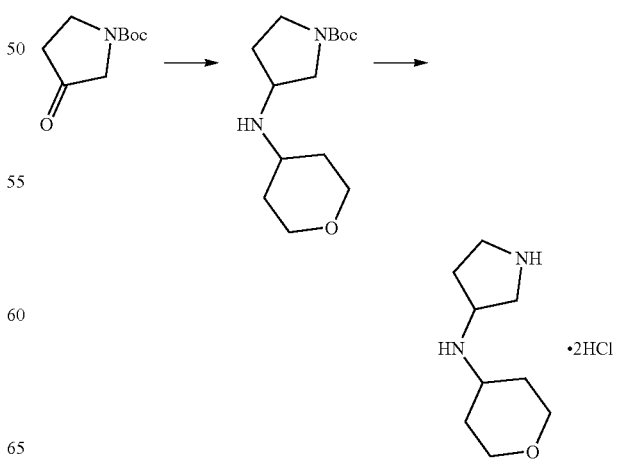

tert-Butyl 3-oxopyrrolidine-1-carboxylate (1.31 g, 7.07 mmol) and tetrahydro-2H-pyran-4-amine (787 mg, 7.78 mmol) were dissolved in DCM (50 mL). Sodium triacetoxyborohydride (3.14 g, 14.84 mmol) was added at r.t. and the reaction was stirred for 18 h. The reaction was diluted with DCM and washed with water and brine, separating the layers using a phase separator. The solvent was removed in vacuo to give the crude tert-butyl 3-((tetrahydro-2H-pyran-4-yl)amino)pyrrolidine-1-carboxylate, which was used without further purification.

tert-butyl 3-((tetrahydro-2H-pyran-4-yl)amino)pyrrolidine-1-carboxylate (1.82 g, 4.74 mmol) was dissolved in methanol (5 mL) and 4M HCl in dioxane (20.0 ml, 80 mmol) was added at r.t. The reaction was stirred for 18 h and the solvent removed in vacuo to give crude N-(tetrahydro-2H-pyran-4-yl)pyrrolidin-3-amine-2HCl, which was used without further purification.

Intermediate 17: 6-bromo-8-methoxy-2-methylimidazo[1,2-a]pyrazine

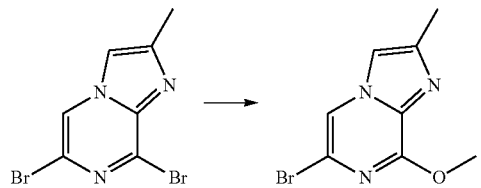

Sodium hydride (60% dispersion in mineral oil, 256 mg, 6.4 mmol) was added portionwise to a mixture of 6,8-dibromo-2-methylimidazo[1,2-a]pyrazine (1.69 g, 5.8 mmol) in methanol (30 mL) and the reaction stirred for 24 hours. The reaction mixture was concentrated under reduced pressure. The residue was taken up in EtOAc and washed with water and brine. The organics were concentrated in vacuo to give 6-bromo-8-methoxy-2-methylimidazo[1,2-a]pyrazine, which was used without further purification.

Intermediate 18: N-(Pyrrolidin-3-ylmethyl)cyclopropanamine-2HCl

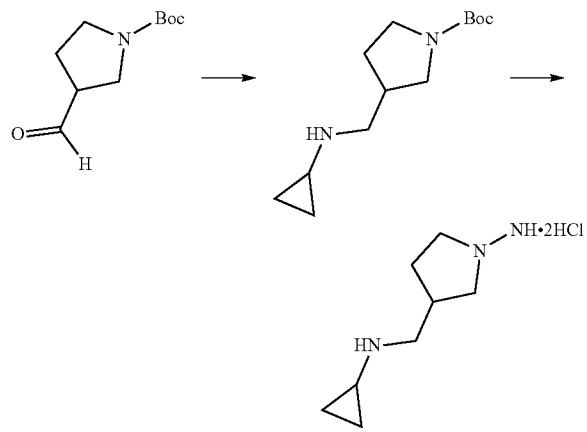

tert-Butyl 3-formylpyrrolidine-1-carboxylate (2 g, 10 mmol), cyclopropylamine (630 mg, 11 mmol), dichloromethane (60 mL) and sodium triacetoxyborohydride (4.45 g, 21 mmol) were combined and stirred at room temperature for 18 hours. Reaction mixture was then quenched with sat. aq. NaHCO₃, extracted with dichloromethane, dried (MgSO₄) and evaporated to dryness to give tert-butyl 3-((cyclopropylamino)methyl)pyrrolidine-1-carboxylate (2.29 g) as a clear oil which was used crude in next step.

tert-Butyl 3-((cyclopropylamino)methyl)pyrrolidine-1-carboxylate (2.29 g, 9.54 mmol), MeOH (20 ml) and 4N HCl in dioxane (10 ml) were combined and stirred at room temperature for 16 hours. Reaction mixture was then evaporated to dryness to give the title compound as a clear oil, which was used crude in next step.

Intermediate 19: N-methyl-N-(pyrrolidin-3-ylmethyl)propan-2-amine-2HCl

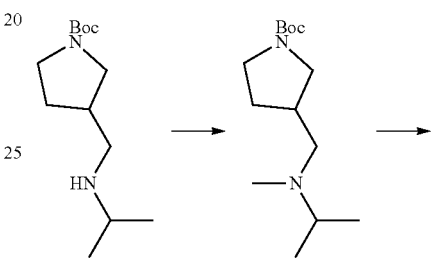

tert-Butyl 3-((isopropylamino)methyl)pyrrolidine-1-carboxylate (200 mg, 0.83 mmol) was dissolved in DMF (3 ml), then sodium hydride (60%, 50 mg, 1.24 mmol) and iodomethane (51 ul, 0.83 mmol) were added at r.t., and stirred for 65 h. Reaction mixture was then quenched with LiCl aqueous solution (4%), extracted with ethyl acetate (×2), dried over a phase separator paper and evaporated to dryness to give tert-butyl 3-((isopropyl(methyl)amino)methyl)pyrrolidine-1-carboxylate (190 mg) as a clear oil which was used crude in next step.

tert-butyl 3-((isopropyl(methyl)amino)methyl)pyrrolidine-1-carboxylate (190 mg, 0.74 mmol), MeOH (3 ml) and 4N HCl in dioxane (1.9 ml) were combined and stirred at room temperature for 19 hours. Reaction mixture was then evaporated to dryness to give the title compound as an oil, which was used crude in next step.

Intermediate 20: N-(pyrrolidin-3-ylmethyl)propan-2-amine-2HCl

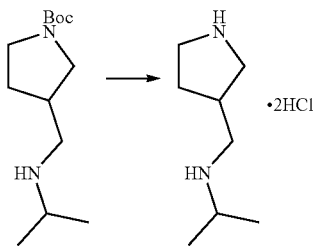

tert-Butyl 3-((isopropylamino)methyl)pyrrolidine-1-carboxylate (300 mg, 1.24 mmol), MeOH (5 ml) and 4N HCl in dioxane (4 ml) were combined and stirred at room temperature for 16 hours. Reaction mixture was then evaporated to dryness to give the title compound as a white solid, which was used crude in next step.

Intermediate 21: 6-methoxy-2-methylpyrazolo[1,5-a]pyridin-5-amine. 2HBr

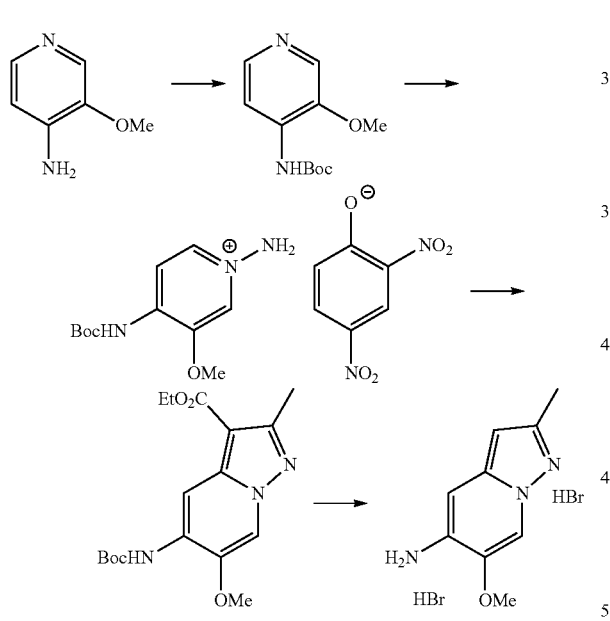

Following Method L Boc protection from 3-methoxypyridin-4-amine (370 mg, 2.98 mmol, 1 eq). The crude was purified using silica chromatography, elution gradient 0-100% EtOAc in cyclohexane. Fractions containing the desired material were combined and the solvent removed in vacuo to give tert-butyl (3-methoxypyridin-4-yl)carbamate (590 mg, 88%) as a white solid LCMS (ES+) 225 (M+H)+

Following Method M Amino pyridinium salt formation from tert-butyl (3-methoxypyridin-4-yl)carbamate (590 mg, 2.63 mmol, 1 eq). LCMS showed consumption of starting material and new peak with correct target mass ion (240). The reaction mixture was taken forward to next step without work up (assumed 100% yield).

Following Method N 1,3 dipolar addition from 1-amino-4-((tert-butoxycarbonyl)amino)-3-methoxypyridin-1-ium 2,4-dinitrophenolate (1114 mg, 2.63 mmol, 1 eq). The reaction mixture was concentrated in vacuo onto silica and the crude purified by silica chromatography, elution gradient 0-75% EtOAc in cyclohexane. Fractions containing the desired material were combined and the solvent removed in vacuo to give ethyl 5-((tert-butoxycarbonyl)amino)-6-methoxy-2-methylpyrazolo[1,5-a]pyridine-3-carboxylate (169 mg, 18%) as an off white solid LCMS (ES+) 350 (M+H)+ $^1$H NMR (400 MHz, CDCl3) δ 8.69 (s, 1H), 7.93 (s, 1H), 7.20 (s, 1H), 4.37 (q, J=7.1 Hz, 2H), 3.91 (s, 3H), 2.62 (s, 3H), 1.55 (s, 9H), 1.44 (t, J=7.1 Hz, 3H).

Following Method O HBr Decarboxylation from ethyl 5-((tert-butoxycarbonyl)amino)-6-methoxy-2-methylpyrazolo[1,5-a]pyridine-3-carboxylate (169 mg, 0.484 mmol, 1 eq). The reaction mixture was concentrated in vacuo to give crude 6-methoxy-2-methylpyrazolo[1,5-a]pyridin-5-amine. 2HBr as a brown oil. Taken forward to the next step without further purification.

Intermediate 22: ethyl 5-((tert-butoxycarbonyl)amino)-6-fluoro-2-methylpyrazolo[1,5-a]pyridine-3-carboxylate and Intermediate 23: ethyl 5-((tert-butoxycarbonyl)amino)-4-fluoro-2-methylpyrazolo[1,5-a]pyridine-3-carboxylate

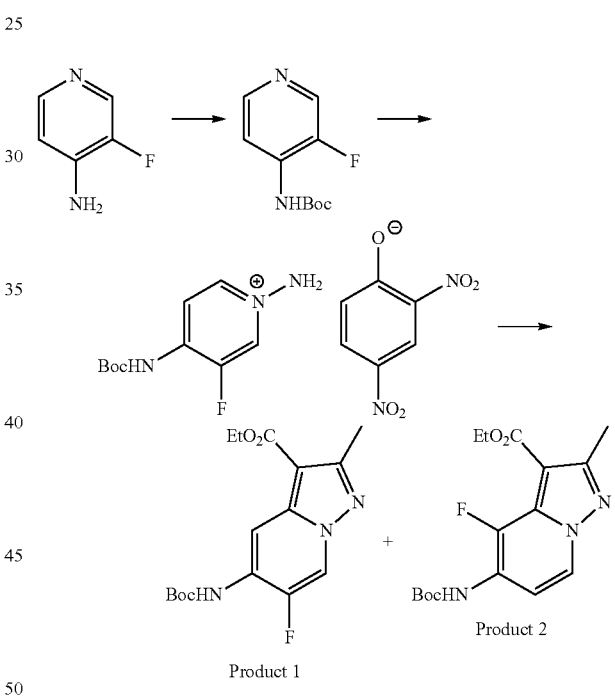

Following Method L Boc protection from 3-fluoropyridin-4-amine (925 mg, 8.25 mmol, 1 eq). The crude was purified using silica chromatography, elution gradient 0-100% EtOAc in cyclohexane. Fractions containing the desired material were combined and the solvent removed in vacuo to tert-butyl (3-fluoropyridin-4-yl)carbamate (1453 mg, 83%) as a white solid LCMS (ES+) 213 (M+H)+

Following Method M Amino pyridinium salt formation from tert-butyl (3-fluoropyridin-4-yl)carbamate (503 mg, 2.37 mmol, 1 eq). LCMS showed consumption of starting material and new peak with correct target mass ion (228). The reaction mixture was taken forward to next step without work up (assumed 100% yield).

Following Method N 1,3 dipolar addition from 1-amino-4-((tert-butoxycarbonyl)amino)-3-fluoropyridin-1-ium 2,4-dinitrophenolate (1278 mg, 3.11 mmol, 1 eq). The reaction mixture was concentrated in vacuo onto silica and the crude purified by silica chromatography, elution gradient 0-20% EtOAc in cyclohexane. Fractions containing target mass combined and the solvent removed in vacuo to give mixture of ethyl 5-((tert-butoxycarbonyl)amino)-6-fluoro-2-methylpyrazolo[1,5-a]pyridine-3-carboxylate and ethyl 5-((tert-butoxycarbonyl)amino)-4-fluoro-2-methylpyrazolo[1,5-a]pyridine-3-carboxylate. The crude was re-purified using silica chromatography, elution gradient 0-18% EtOAc in cyclohexane to give title compounds ethyl 5-((tert-butoxycarbonyl)amino)-6-fluoro-2-methylpyrazolo[1,5-a]pyridine-3-carboxylate (Product 1) as a yellow solid (127 mg, 12%) LCMS (ES+) 338 (M+H)+

Ethyl 5-((tert-butoxycarbonyl)amino)-4-fluoro-2-methylpyrazolo[1,5-a]pyridine-3-carboxylate (Product 2) as a yellow solid (265 mg, 25%) LCMS (ES+) 338 (M+H)+ $^1$H NMR (400 MHz, CDCl3) δ 8.20-8.18 (m, 1H), 7.90 (dd, J=7.0, 7.0 Hz, 1H), 6.90 (d, J=1.9 Hz, 1H), 4.35 (q, J=7.2 Hz, 2H), 2.63 (s, 3H), 1.55 (s, 9H), 1.40 (t, J=7.3 Hz, 3H).

Intermediate 24: 6-fluoro-2-methylpyrazolo[1,5-a]pyridin-5-amine. 2HBr

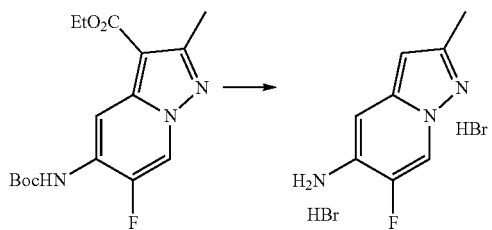 [SMILES: CCOC(=O)c1c(C)nn2cc(F)c(NC(=O)OC(C)(C)C)cc12 ; Br ; Cc1cc2cc(N)c(F)cn2n1 ; Br]

Following Method O HBr Decarboxylation from ethyl 5-((tert-butoxycarbonyl)amino)-6-fluoro-2-methylpyrazolo[1,5-a]pyridine-3-carboxylate (127 mg, 0.376 mmol, 1 eq). The reaction mixture was concentrated in vacuo to give crude 6-fluoro-2-methylpyrazolo[1,5-a]pyridin-5-amine. 2HBr as a brown solid. Taken forward to the next step without further purification.

Intermediate 25: ethyl 5-((tert-butoxycarbonyl)amino)-2,6-dimethylpyrazolo[1,5-a]pyridine-3-carboxylate and Intermediate 26: ethyl 5-((tert-butoxycarbonyl)amino)-2,4-dimethylpyrazolo[1,5-a]pyridine-3-carboxylate

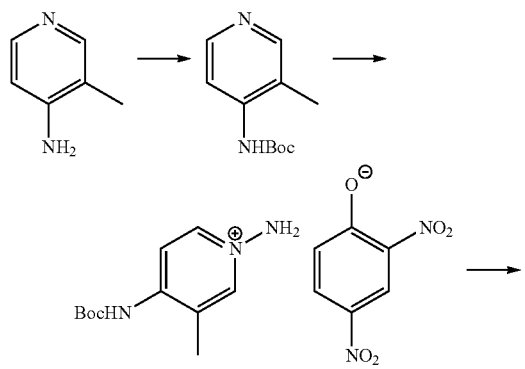

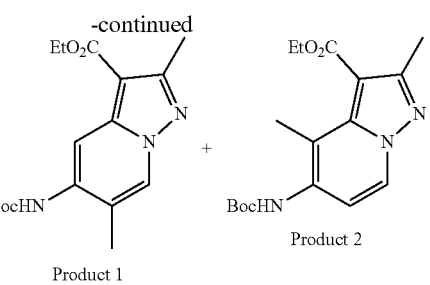

Product 1

Product 2

Following Method L Boc protection 3-methylpyridin-4-amine (600 mg, 5.55 mmol, 1 eq). The crude was purified using silica chromatography, elution gradient 0-100% EtOAc in cyclohexane. Fractions containing the desired material were combined and the solvent removed in vacuo to give tert-butyl (3-methylpyridin-4-yl)carbamate (939 mg, 81%) as a white solid LCMS (ES+) 209 (M+H)+

Following Method M Amino pyridinium salt formation from tert-butyl (3-fluoropyridin-4-yl)carbamate (939 mg, 4.51 mmol, 1 eq). LCMS showed consumption of starting material and new peak with correct target mass ion (224). The reaction mixture was taken forward to next step without work up (assumed 100% yield).

Following Method N 1,3 dipolar addition from 1-amino-4-((tert-butoxycarbonyl)amino)-3-methylpyridin-1-ium 2,4-dinitrophenolate (1835 mjg, 4.51 mmol, 1 eq). The reaction mixture was concentrated in vacuo onto silica and the crude purified by silica chromatography, elution gradient 0-50% EtOAc in cyclohexane. Fractions containing the desired material were combined and the solvent removed in vacuo to give title compounds ethyl 5-((tert-butoxycarbonyl)amino)-2,6-dimethylpyrazolo[1,5-a]pyridine-3-carboxylate (Product 1) as a yellow oil (516 mg, 34%) LCMS (ES+) 334 (M+H)+ $^1$H NMR (400 MHz, CDCl$_3$) δ 8.67 (s, 1H), 8.15 (s, 1H), 6.45 (s, 1H), 4.37 (q, J=7.2 Hz, 2H), 2.63 (s, 3H), 2.26 (s, 3H), 1.56 (s, 9H), 1.44 (dd, J=7.2, 7.2 Hz, 3H).

Ethyl 5-((tert-butoxycarbonyl)amino)-2,4-dimethylpyrazolo[1,5-a]pyridine-3-carboxylate (Product 2) as a yellow solid (253 mg, 18%) LCMS (ES+) 334 (M+H)+ $^1$H NMR (400 MHz, CDCl$_3$) δ 8.23 (d, J=7.4 Hz, 1H), 7.67 (d, J=7.3 Hz, 1H), 6.54 (s, 1H), 4.35 (q, J=7.2 Hz, 2H), 2.58 (s, 3H), 2.57 (s, 3H), 1.54 (s, 9H), 1.40 (t, J=7.1 Hz, 3H).

Intermediate 27: 2,6-dimethylpyrazolo[1,5-a]pyridin-5-amine. 2HBr

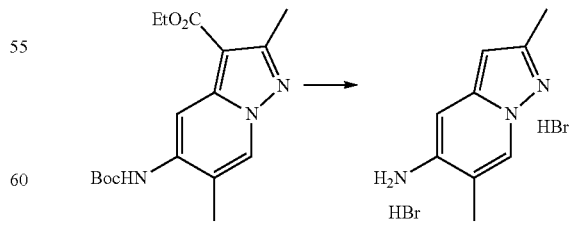

Following Method O HBr Decarboxylation from ethyl 5-((tert-butoxycarbonyl)amino)-2,6-dimethylpyrazolo[1,5-a]pyridine-3-carboxylate (250 mg, 0.750 mmol, 1 eq). The reaction mixture was concentrated in vacuo to give crude 2,6-dimethylpyrazolo[1,5-a]pyridin-5-amine 2HBr as a brown oil. Taken forward to the next step without further purification.

Intermediate 28: 6-ethoxy-2-methylpyrazolo[1,5-a]pyridin-5-amine

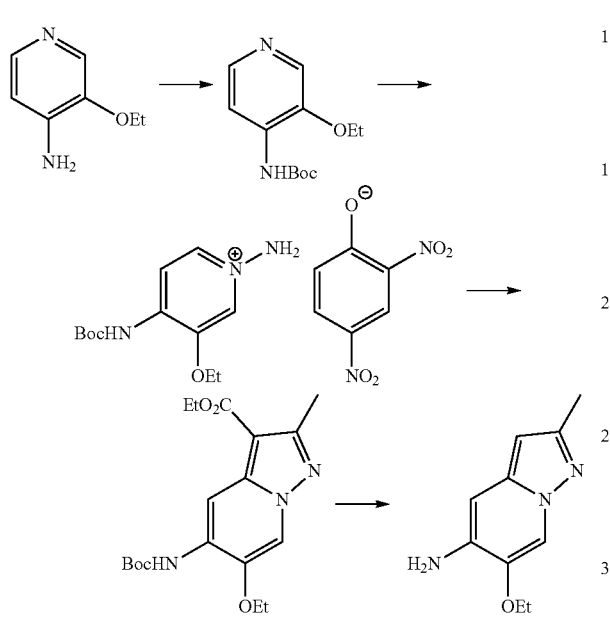

Following Method L Boc protection from 3-ethoxypyridin-4-amine (2200 mg, 15.9 mmol, 1 eq). tert-butyl (3-ethoxypyridin-4-yl)carbamate as a yellow solid. Taken forward to next step without further purification.

Following Method M Amino pyridinium salt formation from tert-butyl (3-ethoxypyridin-4-yl)carbamate (4200 mg, 17.6 mmol, 1 eq). LCMS showed consumption of starting material and new peak with correct target mass ion (254). The reaction mixture was taken forward to next step without work up (assumed 100% yield).

Following Method N 1,3 dipolar addition from 1-amino-4-((tert-butoxycarbonyl)amino)-3-ethoxypyridin-1-ium 2,4-dinitrophenolate (7702 mg, 17.626 mmol, 1 eq). The reaction mixture was concentrated in vacuo onto silica and the crude purified by silica chromatography, elution gradient 0-60% EtOAc in cyclohexane. Fractions containing the desired material were combined and the solvent removed in vacuo to give ethyl 5-((tert-butoxycarbonyl)amino)-6-ethoxy-2-methylpyrazolo[1,5-a]pyridine-3-carboxylate (380 mg, 5%) as a yellow solid LCMS (ES+) 364 (M+H)+ $^1$H NMR (400 MHz, DMSO) δ 8.53 (s, 1H), 8.46 (s, 1H), 8.33 (s, 1H), 4.27 (q, J=7.0 Hz, 2H), 4.16 (dt, J=7.5, 14.6 Hz, 2H), 1.52 (s, 9H), 1.50 (s, 3H), 1.42 (t, J=7.1 Hz, 3H), 1.37-1.33 (m, 3H).

Following Method O HBr Decarboxylation from ethyl 5-((tert-butoxycarbonyl)amino)-6-ethoxy-2-methylpyrazolo[1,5-a]pyridine-3-carboxylate (380 mg, 0.941 mmol, 1 eq). The reaction mixture was concentrated in vacuo to give crude 6-methoxy-2-methylpyrazolo[1,5-a]pyridin-5-amine. 2HBr as a brown oil. The crude was loaded onto a 5 g SCX cartridge (pre-conditioned with MeOH). The residue was eluted with MeOH then 7M NH3 in MeOH. The ammonia fraction was concentrated in vacuo to give 6-ethoxy-2-methylpyrazolo[1,5-a]pyridin-5-amine as a tan oil. Taken forward without further purification to next step.

Intermediate 29: 6-(difluoromethoxy)-2-methyl-2H-indazol-5-amine

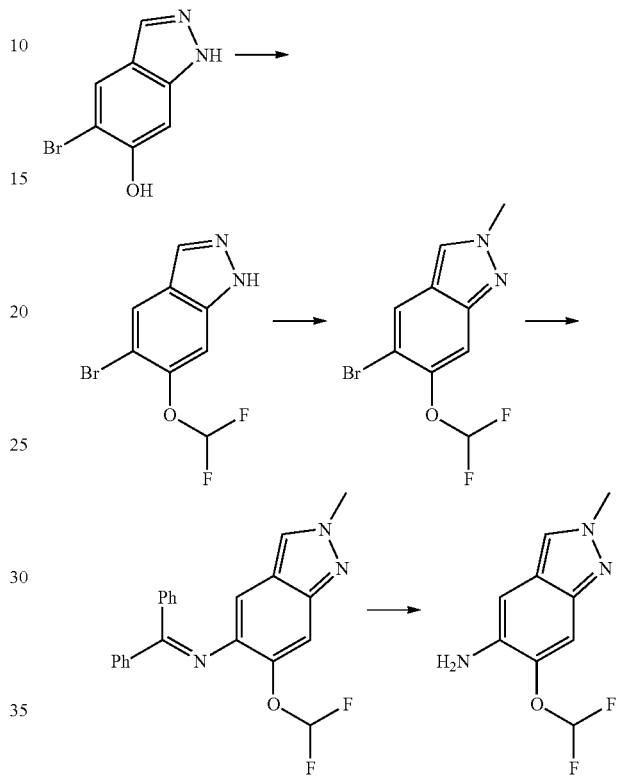

5-Bromo-1H-indazol-6-ol (900 mg, 4.22 mmol, 1 eq), sodium chlorodifluoroacetate (1288 mg, 8.45 mmol, 2 eq), Cs$_2$CO$_3$ (2065 mg, 6.34 mmol, 1.5 eq) were dissolved in DMF (10 mL) and the reaction mixture stirred at 100° C. in a sealed tube for 18 h. EtOAc and H$_2$O were added and the layers separated. The aq. layer was washed with EtOAc (×2) and the combined organics were washed with brine, dried (phase separating filter paper) and concentrated in vacuo. The crude was purified by silica chromatography, elution gradient 5-100% EtOAc in cyclohexane. Fractions containing the desired material were combined and the solvent removed in vacuo to give 5-bromo-6-(difluoromethoxy)-1H-indazole (490 mg, 44%) as a yellow solid LCMS (ES+) 253, 265 (M+H)+(Br)

5-Bromo-6-(difluoromethoxy)-1H-indazole (490 mg, 1.86 mmol, 1 eq) was dissolved in EtOAc (50 mL) and trimethyloxonium tetrafluoroborate (413 mg, 2.79 mmol, 1.5 eq) was added and the R.M stirred at r.t for 16 h. EtOAc and H$_2$O were added and the layers separated. The aq. layer was washed with EtOAc (×2) and the combined organics were washed with brine, dried (phase separating filter paper) and concentrated in vacuo to give 5-bromo-6-(difluoromethoxy)-2-methyl-2H-indazole (400 mg, 77%) LCMS (ES+) 277, 279 (M+H)+(Br) $^1$H NMR (400 MHz, DMSO) δ 8.40 (s, 1H), 8.18 (s, 1H), 7.50 (s, 1H), 7.34 (t, J=74.6 Hz, 1H), 4.18 (s, 3H).

5-Bromo-6-(difluoromethoxy)-2-methyl-2H-indazole (400 mg, 1.44 mmol, 1 eq), diphenylmethanimine (0.24 mL, 1.44 mmol, 1 equiv) Cs$_2$CO$_3$ (706 mg, 2.16 mmol, 1.5 eq), Pd(OAc)$_2$ (32 mg, 0.14 mmol, 0.1 equiv) rac-BINAP (90 mg, 0.14 mmol, 0.1 equiv) were combined in THF (5 mL) and the mixture purged with N$_2$ for 15 minutes. The reaction mixture was stirred at 80° C. for 18 h in a sealed tube. The reaction mixture was allowed to cool to r.t. and the mixture was diluted with water and the aqueous phase was extracted with EtOAc (×3). The combined organic phases were washed with brine, dried (phase separating filter paper) and the solvent was removed in vacuo. The crude was purified using silica chromatography, elution gradient 0-75% EtOAc in cyclohexane. Fractions containing the desired materials were combined and the solvent removed in vacuo to give N-(6-(difluoromethoxy)-2-methyl-2H-indazol-5-yl)-1,1-diphenylmethanimine. Still impurities present, therefore taken forward to next step without further purification.

N-(6-(difluoromethoxy)-2-methyl-2H-indazol-5-yl)-1,1-diphenylmethanimine (220 mg, 0.48 mmol, 1 eq) was dissolved in MeOH (10 mL) and 4M HCl in dioxane (0.48 mL, 1.91 mmol, 4 eq) was added. The reaction mixture was stirred at r.t. for 16 h. The reaction mixture was concentrated in vacuo to give 6-(difluoromethoxy)-2-methyl-2H-indazol-5-amine. 2HCl as a red solid. Taken forward to next step without further purification.

Intermediate 30: 5-chloro-N-(6-methoxy-2-methylpyrazolo[1,5-a]pyridin-5-yl)pyrazine-2-carboxamide

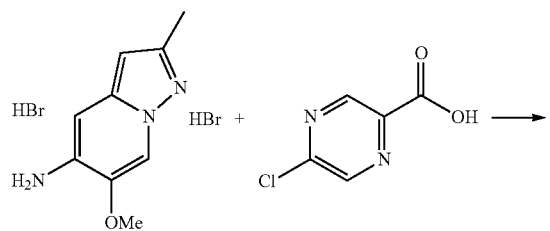

Following Method H TCFH coupling from 5-chloropyrazine-2-carboxylic acid (321 mg, 2.02 mmol, 1 eq) and 6-methoxy-2-methylpyrazolo[1,5-a]pyridin-5-amine. 2HBr (858 mg, 2.02 mmol, 1 eq). The reaction mixture was diluted with H$_2$O and the solid filtered. The solid was washed with MeCN:H$_2$O (1:2) (×3) to give 5-chloro-N-(6-methoxy-2-methylpyrazolo[1,5-a]pyridin-5-yl)pyrazine-2-carboxamide (327 mg 80% pure, 40%) as a yellow solid LCMS (ES+) 318 (M+H)+

Intermediate 31: (6-bromo-8-fluoroimidazo[1,2-a]pyridin-2-yl)methanol

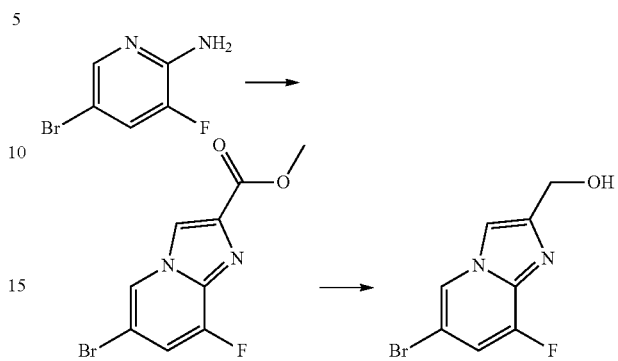

5-Bromo-3-fluoropyridin-2-amine (2 g, 10.47 mmol) and ethyl bromopyruvate (1.4 mL, 11.52 mmol) was dissolved in ethanol (50 mL) and heated at reflux for 18 h. The reaction was cooled to r.t. and the solvent removed in vacuo to give a residue. The residue was dissolved in EtOAc and washed with saturated sodium hydrogencarbonate. The EtOAc layer was dried (MgSO$_4$) and the solvent removed in vacuo to give a residue, which was purified using silica chromatography, elution gradient 0-50% EtOAc/cyclohexane to give the title compound as an off-white solid (1.76 g, 59%).

Methyl 6-bromo-8-fluoroimidazo[1,2-a]pyridine-2-carboxylate (1.76 g, 6.13 mmol) was dissolved in THF (50 mL) and cooled to −78° C. 1M DIBAL in toluene (12.88 mL, 12.88 mmol) was added dropwise and the reaction allowed to warm to r.t. over 18 h. The reaction was cooled to 0° C. in an ice-bath and quenched by addition of water. The aqueous layer was extracted with EtOAc ×3 and the organic layer dried (MgSO$_4$). The solvent was removed in vacuo to give a residue, which was purified using silica chromatography, elution gradient 0-100% EtOAc/cyclohexane to give the title compound as a clear oil (1.1 g, 73%).

Intermediate 32: Lithium (S)-5-(3-(((tert-butoxycarbonyl)(cyclopropyl)amino)methyl)pyrrolidin-1-yl)pyrazine-2-carboxylate

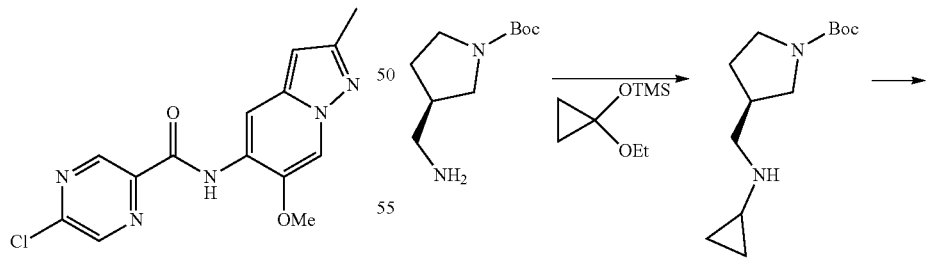

-continued

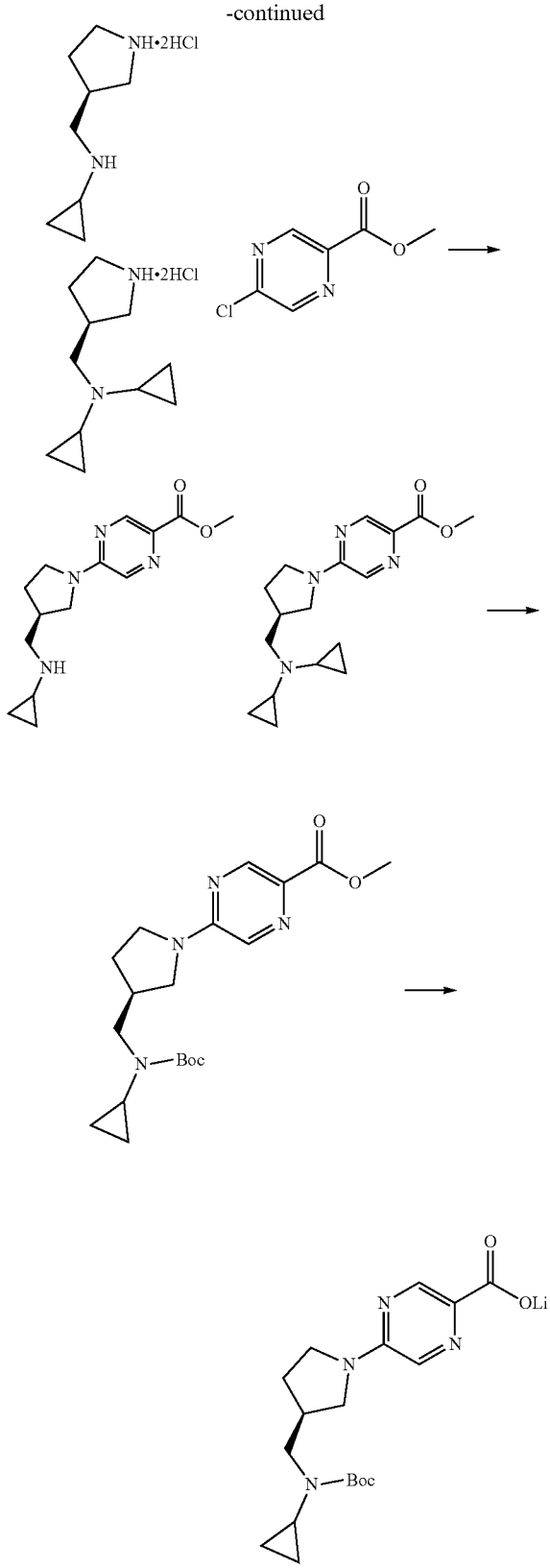

(R)-3-(Aminomethyl)-1-Boc-pyrrolidine (1000 mg, 4.99 mmol, 1.00 eq), (1-ethoxycyclopropoxy)trimethylsilane (1.0 mL, 4.99 mmol, 1.00 eq) and methyl alcohol (50.00 mL) were combined. Sodium cyanoborohydride (345 mg, 5.49 mmol, 1.10 eq) was added followed by acetic acid (0.20 mL). Reaction was then hot block heated to 55° C. for 2 days. Reaction was cooled to room temperature. Diluted with dichloromethane, washed with 10% NaOH solution, dried (MgSO4) and concentrated in vacuo to give a mixture of tert-butyl (3R)-3-[(cyclopropylamino)methyl]pyrrolidine-1-carboxylate and tert-butyl (R)-3-((dicyclopropylamino)methyl)pyrrolidine-1-carboxylate as a clear oil (1.29 g), which was used crude in next step.

Mixture of tert-butyl (3R)-3-[(cyclopropylamino)methyl]pyrrolidine-1-carboxylate and tert-butyl (R)-3-((dicyclopropylamino)methyl)pyrrolidine-1-carboxylate (1.20 g, 4.99 mmol, 1.00 eq), methyl alcohol (10 mL) and 4 M hydrogen chloride in dioxane (5.0 mL, 20.0 mmol, 4.01 eq) were combined and stirred at room temperature for 23 hours. Reaction was then concentrated in vacuo and partitioned between dichloromethane and 15% Aq NaOH soln. The organic layer concentrated in vacuo to give a mixture of N-[[(3S)-pyrrolidin-3-yl]methyl]cyclopropanamine dihydrochloride and (S)—N-cyclopropyl-N-(pyrrolidin-3-ylmethyl)cyclopropanamine dihydrochloride as a clear gum (718 mg), which was used directly in the next step.

A mixture of N-[[(3S)-pyrrolidin-3-yl]methyl]cyclopropanamine and (S)—N-cyclopropyl-N-(pyrrolidin-3-ylmethyl)cyclopropanamine dihydrochloride (700 mg, 4.99 mmol, 1.00 eq), methyl 5-chloro-2-pyrazinecarboxylate (861 mg, 4.99 mmol, 1.00 eq), N,N-diisopropylethylamine (2.0 mL, 11.5 mmol, 2.30 eq) and 1,4-dioxane (100.00 mL) were combined and hot block heated to 100° C. for 16 hours. The reaction was cooled to room temperature and used reaction mixture directly in next step.

Di-tert-butyl dicarbonate (1.1 mL, 5.00 mmol, 1.00 eq) was added to the reaction mixture from previous step and stirred at room temperature for 2 hours. The crude reaction was concentrated in vacuo onto silica and purified by flash chromatography to give methyl 5-[(3S)-3-[[tert-butoxycarbonyl(cyclopropyl)amino]methyl]pyrrolidin-1-yl]pyrazine-2-carboxylate as a clear gum (682 mg). Used directly in next step. LCMS (ES+) 377 (M+H)+

Methyl 5-[(3S)-3-[[tert-butoxycarbonyl(cyclopropyl)amino]methyl]pyrrolidin-1-yl]pyrazine-2-carboxylate (682 mg, 1.81 mmol, 1.00 eq), lithium hydroxide monohydrate (76 mg, 1.81 mmol, 1.00 eq), methyl alcohol (30.00 mL) and water (3.00 mL) were combined and hot block heated to 50° C. for 16 hours. Concentrated in vacuo to give [5-[(3S)-3-[[tert-butoxycarbonyl(cyclopropyl)amino]methyl]pyrrolidin-1-yl]pyrazine-2-carbonyl]oxylithium as a white solid (672 mg). LCMS (ES+) 363 (M+H)+ as acid.

Intermediate 33: N-[[(3R)-pyrrolidin-3-yl]methyl]cyclopropanamine Dihydrochloride

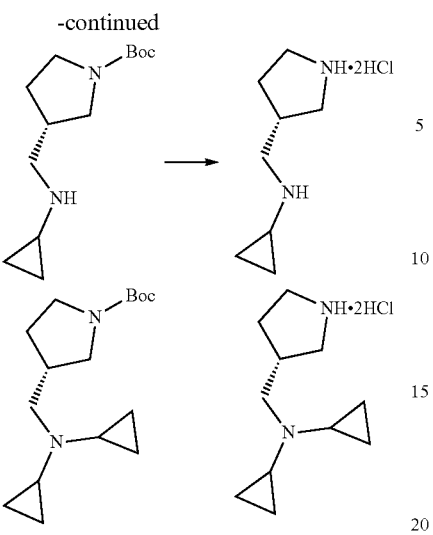

N-[[(3R)-Pyrrolidin-3-yl]methyl]cyclopropanamine dihydrochloride was made using the same chemistry as its enantiomer N-[[(3S)-pyrrolidin-3-yl]methyl]cyclopropanamine dihydrochloride and was used directly in next steps.

Intermediate 34: Lithium (R)-5-(3-((tert-butoxycarbonyl)(cyclopropyl)amino)pyrrolidin-1-yl)pyrazine-2-carboxylate

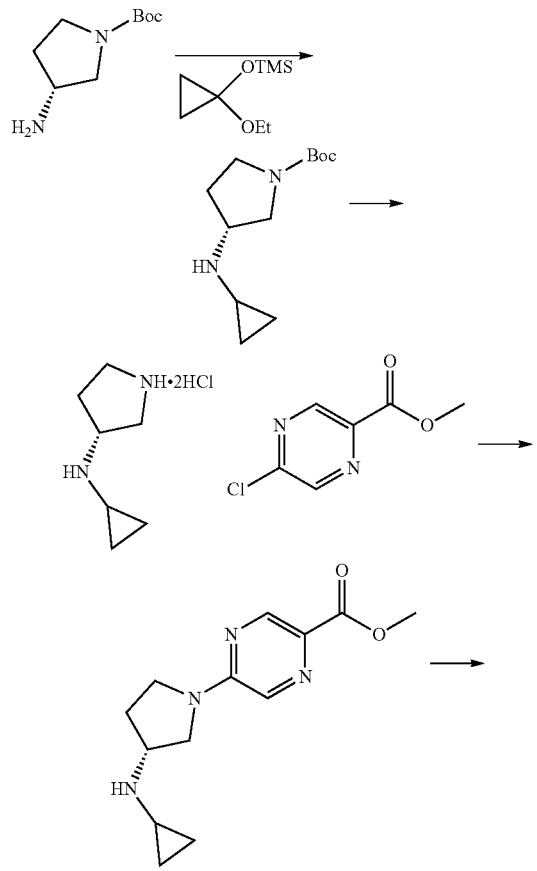

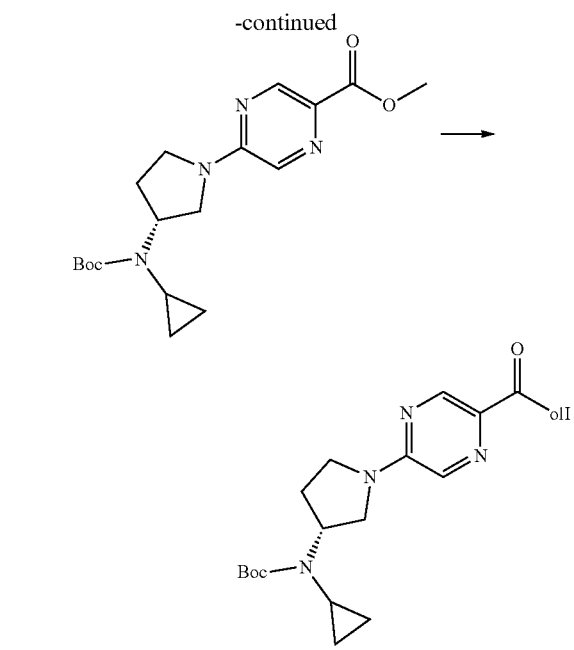

(R)-(+)-1-Boc-3-aminopyrrolidine (1000 mg, 5.37 mmol, 1.00 eq), (1-ethoxycyclopropoxy)trimethylsilane (1.1 mL, 5.37 mmol, 1.00 eq) and methyl alcohol (50.00 mL) were combined. Sodium cyanoborohydride (371 mg, 5.91 mmol, 1.10 eq) was added followed by acetic acid (0.20 mL). Reaction was then hot block heated to 55° C. for 20 hours. The reaction was cooled to room temperature and diluted with dichloromethane, washed with 10% NaOH solution, dried (MgSO$_4$) and concentrated in vacuo to give tert-butyl (3R)-3-(cyclopropylamino)pyrrolidine-1-carboxylate as clear oil (1.11 g), which was used directly in next step.

tert-Butyl (3R)-3-(cyclopropylamino)pyrrolidine-1-carboxylate (1.11 g, 4.91 mmol, 1.00 eq), methyl alcohol (10.00 mL) and 4 M hydrogen chloride in dioxane (5.0 mL, 20.0 mmol, 4.07 eq) were combined and stirred at room temperature for 20 hours. The reaction was concentrated in vacuo to give (3R)—N-cyclopropylpyrrolidin-3-amine; dihydrochloride as a white semi-solid (985 mg), which was used directly in next step.

(3R)—N-Cyclopropylpyrrolidin-3-amine; dihydrochloride (985 mg, 4.95 mmol, 1.00 eq), methyl 5-chloro-2-pyrazinecarboxylate (854 mg, 4.95 mmol, 1.00 eq), 1,4-dioxane (100.00 mL) and N,N-diisopropylethylamine (2.0 mL, 11.5 mmol, 2.32 eq) were combined and hot block heated to 100° C. for 3 days. The reaction was cooled to room temperature and used crude in the next step.

Di-tert-butyl dicarbonate (1.1 mL, 5.00 mmol, 1.01 eq) was added to the reaction mixture from the previous step and stirred for 3 days. The reaction was concentrated in vacuo onto silica and purified by flash chromatography to give methyl 5-[(3R)-3-[tert-butoxycarbonyl(cyclopropyl)amino]pyrrolidin-1-yl]pyrazine-2-carboxylate as a pale yellow gum (436 mg), which was used directly in the next step. LCMS (ES+) 363 (M+H)+

Methyl 5-[(3R)-3-[tert-butoxycarbonyl(cyclopropyl)amino]pyrrolidin-1-yl]pyrazine-2-carboxylate (436 mg, 1.20 mmol, 1.00 eq), lithium hydroxide monohydrate (50 mg, 1.20 mmol, 1.00 eq), methyl alcohol (30.00 mL) and water (3.00 mL) were combined and hot block heated to 55° C. for 20 hours. The reaction was concentrated in vacuo to give [5-[(3R)-3-[tert-butoxycarbonyl(cyclopropyl)amino]

pyrrolidin-1-yl]pyrazine-2-carbonyl]oxylithium as a tan glass (349 mg). LCMS (ES+) 349 (M+H)+ as acid.

Intermediate 35:
N-(azetidin-3-ylmethyl)cyclopropanamine

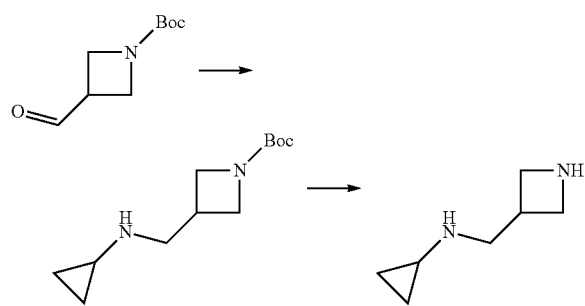

Cyclopropylamine (2.1 mL, 29.7 mmol) tert-butyl 3-formylazetidine-1-carboxylate (5.00 g, 27.0 mmol) and sodium triacetoxyborohydride (12.59 g, 59.4 mmol) were combined in dichloromethane (50.00 mL) and stirred at r.t. for 17 h. Saturated aqueous sodium hydrogen carbonate solution (200 mL) was added to the reaction mixture and stirred vigorously for 10 mins. The organics were collected and washed with water and brine, before passing through a phase separator and concentrating to dryness to give the title compound as a clear oil (5.1 g, 83%) which was progressed to the next step directly.

tert-Butyl 3-[(cyclopropylamino)methyl]azetidine-1-carboxylate (3.00 g, 13.3 mmol, 1.00 eq) and trifluoroacetic acid (5.1 mL, 66.3 mmol, 5.00 eq) were combined in dichloromethane (30 mL) and stirred at r.t. for 72 h. The reaction mixture was concentrated in vacuo and loaded onto an SCX cartridge and washed with DCM/MeOH (1:1). The compound was released using DCM/MeOH/7M ammonia in MeOH (5:5:1) and concentrated to dryness to give N-(azetidin-3-ylmethyl)cyclopropanamine as a colourless oil (1.19 g, 71%). NB: multiple elutions were required to release product from SCX cartridge. ¹H NMR (400 MHz, CDCl3) δ, 3.74 (dd, J=7.8, 7.8 Hz, 2H), 3.44-3.35 (m, 2H), 2.94-2.91 (m, 2H), 2.91-2.83 (m, 1H), 2.13-2.05 (m, 1H), 0.46-0.40 (m, 2H), 0.33-0.28 (m, 2H).

Intermediate 36:
3-(azetidin-3-yl)-1-methylpiperidine hydrochloride

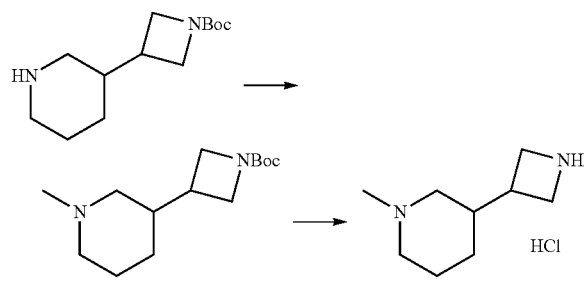

A mixture of tert-butyl 3-(piperidin-3-yl)azetidine-1-carboxylate (250 mg, 1.04 mmol), formaldehyde (37% solution, 3.9 mL, 52.0 mmol) and sodium triacetoxyborohydride (441 mg, 2.08 mmol) in methanol 1 mL) was stirred for 20 hours. Water was added and the organics were extracted with DCM. The combined organics were passed through a phase separator and concentrated under reduced pressure yielding the crude material as an off-white gum, which was taken on without further purification (tert-butyl 3-(1-methylpiperidin-3-yl)azetidine-1-carboxylate; 330 mg).

A solution of tert-butyl 3-(1-methylpiperidin-3-yl)azetidine-1-carboxylate (265 mg, 1.04 mmol) in 4 M HCl in dioxane (8.7 mL, 34.7 mmol) and methanol (8.7 mL) was stirred for 20 hours. The reaction mixture was concentrated under reduced pressure to yield the crude material as a colourless oil which was used without further purification (3-(azetidin-3-yl)-1-methylpiperidine hydrochloride; 310 mg). MS (ES+) 155.1 [M−HCl+H]⁺.

Intermediate 37:
3-(azetidin-3-yl)-1-cyclopropylpiperidine Hydrochloride

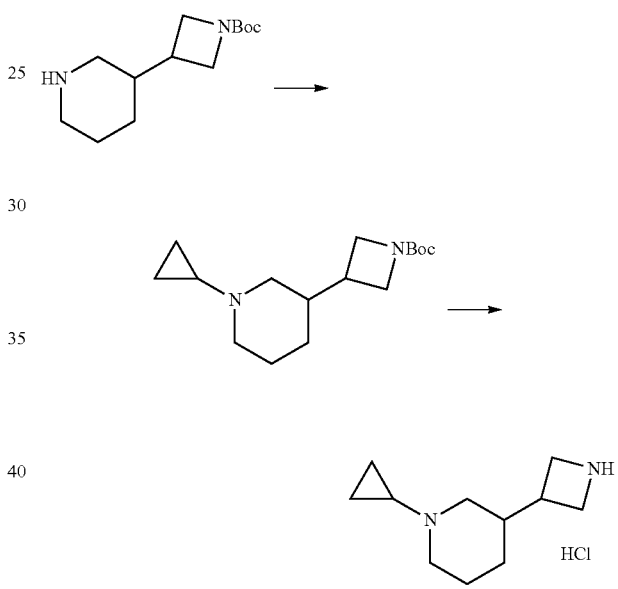

A mixture of tert-butyl 3-(piperidin-3-yl)azetidine-1-carboxylate (250 mg, 1.04 mmol), 1-(ethoxycycloproxy)trimethylsilane (0.23 mL, 1.14 mmol) and sodium cyanoborohydride in methanol (10 mL) and acetic acid (0.1 mL) was heated to 50° C. for 20 hours. The reaction mixture was concentrated under reduced pressure and the residue partitioned between ethyl acetate and water. The organics were separated and washed with brine and dried over sodium sulfate, decanted and concentrated under reduced pressure to yield the crude material as an orange gum, which was taken forward without further purification (tert-butyl 3-(1-cyclopropylpiperidin-3-yl)azetidine-1-carboxylate; 224 mg). MS (ES+) 281.2 [M+H]⁺.

A solution of tert-butyl 3-(1-cyclopropylpiperidin-3-yl)azetidine-1-carboxylate (224 mg, 0.799 mmol) in 4 M HCl in dioxane (6.7 mL, 26.6 mmol) and methanol (6.7 mL) was stirred for 20 hours. The reaction mixture was concentrated under reduced pressure to yield the crude material as a colourless oil, which was used without further purification (3-(azetidin-3-yl)-1-cyclopropylpiperidine hydrochloride; 144 mg). MS (ES+) 181.1 [M−HCl+H]⁺.

Intermediate 38: 5-chloro-N-(6-ethoxy-2-methyl-indazol-5-yl)pyrazine-2-carboxamide

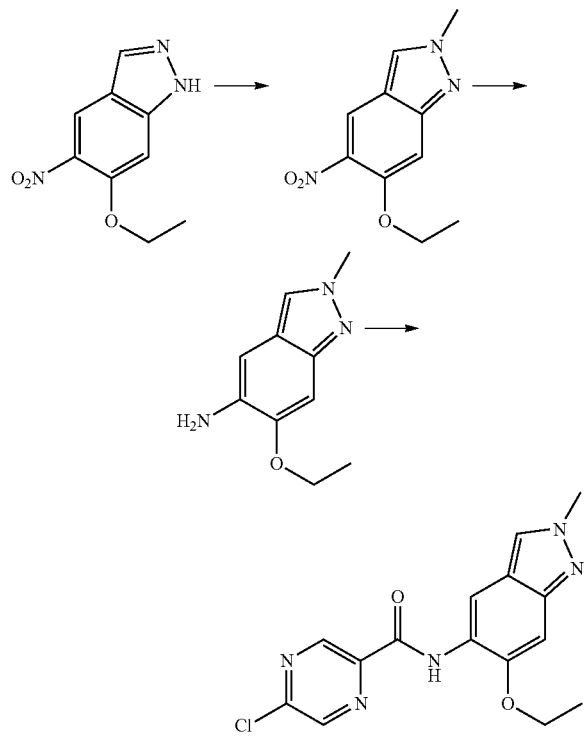

To a suspension of 6-ethoxy-5-nitro-1H-indazole (2.30 g, 11.1 mmol) and potassium carbonate (1.69 g, 12.2 mmol) in N,N-dimethylformamide (20 mL) was added iodomethane (0.76 mL, 12.2 mmol) as drops and the reaction was stirred overnight. The reaction mixture was diluted with EtOAc and water and the organics separated and further extracted with EtOAc. The combined organics were washed with brine, dried over sodium sulfate, decanted and concentrated under reduced pressure. The crude material was purified by flash column chromatography (0 to 100% EtOAc in cyclohexane; 80 g column). The product containing fractions were concentrated under reduced pressure to yield the title compound as a tan solid (586 mg; 23% yield). MS (ES+) 222.2 [M+H]+. $^1$H NMR (400 MHz, CDCl$_3$) δ 8.16 (s, 1H), 8.00 (s, 1H), 7.08 (s, 1H), 4.21-4.15 (m, 5H), 1.49 (t, J=7.0 Hz, 3H).

To a thoroughly degassed suspension of 6-ethoxy-2-methyl-5-nitro-indazole (580 mg, 2.62 mmol) and 1-methyl-1,4-cyclohexadiene (2.9 mL, 26.2 mmol) in ethanol (25 mL) was added 10% palladium on carbon (279 mg, 2.62 mmol) and the reaction was heated to 70° C. overnight. After 24 hours, the reaction was allowed to cool to room temperature and filtered through a pad of Celite and washed with MeOH. The filtrate was concentrated under reduced pressure to yield a brown gum and the crude material was used directly in the next step without further purification (460 mg; 92% yield). MS (ES+) 192.2 [M+H]+. 1H NMR (400 MHz, CDCl$_3$) δ 7.54 (s, 1H), 6.90 (s, 1H), 6.75 (s, 1H), 4.09 (s, 3H), 3.72 (q, J=7.0 Hz, 2H), 1.49 (t, J=7.0 Hz, 3H).

A suspension of 6-ethoxy-2-methyl-indazol-5-amine (460 mg, 2.41 mmol), 5-chloro-2-pyrazinecarboxylic acid (381 mg, 2.41 mmol), chloro-N,N,N',N'-tetramethylformamidinium hexafluorophosphate (810 mg, 2.89 mmol) and 1-methylimidazole (0.58 mL, 7.22 mmol) in acetonitrile (12 mL) was stirred under nitrogen over the weekend. The reaction mixture was diluted with water and stirred for 15 minutes. The reaction mixture was filtered and the filtercake taken and dried under reduced pressure yielding 5-chloro-N-(6-ethoxy-2-methyl-indazol-5-yl)pyrazine-2-carboxamide as a yellow powder (410 mg; 51% yield). MS (ES+) 332.2 [M+H]+. $^1$H NMR (400 MHz, CDCl$_3$) δ 10.39 (s, 1H), 9.27 (d, J=1.4 Hz, 1H), 8.81 (s, 1H), 8.62 (d, J=1.4 Hz, 1H), 7.82 (s, 1H), 7.02 (s, 1H), 4.22 (q, J=7.0 Hz, 2H), 4.16 (s, 3H), 1.57 (t, J=7.0 Hz, 3H).

Intermediate 39: N-(azetidin-3-ylmethyl)cyclopropanamine Dihydrochloride

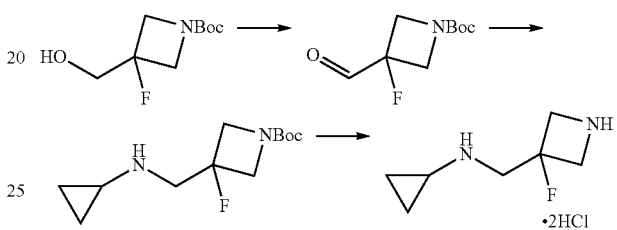

A suspension of tert-butyl 3-fluoro-3-(hydroxymethyl) azetidine-1-carboxylate (500 mg, 2.44 mmol) and Dess-Martin periodinane (1.24 g, 2.92 mmol) in dichloromethane (15 mL) was stirred at room temperature for 2 hours. The reaction mixture was diluted with an aqueous sodium thiosulfate (10% w/v) and sat. aqueous sodium hydrogen carbonate and stirred for 20 minutes. The mixture was passed through a phase separator and the organics concentrated under reduced pressure yielding a colourless oil, which was taken on without further purification (480 mg; 97% yield).

A mixture of tert-butyl 3-fluoro-3-formyl-azetidine-1-carboxylate (240 mg, 1.18 mmol), sodium triacetoxyborohydride (526 mg, 2.48 mmol) and cyclopropylamine (0.090 mL, 1.30 mmol) in dichloromethane (10 mL) was stirred under nitrogen at room temperature overnight. The reaction mixture was diluted with water and stirred for 10 minutes. The mixture was passed through a phase separator and the organics concentrated under reduced pressure yielding the crude material as a pale yellow gum (250 mg; 87% yield).

A solution of tert-butyl 3-[(cyclopropylamino)methyl]-3-fluoro-azetidine-1-carboxylate (250 mg, 1.02 mmol) in 4 M hydrogen chloride in dioxane (5.0 mL, 20.0 mmol) and methanol (5 mL) was stirred at room temperature for three days. The reaction mixture was concentrated under reduced pressure to yield the crude material as a tan solid, which was used without further purification (210 mg; 95% yield).

Intermediate 40: 1-(Azetidin-3-ylmethyl)-3-methoxy-azetidine

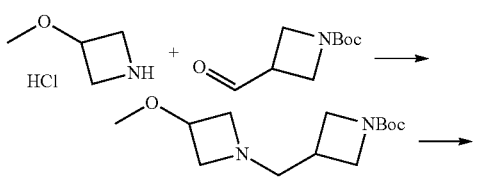

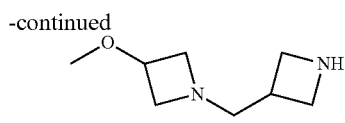

tert-Butyl 3-formylazetidine-1-carboxylate (0.50 g, 2.70 mmol), sodium triacetoxyborohydride (1.26 g, 5.94 mmol) and 3-methoxyazetidine hydrochloride (334 mg, 2.70 mmol) were combined in dichloromethane (50 mL) and stirred at room temperature for 17 hours. Saturated aqueous sodium hydrogen carbonate solution (15 mL) was added to the reaction mixture and stirred vigorously for 10 mins. The organics were collected and washed with water and brine, before passing through a phase separator and concentrating to dryness to give tert-butyl 3-[(3-methoxyazetidin-1-yl)methyl]azetidine-1-carboxylate as a clear oil (700 mg), which was used without further purification.

tert-Butyl 3-[(3-methoxyazetidin-1-yl)methyl]azetidine-1-carboxylate (700 mg, 2.73 mmol) and trifluoroacetic acid (1.0 mL, 13.7 mmol) were combined in dichloromethane (30 mL) and stirred at room temperature for 21 hours. The reaction mixture was concentrated in vacuo, then dissolved in DCM:MeOH (1:1, 20 mL) and passed through an SCX cartridge. The column was eluted with DCM:MeOH (1:1) to remove TFA and the product was released using DCM:MeOH:7M NH₃ in MeOH (5:5:1). The product containing fraction was concentrated to dryness to give 1-(azetidin-3-ylmethyl)-3-methoxy-azetidine as a colourless oil (400 mg).

Intermediate 41: 1-cyclopropyl-3,3'-biazetidine

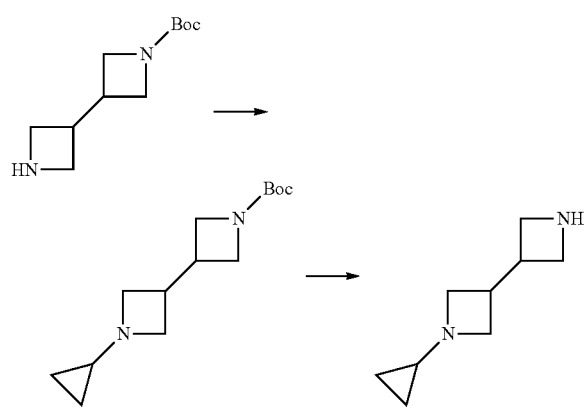

tert-Butyl [3,3'-biazetidine]-1-carboxylate (80 mg, 0.38 mmol), (1-ethoxycyclopropoxy)trimethylsilane (0.15 mL, 0.75 mmol), methanol (2.5 mL), acetic acid (0.01 ml) and sodium cyanoborohydride (47 mg, 0.75 mmol) were combined and stirred at 50° C. for 18 hours. The mixture was partitioned between DCM and saturated sodium bicarbonate, dried and evaporated to afford tert-butyl 1'-cyclopropyl-[3,3'-biazetidine]-1-carboxylate (103 mg) as a colorless oil which was used crude in the next step.

tert-Butyl 1'-cyclopropyl-[3,3'-biazetidine]-1-carboxylate (100 mg, 0.38 mmol), DCM (1 ml) and TFA (1 ml) were combined and stirred at room temperature for 65 hours. The reaction mixture was purified by SCX to give 1-cyclopropyl-3,3'-biazetidine as a crude yellow oil (56 mg) which was used as such in next step.

Intermediate 41a: 2,8-dimethylimidazo[1,2-a]pyrazin-6-amine

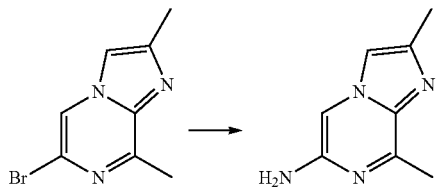

A mixture of 6-bromo-2,8-dimethylimidazo[1,2-a]pyrazine (prepared according to WO 2015/197503, 991 mg, 4.38 mmol) and CuSO₄ (401 mg, 2.51 mmol) in 35% aqueous ammonia solution (8 mL) was heated to 90° C. under microwave irradiation for 3 h. After cooling to rt, the material was filtered through Celite, washing with water and methanol. The filtrate was acidified to pH 4 with 2 M HCl, then concentrated. The residue was applied to a 70 g SCX cartridge, eluting with 100 mL MeOH, then 150 mL 2.3 M NH₃/MeOH. The ammonia fraction was concentrated and the residue purified by silica gel column chromatography (gradient elution, 0-20% MeOH/DCM) to give 2,8-dimethylimidazo[1,2-a]pyrazin-6-amine as a brown powder (450 mg, 2.77 mmol, 63%).

Intermediate H1: 5-Chloro-N-(8-chloro-2-methyl-imidazo[1,2-a]pyridin-6-yl)pyrazine-2-carboxamide

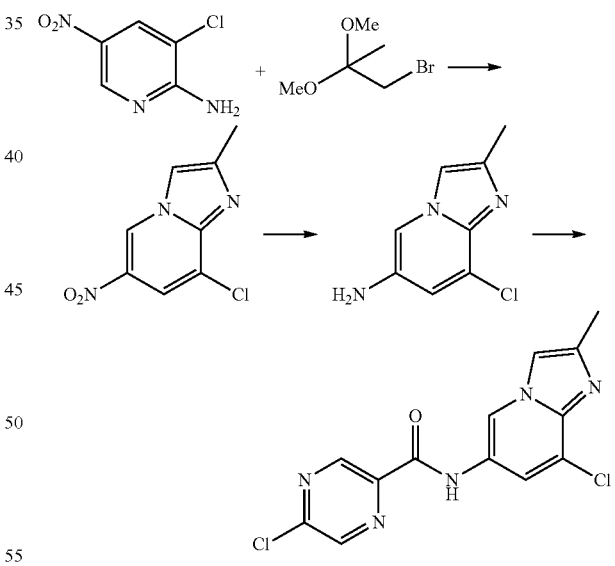

3-Chloro-5-nitro-pyridin-2-amine (0.0010 g, 5.76 μmol), 1-bromo-2,2-dimethoxypropane (0.0012 mL, 9.22 μmol), pyridinium p-toluenesulfonate (0.00014 g, 0.576 μmol) and IPA (10.00 mL) were combined and the R.M was stirred at 95° C. for 4.5 h. The reaction mixture was filtered and washed with IPA to give the desired product (91% purity, 1.5 g, quantitative). LCMS (ES+) 212 (M+H)⁺, RT 1.35 min.

8-Chloro-2-methyl-6-nitro-imidazo[1,2-a]pyridine (300 mg, 1.42 mmol) and iron (396 mg, 7.09 mmol) in acetic acid (1 mL) were stirred at 60° C. for 1 h. The reaction mixture was loaded onto an SCX cartridge and passed through using NH₃ (7 M) in MeOH. The filtrate was concentrated, diluted with DCM and washed with aqueous 15 mol % NaOH. The organic layer was concentrated in vacuo to give the desired product (211 mg, 82%). LCMS (ES⁺) 181 (M+H)⁺, RT 1.05 min.

8-Chloro-2-methyl-imidazo[1,2-a]pyridin-6-amine (211 mg, 1.16 mmol), 5-chloro-2-pyrazinecarboxylic acid (184 mg, 1.16 mmol), chloro-N,N,N',N'-tetramethylformamidinium hexafluorophosphate (489 mg, 1.74 mmol) and 1-methylimidazole (0.28 mL, 3.49 mmol) in acetonitrile (8.00 mL) was stirred under nitrogen for 16 h at RT. The reaction mixture was concentrated, diluted with DCM and washed with aqueous sodium bicarbonate. The organic layer was concentrated onto silica and purified by column chromatography, eluting with cyclohexane/EtOAc (0-100% gradient). The appropriate fractions were combined and concentrated in vacuo to give the desired product (211 mg, 75%). LCMS (ES⁺) 322 (M+H)⁺, RT 1.23 min. ¹H NMR (400 MHz, CDCl₃) δ 9.36 (s, 1H), 9.26 (s, 1H), 9.21 (d, J=1.6 Hz, 1H), 8.60 (s, 1H), 7.47 (s, 1H), 7.19 (d, J=1.6 Hz, 1H), 2.51 (s, 3H).

Intermediate H2 (5-chloro-N-(8-methoxy-2-methyl-imidazo[1,2-a]pyridin-6-yl)pyrazine-2-carboxamide)

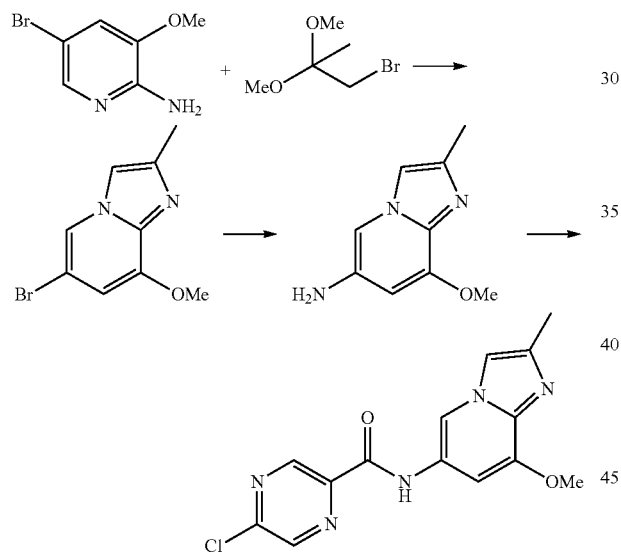

5-Bromo-3-methoxy-pyridin-2-amine (3.57 g, 17.6 mmol), 1-bromo-2,2-dimethoxypropane (3.8 mL, 28.1 mmol), pyridinium p-toluenesulfonate (0.44 g, 1.76 mmol) and IPA (10.00 mL) were combined. The R.M was stirred at 95° C. for 5 h. The reaction mixture was diluted with 3:1 DCM/IPA and washed with brine. The organic layer was concentrated in vacuo to afford 6-bromo-8-methoxy-2-methylimidazo[1,2-a]pyridine (4.2 g, 96%). LCMS (ES⁺) 242 (M+H)⁺, RT 1.02 min. ¹H NMR (400 MHz, DMSO) δ 8.44 (1H, d, J=1.6 Hz), 7.66 (1H, s), 6.81 (1H, d, J=1.5 Hz), 3.95 (3H, s), 2.32 (3H, s).

6-Bromo-8-methoxy-2-methyl-imidazo[1,2-a]pyridine (1.01 g, 4.19 mmol), copper(I) iodide (0.16 g, 0.838 mmol), potassium carbonate (0.87 g, 6.28 mmol), ammonium hydroxide solution (0.26 mL, 6.28 mmol), L-proline (0.19 g, 1.68 mmol) and DMSO (10.00 mL) were added to the reaction flask. The reaction vessel was sealed and heated at 90° C. for 16 h. The reaction mixture was passed through an SCX cartridge with MeOH and NH₃ (7 M) in MeOH and the appropriate fraction was concentrated in vacuo to give the desired product (1.19 g, 99%). LCMS (ES⁺) 179 (M+H)⁺.

8-Methoxy-2-methyl-imidazo[1,2-a]pyridin-6-amine (326 mg, 1.84 mmol), 5-chloro-2-pyrazinecarboxylic acid (292 mg, 1.84 mmol), chloro-N,N,N',N'-tetramethylformamidinium hexafluorophosphate (774 mg, 2.76 mmol) and 1-methylimidazole (0.44 mL, 5.52 mmol) in acetonitrile (8.00 mL) was stirred under nitrogen for 16 h at RT. The reaction mixture was concentrated, diluted with 3:1 DCM:IPA and washed with brine. The crude product was purified by column chromatography eluting with cyclohexane/EtOAc (0-100% gradient) to give 5-chloro-N-(8-methoxy-2-methylimidazo[1,2-a]pyridin-6-yl)pyrazine-2-carboxamide (909 mg, 87%). LCMS (ES⁺) 317 (M+H)⁺.

Intermediate H3: 5-((1H-benzo[d][1,2,3]triazol-1-yl)oxy)-N-(7-fluoro-2-methyl-2H-indazol-5-yl)pyrazine-2-carboxamide

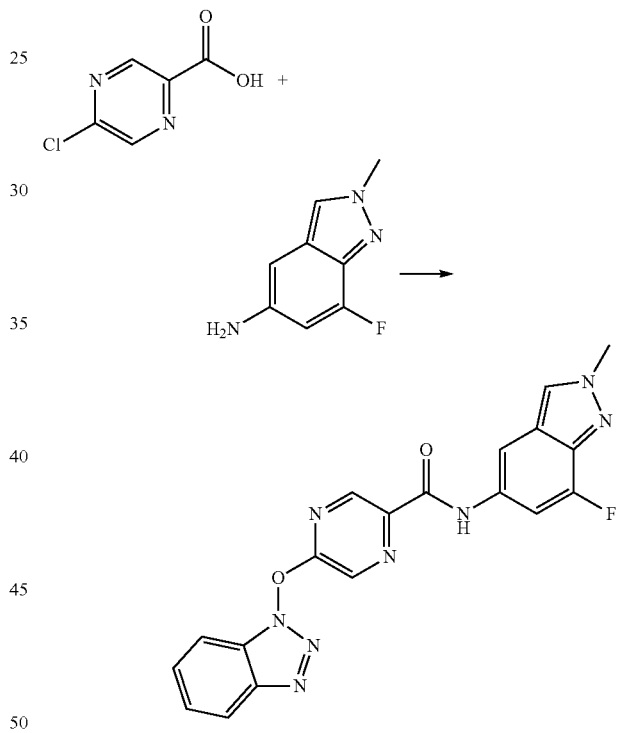

HBTU (1.88 g, 4.96 mmol, 1.00 eq), triethylamine (3.5 mL, 24.8 mmol, 5.00 eq), 5-chloro-2-pyrazinecarboxylic acid (0.79 g, 4.96 mmol, 1.00 eq), N,N-dimethylformamide (10.00 mL) and 7-fluoro-2-methyl-indazol-5-amine; hydrochloride (1.00 g, 4.96 mmol, 1.00 eq) were combined and stirred at room temperature for 17 h. LCMS indicated none of the expected chlorinated material present, and instead the HOBt adduct was formed. The reaction mixture was partitioned between EtOAc and water. The aqueous layer was washed multiple times with EtOAc. The combined organic phases were dried over magnesium sulfate, filtered and concentrated in vacuo. NB. Significant quantities of the HOBt adduct remained in the aqueous layer. The material was purified by flash silica chromatography (gradient elution c-hex to EtOAc) to give 5-(benzotriazol-1-yloxy)-N-(7-fluoro-2-methyl-indazol-5-yl)pyrazine-2-carboxamide as a pale yellow solid (586 mg, 28%). LCMS (ES+) 405 (M+H)+. $^1$H NMR (400 MHz, DMSO) δ 10.81 (s, 1H), 9.16 (s, 1H), 8.82 (s, 1H), 8.48 (d, J=2.7 Hz, 1H), 8.25-8.20 (m, 2H), 7.87 (d, J=8.3 Hz, 1H), 7.71 (dd, J=7.6, 7.6 Hz, 1H), 7.62-7.57 (m, 2H), 4.20 (s, 3H).

Intermediate 42:
7-fluoro-2-methyl-2H-indazol-5-amine Hydrochloride

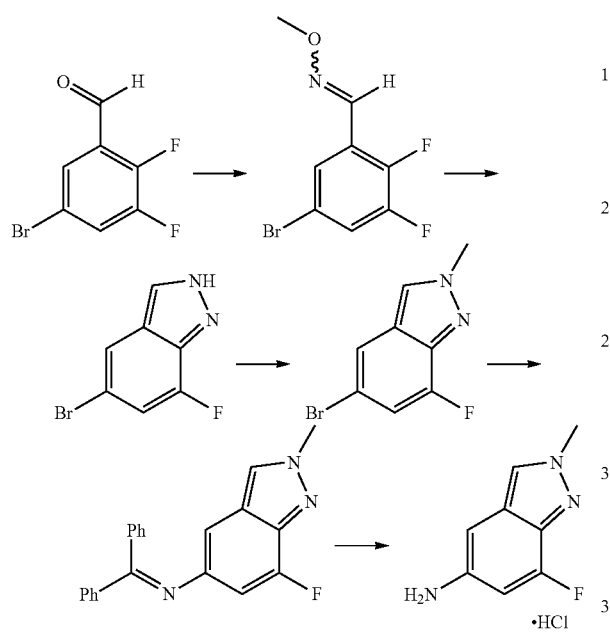

5-Bromo-2,3-difluoro-benzaldehyde (5 g, 22.6 mmol), methoxyamine hydrochloride (2.27 g, 27.1 mmol) and potassium carbonate (6.88 g, 49.8 mmol) were added to ethylene glycol dimethyl ether (100 mL). The reaction was heated to 45° C. for 18 h. The reaction was cooled to r.t. and filtered through a glass sinter and the collected solid was washed with EtOAc. The collected liquid was concentrated in vacuo to give 5-bromo-2,3-difluorobenzaldehyde O-methyl oxime as a pale yellow solid (6.82 g, 100%).

5-Bromo-2,3-difluorobenzaldehyde O-methyl oxime (5.66 g, 22.6 mmol) was dissolved in 1,4-dioxane (150 mL) and hydrazine (3.6 mL, 0.113 mol) was added. The reaction was heated at 90° C. for 5 days. The reaction was cooled to r.t. and concentrated in vacuo. The residue was purified by silica chromatography EtOAc/cyclohexane 0-40% to give 5-bromo-7-fluoro-2H-indazole as an off-white solid (3.83 g, 71%).

5-Bromo-7-fluoro-1H-indazole (3.83 g, 17.8 mmol) was dissolved in ethyl acetate (100 mL) and cooled to 0° C. using an ice-bath. Trimethyloxonium tetrafluoroborate (3.95 g, 26.7 mmol) was added portion wise and once addition was complete the reaction was warmed to r.t. The reaction was stirred for 18 h at r.t. The reaction was quenched with water, extracted with EtOAc and the layers separated. The combined organic phases were dried over magnesium sulfate, filtered and concentrated in vacuo to give a residue. The residue was purified by column chromatography on silica gel, eluting with 0-50% EtOAc in cyclohexane to give 5-bromo-7-fluoro-2-methyl-2H-indazole as an off-white solid (2.42 g, 55%).

5-Bromo-7-fluoro-2-methyl-indazole (2.42 g, 10.6 mmol) was dissolved in degassed tetrahydrofuran (100 mL) and cesium carbonate (5.16 g, 15.8 mmol), palladium(II) acetate (0.24 g, 1.06 mmol), (rac)-2,2'-bis(diphenylphosphino)-1,1'-binaphthalene (0.66 g, 1.06 mmol) and benzophenone imine (1.8 mL, 10.6 mmol) was added. The reaction tube was purged with nitrogen and sealed. The reaction heated at 80° C. for 18 h. The reaction was cooled to r.t. and the solids filtered and washed with EtOAc. The filtrate was concentrated in vacuo to give a residue. The residue was purified by column chromatography on silica gel, eluting with EtOAc/cyclohexane 0-100% to give an oil (3 g). $^1$H NMR analysis showed predominantly starting material, 5-Bromo-7-fluoro-2-methyl-indazole, with 35% conversion to N-(7-fluoro-2-methyl-2H-indazol-5-yl)-1,1-diphenylmethanimine.

The impure material (3.00 g, 4.58 mmol, assume 35% purity) was dissolved in degassed tetrahydrofuran (80 mL) and cesium carbonate (2.24 g, 6.88 mmol), palladium(II) acetate (0.21 g, 0.917 mmol), (rac)-(+)-2,2'-bis(diphenylphosphino)-1,1'-binaphthalene (0.57 g, 0.917 mmol) and benzophenone imine (0.92 mL, 5.50 mmol) was added. The reaction tube was purged with nitrogen and sealed. The reaction was heated at 80° C. for 24 h. The reaction was cooled to r.t. and the solids filtered and washed with EtOAc. The filtrate was concentrated in vacuo to give a residue oil. The residue was purified by column chromatography on silica gel, eluting with EtOAc/cyclohexane 0-100% to give N-(7-fluoro-2-methyl-2H-indazol-5-yl)-1,1-diphenylmethanimine as an off-white solid (2.56 g, >100%).

N-(7-Fluoro-2-methyl-indazol-5-yl)-1,1-diphenyl-methanimine (2.56 g, 7.77 mmol) was suspended in methyl alcohol (10 mL) and 4 N hydrogen chloride in dioxane (19 mL, 77.7 mmol) was added at r.t. The reaction was stirred at r.t. for 18 h. The solvent was removed in vacuo to give a pale yellow solid. EtOAc was added and the formed slurry was stirred for ~10 minutes. The solid was filtered and washed with further EtOAc to give the title compound as an off-white solid (1.66 g, 95%). LCMS (ES+) 166 (M+H)+

Intermediate 43: tert-butyl cyclopropyl((2-oxopyrrolidin-3-yl)methyl)carbamate

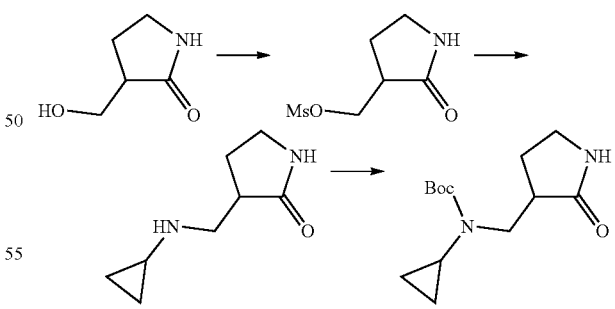

To a stirred solution of 3-(hydroxymethyl)pyrrolidin-2-one (780 mg, 6.77 mmol) in dichloromethane (50 mL) and triethylamine (1.9 mL, 13.5 mmol) at r.t. was added methanesulfonyl chloride (0.58 mL, 7.45 mmol) dropwise. The reaction was stirred for 18 h at r.t. The reaction was quenched by addition of water and the layers separated using a phase separator. The DCM was removed in vacuo to give (2-oxopyrrolidin-3-yl)methyl methanesulfonate as a white solid (800 mg, 61%).

(2-Oxopyrrolidin-3-yl)methyl methanesulfonate (800 mg, 4.14 mmol) was dissolved in acetonitrile (15 mL) and triethylamine (1.7 mL, 12.4 mmol) was added followed by cyclopropylamine (1.7 mL, 24.8 mmol). The reaction tube was sealed and heated in a microwave at 120° C. for 2 h. The solvent was removed in vacuo to give a residue, which was purified by SCX chromatography (5 g, eluting with MeOH/DCM 50% and then 10% 7N NH$_3$ in MeOH/MeOH). The ammonical fractions were combined and the solvent removed in vacuo to give 3-((cyclopropylamino)methyl) pyrrolidin-2-one as a yellow oil (438 mg, 69%).

3-[(Cyclopropylamino)methyl]pyrrolidin-2-one (438 mg, 2.84 mmol) was dissolved in dichloromethane (30 mL). Di-tert-butyl dicarbonate (0.72 mL, 3.12 mmol) and 4-(dimethylamino)pyridine (17 mg, 0.142 mmol) was added. The reaction was stirred at r.t. for 18 h. The solvent was removed in vacuo to give a residue, which was purified by silica chromatography (10 g, eluting with EtOAc) to give the title compound as a clear oil (420 mg, 58%).

Intermediate 44: 5-chloro-N-(7-fluoro-2-methyl-2H-indazol-5-yl)pyrazine-2-carboxamide

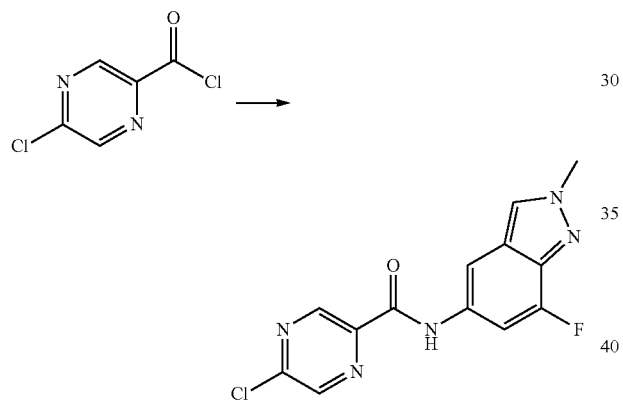

5-Chloropyrazine-2-carbonyl chloride (223 mg, 1.26 mmol) and 7-fluoro-2-methyl-indazol-5-amine hydrochloride (254 mg, 1.26 mmol) was dissolved in dichloromethane (10 mL). Triethylamine (0.53 mL, 3.78 mmol) was added and the reaction stirred at r.t. for 3 h. The reaction was quenched by addition of water and the aqueous layer extracted with DCM. The layers were separated using a phase separator and the DCM removed in vacuo to give the title compound as a light tan solid (280 mg, 65%). Used in next step without further purification.

Intermediate 45:
5-chloro-N-(1H-indazol-5-yl)pyrazine-2-carboxamide

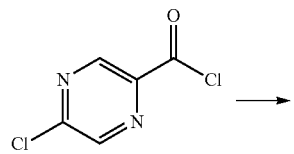

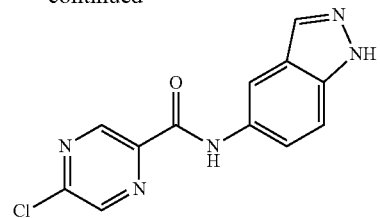

5-Chloropyrazine-2-carbonyl chloride (223 mg, 1.26 mmol) and 2H-indazol-5-amine (168 mg, 1.26 mmol) was dissolved in dichloromethane (10 mL). Triethylamine (0.53 mL, 3.78 mmol) was added at r.t. and the reaction was stirred for 3 h at r.t.

The reaction was quenched with water and the aqueous extracted with DCM ×3. The layers were separated using a phase separator and solvent removed in vacuo to give the title compound as brown solid (305 mg, 79%). Used in the next step without further purification.

Intermediate 46: 5-chloro-N-(4-fluoro-2-methyl-benzo[d]oxazol-6-yl)pyrazine-2-carboxamide

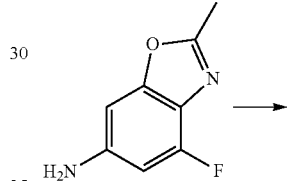

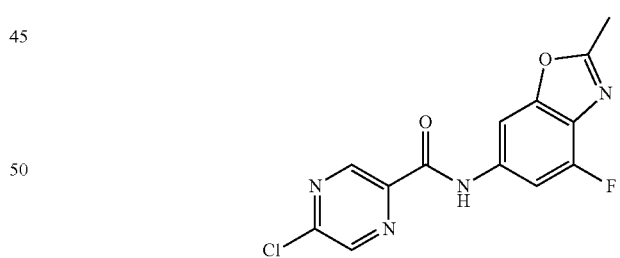

4-Fluoro-2-methyl-1,3-benzoxazol-6-amine (200 mg, 1.20 mmol), 5-chloro-2-pyrazinecarboxylic acid (191 mg, 1.20 mmol) and 1-methylimidazole (0.29 mL, 3.60 mmol) were suspended in acetonitrile (10 mL). Chloro-N,N,N',N'-tetramethylformamidinium hexafluorophosphate (400 mg, 1.43 mmol) was added and the suspension stirred at r.t. for 18 h.

The formed solid was collected by filtration and washed with acetonitrile and water. The solid was dried overnight in a vacuum oven to give the title compound as an off-white solid (250 mg, 67%). Used in the next step without further purification.

Intermediate 47: 5-(3-(((tert-butoxycarbonyl)(methyl)amino)methyl)azetidin-1-yl)pyrazine-2-carboxylic Acid

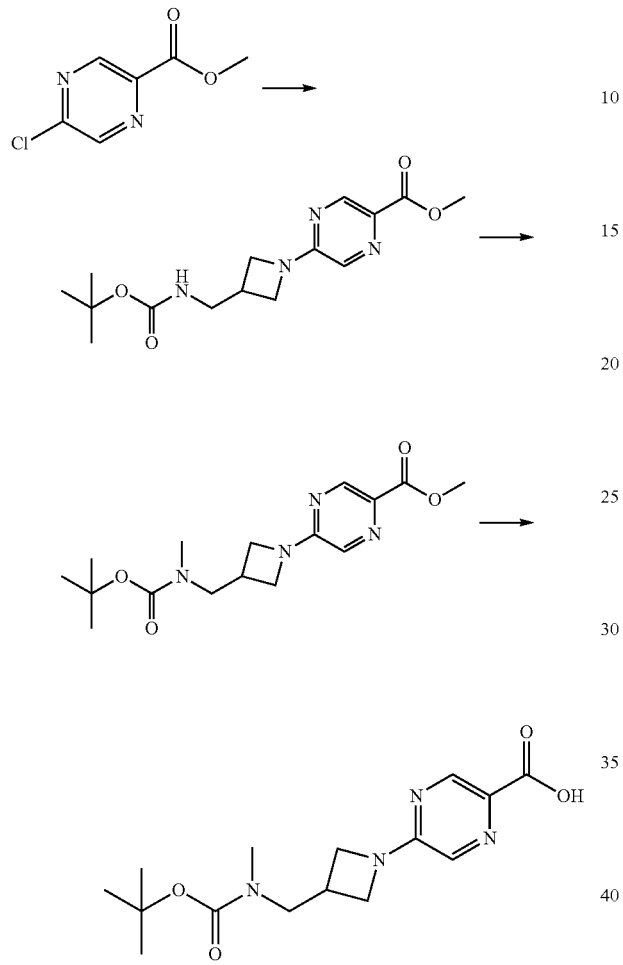

tert-Butyl N-(azetidin-3-ylmethyl)carbamate (675 mg, 3.62 mmol), methyl 5-chloro-2-pyrazinecarboxylate (625 mg, 3.62 mmol), cesium carbonate (2373 mg, 7.28 mmol) and 1,4-dioxane (25 mL) were combined and heated at reflux overnight. The reaction was cooled to r.t. and the solvent removed in vacuo. Residue taken up in DCM and washed with water, the layers were separated using a phase separator. The DCM was removed in vacuo to give a residue. The residue was purified by column chromatography on silica gel (25 g, eluting with EtOAc in cyclohexane 0-100%) to give a yellow oil (870 mg, 74%).

Methyl 5-[3-[(tert-butoxycarbonylamino)methyl]azetidin-1-yl]pyrazine-2-carboxylate (250 mg, 0.776 mmol) was dissolved in N,N-dimethylformamide (5 mL) and sodium hydride (60%, 34 mg, 0.853 mmol) was added. The reaction was stirred at r.t. for 1 h. Iodomethane (0.048 mL, 0.776 mmol) was added and the reaction stirred for 18 h at r.t. The reaction was quenched with MeOH (to avoid ester hydrolysis) and the solvent removed in vacuo to give a residue oil. Used in the next step without further purification. Methyl 5-[3-[[tert-butoxycarbonyl(methyl)amino]methyl]azetidin-1-yl]pyrazine-2-carboxylate (261 mg, 0.776 mmol) was dissolved in methyl alcohol (2 mL) and water (1 mL) and lithium hydroxide monohydrate (33 mg, 0.776 mmol) was added. The reaction was stirred at r.t. for 18 h. The solvent was removed in vacuo and the residue dissolved in water (2 mL). The pH was adjusted to pH=3 with 1M HCl and the aqueous layer extracted with EtOAc ×4. The organic layer was separated and dried by passing through a hydrophobic frit. The solvent was removed in vacuo to give the title compound as a clear oil (155 mg, 61%). Used in the next step without further purification.

Intermediate 48: 7-fluoro-2,8-dimethyl-imidazo[1,2-a]pyridin-6-amine·HCl

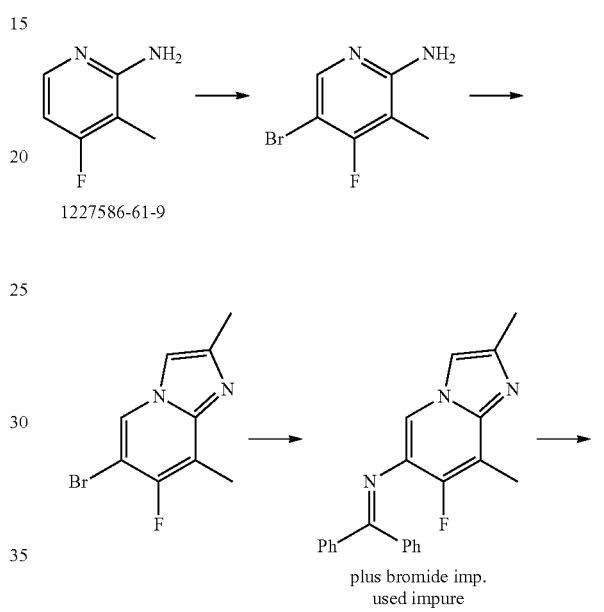

1227586-61-9

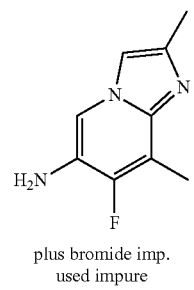

plus bromide imp.
used impure

4-Fluoro-3-methyl-pyridin-2-amine (500 mg, 3.96 mmol, 1.00 eq), N-bromosuccinimide (706 mg, 3.96 mmol) and dichloromethane (20 mL) were combined and stirred at r.t. for 2 h. Reaction mixture was then evaporated to dryness to give a brown solid, which was used crude in next step. LCMS (ES+) 205/207 (M+H)+.

5-Bromo-4-fluoro-3-methyl-pyridin-2-amine (813 mg, 3.96 mmol) (crude from previous step), 1-bromo-2,2-dimethoxypropane (0.80 mL, 5.95 mmol), pyridinium p-toluenesulfonate (100 mg, 0.396 mmol) and 2-propanol (15 mL) were combined in a sealed tube and hot block heated to 85° C. overnight. Off-white precipitate was observed. The reaction mixture was cooled to r.t., concentrated in vacuo, partitioned between ~10% aq. NaOH soln. and dichloromethane. The organic phase was dried (MgSO₄) and concentrated in vacuo to give 6-bromo-7-fluoro-2,8-dimethyl-imidazo[1,2-a]pyridine (856 mg) as a brown solid. LCMS (ES+) 243/245 (M+H)+. ¹H NMR (400 MHz, CDCl₃) δ 8.09 (d, J=6.3 Hz, 1H), 7.25 (s, 1H), 2.53 (d, J=2.5 Hz, 3H), 2.44 (s, 3H).

Cesium carbonate (1721 mg, 5.28 mmol), palladium(II) acetate (79 mg, 0.352 mmol), (±)-2,2'-bis(diphenylphosphino)-1,1'-binaphthalene (219 mg, 0.352 mmol), 6-bromo-7-fluoro-2,8-dimethyl-imidazo[1,2-a]pyridine (856 mg, 3.52 mmol) and tetrahydrofuran (20 mL) were combined and the reaction mixture was degassed by bubbling through nitrogen for 5 mins. Reaction tube was sealed and hot block heated to 85° C. over weekend. The reaction mixture was filtered through a Celite plug to remove Cesium salts, rinsing through with EtOAc. The organic phase was concentrated in vacuo onto silica and purified by flash chromatography. Starting material and target seemed to co-run. 622 mg, tan solid. LCMS basic, RT=1.42 mins, 243/245 M+H starting material, RT=1.70 mins, 344 M+H target. Used as is in next step.

A mixture of 6-bromo-7-fluoro-2,8-dimethyl-imidazo[1,2-a]pyridine and N-(7-fluoro-2,8-dimethyl-imidazo[1,2-a]pyridin-6-yl)-1,1-diphenyl-methanimine (622 mg, from previous step), methyl alcohol (5 mL) and 4 M hydrogen chloride in dioxane (5.0 mL, 20.0 mmol) were combined and stirred at r.t. for 1 h. Reaction mixture was evaporated to dryness to give 767 mg, tan solid. LCMS analysis showed a mixture of 6-bromo-7-fluoro-2,8-dimethyl-imidazo[1,2-a]pyridine and 7-fluoro-2,8-dimethyl-imidazo[1,2-a]pyridin-6-amine·HCl. LCMS basic RT=1.04 mins, 180 M+H target, RT=1.42 mins, 243/245 bromide in starting material. Used as is in next step.

Example 1: (R)-5-(2-ethylpiperazin-1-yl)-N-(8-fluoro-2-methylimidazo[1,2-a]pyridin-6-yl)pyrazine-2-carboxamide

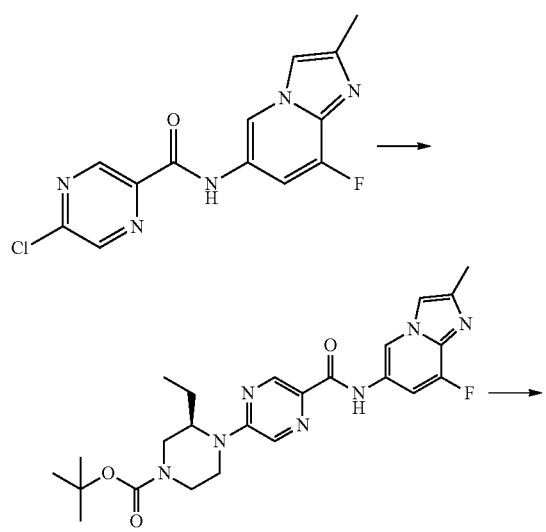

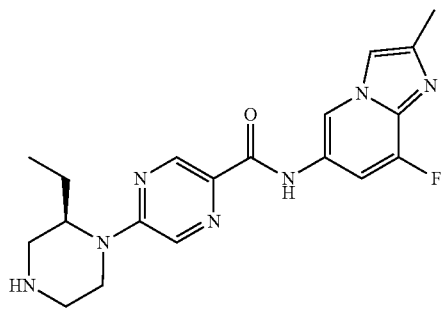

To a solution of Intermediate 1 (150 mg, 0.49 mmol) in dioxane (1 mL) was added tert-butyl (R)-3-ethylpiperazine-1-carboxylate (263 mg, 1.23 mmol). Triethylamine (0.1 mL, 0.74 mmol) was added and the reaction was heated in a microwave at 140° C. for 30 minutes. The solvent was removed in vacuo and the residue purified using silica chromatography elution gradient 0-10% ethyl acetate/cyclohexane to give tert-butyl (R)-3-ethyl-4-(5-((8-fluoro-2-methylimidazo[1,2-a]pyridin-6-yl)carbamoyl)pyrazin-2-yl)piperazine-1-carboxylate. MS (ES+) 484 (M+H).

To a solution of tert-butyl (R)-3-ethyl-4-(5-((8-fluoro-2-methylimidazo[1,2-a]pyridin-6-yl)carbamoyl)pyrazin-2-yl)piperazine-1-carboxylate (140 mg, 0.29 mmol) in methanol (2 mL) was added 4M hydrochloric acid in dioxane (10 mL). The reaction was stirred at r.t. for 1 h. The solvent was removed in vacuo, and the crude product provided was purified by reverse phase HPLC to give a TFA salt of the target. The TFA salt was dissolved in methanol/DCM 1:1 and MP-carbonate was added. The mixture was left standing for 18 h. The MP-carbonate was filtered and the solvent removed in vacuo to give the title compound. LCMS (ES+) 384 (M+H)+, RT 1.85 min (Analytical method AcHSSC18); 1H NMR (400 MHz, DMSO) δ 10.44 (s, 1H), 9.22 (d, J=1.3 Hz, 1H), 8.77 (s, 1H), 8.31 (s, 1H), 7.93 (d, J=2.0 Hz, 1H), 7.60 (dd, J=1.1, 12.7 Hz, 1H), 4.47-4.44 (m, 1H), 4.32 (d, J=12.9 Hz, 1H), 3.14-2.98 (m, 3H), 2.81 (dd, J=2.9, 12.5 Hz, 1H), 2.70-2.64 (m, 1H), 2.39 (s, 3H), 1.92-1.74 (m, 2H), 0.89 (t, J=7.5 Hz, 3H).

Further analogues were prepared using the same chemistry from commercially available or synthesized amines. In some instances, Boc protected amines were used, in which case the Boc group was removed at end of the synthetic sequence using 4N HCl in dioxane (general Method C) or TFA/DCM (general Method E). Final products were isolated by SCX and/or Preparative HPLC. Some enantiomers were separated by chiral SFC, in which case chirality was arbitrarily assigned.

| Ex. | Structure | Amine | Analytical data |
|---|---|---|---|
| 2 | 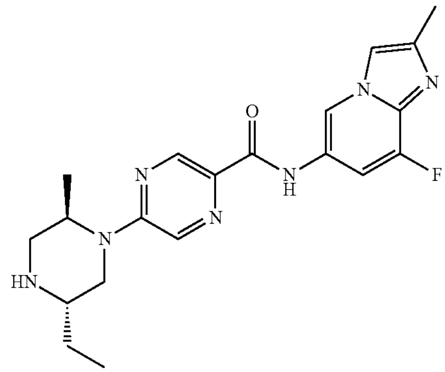 [SMILES: CC[C@H]1CN(c2cnc(C(=O)Nc3cc(F)c4nc(C)cn4c3)cn2)[C@H](C)CN1] | tert-butyl (2S,5R)-2-ethyl-5-methylpiperazine-1-carboxylate | LCMS (ES+) 398 (M + H)+, RT 1.89 min (Analytical method AcHSSC18) <br> ¹H NMR (400 MHz, DMSO) δ 10.32 (s, 1H), 9.11 (d, J = 1.5 Hz, 1H), 8.65 (d, J = 1.3 Hz, 1H), 8.16 (d, J = 1.3 Hz, 1H), 7.82 (d, J = 2.5 Hz, 1H), 7.48 (dd, J = 1.6, 13.2 Hz, 1H), 4.46-4.41 (m, 1H), 4.07 (dd, J = 1.6, 13.3 Hz, 1H), 3.39 (dd, J = 4.2, 13.3 Hz, 1H), 3.04 (dd, J = 4.8, 13.1 Hz, 1H), 2.85-2.80 (m, 1H), 2.52 (dd, J = 2.6, 13.1 Hz, 1H), 2.28 (s, 3H), 1.48-1.33 (m, 2H), 1.19 (d, J = 6.6 Hz, 3H), 0.82 (t, J = 7.5 Hz, 3H). |
| 3 | 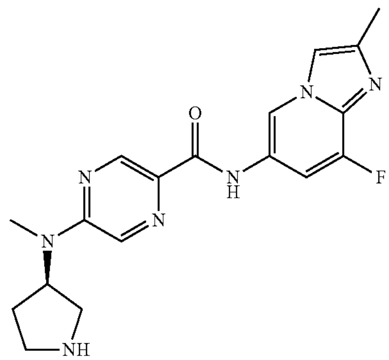 [SMILES: Cc1cn2cc(NC(=O)c3cnc(N(C)[C@@H]4CCNC4)cn3)cc(F)c2n1] | tert-butyl (R)-3-(methylamino)pyrrolidine-1-carboxylate | LCMS (ES+) 370 (M + H)+, RT 1.69 min (Analytical method AcHSSC18) <br> ¹H NMR (400 MHz, DMSO) δ 10.97 (s, 1H), 9.76 (s, 1H), 9.66 (s, 1H), 9.62 (d, J = 1.4 Hz, 1H), 8.85 (d, J = 1.3 Hz, 1H), 8.34 (s, 1H), 8.30-8.25 (m, 2H), 5.49-5.39 (m, 1H), 3.48-3.37 (m, 2H), 3.27-3.14 (m, 5H), 2.51 (s, 3H), 2.27-2.18 (m, 1H), 2.17-2.06 (m, 1H). |
| 4 | 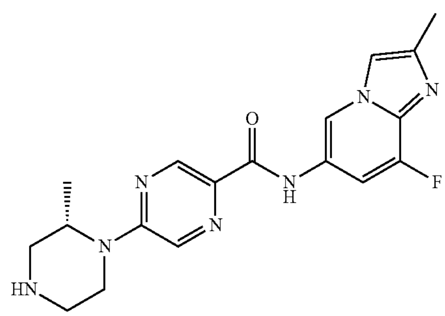 [SMILES: Cc1cn2cc(NC(=O)c3cnc(N4CCNC[C@@H]4C)cn3)cc(F)c2n1] | tert-butyl (S)-3-methylpiperazine-1-carboxylate | LCMS (ES+) 370 (M + H)+, RT 2.98 min (Analytical method BicarbBEHC18) <br> ¹H NMR (400 MHz, DMSO) δ 10.44 (s, 1H), 9.19 (d, J = 1.6 Hz, 1H), 8.75 (s, 1H), 8.25 (s, 1H), 7.90 (d, J = 3.0 Hz, 1H), 7.56 (dd, J = 1.6, 13.1 Hz, 1H), 4.61-4.58 (m, 1H), 4.18 (d, J = 12.5 Hz, 1H), 3.08 (dt, J = 3.6, 12.6 Hz, 1H), 3.01 (dd, J = 3.0, 12.2 Hz, 1H), 2.86-2.82 (m, 2H), 2.64 (ddd, J = 12.2, 12.2, 3.5 Hz, 1H), 2.56 (s, 3H), 2.35 (s, 3H), 1.24 (d, J = 6.7 Hz, 3H). |
| 5 | 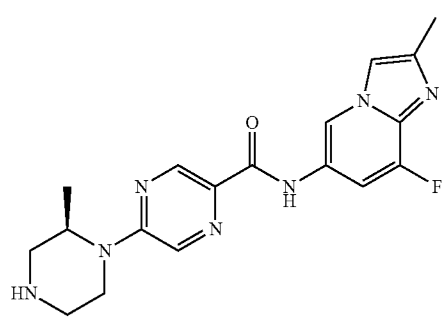 [SMILES: Cc1cn2cc(NC(=O)c3cnc(N4CCNC[C@H]4C)cn3)cc(F)c2n1] | tert-butyl (R)-3-methylpiperazine-1-carboxylate | LCMS (ES+) 370 (M + H)+, RT 2.98 min (Analytical method BicarbBEHC18) <br> ¹H NMR (400 MHz, DMSO) δ 10.44 (s, 1H), 9.19 (d, J = 1.6 Hz, 1H), 8.75 (s, 1H), 8.25 (s, 1H), 7.90 (d, J = 3.0 Hz, 1H), 7.56 (dd, J = 1.7, 13.1 Hz, 1H), 4.62-4.58 (m, 1H), 4.18 (d, J = 12.4 Hz, 1H), 3.09 (ddd, J = 12.4, 12.4, 3.5 Hz, 1H), 3.01 (dd, J = 3.1, 12.4 Hz, 1H), 2.86-2.81 (m, 2H), 2.64 (dt, J = 3.4, 12.0 Hz, 1H), 2.56 (s, 3H), 1.24 (d, J = 6.8 Hz, 3H). |

| Ex. | Structure | Amine | Analytical data |
|---|---|---|---|
| 6 | 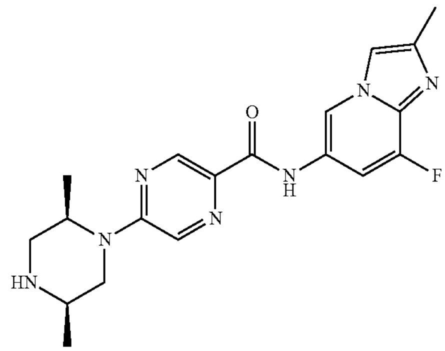 [SMILES: Cc1cn2cc(NC(=O)c3cnc(N4C[C@@H](C)NC[C@H]4C)cn3)cc(F)c2n1] | tert-butyl (2R,5R)-2,5-dimethylpiperazine-1-carboxylate | LCMS (ES+) 384 (M + H)+, RT 1.78 min (Analytical method AcHSSC18) ¹H NMR (400 MHz, DMSO) δ 10.51 (s, 1H), 9.27 (d, J = 1.6 Hz, 1H), 8.83 (d, J = 1.1 Hz, 1H), 8.35 (d, J = 1.1 Hz, 1H), 7.98 (d, J = 2.8 Hz, 1H), 7.64 (dd, J = 1.6, 13.1 Hz, 1H), 4.30 (d, J = 8.9 Hz, 1H), 2.99 (dd, J = 3.9, 12.3 Hz, 1H), 2.93 (dd, J = 1.5, 12.0 Hz, 1H), 2.80-2.68 (m, 3H), 2.42 (d, J = 0.7 Hz, 3H), 1.31 (d, J = 6.8 Hz, 3H), 1.18 (d, J = 5.8 Hz, 3H). |
| 7 | 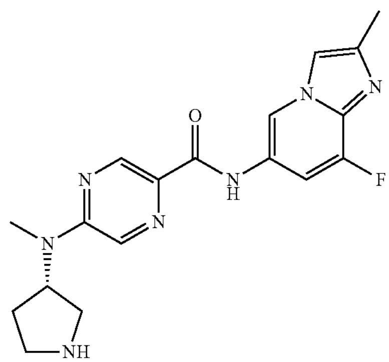 | tert-butyl (S)-3-(methylamino)pyrrolidine-1-carboxylate | LCMS (ES+) 370 (M + H)+, RT 1.69 min (Analytical method AcHSSC18) ¹H NMR (400 MHz, DMSO) δ 10.96 (s, 1H), 9.68-9.63 (m, 1H), 9.60 (d, J = 1.4 Hz, 1H), 9.55-9.55 (m, 1H), 8.85 (d, J = 1.3 Hz, 1H), 8.34-8.32 (m, 1H), 8.28-8.23 (m, 2H), 5.48-5.38 (m, 1H), 3.49-3.38 (m, 2H), 3.26-3.17 (m, 5H), 2.51 (s, 3H), 2.27-2.19 (m, 1H), 2.14-2.05 (m, 1H). |
| 8 | 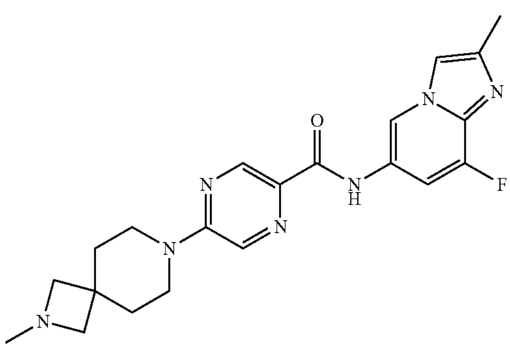 [SMILES: Cc1cn2cc(NC(=O)c3cnc(N4CCC5(CC4)CN(C)C5)cn3)cc(F)c2n1] | 2-methyl-2,7-diazaspiro[3.5]nonane•2HCl | LCMS (ES+) 410 (M + H)+, RT 1.93 min (Analytical method AcHSSC18); ¹H NMR (400 MHz, DMSO) δ 10.43 (s, 1H), 9.19 (d, J = 1.6 Hz, 1H), 8.74 (d, J = 1.1 Hz, 1H), 8.30 (s, 1H), 8.19 (s, 1H), 7.90 (d, J = 2.6 Hz, 1H), 7.56 (dd, J = 1.5, 13.0 Hz, 1H), 4.05 (s, 4H), 3.23 (s, 3H), 2.97-2.90 (m, 2H), 2.73-2.67 (m, 2H), 2.35 (s, 3H), 1.68-1.61 (m, 2H), 1.43-1.35 (m, 2H). |
| 9 | Enantiomer 1 + Enantiomer 2 | 1-methyl-1,7-diazaspiro[4.4]nonane•2HCl | 0.25 equiv formate salt LCMS (ES+) 410 (M + H)+, RT 1.76 min (Analytical method AcHSSC18); ¹H NMR (400 MHz, DMSO) δ 10.43 (s, 1H), 9.19 (d, J = 1.6 Hz, 1H), 8.75 (d, J = 1.3 Hz, 1H), 8.22 (s, 0.25H), 7.99 (d, J = 1.3 Hz, 1H), 7.89 (d, J = 2.8 Hz, 1H), 7.57 (dd, J = 1.8, 13.3 Hz, 1H), 3.82-3.75 (m, 1H), 3.54-3.49 (m, 2H), 3.35-3.30 (m, 1H), 2.81-2.65 (m, 2H), 2.35 (s, 3H), 2.28 (s, 3H), 2.19-2.09 (m, 1H), 1.85-1.72 (m, 5H). |

-continued

| Ex. | Structure | Amine | Analytical data |
|---|---|---|---|
| 10 | 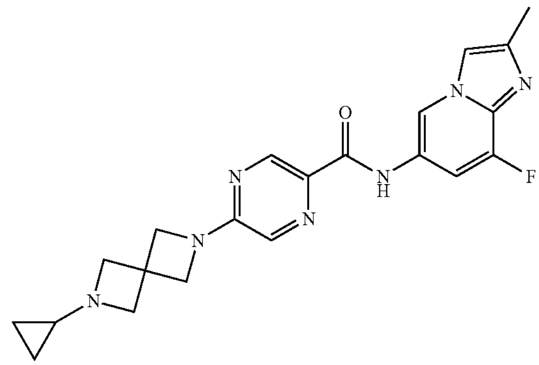 [SMILES: Cc1cn2cc(NC(=O)c3cnc(N4CC5(C4)CN(C4CC4)C5)cn3)cc(F)c2n1] | 2-cyclopropyl-2,6-diazaspiro[3.3]heptane•2TFA | 0.5 eq formate salt<br>LCMS (ES+) 408 (M + H)+, RT 1.76 min (Analytical method AcHSSC18);<br>$^1$H NMR (400 MHz, DMSO) δ 10.41 (s, 1H), 9.15 (d, J = 1.6 Hz, 1H), 8.69 (d, J = 1.3 Hz, 1H), 8.18 (s, 0.5H), 7.87 (d, J = 2.8 Hz, 1H), 7.84 (d, J = 1.4 Hz, 1H), 7.53 (dd, J = 1.9, 12.9 Hz, 1H), 4.23 (s, 4H), 3.39 (s, 4H), 2.32 (s, 3H), 1.87-1.80 (m, 1H), 0.34-0.29 (m, 2H), 0.22-0.25 (m, 2H). |
| 11 | 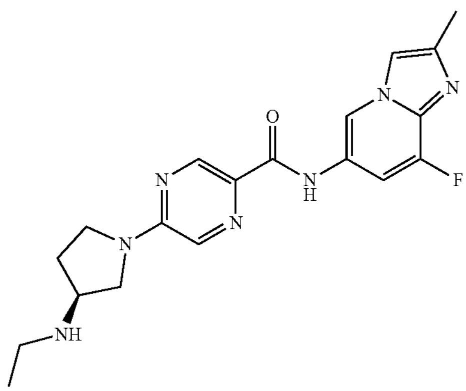 [SMILES: CCN[C@H]1CCN(c2cnc(C(=O)Nc3cc(F)c4nc(C)cn4c3)cn2)C1] | (S)-N-ethylpyrrolidin-3-amine | LCMS (ES+) 384 (M + H)+, RT 1.69 min (Analytical method AcHSSC18)<br>$^1$H NMR (400 MHz, DMSO) δ 8.95 (s, 1H), 8.64 (s, 1H), 7.94 (s, 1H), 7.78 (d, J = 2.0 Hz, 1H), 7.42 (d, J = 12.7 Hz, 1H), 3.72-3.60 (m, 2H), 3.52-3.47 (m, 1H), 3.41 (s, 1H), 3.31-3.27 (m, 1H), 2.58 (d, J = 6.8 Hz, 2H), 2.32 (s, 3H), 2.21-2.15 (m, 1H), 1.84-1.84 (m, 1H), 1.02 (dd, J = 7.1, 7.1 Hz, 3H). |

Example 12: 5-(3-((cyclopropylamino)methyl)pyrrolidin-1-yl)-N-(8-fluoro-2-methylimidazo[1,2-a]pyridin-6-yl)pyrazine-2-carboxamide (Enantiomer 1+Enantiomer 2)

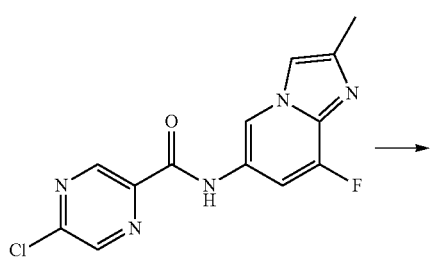

-continued

Prepared using general Method D and the following quantities: Intermediate 1 (127 mg, 0.41 mmol), N-(pyrrolidin-3-ylmethyl)cyclopropanamine dihydrochloride (87 mg, 0.41 mmol), cesium carbonate (487 mg, 1.5 mmol) and DMF (3 mL). The crude material was purified by preparative HPLC to give the title compound. LCMS (ES+) 410.2 (M+H)+, RT 3.59 min (Analytical method BicarbBEHC18). $^1$H NMR (400 MHz, DMSO) δ 10.17 (s, 1H), 8.95 (d, J=1.7 Hz, 1H), 8.50 (d, J=1.4 Hz, 1H), 7.72 (d, J=1.1 Hz, 1H), 7.65 (dd, J=0.8, 3.1 Hz, 1H), 7.33 (dd, J=1.6, 13.1 Hz, 1H), 3.51-3.40 (m, 2H), 3.32-3.24 (m, 1H), 3.03-2.95 (m, 2H), 2.49-2.36 (m, 2H), 2.10 (s, 3H), 1.90-1.82 (m, 2H), 1.55-1.46 (m, 1H), 0.17-0.12 (m, 2H), 0.04--0.04 (in, 2H).

Further analogues were prepared using the same chemistry from commercially available or synthesized amines. In some instances, Boc protected amines were used, in which case the Boc group was removed at end of the synthetic sequence using 4N HCl in dioxane (general Method C) or TFA/DCM (general Method E). Final products were isolated by SCX and/or preparative HPLC. Some enantiomers were separated by chiral SFC, in which case chirality was arbitrarily assigned.

| Ex. | Structure | Amine | Analytical data |
| --- | --- | --- | --- |
| 13 | 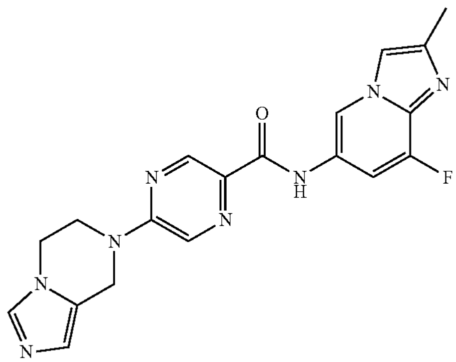 [SMILES: Cc1cn2cc(NC(=O)c3cnc(N4CCn5cncc5C4)cn3)cc(F)c2n1] | 5,6,7,8-tetrahydroimidazo[1,5-a]pyrazine | LCMS (ES+) 393 (M + H)+, RT 3.43 min (Analytical method BicarbBEHC18) $^1$H NMR (400 MHz, DMSO) δ 10.53 (s, 1H), 9.20 (d, J = 1.6 Hz, 1H), 8.82 (d, J = 1.1 Hz, 1H), 8.43 (d, J = 1.1 Hz, 1H), 8.19 (s, 1H), 7.91 (d, J = 2.6 Hz, 1H), 7.68 (s, 1H), 7.58 (dd, J = 1.6, 12.8 Hz, 1H), 6.86 (s, 1H), 4.98 (s, 2H), 4.28-4.23 (m, 2H), 4.18-4.13 (m, 2H), 2.35 (s, 3H). |
| 14 | Enantiomer 2 | 2-methyl-2,7-diazaspiro[4.4]nonane | LCMS (ES+) 440 (M + H)+, RT 2.02 min (Analytical method AcHSSC18); $^1$H NMR (400 MHz, DMSO δ 10.44 (s, 1H), 9.20 (d, J = 1.6 Hz, 1H), 8.75 (d, J = 1.0 Hz, 1H), 7.98 (d, J = 1.1 Hz, 1H), 7.90 (d, J = 2.7 Hz, 1H), 7.58 (dd, J = 1.8, 13.0 Hz, 1H), 3.65-3.56 (m, 3H), 3.48 (d, J = 10.8 Hz, 1H), 2.69-2.54 (m, 1H), 2.54-2.49 (m, 2H, obscured by water), 2.42 (d, J = 9.2 Hz, 1H), 2.35 (s, 3H), 2.27 (s, 3H), 2.03-1.97 (m, 2H), 1.86-1.80 (m, 2H). |
| 15 | Enantiomer 1 | 2-methyl-2,7-diazaspiro[4.4]nonane | LCMS (ES+) 398 (M + H)+, RT 1.91 min (Analytical method AcHSSC18); $^1$H NMR (400 MHz, DMSO δ 10.44 (s, 1H), 9.20 (d, J = 1.6 Hz, 1H), 8.75 (d, J = 1.0 Hz, 1H), 7.98 (d, J = 1.1 Hz, 1H), 7.90 (d, J = 2.7 Hz, 1H), 7.58 (dd, J = 1.8, 13.0 Hz, 1H), 3.65-3.56 (m, 3H), 3.48 (d, J = 10.8 Hz, 1H), 2.69-2.54 (m, 1H), 2.54-2.49 (m, 2H, obscured by water), 2.42 (d, J = 9.2 Hz, 1H), 2.35 (s, 3H), 2.27 (s, 3H), 2.03-1.97 (m, 2H), 1.86-1.80 (m, 2H). |

-continued

| Ex. | Structure | Amine | Analytical data |
|---|---|---|---|
| 16 | Cis Isomer, Enantiomer 1 | Intermediate 8 | LCMS (ES+) 428 (M + H)+, RT 2.25 min (Analytical method AcHSSC18) $^1$H NMR (400 MHz, DMSO) δ 10.47 (s, 1H), 9.20 (d, J = 1.6 Hz, 1H), 8.79 (d, J = 1.3 Hz, 1H), 8.09 (s, 1H), 7.90 (d, J = 2.8 Hz, 1H), 7.57 (dd, J = 1.6, 13.1 Hz, 1H), 5.57 (td, J = 3.0, 51.6 Hz, 1H), 4.03-3.78 (m, 4H), 3.49-3.38 (m, 1H), 2.36 (d, J = 7.2 Hz, 6H), 1.92-1.85 (m, 1H), 0.53-0.48 (m, 2H), 0.39-0.27 (m, 2H). |
| 17 | 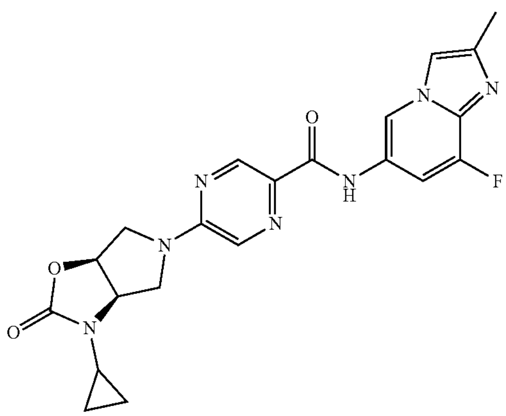 [SMILES: Cc1cn2cc(NC(=O)c3cnc(N4C[C@@H]5OC(=O)N(C6CC6)[C@@H]5C4)cn3)cc(F)c2n1] | Intermediate 9 | LCMS (ES+) 438 (M + H)+, RT 2.46 min (Analytical method AcHSSC18) $^1$H NMR (400 MHz, DMSO) δ 10.54 (s, 1H), 9.23 (s, 1H), 8.85 (s, 1H), 8.27 (s, 1H), 7.94 (d, J = 2.5 Hz, 1H), 7.62 (d, J = 13.1 Hz, 1H), 5.26-5.21 (m, 1H), 4.55 (t, J = 6.6 Hz, 1H), 4.30-4.19 (m, 2H), 3.71 (dd, J = 5.3, 13.1 Hz, 1H), 3.56 (dd, J = 5.9, 12.3 Hz, 1H), 2.74-2.63 (m, 1H), 2.39 (s, 3H), 0.91-0.72 (m, 4H). |
| 18 | Enantiomer 1 + Enantiomer 2 | 2-methyl-2,6-diazaspiro[3.4]octane | LCMS (ES+) 428 (M + H)+, RT 1.99 min (Analytical method AcHSSC18); $^1$H NMR (400 MHz, DMSO) δ 10.43 (s, 1H), 9.20 (d, J = 1.3 Hz, 1H), 8.75 (s, 1H), 7.98 (d, J = 1.9 Hz, 1H), 7.89 (d, J = 3.1 Hz, 1H), 7.57 (dd, J = 1.5, 13.2 Hz, 1H), 3.68 (s, 2H), 3.58 (dd, J = 6.9, 6.9 Hz, 2H), 3.19-3.12 (m, 4H), 2.35 (s, 3H), 2.25 (s, 3H), 2.16 (dd, J = 6.5, 6.5 Hz, 2H). |

-continued

| Ex. | Structure | Amine | Analytical data |
|---|---|---|---|
| 19 | 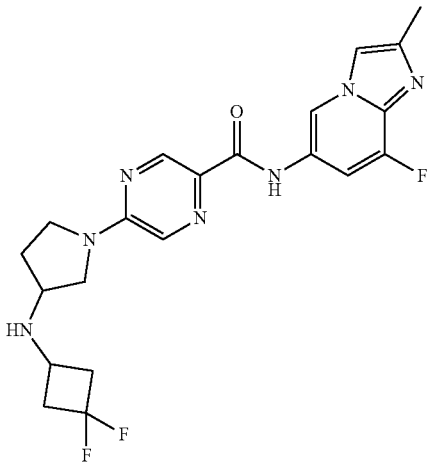<br>Enantiomer 1 | 3-((3,3-difluorocyclobutyl)ammonio)pyrrolidin-1-ium dichloride | LCMS (ES+) 446 (M + H)+, RT 3.63 min (Analytical method BicarbBEHC18) $^1$H NMR (400 MHz, DMSO) δ 10.42 (s, 1H), 9.19 (d, J = 1.6 Hz, 1H), 8.75 (d, J = 1.3 Hz, 1H), 7.98 (d, J = 1.4 Hz, 1H), 7.90 (d, J = 2.8 Hz, 1H), 7.57 (dd, J = 1.6, 13.1 Hz, 1H), 3.73-3.53 (m, 3H), 3.34 (s, 3H), 3.41-3.22 (m, 3H), 3.32-3.30 (m, 3H), 2.86-2.75 (m, 2H), 2.42-2.27 (m, 2H), 2.35 (s, 3H), 2.19-2.09 (m, 1H), 1.87 (s, 1H). |
| 20 | 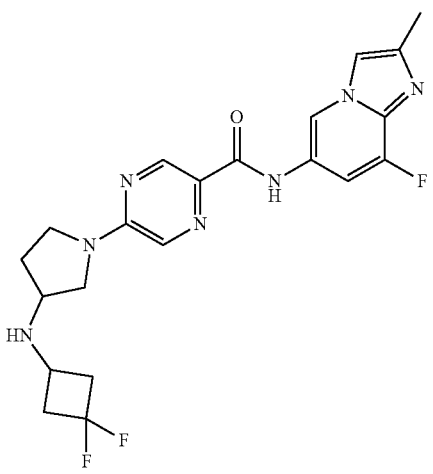<br>Enantiomer 2 | 3-((3,3-difluorocyclobutyl)ammonio)pyrrolidin-1-ium dichloride | LCMS (ES+) 446 (M + H)+, RT 3.63 min (Analytical method BicarbBEHC18) $^1$H NMR (400 MHz, DMSO) δ 10.42 (s, 1H), 9.19 (d, J = 1.6 Hz, 1H), 8.75 (d, J = 1.3 Hz, 1H), 7.98 (d, J = 1.4 Hz, 1H), 7.90 (d, J = 2.8 Hz, 1H), 7.57 (dd, J = 1.6, 13.1 Hz, 1H), 3.73-3.53 (m, 3H), 3.34 (s, 3H), 3.41-3.22 (m, 3H), 3.32-3.30 (m, 3H), 2.86-2.75 (m, 2H), 2.42-2.27 (m, 2H), 2.35 (s, 3H), 2.19-2.09 (m, 1H), 1.87 (s, 1H). |
| 21 | 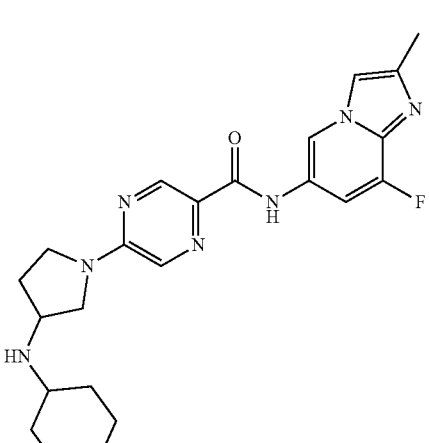<br>Enantiomer 2 | 3-((tetrahydro-2H-pyran-4-yl)ammonio)pyrrolidin-1-ium dichloride | LCMS (ES+) 440 (M + H)+, RT 3.4 min (Analytical method BicarbBEHC18) $^1$H NMR (400 MHz, DMSO δ 10.42 (s, 1H), 9.19 (d, J = 1.5 Hz, 1H), 8.75 (d, J = 1.3 Hz, 1H), 7.98 (d, J = 1.3 Hz, 1H), 7.90 (d, J = 2.8 Hz, 1H), 3.85 (d, J = 11.4 Hz, 2H), 3.79-3.51 (m, 4H), 3.34 (s, 3H), 3.36-3.27 (m, 3H), 2.76-2.68 (m, 1H), 2.35 (s, 3H), 2.20-2.14 (m, 1H), 1.84-1.76 (m, 3H), 1.32-1.20 (m, 2H). |

| Ex. | Structure | Amine | Analytical data |
|---|---|---|---|
| 22 | 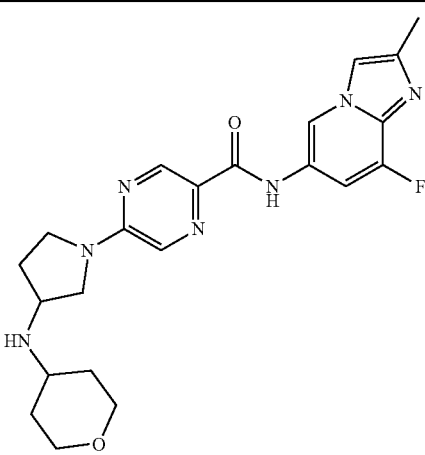<br>Enantiomer 1 | 3-((tetrahydro-2H-pyran-4-yl)ammonio)pyrrolidin-1-ium dichloride | LCMS (ES+) 440 (M + H)+, RT 3.39 min (Analytical method BicarbBEHC18)<br>$^1$H NMR (400 MHz, DMSO) δ 10.42 (s, 1H), 9.19 (d, J = 1.5 Hz, 1H), 8.75 (d, J = 1.3 Hz, 1H), 7.98 (d, J = 1.3 Hz, 1H), 7.90 (d, J = 2.8 Hz, 1H), 3.85 (d, J = 11.4 Hz, 2H), 3.79-3.51 (m, 4H), 3.34 (s, 3H), 3.36-3.27 (m, 3H), 2.76-2.68 (m, 1H), 2.35 (s, 3H), 2.20-2.14 (m, 1H), 1.84-1.76 (m, 3H), 1.32-1.20 (m, 2H). |
| 23 | 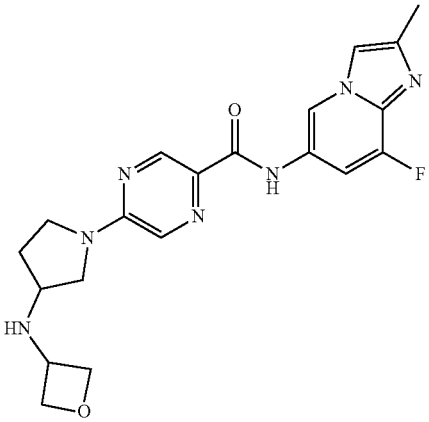<br>Enantiomer 1 + Enantiomer 2 | Intermediate 7 | LCMS (ES+) 412 (M + H)+, RT 1.62 min (Analytical method AcHSSC18)<br>$^1$H NMR (400 MHz, DMSO) δ 10.42 (s, 1H), 9.19 (d, J = 1.6 Hz, 1H), 8.75 (d, J = 1.3 Hz, 1H), 7.97 (d, J = 1.3 Hz, 1H), 7.90 (d, J = 2.8 Hz, 1H), 4.70-4.65 (m, 2H), 4.39-4.32 (m, 2H), 4.04-3.96 (m, 1H), 3.71-3.51 (m, 3H), 3.43-3.38 (m, 1H), 3.32-3.28 (m, 1H), 2.92-2.92 (m, 1H), 2.35 (s, 3H), 2.10-2.06 (m, 1H), 1.82 (d, J = 4.5 Hz, 1H). |
| 24 | 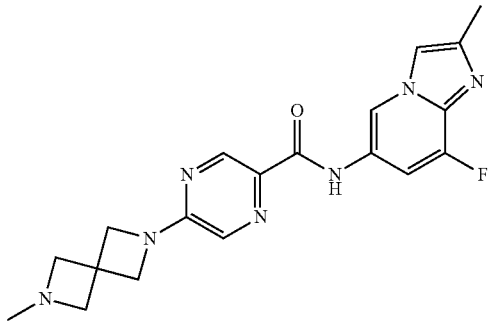 [SMILES: Cc1cn2cc(NC(=O)c3cnc(N4CC5(CN(C)C5)C4)cn3)cc(F)c2n1] | 6-methyl-2,6-diazaspiro[3.3]heptane; dihydrochloride | LCMS (ES+) 382 (M + H)+, RT 1.64 min (Analytical method AcHSSC18)<br>$^1$H NMR (400 MHz, DMSO) δ 10.44 (s, 1H), 9.18 (d, J = 1.6 Hz, 1H), 8.72 (d, J = 1.4 Hz, 1H), 7.89 (d, J = 2.8 Hz, 1H), 7.86 (d, J = 1.4 Hz, 1H), 7.56 (dd, J = 1.8, 12.9 Hz, 1H), 4.26 (s, 4H), 3.31 (s, 4H), 2.35 (s, 3H), 2.20 (s, 3H). |

-continued

| Ex. | Structure | Amine | Analytical data |
|---|---|---|---|
| 25 | 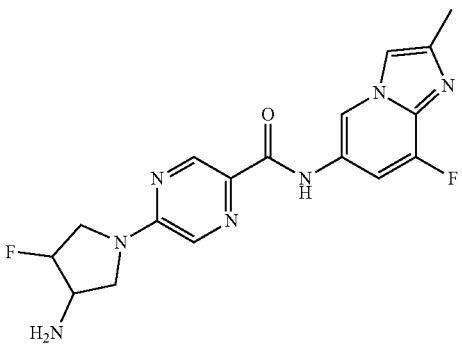<br>Cis Isomers, Enantiomer 1 + Enantiomer 2 | tert-butyl (3R*,4S*)-3-amino-4-fluoropyrrolidine-1-carboxylate | LCMS (ES+) 374 (M + H)+, RT 1.6 min (Analytical method AcHSSC18) $^1$H NMR (400 MHz, DMSO) δ 10.46 (s, 1H), 9.20 (d, J = 1.5 Hz, 1H), 8.77 (d, J = 1.3 Hz, 1H), 8.02 (s, 1H), 7.90 (d, J = 2.8 Hz, 1H), 7.57 (dd, J = 1.6, 13.1 Hz, 1H), 5.09 (d, J = 54.4 Hz, 1H), 3.98-3.86 (m, 2H), 3.79-3.60 (m, 2H), 3.17 (dd, J = 10.2, 10.2 Hz, 1H), 2.35 (s, 3H), 1.86-1.83 (m, 2H). |
| 26 | 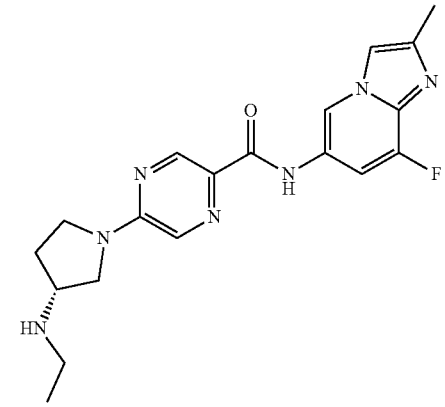 [SMILES: CCN[C@@H]1CCN(c2cnc(C(=O)Nc3cc(F)c4nc(C)cn4c3)cn2)C1] | (R)-N-ethylpyrrolidin-3-amine | LCMS (ES+) 384 (M + H)+, RT 1.7 min (Analytical method AcHSSC18 $^1$H NMR (400 MHz, DMSO) δ 10.41 (s, 1H), 9.19 (d, J = 1.4 Hz, 1H), 8.74 (s, 1H), 7.97 (s, 1H), 7.89 (d, J = 2.6 Hz, 1H), 7.57 (dd, J = 1.5, 13.2 Hz, 1H), 3.73-3.54 (m, 3H), 3.42 (m, 2H), 2.60-2.60 (m, 2H), 2.35 (s, 3H), 2.19-2.08 (m, 1H), 1.89-1.88 (m, 1H), 1.04 (dd, J = 7.0, 7.0 Hz, 3H). |
| 27 | 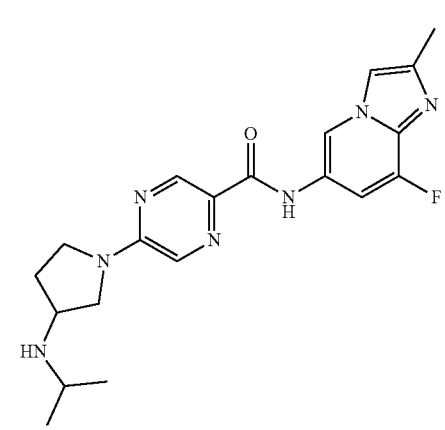<br>Enantiomer 1 | Intermediate 5 | LCMS (ES+) 398 (M + H)+, RT 1.72 min (Analytical method AcHSSC18) $^1$H NMR (400 MHz, DMSO) δ 10.44 (s, 1H), 9.23 (s, 1H), 8.79 (s, 1H), 8.01 (s, 1H), 7.93 (d, J = 2.8 Hz, 1H), 7.61 (dd, J = 0.9, 13.4 Hz, 1H), 3.83-3.68 (m, 2H), 3.63-3.52 (m, 2H), 3.34-3.26 (m, 1H), 2.93-2.85 (m, 1H), 2.39 (s, 3H), 2.23-2.14 (m, 1H), 1.86-1.86 (m, 2H), 1.06 (dd, J = 5.9, 5.9 Hz, 6H). |

| Ex. | Structure | Amine | Analytical data |
|---|---|---|---|
| 28 | 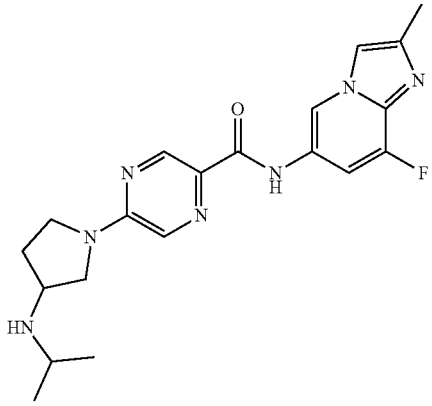<br>Enantiomer 2 | Intermediate 5 | LCMS (ES+) 398 (M + H)+, RT 1.87 min (Analytical method AcHSSC18)<br>$^1$H NMR (400 MHz, DMSO) δ 10.44 (s, 1H), 9.23 (s, 1H), 8.79 (s, 1H), 8.01 (s, 1H), 7.93 (d, J = 2.8 Hz, 1H), 7.61 (dd, J = 0.9, 13.4 Hz, 1H), 3.83-3.68 (m, 2H), 3.63-3.52 (m, 2H), 3.34-3.26 (m, 1H), 2.93-2.85 (m, 1H), 2.39 (s, 3H), 2.23-2.14 (m, 1H), 1.86-1.86 (m, 2H), 1.06 (dd, J = 5.9, 5.9 Hz, 6H). |
| 29 | 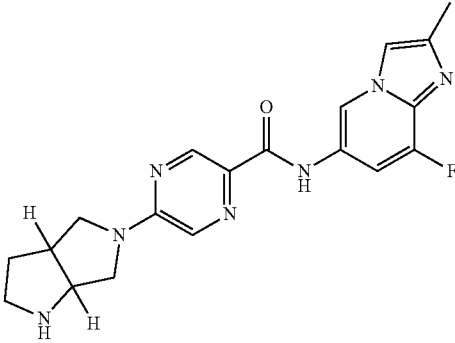<br>Cis Isomer, Enantiomer 1 | tert-butyl hexahydropyrrolo[3,4-b]pyrrole-1(2H)-carboxylate | LCMS (ES+) 382 (M + H)+, RT 1.68 min (Analytical method AcHSSC18)<br>$^1$H NMR (400 MHz, DMSO) δ 10.45 (s, 1H), 9.23 (s, 1H), 8.78 (s, 1H), 8.01 (s, 1H), 7.94-7.91 (m, 1H), 7.61 (d, J = 13.2 Hz, 1H), 3.88 (dd, J = 9.3, 20.7 Hz, 2H), 3.74 (dd, J = 6.2, 11.7 Hz, 1H), 3.56 (d, J = 11.6 Hz, 1H), 2.99-2.88 (m, 3H), 2.75-2.68 (m, 1H), 2.39 (s, 3H), 2.00-1.89 (m, 1H), 1.73-1.71 (m, 1H). |
| 30 | 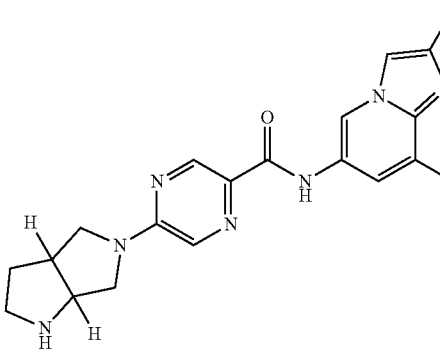<br>Cis Isomer, Enantiomer 2 | tert-butyl hexahydropyrrolo[3,4-b]pyrrole-1(2H)-carboxylate | LCMS (ES+) 382 (M + H)+, RT 1.68 min (Analytical method AcHSSC18)<br>$^1$H NMR (400 MHz, DMSO) δ 10.45 (s, 1H), 9.23 (s, 1H), 8.78 (s, 1H), 8.01 (s, 1H), 7.94-7.91 (m, 1H), 7.61 (d, J = 13.2 Hz, 1H), 3.88 (dd, J = 9.3, 20.7 Hz, 2H), 3.74 (dd, J = 6.2, 11.7 Hz, 1H), 3.56 (d, J = 11.6 Hz, 1H), 2.99-2.88 (m, 3H), 2.75-2.68 (m, 1H), 2.39 (s, 3H), 2.00-1.89 (m, 1H), 1.73-1.71 (m, 1H). |

-continued

| Ex. | Structure | Amine | Analytical data |
|---|---|---|---|
| 31 | Cis Isomer, Enantiomer 1 | 1-methyloctahydropyrrolo[3,4-b]pyrrole | LCMS (ES+) 396 (M + H)+, RT 1.67 min (Analytical method AcHSSC18) $^1$H NMR (400 MHz, DMSO) δ 10.42 (s, 1H), 9.19 (d, J = 1.5 Hz, 1H), 8.75 (d, J = 1.3 Hz, 1H), 7.99 (s, 1H), 7.90 (d, J = 2.8 Hz, 1H), 7.57 (dd, J = 1.6, 13.0 Hz, 1H), 3.89-3.76 (m, 2H), 3.51 (dd, J = 4.6, 12.0 Hz, 1H), 3.40-3.36 (m, 1H), 3.10-3.03 (m, 1H), 2.94-2.88 (m, 2H), 2.35 (s, 3H), 2.29 (s, 3H), 2.32-2.26 (m, 1H), 2.10-2.03 (m, 1H), 1.73-1.63 (m, 1H). |
| 32 | Cis Isomer, Enantiomer 2 | 1-methyloctahydropyrrolo[3,4-b]pyrrole | LCMS (ES+) 396 (M + H)+, RT 1.67 min (Analytical method AcHSSC18) $^1$H NMR (400 MHz, DMSO) δ 10.42 (s, 1H), 9.19 (d, J = 1.5 Hz, 1H), 8.75 (d, J = 1.3 Hz, 1H), 7.99 (s, 1H), 7.90 (d, J = 2.8 Hz, 1H), 7.57 (dd, J = 1.6, 13.0 Hz, 1H), 3.89-3.76 (m, 2H), 3.51 (dd, J = 4.6, 12.0 Hz, 1H), 3.40-3.36 (m, 1H), 3.10-3.03 (m, 1H), 2.94-2.88 (m, 2H), 2.35 (s, 3H), 2.29 (s, 3H), 2.32-2.26 (m, 1H), 2.10-2.03 (m, 1H), 1.73-1.63 (m, 1H). |
| 33 | 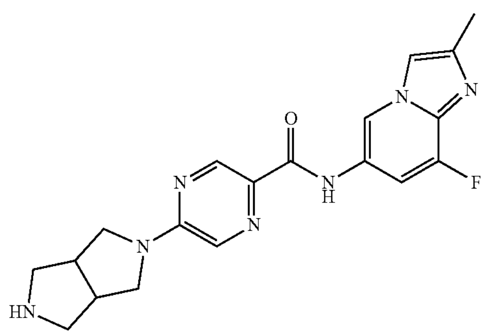 [SMILES: Cc1cn2cc(NC(=O)c3cnc(N4CC5CNCC5C4)cn3)cc(F)c2n1] | tert-butyl hexahydropyrrolo[3,4-c]pyrrole-2(1H)-carboxylate | LCMS (ES+) 382 (M + H)+, RT 1.68 min (Analytical method AcHSSC18) $^1$H NMR (400 MHz, DMSO) δ 10.43 (s, 1H), 9.19 (d, J = 1.6 Hz, 1H), 8.75 (d, J = 1.3 Hz, 1H), 7.99 (d, J = 1.3 Hz, 1H), 7.89 (d, J = 2.6 Hz, 1H), 7.57 (dd, J = 1.8, 13.1 Hz, 1H), 3.82 (dd, J = 7.2, 11.2 Hz, 2H), 3.43 (dd, J = 2.6, 11.0 Hz, 2H), 2.97-2.88 (m, 4H), 2.70 (d, J = 8.4 Hz, 2H), 2.35 (s, 3H). |
| 34 | 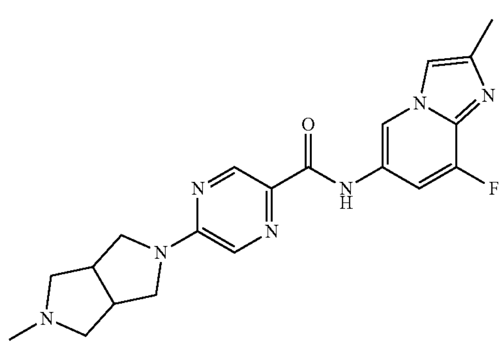 [SMILES: Cc1cn2cc(NC(=O)c3cnc(N4CC5CN(C)CC5C4)cn3)cc(F)c2n1] | 2-methyloctahydropyrrolo[3,4-c]pyrrole | LCMS (ES+) 396.2 (M + H)+, RT 1.64 min (Analytical method AcHSSC18) $^1$H NMR (400 MHz, DMSO) δ 10.44 (s, 1H), 9.19 (d, J = 1.5 Hz, 1H), 8.75 (d, J = 1.1 Hz, 1H), 8.00 (d, J = 1.3 Hz, 1H), 7.89 (d, J = 2.8 Hz, 1H), 7.57 (dd, J = 1.6, 13.2 Hz, 1H), 3.85-3.78 (m, 2H), 3.49 (dd, J = 2.9, 11.5 Hz, 2H), 2.99-2.99 (m, 2H), 2.58 (dd, J = 1.8, 9.6 Hz, 2H), 2.50-2.45 (m, 2H), 2.35 (s, 3H), 2.24 (s, 3H). |

| Ex. | Structure | Amine | Analytical data |
|---|---|---|---|
| 35 | 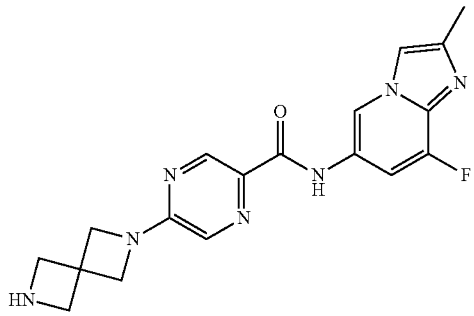 [SMILES: Cc1cn2cc(NC(=O)c3cnc(N4CC5(CNC5)C4)cn3)cc(F)c2n1] | tert-butyl 2,6-diazaspiro[3.3]heptane-2-carboxylate | LCMS (ES+) 368 (M + H)+, RT 1.6 min (Analytical method AcHSSC18) <br> $^1$H NMR (400 MHz, DMSO) δ 10.45 (s, 1H), 9.18 (d, J = 1.6 Hz, 1H), 8.72 (d, J = 1.3 Hz, 1H), 7.90-7.86 (m, 2H), 7.56 (dd, J = 1.6, 13.0 Hz, 1H), 4.28 (s, 4H), 3.64 (s, 4H), 2.35 (s, 3H). |
| 36 | Enantiomer 1 + Enantiomer 2 | Intermediate 15 | LCMS (ES+) 412 (M + H)+, RT 1.94 min (Analytical method AcHSSC18) <br> $^1$H NMR (400 MHz, MeOD) δ 8.98 (d, J = 1.5 Hz, 1H), 8.69 (d, J = 1.0 Hz, 1H), 7.89 (d, J = 1.0 Hz, 1H), 7.66 (d, J = 2.3 Hz, 1H), 7.32 (dd, J = 1.5, 12.2 Hz, 1H), 3.82-3.67 (m, 2H), 3.58-3.47 (m, 2H), 3.41-3.34 (m, 1H), 2.70-2.62 (m, 2H), 2.41 (s, 3H), 2.36-2.26 (m, 1H), 2.02-1.89 (m, 1H), 1.59-1.37 (m, 4H), 0.98 (dd, J = 7.3, 7.3 Hz, 3H). |
| 37 | Cis Isomer, Enantiomer 2 | tert-butyl hexahydropyrrolo[3,2-b]pyrrole-1(2H)-carboxylate | LCMS (ES+) 382 (M + H)+, RT 1.63 min (Analytical method AcHSSC18) <br> $^1$H NMR (400 MHz, DMSO δ 10.42 (s, 1H), 9.20 (d, J = 1.6 Hz, 1H), 8.76 (d, J = 1.1 Hz, 1H), 8.03 (d, J = 1.0 Hz, 1H), 7.90 (d, J = 2.6 Hz, 1H), 4.48-4.42 (m, 1H), 3.91-3.79 (m, 2H), 3.59-3.51 (m, 1H), 2.81 (dd, J = 6.7, 6.7 Hz, 2H), 2.34 (s, 3H), 2.16-1.87 (m, 3H), 1.69-1.63 (m, 1H). |

-continued

| Ex. | Structure | Amine | Analytical data |
|---|---|---|---|
| 38 | Cis Isomer, Enantiomer 1 | tert-butyl hexahydropyrrolo[3,2-b]pyrrole-1(2H)-carboxylate | LCMS (ES+) 382 (M + H)+, RT 1.62 min (Analytical method AcHSSC18) $^1$H NMR (400 MHz, DMSO δ 10.42 (s, 1H), 9.20 (d, J = 1.6 Hz, 1H), 8.76 (d, J = 1.1 Hz, 1H), 8.03 (d, J = 1.0 Hz, 1H), 7.90 (d, J = 2.6 Hz, 1H), 4.48-4.42 (m, 1H), 3.91-3.79 (m, 2H), 3.59-3.51 (m, 1H), 2.81 (dd, J = 6.7, 6.7 Hz, 2H), 2.34 (s, 3H), 2.16-1.87 (m, 3H), 1.69-1.63 (m, 1H). |
| 39 | 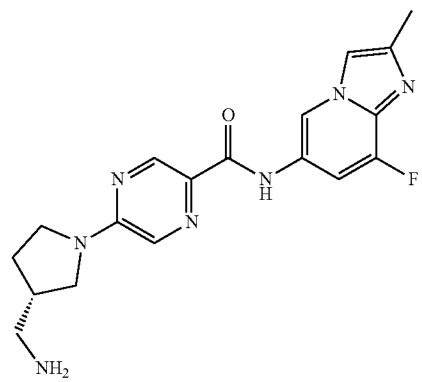 [SMILES: Cc1cn2cc(NC(=O)c3cnc(N4CC[C@@H](CN)C4)cn3)cc(F)c2n1] | tert-butyl (R)-(pyrrolidin-3-ylmethyl)carbamate | LCMS (ES+) 370 (M + H)+, RT 1.67 min (Analytical method AcHSSC18) $^1$H NMR (400 MHz, DMSO δ 10.46 (s, 1H), 9.24 (s, 1H), 8.79 (s, 1H), 8.01 (s, 1H), 7.93 (d, J = 2.0 Hz, 1H), 7.61 (dd, J = 1.3, 13.2 Hz, 1H), 3.81-3.70 (m, 2H), 3.59-3.53 (m, 1H), 3.35 (d, J = 7.8 Hz, 1H), 3.13-3.06 (m, 1H), 2.71 (dd, J = 6.9, 6.9 Hz, 1H), 2.43 (m, 1H), 2.39 (s, 3H), 2.15 (s, 1H), 1.82-1.82 (m, 1H). |
| 40 | 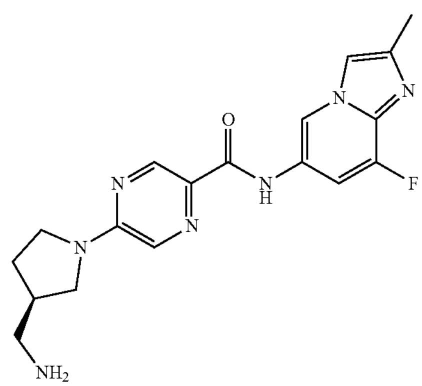 [SMILES: Cc1cn2cc(NC(=O)c3cnc(N4CC[C@H](CN)C4)cn3)cc(F)c2n1] | tert-butyl (S)-(pyrrolidin-3-ylmethyl)carbamate | LCMS (ES+) 370 (M + H)+, RT 1.67 min (Analytical method AcHSSC18) $^1$H NMR (400 MHz, DMSO) δ 10.46 (s, 1H), 9.24 (s, 1H), 8.79 (s, 1H), 8.01 (s, 1H), 7.93 (d, J = 2.0 Hz, 1H), 7.61 (dd, J = 1.3, 13.2 Hz, 1H), 3.81-3.70 (m, 2H), 3.59-3.53 (m, 1H), 3.35 (d, J = 7.8 Hz, 1H), 3.13-3.06 (m, 1H), 2.71 (dd, J = 6.9, 6.9 Hz, 1H), 2.43 (m, 1H), 2.39 (s, 3H), 2.15 (s, 1H), 1.82-1.82 (m, 1H). |

| Ex. | Structure | Amine | Analytical data |
|---|---|---|---|
| 41 | Enantiomer 1 + Enantiomer 2 | 1-(pyrrolidin-3-ylmethyl)pyrrolidine | LCMS (ES+) 424.2 (M + H)+, RT 1.83 min (Analytical method AcHSSC18) $^1$H NMR (400 MHz, DMSO) δ 10.43 (s, 1H), 9.20 (d, J = 1.6 Hz, 1H), 8.74 (d, J = 1.3 Hz, 1H), 7.98 (d, J = 1.0 Hz, 1H), 7.90 (d, J = 2.8 Hz, 1H), 7.57 (dd, J = 1.6, 13.0 Hz, 1H), 3.79-3.65 (m, 2H), 3.57-3.48 (m, 1H), 3.33-3.22 (m, 1H), 2.52 (t, J = 1.9 Hz, 10H), 2.56-2.41 (m, 10H), 2.35 (s, 3H), 2.20-2.09 (m, 1H), 1.70 (dd, J = 2.8, 2.8 Hz, 6H). |
| 42 | Enantiomer 1 + Enantiomer 2 | N,N-dimethyl-1-(pyrrolidin-3-yl)methanamine | LCMS (ES+) 398 (M + H)+, RT 1.69 min (Analytical method AcHSSC18) $^1$H NMR (400 MHz, DMSO) δ 10.46 (s, 1H), 9.23 (d, J = 1.5 Hz, 1H), 8.79 (d, J = 1.3 Hz, 1H), 8.02 (d, J = 1.3 Hz, 1H), 7.93 (d, J = 2.5 Hz, 1H), 7.61 (dd, J = 1.5, 13.1 Hz, 1H), 3.81-3.70 (m, 2H), 3.61-3.53 (m, 1H), 3.35-3.26 (m, 1H), 2.61 (m, 1H), 2.39 (s, 3H), 2.37-2.27 (m, 2H), 2.23 (s, 6H), 2.20-2.16 (m, 1H), 1.80-1.73 (m, 1H). |
| 43 | Enantiomer 1 + Enantiomer 2 | Intermediate 11 | LCMS (ES+) 412 (M + H)+, RT 1.87 min (Analytical method AcHSSC18) $^1$H NMR (400 MHz, DMSO δ 10.41 (s, 1H), 9.19 (d, J = 1.5 Hz, 1H), 7.95 (d, J = 1.3 Hz, 1H), 7.89 (d, J = 2.8 Hz, 1H), 7.57 (dd, J = 1.6, 13.1 Hz, 1H), 3.81 (dd, J = 6.8, 10.7 Hz, 1H), 3.73-3.67 (m, 1H), 3.52-3.44 (m, 2H), 3.12 (dd, J = 7.1, 10.7 Hz, 1H), 2.35 (s, 3H), 2.19-2.16 (m, 1H), 1.77-1.77 (m, 2H), 1.09 (s, 9H). |

| Ex. | Structure | Amine | Analytical data |
|---|---|---|---|
| 44 | 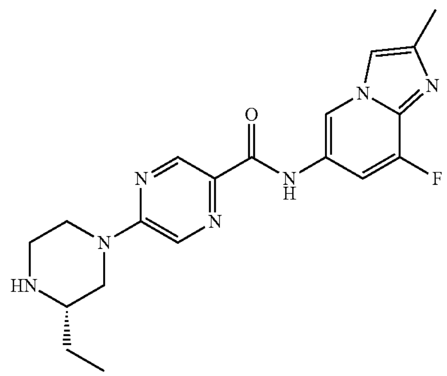 [SMILES: CC[C@H]1CN(c2cnc(C(=O)Nc3cc(F)c4nc(C)cn4c3)cn2)CCN1] | tert-butyl (S)-2-ethylpiperazine-1-carboxylate | LCMS (ES+) 384 (M + H)+, RT 1.8 min (Analytical method AcHSSC18) $^1$H NMR (400 MHz, DMSO) δ10.42 (s, 1H), 9.19 (d, J = 1.6 Hz, 1H), 8.74 (s, 1H), 8.31 (s, 1H), 7.90 (d, J = 3.0 Hz, 1H), 7.56 (dd, J = 1.6, 13.0 Hz, 1H), 4.43-4.30 (m, 2H), 3.04-2.95 (m, 2H), 2.72-2.59 (m, 2H), 2.50-2.35 (m, 1H), 2.35 (s, 3H), 2.19 (s, 1H), 1.47-1.34 (m, 2H), 0.95 (dd, J = 7.5, 7.5 Hz, 3H). |
| 45 | Enantiomer 1 + Enantiomer 2 | tert-butyl (3aR,4S,7R,7a5)-octahydro-1H-4,7-epiminoisoindole-8-carboxylate | LCMS (ES+) 408 (M + H)+, RT 1.73 min (Analytical method AcHSSC18) $^1$H NMR (400 MHz, DMSO) δ 0.37 (s, 1H), 9.10 (d, J = 1.5 Hz, 1H), 8.70 (d, J = 1.3 Hz, 1H), 8.27 (s, 1H), 8.07 (d, J = 1.3 Hz, 1H), 7.81 (d, J = 2.5 Hz, 1H), 7.48 (dd, J = 1.5, 13.1 Hz, 1H), 3.89-3.79 (m, 4H), 3.22-3.14 (m, 2H), 2.91-2.85 (m, 2H), 2.27 (s, 3H), 1.42-1.34 (m, 4H). |
| 46 | 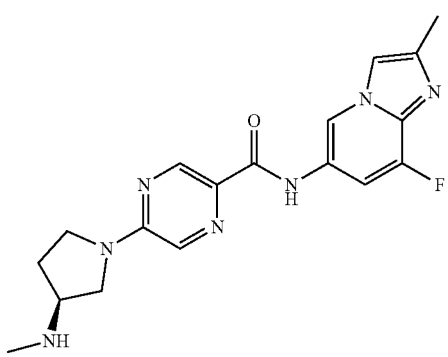 [SMILES: CN[C@H]1CCN(c2cnc(C(=O)Nc3cc(F)c4nc(C)cn4c3)cn2)C1] | (S)-N-methylpyrrolidin-3-amine | LCMS (ES+) 370.2 (M + H)+, RT 1.65 min (Analytical method AcHSSC18) $^1$H NMR (400 MHz, DMSO) δ10.41 (s, 1H), 9.19 (s, 1H), 8.74 (s, 1H), 7.97 (s, 1H), 7.89 (d, J = 2.5 Hz, 1H), 7.56 (d, J = 12.9 Hz, 1H), 3.69-3.57 (m, 2H), 2.33 (d, J = 8.8 Hz, 6H), 2.16-2.09 (m, 2H), 1.93-1.87 (m, 2H). |
| 47 | Cis Isomers, Enantiomer 1 and Enantiomer 2 | 1,1-dimethyloctahydropyrrolo[3,4-c]pyrrole | LCMS (ES+) 410 (M + H)+, RT 1.9 min (Analytical method AcHSSC18) $^1$H NMR (400 MHz, CDCl$_3$) δ 9.22 (s, 1H), 9.09 (s, 1H), 8.92 (s, 1H), 7.76 (s, 1H), 7.41 (d, J = 2.3 Hz, 1H), 6.81 (dd, J = 1.5, 11.0 Hz, 1H), 3.80 (dd, J = 8.2, 11.0 Hz, 1H), 3.69 (dd, J = 8.5, 12.0 Hz, 1H), 3.62-3.50 (m, 2H), 3.40 (dd, J = 8.6, 11.4 Hz, 1H), 3.23-3.15 (m, 1H), 2.86 (dd, J = 4.5, 11.6 Hz, 1H), 2.68-2.60 (m, 1H), 2.47 (s, 3H), 1.24 (s, 3H), 1.21 (s, 3H). |

| Ex. | Structure | Amine | Analytical data |
| --- | --- | --- | --- |
| 48 | 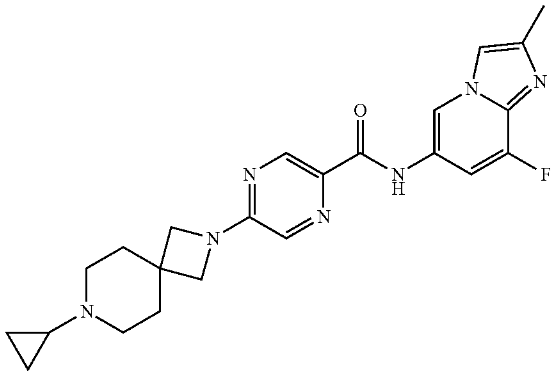 [SMILES: Cc1cn2cc(NC(=O)c3cnc(N4CC5(CCN(C6CC6)CC5)C4)cn3)cc(F)c2n1] | 7-cyclopropyl-2,7-diazaspiro[3.5]nonane•2HCl | LCMS (ES+) 436.2 (M + H)+, RT 3.9 min (Analytical method BicarbBEHC18); $^1$H NMR (400 MHz, DMSO) δ 10.15 (s, 1H), 9.07 (s, 1H), 8.73 (s, 1H), 7.87 (s, 1H), 7.83 (d, J = 2.7 Hz, 1H), 7.52 (dd, J = 1.3, 12.8 Hz, 1H), 3.92 (s, 4H), 2.58-2.52 (m, 4H), 2.37 (s, 3H), 1.78 (dd, J = 5.4, 5.4 Hz, 4H), 1.65-1.59 (m, 1H), 0.47-0.41 (m, 2H), 0.35-0.30 (m, 2H). |
| 49 | 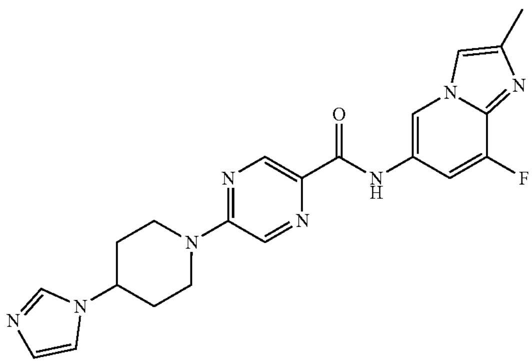 [SMILES: Cc1cn2cc(NC(=O)c3cnc(N4CCC(n5ccnc5)CC4)cn3)cc(F)c2n1] | 4-(1H-imidazol-1-yl)piperidine•2HCl | LCMS (ES+) 421 (M + H)+, RT 3.71 min (Analytical method BicarbBEHC18). $^1$H NMR (400 MHz, DMSO) δ 10.48 (s, 1H), 9.20 (s, 1H), 8.77 (s, 1H), 8.43 (s, 1H), 7.91 (s, 1H), 7.76 (s, 1H), 7.56 (dd, 1H), 7.31 (s, 1H), 6.90 (s, 1H), 4.71 (m, 2H), 4.45 (m, 1H), 3.15 (m, 2H), 2.35 (s, 3H), 2.11 (m, 2H), 1.94 (m, 2H). |
| 50 | 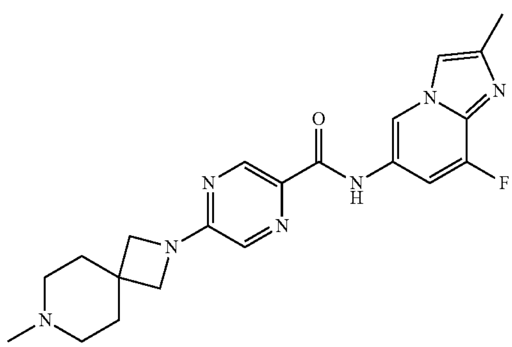 [SMILES: Cc1cn2cc(NC(=O)c3cnc(N4CC5(CCN(C)CC5)C4)cn3)cc(F)c2n1] | 7-methyl-2,7-diazaspiro[3.5]nonane | LCMS (ES+) 410 (M + H)+, RT 1.76 min (Analytical method AcHSSC18); $^1$H NMR (400 MHz, DMSO δ 10.45 (s, 1H), 9.19 (d, J = 1.6 Hz, 1H), 8.72 (d, J = 1.3 Hz, 1H), 7.89 (dd, J = 1.8, 6.1 Hz, 2H), 7.57 (dd, J = 1.7, 13.0 Hz, 1H), 3.90 (s, 4H), 2.35-2.35 (m, 4H), 2.32-2.26 (m, 3H), 2.16 (s, 3H), 1.80 (t, J = 5.0 Hz, 4H). |
| 51 | 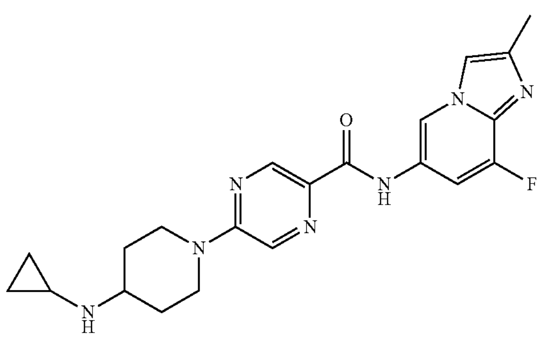 [SMILES: Cc1cn2cc(NC(=O)c3cnc(N4CCC(NC5CC5)CC4)cn3)cc(F)c2n1] | N-cyclopropylpiperidin-4-amine | LCMS (ES+) 410 (M + H)+, RT 1.9 min (Analytical method AcHSSC18); $^1$H NMR (400 MHz, DMSO) δ 10.19 (s, 1H), 8.95 (d, J = 1.6 Hz, 1H), 8.49 (s, 1H), 8.10 (s, 1H), 7.66 (d, J = 2.6 Hz, 1H), 7.33 (dd, J = 1.7, 13.1 Hz, 1H), 4.16-4.10 (m, 2H), 3.02-2.94 (m, 2H), 2.64-2.57 (m, 1H), 2.11 (s, 3H), 1.92-1.86 (m, 1H), 1.76-1.69 (m, 3H), 1.14-1.02 (m, 2H), 0.18-0.13 (m, 2H), 0.01--0.02 (m, 2H). |

Example 52: N-(2,8-dimethylimidazo[1,2-a]pyrazin-6-yl)-5-(3-(pyrrolidin-1-ylmethyl)pyrrolidin-1-yl)pyrazine-2-carboxamide (Enantiomer 1+Enantiomer 2)

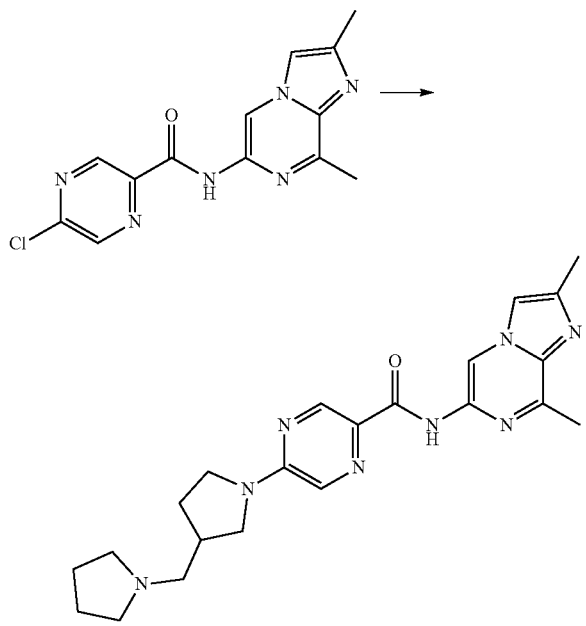

Intermediate 2 (100 mg, 0.3 mmol), 1-(pyrrolidin-3-ylmethyl)pyrrolidine dihydrochloride (94 mg, 0.23 mmol), $Cs_2CO_3$ (487 mg, 1 mmol) and DMF (3 mL) were combined in a sealed tube and hot block heated to 100° C. for 16 hours. The reaction mixture was cooled to room temperature, the cesium salts were removed by filtration, and the reaction mixture was purified by Preparative HPLC to give the title compound. LCMS (ES+) 421.2 (M+H)+, RT 2.04 min (Analytical method AcHSSC18); $^1$H NMR (400 MHz, DMSO) δ 9.66 (s, 1H), 9.15 (s, 1H), 8.75 (d, J=1.3 Hz, 1H), 8.04 (s, 1H), 8.01 (s, 1H), 3.79-3.66 (m, 2H), 3.57-3.49 (m, 1H), 3.33-3.24 (m, 1H), 2.71 (s, 3H), 2.52 (t, J=1.9 Hz, 6H), 2.50-2.42 (m, 6H), 2.40 (s, 3H), 2.15-2.13 (m, 1H), 1.71 (s, 6H).

Further analogues were prepared using the same chemistry from commercially available or synthesized amines. In some instances, Boc protected amines were used, in which case the Boc group was removed at end of the synthetic sequence using 4N HCl in dioxane (general Method C) or TFA/DCM (general Method E). Final products were isolated by SCX and/or Preparative HPLC. Some enantiomers were separated by chiral SFC, in which case chirality was arbitrarily assigned.

| Ex. | Structure | Amine | Analytical data |
| --- | --- | --- | --- |
| 53 | 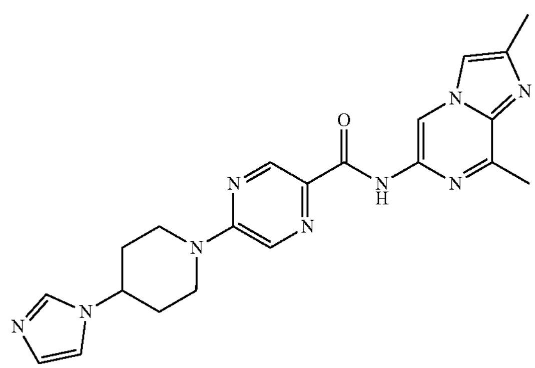 [SMILES: Cc1cn2cc(NC(=O)c3cnc(N4CCC(n5ccnc5)CC4)cn3)nc(C)c2n1] | 4-(1H-imidazol-1-yl)piperidine | LCMS (ES+) 418 (M + H)+, RT 2.15 min (Analytical method AcHSSC18) $^1$H NMR (400 MHz, DMSO) δ 9.69 (s, 1H), 9.15 (s, 1H), 8.78 (d, J = 1.1 Hz, 1H), 8.48 (d, J = 1.1 Hz, 1H), 8.01 (s, 1H), 7.76 (s, 1H), 7.31 (s, 1H), 6.90 (s, 1H), 4.72 (d, J = 13.7 Hz, 2H), 4.51-4.42 (m, 1H), 3.17 (dd, J = 12.0, 12.0 Hz, 2H), 2.71 (s, 3H), 2.40 (s, 3H), 2.11 (d, J = 9.8 Hz, 2H), 1.99-1.86 (m, 2H). |
| 54 | 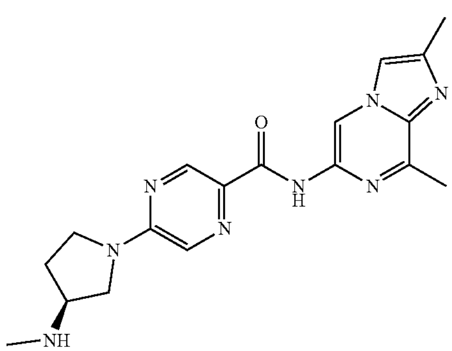 | (S)-N-methylpyrrolidin-3-amine | LCMS (ES+) 367 (M + H)+, RT 1.79 min (Analytical method AcHSSC18) $^1$H NMR (400 MHz, DMSO) δ 9.66 (s, 1H), 9.14 (s, 1H), 8.76 (d, J = 1.4 Hz, 1H), 8.03 (d, J = 1.3 Hz, 1H), 8.01 (d, J = 0.7 Hz, 1H), 3.70-3.55 (m, 3H), 3.42-3.39 (m, 1H), 2.71 (s, 3H), 2.40 (s, 3H), 2.33-2.31 (m, 3H), 2.13-2.07 (m, 2H), 1.88-1.88 (m, 2H). |

| Ex. | Structure | Amine | Analytical data |
|---|---|---|---|
| 55 | Enantiomer 1 | Intermediate 5 | LCMS (ES+) 395 (M + H)+, RT 1.99 min (Analytical method AcHSSC18) $^1$H NMR (400 MHz, DMSO) δ 9.68 (s, 1H), 9.17 (s, 1H), 8.79 (d, J = 1.3 Hz, 1H), 8.06-8.04 (m, 2H), 3.82-3.68 (m, 2H), 3.62-3.52 (m, 2H), 3.31 (dd, J = 5.1, 10.9 Hz, 1H), 2.94-2.83 (m, 1H), 2.74 (s, 3H), 2.44 (s, 3H), 2.20 (dd, J = 5.6, 11.4 Hz, 1H), 1.85-1.85 (m, 2H), 1.06 (dd, J = 5.7, 5.7 Hz, 6H). |
| 56 | Enantiomer 2 | Intermediate 5 | LCMS (ES+) 395 (M + H)+, RT 1.99 min (Analytical method AcHSSC18) $^1$H NMR (400 MHz, DMSO) δ 9.68 (s, 1H), 9.17 (s, 1H), 8.79 (d, J = 1.3 Hz, 1H), 8.06-8.04 (m, 2H), 3.82-3.68 (m, 2H), 3.62-3.52 (m, 2H), 3.31 (dd, J = 5.1, 10.9 Hz, 1H), 2.94-2.83 (m, 1H), 2.74 (s, 3H), 2.44 (s, 3H), 2.20 (dd, J = 5.6, 11.4 Hz, 1H), 1.85-1.85 (m, 2H), 1.06 (dd, J = 5.7, 5.7 Hz, 6H). |
| 57 | Enantiomer 1 + Enantiomer 2 | Intermediate 11 | LCMS (ES+) 409 (M + H)+, RT 2.05 min (Analytical method AcHSSC18) $^1$H NMR (400 MHz, DMSO) δ 9.70-9.67 (m, 1H), 9.18 (s, 1H), 8.79 (d, J = 1.3 Hz, 1H), 8.04 (d, J = 2.5 Hz, 2H), 3.86 (dd, J = 6.8, 10.9 Hz, 1H), 3.78-3.70 (m, 1H), 3.59-3.47 (m, 2H), 3.16 (dd, J = 7.1, 10.6 Hz, 1H), 2.74 (s, 3H), 2.44 (s, 3H), 2.23-2.17 (m, 1H), 1.85-1.79 (m, 2H), 1.13 (s, 9H). |

| Ex. | Structure | Amine | Analytical data |
|---|---|---|---|
| 58 | 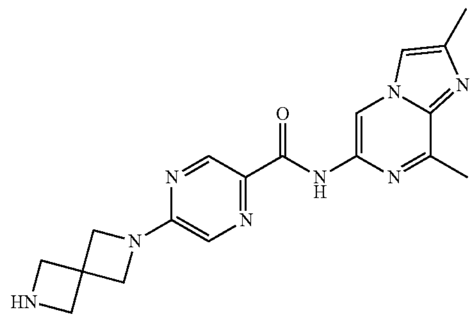 [SMILES: Cc1cn2cc(NC(=O)c3cnc(N4CC5(CNC5)C4)cn3)nc(C)c2n1] | tert-butyl 2,6-diazaspiro[3.3]heptane-2-carboxylate | LCMS (ES+) 365 (M + H)+, RT 1.81 min (Analytical method AcHSSC18) ¹H NMR (400 MHz, MeOD) δ 9.01 (s, 1H), 8.60 (d, J = 1.3 Hz, 1H), 7.73 (d, J = 1.3 Hz, 1H), 7.67 (s, 1H), 4.22 (s, 4H), 3.74 (s, 4H), 2.64 (s, 3H), 2.35 (s, 3H). |
| 59 | 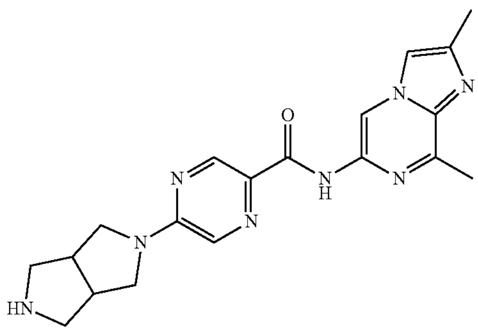 [SMILES: Cc1cn2cc(NC(=O)c3cnc(N4CC5CNCC5C4)cn3)nc(C)c2n1] | octahydropyrrolo[3,4-c]pyrrole | LCMS (ES+) 379 (M + H)+, RT 1.74 min (Analytical method AcHSSC18); ¹H NMR (400 MHz, DMSO) δ 10.72-10.70 (m, 1H), 9.18 (d, J = 0.5 Hz, 1H), 8.98-8.94 (m, 2H), 7.97 (d, J = 0.8 Hz, 1H), 3.87-3.80 (m, 2H), 3.46 (dd, J = 3.5, 12.1 Hz, 2H), 3.01 (dd, J = 6.8, 10.9 Hz, 2H), 2.93-2.87 (m, 2H), 2.74-2.72 (m, 5H), 2.40 (s, 3H). |
| 60 | Enantiomer 2 | Intermediate 12 | LCMS (ES+) 393 (M + H)+, RT 3.93 min (Analytical method BicarbBEHC18) ¹H NMR (400 MHz, DMSO) δ 9.67 (s, 1H), 9.17 (s, 1H), 8.78 (d, J = 1.3 Hz, 1H), 8.05-8.03 (m, 2H), 3.77-3.51 (m, 4H), 3.50-3.41 (m, 1H), 2.74 (s, 3H), 2.60-2.57 (m, 1H), 2.43 (s, 3H), 2.17-2.12 (m, 2H), 2.03-1.95 (m, 1H), 0.46 (d, J = 6.6 Hz, 2H), 0.33-0.23 (m, 2H). |
| 61 | Enantiomer 1 | Intermediate 12 | LCMS (ES+) 393 (M + H)+, RT 3.9 min (Analytical method BicarbBEHC18) ¹H NMR (400 MHz, DMSO) δ 9.67 (s, 1H), 9.17 (s, 1H), 8.78 (d, J = 1.3 Hz, 1H), 8.05-8.03 (m, 2H), 3.77-3.51 (m, 4H), 3.50-3.41 (m, 1H), 2.74 (s, 3H), 2.60-2.57 (m, 1H), 2.43 (s, 3H), 2.17-2.12 (m, 2H), 2.03-1.95 (m, 1H), 0.46 (d, J = 6.6 Hz, 2H), 0.33-0.23 (m, 2H). |

| Ex. | Structure | Amine | Analytical data |
|---|---|---|---|
| 62 | 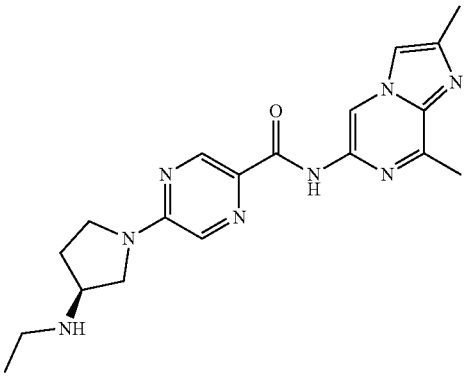 [SMILES: CCN[C@H]1CCN(c2cnc(C(=O)Nc3cn4cc(C)nc4c(C)n3)cn2)C1] | (S)-N-ethylpyrrolidin-3-amine | LCMS (ES+) 381 (M + H)+, RT 1.88 min (Analytical method AcHSSC18) $^1$H NMR (400 MHz, DMSO +D$_2$O) δ 8.98 (s, 1H), 8.62 (s, 1H), 7.91 (s, 1H), 7.85 (s, 1H), 3.70-3.58 (m, 2H), 3.49-3.38 (m, 2H), 3.30-3.23 (m, 1H), 2.65 (s, 3H), 2.59-2.56 (m, 2H), 2.35 (s, 3H), 2.20-2.13 (m, 1H), 1.88-1.83 (m, 1H), 1.02 (t, J = 6.9 Hz, 3H). |
| 63 | 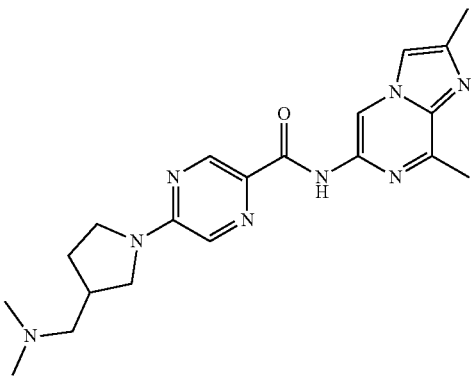<br>Enantiomer 1 + Enantiomer 2 | N,N-dimethyl-1-(pyrrolidin-3-yl)methanamine | LCMS (ES+) 395 (M + H)+, RT 1.96 min (Analytical method AcHSSC18) $^1$H NMR (400 MHz, DMSO) δ 9.72 (s, 1H), 9.22 (s, 1H), 8.83 (d, J = 1.3 Hz, 1H), 8.11 (d, J = 1.0 Hz, 1H), 8.08 (s, 1H), 3.84-3.72 (m, 2H), 3.65-3.56 (m, 1H), 3.33 (dd, J = 7.1, 11.1 Hz, 1H), 2.78 (s, 3H), 2.64 (s, 1H), 2.47 (s, 3H), 2.40-2.32 (m, 2H), 2.26 (s, 6H), 2.20 (s, 1H), 1.85-1.78 (m, 1H). |
| 64 | 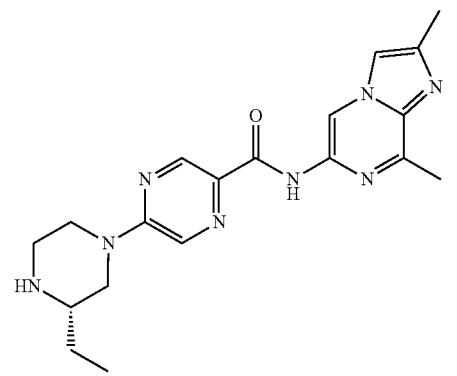 [SMILES: CC[C@H]1CN(c2cnc(C(=O)Nc3cn4cc(C)nc4c(C)n3)cn2)CCN1] | tert-butyl (S)-2-ethylpiperazine-1-carboxylate | LCMS (ES+) 381 (M + H)+, RT 2.02 min (Analytical method AcHSSC18); $^1$H NMR (400 MHz, MeOD) δ 9.17 (s, 1H), 8.81 (s, 1H), 8.30 (s, 1H), 7.82 (s, 1H), 4.49 (dd, J = 14.9, 40.1 Hz, 2H), 3.17-3.07 (m, 2H), 2.91-2.82 (m, 1H), 2.79 (s, 3H), 2.78-2.62 (m, 2H), 2.49 (s, 3H), 1.60-1.51 (m, 2H), 1.07 (dd, J = 7.6, 7.6 Hz, 3H). |

Example 65: N-(2,8-dimethylimidazo[1,2-a]pyrazin-6-yl)-5-(piperazin-1-yl)pyrazine-2-carboxamide

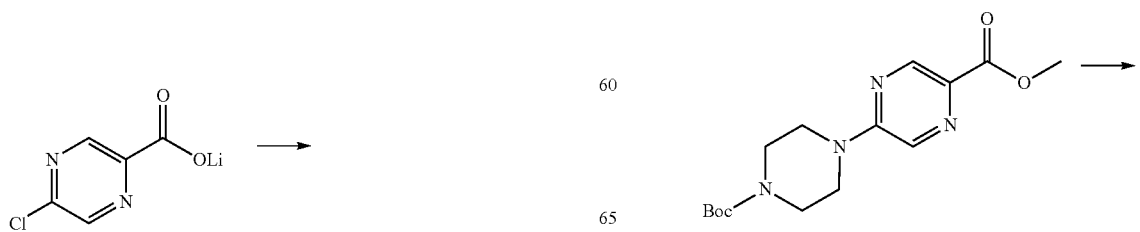

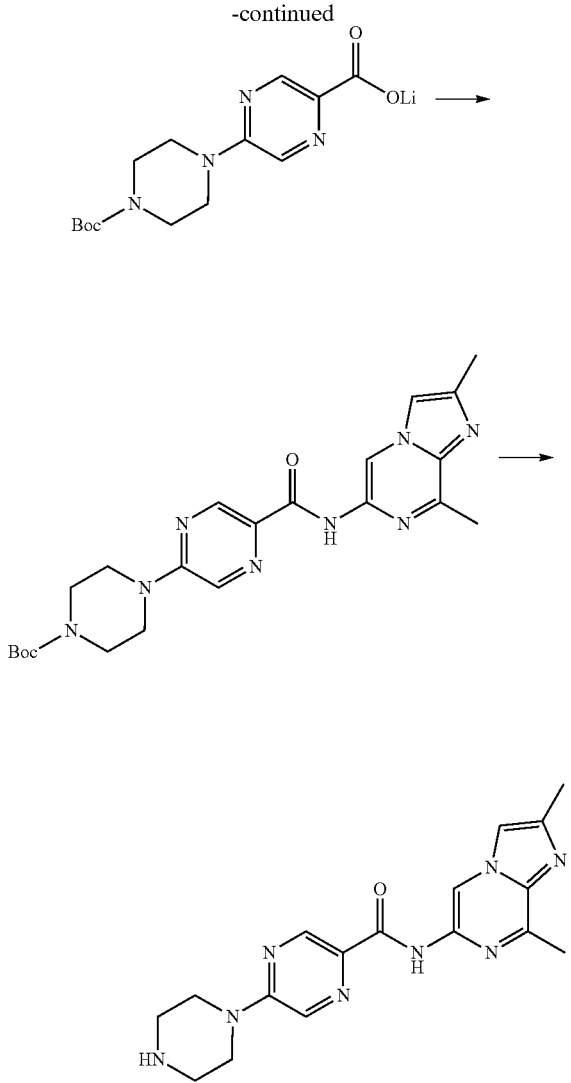

-continued

Methyl 5-chloropyrazine-2-carboxylate (173 mg, 1 mol), N-Boc piperazine (186 mg, 1 mmol), Cs$_2$CO$_3$ (650 mg, 2 mmol) and DMF (5 mL) were combined in a sealed tube and hot block heated to 100° C. for 4 hours. The reaction mixture was diluted with EtOAc, washed with water (×2), brine and evaporated to dryness to give methyl 5-(4-(tert-butoxycarbonyl)piperazin-1-yl)pyrazine-2-carboxylate, which was used crude in next step. MS (ES+) 323 (M+H).

Methyl 5-(4-(tert-butoxycarbonyl)piperazin-1-yl)pyrazine-2-carboxylate, LiOH·H$_2$O (50 mg), methanol (20 mL) and water (2 mL) were combined and stirred at room temperature for 16 hours. The reaction mixture was evaporated to dryness to give lithium 5-(4-(tert-butoxycarbonyl)piperazin-1-yl)pyrazine-2-carboxylate, which was used crude in next step. MS (ES+) 309 (M+H).

Lithium 5-(4-(tert-butoxycarbonyl)piperazin-1-yl)pyrazine-2-carboxylate (157 mg, 0.5 mmol), 2,8-dimethylimidazo[1,2-a]pyrazin-6-amine (81 mg, 0.5 mmol), HBTU (190 mg, 0.5 mmol), triethylamine (0.75 mL) and DMF (2 mL) were combined and stirred at room temperature for 3 days. The reaction mixture was then purified by preparative HPLC to give tert-butyl 4-(5-((2,8-dimethylimidazo[1,2-a]pyrazin-6-yl)carbamoyl)pyrazin-2-yl)piperazine-1-carboxylate. MS (ES+) 453 (M+H).

tert-Butyl 4-(5-((2,8-dimethylimidazo[1,2-a]pyrazin-6-yl)carbamoyl)pyrazin-2-yl)piperazine-1-carboxylate (10.6 mg), dichloromethane (2 mL) and TFA (1 mL) were combined and stirred at room temperature for 1 hour. The reaction mixture was evaporated to dryness then taken up in MeOH. Na$_2$CO$_3$ was added and stirred for 5 mins. The reaction was then filtered, the filtrate evaporated to dryness and purified by preparative HPLC to give the title compound. LCMS (ES+) 353 (M+H)+, RT 1.86 min (Analytical method AcHSSC18). $^1$H NMR (400 MHz, DMSO) δ 9.68 (s, 1H), 9.15 (s, 1H), 8.75 (d, J=1.1 Hz, 1H), 8.37 (d, J=1.1 Hz, 1H), 8.01 (s, 1H), 3.71-3.67 (m, 4H), 2.82 (dd, J=5.1, 5.1 Hz, 4H), 2.71 (s, 3H), 2.40 (s, 3H).

Further analogues were prepared using the same chemistry from commercially available or synthesized amines. In some instances, Boc protected amines were used, in which case the Boc group was removed at end of the synthetic sequence using 4N HCl in dioxane (general Method C) or TFA/DCM (general Method E). Final products were isolated by SCX and/or Preparative HPLC. Some enantiomers were separated by chiral SFC, in which case chirality was arbitrarily assigned.

| Ex. | Structure | Amine | Analytical data |
|---|---|---|---|
| 66 | ![structure] | tert-butyl (2S,5R)-2,5-dimethylpiperazine-1-carboxylate | LCMS (ES+) 381 (M + H)+, RT 2.05 min (Analytical method AcHSSC18) $^1$H NMR (400 MHz, DMSO) δ 9.65 (s, 1H), 9.15 (s, 1H), 8.74 (d, J = 1.1 Hz, 1H), 8.31 (d, J = 1.1 Hz, 1H), 8.00 (s, 1H), 4.55-4.49 (m, 1H), 4.04 (dd, J = 2.0, 13.2 Hz, 1H), 3.38 (m, 1H), 3.26-3.15 (m, 2H), 2.71 (s, 3H), 2.57 (dd, J = 3.1, 12.6 Hz, 1H), 2.40 (s, 3H), 1.26 (d, J = 6.7 Hz, 3H), 1.10 (d, J = 6.7 Hz, 3H). |

| Ex. | Structure | Amine | Analytical data |
|---|---|---|---|
| 67 | 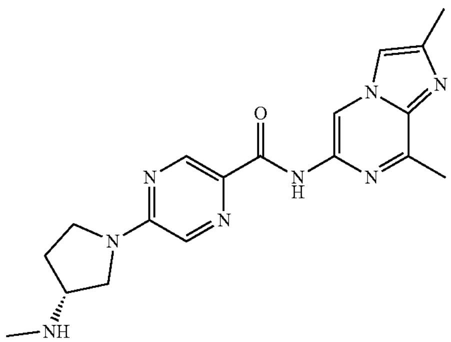 | tert-butyl (R)-methyl (pyrrolidin-3-yl)carbamate | LCMS (ES+) 367 (M + H)+, RT 1.84 min (Analytical method AcHSSC18) ¹H NMR (400 MHz, DMSO) δ 9.59-9.54 (m, 1H), 9.06 (s, 1H), 8.67 (d, J = 1.3 Hz, 1H), 7.95-7.91 (m, 2H), 3.62-3.48 (m, 3H), 3.33-3.28 (m, 1H), 3.22 (m, 1H), 2.62 (s, 3H), 2.45-2.42 (m, 9H), 2.32 (s, 3H), 2.24 (s, 3H), 2.02 (dd, J = 4.8, 11.6 Hz, 1H), 1.83-1.82 (m, 2H). |
| 68 | 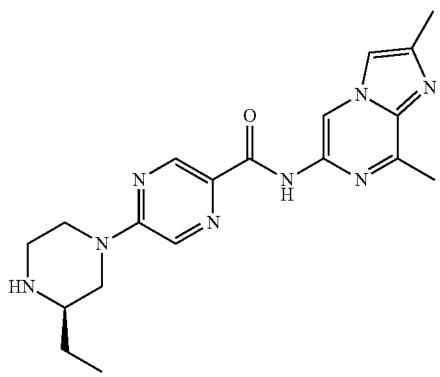 [SMILES: CC[C@@H]1CN(c2cnc(C(=O)Nc3cn4cc(C)nc4c(C)n3)cn2)CCN1] | tert-butyl (R)-2-ethylpiperazine-1-carboxylate | LCMS (ES+) 381 (M + H)+, RT 2.03 min (Analytical method AcHSSC18) ¹H NMR (400 MHz, DMSO) δ 9.65 (s, 1H), 9.14 (s, 1H), 8.74 (d, J = 1.1 Hz, 1H), 8.38 (d, J = 1.1 Hz, 1H), 8.00 (s, 1H), 4.42-4.31 (m, 2H), 3.04-2.94 (m, 2H), 2.71 (s, 3H), 2.70-2.61 (m, 3H), 2.40 (s, 4H), 1.47-1.34 (m, 2H), 0.96 (dd, J = 7.5, 7.5 Hz, 3H). |
| 69 | 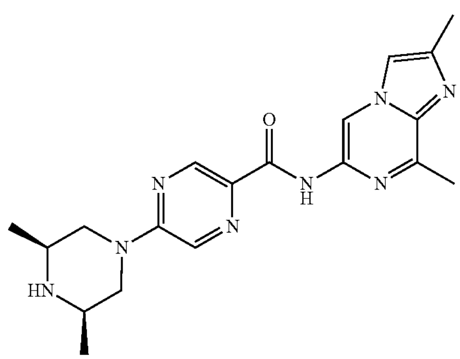 | tert-butyl (2S,6R)-2,6-dimethylpiperazine-1-carboxylate | LCMS (ES+) 381 (M + H)+, RT 1.97 min (Analytical method AcHSSC18) ¹H NMR (400 MHz, DMSO) δ 9.66 (s, 1H), 9.15 (s, 1H), 8.74 (d, J = 1.1 Hz, 1H), 8.39 (d, J = 1.1 Hz, 1H), 8.01 (s, 1H), 4.42 (d, J = 12.0 Hz, 2H), 2.79-2.73 (m, 2H), 2.71 (s, 3H), 2.49-2.44 (m, 2H), 2.40 (s, 3H), 2.37-2.34 (m, 1H), 1.06 (d, J = 6.3 Hz, 6H). |
| 70 | 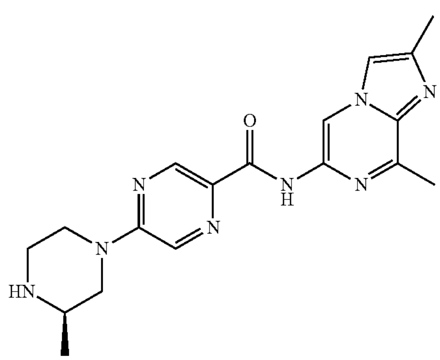 [SMILES: Cc1cn2cc(NC(=O)c3cnc(N4CCN[C@H](C)C4)cn3)nc(C)c2n1] | tert-butyl (R)-2-methylpiperazine-1-carboxylate | LCMS (ES+) 367 (M + H)+, RT 1.9 min (Analytical method AcHSSC18) ¹H NMR (400 MHz, DMSO) δ 9.64 (s, 1H), 9.14 (s, 1H), 8.73 (d, J = 1.1 Hz, 1H), 8.36 (d, J = 1.3 Hz, 1H), 8.00 (s, 1H), 4.41-4.35 (m, 2H), 3.02-2.90 (m, 2H), 2.70 (s, 3H), 2.74-2.66 (m, 2H), 2.62-2.54 (m, 1H), 2.40 (s, 4H), 1.06 (d, J = 6.1 Hz, 3H). |

-continued

| Ex. | Structure | Amine | Analytical data |
|---|---|---|---|
| 71 | 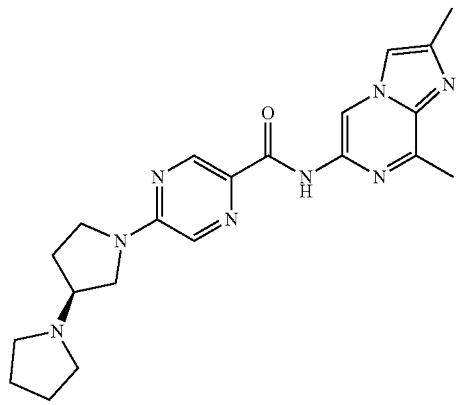 [SMILES: Cc1cn2cc(NC(=O)c3cnc(N4CC[C@H](N5CCCC5)C4)cn3)nc(C)c2n1] | (S)-1,3'-bipyrrolidine | LCMS (ES+) 407 (M + H)+, RT 1.89 min (Analytical method AcHSSC18) ¹H NMR (400 MHz, DMSO) δ 9.68 (s, 1H), 9.17 (s, 1H), 8.79 (s, 1H), 8.07 (s, 1H), 8.04 (s, 1H), 3.87-3.73 (m, 2H), 3.60-3.52 (m, 1H), 3.45-3.41 (m, 1H), 2.93-2.90 (m, 1H), 2.74 (s, 3H), 2.60 (dd, J = 5.9, 9.4 Hz, 4H), 2.44 (s, 3H), 2.23-2.21 (m, 1H), 2.05-1.97 (m, 1H), 1.76 (s, 4H). |
| 72 | Trans Isomers, Enantiomer 1 + Enantiomer 2 | tert-butyl ((3R*,4R*)-4-fluoropyrrolidin-3-yl)carbamate | LCMS (ES+) 371 (M + H)+, RT 2.93 min (Analytical method BicarbBEHC18) ¹H NMR (400 MHz, DMSO) δ 9.69 (s, 1H), 9.15 (s, 1H), 8.78 (d, J = 1.1 Hz, 1H), 8.08 (d, J = 1.1 Hz, 1H), 8.01 (s, 1H), 5.08 (d, J = 51.3 Hz, 1H), 4.02-3.78 (m, 2H), 3.73-3.69 (m, 2H), 3.58-3.55 (m, 1H), 2.71 (s, 3H), 2.40 (s, 3H), 1.94 (d, J = 0.9 Hz, 2H). |
| 73 | 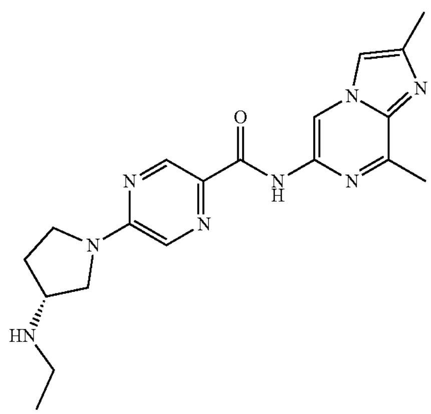 [SMILES: CCN[C@@H]1CCN(c2cnc(C(=O)Nc3cn4cc(C)nc4c(C)n3)cn2)C1] | tert-butyl (R)-ethyl(pyrrolidin-3-yl)carbamate | LCMS (ES+) 381 (M + H)+, RT 1.88 min (Analytical method AcHSSC18) ¹H NMR (400 MHz, DMSO) δ 9.65-9.63 (m, 1H), 9.14 (s, 1H), 8.75 (d, J = 1.1 Hz, 1H), 8.02-7.99 (m, 2H), 3.72-3.48 (m, 3H), 3.41-3.41 (m, 2H), 2.70 (s, 3H), 2.64-2.57 (m, 2H), 2.40 (s, 3H), 2.13 (d, J = 5.4 Hz, 1H), 1.88-1.88 (m, 2H), 1.04 (dd, J = 7.2, 7.2 Hz, 3H). |
| 74 | 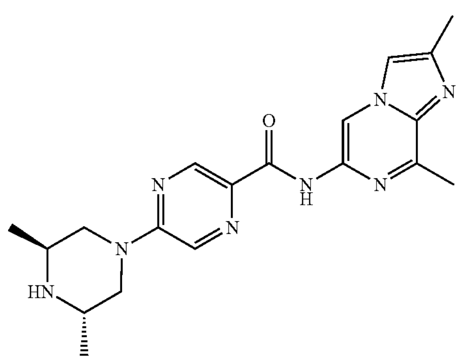 | tert-butyl (2S,6S)-2,6-dimethylpiperazine-1-carboxylate | LCMS (ES+) 381 (M + H)+, RT 1.96 min (Analytical method AcHSSC18) ¹H NMR (400 MHz, DMSO) δ 9.64 (s, 1H), 9.14 (s, 1H), 8.72 (d, J = 1.2 Hz, 1H), 8.38 (d, J = 1.2 Hz, 1H), 8.00 (s, 1H), 3.81 (dd, J = 3.3, 12.7 Hz, 2H), 3.41 (dd, J = 6.5, 12.7 Hz, 2H), 3.21-3.12 (m, 2H), 2.71 (s, 3H), 2.40 (s, 3H), 2.23-2.16 (m, 1H), 1.05 (s, 3H), 1.04 (s, 3H). |

Further analogues were prepared using the same chemistry from commercially available or synthesized amines, however coupling with 8-fluoro-2-methylimidazo[1,2-a]pyridin-6-amine in place of 2,8-dimethylimidazo[1,2-a]pyrazin-6-amine. In some instances, Boc protected amines were used, in which case the Boc group was removed at end of the synthetic sequence using 4N HCl in dioxane (general Method C) or TFA/DCM (general Method E). Final products were isolated by SCX and/or Preparative HPLC. Some enantiomers were separated by chiral SFC, in which case chirality was arbitrarily assigned.

| Ex. | Structure | Amine | Analytical data |
|---|---|---|---|
| 75 | 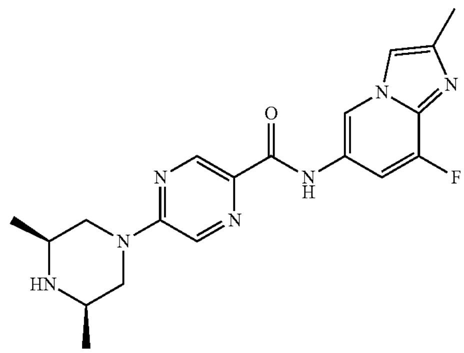 [SMILES: Cc1cn2cc(NC(=O)c3cnc(N4C[C@@H](C)N[C@@H](C)C4)cn3)cc(F)c2n1] | tert-butyl (2S,6R)-2,6-dimethylpiperazine-1-carboxylate | LCMS (ES+) 384 (M + H)+, RT 1.75 min (Analytical method AcHSSC18) $^1$H NMR (400 MHz, DMSO δ 10.42 (s, 1H), 9.18 (d, J = 1.6 Hz, 1H), 8.73 (d, J = 1.1 Hz, 1H), 8.33 (d, J = 1.3 Hz, 1H), 7.90 (d, J = 2.8 Hz, 1H), 7.57 (dd, J = 1.5, 13.2 Hz, 1H), 4.41 (dd, J = 1.8, 12.4 Hz, 2H), 2.80-2.71 (m, 2H), 2.53-2.50 (m, 2H), 2.47 (dd, J = 10.9, 13.0 Hz, 2H), 2.35 (s, 4H), 1.07 (d, J = 6.1 Hz, 6H). |
| 76 | 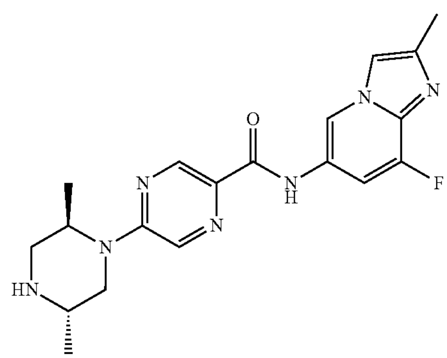 [SMILES: Cc1cn2cc(NC(=O)c3cnc(N4C[C@H](C)NC[C@H]4C)cn3)cc(F)c2n1] | tert-butyl (2S,5R)-2,5-dimethylpiperazine-1-carboxylate | LCMS (ES+) 384 (M + H)+, RT 1.82 min (Analytical method AcHSSC18) $^1$H NMR (400 MHz, DMSO δ 10.40 (s, 1H), 9.19 (d, J = 1.6 Hz, 1H), 8.73 (d, J = 1.1 Hz, 1H), 8.24 (d, J = 1.1 Hz, 1H), 7.89 (d, J = 2.8 Hz, 1H), 7.56 (dd, J = 1.5, 13.0 Hz, 1H), 4.55-4.49 (m, 1H), 4.03 (dd, J = 2.0, 13.2 Hz, 1H), 3.35 (dd, J = 4.1, 13.9 Hz, 1H), 3.25-3.15 (m, 2H), 2.56 (dd, J = 2.8, 13.3 Hz, 1H), 2.35 (s, 3H), 1.25 (d, J = 6.7 Hz, 3H), 1.10 (d, J = 6.8 Hz, 3H). |
| 77 | 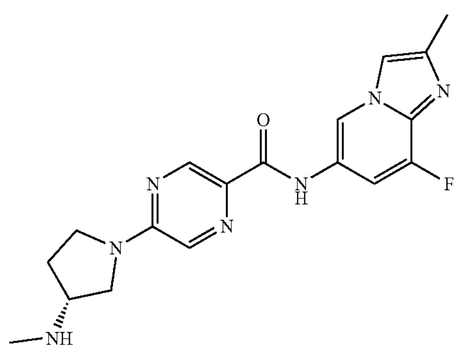 [SMILES: CN[C@@H]1CCN(c2cnc(C(=O)Nc3cc(F)c4nc(C)cn4c3)cn2)C1] | tert-butyl (R)-methyl(pyrrolidin-3-yl)carbamate | LCMS (ES+) 370 (M + H)+, RT 1.66 min (Analytical method AcHSSC18) $^1$H NMR (400 MHz, DMSO δ 10.41 (s, 1H), 9.19 (d, J = 1.6 Hz, 1H), 8.75 (d, J = 1.1 Hz, 1H), 7.98 (d, J = 1.3 Hz, 1H), 7.89 (d, J = 2.8 Hz, 1H), 7.57 (dd, J = 1.6, 13.1 Hz, 1H), 3.70-3.56 (m, 3H), 3.44-3.38 (m, 1H), 3.32-3.27 (m, 1H), 2.35 (s, 3H), 2.32 (s, 3H), 2.17-2.07 (m, 1H), 1.93 (s, 2H). |
| 78 | 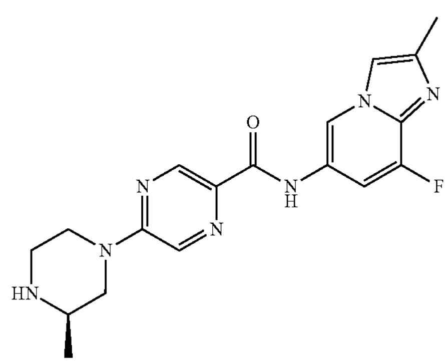 [SMILES: Cc1cn2cc(NC(=O)c3cnc(N4CCN[C@H](C)C4)cn3)cc(F)c2n1] | tert-butyl (R)-2-methylpiperazine-1-carboxylate | LCMS (ES+) 370 (M + H)+, RT 1.71 min (Analytical method AcHSSC18) $^1$H NMR (400 MHz, DMSO δ 10.46 (s, 1H), 9.22 (d, J = 1.5 Hz, 1H), 8.77 (d, J = 1.3 Hz, 1H), 8.36 (d, J = 1.3 Hz, 1H), 7.93 (d, J = 2.3 Hz, 1H), 7.60 (dd, J = 1.6, 13.1 Hz, 1H), 4.45-4.36 (m, 2H), 3.06-2.94 (m, 2H), 2.79-2.71 (m, 2H), 2.62 (dd, J = 10.0, 12.3 Hz, 1H), 2.43 (s, 1H), 2.39 (s, 3H), 1.10 (d, J = 6.3 Hz, 3H). |

| Ex. | Structure | Amine | Analytical data |
| --- | --- | --- | --- |
| 79 | 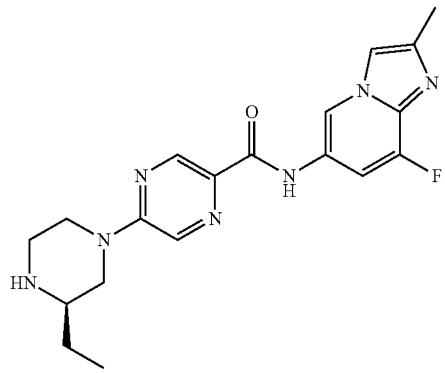 [SMILES: CC[C@@H]1CN(c2cnc(C(=O)Nc3cc(F)c4nc(C)cn4c3)cn2)CCN1] | tert-butyl (R)-2-ethylpiperazine-1-carboxylate | LCMS (ES+) 384 (M + H)+, RT 1.82 min (Analytical method AcHSSC18)<br>¹H NMR (400 MHz, DMSO δ 10.42 (s, 1H), 9.19 (d, J = 1.6 Hz, 1H), 8.74 (d, J = 1.1 Hz, 1H), 8.32 (d, J = 1.1 Hz, 1H), 7.90 (d, J = 2.8 Hz, 1H), 7.56 (dd, J = 1.8, 13.0 Hz, 1H), 4.44-4.30 (m, 2H), 3.04-2.94 (m, 2H), 2.72-2.59 (m, 2H), 2.49 (m, 1H), 2.35 (s, 4H), 1.48-1.34 (m, 2H), 0.96 (dd, J = 7.5, 7.5 Hz, 3H). |
| 80 | 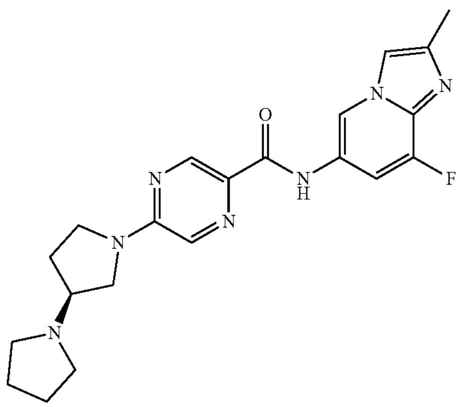 [SMILES: Cc1cn2cc(NC(=O)c3cnc(N4CC[C@H](N5CCCC5)C4)cn3)cc(F)c2n1] | (S)-1,3'-bipyrrolidine | LCMS (ES+) 410 (M + H)+, RT 3.6 min (Analytical method BicarbBEHC18)<br>¹H NMR (400 MHz, DMSO δ 10.42 (s, 1H), 9.19 (d, J = 1.6 Hz, 1H), 8.75 (d, J = 1.1 Hz, 1H), 7.99 (s, 1H), 7.89 (d, J = 2.8 Hz, 1H), 7.57 (dd, J = 1.8, 13.0 Hz, 1H), 3.84-3.70 (m, 2H), 3.58-3.50 (m, 1H), 3.39 (dd, J = 7.3, 10.9 Hz, 1H), 2.90-2.90 (m, 1H), 2.55-2.53 (m, 4H), 2.35 (s, 3H), 2.19-2.18 (m, 1H), 1.99-1.96 (m, 2H), 1.76-1.70 (m, 3H). |
| 81 | 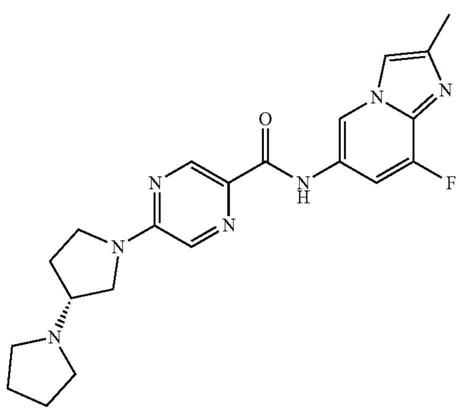 [SMILES: Cc1cn2cc(NC(=O)c3cnc(N4CC[C@@H](N5CCCC5)C4)cn3)cc(F)c2n1] | (R)-1,3'-bipyrrolidine | LCMS (ES+) 410 (M + H)+, RT 3.6 min (Analytical method BicarbBEHC18)<br>¹H NMR (400 MHz, DMSO δ 10.42 (s, 1H), 9.19 (d, J = 1.6 Hz, 1H), 8.75 (d, J = 1.1 Hz, 1H), 7.99 (s, 1H), 7.89 (d, J = 2.8 Hz, 1H), 7.57 (dd, J = 1.8, 13.0 Hz, 1H), 3.84-3.70 (m, 2H), 3.58-3.50 (m, 1H), 3.39 (dd, J = 7.3, 10.9 Hz, 1H), 2.90-2.90 (m, 1H), 2.55-2.53 (m, 4H), 2.35 (s, 3H), 2.19-2.18 (m, 1H), 1.99-1.96 (m, 2H), 1.76-1.70 (m, 3H). |
| 82 | 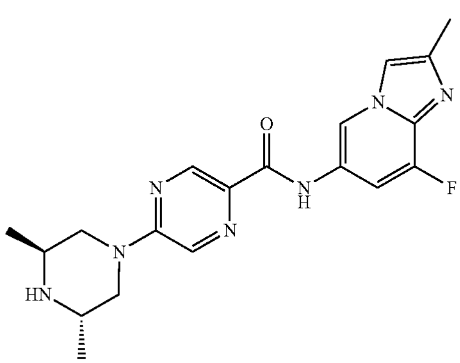 [SMILES: Cc1cn2cc(NC(=O)c3cnc(N4C[C@H](C)N[C@@H](C)C4)cn3)cc(F)c2n1] | tert-butyl (2S,6S)-2,6-dimethylpiperazine-1-carboxylate | LCMS (ES+) 384 (M + H)+, RT 1.79 min (Analytical method AcHSSC18)<br>¹H NMR (400 MHz, DMSO δ 10.39 (s, 1H), 9.18 (d, J = 1.5 Hz, 1H), 8.70 (s, 1H), 8.31 (s, 1H), 7.90 (d, J = 2.6 Hz, 1H), 7.55 (dd, J = 1.6, 13.1 Hz, 1H), 3.81 (dd, J = 3.1, 12.7 Hz, 2H), 3.41 (dd, J = 6.4, 12.7 Hz, 2H), 3.20-3.13 (m, 2H), 2.34 (s, 3H), 1.04 (d, J = 6.5 Hz, 6H). |

Example 83 (R)-5-(3-(ethylamino)pyrrolidin-1-yl)-N-(8-methoxy-2-methylimidazo[1,2-a]pyrazin-6-yl)pyrazine-2-carboxamide

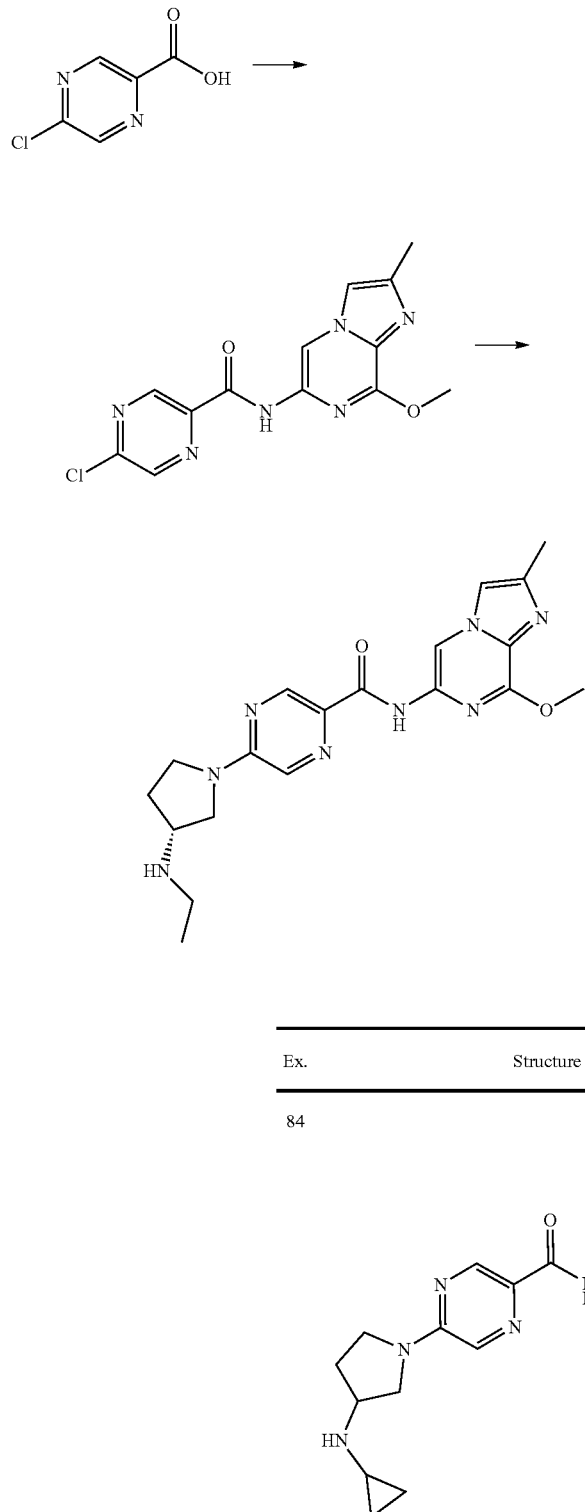

5-Chloropyrazine-2-carboxylic acid (246 mg, 1.55 mmol) and dichloromethane (10 mL) were combined at room temperature under a nitrogen atmosphere. Oxalyl chloride (0.27 mL, 3.1 mmol) was added, followed by 1 drop of DMF. The reaction mixture was stirred for 21 hours and then evaporated to dryness. Intermediate 10 (276 mg, 1.55 mmol), dichloromethane (30 mL) and triethylamine (2 mL) were added and the reaction was stirred for 1 hour. The reaction mixture was evaporated to dryness to give 5-chloro-N-(8-methoxy-2-methylimidazo[1,2-a]pyrazin-6-yl)pyrazine-2-carboxamide, which was used crude in the next step.

5-Chloro-N-(8-methoxy-2-methylimidazo[1,2-a]pyrazin-6-yl)pyrazine-2-carboxamide(125 mg, 0.28 mmol), (R)—N-ethylpyrrolidin-3-amine (32 mg, 0.28 mmol), cesium carbonate (325 mg, 1 mmol) and DMF (3 mL) were combined in a sealed tube and heated to 100° C. for 2 hours. The reaction mixture was then cooled to room temperature, the cesium salts were removed by filtration and the filtrate was purified by prep HPLC to give the title compound. LCMS (ES+) 397 (M+H)+, RT 1.9 min (Analytical method AcHSSC18). $^1$H NMR (400 MHz, DMSO) δ 9.48-9.46 (m, 1H), 8.89 (s, 1H), 8.74 (d, J=1.1 Hz, 1H), 8.02 (d, J=1.3 Hz, 1H), 7.94 (s, 1H), 4.07 (s, 3H), 3.71-3.52 (m, 3H), 3.43-3.38 (m, 2H), 2.64-2.56 (m, 2H), 2.35 (s, 3H), 2.19-2.08 (m, 1H), 1.88-1.88 (m, 2H), 1.04 (dd, J=7.2, 7.2 Hz, 3H).

Further analogues were prepared using the same chemistry and suitable amines. Some enantiomers were separated by chiral SFC, in which case chirality was arbitrarily assigned.

| Ex. | Structure | Amine | Analytical data |
|---|---|---|---|
| 84 | 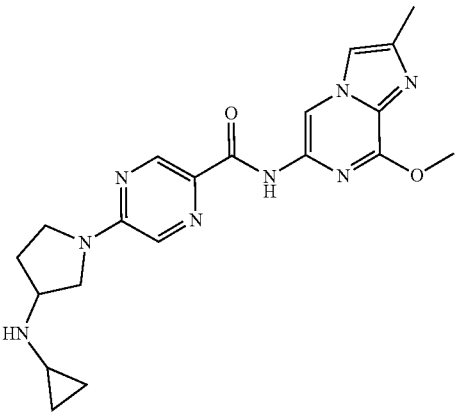<br>Enantiomer 1 | Intermediate 12 | LCMS (ES+) 409 (M + H)+, RT 2.01 min (Analytical method AcHSSC18) $^1$H NMR (400 MHz, DMSO) δ 9.53 (s, 1H), 8.93 (s, 1H), 8.78 (d, J = 1.1 Hz, 1H), 8.06 (d, J = 1.1 Hz, 1H), 7.98 (s, 1H), 4.09 (s, 3H), 3.74-3.56 (m, 4H), 3.47-3.43 (m, 1H), 2.38 (s, 4H), 2.15-2.11 (m, 2H), 2.00-1.98 (m, 1H), 0.44 (d, J = 6.5 Hz, 2H, 0.31-0.24 (m, 2H). |

| Ex. | Structure | Amine | Analytical data |
|---|---|---|---|
| 85 | 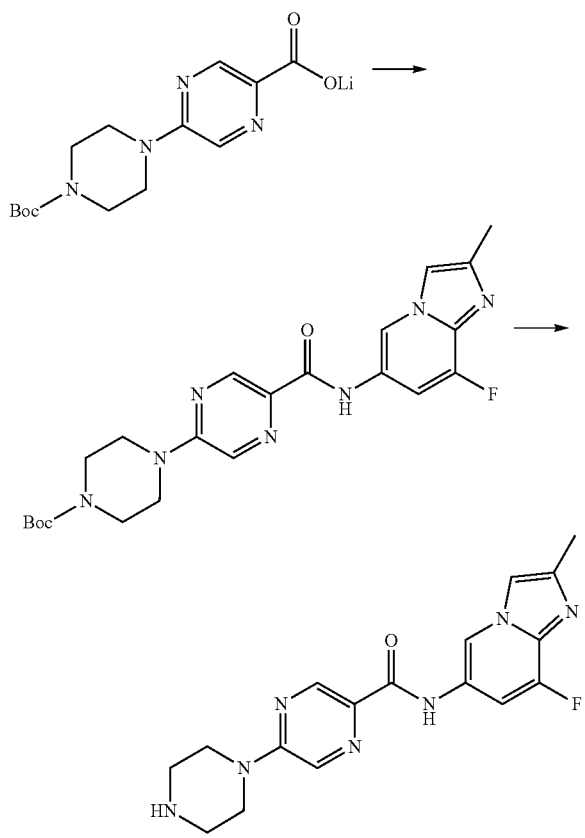<br>Enantiomer 2 | Intermediate 12 | LCMS (ES+) 409 (M + H)+, RT 2.01 min (Analytical method AcHSSC18) $^1$H NMR (400 MHz, DMSO) δ 9.53 (s, 1H), 8.93 (s, 1H), 8.78 (d, J = 1.1 Hz, 1H), 8.06 (d, J = 1.1 Hz, 1H), 7.98 (s, 1H), 4.09 (s, 3H), 3.74-3.56 (m, 4H), 3.47-3.43 (m, 1H), 2.38 (s, 4H), 2.15-2.11 (m, 2H), 2.00-1.98 (m, 1H), 0.44 (d, J = 6.5 Hz, 2H, 0.31-0.24 (m, 2H). |

Example 86: N-(8-fluoro-2-methylimidazo[1,2-a]pyridin-6-yl)-5-(piperazin-1-yl)pyrazine-2-carboxamide Lithium 5-(4-(tert-butoxycarbonyl)piperazin-1-yl)pyrazine-2-carboxylate (157 mg, 0.5 mmol), 8-fluoro-2-methylimidazo[1,2-a]pyridin-6-amine (83 mg, 0.5 mmol), HBTU (190 mg, 0.5 mmol), triethylamine (0.75 mL) and DMF (2 mL) were combine and stirred at room temperature for 2 hours. The reaction mixture was then purified by Preparative HPLC to give tert-butyl 4-(5-((2,8-dimethylimidazo[1,2-a]pyrazin-6-yl)carbamoyl)pyrazin-2-yl)piperazine-1-carboxylate. MS (ES+) 456 (M+H).

tert-Butyl 4-(5-((2,8-dimethylimidazo[1,2-a]pyrazin-6-yl)carbamoyl)pyrazin-2-yl)piperazine-1-carboxylate (80 mg), dichloromethane (2 mL) and TFA (1 mL) were combined and stirred at room temperature for 1 hour. The reaction mixture was evaporated to dryness then taken up in MeOH. Na$_2$CO$_3$ was added and stirred for 5 mins. The reaction was then filtered, and the filtrate evaporated to dryness and purified by Preparative HPLC to give the title compound. LCMS (ES+) 356 (M+H)+, RT 1.67 min (Analytical method AcHSSC18). $^1$H NMR (400 MHz, DMSO) δ 10.45 (s, 1H), 9.19 (d, J=1.6 Hz, 1H), 8.74 (d, J=1.0 Hz, 1H), 8.32 (s, 1H), 7.89 (d, J=2.6 Hz, 1H), 7.57 (dd, J=1.5, 13.0 Hz, 1H), 3.65 (dd, J=5.1, 5.1 Hz, 4H), 3.41 (dd, J=5.1, 5.1 Hz, 4H), 2.35 (s, 3H).

Example 87: N-(2,8-dimethylimidazo[1,2-a]pyrazin-6-yl)-5-((3R,4S)-3-fluoro-4-(methylamino)pyrrolidin-1-yl)pyrazine-2-carboxamide

And Example 88: N-(2,8-dimethylimidazo[1,2-a]pyridin-6-yl)-5-((3S,4R)-3-fluoro-4-(methylamino)pyrrolidin-1-yl)pyrazine-2-carboxamide

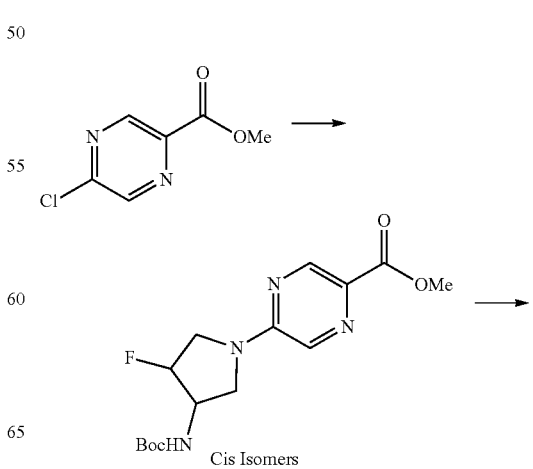

Cis Isomers

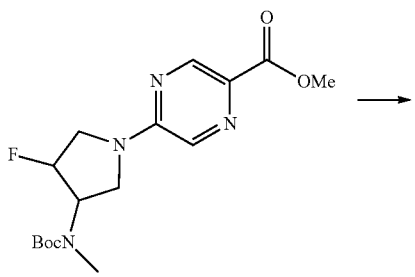

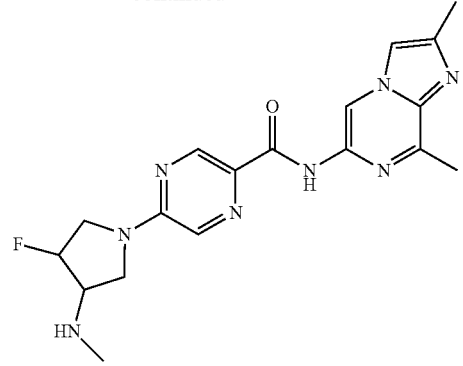

Cis Enantiomer 2

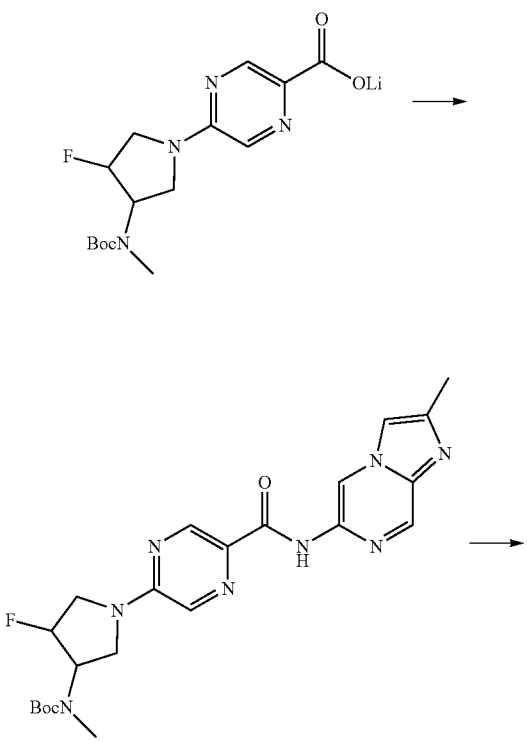

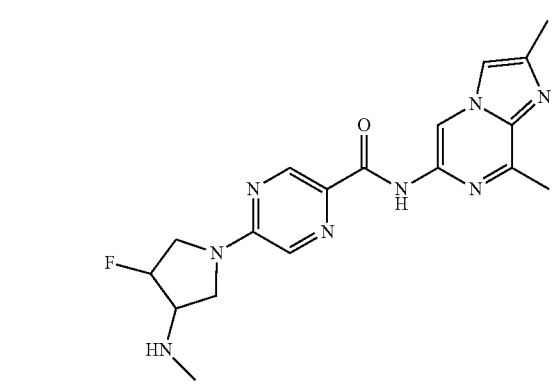

Cis Enantiomer 1

+

Methyl 5-chloropyrazine-2-carboxylate (665 mg, 3.85 mmol), tert-butyl ((3R*,4S*)-4-fluoropyrrolidin-3-yl)carbamate (786 mg, 3.85 mmol), cesium carbonate (1.25 g, 3.85 mmol) and DMF (10 mL) were combined in a sealed tube and heated to 100° C. for 18 hours. The reaction mixture was then diluted with EtOAc, washed with water (3×), brine (1×) and evaporated to dryness to give methyl 5-((3R*,4S*)-3-((tert-butoxycarbonyl)amino)-4-fluoropyrrolidin-1-yl)pyrazine-2-carboxylate, which was used crude without further purification.

Methyl 5-((3R*,4S*)-3-((tert-butoxycarbonyl)amino)-4-fluoropyrrolidin-2-yl)pyrazine-2-carboxylate (630 mg, 1.85 mmol) and DMF (15 mL) were combined under a nitrogen atmosphere at room temperature. NaH (60% in oil, 89 mg, 2.22 mmol) was added to the stirred reaction mixture followed by MeI (0.14 mL, 2.22 mmol). The reaction mixture was stirred for 22 hours then diluted with EtOAc, washed with water (3×) and brine (1×). The organic layer was evaporated to dryness to give methyl 5-((3R*,4S*)-3-((tert-butoxycarbonyl)(methyl)amino)-4-fluoropyrrolidin-1-yl)pyrazine-2-carboxylate, solid which was used crude without further purification.

Methyl 5-((3R*,4S*)-3-((tert-butoxycarbonyl)(methyl)amino)-4-fluoropyrrolidin-1-yl)pyrazine-2-carboxylate, LiOH·H$_2$O (85 mg, 2.03 mmol), methanol (20 mL) and water (2 mL) were combined and stirred at 45° C. for 23 hours. The reaction mixture was then evaporated to dryness to give lithium 5-((3R*,4S*)-3-((tert-butoxycarbonyl)(methyl)amino)-4-fluoropyrrolidin-1-yl)pyrazine-2-carboxylate, which was used crude without further purification.

Lithium 5-((3R*,4S*)-3-((tert-butoxycarbonyl)(methyl)amino)-4-fluoropyrrolidin-1-yl)pyrazine-2-carboxylate, 2,8-dimethylimidazo[1,2-a]pyrazin-6-amine (162 mg, 1 mmol), HBTU (379 mg, 1 mmol), triethylamine (1 mL) and DMF (5 mL) were combined and stirred at room temperature for 1 hour. The reaction mixture was then purified by preparative HPLC to give tert-butyl ((3R*,4S*)-4-fluoro-1-(5-((8-fluoro-2-methylimidazo[1,2-a]pyridin-6-yl)carbamoyl)pyrazin-2-yl)pyrrolidin-3-yl)(methyl)carbamate, which was used without further purification.

tert-Butyl ((3R*,4S*)-4-fluoro-1-(5-((8-fluoro-2-methylimidazo[1,2-a]pyridin-6-yl)carbamoyl)pyrazin-2-yl)pyrrolidin-3-yl)(methyl)carbamate, methanol (3 mL) and 4N HCl in dioxane (3 mL) were combined and stirred at room temperature for 2 hours. The reaction mixture was then evaporated to dryness, dissolved in MeOH, stirred with Na$_2$CO$_3$ for 5 mins, filtered through an Isolute NH$_2$ resin cartridge and the filtrate was evaporated to dryness. The crude solid was purified by preparative HPLC then chiral Preparative HPLC to give;

Cis Isomer, Enantiomer 1
N-(2,8-dimethylimidazo[1,2-a]pyrazin-6-yl)-5-((3R,4S)-3-fluoro-4-(methylamino)pyrrolidin-1-yl)pyrazine-2-carboxamide. LCMS (ES+) 385 (M+H)+, RT 1.77 min (Analytical method AcHSSC18); $^1$H NMR (400 MHz, DMSO) δ 9.69 (s, 1H), 9.15 (s, 1H), 8.78 (s, 1H), 8.10 (s, 1H), 8.01 (s, 1H), 5.39 (d, J=52.3 Hz, 1H), 4.05-3.92 (m, 2H), 3.81 (dd, J=12.7, 39.6 Hz, 1H), 3.48-3.42 (m, 1H), 3.24-3.18 (m, 1H), 2.71 (s, 3H), 2.44-2.39 (m, 6H), 2.01-2.01 (m, 1H).

Cis Isomer, Enantiomer 2
N-(2,8-dimethylimidazo[1,2-a]pyridin-6-yl)-5-((3S,4R)-3-fluoro-4-(methylamino)pyrrolidin-1-yl)pyrazine-2-carboxamide. LCMS (ES+) 385 (M+H)+, RT 1.77 min (Analytical method AcHSSC18); $^1$H NMR (400 MHz, DMSO) δ 9.69 (s, 1H), 9.15 (s, 1H), 8.78 (s, 1H), 8.10 (s, 1H), 8.01 (s, 1H), 5.39 (d, J=52.3 Hz, 1H), 4.05-3.92 (m, 2H), 3.81 (dd, J=12.7, 39.6 Hz, 1H), 3.48-3.42 (m, 1H), 3.24-3.18 (m, 1H), 2.71 (s, 3H), 2.44-2.39 (m, 6H), 2.01-2.01 (m, 1H).

Further analogues were prepared using the same chemistry from commercially available or synthesized amines. In some instances, Boc protected amines were used, in which case the Boc group was removed at end of the synthetic sequence using 4N HCl in dioxane (general Method C) or TFA/DCM (general Method E). Final products were isolated by SCX and/or Preparative HPLC. Some enantiomers were separated by chiral SFC, in which case chirality was arbitrarily assigned.

| Ex. | Structure | Amine | Analytical data |
|---|---|---|---|
| 89 | 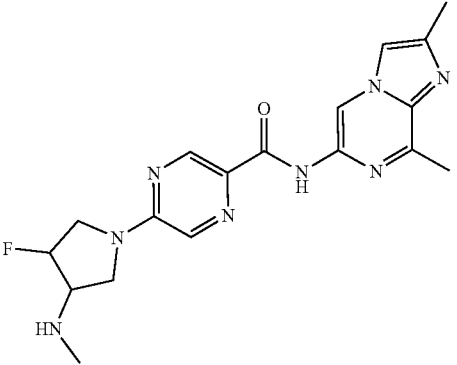 | tert-butyl ((3R*,4R*)-4-fluoropyrrolidin-3-yl)carbamate | LCMS (ES+) 385 (M + H)+, RT 3.19 min (Analytical method BicarbBEHC18) $^1$H NMR (400 MHz, DMSO) δ 9.68 (s, 1H), 9.14 (s, 1H), 8.78 (d, J = 1.3 Hz, 1H), 8.09 (s, 1H), 8.01 (s, 1H), 5.28 (d, J = 50.6 Hz, 1H), 3.91 (s, 1H), 3.83 (s, 1H), 3.74-3.65 (m, 2H), 3.42-3.36 (m, 1H), 2.71 (s, 3H), 2.40 (s, 3H), 2.36 (s, 3H), 2.24-2.19 (m, 1H). |

Trans Isomers, Enantiomer 1 and Enantiomer 2

Further analogues were prepared using the same chemistry with lithium 5-((3R*,4S*)-3-((tert-butoxycarbonyl)(methyl)amino)-4-fluoropyrrolidin-1-yl)pyrazine-2-carboxylate or lithium 5-((3R*,4R*)-3-((tert-butoxycarbonyl)(methyl)amino)-4-fluoropyrrolidin-1-yl)pyrazine-2-carboxylate and 8-fluoro-2-methylimidazo[1,2-a]pyridin-6-amine. In some instances, Boc protected amines were used, in which case the Boc group was removed at end of the synthetic sequence using 4N HCl in dioxane (general Method C) or TFA/DCM (general Method E). Final products were isolated by SCX and/or Preparative HPLC. Some enantiomers were separated by chiral SFC, in which case chirality was arbitrarily assigned.

| Ex. | Structure | Analytical Data |
|---|---|---|
| 90 | 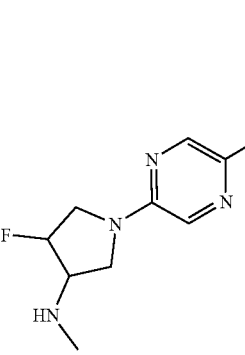 | LCMS (ES+) 388.659 (M + H)+, RT 1.71 min (Analytical method AcHSSC18) $^1$H NMR (400 MHz, DMSO) δ 10.45 (s, 1H), 9.19 (d, J = 1.5 Hz, 1H), 8.77 (s, 1H), 8.04 (s, 1H), 7.90 (d, J = 2.6 Hz, 1H), 7.57 (dd, J = 1.6, 13.2 Hz, 1H), 5.27 (d, J = 51.9 Hz, 1H), 3.90-3.62 (m, 5H), 2.36 (s, 3H), 2.34 (s, 3H), 2.19-2.19 (m, 1H). |

Trans Isomers, Enantiomer 1 and Enantiomer 2

| Ex. | Structure | Analytical Data |
|---|---|---|
| 91 | 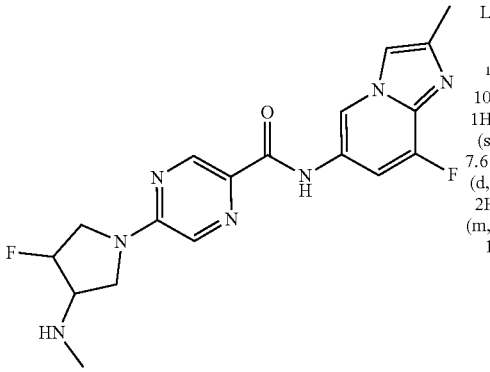<br>Cis Isomer, Enantiomer 1 | LCMS (ES+) 388 (M + H)+, RT 1.67 min (Analytical method AcHSSC18).<br>¹H NMR (400 MHz, DMSO) δ 10.49 (s, 1H), 9.23 (d, J = 1.8 Hz, 1H), 8.81 (d, J = 1.3 Hz, 1H), 8.08 (s, 1H), 7.94 (d, J = 2.3 Hz, 1H), 7.61 (dd, J = 1.4, 13.0 Hz, 1H), 5.44 (d, J = 54.1 Hz, 1H), 4.09-3.96 (m, 2H), 3.91-3.78 (m, 1H), 3.54-3.42 (m, 1H), 3.25 (dd, J = 10.2, 10.2 Hz, 1H), 2.46 (s, 3H), 2.39 (s, 3H), 2.11-2.06 (m, 1H). |

Example 92: (S)-5-([1,3'-Bipyrrolidin]-1'-yl)-N-(6-methoxy-2-methyl-2H-indazol-5-yl)pyrazine-2-carboxamide

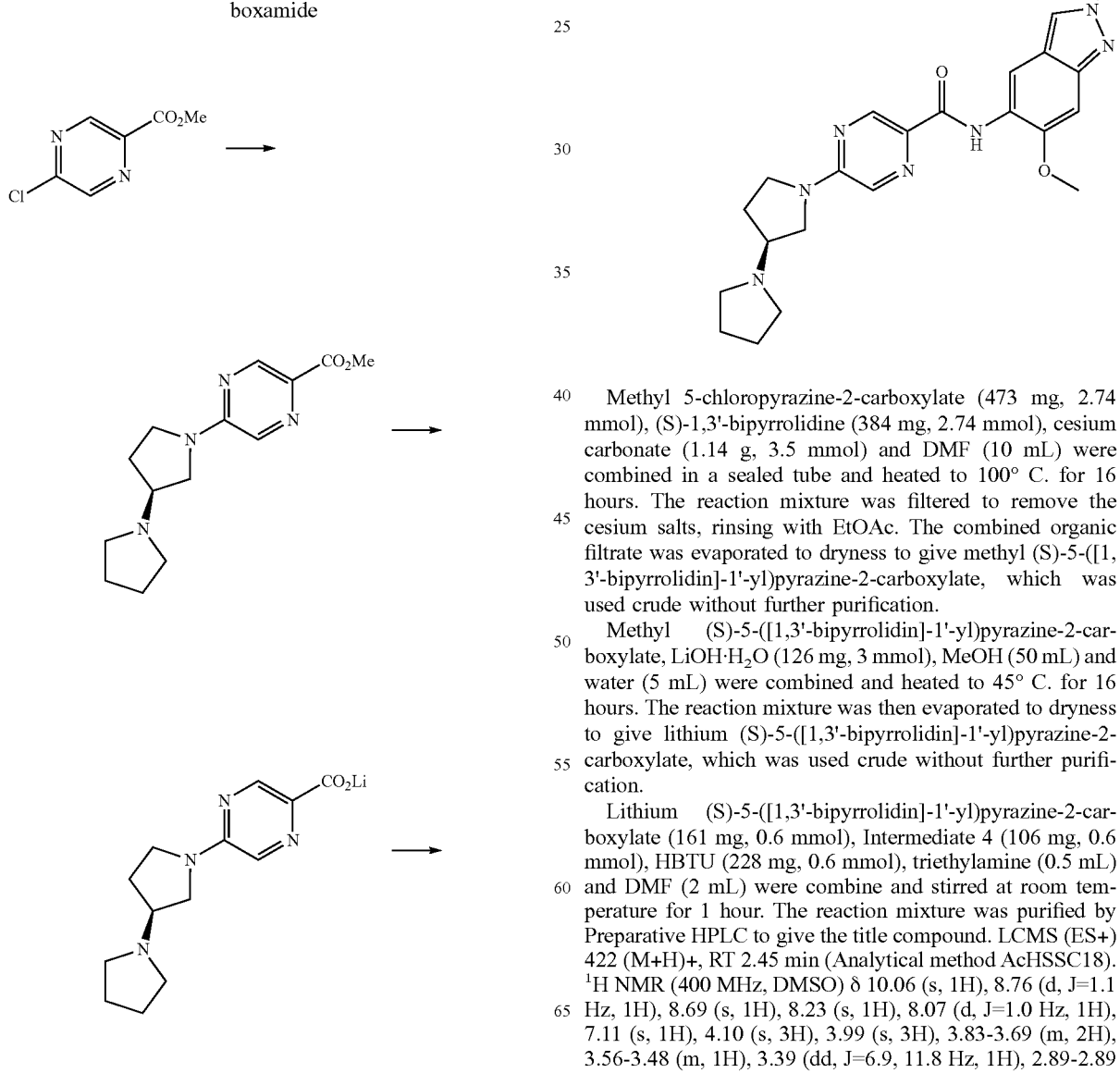

Methyl 5-chloropyrazine-2-carboxylate (473 mg, 2.74 mmol), (S)-1,3'-bipyrrolidine (384 mg, 2.74 mmol), cesium carbonate (1.14 g, 3.5 mmol) and DMF (10 mL) were combined in a sealed tube and heated to 100° C. for 16 hours. The reaction mixture was filtered to remove the cesium salts, rinsing with EtOAc. The combined organic filtrate was evaporated to dryness to give methyl (S)-5-([1,3'-bipyrrolidin]-1'-yl)pyrazine-2-carboxylate, which was used crude without further purification.

Methyl (S)-5-([1,3'-bipyrrolidin]-1'-yl)pyrazine-2-carboxylate, LiOH·H₂O (126 mg, 3 mmol), MeOH (50 mL) and water (5 mL) were combined and heated to 45° C. for 16 hours. The reaction mixture was then evaporated to dryness to give lithium (S)-5-([1,3'-bipyrrolidin]-1'-yl)pyrazine-2-carboxylate, which was used crude without further purification.

Lithium (S)-5-([1,3'-bipyrrolidin]-1'-yl)pyrazine-2-carboxylate (161 mg, 0.6 mmol), Intermediate 4 (106 mg, 0.6 mmol), HBTU (228 mg, 0.6 mmol), triethylamine (0.5 mL) and DMF (2 mL) were combine and stirred at room temperature for 1 hour. The reaction mixture was purified by Preparative HPLC to give the title compound. LCMS (ES+) 422 (M+H)+, RT 2.45 min (Analytical method AcHSSC18). ¹H NMR (400 MHz, DMSO) δ 10.06 (s, 1H), 8.76 (d, J=1.1 Hz, 1H), 8.69 (s, 1H), 8.23 (s, 1H), 8.07 (d, J=1.0 Hz, 1H), 7.11 (s, 1H), 4.10 (s, 3H), 3.99 (s, 3H), 3.83-3.69 (m, 2H), 3.56-3.48 (m, 1H), 3.39 (dd, J=6.9, 11.8 Hz, 1H), 2.89-2.89

(m, 1H), 2.56 (d, J=3.6 Hz, 4H), 2.20-2.19 (m, 1H), 2.01-1.97 (m, 1H), 1.73 (dd, J=5.0, 5.0 Hz, 4H).

Example 93: (S)-5-([1,3'-bipyrrolidin]-1'-yl)-N-(6-ethoxy-2-methyl-2H-indazol-5-yl)pyrazine-2-carboxamide

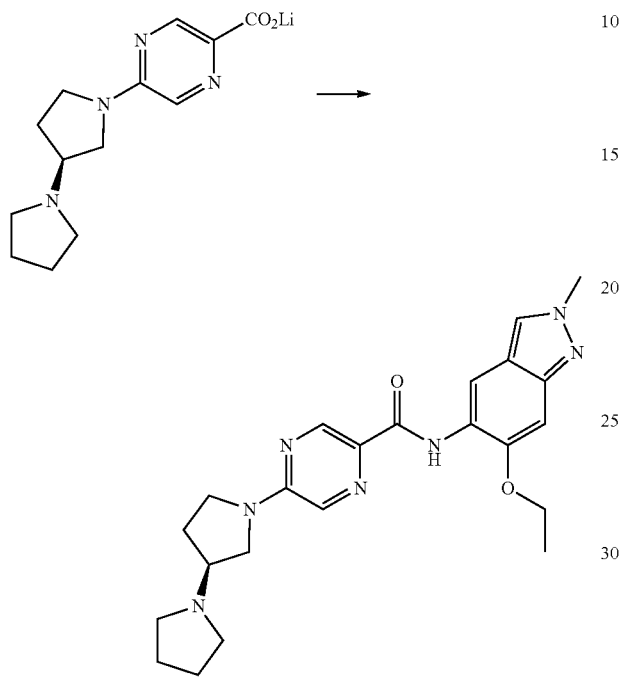

Lithium (S)-5-([1,3'-bipyrrolidin]-1'-yl)pyrazine-2-carboxylate (95 mg, 0.36 mmol), Intermediate 3 (69 mg, 0.36 mmol), HBTU (137 mg, 0.36 mmol), triethylamine (0.5 mL) and DMF (2.5 mL) were combined and stirred at room temperature overnight. The reaction mixture was purified by Preparative HPLC to give the title compound. LCMS (ES+) 436.5 (M+H)+, RT 2.6 min (Analytical method AcHSSC18). $^1$H NMR (400 MHz, DMSO) δ 10.14 (s, 1H), 8.75 (d, J=1.3 Hz, 1H), 8.68 (s, 1H), 8.21 (s, 1H), 8.04 (s, 1H), 7.09 (s, 1H), 4.22 (q, J=6.9 Hz, 2H), 4.09 (s, 3H), 3.83-3.69 (m, 1H), 3.55-3.48 (m, 1H), 3.20 (s, 1H), 2.90-2.82 (m, 2H), 2.19-2.13 (m, 2H), 1.96 (dd, J=3.6, 8.2 Hz, 2H), 1.75-1.69 (m, 4H), 1.51-1.46 (m, 3H).

Example 94: 5-((3S*,4R*)-3-Fluoro-4-(methylamino)pyrrolidin-1-yl)-N-(6-methoxy-2-methyl-2H-indazol-5-yl)pyrazine-2-carboxamide

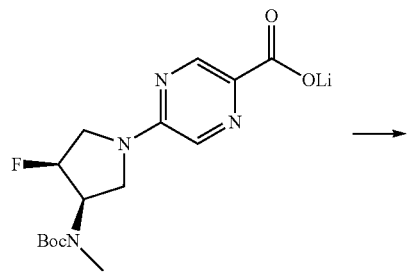

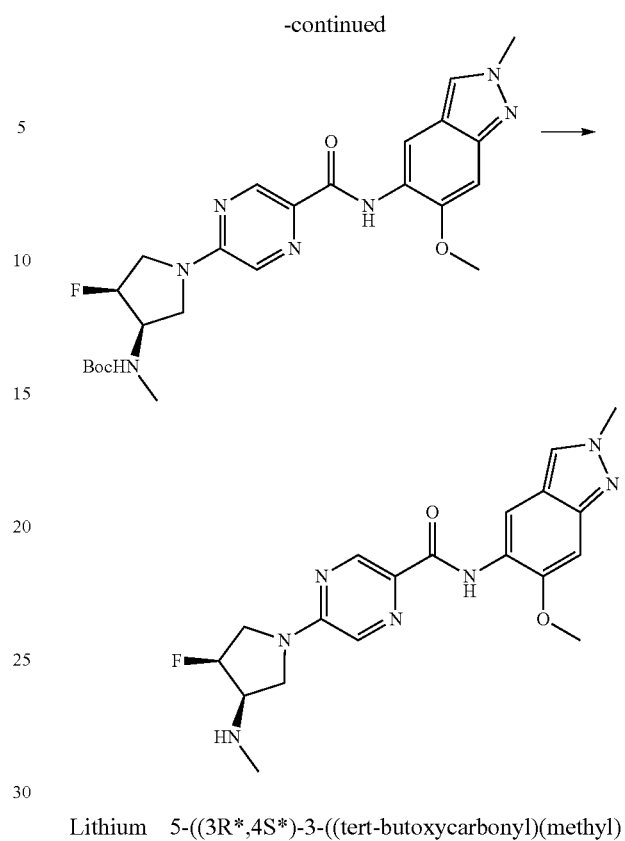

Lithium 5-((3R*,4S*)-3-((tert-butoxycarbonyl)(methyl)amino)-4-fluoropyrrolidin-1-yl)pyrazine-2-carboxylate (187 mg, 0.54 mmol), Intermediate 4 (106 mg, 0.6 mmol), HBTU (228 mg, 0.6 mmol), triethylamine (0.5 mL) and DMF (3 mL) were combined and stirred at room temperature for 3 hours. The reaction mixture was then purified by preparative HPLC to give tert-butyl ((3R*,4S*)-4-fluoro-1-(5-((6-methoxy-2-methyl-2H-indazol-5-yl)carbamoyl)pyrazin-2-yl)pyrrolidin-3-yl)(methyl)carbamate, which was used without further purification.

tert-butyl ((3R*,4S*)-4-fluoro-1-(5-((6-methoxy-2-methyl-2H-indazol-5-yl)carbamoyl)pyrazin-2-yl)pyrrolidin-3-yl)(methyl)carbamate was deprotected using general method C (HCl Boc deprotection) to give the title compound. LCMS (ES+) 400 (M+H)+, RT 2.3 min (Analytical method AcHSSC18). 1H NMR (400 MHz, DMSO) δ 10.07 (s, 1H), 8.78 (s, 1H), 8.69 (s, 1H), 8.23 (s, 1H), 8.12 (s, 1H), 7.12 (s, 1H), 5.39 (d, J=55.2 Hz, 1H), 4.10 (s, 3H), 3.99 (s, 3H), 4.04-3.70 (m, 4H), 3.20 (dd, J=10.2, 10.2 Hz, 1H), 2.42 (s, 3H).

Example 95: (S)—N-(8-fluoro-2-methylimidazo[1,2-a]pyridin-6-yl)-5-(pyrrolidin-3-yloxy)pyrazine-2-carboxamide

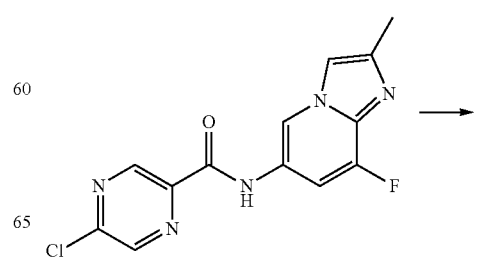

427
-continued

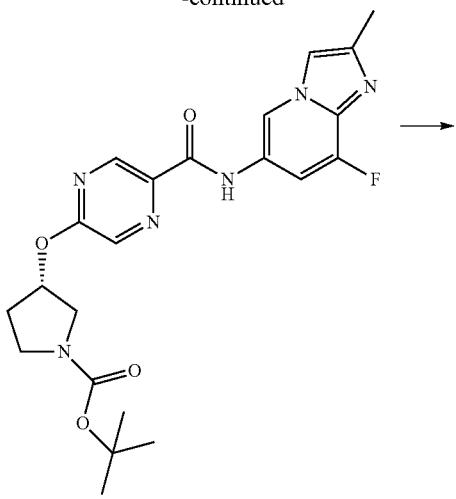

→

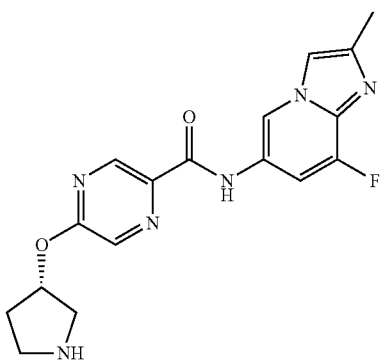

tert-butyl (S)-3-hydroxypyrrolidine-1-carboxylate (100 mg, 0.53 mmol) in DMF (2 mL) was added to a suspension of NaH (32 mg, 0.801 mmol) in DMF (1 mL) and the reaction was stirred at room temperature for 30 minutes. Intermediate 1 (163 mg, 0.534 mmol) was added and the reaction was heated to 90° C. for 5.5 hours. The reaction mixture was cooled to room temperature and partitioned between dichloromethane and water. The aqueous layer was extracted with dichloromethane (×2) and the combined organic solution dried with MgSO₄ and evaporated to dryness. The crude mixture was purified by flash chromatography to give tert-butyl (S)-3-((5-((8-fluoro-2-methylimidazo[1,2-a]pyridin-6-yl)carbamoyl)pyrazin-2-yl)oxy)pyrrolidine-1-carboxylate. MS (ES+) 457 (M+H).

tert-butyl (S)-3-((5-((8-fluoro-2-methylimidazo[1,2-a]pyridin-6-yl)carbamoyl)pyrazin-2-yl)oxy)pyrrolidine-1-carboxylate (63 mg, 0.14 mmol), methanol (1 mL) and 4N HCl in dioxane (0.35 mL, 1.38 mmol) were combined and stirred at room temperature for 17 hours. The reaction mixture was evaporated to dryness and the crude material was purified by Preparative HPLC to give the title compound. LCMS (ES+) 357 (M+H)+, RT 1.62 min (Analytical method AcHSSC18). ¹H NMR (400 MHz, DMSO) δ 10.74 (s, 1H), 9.21 (d, J=1.6 Hz, 1H), 8.90 (s, 1H), 8.38 (s, 1H), 7.92 (d, J=2.8 Hz, 1H), 7.57 (dd, J=1.5, 13.0 Hz, 1H), 5.50 (dd, J=5.8, 5.8 Hz, 1H), 3.68-3.52 (m, 1H), 3.15 (dd, J=5.2, 12.5 Hz, 1H), 3.00-2.92 (m, 2H), 2.88-2.81 (m, 1H), 2.35 (s, 3H), 2.19-2.05 (m, 1H), 1.91-1.87 (m, 1H).

Further analogues were prepared using the same chemistry from commercially available or synthesized amines. In some instances, Boc protected amines were used, in which case the Boc group was removed at end of the synthetic sequence using 4N HCl in dioxane (general Method C) or TFA/DCM (general Method E). Final products were isolated by Preparative HPLC.

| Ex. | Structure | Amine | Analytical data |
|---|---|---|---|
| 96 | ![structure] | tert-butyl (R)-3-hydroxypyrrolidine-1-carboxylate | LCMS (ES+) 357 (M + H)+, RT 1.66 min (Analytical method AcHSSC18) ¹H NMR (400 MHz, DMSO) δ 10.74 (s, 1H), 9.22 (d, J = 1.6 Hz, 1H), 8.90 (d, J = 1.3 Hz, 1H), 8.38 (d, J = 1.3 Hz, 1H), 7.92 (d, J = 2.8 Hz, 1H), 7.57 (dd, J = 1.6, 13.0 Hz, 1H), 5.53-5.47 (m, 1H), 3.14 (dd, J = 5.4, 12.5 Hz, 1H, 3.00-2.90 (m, 2H), 2.88-2.80 (m, 1H), 2.35 (s, 3H), 2.15-2.05 (m, 1H), 1.92-1.84 (m, 1H). |

Example 97 N-(8-fluoro-2-methylimidazo[1,2-a]pyridin-6-yl)-5-((3R,4R)-3-methyl-4-(methylamino)pyrrolidin-1-yl)pyrazine-2-carboxamide

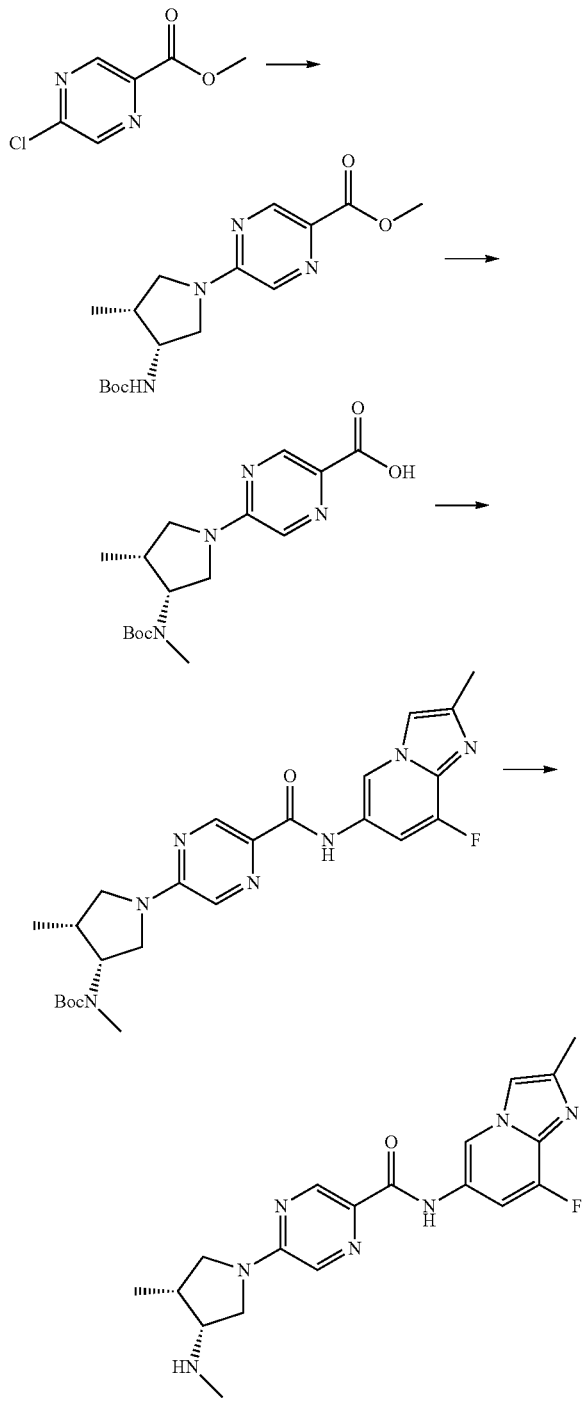

tert-Butyl ((3R,4R)-4-methylpyrrolidin-3-yl)carbamate (251 mg, 1.25 mmol) and methyl 5-chloropyrazine-2-carboxylate (216 mg, 1.25 mmol) were dissolved in DMF (4 mL) and the reaction was heated to 100° C. for 18 h. The reaction was cooled to r.t., diluted with EtOAc and filtered through Celite. The solvent was removed in vacuo to give crude product. The crude was purified using silica chromatography, elution gradient 0-100% EtOAc/cyclohexane to give methyl 5-((3R,4R)-3-((tert-butoxycarbonyl)amino)-4-methylpyrrolidin-1-yl)pyrazine-2-carboxylate. MS (ES+) 337 (M+H).

Methyl 5-((3R,4R)-3-((tert-butoxycarbonyl)amino)-4-methylpyrrolidin-1-yl)pyrazine-2-carboxylate (344 mg, 1.02 mmol) was dissolved in DMF (2 mL) and cooled in an ice bath. Sodium hydride/60% in mineral oil (45 mg, 1.12 mmol) was added and the reaction stirred for 15 minutes. Methyl iodide (145 mg, 1.02 mmol) was added and the reaction allowed to warm to r.t. over 3 h. LCMS indicated starting material. Further sodium hydride/60% in mineral oil (45 mg, 1.12 mmol) was added followed by methyl iodide (145 mg, 1.02 mmol) and the reaction stirred for a further 18 h. Water (1 mL) was added followed by sodium hydroxide (82 mg, 1.04 mmol) and the reaction stirred for 18 h. The reaction was acidified with 1M HCl to pH=5 and the aqueous layer extracted with EtOAc ×3. The organic layer was dried (MgSO$_4$) and the solvent removed in vacuo to give 5-((3R,4R)-3-((tert-butoxycarbonyl)(methyl)amino)-4-methylpyrrolidin-1-yl)pyrazine-2-carboxylic acid. MS (ES+) 337 (M+H).

5-((3R,4R)-3-((tert-butoxycarbonyl)(methyl)amino)-4-methylpyrrolidin-1-yl)pyrazine-2-carboxylic acid (343 mg, 1.02 mmol) and 8-fluoro-2-methylimidazo[1,2-a]pyridin-6-amine (168 mg, 1.02 mmol) were dissolved in DMF (2 mL). HBTU (426 mg, 1.12 mmol) and trimethylamine (0.5 mL) were added and the reaction stirred overnight at r.t. The solvent was removed in vacuo to give crude product. Purification using silica chromatography elution gradient 0-100% EtOAc/cyclohexane gave tert-butyl ((3R,4R)-1-(5-((8-fluoro-2-methylimidazo[1,2-a]pyridin-6-yl)carbamoyl)pyrazin-2-yl)-4-methylpyrrolidin-3-yl)(methyl)carbamate. MS (ES+) 484 (M+H).

tert-Butyl ((3R,4R)-1-(5-((8-fluoro-2-methylimidazo[1,2-a]pyridin-6-yl)carbamoyl)pyrazin-2-yl)-4-methylpyrrolidin-3-yl)(methyl)carbamate (610 mg, 1.02 mmol) was dissolved in methanol (2 mL) and 4M HCl in dioxane (10 mL) was added. The reaction was stirred overnight at r.t. The solvent was removed in vacuo to give crude product. The crude was purified by SCX 5 g SCX cartridge (pre-conditioned with MeOH), eluting with 1:1 MeOH/DCM (2 CV) then 2.3 M NH$_3$/MeOH (3 CV). The ammonia fraction was concentrated in vacuo to give a residue. Further purification by reverse phase HPLC gave the title compound. LCMS (ES+) 384.2 (M+H)+, RT 1.72 min (Analytical method AcHSSC18); $^1$H NMR (400 MHz, DMSO) δ 10.45 (s, 1H), 9.20 (d, J=1.5 Hz, 1H), 8.74 (d, J=1.1 Hz, 1H), 7.96 (s, 1H), 7.90 (d, J=2.6 Hz, 1H), 7.57 (dd, J=1.6, 13.1 Hz, 1H), 3.70-3.63 (m, 2H), 3.26-3.08 (m, 3H), 2.32 (m, 6H), 1.02 (d, J=5.9 Hz, 3H) NH obscured under DMSO peak.

The following examples were prepared using an analogous procedure starting from methyl 5-chloropyrazine-2-carboxylate and the stated amine. Final products were isolated by SCX and/or Preparative HPLC. Some enantiomers were separated by chiral SFC, in which case chirality was arbitrarily assigned.

| Ex. | Structure | Amine | Analytical data |
|---|---|---|---|
| 98 | 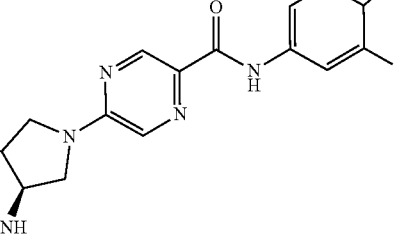 | (3S,4S)-N,4-dimethylpyrrolidin-3-amine | LCMS (ES+) 384 (M + H)+, RT 1.73 min (Analytical method AcHSSC18)<br>¹H NMR (400 MHz, DMSO) δ 10.42 (s, 1H), 9.20 (d, J = 1.6 Hz, 1H), 8.74 (d, J = 1.3 Hz, 1H), 7.96 (s, 1H), 7.89 (d, J = 2.8 Hz, 1H), 7.57 (dd, J = 1.6, 13.1 Hz, 1H), 3.70-3.42 (m, 3H), 3.41-3.34 (m, 1H), 3.20 (s, 1H, 2.51 (s, 1H), 2.35-2.33 (m, 6H), 1.80 (s, 1H), 1.02 (d, J = 6.8 Hz, 3H). |
| 99 | 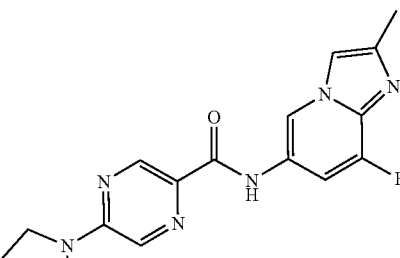 | (3S,4R)-N,4-dimethylpyrrolidin-3-amine | LCMS (ES+) 384 (M + H)+, RT 1.83 min (Analytical method AcHSSC18)<br>¹H NMR (400 MHz, DMSO) δ 10.46 (s, 1H), 9.23 (d, J = 1.5 Hz, 1H), 8.79 (d, J = 1.3 Hz, 1H), 8.02 (d, J = 1.3 Hz, 1H, 7.94 (d, J = 2.5 Hz, 1H), 7.61 (dd, J = 1.4, 13.0 Hz, 1H), 3.92-3.82 (m, 2H), 3.36-3.31 (m, 2H), 3.24 (dd, J = 6.6, 10.9 Hz, 1H), 2.93-2.90 (m, 1H), 2.40-2.38 (m, 6H), 2.23-2.20 (m, 1H), 1.12 (d, J = 6.8 Hz, 3H). |
| 100 | 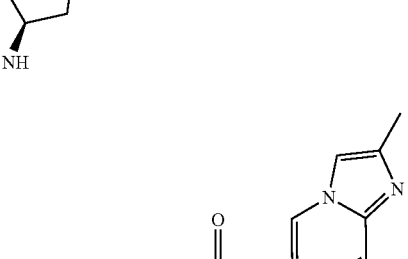 | (3R,4S)-N,4-dimethylpyrrolidin-3-amine | LCMS (ES+) 384.2 (M + H)+, RT 1.79 min (Analytical method AcHSSC18)<br>¹H NMR (400 MHz, DMSO) δ 10.45 (s, 1H), 9.21 (d, J = 1.5 Hz, 1H), 8.74 (d, J = 1.3 Hz, 1H), 7.97 (s, 1H), 7.90 (d, J = 2.8 Hz, 1H), 7.57 (dd, J = 1.7, 13.2 Hz, 1H), 3.88-3.77 (m, 2H, 3.30 (dd, J = 5.6, 11.2 Hz, 1H), 3.19 (dd, J = 6.5, 10.8 Hz, 1H), 2.88-2.85 (m, 1H), 2.35 (s, 6H), 2.21-2.18 (m, 1H), 1.96-1.96 (m, 1H), 1.08 (d, J = 6.8 Hz, 3H). |
| 101 | 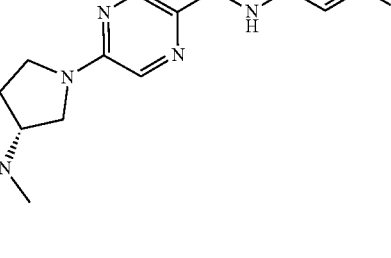 | tert-butyl (S)-(pyrrolidin-3-ylmethyl)carbamate | LCMS (ES+) 381 (M + H)+, RT 1.87 min (Analytical method AcHSSC18)<br>¹H NMR (400 MHz, DMSO and D₂O) δ 8.94 (s, 1H), 8.58 (s, 1H), 7.87 (s, 1H), 7.83 (s, 1H), 3.66-3.53 (m, 2H), 3.41-3.37 (m, 1H), 3.12-3.06 (m, 1H), 2.64 (s, 3H), 2.51 (s, 0H), 2.46-2.41 (m, 1H), 2.35 (s, 3H), 2.27 (s, 3H), 2.13-2.07 (m, 1H), 1.68-1.61 (m, 1H). |

-continued

| Ex. | Structure | Amine | Analytical data |
|---|---|---|---|
| 102 | 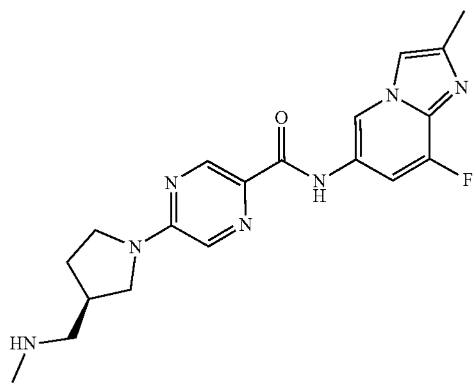 [SMILES: CNC[C@H]1CCN(c2cnc(C(=O)Nc3cc(F)c4nc(C)cn4c3)cn2)C1] | tert-butyl (S)-(pyrrolidin-3-ylmethyl)carbamate | LCMS (ES+) 384.7 (M + H)+, RT 1.69 min (Analytical method AcHSSC18)<br>$^1$H NMR (400 MHz, DMSO and D$_2$O) δ 8.94 (d, J = 1.3 Hz, 1H), 8.63 (d, J = 1.2 Hz, 1H, 7.93 (s, 1H), 7.78 (d, J = 2.3 Hz, 1H), 7.41 (dd, J = 1.4, 12.5 Hz, 1H), 3.71-3.59 (m, 1H), 3.44 (dd, J = 8.0, 8.0 Hz, 1H), 3.14 (dd, J = 7.9, 10.8 Hz, 1H), 2.48-2.42 (m, 1H), 2.29 (d, J = 19.3 Hz, 6H, 2.16-2.12 (m, 1H, 1.74-1.64 (m, 1H). |
| 103 | 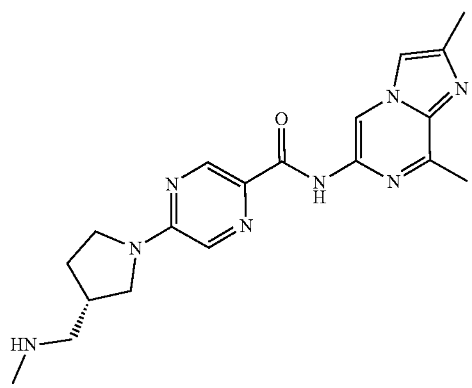 | tert-butyl (R)-(pyrrolidin-3-ylmethyl)carbamate | LCMS (ES+) 381.2 (M + H)+, RT 1.93 min (Analytical method AcHSSC18)<br>$^1$H NMR (400 MHz, DMSO) δ 8.96 (s, 1H, 8.59 (s, 1H), 7.88 (s, 1H), 7.84 (s, 1H), 3.67-3.63 (m, 1H), 3.59-3.56 (m, 1H), 3.40-3.37 (m, 1H), 3.12-3.07 (m, 1H), 2.64 (s, 3H), 2.45-2.41 (m, 1H), 2.34 (s, 3H), 2.25 (s, 3H), 2.11-2.11 (m, 1H), 1.68-1.62 (m, 1H). |
| 104 | 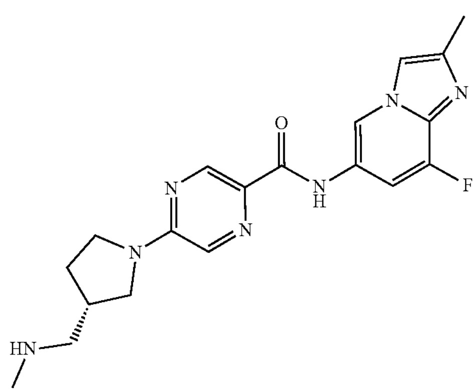 [SMILES: CNC[C@@H]1CCN(c2cnc(C(=O)Nc3cc(F)c4nc(C)cn4c3)cn2)C1] | tert-butyl (R)-(pyrrolidin-3-ylmethyl)carbamate | LCMS (ES+) 384.2 (M + H)+, RT 1.68 min (Analytical method AcHSSC18)<br>$^1$H NMR (400 MHz, DMSO) δ 8.98 (s, 1H), 8.65 (s, 1H), 7.94 (s, 1H), 7.79 (d, J = 2.6 Hz, 1H), 7.44 (d, J = 12.5 Hz, 1H, 3.72-3.60 (m, 2H), 3.48-3.41 (m, 1H), 3.16 (dd, J = 8.1, 10.5 Hz, 1H), 2.46-2.41 (m, 1H), 2.32 (s, 3H), 2.25 (s, 3H), 2.12-2.10 (m, 1H), 1.72-1.64 (m, 1H). |
| 105 | Cis Isomer, Enantiomer 1 + Enantiomer 2 | tert-butyl ((3R*,4S*)-4-fluoropyrrolidin-3-yl)carbamate | LCMS (ES+) 388 (M + H)+, RT 1.67 min (Analytical method AcHSSC18)<br>$^1$H NMR (400 MHz, DMSO) δ 10.49 (s, 1H, 9.23 (d, J = 1.8 Hz, 1H, 8.81 (d, J = 1.3 Hz, 1H), 8.08 (s, 1H), 7.94 (d, J = 2.3 Hz, 1H), 7.61 (dd, J = 1.4, 13.0 Hz, 1H), 5.44 (d, J = 54.1 Hz, 1H), 4.09-3.96 (m, 2H), 3.91-3.78 (m, 1H), 3.54-3.42 (m, 1H, 3.25 (dd, J = 10.2, 10.2 Hz, 1H, 2.46 (s, 3H), 2.39 (s, 3H), 2.11-2.06 (m, 1H). |

Example 106: (R)—N-(8-fluoro-2-methylimidazo[1,2-a]pyridin-6-yl)-5-(3-(1-(methylamino)cyclopropyl)pyrrolidin-1-yl)pyrazine-2-carboxamide
and Example 107: (R)-5-(3-(1-aminocyclopropyl)pyrrolidin-1-yl)-N-(8-fluoro-2-methylimidazo[1,2-a]pyridin-6-yl)pyrazine-2-carboxamide
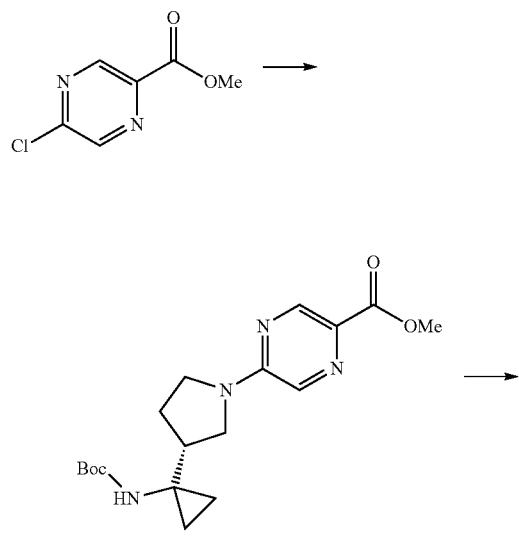
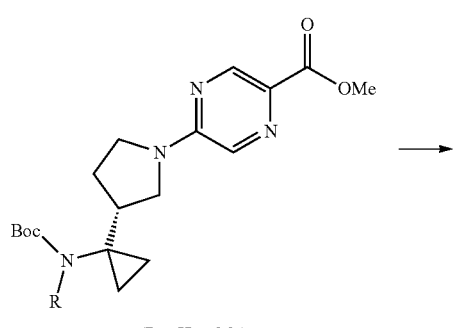
(R = H or Me)
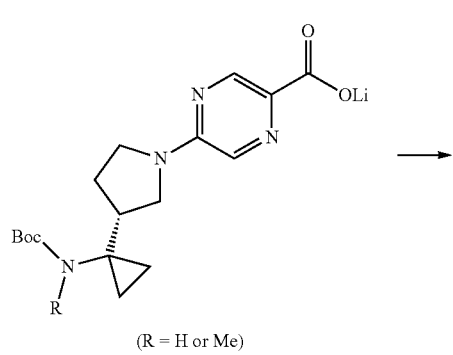
(R = H or Me)
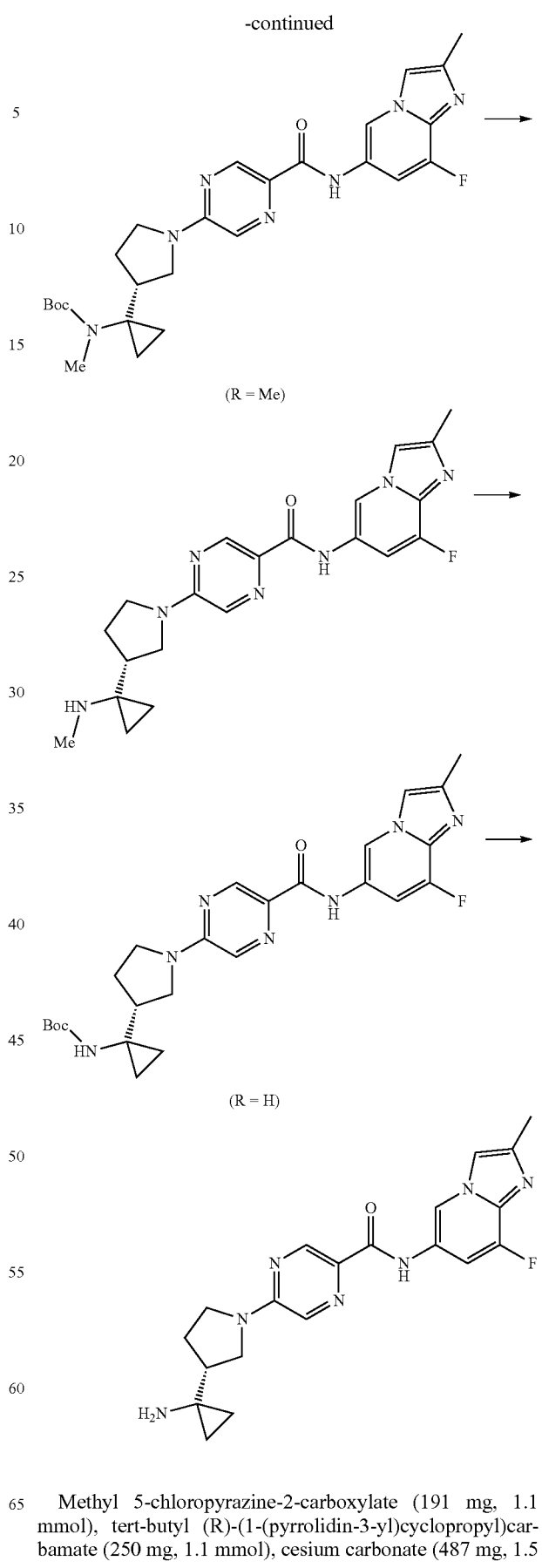
Methyl 5-chloropyrazine-2-carboxylate (191 mg, 1.1 mmol), tert-butyl (R)-(1-(pyrrolidin-3-yl)cyclopropyl)carbamate (250 mg, 1.1 mmol), cesium carbonate (487 mg, 1.5 mmol) and DMF (4 mL) were combined in a sealed tube and hot block heated to 100° C. for 23 hours. The reaction mixture was then diluted with EtOAc, washed with water (3×), brine (1×) and evaporated to dryness to give methyl (R)-5-(3-(1-((tert-butoxycarbonyl)amino)cyclopropyl)pyrrolidin-1-yl)pyrazine-2-carboxylate, which was used crude without further purification.

Methyl (R)-5-(3-(1-((tert-butoxycarbonyl)amino)cyclopropyl)pyrrolidin-1-yl)pyrazine-2-carboxylate (341 mg, 0.91 mmol) and DMF (10 mL) were combined at room temperature under nitrogen atmosphere. NaH (60% in oil, 45 mg, 1.13 mmol) was added followed by MeI (0.07 mL, 1.13 mmol) and stirring continued for 10 days. The reaction mixture was then diluted with EtOAc, washed with water (3×), brine (1×), dried (MgSO$_4$) and evaporated to dryness to give a mixture of methyl (R)-5-(3-(1-((tert-butoxycarbonyl)(methyl)amino)cyclopropyl)pyrrolidin-1-yl)pyrazine-2-carboxylate and methyl (R)-5-(3-(1-((tert-butoxycarbonyl)amino)cyclopropyl)pyrrolidin-1-yl)pyrazine-2-carboxylate, which was used crude without further purification.

The mixture of methyl (R)-5-(3-(1-((tert-butoxycarbonyl)(methyl)amino)cyclopropyl)pyrrolidin-1-yl)pyrazine-2-carboxylate and methyl (R)-5-(3-(1-((tert-butoxycarbonyl)amino)cyclopropyl)pyrrolidin-1-yl)pyrazine-2-carboxylate (169 mg), LiOH·H$_2$O (19 mg, 0.45 mmol), methanol (15 mL) and water (2 mL) were combined and hot block heated to 45° C. for 18 hours. The reaction mixture was then evaporated to dryness to give a mixture of lithium (R)-5-(3-(1-((tert-butoxycarbonyl)(methyl)amino)cyclopropyl)pyrrolidin-1-yl)pyrazine-2-carboxylate and lithium (R)-5-(3-(1-((tert-butoxycarbonyl)amino)cyclopropyl)pyrrolidin-1-yl)pyrazine-2-carboxylate, which was used crude without further purification.

The mixture of lithium (R)-5-(3-(1-((tert-butoxycarbonyl)(methyl)amino)cyclopropyl)pyrrolidin-1-yl)pyrazine-2-carboxylate and lithium (R)-5-(3-(1-((tert-butoxycarbonyl)amino)cyclopropyl)pyrrolidin-1-yl)pyrazine-2-carboxylate, 8-fluoro-2-methylimidazo[1,2-a]pyridin-6-amine (74 mg, 0.45 mmol), HBTU (171 mg, 0.45 mmol), triethylamine (0.5 mL) and DMF (2 mL) were combined and stirred at room temperature for 2 hours. The reaction mixture was then purified by preparative HPLC to give;

tert-butyl (R)-(1-(1-(5-((8-fluoro-2-methylimidazo[1,2-a]pyridin-6-yl)carbamoyl)pyrazin-2-yl)pyrrolidin-3-yl)cyclopropyl)(methyl)carbamate, which was used without further purification.

tert-Butyl (R)-(1-(1-(5-((8-fluoro-2-methylimidazo[1,2-a]pyridin-6-yl)carbamoyl)pyrazin-2-yl)pyrrolidin-3-yl)cyclopropyl)carbamate, which was used without further purification.

tert-Butyl (R)-(1-(1-(5-((8-fluoro-2-methylimidazo[1,2-a]pyridin-6-yl)carbamoyl)pyrazin-2-yl)pyrrolidin-3-yl)cyclopropyl)(methyl)carbamate (65.1 mg), methanol (3 mL) and 4N HCl in dioxane (3 mL) were combined and stirred at room temperature for 7 hours. The reaction mixture was then evaporated to dryness and purified by preparative HPLC to give (R)—N-(8-fluoro-2-methylimidazo[1,2-a]pyridin-6-yl)-5-(3-(1-(methylamino)cyclopropyl)pyrrolidin-1-yl)pyrazine-2-carboxamide. LCMS (ES+) 410 (M+H)+, RT 1.93 min (Analytical method AcHSSC18). $^1$H NMR (400 MHz, DMSO) δ 10.42 (s, 1H), 9.19 (d, J=1.5 Hz, 1H), 8.74 (d, J=1.1 Hz, 1H), 7.97 (d, J=1.3 Hz, 1H), 7.89 (d, J=2.8 Hz, 1H), 7.57 (dd, J=1.7, 13.0 Hz, 1H), 3.81-3.73 (m, 2H), 3.46-3.42 (m, 1H), 3.13 (dd, J=10.2, 10.2 Hz, 1H), 2.73-2.68 (m, 1H), 2.35 (s, 3H), 2.29 (s, 3H), 2.00 (s, 1H), 1.65 (s, 1H), 0.51 (s, 4H).

tert-Butyl (R)-(1-(1-(5-((8-fluoro-2-methylimidazo[1,2-a]pyridin-6-yl)carbamoyl)pyrazin-2-yl)pyrrolidin-3-yl)cyclopropyl)carbamate (41.9 mg), methanol (3 mL) and 4N HCl in dioxane (3 mL) were combined and stirred at room temperature for 7 hours. The reaction mixture was then evaporated to dryness and purified by preparative HPLC to give (R)-5-(3-(1-aminocyclopropyl)pyrrolidin-1-yl)-N-(8-fluoro-2-methylimidazo[1,2-a]pyridin-6-yl)pyrazine-2-carboxamide. LCMS (ES+) 396 (M+H)+, RT 1.9 min (Analytical method AcHSSC18). $^1$H NMR (400 MHz, DMSO) δ 10.42 (s, 1H), 9.19 (d, J=1.6 Hz, 1H), 8.74 (d, J=1.1 Hz, 1H), 7.97 (d, J=1.3 Hz, 1H), 7.89 (d, J=2.8 Hz, 1H), 7.57 (dd, J=1.7, 13.1 Hz, 1H), 3.82-3.69 (m, 2H), 3.50-3.41 (m, 2H), 2.35 (s, 3H), 2.09 (d, J=8.3 Hz, 1H), 2.00 (s, 1H), 1.93 (d, J=9.8 Hz, 1H), 0.49 (d, J=6.4 Hz, 4H).

Example 108: (R)—N-(6-ethoxy-2-methyl-2H-indazol-5-yl)-5-(3-(methylamino)pyrrolidin-1-yl)pyrazine-2-carboxamide

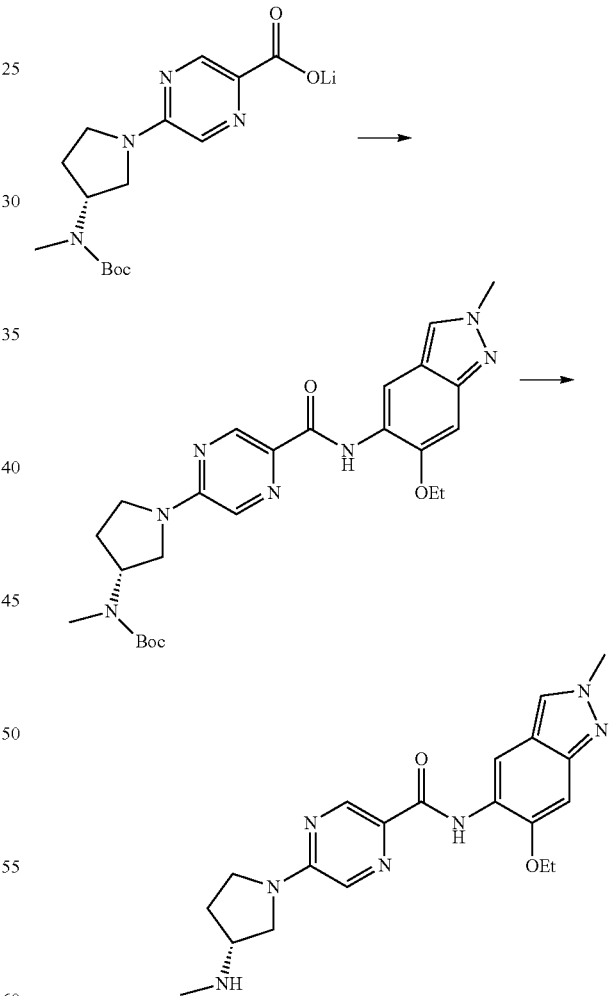

Intermediate 3 (0.32 mmol), lithium (R)-5-(3-((tert-butoxycarbonyl)(methyl)amino)pyrrolidin-1-yl)pyrazine-2-carboxylate (100 mg, 0.32 mmol), HBTU (137 mg, 0.36 mmol), triethylamine (0.5 mL) and DMF (2.5 mL) were combined and stirred at room temperature for 18 hours. The reaction mixture was then purified by preparative HPLC to give tert-butyl (R)-(1-(5-((6-ethoxy-2-methyl-2H-indazol-5-yl)carbamoyl)pyrazin-2-yl)pyrrolidin-3-yl)(methyl)carbamate as an off white solid which was used without further purification.

tert-butyl (R)-(1-(5-((6-ethoxy-2-methyl-2H-indazol-5-yl)carbamoyl)pyrazin-2-yl)pyrrolidin-3-yl)(methyl)carbamate, methanol (3 mL) and 4N HCl in dioxane (3 mL) were combined and stirred at room temperature for 2 hours. The reaction mixture was then evaporated to dryness then taken up in MeOH and stirred over sodium carbonate for 5 mins, then filtered through an Isolute $NH_2$ resin cartridge. The filtrate was evaporated to dryness to give the title compound. LCMS (ES+) 396 (M+H)+, RT 2.5 min (Analytical method AcHSSC18). $^1$H NMR (400 MHz, DMSO) δ 10.18 (s, 1H), 8.79 (d, J=1.3 Hz, 1H), 8.72 (s, 1H), 8.25 (s, 1H), 8.07 (d, J=1.3 Hz, 1H), 7.13 (s, 1H), 4.27 (q, J=7.0 Hz, 2H), 4.13 (s, 3H), 3.73-3.60 (m, 3H), 3.45-3.40 (m, 1H), 3.34-3.32 (m, 1H), 2.38-2.34 (m, 3H), 2.17-2.09 (m, 1H), 1.94-1.91 (m, 2H), 1.53 (dd, J=6.9, 6.9 Hz, 3H).

Further analogues were prepared using Method H (TCFH coupling) starting from (R)-5-(3-((tert-butoxycarbonyl)(methyl)amino)pyrrolidin-1-yl)pyrazine-2-carboxylic acid and the stated amine. In some instances, Boc protected amines were used, in which case the Boc group was removed at end of the synthetic sequence using 4N HCl in dioxane (general Method C) or TFA/DCM (general Method E). Final products were isolated by SCX and/or Preparative HPLC.

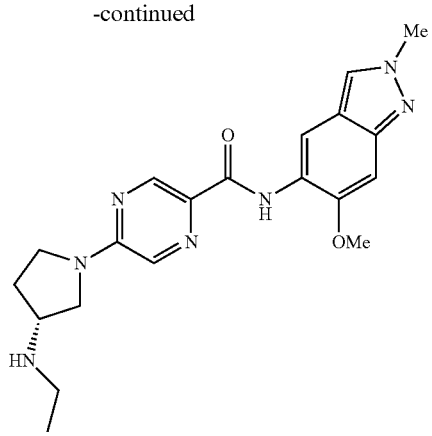

5-Chloropyrazine-2-carboxylic acid (159 mg, 1 mmol) and dichloromethane (10 mL) were combined under nitrogen atmosphere. Oxalyl chloride (0.17 mL, 2 mmol) was added followed by DMF (1 drop). The reaction mixture was stirred at room temperature for 16 hours. The reaction mixture was evaporated to dryness. Intermediate 4 (1.08 mmol), dichloromethane (20 mL) and triethylamine (2 mL) were added and the reaction mixture was stirred for 1.5 hours. The reaction was then evaporated to dryness to give 5-chloro-N-(6-methoxy-2-methyl-2H-indazol-5-yl)pyrazine-2-carboxamide, which was used crude without further purification. MS (ES+) 318/320 (M+H).

| Ex. | Structure | Amine | Analytical data |
|---|---|---|---|
| 109 | 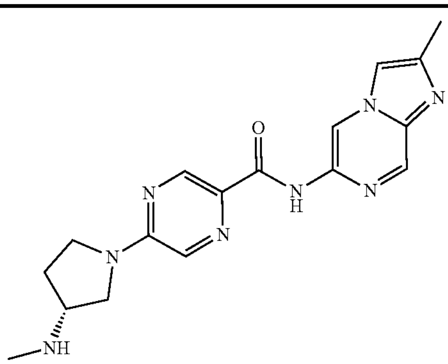 | 2-methylimidazo[1,2-a]pyrazin-6-amine | LCMS (ES+) 353 (M + H)+, RT 1.76 min (Analytical method AcHSSC18); $^1$H NMR (400 MHz, DMSO) δ 9.80 (s, 1H), 9.31 (d, J = 1.3 Hz, 1H), 8.83 (s, 1H), 8.79 (d, J = 1.0 Hz, 1H), 8.08 (d, J = 4.6 Hz, 2H, 3.78-3.53 (m, 6H, 2.47 (s, 3H), 2.42 (s, 3H), 2.23 (s, 1H), 2.04 (s, 1H). |

Example 110: (R)-5-(3-(ethylamino)pyrrolidin-1-yl)-N-(6-methoxy-2-methyl-2H-indazol-5-yl)pyrazine-2-carboxamide

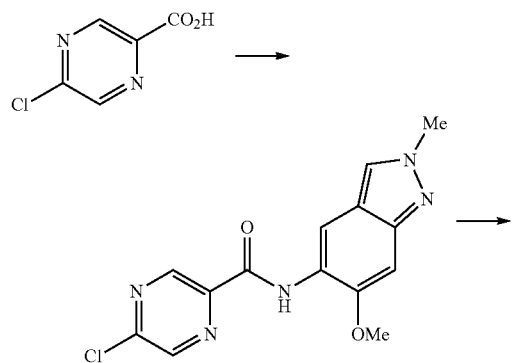

5-Chloro-N-(6-methoxy-2-methyl-2H-indazol-5-yl)pyrazine-2-carboxamide (150 mg, 0.25 mmol), (R)—N-ethylpyrrolidin-3-amine (28 mg, 0.25 mmol), $Cs_2CO_3$ (325 mg, 1 mmol) and DMF (2 mL) were combined in a sealed tube and hot block heated to 100° C. for 1 hour. The reaction mixture was cooled to room temperature, the cesium salts were removed by filtration and the reaction mixture was purified by Preparative HPLC to give the title compound. LCMS (ES+) 396 (M+H)+, RT 2.36 min (Analytical method AcHSSC18). $^1$H NMR (400 MHz, DMSO) δ 10.05 (s, 1H), 8.75 (d, J=1.3 Hz, 1H), 8.69 (s, 1H), 8.23 (s, 1H), 8.04 (d, J=1.3 Hz, 1H), 7.11 (s, 1H), 4.10 (s, 3H), 3.99 (s, 3H), 3.71-3.52 (m, 3H), 3.42-3.37 (m, 2H), 2.63-2.58 (m, 2H), 2.17-2.09 (m, 1H), 1.86-1.81 (m, 2H), 1.04 (dd, J=7.1, 7.1 Hz, 3H).

Further analogues were prepared using the same chemistry from commercially available or synthesized amines. In some instances, Boc protected amines were used, in which case the Boc group was removed at end of the synthetic sequence using 4N HCl in dioxane (general Method C) or TFA/DCM (general Method E) Final products were isolated by SCX and/or Preparative HPLC.

| Ex. | Structure | Amine | Analytical data |
|---|---|---|---|
| 111 | 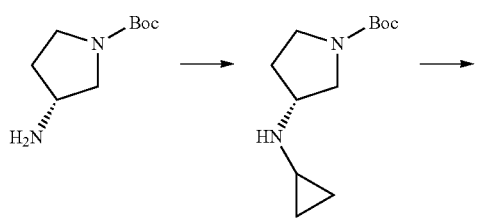 | tert-butyl (R)-methyl(pyrrolidin-3-yl)carbamate | LCMS (ES+) 382 (M + H)+, RT 3.1 min (Analytical method BicarbBEHC18)<br>$^1$H NMR (400 MHz, DMSO) δ 10.06 (s, 1H), 8.75 (d, J = 1.1 Hz, 1H), 8.69 (s, 1H), 8.23 (s, 1H), 8.06 (d, J = 1.3 Hz, 1H), 7.11 (s, 1H), 4.10 (s, 3H), 3.99 (s, 3H), 3.70-3.55 (m, 3H), 3.46-3.39 (m, 2H), 2.34 (s, 3H), 2.17-2.09 (m, 1H), 1.92-1.92 (m, 1H). |

Example 112: (R)-5-(3-(cyclopropylamino)pyrrolidin-1-yl)-N-(8-fluoro-2-methylimidazo[1,2-a]pyridin-6-yl)pyrazine-2-carboxamide

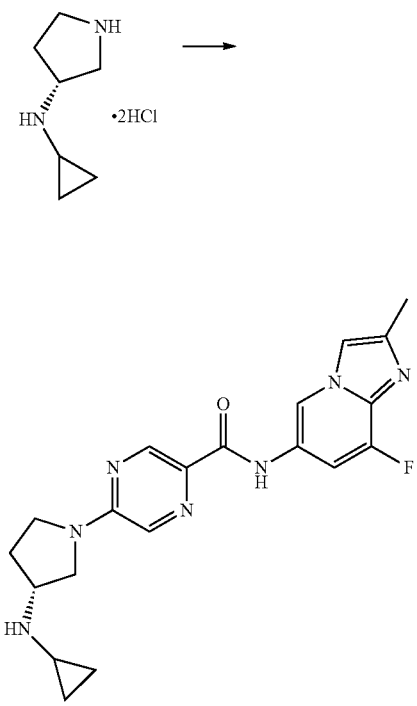

(R)-(+)-1-Boc-3-aminopyrrolidine (400 mg, 2.15 mmol) and (1-ethoxycyclopropoxy)trimethylsilane (0.48 mL, 2.37 mmol) were combined in MeOH (30 mL). NaBH$_3$CN (162 mg, 2.58 mmol) was added followed by AcOH (0.2 mL). The reaction mixture was then heated to 55° C. for 16 hours. The reaction was then diluted with dichloromethane, washed with sat. aq. NaHCO$_3$ solution, dried (MgSO$_4$) and evaporated to dryness to give tert-butyl (R)-3-(cyclopropylamino)pyrrolidine-1-carboxylate, which was used crude in next step.

tert-Butyl (R)-3-(cyclopropylamino)pyrrolidine-1-carboxylate (455 mg, 2 mmol), MeOH (15 mL) and 4N HCl in dioxane (15 mL) were combined and stirred at room temperature for 24 hours. The reaction mixture was then evaporated to dryness to give (R)—N-cyclopropylpyrrolidin-3-amine-2HCl, which was used crude in next step.

(R)—N-cyclopropylpyrrolidin-3-amine-2HCl (500 mg), Intermediate 1 (400 mg, 1.3 mmol), cesium carbonate (1.63 g, 5 mmol) and DMF (7 mL) were combined and heated to 100° C. for 20 hours. The cesium salts were then filtered off and the filtrate was purified by preparative HPLC to give the title compound. LCMS (ES+) 396 (M+H)+, RT 1.75 min (Analytical method AcHSSC18). $^1$H NMR (400 MHz, DMSO) δ 10.44 (s, 1H), 9.23 (d, J=1.8 Hz, 1H), 8.78 (d, J=1.3 Hz, 1H), 8.00 (d, J=1.3 Hz, 1H), 7.93 (d, J=2.5 Hz, 1H), 7.60 (dd, J=1.5, 13.0 Hz, 1H), 3.78-3.53 (m, 4H), 3.51-3.42 (m, 1H), 2.61-2.58 (m, 1H), 2.39 (s, 3H), 2.21-2.12 (m, 2H), 1.99-1.99 (m, 1H), 0.45 (d, J=6.6 Hz, 2H), 0.33-0.25 (m, 2H).

Further analogues were prepared using the same chemistry from commercially available or synthesized amines. Final products were isolated by Preparative HPLC.

| Ex. | Structure | Amine | Analytical data |
|---|---|---|---|
| 113 | 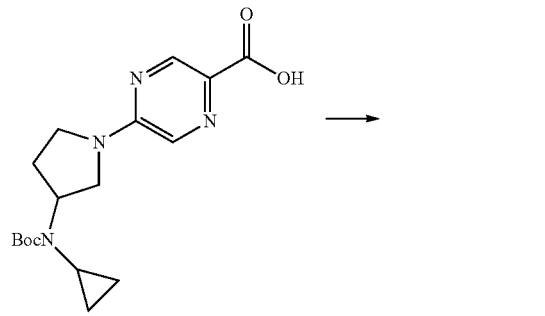 | (S)-1-Boc-3-aminopyrrolidine | LCMS (ES+) 396 (M + H)+, RT 1.75 min (Analytical method AcHSSC18) ¹H NMR (400 MHz, DMSO) δ 10.44 (s, 1H), 9.23 (d, J = 1.8 Hz, 1H), 8.78 (d, J = 1.3 Hz, 1H), 8.00 (d, J = 1.3 Hz, 1H), 7.93 (d, J = 2.5 Hz, 1H), 7.60 (dd, J = 1.5, 13.0 Hz, 1H), 3.78-3.53 (m, 4H), 3.51-3.42 (m, 1H), 2.61-2.58 (m, 1H), 2.39 (s, 3H), 2.21-2.12 (m, 2H), 1.99-1.99 (m, 1H), 0.45 (d, J = 6.6 Hz, 2H), 0.33-0.25 (m, 2H). |

Example 114 5-[3-(cyclopropylamino)pyrrolidin-1-yl]-N-(5-fluoro-2-methyl-1,3-benzoxazol-6-yl)pyrazine-2-carboxamide (Enantiomer 1+Enantiomer 2)

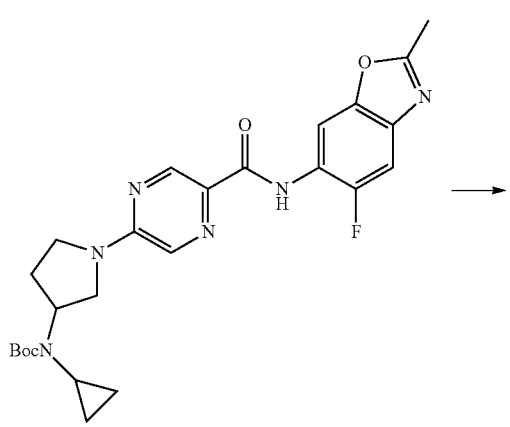

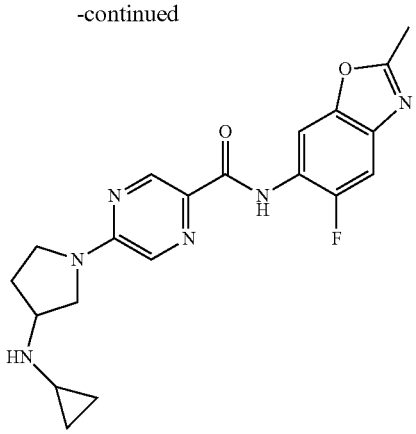

Following Method H from 5-(3-((tert-butoxycarbonyl)(cyclopropyl)amino)pyrrolidin-1-yl)pyrazine-2-carboxylic acid (126 mg, 0.361 mmol, 1 equiv) and 5-fluoro-2-methylbenzo[d]oxazol-6-amine (60 mg, 0.361 mmol, 1 equiv) in DMF (2.0 mL). The reaction mixture was diluted with water and the solids filtered and washed with 1:1 MeCN/H₂O. The solid was purified using silica chromatography, elution gradient 0-10% EtOAc in cyclohexane. Fractions containing the desired material were combined and the solvent removed in vacuo to give tert-butyl cyclopropyl(1-(5-((5-fluoro-2-methylbenzo[d]oxazol-6-yl)carbamoyl)pyrazin-2-yl)pyrrolidin-3-yl)carbamate. LCMS (ES+) 497 (M+H)+.

Following Method E TFA Boc deprotection from tert-butyl cyclopropyl(1-(5-((5-fluoro-2-methylbenzo[d]oxazol-6-yl)carbamoyl)pyrazin-2-yl)pyrrolidin-3-yl)carbamate (26 mg, 0.0511 mmol). The reaction mixture was concentrated in vacuo and the residue applied to a 2 g SCX cartridge, eluting with 2 column volumes methanol, then 3 column volumes 2 M methanolic ammonia. The ammonia fraction was concentrated in vacuo to give 5-[3-(cyclopropylamino)pyrrolidin-1-yl]-N-(5-fluoro-2-methyl-1,3-benzoxazol-6-yl)pyrazine-2-carboxamide. LCMS (ES+) 397 (M+H)+, RT 4.57 min (Analytical method BicarbBEHC18) ¹H NMR (400 MHz, DMSO) δ 9.91 (d, J=2.4 Hz, 1H), 8.75 (s, 1H), 8.47 (d, J=6.5 Hz, 1H), 8.04 (s, 1H), 7.71 (d, J=10.9 Hz, 1H), 3.74-3.50 (m, 4H), 3.45 (s, 1H), 2.63 (s, 3H), 2.19-2.10 (m, 2H), 1.96 (s, 1H), 0.43 (d, J=6.7 Hz, 2H), 0.32-0.23 (m, 2H).

Example 115 5-[3-(cyclopropylamino)pyrrolidin-1-yl]-N-(2,6-dimethylindazol-5-yl)pyrazine-2-carboxamide (Enantiomer 1+Enantiomer 2)

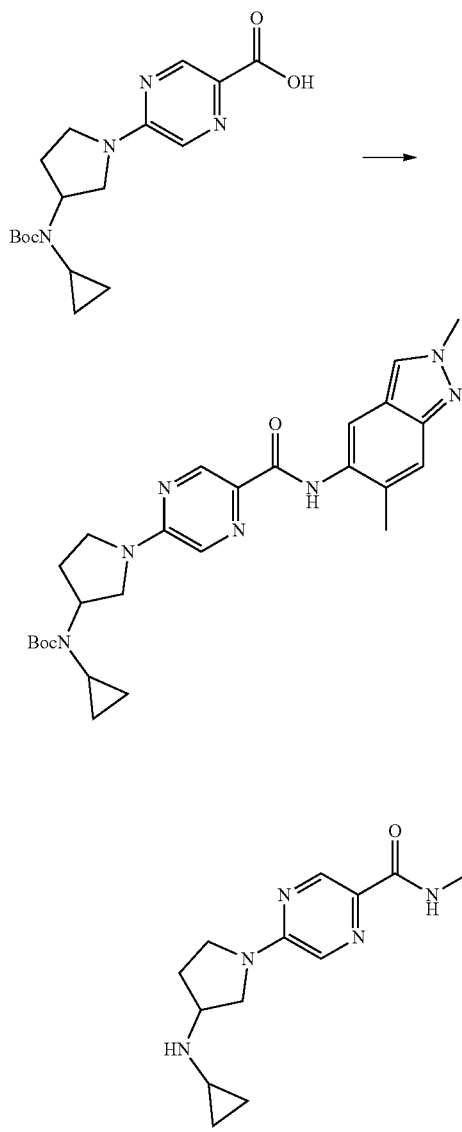

Following Method H from 5-(3-((tert-butoxycarbonyl)(cyclopropyl)amino)pyrrolidin-1-yl)pyrazine-2-carboxylic acid (140 mg, 0.403 mmol, 1 equiv) and 2,6-dimethyl-2H-indazol-5-amine (65 mg, 0.403 mmol, 1 equiv) in DMF (2.0 mL). The reaction mixture was diluted with water and the solid filtered and washed with 1:1 MeCN/H₂O to give crude tert-butyl cyclopropyl(1-(5-((2,6-dimethyl-2H-indazol-5-yl)carbamoyl)pyrazin-2-yl)pyrrolidin-3-yl)carbamate which was taken forward without further purification.

Following Method E TFA Boc deprotection from tert-butyl cyclopropyl(1-(5-((2,6-dimethyl-2H-indazol-5-yl)carbamoyl)pyrazin-2-yl)pyrrolidin-3-yl)carbamate (36 mg, 0.0732 mmol). The reaction mixture was concentrated in vacuo and the residue applied to a 2 g SCX cartridge, eluting with 2 column volumes methanol, then 3 column volumes 2 M methanolic ammonia. The ammonia fraction was concentrated in vacuo and the residue purified by reverse phase HPLC to give 5-[3-(cyclopropylamino)pyrrolidin-1-yl]-N-(2,6-dimethylindazol-5-yl)pyrazine-2-carboxamide. LCMS (ES+) 392 (M+H)+, RT 2.38 min (Analytical method AcHSSC18) ¹H NMR (400 MHz, DMSO) δ 9.74 (s, 1H), 8.77 (s, 1H), 8.30 (s, 1H), 8.26-8.22 (m, 1H), 8.05 (s, 1H), 7.52 (s, 1H), 4.18 (s, 3H), 3.77-3.55 (m, 4H), 3.51-3.45 (m, 1H), 2.43 (s, 3H), 2.21-2.15 (m, 2H), 2.01-1.99 (m, 1H), 0.48 (d, J=6.6 Hz, 2H), 0.36-0.28 (m, 2H).

Example 116 5-[3-(cyclopropylamino)pyrrolidin-1-yl]-N-(2,7-dimethylimidazo[1,2-a]pyridin-6-yl)pyrazine-2-carboxamide (Enantiomer 1+Enantiomer 2)

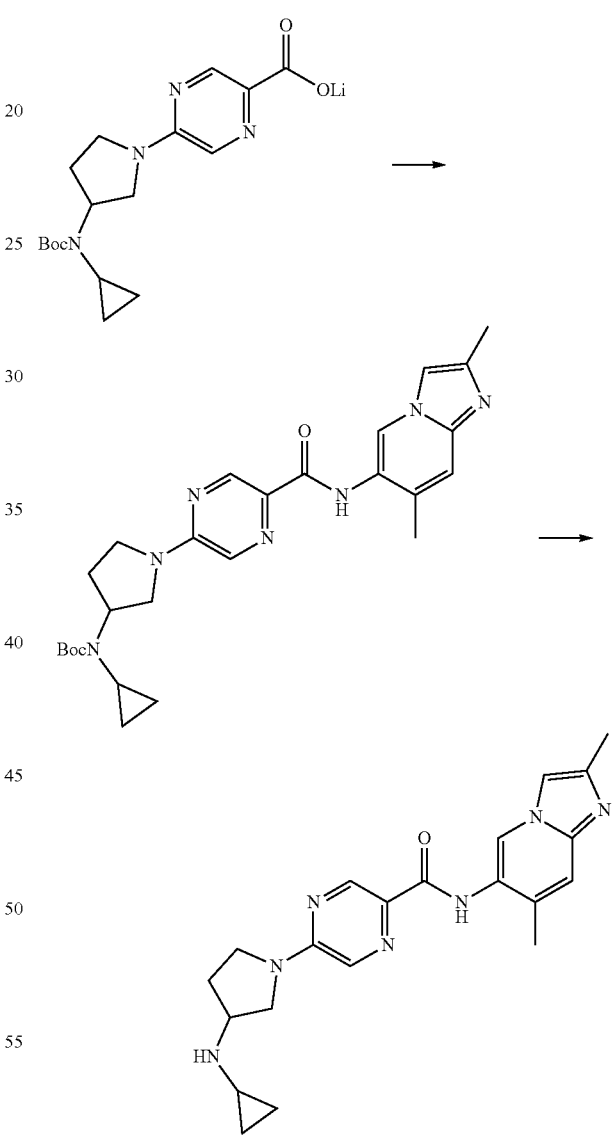

Following method H, lithium 5-(3-((tert-butoxycarbonyl)(cyclopropyl)amino)pyrrolidin-1-yl)pyrazine-2-carboxylate (97 mg, 0.273 mmol) was reacted with 2,7-dimethylimidazo[1,2-a]pyridin-6-amine (44 mg, 0.273 mmol) in DMF (2.0 mL). The reaction mixture was diluted with water and the solid filtered and washed with 1:1 MeCN/H₂O and purified by reverse phase HPLC to give tert-butyl cyclopropyl(1-(5-

((2,7-dimethylimidazo[1,2-a]pyridin-6-yl)carbamoyl) pyrazin-2-yl)pyrrolidin-3-yl)carbamate. LCMS (ES+) 492 (M+H)+.

Following method E, tert-butyl cyclopropyl(1-(5-((2,7-dimethylimidazo[1,2-a]pyridin-6-yl)carbamoyl)pyrazin-2-yl)pyrrolidin-3-yl)carbamate (9.4 mg, 0.020 mmol) was treated with TFA. The reaction mixture was concentrated in vacuo and the residue applied to a 2 g SCX cartridge, eluting with 2 column volumes methanol, then 3 column volumes 2 M methanolic ammonia. The ammonia fraction was concentrated in vacuo to give the title compound. LCMS (ES+) 392 (M+H)+, RT 3.95 min (Analytical method BicarbBEHC18) $^1$H NMR (400 MHz, MeOD) δ 8.78 (s, 1H), 8.65 (d, J=1.3 Hz, 1H), 7.87 (d, J=1.3 Hz, 1H), 7.44 (s, 1H), 7.23 (s, 1H), 3.76-3.45 (m, 4H), 3.42-3.37 (m, 1H), 2.31 (d, J=0.8 Hz, 3H), 2.29 (d, J=0.7 Hz, 3H), 2.26-2.12 (m, 2H), 2.01-1.91 (m, 1H), 0.47-0.44 (m, 2H), 0.35-0.31 (m, 2H).

Example 117 (R)—N-(8-fluoro-2-methylimidazo[1,2-a]pyridin-6-yl)-5-(3-((2,2,2-trifluoroethyl)amino)pyrrolidin-1-yl)pyrazine-2-carboxamide

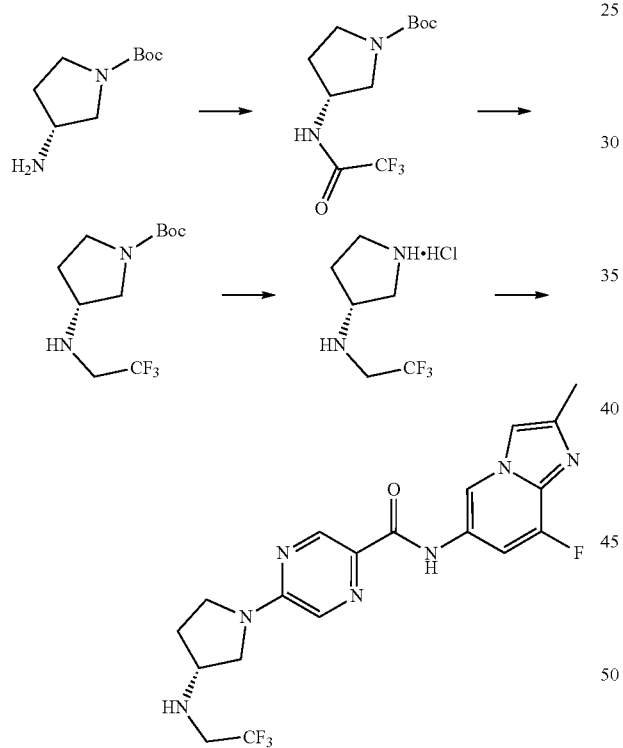

tert-Butyl (R)-3-aminopyrrolidine-1-carboxylate (1.0 g, 5.37 mmol) and ethyl trifluoroacetate (2.29 g, 16.1 mmol) were stirred in ethanol (20 mL) at 60° C. for 17 h. The reaction mixture was concentrated to dryness and the crude tert-butyl (R)-3-(2,2,2-trifluoroacetamido)pyrrolidine-1-carboxylate used in the next step. LCMS (ES+) 283 (M+H)+.

To a stirred solution of tert-butyl (R)-3-(2,2,2-trifluoroacetamido)pyrrolidine-1-carboxylate (5.37 mmol) in THF (10 mL) was added borane-THF (21.5 mL, 1 M, 21.5 mmol) dropwise. After addition the mixture was refluxed for 17 h. The reaction mixture was cooled to r.t. and sat. aq. NH$_4$Cl (20 mL) was added, before heating to 60° C. for 2 h. The mixture was concentrated and the resulting aqueous solution was extracted with EtOAc (2×30 mL). The organic layer was collected, dried (MgSO$_4$), filtered and concentrated. Purification by flash silica column chromatography (gradient, DCM to DCM/MeOH/7 M NH$_3$ in MeOH [89:10:1]), gave tert-butyl (R)-3-((2,2,2-trifluoroethyl)amino)pyrrolidine-1-carboxylate. LCMS (ES+) 213 (M+H)+.

tert-Butyl (R)-3-((2,2,2-trifluoroethyl)amino)pyrrolidine-1-carboxylate (600 mg, 3.29 mmol) and HCl in dioxane (4 M, 4 mL, 16 mmol) were stirred in MeOH (10 mL) for 17 h. The mixture was concentrated to dryness and the crude (R)—N-(2,2,2-trifluoroethyl)pyrrolidin-3-amine·HCl was used in the next step.

To a stirred solution of Intermediate 1 (100 mg, 0.33 mmol) in DMF (4 mL) was added (R)—N-(2,2,2-trifluoroethyl)pyrrolidin-3-amine·HCl (87 mg, 0.36 mmol) and Cs$_2$CO$_3$ (533 mg, 1.64 mmol). The mixture was stirred at 100° C. for 17 h and then cooled to r.t. The reaction mixture was partitioned between EtOAc (10 mL) and water (10 mL). The organics were separated from the aqueous layer, which was extracted with further EtOAc (10 mL). The combined organic layers were washed with water (3×30 mL), dried (MgSO$_4$), filtered and concentrated to dryness. Purification by preparative HPLC gave the title compound. LCMS (ES+) 438 (M+H)+, RT 2.64 min (Analytical method AcHSSC18); $^1$H NMR (400 MHz, DMSO) δ 10.42 (s, 1H), 9.19 (d, J=1.2 Hz, 1H), 8.75 (s, 1H), 7.98 (d, J=1.6 Hz, 1H), 7.90 (t, J=8 Hz, 1H), 7.56 (dd, J=1.6, 13.2 Hz, 1H), 3.68-3.49 (m, 4H), 3.41-3.21 (m, 2H), 2.82-2.73 (m, 1H), 2.34 (s, 3H), 2.20-2.11 (m, 1H), 2.01-1.85 (m, 1H), 1 proton obscured by water peak.

Example 118 N-(8-fluoro-2-methylimidazo[1,2-a]pyridin-6-yl)-5-((3'S,4'R)-4'-fluoro-[1,3'-bipyrrolidin]-1'-yl)pyrazine-2-carboxamide and Example 119 N-(8-fluoro-2-methylimidazo[1,2-a]pyridin-6-yl)-5-((3'R,4'S)-4'-fluoro-[1,3'-bipyrrolidin]-1'-yl)pyrazine-2-carboxamide

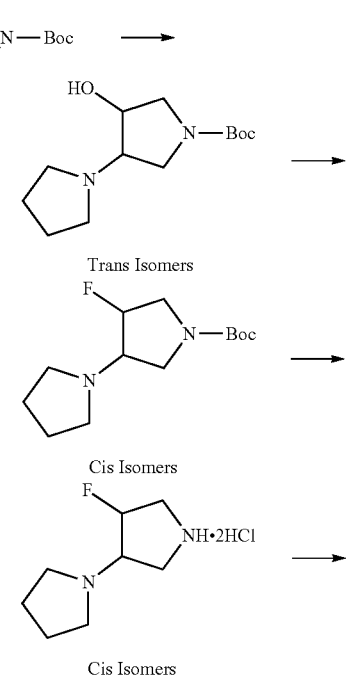

Trans Isomers

Cis Isomers

Cis Isomers

-continued

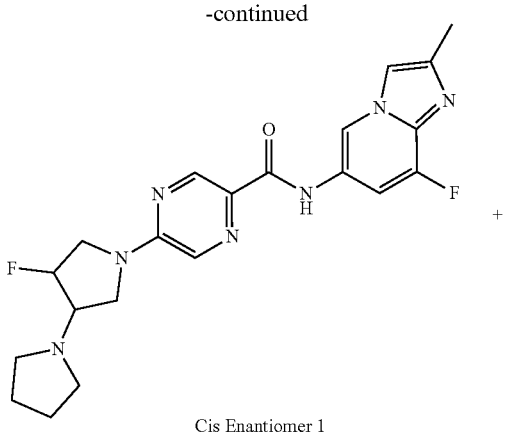

Cis Enantiomer 1

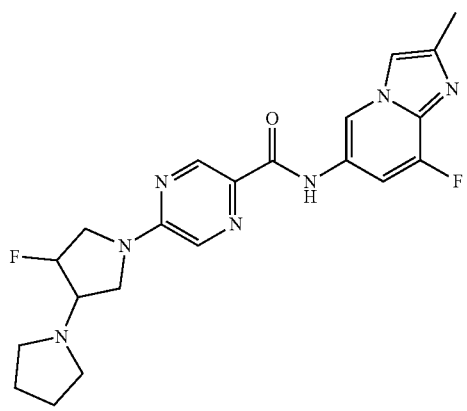

Cis Enantiomer 2 tert-Butyl 6-oxa-3-azabicyclo[3.1.0]hexane-3-carboxylate (1.25 g, 6.75 mmol), pyrrolidine (6.816 g, 95.84 mmol) and water (12 mL) were combined in a sealed tube and heated to 50° C. for 5 days. The reaction was quenched with sat. aq. NaHCO₃ solution and extracted with dichloromethane (2×). The combined organic layers were dried (MgSO₄) and evaporated to dryness onto silica which was purified by flash chromatography eluting with 1% NH₄OH/10% MeOH/CH₂Cl₂ to give tert-butyl (3'R*,4'R*)-4'-hydroxy-[1,3'-bipyrrolidine]-1'-carboxylate, which was used crude in the next step.

tert-Butyl (3'R*,4'R*)-4'-hydroxy-[1,3'-bipyrrolidine]-1'-carboxylate (200 mg, 0.78 mmol), dichloromethane (10 mL) and Deoxy-Fluor® (50% in THF) (0.32 mL, 0.86 mmol) were combined under a nitrogen atmosphere at room temperature and stirred for 2 days. The reaction was quenched with sat. aq. NaHCO₃ solution and extracted with dichloromethane (2×). The combined organic layers were dried (MgSO₄) and evaporated to dryness to give tert-butyl (3'R*,4'S*)-4'-fluoro-[1,3'-bipyrrolidine]-1'-carboxylate, which was used crude in the next step.

tert-Butyl (3'R*,4'S*)-4'-fluoro-[1,3'-bipyrrolidine]-1'-carboxylate, methanol (3 mL) and 4N HCl in dioxane (3 mL) were combined and stirred for 16 hours. The reaction mixture was evaporated to dryness to give (3'R*,4'S*)-4'-fluoro-1,3'-bipyrrolidine-2HCl, which was used crude in the next step without further purification.

(3'R*,4'S*)-4'-Fluoro-1,3'-bipyrrolidine-2HCl, Intermediate 1 (200 mg, 0.65 mmol), cesium carbonate (800 mg, 2.45 mmol) and DMF (4 mL) were combined in a sealed tube and heated to 100° C. for 6 hours. The reaction mixture was cooled to room temperature, the cesium salts were removed by filtration and the filtrate was purified by preparative HPLC followed by chiral prep HPLC to give Example 118, Cis Isomer, Enantiomer 1

N-(8-fluoro-2-methylimidazo[1,2-a]pyridin-6-yl)-5-((3'S,4'R)-4'-fluoro-[1,3'-bipyrrolidin]-1'-yl)pyrazine-2-carboxamide. LCMS (ES+) 428 (M+H)+, RT 1.82 min (Analytical method AcHSSC18). ¹H NMR (400 MHz, DMSO) δ 10.47 (s, 1H), 9.20 (d, J=1.5 Hz, 1H), 8.78 (d, J=1.3 Hz, 1H), 8.08 (s, 1H), 7.90 (d, J=2.8 Hz, 1H), 7.58 (dd, J=1.6, 13.0 Hz, 1H), 5.47 (td, J=1.9, 51.0 Hz, 1H), 3.97-3.78 (m, 4H), 3.20-3.15 (m, 1H), 2.66-2.59 (m, 4H), 2.35 (s, 3H), 1.71 (dd, J=4.5, 4.5 Hz, 4H).

Example 119, Cis Isomer, Enantiomer 2

N-(8-fluoro-2-methylimidazo[1,2-a]pyridin-6-yl)-5-((3'R,4'S)-4'-fluoro-[1,3'-bipyrrolidin]-1'-yl)pyrazine-2-carboxamide. LCMS (ES+) 428 (M+H)+, RT 1.82 min (Analytical method AcHSSC18). ¹H NMR (400 MHz, DMSO) δ 10.47 (s, 1H), 9.20 (d, J=1.5 Hz, 1H), 8.78 (d, J=1.3 Hz, 1H), 8.08 (s, 1H), 7.90 (d, J=2.8 Hz, 1H), 7.58 (dd, J=1.6, 13.0 Hz, 1H), 5.47 (td, J=1.9, 51.0 Hz, 1H), 3.97-3.78 (m, 4H), 3.20-3.15 (m, 1H), 2.66-2.59 (m, 4H), 2.35 (s, 3H), 1.71 (dd, J=4.5, 4.5 Hz, 4H).

Further analogues were prepared using the same chemistry and suitable amines. Some enantiomers were separated by chiral SFC, in which case chirality was arbitrarily assigned.

| Ex. | Structure | Amine | Analytical data |
| --- | --- | --- | --- |
| 120 | ![structure] Cis Isomer, Enantiomer 1 | Ethylamine | LCMS (ES+) 402 (M + H)+, RT 3.17 min (Analytical method BicarbBEHC18); ¹H NMR (400 MHz, DMSO) δ 10.46 (s, 1H, 9.20 (d, J = 1.6 Hz, 1H), 8.77 (d, J = 1.4 Hz, 1H, 8.04 (s, 1H), 7.90 (d, J = 2.4 Hz, 1H), 7.59-7.55 (m, 1H), 5.35 (d, J = 54.6 Hz, 1H), 4.06-3.90 (m, 2H), 3.89-3.71 (m, 1H), 3.63-3.46 (m, 1H), 3.21 (t, J = 10.4 Hz, 1H), 2.79-2.62 (m, 2H, 2.35 (d, J = 0.8 Hz, 3H), 1.08 (t, J = 7.2 Hz, 3H). |

Example 121 (R)—N-(6-fluoro-2-methyl-2H-indazol-5-yl)-5-(3-(methylamino)pyrrolidin-1-yl)pyrazine-2-carboxamide

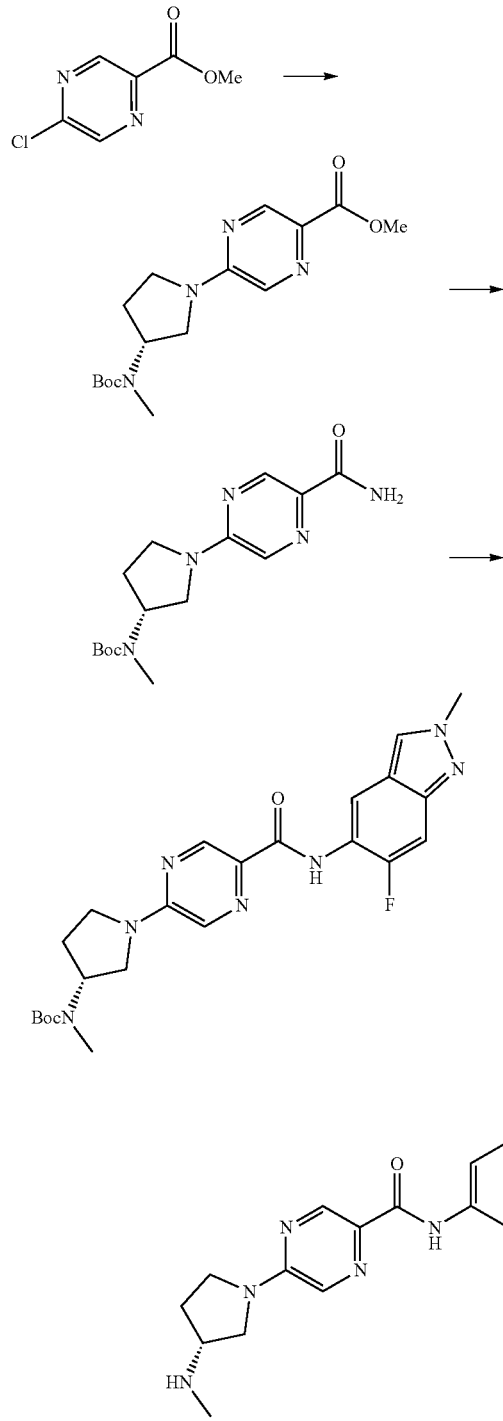

A mixture of tert-butyl (R)-methyl(pyrrolidin-3-yl)carbamate (400 mg, 2.0 mmol), methyl 5-chloropyrazine-2-carboxylate (350 mg, 2.0 mmol), Cs₂CO₃ (976 mg, 3.0 mmol) and DMF (6 mL) was heated in a sealed tube to 110° C. for 17 hours. The reaction was cooled to room temperature and diluted with EtOAc, washed with water and brine and the organics concentrated in vacuo to give methyl (R)-5-(3-((tert-butoxycarbonyl)(methyl)amino)pyrrolidin-1-yl)pyrazine-2-carboxylate.

A mixture of methyl (R)-5-(3-((tert-butoxycarbonyl)(methyl)amino)pyrrolidin-1-yl)pyrazine-2-carboxylate (671 mg) and ammonia in methanol (4N, 20 mL) was heated to 90° C. for 19 hours. The reaction was cooled to room temperature and concentrated in vacuo to give tert-butyl (R)-(1-(5-carbamoylpyrazin-2-yl)pyrrolidin-3-yl)(methyl)carbamate.

Following Method F, tert-butyl (R)-(1-(5-carbamoylpyrazin-2-yl)pyrrolidin-3-yl)(methyl)carbamate (308 mg, 0.96 mmol) and 5-bromo-6-fluoro-2-methyl-2H-indazole (229 mg, 1.0 mmol) were coupled. The crude material was purified by preparative HPLC to give tert-butyl (R)-(1-(5-(((6-fluoro-2-methyl-2H-indazol-5-yl)carbamoyl)pyrazin-2-yl)pyrrolidin-3-yl)(methyl)carbamate.

Following Method E, tert-butyl (R)-(1-(5-((6-fluoro-2-methyl-2H-indazol-5-yl)carbamoyl)pyrazin-2-yl)pyrrolidin-3-yl)(methyl)carbamate (78 mg, 0.17 mmol) was treated with TFA. The reaction mixture was concentrated in vacuo and the residue taken up in MeOH and stirred with Na₂CO₃ for 5 minutes, filtered and the filtrate was purified by preparative HPLC to give the title compound. LCMS (ES+) 370 (M+H)+, RT 2.37 min (Analytical method AcHSSC18). ¹H NMR (400 MHz, DMSO) δ 9.82 (d, J=2.8 Hz, 1H), 8.75 (d, J=1.0 Hz, 1H), 8.49 (d, J=7.9 Hz, 1H), 8.39 (s, 1H), 8.04 (s, 1H), 7.51 (d, J=12.1 Hz, 1H), 4.16 (s, 3H), 3.69-3.56 (m, 4H), 2.32 (s, 3H), 2.17-2.04 (m, 1H), 1.99-1.80 (m, 2H).

Example 122 (R)—N-(8-methoxy-2-methylimidazo[1,2-a]pyrazin-6-yl)-5-(3-(methylamino)pyrrolidin-1-yl)pyrazine-2-carboxamide

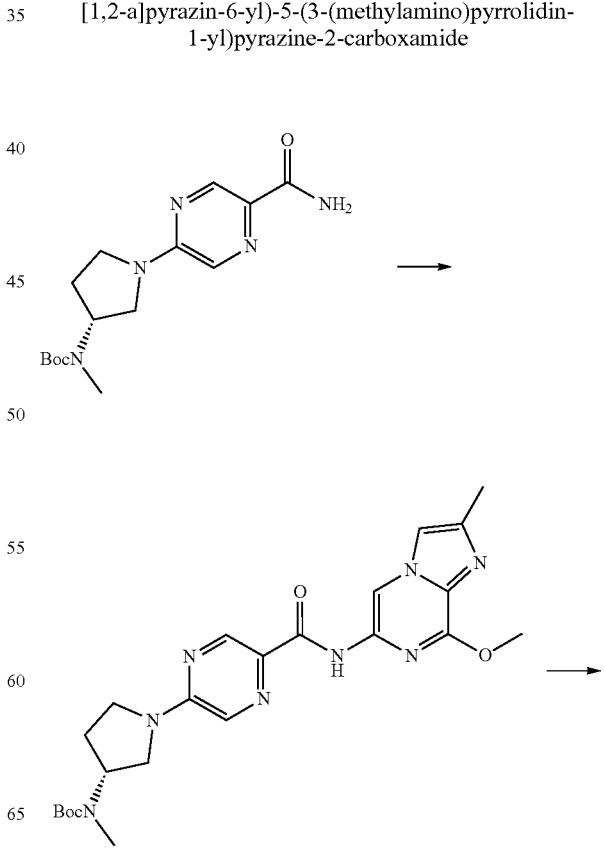

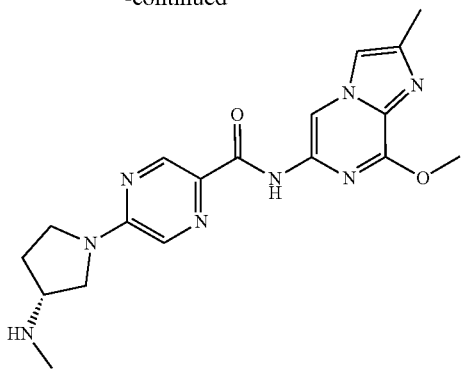

Following Method F, tert-butyl (R)-(1-(5-carbamoylpyrazin-2-yl)pyrrolidin-3-yl)(methyl)carbamate (150 mg, 0.47 mmol) and Intermediate 17 (119 mg, 0.49 mmol) were coupled. The crude material was purified by preparative HPLC to give tert-butyl (R)-(1-(5-((8-methoxy-2-methylimidazo[1,2-a]pyrazin-6-yl)carbamoyl)pyrazin-2-yl)pyrrolidin-3-yl)(methyl)carbamate.

Following Method E, tert-butyl (R)-(1-(5-((8-methoxy-2-methylimidazo[1,2-a]pyrazin-6-yl)carbamoyl)pyrazin-2-yl)pyrrolidin-3-yl)(methyl)carbamate (24 mg, 0.050 mmol) was treated with TFA. The reaction mixture was concentrated in vacuo and the residue taken up in MeOH and stirred with $Na_2CO_3$ for 5 minutes, filtered and the filtrate was purified by preparative HPLC to give the title compound. LCMS (ES+) 383 (M+H)+, RT 1.9 min (Analytical method AcHSSC18). $^1$H NMR (400 MHz, DMSO) δ 9.47 (s, 1H), 8.89 (s, 1H), 8.74 (s, 1H), 8.02 (s, 1H), 7.94 (s, 1H), 4.07 (s, 3H), 3.65-3.54 (m, 4H), 2.35 (s, 3H), 2.31 (s, 3H), 2.10 (s, 1H), 1.94-1.94 (m, 2H).

Further analogues were prepared using the same chemistry from commercially available or synthesized amines. In some instances, Boc protected amines were used, in which case the Boc group was removed at end of the synthetic sequence using 4N HCl in dioxane (general Method C) or TFA/DCM (general Method E). Final products were isolated by SCX and/or preparative HPLC. Some enantiomers were separated by chiral SFC, in which case chirality was arbitrarily assigned.

| Ex. | Structure | Amine | Analytical data |
|---|---|---|---|
| 123 | 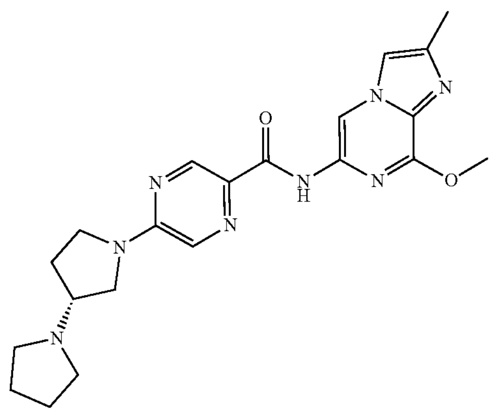 [SMILES: COc1nc(NC(=O)c2cnc(N3CC[C@@H](N4CCCC4)C3)cn2)cn2cc(C)nc12] | (R)-1,3'-bipyrrolidine; dihydrochloride | LCMS (ES+) 423 (M + H)+, RT 1.98 min (Analytical method AcHSSC18) $^1$H NMR (400 MHz, MeOD) δ 8.77 (1H, s), 8.66 (1H, d, J = 1.3 Hz), 7.88 (1H, d, J = 1.3 Hz), 7.61 (1H, d, J = 0.8 Hz), 4.05 (3H, s), 3.84-3.68 (2H, m), 3.50-3.40 (1H, m), 3.36-3.29 (1H, m), 2.96-2.86 (1H, m), 2.65-2.53 (4H, m), 2.31 (3H, s), 2.28-2.18 (1H, m), 2.00-1.90 (1H, m), 1.81-1.73 (4H, m). |
| 124 | 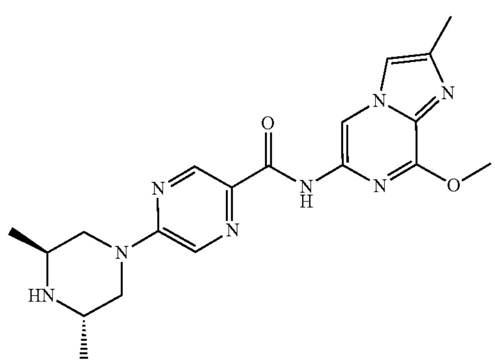 | tert-butyl (2S,6S)-2,6-dimethylpiperazine-1-carboxylate | LCMS (ES+) 397 (M + H)+, RT 2.02 min (Analytical method AcHSSC18) $^1$H NMR (400 MHz, DMSO) δ 9.48 (s, 1H), 8.90 (s, 1H, 8.72 (d, J = 1.1 Hz, 1H), 8.38 (s, 1H), 7.95 (s, 1H, 6.64-6.63 (m, 1H, 4.07 (s, 3H), 3.85-3.78 (m, 2H), 3.45-3.40 (m, 2H), 3.18 (m, 2H), 2.35 (s, 3H, 1.05 (s, 3H), 1.04 (s, 3H). |

Example 125: N-(8-fluoro-2-methylimidazo[1,2-a]pyridin-6-yl)-5-(piperidin-4-yl)pyrazine-2-carboxamide

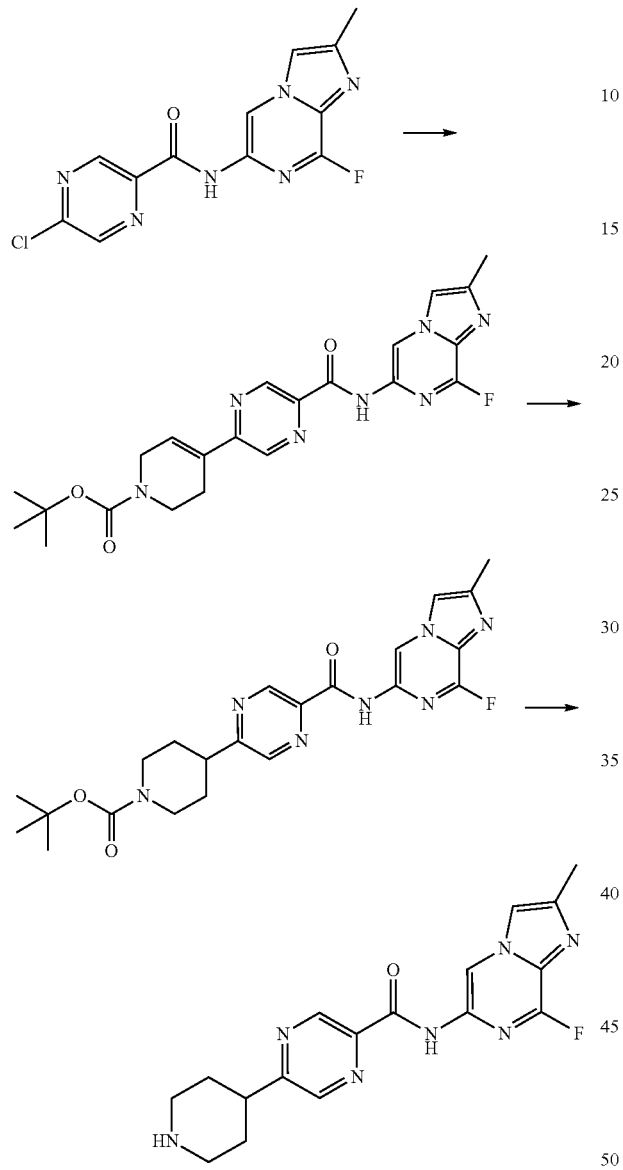

To a solution of Intermediate 1 (200 mg, 0.65 mmol) in dioxane (15 mL) and water (2 mL) was added sodium carbonate (500 mg, 4.71 mmol) and tert-butyl 4-(4,4,5,5-tetramethyl-1,3,2-dioxaborolan-2-yl)-3,6-dihydropyridine-1(2H)-carboxylate (202 mg, 0.65 mmol). Bis(triphenylphosphine)palladium(II) dichloride (20 mg, 0.03 mmol) was added and the reaction tube was sealed and heated at 100° C. for 22 h. The reaction was cooled to r.t. and the solvent removed in vacuo to give a residue, which was purified by silica chromatography to give tert-butyl 4-(5-((8-fluoro-2-methylimidazo[1,2-a]pyridin-6-yl)carbamoyl)pyrazin-2-yl)-3,6-dihydropyridine-1(2H)-carboxylate. MS (ES+) 453 (M+H).

A solution of tert-butyl 4-(5-((8-fluoro-2-methylimidazo[1,2-a]pyridin-6-yl)carbamoyl)pyrazin-2-yl)-3,6-dihydropyridine-1(2H)-carboxylate (150 mg, 0.33 mmol) in ethyl acetate (15 mL) was hydrogenated using the H-cube and a 20% Pd(OH)$_2$/C cartridge, in recycling mode at 1 mL/min, 40° C., 40 bars for 6 h, after which LCMS analysis showed near complete conversion. The solvent was removed in vacuo to give tert-butyl 4-(5-((8-fluoro-2-methylimidazo[1,2-a]pyridin-6-yl)carbamoyl)pyrazin-2-yl)piperidine-1-carboxylate, which was used in the next step without further purification.

Prepared using general Method E and the following quantities: tert-butyl 4-(5-((8-fluoro-2-methylimidazo[1,2-a]pyridin-6-yl)carbamoyl)pyrazin-2-yl)piperidine-1-carboxylate, DCM (3 mL) and TFA (1 mL). The reaction mixture was evaporated to dryness, taken up in MeOH, treated with Na$_2$CO$_3$, and then filtered. Purification by reverse phase HPLC followed by achiral SFC gave N-(8-fluoro-2-methylimidazo[1,2-a]pyridin-6-yl)-5-(piperidin-4-yl)pyrazine-2-carboxamide. LCMS (ES+) 355.2 (M+H)+, RT 1.61 min (Analytical method AcHSSC18) $^1$H NMR (400 MHz, DMSO) δ 10.92-10.90 (m, 1H), 9.23 (d, J=1.6 Hz, 2H), 8.76 (s, 1H), 7.94 (d, J=2.8 Hz, 1H), 7.57 (dd, J=2.0, 12.9 Hz, 1H), 3.10-3.00 (m, 3H), 2.63 (dd, J=10.5, 12.0 Hz, 2H), 2.36 (s, 3H), 1.84-1.81 (m, 2H), 1.70 (dq, J=3.9, 12.2 Hz, 2H).

Example 126: N-(8-fluoro-2-methylimidazo[1,2-a]pyridin-6-yl)-2-(piperazin-1-yl)pyrimidine-5-carboxamide

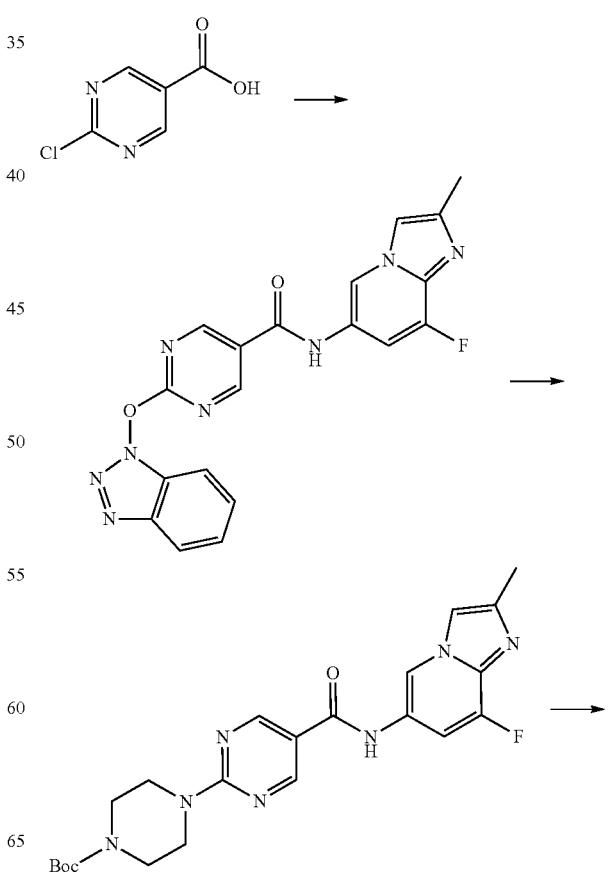

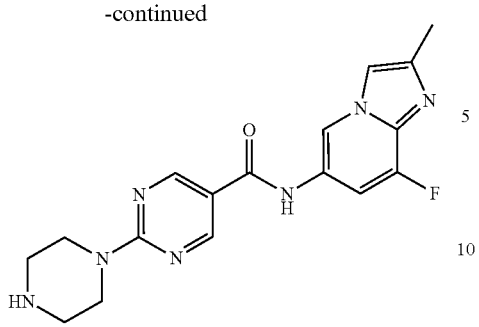

2-Chloropyrimidine-5-carboxylic acid (159 mg, 1 mmol), 8-fluoro-2-methylimidazo[1,2-a]pyridin-6-amine-2HCl (238 mg, 1 mmol), HBTU (379 mg, 1 mmol), triethylamine (0.5 mL) and DMF (4 mL) were combine and stirred at room temperature for 2 hours. The reaction mixture was then purified by Preparative HPLC to give 2-((1H-benzo[d][1,2,3]triazol-1-yl)oxy)-N-(8-fluoro-2-methylimidazo[1,2-a]pyridin-6-yl)pyrimidine-5-carboxamide. MS (ES+) 405 (M+H).

2-((1H-Benzo[d][1,2,3]triazol-1-yl)oxy)-N-(8-fluoro-2-methylimidazo[1,2-a]pyridin-6-yl)pyrimidine-5-carboxamide (113 mg, 0.28 mmol), N-Boc piperazine (52 mg, 0.28 mmol), $Cs_2CO_3$ (162 mg, 0.5 mmol) and DMF (4 mL) were combined in a sealed tube and hot block heated to 100° C. for 3 days. The reaction mixture was purified by preparative HPLC to give tert-butyl 4-(5-((8-fluoro-2-methylimidazo[1,2-a]pyridin-6-yl)carbamoyl)pyrimidin-2-yl)piperazine-1-carboxylate. MS (ES+) 456 (M+H).

tert-Butyl 4-(5-((8-fluoro-2-methylimidazo[1,2-a]pyridin-6-yl)carbamoyl)pyrimidin-2-yl)piperazine-1-carboxylate (27.5 mg), dichloromethane (2 mL) and TFA (1 mL) were combined and stirred at room temperature for 16 hours. The reaction mixture was evaporated to dryness then taken up in MeOH. $Na_2CO_3$ was added and stirred for 5 mins. The reaction was then filtered, the filtrate evaporated to dryness and purified by preparative HPLC to give the title compound. LCMS (ES+) 356 (M+H)+, RT 1.61 min (Analytical method AcHSSC18). $^1$H NMR (400 MHz, DMSO) δ 10.22-10.21 (m, 1H), 9.05 (d, J=1.6 Hz, 1H), 8.89 (s, 2H), 7.91 (d, J=2.8 Hz, 1H), 7.28 (dd, J=1.4, 12.7 Hz, 1H), 3.81-3.77 (m, 4H), 2.76 (dd, J=5.0, 5.0 Hz, 4H), 2.45 (s, 1H), 2.35 (s, 3H).

Example 127: (R)—N-(2,8-dimethylimidazo[1,2-a]pyrazin-6-yl)-2-(3-(methylamino)pyrrolidin-1-yl)pyrimidine-5-carboxamide

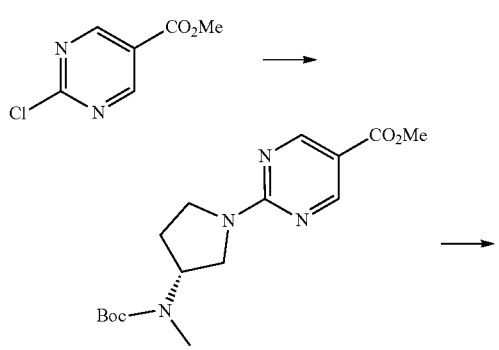

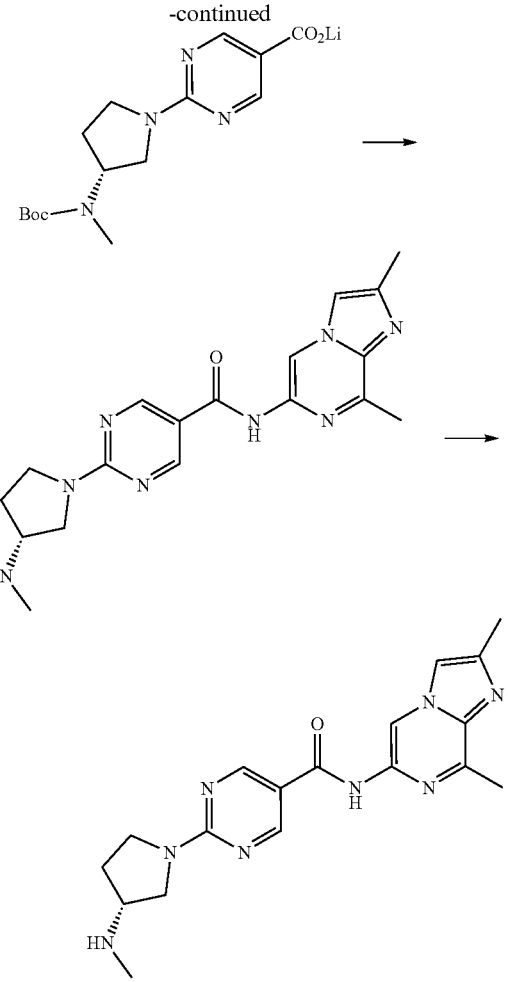

Methyl 2-chloropyrimidine-5-carboxylate (345 mg, 2 mmol), tert-butyl (R)-methyl(pyrrolidin-3-yl)carbamate (400 mg, 2 mmol), $Cs_2CO_3$ (975 mg, 3 mmol) and DMF (10 mL) were combined in a sealed tube and hot block heated to 100° C. for 1 hour. The reaction mixture was diluted with EtOAc, washed with water (×4), brine (×1) and evaporated to dryness to give methyl (R)-2-(3-((tert-butoxycarbonyl)(methyl)amino)pyrrolidin-1-yl)pyrimidine-5-carboxylate. MS RT (ES+) 337 (M+H).

Methyl (R)-2-(3-((tert-butoxycarbonyl)(methyl)amino)pyrrolidin-1-yl)pyrimidine-5-carboxylate (400 mg, 1.19 mmol), LiOH·$H_2O$ (55 mg, 1.3 mmol), MeOH (20 mL) and water (2 mL) were combined and hot block heated to 50° C. for 3 days. The reaction mixture was then evaporated to dryness to give lithium (R)-2-(3-((tert-butoxycarbonyl)(methyl)amino)pyrrolidin-1-yl)pyrimidine-5-carboxylate which was used crude in next reaction. MS (ES+) 323 (M+H).

Lithium (R)-2-(3-((tert-butoxycarbonyl)(methyl)amino)pyrrolidin-1-yl)pyrimidine-5-carboxylate (200 mg, 0.62 mmol), 2,8-dimethylimidazo[1,2-a]pyrazin-6-amine (100 mg, 0.62 mmol), HBTU (235 mg, 0.62 mmol), triethylamine (0.5 mL) and DMF (3 mL) were combined and stirred at room temperature for 1.5 hours. The reaction mixture was then purified by Preparative HPLC to give tert-butyl (R)-(1-(5-((2,8-dimethylimidazo[1,2-a]pyrazin-6-yl)carbamoyl)pyrimidin-2-yl)pyrrolidin-3-yl)(methyl)carbamate. MS (ES+) 467 (M+H).

tert-Butyl (R)-(1-(5-((2,8-dimethylimidazo[1,2-a]pyrazin-6-yl)carbamoyl)pyrimidin-2-yl)pyrrolidin-3-yl)(methyl)carbamate (49 mg), dichloromethane (3 mL) and TFA (1 mL) were combined and stirred at room temperature for 1 hour. The reaction mixture was evaporated to dryness then taken up in MeOH. Na₂CO₃ was added and stirred for 5 mins. The reaction was then filtered, the filtrate evaporated to dryness and purified by Preparative HPLC to give the title compound. LCMS (ES+) 367 (M+H)+, RT 1.73 min (Analytical method AcHSSC18). ¹H NMR (400 MHz, DMSO) δ 10.69 (s, 1H), 9.18 (s, 1H), 8.95 (s, 2H), 7.96 (s, 1H), 3.69-3.57 (m, 3H), 3.40 (dd, J=4.2, 11.7 Hz, 1H), 3.29-3.23 (m, 1H), 2.73 (s, 3H), 2.40 (s, 3H), 2.31 (s, 3H), 2.12-2.03 (m, 1H), 1.90-1.80 (m, 2H).

Further analogues were prepared using the same chemistry using commercially available or synthesized amines.

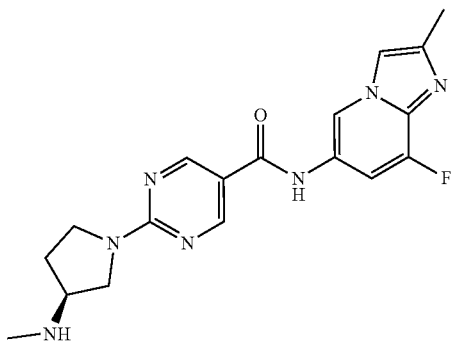

| Ex. | Structure | Amine | Analytical data |
|---|---|---|---|
| 128 | 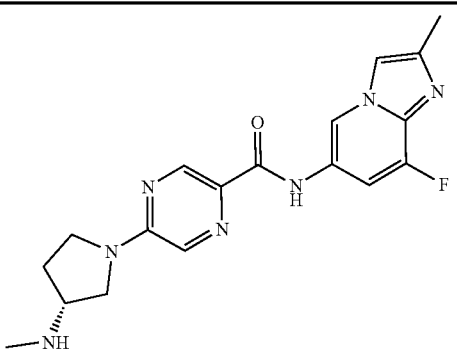 | 8-fluoro-2-methylimidazo[1,2-a]pyridin-6-amine | LCMS (ES+) 370 (M + H)+, RT 1.62 min (Analytical method AcHSSC18) ¹H NMR (400 MHz, DMSO) δ 10.16 (s, 1H), 9.05 (d, J = 1.6 Hz, 1H), 8.88 (s, 2H), 7.91 (d, J = 2.9 Hz, 1H, 7.28 (dd, J = 1.7, 12.9 Hz, 1H), 3.70-3.58 (m, 3H), 3.41 (dd, J = 4.1, 11.7 Hz, 1H), 3.30-3.23 (m, 1H), 2.35 (d, J = 0.7 Hz, 3H), 2.31 (s, 3H), 2.13-2.03 (m, 1H), 1.94 (s, 1H), 1.89-1.80 (m, 1H). |

Example 129: (S)—N-(8-fluoro-2-methylimidazo[1,2-a]pyridin-6-yl)-2-(3-(methylamino)pyrrolidin-1-yl)pyrimidine-5-carboxamide

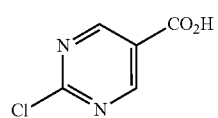

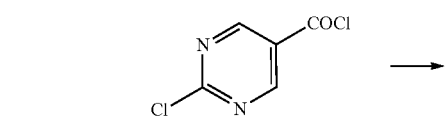

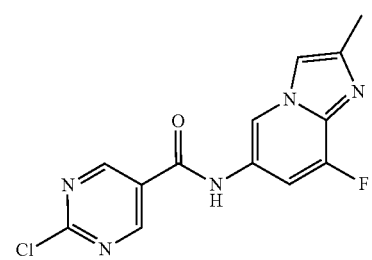

2-chloropyrimidine-5-carboxylic acid (500 mg, 3.15 mmol), and dichloromethane (10 mL) were combined under nitrogen atmosphere. Oxalyl chloride (0.55 mL, 6.3 mmol) was added followed by DMF (1 drop). The reaction mixture was stirred at room temperature for 16 hours. The reaction mixture was evaporated to dryness. 8-fluoro-2-methylimidazo[1,2-a]pyridin-6-amine (750 mg, 3.15 mmol), dichloromethane (30 mL) and triethylamine (3 mL) were added and the reaction mixture was stirred for 1.5 hours. The reaction was then evaporated to dryness to give 2-chloro-N-(8-fluoro-2-methylimidazo[1,2-a]pyridin-6-yl)pyrimidine-5-carboxamide, which was used crude in next reaction. MS (ES+) 306/308 (M+H).

2-chloro-N-(8-fluoro-2-methylimidazo[1,2-a]pyridin-6-yl)pyrimidine-5-carboxamide (150 mg, 0.23 mmol), (S)—N-methylpyrrolidin-3-amine (23 mg, 0.23 mmol), Cs₂CO₃ (325 mg, 1 mmol) and DMF (2 mL) were combined in a sealed tube and hot block heated to 100° C. for 16 hours. The reaction mixture was cooled to room temperature, the cesium salts were removed by filtration and the reaction mixture was purified by preparative HPLC to give the title compound. LCMS (ES+) 370 (M+H)+, RT 1.61 min (Analytical method AcHSSC18). ¹H NMR (400 MHz, DMSO) δ 9.95 (s, 1H), 8.94 (d, J=1.6 Hz, 1H), 8.89 (s, 2H), 7.84 (d, J=2.8 Hz, 1H), 7.28 (dd, J=1.5, 12.7 Hz, 1H), 3.76-3.59 (m, 3H), 3.42 (dd, J=4.6, 11.7 Hz, 1H), 3.35-3.28 (m, 1H), 2.37 (d, J=0.7 Hz, 3H), 2.36 (s, 3H), 2.24-2.08 (m, 1H), 1.90-1.81 (m, 1H).

Further analogues were prepared using the same chemistry from commercially available or synthesized amines. In some instances, Boc protected amines were used, in which case the Boc group was removed at end of the synthetic sequence using 4N HCl in dioxane (general Method C) or TFA/DCM (general Method E). Final products were isolated by SCX and/or preparative HPLC. Some enantiomers were separated by chiral SFC, in which case chirality was arbitrarily assigned.

| Ex. | Structure | Amine | Analytical data |
|---|---|---|---|
| 130 | 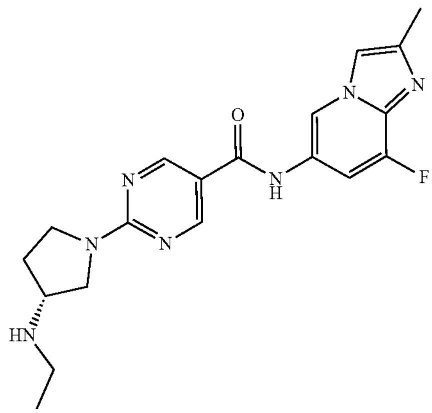 [SMILES: CCN[C@@H]1CCN(c2ncc(C(=O)Nc3cc(F)c4nc(C)cn4c3)cn2)C1] | (R)-N-ethylpyrrolidin-3-amine | LCMS (ES+) 384 (M + H)+, RT 1.63 min (Analytical method AcHSSC18) <sup>1</sup>H NMR (400 MHz, DMSO) δ 10.17-10.16 (m, 1H), 9.05 (d, J = 1.6 Hz, 1H), 8.89 (s, 2H), 7.91 (d, J = 2.8 Hz, 1H), 7.28 (dd, J = 1.6, 13.0 Hz, 1H), 3.73-3.54 (m, 3H), 3.42-3.37 (m, 2H), 3.34 (s, 2H), 2.64-2.54 (m, 2H), 2.35 (s, 3H), 2.15-2.05 (m, 1H), 1.88-1.79 (m, 2H), 1.04 (t, J = 7.1 Hz, 3H). |
| 131 | Enantiomer 1 + Enantiomer 2 | Intermediate 12 | LCMS (ES+) 396 (M + H)+, RT 1.7 min (Analytical method AcHSSC18) <sup>1</sup>H NMR (400 MHz, MeOD) δ 8.98 (d, J = 1.5 Hz, 1H), 8.90 (s, 2H), 7.73 (d, J = 2.5 Hz, 1H), 7.25 (dd, J = 1.6, 12.0 Hz, 1H), 3.95-3.78 (m, 2H), 3.70-3.51 (m, 3H), 2.45 (s, 3H), 2.34-2.21 (m, 2H), 2.06-1.97 (m, 1H), 0.57-0.54 (m, 2H), 0.45-0.41 (m, 2H). |
| 132 | Enantiomer 1 + Enantiomer 2 | Intermediate 5 | LCMS (ES+) 398 (M + H)+, RT 1.73 min (Analytical method AcHSSC18) <sup>1</sup>H NMR (400 MHz, MeOD) δ 8.98 (d, J = 1.5 Hz, 1H), 8.90 (s, 2H), 7.73 (d, J = 2.6 Hz, 1H), 7.25 (dd, J = 1.6, 12.0 Hz, 1H), 3.98 (dd, J = 6.7, 11.5 Hz, 1H), 3.91-3.83 (m, 1H), 3.66-3.57 (m, 2H), 3.38 (dd, J = 6.8, 11.5 Hz, 1H), 3.03-2.95 (m, 1H), 2.44 (s, 3H), 2.38-2.29 (m, 1H), 1.97-1.86 (m, 1H), 1.16 (dd, J = 4.3, 6.3 Hz, 6H). |

| Ex. | Structure | Amine | Analytical data |
| --- | --- | --- | --- |
| 133 | 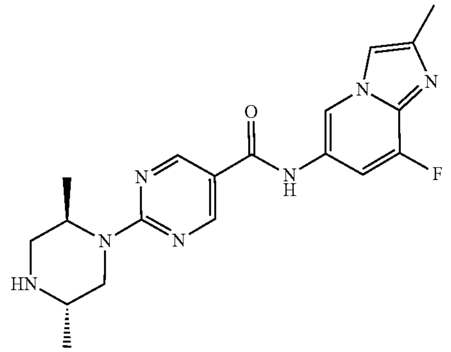 [SMILES: Cc1cn2cc(NC(=O)c3cnc(N4C[C@H](C)NC[C@H]4C)nc3)cc(F)c2n1] | tert-butyl (2S,5R)-2,5-dimethylpiperazine-1-carboxylate | LCMS (ES+) 384 (M + H)+, RT 1.77 min (Analytical method AcHSSC18) <br> $^1$H NMR (400 MHz, DMSO) δ 10.20-10.19 (m, 1H), 9.04 (d, J = 1.6 Hz, 1H), 8.89 (s, 2H), 7.91 (d, J = 2.9 Hz, 1H), 7.28 (dd, J = 1.7, 12.9 Hz, 1H), 4.86-4.80 (m, 1H), 4.48 (d, J = 9.8 Hz, 1H), 2.83 (s, 2H), 2.65-2.60 (m, 2H), 2.35 (s, 3H), 1.22 (d, J = 6.8 Hz, 3H), 1.08 (d, J = 5.6 Hz, 3H). |
| 134 | 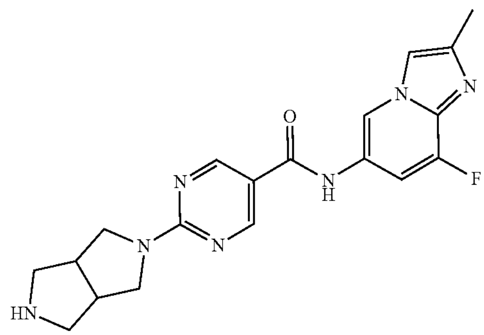 | tert-butyl hexahydropyrrolo[3,4-c]pyrrole-2(1H)-carboxylate | LCMS (ES+) 395 (M + H)+, RT 2.04 min (Analytical method AcHSSC18) <br> $^1$H NMR (400 MHz, DMSO) δ 10.21-10.16 (m, 1H), 9.05 (d, J = 1.5 Hz, 1H), 8.89 (s, 2H), 7.91 (d, J = 2.8 Hz, 1H), 7.28 (dd, J = 1.4, 13.1 Hz, 1H), 3.84 (dd, J = 7.8, 12.0 Hz, 2H), 3.44 (dd, J = 3.5, 12.0 Hz, 2H), 2.96-2.85 (m, 4H), 2.67 (dd, J = 2.5, 10.7 Hz, 2H), 2.35 (s, 3H). |
| 135 | 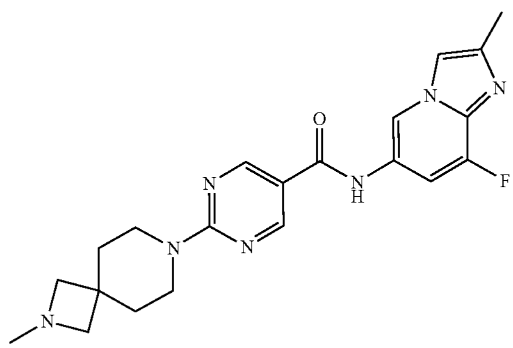 [SMILES: Cc1cn2cc(NC(=O)c3cnc(N4CCC5(CC4)CN(C)C5)nc3)cc(F)c2n1] | 2-methyl-2,7-diazaspiro[3.5]nonane | Formate salt. LCMS (ES+) 410 (M + H)+, RT 1.71 min (Analytical method AcHSSC18) <br> $^1$H NMR (400 MHz, DMSO) 10.23 (s, 1H), 9.06 (d, J = 1.6 Hz, 1H), 8.89 (s, 2H), 8.35 (s, 1H), 7.96 (d, J = 2 Hz, 1H), 7.29 (dd, J = 1.2, 12.4 Hz, 1H), 3.67-3.52 (m, 4H), 3.50 (d, J = 11.2 Hz, 2H), 2.59-2.41 (m, 2H), 2.35 (s, 3H), 2.27 (s, 3H), 2.06-1.91 (m, 2H), 1.82-1.72 (m, 2H). |

Example 136 (R)—N-(2,8-dimethylimidazo[1,2-a]pyrazin-6-yl)-2-(3-(ethylamino)pyrrolidin-1-yl)pyrimidine-5-carboxamide -continued

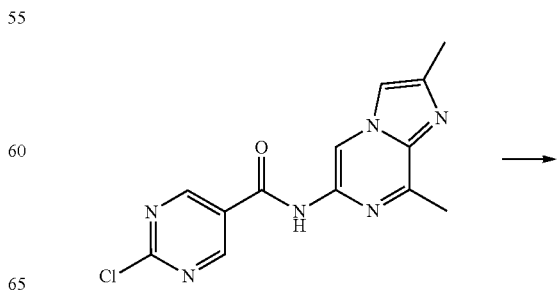

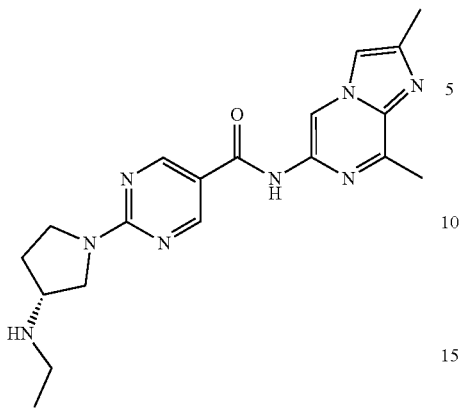

2-Chloropyrimidine-5-carboxylic acid (317 mg, 2 mmol) and dichloromethane (5 mL) were combined at room temperature under a nitrogen atmosphere. Oxalyl chloride (0.35 mL, 4 mmol) was added followed by 1 drop of DMF. The reaction mixture was stirred for 21 hours and then evaporated to dryness. 2,8-dimethylimidazo[1,2-a]pyrazin-6-amine (324 mg, 2 mmol), dichloromethane (30 mL) and triethylamine (2 mL) were added and the reaction was stirred for 2 hours. The reaction mixture was then evaporated to dryness to give 2-chloro-N-(2,8-dimethylimidazo[1,2-a]pyrazin-6-yl)pyrimidine-5-carboxamide, which was used crude in the next step.

2-Chloro-N-(2,8-dimethylimidazo[1,2-a]pyrazin-6-yl)pyrimidine-5-carboxamide (156 mg, 0.5 mmol), (R)—N-ethylpyrrolidin-3-amine (57 mg, 0.5 mmol), cesium carbonate (325 mg, 1 mmol) and DMF (3 mL) were combined in a sealed tube and hot block heated to 100° C. for 2 hours. The reaction mixture was then cooled to room temperature, the cesium salts were removed by filtration and the filtrate was purified by preparative HPLC to give the title compound. LCMS (ES+) 381 (M+H)+, RT 1.79 min (Analytical method AcHSSC18). $^1$H NMR (400 MHz, DMSO) δ 10.69 (s, 1H), 9.17 (s, 1H), 8.95 (s, 2H), 7.97 (s, 1H), 3.73-3.53 (m, 3H), 3.40-3.36 (m, 2H), 2.73 (s, 3H), 2.64-2.55 (m, 2H), 2.40 (s, 3H), 2.14-2.05 (m, 1H), 1.88-1.78 (m, 2H), 1.04 (dd, J=7.1, 7.1 Hz, 3H).

Example 137 2-((3S,4R)-3-(ethylamino)-4-fluoropyrrolidin-1-yl)-N-(8-fluoro-2-methylimidazo[1,2-a]pyridin-6-yl)pyrimidine-5-carboxamide and Example 138 2-((3R,4S)-3-(ethylamino)-4-fluoropyrrolidin-1-yl)-N-(8-fluoro-2-methylimidazo[1,2-a]pyridin-6-yl)pyrimidine-5-carboxamide

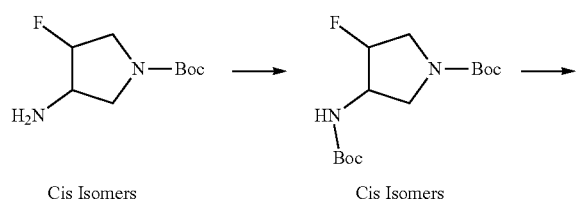

Cis Isomers

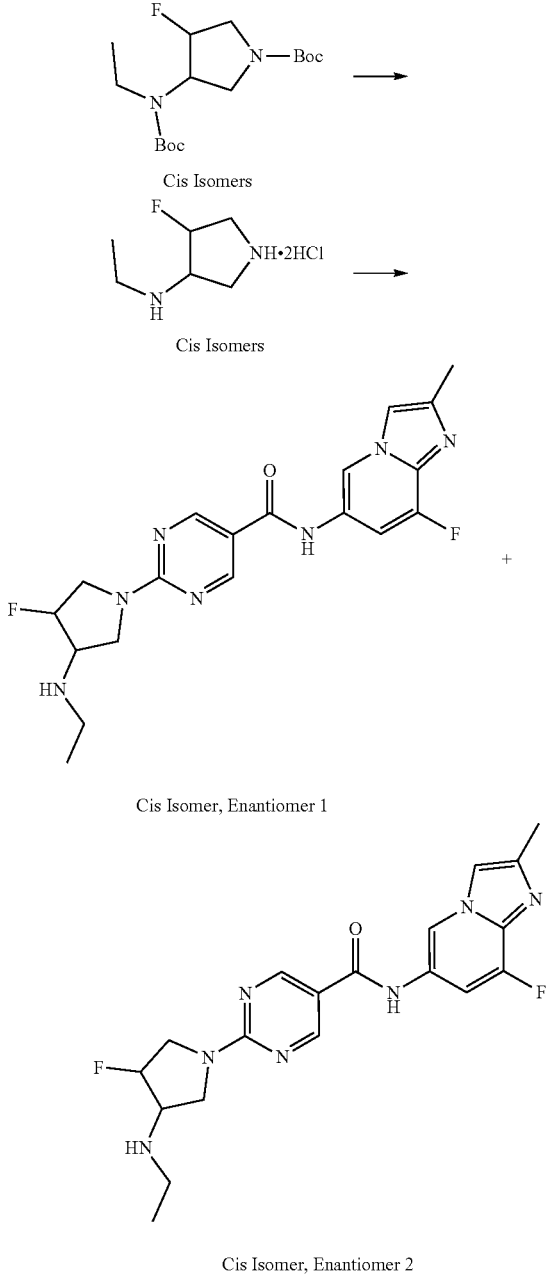

Cis-tert-butyl-3-amino-4-fluoropyrrolidine-1-carboxylate (2.17 g, 10.64 mmol), dichloromethane (40 mL), triethylamine (2 mL) and di-tert-butyl decarbonate (2.55 g, 11.7 mmol) were combined and stirred at room temperature for 18 hours. The reaction mixture was then evaporated to dryness to give tert-butyl (3R*,4S*)-3-((tert-butoxycarbonyl)amino)-4-fluoropyrrolidine-1-carboxylate, which was used crude in the next step without further purification.

tert-Butyl (3R*,4S*)-3-((tert-butoxycarbonyl)amino)-4-fluoropyrrolidine-1-carboxylate and DMF (20 mL) were combined at room temperature under a nitrogen atmosphere. NaH (60% in oil, 511 mg, 12.77 mmol) was added, followed by EtI (1 mL, 12.77 mmol). The reaction mixture was stirred for 3 days then diluted with EtOAc, washed with water (4×), brine (1×) and evaporated to dryness to give tert-butyl (3R*,4S*)-3-((tert-butoxycarbonyl)(ethyl)amino)-4-fluoropyrrolidine-1-carboxylate, which was used crude in the next step without further purification.

tert-Butyl (3R*,4S*)-3-((tert-butoxycarbonyl)(ethyl)amino)-4-fluoropyrrolidine-1-carboxylate, methanol (15 mL) and 4N HCl in dioxane (15 mL) were combined and stirred for 16 hours. The reaction mixture was then evaporated to dryness to give (3R*,4S*)—N-ethyl-4-fluoropyrrolidin-3-amine-2HCl, which was used crude in the next step without further purification.

(3R*,4S*)—N-ethyl-4-fluoropyrrolidin-3-amine-2HCl (133 mg, 0.65 mmol), 2-chloro-N-(8-fluoro-2-methylimidazo[1,2-a]pyridin-6-yl)pyrimidine-5-carboxamide (200 mg, 0.65 mmol), cesium carbonate (487 mg, 1.5 mmol) and DMF (3 mL) were combined in a sealed tube and hot block heated to 100° C. for 20 hours. The reaction mixture was then cooled to room temperature, the cesium salts were removed by filtration and the filtrate was purified by preparative HPLC followed by chiral preparative HPLC to give;

Cis Isomer, Enantiomer 1
2-((3S,4R)-3-(ethylamino)-4-fluoropyrrolidin-1-yl)-N-(8-fluoro-2-methylimidazo[1,2-a]pyridin-6-yl)pyrimidine-5-carboxamide. LCMS (ES+) 402.3 (M+H)+, RT 1.62 min (Analytical method AcHSSC18). ¹H NMR (400 MHz, DMSO) δ 10.25 (s, 1H), 9.06 (d, J=1.6 Hz, 1H), 8.92 (d, J=4.0 Hz, 2H), 7.92 (d, J=2.8 Hz, 1H), 7.29 (dd, J=1.7, 12.6 Hz, 1H), 5.30 (td, J=3.1, 54.4 Hz, 1H), 4.05-3.89 (m, 2H), 3.78 (ddt, J=3.0, 18.3, 20.3 Hz, 1H), 3.58-3.44 (m, 1H), 3.20 (dd, J=10.7, 10.7 Hz, 1H), 2.77-2.59 (m, 2H), 2.35 (s, 3H), 2.06-2.05 (m, 1H), 1.08 (dd, J=7.1, 7.1 Hz, 3H).

Cis Isomer, Enantiomer 2
2-((3R,4S)-3-(ethylamino)-4-fluoropyrrolidin-1-yl)-N-(8-fluoro-2-methylimidazo[1,2-a]pyridin-6-yl)pyrimidine-5-carboxamide. LCMS (ES+) 402 (M+H)+, RT 1.62 min (Analytical method AcHSSC18). ¹H NMR (400 MHz, DMSO) δ 10.25 (s, 1H), 9.06 (d, J=1.6 Hz, 1H), 8.92 (d, J=4.0 Hz, 2H), 7.92 (d, J=2.8 Hz, 1H), 7.29 (dd, J=1.7, 12.6 Hz, 1H), 5.30 (td, J=3.1, 54.4 Hz, 1H), 4.05-3.89 (m, 2H), 3.78 (ddt, J=3.0, 18.3, 20.3 Hz, 1H), 3.58-3.44 (m, 1H), 3.20 (dd, J=10.7, 10.7 Hz, 1H), 2.77-2.59 (m, 2H), 2.35 (s, 3H), 2.06-2.05 (m, 1H), 1.08 (dd, J=7.1, 7.1 Hz, 3H).

Further analogues were prepared using the same chemistry.

Examples 140-141

Examples 140-141 were conducted in accordance with the following:

Unless otherwise noted, reagents and solvents were used as received from commercial suppliers. All non-aqueous reactions were carried out under an atmosphere of dry nitrogen (unless otherwise noted). Proton nuclear magnetic resonance spectra were obtained on a Bruker AVANCE 300 spectrometer at 300 MHz, on a Bruker AVANCE 500 spectrometer at 500 MHz, or on a Bruker ASCEND 500 spectrometer at 500 MHz. Spectra are given in ppm (δ) and coupling constants, J values, are reported in hertz (Hz). Tetramethylsilane was used as an internal standard for proton nuclear magnetic resonance. Mass spectra and LCMS analyses were obtained using a Waters Acquity SQD (ESI, UP-LCMS) or a Shimadzu 2020 UP-LCMS instrument. UPLC analyses were obtained using an Acquity UPLC BEH C18 column, 1.7 μm (2.1×75 mm), eluted according to solvent gradient Method 1. HPLC analyses were obtained using a Phenomenex C18 Kinetex column, 5 μm (4.6×150 mm), eluted according to solvent gradient Method 2. Detection was by UV at 254 and 215 nm. UPLC-MS data were obtained using standard methods: (a) low pH, Waters CSHC18 column (1.7 μm, 2.1×50 mm), column temperature of 55° C., sample concentration of 0.5 mM in DMSO, ESI mass detection, UV DAD detection for the wavelength range 210-400 nm, and elution according to solvent gradient Method 3, or (b) high pH, Waters UPLC Xbridge BEH C18 column (2.5 μm, 2.1×50 mm), column temperature of 45° C., sample concentration of 0.5 mM in DMSO, ESI mass detection, UV DAD detection for the wavelength range 210-400 nm, and elution according to solvent gradient Method 4.

Method 1

| Time (min) | Flow (mL/min) | % A | % B |
| --- | --- | --- | --- |
| 0.0 | 0.5 | 95 | 5 |
| 6.0 | 0.5 | 0 | 100 |

| Ex. | Structure | Amine | Analytical data |
| --- | --- | --- | --- |
| 139 | Cis Isomer, Enantiomer 1 + Enantiomer 2 | (3R*,4S*)-N-methyl-4-fluoropyrrolidin-3-amine•2HCl | LCMS (ES+) 388 (M + H)+, RT 1.59 min (Analytical method AcHSSC18) ¹H NMR (400 MHz, DMSO) δ 10.24 (s, 1H), 9.06 (d, J = 1.5 Hz, 1H), 8.93-8.91 (m, 2H), 7.92 (d, J = 2.8 Hz, 1H), 7.29 (dd, J = 1.8, 12.6 Hz, 1H, 5.35 (td, J = 3.0, 54.2 Hz, 1H), 4.05-3.71 (m, 3H), 3.34 (s, 2H), 3.36-3.16 (m, 2H), 2.41 (s, 3H), 2.36 (s, 3H). |

-continued

| Time (min) | Flow (mL/min) | % A | % B |
|---|---|---|---|
| 8.0 | 0.5 | 0 | 100 |
| 9.0 | 0.5 | 95 | 5 |

A=Water with 0.1% v/v Trifluoroacetic Acid
B=Acetonitrile with 0.1% v/v Trifluoroacetic Acid
Method 2

| Time (min) | Flow (mL/min) | % A | % B |
|---|---|---|---|
| 0.01 | 2.0 | 95 | 5 |
| 10.0 | 2.0 | 0 | 100 |
| 13.0 | 2.0 | 0 | 100 |
| 14.0 | 2.0 | 95 | 5 |

A=Water with 0.1% v/v Trifluoroacetic Acid
B=Acetonitrile with 0.1% v/v Trifluoroacetic Acid
Method 3

| Time (min) | Flow (mL/min) | % A | % B |
|---|---|---|---|
| 0.0 | 1.0 | 95 | 5 |
| 2.0 | 1.0 | 0 | 100 |
| 2.5 | 1.0 | 0 | 100 |
| 2.6 | 1.0 | 95 | 5 |
| 3.0 | 1.0 | 95 | 5 |

A=Water with 0.02% v/v Formic Acid
B=Acetonitrile with 0.02% v/v Formic Acid
Method 4

| Time (min) | Flow (mL/min) | % A | % B |
|---|---|---|---|
| 0.0 | 1.0 | 95 | 5 |
| 0.1 | 1.0 | 95 | 5 |
| 2.1 | 1.0 | 5 | 95 |
| 2.3 | 1.0 | 5 | 95 |
| 2.35 | 1.0 | 95 | 5 |
| 2.8 | 1.0 | 95 | 5 |

A=1 mM Ammonium Formate in Water
Modified to pH 10 With NH$_4$OH
B=95:5 Acetonitrile/Water Example 140 (R)—N-(8-Fluoro-2-methylimidazo[1,2-a]pyridin-6-yl)-6-(3-(methyl-amino)pyrrolidin-1-yl)pyridazine-3-carboxamide

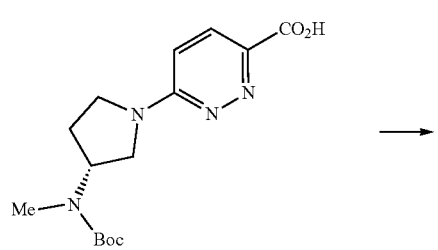

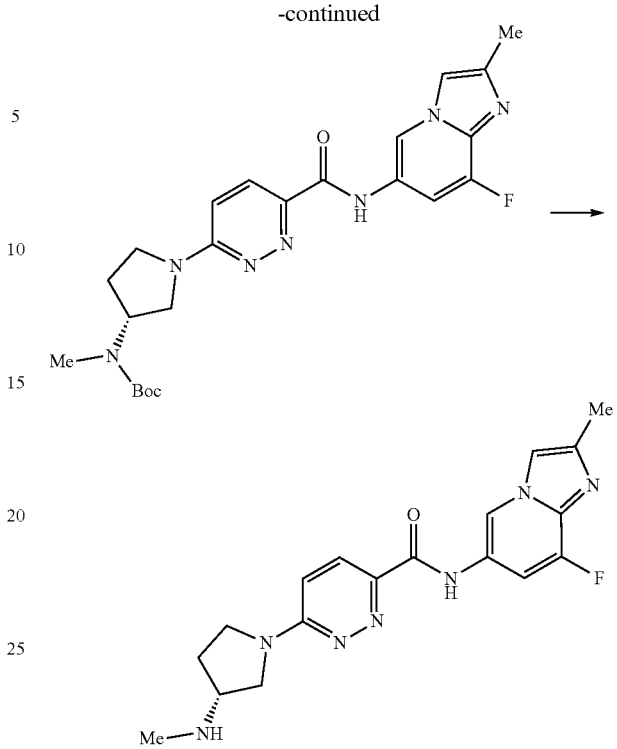

To a solution of (R)-6-(3-(((tert-butoxycarbonyl)(methyl)amino)pyrrolidin-1-yl)pyridazine-3-carboxylic acid (0.050 g, 0.16 mmol) and 8-fluoro-2-methylimidazo[1,2-a]pyridin-6-amine (0.026 g, 0.16 mmol) in N,N-dimethylformamide (5.0 mL) was added N,N-diisopropylethylamine (0.13 mL, 0.78 mmol), followed by 1-[bis(dimethyl-amino)methyl-ene]-1H-1,2,3-triazolo[4,5-b]pyridinium 3-oxide hexafluorophosphate (HATU, 0.071 g, 0.19 mmol). The mixture was stirred at room temperature for 16 h. After this time, water (30 mL) was added, followed by saturated aqueous sodium bicarbonate (30 mL). The resulting suspension was extracted with ethyl acetate (3×30 mL), and the combined organic layers were washed with brine (2×30 mL), dried over sodium sulfate, filtered, and concentrated under reduced pressure. The residue obtained was purified by chromatography (silica gel; dichloromethane to 95:5 dichloro-methane/methanol; gradient elution) to afford tert-butyl (R)-(1-(6-((8-fluoro-2-methylimidazo[1,2-a]pyridin-6-yl)carbamoyl)pyridazin-3-yl)pyrrolidin-3-yl)(methyl)carbamate. $^1$H NMR (500 MHz, CDCl$_3$) δ 9.71 (s, 1H), 9.04 (d, J=1.5 Hz, 1H), 8.06 (d, J=9.5 Hz, 1H), 7.43 (d, J=2.5 Hz, 1H), 6.83 (dd, J=11.0 Hz, 1.5 Hz, 1H), 6.77 (d, J=9.5 Hz, 1H), 5.00-4.80 (m, 1H), 4.06-3.73 (m, 2H), 3.72-3.42 (m, 2H), 2.86 (s, 3H), 2.48 (s, 3H), 2.23-2.17 (m, 2H), 1.50 (s, 9H); MS (ESI) m/z 470 [M+H]$^+$.

To a solution of tert-butyl (R)-(1-(6-((8-fluoro-2-methyl-imidazo[1,2-a]pyridin-6-yl)carbamoyl)pyridazin-3-yl)pyrrolidin-3-yl)(methyl)carbamate (0.061 g, 0.13 mmol) in dichloro-methane (4.5 mL) was added trifluoroacetic acid (0.50 mL, 6.5 mmol), and the mixture was stirred at room temperature for 90 min. After this time, the volatiles were removed under reduced pressure, and the residue obtained was taken up in 80:18:2 dichloro-methane/methanol/ammonium hydroxide and concentrated again (2×25 mL). The crude product was purified by chromatography (silica gel; dichloromethane to 80:18:2 dichloromethane/methanol/ammonium hydroxide; gradient elution). The product obtained was combined with another batch and triturated with 90:10 heptane/dichloromethane to afford (R)—N-(8-fluoro-2-methylimidazo[1,2-a]pyridin-6-yl)-6-(3-(methylamino)pyrrolidin-1-yl)pyridazine-3-carboxamide. mp 198-200° C., dec; ¹H NMR (500 MHz, DMSO-d₆) δ 10.89 (s, 1H), 9.21 (d, J=1.5 Hz, 1H), 7.92 (d, J=9.4 Hz, 1H), 7.90 (d, J=2.5 Hz, 1H), 7.60 (dd, J=13.0, 1.5 Hz, 1H), 7.02 (d, J=9.4 Hz, 1H), 3.87-3.33 (m, 5H), 2.34 (s, 3H), 2.32 (s, 3H), 2.17-2.08 (m, 1H), 1.94-1.85 (m, 1H); MS (ESI) m/z 370 [M+H]⁺; HPLC: Method 2, $t_R$=3.00 min, >99% (AUC) at 254 and 215 nm.

Example 141 (R)—N-(2,8-Dimethylimidazo[1,2-a]pyrazin-6-yl)-5-(3-(methylamino)-pyrrolidin-1-yl)pyrimidine-2-carboxamide

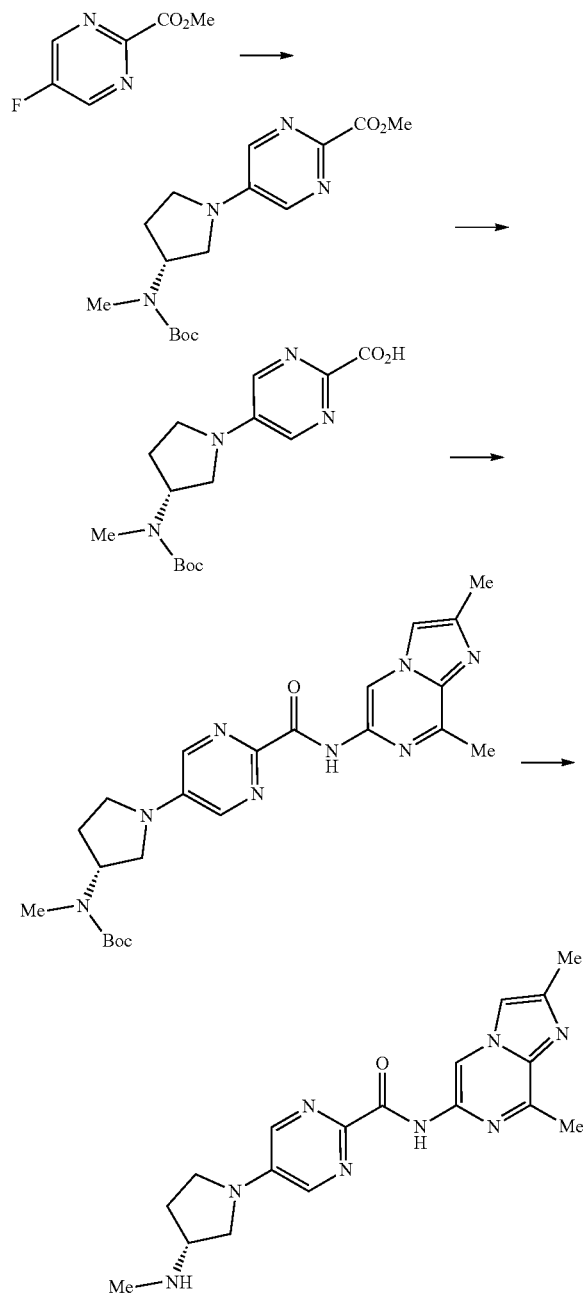

Pyridine (0.031 mL, 0.39 mmol) and tert-butyl (R)-methyl(pyrrolidin-3-yl)carbamate (0.128 g, 0.641 mmol) were added to a solution of methyl 5-fluoropyrimidine-2-carboxylate (0.050 g, 0.32 mmol) in dimethyl sulfoxide (0.4 mL), and the mixture was stirred at room temperature for 1 h and at 80° C. for 18 h. After this time, the mixture was cooled, water (8 mL) was added, and the mixture was added to saturated aqueous sodium bicarbonate (20 mL) and extracted with dichloromethane (3×20 mL). The combined organic layers were dried over sodium sulfate, filtered, and the filtrate was concentrated in vacuo. The residue obtained was purified by chromatography (silica gel; dichloromethane to 95:5 dichloromethane/methanol; gradient elution) to afford methyl (R)-5-(3-((tert-butoxycarbonyl)(methyl)amino)pyrrolidin-1-yl)pyrimidine-2-carboxylate. ¹H NMR (500 MHz, CDCl₃) δ 8.14 (s, 2H), 4.96 (br s, 1H), 4.02 (s, 3H), 3.64-3.59 (m, 2H), 3.46-3.41 (m, 1H), 3.34-3.30 (m, 1H), 2.84 (s, 3H), 2.31-2.16 (m, 2H), 1.49 (s, 9H); MS (ESI) m/z 337 [M+H]⁺.

A solution of lithium hydroxide monohydrate (0.013 g, 0.32 mmol) in water (6.9 mL) was added to a solution of methyl (R)-5-(3-((tert-butoxycarbonyl)(methyl)amino)pyrrolidin-1-yl)pyrimidine-2-carboxylate (0.107 g, 0.318 mmol) in tetrahydrofuran (6.9 mL), and the mixture was stirred at room temperature for 16 h. After this time, the volatiles were removed in vacuo, and water (5 mL) was added. The mixture was washed with dichloromethane (10 mL). The pH of the aqueous layer was adjusted to 3 with 2.0 N hydrochloric acid, and the solid that formed was collected by filtration, washed with water and dried in vacuo to afford (R)-5-(3-((tert-butoxycarbonyl)(methyl)amino)-pyrrolidin-1-yl)pyrimidine-2-carboxylic acid. The aqueous layer was extracted with 3:1 chloroform/2-propanol (3×20 mL), and the combined organic layers were dried over sodium sulfate, filtered, and the filtrate was concentrated in vacuo to afford a second crop of (R)-5-(3-((tert-butoxycarbonyl)(methyl)-amino)pyrrolidin-1-yl)pyrimidine-2-carboxylic acid. ¹H NMR (500 MHz, DMSO-d₆) δ 12.63 (br s, 1H), 8.20 (s, 2H), 4.80 (br s, 1H), 3.61-3.53 (m, 2H), 3.40-3.35 (m, 2H), 2.75 (s, 3H), 2.17-2.07 (m, 2H), 1.42 (s, 9H); MS (ESI) m/z 323 [M+H]⁺.

N,N-Diisopropylethylamine (0.203 mL, 1.17 mmol) and 2-(1H-benzo[d][1,2,3]triazol-1-yl)-1,1,3,3-tetramethyluronium hexafluorophosphate (HBTU, 0.166 g, 0.437 mmol) were added to a solution of (R)-5-(3-((tert-butoxycarbonyl)(methyl)amino)-pyrrolidin-1-yl)pyrimidine-2-carboxylic acid (0.094 g, 0.29 mmol) and 2,8-dimethylimidazo[1,2-a]pyrazin-6-amine (0.047 g, 0.29 mmol) in N,N-dimethylformamide (2.4 mL), and the mixture was stirred at room temperature for 16 h. After this time, water (20 mL) was added. The solid that formed was collected by filtration, washed with water (10 mL) and dried in vacuo to afford tert-butyl (R)-(1-(2-((2,8-dimethylimidazo[1,2-a]pyrazin-6-yl)carbamoyl)pyrimidin-5-yl)pyrrolidin-3-yl)(methyl)carbamate. ¹H NMR (500 MHz, DMSO-d₆) δ 9.98 (s, 1H), 9.17 (s, 1H), 8.29 (s, 2H), 8.01 (s, 1H), 4.82 (br s, 1H), 3.65-3.57 (m, 2H), 3.44-3.28 (m, 2H), 2.77 (s, 3H), 2.70 (s, 3H), 2.39 (s, 3H), 2.19-2.11 (m, 2H), 1.43 (s, 9H); MS (ESI) m/z 467 [M+H]⁺.

Trifluoroacetic acid (0.348 mL, 4.54 mmol) was added to a solution of tert-butyl (R)-(1-(2-((2,8-dimethylimidazo[1,2-a]pyrazin-6-yl)carbamoyl)pyrimidin-5-yl)pyrrolidin-3-yl)(methyl)carbamate (0.106 g, 0.227 mmol) in dichloromethane (4.7 mL), and the mixture was stirred at room temperature for 2 h. After this time, the solvent was removed in vacuo, dichloromethane (40 mL) was added, and the mixture was concentrated to dryness again. The residue obtained was dissolved in dichloromethane (40 mL) and washed with saturated aqueous sodium bicarbonate (50 mL). The organic layer was dried over sodium sulfate, filtered, and the filtrate was concentrated in vacuo. The crude product was purified by chromatography (silica gel; dichloromethane to 85:14:1 dichloromethane/methanol/ammonium hydroxide; gradient elution) to afford (R)—N-(2,8-dimethylimidazo[1,2-a]pyrazin-6-yl)-5-(3-(methylamino)pyrrolidin-1-yl)pyrimidine-2-carboxamide. The product was dissolved in dichloromethane (4 mL), the solution was added to hexanes (100 mL), and the suspension was concentrated in vacuo to afford (R)—N-(2,8-dimethylimidazo[1,2-a]pyrazin-6-yl)-5-(3-(methylamino)pyrrolidin-1-yl)pyrimidine-2-carboxamide. mp 266-268° C.; $^1$H NMR (500 MHz, DMSO-d$_6$) δ 9.96 (br s, 1H), 9.17 (s, 1H), 8.24 (s, 2H), 8.01 (s, 1H), 3.56-3.40 (m, 3H), 3.23-3.20 (m, 1H), 2.70 (s, 3H), 2.39 (s, 3H), 2.32 (s, 3H), 2.14-1.84 (m, 3H); MS (ESI) m/z 367 [M+H]$^+$; UPLC: Method 1, t$_R$=2.69 min, 98.7% (AUC) at 254 nm and >99% (AUC) at 215 nm; UPLC-MS: Method 4, t$_R$=0.83 min, >99% (AUC), MS (ESI) m/z 367 [M+H]$^+$.

Example 142: (S)—N-(8-fluoro-2-methylimidazo[1,2-a]pyridin-6-yl)-5-(3-(piperidin-2-yl)azetidin-1-yl)pyrazine-2-carboxamide 2-(azetidin-3-yl)-11-benzylpiperidine

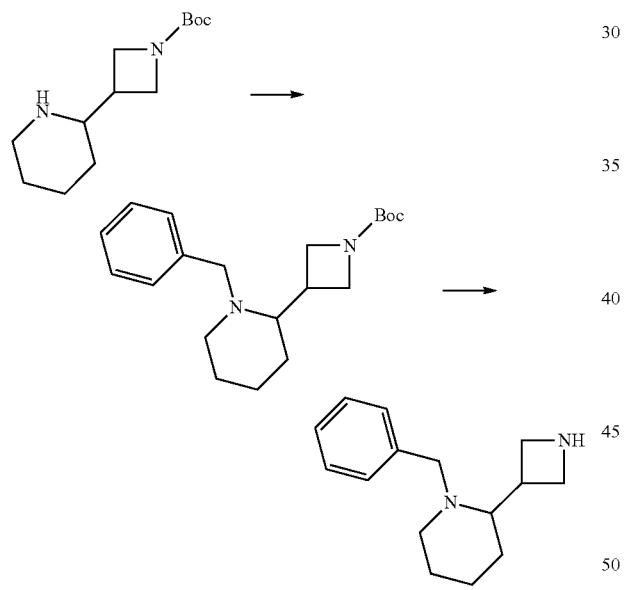

To a solution of tert-butyl 3-(piperidin-2-yl)azetidine-1-carboxylate (500 mg, 2.08 mmol) in DCM (7 mL) then benzyl bromide added (0.37 mL, 3.12 mmol) followed by sodium carbonate saturated solution (7 mL) and the resulting mixture was stirred at rt for 19 h. The mixture was then partitioned between DCM and water. The aqueous phase was reextracted (×1) and the combined organic phases were passed through a phase separator paper and evaporated to dryness. The crude was purified using silica chromatography, elution gradient 0-100% [EtOAc+5% NH$_3$ in MeOH]/cyclohexane to give tert-butyl 3-(1-benzylpiperidin-2-yl)azetidine-1-carboxylate.

tert-butyl 3-(1-benzylpiperidin-2-yl)azetidine-1-carboxylate (540 mg, 1.63 mmol) was dissolved in a mixture of DCM (5 mL) and TFA (5 mL) and the resulting mixture was stirred at rt for 18 h. The mixture was evaporated to dryness to give an oil which was partitioned between DCM and aqueous sodium carbonate. The aqueous was extracted with DCM (×1) and the combined organic phases were passed through a phase separator paper and evaporated to dryness to afford 2-(azetidin-3-yl)-1-benzylpiperidine.

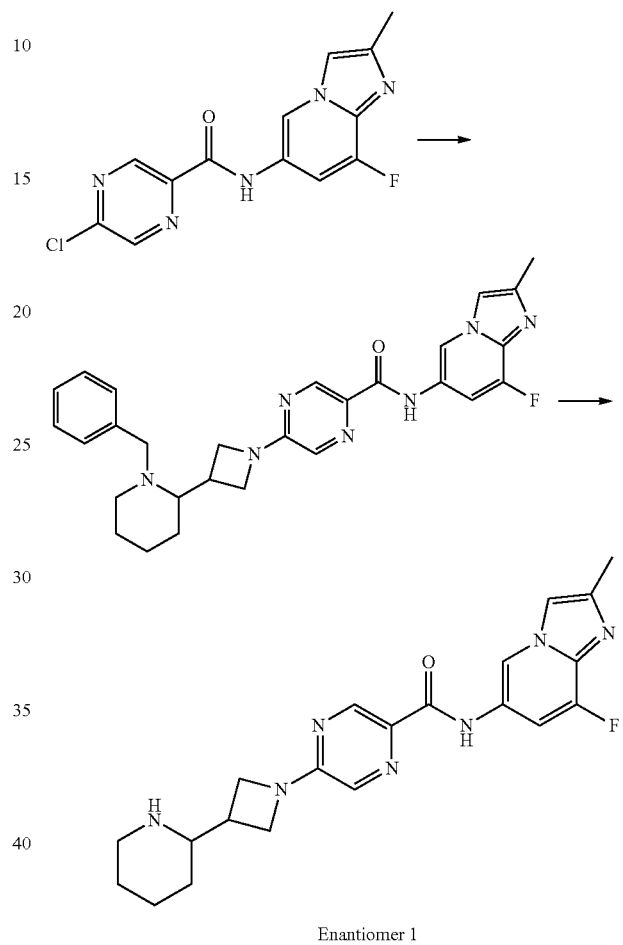

Enantiomer 1

Following method D for 22 h and the following quantities: 5-chloro-N-(8-fluoro-2-methylimidazo[1,2-a]pyridin-6-yl)pyrazine-2-carboxamide (119 mg, 0.39 mmol), 2-(azetidin-3-yl)-1-benzylpiperidine (90 mg, 0.39 mmol), cesium carbonate (191 mg, 0.59 mmol) and DMF (2 mL). To the reaction mixture was then added LiCl aqueous solution (4%), which was extracted with DCM (×2). The organic was then dried over a phase separator paper and evaporated to dryness. The crude was purified using silica chromatography, elution gradient 25-100% EtOAc/cyclohexane then 0-1% NH$_3$ in MeOH (7N)/EtOAc. The material was then purified by chiral SFC to afford 5-(3-(1-benzylpiperidin-2-yl)azetidin-1-yl)-N-(8-fluoro-2-methylimidazo[1,2-a]pyridin-6-yl)pyrazine-2-carboxamide (Enantiomer 1).

Enantiomer 1, 5-(3-(1-benzylpiperidin-2-yl)azetidin-1-yl)-N-(8-fluoro-2-methylimidazo[1,2-a]pyridin-6-yl)pyrazine-2-carboxamide (34 mg, 0.068 mmol) was dissolved in MeOH (1 mL) and degassed for 20 min by sparging N$_2$ gas. Pd/C (10%, 5 mg) was then added followed by 1-methyl-1,4-cyclohexadiene (76 uL, 0.68 mmol) and the resulting mixture was heated to 60° C. for 3 h. More 1-methyl-1,4-cyclohexadiene (76 uL, 0.68 mmol) was added and left overnight at 60° C. Additional 1-methyl-1,4-cyclohexadiene (76 uL, 0.68 mmol) and Pd/C (10%, 5 mg) were added and left again overnight at 60° C. after which full conversion was reached. The mixture was filtered over celite, washed with copious MeOH and evaporated to give a crude residue which was purified by reverse phase HPLC to afford (S)—N-(8-fluoro-2-methylimidazo[1,2-a]pyridin-6-yl)-5-(3-(piperidin-2-yl)azetidin-1-yl)pyrazine-2-carboxamide. LCMS (ES+) 410 (M+H)+, RT 1.81 min (Analytical method AcHSSC18); $^1$H NMR (400 MHz, DMSO) δ 10.44 (s, 1H), 9.19 (d, J=1.5 Hz, 1H), 8.73 (d, J=1.3 Hz, 1H), 7.90 (d, J=2.8 Hz, 1H), 7.86 (d, J=1.3 Hz, 1H), 7.56 (dd, J=1.6, 13.1 Hz, 1H), 4.26-4.17 (m, 2H), 4.10 (dd, J=5.6, 9.1 Hz, 1H), 4.00 (dd, J=5.7, 9.0 Hz, 1H), 3.06 (d, J=11.0 Hz, 1H), 2.90-2.85 (m, 1H), 2.80-2.74 (m, 1H), 2.69-2.60 (m, 1H), 2.35 (s, 3H), 1.79-1.78 (m, 1H), 1.71-1.68 (m, 1H), 1.61-1.59 (m, 1H), 1.42-1.34 (m, 2H), 1.13-1.05 (m, 1H).

Example 143 5-[3-(cyclopropylamino)pyrrolidin-1-yl]-N-(2-methylpyrazolo[1,5-a]pyridin-5-yl)pyrazine-2-carboxamide (Enantiomer 1+Enantiomer 2)

2-Methylpyrazolo[1,5-a]pyridin-5-amine

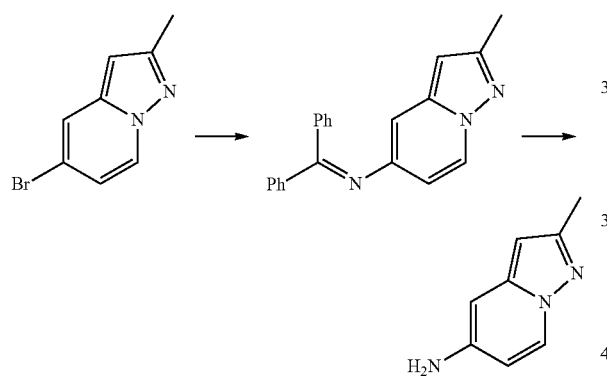

5-bromo-2-methylpyrazolo[1,5-a]pyridine (120 mg, 0.569 mmol, 1 equiv), benzophenone imine (0.095 mL, 0.569 mmol, 1 equiv), rac-BINAP (35 mg, 0.0569 mmol, 0.1 equiv), Pd(OAc)$_2$ (13 mg, 0.0569 mmol, 0.1 equiv) and cesium carbonate (278 mg, 0.853 mmol, 1.5 equiv) were suspended in THF and the reaction mixture purged with N$_2$ for 15 minutes. The tube was sealed and the reaction mixture was stirred at 100° C. for 16 hours. The mixture was allowed to cool to room temperature and the mixture was diluted with water and washed with EtOAc (×3). The combined organics were washed with brine, dried and the solvent removed in vacuo. The crude was purified using silica chromatography, elution gradient 5-60% EtOAc in cyclohexane. Fractions containing the desired compound were combined and the solvent removed in vacuo to give N-(2-methylpyrazolo[1,5-a]pyridin-5-yl)-1,1-diphenylmethanimine. LCMS (ES+) 312 (M+H)+

2-Methylpyrazolo[1,5-a]pyridin-5-amine (185 mg, 0.529 mmol, 1 equiv) was dissolved in MeOH (2.0 mL) and 4M HCl in dioxane (1.3 mL, 5.29 mmol, 10 equiv) was added. The reaction mixture was stirred at room temperature for 16 hours. The mixture was concentrated in vacuo and the residue was applied to a 2 g SCX cartridge, eluting with 2 column volumes methanol, then 3 column volumes 2 M methanolic ammonia. The ammonia fraction was concentrated in vacuo to give 2-Methylpyrazolo[1,5-a]pyridin-5-amine. LCMS (ES+) 148 (M+H)+

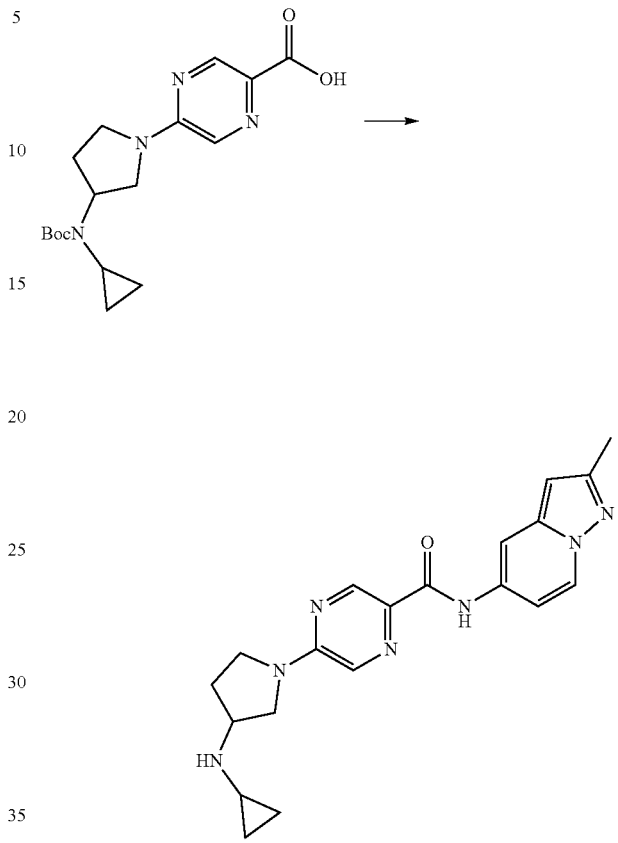

Following Method H from 5-(3-((tert-butoxycarbonyl) (cyclopropyl)amino)pyrrolidin-1-yl)pyrazine-2-carboxylic acid (188 mg, 0.530 mmol, 1 equiv) and 2-methylpyrazolo [1,5-a]pyridin-5-amine (78 mg, 0.530 mmol, 1 equiv) in DMF (2.0 mL). The reaction mixture was diluted with water and the solid filtered and washed with 1:2 MeCN/H$_2$O to give tert-butyl cyclopropyl(1-(5-((2-methylpyrazolo[1,5-a] pyridin-5-yl)carbamoyl)pyrazin-2-yl)pyrrolidin-3-yl)carbamate which was taken forward without further purification to the next step.

Following Method E from tert-butyl cyclopropyl(1-(5-((2-methylpyrazolo[1,5-a]pyridin-5-yl)carbamoyl)pyrazin-2-yl)pyrrolidin-3-yl)carbamate (71 mg, 0.149 mmol). The reaction mixture was concentrated in vacuo and the residue applied to a 2 g SCX cartridge, eluting with 2 column volumes methanol, then 3 column volumes 2 M methanolic ammonia. The ammonia fraction was concentrated in vacuo to give crude 5-[3-(cyclopropylamino)pyrrolidin-1-yl]-N-(2-methylpyrazolo[1,5-a]pyridin-5-yl)pyrazine-2-carboxamide which was purified by HPLC to give 5-[3-(cyclopropylamino)pyrrolidin-1-yl]-N-(2-methylpyrazolo[1,5-a] pyridin-5-yl)pyrazine-2-carboxamide (Enantiomer 1+Enantiomer 2). LCMS (ES+) 378 (M+H)+, RT 4.32 min (Analytical method BicarbBEHC18) $^1$H NMR (400 MHz, DMSO) δ 10.22 (s, 1H), 8.56 (s, 1H), 8.29 (d, J=7.6 Hz, 1H), 8.03 (s, 1H), 7.78 (s, 1H), 7.07 (dd, J=2.0, 7.6 Hz, 1H), 6.08 (s, 1H), 3.56-3.25 (m, 6H), 2.16 (s, 3H), 1.98-1.93 (m, 2H), 1.79 (s, 1H), 0.26 (d, J=6.6 Hz, 2H), 0.15-0.06 (m, 2H).

Example 144 Tert-butyl 3-(6-((2-methylimidazo[1,2-a]pyridin-6-yl)carbamoyl)pyridazin-3-yl)-3,8-diazabicyclo[3.2.1]octane-8-carboxylate

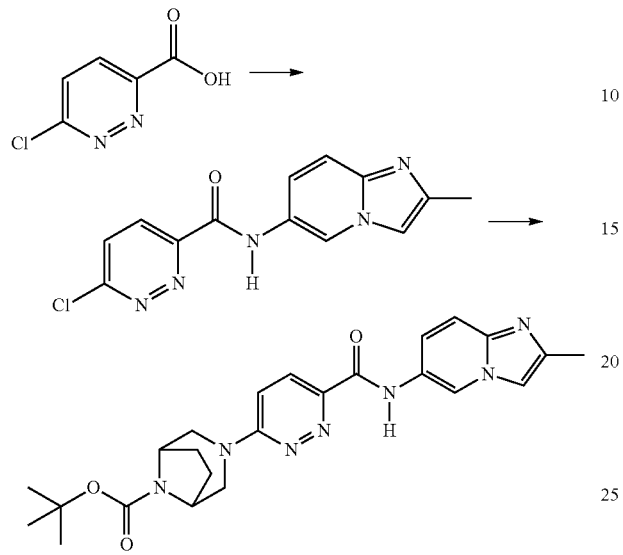

6-chloropyridazine-3-carboxylic acid (270 mg, 1.7 mmol), 2-methylimidazo[1,2-a]pyridin-6-amine (250 mg, 1.7 mmol), HBTU (683 mg, 1.8 mmol) and triethylamine (1 mL, 7.2 mmol) were dissolved in DMF (6 mL) and stirred at RT for 24 h. The solution, containing crude 6-chloro-N-(2-methylimidazo[1,2-a]pyridin-6-yl)pyridazine-3-carboxamide, was used without further purification. 6-chloro-N-(2-methylimidazo[1,2-a]pyridin-6-yl)pyridazine-3-carboxamide (1 mL of solution from previous step, ~0.24 mmol), tert-butyl 3,8-diazabicyclo[3.2.1]octane-8-carboxylate (64 mg, 0.3 mmol) and cesium carbonate (98 mg, 0.3 mmol) were stirred in DMF (1 mL) at 110° C. for 1.5 h. After cooling to RT, the solids were removed by filtration and the filtrate purified by preparative HPLC to give tert-butyl 3-(6-((2-methylimidazo[1,2-a]pyridin-6-yl)carbamoyl)pyridazin-3-yl)-3,8-diazabicyclo[3.2.1]octane-8-carboxylate. LCMS (ES+) 464 (M+H)+, RT 2.75 min (Analytical method 10 cm_Formic_AQ). $^1$H NMR (400 MHz, DMSO) δ 10.91 (s, 1H), 9.32 (s, 1H), 8.04-8.00 (m, 1H), 7.80 (s, 1H), 7.63 (dd, J=1.8, 9.6 Hz, 1H), 7.47 (d, J=9.6 Hz, 1H), 7.41 (d, J=9.6 Hz, 1H), 4.36 (s, 2H), 4.28 (d, J=12.4 Hz, 2H), 3.21 (d, J=12.0 Hz, 2H), 2.37 (s, 3H), 1.99-1.94 (m, 2H), 1.72 (d, J=4.6 Hz, 2H), 1.50 (s, 9H).

COMPARATIVE EXAMPLES

Comparative Example 145 N-(2,8-dimethylimidazo[1,2-a]pyrazin-6-yl)-2-methoxy-6-(piperazin-1-yl)nicotinamide

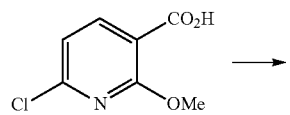

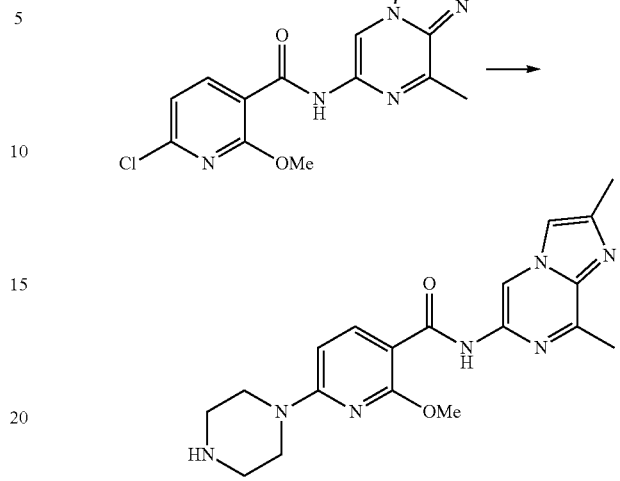

6-Chloro-2-methoxynicotinic acid (188 mg, 1 mmol), 2,8-dimethylimidazo[1,2-a]pyrazin-6-amine (162 mg, 1 mmol), HBTU (379 mg, 1 mmol), triethylamine (1 mL) and DMF (4 mL) were combined and stirred for 17 hours. Reaction was diluted with EtOAc, washed with water (2×) and evaporated to dryness to give 6-chloro-N-(2,8-dimethylimidazo[1,2-a]pyrazin-6-yl)-2-methoxynicotinamide, which was used crude in next step.

6-Chloro-N-(2,8-dimethylimidazo[1,2-a]pyrazin-6-yl)-2-methoxynicotinamide (70 mg, 0.21 mmol), piperazine (45 mg, 0.52 mmol), triethylamine (1 mL) and dioxane (6 mL) were combined in a sealed tube and heated to 100° C. for 17 hours. Reaction mixture was cooled to room temperature, evaporated to dryness and purified by prep HPLC to give the title compound. LCMS (ES+) 382 (M+H)+, RT 2.07 min (Analytical method AcHSSC18). $^1$H NMR (400 MHz, DMSO) δ 9.86 (s, 1H), 9.19 (s, 1H), 8.13 (d, J=8.8 Hz, 1H), 7.97 (s, 1H), 6.56 (d, J=8.8 Hz, 1H), 4.08 (s, 3H), 3.59 (dd, J=5.0, 5.0 Hz, 4H), 2.80 (dd, J=5.0, 5.0 Hz, 4H), 2.70 (s, 3H), 2.39 (s, 3H).

Comparative Example 146 N-(8-Fluoro-2-methylimidazo[1,2-a]pyridin-6-yl)-2-methoxy-6-(piperazin-1-yl)nicotinamide

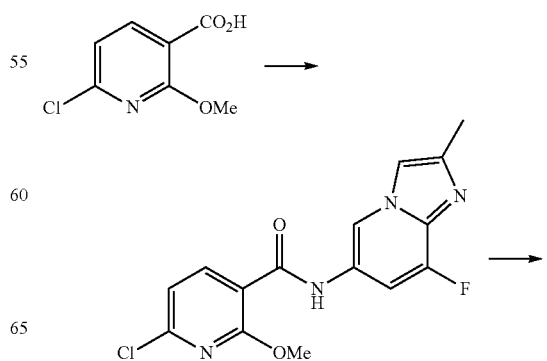

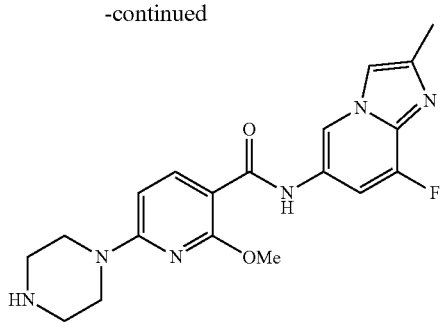

6-Chloro-2-methoxynicotinic acid (188 mg, 1 mmol), 8-fluoro-2-methylimidazo[1,2-a]pyridin-6-amine-2HCl (238 mg, 1 mmol), HBTU (379 mg, 1 mmol), triethylamine (1 mL) and DMF (4 mL) were combined and stirred for 17 hours. Reaction was diluted with EtOAc, washed with water (2×) and evaporated to dryness to give 6-chloro-N-(8-fluoro-2-methylimidazo[1,2-a]pyridin-6-yl)-2-methoxynicotinamide, which was used crude in next step.

Crude product from previous step, piperazine (86 mg, 1 mmol), triethylamine (1 mL) and dioxane (10 mL) were combined in a sealed tube and heated to 100° C. for 17 hours. Reaction mixture was cooled to room temperature, evaporated to dryness and purified by prep HPLC to give the title compound. LCMS (ES+) 385 (M+H)+, RT 1.89 min (Analytical method AcHSSC18). ¹H NMR (400 MHz, DMSO) δ 9.68 (s, 1H), 9.11 (d, J=1.6 Hz, 1H), 8.03 (d, J=8.7 Hz, 1H), 7.88 (d, J=2.8 Hz, 1H), 7.37 (dd, J=1.6, 12.9 Hz, 1H), 6.50 (d, J=8.8 Hz, 1H), 4.03 (s, 3H), 3.57 (dd, J=5.0, 5.0 Hz, 4H), 2.79 (dd, J=5.0, 5.0 Hz, 4H), 2.35 (s, 3H).

Comparative Example 147 N-(2-Methylimidazo[1,2-a]pyridin-6-yl)-6-(4-methylpiperazin-1-yl)nicotinamide

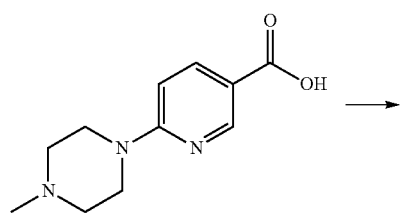

6-(4-Methylpiperazin-1-yl)pyridine-3-carboxylic acid (50 mg, 0.23 mmol), 2-methylimidazo[1,2-a]pyridin-6-amine (33 mg, 0.23 mmol), HBTU (95 mg, 0.25 mmol), DMF (1 mL) and triethylamine (0.25 mL) were combined and stirred at room temperature for 18 hours. Reaction mixture was then purified by prep HPLC to give the title compound. LCMS (ES+) 351 (M+H)+, RT 2.89 min (Analytical method BicarbBEHC18). ¹H NMR (400 MHz, DMSO) δ 10.04 (s, 1H), 9.19 (s, 1H), 8.76 (d, J=2.3 Hz, 1H), 8.10 (dd, J=2.6, 9.1 Hz, 1H), 7.74 (s, 1H), 7.44 (d, J=9.5 Hz, 1H), 7.35 (dd, J=2.0, 9.5 Hz, 1H), 6.94 (d, J=9.0 Hz, 1H), 3.65 (dd, J=5.0, 5.0 Hz, 4H), 2.41 (dd, J=5.1, 5.1 Hz, 4H), 2.33 (s, 3H), 2.23 (s, 3H).

Examples 148 and 149: (R)-5-(3-(((Cyclopropylamino)methyl)pyrrolidin-1-yl)-N-(8-fluoro-2-methylimidazo[1,2-a]pyridin-6-yl)pyrazine-2-carboxamide (S)-5-(3-(((Cyclopropylamino)methyl)pyrrolidin-1-yl)-N-(8-fluoro-2-methylimidazo[1,2-a]pyridin-6-yl)pyrazine-2-carboxamide

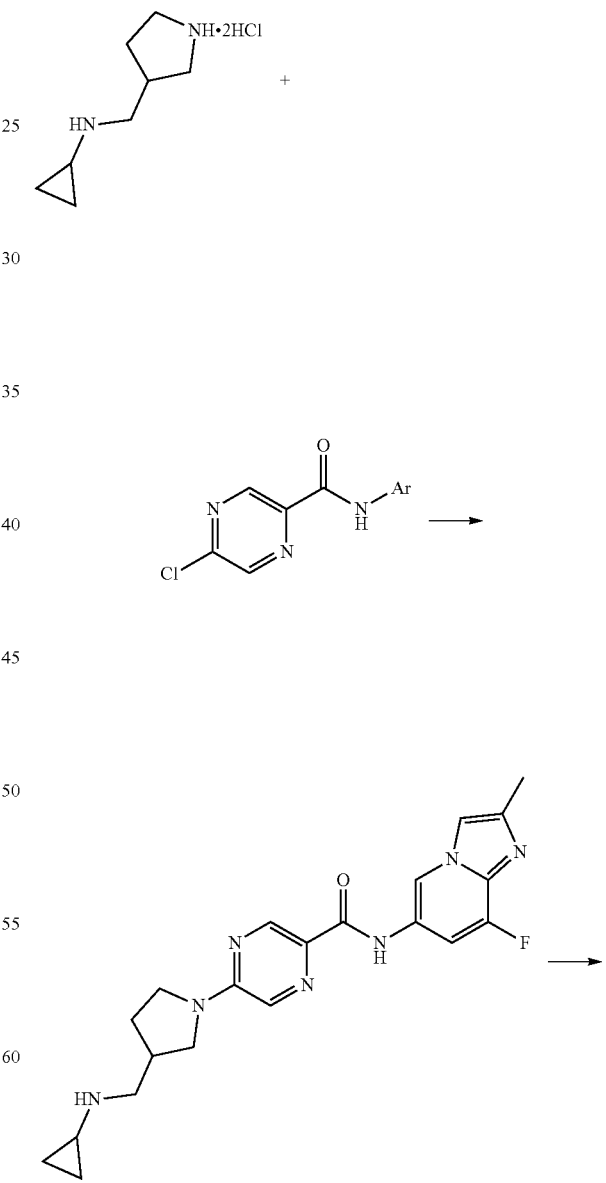

-continued

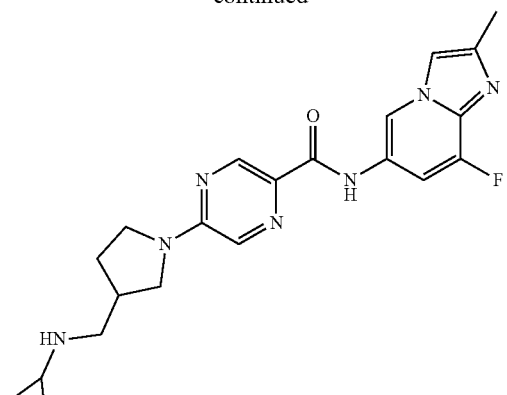

Enantiomer 1

+

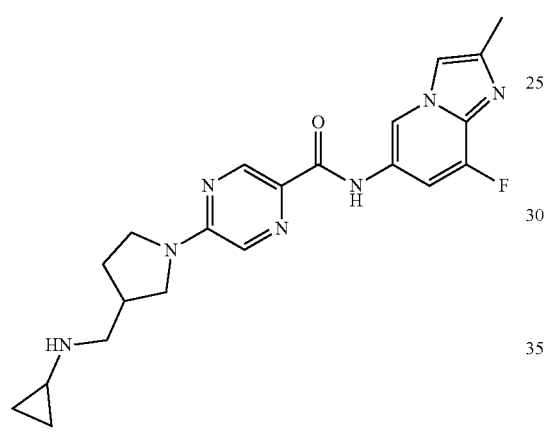

Enantiomer 2

N-(Pyrrolidin-3-ylmethyl)cyclopropanamine-2HCl (488 mg, 2.29 mmol), 5-chloro-N-(8-fluoro-2-methylimidazo[1,2-a]pyridin-6-yl)pyrazine-2-carboxamide (700 mg, 2.29 mmol), cesium carbonate (2.98 g, 9.16 mmol) and DMF (8 ml) were combined and heated to 100° C. for 4 hours. Cesium salts were then filtered off and filtrate was purified by preparative HPLC followed by chiral preparative HPLC to give:

Example 148

Enantiomer 1

5-(3-(((Cyclopropylamino)methyl)pyrrolidin-1-yl)-N-(8-fluoro-2-methylimidazo[1,2-a]pyridin-6-yl)pyrazine-2-carboxamide. LCMS (ES+) 410 (M+H)+, RT 1.83 min (Analytical method AcHSSC18). $^1$H NMR (400 MHz, DMSO) δ 10.44 (s, 1H), 9.22 (d, J=1.6 Hz, 1H), 8.77 (d, J=1.3 Hz, 1H), 7.99 (d, J=1.3 Hz, 1H), 7.92 (d, J=2.8 Hz, 1H), 7.59 (dd, J=1.8, 13.0 Hz, 1H), 3.78-3.67 (m, 2H), 3.58-3.45 (m, 1H), 3.28 (dd, J=7.3, 11.0 Hz, 1H), 2.76-2.63 (m, 3H), 2.37 (s, 3H), 2.17-2.08 (m, 2H), 1.79-1.74 (m, 1H), 0.40 (dd, J=1.6, 6.6 Hz, 2H), 0.27-0.23 (m, 2H).

Example 149

Enantiomer 2

5-(3-(((Cyclopropylamino)methyl)pyrrolidin-1-yl)-N-(8-fluoro-2-methylimidazo[1,2-a]pyridin-6-yl)pyrazine-2-carboxamide. LCMS (ES+) 410 (M+H)+, RT 1.83 min (Analytical method AcHSSC18). $^1$H NMR (400 MHz, DMSO) δ 10.44 (s, 1H), 9.22 (d, J=1.6 Hz, 1H), 8.77 (d, J=1.3 Hz, 1H), 7.99 (d, J=1.3 Hz, 1H), 7.92 (d, J=2.8 Hz, 1H), 7.59 (dd, J=1.8, 13.0 Hz, 1H), 3.78-3.67 (m, 2H), 3.58-3.45 (m, 1H), 3.28 (dd, J=7.3, 11.0 Hz, 1H), 2.76-2.63 (m, 3H), 2.37 (s, 3H), 2.17-2.08 (m, 2H), 1.79-1.74 (m, 1H), 0.40 (dd, J=1.6, 6.6 Hz, 2H), 0.27-0.23 (m, 2H).

Further analogues were prepared using the same chemistry from commercially available or synthesised amines. Final products were isolated by Preparative HPLC.

| Example | Structure | Analytical data |
| --- | --- | --- |
| Example 150 | 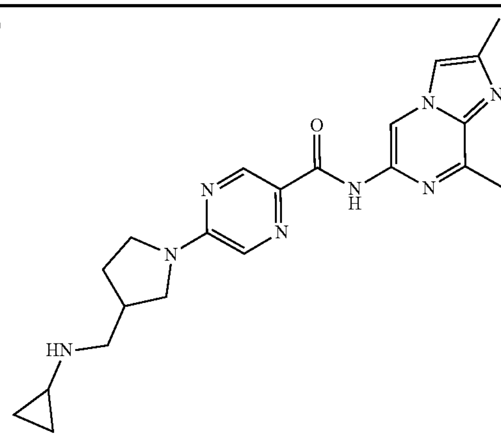 | LCMS (ES+) 407 (M + H)+, RT 2.04 min (Analytical method AcHSSC18) $^1$H NMR (400 MHz, DMSO) δ 9.68 (s, 1H), 9.16 (s, 1H), 8.78 (d, J = 1.3 Hz, 1H), 8.05-8.03 (m, 2H), 3.78-3.66 (m, 2H), 3.58-3.50 (m, 1H), 3.34-3.25 (m, 1H), 2.73 (s, 3H), 2.76-2.62 (m, 3H), 2.43 (s, 3H), 2.14-2.08 (m, 2H), 1.78 (s, 1H), 0.42-0.39 (m, 2H), 0.27-0.23 (m, 2H). |

Examples 151 and 152: (R)-5-(3-((cyclopropyl (methyl)amino)methyl)pyrrolidin-1-yl)-N-(8-fluoro-2-methylimidazo[1,2-a]pyridin-6-yl)pyrazine-2-carboxamide (S)-5-(3-((cyclopropyl(methyl)amino)methyl)pyrrolidin-1-yl)-N-(8-fluoro-2-methylimidazo[1,2-a]pyridin-6-yl)pyrazine-2-carboxamide

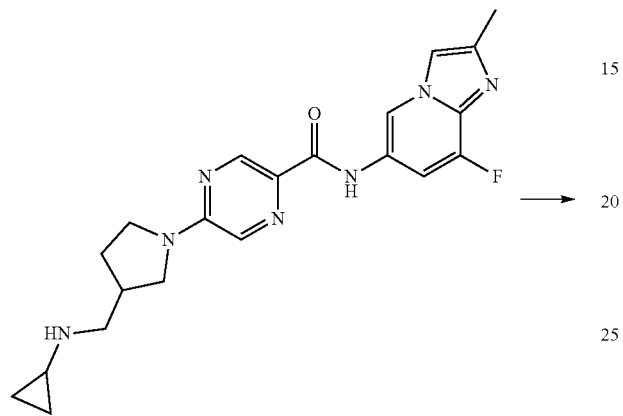

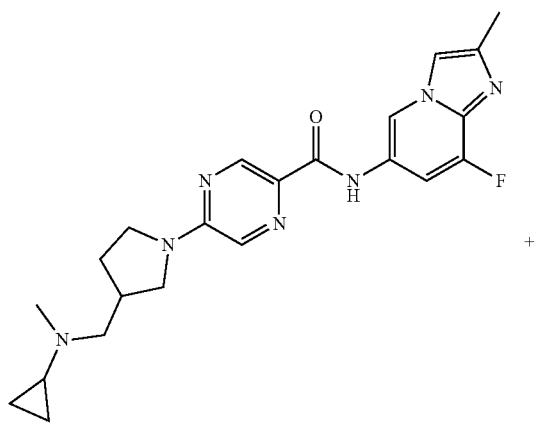

Enantiomer 1

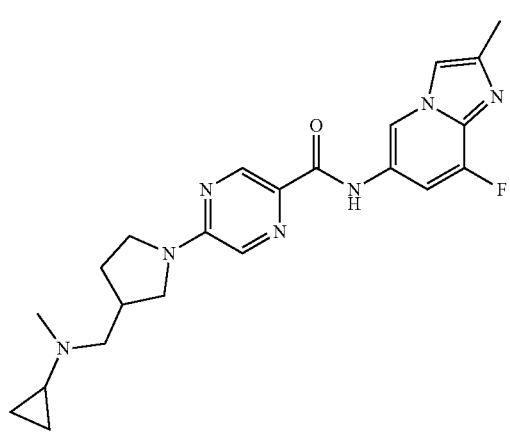

Enantiomer 2

5-(3-((Cyclopropylamino)methyl)pyrrolidin-1-yl)-N-(8-fluoro-2-methylimidazo[1,2-a]pyridin-6-yl)pyrazine-2-carboxamide was reacted with formaldehyde (37 wt. % in H₂O, 10-15% Methanol, 1.5 mL) and sodium triacetoxyborohydride (168 mg, 0.794 mmol) and stirred at r.t. for 18 h. The mixture was then partitioned between DCM and sodium bicarbonate aqueous solution. The aqueous phase was then reextracted with DCM (×1) and the combined organic phases were passed through a phase separator paper and evaporated to dryness to afford the crude residue. The crude was purified using silica chromatography, elution gradient 0-4% NH₃ in MeOH (7N)/EtOAc. The material was then purified by chiral SFC, followed by HPLC chromatography to provide:

Example 151

Enantiomer 1

5-(3-((Cyclopropyl(methyl)amino)methyl)pyrrolidin-1-yl)-N-(8-fluoro-2-methylimidazo[1,2-a]pyridin-6-yl)pyrazine-2-carboxamide. LCMS (ES+) 424 (M+H)+, RT 1.92 min (Analytical method AcHSSC18); $^1$H NMR (400 MHz, DMSO) δ 10.42 (s, 1H), 9.19 (d, J=1.5 Hz, 1H), 8.75 (d, J=1.3 Hz, 1H), 7.98 (d, J=1.4 Hz, 1H), 7.90 (d, J=2.8 Hz, 1H), 7.57 (dd, J=1.6, 13.2 Hz, 1H), 3.73-3.64 (m, 2H), 3.57-3.49 (m, 1H), 3.23 (dd, J=6.8, 11.1 Hz, 1H), 2.35 (s, 3H), 2.31 (s, 3H), 2.15-2.09 (z, 1H), 1.75-1.63 (m, 2H), 0.48-0.43 (m, 2H), 0.36-0.27 (in, 2H).

Example 152

Enantiomer 2

5-(3-((cyclopropyl(methyl)amino)methyl)pyrrolidin-1-yl)-N-(8-fluoro-2-methylimidazo[1,2-a]pyridin-6-yl)pyrazine-2-carboxamide. LCMS (ES+) 424 (M+H)+, RT 1.92 mi 2 (Analytical method AcHSSC18); $^1$H NMR (400 MHz, DMSO) δ 10.42 (s, 1H), 9.19 (d, J=1.6 Hz, 1H), 8.75 (d, J=1.3 Hz, 1H), 7.98 (d, J=1.4 Hz, 1H), 7.90 (dd, J=0.8, 3.2 Hz, 1H), 7.57 (dd, J=1.7, (13.1 Hz, 1H), 3.73-3.64 (m, 2H), 3.57-3.50 (m, 1H), 3.22 (dd, J=6.7, 11.0 Hz, 1H), 2.65-2.59 (m, 1H), 2.52 (t, J=1.8 Hz, OH), 2.35 (s, 3H), 2.31 (s, 3H), 2.15-2.07 (m, 1H), 1.73-1.63 (m, 2H), 0.48-0.42 (m, 2H), 0.36-0.27 (in, 2H).

Further analogues were prepared using the same chemistry and the stated amines either commercial or described in the intermediates section. When Boc protected amines were used the Boc group was subsequently removed with TFA or HCl using standard methods C or D.

| Example | Structure | Amine | Analytical data |
| --- | --- | --- | --- |
| Example 153 (Absolute stereochemistry arbitrarily assigned) | 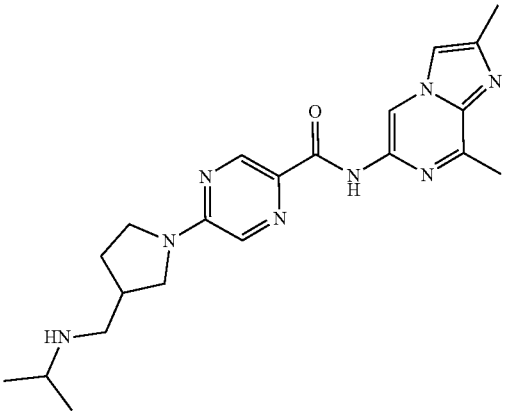<br>Enantiomer 1 | N-(pyrrolidin-3-ylmethyl)propan-2-amine•2HCl | LCMS (ES+) 409 (M + H)+, RT 2.11 min (Analytical method AcHSSC18); RT 12.63 min (SFC4, YMC CELLULOSE-SC + 0.1% DEAISO 35% IPA SOL3); $^1$H NMR (400 MHz, DMSO) δ 9.67 (s, 1H), 9.14 (s, 1H), 8.76 (d, J = 1.3 Hz, 1H), 8.03 (d, J = 1.6 Hz, 1H), 8.01 (d, J = 0.6 Hz, 1H), 3.78-3.66 (m, 2H), 3.57-3.49 (m, 1H), 3.31-3.21 (m, 1H), 2.71-2.70 (m, 4H), 2.66-2.57 (m, 2H), 2.46-2.41 (m, 4H), 2.18-2.11 (m, 1H), 1.77-1.74 (m, 1H), 1.01 (d, J = 3.4 Hz, 3H), 0.99 (d, J = 3.2 Hz, 3H). |
| Example 154 (Absolute stereochemistry arbitrarily assigned) | 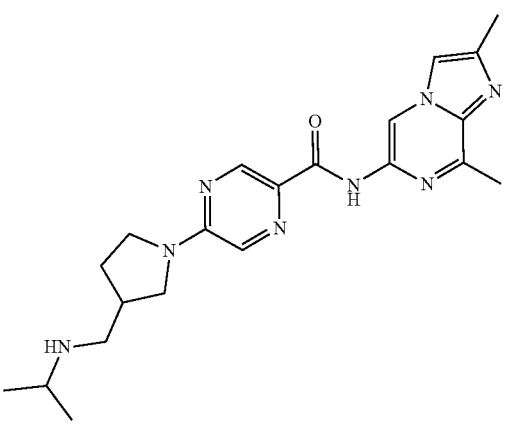<br>Enantiomer 2 | N-(pyrrolidin-3-ylmethyl)propan-2-amine•2HCl | LCMS (ES+) 409 (M + H)+, RT 2.12 min (Analytical method AcHSSC18); RT 15.06 min (SFC4, YMC CELLULOSE-SC + 0.1% DEAISO 35% IPA SOL3); $^1$H NMR (400 MHz, DMSO) δ 9.66 (s, 1H), 9.15 (s, 1H), 8.76 (d, J = 1.1 Hz, 1H), 8.03 (d, J = 1.3 Hz, 1H), 8.01 (d, J = 0.7 Hz, 1H, 3.79-3.65 (m, 2H, 3.57-3.48 (m, 1H), 3.34 (s, 1H), 2.71-2.70 (m, 4H), 2.66-2.54 (m, 2H), 2.44-2.40 (m, 4H), 2.14-2.09 (m, 1H), 1.80-1.74 (m, 1H), 1.00 (dd, J = 3.3, 6.2 Hz, 3H). |
| Example 155 (Absolute stereochemistry arbitrarily assigned) | 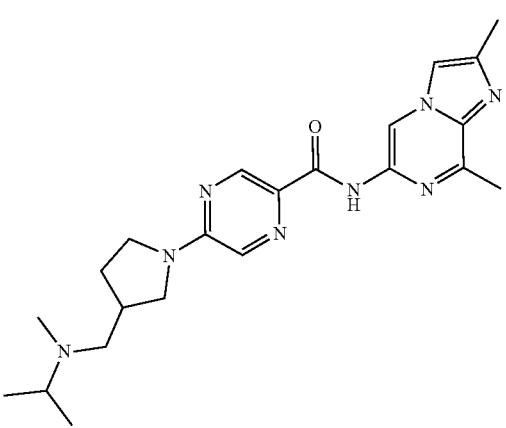<br>Enantiomer 1 | N-methyl-N-(pyrrolidin-3-ylmethyl)propan-2-amine•2HCl | LCMS (ES+) 423 (M + H)+, RT 2.14 min (Analytical method AcHSSC18); RT 17.27 min (SFC1, LUX CELLULOSE-4 + 0.1% DEAISO 55% IPA SOL3); $^1$H NMR in d6 DMSO 9.66 (s, 1H), 9.15 (s, 1H), 8.76 (d, J = 1.3 Hz, 1H), 8.04 (d, J = 1.0 Hz, 1H), 8.01 (d, J = 0.6 Hz, 1H), 3.73-3.64 (m, 2H), 3.58-3.51 (m, 1H), 2.83-2.76 (m, 1H), 2.71 (s, 3H), 2.40 (s, 3H, 2.38-2.34 (m, 2H), 2.18 (s, 3H), 2.14-2.09 (m, 1H), 1.79-1.73 (m, 1H), 0.95 (d, J = 1.8 Hz, 3H), 0.94 (d, J = 1.8 Hz, 3H). |

| Example | Structure | Amine | Analytical data |
| --- | --- | --- | --- |
| Example 156 (Absolute stereochemistry arbitrarily assigned) | 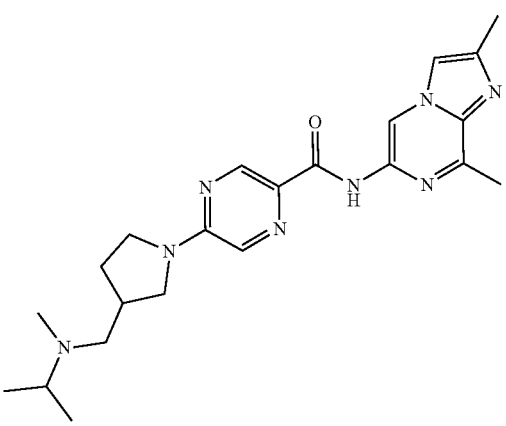<br>Enantiomer 2 | N-methyl-N-(pyrrolidin-3-ylmethyl)propan-2-amine•2HCl | LCMS (ES+) 423 (M + H)+, RT 2.15 min (Analytical method AcHSSC18); RT 19.64 min (SFC1, LUX CELLULOSE-4 + 0.1% DEAISO 55% IPA SOL3); $^1$H NMR (400 MHz, DMSO) δ 9.67 (s, 1H), 9.15 (s, 1H), 8.76 (d, J = 1.1 Hz, 1H), 8.04 (d, J = 1.0 Hz, 1H), 8.01 (s, 1H), 3.73-3.65 (m, 2H), 3.58-3.53 (m, 1H), 2.83-2.76 (m, 1H), 2.71 (s, 3H), 2.41-2.34 (m, 2H), 2.18 (s, 3H), 2.14-2.09 (m, 1H), 1.80-1.76 (m, 1H), 0.96 (d, J = 1.8 Hz, 3H), 0.94 (d, J = 1.9 Hz, 3H). |
| Example 157 (Absolute stereochemistry from commercial SM) | 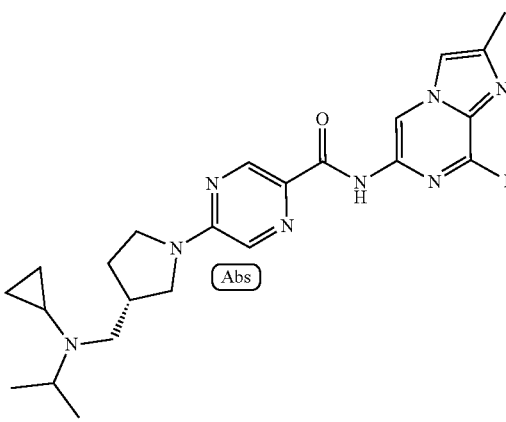 | (R)-N-cyclopropyl-N-(pyrrolidin-3-ylmethyl)cyclo-propanamine•2HCl | LCMS (ES+) 450 (M + H)+, RT 2.06 min (Analytical method AcHSSC18); $^1$H NMR (400 MHz, DMSO) δ 10.43 (s, 1H), 9.20 (d, J = 1.5 Hz, 1H), 8.77 (d, J = 1.5 Hz, 1H), 8.01 (d, J = 1.3 Hz, 1H), 7.92 (d, J = 2.3 Hz, 1H), 7.59 (dd, J = 1.7, 13.0 Hz, 1H), 3.78-3.65 (m, 2H), 3.58-3.50 (m, 0H), 3.46 (s, 0H), 3.31-3.21 (m, 1H), 2.86-2.71 (m, 3H), 2.39 (s, 3H), 2.21-2.13 (m, 1H), 1.99-1.93 (m, 2H), 1.80-1.71 (m, 1H), 0.52-0.34 (m, 8H). |
| Example 158 (Absolute stereochemistry arbitrarily assigned) | 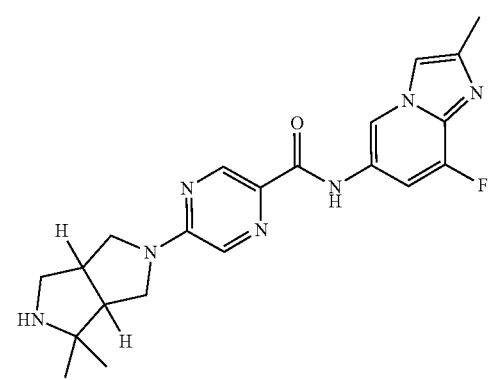 [SMILES: Cc1cn2cc(NC(=O)c3cnc(N4CC5CNC(C)(C)C5C4)cn3)cc(F)c2n1] | 1,1-dimethylocta-hydropyrrolo[3,4-c]pyrrole (synthesised according to ref: PCT Int. Appl., 2019076358, 25 Apr 2019) | LCMS (ES+) 410 (M + H)+, RT 1.8 min (Analytical method AcHSSC18); RT 15.9 min (SFC1, YMC CELLULOSE-SC + 0.1% DEAISO 55% MeOH SOL1); $^1$H NMR (400 MHz, DMSO) δ 10.45 (s, 1H), 9.22 (d, J = 1.3 Hz, 1H), 8.79 (d, J = 1.0 Hz, 1H), 8.03 (s, 1H), 7.93 (d, J = 2.5 Hz, 1H), 7.61 (dd, J = 1.4, 13.0 Hz, 1H), 3.80 (dd, J = 7.8, 11.4 Hz, 1H), 3.69 (dd, J = 8.6, 11.6 Hz, 1H), 3.60-3.52 (m, 2H), 3.20 (dd, J = 8.6, 10.9 Hz, 1H), 3.16-3.08 (m, 1H), 2.72 (dd, J = 4.2, 11.0 Hz, 1H), 2.56 (s, 1H), 2.38 (s, 3H), 1.14 (s, 3H), 1.12 (s, 3H). |

| Example | Structure | Amine | Analytical data |
|---|---|---|---|
| Example 159 (Absolute stereochemistry arbitrarily assigned) | 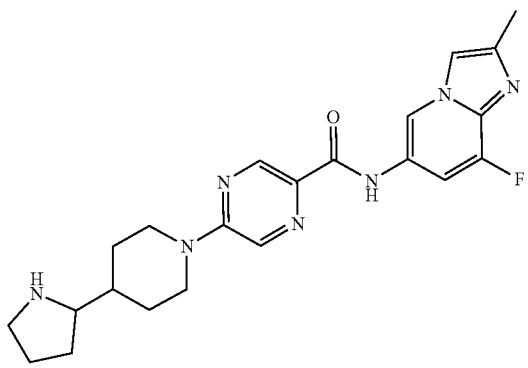<br>Enantiomer 1 | tert-butyl 2-(piperidin-4-yl)pyrrolidine-1-carboxylate (chiral separation at Boc stage) | LCMS (ES+) 424.216 (M + H)+, RT 2 min (Analytical method AcHSSC18); $^1$H NMR (400 MHz, DMSO) δ 10.42 (s, 1H), 9.19 (d, J = 1.6 Hz, 1H), 8.73 (d, J = 1.1 Hz, 1H), 8.33 (d, J = 1.3 Hz, 1H), 7.90 (dd, J = 0.8, 3.1 Hz, 1H), 7.57 (dd, J = 1.5, 13.1 Hz, 1H), 4.57 (d, J = 13.1 Hz, 2H), 3.02-2.93 (m, 2H), 2.84-2.55 (m, 2H), 2.35 (s, 3H), 1.97-1.94 (m, 1H), 1.81-1.72 (m, 2H), 1.64-1.59 (m, 2H), 1.50-1.46 (m, 1H, 1.32-1.16 (m, 3H). |
| Example 160 (Stereochemistry arbitrarily assigned) | 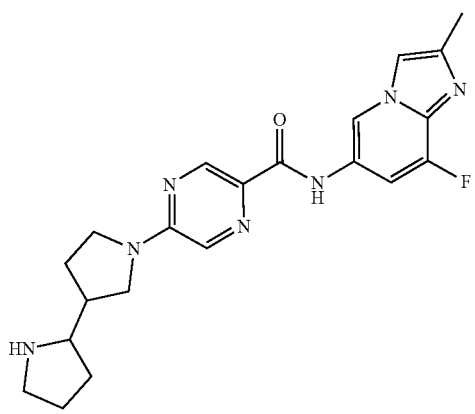<br>Stereoisomer 1 | tert-butyl [2,3'-bipyrrolidine]-1-carboxylate (chiral separation of 4 diastereomers at Boc stage) | LCMS (ES+) 410 (M + H)+, RT 1.89 min (Analytical method AcHSSC18); $^1$H NMR (400 MHz, DMSO) δ 10.43 (s, 1H), 9.19 (d, J = 1.6 Hz, 1H), 8.74 (d, J = 1.1 Hz, 1H), 7.96 (s, 1H), 7.89 (d, J = 2.8 Hz, 1H), 7.57 (dd, J = 1.6, 13.1 Hz, 1H), 3.82-3.71 (m, 2H, 3.52-3.45 (m, 1H), 3.01-2.89 (m, 2H), 2.87-2.80 (m, 1H), 2.34 (s, 3H), 2.30-2.27 (m, 1H), 2.13-2.08 (m, 1H), 1.95-1.88 (m, 1H), 1.78-1.67 (m, 3H, 1.45-1.35 (m, 1H). $^{19}$F NMR (376 MHz, d6 DMSO) δ −132 ppm. |
| Example 161 (Stereochemistry arbitrarily assigned) | 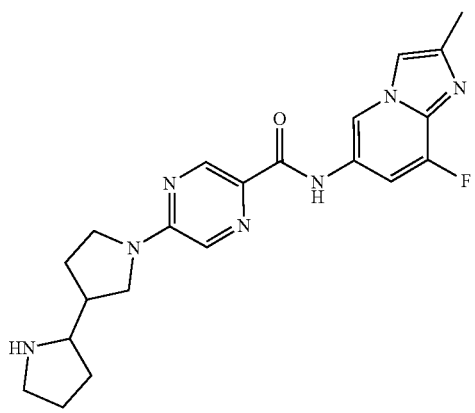<br>Stereoisomer 2 | tert-butyl [2,3'-bipyrrolidine]-1-carboxylate (chiral separation of 4 diastereomers at Boc stage) | LCMS (ES+) 410 (M + H)+, RT 1.88 min (Analytical method AcHSSC18); $^1$H NMR (400 MHz, DMSO) δ 10.42 (s, 1H), 9.19 (d, J = 1.6 Hz, 1H), 8.74 (d, J = 1.1 Hz, 1H), 7.95 (d, J = 1.1 Hz, 1H), 7.89 (d, J = 2.6 Hz, 1H), 7.57 (dd, J = 1.6, 13.1 Hz, 1H), 3.81-3.70 (m, 2H), 3.37 (s, 2H), 2.98-2.87 (m, 2H), 2.85-2.77 (m, 1H), 2.34 (s, 3H), 2.30-2.22 (m, 1H), 2.11-2.06 (m, 1H), 1.95-1.86 (m, 1H), 1.77-1.66 (m, 3H, 1.44-1.34 (m, 1H). $^{19}$F NMR (376 MHz, d6 DMSO) δ −132 ppm. |

-continued

| Example | Structure | Amine | Analytical data |
|---|---|---|---|
| Example 162 (Absolute stereochemistry arbitrarily assigned) | 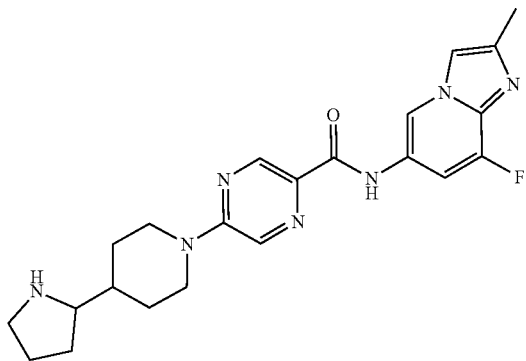<br>Stereoisomer 2 | tert-butyl 2-(piperidin-4-yl)pyrrolidine-1-carboxylate (chiral separation at Boc stage) | LCMS (ES+) 424.309 (M + H)+, RT 2 min (Analytical method AcHSSC18); $^1$H NMR (400 MHz, DMSO) δ 10.43 (s, 1H), 9.19 J = 1.5 Hz 1H), 8.73 (d, J = 1.1 Hz, 1H), 8.33 (d, J = 1.1 Hz, 1H), 7.90 (d, J = 2.8 Hz, 1H), 7.57 (dd, J = 1.6, 13.1 Hz, 1H), 4.57 (d, J = 13.2 Hz, 2H), 3.03-2.93 (m, 2H), 2.84-2.77 (m, 1H), 2.75-2.61 (m, 2H), 2.35 (s, 3H), 1.95 (d, J = 12.3 Hz, 1H), 1.82-1.72 (m, 2H), 1.68-1.58 (m, 2H), 1.49-1.43 (m, 1H), 1.34-1.16 (m, 3H). |
| Example 163 (Stereochemistry arbitrarily assigned) | 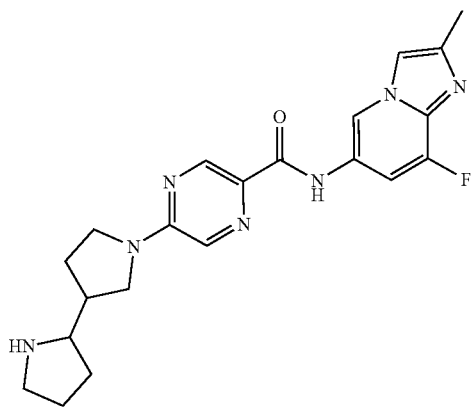<br>Stereoisomer 3 | tert-butyl [2,3'-bipyrrolidine]-1-carboxylate (chiral separation of 4 diastereomers at Boc stage) | LCMS (ES+) 410 (M + H)+, RT 1.79 min (Analytical method AcHSSC18); $^1$HNMR (400 MHz, DMSO) δ 10.45 (s, 1H), 9.22 (d, J = 1.5 Hz, 1H), 8.78 (d, J = 1.3 Hz, 1H), 8.01 (d, J = 1.2 Hz, 1H), 7.92 (dd, J = 0.7, 3.1 Hz, 1H), 7.61 (dd, J = 1.6, 13.2 Hz, 1H), 3.80-3.74 (m, 2H), 3.57-3.52 (m, 1H), 3.28 (d, J = 8.3 Hz, 1H), 3.08 (q, J = 7.8 Hz, 1H), 3.01-2.88 (m, 2H), 2.39 (s, 4H), 2.29-2.21 (m, 1H), 2.00-1.72 (m, 4H), 1.46 (dd, J = 8.5, 12.0 Hz, 1H). $^{19}$F NMR (376 MHz, d6 DMSO) δ −132 ppm |
| Example 164 (Stereochemistry arbitrarily assigned) | 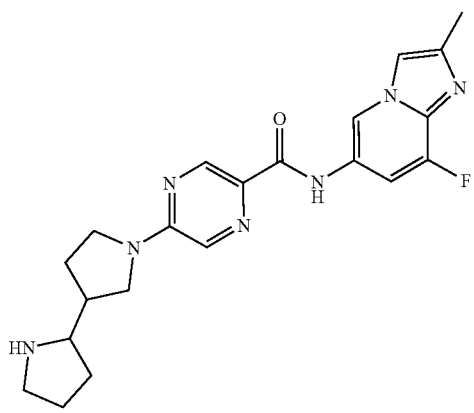<br>Stereoisomer 4 | tert-butyl [2,3'-bipyrrolidine]-1-carboxylate (chiral separation of 4 diastereomers at Boc stage) | LCMS (ES+) 410 (M + H)+, RT 1.78 min (Analytical method AcHSSC18); $^1$H NMR (400 MHz, DMSO) δ 10.45 (s, 1H), 9.22 (d, J = 1.5 Hz, 1H), 8.78 (d, J = 1.3 Hz, 1H), 8.02 (d, J = 1.3 Hz, 1H), 7.93 (d, J = 2.5 Hz, 1H), 7.61 (dd, J = 1.5, 12.7 Hz, 1H), 3.80-3.73 (m, 2H), 3.57-3.49 (m, 1H), 3.30-3.23 (m, 1H), 3.08-2.84 (m, 3H), 2.38 (s, 4H), 2.24-2.22 (m, 1H), 1.98-1.91 (m, 2H), 1.82-1.72 (m, 2H), 1.48-1.40 (m, 1H). $^{19}$F NMR (376 MHz, d6 DMSO) δ −132 ppm |

-continued

| Example | Structure | Amine | Analytical data |
|---|---|---|---|
| Example 165 (Absolute stereochemistry arbitrarily assigned) | 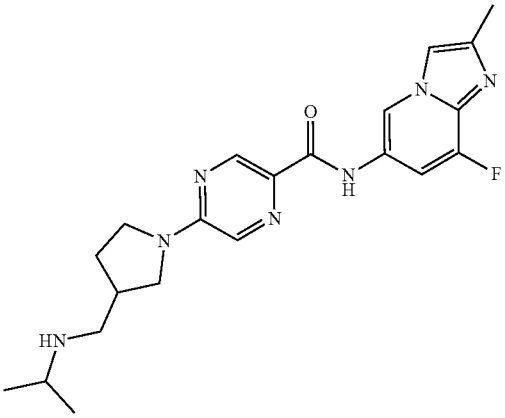<br>Enantiomer 1 | N-(pyrrolidin-3-ylmethyl)propan-2-amine•2HCl | LCMS (ES+) 412.2 (M + H)+, RT 1.91 min (Analytical method AcHSSC18); RT 9.26 min (SFC1, YMC CELLULOSE-C + 0.1% DEAISO 20% MeOH SOL4); $^1$H NMR (400 MHz, DMSO) δ 10.43 (s, 1H), 9.19 (d, J = 1.6 Hz, 1H), 8.75 (d, J = 1.3 Hz, 1H), 7.98 (d, J = 1.3 Hz, 1H), 7.90 (dd, J = 0.8, 3.1 Hz, 1H), 7.57 (dd, J = 1.6, 13.2 Hz, 1H), 3.80-3.67 (m, 2H), 3.57-3.49 (m, 1H), 3.33 (s, 0H), 2.85-2.78 (m, 1H), 2.72-2.61 (m, 2H), 2.35 (s, 3H), 2.19-2.06 (m, 1H), 1.81-1.75 (m, 1H), 1.04 (dd, J = 3.0, 6.3 Hz, 3H). $^{19}$F NMR (376 MHz, d6 DMSO) δ −132 ppm. |
| Example 166 (Absolute stereochemistry arbitrarily assigned) | 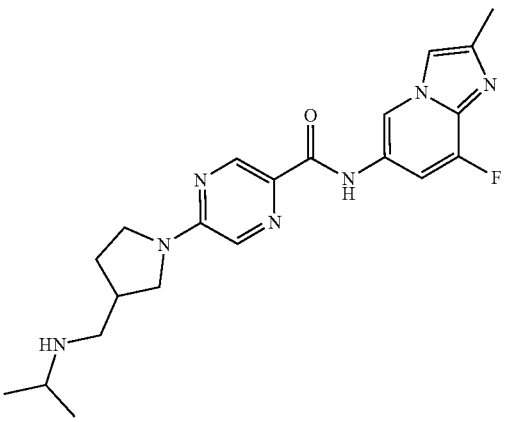<br>Enantiomer 2 | N-(pyrrolidin-3-ylmethyl)propan-2-amine•2HCl | LCMS (ES+) 412 (M + H)+, RT 1.85 min (Analytical method AcHSSC18); RT 12.34 min (SFC1, YMC CELLULOSE-C + 0.1% DEAISO 20% MeOH SOL4); $^1$H NMR (400 MHz, DMSO) δ 10.43 (s, 1H), 9.20 (d, J = 1.6 Hz, 1H), 8.75 (d, J = 1.3 Hz, 1H), 7.98 (d, J = 1.3 Hz, 1H), 7.90 (dd, J = 0.8, 3.0 Hz, 1H), 7.57 (dd, J = 1.6, 13.0 Hz, 1H), 3.79-3.66 (m, 1H), 3.57-3.49 (m, 1H), 3.28 (dd, J = 7.3, 11.2 Hz, 1H), 2.77-2.54 (m, 3H), 2.46-2.40 (m, 1H), 2.35 (s, 3H), 2.19-2.10 (m, 1H), 1.82-1.72 (m, 1H), 1.02 (d, J = 3.3 Hz, 3H), 1.00 (d, J = 3.3 Hz, 3H). $^{19}$F NMR (376 MHz, d6 DMSO) δ −132 ppm. |
| Example 167 (Absolute stereochemistry arbitrarily assigned) | 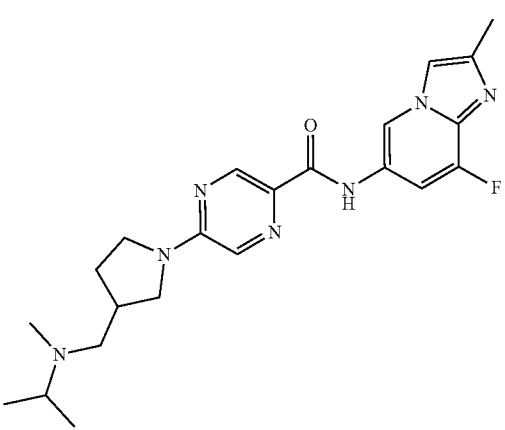<br>Enantiomer 1 | N-methyl-N-(pyrrolidin-3-ylmethyl)propan-2-amine | LCMS (ES+) 426.2 (M + H)+, RT 1.93 min (Analytical method AcHSSC18); RT 15.92 min (SFC1, YMC CELLULOSE-C + 0.1% DEAISO 25% IPA SOL6); $^1$H NMR (400 MHz, DMSO) δ 10.42 (s, 1H), 9.20 (d, J = 1.5 Hz, 1H), 8.75 (d, J = 1.3 Hz, 1H), 7.98 (d, J = 1.3 Hz, 1H), 7.90 (dd, J = 0.9, 3.2 Hz, 1H), 7.57 (dd, J = 1.6, 13.2 Hz, 1H), 3.73-3.64 (m, 2H), 3.59-3.51 (m, 1H), 3.34 (s, 1H), 3.32-3.26 (m, 1H), 2.84-2.76 (m, 1H), 2.38-2.35 (m, 5H), 2.19 (s, 3H), 2.13-2.09 (m, 1H), 1.74-1.74 (m, 1H), 0.96 (d, J = 2.3 Hz, 3H), 0.94 (d, J = 2.3 Hz, 3H). |

-continued

| Example | Structure | Amine | Analytical data |
|---|---|---|---|
| Example 168 (Absolute stereochemistry arbitrarily assigned) Enantiomer 2 | | N-methyl-N-(pyrrolidin-3-ylmethyl)propan-2-amine | LCMS (ES+) 426.2 (M + H)+, RT 1.93 min (Analytical method AcHSSC18); RT 18.92 min (SFC1, YMC CELLULOSE-C + 0.1% DEAISO 25% IPA SOL6); ¹H NMR (400 MHz, DMSO) δ 10.42 (s, 1H), 9.20 (d, J = 1.6 Hz, 1H), 8.75 (d, J = 1.3 Hz, 1H), 7.98 (d, J = 1.3 Hz, 1H), 7.90 (dd, J = 0.7, 3.1 Hz, 1H), 7.57 (dd, J = 1.6, 13.1 Hz, 1H), 3.73-3.64 (m, 2H), 3.59-3.51 (m, 1H), 3.30-3.26 (m, 1H), 2.85-2.77 (m, 1H), 2.39-2.35 (m, 5H), 2.19 (s, 3H), 2.13-2.09 (m, 1H), 1.77-1.77 (m, 1H), 0.96 (d, J = 2.3 Hz, 3H), 0.94 (d, J = 2.3 Hz, 3H). |
| Example 169 | 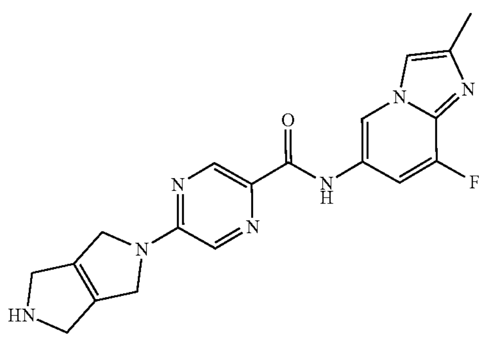 [SMILES: Cc1cn2cc(NC(=O)c3cnc(N4CC5=C(CNC5)C4)cn3)cc(F)c2n1] | tert-butyl 3,4,5,6-tetrahydropyrrolo[3,4-c]pyrrole-2(1H)-carboxylate | LCMS (ES+) 380 (M + H)+, RT 1.67 min (Analytical method AcHSSC18); ¹H NMR (400 MHz, DMSO) δ 10.47-10.44 (m, 1H), 9.21 (d, J = 1.3 Hz, 1H), 8.80 (s, 1H), 8.02 (s, 1H), 7.91 (d, J = 2.5 Hz, 1H), 7.59 (dd, J = 1.3, 13.5 Hz, 1H), 4.36 (s, 4H), 4.18 (s, 1H), 3.74 (s, 4H), 2.37 (s, 3H); ¹⁹F NMR (376 MHz, d6 DMSO) δ -132 ppm. |

Example 170: (R)-5-(3-(1-(cyclopropylamino)cyclopropyl)pyrrolidin-1-yl)-N-(8-fluoro-2-methylimidazo[1,2-a]pyridin-6-yl)pyrazine-2-carboxamide (R)-5-(3-(1-Aminocyclopropyl)pyrrolidin-1-yl)-N-(8-fluoro-2-methylimidazo[1,2-a]pyridin-6-yl)pyrazine-2-carboxamide (60 mg, 0.15 mmol) was dissolved in methanol (2 mL) and (1-ethoxycyclopropoxy)trimethylsilane (29 mg, 0.21 mmol) and sodium cyanoborohydride (11 mg, 0.18 mmol) was added. Acetic acid (20 μL) was added and the reaction heated at 50° C. overnight. The reaction was cooled to r.t. and the solvent removed in vacuo to give a residue, which was purified preparative HPLC to give (R)-5-(3-(1-(cyclopropylamino)cyclopropyl)pyrrolidin-1-yl)-N-(8-fluoro-2-methylimidazo[1,2-a]pyridin-6-yl)pyrazine-2-carboxamide. LCMS (ES+) 436 (M+H)+, RT 1.98 min (Analytical method AcHSSC18); $^1$H NMR (400 MHz, DMSO) δ 10.44 (s, 1H), 9.23 (d, J=1.5 Hz, 1H), 8.78 (d, J=1.3 Hz, 1H), 8.00 (d, J=1.5 Hz, 1H), 7.93 (d, J=2.3 Hz, 1H), 7.61 (dd, J=1.5, 13.1 Hz, 1H), 3.88-3.76 (m, 2H), 3.54-3.46 (m, 1H), 3.23-3.16 (m, 1H), 2.92-2.66 (m, 2H), 2.39-2.38 (m, 3H), 2.20-2.14 (m, 1H), 2.06 (s, 1H), 1.76-1.63 (m, 1H), 0.63-0.54 (m, 4H), 0.44-0.40 (m, 2H), 0.30-0.25 (m, 2H).

Example 171: N-(8-fluoro-2-methylimidazo[1,2-a]pyridin-6-yl)-5-(6-methyl-2,6-diazaspiro[3.5]nonan-2-yl)pyrazine-2-carboxamide

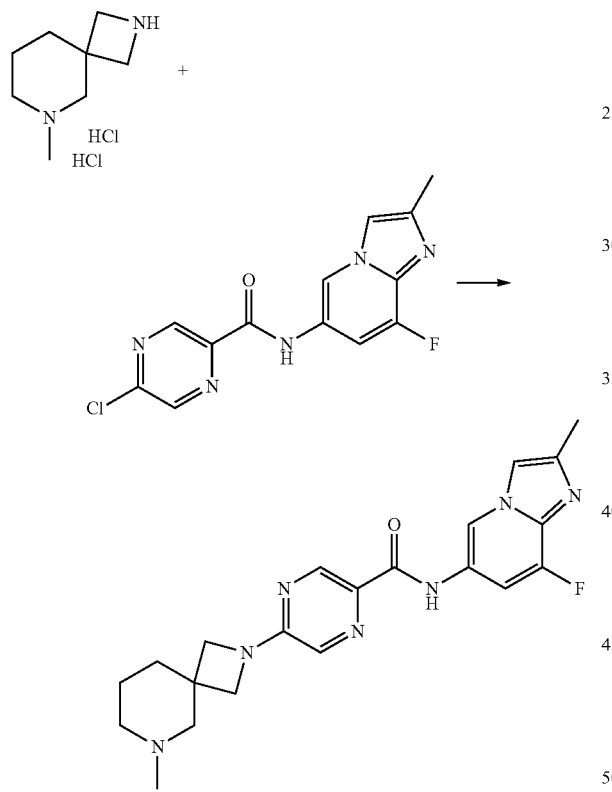

A mixture of 5-chloro-N-(8-fluoro-2-methylimidazo[1,2-a]pyridin-6-yl)pyrazine-2-carboxamide (55 mg, 0.18 mmol), 6-methyl-2,6-diazaspiro[3.5]nonane dihydrochloride (50 mg, 0.24 mmol) and cesium carbonate (235 mg, 0.722 mmol) in DMF (1.5 mL) was heated to 100° C. and stirred overnight. The reaction was cooled to room temperature, filtered and submitted to achiral reverse phase HPLC purification (Xbridge Phenyl 19×150 mm, 10 μm 40-100% MeOH/H$_2$O (10 mM NH$_4$CO$_3$), 20 mL/min, RT) to yield N-(8-fluoro-2-methylimidazo[1,2-a]pyridin-6-yl)-5-(6-methyl-2,6-diazaspiro[3.5]nonan-2-yl)pyrazine-2-carboxamide. LCMS (ES+) 410.3 [M+H]+, RT 1.83 minutes (Analytical method AcHSSC18). $^1$H NMR (400 MHz, DMSO) δ 10.44 (s, 1H), 9.19 (d, J=1.6 Hz, 1H), 8.72 (d, J=1.3 Hz, 1H), 7.90-7.87 (m, 2H), 7.56 (dd, J=1.6, 13.1 Hz, 1H), 3.90 (d, J=9.0 Hz, 2H), 3.86 (d, J=9.0 Hz, 2H), 2.50-2.40 (m, 2H), 2.35 (s, 3H), 2.29-2.21 (m, 2H), 2.21 (s, 3H), 1.70-1.60 (m, 2H), 1.57-1.50 (m, 2H).

Example 172: N-(8-fluoro-2-methylimidazo[1,2-a]pyridin-6-yl)-5-(2,6-diazaspiro[3.5]nonan-2-yl)pyrazine-2-carboxamide

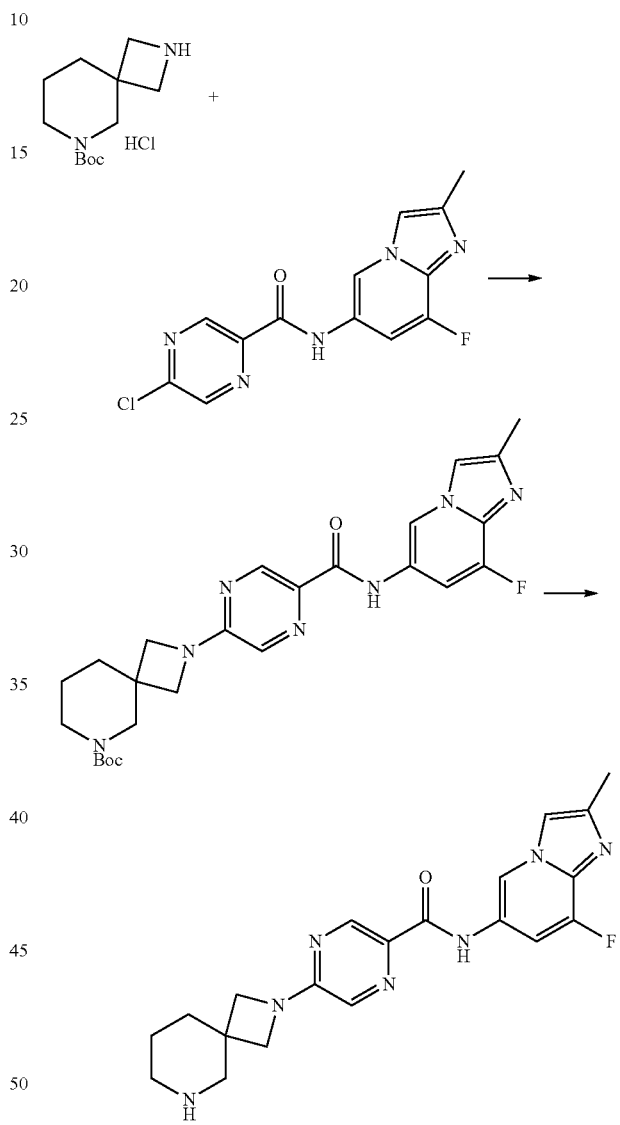

A mixture of 5-chloro-N-(8-fluoro-2-methylimidazo[1,2-a]pyridin-6-yl)pyrazine-2-carboxamide (89 mg, 0.29 mmol), tert-butyl 2,6-diazaspiro[3.5]nonane-6-carboxylate hydrochloride (100 mg, 0.38 mmol) and cesium carbonate (382 mg, 1.17 mmol) in DMF (3 mL) was heated to 100° C. and stirred overnight. The reaction was cooled to room temperature, filtered and the solids washed with EtOAc. The combined filtrates were concentrated under reduced pressure yielding the crude material, which was taken on without further purification assuming a quantitative yield. MS (ES+) 496.3 [M+H]+.

To a solution of tert-butyl 2-(5-((8-fluoro-2-methylimidazo[1,2-a]pyridin-6-yl)carbamoyl)pyrazin-2-yl)-2,6-diazaspiro[3.5]nonane-6-carboxylate (145 mg, 0.293 mmol) in methanol (2.5 mL) was added hydrogen chloride (4 M in dioxane, 2.4 mL, 9.75 mmol) and the reaction stirred at room temperature overnight. The reaction mixture was concentrated under reduced pressure. The crude material was purified by reverse phase HPLC (Xbridge Phenyl 19×150 mm, 10 μm 20-80% MeOH/H$_2$O (10 mM NH$_4$CO$_3$), 20 mL/min, RT) to yield N-(8-fluoro-2-methylimidazo[1,2-a]pyridin-6-yl)-5-(2,6-diazaspiro[3.5]nonan-2-yl)pyrazine-2-carboxamide. LCMS (ES+) 396.0 [M+H]+, RT 1.80 minutes (Analytical method AcHSSC18). $^1$H NMR (400 MHz, DMSO) δ 10.44 (s, 1H), 9.19 (d, J=1.5 Hz, 1H), 8.72 (d, J=1.3 Hz, 1H), 7.90-7.86 (m, 2H), 7.58 (d, J=1.5 Hz, 1H), 7.56 (dd, J=1.6, 13.1 Hz, 1H), 7.55 (d, J=1.6 Hz, 1H), 3.90 (d, J=8.9 Hz, 2H), 3.83 (d, J=8.9 Hz, 2H), 2.84 (s, 2H), 2.67-2.61 (m, 2H), 2.35 (s, 3H), 1.80-1.71 (m, 2H), 1.50-1.41 (m, 2H).

Example 173: N-(8-fluoro-2-methylimidazo[1,2-a]pyridin-6-yl)-5-((2,2,6,6-tetramethylpiperidin-4-yl)oxy)pyrazine-2-carboxamide Example 174: 5-(5-cyclopropylhexahydropyrrolo[3,4-c]pyrrol-2(1H)-yl)-N-(8-fluoro-2-methylimidazo[1,2-a]pyridin-6-yl)pyrazine-2-carboxamide

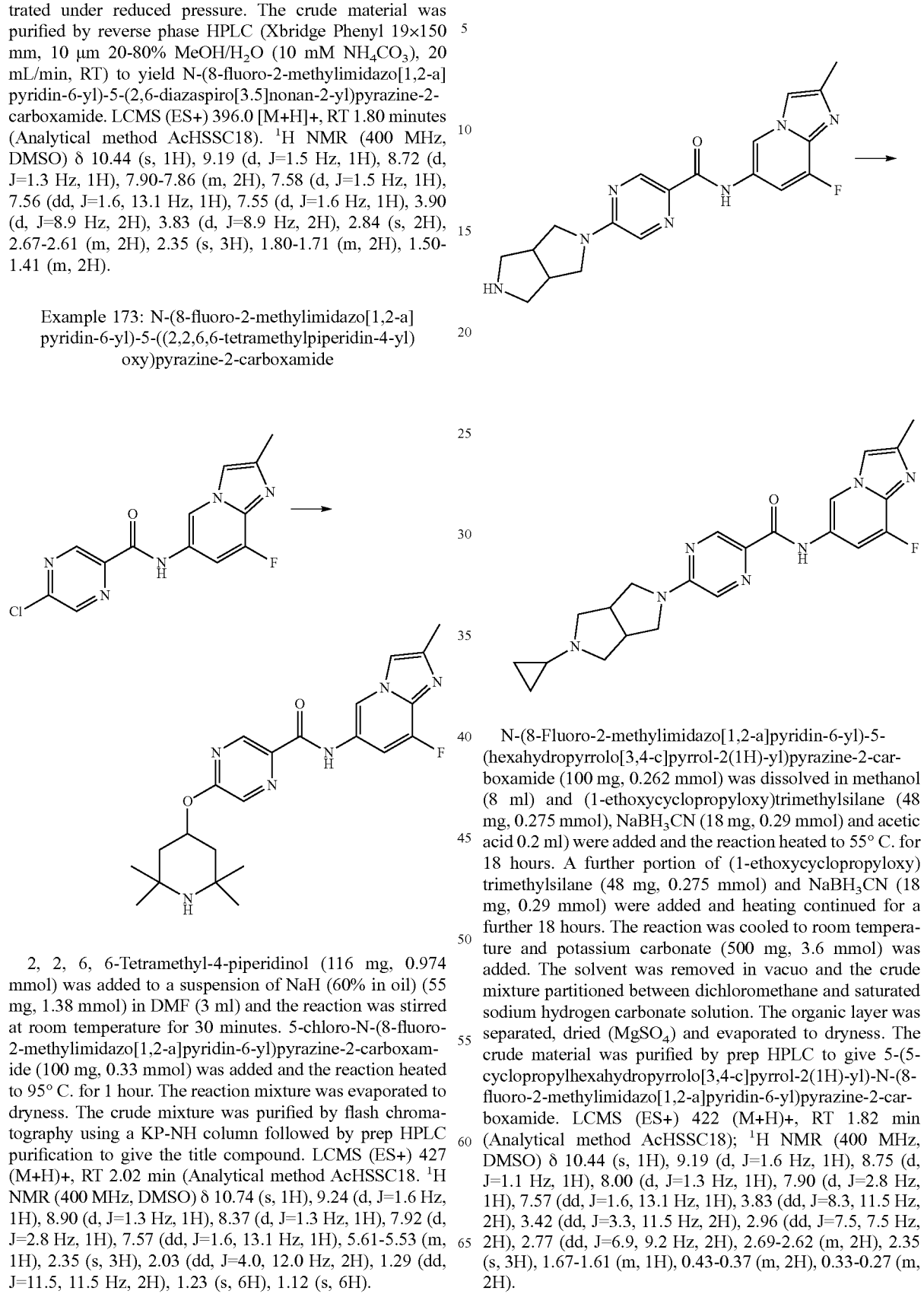

2, 2, 6, 6-Tetramethyl-4-piperidinol (116 mg, 0.974 mmol) was added to a suspension of NaH (60% in oil) (55 mg, 1.38 mmol) in DMF (3 ml) and the reaction was stirred at room temperature for 30 minutes. 5-chloro-N-(8-fluoro-2-methylimidazo[1,2-a]pyridin-6-yl)pyrazine-2-carboxamide (100 mg, 0.33 mmol) was added and the reaction heated to 95° C. for 1 hour. The reaction mixture was evaporated to dryness. The crude mixture was purified by flash chromatography using a KP-NH column followed by prep HPLC purification to give the title compound. LCMS (ES+) 427 (M+H)+, RT 2.02 min (Analytical method AcHSSC18. $^1$H NMR (400 MHz, DMSO) δ 10.74 (s, 1H), 9.24 (d, J=1.6 Hz, 1H), 8.90 (d, J=1.3 Hz, 1H), 8.37 (d, J=1.3 Hz, 1H), 7.92 (d, J=2.8 Hz, 1H), 7.57 (dd, J=1.6, 13.1 Hz, 1H), 5.61-5.53 (m, 1H), 2.35 (s, 3H), 2.03 (dd, J=4.0, 12.0 Hz, 2H), 1.29 (dd, J=11.5, 11.5 Hz, 2H), 1.23 (s, 6H), 1.12 (s, 6H).

N-(8-Fluoro-2-methylimidazo[1,2-a]pyridin-6-yl)-5-(hexahydropyrrolo[3,4-c]pyrrol-2(1H)-yl)pyrazine-2-carboxamide (100 mg, 0.262 mmol) was dissolved in methanol (8 ml) and (1-ethoxycyclopropyloxy)trimethylsilane (48 mg, 0.275 mmol), NaBH$_3$CN (18 mg, 0.29 mmol) and acetic acid 0.2 ml) were added and the reaction heated to 55° C. for 18 hours. A further portion of (1-ethoxycyclopropyloxy)trimethylsilane (48 mg, 0.275 mmol) and NaBH$_3$CN (18 mg, 0.29 mmol) were added and heating continued for a further 18 hours. The reaction was cooled to room temperature and potassium carbonate (500 mg, 3.6 mmol) was added. The solvent was removed in vacuo and the crude mixture partitioned between dichloromethane and saturated sodium hydrogen carbonate solution. The organic layer was separated, dried (MgSO$_4$) and evaporated to dryness. The crude material was purified by prep HPLC to give 5-(5-cyclopropylhexahydropyrrolo[3,4-c]pyrrol-2(1H)-yl)-N-(8-fluoro-2-methylimidazo[1,2-a]pyridin-6-yl)pyrazine-2-carboxamide. LCMS (ES+) 422 (M+H)+, RT 1.82 min (Analytical method AcHSSC18); $^1$H NMR (400 MHz, DMSO) δ 10.44 (s, 1H), 9.19 (d, J=1.6 Hz, 1H), 8.75 (d, J=1.1 Hz, 1H), 8.00 (d, J=1.3 Hz, 1H), 7.90 (d, J=2.8 Hz, 1H), 7.57 (dd, J=1.6, 13.1 Hz, 1H), 3.83 (dd, J=8.3, 11.5 Hz, 2H), 3.42 (dd, J=3.3, 11.5 Hz, 2H), 2.96 (dd, J=7.5, 7.5 Hz, 2H), 2.77 (dd, J=6.9, 9.2 Hz, 2H), 2.69-2.62 (m, 2H), 2.35 (s, 3H), 1.67-1.61 (m, 1H), 0.43-0.37 (m, 2H), 0.33-0.27 (m, 2H).

501

Example 175: (R)—N-(6,8-dimethylimidazo[1,2-a]pyrazin-2-yl)-5-(3-(methylamino)pyrrolidin-1-yl)pyrazine-2-carboxamide

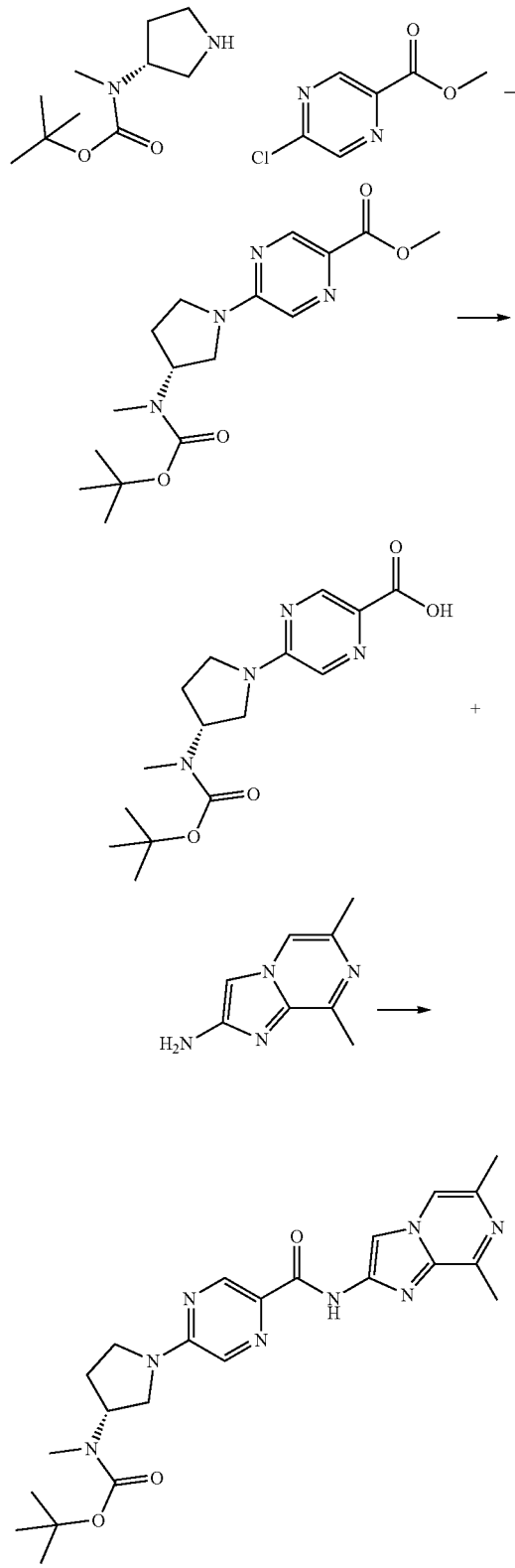

502

-continued

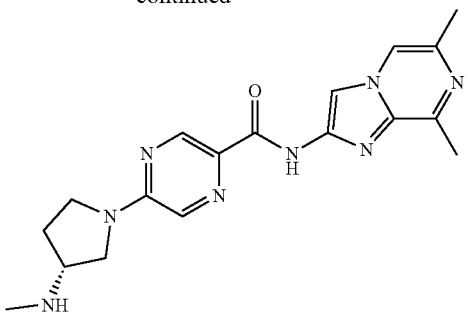

To a solution of methyl 5-chloropyrazine-2-carboxylate (500 mg, 2.9 mmol) in dioxane (10 mL) was added tert-butyl (R)-methyl(pyrrolidin-3-yl)carbamate (696 mg, 3.48 mmol). Triethylamine (0.61 mL, 4.35 mmol) was added and the reaction was heated in a microwave at 140° C. for 30 minutes. The solvent was removed in vacuo and a portion of the residue was purified by flash chromatography with an elution gradient of 20-100% EtOAc in cyclohexane to give methyl (R)-5-(3-((tert-butoxycarbonyl)(methyl)amino)pyrrolidin-1-yl)pyrazine-2-carboxylate lithium salt. LCMS (AQ6 generic acidic run) RT 1.54 min, (ES+) 337 (M+H). $^1$H NMR (400 MHz, CDCl3) δ 8.79 (s, 1H), 7.89 (s, 1H), 4.89-4.80 (m, 1H), 3.93 (s, 3H), 3.83-3.76 (m, 2H), 3.58-3.45 (m, 2H), 2.82 (s, 3H), 2.27-2.13 (m, 2H), 1.48 (s, 9H).

Methyl (R)-5-(3-((tert-butoxycarbonyl)(methyl)amino)pyrrolidin-1-yl)pyrazine-2-carboxylate (194 mg, 0.577 mmol, 1 equiv) was dissolved in MeOH (5 mL) and H$_2$O (0.5 mL) and lithium hydroxide monohydrate (36 mg, 0.865 mmol, 1.50 equiv) was added and the reaction mixture stirred for 16 hours. An additional portion of lithium hydroxide monohydrate (45 mg, 1.1 mmol) was added and the reaction mixture stirred at 45° C. for 1 hour. The reaction mixture was allowed to cool to room temperature and the solvent removed in vacuo. The resulting material was used without further purification. LCMS (AQ6 generic acidic run) RT 1.4 min, (ES+) 323 (M+H).

6,8-Dimethylimidazo[1,2-a]pyrazin-2-amine (50 mg, 0.31 mmol), methyl (R)-5-(3-((tert-butoxycarbonyl)(methyl)amino)pyrrolidin-1-yl)pyrazine-2-carboxylate lithium salt (99 mg, 0.31 mmol), HBTU (129 mg, 0.339 mmol), triethylamine (0.064 ml, 0.46 mmol) and DMF (1 mL) were combined and stirred at room temperature for 18 hour. An additional portion of HBTU (160 mg, 0.422 mmol) was added and the reaction heated to 50° C. for 2.5 hours. The solvent was removed in vacuo and the residue partitioned between dichloromethane and water. The layers were separated and the aqueous extracted with dichloromethane. The combined extracts were dried (MgSO$_4$), evaporated and the crude purified by flash chromatography elution gradient 20-100% EtOAc in cyclohexane followed by 10% ethanol/ethyl acetate, then using flash chromatography on KP-NH elution gradient 20-100% EtOAc to give tert-butyl (R)-(1-(5-(((6,8-dimethylimidazo[1,2-a]pyrazin-2-yl)carbamoyl)pyrazin-2-yl)pyrrolidin-3-yl)(methyl)carbamate. LCMS (AQ6 generic acidic run) RT 1.53 min, (ES+) 467 (M+H).

tert-Butyl (R)-(1-(5-(((6,8-dimethylimidazo[1,2-a]pyrazin-2-yl)carbamoyl)pyrazin-2-yl)pyrrolidin-3-yl)(methyl)carbamate (35 mg, 0.07 mmol), methanol (1 mL), dioxane (1 mL) and 4N HCl in dioxane (0.5 mL, 2.0 mmol) were combined and stirred at room temperature for 3 hours. The reaction mixture was evaporated to dryness and the crude material was dissolved in methanol (2 mL) and stirred with potassium carbonate, re-evaporated and purified by Prep HPLC to give the title product. LCMS (ES+) 367 (M+H)+, RT 1.88 min (Analytical method AcHSSC18); ¹H NMR (400 MHz, DMSO) δ 10.25 (s, 1H), 8.76 (d, J=1.3 Hz, 1H), 8.34 (s, 1H), 8.29 (s, 1H), 8.03 (d, J=1.4 Hz, 1H), 3.69-3.59 (m, 3H), 3.42-3.38 (m, 1H), 2.68 (s, 3H), 2.38 (s, 3H), 2.32 (s, 3H), 2.15-2.08 (m, 2H), 1.90 (s, 1H).

Example 176 (R)—N-(6-methoxy-2-methylpyrazolo[1,5-a]pyridin-5-yl)-5-(3-(methylamino)pyrrolidin-1-yl)pyrazine-2-carboxamide Following Method H TCFH coupling from (R)-5-(3-((tert-butoxycarbonyl)(methyl)amino)pyrrolidin-1-yl)pyrazine-2-carboxylic acid (156 mg, 0.485 mmol, 1 eq) and 6-methoxy-2-methylpyrazolo[1,5-a]pyridin-5-amine 2HBr (164 mg, 0.485 mmol, 1 eq). The reaction mixture was diluted with H₂O and the solid filtered. The solid was washed with MeCN:H₂O (1:2) (×3) to give tert-butyl (R)-(1-(5-((6-methoxy-2-methylpyrazolo[1,5-a]pyridin-5-yl)carbamoyl)pyrazin-2-yl)pyrrolidin-3-yl)(methyl)carbamate. LCMS (ES+) 482 (M+H)+.

Following Method E TFA Boc deprotection from tert-butyl (R)-(1-(5-((6-methoxy-2-methylpyrazolo[1,5-a]pyridin-5-yl)carbamoyl)pyrazin-2-yl)pyrrolidin-3-yl)(methyl)carbamate (50 mg, 0.104 mmol, 1 eq). The reaction mixture was concentrated in vacuo and the crude was purified by HPLC to give (R)—N-(6-methoxy-2-methylpyrazolo[1,5-a]pyridin-5-yl)-5-(3-(methylamino)pyrrolidin-1-yl)pyrazine-2-carboxamide. LCMS (ES+) 382 (M+H)+, RT 2.76 min (Analytical method AcHSSC18) ¹H NMR (400 MHz, DMSO) δ 10.02 (s, 1H), 8.76 (d, J=1.1 Hz, 1H), 8.48 (s, 1H), 8.41 (s, 1H), 8.06 (d, J=1.3 Hz, 1H), 6.28 (s, 1H), 3.98 (s, 3H), 3.68-3.57 (m, 3H), 3.45-3.39 (m, 2H), 2.34 (s, 3H), 2.32 (s, 3H), 2.12-2.09 (m, 1H), 1.94-1.86 (m, 1H).

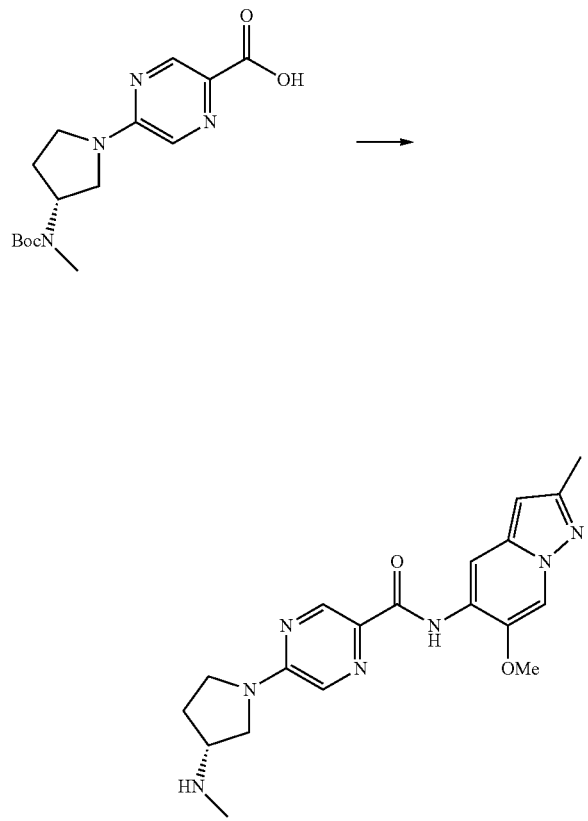

The following examples were prepared using an analogous procedure starting from (R)-5-(3-((tert-butoxycarbonyl)(methyl)amino)pyrrolidin-1-yl)pyrazine-2-carboxylic acid and the stated amine.

| Example | Structure | Amine | Analytical data |
|---|---|---|---|
| Example 177 | 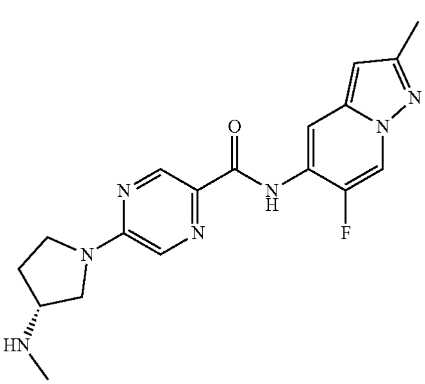 | 6-fluoro-2-methylpyrazolo[1,5-a]pyridin-5-amine. 2HBr | LCMS (ES+) 370 (M + H)+, RT 2.74 min (Analytical method AcHSSC18)<br>¹H NMR (400 MHz, DMSO) δ 9.90 (d, J = 2.3 Hz, 1H), 9.01 (d, J = 6.3 Hz, 1H), 8.77 (d, J = 1.3 Hz, 1H), 8.34 (d, J = 7.9 Hz, 1H), 8.06 (d, J = 1.3 Hz, 1H), 6.42 (s, 1H), 3.69-3.57 (m, 3H), 3.43-3.39 (m, 2H), 2.37 (s, 3H), 2.33 (s, 3H), 2.12 (dd, J = 7.8, 17.9 Hz, 1H), 1.92 (s, 1H). |

-continued

| Example | Structure | Amine | Analytical data |
|---|---|---|---|
| Example 178 | 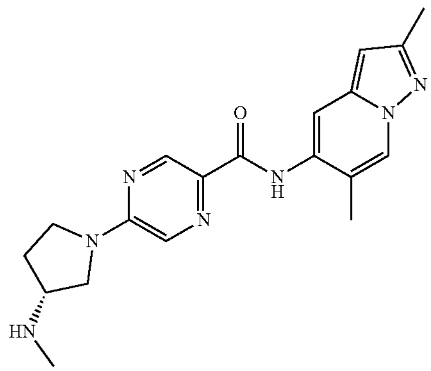 [SMILES: CN[C@@H]1CCN(c2cnc(C(=O)Nc3cc4cc(C)nn4cc3C)cn2)C1] | 2,6-dimethylpyrazolo[1,5-a]pyridin-5-amine 2HBr | LCMS (ES+) 366 (M + H)+, RT 2.66 min (Analytical method AcHSSC18)<br>$^1$H NMR (400 MHz, DMSO) δ 9.75 (s, 1H), 8.76 (d, J = 1.1 Hz, 1H), 8.49 (s, 1H), 8.25 (s, 1H), 8.05 (d, J = 1.3 Hz, 1H), 6.28 (s, 1H), 3.69-3.57 (m, 3H), 3.44-3.38 (m, 2H), 2.36 (s, 3H), 2.33-2.31 (m, 6H), 2.16-2.09 (m, 1H), 1.93-1.88 (m, 1H). |
| Example 179 | 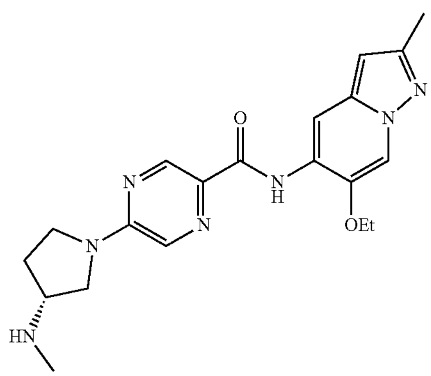 [SMILES: CCOc1cn2nc(C)cc2cc1NC(=O)c1cnc(N2CC[C@@H](NC)C2)cn1] | 6-ethoxy-2-methylpyrazolo[1,5-a]pyridin-5-amine 2HBr | LCMS (ES+) 396 (M + H)+, RT 2.95 min (Analytical method AcHSSC18)<br>$^1$H NMR (400 MHz, DMSO) δ 10.10 (s, 1H), 8.76 (d, J = 1.3 Hz, 1H), 8.48 (s, 1H), 8.42 (s, 1H), 8.05 (d, J = 1.1 Hz, 1H), 6.27 (s, 1H), 4.21 (q, J = 7.0 Hz, 2H), 3.69-3.58 (m, 3H), 2.35 (s, 3H), 2.33 (s, 3H), 2.16-2.09 (m, 1H), 1.92-1.89 (m, 1H), 1.47 (t, J = 6.9 Hz, 3H). |
| Example 180 | 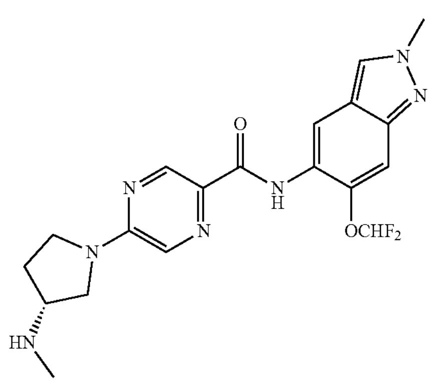 [SMILES: CN[C@@H]1CCN(c2cnc(C(=O)Nc3cc4cn(C)nc4cc3OC(F)F)cn2)C1] | 6-(difluoromethoxy)-2-methyl-2H-indazol-5-amine 2HCl | LCMS (ES+) 418 (M + H)+, RT 3.27 min (Analytical method BicarbBEHC18)<br>$^1$H NMR (400 MHz, DMSO) δ 9.93 (s, 1H), 8.75 (D, J = 1.0 Hz, 1H), 8.70 (s, 1H), 8.38 (s, 1H), 8.05 (d, J = 1.1 Hz, 1H), 7.48 (s, 1H), 7.41 (t, J = 73.7 Hz, 0H), 4.16 (s, 3H), 3.70-3.55 (m, 3H), 2.33 (s, 3H), 2.17-2.09 (m, 1H), 1.93-1.92 (m, 1H). |

Example 181: (R)-5-(3-(cyclopropylamino)pyrrolidin-1-yl)-N-(2,8-dimethylimidazo[1,2-a]pyridin-6-yl)pyrazine-2-carboxamide

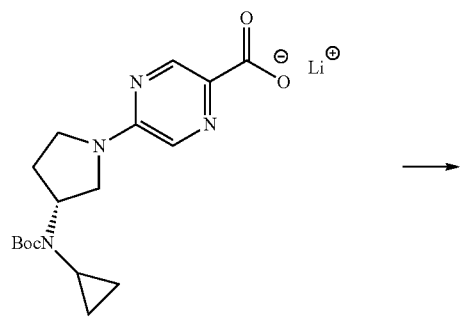

Following HBTU coupling from (R)-5-(3-((tert-butoxycarbonyl)(cyclopropyl)amino)pyrrolidin-1-yl)pyrazine-2-carboxylate lithium salt (100 mg, 0.282 mmol, 1 eq) and 2,8-dimethylimidazo[1,2-a]pyridin-6-amine (68 mg, 0.339 mmol, 1.2 eq). The R.M was filtered and purified by HPLC to give tert-butyl (R)-cyclopropyl(1-(5-((2,8-dimethylimidazo[1,2-a]pyridin-6-yl)carbamoyl)pyrazin-2-yl)pyrrolidin-3-yl)carbamate. LCMS (ES+) 492 (M+H)+

Following Method E TFA Boc deprotection from tert-butyl (R)-cyclopropyl(1-(5-((2,8-dimethylimidazo[1,2-a]pyridin-6-yl)carbamoyl)pyrazin-2-yl)pyrrolidin-3-yl)carbamate (25 mg, 0.0509 mmol, 1 eq). The R.M was purified by HPLC to give (R)-5-(3-(cyclopropylamino)pyrrolidin-1-yl)-N-(2,8-dimethylimidazo[1,2-a]pyridin-6-yl)pyrazine-2-carboxamide. LCMS (ES+) 392 (M+H)+, RT 1.85 min (Analytical method AcHSSC18) $^1$H NMR (400 MHz, DMSO) δ 10.15 (s, 1H), 9.07 (d, J=1.5 Hz, 1H), 8.72 (d, J=1.3 Hz, 1H), 7.96 (d, J=1.3 Hz, 1H), 7.69 (d, J=0.9 Hz, 1H), 7.33 (dd, J=1.2, 1.9 Hz, 1H), 3.72-3.51 (m, 4H), 3.42-3.36 (m, 1H), 2.43 (s, 3H), 2.31 (s, 3H), 2.15-2.07 (m, 2H), 1.94 (s, 1H), 0.40 (d, J=6.5 Hz, 2H), 0.27-0.19 (m, 2H).

The following examples were prepared using an analogous procedure starting from (R)-5-(3-((tert-butoxycarbonyl)(methyl)amino)pyrrolidin-1-yl)pyrazine-2-carboxylic acid and the stated amine. Final products were isolated by SCX and/or Preparative HPLC.

| Example | Structure | Amine | Analytical data |
|---|---|---|---|
| Example 182 | 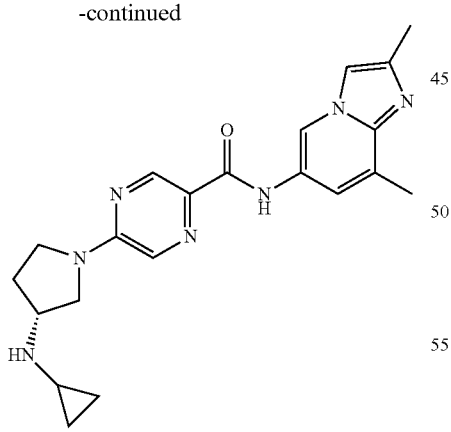 | 6-methoxy-2-methylpyrazolo[1,5-a]pyridin-5-amine. 2HBr | LCMS (ES+) 408 (M + H)+, RT 2.94 min (Analytical method AcHSSC18) $^1$H NMR (400 MHz, DMSO) δ 10.00 (s, 1H), 8.77 (s, 1H), 8.46 (s, 1H), 8.39 (s, 1H), 8.08 (s, 1H), 6.26 (s, 1H), 3.97 (s, 3H), 3.83-3.61 (m, 6H), 2.33 (s, 3H), 2.20-2.14 (m, 1H), 1.75-1.69 (m, 1H), 0.63-0.62 (m, 4H). |

Example 183 (R)—N-(7-methoxy-2-methylimidazo[1,2-a]pyridin-6-yl)-5-(3-(methylamino)pyrrolidin-1-yl)pyrazine-2-carboxamide

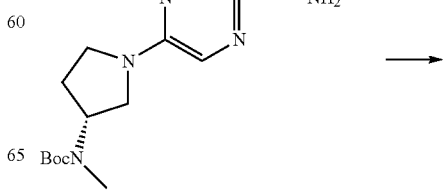

-continued

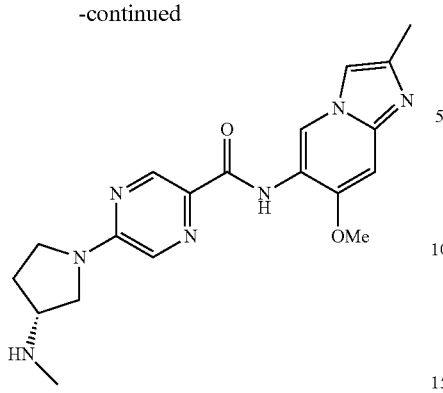

Following Method F CuI coupling conditions from tert-butyl (R)-(1-(5-carbamoylpyrazin-2-yl)pyrrolidin-3-yl)(methyl)carbamate (100 mg, 0.311 mmol, 1 eq) and 6-bromo-7-methoxy-2-methylimidazo[1,2-a]pyridine (97 mg, 0.404 mmol, 1.3 eq). After the reaction was complete, the R.M was diluted with water and the aqueous layer washed with EtOAc (×3). The combined organics were washed with brine, dried (phase separating filter paper) and the solvent removed in vacuo. The residue was purified by HPLC to give tert-butyl (R)-(1-(5-((7-methoxy-2-methyl-imidazo[1,2-a]pyridin-6-yl)carbamoyl)pyrazin-2-yl)pyrrolidin-3-yl)(methyl)carbamate. LCMS (ES+) 482 (M+H)+.

Following Method E TFA Boc deprotection from tert-butyl (R)-(1-(5-((7-methoxy-2-methylimidazo[1,2-a]pyridin-6-yl)carbamoyl)pyrazin-2-yl)pyrrolidin-3-yl)(methyl)carbamate (21 mg, 0.0436 mmol, 1 eq). The R.M was concentrated in vacuo. The residue was loaded onto a 1 g SCX and eluted with MeOH then 7M $NH_3$ in MeOH. The ammonia fraction was concentrated in vacuo to give (R)—N-(7-methoxy-2-methylimidazo[1,2-a]pyridin-6-yl)-5-(3-(methylamino)pyrrolidin-1-yl)pyrazine-2-carboxamide. LCMS (ES+) 382 (M+H)+, RT 1.86 min (Analytical method AcHSSC18) $^1$H NMR (400 MHz, DMSO) δ 9.76 (s, 1H), 9.36 (s, 1H), 8.74 (d, J=1.0 Hz, 1H), 8.05 (s, 1H), 7.60 (s, 1H), 7.00 (s, 1H), 3.99 (s, 3H), 3.69-3.57 (m, 5H), 2.34 (s, 3H), 2.28 (s, 3H), 2.10 (s, 1H), 1.92 (s, 1H).

The following examples were prepared using an analogous procedure starting from tert-butyl (R)-(1-(5-carbamoylpyrazin-2-yl)pyrrolidin-3-yl)(methyl)carbamate and the stated bromo heterocycle.

Example 185: 5-(3-((cyclopropylamino)methyl)azetidin-1-yl)-N-(6-methoxy-2-methylpyrazolo[1,5-a]pyridin-5-yl)pyrazine-2-carboxamide

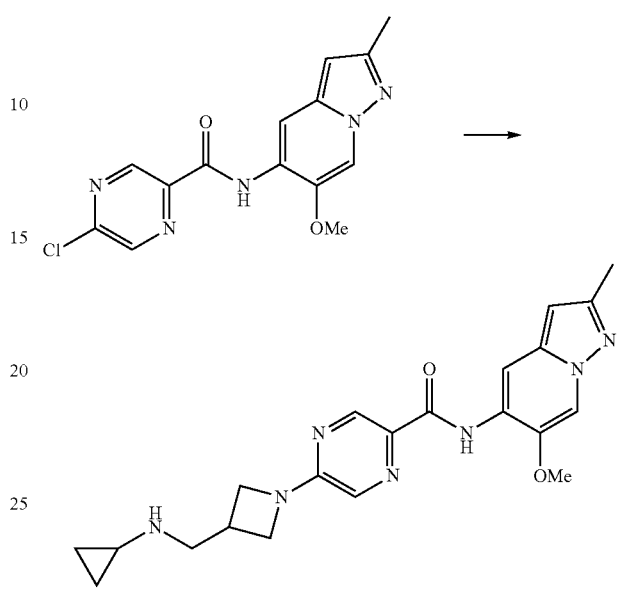

Following Method D (SNAr displacement) from 5-chloro-N-(6-methoxy-2-methylpyrazolo[1,5-a]pyridin-5-yl)pyrazine-2-carboxamide (150 mg, 0.312 mmol, 1 eq) and N-(azetidin-3-ylmethyl)cyclopropanamine 2HCl (124 mg, 0.623 mmol, 2 eq). After the reaction was complete, the reaction mixture was diluted with water and EtOAc and the layers separated. The aqueous layer was washed with EtOAc (×2), and the combined organics were washed with brine, dried (phase separating filter paper) and the solvent removed in vacuo. The residue was purified by HPLC to give 5-(3-((cyclopropylamino)methyl)azetidin-1-yl)-N-(6-methoxy-2-methylpyrazolo[1,5-a]pyridin-5-yl)pyrazine-2-carboxamide. LCMS (ES+) 408 (M+H)+, RT 4.04 min (Analytical method BicarbBEHC18). $^1$H NMR (400 MHz, DMSO) δ 9.98 (s, 1H), 8.71 (d, J=1.3 Hz, 1H), 8.45 (s, 1H), 8.40 (s, 1H), 7.89 (d, J=1.4 Hz, 1H), 6.26 (s, 1H), 4.21 (dd, J=8.3, 8.3 Hz, 2H), 3.95 (s, 3H), 3.85 (dd, J=5.0, 9.2 Hz, 2H),

| Example | Structure | Het-Br | Analytical data |
| --- | --- | --- | --- |
| Example 184 | ![structure] | 6-bromo-4-fluoro-2-methylbenzo[d]oxazole | LCMS (ES+) 371 (M + H)+, RT 2.58 min (Analytical method AcHSSC18) $^1$H NMR (400 MHz, DMSO) δ 10.58 (s, 1H), 8.77 (d, J = 1.3 Hz, 1H), 8.20 (d, J = 1.6 Hz, 1H), 7.98 (d, J = 1.3 Hz, 1H), 7.85 (dd, J = 2.2, 12.9 Hz, 1H), 3.70-3.57 (m, 3H), 3.40 (d, J = 11.2 Hz, 1H), 2.63 (s, 3H), 2.33 (s, 3H), 2.17-2.08 (m, 2H), 1.92-1.92 (m, 1H). |

2.90-2.84 (m, 2H), 2.38-2.38 (m, 1H), 2.33 (s, 3H), 2.08-2.02 (m, 1H), 0.39-0.34 (m, 2H), 0.22-0.18 (m, 2H).

Example 186: (R)-5-(3-(cyclopropylamino)pyrrolidin-1-yl)-N-(8-fluoro-2-(fluoromethyl)imidazo[1,2-a]pyridin-6-yl)pyrazine-2-carboxamide

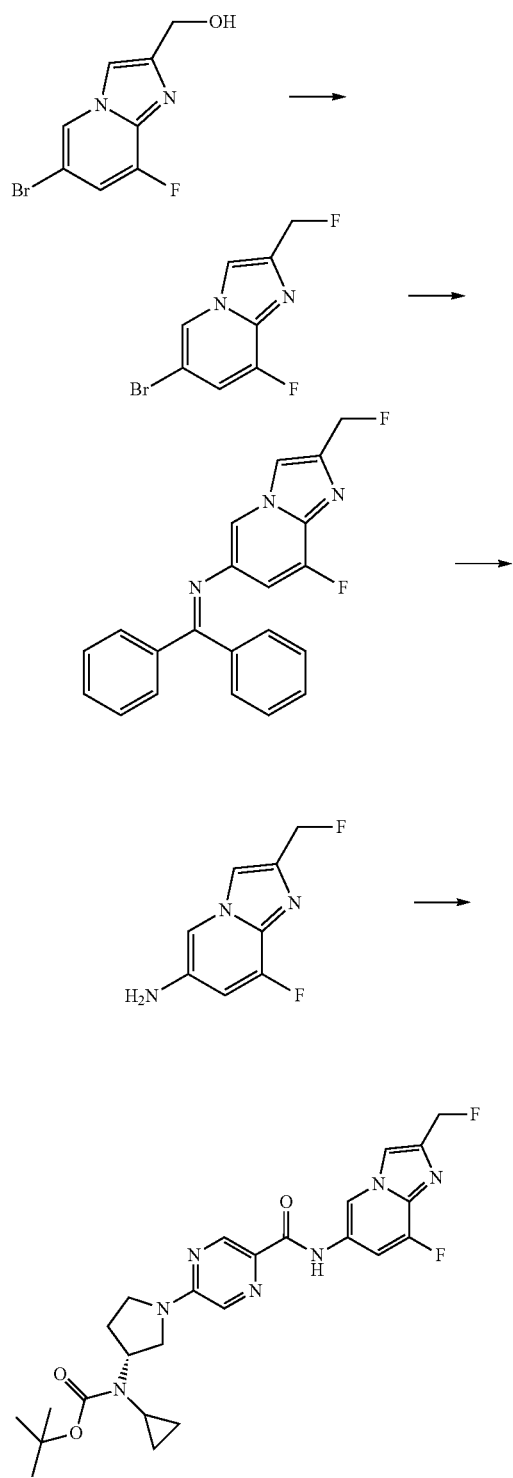

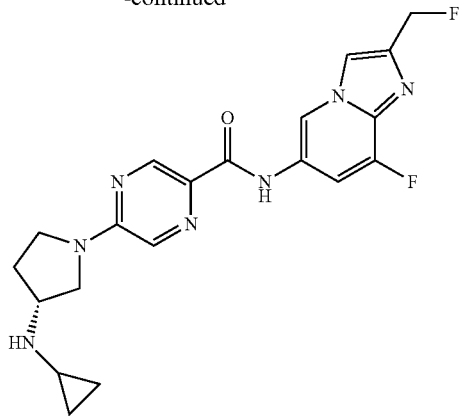

(6-Bromo-8-fluoroimidazo[1,2-a]pyridin-2-yl)methanol (200 mg, 0.82 mmol) was dissolved in DCM (5 mL) and the mixture cooled in an ice-bath. DAST (0.16 mL, 1.22 mmol) was added dropwise and the reaction allowed to warm to r.t. over 18 h. The reaction was cooled in an ice-bath and quenched with saturated sodium hydrogencarbonate. The aqueous layer was extracted with DCM (×2), the layers being separated using a phase separator. The solvent was removed in vacuo to give a residue, which was purified using silica chromatography, elution gradient 0-50% EtOAc/cyclohexane to give the product.

6-Bromo-8-fluoro-2-(fluoromethyl)imidazo[1,2-a]pyridine (118 mg, 0.48 mmol) was dissolved in THF (4 mL). Benzophenone imine (87 mg, 0.48 mmol) and cesium carbonate (233 mg, 0.72 mmol) was added and the reaction degassed with nitrogen for 15 minutes. To the mixture was added rac-BINAP (30 mg, 0.048 mmol) and palladium acetate (11 mg, 0.048 mmol) and the mixture degassed with nitrogen for a further 15 minutes. The reaction tube was sealed and heated at 70° C. for 18 h. The reaction was cooled to r.t. and the solvent removed in vacuo. The residue was purified by silica chromatography, elution gradient 0-100% EtOAc/cyclohexane to give the product.

N-(8-Fluoro-2-(fluoromethyl)imidazo[1,2-a]pyridin-6-yl)-1,1-diphenylmethanimine (127 mg, 0.37 mmol) was dissolved in methanol (2 mL) and 4M HCl in dioxane (4 mL) was added. The reaction was stirred at r.t. for 4 h. The solvent was removed in vacuo to give a residue, which was further purified by SCX chromatography, eluting with methanol and then 10% 7N ammonia in methanol/methanol. The ammonical fractions were combined and the solvent removed in vacuo to give the product.

8-Fluoro-2-(fluoromethyl)imidazo[1,2-a]pyridin-6-amine (31 mg, 0.17 mmol) and lithium (R)-5-(3-((tert-butoxycarbonyl)(cyclopropyl)amino)pyrrolidin-1-yl)pyrazine-2-carboxylate (60 mg, 0.17 mmol) were dissolved in DMF (2 mL), then TEA (0.5 mL) and HBTU (71 mg, 0.18 mmol) were added. The reaction was stirred at r.t. for 18 h. The solvent was removed in vacuo and the residue purified by preparative HPLC to give the product.

tert-Butyl (R)-cyclopropyl(1-(5-((8-fluoro-2-(fluoromethyl)imidazo[1,2-a]pyridin-6-yl)carbamoyl)pyrazin-2-yl)pyrrolidin-3-yl)carbamate (21 mg, 0.04 mmol) was dissolved in DCM (1.7 mL) and TFA (0.3 mL) was added. The reaction was stirred at r.t. for 3 h and the solvent removed in vacuo to give a residue, which was further purified by SCX chromatography, eluting with methanol and then 10% 7N ammonia in methanol/methanol. The ammonical fractions were combined and the solvent removed in vacuo to give a residue, which was further purified by silica chromatography, elution gradient 0-100% 3:1 EtOAc:ethanol/cyclohexane to give the title compound. LCMS (ES+) 413 (M+H)+, RT 2.25 min (Analytical method AcHSSC18); $^1$H NMR (400 MHz, DMSO) δ 10.48 (s, 1H), 9.32 (d, J=1.5 Hz, 1H), 8.74 (d, J=1.4 Hz, 1H), 8.30 (t, J=3.3 Hz, 1H), 7.96 (d, J=1.3 Hz, 1H), 7.68 (dd, J=1.5, 13.1 Hz, 1H), 5.49 (d, J=48.6 Hz, 1H), 3.71-3.51 (m, 4H), 3.45-3.37 (m, 1H), 2.14-2.07 (m, 2H), 1.95 (brs, 1H), 0.42-0.39 (m, 2H), 0.27-0.20 (m, 2H).

Example 187: (R)-5-(3-(Cyclopropyl(methyl)amino) pyrrolidin-1-yl)-N-(8-fluoro-2-methylimidazo[1,2-a] pyridin-6-yl)pyrazine-2-carboxamide

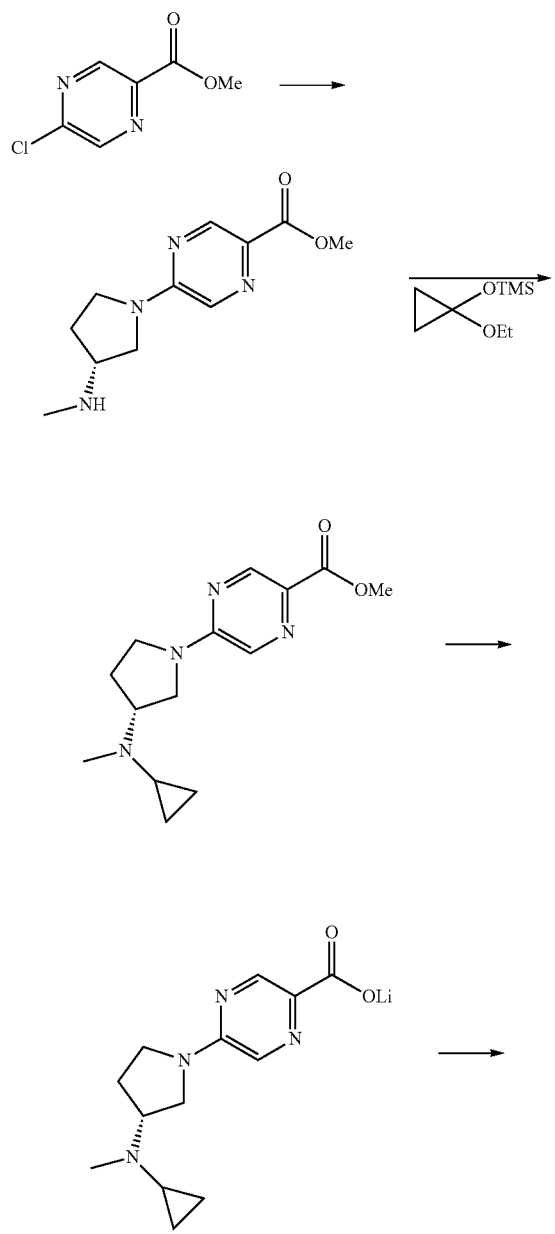

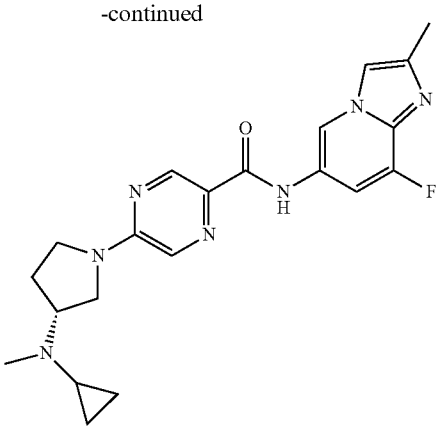

Methyl 5-chloropyrazine-2-carboxylate (377 mg, 2.19 mmol), (R)—N-methylpyrrolidin-3-amine (219 mg, 2.19 mmol), cesium carbonate (775 mg, 3 mmol) and DMF (15 mL) were combined in a sealed tube and hot block heated to 100° C. for 22 hours. Cesium salts were removed by filtration, rinsing with EtOAc. Combined organic filtrate was evaporated to dryness in vacuo to give methyl (R)-5-(3-(methylamino)pyrrolidin-1-yl)pyrazine-2-carboxylate, which was used crude in next step.

(R)-5-(3-(methylamino)pyrrolidin-1-yl)pyrazine-2-carboxylate (crude from previous step), (1-ethoxycyclopropoxy)trimethylsilane (0.44 ml, 2.19 mmol) and MeOH (30 mL) were combined. Sodium cyanoborohydride (151 mg, 2.4 mmol) was added, followed by AcOH (0.2 mL), and the mixture was hot block heated to 55° C. for 3 days. The reaction mixture was then diluted with dichloromethane, washed with sat. aq. NaHCO$_3$ (1×), dried (MgSO$_4$) and evaporated in vacuo to give methyl (R)-5-(3-(cyclopropyl(methyl)amino)pyrrolidin-1-yl)pyrazine-2-carboxylate, which was used crude in next step.

Methyl (R)-5-(3-(cyclopropyl(methyl)amino)pyrrolidin-1-yl)pyrazine-2-carboxylate (crude from previous step), lithium hydroxide monohydrate (81 mg, 1.92 mmol), methanol (15 mL) and water (2 mL) were combined and hot block heated to 50° C. for 23 hours. The reaction mixture was then evaporated to dryness in vacuo to give lithium (R)-5-(3-(cyclopropyl(methyl)amino)pyrrolidin-1-yl)pyrazine-2-carboxylate, which was used crude in next step. LCMS (ES+) 263 (M+H)+ for acid.

Lithium (R)-5-(3-(cyclopropyl(methyl)amino)pyrrolidin-1-yl)pyrazine-2-carboxylate (107 mg, 0.4 mmol), 8-fluoro-2-methylimidazo[1,2-a]pyridin-6-amine (66 mg, 0.4 mmol), HBTU (152 mg, 0.4 mmol), triethylamine (0.5 mL) and DMF (3 mL) were combined and stirred at room temperature for 18 hours. The reaction mixture was purified by preparative HPLC to give the title compound. LCMS (ES+) 410 (M+H)+, RT 1.81 min (Analytical method AcHSSC18). $^1$H NMR (400 MHz, DMSO) δ 10.42 (s, 1H), 9.19 (d, J=1.6 Hz, 1H), 8.76 (d, J=1.3 Hz, 1H), 8.00 (s, 1H), 7.90 (d, J=2.8 Hz, 1H), 7.57 (dd, J=1.7, 13.1 Hz, 1H), 3.89-3.84 (m, 1H), 3.79-3.72 (m, 1H), 3.56-3.39 (m, 2H), 3.27-3.25 (m, 1H), 2.34 (d, J=3.3 Hz, 6H), 2.22-2.22 (m, 1H), 2.05-1.97 (m, 1H), 1.80-1.74 (m, 1H), 0.52-0.49 (m, 2H), 0.42-0.34 (m, 2H).

Further analogues were prepared using the same chemistry from commercially available or synthesised amines. Final products were isolated by Preparative HPLC.

| Example | Structure | Analytical data |
|---|---|---|
| Example 188 | 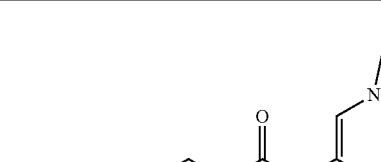 | LCMS (ES+) 410 (M + H)+, RT 1.80 min (Analytical method AcHSSC18). ¹H NMR (400 MHz, DMSO) δ 10.42 (s, 1H), 9.19 (d, J = 1.6 Hz, 1H), 8.76 (d, J = 1.3 Hz, 1H), 8.00 (s, 1H), 7.90 (d, J = 2.8 Hz, 1H), 7.57 (dd, J = 1.6, 13.2 Hz, 1H), 3.88-3.83 (m, 1H), 3.78-3.73 (m, 1H), 3.55-3.48 (m, 1H), 3.44-3.36 (m, 1H), 3.29 (s, 1H), 3.29-3.24 (m, 1H), 2.34 (d, J = 3.4 Hz, 6H), 2.27-2.23 (m, 1H), 2.11-1.95 (m, 1H), 1.80-1.74 (m, 1H), 0.51 (dd, J = 1.8, 6.5 Hz, 2H), 0.43-0.35 (m, 2H). |
Example 189: (S)-5-(3-((cyclopropylamino)methyl)pyrrolidin-1-yl)-N-(8-methoxy-2-methylimidazo[1,2-a]pyrazin-6-yl)pyrazine-2-carboxamide
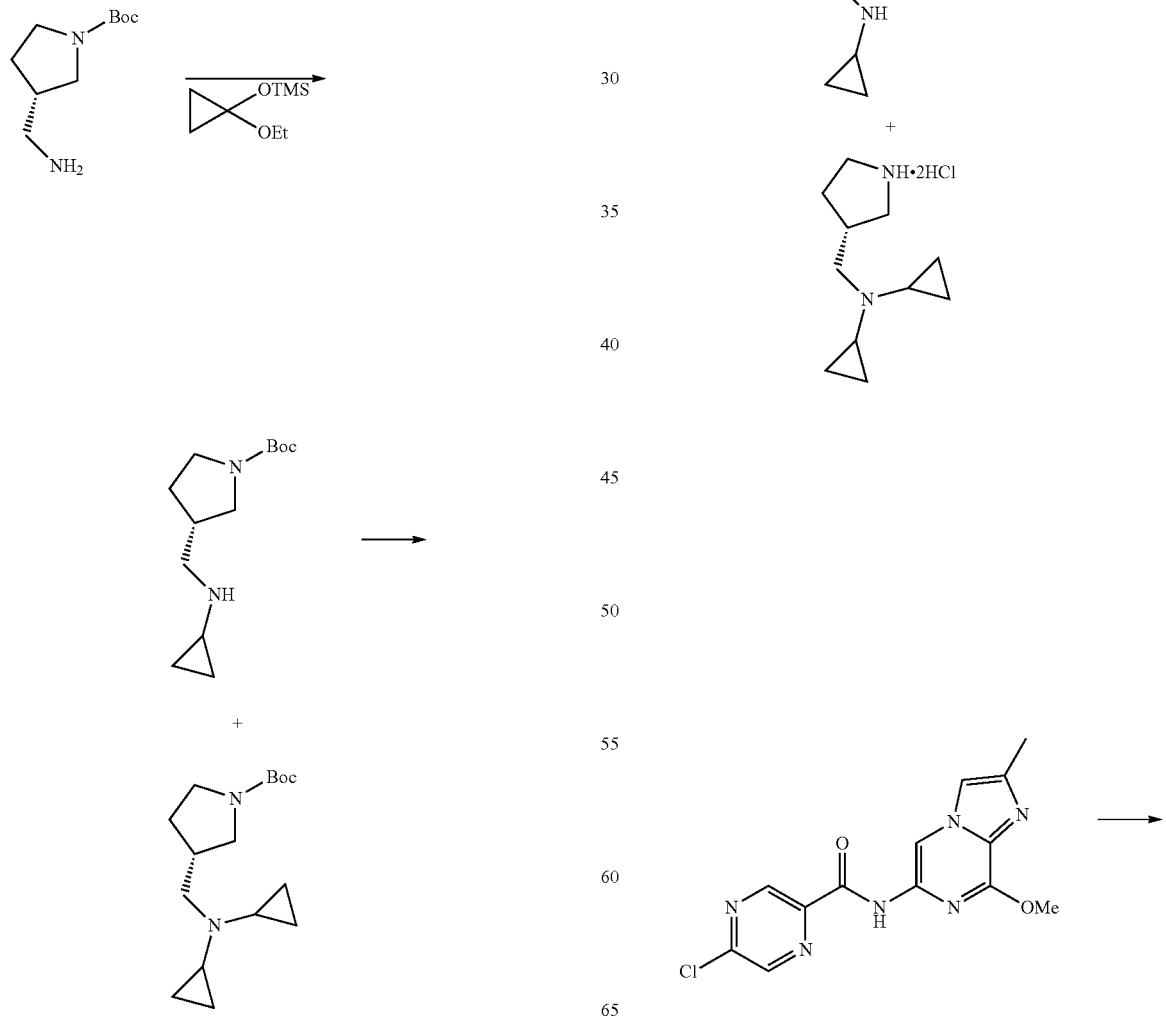

517

-continued

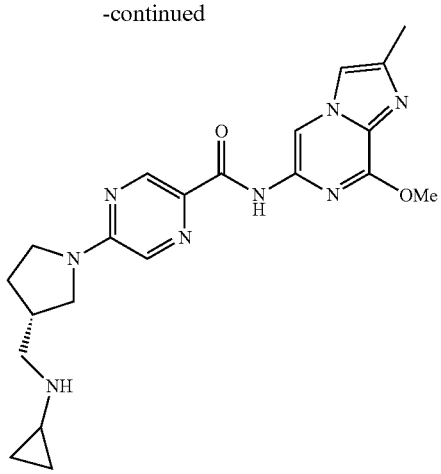

(S)-3-(Aminomethyl)-1-Boc-pyrrolidine (855 mg, 4.27 mmol, 1.00 eq), (1-ethoxycyclopropoxy)trimethylsilane (0.86 mL, 4.27 mmol, 1.00 eq), and methyl alcohol (50.00 mL) were combined. Sodium cyanoborohydride (295 mg, 4.70 mmol, 1.10 eq) was added, followed by acetic acid (0.20 mL). The reaction was then hot block heated to 55° C. for 18 hours. The reaction was then cooled to room temperature, diluted with dichloromethane, washed with 10% NaOH solution, dried (MgSO$_4$) and concentrated in vacuo to give a mixture of tert-butyl (3S)-3-[(cyclopropylamino) methyl]pyrrolidine-1-carboxylate and tert-butyl (S)-3-((dicyclopropylamino)methyl)pyrrolidine-1-carboxylate, which was used directly in next step.

A mixture of tert-butyl (3S)-3-[(cyclopropylamino) methyl]pyrrolidine-1-carboxylate and tert-butyl (S)-3-((dicyclopropylamino)methyl)pyrrolidine-1-carboxylate (868 mg, 3.61 mmol, 1.00 eq), methyl alcohol (10.00 mL), and 4 M Hydrogen chloride in dioxane (5.0 mL, 20.0 mmol, 5.54 eq) were combined and stirred at room temperature for 20 hours. The reaction mixture was concentrated in vacuo to give a mixture of N-[[(3R)-pyrrolidin-3-yl]methyl]cyclopropanamine dihydrochloride and (R)—N-cyclopropyl-N-(pyrrolidin-3-ylmethyl)cyclopropanamine dihydrochloride, which was used directly in the next step. 5-Chloro-N-(8-methoxy-2-methyl-imidazo[1,2-a]pyrazin-6-yl)pyrazine-2-carboxamide (67 mg, 0.210 mmol, 1.00 eq), a mixture of N-[[(3R)-pyrrolidin-3-yl]methyl]cyclopropanamine dihydrochloride and (R)—N-cyclopropyl-N-(pyrrolidin-3-ylmethyl)cyclopropanamine dihydrochloride (93 mg, 0.436 mmol, 2.08 eq), cesium carbonate (200 mg, 0.614 mmol, 2.92 eq) and N,N-dimethylformamide (3.00 mL) were combined in a sealed tube and heated to 100° C. for 3.5 hours. The reaction was then cooled to room temperature. The cesium salts were removed by filtration and purified by prep HPLC to give 5-[(3S)-3-[(cyclopropylamino)methyl]pyrrolidin-1-yl]-N-(8-methoxy-2-methyl-imidazo[1,2-a]pyrazin-6-yl)pyrazine-2-carboxamide. LCMS (ES+) 423 (M+H)+, RT 2.15 min (Analytical method AcHSSC18). $^1$H NMR (400 MHz, DMSO) δ 9.52 (s, 1H), 8.93 (s, 1H), 8.77 (d, J=1.3 Hz, 1H), 8.05 (d, J=1.1 Hz, 1H), 7.98 (s, 1H), 4.09 (s, 3H), 3.78-3.66 (m, 2H), 3.57-3.41 (m, 1H), 3.34-3.25 (m, 1H), 2.76-2.62 (m, 2H), 2.50 (t, J=3.6 Hz, 1H), 2.38 (s, 4H), 2.14-2.08 (m, 2H), 1.77 (t, J=5.4 Hz, 1H), 0.42-0.39 (m, 2H), 0.26 (dd, J=1.6, 3.5 Hz, 2H).

518

Example 190: 5-(3-((cyclopropylamino)methyl) azetidin-1-yl)-N-(8-fluoro-2-methylimidazo[1,2-a] pyridin-6-yl)pyrazine-2-carboxamide

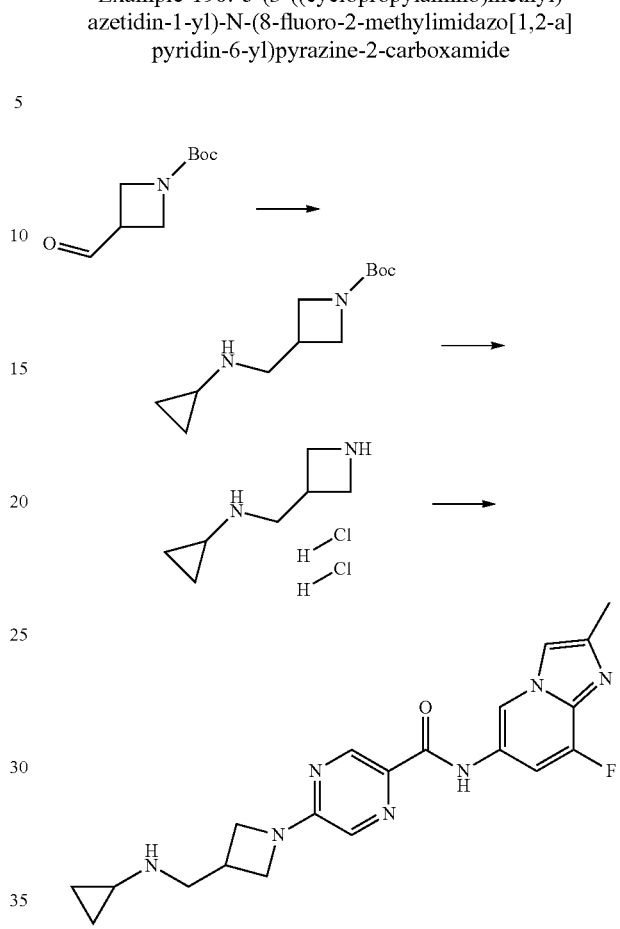

Tert-Butyl 3-((cyclopropylamino)methyl)azetidine-1-carboxylate

Cyclopropylamine (2.1 mL, 29.7 mmol), tert-butyl 3-formylazetidine-1-carboxylate (5.00 g, 27.0 mmol) and sodium triacetoxyborohydride (12.59 g, 59.4 mmol) were combined in dichloromethane (50.00 mL) and stirred at r.t. for 17 h. Saturated aqueous sodium hydrogen carbonate solution (200 mL) was added to the reaction mixture and stirred vigorously for 10 mins. The organics were collected and washed with water and brine, before passing through a phase separator and concentrating to dryness to give the title compound, which was progressed to the next step directly.

N-(Azetidin-3-ylmethyl)cyclopropanamine tert-Butyl 3-[(cyclopropylamino)methyl]azetidine-1-carboxylate (2.15 g, 9.50 mmol, 1.00 eq) and 4 M hydrogen chloride in dioxane (12 mL, 47.5 mmol, 5.00 eq) were stirred in methyl alcohol (15.00 mL) at r.t. for 6 h, before concentrating to dryness to give title compound, which was progressed to the next step directly.

N-(Azetidin-3-ylmethyl)cyclopropanamine dihydrochloride (129 mg, 0.650 mmol, 1.00 eq), cesium carbonate (847 mg, 2.60 mmol, 4.00 eq) and 5-chloro-N-(8-fluoro-2-methyl-imidazo[1,2-a]pyridin-6-yl)pyrazine-2-carboxamide (199 mg, 0.650 mmol, 1.00 eq) were combined in N,N-dimethylformamide (5.00 mL) and stirred at 100° C. for 17 h. LCMS showed product to be present. The residue was partitioned between EtOAc and water. The aqueous phase was extracted with EtOAc. The combined organic phases were dried over magnesium sulfate, filtered and concentrated in vacuo. Purification by preparative HPLC followed by Et₂O trituration gave 5-(3-((cyclopropylamino)methyl)azetidin-1-yl)-N-(8-fluoro-2-methylimidazo[1,2-a]pyridin-6-yl)pyrazine-2-carboxamide. LCMS (ES+) 396 (M+H)+, RT 1.8 min (Analytical method AcHSSC18). ¹H NMR (400 MHz, DMSO) δ 10.45 (s, 1H), 9.20 (d, J=1.5 Hz, 1H), 8.73 (d, J=1.3 Hz, 1H), 7.91 (d, J=2.8 Hz, 1H), 7.86 (d, J=1.4 Hz, 1H), 7.58 (dd, J=1.7, 12.9 Hz, 1H), 4.23 (dd, J=8.3, 8.3 Hz, 2H), 3.88 (dd, J=5.0, 9.0 Hz, 2H), 2.95-2.88 (m, 3H), 2.42 (s, 1H), 2.37 (s, 3H), 2.12-2.09 (m, 1H), 0.42-0.38 (m, 2H), 0.25-0.22 (m, 2H).

Further analogues were prepared using the similar chemistry except using method C for the Boc deprotection from commercially available or synthesised amines. Some amines were used as the HCl salts. Final products were isolated by Preparative HPLC.

| Example | Structure | Amine | Analytical data |
|---------|-----------|-------|-----------------|
| Example 191 | 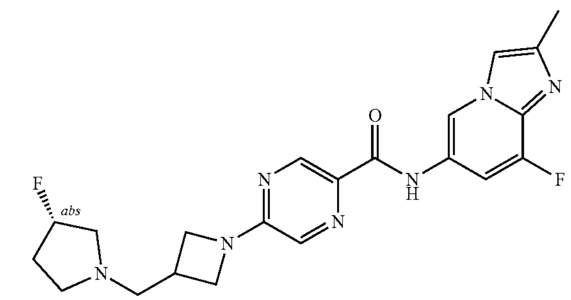 | (S)-1-(azetidin-3-ylmethyl)-3-fluoropyrrolidine dihydrochloride | LCMS (ES+) 428 (M + H)+, RT 1.76 min (Analytical method AcHSSC18) ¹H NMR (400 MHz, DMSO) δ 10.45 (s, 1H), 9.19 (d, J = 1.5 Hz, 1H), 8.72 (d, J = 1.4 Hz, 1H), 7.90-7.87 (m, 2H), 7.57 (dd, J = 2.0, 12.9 Hz, 1H), 5.30-5.26 (m, 0.5H), 5.16-5.12 (m, 0.5H), 4.29 (dd, J = 8.6, 8.6 Hz, 2H), 3.87 (dd, J = 5.6, 9.1 Hz, 2H), 3.04-2.95 (m, 1H), 2.90-2.57 (m, 6H), 2.35 (s, 3H), 2.23-2.06 (m, 1H), 1.96-1.79 (m, 1H). |
| Example 192 | 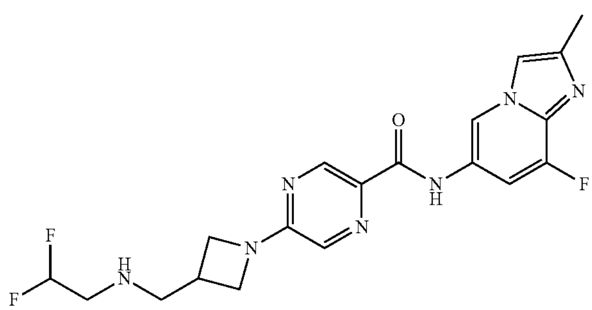 [SMILES: Cc1cn2cc(NC(=O)c3cnc(N4CC(CNCC(F)F)C4)cn3)cc(F)c2n1] | N-(azetidin-3-ylmethyl)-2,2-difluoroethan-1-amine dihydrochloride | LCMS (ES+) 420 (M + H)+, RT 1.77 min (Analytical method AcHSSC18) ¹H NMR (400 MHz, DMSO) δ 10.44 (s, 1H), 9.19 (d, J = 1.5 Hz, 1H), 8.72 (d, J = 1.3 Hz, 1H), 7.90 (d, J = 2.6 Hz, 1H), 7.86 (d, J = 1.4 Hz, 1H), 7.56 (dd, J = 1.7, 13.4 Hz, 1H), 6.01 (tt, J = 4.6, 56.1 Hz, 1H), 4.24 (dd, J = 8.2, 8.2 Hz, 2H), 3.89 (dd, J = 4.6, 9.0 Hz, 2H), 2.98-2.85 (m, 5H), 2.35 (s, 3H), 2.23 (s, 1H). |
| Example 193 | 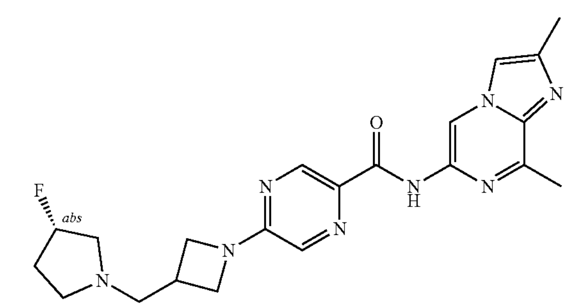 | (S)-1-(azetidin-3-ylmethyl)-3-fluoropyrrolidine-dihydrochloride | LCMS (ES+) 425.385 (M+ H)+, RT 1.97 min (Analytical method AcHSSC18). ¹H NMR (400 MHz, DMSO) δ 9.68 (s, 1H), 9.14 (s, 1H), 8.73 (d, J = 1.4 Hz, 1H), 8.01 (s, 1H), 7.92 (d, J = 1.4 Hz, 1H), 5.30-5.12 (m, 1H), 4.29 (dd, J = 8.6, 8.6 Hz, 2H), 3.87 (dd, J = 5.4, 9.0 Hz, 2H), 3.04-2.96 (m, 1H), 2.89-2.74 (m, 4H), 2.71 (s, 3H), 2.69-2.57 (m, 1H), 2.40 (s, 3H), 2.37-2.31 (m, 1H), 2.23-2.06 (m, 1H), 1.96-1.80 (m, 1H). |

-continued

| Example | Structure | Amine | Analytical data |
|---|---|---|---|
| Example 194 | 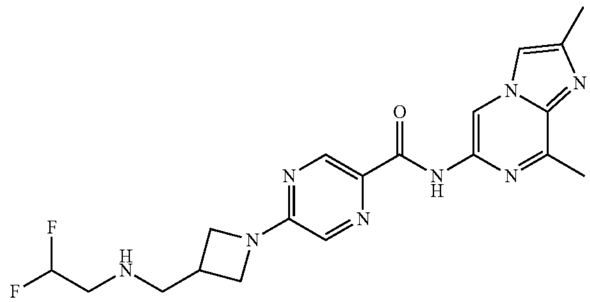 [SMILES: Cc1cn2cc(NC(=O)c3cnc(N4CC(CNCC(F)F)C4)cn3)nc(C)c2n1] | N-(azetidin-3-ylmethyl)-2,2-difluoroethan-1-amine dihydrochloride | LCMS (ES+) 417.36 (M + H)+, RT 3.43 min (Analytical method BicarbBEHC18). $^1$H NMR (400 MHz, DMSO) δ 9.67 (s, 1H), 9.14 (s, 1H), 8.72 (d, J = 1.3 Hz, 1H), 8.01 (s, 1H), 7.90 (d, J = 1.4 Hz, 1H), 6.01 (tt, J = 4.2, 56.5 Hz, 1H), 4.24 (dd, J = 8.3, 8.3 Hz, 2H), 3.89 (dd, J = 4.8, 9.0 Hz, 2H), 2.98-2.84 (m, 5H), 2.71 (s, 3H), 2.40 (s, 3H), 2.26-2.23 (m, 1H). |
| Example 195 | Enantiomer 1 | rac-N-(1-(azetidin-3-yl)ethyl)cyclopropanamine dihydrochloride | LCMS (ES+) 423.425 (M + H)+, RT 3.86 min (Analytical method BicarbBEHC18). RT 19.7 min (SFC1, YMC AMYLOSE-C + 0.1% DEAISO 20% IPA SOL3). $^1$H NMR (400 MHz, DMSO) δ 8.88 (s, 1H), 8.69 (d, J = 1.4 Hz, 1H), 7.89 (s, 1H), 7.84 (d, J = 1.4 Hz, 1H), 4.21-4.13 (m, 2H), 4.04 (s, 3H), 3.99-3.84 (m, 2H), 2.90-2.81 (m, 1H), 2.74-2.65 (m, 1H), 2.33 (s, 3H), 2.12-2.05 (m, 1H), 1.03 (d, J = 6.3 Hz, 3H), 0.43-0.12 (m, 4H). |
| Example 196 | Enantiomer 2 | rac-N-(1-(azetidin-3-yl)ethyl)cyclopropanamine dihydrochloride | LCMS (ES+) 423.425 (M + H)+, RT 3.86 min (Analytical method BicarbBEHC18). RT 15.88 min (SFC1, YMC AMYLOSE-C + 0.1% DEAISO 20% IPA SOL3). $^1$H NMR (400 MHz, DMSO) δ 8.89 (s, 1H), 8.70 (d, J = 1.4 Hz, 1H), 7.91 (s, 1H), 7.86 (d, J = 1.3 Hz, 1H), 3.99-3.85 (m, 2H), 2.89-2.82 (m, 1H), 2.74-2.65 (m, 1H), 2.33 (s, 3H), 2.12-2.05 (m, 1H), 1.23 (s, 1H), 1.03 (d, J = 6.3 Hz, 3H), 0.43-0.12 (m, 4H). |
| Example 197 | 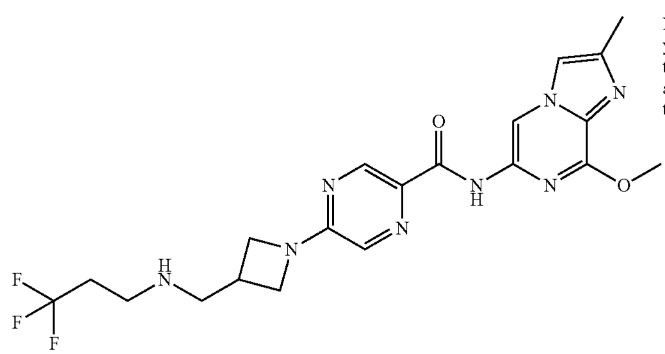 | N-(azetidin-3-ylmethyl)-3,3,3-trifluoropropan-1-amine bis trifluoroacetate | LCMS (ES+) 465 (M + H)+, RT 2.25 min (Analytical method AcHSSC18). $^1$H NMR (400 MHz, DMSO) 9.51 (s, 1H), 8.91 (s, 1H), 8.72 (d, J = 1.3 Hz, 1H), 7.95 (s, 1H), 7.91 (d, J = 1.4 Hz, 1H), 4.24 (dd, J = 8.6, 8.6 Hz, 2H), 4.07 (s, 3H), 3.89 (dd, J = 5.3, 9.2 Hz, 2H), 3.32-3.30 (m, 1H), 3.29 (s, 1H), 2.90 (dd, J = 7.7, 14.6 Hz, 1H), 2.83-2.73 (m, 4H), 2.47-2.37 (m, 3H), 2.35 (s, 3H). |

-continued

| Example | Structure | Amine | Analytical data |
|---|---|---|---|
| Example 198 | 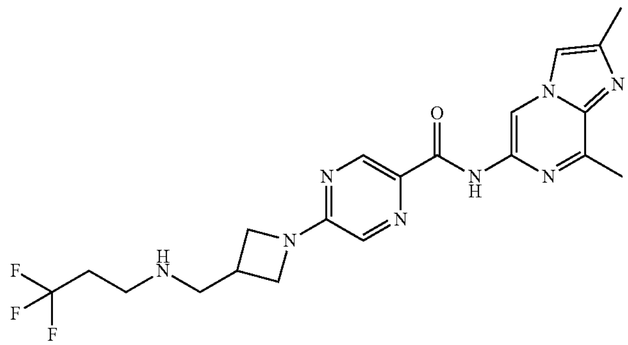 [SMILES: Cc1cn2cc(NC(=O)c3cnc(N4CC(CNCCC(F)(F)F)C4)cn3)nc(C)c2n1] | N-(azetidin-3-ylmethyl)-3,3,3-trifluoropropan-1-amine bis trifluoroacetate | LCMS (ES+) 449 (M + H)+, RT 2.19 min (Analytical method AcHSSC18). $^1$H NMR (400 MHz, DMSO) 9.67 (s, 1H), 9.15 (s, 1H), 8.73 (d, J = 1.3 Hz, 1H), 8.01 (s, 1H), 7.90 (d, J = 1.4 Hz, 1H), 4.25 (dd, J = 8.6, 8.6 Hz, 2H), 3.89 (dd, J = 5.4, 9.0 Hz, 2H), 2.93-2.89 (m, 1H), 2.83-2.73 (m, 4H), 2.71 (s, 3H), 2.41-2.40 (m, 5H), 2.03 (s, 1H). |
| Example 199 | 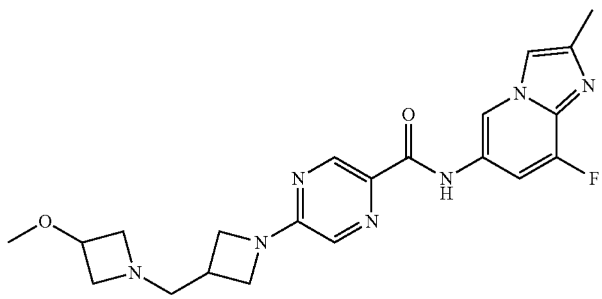 [SMILES: COC1CN(CC2CN(c3cnc(C(=O)Nc4cc(F)c5nc(C)cn5c4)cn3)C2)C1] | 1-(azetidin-3-ylmethyl)-3-methoxyazetidine | LCMS (ES+) 426 (M + H)+, RT 1.79 min (Analytical method AcHSSC18). $^1$H NMR (400 MHz, DMSO) δ 10.43 (s, 1H), 9.18 (d, J = 1.5 Hz, 1H), 8.71 (d, J = 1.3 Hz, 1H), 7.90 (d, J = 2.8 Hz, 1H), 7.85 (d, J = 1.4 Hz, 1H), 7.56 (dd, J = 2.1, 13.2 Hz, 1H), 4.22 (dd, J = 8.5, 8.5 Hz, 2H), 3.96 (dd, J = 5.8, 5.8 Hz, 1H), 3.84 (dd, J = 5.4, 9.0 Hz, 2H), 3.54-3.49 (m, 2H), 3.16 (s, 3H), 2.87-2.78 (m, 3H), 2.69 (d, J = 7.5 Hz, 2H), 2.35 (s, 3H). |
| Example 200 | 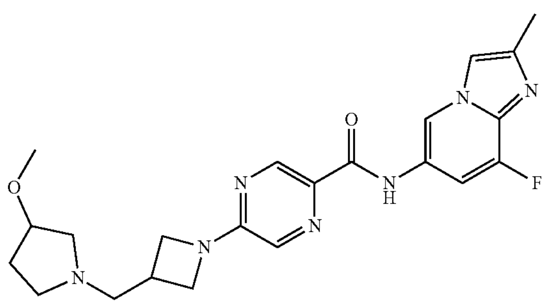 [SMILES: COC1CCN(CC2CN(c3cnc(C(=O)Nc4cc(F)c5nc(C)cn5c4)cn3)C2)C1] | 1-(azetidin-3-ylmethyl)-3-methoxypyrrolidine dihydrochloride | LCMS (ES+) 440 (M + H)+, RT 1.83 min (Analytical method AcHSSC18). $^1$H NMR (400 MHz, DMSO) δ 10.44 (s, 1H), 9.19 (d, J = 1.4 Hz, 1H), 8.71 (s, 1H), 7.91-7.86 (m, 2H), 7.56 (dd, J = 1.5, 12.9 Hz, 1H), 4.27 (dd, J = 8.5, 8.5 Hz, 2H), 3.90-3.83 (m, 2H), 3.18 (s, 3H), 3.02-2.95 (m, 1H), 2.73-2.67 (m, 2H), 2.61-2.55 (m, 1H), 2.48-2.40 (m, 2H), 2.34 (s, 3H), 2.03-1.93 (m, 2H), 1.70-1.61 (m, 2H). |
| Example 201 | 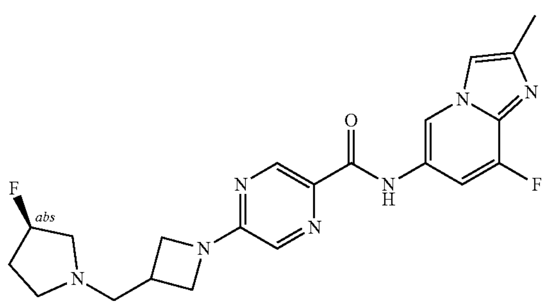 [SMILES: Cc1cn2cc(NC(=O)c3cnc(N4CC(CN5CC[C@@H](F)C5)C4)cn3)cc(F)c2n1] | (R)-1-(azetidin-3-ylmethyl)-3-fluoropyrrolidine dihydrochloride | LCMS (ES+) 428 (M + H)+, RT 3.41 min (Analytical method BicarbBEHC18). $^1$H NMR (400 MHz, DMSO) δ 10.44 (s, 1H), 9.19 (d, J = 1.6 Hz, 1H), 8.72 (d, J = 1.3 Hz, 1H), 7.90-7.87 (m, 2H), 7.56 (dd, J = 1.9, 13.2 Hz, 1H), 5.31-5.26 (m, 1H), 5.16-5.11 (m, 1H), 4.28 (dd, J = 8.6, 8.6 Hz, 2H), 3.87 (dd, J = 5.6, 9.1 Hz, 2H), 3.04-2.95 (m, 1H), 2.89-2.57 (m, 3H), 2.34 (s, 4H), |

-continued

| Example | Structure | Amine | Analytical data |
|---|---|---|---|
| | | | 2.23-2.06 (m, 2H), 1.96-1.79 (m, 2H). |
| Example 202 | 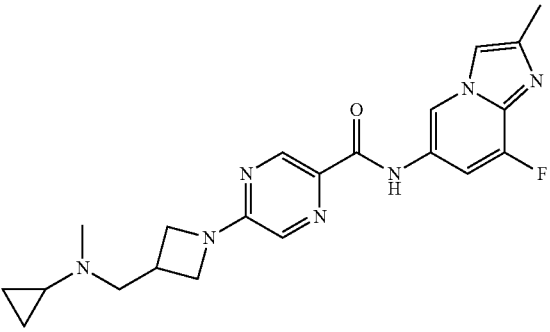 [SMILES: Cc1cn2cc(NC(=O)c3cnc(N4CC(CN(C)C5CC5)C4)cn3)cc(F)c2n1] | N-(azetidin-3-ylmethyl)-N-methylcyclopropanamine dihydrochloride | LCMS (ES+) 410 (M + H)+, RT 3.76 min (Analytical method BicarbBEHC18). $^1$H NMR (400 MHz, DMSO) δ 10.44 (s, 1H), 9.19 (d, J = 1.5 Hz, 1H), 8.72 (d, J = 1.4 Hz, 1H), 7.90 (d, J = 2.8 Hz, 1H), 7.86 (d, J = 1.4 Hz, 1H), 7.57 (dd, J = 1.4, 13.0 Hz, 1H), 4.26 (dd, J = 8.6, 8.6 Hz, 2H), 3.82 (dd, J = 5.5, 9.1 Hz, 2H), 3.10-3.03 (m, 1H), 2.79 (d, J = 7.7 Hz, 2H), 2.35 (s, 3H), 2.28 (s, 3H), 1.69-1.63 (m, 1H), 0.49-0.44 (m, 2H), 0.33-0.28 (m, 2H). |
| Example 203 | 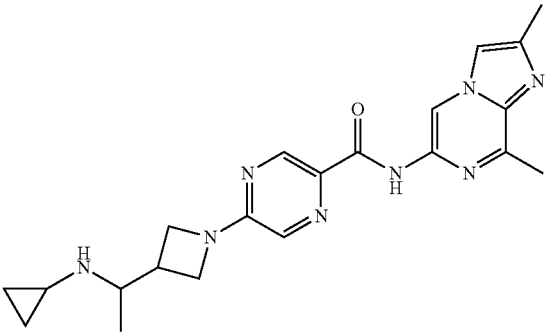<br>Enantiomer 1 | rac-N-(1-(azetidin-3-yl)ethyl)cyclopropanamine dihydrochloride | LCMS (ES+) 407 (M + H)+, RT 3.69 min (Analytical method BicarbBEHC18). RT 5.91 min (SFC1, YMC AMYLOSE-C + 0.1% DEAISO 45% EtOH SOL2). $^1$H NMR (400 MHz, DMSO) δ 9.65 (s, 1H), 9.12 (s, 1H), 8.70 (d, J = 1.4 Hz, 1H), 7.99 (s, 1H), 7.87 (d, J = 1.3 Hz, 1H), 4.22-4.14 (m, 2H), 3.99-3.85 (m, 2H), 2.89-2.83 (m, 1H), 2.69 (s, 4H), 2.38 (s, 3H), 2.17-2.07 (m, 2H), 1.03 (d, J = 6.3 Hz, 3H), 0.44-0.12 (m, 4H). |
| Example 204 | 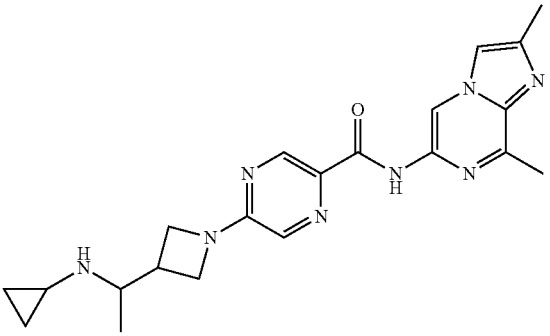<br>Enantiomer 2 | rac-N-(1-(azetidin-3-yl)ethyl)cyclopropanamine dihydrochloride | LCMS (ES+) 407 (M + H)+, RT 3.69 min (Analytical method BicarbBEHC18). RT 3.08 min (SFC1, YMC AMYLOSE-C + 0.1% DEAISO 45% EtOH SOL2). $^1$H NMR (400 MHz, DMSO) δ 9.65 (s, 1H), 9.12 (s, 1H), 8.70 (d, J = 1.4 Hz, 1H), 7.99 (s, 1H), 7.87 (d, J = 1.4 Hz, 1H), 4.22-4.14 (m, 2H), 3.99-3.86 (m, 2H), 2.89-2.82 (m, 1H), 2.69 (s, 4H), 2.38 (s, 3H), 2.15-2.08 (m, 2H), 1.03 (d, J = 6.3 Hz, 3H), 0.44-0.12 (m, 4H). |

| Example | Structure | Amine | Analytical data |
|---|---|---|---|
| Example 205 | 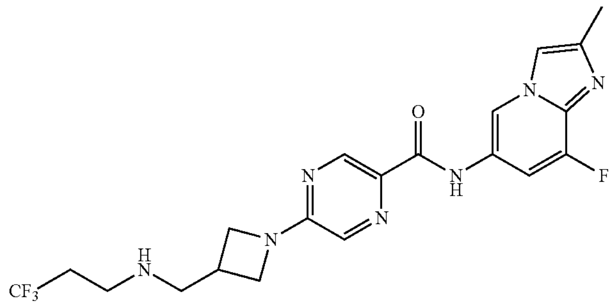 [SMILES: Cc1cn2cc(NC(=O)c3cnc(N4CC(CNCCC(F)(F)F)C4)cn3)cc(F)c2n1] | N-(azetidin-3-ylmethyl)-3,3,3-trifluoropropan-1-amine bis trifluoroacetate | LCMS (ES +) 452 (M + H)+, RT 1.97 min (Analytical method AcHSSC18) ¹H NMR (400 MHz, DMSO) δ 10.44 (s, 1H), 9.19 (d, J = 1.6 Hz, 1H), 8.72 (d, J = 1.3 Hz, 1H), 7.90 (d, J = 3.0 Hz, 1H), 7.86 (d, J = 1.4 Hz, 1H), 7.56 (dd, J = 1.7, 13.1 Hz, 1H), 4.24 (dd, J = 8.5, 8.5 Hz, 2H), 3.88 (dd, J = 5.3, 9.1 Hz, 2H), 2.94-2.88 (m, 1H), (m, 1H), 2.83-2.73 (m, 3H), 2.48-2.36 (m, 3H), 2.35 (s, 3H), 2.03-2.03 (m, 2H). |
| Example 206 | 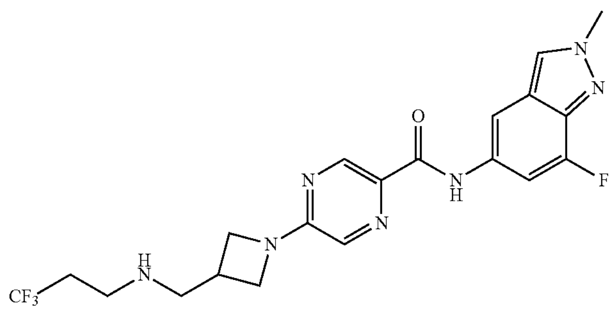 [SMILES: Cn1cc2cc(NC(=O)c3cnc(N4CC(CNCCC(F)(F)F)C4)cn3)cc(F)c2n1] | N-(azetidin-3-ylmethyl)-3,3,3-trifluoropropan-1-amine bis trifluoroacetate | LCMS (ES+) 452 (M + H)+, RT 2.65 min (Analytical method AcHSSC18) ¹H NMR (400 MHz, DMSO) δ 10.27 (s, 1H), 8.72 (d, J = 1.3 Hz, 1H), 8.43 (d, J = 2.8 Hz, 1H), 8.16 (d, J = 1.6 Hz, 1H), 7.86 (d, J = 1.4 Hz, 1H), 7.58 (dd, J = 1.5, 13.7 Hz, 1H), 4.24 (dd, J = 8.5, 8.5 Hz, 2H), 4.19 (s, 3H), 3.88 (dd, J = 5.2, 9.1 Hz, 2H), 2.94-2.86 (m, 1H), 2.84-2.74 (m, 3H), 2.48-2.34 (m, 3H), 2.00-1.99 (m, 1H). |

Example 207: (R)—N-(2,8-dimethylimidazo[1,2-a]pyrazin-6-yl)-5-(7-(methylamino)-5-azaspiro[2.4]heptan-5-yl pyrazine-2-carboxamide

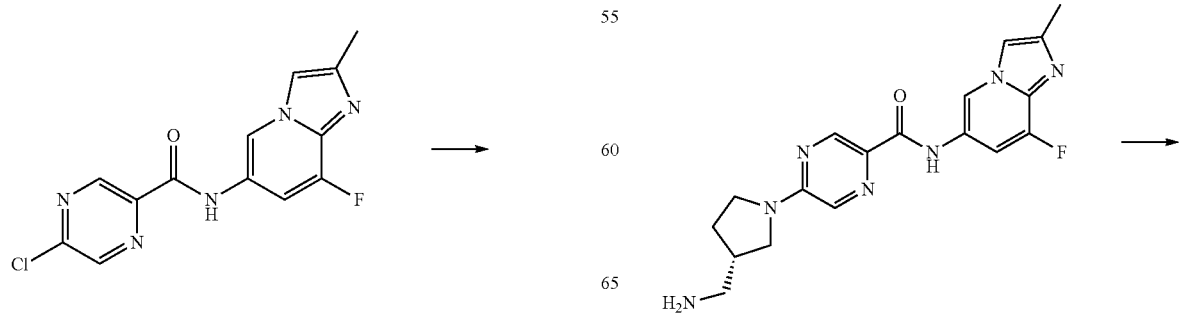

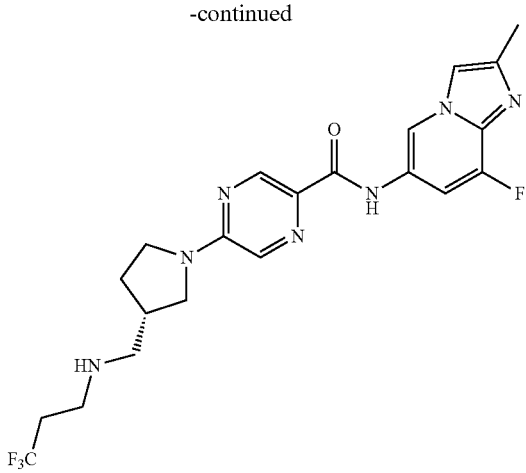

5-Chloro-N-(8-fluoro-2-methylimidazo[1,2-a]pyridin-6-yl)pyrazine-2-carboxamide (300 mg, 0.98 mmol), tert-butyl (R)-(pyrrolidin-3-ylmethyl)carbamate (272 mg, 1.36 mmol) and triethylamine (0.19 mL, 1.40 mol) were suspended in dioxane (3.5 mL) and heated to 140° C. in a microwave reactor for 30 min. The mixture was concentrated to give crude tert-butyl (S)-((1-(5-((8-fluoro-2-methylimidazo[1,2-a]pyridin-6-yl)carbamoyl)pyrazin-2-yl)pyrrolidin-3-yl)methyl)carbamate, which was used immediately in the next step.

tert-Butyl (S)-((1-(5-((8-fluoro-2-methylimidazo[1,2-a]pyridin-6-yl)carbamoyl)pyrazin-2-yl)pyrrolidin-3-yl)methyl)carbamate (crude material from previous step) was dissolved in MeOH (10 mL) and treated with 4 M HCl/dioxane (2.3 mL, 9.11 mmol). After stirring at RT for 24 h, the reaction mixture was concentrated. The residue was partitioned between DCM (10 mL) and aqueous NaHCO₃ (10 mL) and the aqueous layer was extracted with DCM (10 mL). The combined DCM extracts were dried (MgSO₄) and concentrated to give crude (S)-5-(3-(aminomethyl)pyrrolidin-1-yl)-N-(8-fluoro-2-methylimidazo[1,2-a]pyridin-6-yl)pyrazine-2-carboxamide, which was used in the next step.

(S)-5-(3-(Aminomethyl)pyrrolidin-1-yl)-N-(8-fluoro-2-methylimidazo[1,2-a]pyridin-6-yl)pyrazine-2-carboxamide (49.7 mg of crude material from previous step) was dissolved in MeOH (1 mL) and CHCl₃ (1 mL) at RT. NaBH₃CN (14.9 mg, 0.24 mmol), AcOH (10 mg, 0.17 mmol) and 3,3,3-trifluoropropanal (30.3 mg, 0.27 mmol) were added and the mixture was stirred at RT for 48 h. The mixture was concentrated and purified by reverse phase HPLC to yield (S)—N-(8-fluoro-2-methylimidazo[1,2-a]pyridin-6-yl)-5-(3-(((3,3,3-trifluoropropyl)amino)methyl)pyrrolidin-1-yl)pyrazine-2-carboxamide. LCMS (ES+) 466 (M+H)+, RT 2.05 min (Analytical method AcHSSC18); ¹H NMR (400 MHz, DMSO) δ 10.43 (s, 1H), 9.20 (d, J=1.5 Hz, 1H), 8.76-8.75 (m, 1H), 7.97 (d, J=1.3 Hz, 1H), 7.90 (d, J=2.4 Hz, 1H), 7.60-7.55 (m, 1H), 3.78-3.66 (m, 2H), 3.57-3.50 (m, 1H), 3.31-3.26 (m, 1H), 2.79-2.56 (m, 4H), 2.49-2.37 (m, 2H), 2.35 (d, J=0.7 Hz, 3H), 2.19-2.06 (m, 2H), 1.81-1.71 (m, 2H).

Example 208: N-(8-fluoro-2-methylimidazo[1,2-a]pyridin-6-yl)-5-(3-(1-(methylamino)cyclopropyl)azetidin-1-yl)pyrazine-2-carboxamide

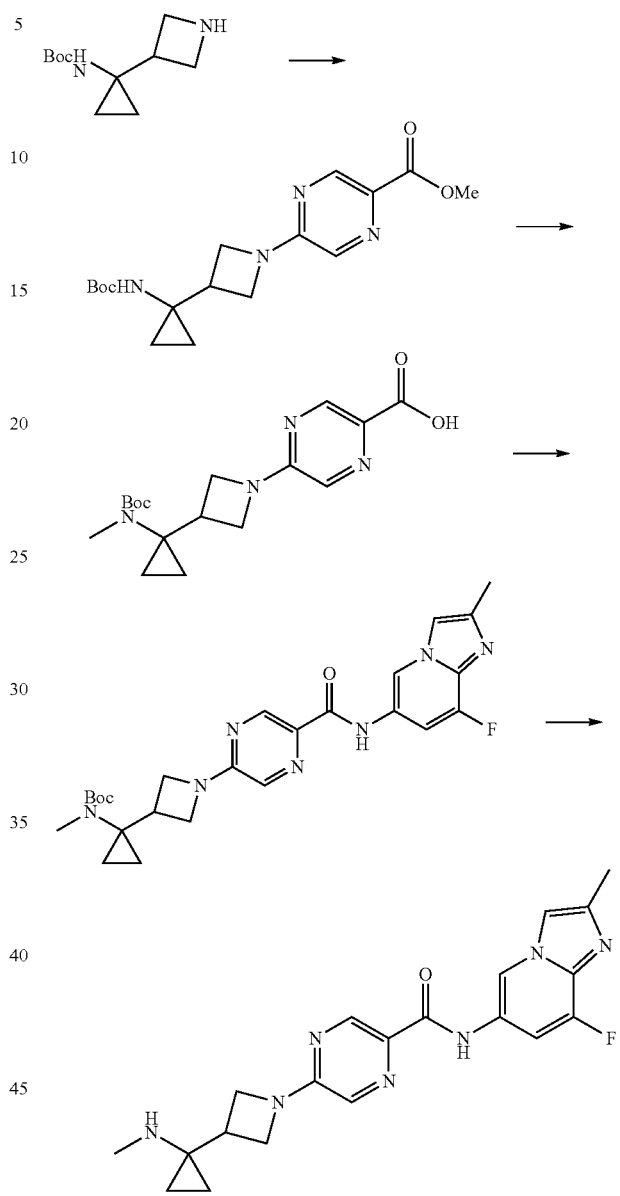

Following Method D from tert-butyl (1-(azetidin-3-yl)cyclopropyl)carbamate (229 mg, 1.08 mmol) and methyl 5-chloropyrazine-2-carboxylate (193 mg, 1.12 mmol), to give crude methyl 5-(3-(1-((tert-butoxycarbonyl)amino)cyclopropyl)azetidin-1-yl)pyrazine-2-carboxylate, which was used in the next step.

A solution of methyl 5-(3-(1-((tert-butoxycarbonyl)amino)cyclopropyl)azetidin-1-yl)pyrazine-2-carboxylate (80 mg, 0.23 mmol) in DMF (4 mL) was treated with NaH (60 wt % in oil, 38 mg, 0.95 mmol) under N₂ at RT. After stirring for 10 min, MeI (30 μL, 0.48 mmol) was added and the mixture stirred for 16 h. NaOH (3.75 M in H₂O, 0.5 mL) was added (CAUTION: gas evolved) and stirring continued for 1.5 h. After this time, LCMS analysis indicated complete hydrolysis of the ester to the carboxylic acid. The mixture was acidified to pH 1 with 2 M HCl and extracted with EtOAc (2×20 mL); the combined extracts were dried (Na₂SO₄) and concentrated to give crude 5-(3-(1-((tert-butoxycarbonyl)(methyl)amino)cyclopropyl)azetidin-1-yl)pyrazine-2-carboxylic acid, which was used in the next step.

Following Method H from 5-(3-(1-((tert-butoxycarbonyl)(methyl)amino)cyclopropyl)azetidin-1-yl)pyrazine-2-carboxylic acid (120 mg of material from previous step) and 8-fluoro-2-methylimidazo[1,2-a]pyridin-6-amine (38 mg, 0.23 mmol) to give crude tert-butyl (1-(1-(5-((8-fluoro-2-methylimidazo[1,2-a]pyridin-6-yl)carbamoyl)pyrazin-2-yl)azetidin-3-yl)cyclopropyl)(methyl)carbamate, which was used in the next step.

Following Method E from tert-butyl (1-(1-(5-((8-fluoro-2-methylimidazo[1,2-a]pyridin-6-yl)carbamoyl)pyrazin-2-yl)azetidin-3-yl)cyclopropyl)(methyl)carbamate (crude material from previous step) gave N-(8-fluoro-2-methylimidazo[1,2-a]pyridin-6-yl)-5-(3-(1-(methylamino)cyclopropyl)azetidin-1-yl)pyrazine-2-carboxamide. LCMS (ES+) 396 (M+H)+, RT 1.82 min (Analytical method AcHSSC18); $^1$H NMR (400 MHz, DMSO) δ 9.21 (s, 1H), 9.09 (d, J=1.6 Hz, 1H), 8.88 (d, J=1.4 Hz, 1H), 7.61 (d, J=1.4 Hz, 1H), 7.42 (d, J=2.3 Hz, 1H), 6.83-6.79 (m, 1H), 4.29-4.23 (m, 2H), 3.82-3.77 (m, 2H), 3.43-3.34 (m, 1H), 2.47 (s, 3H), 2.43 (s, 3H), 0.73-0.63 (m, 4H).

Example 209: N-(8-methoxy-2-methylimidazo[1,2-a]pyrazin-6-yl)-5-(2,6-diazaspiro[3.3]heptan-2-yl)pyrazine-2-carboxamide

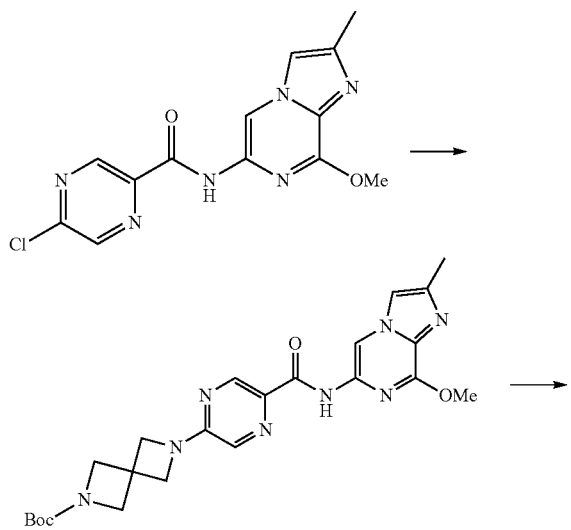

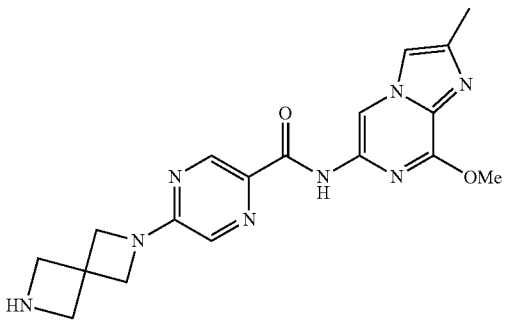

5-Chloro-N-(8-methoxy-2-methylimidazo[1,2-a]pyrazin-6-yl)pyrazine-2-carboxamide (115 mg, 0.36 mmol), tert-butyl 2,6-diazaspiro[3.3]heptane-2-carboxylate·hemioxalate salt (88 mg, 0.36 mmol), cesium carbonate (325 mg, 1 mmol) and dioxane (10 mL) were combined in a sealed tube and hot block heated to 100° C. for 3 days. Reaction mixture was diluted with EtOAc and filtered to remove cesium salts. Filtrate was evaporated to dryness in vacuo to give tert-butyl 6-(5-((8-methoxy-2-methylimidazo[1,2-a]pyrazin-6-yl)carbamoyl)pyrazin-2-yl)-2,6-diazaspiro[3.3]heptane-2-carboxylate, which was used directly in next step.

tert-Butyl 6-(5-((8-methoxy-2-methylimidazo[1,2-a]pyrazin-6-yl)carbamoyl)pyrazin-2-yl)-2,6-diazaspiro[3.3]heptane-2-carboxylate (crude from previous step), dichloromethane (10 mL) and TFA (2 mL) were combined and stirred at room temperature for 1.5 hours. Reaction mixture was evaporated to dryness in vacuo, then dissolved in MeOH and stirred over $Na_2CO_3$ for 5 mins. The mixture was passed through an isolute $NH_2$ cartridge rinsing with MeOH and filtrate was evaporated to dryness. The residue was purified by prep HPLC to give the title compound. LCMS (ES+) 381 (M+H)+, RT 1.91 min (Analytical method AcHSSC18). $^1$H NMR (400 MHz, DMSO) δ 9.52 (s, 1H), 8.90 (s, 1H), 8.73 (d, J=1.3 Hz, 1H), 7.96 (s, 1H), 7.92 (d, J=1.1 Hz, 1H), 4.28 (s, 4H), 4.07 (s, 3H), 3.65 (s, 4H), 2.35 (s, 3H).

Further analogues were prepared using the same chemistry from commercially available or synthesised amines. Final products were isolated by Preparative HPLC.

| Example | Structure | Analytical data |
|---|---|---|
| Example 210 | ![structure] | LCMS (ES+) 409 (M + H)+, RT 2.05 min (Analytical method AcHSSC18). $^1$H NMR (400 MHz, DMSO) δ 9.53 (s, 1H), 8.93 (s, 1H), 8.74 (d, J = 1.4 Hz, 1H), 7.98 (s, 1H), 7.92 (d, J = 1.4 Hz, 1H), 4.25 (dd, J = 8.4, 8.4 Hz, 2H), 4.09 (s, 3H), 3.89 (dd, J = 5.0, 9.2 Hz, 2H), 2.91-2.88 (m, 3H), 2.37 (s, 4H), 2.13-2.07 (m, 1H), 0.43-0.38 (m, 2H), 0.26-0.22 (m, 2H). |

| Example | Structure | Analytical data |
| --- | --- | --- |
| Example 211 | 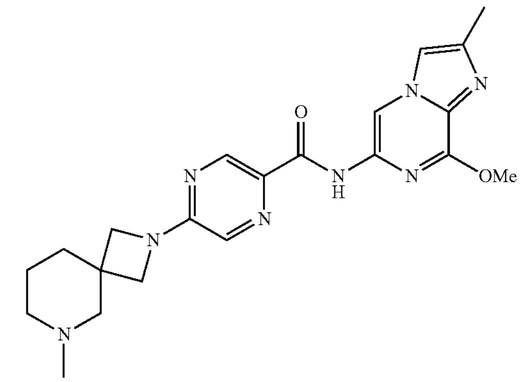 [SMILES: COc1nc(NC(=O)c2cnc(N3CC4(CCCN(C)C4)C3)cn2)cn2cc(C)nc12] | LCMS (ES+) 423 (M + H)+, RT 3.63 min (Analytical method BicarbBEHC18).<br>¹H NMR (400 MHz, DMSO) δ 9.50 (s, 1H), 8.90 (s, 1H), 8.72 (d, J = 1.3 Hz, 1H), 7.95 (s, 1H), 7.91 (d, J = 1.3 Hz, 1H), 4.07 (s, 3H), 3.92-3.83 (m, 4H), 2.46 (s, 2H), 2.35 (s, 3H), 2.25 (s, 2H), 2.21 (s, 3H), 1.65-1.65 (m, 2H), 1.53 (dd, J = 5.4, 5.4 Hz, 2H). |
| Example 212 | 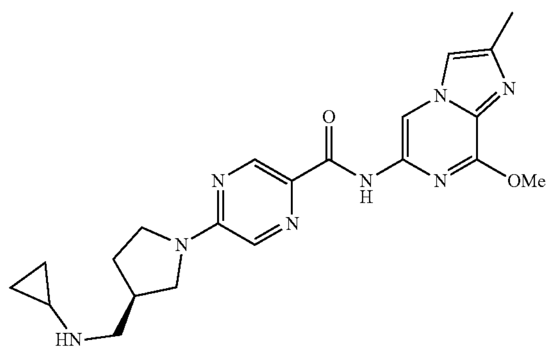 [SMILES: COc1nc(NC(=O)c2cnc(N3CC[C@H](CNC4CC4)C3)cn2)cn2cc(C)nc12] | LCMS (ES+) 423 (M + H)+, RT 2.15 min (Analytical method AcHSSC18).<br>¹H NMR (400 MHz, DMSO) δ 9.52 (s, 1H), 8.93 (s, 1H), 8.78 (d, J = 1.3 Hz, 1H), 8.05 (d, J = 1.3 Hz, 1H), 7.98 (s, 1H), 4.09 (s, 3H), 3.78-3.66 (m, 2H), 3.58-3.50 (m, 1H), 3.31-3.23 (m, 1H), 2.76-2.62 (m, 2H), 2.51-2.50 (m, 1H), 2.38 (s, 3H), 2.15-2.08 (m, 2H), 1.80-1.75 (m, 1H), 0.42-0.39 (m, 2H), 0.27-0.24 (m, 2H). |

Example 213: 5-((3,3-difluoropiperidin-4-yl)oxy)-N-(8-fluoro-2-methylimidazo[1,2-a]pyridin-6-yl)pyrazine-2-carboxamide

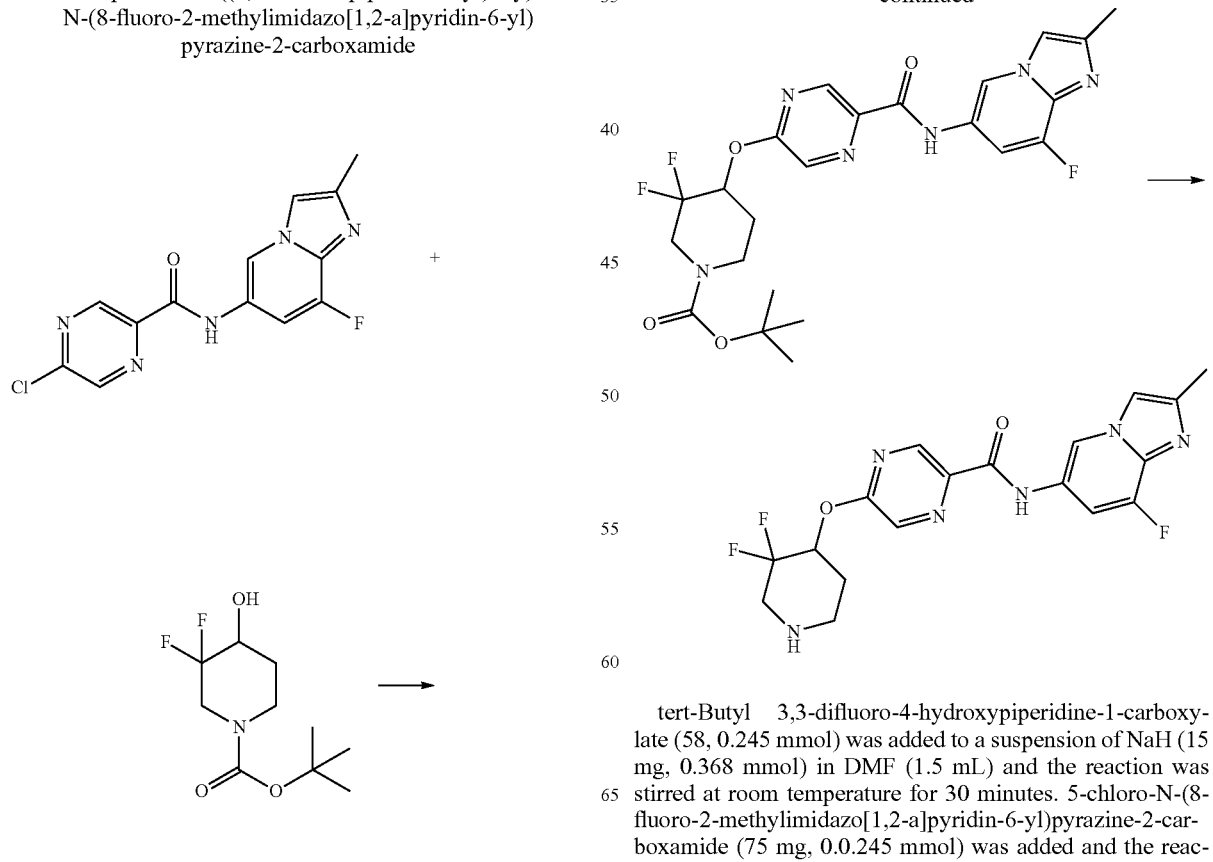

tert-Butyl 3,3-difluoro-4-hydroxypiperidine-1-carboxylate (58, 0.245 mmol) was added to a suspension of NaH (15 mg, 0.368 mmol) in DMF (1.5 mL) and the reaction was stirred at room temperature for 30 minutes. 5-chloro-N-(8-fluoro-2-methylimidazo[1,2-a]pyridin-6-yl)pyrazine-2-carboxamide (75 mg, 0.0.245 mmol) was added and the reaction stirred for at 90° C. for 2 hours. The reaction mixture was quenched with water and extracted with dichloromethane (×2) and the combined organic solution dried with MgSO$_4$ and evaporated to dryness. The crude mixture was purified by flash chromatography to give tert-butyl 3,3-difluoro-4-((5-((8-fluoro-2-methylimidazo[1,2-a]pyridin-6-yl)carbamoyl)pyrazin-2-yl)oxy)piperidine-1-carboxylate.
$^1$H NMR (400 MHz, DMSO) δ 10.83 (s, 1H), 9.22 (d, J=1.5 Hz, 1H), 8.92 (d, J=1.3 Hz, 1H), 8.57 (d, J=1.3 Hz, 1H), 7.93 (d, J=2.8 Hz, 1H), 7.57 (dd, J=1.6, 12.9 Hz, 1H), 5.81-5.72 (m, 1H), 4.13-4.06 (m, 1H), 3.81 (d, J=13.9 Hz, 1H), 3.75-3.67 (m, 1H), 2.36 (s, 3H), 2.21-2.15 (m, 1H), 1.86-1.81 (m, 1H), 1.44 (s, 9H).

tert-Butyl 3,3-difluoro-4-((5-((8-fluoro-2-methylimidazo[1,2-a]pyridin-6-yl)carbamoyl)pyrazin-2-yl)oxy)piperidine-1-carboxylate (117 mg, 0.231 mmol), methanol (1 mL), dioxane (3 mL) and 4N HCl in dioxane (0.72 mL, 2.9 mmol) were combined and stirred at room temperature for 4.5 hours. The reaction mixture was evaporated to dryness and the crude material was purified by Prep HPLC to give 5-((3,3-difluoropiperidin-4-yl)oxy)-N-(8-fluoro-2-methylimidazo[1,2-a]pyridin-6-yl)pyrazine-2-carboxamide.
LCMS (ES+) 407 (M+H)+, RT 1.92 min (Analytical method AcHSSC18); $^1$H NMR (400 MHz, DMSO) δ 10.80 (s, 1H), 9.21 (d, J=1.5 Hz, 1H), 8.91 (d, J=1.3 Hz, 1H), 8.56 (d, J=1.3 Hz, 1H), 7.93 (d, J=2.6 Hz, 1H), 7.57 (dd, J=1.5, 13.1 Hz, 1H), 5.69-5.59 (m, 1H), 3.22-3.13 (m, 1H), 3.03-2.92 (m, 2H), 2.75-2.70 (m, 1H), 2.57-2.54 (m, 1H), 2.16-2.11 (m, 1H), 1.85-1.79 (m, 1H).

Further analogues were prepared using the same chemistry and commercially available alcohols.

| Example | Structure | Analytical data |
| --- | --- | --- |
| Example 214 | 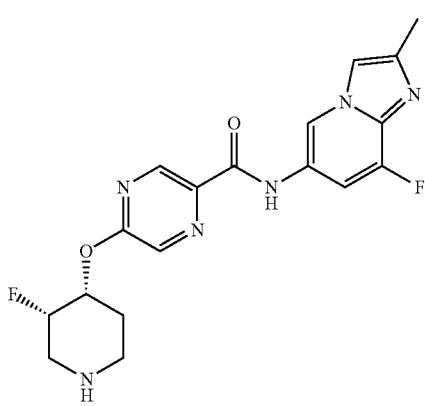 [SMILES: Cc1cn2cc(NC(=O)c3cnc(O[C@@H]4CCNC[C@@H]4F)cn3)cc(F)c2n1] | LCMS (ES+) 389 (M + H)+, RT 1.72 min (Analytical method AcHSSC18. $^1$H NMR (400 MHz, DMSO) δ 10.77 (s, 1H), 9.21 (d, J = 1.6 Hz, 1H), 8.89 (d, J = 1.3 Hz, 1H), 8.49 (d, J = 1.3 Hz, 1H), 7.93 (d, J = 2.8 Hz, 1H), 7.57 (dd, J = 1.6, 13.0 Hz, 1H), 5.43-5.33 (m, 1H), 4.97-4.81 (m, 1H), 3.19-3.12 (m, 1H), 2.98-2.93 (m, 1H), 2.85 (dd, J = 14.0, 32.0 Hz, 1H), 2.70-2.59 (m, 1H), 2.35 (s, 3H), 1.91-1.84 (m, 2H). |
| Example 215 | 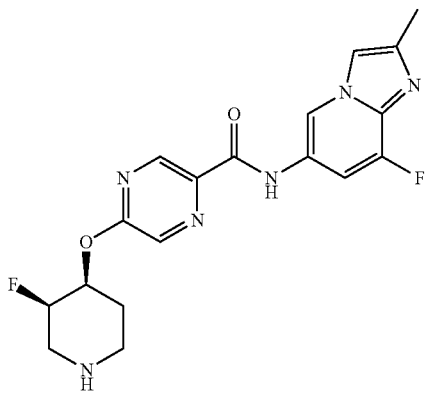 [SMILES: Cc1cn2cc(NC(=O)c3cnc(O[C@H]4CCNC[C@H]4F)cn3)cc(F)c2n1] | LCMS (ES+) 389 (M + H)+, RT 1.72 min (Analytical method AcHSSC18. $^1$H NMR (400 MHz, DMSO) δ 10.77 (s, 1H), 9.22 (d, J = 1.6 Hz, 1H), 8.89 (d, J = 1.3 Hz, 1H), 8.49 (d, J = 1.3 Hz, 1H), 7.93 (d, J = 2.8 Hz, 1H), 7.57 (dd, J = 1.6, 13.0 Hz, 1H), 5.44-5.33 (m, 1H), 4.97-4.81 (m, 1H), 3.19-3.11 (m, 1H), 2.98-2.92 (m, 1H), 2.91-2.79 (m, 1H), 2.67-2.59 (m, 1H), 2.36 (s, 3H), 1.91-1.84 (m, 2H). |

Example 216: N-(8-methoxy-2-methylimidazo[1,2-a]pyrazin-6-yl)-5-(methyl(2,2,6,6-tetramethylpiperidin-4-yl)amino)pyrazine-2-carboxamide

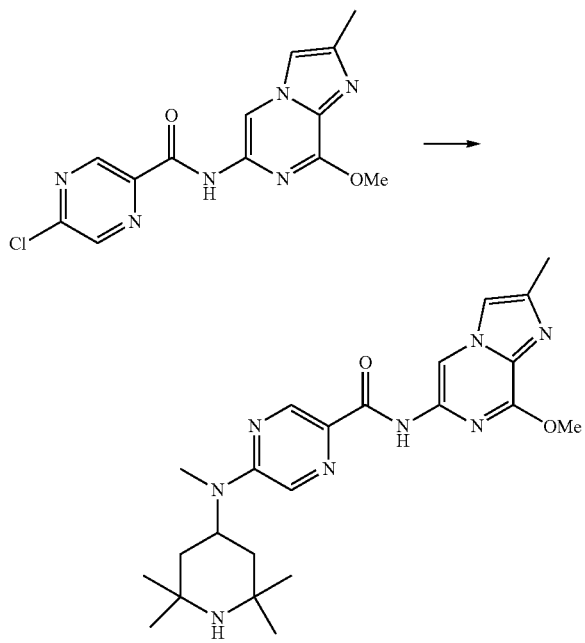

5-Chloro-N-(8-methoxy-2-methyl-imidazo[1,2-a]pyrazin-6-yl)pyrazine-2-carboxamide (100 mg, 0.314 mmol, 1.00 eq), N,2,2,6,6-pentamethylpiperidin-4-amine (100 mg, 0.587 mmol, 1.87 eq), 1,4-dioxane (5.00 mL) and triethylamine (0.25 mL, 1.79 mmol, 5.72 eq) were combined in a sealed tube and microwave heated to 145° C. for 45 mins. Reaction would not reach temperature—due to poor microwave absorber. Water (0.5 mL) was added and the reaction heated to 145° C. for 1 hour 45 mins. The reaction was concentrated in vacuo, triturated with water and dried in a vac oven to give N-(8-methoxy-2-methyl-imidazo[1,2-a]pyrazin-6-yl)-5-[methyl-(2,2,6,6-tetramethyl-4-piperidyl)amino]pyrazine-2-carboxamide. LCMS (ES+) 453 (M+H)+, RT 2.42 mi (Analytical method AcHSSC18). $^1$H NMR (400 MHz, DMSO) δ 9.52 (s, 1H), 8.93 (s, 1H), 8.78 (d, J=1.1 Hz, 1H), 8.24 (s, 1H), 7.95 (s, 1H), 5.04 (s, 1H), 4.07 (s, 3H), 3.04 (s, 3H), 2.36 (s, 3H), 1.53-1.51 (m, 4H), 1.27 (s, 6H), 1.12 (s, 6H).

Further analogues were prepared using the same chemistry from commercially available or synthesised amines. Final products were isolated by Preparative HPLC.

| Example | Structure | Analytical data |
|---|---|---|
| Example 217 | 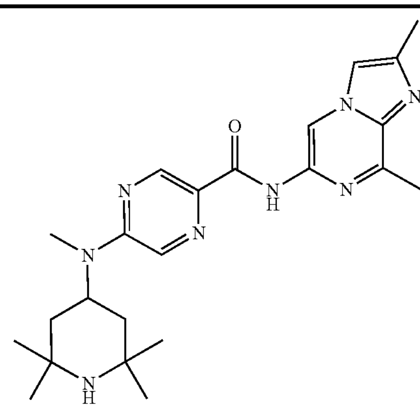 | LCMS (ES+) 437 (M + H)+, RT 3.36 min (Analytical method BicarbBEHCl8). $^1$H NMR (400 MHz, DMSO) δ 9.66 (s, 1H), 9.16 (s, 1H), 8.78 (d, J = 1.3 Hz, 1H), 8.21 (s, 1H), 8.00 (s, 1H), 5.05 (s, 1H), 3.03 (s, 3H), 2.71 (s, 3H), 2.40 (s, 3H), 1.54-1.43 (m, 4H), 1.26 (s, 6H), 1.11 (s, 6H). |
| Example 218 | 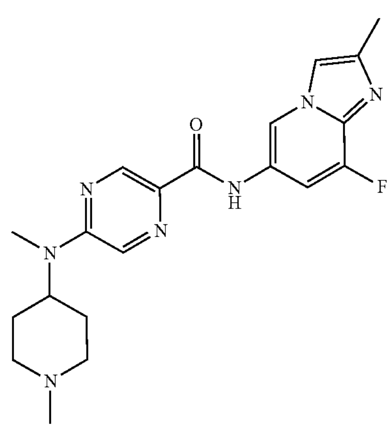 [SMILES: Cc1cn2cc(NC(=O)c3cnc(N(C)C4CCN(C)CC4)cn3)cc(F)c2n1] | LCMS (ES+) 398 (M + H)+, RT 1.82 min (Analytical method AcHSSC18). $^1$H NMR (400 MHz, DMSO) δ 10.42 (s, 1H), 9.20 (d, J = 1.6 Hz, 1H), 8.76 (d, J = 1.3 Hz, 1H), 8.17 (d, J = 1.3 Hz, 1H), 7.90 (d, J = 2.8 Hz, 1H), 7.56 (dd, J = 1.6, 13.1 Hz, 1H), 4.52-4.52 (m, 1H), 3.06 (s, 3H), 2.89 (d, J = 11.3 Hz, 2H), 2.35 (s, 3H), 2.21 (s, 3H), 2.09-2.01 (m, 2H), 1.91-1.80 (m, 2H), 1.60 (d, J = 10.2 Hz, 2H). |

| Example | Structure | Analytical data |
|---|---|---|
| Example 219 | 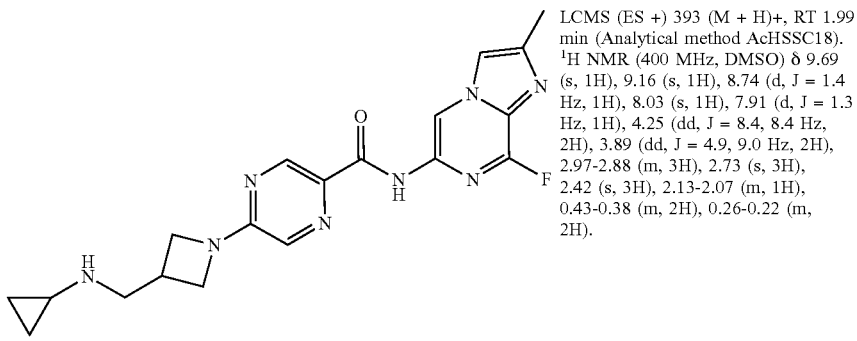 | LCMS (ES +) 393 (M + H)+, RT 1.99 min (Analytical method AcHSSC18). ¹H NMR (400 MHz, DMSO) δ 9.69 (s, 1H), 9.16 (s, 1H), 8.74 (d, J = 1.4 Hz, 1H), 8.03 (s, 1H), 7.91 (d, J = 1.3 Hz, 1H), 4.25 (dd, J = 8.4, 8.4 Hz, 2H), 3.89 (dd, J = 4.9, 9.0 Hz, 2H), 2.97-2.88 (m, 3H), 2.73 (s, 3H), 2.42 (s, 3H), 2.13-2.07 (m, 1H), 0.43-0.38 (m, 2H), 0.26-0.22 (m, 2H). |

Example 220: (R)-5-(3-Aminopyrrolidin-1-yl)-N-(8-fluoro-2-methylimidazo[1,2-a]pyridin-6-yl)pyrazine-2-carboxamide

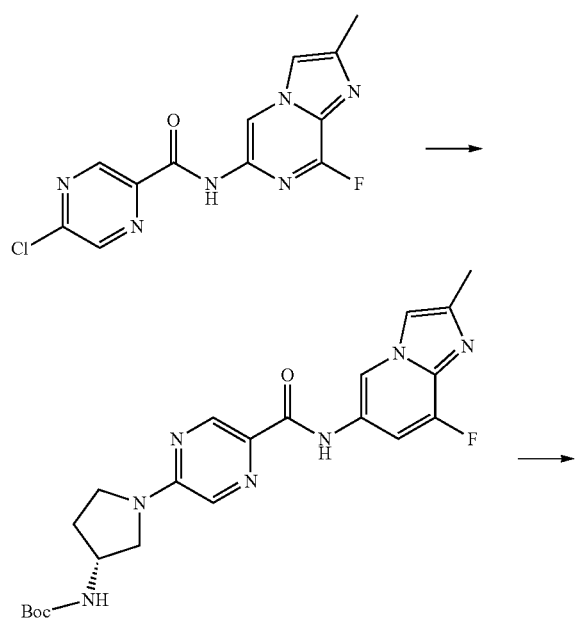

5-Chloro-N-(8-fluoro-2-methyl-imidazo[1,2-a]pyridin-6-yl)pyrazine-2-carboxamide (127 mg, 0.415 mmol, 1.00 eq), cesium carbonate (271 mg, 0.831 mmol, 2.00 eq), (R)-3-(Boc-amino)pyrrolidine (77 mg, 0.415 mmol, 1.00 eq) and 1,4-dioxane (15 mL) were combined in a sealed tube and hot block heated to 100° C. for 4 hours. The reaction was cooled to room temperature and the cesium salts removed by filtration. The filtrate was concentrated in vacuo to give tert-butyl N-[(3R)-1-[5-[(8-fluoro-2-methyl-imidazo[1,2-a]pyridin-6-yl)carbamoyl]pyrazin-2-yl]pyrrolidin-3-yl]carbamate. LCMS (ES+) 456 (M+H)+.

tert-Butyl N-[(3R)-1-[5-[(8-fluoro-2-methyl-imidazo[1,2-a]pyridin-6-yl)carbamoyl]pyrazin-2-yl]pyrrolidin-3-yl]carbamate (189 mg, 0.415 mmol, 1.00 eq), methyl alcohol (10 mL) and 4 M hydrogen chloride in dioxane (0.10 mL, 0.415 mmol, 1.00 eq) were combined and stirred at room temperature for 20 hours. The reaction was concentrated in vacuo and purified by prep HPLC to give 5-[(3R)-3-aminopyrrolidin-1-yl]-N-(8-fluoro-2-methyl-imidazo[1,2-a]pyridin-6-yl)pyrazine-2-carboxamide. LCMS (ES+) 356 (M+H)+, RT 1.67 min (Analytical method AcHSSC18). ¹H NMR (400 MHz, DMSO) δ 10.42 (s, 1H), 9.20 (d, J=1.6 Hz, 1H), 8.75 (d, J=1.3 Hz, 1H), 7.97 (s, 1H), 7.90 (d, J=2.8 Hz, 1H), 7.57 (dd, J=1.7, 13.3 Hz, 1H), 3.73-3.55 (m, 4H), 3.28-3.26 (m, 1H), 2.35 (s, 3H), 2.12-1.75 (m, 4H).

Example 221: N-(8-Fluoro-2-methylimidazo[1,2-a]pyridin-6-yl)-5-(methyl(piperidin-4-yl)amino)pyrazine-2-carboxamide

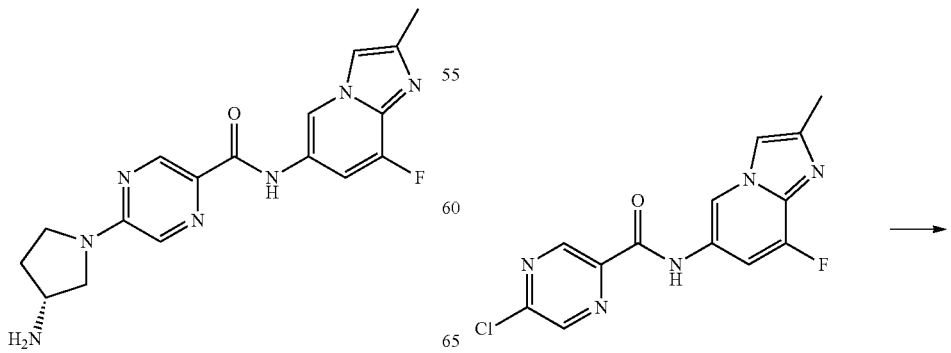

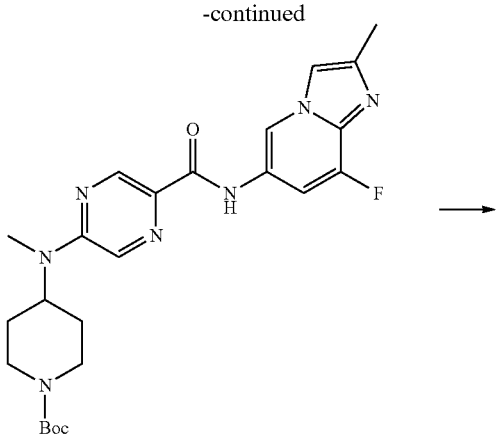

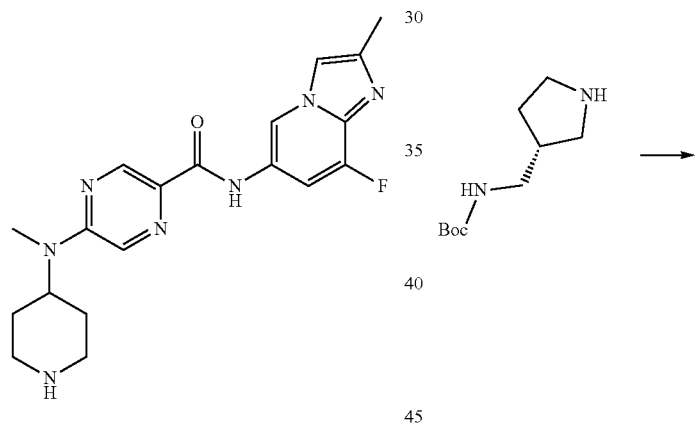

5-Chloro-N-(8-fluoro-2-methyl-imidazo[1,2-a]pyridin-6-yl)pyrazine-2-carboxamide (100 mg, 0.327 mmol, 1.00 eq), 1-Boc-4-(methylamino)piperidine (0.075 mL, 0.350 mmol, 1.07 eq), cesium carbonate (200 mg, 0.614 mmol, 1.88 eq) and 1,4-dioxane (15.00 mL) were combined in a sealed tube and hot block heated to 100° C. for 20 hours. LCMS (acidic) indicated mostly starting material RT=1.16 mins 306/308, small target peak RT=1.54 mins 484. Diisopropylethylamine (0.5 mL) was added and the reaction was hot block heated to 100° C. for 4 days. The reaction was cooled to room temperature. Filtered off cesium salts, rinsing with EtOAc. The filtrate was concentrated in vacuo and purified by prep HPLC to give tert-butyl 4-[[5-[(8-fluoro-2-methyl-imidazo[1,2-a]pyridin-6-yl)carbamoyl]pyrazin-2-yl]-methyl-amino]piperidine-1-carboxylate. LCMS (ES+) 484 (M+H)+.

tert-Butyl 4-[[5-[(8-fluoro-2-methyl-imidazo[1,2-a]pyridin-6-yl)carbamoyl]pyrazin-2-yl]-methyl-amino]piperidine-1-carboxylate (30 mg, 0.0620 mmol, 1.00 eq), methyl alcohol (3.00 mL) and 4 M hydrogen chloride in dioxane (3.0 mL, 12.0 mmol, 193 eq) were combined and stirred at room temperature for 4 hours. The reaction was concentrated in vacuo and purified by prep HPLC to give N-(8-fluoro-2-methyl-imidazo[1,2-a]pyridin-6-yl)-5-[methyl(4-piperidyl)amino]pyrazine-2-carboxamide. LCMS (ES+) 384 (M+H)+, RT 1.80 min (Analytical method AcHSSC18). $^1$H NMR (400 MHz, DMSO) δ 10.42 (s, 1H), 9.19 (d, J=1.6 Hz, 1H), 8.76 (d, J=1.3 Hz, 1H), 8.32 (s, 1H), 8.19 (d, J=0.9 Hz, 1H), 7.90 (d, J=2.6 Hz, 1H), 7.56 (dd, J=1.7, 13.1 Hz, 1H), 4.71 (dd, J=12.0, 12.0 Hz, 1H), 3.23-3.14 (m, 2H), 3.05 (s, 3H), 2.78 (dd, J=10.4, 12.4 Hz, 2H), 2.35 (s, 3H), 1.87-1.76 (m, 2H), 1.66 (d, J=10.3 Hz, 2H).

Example 222: (S)-5-(3-(((2,2-difluoroethyl)amino)methyl)pyrrolidin-1-yl)-N-(2,8-dimethylimidazo[1,2-a]pyrazin-6-yl)pyrazine-2-carboxamide

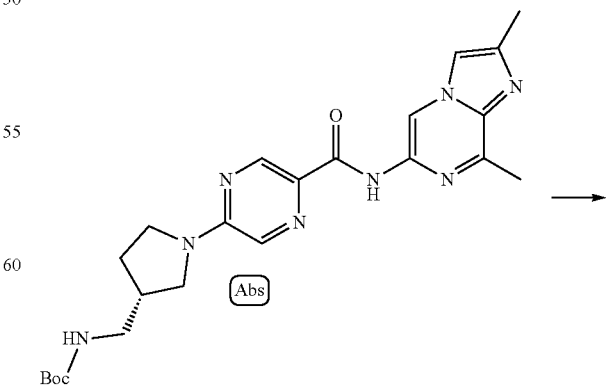

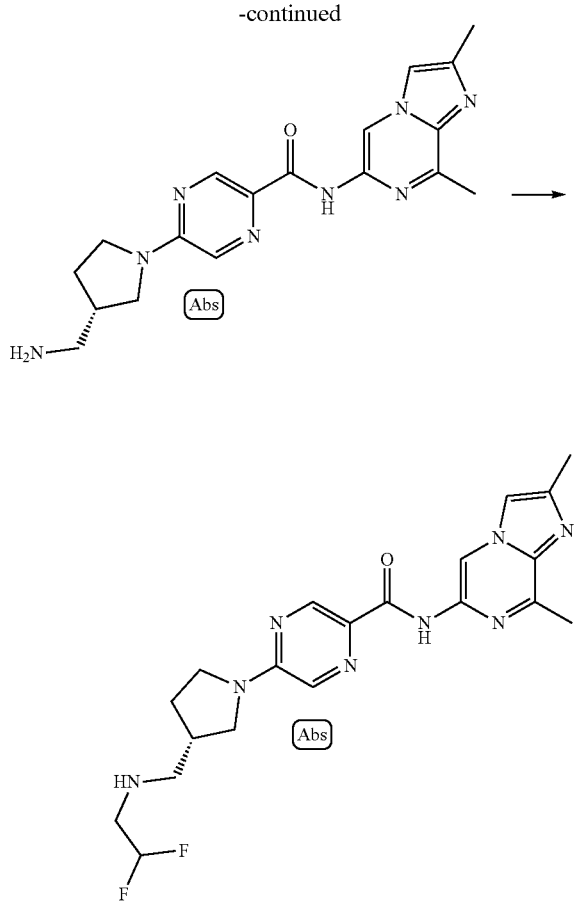

Following Method D (SNAr displacement) starting from 5-chloro-N-(2,8-dimethylimidazo[1,2-a]pyrazin-6-yl)pyrazine-2-carboxamide (300 mg, 1.00 mmol) and tert-butyl (R)-(pyrrolidin-3-ylmethyl)carbamate (238 mg, 1.20 mmol), the mixture was heated for 24 h, and afforded tert-butyl (S)-((1-(5-((2,8-dimethylimidazo[1,2-a]pyrazin-6-yl)carbamoyl)pyrazin-2-yl)pyrrolidin-3-yl)methyl)carbamate.

Following Method L (HCl Boc deprotection) from tert-butyl (S)-((1-(5-((2,8-dimethylimidazo[1,2-a]pyrazin-6-yl)carbamoyl)pyrazin-2-yl)pyrrolidin-3-yl)methyl)carbamate (130 mg, 0.28 mmol) and stirring at r.t. for 67 h. SCX purification afforded (S)-5-(3-(aminomethyl)pyrrolidin-1-yl)-N-(2,8-dimethylimidazo[1,2-a]pyrazin-6-yl)pyrazine-2-carboxamide, which was used as such in the next step.

(S)-5-(3-(Aminomethyl)pyrrolidin-1-yl)-N-(2,8-dimethylimidazo[1,2-a]pyrazin-6-yl)pyrazine-2-carboxamide (150 mg, 0.41 mmol) was dissolved in acetonitrile (2 mL). Triethylamine (0.13 mL, 0.90 mmol), potassium carbonate (85 mg, 0.61 mmol) and 2,2-difluoroethyl trifluoromethanesulfonate (0.076 mL, 0.57 mmol) were then added and the resulting mixture was heated to 70° C. for 20 hours. The mixture was then loaded onto silica and purified using silica chromatography, elution gradient 0-100% [EtOAc:EtOH=3:1]/cyclohexane to afford (S)-5-(3-(((2,2-difluoroethyl)amino)methyl)pyrrolidin-1-yl)-N-(2,8-dimethylimidazo[1,2-a]pyrazin-6-yl)pyrazine-2-carboxamide. LCMS (ES+) 431 (M+H)+, RT 2.04 min (Analytical method AcHSSC18); $^1$H NMR (400 MHz, DMSO) δ 9.69 (s, 1H), 9.18 (s, 1H), 8.79 (d, J=1.3 Hz, 1H), 8.06-8.04 (m, 2H), 6.07 (tt, J=4.2, 56.5 Hz, 1H), 3.81-3.68 (m, 2H), 3.61-3.53 (m, 1H), 3.33 (dd, J=7.1, 11.1 Hz, 1H), 2.98 (ddd, J=16.0, 16.0, 4.3 Hz, 2H), 2.79-2.65 (m, 5H), 2.44 (s, 3H), 2.21-2.13 (m, 1H), 1.85-1.77 (m, 1H).

The following analogue was prepared using reductive amination with the same aldehyde but starting with a different amine.

| Example | Structure | Amine | Analytical data |
|---|---|---|---|
| Example 223 (Absolute stereochemistry from commercial SM) | 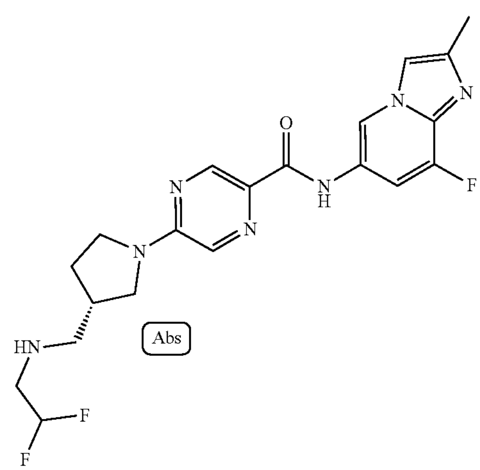 [SMILES: Cc1cn2cc(NC(=O)c3cnc(N4CC[C@@H](CNCC(F)F)C4)cn3)cc(F)c2n1] | (S)-5-(3-(aminomethyl) pyrrolidin-1-yl)-N-(8-fluoro-2-methylimidazo [1,2-a]pyridin-6-yl)pyrazine-2-carboxamide | LCMS (ES+) 434 (M + H)+, RT 1.85 min (Analytical method AcHSSC18); $^1$H NMR (400 MHz, DMSO) δ 10.43-10.40 (m, 1H), 9.19 (d, J = 1.5 Hz, 1H), 8.76-8.74 (m, 1H), 7.98-7.96 (m, 1H), 7.91-7.88 (m, 1H), 7.57 (dd, J = 1.6, 13.1 Hz, 1H), 6.09 (tt, J = 4.0, 56.2 Hz, 1H), 3.79-3.64 (m, 2H), 3.56-3.48 (m, 1H), 3.09-2.97 (m, 2H), 2.81-2.69 (m, 2H), 2.34 (s, 3H), 2.15 (s, 1H), 1.77 (s, 1H) |

Example 224: (S)—N-(2,8-dimethylimidazo[1,2-a]pyrazin-6-yl)-5-(3-(((3,3,3-trifluoropropyl)amino)methyl)pyrolidin-1-yl)pyrazine-2-carboxamide

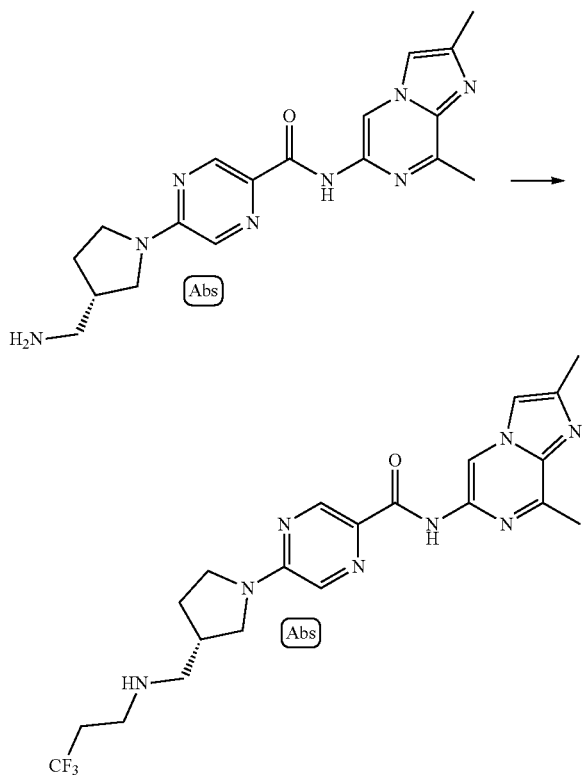

(S)-5-(3-(Aminomethyl)pyrrolidin-1-yl)-N-(2,8-dimethylimidazo[1,2-a]pyrazin-6-yl)pyrazine-2-carboxamide (150 mg, 0.41 mmol) was dissolved in a mixture of methanol (1 mL) and chloroform (1 mL) before 3,3,3-trifluoropropanal (92 mg, 0.82 mmol) and sodium cyanoborohydride (39 mg, 0.61 mmol) were added, as well as a drop of acetic acid. The resulting mixture was stirred at r.t. for 17 h before it was partitioned between DCM and saturated sodium bicarbonate, dried and evaporated to afford crude product, which was used in the next step. The crude material was then loaded onto silica in DCM and purified using silica chromatography, elution gradient 0-100% [EtOAc:EtOH=3:1]/cyclohexane to afford (S)—N-(2,8-dimethylimidazo[1,2-a]pyrazin-6-yl)-5-(3-(((3,3,3-trifluoropropyl)amino)methyl)pyrolidin-1l-yl)pyrazine-2-carboxamide, which was registered together with less clean fractions which were used for subsequent chemistry. LCMS (ES+) 463 (M+H)+, RT 2.27 min (Analytical method AcHSSC18); $^1$H NMR (400 MHz, DMSO) δ 9.62 (s, 1H), 9.12 (s, 1H), 8.73 (d, J=1.1 Hz, 1H), 7.99-7.98 (m, 2H), 3.75-3.63 (m, 2H), 3.55-3.46 (m, 1H), 3.26 (dd, J=7.2, 11.1 Hz, 1H), 2.79-2.73 (m, 2H), 2.69 (s, 3H), 2.66-2.54 (m, 2H), 2.48-2.36 (m, 6H), 2.13-2.12 (m, 1H), 1.77-1.73 (m, 1H).

The following lactam analogues were prepared using Method P (Pd catalyzed amidation) using commercial amides, followed by Boc deprotection using method C (HCl Boc deprotection) and the final compounds were purified by achiral SFC.

| Example | Structure | Amide | Analytical data |
|---|---|---|---|
| Example 225 (rac, cis) | 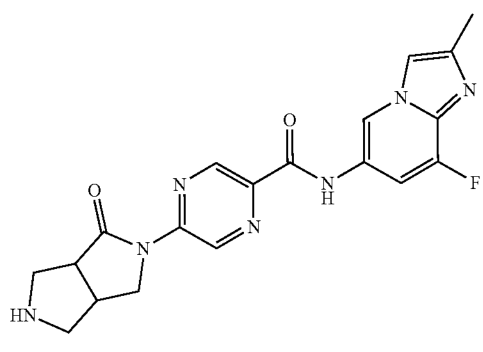 [SMILES: Cc1cn2cc(NC(=O)c3cnc(N4CC5CNCC5C4=O)cn3)cc(F)c2n1] | tert-butyl 4-oxohexahydropyrrolo[3,4-c]pyrrole-2(1H)-carboxylate | LCMS (ES+) 396 (M + H)+, RT 2.75 min (Analytical method BicarbBEHCl8); $^1$H NMR (400 MHz, DMSO) δ 10.90 (s, 1H), 9.73 (d, J = 1.4 Hz, 1H), 9.23 (d, J = 1.5 Hz, 1H), 9.11 (d, J = 1.4 Hz, 1H), 7.94 (d, J = 2.6 Hz, 1H), 7.59 (dd, J = 1.6, 13.0 Hz, 1H), 4.25-4.19 (m, 1H), 3.76 (dd, J = 3.1, 11.5 Hz, 1H), 3.22-3.17 (m, 3H), 2.96-2.86 (m, 4H), 2.36 (s, 3H). $^{19}$F NMR (376 MHz, d6 DMSO) δ −132 ppm. |
| Example 226 (rac, cis) | 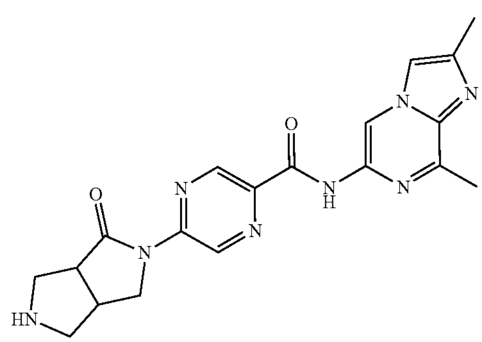 [SMILES: Cc1cn2cc(NC(=O)c3cnc(N4CC5CNCC5C4=O)cn3)nc(C)c2n1] | tert-butyl 4-oxohexahydropyrrolo[3,4-c]pyrrole-2(1H)-carboxylate | LCMS (ES+) 393 (M + H)+, RT 1.93 min (Analytical method AcHSSC18); $^1$H NMR (400 MHz, DMSO) δ 10.08 (br s, 1H) 9.70 (d, J = 1.4 Hz, 1H), 9.18 (s, 1H), 9.12 (d, J = 1.5 Hz, 1H), 8.04 (s, 1H), 4.25-4.18 (m, 1H), 3.75 (dd, J = 2.9, 11.4 Hz, 1H), 3.30-3.27 (m, 1H), 3.23-3.17 (m, 3H), 2.97-2.85 (m, 4H), 2.72 (s, 3H), 2.41 (s, 3H) |

Further analogues were prepared following Method D ($S_NAr$ displacement) with the corresponding chloropyrazine moiety and the stated amines either commercial or described in the intermediates section.

| Example | | | |
|---|---|---|---|
| Example 227 (Absolute stereochemistry arbitrarily assigned) | 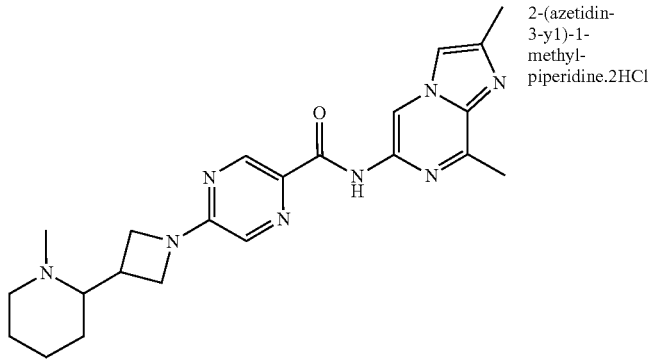<br>Enantiomer 1 | 2-(azetidin-3-yl)-1-methyl-piperidine.2HCl | LCMS (ES+) 421 (M + H)+, RT 2.06 min (Analytical method AcHSSC18); RT 5.39 min (SFCl, YMC AMYLOSE-C + 0.1% DEAISO 30% IPA SOL3); $^1$H NMR (400 MHz, DMSO) δ 9.68 (s, 1H), 9.14 (s, 1H), 8.73 (d, J = 1.3 Hz, 1H), 8.01 (s, 1H), 7.92 (d, J = 1.4 Hz, 1H), 4.34 (dd, J = 8.6, 8.6 Hz, 1H), 4.20 (dd, J = 8.8, 8.8 Hz, 1H), 4.06-3.94 (m, 2H), 2.96-2.92 (m, 1H), 2.76-2.67 (m, 4H), 2.40 (s, 3H), 2.18-2.06 (m, 5H), 1.71-1.61 (m, 2H), 1.55-1.41 (m, 2H), 1.25-1.21 (m, 1H), 1.11-1.08 (m, 1H). |
| Example 228 (Absolute stereochemistry arbitrarily assigned) | 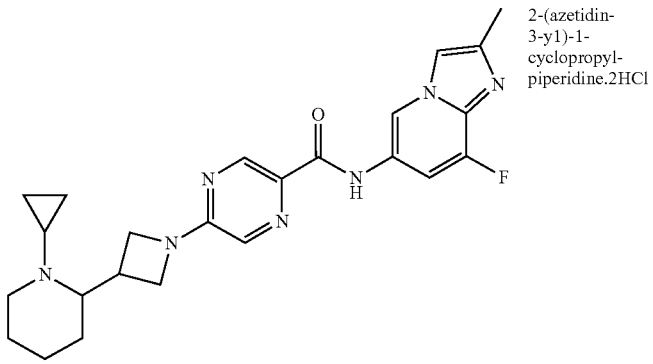<br>Enantiomer 1 | 2-(azetidin-3-yl)-1-cyclopropyl-piperidine.2HCl | LCMS (ES+) 450 (M + H)+, RT 1.96 min (Analytical method AcHSSC18); RT 18.01 min (SFCl, YMC CELLULOSE-SC + 0.1% DEAISO 50% IPA SOL3); $^1$H NMR (400 MHz, DMSO) δ 10.43 (s, 1H), 9.17 (d, J = 1.6 Hz, 1H), 8.70 (d, J = 1.3 Hz, 1H), 7.88 (dd, J = 0.8, 3.2 Hz, 1H), 7.86 (d, J = 1.3 Hz, 1H), 7.55 (dd, J = 1.6, 13.0 Hz, 1H), 4.36 (dd, J = 8.7, 8.7 Hz, 1H), 4.19 (dd, J = 8.7, 8.7 Hz, 1H), 4.10 (dd, J = 6.5, 9.0 Hz, 1H), 3.93-3.87 (m, 1H), 3.16-3.07 (m, 1H), 2.95-2.89 (m, 1H), 2.61-2.55 (m, 1H), 2.33 (s, 3H), 2.31-2.25 (m, 1H), 1.78-1.71 (m, 1H), 1.68-1.61 (m, 2H), 1.51-1.49 (m, 1H), 1.40-1.23 (m, 2H), 1.15-1.05 (m, 1H), 0.57-0.51 (m, 1H), 0.46-0.38 (m, 2H), 0.24-0.18 (m, 1H). |
| Example 229 (Absolute stereochemistry arbitrarily assigned) | 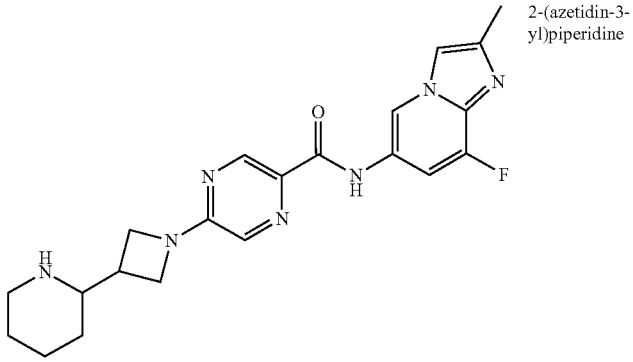<br>Enantiomer 1 | 2-(azetidin-3-yl)piperidine | LCMS (ES+) 410 (M + H)+, RT 1.88 min (Analytical method AcHSSC18); RT 27.16 min (SFC1, YMC CELLULOSE-SC + 0.1% DEAISO 45% EtOH SOL2); $^1$H NMR (400 MHz, DMSO) δ 10.44 (s, 1H), 9.19 (d, J = 1.6 Hz, 1H), 8.71 (d, J = 1.3 Hz, 1H), 7.90 (dd, J = 0.8, 3.1 Hz, 1H), 7.84 (d, J = 1.4 Hz, 1H), 7.57 (dd, J = 1.5, 13.2 Hz, 1H), 4.23-4.14 (m, 2H), 4.07 (dd, J = 5.7, 9.1 Hz, 1H), 3.98 (dd, J = 5.5, 9.1 Hz, 1H), 2.96 (d, J = 12.4 Hz, 1H), 2.71-2.59 (m, 2H), 2.35 (s, 3H), 1.79-1.76 (m, 1H), 1.63-1.59 (m, 1H), 1.53-1.50 (m, 1H), 1.36-1.24 (m, 2H), 1.01-0.93 (m, 1H). |

| Example | Structure | Name | Data |
|---|---|---|---|
| Example 230 (Absolute stereochemistry arbitrarily assigned) | 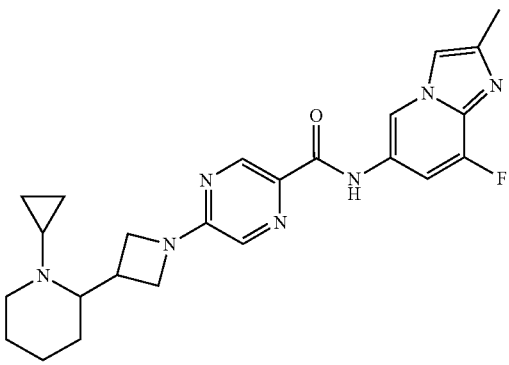 Enantiomer 2 | 2-(azetidin-3-yl)-1-cyclopropyl-piperidine.2 HCl | LCMS (ES+) 450 (M + H)+, RT 1.96 min (Analytical method AcHSSC18); $^1$H NMR (400 MHz, DMSO) δ 10.43 (s, 1H), 9.17 (d, J = 1.6 Hz, 1H), 8.70 (d, J = 1.3 Hz, 1H), 7.88 (dd, J = 0.7, 3.1 Hz, 1H), 7.86 (d, J = 1.4 Hz, 1H), 7.55 (dd, J = 1.6, 13.1 Hz, 1H), 4.37 (dd, J = 8.8, 8.8 Hz, 1H), 4.20 (dd, J = 8.8, 8.8 Hz, 1H), 4.10 (dd, J = 6.6, 9.0 Hz, 1H), 3.89 (dd, J = 6.7, 8.7 Hz, 1H), 3.13-3.07 (m, 1H), 2.94-2.89 (m, 1H), 2.60-2.55 (m, 1H), 2.33 (s, 3H), 2.31-2.25 (m, 1H), 1.78-1.72 (m, 1H), 1.69-1.60 (m, 2H), 1.54-1.48 (m, 1H), 1.42-1.22 (m, 2H), 1.15-1.04 (m, 1H), 0.58-0.52 (m, 1H), 0.46-0.38 (m, 2H), 0.23-0.18 (m, 1H). |
| Example 231 (Absolute stereochemistry arbitrarily assigned) | 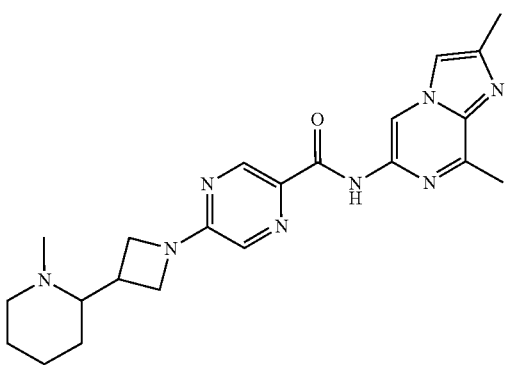 Enantiomer 2 | 2-(azetidin-3-yl)-1-methyl-piperidine.2HCl | LCMS (ES+) 421 (M + H)+, RT 2.07 min (Analytical method AcHSSC18); $^1$H NMR (400 MHz, DMSO) δ 9.68 (s, 1H), 9.14 (d, J = 0.6 Hz, 1H), 8.73 (d, J = 1.4 Hz, 1H), 8.01 (d, J = 0.7 Hz, 1H), 7.92 (d, J = 1.4 Hz, 1H), 4.34 (dd, J = 8.5, 8.5 Hz, 1H), 4.20 (dd, J = 8.8, 8.8 Hz, 1H), 4.07-3.93 (m, 2H), 2.98-2.92 (m, 1H), 2.76-2.68 (m, 4H), 2.40 (s, 3H), 2.18-2.05 (m, 5H), 1.72-1.61 (m, 2H), 1.55-1.43 (m, 2H), 1.28-1.21 (m, 1H), 1.14-1.02 (m, 1H). |
| Example 232 (Absolute stereochemistry arbitrarily assigned) | 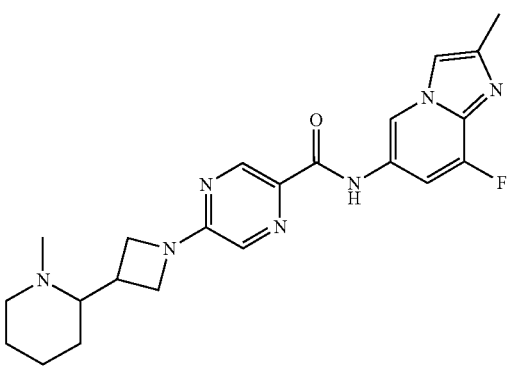 Enantiomer 1 | 2-(azetidin-3-yl)-1-methyl-piperidine.2HCl | LCMS (ES+) 424 (M + H)+, RT 1.88 min (Analytical method AcHSSC18); RT 5.92 min (SFC1, YMC AMYLOSE-C + 0.1% DEAISO 40% IPA SOL3); $^1$H NMR (400 MHz, DMSO) δ 10.46 (s, 1H), 9.19 (d, J =1.6 Hz, 1H), 8.72 (d, J = 1.4 Hz, 1H), 7.90-7.88 (m, 2H), 7.57 (dd, J = 1.7, 13.1 Hz, 1H), 4.34 (dd, J = 8.5, 8.5 Hz, 1H), 4.20 (dd, J = 8.8, 8.8 Hz, 1H), 4.06-4.01 (m, 1H), 3.96 (t, J = .0 Hz, 1H), 2.98-2.92 (m, 1H), 2.76-2.70 (m, 1H), 2.35 (d, J = 0.8 Hz, 3H), 2.18-2.11 (m, 4H), 2.08 (dd, J = 3.3, 11.5 Hz, 1H), 1.72-1.62 (m, 2H), 1.55-1.44 (m, 2H), 1.28-1.21 (m, 1H), 1.14-1.02 (m, 1H). $^{19}$F NMR (376 MHz, d6 DMSO) δ −132 ppm. |

| Example | Structure | Name | Data |
|---|---|---|---|
| Example 233 (Absolute stereochemistry arbitrarily assigned) Enantiomer 2 | 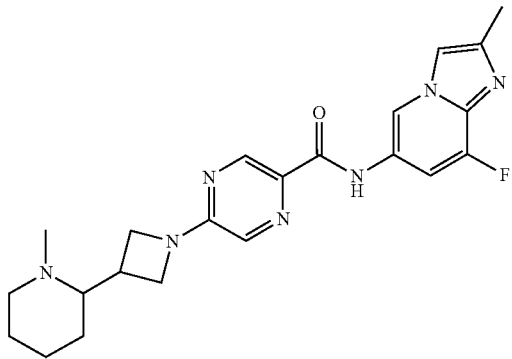 | 2-(azetidin-3-yl)-1-methyl-piperidine.2HCl | LCMS (ES+) 424 (M + H)+, RT 1.87 min (Analytical method AcHSSC18); $^1$H NMR (400 MHz, DMSO) δ 10.46 (s, 1H), 9.19 (d, J = 1.6 Hz, 1H), 8.72 (d, J = 1.4 Hz, 1H), 7.90-7.88 (m, 2H), 7.57 (dd, J = 1.7, 13.1 Hz, 1H), 4.34 (dd, J = 8.6, 8.6 Hz, 1H), 4.20 (dd, J = 8.9, 8.9 Hz, 1H), 4.05 (t, J = 7.6 Hz, 1H), 3.95 (t, J = 8.1 Hz, 1H), 2.99-2.93 (m, 1H), 2.76-2.73 (m, 1H), 2.35 (s, 3H), 2.16 (s, 4H), 2.09 (d, J = 11.7 Hz, 4H), 1.72-1.62 (m, 2H), 1.55-1.41 (m, 2H), 1.29-1.08 (m, 2H). |
| Example 234 | 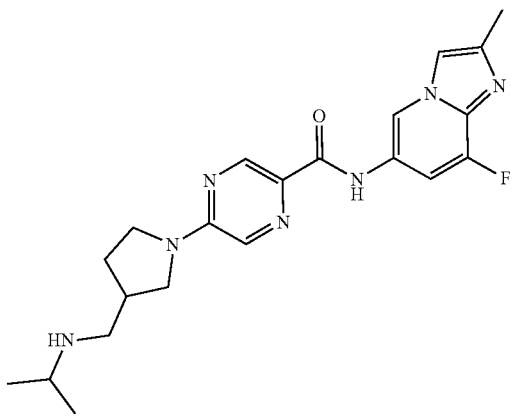 [SMILES: Cc1cn2cc(NC(=O)c3cnc(N4CCC(CNC(C)C)C4)cn3)cc(F)c2n1] | N-(pyrrolidin-3-ylmethyl)propan-2-amine | LCMS (ES+) 412 (M + H)+, RT 1.85 min (Analytical method AcHSSC18); $^1$H NMR (400 MHz, DMSO) δ 10.44 (s, 1H), 9.23 (d, J = 1.5 Hz, 1H), 8.78 (d, J = 1.3 Hz, 1H), 8.00 (d, J = 1.3 Hz, 1H), 7.92 (d, J = 2.5 Hz, 1H), 7.61 (dd, J = 1.5, 13.0 Hz, 1H), 3.82-3.68 (m, 2H), 3.60-3.50 (m, 1H), 3.30 (dd, J = 7.2, 11.0 Hz, 1H), 2.48-2.41 (m, 1H), 2.38 (s, 3H), 2.23-2.16 (m, 1H), 1.85-1.76 (m, 1H), 1.04 (dd, J = 3.4, 6.2 Hz, 6H). $^{19}$F NMR (376 MHz, DMSO) δ −132.1 ppm. |

The following compounds were prepared from chirally pure reported compounds using Method Q (Formaldehyde reductive amination).

| Example | Structure | Name | Data |
|---|---|---|---|
| Example 235 (Absolute stereochemistry arbitrarily assigned) Stereoisomer 1 | 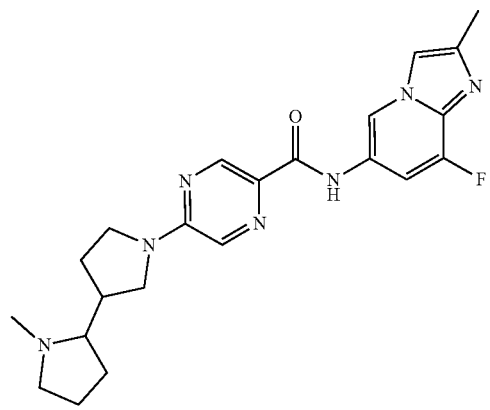 | By methylation of reported amine NH | LCMS (ES+) 424 (M + H)+, RT 1.88 min (Analytical method AcHSSC18); $^1$H NMR (400 MHz, DMSO) δ 10.42 (s, 1H), 9.19 (d, J = 1.6 Hz, 1H), 8.75 (d, J = 1.3 Hz, 1H), 8.00 (d, J = 1.0 Hz, 1H), 7.90 (dd, J = 0.8, 3.2 Hz, 1H), 7.57 (dd, J = 1.6, 13.1 Hz, 1H), 3.85 (dd, J = 7.8, 10.6 Hz, 1H), 3.74 (dd, J = 9.1, 9.1 Hz, 1H), 3.48-3.41 (m, 1H), 3.22 (dd, J = 10.0, 10.0 Hz, 1H), 3.00-2.95 (m, 1H), 2.48-2.42 (m, 1H), 2.35 (d, J = 0.7 Hz, 3H), 2.31 (s, 3H), 2.22-2.15 (m, 1H), 2.06-2.01 (m, 1H), 1.88-1.74 (m, 2H), 1.70-1.56 (m, 3H). $^{19}$F NMR (376 MHz, d6 DMSO) δ −132 ppm. |

-continued

| Example 236 (Absolute stereochemistry arbitrarily assigned) 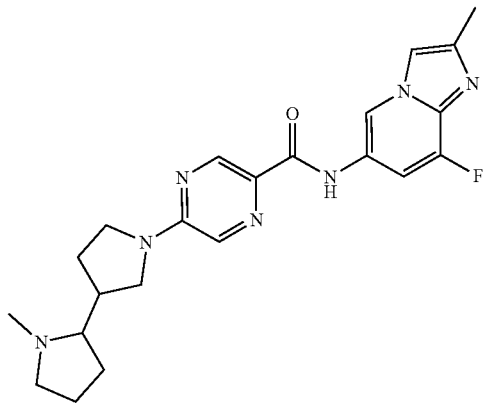 Stereoisomer 2 | By methylation of reported amine NH | LCMS (ES+) 424 (M + H)+, RT 1.88 min (Analytical method AcHSSC18); ¹H NMR (400 MHz, DMSO) δ 10.42 (s, 1H), 9.19 (d, J = 1.6 Hz, 1H), 8.75 (d, J = 1.3 Hz, 1H), 8.00 (d, J = 0.9 Hz, 1H), 7.90 (dd, J = 0.8, 3.2 Hz, 1H), 7.57 (dd, J = 1.6, 13.1 Hz, 1H), 3.85 (dd, J = 7.8, 10.7 Hz, 1H), 3.77-3.72 (m, 1H), 3.46 (dd, J = 7.5, 10.3 Hz, 1H), 3.23 (dd, J = 10.2, 10.2 Hz, 1H), 3.00-2.95 (m, 1H), 2.48-2.40 (m, 1H), 2.35 (d, J = 0.7 Hz, 3H), 2.31 (s, 3H), 2.22-2.15 (m, 1H), 2.07-2.00 (m, 1H), 1.88-1.74 (m, 2H), 1.71-1.58 (m, 3H). ¹⁹F NMR (376 MHz, d6 DMSO) δ −132 ppm. |
| Example 237 (Absolute stereochemistry arbitrarily assigned) 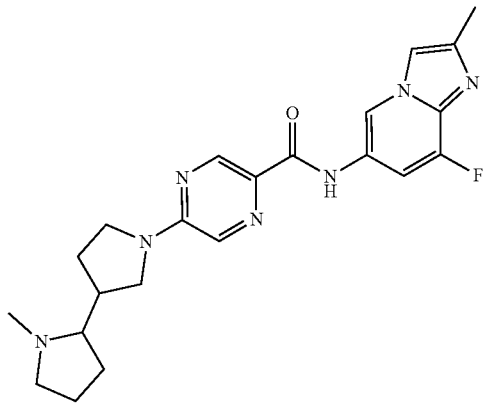 Stereoisomer 3 | By methylation of reported amine NH | LCMS (ES+) 424 (M + H)+, RT 3.36 min (Analytical method BicarbBEHC18); ¹H NMR (400 MHz, DMSO) δ 10.44 (s, 1H), 9.20 (d, J= 1.5 Hz, 1H), 8.75 (d, J = 1.1 Hz, 1H), 7.99 (d, J = 1.1 Hz, 1H), 7.90 (dd, J = 0.7, 3.2 Hz, 1H), 7.58 (dd, J = 1.6, 13.1 Hz, 1H), 3.77 (dd, J = 8.7, 8.7 Hz, 1H), 3.61 (dd, J = 8.4, 10.9 Hz, 1H), 3.54-3.46 (m, 1H), 3.26 (t, J = 9.9 Hz, 1H), 3.00-2.94 (m, 1H), 2.64-2.56 (m, 1H), 2.35-2.31 (m, 6H), 2.19-2.10 (m, 2H), 1.87-1.75 (m, 2H), 1.70-1.52 (m, 3H). ¹⁹F NMR (376 MHz, d6 DMSO) δ −132 ppm. |
| Example 238 (Absolute stereochemistry arbitrarily assigned) 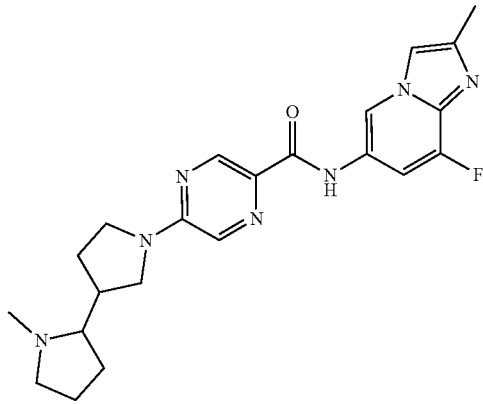 Stereoisomer 4 | By methylation of reported amine NH | LCMS (ES+) 424 (M + H)+, RT 1.88 min (Analytical method AcHSSC18); ¹H NMR (400 MHz, DMSO) δ 10.44 (s, 1H), 9.20 (d, J = 1.6 Hz, 1H), 8.75 (d, J = 1.1 Hz, 1H), 7.99 (d, J = 1.1 Hz, 1H), 7.90 (d, J = 2.8 Hz, 1H), 7.58 (dd, J = 1.6, 13.0 Hz, 1H), 3.77 (dd, J = 8.7, 8.7 Hz, 1H), 3.65-3.60 (m, 1H), 3.54-3.46 (m, 1H), 3.26 (dd, J = 9.0, 11.5 Hz, 1H), 3.00-2.94 (m, 1H), 2.67-2.58 (m, 0H), 2.33 (d, J = 15.1 Hz, 6H), 2.18-2.10 (m, 2H), 1.86-1.72 (m, 2H), 1.70-1.52 (m, 3H). ¹⁹F NMR (376 MHz, d6 DMSO) δ −132 ppm. |

| Example 239 (Absolute stereochemistry from commercial SM) | 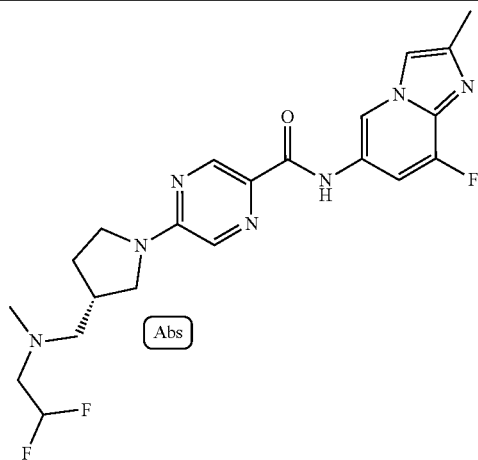 | Reductive amination on secondary amine | LCMS (ES+) 448 (M + H)+, RT 2.04 min (Analytical method AcHSSC18); $^1$H NMR (400 MHz, DMSO) δ 10.43 (s, 1H), 9.20 (d, J = 1.6 Hz, 1H), 8.75 (d, J = 1.3 Hz, 1H), 7.98 (d, J = 1.3 Hz, 1H), 7.90 (d, J = 2.8 Hz, 1H), 7.57 (dd, J = 1.6, 13.0 Hz, 1H), 6.13 (tt, J = 4.3, 55.9 Hz, 1H), 3.77-3.65 (m, 2H), 3.58-3.51 (m, 1H), 3.31-3.24 (m, 1H), 2.86-2.74 (m, 2H), 2.62-2.55 (m, 1H), 2.36-2.35 (m, 6H), 2.18-2.10 (m, 1H), 1.77-1.75 (m, 1H). |

The following compounds were prepared from racemic secondary amine using Method Q (Formaldehyde reductive amination) followed by chiral SFC resolution.

| Example 240 (Absolute stereochemistry arbitrarily assigned) | 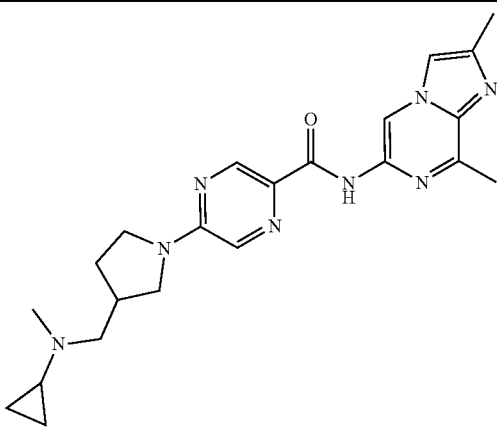<br>Enantiomer 1 | Reductive amination on secondary amine | LCMS (ES+) 421 (M + H)+, RT 2.11 min (Analytical method AcHSSC18); $^1$H NMR (400 MHz, DMSO) δ 9.66 (s, 1H), 9.14 (s, 1H), 8.76 (d, J = 1.1 Hz, 1H), 8.04 (d, J = 1.1 Hz, 1H), 8.01 (s, 1H), 3.73-3.64 (m, 2H), 3.57-3.50 (m, 1H), 3.22 (dd, J = 7.7, 10.8 Hz, 1H), 2.71 (s, 3H), 2.64-2.58 (m, 1H), 2.40 (s, 3H), 2.31 (s, 3H), 2.15-2.08 (m, 1H), 1.78-1.63 (m, 2H), 0.48-0.43 (m, 2H), 0.36-0.27 (m, 2H) |
| Example 241 (Absolute stereochemistry arbitrarily assigned) | 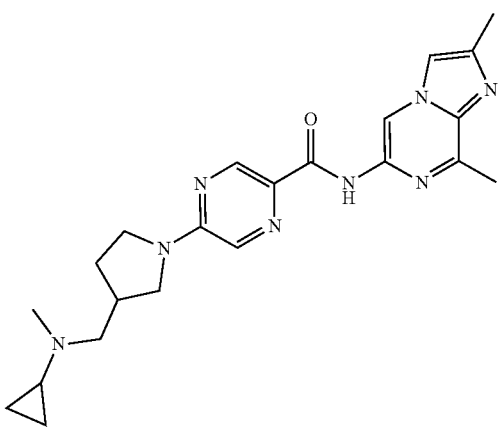<br>Enantiomer 2 | Reductive amination on secondary amine | LCMS (ES+) 421 (M + H)+, RT 2.13 min (Analytical method AcHSSC18); $^1$NMR (400 MHz, DMSO) δ 9.66 (s, 1H), 9.15 (d, J = 0.6 Hz, 1H), 8.76 (d, J = 1.3 Hz, 1H), 8.04 (d, J = 1.1 Hz, 1H), 8.01 (d, J = 0.7 Hz, 1H), 3.73-3.64 (m, 2H), 3.57-3.49 (m, 1H), 3.22 (dd, J = 6.7, 11.1 Hz, 1H), 2.71 (s, 3H), 2.40 (s, 3H), 2.31 (s, 3H), 2.15-2.09 (m, 1H), 1.71-1.63 (m, 2H), 0.48-0.43 (m, 2H), 0.36-0.27 (m, 2H) |

Example 242: 5-(6-cyclopropyl-2,6-diazaspiro[3.5] nonan-2-yl)-N-(8-fluoro-2-methylimidazo[1,2-a]pyridin-6-yl)pyrazine-2-carboxamide

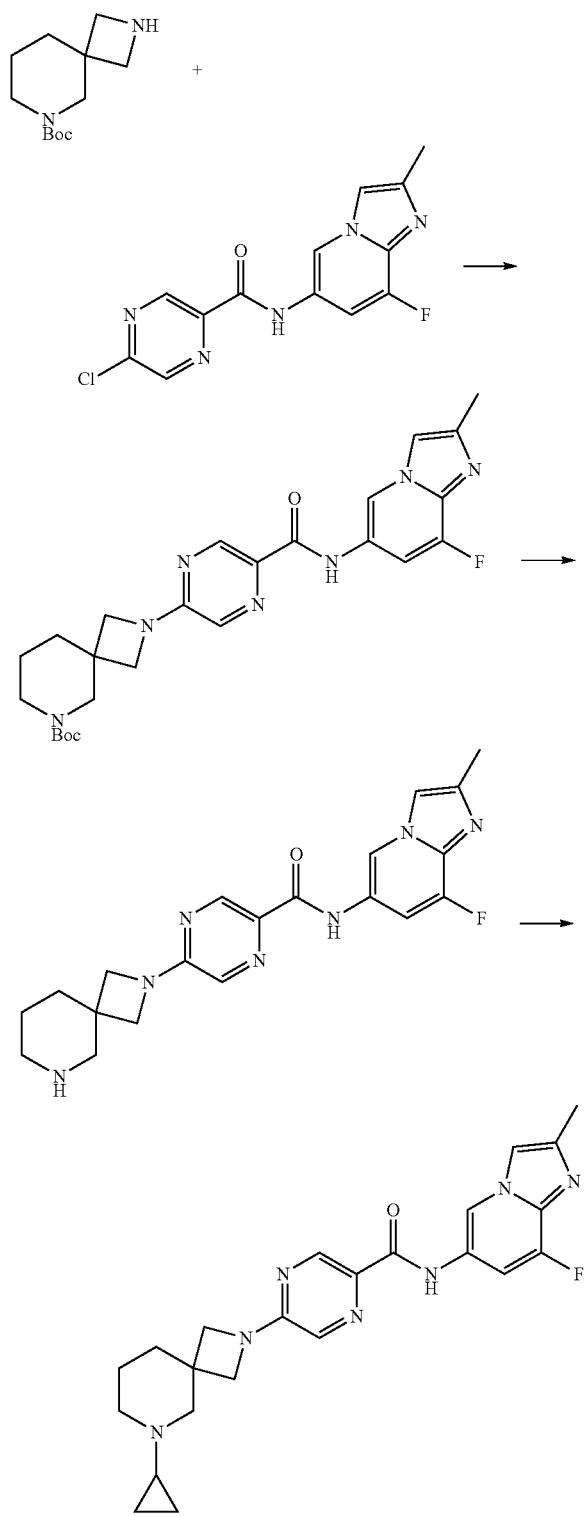

A suspension of tert-butyl 2,6-diazaspiro[3.5]nonane-6-carboxylate hydrochloride (174 mg, 0.663 mmol), 5-chloro-N-(8-fluoro-2-methyl-imidazo[1,2-a]pyridin-6-yl)pyrazine-2-carboxamide (156 mg, 0.510 mmol) and triethylamine (0.21 mL, 1.53 mmol) in 1,4-dioxane (4.70 mL) was heated to 140° C. in a microwave for 40 minutes. The reaction mixture was concentrated under reduced pressure yielding the crude material, which was used without further purification, assuming a quantitative yield. MS (ES+) 496.5 [M+H]+.

A mixture of tert-butyl 2-[5-[(8-fluoro-2-methyl-imidazo[1,2-a]pyridin-6-yl)carbamoyl]pyrazin-2-yl]-2,8-diazaspiro[3.5]nonane-8-carboxylate (252 mg, 0.509 mmol) in 4 M hydrogen chloride in 1,4-dioxane (2.5 mL, 10.2 mmol) and methyl alcohol (2.50 mL) was stirred overnight at room temperature. The reaction mixture was concentrated under reduced pressure. The crude material was taken up in methanol and passed through an SCX-2 cartridge (10 g) with the product eluted in 2 M $NH_3$ in methanol and concentrated under reduced pressure to yield 5-(2,8-diazaspiro[3.5]nonan-2-yl)-N-(8-fluoro-2-methyl-imidazo[1,2-a]pyridin-6-yl)pyrazine-2-carboxamide, which was used without further purification. MS (ES+) 396.4 [M+H]+.

A suspension of 5-(2,8-diazaspiro[3.5]nonan-2-yl)-N-(8-fluoro-2-methyl-imidazo[1,2-a]pyridin-6-yl)pyrazine-2-carboxamide (250 mg, 0.632 mmol), (1-ethoxycyclopropoxy)trimethylsilane (0.14 mL, 0.695 mmol) and sodium cyanoborohydride (48 mg, 0.759 mmol) in methanol (6 mL) and acetic acid (0.1 mL) was stirred under nitrogen at 50° C. overnight. The reaction mixture was concentrated under reduced pressure and the crude material purified by reverse phase HPLC (Xbridge Phenyl 19×150 mm, 10 µm 40-100% MeOH/$H_2O$ (10 mM $NH_4CO_3$), 20 mL/min, RT) to yield 5-(8-cyclopropyl-2,8-diazaspiro[3.5]nonan-2-yl)-N-(8-fluoro-2-methyl-imidazo[1,2-a]pyridin-6-yl)pyrazine-2-carboxamide. LCMS (ES+) 436.4 [M+H]+, RT 1.92 min (Analytical method AcHSSC18). $^1$H NMR (400 MHz, DMSO) δ 10.45 (s, 1H), 9.19 (d, J=1.6 Hz, 1H), 8.71 (d, J=1.3 Hz, 1H), 7.90 (dd, J=0.8, 3.2 Hz, 1H), 7.87 (d, J=1.4 Hz, 1H), 7.57 (dd, J=1.6, 13.1 Hz, 1H), 3.85 (d, J=8.9 Hz, 2H), 3.81 (d, J=8.9 Hz, 2H), 2.74-2.53 (m, 4H), 2.35 (s, 3H), 1.69-1.63 (m, 3H), 1.51-1.46 (m, 2H), 0.47-0.41 (m, 2H), 0.34-0.29 (m, 2H).

Example 243: N-(8-fluoro-2-methylimidazo[1,2-a]pyridin-6-yl)-5-(3-(1-methylpiperidin-3-yl)azetidin-1-yl)pyrazine-2-carboxamide

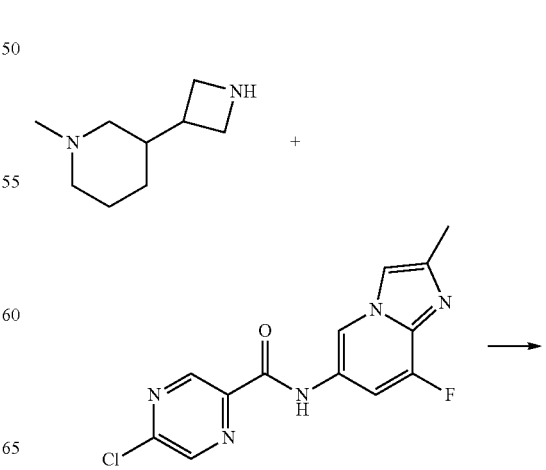

-continued

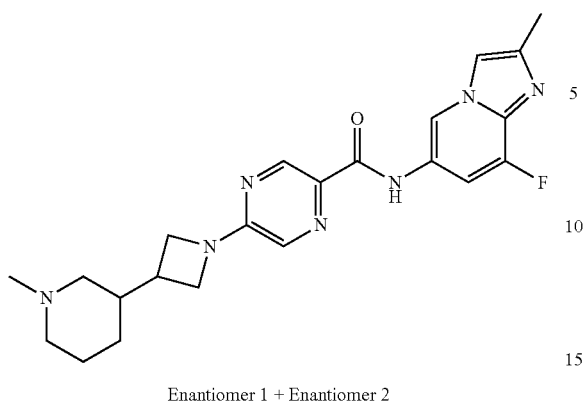

Enantiomer 1 + Enantiomer 2

A suspension of 5-chloro-N-(8-fluoro-2-methylimidazo[1,2-a]pyridin-6-yl)pyrazine-2-carboxamide (122 mg, 0.399 mmol), 3-(azetidin-3-yl)-1-methylpiperidine hydrochloride (80 mg, 0.421 mmol) and cesium carbonate (520 mg, 1.60 mmol) in DMF (3 mL) was heated to 100° C. for 24 hours. The reaction mixture was filtered and the crude material purified by reverse phase HPLC (Sunfire C18 19×150 mm, 10 μm 5-60% ACN/H$_2$O (10 mM NH$_4$CO$_3$), 20 mL/min, RT) to yield N-(8-fluoro-2-methylimidazo[1,2-a]pyridin-6-yl)-5-(3-(1-methylpiperidin-3-yl)azetidin-1-yl)pyrazine-2-carboxamide. LCMS (ES+) 424.4 [M+H]+, RT 1.91 min (Analytical method AcHSSC18). $^1$H NMR (400 MHz, DMSO) δ 10.44 (s, 1H), 9.19 (d, J=1.5 Hz, 1H), 8.72 (d, J=1.3 Hz, 1H), 7.90 (d, J=2.8 Hz, 1H), 7.85 (d, J=1.4 Hz, 1H), 7.56 (dd, J=1.6, 13.1 Hz, 1H), 4.27-4.20 (m, 2H), 3.95 (dd, J=6.0, 8.8 Hz, 2H), 2.70-2.64 (m, 3H), 2.35 (s, 3H), 2.16 (s, 3H), 1.89-1.42 (m, 6H), 0.87-0.84 (m, 1H).

Example 244: 5-(3-(1-cyclopropylpiperidin-3-yl)azetidin-1-yl)-N-(8-fluoro-2-methylimidazo[1,2-a]pyridin-6-yl)pyrazine-2-carboxamide -continued

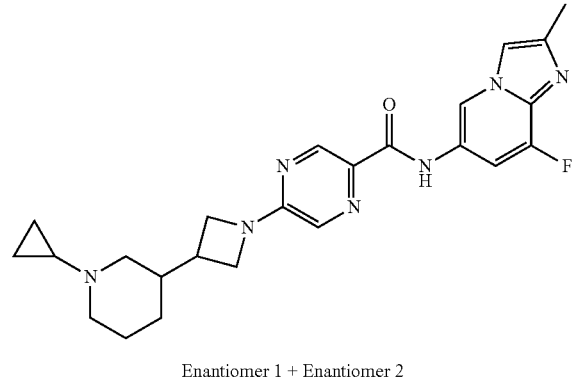

Enantiomer 1 + Enantiomer 2

A mixture of 5-chloro-N-(8-fluoro-2-methylimidazo[1,2-a]pyridin-6-yl)pyrazine-2-carboxamide (91 mg, 0.299 mmol), (3-(azetidin-3-yl)-1-cyclopropylpiperidine hydrochloride (70 mg, 0.324 mmol) and cesium carbonate (389 mg, 1.19 mmol) in DMF (3.0 mL) was heated to 100° C. overnight. The reaction mixture was allowed to cool to room temperature, filtered and purified by reverse phase HPLC (Xbridge Phenyl 19×150 mm, 10 μm 40-100% MeOH/H$_2$O (10 mM NH$_4$CO$_3$), 20 mL/min, RT) to yield 5-(3-(1-cyclopropylpiperidin-3-yl)azetidin-1-yl)-N-(8-fluoro-2-methylimidazo[1,2-a]pyridin-6-yl)pyrazine-2-carboxamide. LCMS (ES+) 450.3 [M+H]+, RT 2.00 min (Analytical method AcHSSC18). $^1$H NMR (400 MHz, DMSO) δ 10.45 (s, 1H), 9.19 (d, J=1.6 Hz, 1H), 8.71 (d, J=1.4 Hz, 1H), 7.90 (d, J=2.8 Hz, 1H), 7.86 (d, J=1.4 Hz, 1H), 7.56 (dd, J=1.6, 13.0 Hz, 1H), 4.28-4.21 (m, 2H), 3.98-3.90 (m, 2H), 2.84 (dd, J=11.0, 11.0 Hz, 2H), 2.67-2.60 (m, 1H), 2.34 (s, 3H), 2.18-2.11 (m, 1H), 1.87 (dd, J=10.2, 10.2 Hz, 1H), 1.75-1.55 (m, 4H), 1.44-1.37 (m, 1H), 0.96-0.89 (m, 1H), 0.44-0.40 (m, 2H), 0.35-0.25 (m, 2H).

Example 245: N-(8-fluoro-2-methylimidazo[1,2-a]pyridin-6-yl)-5-(3-(pyrrolidin-1-ylmethyl)azetidin-1-yl)pyrazine-2-carboxamide

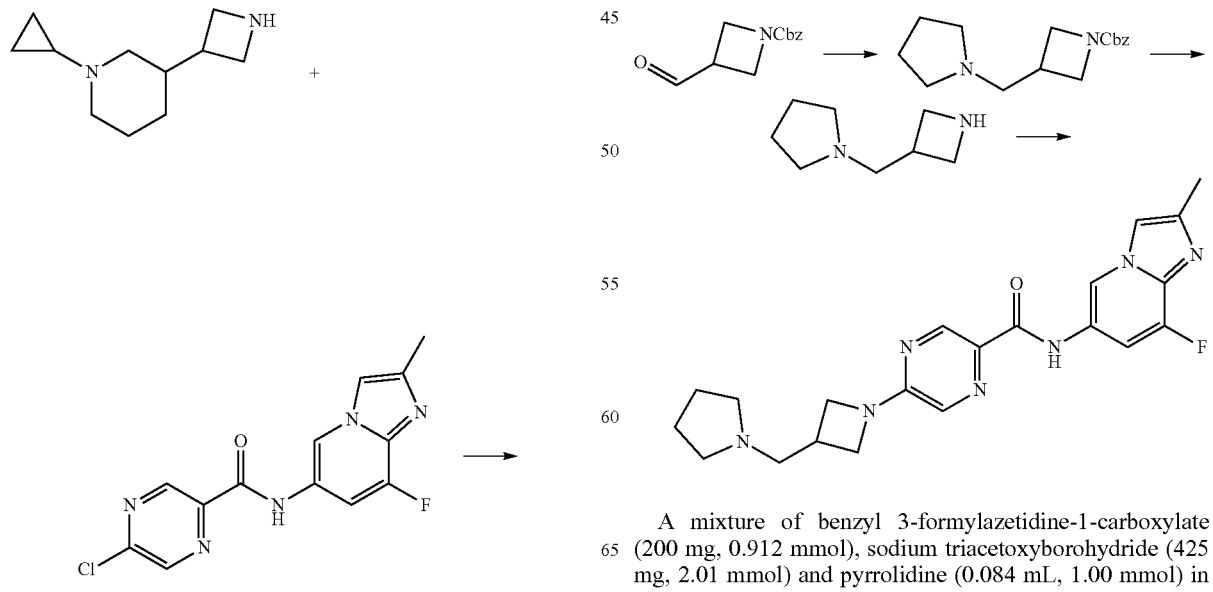

A mixture of benzyl 3-formylazetidine-1-carboxylate (200 mg, 0.912 mmol), sodium triacetoxyborohydride (425 mg, 2.01 mmol) and pyrrolidine (0.084 mL, 1.00 mmol) in DCM (10 mL) was stirred at room temperature overnight.

The reaction was diluted with sat. aq. NaHCO₃ and water. The mixture was passed through a phase separator and concentrated under reduced pressure to yield the crude material.

To a degassed solution of benzyl 3-(pyrrolidin-1-ylmethyl)azetidine-1-carboxylate (130 mg, 0.474 mmol) and 1-methyl-1,4-cyclohexadiene (1.1 mL, 9.48 mmol) in ethanol (5.0 mL) under nitrogen was added 10% palladium on carbon (50 mg, 0.474 mmol) and the reaction was heated to 70° C. overnight. The reaction was allowed to cool to room temperature and filtered through celite. The eluent was concentrated under reduced pressure to yield the crude material, which was taken forward without further purification. MS (ES+) 141.1 [M+H]+.

A mixture of 5-chloro-N-(8-fluoro-2-methylimidazo[1,2-a]pyridin-6-yl)pyrazine-2-carboxamide (111 mg, 0.362 mmol), 1-(azetidin-3-ylmethyl)pyrrolidine (66 mg, 0.471 mmol) and cesium carbonate (472 mg, 1.45 mmol) in DMF (3.0 mL) was heated to 100° C. overnight. The reaction mixture was allowed to cool to room temperature, filtered and purified by reverse phase HPLC (Sunfire C18 19×150 mm, 10 μm 5-60% ACN/H₂O (10 mM NH₄CO₃), 20 mL/min, RT) to yield N-(8-fluoro-2-methylimidazo[1,2-a]pyridin-6-yl)-5-(3-(pyrrolidin-1-ylmethyl)azetidin-1-yl)pyrazine-2-carboxamide. LCMS (ES+) 410.4 [M+H]+, RT 1.78 min (Analytical method AcHSSC18). ¹H NMR (400 MHz, DMSO) δ 10.44 (s, 1H), 9.18 (d, J=1.6 Hz, 1H), 8.71 (d, J=1.3 Hz, 1H), 7.89 (dd, J=0.8, 3.2 Hz, 1H), 7.87 (d, J=1.2 Hz, 1H), 7.56 (dd, J=1.6, 13.0 Hz, 1H), 4.28 (dd, J=8.6, 8.6 Hz, 2H), 3.86 (dd, J=5.6, 9.0 Hz, 2H), 3.04-2.94 (m, 2H), 2.72 (d, J=7.7 Hz, 2H), 2.49-2.43 (m, 4H), 2.35 (s, 3H), 1.72-1.67 (m, 4H).

Example 246: N-(8-fluoro-2-methylimidazo[1,2-a]pyridin-6-yl)-5-(3-(morpholinomethyl)azetidin-1-yl)pyrazine-2-carboxamide

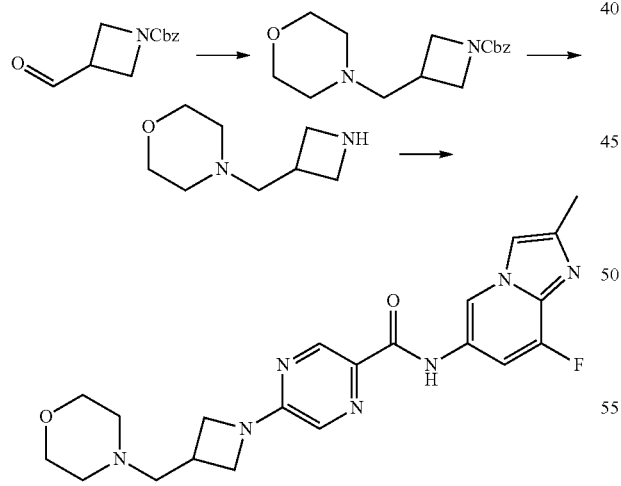

A mixture of benzyl 3-formylazetidine-1-carboxylate (200 mg, 0.912 mmol), sodium triacetoxyborohydride (425 mg, 2.01 mmol) and morpholine (0.088 mL, 1.00 mmol) in DCM (10 mL) was stirred at room temperature overnight. The reaction was diluted with sat. aq. NaHCO₃ and water. The mixture was passed through a phase separator and concentrated under reduced pressure to yield the crude material.

To a degassed solution of benzyl 3-(morpholinomethyl)azetidine-1-carboxylate (160 mg, 0.551 mmol) and 1-methyl-1,4-cyclohexadiene (1.2 mL, 11.0 mmol) in ethanol (6.0 mL) under nitrogen was added 10% palladium on carbon (59 mg, 0.551 mmol) and the reaction was heated to 70° C. overnight. The reaction was allowed to cool to room temperature and was filtered through celite. The eluent was concentrated under reduced pressure to yield the crude material, which was taken forward without further purification. MS (ES+) 157.1 [M+H]+.

A mixture of 5-chloro-N-(8-fluoro-2-methylimidazo[1,2-a]pyridin-6-yl)pyrazine-2-carboxamide (117 mg, 0.384 mmol), 4-(azetidin-3-ylmethyl)morpholine (78 mg, 0.499 mmol) and cesium carbonate (501 mg, 1.54 mmol) in DMF (3.0 mL) was heated to 100° C. overnight. The reaction mixture was allowed to cool to room temperature, filtered and purified by reverse phase HPLC (Xbridge Phenyl 19×150 mm, 10 μm 40-100% MeOH/H₂O (10 mM NH₄CO₃), 20 mL/min, RT) to yield N-(8-fluoro-2-methylimidazo[1,2-a]pyridin-6-yl)-5-(3-(morpholinomethyl)azetidin-1-yl)pyrazine-2-carboxamide. LCMS (ES+) 426.4 [M+H]+, RT 1.73 min (Analytical method AcHSSC18). ¹H NMR (400 MHz, DMSO) δ 10.46 (s, 1H), 9.19 (d, J=1.5 Hz, 1H), 8.72 (d, J=1.4 Hz, 1H), 7.90 (dd, J=0.8, 3.2 Hz, 1H), 7.88 (d, J=1.3 Hz, 1H), 7.56 (dd, J=1.6, 13.1 Hz, 1H), 4.28 (dd, J=8.5, 8.5 Hz, 2H), 3.86 (dd, J=5.6, 8.9 Hz, 2H), 3.58 (dd, J=4.6, 4.6 Hz, 4H), 3.10-3.02 (m, 1H), 2.63 (d, J=7.7 Hz, 2H), 2.42-2.36 (m, 4H), 2.34 (d, J=0.7 Hz, 3H).

Example 247: 5-(3-((cyclopropylamino)methyl)-3-fluoroazetidin-1-yl)-N-(8-fluoro-2-methylimidazo[1,2-a]pyridin-6-yl)pyrazine-2-carboxamide

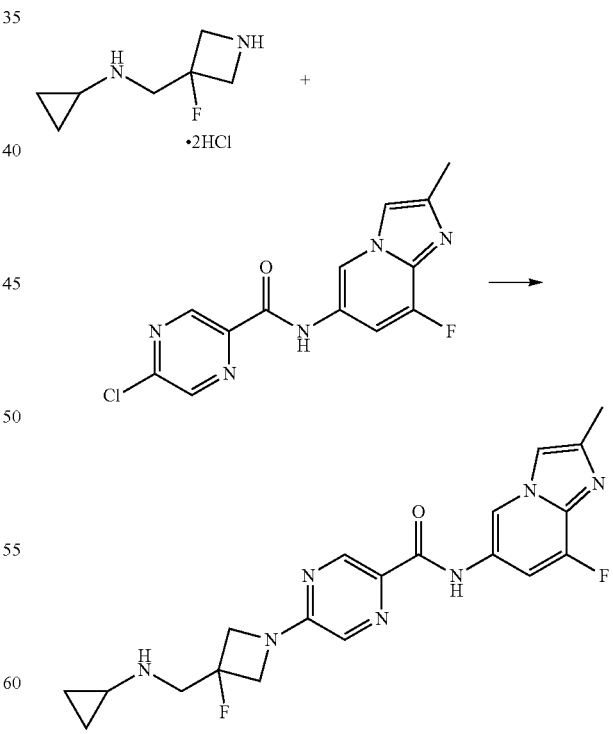

A mixture of N-[(3-fluoroazetidin-3-yl)methyl]cyclopropanamine dihydrochloride (92 mg, 0.425 mmol), 5-chloro-N-(8-fluoro-2-methyl-imidazo[1,2-a]pyridin-6-yl)pyrazine-2-carboxamide (100 mg, 0.327 mmol) and triethylamine (0.14 mL, 0.981 mmol) in 1,4-dioxane (3.20 mL) was heated to 140° C. in a microwave for 80 minutes. The reaction mixture was allowed to cool to room temperature and was concentrated under reduced pressure. The crude material was submitted to achiral reverse phase HPLC for purification (Xbridge Phenyl 19×150 mm, 10 µm 20-80% MeOH/H$_2$O (10 mM NH$_4$CO$_3$), 20 mL/min, RT) to yield 5-[3-[(cyclopropylamino)methyl]-3-fluoro-azetidin-1-yl]-N-(8-fluoro-2-methyl-imidazo[1,2-a]pyridin-6-yl)pyrazine-2-carboxamide. LCMS (ES+) 414.2 [M+H]+, RT 3.59 min (Analytical method BicarbBEHC18). $^1$H NMR (400 MHz, DMSO) δ 10.50 (1H, s), 9.19 (1H, d, J=1.5 Hz), 8.76 (1H, d, J=1.4 Hz), 7.97 (1H, d, J=1.4 Hz), 7.90 (1H, d, J=2.8 Hz), 7.57 (1H, dd, J=1.6, 13.0 Hz), 4.40-4.20 (4H, m), 3.09 (2H, d, J=22.8 Hz), 2.58-2.55 (1H, m), 2.35 (3H, s), 2.20-2.14 (1H, m), 0.43-0.37 (2H, m), 0.28-0.24 (2H, m).

Example 248: 5-(3-((cyclopropylamino)methyl)-3-fluoroazetidin-1-yl)-N-(2,8-dimethylimidazo[1,2-a]pyrazin-6-yl)pyrazine-2-carboxamide

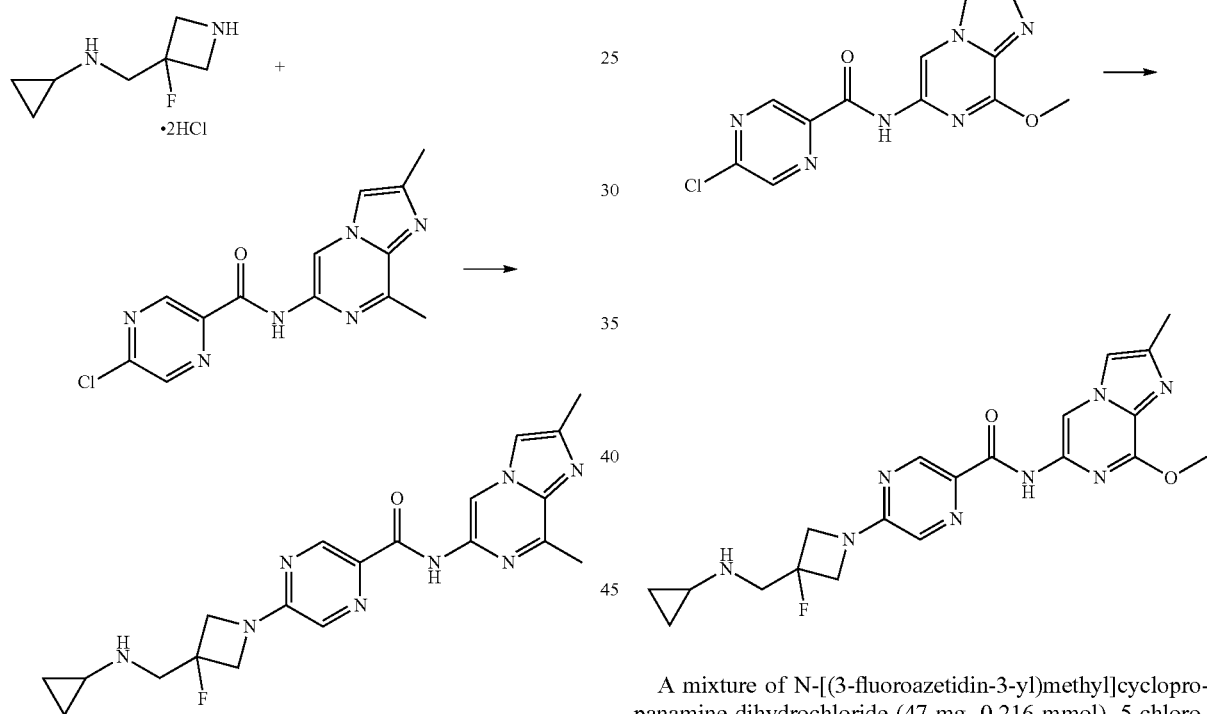

A mixture of N-[(3-fluoroazetidin-3-yl)methyl]cyclopropanamine dihydrochloride (65 mg, 0.301 mmol), 5-chloro-N-(2,8-dimethylimidazo[1,2-a]pyrazin-6-yl)pyrazine-2-carboxamide (70 mg, 0.231 mmol) and triethylamine (0.097 mL, 0.694 mmol) in 1,4-dioxane (2.50 mL) was heated to 140° C. in a microwave for 1 hour. The reaction mixture was concentrated under reduced pressure. The crude material was submitted to achiral reverse phase HPLC for purification (Xbridge Phenyl 19×150 mm, 10 µm 40-100% MeOH/H$_2$O (10 mM NH$_4$CO$_3$), 20 mL/min, RT then Xbridge Phenyl 19×150 mm, 10 µm 40-100% MeOH/H$_2$O (10 mM NH$_4$CO$_3$), 20 mL/min, RT) to yield 5-[3-[(cyclopropylamino)methyl]-3-fluoro-azetidin-1-yl]-N-(2,8-dimethyl-imidazo[1,2-a]pyrazin-6-yl)pyrazine-2-carboxamide. LCMS (ES+) 411.3 [M+H]+, RT 2.01 min (Analytical method AcHSSC18). 1H NMR (400 MHz, DMSO) δ 9.70 (s, 1H), 9.13 (s, 1H), 8.75 (d, J=1.1 Hz, 1H), 7.99 (s, 1H), 7.98 (d, J=1.3 Hz, 1H), 4.38-4.18 (m, 4H), 3.06 (dd, J=6.6, 22.5 Hz, 2H), 2.69 (s, 3H), 2.57-2.53 (m, 1H), 2.38 (s, 3H), 2.15 (dd, J=6.1, 6.1 Hz, 1H), 0.41-0.35 (m, 2H), 0.27-0.22 (m, 2H).

Example 249: 5-(3-((cyclopropylamino)methyl)-3-fluoroazetidin-1-yl)-N-(8-methoxy-2-methylimidazo[1,2-a]pyrazin-6-yl)pyrazine-2-carboxamide

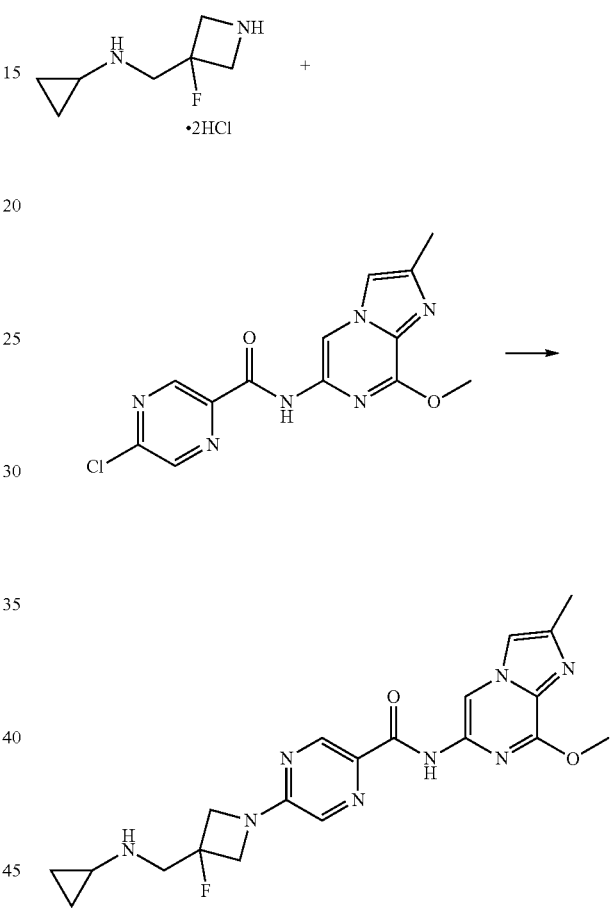

A mixture of N-[(3-fluoroazetidin-3-yl)methyl]cyclopropanamine dihydrochloride (47 mg, 0.216 mmol), 5-chloro-N-(8-methoxy-2-methyl-imidazo[1,2-a]pyrazin-6-yl)pyrazine-2-carboxamide (53 mg, 0.166 mmol) and triethylamine (0.070 mL, 0.499 mmol) in 1,4-dioxane (2.50 mL) was heated to 140° C. in a microwave for 1 hour. The reaction mixture was concentrated under reduced pressure. The crude material was submitted to achiral reverse phase HPLC for purification (Xbridge Phenyl 19×150 mm, 10 µm 40-100% MeOH/H$_2$O (10 mM NH$_4$CO$_3$), 20 mL/min, RT) to yield 5-[3-[(cyclopropylamino)methyl]-3-fluoro-azetidin-1-yl]-N-(8-methoxy-2-methyl-imidazo[1,2-a]pyrazin-6-yl)pyrazine-2-carboxamide. LCMS (ES+) 427.3 [M+H]+, RT 2.08 min (Analytical method AcHSSC18). $^1$H NMR (400 MHz, DMSO) δ 9.54 (s, 1H), 8.89 (s, 1H), 8.75 (d, J=1.4 Hz, 1H), 7.98 (d, J=1.4 Hz, 1H), 7.94 (s, 1H), 4.38-4.18 (m, 4H), 4.05 (s, 3H), 3.06 (dd, J=6.2, 22.6 Hz, 2H), 2.57-2.54 (m, 1H), 2.34 (s, 3H), 2.16 (s, 1H), 0.41-0.36 (m, 2H), 0.26-0.22 (m, 2H).

Example 250: 5-(3-((cyclopropylamino)methyl)-3-fluoropyrrolidin-1-yl)-N-(2,8-dimethylimidazo[1,2-a]pyrazine-6-yl)pyrazine-2-carboxamide

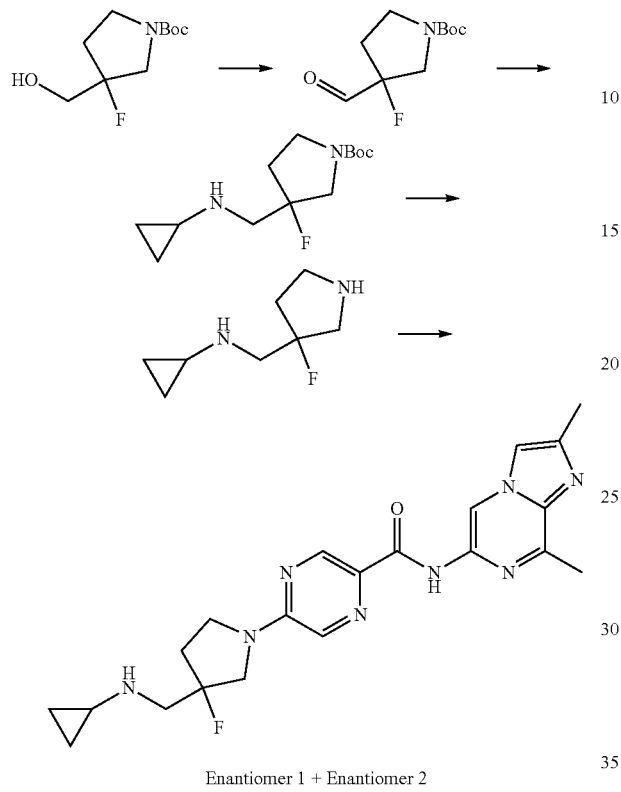

Enantiomer 1 + Enantiomer 2

A suspension of tert-butyl 3-fluoro-3-(hydroxymethyl)pyrrolidine-1-carboxylate (1.00 g, 4.56 mmol) and Dess-Martin periodinane (2.32 g, 5.47 mmol) in dichloromethane (23 mL) was stirred at room temperature overnight. The reaction mixture was diluted with an aqueous sodium thiosulfate (10% w/v) and sat. aqueous sodium hydrogen carbonate and stirred for 20 minutes. The mixture was passed through a phase separator and the organics concentrated under reduced pressure. The crude material was purified by flash column chromatography (0 to 100% EtOAc in cyclohexane; 40 g column). The product containing fractions were concentrated under reduced pressure to yield the product.

A mixture of tert-butyl 3-fluoro-3-formylpyrrolidine-1-carboxylate (215 mg, 0.990 mmol), sodium triacetoxyborohydride (440 mg, 2.08 mmol) and cyclopropylamine (0.075 mL, 1.09 mmol) in DCM (10 mL) was stirred at room temperature for three days. The reaction was diluted with water and stirred for 10 minutes. The mixture was passed through a phase separator and concentrated under reduced pressure to yield the crude material.

A mixture of tert-butyl 3-((cyclopropylamino)methyl)-3-fluoropyrrolidine-1-carboxylate (207 mg, 0.801 mmol) in 4 M hydrogen chloride in 1,4-dioxane (2.0 mL, 8.01 mmol) and methyl alcohol (2.0 mL) was stirred overnight at room temperature. The reaction mixture was concentrated under reduced pressure. The crude material was taken up in methanol and passed through an SCX-2 cartridge (5 g) with the product eluted in 2 M $NH_3$ in methanol and concentrated under reduced pressure to yield N-((3-fluoropyrrolidin-3-yl)methyl)cyclopropanamine. MS (ES+) 159.2 [M+H]+.

A suspension of 5-chloro-N-(2,8-dimethylimidazo[1,2-a]pyrazin-6-yl)pyrazine-2-carboxamide (140 mg, 0.462 mmol), N-((3-fluoropyrrolidin-3-yl)methyl)cyclopropanamine (95 mg, 0.600 mmol) and triethylamine (0.19 mL, 1.39 mmol) in 1,4-dioxane (4.50 mL) was heated in a microwave to 140° C. for 30 minutes. The reaction mixture was concentrated under reduced pressure and the crude material submitted to achiral reverse phase HPLC for purification (Xbridge Phenyl 19×150 mm, 10 μm 40-100% MeOH/$H_2O$ (10 mM $NH_4CO_3$), 20 mL/min, RT) to provide 5-(3-((cyclopropylamino)methyl)-3-fluoropyrrolidin-1-yl)-N-(2,8-dimethylimidazo[1,2-a]pyrazin-6-yl)pyrazine-2-carboxamide. LCMS (ES+) 425 [M+H]+, RT 2.06 min (Analytical method AcHSSC18). $^1$H NMR (400 MHz, DMSO) δ 9.70 (s, 1H), 9.16 (s, 1H), 8.79 (d, J=1.1 Hz, 1H), 8.09 (s, 1H), 8.02 (s, 1H), 3.93-3.61 (m, 4H), 3.14-2.97 (m, 2H), 2.72 (s, 3H), 2.41 (s, 3H), 2.33-2.15 (m, 3H), 0.44-0.39 (m, 2H), 0.32-0.27 (m, 2H).

Example 251: N-(8-fluoro-2-methylimidazo[1,2-a]pyridin-6-yl)-5-(3-fluoro-3-((methylamino)methyl)pyrrolidin-1-yl)pyrazine-2-carboxamide

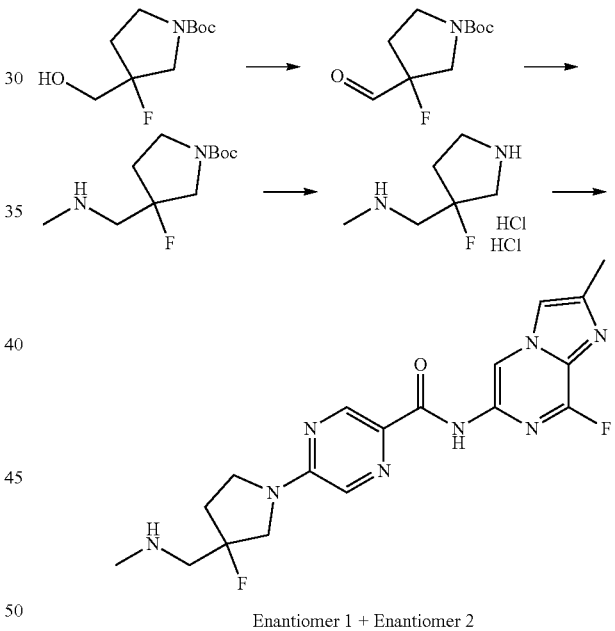

Enantiomer 1 + Enantiomer 2

A suspension of tert-butyl 3-fluoro-3-(hydroxymethyl)pyrrolidine-1-carboxylate (1.00 g, 4.56 mmol) and Dess-Martin periodinane (2.32 g, 5.47 mmol) in dichloromethane (23 mL) was stirred at room temperature overnight. The reaction mixture was diluted with aqueous sodium thiosulfate (10% w/v) and sat. aqueous sodium hydrogen carbonate and stirred for 20 minutes. The mixture was passed through a phase separator and the organics concentrated under reduced pressure. The resulting crude material was purified by flash column chromatography (0 to 100% EtOAc in cyclohexane; 40 g column). The product containing fractions were concentrated under reduced pressure to yield the product.

A suspension of tert-butyl 3-fluoro-3-formyl-pyrrolidine-1-carboxylate (270 mg, 1.24 mmol), 2 M methylamine in THF (0.62 mL, 1.24 mmol) and sodium triacetoxyborohydride (263 mg, 1.24 mmol) in dichloromethane (12 mL) under nitrogen was stirred at room temperature overnight. The reaction mixture was diluted with saturated aqueous sodium hydrogen carbonate and stirred for 10 minutes. The mixture was passed through a phase separator and the organics concentrated under reduced pressure, yielding the crude material, which was taken on without further purification.

A solution of tert-butyl 3-fluoro-3-(methylaminomethyl)pyrrolidine-1-carboxylate (210 mg, 0.904 mmol, 1.00 eq) in 4 M hydrogen chloride in dioxane (4.5 mL, 18.1 mmol, 20.0 eq) and methyl alcohol (4.50 mL) was stirred at room temperature overnight. The reaction mixture was concentrated under reduced pressure and taken on without further purification.

A mixture of 1-(3-fluoropyrrolidin-3-yl)-N-methyl-methanamine dihydrochloride (87 mg, 0.425 mmol), 5-chloro-N-(8-fluoro-2-methyl-imidazo[1,2-a]pyridin-6-yl)pyrazine-2-carboxamide (100 mg, 0.327 mmol) and triethylamine (0.14 mL, 0.981 mmol) in 1,4-dioxane (3.20 mL) was heated in a microwave to 140° C. for 30 minutes. The reaction mixture was concentrated under reduced pressure and the crude material submitted to achiral reverse phase HPLC for purification (Sunfire C18 19×150 mm, 10 µm 50-60% MeOH/H$_2$O (10 mM NH$_4$CO$_3$), 20 mL/min, RT) to yield 5-[3-fluoro-3-(methylaminomethyl)pyrrolidin-1-yl]-N-(8-fluoro-2-methyl-imidazo[1,2-a]pyridin-6-yl)pyrazine-2-carboxamide. LCMS (ES+) 402.3 [M+H]+, RT 1.78 min (Analytical method AcHSSC18). $^1$H NMR (400 MHz, DMSO) δ 10.47 (s, 1H), 9.20 (d, J=1.5 Hz, 1H), 8.78 (d, J=1.3 Hz, 1H), 8.04 (s, 1H), 7.90 (d, J=2.6 Hz, 1H), 7.58 (dd, J=1.6, 13.1 Hz, 1H), 3.94-3.62 (m, 4H), 2.98-2.84 (m, 2H), 2.38 (s, 3H), 2.34 (s, 3H), 2.32-2.15 (m, 2H), 1.93 (s, 1H).

Example 252: N-(6-ethoxy-2-methyl-2H-indazol-5-yl)-5-(6-methyl-2,6-diazaspiro[3.5]nonan-2-yl)pyrazine-2-carboxamide

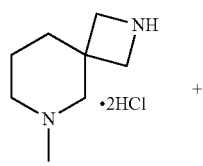

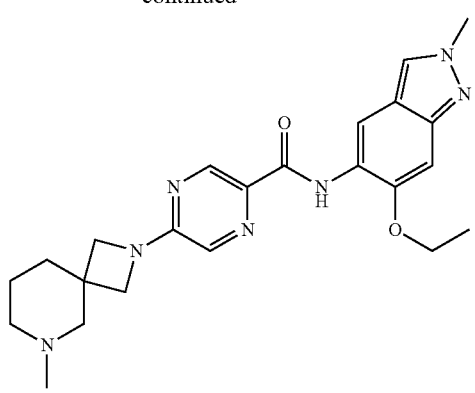

A suspension of 5-chloro-N-(6-ethoxy-2-methyl-indazol-5-yl)pyrazine-2-carboxamide (91 mg, 0.274 mmol), 6-methyl-2,6-diazaspiro[3.5]nonane dihydrochloride (45 mg, 0.211 mmol) and triethylamine (0.11 mL, 0.823 mmol) in 1,4-dioxane (3.00 mL) was heated in a microwave to 140° C. for 1 hour. The reaction mixture was concentrated under reduced pressure and the crude material submitted to achiral reverse phase HPLC for purification (Sunfire C18 19×150 mm, 10 µm 20-80% ACN/H$_2$O (10 mM NH$_4$CO$_3$), 20 mL/min, RT) to yield N-(6-ethoxy-2-methyl-indazol-5-yl)-5-(8-methyl-2,8-diazaspiro[3.5]nonan-2-yl)pyrazine-2-carboxamide. LCMS (ES+) 436.3 [M+H]+, RT 2.74 min (Analytical method AcHSSC18). $^1$H NMR (400 MHz, DMSO) δ 10.13 (s, 1H), 8.72 (d, J=1.4 Hz, 1H), 8.67 (s, 1H), 8.22 (s, 1H), 7.93 (d, J=1.3 Hz, 1H), 7.09 (s, 1H), 4.22 (q, J=6.9 Hz, 2H), 4.09 (s, 3H), 3.91-3.82 (m, 4H), 2.48-2.41 (m, 2H), 2.29-2.22 (m, 2H), 2.20 (s, 3H), 1.67-1.60 (m, 2H), 1.57-1.51 (m, 2H), 1.48 (t, J=6.9 Hz, 3H).

Example 253: (S)-5-(3-((cyclopropylamino)methyl)pyrrolidin-1-yl)-N-(6-ethoxy-2-methyl-2H-indazol-5-yl)pyrazine-2-carboxamide

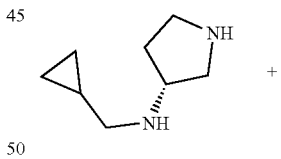

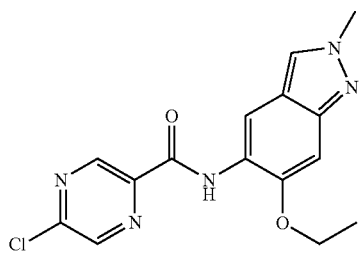

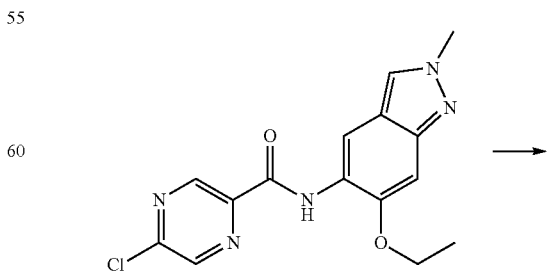

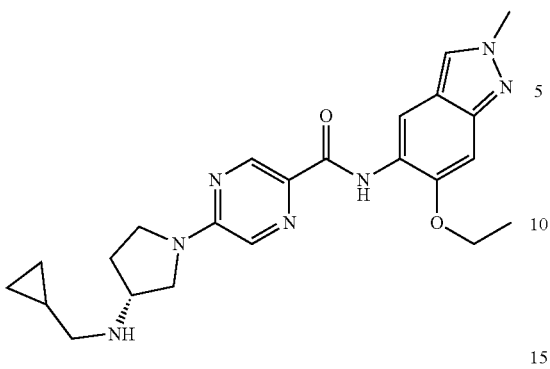

A mixture of 5-chloro-N-(6-ethoxy-2-methyl-indazol-5-yl)pyrazine-2-carboxamide (80 mg, 0.241 mmol), N-[[(3R)-pyrrolidin-3-yl]methyl]cyclopropanamine dihydrochloride (51 mg, 0.241 mmol) and triethylamine (0.10 mL, 0.723 mmol) in 1,4-dioxane (2.50 mL) was heated to 140° C. in a microwave for 40 minutes. The reaction was allowed to cool to room temperature and concentrated under reduced pressure. The crude material was submitted to achiral reverse phase for HPLC for purification (Sunfire C18 19×150 mm, 10 μm 20-80% ACN/H$_2$O (10 mM NH$_4$CO$_3$), 20 mL/min, RT) to yield N-(6-ethoxy-2-methyl-indazol-5-yl)-5-[-(3S)-3-[(cyclopropylamino)methyl]pyrrolidin-1-yl]pyrazine-2-carboxamide. LCMS (ES+) 436.3 [M+H]+, RT 2.82 min (Analytical method AcHSSC18). $^1$H NMR (400 MHz, DMSO) δ 10.13 (1H, s), 8.73 (1H, d, J=1.3 Hz), 8.66 (1H, s), 8.20 (1H, s), 8.00 (1H, d, J=1.3 Hz), 7.07 (1H, s), 4.21 (2H, q, J=6.9 Hz), 4.07 (3H, s), 3.74-3.62 (2H, m), 3.54-3.46 (1H, m), 3.24 (1H, dd, J=7.3, 11.2 Hz), 2.71-2.57 (2H, m), 2.45-2.42 (1H, m), 2.33 (1H, dd, J=1.9, 3.6 Hz), 2.15-2.04 (2H, m), 1.78-1.67 (1H, m), 1.47 (3H, t, J=7.0 Hz), 0.38-0.35 (2H, m), 0.24-0.19 (2H, m).

Example 254: (R)—N-(6-ethoxy-2-methyl-2H-indazol-5-yl)-5-(3-(ethylamino)pyrrolidin-1-yl)pyrazine-2-carboxamide A mixture of 5-chloro-N-(6-ethoxy-2-methyl-indazol-5-yl)pyrazine-2-carboxamide (80 mg, 0.241 mmol), (3R)—N-ethylpyrrolidin-3-amine (28 mg, 0.241 mmol) and triethylamine (0.10 mL, 0.723 mmol) in 1,4-dioxane (2.50 mL) was heated to 140° C. in a microwave for 40 minutes. The reaction was allowed to cool to room temperature and concentrated under reduced pressure. The crude material was submitted to achiral reverse phase HPLC for purification (Sunfire C18 19×150 mm, 10 μm 20-80% ACN/H$_2$O (10 mM NH$_4$CO$_3$), 20 mL/min, RT) to yield (R)—N-(6-ethoxy-2-methyl-2H-indazol-5-yl)-5-(3-(ethylamino)pyrrolidin-1-yl)pyrazine-2-carboxamide. LCMS (ES+) 410.3 [M+H]+, RT 2.66 min (Analytical method AcHSSC18). $^1$H NMR (400 MHz, DMSO) δ 10.14 (s, 1H), 8.75 (d, J=1.1 Hz, 1H), 8.68 (s, 1H), 8.22 (s, 1H), 8.03 (d, J=1.3 Hz, 1H), 7.09 (s, 1H), 4.24 (q, J=7.0 Hz, 2H), 4.09 (s, 3H), 3.72-3.54 (m, 3H), 3.48-3.37 (m, 2H), 2.66-2.55 (m, 2H), 2.17-2.06 (m, 1H), 1.93-1.78 (m, 2H), 1.49 (t, J=7.0 Hz, 3H), 1.04 (t, J=7.1 Hz, 3H).

Example 255: 5-(3-((cyclopropylamino)methyl)azetidin-1-yl)-N-(6-ethoxy-2-methyl-2H-indazol-5-yl)pyrazine-2-carboxamide

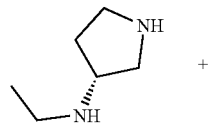

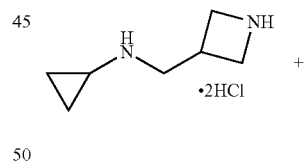

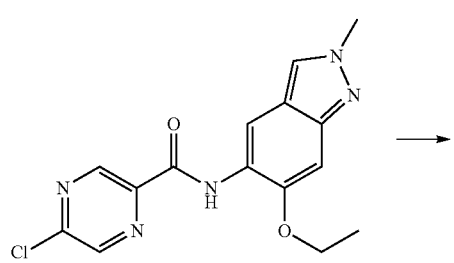

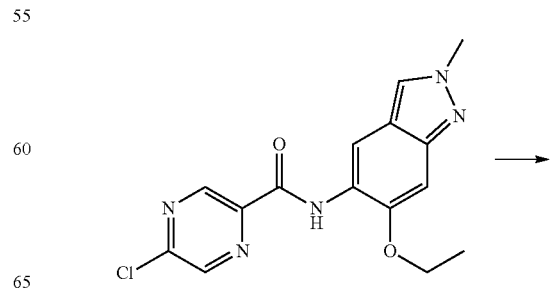

571
-continued

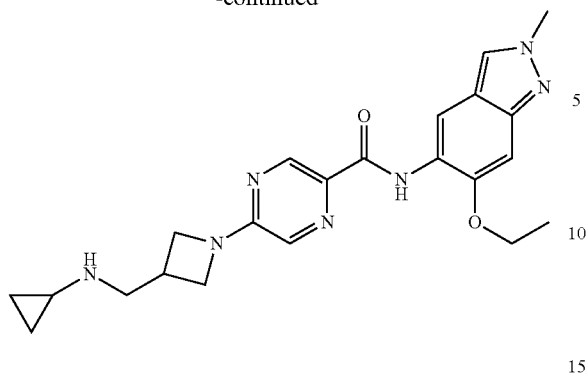

A suspension of 5-chloro-N-(6-ethoxy-2-methyl-indazol-5-yl)pyrazine-2-carboxamide (50 mg, 0.151 mmol), N-(azetidin-3-ylmethyl)cyclopropanamine dihydrochloride (39 mg, 0.196 mmol) and cesium carbonate (196 mg, 0.603 mmol) in DMF (1.50 mL) was heated at 100° C. overnight. The reaction mixture was allowed to cool to room temperature, filtered and sent to achiral reverse phase HPLC for purification (Xbridge Phenyl 19×150 mm, 10 μm 40-100% MeOH/H$_2$O (10 mM NH$_4$CO$_3$), 20 mL/min, RT) to yield 5-[3-[(cyclopropylamino)methyl]azetidin-1-yl]-N-(6-ethoxy-2-methyl-indazol-5-yl)pyrazine-2-carboxamide. LCMS (ES+) 422.4 [M+H]+, RT 2.70 min (Analytical method AcHSSC18). $^1$H NMR (400 MHz, DMSO) δ 10.12 (s, 1H), 8.70 (d, J=1.3 Hz, 1H), 8.65 (s, 1H), 8.20 (s, 1H), 7.88 (d, J=1.3 Hz, 1H), 7.07 (s, 1H), 4.25-4.17 (m, 4H), 4.08 (s, 3H), 3.84 (dd, J=4.8, 8.9 Hz, 2H), 2.89-2.84 (m, 3H), 2.37-2.32 (m, 1H), 2.09-2.03 (m, 1H), 1.46 (t, J=6.9 Hz, 3H), 0.39-0.34 (m, 2H), 0.22-0.17 (m, 2H).

Example 256: (R)-5-(3-(cyclopropylamino)pyrrolidin-1-yl)-N-(8-methoxy-2-methylimidazo[1,2-a]pyridin-6-yl)pyrazine-2-carboxamide

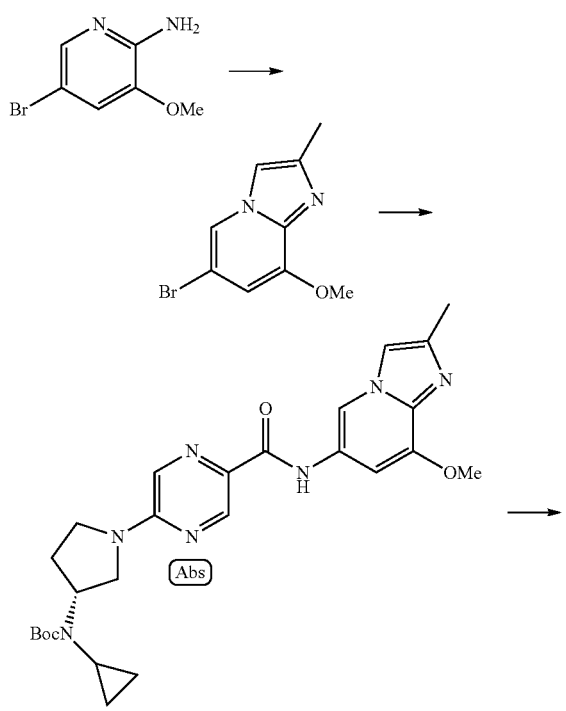

572
-continued

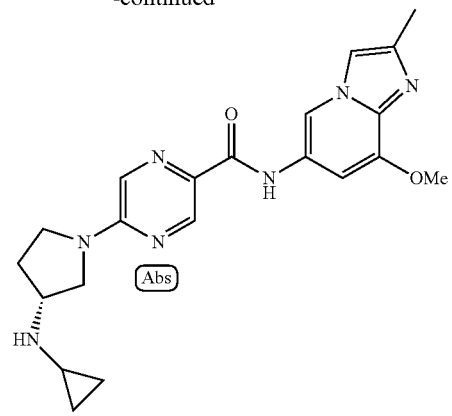

5-Bromo-3-methoxy-pyridin-2-amine (1000 mg, 4.93 mmol), 1-Bromo-2,2-dimethoxypropane (1.1 mL, 7.88 mmol), pyridinium para-toluenesulfonate (124 mg, 0.493 mmol) and 2-propanol (8.00 mL) were combined. The reaction was heated at 95° C. for 16 h. After cooling, the reaction mixture was diluted with water and washed with 3:1 CHCl$_3$/IPA (×3). The combined organics were washed with brine, dried (phase separating filter paper) and the solvent removed in vacuo to give the desired cyclised product. LCMS (ES+) 241, 243 (M+H)+(Br isotope). tert-Butyl N-[(3R)-1-(5-carbamoylpyrazin-2-yl)pyrrolidin-3-yl]-N-cyclopropyl-carbamate (120 mg, 0.345 mmol) and 6-bromo-8-methoxy-2-methyl-imidazo[1,2-a]pyridine (95%, 125 mg, 0.493 mmol) were coupled together using Method F to give tert-butyl N-cyclopropyl-N-[(3R)-1-[5-[(8-methoxy-2-methyl-imidazo[1,2-a]pyridin-6-yl)carbamoyl]pyrazin-2-yl]pyrrolidin-3-yl]carbamate. LCMS (ES$^+$) 507 (M+H)$^+$.

tert-Butyl N-cyclopropyl-N-[(3R)-1-[5-[(8-methoxy-2-methyl-imidazo[1,2-a]pyridin-6-yl)carbamoyl]pyrazin-2-yl]pyrrolidin-3-yl]carbamate (23 mg) was subjected to Method E conditions to give the final compound (R)-5-(3-(cyclopropylamino)pyrrolidin-1-yl)-N-(8-methoxy-2-methylimidazo[1,2-a]pyridin-6-yl)pyrazine-2-carboxamide.
LCMS (ES+) 408 (M+H)+, rt 3.32 min (Analytical method BicarbBEHC18). $^1$H NMR (400 MHz, DMSO) δ 10.16 (s, 1H), 8.93 (d, J=1.6 Hz, 1H), 8.72 (d, J=1.3 Hz, 1H), 7.95 (d, J=1.3 Hz, 1H), 7.68 (s, 1H), 7.10 (d, J=1.6 Hz, 1H), 3.90 (s, 3H), 3.72-3.51 (m, 6H), 3.43-3.37 (m, 1H), 2.28 (s, 3H), 2.15-2.08 (m, 2H), 0.40 (d, J=6.5 Hz, 2H), 0.28-0.19 (m, 2H).

Example 257: (R)-5-(3-((cyclopropylamino)methyl)pyrrolidin-1-yl)-N-(6-methoxy-2-methylpyrazolo[1,5-a]pyridin-5-yl)pyrazine-2-carboxamide

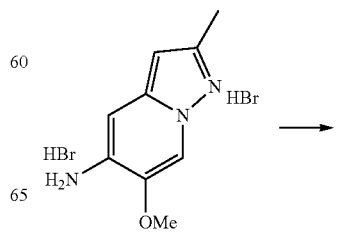

573
-continued

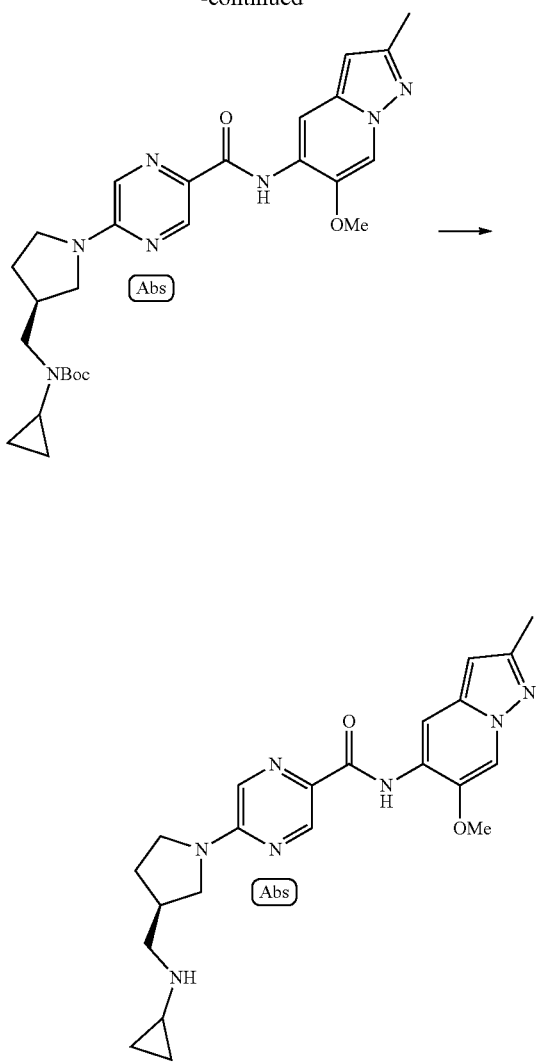

Following Method H 6-methoxy-2-methylpyrazolo[1,5-a]pyridin-5-amine and (S)-5-(3-(((tert-butoxycarbonyl)(cyclopropyl)amino)methyl)pyrrolidin-1-yl)pyrazine-2-carboxylic acid were coupled together to give the product.

Following Method E tert-butyl N-cyclopropyl-N-[[(3S)-1-[5-[(6-methoxy-2-methyl-pyrazolo[1,5-a]pyridin-5-yl)carbamoyl]pyrazin-2-yl]pyrrolidin-3-yl]methyl]carbamate (70 mg, 0.134 mmol) was treated with trifluoroacetic acid (1.0 mL, 13.1 mmol) and $CH_2C_2$ (5 mL). The reaction mixture was stirred at r.t. for 3 h. The reaction mixture was concentrated in vacuo and the residue loaded onto a 2 g SCX cartridge eluting with MeOH then $NH_3$ (7 M) in MeOH. The ammonia fraction was concentrated in vacuo and submitted to prep for achiral purification to give (R)-5-(3-((cyclopropylamino)methyl)pyrrolidin-1-yl)-N-(6-methoxy-2-methylpyrazolo[1,5-a]pyridin-5-yl)pyrazine-2-carboxamide. (ES+) 422.352 (M+H)+, RT 4.36 min (Analytical method BicarbBEHC18). $^1$H NMR (400 MHz, DMSO) δ 8.74 (d, J=1.1 Hz, 1H), 8.46 (s, 1H), 8.36 (s, 1H), 8.00 (s, 1H), 6.25 (s, 1H), 3.95 (s, 3H), 3.74-3.62 (m, 2H), 3.54-3.43 (m, 1H), 3.24 (dd, J=7.3, 11.1 Hz, 1H), 3.12 (s, 3H), 2.70-2.54 (m, 3H), 2.32 (s, 3H), 2.09-2.03 (m, 2H), 0.36 (dd, J=1.7, 6.6 Hz, 2H), 0.23-0.19 (m, 2H).

574

Example 258: (R)-5-(3-((cyclopropylamino)methyl)pyrrolidin-1-yl)-N-(7-fluoro-6-methoxy-2-methyl-2H-indazol-5-yl)pyrazine-2-carboxamide

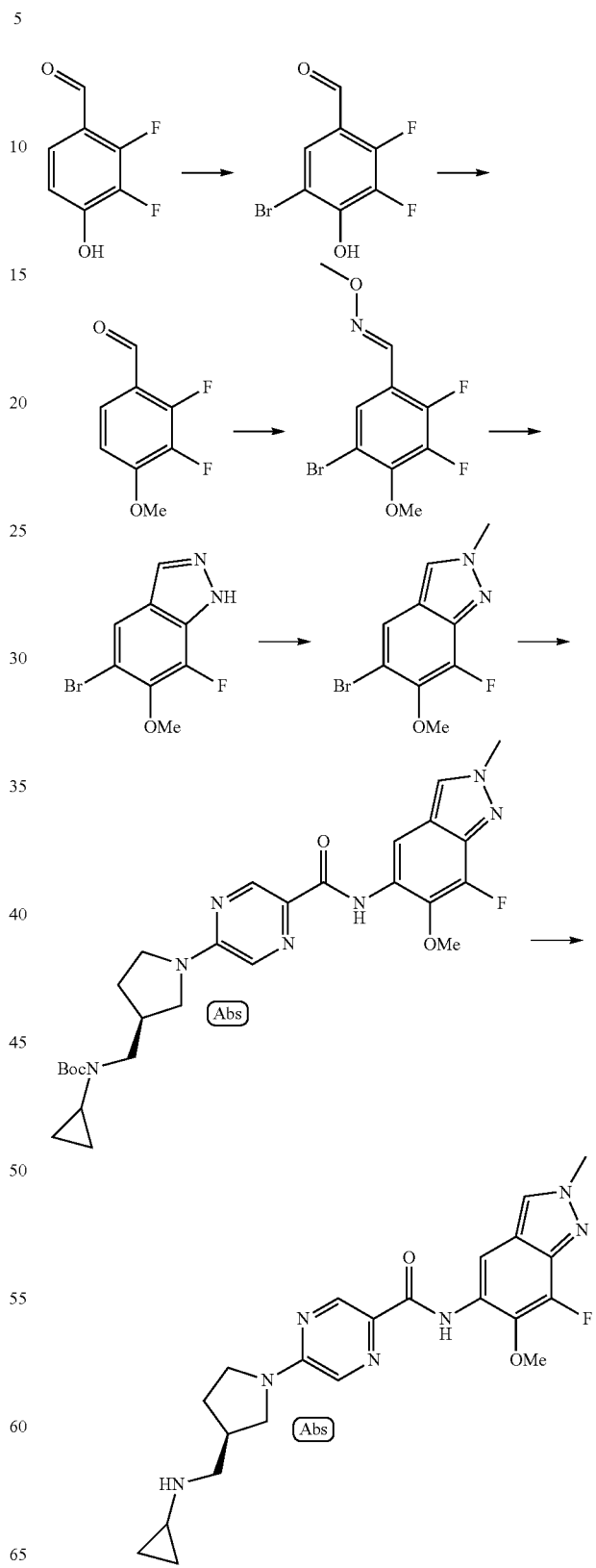

2,3-Difluoro-4-hydroxy-benzaldehyde (1000 mg, 6.33 mmol), diisopropylamine (0.089 mL, 0.633 mmol), N-bromosuccinimide (1182 mg, 6.64 mmol) were dissolved in CH$_2$Cl$_2$ at 0° C. The reaction mixture was allowed to warm to r.t. and stirred for 1 h. The reaction mixture was diluted with water and the layers separated. The organic layer was concentrated in vacuo to give the desired product. LCMS (ES$^+$) 235, 237 (M+H)$^+$.

5-Bromo-2,3-difluoro-4-hydroxy-benzaldehyde (1180 mg, 4.48 mmol), cesium carbonate (1752 mg, 5.38 mmol) N,N-dimethylformamide (10.00 mL) were combined and stirred for 20 mins at r.t. Iodomethane (0.96 mL) was added and the reaction was stirred for 16 h at r.t. The reaction mixture was diluted with water and Et$_2$O and the layers separated. The combined organics were collected, and the solvent removed in vacuo. The crude product was purified by silica chromatography, elution gradient 0-50% EtOAc in cyclohexane. The appropriate fractions were combined and concentrated in vacuo to give the desired product. Product consistent with $^1$H NMR analysis.

5-Bromo-2,3-difluoro-4-methoxy-benzaldehyde (272 mg, 1.08 mmol), methoxyamine hydrochloride (109 mg, 1.30 mmol), potassium carbonate (329 mg, 2.38 mmol) and ethylene glycol dimethyl ether (5 mL) were stirred at 50° C. for 16 h. The reaction mixture was filtered and the solid was washed with EtOAc. The filtrate was concentrated in vacuo and purified using silica chromatography, elution gradient 0-50% EtOAc in cyclohexane. The appropriate fractions were combined and concentrated in vacuo to give the desired product. Product consistent with $^1$H NMR analysis.

(E)-1-(5-Bromo-2,3-difluoro-4-methoxy-phenyl)-N-methoxy-methanimine (1800 mg, 6.43 mmol), hydrazine monohydrate (6.2 mL, 0.129 mol) and tetrahydrofuran (8 mL) were combined and the reaction stirred at 90° C. for 48 h. The reaction mixture was concentrated in vacuo. The crude product was purified by silica chromatography, elution gradient (0-50%) EtOAc in cyclohexane. The appropriate fractions were combined and concentrated in vacuo to give the desired product. Product consistent with $^1$H NMR analysis.

5-Bromo-7-fluoro-6-methoxy-1H-indazole (750 mg, 3.06 mmol), trimethyloxonium tetrafluoroborate (589 mg, 3.98 mmol) and ethyl acetate (30 mL) were stirred at r.t. for 18 h. The reaction mixture was washed with water and the organic layer was concentrated in vacuo. The crude product was purified using silica chromatography, elution gradient 0-40% EtOAc in cyclohexane. The appropriate fractions were combined and concentrated in vacuo to give the desired product. Product consistent with $^1$H NMR analysis.

tert-Butyl N-[[(3S)-1-(5-carbamoylpyrazin-2-yl)pyrrolidin-3-yl]methyl]-N-cyclopropyl-carbamate (120 mg, 0.282 mmol) and 5-bromo-7-fluoro-6-methoxy-2-methyl-indazole (95 mg, 0.367 mmol) were coupled together following Method F experimental conditions to afford tert-butyl N-cyclopropyl-N-[[(3S)-1-[5-[(7-fluoro-6-methoxy-2-methyl-indazol-5-yl)carbamoyl]pyrazin-2-yl]pyrrolidin-3-yl]methyl] carbamate.

Following Method E, tert-butyl N-cyclopropyl-N-[[(3S)-1-[5-[(7-fluoro-6-methoxy-2-methyl-indazol-5-yl)carbamoyl]pyrazin-2-yl]pyrrolidin-3-yl]methyl] (120 mg) was treated with trifluoroacetic acid to give (R)-5-(3-((cyclopropylamino)methyl)pyrrolidin-1-yl)-N-(7-fluoro-6-methoxy-2-methyl-2H-indazol-5-yl)pyrazine-2-carboxamide. LCMS (ES+) 440 (M+H)+, RT 2.8 min (Analytical method AcHSSC18). $^1$H NMR (400 MHz, DMSO) δ 10.02 (s, 1H), 8.74 (d, J=1.1 Hz, 1H), 8.47 (s, 1H), 8.40 (d, J=2.9 Hz, 1H), 8.04 (d, J=1.1 Hz, 1H), 4.14 (s, 3H), 4.06 (d, J=1.8 Hz, 3H), 3.74-3.62 (m, 2H), 3.54-3.46 (m, 1H), 3.25 (dd, J=7.2, 11.3 Hz, 1H), 2.71-2.59 (m, 2H), 2.33 (dd, J=1.6, 3.4 Hz, 1H), 2.11-2.05 (m, 2H), 1.71-1.71 (m, 1H), 0.36 (dd, J=1.6, 6.5 Hz, 2H), 0.24-0.19 (m, 2H).

The synthesis of further target compounds followed the same synthetic sequence as described above using Method E and Method F. The coupling partner varied only in the primary amide as shown below.

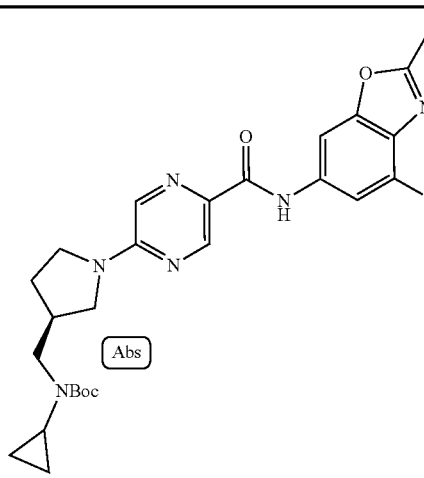

| | Structure | Aryl halide | Primary amide | Analytical data |
|---|---|---|---|---|
| Example 259: | 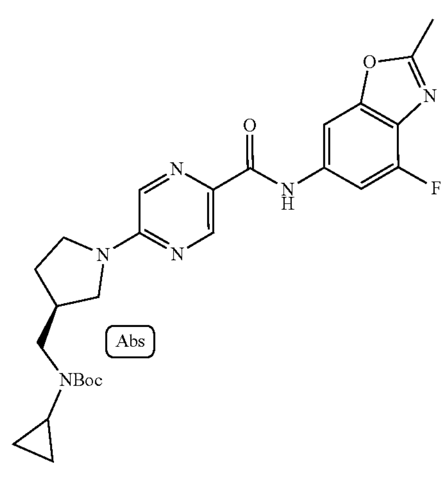 | 6-bromo-4-fluoro-2-methylbenzo[d]oxazole | tert-butyl (S)-((1-(5-carbamoylpyrazin-2-yl)pyrrolidin-3-yl)methyl)(cyclopropyl) carbamate | LCMS (ES+) 408 (M + H)+, RT 3.32 min (Analytical method BicarbBEHCl8). $^1$H NMR (400 MHz, DMSO) δ 10.16 (s, 1H), 8.93 (d, J = 1.6 Hz, 1H), 8.72 (d, J = 1.3 Hz, 1H), 7.95 (d, J = 1.3 Hz, 1H), 7.68 (s, 1H), 7.10 (d, J = 1.6 Hz, 1H), 3.90 (s, 3H), 3.72-3.51 (m, 6H), 3.43-3.37 (m, 1H), 2.28 (s, 3H), 2.15-2.08 (m, 2H), 0.40 (d, J = 6.5 Hz, 2H), 0.28-0.19 (m, 2H). |

-continued

| | Structure | Aryl halide | Primary amide | Analytical data |
|---|---|---|---|---|
| Example 260: | 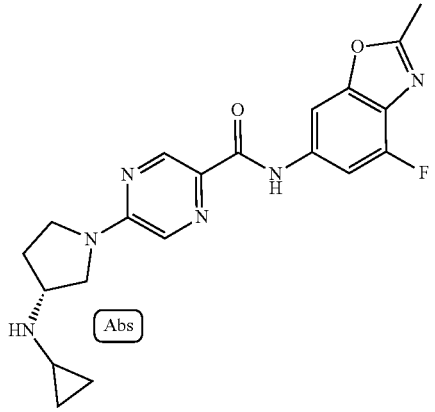 [SMILES: Cc1nc2c(F)cc(NC(=O)c3cnc(N4CC[C@@H](NC5CC5)C4)cn3)cc2o1] | 6-bromo-4-fluoro-2-methylbenzo[d]oxazole | tert-butyl (R)-(1-(5-carbamoylpyrazin-2-yl)pyrrolidin-3-yl)(cyclopropyl)carbamate | LCMS (ES+) 397 (M + H)+, RT 2.73 min (Analytical method AcHSSC18). $^1$H NMR (400 MHz, DMSO) δ 10.57 (s, 1H), 8.75 (d, J = 1.3 Hz, 1H), 8.19 (d, J = 1.6 Hz, 1H), 7.96 (d, J = 1.3 Hz, 1H), 7.83 (dd, J = 1.8, 12.6 Hz, 1H), 3.72-3.60 (m, 2H), 3.60-3.49 (m, 2H), 3.44-3.38 (m, 1H), 2.61 (s, 3H), 2.15-2.07 (m, 2H), 1.98-1.92 (m, 1H), 0.43-0.36 (m, 2H), 0.27 - 0.19 (m, 2H). |
| Example 261: | 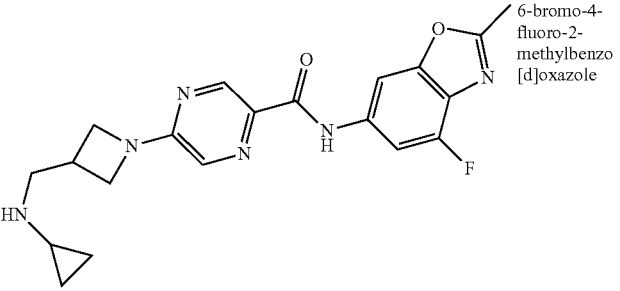 | 6-bromo-4-fluoro-2-methylbenzo[d]oxazole | tert-butyl ((1-(5-carbamoylpyrazin-2-yl)azetidin-3-yl)methyl)(cyclopropyl)carbamate | LCMS (ES+) 397 (M + H)+, RT 3.87 min (Analytical method BicarbBEHCl8). $^1$H NMR (400 MHz, DMSO) δ 10.38 (s, 1H), 8.51 (d, J = 1.4 Hz, 1H), 7.97 (d, J = 1.8 Hz, 1H), 7.64-7.59 (m, 2H), 4.01 (dd, J = 8.3, 8.3 Hz, 2H), 3.64 (dd, J = 4.9, 9.0 Hz, 2H), 2.72-2.63 (m, 3H), 2.40 (s, 3H), 2.17 (s, 1H), 1.88-1.82 (m, 1H), 0.17-0.13 (m, 2H), 0.01--0.03 (m, 2H). |
| Example 262 | 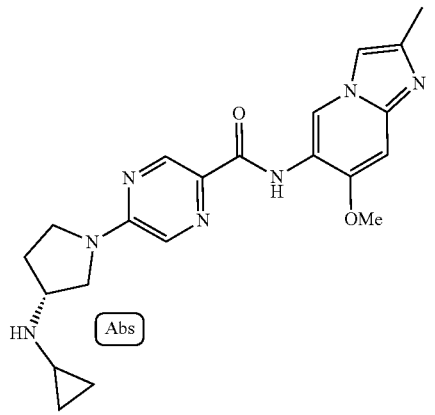 [SMILES: COc1cc2nc(C)cn2cc1NC(=O)c1cnc(N2CC[C@@H](NC3CC3)C2)cn1] | 6-bromo-7-methoxy-2-methylimidazo[1,2-a]pyridine | tert-butyl (R)-(1-(5-carbamoylpyrazin-2-yl)pyrrolidin-3-yl)(cyclopropyl)carbamate | LCMS (ES+) 408 (M + H)+, RT 1.94 min (Analytical method AcHS SC18). $^1$H NMR (400 MHz, DMSO) δ 9.74 (s, 1H), 9.35 (s, 1H), 8.73 (d, J = 1.1 Hz, 1H), 8.03 (d, J = 1.3 Hz, 1H), 7.58 (s, 1H), 6.99 (s, 1H), 3.98 (s, 3H), 3.70-3.50 (m, 4H), 3.42-3.41 (m, 1H), 2.26 (s, 3H), 2.09 (dd, J = 3.7, 3.7 Hz, 2H), 2.00-1.88 (m, 1H), 0.44-0.36 (m, 2H), 0.27-0.21 (m, 2H). |

Example 263: N-(8-fluoro-2-methylimidazo[1,2-a]pyridin-6-yl)-5-(((3S,4R)-3-fluoropiperidin-4-yl)amino)pyrazine-2-carboxamide

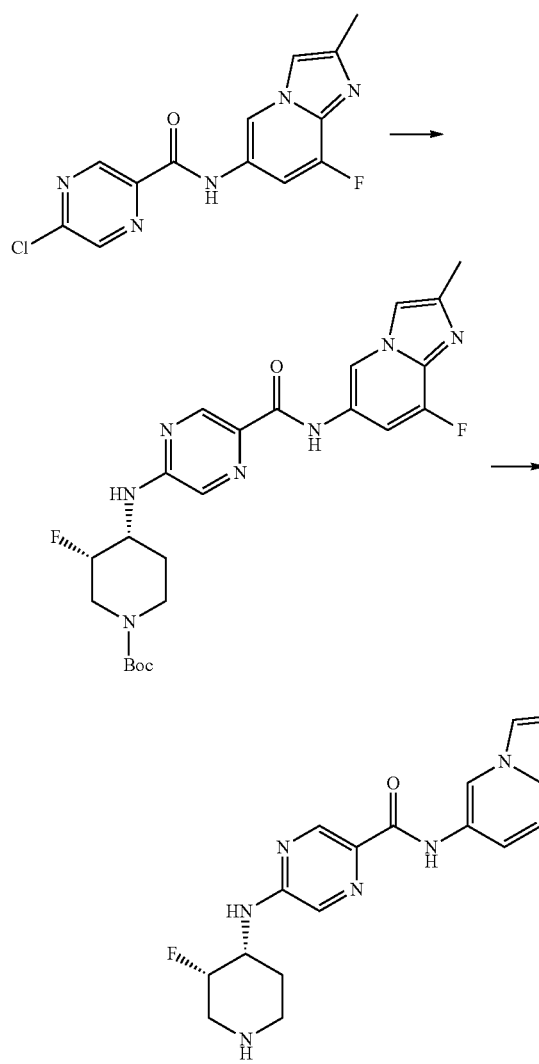

5-Chloro-N-(8-fluoro-2-methyl-imidazo[1,2-a]pyridin-6-yl)pyrazine-2-carboxamide (224 mg, 0.733 mmol, 1.00 eq), cesium carbonate (478 mg, 1.47 mmol, 2.00 eq), tert-butyl (3S,4R)-4-amino-3-fluoro-piperidine-1-carboxylate (160 mg, 0.733 mmol, 1.00 eq), and 1,4-dioxane (15.00 mL) were combined in a sealed tube and hot block heated to 100° C. for 9 days. The reaction mixture was cooled to room temperature, cesium salts were filtered off, and the reaction mixture was concentrated in vacuo. The residue was purified by prep HPLC to give tert-butyl (3S,4R)-3-fluoro-4-((5-((8-fluoro-2-methylimidazo[1,2-a]pyridin-6-yl)carbamoyl)pyrazin-2-yl)amino)piperidine-1-carboxylate, which was used directly in the next step. LCMS (ES+) 488 (M+H)+.

tert-Butyl (3S,4R)-3-fluoro-4-[[5-[(8-fluoro-2-methyl-imidazo[1,2-a]pyridin-6-yl)carbamoyl]pyrazin-2-yl]amino]piperidine-1-carboxylate (16 mg, 0.0328 mmol, 1.00 eq), methyl alcohol (3.00 mL), and 4 M hydrogen chloride in dioxane (1.0 mL, 4.00 mmol, 122 eq) were combined and stirred at room temperature for 2 days. The reaction mixture was concentrated in vacuo and the residue was purified by prep HPLC to give the title compound. LCMS (ES+) 388 (M+H)+, RT 2.68 min (Analytical method BicarbBEHC18). $^1$H NMR (400 MHz, DMSO) δ 10.40 (s, 1H), 9.20 (s, 1H), 8.67 (s, 1H), 8.15 (s, 1H), 8.02 (d, J=7.9 Hz, 1H), 7.89 (d, J=2.5 Hz, 1H), 7.56 (dd, J=1.6, 13.4 Hz, 1H), 4.72 (d, J=54.4 Hz, 1H), 4.23-4.14 (m, 2H), 3.19-3.11 (m, 1H), 2.98-2.95 (m, 1H), 2.79-2.67 (m, 1H), 2.34 (s, 3H), 1.98-1.98 (m, 1H), 1.69-1.64 (m, 2H).

Example 264: (R)-5-(3-((cyclopropylamino)methyl)pyrrolidin-1-yl)-N-(2,8-dimethylimidazo[1,2-a]pyridin-6-yl)pyrazine-2-carboxamide

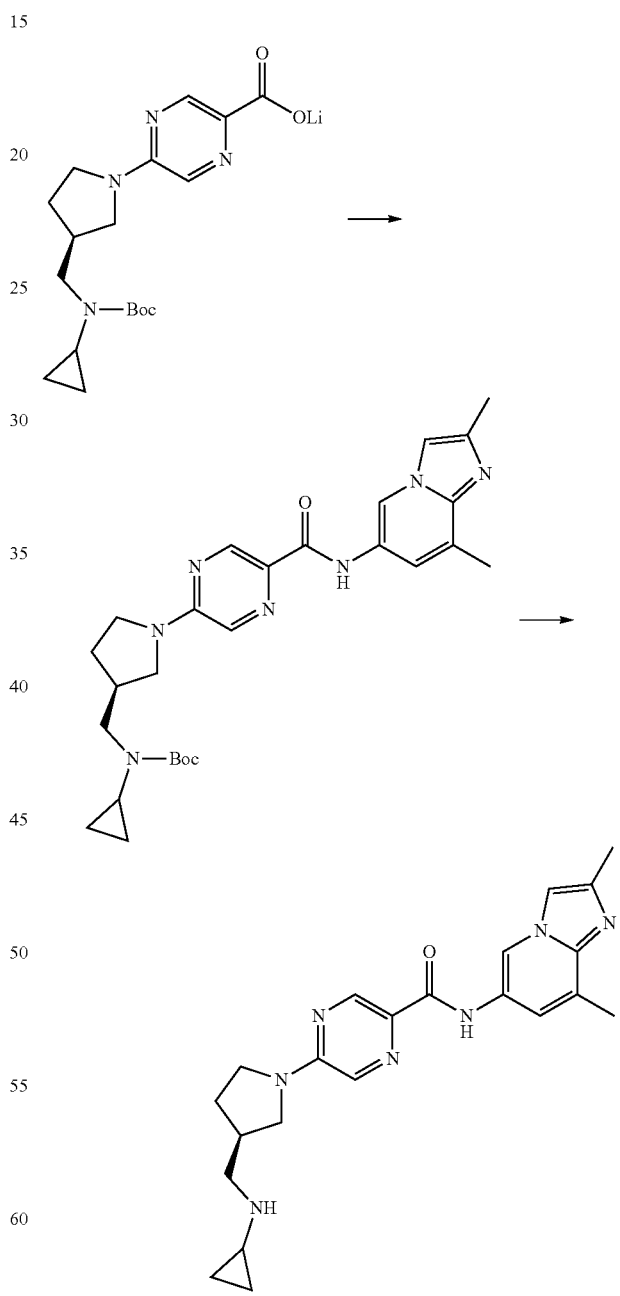

[5-[(3S)-3-[[tert-Butoxycarbonyl(cyclopropyl)amino]methyl]pyrrolidin-1-yl]pyrazine-2-carbonyl]oxylithium (100 mg, 0.271 mmol, 1.00 eq), 2,8-dimethylimidazo[1,2- a]pyridin-6-amine (44 mg, 0.271 mmol, 1.00 eq), HBTU (103 mg, 0.271 mmol, 1.00 eq), triethylamine (0.25 mL, 1.79 mmol, 6.61 eq), and N,N-dimethylformamide (3.75 mL) were combined and stirred at room temperature for 18 hours. The reaction mixture was purified by prep HPLC to give tert-butyl N-cyclopropyl-N-[[(3S)-1-[5-[(2,8-dimethyl-imidazo[1,2-a]pyridin-6-yl)carbamoyl]pyrazin-2-yl]pyrrolidin-3-yl]methyl]carbamate, which was used in the next step. LCMS (ES+) 506 (M+H)+.

tert-Butyl N-cyclopropyl-N-[[(3S)-1-[5-[(2,8-dimethyl-imidazo[1,2-a]pyridin-6-yl)carbamoyl]pyrazin-2-yl]pyrrolidin-3-yl]methyl]carbamate (50 mg, 0.0989 mmol, 1.00 eq), methyl alcohol (2.00 mL) and 4 M hydrogen chloride in dioxane (1.0 mL, 4.00 mmol, 40.4 eq) were combined and stirred at room temperature for 3 hours. The reaction mixture was concentrated in vacuo, purified by prep HPLC to give the title compound. LCMS (ES+) 406 (M+H)+, RT 1.93 min (Analytical method AcHSSC18). $^1$H NMR (400 MHz, DMSO) δ 10.19 (s, 1H), 9.11 (d, J=1.5 Hz, 1H), 8.75 (d, J=1.3 Hz, 1H), 7.99 (d, J=1.3 Hz, 1H), 7.73 (s, 1H), 7.37 (s, 1H), 3.78-3.66 (m, 2H), 3.58-3.49 (m, 1H), 3.27 (dd, J=7.2, 11.1 Hz, 1H), 2.76-2.62 (m, 2H), 2.50 (s, 1H), 2.47 (s, 3H), 2.35 (s, 3H), 2.17-2.08 (m, 2H), 1.81-1.73 (m, 1H), 0.40 (dd, J=1.6, 6.5 Hz, 2H), 0.28-0.23 (m, 2H).

Example 265: 5-[(3R)-3-(cyclopropylmethylamino) pyrrolidin-1-yl]-N-(8-fluoro-2-methyl-imidazo[1,2-a]pyridin-6-yl)pyrazine-2-carboxamide

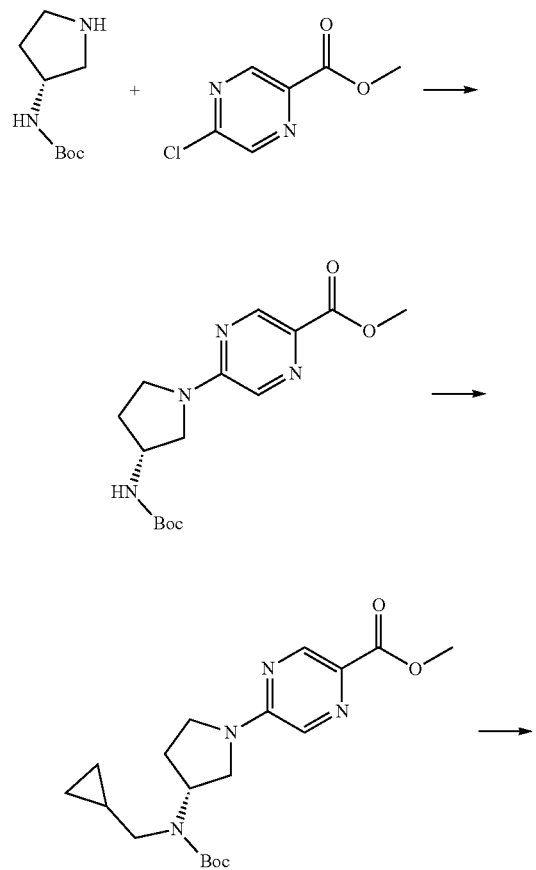

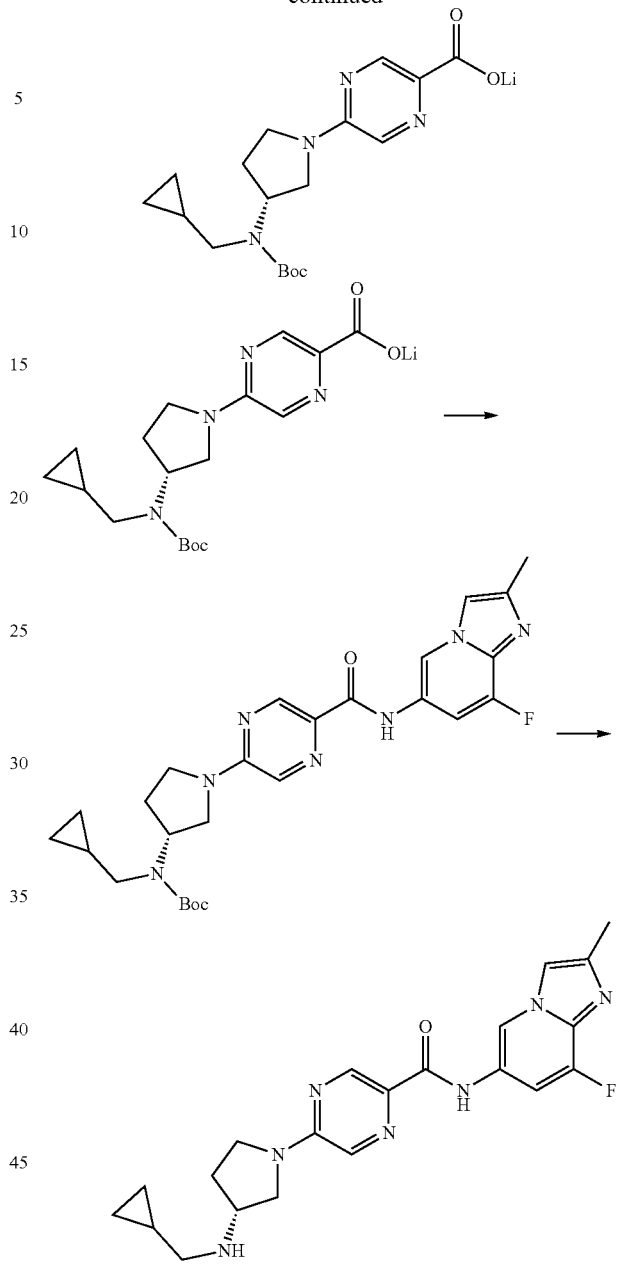

Methyl 5-chloro-2-pyrazinecarboxylate (2.00 g, 11.6 mmol, 1.00 eq), (R)-3-(Boc-amino)pyrrolidine (2.16 g, 11.6 mmol, 1.00 eq), 1,4-dioxane (100.00 mL), and N,N-diisopropylethylamine (3.0 mL, 17.2 mmol, 1.49 eq) were combined and hot block heated to 100° C. for 18 hours. The reaction mixture was concentrated in vacuo, diluted with EtOAc, washed with water (3×), dried (MgSO$_4$) and concentrated in vacuo to give methyl 5-[(3R)-3-(tert-butoxycarbonylamino)pyrrolidin-1-yl]pyrazine-2-carboxylate. LCMS (ES+) 323 (M+H)+. Used in next step.

Methyl 5-[(3R)-3-(tert-butoxycarbonylamino)pyrrolidin-1-yl]pyrazine-2-carboxylate (1500 mg, 4.65 mmol, 1.00 eq), N,N-dimethylformamide (20.00 mL), and (Bromomethyl) cyclopropane (0.54 mL, 5.58 mmol, 1.20 eq) were combined under a nitrogen atmosphere. Sodium hydride (60%, 223 mg, 5.58 mmol, 1.20 eq) was added and reaction stirred at room temperature for 1 hour, then hot block heated to 55° C.

for 18 hours. The reaction mixture was concentrated in vacuo, diluted with EtOAc, washed with water (3×) and brine (1×), and concentrated in vacuo onto silica. The material was purified by flash chromatography to give a mixture of methyl 5-[(3R)-3-[tert-butoxycarbonyl(cyclopropylmethyl) amino]pyrrolidin-1-yl]pyrazine-2-carboxylate and 5-[(3R)-3-[tert-butoxycarbonyl(cyclopropylmethyl) amino]pyrrolidin-1-yl]pyrazine-2-carboxylic acid. LCMS (ES+) 377 and 363 (M+H)+. Used in next step.

Methyl 5-[(3R)-3-[tert-butoxycarbonyl(cyclopropylmethyl)amino]pyrrolidin-1-yl]pyrazine-2-carboxylate and 5-[(3R)-3-[tert-butoxycarbonyl(cyclopropylmethyl)amino]pyrrolidin-1-yl]pyrazine-2-carboxylic acid (252 mg, 0.669 mmol, 1.00 eq), lithium hydroxide monohydrate (28 mg, 0.669 mmol, 1.00 eq), methyl alcohol (30.00 mL), and water (3.00 mL) were combined and hot block heated to 50° C. for 3 days. The reaction mixture was concentrated in vacuo to give [5-[(3R)-3-[tert-butoxycarbonyl(cyclopropylmethyl)amino]pyrrolidin-1-yl]pyrazine-2-carbonyl]oxylithium. LCMS (ES+) 363 (M+H)+. Used in next step.

[5-[(3R)-3-[tert-Butoxycarbonyl(cyclopropylmethyl)amino]pyrrolidin-1-yl]pyrazine-2-carbonyl]oxylithium (90 mg, 0.244 mmol, 1.00 eq), 8-fluoro-2-methyl-imidazo[1,2-a]pyridin-6-amine (40 mg, 0.244 mmol, 1.00 eq), HBTU (93 mg, 0.244 mmol, 1.00 eq), N,N-dimethylformamide (3.00 mL), and triethylamine (0.50 mL, 3.59 mmol, 14.7 eq) were combine and stirred at room temperature for 2 hours. Reaction mixture was purified by prep HPLC to give tert-butyl N-(cyclopropylmethyl)-N-[(3R)-1-[5-[(8-fluoro-2-methyl-imidazo[1,2-a]pyridin-6-yl)carbamoyl]pyrazin-2-yl]pyrrolidin-3-yl] carbamate. LCMS (ES+) 510 (M+H)+. Used in next step.

tert-Butyl N-(cyclopropylmethyl)-N-[(3R)-1-[5-[(8-fluoro-2-methyl-imidazo[1,2-a]pyridin-6-yl)carbamoyl]pyrazin-2-yl]pyrrolidin-3-yl]carbamate (69 mg, 0.135 mmol, 1.00 eq), methyl alcohol (2.00 mL), and 4 M hydrogen chloride in dioxane (2.0 mL, 8.00 mmol, 59.1 eq) were combined and stirred at room temperature for 1 hour. The reaction mixture was concentrated in vacuo, and the residue was purified by prep HPLC to give the title compound. LCMS (ES+) 410 (M+H)+, RT 1.88 min (Analytical method AcHSSC18). $^1$H NMR (400 MHz, DMSO) δ 10.19 (s, 1H), 9.11 (d, J=1.5 Hz, 1H), 8.75 (d, J=1.3 Hz, 1H), 7.99 (d, J=1.3 Hz, 1H), 7.73 (s, 1H), 7.37 (s, 1H), 3.78-3.66 (m, 2H), 3.58-3.49 (m, 1H), 3.27 (dd, J=7.2, 11.1 Hz, 1H), 2.76-2.62 (3, 2H), 2.50 (s, 1H), 2.47 (s, 3H), 2.35 (s, 3H), 2.17-2.08 (m, 2H), 1.81-1.73 (m, 1H), 0.40 (dd, J=1.6, 6.5 Hz, 2H), 0.28-0.23 (m, 2H).

Further analogues were prepared using the same chemistry from commercially available or synthesised amines. Final products were isolated by Preparative HPLC.

| Example | Structure | Analytical data |
|---|---|---|
| Example 266 | 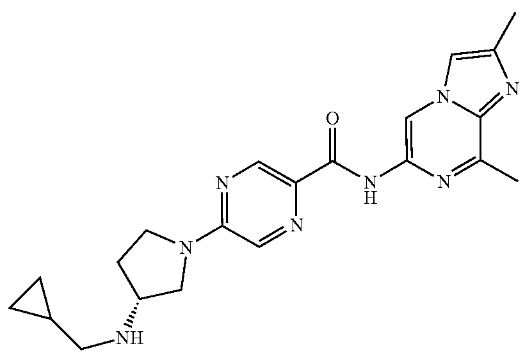 [SMILES: Cc1cn2cc(NC(=O)c3cnc(N4CC[C@@H](NCC5CC5)C4)cn3)nc(C)c2n1] | LCMS (ES+) 407 (M + H)+, RT 2.08 min (Analytical method AcHSSC18) $^1$H NMR (400 MHz, DMSO) δ 9.69 (s, 1H), 9.17 (s, 1H), 8.78 (d, J = 1.3 Hz, 1H), 8.06-8.03 (m, 2H), 3.76-3.56 (m, 3H), 3.50-3.42 (m, 2H), 2.73 (s, 3H), 2.48 (d, J = 6.7 Hz, 2H), 2.43 (s, 3H), 2.17-2.12 (m, 1H), 2.00-1.91 (m, 2H), 0.95-0.88 (m, 1H), 0.44 (ddd, J = 4.0, 5.6, 8.0 Hz, 2H), 0.18-0.13 (m, 2H). |
| Example 267 | 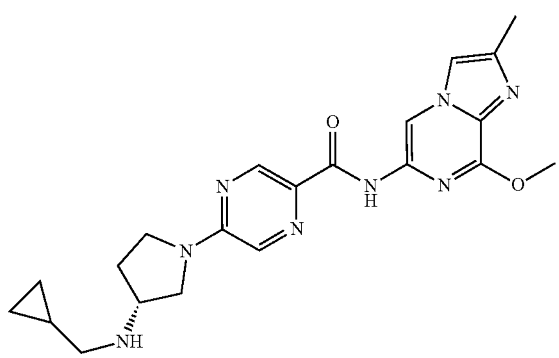 [SMILES: COc1nc(NC(=O)c2cnc(N3CC[C@@H](NCC4CC4)C3)cn2)cn2cc(C)nc12] | LCMS (ES+) 423 (M + H)+, RT 2.13 min (Analytical method AcHSSC18) $^1$H NMR (400 MHz, DMSO) δ 9.53 (s, 1H), 8.93 (s, 1H), 8.78 (d, J = 1.3 Hz, 1H), 8.06 (d, J = 1.3 Hz, 1H), 7.98 (s, 1H), 4.09 (s, 3H), 3.75-3.56 (m, 3H), 3.50 (s, 2H), 2.48 (d, J = 6.7 Hz, 2H), 2.37 (s, 3H), 2.24-2.12 (m, 2H), 1.94-1.90 (m, 1H), 0.95-0.87 (m, 1H), 0.45 (ddd, J = 4.0, 5.7, 8.0 Hz, 2H), 0.18-0.13 (m, 2H). |

-continued

| Example | Structure | Analytical data |
|---|---|---|
| Example 268 | 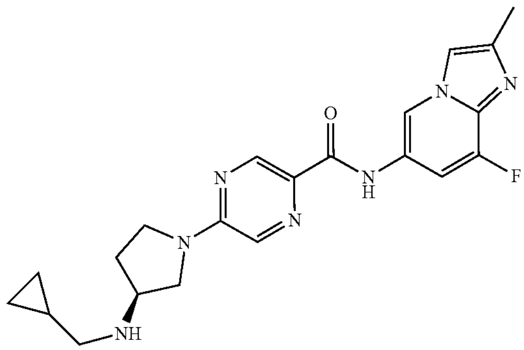 [SMILES: Cc1cn2cc(NC(=O)c3cnc(N4CC[C@H](NCC5CC5)C4)cn3)cc(F)c2n1] | LCMS (ES+) 410 (M + H)+, RT 1.88 min (Analytical method AcHSSC18) ¹H NMR (400 MHz, DMSO) δ 10.19 (s, 1H), 9.11 (d, J = 1.5 Hz, 1H), 8.75 (d, J = 1.3 Hz, 1H), 7.99 (d, J = 1.3 Hz, 1H), 7.73 (s, 1H), 7.37 (s, 1H), 3.78-3.66 (m, 2H), 3.58-3.49 (m, 1H), 3.27 (dd, J = 7.2, 11.1 Hz, 1H), 2.76-2.62 (m, 2H), 2.50 (s, 1H), 2.47 (s, 3H), 2.35 (s, 3H), 2.17-2.08 (m, 2H), 1.81-1.73 (m, 1H), 0.40 (dd, J = 1.6, 6.5 Hz, 2H), 0.28-0.23 (m, 2H). |
| Example 269 | 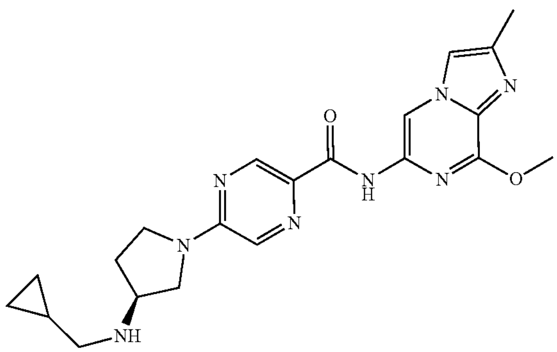 [SMILES: COc1nc(NC(=O)c2cnc(N3CC[C@H](NCC4CC4)C3)cn2)cn2cc(C)nc12] | LCMS (ES+) 423 (M + H)+, RT 2.13 min (Analytical method AcHSSC18) ¹H NMR (400 MHz, DMSO) 9.53 (s, 1H), 8.93 (s, 1H), 8.78 (d, J = 1.3 Hz, 1H), 8.06 (d, J = 1.3 Hz, 1H), 7.98 (s, 1H), 4.09 (s, 3H), 3.75-3.56 (m, 3H), 3.50 (s, 2H), 2.48 (d, J = 6.7 Hz, 2H), 2.37 (s, 3H), 2.24-2.12 (m, 2H), 1.94-1.90 (m, 1H), 0.95-0.87 (m, 1H), 0.45 (ddd, J = 4.0, 5.7, 8.0 Hz, 2H), 0.18-0.13 (m, 2H). |
| Example 270 | 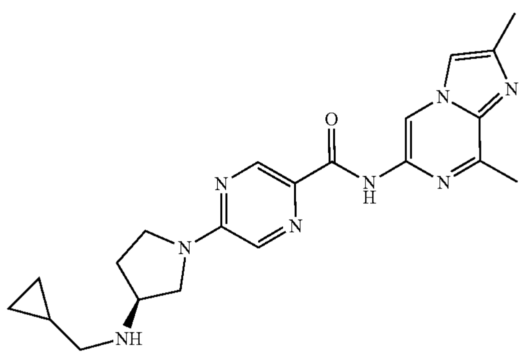 [SMILES: Cc1cn2cc(NC(=O)c3cnc(N4CC[C@H](NCC5CC5)C4)cn3)nc(C)c2n1] | LCMS (ES+) 407 (M + H)+, RT 2.08 min (Analytical method AcHSSC18) ¹H NMR (400 MHz, DMSO) δ 9.69 (s, 1H), 9.17 (s, 1H), 8.78 (d, J = 1.3 Hz, 1H), 8.06-8.03 (m, 2H), 3.76-3.56 (m, 3H), 3.50-3.42 (m, 2H), 2.73 (s, 3H), 2.48 (d, J = 6.7 Hz, 2H), 2.43 (s, 3H), 2.17-2.12 (m, 1H), 2.00-1.91 (m, 2H), 0.95-0.88 (m, 1H), 0.44 (ddd, J = 4.0, 5.6, 8.0 Hz, 2H), 0.18-0.13 (m, 2H). |

Example 271: 5-[(3R)-3-(cyclopropylamino)pyrrolidin-1-yl]-N-(6-methoxy-2-methyl-indazol-5-yl)pyrazine-2-carboxamide -continued

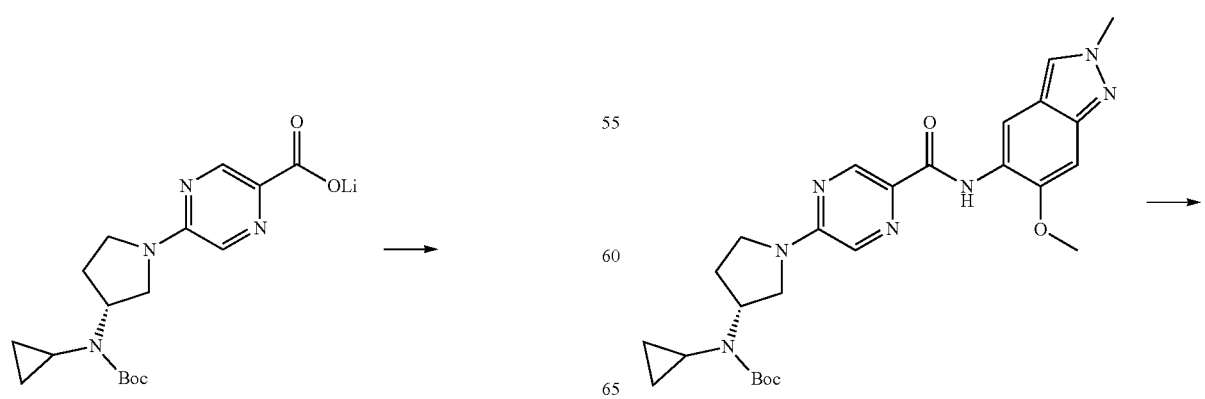

-continued

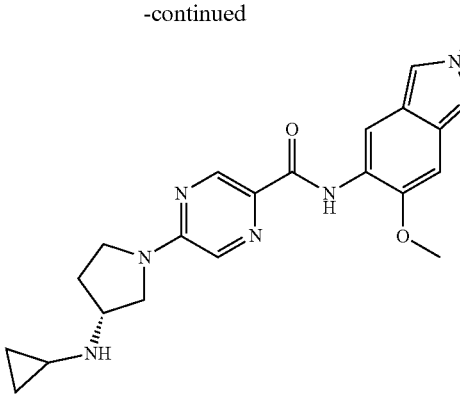

[5-[(3R)-3-[tert-butoxycarbonyl(cyclopropyl)amino]pyrrolidin-1-yl]pyrazine-2-carbonyl]oxylithium (175 mg, 0.494 mmol, 1.00 eq), 6-methoxy-2-methyl-indazol-5-amine (88 mg, 0.494 mmol, 1.00 eq), HBTU (187 mg, 0.494 mmol, 1.00 eq), triethylamine (0.50 mL, 3.59 mmol, 7.26 eq), and N,N-dimethylformamide (4.00 mL) were combined and stirred at room temperature for 4 hours. The reaction mixture was then purified by prep HPLC to give tert-butyl N-cyclopropyl-N-[(3R)-1-[5-[(6-methoxy-2-methyl-indazol-5-yl)carbamoyl]pyrazin-2-yl]pyrrolidin-3-yl]carbamate which was used in the next step. LCMS (ES+) 508 (M+H)+.

tert-butyl N-cyclopropyl-N-[(3R)-1-[5-[(6-methoxy-2-methyl-indazol-5-yl)carbamoyl]pyrazin-2-yl]pyrrolidin-3-yl]carbamate (117 mg, 0.230 mmol, 1.00 eq), methyl alcohol (2.00 mL), and 4 M hydrogen chloride in dioxane (2.0 mL, 8.00 mmol, 34.8 eq) were combined and stirred at room temperature for 4 hours. The reaction mixture was concentrated in vacuo, then purified by prep HPLC to give the title compound. LCMS (ES+) 408 (M+H)+, RT 2.53 min (Analytical method AcHSSC18). $^1$H NMR (400 MHz, DMSO) δ 10.08 (s, 1H), 8.78 (d, J=1.3 Hz, 1H), 8.71 (s, 1H), 8.25 (s, 1H), 8.07 (d, J=1.3 Hz, 1H), 7.14 (s, 1H), 4.12 (s, 3H), 4.01 (s, 3H), 3.75-3.42 (m, 5H), 2.16-1.96 (m, 3H), 0.44 (d, J=6.5 Hz, 2H), 0.31-0.26 (m, 2H).

Further analogues were prepared using the same chemistry from commercially available or synthesised amines. Final products were isolated by Preparative HPLC.

| Example | Structure | Analytical data |
|---|---|---|
| Example 272 | 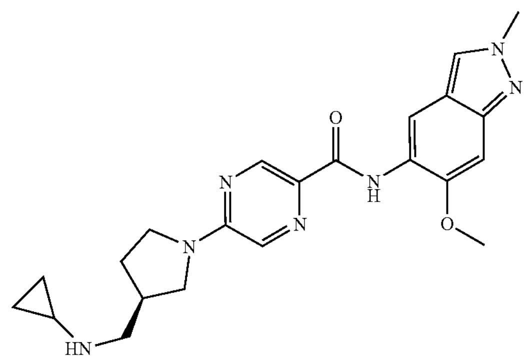 [SMILES: COc1cc2nn(C)cc2cc1NC(=O)c1cnc(N2CC[C@H](CNC3CC3)C2)cn1] | LCMS (ES+) 422.248 (M + H)+, RT 2.63 min (Analytical method AcHSSC18). $^1$H NMR (400 MHz, DMSO) δ 10.07 (s, 1H), 8.77 (d, J = 1.5 Hz, 1H), 8.70 (s, 1H), 8.25 (s, 1H), 8.05 (d, J = 1.3 Hz, 1H), 7.13 (s, 1H), 4.12 (s, 3H), 4.01 (s, 3H), 3.78-3.65 (m, 2H), 3.57-3.49 (m, 1H), 3.27 (dd, J = 7.1, 11.1 Hz, 1H), 2.75-2.61 (m, 2H), 2.50-2.48 (m, 1H), 2.37-2.31 (m, 1H), 2.16-2.07 (m, 2H), 1.81-1.72 (m, 1H), 0.40 (dd, J = 1.8, 6.6 Hz, 2H), 0.28-0.23 (m, 2H). |
| Example 273 | 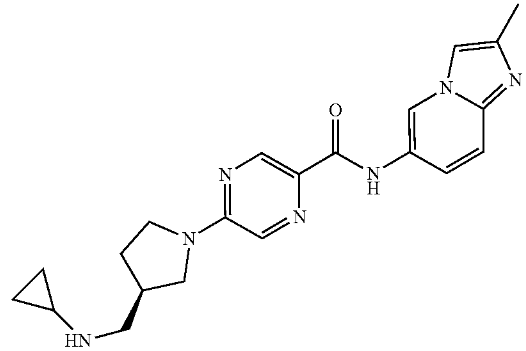 [SMILES: Cc1cn2cc(NC(=O)c3cnc(N4CC[C@H](CNC5CC5)C4)cn3)ccc2n1] | LCMS (ES+) 392 (M + H)+, RT 3.41 min (Analytical method BicarbBEHCl8). $^1$H NMR (400 MHz, DMSO) δ 10.34 (s, 1H), 9.28 (d, J = 1.3 Hz, 1H), 8.77 (d, J = 1.3 Hz, 1H), 7.99 (d, J = 1.4 Hz, 1H), 7.76 (s, 1H), 7.56 (dd, J = 2.0, 9.7 Hz, 1H), 7.44 (d, J = 9.7 Hz, 1H), 3.78-3.66 (m, 2H), 3.58-3.50 (m, 1H), 3.34-3.25 (m, 2H), 2.75-2.63 (m, 2H), 2.35 (s, 3H), 2.16-2.08 (m, 2H), 1.80-1.74 (m, 1H), 0.40 (dd, J = 1.6, 6.6 Hz, 2H), 0.28-0.23 (m, 2H). |

Example 274: N-(2,8-dimethylimidazo[1,2-a]pyrazin-6-yl)-5-[3-[[(3R)-3-fluoropyrrolidin-1-yl]methyl]azetidin-1-yl]pyrazine-2-carboxamide

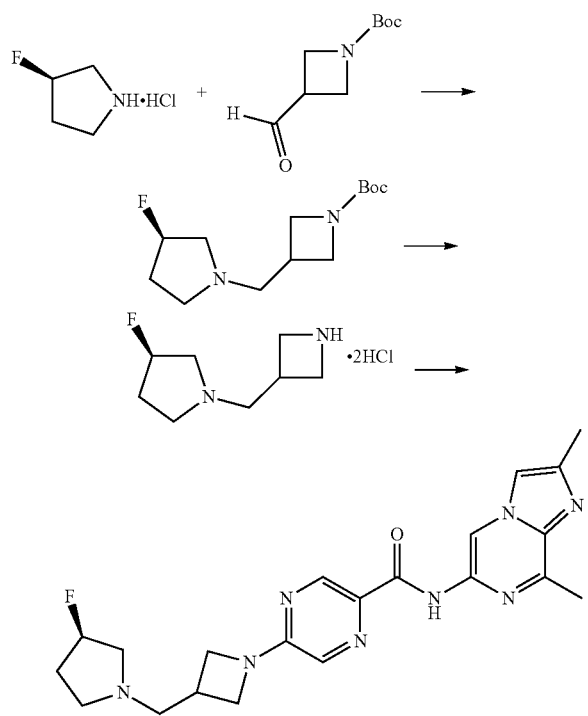

tert-Butyl 3-formylazetidine-1-carboxylate (120 mg, 0.650 mmol, 1.00 eq), sodium triacetoxyborohydride (303 mg, 1.43 mmol, 2.20 eq), and (R)-(−)-3-fluoropyrrolidine hydrochloride (200 mg, 1.59 mmol, 2.45 eq) were combined in dichloromethane (10.00 mL) and stirred at room temperature for 20 hours. Saturated aqueous sodium hydrogen carbonate solution was added to the reaction mixture and stirred vigorously for 10 mins. The reaction mixture was basified further with ~10% NaOH. The mixture was extracted with DCM, dried (MgSO$_4$), and concentrated in vacuo to give tert-butyl (R)-3-((3-fluoropyrrolidin-1-yl)methyl)azetidine-1-carboxylate, which was used directly in next step.

tert-Butyl (R)-3-((3-fluoropyrrolidin-1-yl)methyl)azetidine-1-carboxylate (225 mg), methyl alcohol (5.00 mL), and 4 M hydrogen chloride in dioxane (2.0 mL, 8.00 mmol, 12.3 eq) were combined and stirred at room temperature for 2.5 hours. The reaction mixture was concentrated in vacuo to give (3R)-1-(azetidin-3-ylmethyl)-3-fluoropyrrolidine 2HCl, which was used directly in next step. (3R)-1-(Azetidin-3-ylmethyl)-3-fluoro-pyrrolidine dihydrochloride (100 mg, 0.433 mmol, 1.00 eq), 5-chloro-N-(2,8-dimethylimidazo[1,2-a]pyrazin-6-yl)pyrazine-2-carboxamide (100 mg, 0.330 mmol, 0.764 eq), cesium carbonate (493 mg, 1.51 mmol, 3.50 eq), and N,N-dimethylformamide (4.00 mL) were combined in a sealed tube and hot block heated to 100° C. for 2 hours. The reaction mixture was cooled to room temperature, cesium salts were filtered off, and the residue was purified by prep HPLC to give the title compound. LCMS (ES+) 425 (M+H)+, RT 1.97 min (Analytical method AcHSSC18). $^1$H NMR (400 MHz, DMSO) δ 9.68 (s, 1H), 9.14 (s, 1H), 8.73 (d, J=1.4 Hz, 1H), 8.01 (s, 1H), 7.92 (d, J=1.4 Hz, 1H), 5.30-5.12 (m, 1H), 4.29 (dd, J=8.6, 8.6 Hz, 2H), 3.87 (dd, J=5.5, 9.0 Hz, 2H), 3.04-2.96 (m, 1H), 2.71-2.70 (m, 8H), 2.40 (s, 3H), 2.37-2.31 (m, 1H), 2.23-2.06 (m, 1H), 1.95-1.80 (m, 1H).

Further analogues were prepared using the same chemistry from commercially available or synthesised amines. Final products were isolated by Preparative HPLC.

| Example | Structure | Analytical data |
|---|---|---|
| Example 275 | 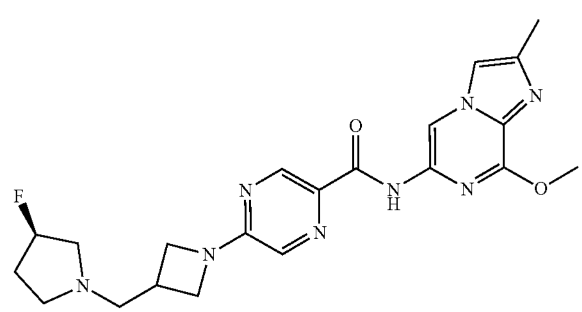 [SMILES: COc1nc(NC(=O)c2cnc(N3CC(CN4CC[C@@H](F)C4)C3)cn2)cn2cc(C)nc12] | LCMS (ES+) 441 (M + H)+, RT 2.03 min (Analytical method AcHSSC18). $^1$H NMR (400 MHz, DMSO) δ 9.51 (s, 1H), 8.90 (s, 1H), 8.73 (d, J = 1.3 Hz, 1H), 7.96 (s, 1H), 7.92 (d, J = 1.4 Hz, 1H), 5.30-5.13 (m, 1H), 4.29 (dd, J = 8.5, 8.5 Hz, 2H), 4.07 (s, 3H), 3.87 (dd, J = 5.6, 9.1 Hz, 2H), 3.04-2.96 (m, 1H), 2.89-2.57 (m, 5H), 2.35 (s, 4H), 2.23-2.09 (m, 1H), 1.95-1.80 (m, 1H). |
| Example 276 | 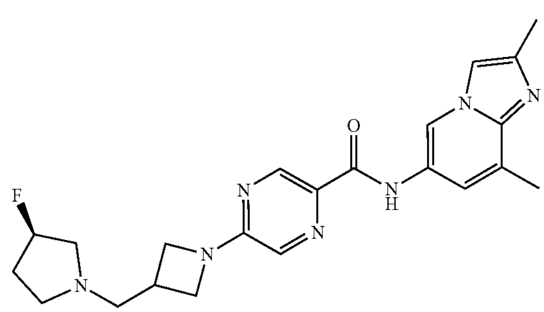 [SMILES: Cc1cn2cc(NC(=O)c3cnc(N4CC(CN5CC[C@@H](F)C5)C4)cn3)cc(C)c2n1] | LCMS (ES+) 424 (M + H)+, RT 1.84 min (Analytical method AcHSSC18). $^1$H NMR (400 MHz, DMSO) δ 10.20 (s, 1H), 9.08 (d, J = 1.5 Hz, 1H), 8.71 (d, J = 1.4 Hz, 1H), 7.88 (d, J = 1.4 Hz, 1H), 7.71 (s, 1H), 7.35 (s, 1H), 5.30-5.13 (m, 1H), 4.28 (dd, J = 8.6, 8.6 Hz, 2H), 3.87 (dd, J = 5.6, 9.0 Hz, 2H), 3.03-2.96 (m, 1H), 2.89-2.56 (m, 5H), 2.44 (s, 3H), 2.33 (s, 4H), 2.23-2.06 (m, 1H), 1.95-1.79 (m, 1H). |

| Example | Structure | Analytical data |
|---|---|---|
| Example 277 | 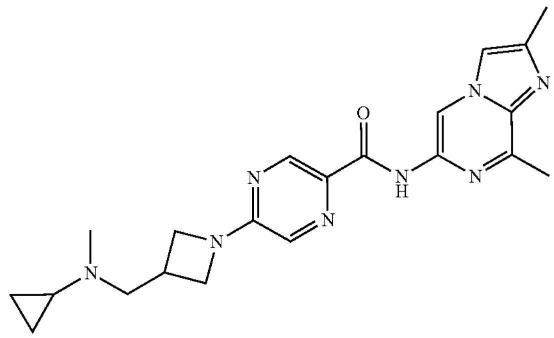 [SMILES: Cc1cn2cc(NC(=O)c3cnc(N4CC(CN(C)C5CC5)C4)cn3)nc(C)c2n1] | LCMS (ES+) 407 (M + H)+, RT 2.02 min (Analytical method AcHSSC18). ¹H NMR (400 MHz, DMSO) δ 9.67 (s, 1H), 9.14 (s, 1H), 8.72 (d, J = 1.4 Hz, 1H), 8.01 (s, 1H), 7.90 (d, J = 1.4 Hz, 1H), 4.26 (dd, J = 8.6, 8.6 Hz, 2H), 3.82 (dd, J = 5.5, 9.0 Hz, 2H), 3.10-3.02 (m, 1H), 2.78 (d, J = 7.7 Hz, 2H), 2.71 (s, 3H), 2.40 (s, 3H), 2.28 (s, 3H), 1.69-1.62 (m, 1H), 0.48-0.43 (m, 2H), 0.33-0.28 (m, 2H). |
| Example 278 | 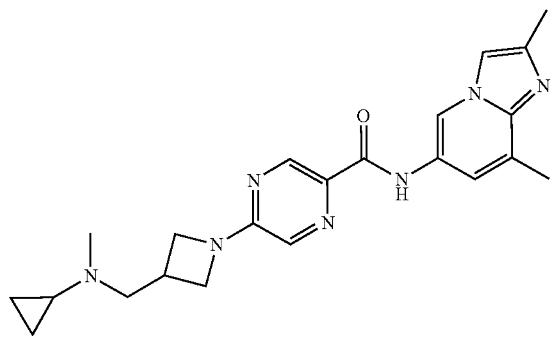 [SMILES: Cc1cn2cc(NC(=O)c3cnc(N4CC(CN(C)C5CC5)C4)cn3)cc(C)c2n1] | LCMS (ES+) 406 (M + H)+, RT 1.91 min (Analytical method AcHSSC18). ¹H NMR (400 MHz, DMSO) δ 10.22 (s, 1H), 9.10 (d, J = 1.5 Hz, 1H), 8.72 (d, J = 1.4 Hz, 1H), 7.89 (d, J = 1.4 Hz, 1H), 7.73 (s, 1H), 7.37 (s, 1H), 4.28 (dd, J = 8.6, 8.6 Hz, 2H), 3.84 (dd, J = 5.5, 9.0 Hz, 2H), 3.12-3.05 (m, 1H), 2.81 (d, J = 7.8 Hz, 2H), 2.47 (s, 3H), 2.35 (s, 3H), 2.31 (s, 3H), 1.71-1.65 (m, 1H), 0.51-0.46 (m, 2H), 0.35-0.30 (m, 2H). |

Example 279: 5-(3-((cyclopropylamino)methyl) azetidin-1-yl)-N-(2,8-dimethylimidazo[1,2-a]pyridin-6-yl)pyrazine-2-carboxamide

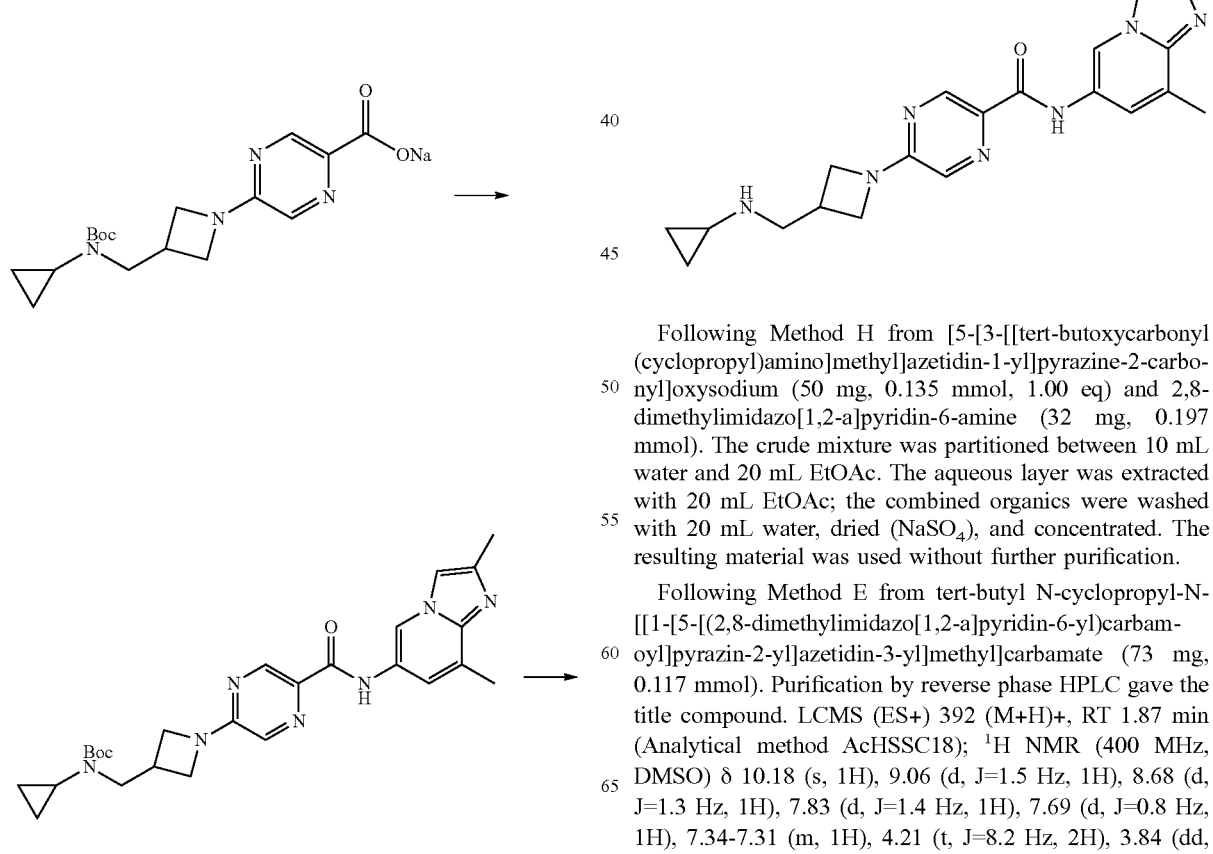

Following Method H from [5-[3-[[tert-butoxycarbonyl(cyclopropyl)amino]methyl]azetidin-1-yl]pyrazine-2-carbonyl]oxysodium (50 mg, 0.135 mmol, 1.00 eq) and 2,8-dimethylimidazo[1,2-a]pyridin-6-amine (32 mg, 0.197 mmol). The crude mixture was partitioned between 10 mL water and 20 mL EtOAc. The aqueous layer was extracted with 20 mL EtOAc; the combined organics were washed with 20 mL water, dried (NaSO₄), and concentrated. The resulting material was used without further purification.

Following Method E from tert-butyl N-cyclopropyl-N-[[1-[5-[(2,8-dimethylimidazo[1,2-a]pyridin-6-yl)carbamoyl]pyrazin-2-yl]azetidin-3-yl]methyl]carbamate (73 mg, 0.117 mmol). Purification by reverse phase HPLC gave the title compound. LCMS (ES+) 392 (M+H)+, RT 1.87 min (Analytical method AcHSSC18); ¹H NMR (400 MHz, DMSO) δ 10.18 (s, 1H), 9.06 (d, J=1.5 Hz, 1H), 8.68 (d, J=1.3 Hz, 1H), 7.83 (d, J=1.4 Hz, 1H), 7.69 (d, J=0.8 Hz, 1H), 7.34-7.31 (m, 1H), 4.21 (t, J=8.2 Hz, 2H), 3.84 (dd, J=4.8, 9.0 Hz, 2H), 2.90-2.82 (m, 3H), 2.43 (s, 3H), 2.31 (s, 3H), 2.09-2.03 (m, 1H), 0.39-0.34 (m, 2H), 0.22-0.18 (m, 2H).

Example 280: (R)—N-(8-methoxy-2-methylimidazo[1,2-a]pyrazin-6-yl)-5-(1-(methylamino)-5-azaspiro[2.3]hexan-5-yl)pyrazine-2-carboxamide

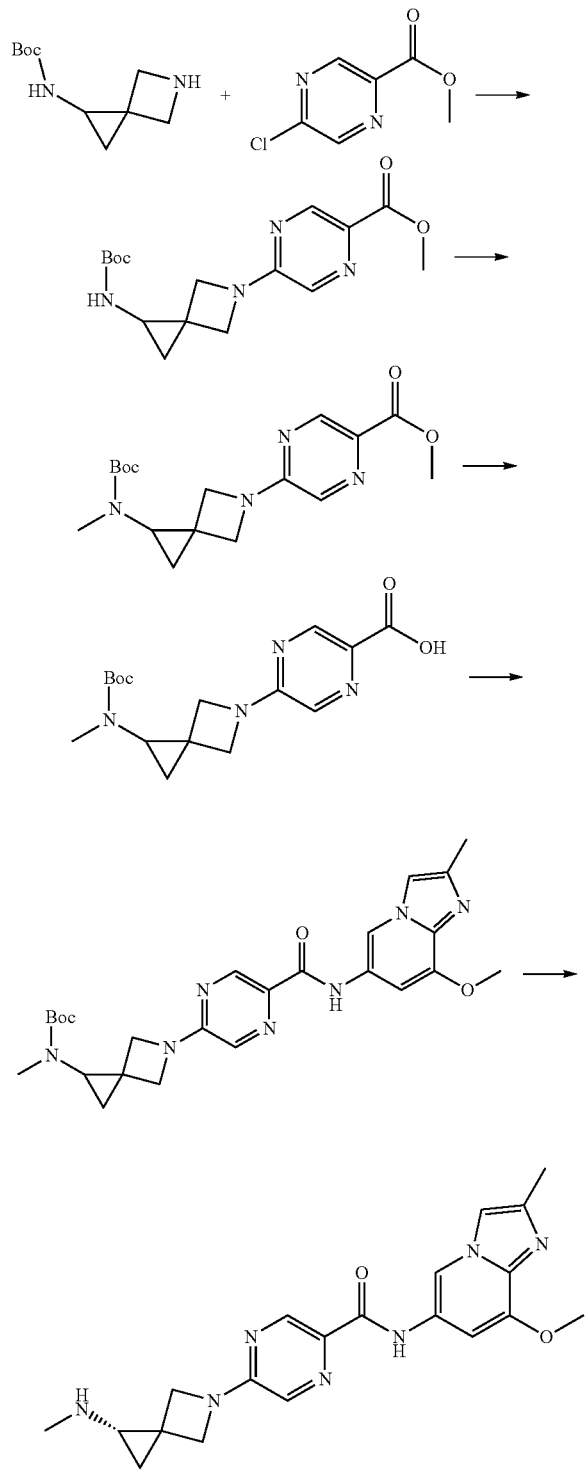

Following Method D from tert-butyl N-(5-azaspiro[2.3]hexan-2-yl)carbamate (273 mg, 1.38 mmol, 1.00 eq) and methyl 5-chloro-2-pyrazinecarboxylate (238 mg, 1.38 mmol, 1.00 eq). The reaction mixture was partitioned between EtOAc and water. The aqueous phase was extracted with EtOAc. The combined organic phases were dried over magnesium sulfate, filtered, and concentrated in vacuo to give methyl 5-(1-((tert-butoxycarbonyl)amino)-5-azaspiro[2.3]hexan-5-yl)pyrazine-2-carboxylate, which was progressed to the next step directly. LCMS (ES+) 335 (M+H)+.

To a stirred solution of methyl 5-[2-(tert-butoxycarbonylamino)-5-azaspiro[2.3]hexan-5-yl]pyrazine-2-carboxylate (462 mg, 1.38 mmol, 1.00 eq) in tetrahydrofuran (10.00 mL) at 0° C., was added sodium hydride (133 mg, 5.53 mmol, 4.00 eq). The reaction mixture was stirred for 15 min before addition of iodomethane (0.17 mL, 2.76 mmol, 2.00 eq), and the mixture stirred at r.t. for 20 h. No reaction was observed by LCMS. N,N-Dimethylformamide (10.00 mL) was added, followed by additional sodium hydride (133 mg, 5.53 mmol, 4.00 eq) and iodomethane (0.17 mL, 2.76 mmol, 2.00 eq). The reaction mixture was heated to 80° C. for 24 h. The reaction mixture was partitioned between EtOAc and water. The organics were collected and washed with water, before drying over magnesium sulfate, filtering, and concentrating to dryness to give methyl 5-[2-[tert-butoxycarbonyl(methyl)amino]-5-azaspiro[2.3]hexan-5-yl]pyrazine-2-carboxylate. LCMS (ES+) 349 (M+H)+.

Aqueous sodium hydroxide (0.45 mL, 0.896 mmol, 1.20 eq) and methyl 5-[2-[tert-butoxycarbonyl(methyl)amino]-5-azaspiro[2.3]hexan-5-yl]pyrazine-2-carboxylate (260 mg, 0.746 mmol, 1.00 eq) were stirred in methyl alcohol (5.00 mL) at 50° C. for 16 h. The reaction mixture was concentrated to dryness to give [5-[2-[tert-butoxycarbonyl(methyl)amino]-5-azaspiro[2.3]hexan-5-yl]pyrazine-2-carbonyl]oxysodium, which was progressed to next step without further purification. LCMS (ES+) 335 (M+H)+.

Following Method B from 8-methoxy-2-methyl-imidazo[1,2-a]pyrazin-6-amine (140 mg, 0.786 mmol, 1.00 eq) and [5-[2-[tert-butoxycarbonyl(methyl)amino]-5-azaspiro[2.3]hexan-5-yl]pyrazine-2-carbonyl]oxysodium (280 mg, 0.786 mmol, 1.00 eq). The reaction mixture was partitioned between EtOAc and water. The aqueous phase was extracted with further EtOAc and water. The combined organic phases were dried over magnesium sulfate, filtered, and concentrated in vacuo. Purification by preparative HPLC gave tert-butyl (5-(5-((8-methoxy-2-methylimidazo[1,2-a]pyrazin-6-yl)carbamoyl)pyrazin-2-yl)-5-azaspiro[2.3]hexan-1-yl)(methyl)carbamate. LCMS (ES+) 495 (M+H)+.

Following Method E from tert-butyl N-[5-[5-[(8-methoxy-2-methyl-imidazo[1,2-a]pyrazin-6-yl)carbamoyl]pyrazin-2-yl]-5-azaspiro[2.3]hexan-2-yl]-N-methyl-carbamate (14 mg, 0.0283 mmol, 1.00 eq). The reaction mixture was concentrated to dryness. Purification by chiral SFC gave (R)—N-(8-methoxy-2-methylimidazo[1,2-a]pyrazin-6-yl)-5-(1-(methylamino)-5-azaspiro[2.3]hexan-5-yl)pyrazine-2-carboxamide. LCMS (ES+) 395 (M+H)+, RT 3.33 min (Analytical method BicarbBEHC18). ¹H NMR (400 MHz, DMSO) δ 9.53 (s, 1H), 8.91 (s, 1H), 8.75 (d, J=1.0 Hz, 1H), 7.96 (d, J=3.7 Hz, 2H), 4.30 (d, J=8.9 Hz, 1H), 4.18 (d, J=6.6 Hz, 2H), 4.07 (s, 4H), 2.36 (d, J=6.5 Hz, 6H), 2.19-2.13 (m, 1H), 0.87 (dd, J=6.4, 6.4 Hz, 1H), 0.53 (dd, J=4.8, 4.8 Hz, 1H).

Example 281: (R)-5-(3-((cyclopropylamino)methyl)pyrrolidin-1-yl)-N-(7-fluoro-2-methyl-2H-indazol-5-yl)pyrazine-2-carboxamide

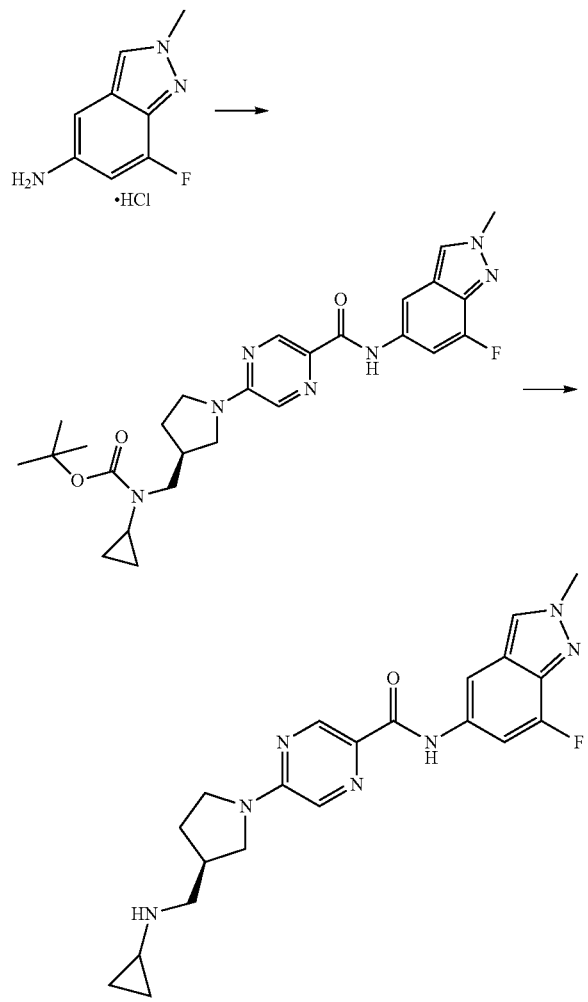 [SMILES: Cn1cc2cc(N)cc(F)c2n1 ; Cl ; Cn1cc2cc(NC(=O)c3cnc(N4CC[C@H](CN(C(=O)OC(C)(C)C)C5CC5)C4)cn3)cc(F)c2n1 ; Cn1cc2cc(NC(=O)c3cnc(N4CC[C@H](CNC5CC5)C4)cn3)cc(F)c2n1]

To a solution of [5-[(3S)-3-[[tert-butoxycarbonyl(cyclopropyl)amino]methyl]pyrrolidin-1-yl]pyrazine-2-carbonyl]oxylithium (100 mg, 0.271 mmol) in N,N-dimethylformamide (4 mL) was added 7-fluoro-2-methyl-indazol-5-amine hydrochloride (60 mg, 0.299 mmol), HBTU (103 mg, 0.271 mmol), and triethylamine (0.5 mL, 3.59 mmol), and the reaction was stirred at room temperature for 18 h. The crude reaction mixture was purified by preparative HPLC to give tert-butyl (S)-cyclopropyl((1-(5-((7-fluoro-2-methyl-2H-indazol-5-yl)carbamoyl)pyrazin-2-yl)pyrrolidin-3-yl)methyl)carbamate.

To a solution of tert-butyl (S)-cyclopropyl((1-(5-((7-fluoro-2-methyl-2H-indazol-5-yl)carbamoyl)pyrazin-2-yl)pyrrolidin-3-yl)methyl)carbamate (65 mg, 0.128 mmol) in dichloromethane (1.7 mL) was added trifluoroacetic acid (0.3 mL, 3.92 mmol) at RT. The reaction was stirred at RT for 2 h. The solvent was removed by blowing nitrogen over the sample to give residue. The residue was purified by SCX chromatography (2 g, eluting with MeOH and then 10% 7N $NH_3$ in MeOH/MeOH). The ammonical fractions were combined and the solvent removed in vacuo to give the title compound. LCMS (ES+) 410 (M+H)+, RT 3.68 min (Analytical method BicarbBEHC18). $^1$H NMR (400 MHz, DMSO) δ 10.23 (s, 1H), 8.73 (d, J=1.4 Hz, 1H), 8.41 (d, J=2.9 Hz, 1H), 8.15 (d, J=1.5 Hz, 1H), 7.94 (d, J=1.3 Hz, 1H), 7.57 (dd, J=1.6, 13.8 Hz, 1H), 4.16 (s, 3H), 3.73-3.63 (m, 2H), 3.54-3.45 (m, 1H), 3.32 (s, 1H), 3.27-3.20 (m, 1H), 2.73-2.59 (m, 2H), 2.13-2.05 (m, 2H), 1.77-1.68 (m, 1H), 0.39-0.36 (m, 2H), 0.26-0.19 (m, 2H) NH partially obscured by DMSO peak.

The following examples were prepared using an analogous procedure.

| Example | Structure | Carboxylate salt used | Analytical data |
|---|---|---|---|
| Example 282 | 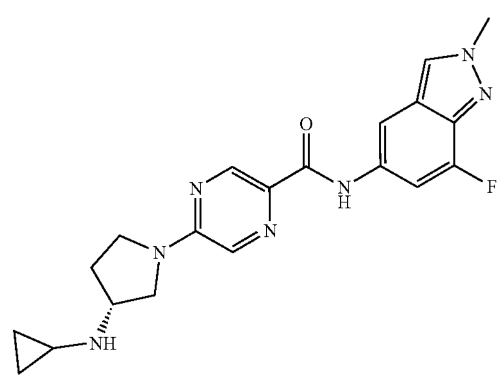 [SMILES: Cn1cc2cc(NC(=O)c3cnc(N4CC[C@@H](NC5CC5)C4)cn3)cc(F)c2n1] | lithium (R)-4-(3-(tert-butoxycarbonyl)(cyclopropyl)amino)pyrrolidin-1-yl)benzoate | LCMS (ES+) 396 (M + H)+, RT 3.53 min (Analytical method BicarbBEHCl8) $^1$H NMR (400 MHz, DMSO) δ 10.23 (s, 1H), 8.73 (d, J = 1.4 Hz, 1H), 8.41 (d, J = 2.9 Hz, 1H), 8.15 (d, J = 1.5 Hz, 1H), 7.95 (d, J = 1.4 Hz, 1H), 7.57 (dd, J = 1.6, 13.7 Hz, 1H), 4.17 (s, 3H), 3.72-3.49 (m, 4H), 3.43-3.40 (m, 1H) 3.32-3.31 (m, 1H), 2.14-2.09 (m, 2H), 1.95-1.88 (m, 1H), 0.42-0.39 (m, 2H), 0.28-0.20 (m, 2H). |

| Example | Structure | Carboxylate salt used | Analytical data |
|---|---|---|---|
| Example 283 | 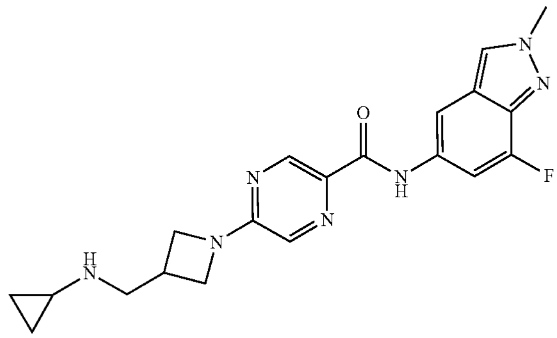 [SMILES: Cn1cc2cc(NC(=O)c3cnc(N4CC(CNC5CC5)C4)cn3)cc(F)c2n1] | sodium 4-(3-(tert-butoxycarbonyl)(cyclopropyl)amino)methyl)azetidin-1-yl)benzoate | LCMS (ES+) 396 (M + H)+, RT 2.43 min (Analytical method AcHSSC18) $^1$H NMR (400 MHz, DMSO) δ 10.27 (s, 1H), 8.72 (d, J = 1.4 Hz, 1H), 8.43 (d, J = 2.9 Hz, 1H), 8.16 (d, J = 1.5 Hz, 1H), 7.85 (d, J = 1.3 Hz, 1H), 7.58 (dd, J = 1.6, 13.7 Hz, 1H), 4.19-4.18 (m, 6H), 3.89-3.84 (m, 2H), 2.92-2.86 (m, 3H), 2.13-2.07 (m, 1H), 0.43-0.37 (m, 2H), 0.27-0.22 (m, 2H) |

Example 284: (R)—N-(7-fluoro-2-methyl-2H-indazol-5-yl)-5-(3-(methylamino)pyrrolidin-1-yl)pyrazine-2-carboxamide

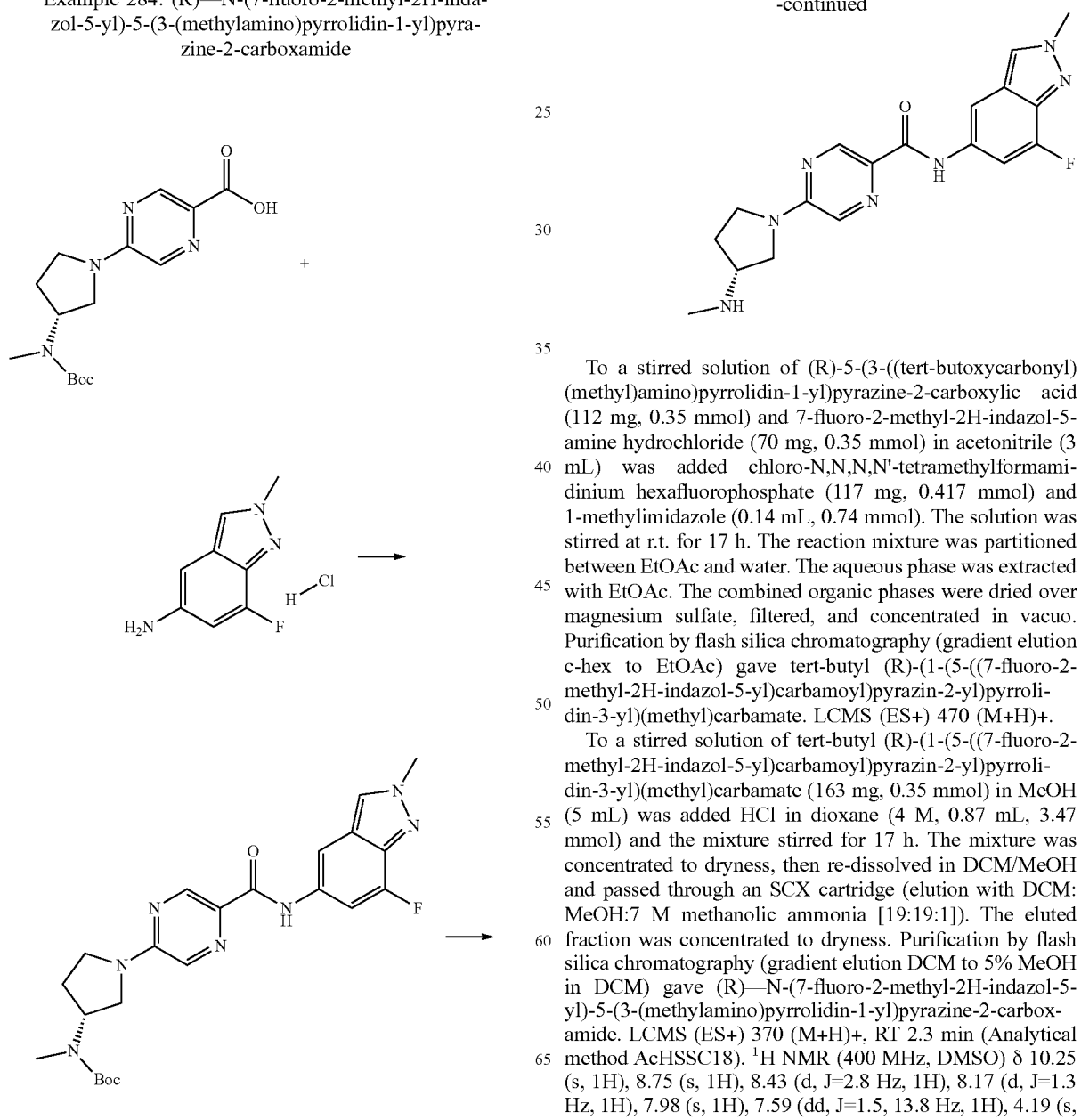

To a stirred solution of (R)-5-(3-((tert-butoxycarbonyl)(methyl)amino)pyrrolidin-1-yl)pyrazine-2-carboxylic acid (112 mg, 0.35 mmol) and 7-fluoro-2-methyl-2H-indazol-5-amine hydrochloride (70 mg, 0.35 mmol) in acetonitrile (3 mL) was added chloro-N,N,N',N'-tetramethylformamidinium hexafluorophosphate (117 mg, 0.417 mmol) and 1-methylimidazole (0.14 mL, 0.74 mmol). The solution was stirred at r.t. for 17 h. The reaction mixture was partitioned between EtOAc and water. The aqueous phase was extracted with EtOAc. The combined organic phases were dried over magnesium sulfate, filtered, and concentrated in vacuo. Purification by flash silica chromatography (gradient elution c-hex to EtOAc) gave tert-butyl (R)-(1-(5-((7-fluoro-2-methyl-2H-indazol-5-yl)carbamoyl)pyrazin-2-yl)pyrrolidin-3-yl)(methyl)carbamate. LCMS (ES+) 470 (M+H)+.

To a stirred solution of tert-butyl (R)-(1-(5-((7-fluoro-2-methyl-2H-indazol-5-yl)carbamoyl)pyrazin-2-yl)pyrrolidin-3-yl)(methyl)carbamate (163 mg, 0.35 mmol) in MeOH (5 mL) was added HCl in dioxane (4 M, 0.87 mL, 3.47 mmol) and the mixture stirred for 17 h. The mixture was concentrated to dryness, then re-dissolved in DCM/MeOH and passed through an SCX cartridge (elution with DCM:MeOH:7 M methanolic ammonia [19:19:1]). The eluted fraction was concentrated to dryness. Purification by flash silica chromatography (gradient elution DCM to 5% MeOH in DCM) gave (R)—N-(7-fluoro-2-methyl-2H-indazol-5-yl)-5-(3-(methylamino)pyrrolidin-1-yl)pyrazine-2-carboxamide. LCMS (ES+) 370 (M+H)+, RT 2.3 min (Analytical method AcHSSC18). $^1$H NMR (400 MHz, DMSO) δ 10.25 (s, 1H), 8.75 (s, 1H), 8.43 (d, J=2.8 Hz, 1H), 8.17 (d, J=1.3 Hz, 1H), 7.98 (s, 1H), 7.59 (dd, J=1.5, 13.8 Hz, 1H), 4.19 (s, 3H), 3.70-3.56 (m, 3H), 3.39 (d, J=11.0 Hz, 1H), 3.34 (s, 1H), 3.33-3.27 (m, 1H), 2.33 (s, 3H), 2.16-2.07 (m, 1H), 1.97-1.90 (m, 1H).

Example 285: N-(2,8-dimethylimidazo[1,2-a]pyrazin-6-yl)-5-(3-fluoro-3-((methylamino)methyl)pyrrolidin-1-yl)pyrazine-2-carboxamide (Enantiomer 1+Enantiomer 2)

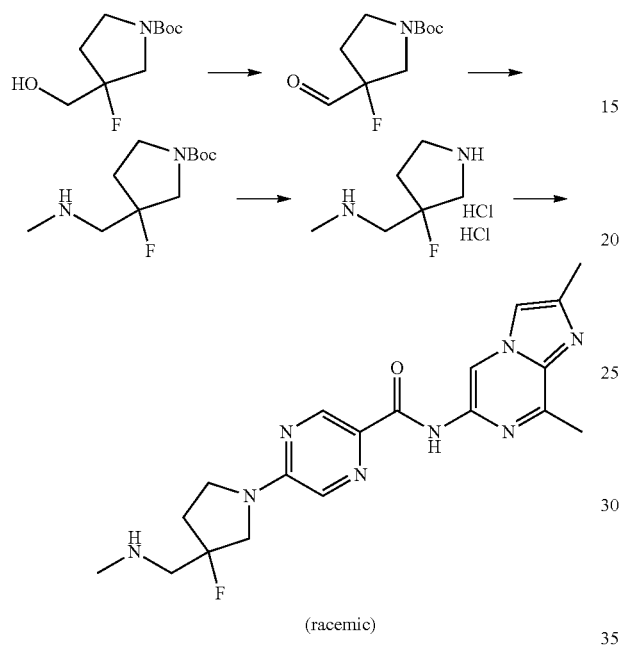

A suspension of tert-butyl 3-fluoro-3-(hydroxymethyl)pyrrolidine-1-carboxylate (1.00 g, 4.56 mmol) and Dess-Martin periodinane (2.32 g, 5.47 mmol) in dichloromethane (23 mL) was stirred at room temperature overnight. The reaction mixture was diluted with aqueous sodium thiosulfate (10% w/v) and sat. aqueous sodium hydrogen carbonate and stirred for 20 minutes. The mixture was passed through a phase separator and the organics concentrated under reduced pressure. The crude material was purified by flash column chromatography (0 to 100% EtOAc in cyclohexane; 40 g column). The product containing fractions were concentrated under reduced pressure to yield the product.

A suspension of tert-butyl 3-fluoro-3-formyl-pyrrolidine-1-carboxylate (270 mg, 1.24 mmol), 2 M methylamine in THF (0.62 mL, 1.24 mmol), and sodium triacetoxyborohydride (263 mg, 1.24 mmol) in dichloromethane (12 mL) under nitrogen was stirred at room temperature overnight. The reaction mixture was diluted with saturated aqueous sodium hydrogen carbonate and stirred for 10 minutes. The mixture was passed through a phase separator and the organics concentrated under reduced pressure yielding the crude material, which was taken on without further purification.

A solution of tert-butyl 3-fluoro-3-(methylaminomethyl)pyrrolidine-1-carboxylate (210 mg, 0.904 mmol) in 4 M hydrogen chloride in dioxane (4.5 mL, 18.1 mmol) and methyl alcohol (4.50 mL) was stirred at room temperature overnight. The reaction mixture was concentrated under reduced pressure and taken on without further purification.

A mixture of 1-(3-fluoropyrrolidin-3-yl)-N-methyl-methanamine dihydrochloride (62 mg, 0.301 mmol), 5-chloro-N-(2,8-dimethylimidazo[1,2-a]pyrazin-6-yl)pyrazine-2-carboxamide (70 mg, 0.231 mmol) and triethylamine (0.097 mL, 0.694 mmol, 3.00 eq) in 1,4-dioxane (2.50 mL) was heated in a microwave to 140° C. for 1 hour. The reaction mixture was concentrated under reduced pressure and the crude material submitted to achiral reverse phase HPLC for purification (Sunfire C18 19×150 mm, 10 μm 5-60% ACN/H$_2$O (10 mM NH$_4$CO$_3$), 20 mL/min, RT) to yield N-(2,8-dimethylimidazo[1,2-a]pyrazin-6-yl)-5-[3-fluoro-3-(methylaminomethyl)pyrrolidin-1-yl]pyrazine-2-carboxamide. LCMS (ES+) 399.3 [M+H]+, RT 1.96 min (Analytical method AcHSSC18). $^1$H NMR (400 MHz, DMSO) δ 9.69 (s, 1H), 9.15 (s, 1H), 8.78 (d, J=1.2 Hz, 1H), 8.09 (s, 1H), 8.01 (s, 1H), 3.95-3.62 (m, 4H), 3.02-2.86 (m, 2H), 2.71 (s, 3H), 2.40 (s, 3H), 2.39 (s, 3H), 2.33-2.15 (m, 2H).

Example 286: (R)-5-(3-((cyclopropylamino)methyl)pyrrolidin-1-yl)-N-(2,8-dimethylimidazo[1,2-a]pyrazin-6-yl)pyrazine-2-carboxamide

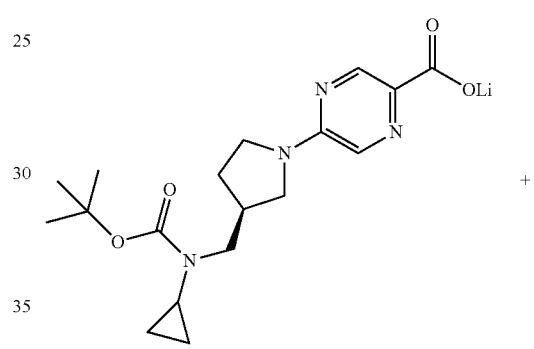

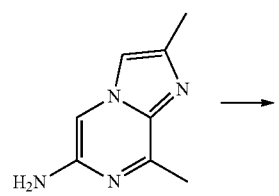

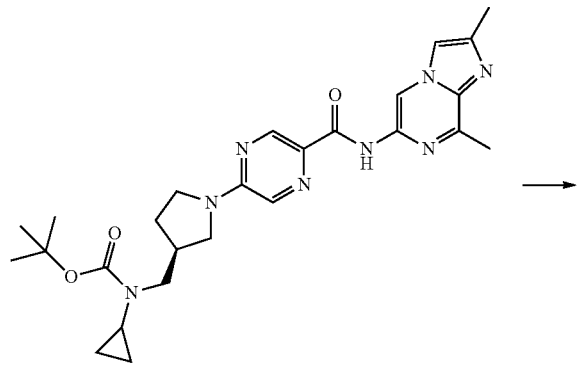

601

-continued

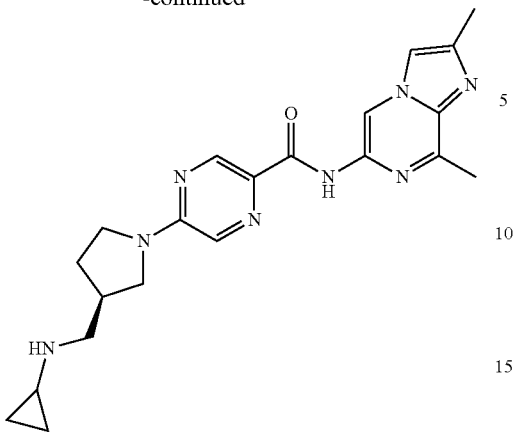

A mixture of [5-[(3S)-3-[[tert-butoxycarbonyl(cyclopropyl)amino]methyl]pyrrolidin-1-yl]pyrazine-2-carbonyl]oxylithium (100 mg, 0.271 mmol), 2,8-dimethylimidazo[1,2-a]pyrazin-6-amine (44 mg, 0.271 mmol), HBTU (103 mg, 0.271 mmol), and triethylamine (0.038 mL, 0.271 mmol) in N,N-dimethylformamide (2.50 mL) was stirred at room temperature overnight. The reaction mixture was filtered and submitted to reverse phase HPLC for purification (Sunfire C18 19×150 mm, 10 µm 20-80% ACN/H$_2$O (10 mM NH$_4$CO$_3$), 20 mL/min, rt) to yield tert-butyl N-cyclopropyl-N-[[(3S)-1-[5-[(2,8-dimethylimidazo[1,2-a]pyrazin-6-yl)carbamoyl]pyrazin-2-yl]pyrrolidin-3-yl]methyl]carbamate. MS (ES+) 507 [M+H]+.

tert-Butyl N-cyclopropyl-N-[[(3S)-1-[5-[(2,8-dimethylimidazo[1,2-a]pyrazin-6-yl)carbamoyl]pyrazin-2-yl]pyrrolidin-3-yl]methyl]carbamate (22 mg, 0.0434 mmol), methanol (0.50 mL), and 4N hydrogen chloride in 1,4-dioxane (0.50 mL, 2.00 mmol) were combined and stirred at room temperature overnight. The reaction was concentrated under reduced pressure and the crude material purified by prep HPLC (Xbridge Phenyl 19×150 mm, 10 µm 40-100% MeOH/H$_2$O (10 mM NH$_4$CO$_3$), 20 mL/min, rt) to yield 5-[(3R)-3-[(cyclopropylamino)methyl]pyrrolidin-1-yl]-N-(2,8-dimethylimidazo[1,2-a]pyrazin-6-yl)pyrazine-2-carboxamide. LCMS (ES+) 407.4 [M+H]+, RT 2.09 min (Analytical method AcHSSC18). $^1$H NMR (400 MHz, DMSO) δ 9.67 (s, 1H), 9.16 (s, 1H), 8.77 (d, J=1.1 Hz, 1H), 8.03 (d, J=1.4 Hz, 1H), 8.02 (d, J=0.7 Hz, 1H), 3.77-3.66 (m, 2H), 3.58-3.49 (m, 1H), 3.28 (dd, J=7.2, 11.2 Hz, 1H), 2.72 (s, 3H), 2.71-2.68 (m, 1H), 2.68-2.61 (m, 1H), 2.50-2.47 (m, 1H), 2.42 (s, 3H), 2.36 (dd, J=1.9, 1.9 Hz, 1H), 2.13-2.07 (m, 2H), 1.76 (s, 1H), 0.41-0.38 (m, 2H), 0.26-0.22 (m, 2H).

Example 287: 5-[(3S)-3-[(cyclopropylamino)methyl]pyrrolidin-1-yl]-N-(2,8-dimethylimidazo[1,2-a]pyrazin-6-yl)pyrazine-2-carboxamide

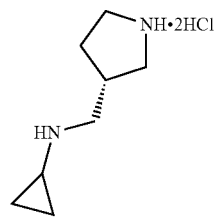

+

602

-continued

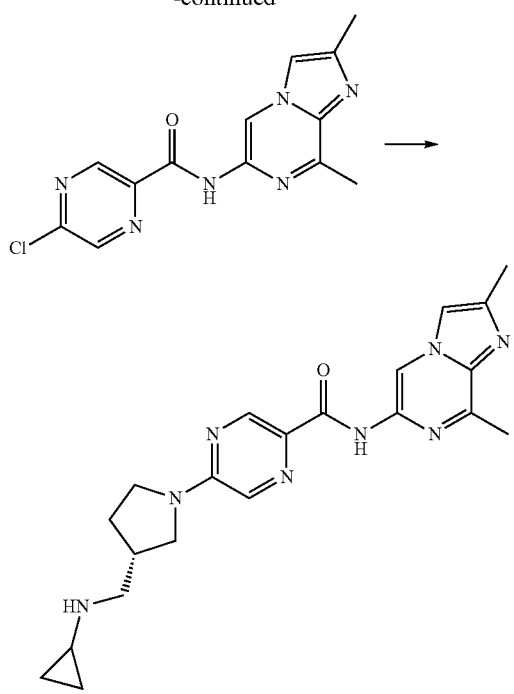

5-Chloro-N-(2,8-dimethyl-1,8a-dihydroimidazo[1,2-a]pyrazin-6-yl)pyrazine-2-carboxamide (100 mg, 0.328 mmol, 1.00 eq) and N-[[(3R)-pyrrolidin-3-yl]methyl]cyclopropanamine dihydrochloride (91 mg, 0.427 mmol, 1.30 eq) were suspended in 1,4-dioxane (3.00 mL) and triethylamine (183 uL, 1.31 mmol, 4.00 eq) was added. The mixture was heated to 140° C. for 40 min in the microwave. The solvent was evaporated and partitioned between DCM (15 mL) and water (5 mL), the layers were separated and the aqueous extracted with DCM (2×5 mL). The combined organic phases were dried over magnesium sulfate, filtered, and concentrated in vacuo and evaporated. The crude material was purified by preparative HPLC to give the title compound. LCMS (ES+) 407 (M+H)+, RT 2.09 min (Analytical method AcHSSC18). $^1$H NMR (400 MHz, DMSO) δ 9.65 (s, 1H), 9.14 (s, 1H), 8.74 (s, 1H), 8.00 (d, J=5.1 Hz, 2H), 3.75-3.64 (m, 2H), 3.54-3.46 (m, 1H), 3.30-3.21 (m, 1H), 2.69 (s, 4H), 2.66-2.59 (m, 2H), 2.39 (s, 3H), 2.33 (s, 1H), 2.08-2.07 (m, 2H), 1.73 (s, 1H), 0.36 (d, J=6.4 Hz, 2H), 0.24-0.19 (m, 2H).

Example 288: 5-(3-((cyclopropylamino)methyl)azetidin-1-yl)-N-(6-methoxy-2-methyl-2H-indazol-5-yl)pyrazine-2-carboxamide

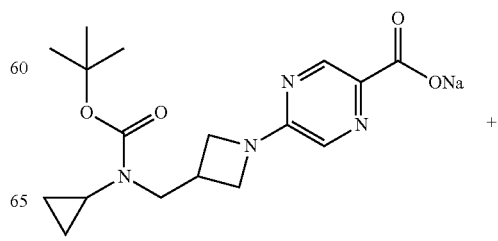

+

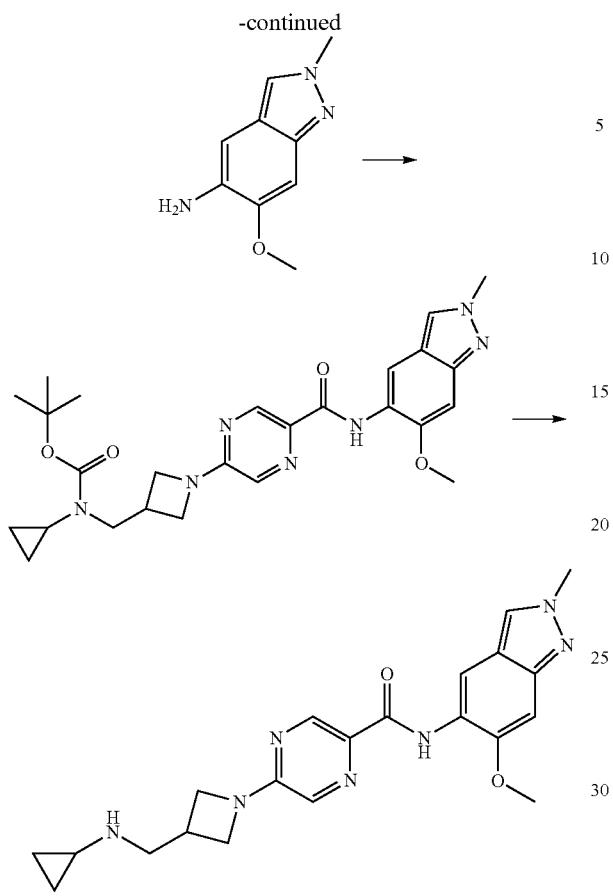

A mixture of 6-methoxy-2-methyl-indazol-5-amine (80 mg, 0.45 mmol), [4-[3-[[tert-butoxycarbonyl(cyclopropyl)amino]methyl]azetidin-1-yl]benzoyl]oxysodium (166 mg, 0.451 mmol), HBTU (171 mg, 0.451 mmol), and triethylamine (0.31 mL, 2.26 mmol) in N,N-dimethylformamide (2.50 mL) was stirred at room temperature overnight. The reaction mixture was diluted with water and the organics extracted with EtOAc (3×). The combined organics were washed with brine, dried over MgSO4, decanted, and concentrated under reduced pressure to yield the crude material, which was taken on without further purification. MS (ES+) 507.0 [M]+.

A solution of tert-butyl N-cyclopropyl-N-[[1-[5-[(6-methoxy-2-methyl-indazol-5-yl)carbamoyl]pyrazin-2-yl]azetidin-3-yl]methyl]carbamate (280 mg, 0.552 mmol) and 4N hydrogen chloride in 1,4-dioxane (3.0 mL, 12.0 mmol) in methanol (3.00 mL) was stirred at room temperature over the weekend. The reaction mixture was concentrated under reduced pressure and the crude material submitted to prep HPLC for purification (Xbridge Phenyl 19×150 mm, 10 um 20-80% MeOH/H2O (10 mM NH4CO3), 20 ml/min, rt) to yield 5-[3-[(cyclopropylamino)methyl]azetidin-1-yl]-N-(6-methoxy-2-methyl-indazol-5-yl)pyrazine-2-carboxamide. LCMS (ES+) 408.4 [M+H]+, RT 2.53 min (Analytical method AcHSSC18). $^1$H NMR (400 MHz, DMSO) δ 10.02 (s, 1H), 8.70 (d, J=1.4 Hz, 1H), 8.66 (s, 1H), 8.21 (s, 1H), 7.89 (d, J=1.4 Hz, 1H), 7.09 (s, 1H), 4.21 (dd, J=8.2, 8.2 Hz, 2H), 4.08 (s, 3H), 3.96 (s, 3H), 3.84 (dd, J=4.9, 9.0 Hz, 2H), 2.94-2.83 (m, 3H), 2.10-2.04 (m, 1H), 0.40-0.35 (m, 2H), 0.23-0.19 (m, 2H).

Example 289: 5-(3-fluoro-3-((methylamino)methyl)azetidin-1-yl)-N-(8-methoxy-2-methylimidazo[1,2-a]pyrazin-6-yl)pyrazine-2-carboxamide

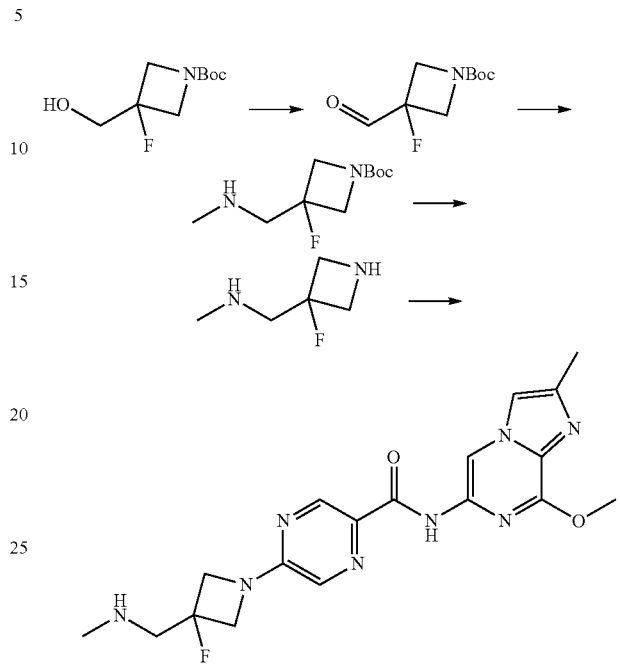

A suspension of tert-butyl 3-fluoro-3-(hydroxymethyl)azetidine-1-carboxylate (500 mg, 2.44 mmol) and Dess-Martin periodinane (1.24 g, 2.92 mmol) in dichloromethane (15 mL) was stirred at room temperature for 2 hours. The reaction mixture was diluted with aqueous sodium thiosulfate (10% w/v) and sat. aqueous sodium hydrogen carbonate and stirred for 20 minutes. The mixture was passed through a phase separator and the organics concentrated under reduced pressure, yielding the product material, which was taken on without further purification.

To a mixture of tert-butyl 3-fluoro-3-formyl-azetidine-1-carboxylate (610 mg, 3.00 mmol) and 2M methylamine (1.5 mL, 3.00 mmol) in dichloromethane (30 mL) was added sodium triacetoxyborohydride (636 mg, 3.00 mmol), and the reaction was stirred at room temperature over the weekend. The reaction mixture was diluted with sat. aq. NaHCO3 and water, and stirred for 15 minutes. The mixture was passed through a phase separator and concentrated under reduced pressure. The residue was taken up in MeOH and passed through an SCX-2 cartridge (5 g). The product eluted using 2M NH3 in MeOH, and was concentrated under reduced pressure, yielding the product. $^1$H NMR (400 MHz, DMSO) δ 4.08-3.92 (m, 4H), 2.95 (d, J=22.9 Hz, 2H), 2.49 (s, 3H), 1.44 (s, 9H).

A solution of tert-butyl 3-fluoro-3-(methylaminomethyl)azetidine-1-carboxylate (211 mg, 0.967 mmol), 4N hydrogen chloride in 1,4-dioxane (5.0 mL, 20.0 mmol), and methanol (5.00 mL) was stirred at room temperature overnight. The reaction mixture was concentrated under reduced pressure and the residue taken up in MeOH. The mixture was passed through an SCX-2 cartridge (5 g) and the product eluted with 2M NH3 in MeOH. The product eluent was concentrated under reduced pressure, which was taken on without further purification.

A suspension of 1-(3-fluoroazetidin-3-yl)-N-methyl-methanamine (44 mg, 0.372 mmol), 5-chloro-N-(8- methoxy-2-methyl-imidazo[1,2-a]pyrazin-6-yl)pyrazine-2-carboxamide (119 mg, 0.372 mmol), and cesium carbonate (121 mg, 0.372 mmol) in N,N-dimethylformamide (4.00 mL) was heated to 100° C. and stirred overnight. The reaction mixture was concentrated under reduced pressure and submitted to reverse phase HPLC for purification (Xbridge Phenyl 19×150 mm, 10 um 20-80% MeOH/H2O (10 mM NH4CO3), 20 mL/min, rt then Luna Phenyl-Hexyl 21.2×150 mm, 10 um 5-60% MeOH/H2O (0.1% FA), 20 mL/min, rt) to yield 5-[3-fluoro-3-(methylaminomethyl)azetidin-1-yl]-N-(8-methoxy-2-methyl-imidazo[1,2-a]pyrazin-6-yl)pyrazine-2-carboxamide. LCMS (ES+) 401.3 [M+H]+, RT 1.99 min (Analytical method AcHSSC18). ¹H NMR (400 MHz, DMSO) δ 9.56 (s, 1H), 8.91 (s, 1H), 8.77 (d, J=1.3 Hz, 1H), 8.01 (d, J=1.4 Hz, 1H), 7.96 (d, J=0.8 Hz, 1H), 4.41-4.21 (m, 4H), 4.07 (s, 3H), 2.97 (d, J=22.4 Hz, 1H), 2.37 (s, 3H), 2.35 (s, 3H).

Example 290: 5-(3-((cyclopropylamino)methyl)azetidin-1-yl)-N-(8-fluoro-2-(fluoromethyl)imidazo[1,2-a]pyridin-6-yl)pyrazine-2-carboxamide

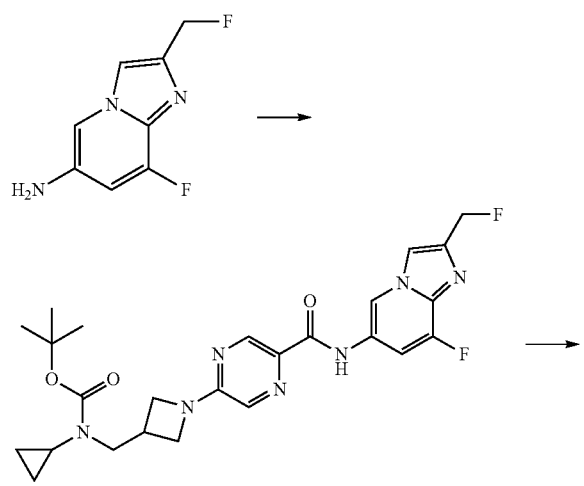

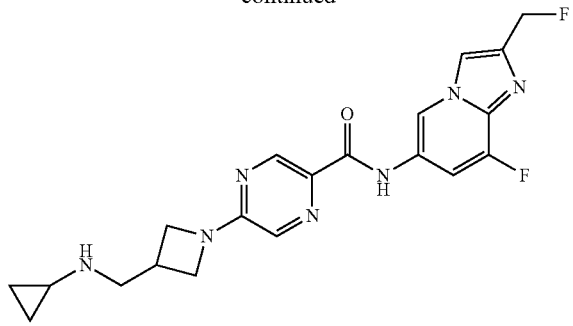

A mixture of 8-fluoro-2-(fluoromethyl)imidazo[1,2-a]pyridin-6-amine (53 mg, 0.287 mmol), 5-[3-[[tert-butoxycarbonyl(cyclopropyl)amino]methyl]azetidin-1-yl]pyrazine-2-carboxylic acid (100 mg, 0.287 mmol, 1.00 eq), HBTU (109 mg, 0.287 mmol), and triethylamine (0.2 mL, 1.44 mmol) in N,N-dimethylformamide (2.50 mL) was stirred at room temperature for 18 h. The reaction mixture was concentrated under reduced pressure to give a residue. The residue was purified by HPLC reverse phase chromatography to give tert-butyl cyclopropyl((1-(5-((8-fluoro-2-(fluoromethyl)imidazo[1,2-a]pyridin-6-yl)carbamoyl)pyrazin-2-yl)azetidin-3-yl)methyl)carbamate.

To a solution of tert-butyl cyclopropyl((1-(5-((8-fluoro-2-(fluoromethyl)imidazo[1,2-a]pyridin-6-yl)carbamoyl)pyrazin-2-yl)azetidin-3-yl)methyl)carbamate (42 mg, 0.0818 mmol) in dichloromethane (2 mL) was added trifluoroacetic acid (1.0 mL, 13.1 mmol) and the reaction mixture stirred for 1.5 hours. The reaction mixture was concentrated under reduced pressure to give a residue, which was purified by achiral SFC to give the title compound. LCMS (ES+) 414 (M+H)+, RT 2.28 min (Analytical method AcHSSC18); ¹H NMR (400 MHz, DMSO) δ 10.50 (s, 1H), 9.31 (d, J=1.6 Hz, 1H), 8.71-8.70 (m, 1H), 8.30 (t, J=3.2 Hz, 1H), 7.84 (d, J=1.4 Hz, 1H), 7.68 (dd, J=1.5, 13.1 Hz, 1H), 5.48 (d, J=48.3 Hz, 2H), 4.25-4.19 (m, 2H), 3.86 (dd, J=4.7, 9.0 Hz, 2H), 2.91-2.86 (m, 3H), 2.11-2.06 (m, 1H), 0.41-0.35 (m, 2H), 0.24-0.19 (m, 2H).

The following compound was prepared from example 225, using the same cyclopropanation method described for making 1-cyclopropyl-3,3'-biazetidine (intermediate 41). Chiral SFC was used to separate the enantiomers.

| Example | Structure | Analytical data |
| --- | --- | --- |
| Example 291 (Stereochemistry arbitrarily assigned) | Cis Isomer, Enantiomer 1 | LCMS (ES+) 436 (M + H)+, RT 4 min (Analytical method BicarbBEHC18); RT 1.64 min (SFC4, YMC CELLULOSE-C + 0.1% DEAISO 55% MeOH SOL1); ¹H NMR (400 MHz, DMSO) δ 10.88 (s, 1H), 9.70 (d, J = 1.5 Hz, 1H), 9.21 (d, J = 1.5 Hz, 1H), 9.09 (d, J = 1.5 Hz, 1H), 7.92 (d, J = 2.8 Hz, 1H), 7.57 (dd, J = 1.6, 12.9 Hz, 1H), 4.19 (dd, J = 9.1, 11.4 Hz, 1H), 3.75 (dd, J = 3.3, 11.5 Hz, 1H), 3.29-3.27 (m, 1H), 3.11 (d, J = 8.9 Hz, 1H), 2.99 (d, J = 8.8 Hz, 1H), 2.91-2.88 (m, 1H), 2.70-2.63 (m, 2H), 2.34 (s, 3H), 1.64-1.58 (m, 1H), 0.40-0.37 (m, 2H), 0.29-0.24 (m, 2H). |

The following lactam analogues were prepared using Method H (TCFH coupling) using acids described in the intermediate section and 2,8-dimethylimidazo[1,2-a]pyrazin-6-amine (intermediate 41a), followed by Boc deprotection using method C (HCl Boc deprotection) or method E (TFA/DCM Boc deprotection), and the final compounds were purified by SCX.

| Example | Structure | Analytical data |
|---|---|---|
| Example 292 (Stereochemistry arbitrarily assigned) | Cis Isomer, Enantiomer 1 | LCMS (ES+) 393 (M + H)+, RT 1.96 min (Analytical method AcHSSC18); $^1$H NMR (400 MHz, DMSO) δ 10.08 (br s, 1H), 9.69 (d, J = 1.4 Hz, 1H), 9.18 (s, 1H), 9.12 (d, J = 1.5 Hz, 1H), 8.03 (s, 1H), 4.24-4.17 (m, 1H), 3.80 (dd, J = 2.4, 11.5 Hz, 1H), 3.30-3.25 (m, 1H), 3.10-2.94 (m, 5H), 2.72 (s, 3H), 2.41 (s, 3H). |

The following lactam analogues were prepared using Method P (Pd catalyzed amidation) using commercial amides or those described in the intermediate section, and when applicable, followed by Boc deprotection using method C (HCl Boc deprotection). The final compounds were purified by achiral SFC, followed by chiral SFC.

| Example | Structure | Amide | Analytical data |
|---|---|---|---|
| Example 293 (Stereochemistry arbitrarily assigned) | Cis Isomer, Enantiomer 1 | tert-butyl 4-oxohexahydro-pyrrolo[3,4-c]pyrrole-2(1H)-carboxylate | LCMS (ES+) 396 (M + H)+, RT 1.73 min (Analytical method AcHSSC18); RT 7.06 min (SFC1, YMC CELLULOSE-SC + 0.1% DEAISO 55% EtOH SOL2); $^1$H NMR (400 MHz, DMSO) δ 10.90 (s, 1H), 9.73 (d, J = 1.4 Hz, 1H), 9.23 (d, J = 1.6 Hz, 1H), 9.11 (d, J = 1.4 Hz, 1H), 7.94 (dd, J = 0.8, 3.2 Hz, 1H), 7.59 (dd, J = 1.6, 13.0 Hz, 1H), 4.25-4.18 (m, 1H), 3.75 (dd, J = 3.1, 11.5 Hz, 1H), 3.31-3.25 (m, 1H), 3.22-3.17 (m, 1H), 2.96-2.85 (m, 4H), 2.36 (d, J = 0.7 Hz, 3H). |
| Example 294 (Stereochemistry arbitrarily assigned) | Cis Isomer, Enantiomer 2 | tert-butyl 4-oxohexahydro-pyrrolo[3,4-c]pyrrole-2(1H)-carboxylate | LCMS (ES+) 396 (M + H)+, RT 1.72 min (Analytical method AcHSSC18); RT 10.65 min (SFC1, YMC CELLULOSE-SC + 0.1% DEAISO 55% EtOH SOL2); $^1$H NMR (400 MHz, DMSO) δ 10.90 (s, 1H), 9.73 (d, J = 1.5 Hz, 1H), 9.23 (d, J = 1.6 Hz, 1H), 9.11 (d, J = 1.5 Hz, 1H), 7.94 (dd, J = 0.8, 3.2 Hz, 1H), 7.59 (dd, J = 1.6, 12.9 Hz, 1H), 4.25-4.19 (m, 1H), 3.75 (dd, J = 3.1, 11.6 Hz, 1H), 3.28 (dt, J = 1.9, 8.5 Hz, 1H), 3.22-3.17 (m, 1H), 2.96-2.85 (m, 4H), 2.35 (s, 3H). |

Example 295: N-(7-fluoro-2-methyl-2H-indazol-5-yl)-5-(3-(((1-methylcyclopropyl)amino)methyl)azetidin-1-yl)pyrazine-2-carboxamide

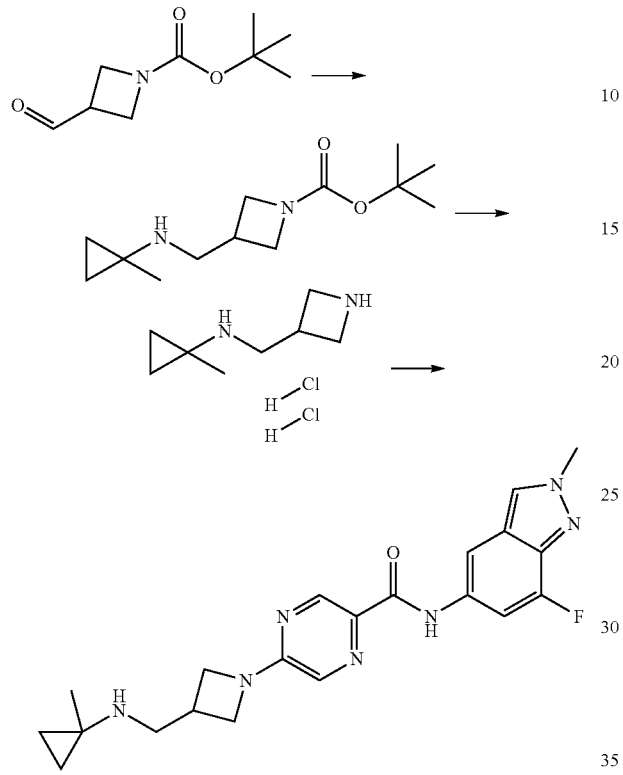

1-Methylcyclopropanamine hydrochloride (581 mg, 5.40 mmol, 1.00 eq), tert-butyl 3-formylazetidine-1-carboxylate (1.00 g, 5.40 mmol, 1.00 eq), and sodium triacetoxyborohydride (3.28 g, 15.5 mmol, 2.86 eq) were combined in dichloromethane (50.00 mL) and stirred at r.t. for 17 h. Saturated aqueous sodium hydrogen carbonate solution (100 mL) was added to the reaction mixture and stirred vigorously for 10 mins. The organics were collected and washed with water and brine, before passing through a phase separator and concentrating to dryness to give the tert-butyl 3-(((1-methylcyclopropyl)amino)methyl)azetidine-1-carboxylate, which was progressed to the next step directly.

tert-Butyl 3-[[(1-methylcyclopropyl)amino]methyl]azetidine-1-carboxylate (1.40 g, 5.83 mmol, 1.00 eq) and 4 M hydrogen chloride in dioxane (7.3 mL, 29.1 mmol, 5.00 eq) were stirred in methyl alcohol (15 mL) at r.t. for 21 h, before concentrating to dryness to give N-(azetidin-3-ylmethyl)-1-methylcyclopropan-1-amine, which was progressed to the next step directly.

N-(Azetidin-3-ylmethyl)cyclopropanamine dihydrochloride (129 mg, 0.650 mmol, 1.00 eq), cesium carbonate (847 mg, 2.60 mmol, 4.00 eq), and 5-(benzotriazol-1-yloxy)-N-(7-fluoro-2-methyl-indazol-5-yl)pyrazine-2-carboxamide (150 mg, 0.371 mmol, 1.00 eq) were combined in N,N-dimethylformamide (5.00 mL) and stirred at 100° C. for 17 h. The reaction mixture was partitioned between EtOAc and water. The aqueous phase was extracted with EtOAc. The combined organic phases were dried over magnesium sulfate, filtered, and concentrated in vacuo. Purification by preparative HPLC gave N-(7-fluoro-2-methyl-2H-indazol-5-yl)-5-(3-(((1-methylcyclopropyl)amino)methyl)azetidin-1-yl)pyrazine-2-carboxamide. LCMS (ES+) 410 (M+H)+, RT 2.55 min (Analytical method AcHSSC18). $^1$H NMR (400 MHz, DMSO) δ 9.56 (s, 1H), 8.91 (s, 1H), 8.77 (d, J=1.4 Hz, 1H), 8.02 (d, J=1.4 Hz, 1H), 7.96 (s, 1H), 4.41-4.23 (m, 4H), 4.07 (s, 3H), 3.00 (d, J=26.4 Hz, 2H), 2.59 (dd, J=5.8, 5.8 Hz, 4H), 2.36 (s, 3H), 1.73-1.69 (m, 4H).

Example 296: 5-(3-fluoro-3-(pyrrolidin-1-ylmethyl)azetidin-1-yl)-N-(8-methoxy-2-methylimidazo[1,2-a]pyrazin-6-yl)pyrazine-2-carboxamide

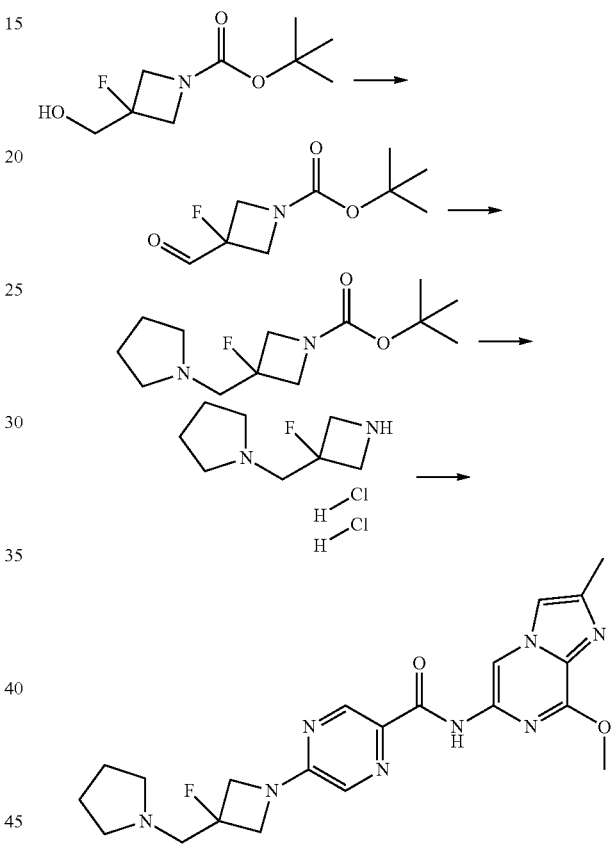

A suspension of tert-butyl 3-fluoro-3-(hydroxymethyl)azetidine-1-carboxylate (500 mg, 2.44 mmol) and Dess-Martin periodinane (1.24 g, 2.92 mmol) in dichloromethane (15 mL) was stirred at room temperature for 2 hours. The reaction mixture was diluted with aqueous sodium thiosulfate (10% w/v) and sat. aqueous sodium hydrogen carbonate and stirred for 20 minutes. The mixture was passed through a phase separator and the organics concentrated under reduced pressure, yielding tert-butyl 3-fluoro-3-formylazetidine-1-carboxylate, which was taken on without further purification.

A mixture of tert-butyl 3-fluoro-3-formyl-azetidine-1-carboxylate (480 mg, 2.36 mmol, 1.00 eq), sodium triacetoxyborohydride (1.00 g, 4.72 mmol, 2.00 eq), and pyrrolidine (0.20 mL, 2.36 mmol, 1.00 eq) in dichloromethane (50 mL) was stirred under nitrogen at room temperature overnight. Saturated aqueous sodium hydrogen carbonate solution (50 mL) was added to the reaction mixture and stirred vigorously for 10 mins. The bi-phasic mixture was passed through a phase separator and the organics concentrated under reduced pressure, yielding tert-butyl 3-fluoro-3-(pyrrolidin-1-ylmethyl)azetidine-1-carboxylate.

4 M Hydrogen chloride in dioxane (2.0 mL, 7.94 mmol, 5.00 eq) and tert-butyl 3-fluoro-3-(pyrrolidin-1-ylmethyl)azetidine-1-carboxylate (410 mg, 1.59 mmol, 1.00 eq) were stirred in methyl alcohol (5.00 mL) at r.t. for 21 h. The reaction mixture was concentrated to dryness to give 1-[(3-fluoroazetidin-3-yl)methyl]pyrrolidine dihydrochloride, which was used in the next step as crude.

1-[(3-fluoroazetidin-3-yl)methyl]pyrrolidine dihydrochloride (120 mg, 0.519 mmol, 1.00 eq), cesium carbonate (677 mg, 2.08 mmol, 4.00 eq), and 5-chloro-N-(8-methoxy-2-methyl-imidazo[1,2-a]pyrazin-6-yl)pyrazine-2-carboxamide (165 mg, 0.519 mmol, 1.00 eq) were combined in N,N-dimethylformamide (5.00 mL) and stirred at 100° C. for 17 h. LCMS showed product to be present. The residue was partitioned between EtOAc and water. The aqueous phase was extracted with EtOAc. The combined organic phases were dried over magnesium sulfate, filtered, and concentrated in vacuo. Purification by preparative HPLC followed by Et₂O trituration gave 5-(3-fluoro-3-(pyrrolidin-1-ylmethyl)azetidin-1-yl)-N-(8-methoxy-2-methylimidazo[1,2-a]pyrazin-6-yl)pyrazine-2-carboxamide. LCMS (ES+) 441 (M+H)+, RT 2.14 min (Analytical method AcHSSC18). ¹H NMR (400 MHz, DMSO) δ 9.56 (s, 1H), 8.91 (s, 1H), 8.77 (d, J=1.4 Hz, 1H), 8.02 (d, J=1.4 Hz, 1H), 7.96 (s, 1H), 4.41-4.23 (m, 4H), 4.07 (s, 3H), 3.00 (d, J=26.4 Hz, 2H), 2.59 (dd, J=5.8, 5.8 Hz, 4H), 2.36 (s, 3H), 1.73-1.69 (m, 4H).

The following example was prepared by the same route, using 5-chloro-N-(8-fluoro-2-methylimidazo[1,2-a]pyridin-6-yl)pyrazine-2-carboxamide in place of 5-chloro-N-(8-methoxy-2-methyl-imidazo[1,2-a]pyrazin-6-yl)pyrazine-2-carboxamide.

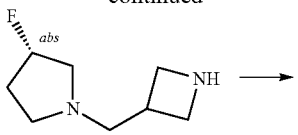

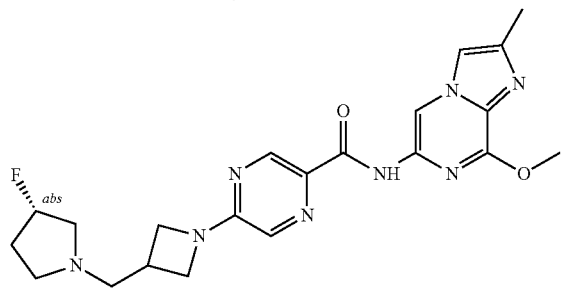

tert-Butyl 3-formylazetidine-1-carboxylate (1.00 g, 5.40 mmol, 1.00 eq), sodium triacetoxyborohydride (2.52 g, 11.9 mmol, 2.20 eq), and (S)-(+)-3-fluoropyrrolidine hydrochloride (678 mg, 5.40 mmol, 1.00 eq) were combined in dichloromethane (10.00 mL) and stirred at r.t. for 26 h. Saturated aqueous sodium hydrogen carbonate solution (20 mL) was added to the reaction mixture and stirred vigorously for 10 mins. The organics were collected and washed with water and brine, before passing through a phase separator and concentrating to dryness to give tert-butyl 3-[[(3S)-3-fluoropyrrolidin-1-yl]methyl]azetidine-1-carboxylate.

tert-Butyl 3-[[(3S)-3-fluoropyrrolidin-1-yl]methyl]azetidine-1-carboxylate (698 mg, 2.70 mmol, 1.00 eq) and 4 M HCl in dioxane (1.4 mL, 5.40 mmol, 2.00 eq) were combined in dichloromethane (10.00 mL) and stirred at r.t. for 17

| Example | Structure | Analytical data |
| --- | --- | --- |
| Example 297 | 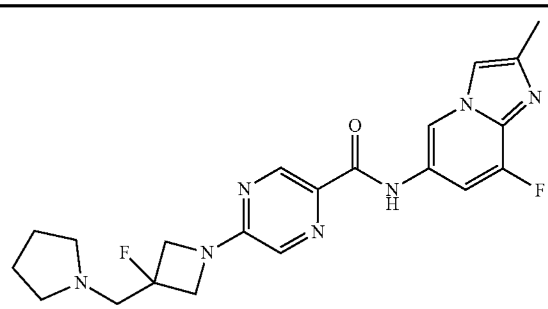 | LCMS (ES+) 428 (M + H)+, RT 1.87 min (Analytical method AcHSSC18). ¹H NMR (400 MHz, DMSO) δ 10.51 (s, 1H), 9.19 (d, J = 1.6 Hz, 1H), 8.76 (d, J = 1.4 Hz, 1H), 7.99 (d, J = 1.4 Hz, 1H), 7.90 (d, J = 2.8 Hz, 1H), 7.57 (dd, J = 1.3, 13.1 Hz, 1H), 4.41-4.23 (m, 4H), 3.00 (d, J = 27.0 Hz, 2H), 2.60-2.57 (m, 4H), 2.35 (s, 3H), 1.73-1.68 (m, 4H). |

Example 298: 5-[3-[[(3S)-3-fluoropyrrolidin-1-yl]methyl]azetidin-1-yl]-N-(8-methoxy-2-methyl-imidazo[1,2-a]pyrazin-6-yl)pyrazine-2-carboxamide

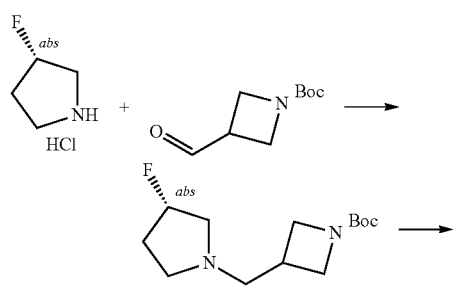

h. The reaction mixture was concentrated to dryness to give (3S)-1-(azetidin-3-ylmethyl)-3-fluoro-pyrrolidine dihydrochloride, which was progressed to the next step without further purification.

5-Chloro-N-(8-methoxy-2-methyl-imidazo[1,2-a]pyrazin-6-yl)pyrazine-2-carboxamide (150 mg, 0.471 mmol, 1.00 eq), cesium carbonate (613 mg, 1.88 mmol, 4.00 eq), and (3S)-1-(azetidin-3-ylmethyl)-3-fluoro-pyrrolidine dihydrochloride (109 mg, 0.471 mmol, 1.00 eq) were combined in N,N-dimethylformamide (5.00 mL) and stirred at 100° C. for 17 h. The residue was partitioned between EtOAc and water. The aqueous phase was extracted with EtOAc. The combined organic phases were dried over magnesium sulfate, filtered, and concentrated in vacuo. The residue was purified by preparative HPLC to give 5-[3-[[(3S)-3-fluoropyrrolidin-1-yl]methyl]azetidin-1-yl]-N-(8-methoxy-2-methyl-imidazo[1,2-a]pyrazin-6-yl)pyrazine-2-carboxamide. LCMS (ES+) 441 (M+H)+, RT 2.05 min (Analytical method AcHSSC18). ¹H NMR (400 MHz, DMSO) δ 9.53 (s, 1H), 8.90 (s, 1H), 8.73 (d, J=1.4 Hz, 1H), 7.94 (dd, J=1.1, 13.1 Hz, 2H), 5.30-5.11 (m, 1H), 4.29 (dd, J=8.6, 8.6 Hz, 2H), 4.07 (s, 3H), 3.87 (dd, J=5.7, 9.0 Hz, 2H), 3.04-2.96 (m, 1H), 2.89-2.59 (m, 5H), 2.35 (s, 4H), 2.23-2.08 (m, 1H), 1.95-1.81 (m, 1H).

Example 299: 5-(3-((cyclopropyl(2-methoxyethyl) amino)methyl)azetidin-1-yl)-N-(8-fluoro-2-methyl-imidazo[1,2-a]pyridin-6-yl)pyrazine-2-carboxamide

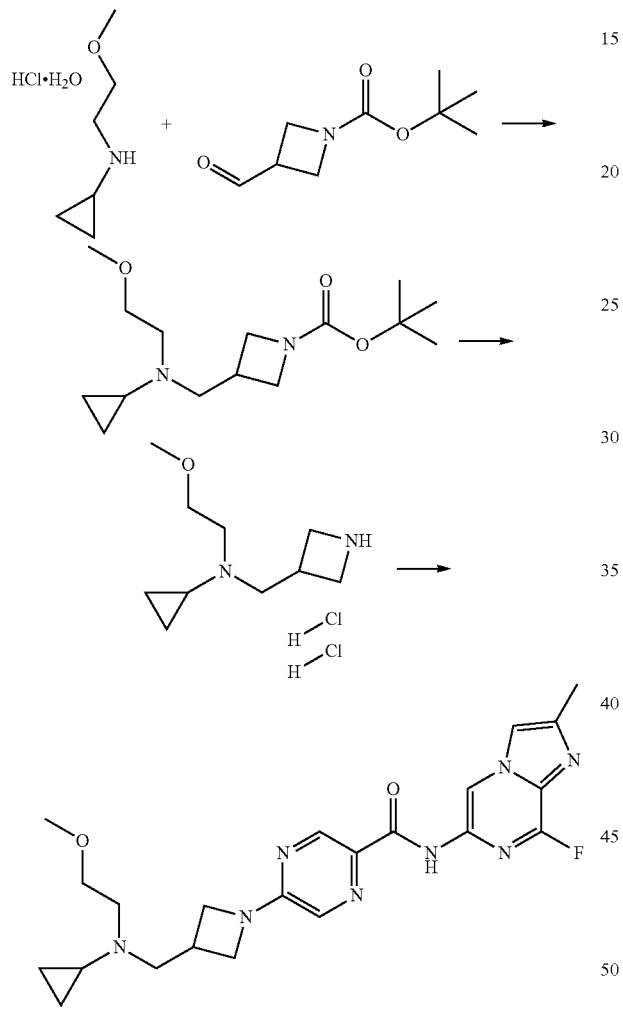

N-(2-Methoxyethyl)cyclopropanamine hydrate hydrochloride (250 mg, 1.47 mmol, 1.00 eq), tert-butyl 3-formylazetidine-1-carboxylate (0.25 g, 1.34 mmol, 0.909 eq), and sodium triacetoxyborohydride (0.62 g, 2.95 mmol, 2.00 eq) were combined in dichloromethane (50.00 mL) and stirred at r.t. for 19 h. Saturated aqueous sodium hydrogen carbonate solution (20 mL) was added to the reaction mixture and stirred vigorously for 10 mins. The organics were collected by passing through a phase separator and concentrating to dryness to give tert-butyl 3-[[cyclopropyl(2-methoxyethyl) amino]methyl]azetidine-1-carboxylate, which was used in the next step as crude.

4 M Hydrogen chloride in dioxane (1.0 mL, 4.04 mmol, 5.00 eq) and tert-butyl 3-[[cyclopropyl(2-methoxyethyl) amino]methyl]azetidine-1-carboxylate (230 mg, 0.809 mmol, 1.00 eq) were stirred in methyl alcohol (5.00 mL) at r.t. for 21 h. The reaction mixture was concentrated to dryness to give N-(azetidin-3-ylmethyl)-N-(2-methoxyethyl)cyclopropanamine dihydrochloride, which was used in the next step as crude.

5-Chloro-N-(8-fluoro-2-methyl-imidazo[1,2-a]pyridin-6-yl)pyrazine-2-carboxamide (226 mg, 0.739 mmol, 1.00 eq), cesium carbonate (963 mg, 2.95 mmol, 4.00 eq), and N-(azetidin-3-ylmethyl)-N-(2-methoxyethyl)cyclopropanamine dihydrochloride (190 mg, 0.739 mmol, 1.00 eq) were combined in N,N-dimethylformamide (5.00 mL) and stirred at 100° C. for 17 h. The reaction mixture was partitioned between EtOAc and water. The aqueous phase was extracted with EtOAc (3×). The combined organic phases were washed with brine. The combined organic phases were dried over magnesium sulfate, filtered and concentrated in vacuo. The residue was submitted for purification by preparative HPLC to give 5-[3-[[cyclopropyl(2-methoxyethyl)amino] methyl]azetidin-1-yl]-N-(8-fluoro-2-methyl-imidazo[1,2-a] pyridin-6-yl)pyrazine-2-carboxamide. LCMS (ES+) 454 (M+H)+, RT 1.94 min (Analytical method AcHSSC18). ¹H NMR (400 MHz, DMSO) δ 10.44 (s, 1H), 9.19 (d, J=1.5 Hz, 1H), 8.71 (d, J=1.4 Hz, 1H), 7.90 (d, J=2.8 Hz, 1H), 7.87 (d, J=1.4 Hz, 1H), 7.57 (dd, J=1.5, 13.0 Hz, 1H), 4.25 (dd, J=8.6, 8.6 Hz, 2H), 3.81 (dd, J=5.5, 9.0 Hz, 2H), 3.46 (dd, J=6.1, 6.1 Hz, 2H), 3.25 (s, 3H), 3.14-3.06 (m, 1H), 2.90 (d, J=7.7 Hz, 2H), 2.74 (dd, J=6.2, 6.2 Hz, 2H), 2.35 (s, 3H), 1.87-1.80 (m, 1H), 0.51-0.45 (m, 2H), 0.33-0.28 (m, 2H).

Example 300: (R)—N-(4-fluoro-2-methylbenzo[d] oxazol-6-yl)-5-(3-((3-fluoropyrrolidin-1-yl)methyl) azetidin-1-yl)pyrazine-2-carboxamide

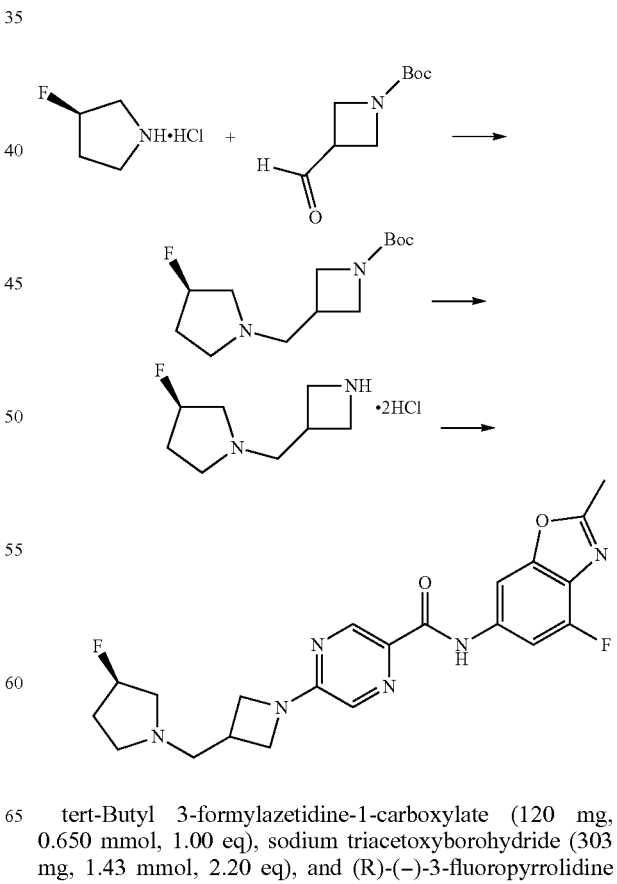

tert-Butyl 3-formylazetidine-1-carboxylate (120 mg, 0.650 mmol, 1.00 eq), sodium triacetoxyborohydride (303 mg, 1.43 mmol, 2.20 eq), and (R)-(−)-3-fluoropyrrolidine hydrochloride (200 mg, 1.59 mmol, 2.45 eq) were combined in dichloromethane (10.00 mL) and stirred at room temperature for 17 hours. Saturated aqueous sodium hydrogen carbonate solution was added to the reaction mixture and stirred vigorously for 10 mins. The reaction mixture was basified further with ~10% NaOH. The mixture was extracted with CH$_2$Cl$_2$, dried (MgSO$_4$), and concentrated in vacuo to give the desired product. To the crude product was added methyl alcohol (5.00 mL) and 4 M hydrogen chloride in dioxane (2.0 mL, 8.00 mmol, 12.3 eq). The mixture was stirred at room temperature for 1.5 hours, then concentrated in vacuo to give (R)-1-(azetidin-3-ylmethyl)-3-fluoropyrrolidine 2HCl, which was used directly in next step.

(3R)-1-(Azetidin-3-ylmethyl)-3-fluoro-pyrrolidine dihydrochloride (150 mg, 0.650 mmol, 1.33 eq), 5-chloro-N-(4-fluoro-2-methyl-1,3-benzoxazol-6-yl)pyrazine-2-carboxamide (150 mg, 0.489 mmol, 1.00 eq), cesium carbonate (319 mg, 0.978 mmol, 2.00 eq), and N,N-dimethylformamide (4.00 mL) were combined and hot block heated to 100° C. for 3 days. The mixture was then cooled to room temperature. The cesium salts were filtered off and the product was purified by prep HPLC to give the title compound. LCMS (ES+) 429 (M+H)+, RT 2.78 min (Analytical method AcHSSC18. $^1$H NMR (400 MHz, DMSO) δ 10.61 (s, 1H), 8.74 (d, J=1.4 Hz, 1H), 8.20 (d, J=1.5 Hz, 1H), 7.88 (d, J=1.2 Hz, 1H), 7.84 (dd, J=1.8, 12.7 Hz, 1H), 5.30-5.12 (m, 1H), 4.29 (dd, J=8.6, 8.6 Hz, 2H), 3.88 (dd, J=5.6, 8.9 Hz, 2H), 3.03-2.98 (m, 1H), 2.88-2.74 (m, 3H), 2.70-2.57 (m, 2H), 2.63 (s, 3H), 2.37-2.30 (m, 1H), 2.19-2.09 (m, 1H), 1.95-1.80 (m, 1H).

Example 301: N-(8-fluoro-2-methylimidazo[1,2-a]pyridin-6-yl)-5-((3R,3'R)-3-fluoro-[1,3'-bipyrrolidin]-1'-yl)pyrazine-2-carboxamide and Example 302: N-(8-fluoro-2-methylimidazo[1,2-a]pyridin-6-yl)-5-((3R,3'S)-3-fluoro-[1,3'-bipyrrolidin]-1'-yl)pyrazine-2-carboxamide

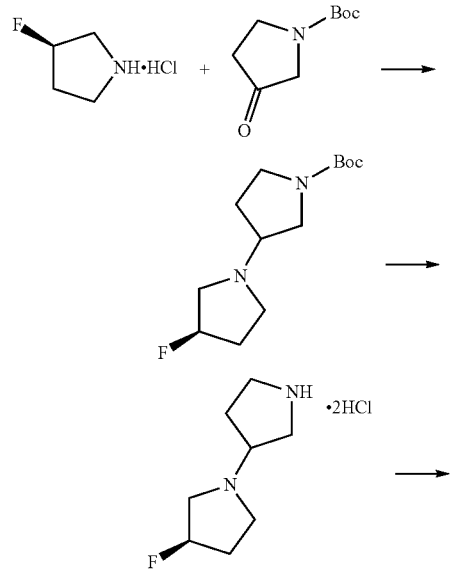

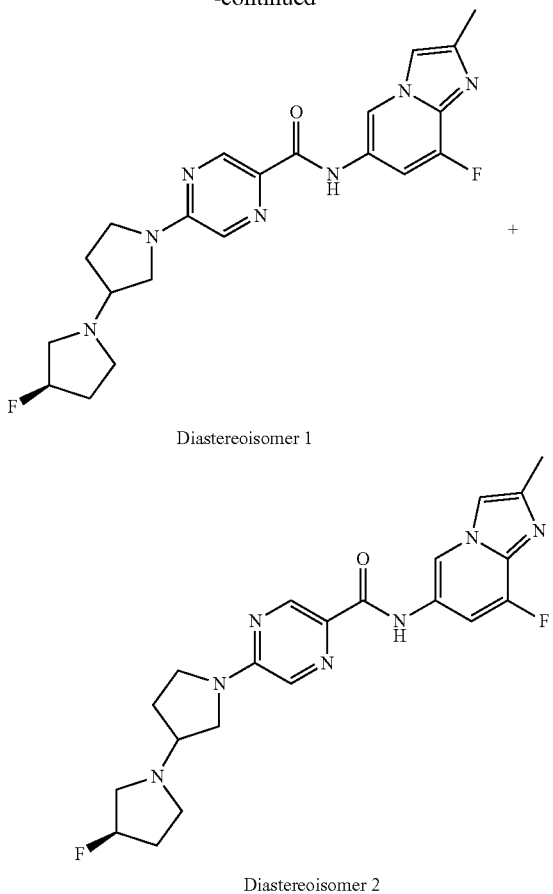

Diastereoisomer 1

Diastereoisomer 2

N-Boc-3-pyrrolidinone (1097 mg, 5.92 mmol, 1.00 eq), sodium triacetoxyborohydride (3764 mg, 17.8 mmol, 3.00 eq), and (R)-(−)-3-fluoropyrrolidine hydrochloride (818 mg, 6.51 mmol, 1.10 eq) were combined in dichloromethane (50.00 mL) and stirred at room temperature for 3 days. Saturated aqueous sodium hydrogen carbonate solution was added to the reaction mixture and stirred vigorously for 10 mins. The mixture was basified further with ~10% NaOH, then extracted with CH$_2$Cl$_2$, dried (MgSO$_4$), and concentrated in vacuo to give product. To this product was added methyl alcohol (5.00 mL) and 4 M hydrogen chloride in dioxane (2.0 mL, 8.00 mmol, 12.3 eq). The resulting mixture was stirred at room temperature for 18 hours, then concentrated in vacuo to give (3R)-3-fluoro-1,3'-bipyrrolidine 2HCl, which was used directly in next step.

(3R)-3-Fluoro-1-pyrrolidin-3-yl-pyrrolidine dihydrochloride (238 mg, 1.03 mmol, 1.21 eq), 5-chloro-N-(8-fluoro-2-methyl-imidazo[1,2-a]pyridin-6-yl)pyrazine-2-carboxamide (260 mg, 0.851 mmol, 1.00 eq), N,N-dimethylformamide (4.50 mL), and cesium carbonate (970 mg, 2.98 mmol, 3.50 eq) were combined and hot block heated to 100° C. for 3 hours. The mixture was then cooled to room temperature. The cesium salts were filtered off, and the product was purified by achiral Prep HPLC, then further purified by chiral SFC to give:

Diastereoisomer 1, arbitrarily assigned as N-(8-fluoro-2-methylimidazo[1,2-a]pyridin-6-yl)-5-((3R,3'R)-3-fluoro-[1,3'-bipyrrolidin]-1'-yl)pyrazine-2-carboxamide. LCMS (ES+) 428 (M+H)+, RT 1.76 min (Analytical method AcHSSC18). $^1$H NMR (400 MHz, DMSO) δ 10.43 (s, 1H), 9.19 (d, J=1.6 Hz, 1H), 8.76 (d, J=1.3 Hz, 1H), 8.01 (d, J=1.0 Hz, 1H), 7.90 (d, J=2.8 Hz, 1H), 7.57 (dd, J=1.6, 13.2 Hz, 1H), 5.34-5.15 (m, 1H), 3.85-3.71 (m, 2H), 3.59-3.51 (m, 1H), 3.41 (dd, J=7.0, 10.9 Hz, 1H), 3.01-2.86 (m, 3H), 2.81-2.67 (m, 1H), 2.48-2.41 (m, 1H), 2.35 (s, 3H), 2.25-2.09 (m, 2H), 1.99-1.83 (m, 2H).

Diastereoisomer 2, arbitrarily assigned as N-(8-fluoro-2-methylimidazo[1,2-a]pyridin-6-yl)-5-((3R,3'S)-3-fluoro-[1,3'-bipyrrolidin]-1'-yl)pyrazine-2-carboxamide. LCMS (ES+) 428 (M+H)+, RT 1.76 min (Analytical method AcHSSC18). ¹H NMR (400 MHz, DMSO) δ 10.43 (s, 1H), 9.19 (d, J=1.6 Hz, 1H), 8.76 (d, J=1.3 Hz, 1H), 8.01 (d, J=1.0 Hz, 1H), 7.90 (d, J=2.8 Hz, 1H), 7.57 (dd, J=1.6, 13.2 Hz, 1H), 5.34-5.15 (m, 1H), 3.85-3.71 (m, 2H), 3.59-3.51 (m, 1H), 3.41 (dd, J=7.0, 10.9 Hz, 1H), 3.01-2.86 (m, 3H), 2.81-2.67 (m, 1H), 2.48-2.41 (m, 1H), 2.35 (s, 3H), 2.25-2.09 (m, 2H), 1.99-1.83 (m, 2H).

Example 303: (R)—N-(7-fluoro-2-methyl-2H-indazol-5-yl)-5-(3-(((3-fluoropyrrolidin-1-yl)methyl)azetidin-1-yl)pyrazine-2-carboxamide

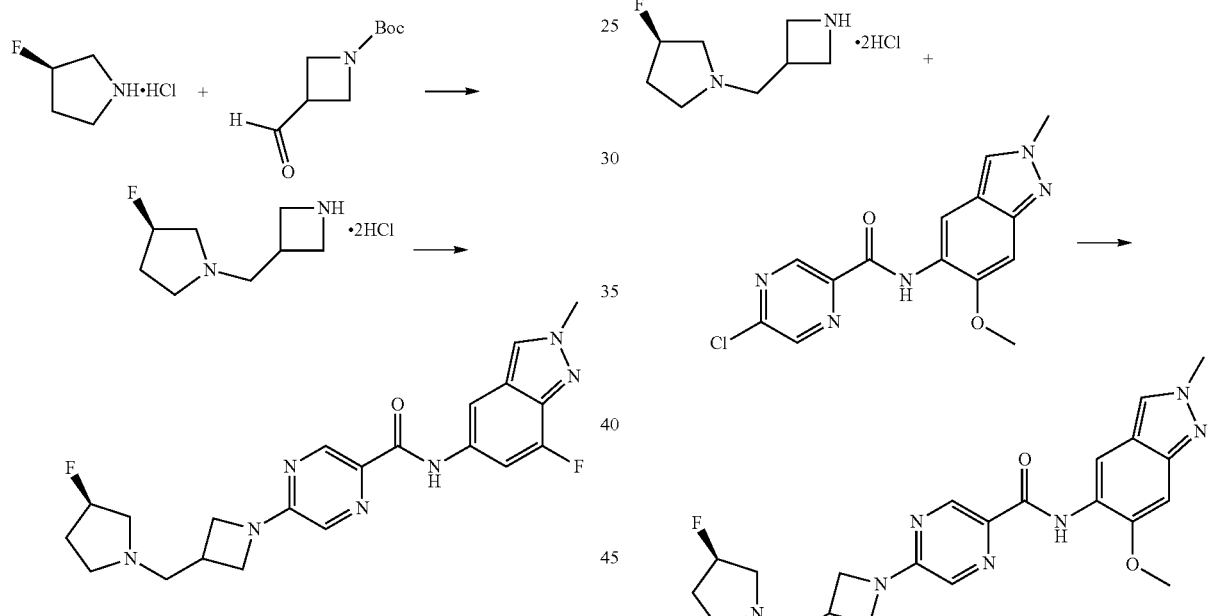

tert-Butyl 3-formylazetidine-1-carboxylate (1180 mg, 6.37 mmol, 1.00 eq), sodium triacetoxyborohydride (2971 mg, 14.0 mmol, 2.20 eq), and (R)-(−)-3-fluoropyrrolidine hydrochloride (800 mg, 6.37 mmol, 1.00 eq) were combined in dichloromethane (10.00 mL) and stirred at room temperature overnight. Saturated aqueous sodium hydrogen carbonate was added and the reaction mixture stirred vigorously for 10 mins. The mixture was then basified with aqueous 2M NaOH solution, extracted with CH₂Cl₂, dried over a hydrophobic frit, and concentrated under reduced pressure. Methanol (30.00 mL) and 4 M hydrogen chloride in dioxane (20 mL, 78.4 mmol, 12.3 eq) were then added, and the mixture was stirred at room temperature for 2 hours. The reaction mixture was then concentrated under reduced pressure to yield (R)-1-(azetidin-3-ylmethyl)-3-fluoropyrrolidine dihydrochloride, which was used directly in the next step.

(3R)-1-(Azetidin-3-ylmethyl)-3-fluoro-pyrrolidine dihydrochloride (150 mg, 0.608 mmol, 2.00 eq), 5-(benzotriazol-1-yloxy)-N-(7-fluoro-2-methyl-indazol-5-yl)pyrazine-2-carboxamide (125 mg, 0.310 mmol, 1.00 eq), cesium carbonate (935 mg, 2.87 mmol, 9.44 eq), and N,N-dimethylformamide (4.00 mL) were combined and heated to 100° C. overnight. The reaction mixture cooled to room temperature, was filtered and purified by prep-HPLC to yield the title compound. LCMS (ES+) 428 (M+H)+, RT 3.56 min (Analytical method BicarbBEHC18). ¹H NMR (400 MHz, DMSO) δ 10.28 (s, 1H), 8.72 (d, J=1.4 Hz, 1H), 8.43 (d, J=2.8 Hz, 1H), 8.16 (d, J=1.6 Hz, 1H), 7.87 (d, J=1.4 Hz, 1H), 7.58 (dd, J=1.6, 13.7 Hz, 1H), 5.30-5.12 (m, 1H), 4.28 (t, J=8.5 Hz, 2H), 4.18 (s, 3H), 3.86 (dd, J=5.5, 9.0 Hz, 2H), 3.04-2.95 (m, 1H), 2.86-2.59 (m, 3H), 2.37-2.30 (m, 2H), 2.23-2.06 (m, 2H), 1.96-1.80 (m, 2H). ¹⁹F NMR (376 MHz, DMSO) δ −128.40 (dd, J=3.0, 13.7 Hz, 1F), −166.00-−166.50 (m, 1F).

Example 304: (R)-5-(3-(((3-fluoropyrrolidin-1-yl)methyl)azetidin-1-yl)-N-(6-methoxy-2-methyl-2H-indazol-5-yl)pyrazine-2-carboxamide

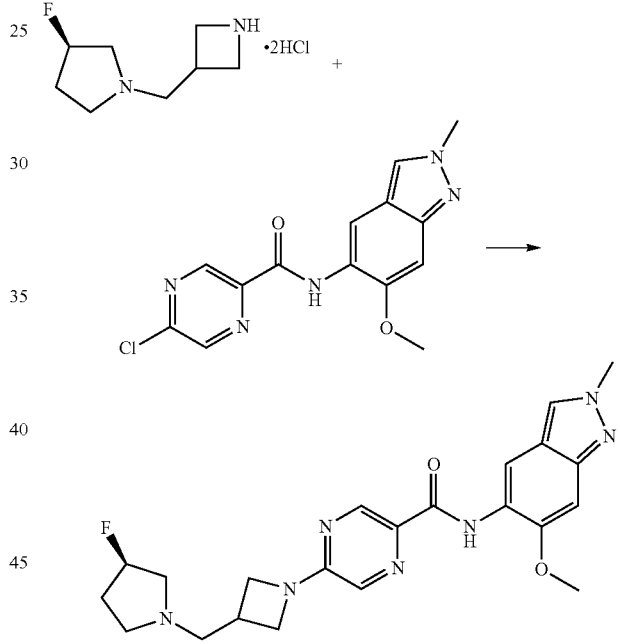

(3R)-1-(Azetidin-3-ylmethyl)-3-fluoro-pyrrolidine dihydrochloride (150 mg, 0.650 mmol, 1.96 eq), 5-chloro-N-(6-methoxy-2-methyl-indazol-5-yl)pyrazine-2-carboxamide (105 mg, 0.331 mmol, 1.00 eq), cesium carbonate (1000 mg, 3.07 mmol, 9.26 eq), and N,N-dimethylformamide (4.00 mL) were combined and stirred at 100° C. overnight. The reaction mixture was cooled to room temperature, filtered, and purified by prep-HPLC. This yielded the title compound. LCMS (ES+) 440 (M+H)+, RT 2.54 min (Analytical method AcHSSC18). ¹H NMR (400 MHz, DMSO) δ 10.04 (s, 1H), 8.72 (d, J=1.4 Hz, 1H), 8.67 (s, 1H), 8.23 (s, 1H), 7.93 (d, J=1.4 Hz, 1H), 7.11 (s, 1H), 5.30-5.12 (m, 1H), 4.27 (t, J=8.6 Hz, 2H), 4.10 (s, 3H), 3.98 (s, 3H), 3.88-3.82 (m, 2H), 3.03-2.95 (m, 1H), 2.89-2.77 (m, 2H), 2.74 (d, J=8.2 Hz, 2H), 2.71-2.57 (m, 1H), 2.37-2.30 (m, 1H), 2.23-2.06 (m, 1H), 1.93-1.79 (m, 1H). ¹⁹F NMR (376 MHz, DMSO) δ −166.00-−166.50 (m, 1F).

Example 305: N-(8-fluoro-2-methylimidazo[1,2-a]pyridin-6-yl)-5-((S)-3-(((R)-3-fluoropyrrolidin-1-yl)methyl)pyrrolidin-1-yl)pyrazine-2-carboxamide

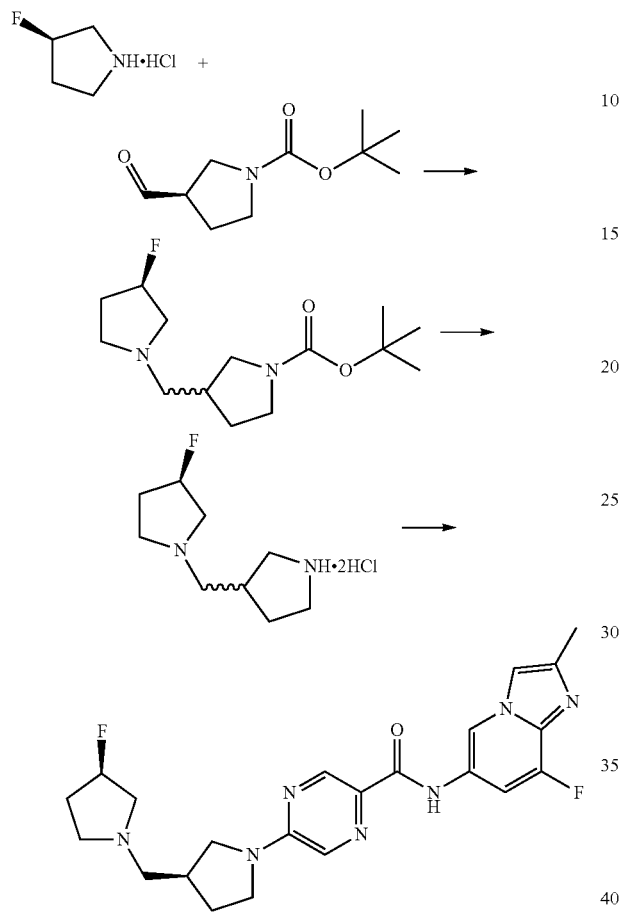

tert-Butyl (3R)-3-formylpyrrolidine-1-carboxylate (317 mg, 1.59 mmol, 1.00 eq), sodium triacetoxyborohydride (743 mg, 3.50 mmol, 2.20 eq), and (R)-(−)-3-fluoropyrrolidine hydrochloride (200 mg, 1.59 mmol, 1.00 eq) were combined in dichloromethane (10.00 mL) and stirred at room temperature overnight. Saturated aqueous sodium hydrogen carbonate was added and reaction mixture stirred vigorously for 10 mins. The mixture was basified with aqueous 2M NaOH solution, extracted with CH$_2$Cl$_2$, dried over a hydrophobic frit, and concentrated under reduced pressure. Methanol (30.00 mL) and 4 M hydrogen chloride in dioxane (4.9 mL, 19.6 mmol, 12.3 eq) was then added, and the mixture was stirred at room temperature for 2 hours. The reaction mixture was concentrated under reduced pressure to yield (3R)-3-fluoro-1-(pyrrolidin-3-ylmethyl)pyrrolidine dihydrochloride, which was used directly in the next step.

(3R)-3-Fluoro-1-(pyrrolidin-3-ylmethyl)pyrrolidine dihydrochloride (100 mg, 0.408 mmol, 1.00 eq), 5-chloro-N-(8-fluoro-2-methyl-imidazo[1,2-a]pyridin-6-yl)pyrazine-2-carboxamide (125 mg, 0.408 mmol, 1.00 eq), and cesium carbonate (266 mg, 0.816 mmol, 2.00 eq) in N,N-dimethylformamide (1.00 mL) were stirred overnight at 100° C. The reaction mixture was filtered, diluted with DMSO, and submitted for prep-HPLC purification. This yielded a product. Chiral QC analysis indicated the presence of two peaks observed in a 40:60 ratio. This product was submitted for chiral SFC separation, which yielded the title compound. LCMS (ES+) 442 (M+H)+, RT 1.9 min (Analytical method AcHSSC18). SFC RT 6.9 min (SFC1, YMC AMYLOSE-C+0.1% DEAISO 50% EtOH SOL5). $^1$H NMR (400 MHz, DMSO) δ 10.43 (s, 1H), 9.20 (d, J=1.5 Hz, 1H), 8.75 (d, J=1.3 Hz, 1H), 7.99 (d, J=1.4 Hz, 1H), 7.90 (d, J=2.4 Hz, 1H), 7.57 (dd, J=1.6, 13.1 Hz, 1H), 5.31-5.13 (m, 1H), 3.80-3.67 (m, 2H), 3.58-3.50 (m, 1H), 3.32-3.25 (m, 1H), 2.94-2.89 (m, 1H), 2.88-2.79 (m, 2H), 2.69-2.58 (m, 2H), 2.48 (d, J=4.1 Hz, 1H), 2.36-2.35 (m, 4H), 2.22-2.09 (m, 2H), 1.97-1.72 (m, 2H). $^{19}$F NMR (376 MHz, DMSO) δ −132.19 (dd, J=3.0, 12.2 Hz, 1F), −165.90−−166.36 (m, 1F).

Example 306: N-(8-fluoro-2-methylimidazo[1,2-a]pyridin-6-yl)-5-((R)-3-(((R)-3-fluoropyrrolidin-1-yl)methyl)pyrrolidin-1-yl)pyrazine-2-carboxamide

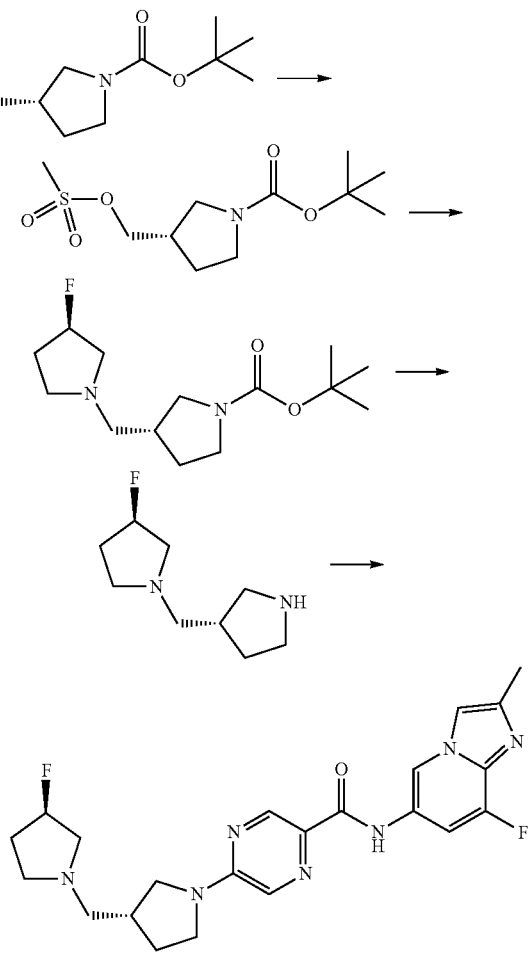

To a solution of tert-butyl (3S)-3-(hydroxymethyl)pyrrolidine-1-carboxylate (300 mg, 1.49 mmol, 1.00 eq) and triethylamine (0.42 mL, 2.98 mmol, 2.00 eq) in dichloromethane (10.00 mL), was added methanesulfonyl chloride (0.13 mL, 1.64 mmol, 1.10 eq) dropwise and the reaction stirred for 18 hours at room temperature. The reaction was quenched with water and the organic phase dried over a hydrophobic frit. The organic phase was concentrated under reduced pressure to yield tert-butyl (3S)-3-(methylsulfonyloxymethyl)pyrrolidine-1-carboxylate, which was used directly in the next step.

tert-Butyl (3S)-3-(methylsulfonyloxymethyl)pyrrolidine-1-carboxylate (400 mg, 1.43 mmol, 1.00 eq) was dissolved in acetonitrile (4.00 mL), and triethylamine (0.60 mL, 4.30 mmol, 3.00 eq) was added, followed by (R)-(–)-3-fluoropyrrolidine hydrochloride (360 mg, 2.86 mmol, 2.00 eq). The reaction was heated in a microwave to 120° C. for 2 h. Water was added and the product extracted into ethyl acetate. The organic phase was dried over a hydrophobic frit and concentrated under reduced pressure to yield tert-butyl (3R)-3-[[(3R)-3-fluoropyrrolidin-1-yl]methyl]pyrrolidine-1-carboxylate, which was used directly in the next step.

tert-Butyl (3R)-3-[[(3R)-3-fluoropyrrolidin-1-yl]methyl]pyrrolidine-1-carboxylate (290 mg, 1.06 mmol, 1.00 eq), 4M hydrogen chloride in 1,4-dioxane (2.7 mL, 10.6 mmol, 10.0 eq), and 1,4-dioxane (5.00 mL) were stirred overnight at room temperature. The reaction mixture was concentrated under reduced pressure to yield (3R)-3-fluoro-1-[[(3S)-pyrrolidin-3-yl]methyl]pyrrolidine dihydrochloride, which was used directly in the next step.

(3R)-3-Fluoro-1-[[(3S)-pyrrolidin-3-yl]methyl]pyrrolidine dihydrochloride (100 mg, 0.408 mmol, 1.00 eq), 5-chloro-N-(8-fluoro-2-methyl-imidazo[1,2-a]pyridin-6-yl)pyrazine-2-carboxamide (125 mg, 0.408 mmol, 1.00 eq), and cesium carbonate (266 mg, 0.816 mmol, 2.00 eq) in N,N-dimethylformamide (1.00 mL) were stirred at 100° C. for 18 hours. The reaction mixture was filtered and purified by prep-HPLC. This yielded the title compound. LCMS (ES+) 442 (M+H)+, RT 1.89 min (Analytical method AcHSSC18), SFC RT 4.8 min (SFC1, YMC AMYLOSE-C+0.1% DEAISO 50% EtOH SOL5). $^1$H NMR (400 MHz, DMSO) δ 10.43 (s, 1H), 9.20 (d, J=1.6 Hz, 1H), 8.75 (d, J=1.4 Hz, 1H), 7.99 (d, J=1.4 Hz, 1H), 7.90 (d, J=2.4 Hz, 1H), 7.57 (dd, J=1.6, 13.1 Hz, 1H), 5.31-5.13 (m, 1H), 3.81-3.66 (m, 2H), 3.58-3.49 (m, 1H), 3.31-3.28 (m, 1H), 2.91-2.79 (m, 2H), 2.73-2.54 (m, 3H), 2.46 (d, J=7.0 Hz, 1H), 2.35-2.35 (m, 4H), 2.24-2.08 (m, 2H), 1.98-1.73 (m, 2H). $^{19}$F NMR (376 MHz, DMSO) δ −132.2 (dd, J=3.0, 12.2 Hz, 1F), −165.9-−166.4 (m, 1F).

Example 307: N-(8-Fluoro-2-methylimidazo[1,2-a]pyridin-6-yl)-5-(3-((3-fluoroazetidin-1-yl)methyl)azetidin-1-yl)pyrazine-2-carboxamide

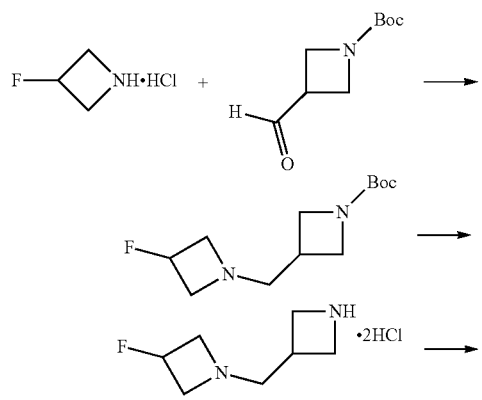

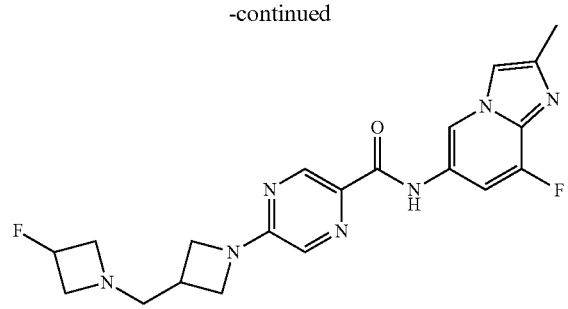

tert-Butyl 3-formylazetidine-1-carboxylate (332 mg, 1.79 mmol, 1.00 eq), sodium triacetoxyborohydride (836 mg, 3.94 mmol, 2.20 eq), and 3-fluoroazetidine hydrochloride (200 mg, 1.79 mmol, 1.00 eq) were combined in dichloromethane (5.00 mL) and stirred at room temperature overnight. Saturated aqueous sodium hydrogen carbonate was added and reaction mixture stirred vigorously for 10 mins. The reaction mixture was basified with aqueous 2M NaOH solution, extracted with DCM, and dried over a hydrophobic frit. The organic phase was concentrated under reduced pressure. Methanol (10.00 mL) and 4 M hydrochloric acid in dioxane (5.5 mL, 22.1 mmol, 12.3 eq) were added and stirred at room temperature for 2 hours. The mixture was concentrated under reduced pressure to yield 1-(azetidin-3-ylmethyl)-3-fluoro-azetidine dihydrochloride, which was used directly in the next step.

1-(Azetidin-3-ylmethyl)-3-fluoro-azetidine dihydrochloride (100 mg, 0.461 mmol, 1.00 eq), cesium carbonate (300 mg, 0.921 mmol, 2.00 eq), and 5-chloro-N-(8-fluoro-2-methyl-imidazo[1,2-a]pyridin-6-yl)pyrazine-2-carboxamide (141 mg, 0.461 mmol, 1.00 eq) in N,N-dimethylformamide (1.00 mL) were stirred overnight at 100° C. The reaction mixture was filtered and purified by prep-HPLC, followed by further achiral SFC purification. This yielded the title compound. LCMS (ES+) 414 (M+H)+, RT 3.35 min (Analytical method BicarbBEHC18). $^1$H NMR (400 MHz, DMSO) δ 10.44 (s, 1H), 9.18 (d, J=1.5 Hz, 1H), 8.71 (d, J=1.4 Hz, 1H), 7.90 (dd, J=0.9, 3.1 Hz, 1H), 7.86 (d, J=1.4 Hz, 1H), 7.56 (dd, J=1.5, 13.1 Hz, 1H), 5.27-5.07 (m, 1H), 4.23 (t, J=8.3 Hz, 2H), 3.88-3.82 (m, 2H), 3.63-3.55 (m, 2H), 3.20-3.09 (m, 2H), 2.77-2.74 (m, 3H), 2.35 (s, 3H). $^{19}$F NMR (376 MHz, DMSO) δ −132.3 (dd, J=3.1, 13.6, Hz, 1F), −177.46-−177.86 (m, 1F).

Example 308: 5-(2,6-diazabicyclo[3.2.0]heptan-6-yl)-N-(8-fluoro-2-methylimidazo[1,2-a]pyridin-6-yl)pyrazine-2-carboxamide, Examples 309 and 310: N-(8-fluoro-2-methylimidazo[1,2-a]pyridin-6-yl)-5-((1S,5S)-2-methyl-2,6-diazabicyclo[3.2.0]heptan-6-yl)pyrazine-2-carboxamide, and N-(8-fluoro-2-methylimidazo[1,2-a]pyridin-6-yl)-5-((1R,5R)-2-methyl-2,6-diazabicyclo[3.2.0]heptan-6-yl)pyrazine-2-carboxamide

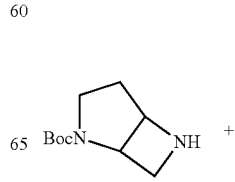

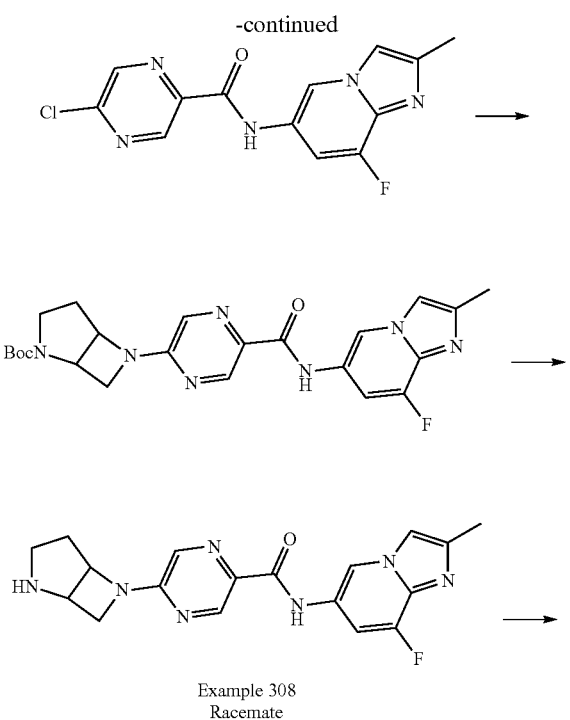

Example 308
Racemate

Enantiomer 1
+
Enantiomer 2 tert-Butyl 2,6-diazabicyclo[3.2.0]heptane-2-carboxylate (105 mg, 0.530 mmol), 5-chloro-N-(8-fluoro-2-methyl-imidazo[1,2-a]pyridin-6-yl)pyrazine-2-carboxamide (162 mg, 0.530 mmol), cesium carbonate (259 mg, 0.794 mmol), and N,N-dimethylformamide (1 mL) were combined and heated at 100° C. for 16 h. The reaction mixture was diluted with DCM and washed with brine/aqueous sodium bicarbonate solution. The organic layer was concentrated in vacuo. The crude product was purified by column chromatography, eluting with cyclohexane/EtOAc (0-100% gradient). The appropriate fractions were combined and concentrated in vacuo to give the desired product. LCMS (ES+) 469 (M+H)+, RT 1.43 min.

tert-Butyl 6-[5-[(8-fluoro-2-methyl-imidazo[1,2-a]pyridin-6-yl)carbamoyl]pyrazin-2-yl]-2,6-diazabicyclo[3.2.0]heptane-2-carboxylate (163 mg, 0.349 mmol) was subjected to Method C. Product was purified by achiral SFC to give 5-(2,6-diazabicyclo[3.2.0]heptan-6-yl)-N-(8-fluoro-2-methylimidazo[1,2-a]pyridin-6-yl)pyrazine-2-carboxamide. LCMS (ES+) 368 (M+H)+, RT 1.7 min (Analytical method AcHSSC18). $^1$H NMR (400 MHz, CDCl$_3$) δ 9.20 (s, 1H), 9.09 (s, 1H), 8.90 (s, 1H), 7.65 (s, 1H), 7.41 (d, J=3.5 Hz, 1H), 6.81 (d, J=10.4 Hz, 1H), 5.08-5.06 (m, 1H), 4.40-4.33 (m, 2H), 3.89 (q, J=7.0 Hz, 1H), 3.49-3.42 (m, 1H), 3.26-3.18 (m, 1H), 2.48 (s, 3H), 2.33-2.25 (m, 1H), 1.30-1.24 (m, 2H).

To a solution of 5-(2,6-diazabicyclo[3.2.0]heptan-6-yl)-N-(8-fluoro-2-methyl-imidazo[1,2-a]pyridin-6-yl)pyrazine-2-carboxamide (173 mg, 0.471 mmol) in methyl alcohol (5 mL) was added formaldehyde solution (37% wt in water; stabilised with 7-8% methanol) (0.65 mL, 23.5 mmol), followed by sodium triacetoxyborohydride (200 mg, 0.942 mmol). The reaction mixture was stirred at room temperature for 16 h. The mixture was partitioned between DCM and saturated aqueous sodium bicarbonate. The organic phase was concentrated in vacuo and purified by chiral SFC to give the two enantiomers:

Example 309

N-(8-Fluoro-2-methyl-imidazo[1,2-a]pyridin-6-yl)-5-[(1S,5S)-2-methyl-2,6-diazabicyclo[3.2.0]heptan-6-yl]pyrazine-2-carboxamide Enantiomer 1. LCMS (ES+) 382 (M+H)+, RT 3.11 min (Analytical method BicarbBEHC18). $^1$H NMR (400 MHz, DMSO) δ 10.43 (s, 1H), 9.18 (d, J=1.6 Hz, 1H), 8.72 (d, J=1.4 Hz, 1H), 7.90 (dd, J=0.6, 3.2 Hz, 1H), 7.87 (s, 1H), 7.56 (dd, J=2.3, 13.4 Hz, 1H), 5.05 (dd, J=5.3, 5.3 Hz, 1H), 4.15 (d, J=10.4 Hz, 1H), 4.08-4.03 (m, 1H), 3.88 (dd, J=6.1, 9.9 Hz, 1H), 2.98 (dd, J=6.8, 9.7 Hz, 1H), 2.76-2.68 (m, 1H), 2.37 (s, 3H), 2.34 (s, 3H), 2.03 (dd, J=5.3, 13.2 Hz, 1H), 1.87-1.80 (m, 1H). $^{19}$F NMR (376 MHz, DMSO) δ −132 (s, 1F).

Example 310

N-(8-Fluoro-2-methyl-imidazo[1,2-a]pyridin-6-yl)-5-[(1R,5R)-2-methyl-2,6-diazabicyclo[3.2.0]heptan-6-yl]pyrazine-2-carboxamide Enantiomer 2. LCMS (ES+) 382 (M+H)+, RT 1.7 min (Analytical method AcHSSC18). $^1$H NMR (400 MHz, DMSO) δ 10.43 (s, 1H), 9.18 (d, J=1.5 Hz, 1H), 8.72 (d, J=1.3 Hz, 1H), 7.90 (dd, J=0.8, 3.0 Hz, 1H), 7.87 (s, 1H), 7.56 (dd, J=2.3, 13.2 Hz, 1H), 5.04 (dd, J=5.4, 5.4 Hz, 1H), 4.14 (s, 1H), 4.08-4.03 (m, 1H), 3.88 (dd, J=6.1, 9.9 Hz, 1H), 3.01-2.96 (m, 1H), 2.74-2.68 (m, 1H), 2.37 (s, 3H), 2.34 (d, J=0.7 Hz, 3H), 2.03 (dd, J=4.8, 13.1 Hz, 1H), 1.87-1.81 (m, 1H). $^{19}$F NMR (376 MHz, DMSO) δ −132 (s, 1F).

Compounds in the table below were prepared from intermediate H1 (5-chloro-N-(8-chloro-2-methylimidazo[1,2-a]pyridin-6-yl)pyrazine-2-carboxamide) and the stated amine using method D2.

| | Structure | Amine intermediate | Analytical data |
|---|---|---|---|
| Example 311: | 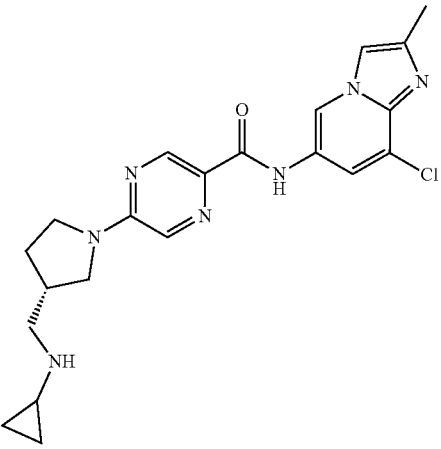 [SMILES: Cc1cn2cc(NC(=O)c3cnc(N4CC[C@@H](CNC5CC5)C4)cn3)cc(Cl)c2n1] | (R)-N-(pyrrolidin-3-ylmethyl)cyclopropanamine | LCMS (ES+) 426 (M + H)+, RT 1.97 min (Analytical method AcHSSC18. ¹H NMR (400 MHz, DMSO) δ 10.19 (s, 1H), 9.05 (d, J = 1.8 Hz, 1H), 8.51 (d, J = 1.1 Hz, 1H), 7.74 (d, J = 1.3 Hz, 1H), 7.66 (s, 1H), 7.60 (d, J = 1.8 Hz, 1H), 3.53-3.41 (m, 2H), 3.33-3.26 (m, 1H), 3.03 (dd, J = 7.3, 11.0 Hz, 2H), 2.50-2.34 (m, 1H), 2.12-2.12 (m, 4H), 1.91-1.81 (m, 3H), 1.54-1.51 (m, 1H), 0.15 (dd, J = 1.5, 6.5 Hz, 2H), 0.01 - -0.02 (m, 2H). |
| Example 312: | 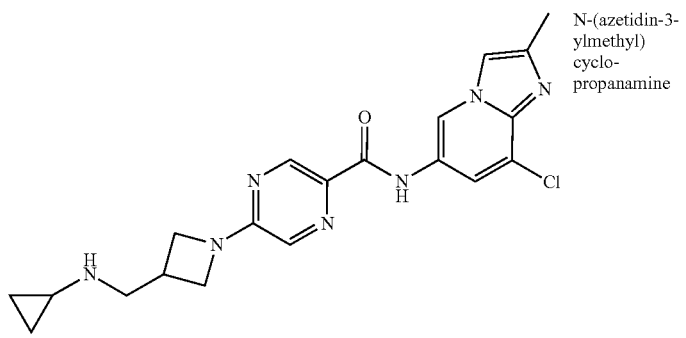 | N-(azetidin-3-ylmethyl)cyclopropanamine | LCMS (ES+) 412 (M + H)+, RT 1.89 min (Analytical method AcHSSC18). ¹H NMR (400 MHz, DMSO) δ 10.21 (s, 1H), 9.05 (d, J = 1.8 Hz, 1H), 8.48 (d, J = 1.3 Hz, 1H), 7.66 (d, J = 0.9 Hz, 1H), 7.62 (d, J = 1.6 Hz, 1H), 7.60 (d, J = 2.1 Hz, 1H), 4.00 (dd, J = 8.3, 8.3 Hz, 2H), 3.64 (dd, J = 4.9, 9.0 Hz, 2H), 2.72-2.63 (m, 3H), 2.17-2.17 (m, 1H), 2.13 (s, 3H), 1.88-1.82 (m, 1H), 0.17-0.13 (m, 2H), 0.01 - -0.02 (m, 2H). |

Compounds in the table below were prepared from intermediate H2 (5-chloro-N-(8-methoxy-2-methylimidazo[1,2-a]pyridin-6-yl)pyrazine-2-carboxamide) and the stated amine using method D2.

| | Structure | Amine intermediate | Analytical data |
|---|---|---|---|
| Example 313 | 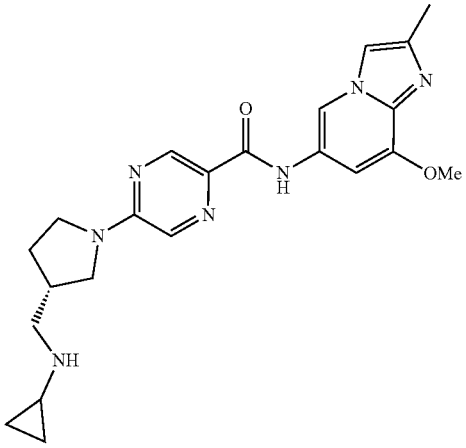 [SMILES: COc1cc(NC(=O)c2cnc(N3CC[C@@H](CNC4CC4)C3)cn2)cn2cc(C)nc12] | (R)-N-(pyrrolidin-3-ylmethyl)cyclopropanamine | LCMS (ES+) 422 (M + H)+, RT 1.97 min (Analytical method AcHSSC18. ¹H NMR (400 MHz, DMSO) δ 10.19 (s, 1H), 8.95 (d, J = 1.5 Hz, 1H), 8.74 (d, J = 1.4 Hz, 1H), 7.97 (d, J = 1.3 Hz, 1H), 7.70 (s, 1H), 7.13 (d, J = 1.5 Hz, 1H), 3.93 (s, 3H), 3.73 - 3.67 (m, 2H), 3.57-3.49 (m, 1H), 3.29-3.25 (m, 2H), 2.79-2.72 (m, 2H), 2.30 (s, 3H), 2.21-2.13 (m, 3H), 1.82-1.73 (m, 1H), 0.47-0.42 (m, 2H), 0.34-0.30 (m, 2H). |
| Example 314 | 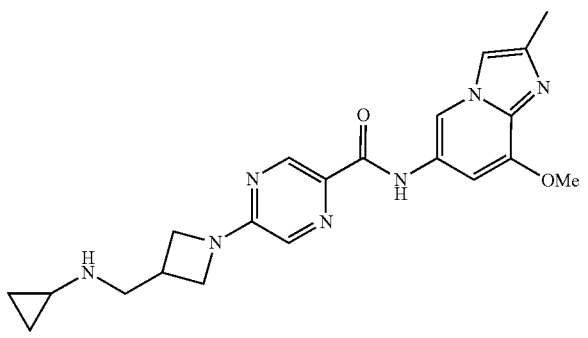 | N-(azetidin-3-ylmethyl)cyclopropanamine | LCMS (ES+) 408 (M + H)+, RT 1.9 min (Analytical method AcHSSC18). ¹H NMR (400 MHz, DMSO) δ 9.97 (s, 1H), 8.71 (d, J = 1.6 Hz, 1H), 8.48 (d, J = 1.4 Hz, 1H), 7.62 (d, J = 1.4 Hz, 1H), 7.48 (s, 1H), 6.89 (d, J = 1.6 Hz, 1H), 4.00 (dd, J = 8.2, 8.2 Hz, 2H), 3.69 (s, 3H), 3.64 (ddd, J = 4.8, 4.8, 4.8 Hz, 2H), 2.71-2.62 (m, 3H), 2.07 (d, J = 0.8 Hz, 3H), 1.89-1.83 (m, 1H), 0.18-0.14 (m, 2H), 0.02 - -0.03 (m, 2H). |

Example 315: 5-(3-((cyclopropylamino)methyl)
azetidin-1-yl)-N-(2-(fluoromethyl)-8-methylimidazo
[1,2-a]pyridin-6-yl)pyrazine-2-carboxamide

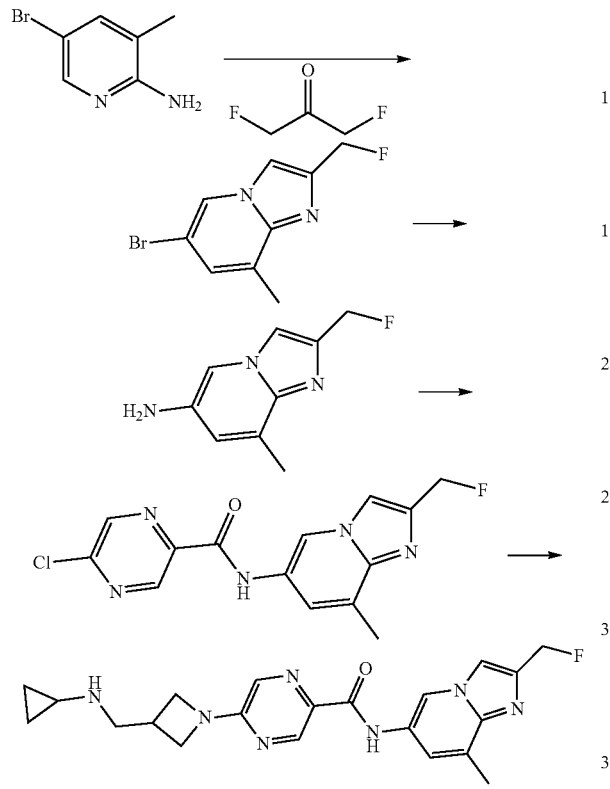

2-Amino-5-bromo-3-methylpyridine (65 mg, 0.348 mmol), 1,3-difluoroacetone (0.13 mL, 1.81 mmol), and IPA (1.00 mL) were combined and the R.M was stirred at 95° C. for 16 h. The reaction mixture was diluted with DCM and washed with aqueous 15 mol % NaOH. The organic layer was concentrated, diluted with DCM, and passed through an SCX cartridge, eluting with MeOH and NH$_3$ (7 M) in MeOH. The appropriate fraction was concentrated in vacuo to give the desired product. LCMS (ES+) 244 (M+H)+, RT 1.18 min. $^1$H NMR (400 MHz, CDCl$_3$) δ 8.13 (s, 1H), 7.61 (d, J=2.8 Hz, 1H), 7.09 (s, 1H), 5.56 (d, J=48.4 Hz, 2H), 2.60 (s, 3H). $^{19}$F NMR (376 MHz, CDCl3) δ −209.95 (t, J=45.5 Hz, 1F). Note: extended fluorine ppm range required to observe signal.

6-Bromo-2-(fluoromethyl)-8-methyl-imidazo[1,2-a]pyridine (78 mg, 0.321 mmol), copper(I) iodide (12 mg, 0.0642 mmol), potassium carbonate (67 mg, 0.481 mmol), ammonium hydroxide solution (0.020 mL, 0.481 mmol), L-proline (15 mg, 0.128 mmol), and DMSO (3.00 mL) were added to the reaction flask. The reaction vessel was sealed and heated at 90° C. for 16 h. The reaction mixture was passed through an SCX cartridge, eluting with DCM/MeOH 1:1 and NH$_3$ (7 M) in MeOH. The appropriate fraction was concentrated in vacuo to give the desired product. LCMS (ES+) 180 (M+H)+, RT 0.69 min.

2-(Fluoromethyl)-8-methyl-imidazo[1,2-a]pyridin-6-amine (50 mg, 0.279 mmol), 5-chloro-2-pyrazinecarboxylic acid (44 mg, 0.279 mmol), chloro-N,N,N',N'-tetramethyl-formamidinium hexafluorophosphate (117 mg, 0.419 mmol), and 1-methylimidazole (0.067 mL, 0.837 mmol) in acetonitrile (5.00 mL) were stirred under nitrogen for 3 h at RT. The reaction was concentrated, diluted with DCM and washed with brine. The organic layer was concentrated onto silica and purified by column chromatography, eluting with cyclohexane/ethyl acetate (0-60% gradient). The appropriate fractions were combined and concentrated in vacuo to give the desired product. LCMS (ES+) 320 (M+H)+, RT 1.22 min. $^1$H NMR (400 MHz, CDCl3) δ 9.38 (s, 1H), 9.28 (s, 1H), 9.23 (s, 1H), 8.60 (s, 1H), 7.72 (d, J=2.5 Hz, 1H), 6.92 (s, 1H), 5.58 (d, J=47.5 Hz, 2H), 2.64 (s, 3H).

N-(Azetidin-3-ylmethyl)cyclopropanamine (18 mg, 0.144 mmol), triethylamine (0.14 mL, 1.01 mmol), and 5-chloro-N-[2-(fluoromethyl)-8-methyl-imidazo[1,2-a]pyridin-6-yl]pyrazine-2-carboxamide (46 mg, 0.144 mmol) were combined in acetonitrile (2.00 mL) and stirred at 55° C. for 16 h. The reaction mixture was concentrated in vacuo and submitted for achiral reverse phase chromatography. LCMS (ES+) 410 (M+H)+, RT 1.93 min (Analytical method AcHSSC18. 1H NMR (400 MHz, DMSO) δ 10.06 (s, 1H), 8.99 (s, 1H), 8.48 (d, J=1.3 Hz, 1H), 7.92 (d, J=3.8 Hz, 1H), 7.63 (d, J=1.3 Hz, 1H), 7.25 (s, 1H), 5.25 (d, J=49.1 Hz, 2H), 4.00 (dd, J=8.3, 8.3 Hz, 2H), 3.64 (dd, J=4.9, 9.0 Hz, 2H), 2.70-2.62 (m, 3H), 2.25 (s, 3H), 1.85 (ddd, J=3.5, 6.6, 10.0 Hz, 2H), 0.17-0.13 (m, 2H), 0.01--0.02 (m, 2H). $^{19}$F NMR (376 MHz, DMSO) δ −202.65 (t, J=45.5 Hz, 1F).

Example 316: 5-(3-((cyclopropylamino)methyl)-2-oxopyrrolidin-1-yl)-N-(8-fluoro-2-methylimidazo[1,2-a]pyridin-6-yl)pyrazine-2-carboxamide

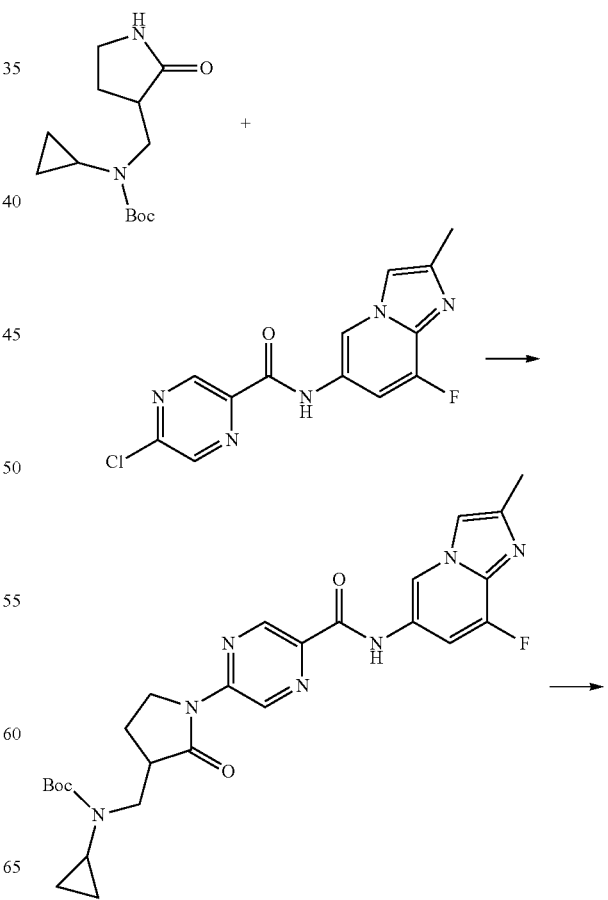

-continued

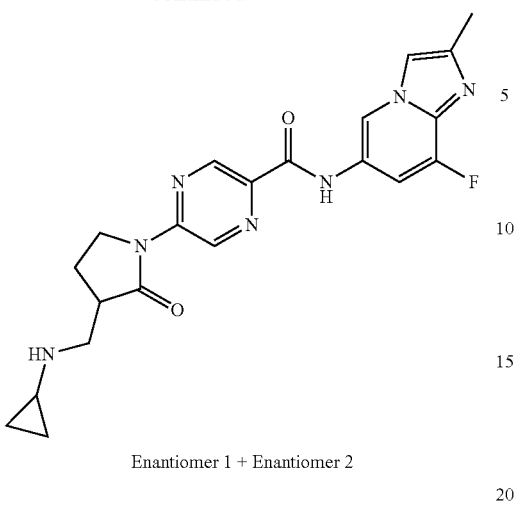

Enantiomer 1 + Enantiomer 2

To a solution of tert-butyl N-cyclopropyl-N-[(2-oxopyrrolidin-3-yl)methyl]carbamate (202 mg, 0.794 mmol) and 5-chloro-N-(8-fluoro-2-methyl-imidazo[1,2-a]pyridin-6-yl) pyrazine-2-carboxamide (243 mg, 0.794 mmol) in 1,4-dioxane (5 mL) was added cesium carbonate (388 mg, 1.19 mmol), and the mixture was degassed under nitrogen by sparging for 20 min. Xantphos (46 mg, 0.0794 mmol) and tris(dibenzylideneacetone)dipalladium(0) (18 mg, 0.0199 mmol) was added, and the mixture heated to 100° C. under inert atmosphere for 18 h. The reaction was cooled to r.t., filtered, and the collected solid washed with DCM. The collected liquid was concentrated in vacuo to give a residue, which was purified by achiral SFC to give tert-butyl cyclopropyl((1-(5-((8-fluoro-2-methylimidazo[1,2-a]pyridin-6-yl)carbamoyl)pyrazin-2-yl)-2-oxopyrrolidin-3-yl)methyl) carbamate. LCMS (ES+) 523 (M+H)+.

tert-Butyl cyclopropyl((1-(5-((8-fluoro-2-methylimidazo[1,2-a]pyridin-6-yl)carbamoyl)pyrazin-2-yl)-2-oxopyrrolidin-3-yl)methyl)carbamate (195 mg, 0.372 mmol) was dissolved in dichloromethane (3 mL), and trifluoroacetic acid (1 mL) was added at r.t. The reaction was stirred at r.t. for 1 h. The solvent was removed in vacuo to give a residue, which was purified by SCX chromatography (5 g, eluting with MeOH/DCM 50% and then 10% 7N NH$_3$ in MeOH/ MeOH. The ammonical fractions were combined and the solvent removed in vacuo to give the title compound. The sample was further purified by achiral SFC to give the title compound. LCMS (ES+) 424 (M+H)+, RT 1.91 min (Analytical method AcHSSC18); $^1$H NMR (400 MHz, DMSO) δ 10.92 (s, 1H), 9.74 (s, 1H), 9.27 (s, 1H), 9.15 (s, 1H), 7.99-7.96 (m, 1H), 4.16-4.09 (m, 1H), 3.97-3.89 (m, 1H), 3.12-3.02 (m, 2H), 2.90 (dd, J=7.1, 10.9 Hz, 1H), 2.42-2.31 (m, 5H), 2.23-2.21 (m, 1H), 2.08-1.97 (m, 1H), 0.50-0.44 (m, 2H), 0.39-0.29 (m, 2H); $^{19}$F NMR (400 MHz, DMSO), d −131.83 (dd, J=3.5, 12.3 Hz, 1H).

Example 317: N-(8-fluoro-2-methylimidazo[1,2-a] pyridin-6-yl)-5-((3aR,6aS)-5-methyl-1-oxohexahydropyrrolo[3,4-c]pyrrol-2(1H)-yl)pyrazine-2-carboxamide

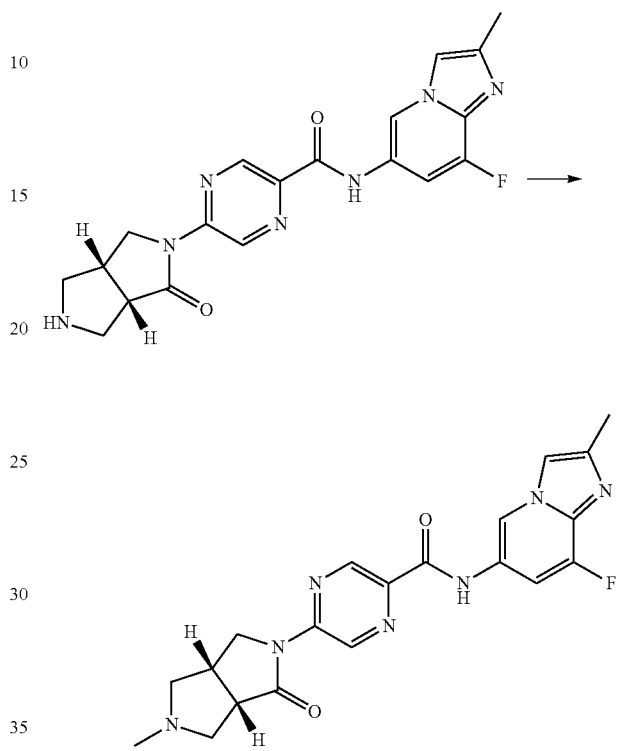

Using Method Q from N-(8-fluoro-2-methylimidazo[1,2-a]pyridin-6-yl)-5-((3aR,6aS)-1-oxohexahydropyrrolo[3,4-c] pyrrol-2(1H)-yl)pyrazine-2-carboxamide. The product was purified by SFC. LCMS (ES+) 410 (M+H)+, RT 1.71 min (Analytical method AcHSSC18); $^1$H NMR (400 MHz, DMSO) δ 10.91 (s, 1H), 9.74 (d, J=1.5 Hz, 1H), 9.23 (d, J=1.5 Hz, 1H), 9.12 (d, J=1.5 Hz, 1H), 7.94 (d, J=2.6 Hz, 1H), 7.59 (dd, J=1.7, 12.9 Hz, 1H), 4.23 (dd, J=9.2, 11.5 Hz, 1H), 3.83 (dd, J=2.9, 11.5 Hz, 1H), 3.35-3.32 (m, 1H), 3.11 (d, J=8.8 Hz, 1H), 3.04-2.98 (m, 1H), 2.88 (d, J=9.4 Hz, 1H), 2.39-2.31 (m, 5H), 2.24 (s, 3H).

Example 318 and Example 319: (S)—N-(8-fluoro-2-methylimidazo[1,2-a]pyridin-6-yl)-5-(methyl(4-azaspiro[2.5]octan-7-yl)amino)pyrazine-2-carboxamide and (R)—N-(8-fluoro-2-methylimidazo[1,2-a]pyridin-6-yl)-5-(methyl(4-azaspiro[2.5]octan-7-yl) amino)pyrazine-2-carboxamide

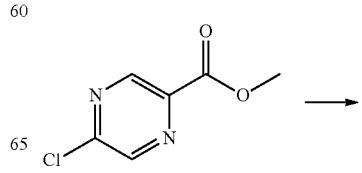

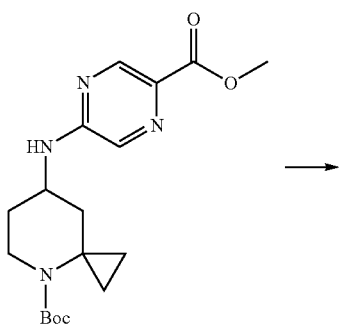

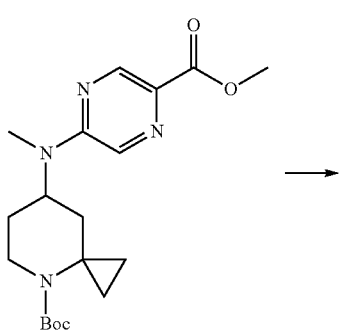

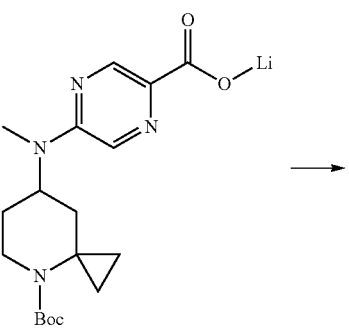

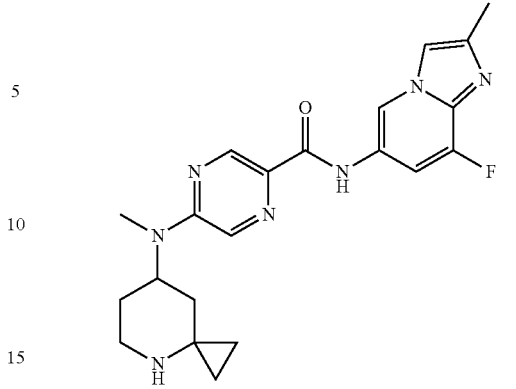

Enantiomer 1

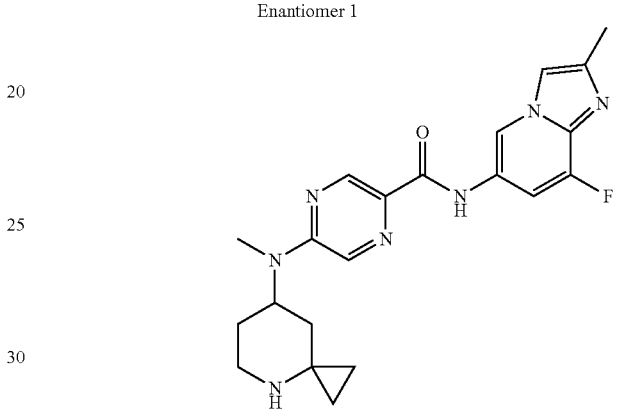

Enantiomer 2 tert-Butyl 7-amino-4-azaspiro[2.5]octane-4-carboxylate (500 mg, 2.21 mmol), methyl 5-chloro-2-pyrazinecarboxylate (381 mg, 2.21 mmol), cesium carbonate (1447 mg, 4.44 mmol, 2.01 eq), and 1,4-dioxane (20 mL) were combined and heated at reflux for 18 h. The reaction was cooled to r.t. and the solvent removed in vacuo. The residue was taken up in DCM and washed with water, then the layers were separated using a phase separator. The DCM was removed in vacuo to give a residue. The residue was purified by column chromatography on silica gel (10 g, eluting with EtOAc in cyclohexane 0-100%) to give tert-butyl 7-((5-(methoxycarbonyl)pyrazin-2-yl)amino)-4-azaspiro[2.5]octane-4-carboxylate.

tert-Butyl 7-[(5-methoxycarbonylpyrazin-2-yl)amino]-4-azaspiro[2.5]octane-4-carboxylate (417 mg, 1.15 mmol) and N,N-dimethylformamide (7 mL) were combined under nitrogen. Iodomethane (0.072 mL, 1.15 mmol) and sodium hydride (60%, 51 mg, 1.27 mmol) was added. The reaction was stirred at room temperature for 18 h. The reaction was then cooled in an ice-bath and quenched by addition of MeOH (to avoid ester hydrolysis). The solvent was removed in vacuo to give a residue. The residue was purified by silica chromatography (25 g, eluting with EtOAc/cyclohexane 0-90%) to give tert-butyl 7-((5-(methoxycarbonyl)pyrazin-2-yl)(methyl)amino)-4-azaspiro[2.5]octane-4-carboxylate. tert-Butyl 7-[(5-methoxycarbonylpyrazin-2-yl)-methyl-amino]-4-azaspiro[2.5]octane-4-carboxylate (322 mg, 0.855 mmol) was dissolved in methyl alcohol (5 mL) and water (1 mL). Lithium hydroxide monohydrate (39 mg, 0.941 mmol) was added and the reaction was heated at 50° C. The solvent was removed in vacuo to give lithium 5-((4-(tert-butoxycarbonyl)-4-azaspiro[2.5]octan-7-yl)(methyl)amino)pyrazine-2-carboxylate.

8-Fluoro-2-methyl-imidazo[1,2-a]pyridin-6-amine (49 mg, 0.299 mmol) and [5-[(4-tert-butoxycarbonyl-4-azaspiro[2.5]octan-7-yl)-methyl-amino]pyrazine-2-carbonyl]oxylithium (100 mg, 0.271 mmol) were dissolved in N,N-dimethylformamide (4 mL). Triethylamine (0.50 mL, 3.59 mmol) and HBTU (103 mg, 0.271 mmol) were added and the reaction was stirred at RT for 18 h. The crude reaction mixture was purified by preparative HPLC to give tert-butyl 7-((5-((8-fluoro-2-methylimidazo[1,2-a]pyridin-6-yl)carbamoyl)pyrazin-2-yl)(methyl)amino)-4-azaspiro[2.5]octane-4-carboxylate.

tert-Butyl 7-[[5-[(8-fluoro-2-methyl-imidazo[1,2-a]pyridin-6-yl)carbamoyl]pyrazin-2-yl]-methyl-amino]-4-azaspiro[2.5]octane-4-carboxylate (73 mg, 0.143 mmol) was dissolved in dichloromethane (3 mL) and trifluoroacetic acid (1.0 mL). The reaction was stirred at RT for 2 h. The solvent was removed by blowing a stream of nitrogen over the sample to give a residue, which was purified by SCX chromatography (eluting with MeOH and 10% 7N NH$_3$ in MeOH/MeOH). The ammonical fractions were combined and solvent removed in vacuo. The residue was freeze dried from 1:1 CH$_3$CN/water to give the desired product mixture. The enantiomers were separated by chiral SFC to give:

Example 318 Enantiomer 1

N-(8-fluoro-2-methylimidazo[1,2-a]pyridin-6-yl)-5-(methyl(4-azaspiro[2.5]octan-7-yl)amino)pyrazine-2-carboxamide. LCMS (ES+) 410 (M+H)+, RT 1.99 min (Analytical method AcHSSC18); RT 9.2 min (SFC1, LUX CELLULOSE-4+0.1% DEAISO 50% MeOH SOL4); $^1$H NMR (400 MHz, DMSO) δ 10.38 (s, 1H), 9.18 (d, J=1.5 Hz, 1H), 8.74 (d, J=1.3 Hz, 1H), 8.12 (d, J=1.5 Hz, 1H), 7.88 (d, J=2.5 Hz, 1H), 7.54 (dd, J=1.6, 13.0 Hz, 1H), 4.83-4.75 (m, 1H), 3.04 (s, 3H), 2.99-2.92 (m, 1H), 2.73-2.64 (m, 1H), 2.34-2.33 (m, 3H), 2.13 (t, J=11.7 Hz, 1H), 1.72-1.58 (m, 2H), 0.99 (dd, J=3.0, 11.9 Hz, 1H), 0.57-0.52 (m, 1H), 0.43-0.30 (m, 3H); $^{19}$F NMR (400 MHz, DMSO) δ −132.13 (dd, J=2.9, 13.0 Hz, 1H).

Example 319 Enantiomer 2

N-(8-fluoro-2-methylimidazo[1,2-a]pyridin-6-yl)-5-(methyl(4-azaspiro[2.5]octan-7-yl)amino)pyrazine-2-carboxamide. LCMS (ES+) 410 (M+H)+, RT 1.98 min (Analytical method AcHSSC18); RT 13.5 min (SFC1, LUX CELLULOSE-4+0.1% DEAISO 50% MeOH SOL4); $^1$H NMR (400 MHz, DMSO) δ 10.38 (s, 1H), 9.18 (d, J=1.5 Hz, 1H), 8.74 (d, J=1.3 Hz, 1H), 8.12 (d, J=1.5 Hz, 1H), 7.88 (d, J=2.5 Hz, 1H), 7.54 (dd, J=1.6, 13.0 Hz, 1H), 4.83-4.75 (m, 1H), 3.04 (s, 3H), 2.99-2.92 (m, 1H), 2.73-2.64 (m, 1H), 2.34-2.33 (m, 3H), 2.13 (t, J=11.7 Hz, 1H), 1.72-1.58 (m, 2H), 0.99 (dd, J=3.0, 11.9 Hz, 1H), 0.57-0.52 (m, 1H), 0.43-0.30 (m, 3H); $^{19}$F NMR (400 MHz, DMSO) δ −132.13 (dd, J=2.9, 13.0 Hz, 1H).

Example 320: 5-(3-(((cyclopropyl(methyl)amino)methyl)azetidin-1-yl)-N-(7-fluoro-2-methyl-2H-indazol-5-yl)pyrazine-2-carboxamide

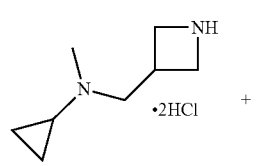

+

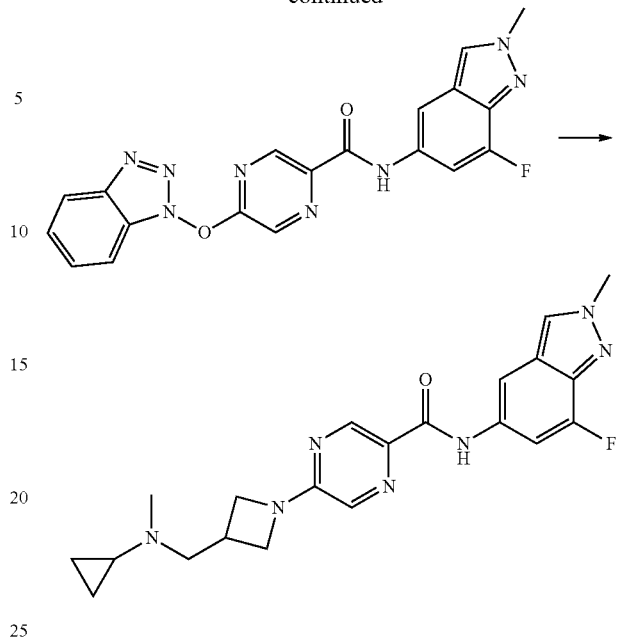

Cesium carbonate (322 mg, 0.989 mmol), 5-(benzotriazol-1-yloxy)-N-(7-fluoro-2-methyl-indazol-5-yl)pyrazine-2-carboxamide (intermediate H3, 100 mg, 0.247 mmol), and N-(azetidin-3-ylmethyl)-N-methyl-cyclopropanamine dihydrochloride (53 mg, 0.247 mmol) were combined in N,N-dimethylformamide (3 mL) and stirred at 100° C. for 17 h. The reaction was cooled to r.t. and filtered. The collected liquid was purified by preparative HPLC to give the title compound. LCMS (ES+) 410 (M+H)+, RT 2.48 min (Analytical method AcHSSC18); $^1$H NMR (400 MHz, DMSO) δ 10.27 (s, 1H), 8.72 (d, J=1.4 Hz, 1H), 8.44-8.42 (m, 1H), 8.16 (d, J=1.6 Hz, 1H), 7.86 (d, J=1.4 Hz, 1H), 7.58 (dd, J=1.6, 13.7 Hz, 1H), 4.26-4.18 (m, 5H), 3.84-3.79 (m, 2H), 3.11-3.02 (m, 1H), 2.80-2.77 (m, 2H), 2.29-2.28 (m, 3H), 1.69-1.62 (m, 1H), 0.49-0.44 (m, 2H), 0.33-0.28 (m, 2H); $^{19}$F NMR (400 MHz, DMSO) δ −128.42 (dd, J=2.7, 13.8 Hz, 1H).

Example 321: 5-(3-(2-(cyclopropylamino)ethyl)azetidin-1-yl)-N-(7-fluoro-2-methyl-2H-indazol-5-yl)pyrazine-2-carboxamide

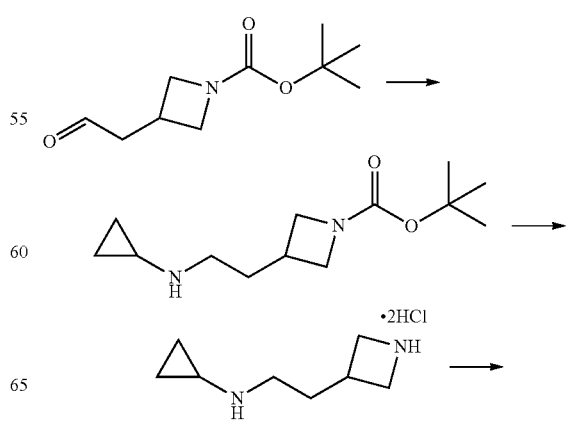

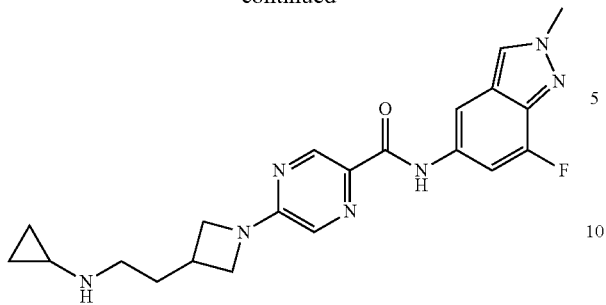

Sodium triacetoxyborohydride (702 mg, 3.31 mmol, 2.20 eq), cyclopropylamine (0.11 mL, 1.66 mmol, 1.10 eq), and tert-butyl 3-(2-oxoethyl)azetidine-1-carboxylate (300 mg, 1.51 mmol, 1.00 eq) were combined in dichloromethane (10 mL) and stirred at r.t. for 20 h. Saturated aqueous sodium hydrogen carbonate solution (20 mL) was added to the reaction mixture and stirred vigorously for 10 mins. The organics were collected and washed with water and brine, before passing through a phase separator and concentrating to dryness to give tert-butyl 3-[2-(cyclopropylamino)ethyl]azetidine-1-carboxylate, which was progressed to the next step directly.

tert-Butyl 3-[2-(cyclopropylamino)ethyl]azetidine-1-carboxylate (300 mg, 1.25 mmol, 1.00 eq) and 4 M hydrogen chloride in dioxane (1.6 mL, 6.24 mmol, 5.00 eq) were combined in methyl alcohol and stirred at r.t. for 18 h. The reaction mixture was concentrated to dryness to give N-[2-(azetidin-3-yl)ethyl]cyclopropanamine dihydrochloride, which was progressed to the next step without further purification.

Cesium carbonate (483 mg, 1.48 mmol, 4.00 eq), 5-(benzotriazol-1-yloxy)-N-(7-fluoro-2-methyl-indazol-5-yl)pyrazine-2-carboxamide (150 mg, 0.371 mmol, 1.00 eq), and N-[2-(azetidin-3-yl)ethyl]cyclopropanamine dihydrochloride (79 mg, 0.371 mmol, 1.00 eq) were combined in N,N-dimethylformamide (5.00 mL) and stirred at 100° C. for 17 h. The residue was partitioned between EtOAc and water. The aqueous phase was extracted with EtOAc. The combined organic phases were dried over magnesium sulfate, filtered, and concentrated in vacuo. The residue was submitted for purification by preparative HPLC to give 5-(3-(2-(cyclopropylamino)ethyl)azetidin-1-yl)-N-(7-fluoro-2-methyl-2H-indazol-5-yl)pyrazine-2-carboxamide. LCMS (ES+) 410 (M+H)+, RT 2.53 min (Analytical method AcHSSC18). $^1$H NMR (400 MHz, DMSO) δ 10.25 (s, 1H), 8.70 (d, J=1.3 Hz, 1H), 8.41 (d, J=2.8 Hz, 1H), 8.14 (d, J=1.6 Hz, 1H), 7.83 (d, J=1.3 Hz, 1H), 7.56 (dd, J=1.7, 13.6 Hz, 1H), 4.25 (dd, J=8.5, 8.5 Hz, 2H), 4.17 (s, 3H), 3.81 (dd, J=5.7, 9.0 Hz, 2H), 2.89-2.81 (m, 1H), 2.57 (dd, J=5.7, 17.2 Hz, 2H), 2.11-2.01 (m, 2H), 1.77 (q, J=7.2 Hz, 2H), 0.37-0.31 (m, 2H), 0.21-0.17 (m, 2H).

Example 322: 5-(3-(2-(cyclopropylamino)ethyl)azetidin-1-yl)-N-(7-fluoro-2-methyl-2H-indazol-5-yl)pyrazine-2-carboxamide

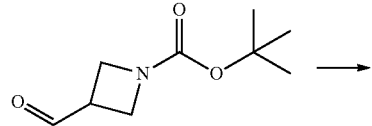

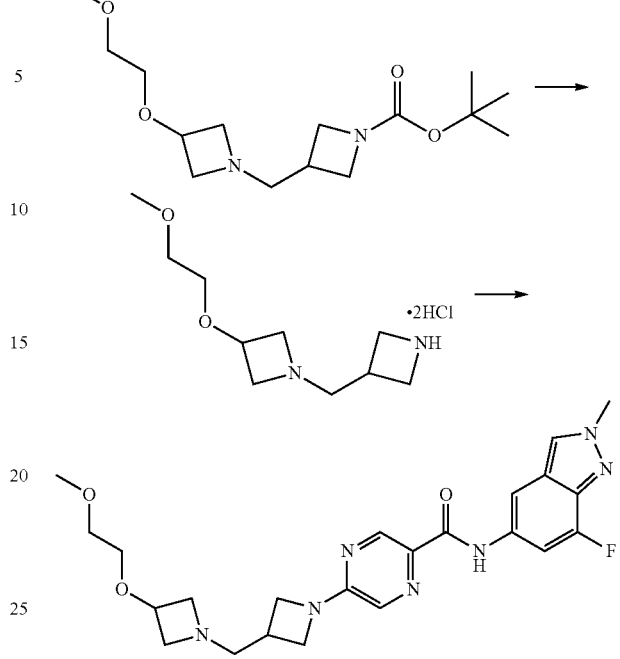

tert-Butyl 3-formylazetidine-1-carboxylate (0.28 g, 1.49 mmol, 1.00 eq), sodium triacetoxyborohydride (0.70 g, 3.28 mmol, 2.20 eq), and 3-(2-methoxyethoxy)azetidine hydrochloride (250 mg, 1.49 mmol, 1.00 eq) were combined in dichloromethane (10.00 mL) and stirred at r.t. for 18 h. Saturated aqueous sodium hydrogen carbonate solution (20 mL) was added to the reaction mixture and stirred vigorously for 10 mins. The organics were collected and washed with water and brine, before passing through a phase separator and concentrating to dryness to give tert-butyl 3-[[3-(2-methoxyethoxy)azetidin-1-yl]methyl]azetidine-1-carboxylate, which was progressed to the next step directly.

4 M Hydrogen chloride in dioxane (0.98 mL, 3.91 mmol, 5.00 eq) and tert-butyl 3-[[3-(2-methoxyethoxy)azetidin-1-yl]methyl]azetidine-1-carboxylate (235 mg, 0.782 mmol, 1.00 eq) were combined in methyl alcohol and stirred at r.t. for 66 h. The reaction mixture was concentrated to dryness to give 1-(azetidin-3-ylmethyl)-3-(2-methoxyethoxy)azetidine dihydrochloride and progressed to the next step directly.

5-Chloro-N-(8-fluoro-2-methyl-imidazo[1,2-a]pyridin-6-yl)pyrazine-2-carboxamide (241 mg, 0.787 mmol, 1.00 eq), cesium carbonate (1026 mg, 3.15 mmol, 4.00 eq), and 1-(azetidin-3-ylmethyl)-3-(2-methoxyethoxy)azetidine·dihydrochloride (215 mg, 0.787 mmol, 1.00 eq) were combined in N,N-dimethylformamide (5.00 mL) and stirred at 110° C. for 17 h. The residue was partitioned between EtOAc and water. The aqueous phase was extracted with EtOAc. The combined organic phases were dried over magnesium sulfate, filtered, and concentrated in vacuo. The residue was purified by preparative HPLC to give N-(8-fluoro-2-methyl-imidazo[1,2-a]pyridin-6-yl)-5-[3-[[3-(2-methoxyethoxy)azetidin-1-yl]methyl]azetidin-1-yl]pyrazine-2-carboxamide. LCMS (ES+) 470 (M+H)+, RT 1.93 min (Analytical method AcHSSC18). $^1$H NMR (400 MHz, DMSO) δ 10.44 (s, 1H), 9.18 (d, J=1.6 Hz, 1H), 8.71 (d, J=1.3 Hz, 1H), 7.90 (d, J=2.8 Hz, 1H), 7.85 (d, J=1.4 Hz, 1H), 7.56 (dd, J=2.1, 13.7 Hz, 1H), 4.23 (dd, J=8.6, 8.6 Hz, 2H), 4.09-4.02 (m, 1H), 3.84 (dd, J=5.4, 9.0 Hz, 2H), 3.55-3.50 (m, 2H), 3.43 (dd, J=4.8, 4.8 Hz, 4H), 3.25 (s, 3H), 2.87-2.76 (m, 3H), 2.69 (d, J=7.4 Hz, 2H), 2.35 (s, 3H).

Example 323: 5-(3-(((2,2-difluoroethyl)amino)methyl)azetidin-1-yl)-N-(7-fluoro-2-methyl-2H-indazol-5-yl)pyrazine-2-carboxamide

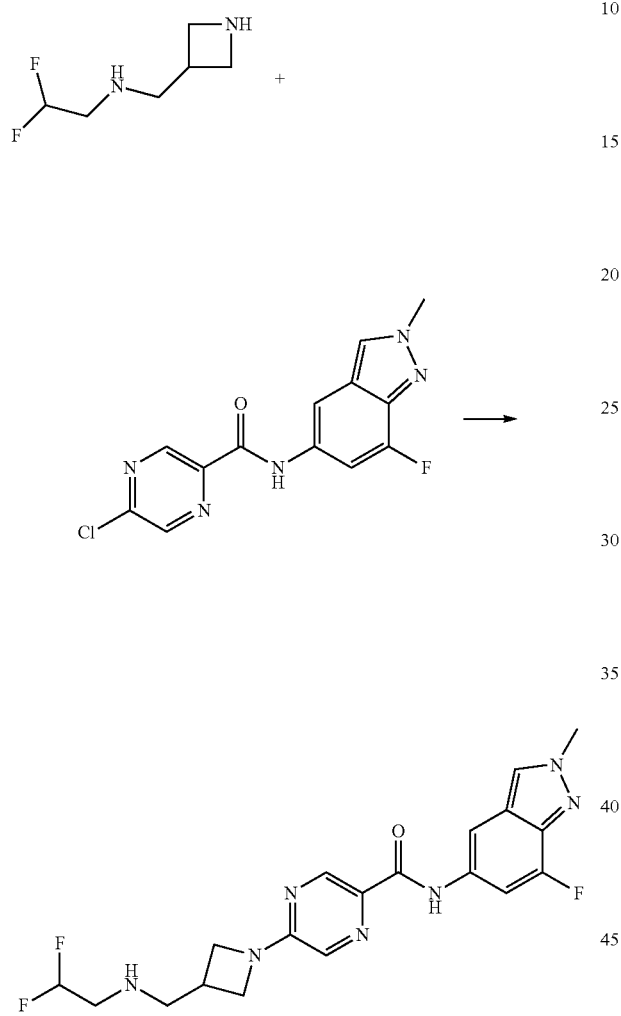

5-Chloro-N-(7-fluoro-2-methyl-indazol-5-yl)pyrazine-2-carboxamide (50 mg, 0.164 mmol) and N-(azetidin-3-ylmethyl)-2,2-difluoroethan-1-amine dihydrochloride (40 mg, 0.18 mmol) were dissolved in acetonitrile (2 mL), and triethylamine (0.068 mL, 0.491 mmol) was added. The reaction was stirred at 45° C. for 18 h. The reaction was cooled to r.t. and the formed solid was collected by filtration. The solid was washed with water and acetonitrile, then was dried in vac oven overnight to give the title compound. LCMS (ES+) 420 (M+H)+, RT 2.42 min (Analytical method AcHSSC18); $^1$H NMR (400 MHz, DMSO) δ 10.27 (1H, s), 8.72-8.72 (1H, m), 8.43 (1H, d, J=2.8 Hz), 8.16 (1H, d, J=1.6 Hz), 7.86-7.85 (1H, m), 7.58 (1H, dd, J=1.6, 13.7 Hz), 6.01 (1H, tt, J=4.3, 56.2 Hz), 4.19-4.18 (5H, m), 3.88 (2H, dd, J=4.6, 8.9 Hz), 2.96-2.88 (6H, m); $^{19}$F NMR (400 MHz, DMSO) δ −120.45 (td, J=16.2, 56.8 Hz, 2F), −128.42 (dd, J=3.5, 13.8 Hz, 1F).

Example 324 and Example 325: 5-((3S,4R)-3-(ethylamino)-4-fluoropyrrolidin-1-yl)-N-(8-methoxy-2-methylimidazo[1,2-a]pyrazin-6-yl)pyrazine-2-carboxamide and 5-((3R,4S)-3-(ethylamino)-4-fluoropyrrolidin-1-yl)-N-(8-methoxy-2-methylimidazo[1,2-a]pyrazin-6-yl)pyrazine-2-carboxamide

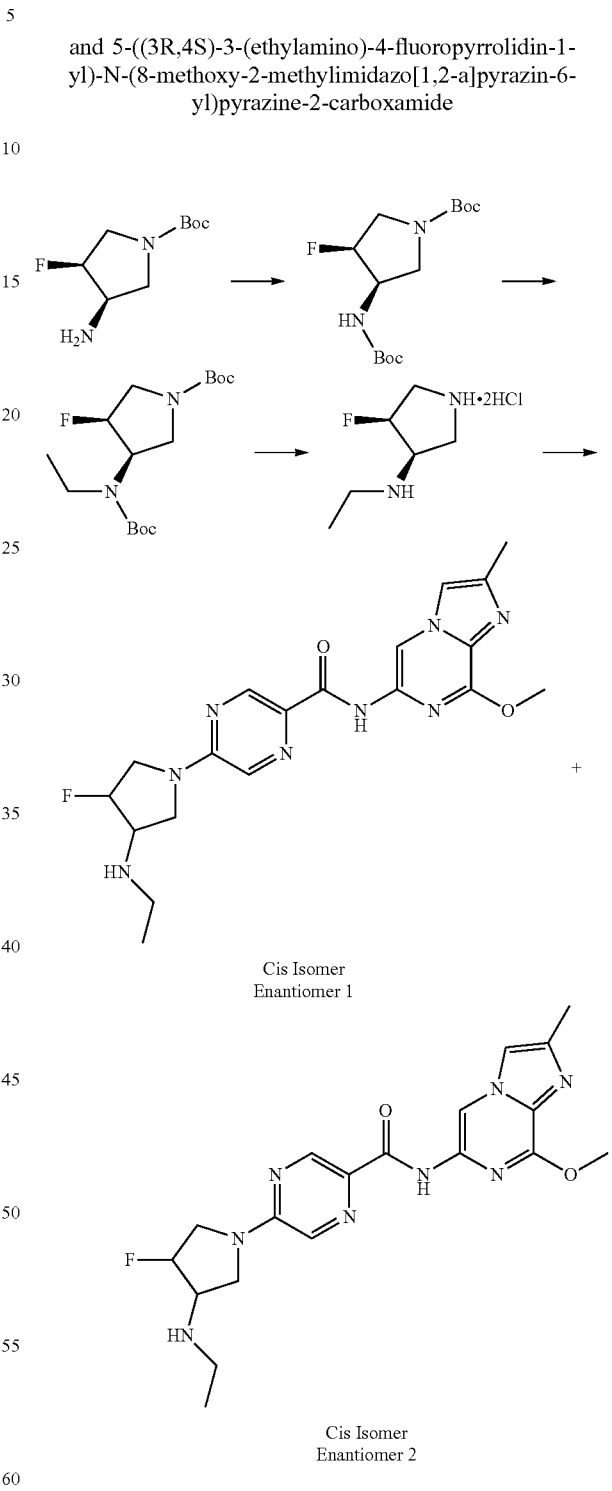

Cis-tert-butyl-3-amino-4-fluoropyrrolidine-1-carboxylate (2.17 g, 10.64 mmol), dichloromethane (40 mL), triethylamine (2 mL), and di-tert-butyl decarbonate (2.55 g, 11.7 mmol) were combined and stirred at room temperature for 18 hours. The reaction mixture was then evaporated to dryness to give tert-butyl (3R*,4S*)-3-((tert-butoxycarbonyl)amino)-4-fluoropyrrolidine-1-carboxylate, which was used crude in the next step without further purification.

tert-Butyl (3R*,4S*)-3-((tert-butoxycarbonyl)amino)-4-fluoropyrrolidine-1-carboxylate (crude from previous step) and DMF (20 mL) were combined at room temperature under a nitrogen atmosphere. NaH (60% in oil) (511 mg, 12.77 mmol) was added, followed by EtI (1 mL, 12.77 mmol). The reaction mixture was stirred for 3 days, then diluted with EtOAc, washed with water (4×), brine (1×), and evaporated to dryness to give tert-butyl (3R*,4S*)-3-((tert-butoxycarbonyl)(ethyl)amino)-4-fluoropyrrolidine-1-carboxylate, which was used crude in the next step without further purification.

tert-Butyl (3R*,4S*)-3-((tert-butoxycarbonyl)(ethyl)amino)-4-fluoropyrrolidine-1-carboxylate (crude from previous step), methanol (15 mL), and 4N HCl in dioxane (15 mL) were combined and stirred for 16 hours. The reaction mixture was then evaporated to dryness to give (3R*,4S*)—N-ethyl-4-fluoropyrrolidin-3-amine 2HCl, which was used crude in the next step without further purification.

(3R*,4S*)—N-ethyl-4-fluoropyrrolidin-3-amine 2HCl (234 mg, 1.14 mmol), 5-chloro-N-(8-methoxy-2-methylimidazo[1,2-a]pyrazin-6-yl)pyrazine-2-carboxamide (364 mg, 1.14 mmol), cesium carbonate (1.48 g, 4.56 mmol), and dioxane (20 mL) were combined in a sealed tube and hot block heated to 100° C. overnight. The cesium salts were then filtered off, rinsing with EtOAc. The organic filtrate was evaporated to dryness and purified by prep HPLC, followed by chiral SFC purification to give:

Example 324 Cis Isomer, Enantiomer 1

5-(3-(ethylamino)-4-fluoropyrrolidin-1-yl)-N-(8-methoxy-2-methylimidazo[1,2-a]pyrazin-6-yl)pyrazine-2-carboxamide. LCMS (ES+) 415 (M+H)+, RT 1.95 min (Analytical method AcHSSC18). $^1$H NMR (400 MHz, DMSO) δ 9.56 (s, 1H), 8.94 (s, 1H), 8.81 (d, J=1.1 Hz, 1H), 8.12 (s, 1H), 7.98 (s, 1H), 5.37 (d, J=54.4 Hz, 1H), 4.10 (s, 3H), 4.07-3.93 (m, 2H), 3.24 (dd, J=10.1, 10.1 Hz, 2H), 2.80-2.67 (m, 3H), 2.37 (s, 3H), 2.01 (s, 1H), 1.11 (dd, J=7.1, 7.1 Hz, 3H).

Example 325 Cis Isomer, Enantiomer 2

5-(3-(ethylamino)-4-fluoropyrrolidin-1-yl)-N-(8-methoxy-2-methylimidazo[1,2-a]pyrazin-6-yl)pyrazine-2-carboxamide. LCMS (ES+) 415 (M+H)+, RT 1.95 min (Analytical method AcHSSC18). $^1$H NMR (400 MHz, DMSO) δ 9.56 (s, 1H), 8.94 (s, 1H), 8.81 (d, J=1.1 Hz, 1H), 8.12 (s, 1H), 7.98 (s, 1H), 5.37 (d, J=54.4 Hz, 1H), 4.10 (s, 3H), 4.07-3.93 (m, 2H), 3.24 (dd, J=10.1, 10.1 Hz, 2H), 2.80-2.67 (m, 3H), 2.37 (s, 3H), 2.01 (s, 1H), 1.11 (dd, J=7.1, 7.1 Hz, 3H).

The following examples were prepared by the same route, using 5-chloro-N-(8-fluoro-2-methylimidazo[1,2-a]pyridin-6-yl)pyrazine-2-carboxamide in place of 5-chloro-N-(8-methoxy-2-methyl-imidazo[1,2-a]pyrazin-6-yl)pyrazine-2-carboxamide.

| Example | Structure | Analytical data |
|---|---|---|
| Example 326 (chiral separation, chirality arbitrarily assigned) | 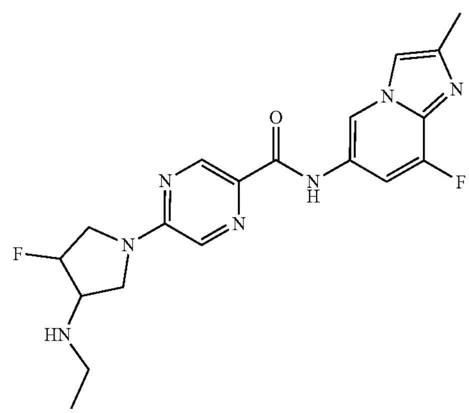 | LCMS (ES+) 402 (M + H)+, RT 1.71 min (Analytical method AcHSSC18) $^1$H NMR (400 MHz, DMSO) d 10.49 (s, 1H), 9.22 (d, J = 1.6 Hz, 1H), 8.80 (d, J = 1.3 Hz, 1H), 8.06 (s, 1H), 7.92 (d, J = 2.8 Hz, 1H), 7.60 (dd, J = 1.5, 13.0 Hz, 1H), 5.38 (d, J = 54.6 Hz, 1H), 4.08-3.93 (m, 2H), 3.90-3.75 (m, 1H), 3.63-3.53 (m, 1H), 3.24 (dd, J = 10.4, 10.4 Hz, 1H), 2.81-2.64 (m, 2H), 2.37 (s, 3H), 2.02-1.98 (m, 1H), 1.11 (dd, J = 7.2, 7.2 Hz, 3H). |
| | Cis Isomer, Enantiomer 1 | |
| Example 327 | 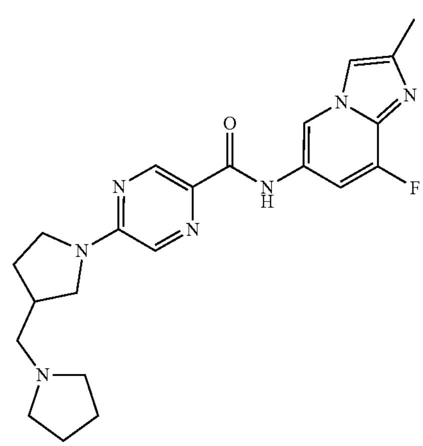 [SMILES: Cc1cn2cc(NC(=O)c3cnc(N4CCC(CN5CCCC5)C4)cn3)cc(F)c2n1] | LCMS (ES+) 424.309 (M + H)+, RT 1.87 min (Analytical method AcHSSC18) $^1$H NMR (400 MHz, DMSO) d 10.45 (s, 1H), 9.22 (d, J = 1.5 Hz, 1H), 8.77 (d, J = 1.3 Hz, 1H), 8.01 (d, J = 1.1 Hz, 1H), 7.92 (d, J = 2.8 Hz, 1H), 7.60 (dd, J = 1.6, 13.2 Hz, 1H), 3.82-3.69 (m, 2H), 3.59-3.52 (m, 1H), 3.33-3.27 (m, 1H), 2.55-2.53 (m, 7H), 2.59-2.47 (m, 7H), 2.37 (s, 3H), 2.18 (s, 1H), 1.74 (s, 4H). |

Example 328 and Example 329: (R)-2-(3-(cyclopropylamino)pyrrolidin-1-yl)-N-(2,8-dimethylimidazo[1,2-a]pyrazin-6-yl)pyrimidine-5-carboxamide and (S)-2-(3-(cyclopropylamino)pyrrolidin-1-yl)-N-(2,8-dimethylimidazo[1,2-a]pyrazin-6-yl)pyrimidine-5-carboxamide

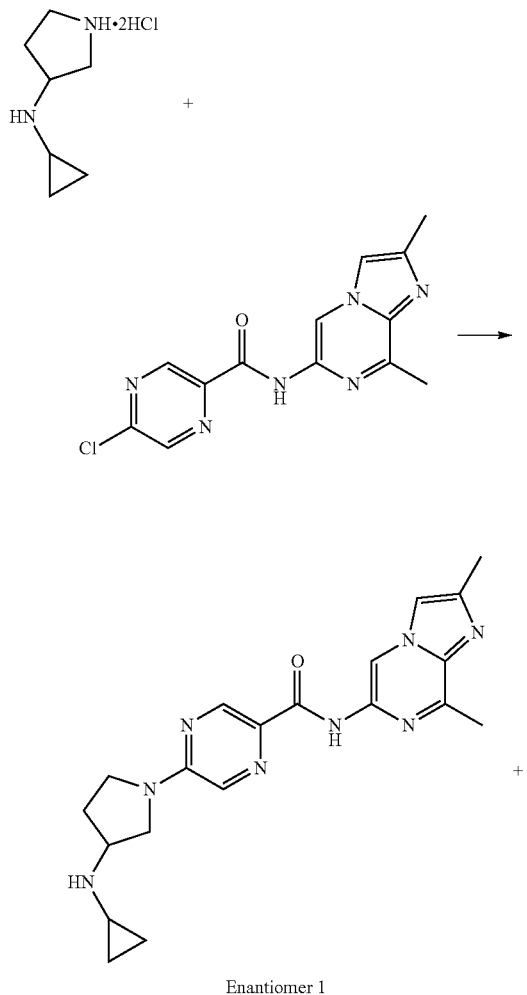

Enantiomer 1

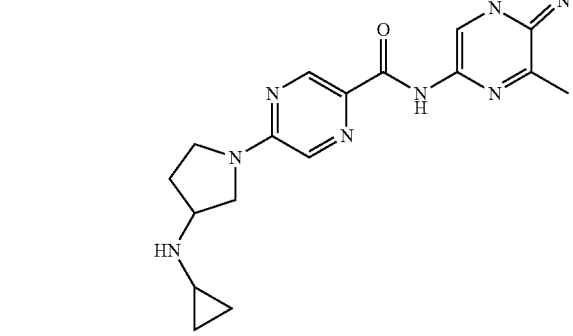

Enantiomer 2

N-Cyclopropylpyrrolidin-3-amine 2HCl (157 mg, 0.79 mmol), 2-chloro-N-(2,8-dimethylimidazo[1,2-a]pyrazin-6-yl)pyrimidine-5-carboxamide (240 mg, 0.79 mmol), cesium carbonate (650 mg, 2 mmol), and DMF (5 mL) were combined and hot block heated to 100° C. for 1 hour. The reaction mixture was cooled to room temperature. Cesium salts were filtered off, and the product mixture was purified by prep HPLC, followed by chiral SFC purification to give:

Example 328

Enantiomer 1 2-(3-(cyclopropylamino)pyrrolidin-1-yl)-N-(2,8-dimethylimidazo[1,2-a]pyrazin-6-yl)pyrimidine-5-carboxamide. LCMS (ES+) 393 (M+H)+, RT 1.85 min (Analytical method AcHSSC18). $^1$H NMR (400 MHz, DMSO) δ 10.72 (s, 1H), 9.20 (s, 1H), 8.97 (s, 2H), 7.99 (s, 1H), 3.76-3.41 (m, 6H), 2.75 (s, 3H), 2.42 (s, 3H), 2.16-2.09 (m, 2H), 1.97-1.88 (m, 1H), 0.43 (d, J=6.5 Hz, 2H), 0.31-0.22 (m, 2H).

Example 329

Enantiomer 2 2-(3-(cyclopropylamino)pyrrolidin-1-yl)-N-(2,8-dimethylimidazo[1,2-a]pyrazin-6-yl)pyrimidine-5-carboxamide. LCMS (ES+) 393 (M+H)+, RT 1.85 min (Analytical method AcHSSC18). $^1$H NMR (400 MHz, DMSO) δ 10.72 (s, 1H), 9.20 (s, 1H), 8.97 (s, 2H), 7.99 (s, 1H), 3.76-3.41 (m, 6H), 2.75 (s, 3H), 2.42 (s, 3H), 2.16-2.09 (m, 2H), 1.97-1.88 (m, 1H), 0.43 (d, J=6.5 Hz, 2H), 0.31-0.22 (m, 2H).

The following examples were prepared by the same route using cis-4-fluoro-N-methylpyrrolidin-3-amine 2HCl.

| Example | Structure | Analytical data |
|---|---|---|
| Example 330 (chiral separation, chirality arbitrarily assigned) | Cis Isomer, Enantiomer 1 | LCMS (ES+) 385 (M + H)+, RT 1.74 min (Analytical method AcHSSC18) $^1$H NMR (400 MHz, DMSO) δ 10.76 (s, 1H), 9.19 (s, 1H), 8.99-8.97 (m, 2H), 7.98 (s, 1H), 5.34 (td, J = 3.1, 54.5 Hz, 1H), 4.04-3.89 (m, 2H), 3.86-3.70 (m, 1H), 3.46-3.39 (m, 1H), 3.18 (dd, J = 10.6, 10.6 Hz, 1H), 2.73 (s, 3H), 2.41 (s, 3H), 2.4 (s, 3H), 2.01 (s, 1H). |

| Example | Structure | Analytical data |
|---|---|---|
| Example 331 (chiral separation, chirality arbitrarily assigned) | 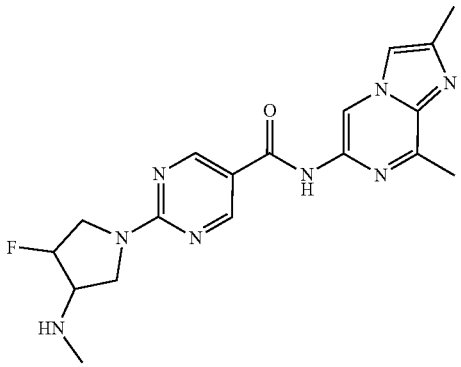<br>Cis Isomer, Enantiomer 2 | LCMS (ES+) 385 (M + H)+, RT 1.74 min (Analytical method AcHSSC18)<br>$^1$H NMR (400 MHz, DMSO) δ 10.76 (s, 1H), 9.19 1H), 8.99-8.97 (m, 2H), 7.98 (s, 1H), 5.34 (td, J = 3.1, 54.5 Hz, 1H), 4.04-3.89 (m, 2H), 3.86-3.70 (m, 1H), 3.46-3.39 (m, 1H), 3.18 (dd, J = 10.6, 10.6 Hz, 1H), 2.73 (s, 3H), 2.41 (s, 3H), 2.40 (s, 3H), 2.01 (s, 1H). |

The following example was prepared by the same route using 2-chloro-N-(8-fluoro-2-methylimidazo[1,2-a]pyridin-6-yl)pyrimidine-5-carboxamide and cis-4-fluoro-N-methylpyrrolidin-3-amine 2HCl.

| Example | Structure | Analytical data |
|---|---|---|
| Example 332 (chiral separation, chirality arbitrarily assigned) | 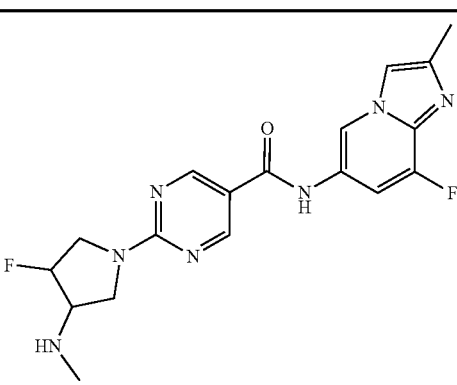<br>Cis Isomer, Enantiomer 1 | LCMS (ES+) 388 (M + H)+, RT 3.29 min (Analytical method BicarbBEHC18)<br>$^1$H NMR (400 MHz, DMSO) δ 10.27 (s, 1H), 9.08 (d, J = 1.6 Hz, 1H), 8.96-8.94 (m, 2H), 7.94 (d, J = 2.8 Hz, 1H), 7.31 (dd, J = 1.5, 12.8 Hz, 1H), 5.37 (td, J = 3.0, 54.5 Hz, 1H), 4.07-3.93 (m, 2H), 3.88-3.73 (m, 1H), 3.49-3.41 (m, 1H), 3.21 (dd, J = 10.6, 10.6 Hz, 1H), 2.43 (s, 3H), 2.43 (s, 3H), 2.38 (s, 3H), 2.03 (s, 1H). |

The following examples were prepared by the same route using 2-chloro-N-(8-fluoro-2-methylimidazo[1,2-a]pyridin-6-yl)pyrimidine-5-carboxamide and cis-4-fluoro-N-methylpyrrolidin-3-amine 2HCl.

| Example | Structure | Analytical data |
|---|---|---|
| Example 333 (chiral separation, chirality arbitrarily assigned) | Cis Isomer, Enantiomer 1 | LCMS (ES+) 399 (M + H)+, RT 1.74 min (Analytical method AcHSSC18) <br> $^1$H NMR (400 MHz, DMSO) δ 10.76 (s, 1H), 9.18 (s, 1H), 8.98 (d, J = 2.6 Hz, 2H), 7.97 (s, 1H), 5.30 (td, J = 3.0, 54.1 Hz, 1H), 4.04-3.89 (m, 2H), 3.84-3.69 (m, 1H), 3.57-3.44 (m, 1H), 3.19 (dd, J = 10.7, 10.7 Hz, 1H), 2.73 (s, 2H), 2.40 (s, 3H), 1.08 (dd, J = 7.1, 7.1 Hz, 3H). |
| Example 334 (chiral separation, chirality arbitrarily assigned) | Cis Isomer, Enantiomer 2 | LCMS (ES+) 399 (M + H)+, RT 1.74 min (Analytical method AcHSSC18) <br> $^1$H NMR (400 MHz, DMSO) δ 10.76 (s, 1H), 9.18 (s, 1H), 8.98 (d, J = 2.6 Hz, 2H), 7.97 (s, 1H), 5.30 (td, J = 3.0, 54.1 Hz, 1H), 4.04-3.89 (m, 2H), 3.84-3.69 (m, 1H), 3.57-3.44 (m, 1H), 3.19 (dd, J = 10.7, 10.7 Hz, 1H), 2.73 (s, 2H), 2.40 (s, 3H), 1.08 (dd, J = 7.1, 7.1 Hz, 3H). |

Example 335: 2-[3-[[cyclopropyl(methyl)amino]methyl]azetidin-1-yl]-N-(8-fluoro-2-methyl-imidazo[1,2-a]pyridin-6-yl)pyrimidine-5-carboxamide

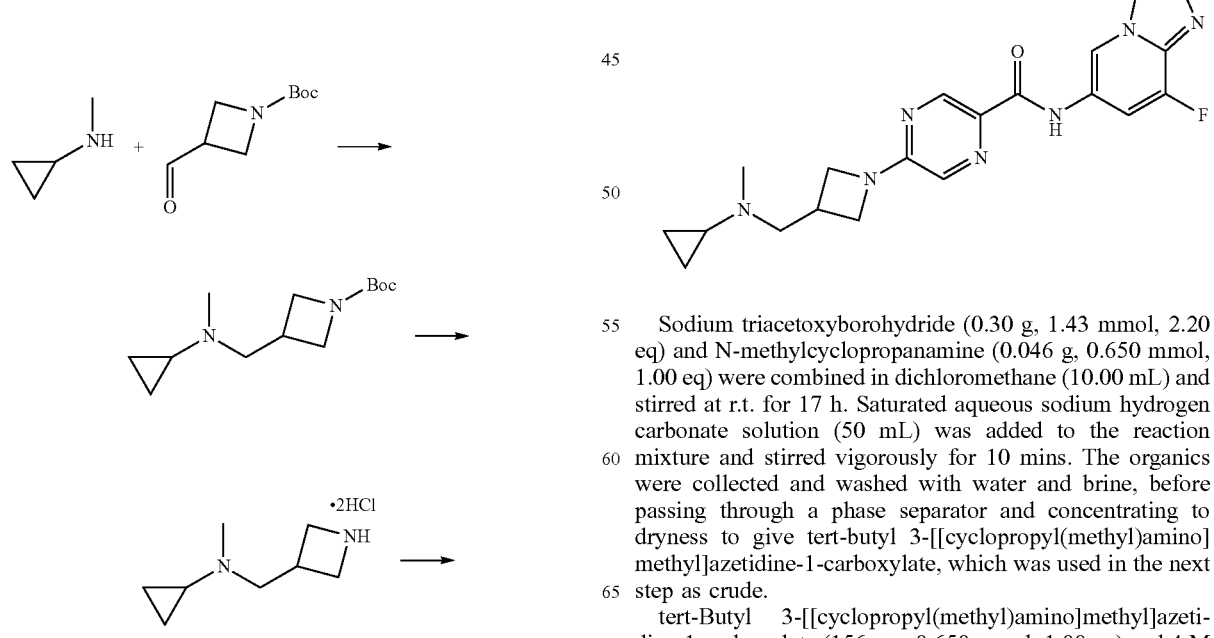

Sodium triacetoxyborohydride (0.30 g, 1.43 mmol, 2.20 eq) and N-methylcyclopropanamine (0.046 g, 0.650 mmol, 1.00 eq) were combined in dichloromethane (10.00 mL) and stirred at r.t. for 17 h. Saturated aqueous sodium hydrogen carbonate solution (50 mL) was added to the reaction mixture and stirred vigorously for 10 mins. The organics were collected and washed with water and brine, before passing through a phase separator and concentrating to dryness to give tert-butyl 3-[[cyclopropyl(methyl)amino]methyl]azetidine-1-carboxylate, which was used in the next step as crude.

tert-Butyl 3-[[cyclopropyl(methyl)amino]methyl]azetidine-1-carboxylate (156 mg, 0.650 mmol, 1.00 eq) and 4 M hydrogen chloride in dioxane (0.81 mL, 3.25 mmol, 5.00 eq) were stirred in methyl alcohol (5.00 mL) at r.t. for 6 h, before concentrating to dryness to give N-(azetidin-3-ylmethyl)-N-methylcyclopropanamine dihydrochloride, which was used in the next step as crude.

2-Chloro-N-(8-fluoro-2-methyl-imidazo[1,2-a]pyridin-6-yl)pyrimidine-5-carboxamide (100 mg, 0.327 mmol, 1.00 eq), cesium carbonate (426 mg, 1.31 mmol, 4.00 eq), and N-(azetidin-3-ylmethyl)-N-methyl-cyclopropanamine dihydrochloride (70 mg, 0.327 mmol, 1.00 eq) were combined in N,N-dimethylformamide (5.00 mL) and stirred at 110° C. for 17 h. The reaction mixture was partitioned between EtOAc and water. The aqueous phase was extracted with EtOAc. The combined organic phases were dried over magnesium sulfate, filtered, and concentrated in vacuo. The residue was purified by preparative HPLC to give 2-[3-[[cyclopropyl(methyl)amino]methyl]azetidin-1-yl]-N-(8-fluoro-2-methyl-imidazo[1,2-a]pyridin-6-yl)pyrimidine-5-carboxamide. LCMS (ES+) 410 (M+H)+, RT 1.74 min (Analytical method AcHSSC18). ¹H NMR (400 MHz, DMSO) δ 10.18 (s, 1H), 9.04 (d, J=1.6 Hz, 1H), 8.86 (s, 2H), 7.92 (d, J=2.8 Hz, 1H), 7.28 (dd, J=1.6, 12.8 Hz, 1H), 4.22 (dd, J=8.9, 8.9 Hz, 2H), 3.76 (dd, J=5.5, 9.6 Hz, 2H), 3.02-2.93 (m, 1H), 2.77 (d, J=7.5 Hz, 2H), 2.35 (s, 3H), 2.28 (s, 3H), 1.68-1.62 (m, 1H), 0.48-0.43 (m, 2H), 0.32-0.27 (m, 2H).

Example 336 and Example 337: (S)-5-(3-((cyclopropylamino)methyl)-2-oxopyrrolidin-1-yl)-N-(8-fluoro-2-methylimidazo[1,2-a]pyridin-6-yl)pyrazine-2-carboxamide and and (R)-5-(3-((cyclopropylamino)methyl)-2-oxopyrrolidin-1-yl)-N-(8-fluoro-2-methylimidazo[1,2-a]pyridin-6-yl)pyrazine-2-carboxamide

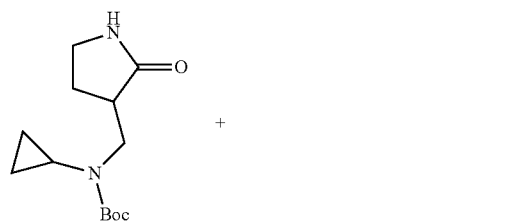

+

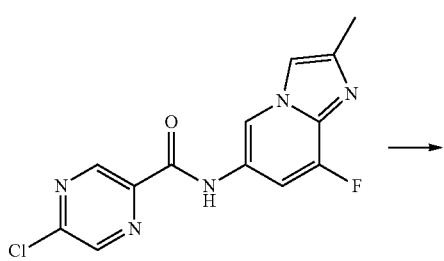

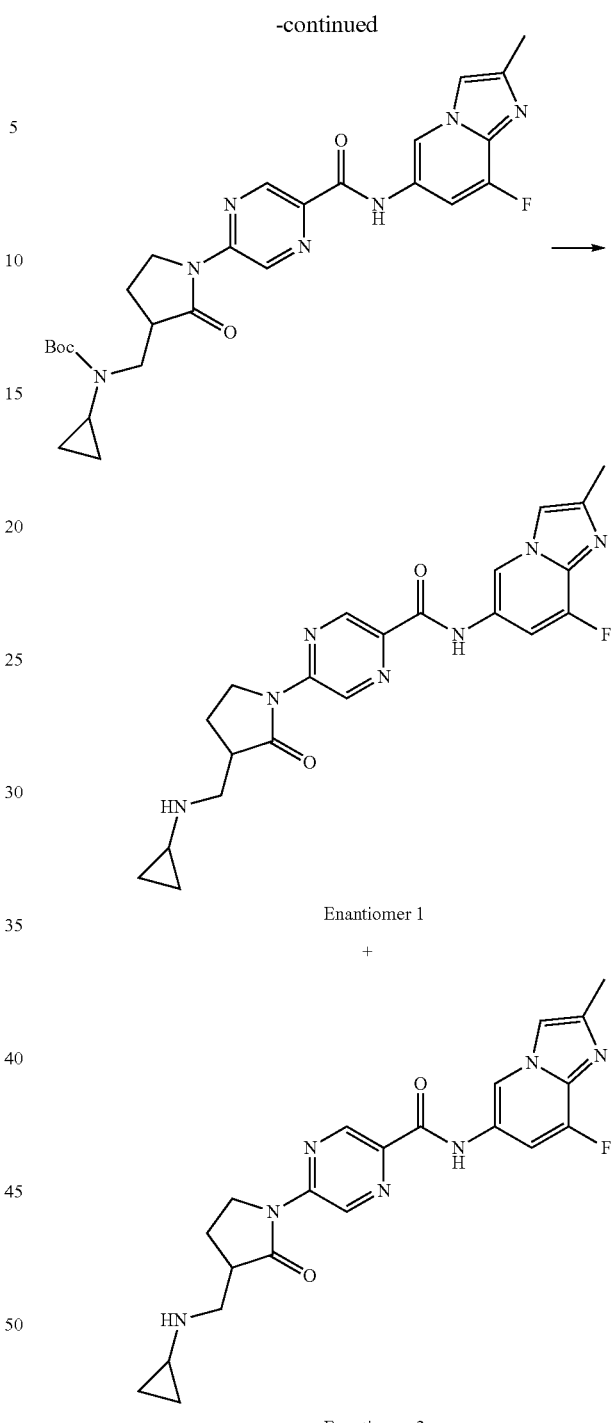

Enantiomer 1

+

Enantiomer 2

To a solution of tert-butyl N-cyclopropyl-N-[(2-oxopyrrolidin-3-yl)methyl]carbamate (intermediate 2, 202 mg, 0.794 mmol) and 5-chloro-N-(8-fluoro-2-methyl-imidazo[1,2-a]pyridin-6-yl)pyrazine-2-carboxamide (243 mg, 0.74 mmol) in 1,4-dioxane (5 mL), was added cesium carbonate (388 mg, 1.19 mmol), and the mixture was degassed under nitrogen by sparging for 20 min Xantphos (46 mg, 0.0794 mmol) and tris(dibenzylideneacetone)dipalladium(0) (18 mg, 0.0199 mmol) were added and the mixture heated to 100° C. under inert atmosphere for 18 h. The reaction mixture was cooled to r.t., filtered, and the collected solid washed with DCM. The collected liquid was concentrated in vacuo to give a residue, which was purified by achiral SFC to give tert-butyl cyclopropyl((1-(5-((8-fluoro-2-methylimidazo[1,2-a]pyridin-6-yl)carbamoyl)pyrazin-2-yl)-2-oxopyrrolidin-3-yl)methyl)carbamate. LCMS (ES+) 523 (M+H)+.

tert-Butyl cyclopropyl((1-(5-((8-fluoro-2-methylimidazo[1,2-a]pyridin-6-yl)carbamoyl)pyrazin-2-yl)-2-oxopyrrolidin-3-yl)methyl)carbamate (195 mg, 0.372 mmol) was dissolved in dichloromethane (3 mL), and trifluoroacetic acid (1 mL) was added at r.t. The reaction was stirred at r.t. for 1 h. The solvent was removed in vacuo to give a residue, which was purified by SCX chromatography (5 g, eluting with MeOH/DCM 50% and then 10% 7N NH$_3$ in MeOH/MeOH. The ammonical fractions were combined and the solvent removed in vacuo to give a mixture of the title compounds. The sample was further purified by achiral SFC. The enantiomers were separated by chiral SFC, to give:

Example 336, Enantiomer 1

5-(3-((cyclopropylamino)methyl)-2-oxopyrrolidin-1-yl)-N-(8-fluoro-2-methylimidazo[1,2-a]pyridin-6-yl)pyrazine-2-carboxamide. LCMS (ES+) 424 (M+H)+, RT 3.73 min (Analytical method BicarbBEHC18); RT 5.59 min (SFC1, LUX CELLULOSE-3+0.5% DEAISO 25% IPA SOL6); $^1$H NMR (400 MHz, DMSO) δ 10.92 (s, 1H), 9.74 (s, 1H), 9.27 (s, 1H), 9.15 (s, 1H), 7.99-7.96 (m, 1H), 4.16-4.09 (m, 1H), 3.97-3.89 (m, 1H), 3.12-3.02 (m, 2H), 2.90 (dd, J=7.1, 10.9 Hz, 1H), 2.42-2.31 (m, 5H), 2.23-2.21 (m, 1H), 2.08-1.97 (m, 1H), 0.50-0.44 (m, 2H), 0.39-0.29 (m, 2H); $^{19}$F NMR (400 MHz, DMSO) δ −131.83 (dd, J=3.5, 12.3 Hz, 1F).

Example 337, Enantiomer 2

5-(3-((cyclopropylamino)methyl)-2-oxopyrrolidin-1-yl)-N-(8-fluoro-2-methylimidazo[1,2-a]pyridin-6-yl)pyrazine-2-carboxamide. LCMS (ES+) 424 (M+H)+, RT 3.73 min (Analytical method BicarbBEHC18); RT 6.95 min (SFC1, LUX CELLULOSE-3+0.5% DEAISO 25% IPA SOL6); 1H NMR (400 MHz, DMSO) δ 10.92 (s, 1H), 9.74 (s, 1H), 9.27 (s, 1H), 9.15 (s, 1H), 7.99-7.96 (m, 1H), 4.16-4.09 (m, 1H), 3.97-3.89 (m, 1H), 3.12-3.02 (m, 2H), 2.90 (dd, J=7.1, 10.9 Hz, 1H), 2.42-2.31 (m, 5H), 2.23-2.21 (m, 1H), 2.08-1.97 (m, 1H), 0.50-0.44 (m, 2H), 0.39-0.29 (m, 2H); $^{19}$F NMR (400 MHz, DMSO) δ −131.83 (dd, J=3.5, 12.3 Hz, 1F).

Example 338: N-(8-fluoro-2-methylimidazo[1,2-a]pyridin-6-yl)-5-(5-oxa-2,8-diazaspiro[3.5]nonan-2-yl)pyrazine-2-carboxamide

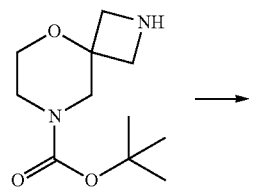

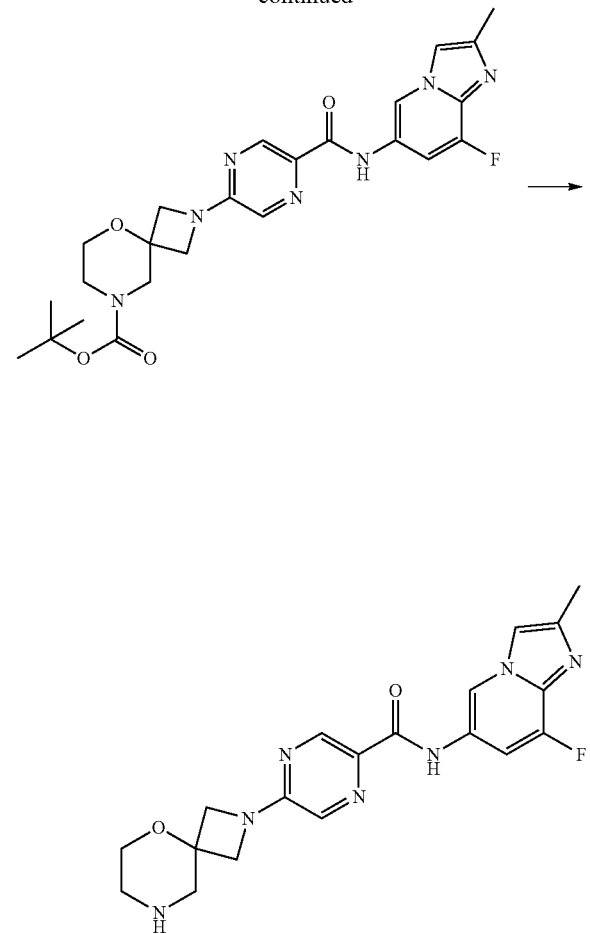

Cesium carbonate (426 mg, 1.31 mmol), 5-chloro-N-(8-fluoro-2-methyl-imidazo[1,2-a]pyridin-6-yl)pyrazine-2-carboxamide (100 mg, 0.327 mmol), and tert-butyl 5-oxa-2,8-diazaspiro[3.5]nonane-8-carboxylate (75 mg, 0.327 mmol) were combined in N,N-dimethylformamide (3 mL) and stirred in a sealed reaction tube at 100° C. for 3 h. The reaction was cooled to r.t. and filtered. The DMF was removed in vacuo and the residue was purified by preparative HPLC to give the desired product.

tert-Butyl 2-[5-[(8-fluoro-2-methyl-imidazo[1,2-a]pyridin-6-yl)carbamoyl]pyrazin-2-yl]-5-oxa-2,8-diazaspiro[3.5]nonane-8-carboxylate (195 mg, 0.392 mmol) was dissolved in dichloromethane (3 mL), and trifluoroacetic acid (1 mL) added at r.t. The reaction was stirred at r.t. for 1 h. The solvent was removed in vacuo to give a residue. The residue was purified by passing through an SCX column (2 g, eluting with MeOH and 10% 7N NH$_3$ in MeOH/MeOH). The ammonical fractions were combined and the solvent removed in vacuo. The residue was freeze-dried from 1:1 CH$_3$CN/H$_2$O to give the title compound. LCMS (ES+) 398 (M+H)+, RT 1.82 min (Analytical method AcHSSC18); $^1$H NMR (400 MHz, DMSO) δ 10.50 (s, 1H), 9.22 (d, J=1.5 Hz, 1H), 8.78 (d, J=1.3 Hz, 1H), 7.97 (d, J=1.3 Hz, 1H), 7.94 (d, J=2.3 Hz, 1H), 7.61 (dd, J=1.5, 13.1 Hz, 1H), 4.16 (d, J=10.1 Hz, 2H), 4.06 (d, J=9.9 Hz, 2H), 3.66 (dd, J=4.5, 4.5 Hz, 2H), 2.96 (s, 2H), 2.75 (dd, J=4.5, 4.5 Hz, 2H), 2.39 (s, 3H). $^{19}$F NMR (400 MHz, DMSO) δ −132.14 (dd, J=3.2, 13.3 Hz, 1F).

Example 339: N-(4-fluoro-2-methylbenzo[d]oxazol-6-yl)-5-(3-methylpiperazin-1-yl)pyrazine-2-carboxamide

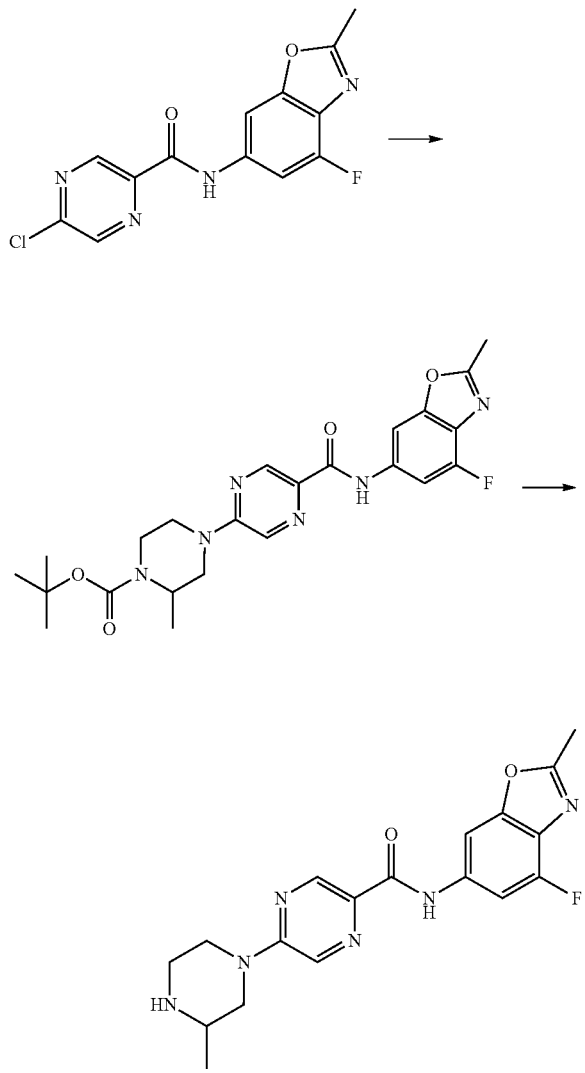

5-Chloro-N-(4-fluoro-2-methyl-1,3-benzoxazol-6-yl)pyrazine-2-carboxamide (150 mg, 0.489 mmol) and Boc-2-methylpiperazine (98 mg, 0.489 mmol) were dissolved in 1,4-dioxane (4 mL), and triethylamine (0.20 mL, 1.47 mmol) was added. The reaction was heated in a sealed tube at 100° C. overnight. The reaction was cooled to r.t. to form a solid suspension. The solid precipitate was collected by filtration and washed with EtOAc to give the desired product.

tert-Butyl 4-[5-[(4-fluoro-2-methyl-1,3-benzoxazol-6-yl)carbamoyl]pyrazin-2-yl]-2-methyl-piperazine-1-carboxylate (100 mg, 0.213 mmol) was dissolved in dichloromethane (3 mL), and trifluoroacetic acid (1.0 mL) was added. The reaction was stirred at r.t. for 1 h. The solvent was removed in vacuo to give a residue. The residue was dissolved in DCM (3 mL) and treated with MP-carbonate (to free base the TFA salt) at r.t. overnight. The solid MP-carbonate was removed by filtration, and the DCM removed in vacuo to give a residue. The residue was freeze dried from 1:1 $CH_3CN/H_2O$ to give the title compound. LCMS (ES+) 371.2 (M+H)+, RT 2.69 min (Analytical method AcHSSC18); $^1$H NMR (400 MHz, DMSO) δ 10.62 (s, 1H), 8.80 (d, J=1.3 Hz, 1H), 8.36 (d, J=1.3 Hz, 1H), 8.24 (d, J=1.5 Hz, 1H), 7.88 (dd, J=1.7, 12.6 Hz, 1H), 4.46-4.37 (m, 2H), 3.07-2.96 (m, 2H), 2.84-2.62 (m, 6H), 1.11 (d, J=6.3 Hz, 3H), 1.08-1.02 (m 1H); $^{19}$F NMR (400 MHz, DMSO) δ −126.12 (s, 1F).

The following examples were prepared using an analogous procedure:

| | Structure | Amine | Analytical data |
|---|---|---|---|
| Example 340 | 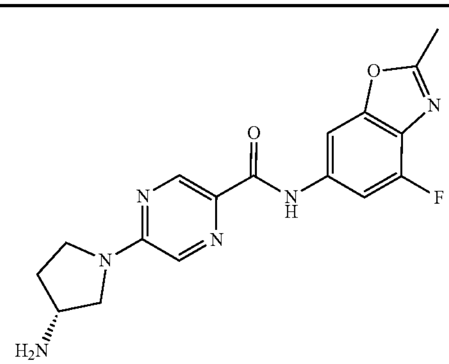 | tert-butyl (R)-pyrrolidin-3-ylcarbamate | LCMS (ES+) 357 (M + H)+, RT 3.14 min (Analytical method BicarbBEHC18); $^1$H NMR (400 MHz, DMSO) δ 10.61 (s, 1H), 8.81 (d, J = 1.5 Hz, 1H), 8.24 (d, J = 1.8 Hz, 1H), 8.01 (d, J = 1.3 Hz, 1H), 7.88 (dd, J = 1.8, 12.6 Hz, 1H), 3.87-3.60 (m, 4H), 2.67 (s, 3H), 2.42-2.25 (m, 2H), 2.20-2.12 (m, 1H), 1.85 (brs, 1H); $^{19}$F NMR (400 MHz, DMSO) δ −126.13 (d, J = 13.0 Hz, 1F). |

The following examples were prepared using an analogous procedure using the stated chloropyrazine and the appropriate amine partner:

| | Structure | Pyrazine intermediate | Analytical data |
|---|---|---|---|
| Example 341 | 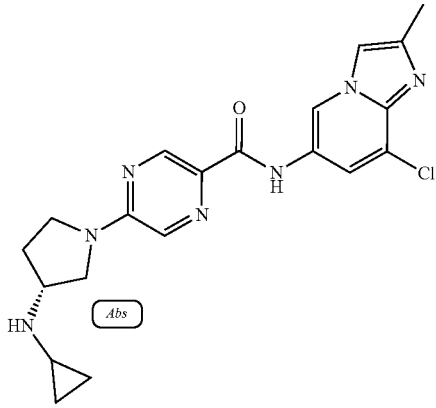 [SMILES: Cc1cn2cc(NC(=O)c3cnc(N4CC[C@@H](NC5CC5)C4)cn3)cc(Cl)c2n1] | 5-Chloro-N-(8-chloro-2-methylimidazo[1,2-a]pyridin-6-yl)pyrazine-2-carboxamide | LCMS (ES+) 412 (M + H)+, RT 1.85 min (Analytical method AcHSSC18). $^1$H NMR (400 MHz, DMSO) δ 10.18 (s, 1H), 9.04 (d, J = 1.8 Hz, 1H), 8.50 (d, J = 1.3 Hz, 1H), 7.73 (d, J = 1.3 Hz, 1H), 7.65 (s, 1H), 7.59 (d, J = 1.8 Hz, 1H), 3.49-3.39 (m, 2H), 3.36-3.29 (m, 2H), 2.11 (s, 3H), 1.92-1.88 (m, 2H), 1.72-1.71 (m, 1H), 0.18 (d, J = 6.5 Hz, 2H), 0.04 - -0.03 (m, 2H). |
| Example 342 | 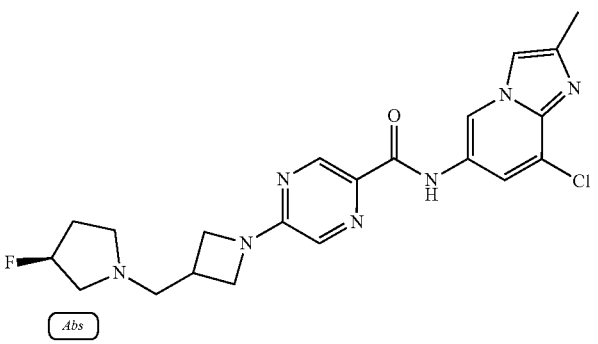 [SMILES: Cc1cn2cc(NC(=O)c3cnc(N4CC(CN5CC[C@H](F)C5)C4)cn3)cc(Cl)c2n1] | 5-Chloro-N-(8-chloro-2-methylimidazo[1,2-a]pyridin-6-yl)pyrazine-2-carboxamide | LCMS (ES+) 444 (M + H)+, RT 1.93 min (Analytical method AcHSSC18). $^1$H NMR (400 MHz, DMSO) δ 10.48 (s, 1H), 9.31 (d, J = 1.8 Hz, 1H), 8.76 (d, J = 1.3 Hz, 1H), 7.93-7.92 (m, 2H), 7.87 (d, J = 1.8 Hz, 1H), 5.26 (d, J = 58.1 Hz, 1H), 4.34 (dd, J = 8.2, 8.2 Hz, 2H), 3.93-3.93 (m, 2H), 3.09-3.03 (m, 1H), 2.89-2.75 (m, 4H), 2.39-2.36 (m, 4H), 2.25-2.13 (m, 1H), 1.99-1.86 (m, 1H). $^{19}$F NMR (376 MHz, DMSO) δ -73.35 (s, 1F). |

Example 343: N-(8-fluoro-2-methylimidazo[1,2-a]pyridin-6-yl)-5-(3-(((1R)-1-fluoro-3-azabicyclo[3.1.0]hexan-3-yl)methyl)azetidin-1-yl)pyrazine-2-carboxamide

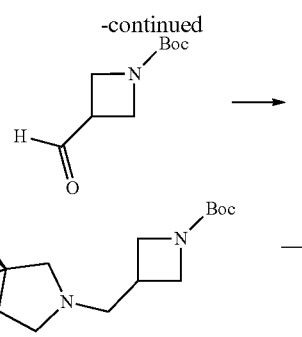

-continued

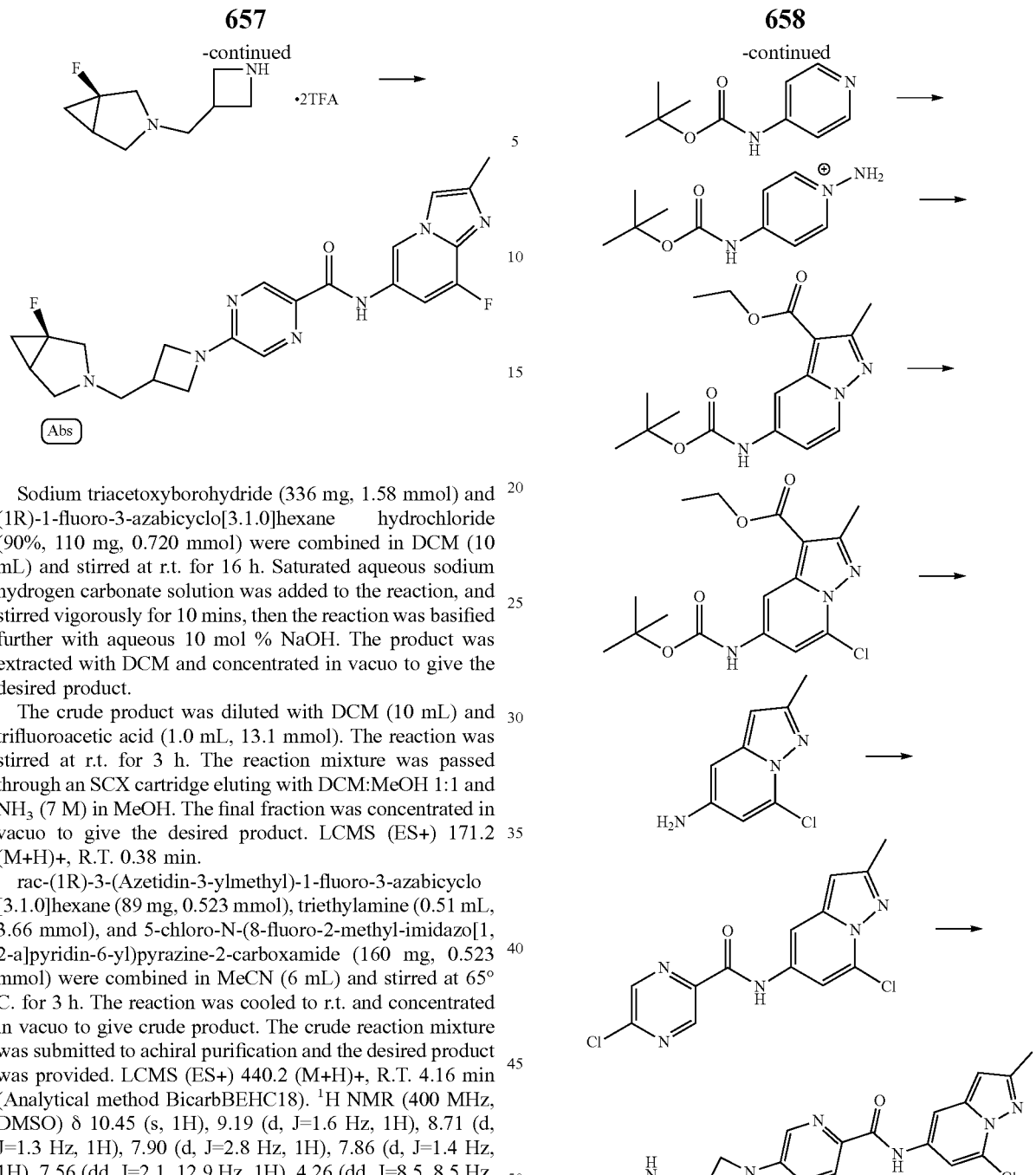

Sodium triacetoxyborohydride (336 mg, 1.58 mmol) and (1R)-1-fluoro-3-azabicyclo[3.1.0]hexane hydrochloride (90%, 110 mg, 0.720 mmol) were combined in DCM (10 mL) and stirred at r.t. for 16 h. Saturated aqueous sodium hydrogen carbonate solution was added to the reaction, and stirred vigorously for 10 mins, then the reaction was basified further with aqueous 10 mol % NaOH. The product was extracted with DCM and concentrated in vacuo to give the desired product.

The crude product was diluted with DCM (10 mL) and trifluoroacetic acid (1.0 mL, 13.1 mmol). The reaction was stirred at r.t. for 3 h. The reaction mixture was passed through an SCX cartridge eluting with DCM:MeOH 1:1 and NH$_3$ (7 M) in MeOH. The final fraction was concentrated in vacuo to give the desired product. LCMS (ES+) 171.2 (M+H)+, R.T. 0.38 min.

rac-(1R)-3-(Azetidin-3-ylmethyl)-1-fluoro-3-azabicyclo[3.1.0]hexane (89 mg, 0.523 mmol), triethylamine (0.51 mL, 3.66 mmol), and 5-chloro-N-(8-fluoro-2-methyl-imidazo[1,2-a]pyridin-6-yl)pyrazine-2-carboxamide (160 mg, 0.523 mmol) were combined in MeCN (6 mL) and stirred at 65° C. for 3 h. The reaction was cooled to r.t. and concentrated in vacuo to give crude product. The crude reaction mixture was submitted to achiral purification and the desired product was provided. LCMS (ES+) 440.2 (M+H)+, R.T. 4.16 min (Analytical method BicarbBEHC18). $^1$H NMR (400 MHz, DMSO) δ 10.45 (s, 1H), 9.19 (d, J=1.6 Hz, 1H), 8.71 (d, J=1.3 Hz, 1H), 7.90 (d, J=2.8 Hz, 1H), 7.86 (d, J=1.4 Hz, 1H), 7.56 (dd, J=2.1, 12.9 Hz, 1H), 4.26 (dd, J=8.5, 8.5 Hz, 2H), 3.87-3.80 (m, 2H), 3.29 (dd, J=2.4, 7.8 Hz, 1H), 2.98-2.90 (m, 1H), 2.81-2.71 (m, 4H), 2.59 (dd, J=3.6, 8.8 Hz, 1H), 2.35 (s, 3H), 1.87-1.78 (m, 1H), 1.28-1.18 (m, 1H), 1.03 (q, J=5.6 Hz, 1H). $^{19}$F NMR (400 MHz, DMSO) δ. −132.2 (dd, J=16.5, 3 Hz, 1° F.), −200.6-200.8 (m, 1F).

Example 344: N-(7-chloro-2-methylpyrazolo[1,5-a]pyridin-5-yl)-5-(3-((cyclopropylamino)methyl) azetidin-1-yl)pyrazine-2-carboxamide

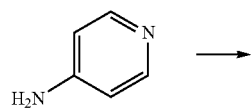

4-Aminopyridine (3 g, 31.9 mmol) was dissolved in EtOAc and di-tert-butyl dicarbonate (7.3 mL, 31.9 mmol) was added. The reaction mixture was stirred at r.t. for 1.5 h. The reaction mixture was partitioned between EtOAc and water. The aqueous phase was extracted with EtOAc (×3) and the combined organic phases were filtered through a hydrophobic frit. The solvent was concentrated in vacuo to give the desired product. LCMS (ES+) 195.3 (M+H)+, R.T. 1.06 min. $^1$H NMR (400 MHz, CDCl3) δ 8.44 (dd, J=1.5, 4.8 Hz, 2H), 7.33-7.29 (m, 2H), 6.83 (s, 1H), 1.53 (s, 9H).

4-(Boc-amino)pyridine (7.22 g, 37.1 mmol) was dissolved in N,N-dimethylformamide (50.00 mL) and O-(2,4-dinitrophenyl)hydroxylamine (8.14 g, 40.9 mmol) was added at r.t. The reaction mixture was stirred at r.t. for 16 h, and this was used directly in the next step. LCMS (ES+) 210 (M+H)+, R.T. 1.05 min (broad signal).

To tert-butyl N-(1-aminopyridin-1-ium-4-yl)carbamate 2,4-dinitrophenolate (14 g, 35.6 mmol) in N,N-dimethylformamide (50 mL) were added ethyl 2-butynoate (2.0 mL, 17.2 mmol) and potassium carbonate (7.38 g, 53.4 mmol) at r.t. The reaction was stirred at r.t. for 48 h. The reaction mixture was filtered, and the precipitate was washed with EtOAc. The filtrate was concentrated in vacuo to give a residue. The crude was purified by column chromatography on silica gel, eluting with EtOAc/cyclohexane 0-100% to give the desired product. LCMS (ES+) 319 (M+H)+, R.T. 1.66 min.

Ethyl 5-(tert-butoxycarbonylamino)-2-methyl-pyrazolo[1,5-a]pyridine-3-carboxylate (537 mg, 1.68 mmol) was stirred in dry THF (10 mL) at −80° C. To this, n-butyllithium solution (1.4 mL, 3.53 mmol, 2.5 M) was added dropwise, and the reaction was stirred at −80° C. for 15 mins. p-Toluenesulfonyl chloride (1.3 g, 6.73 mmol) in dry THF (1 mL) was added to the reaction at −80° C. The reaction was stirred for 5 mins and the ice bath was removed. The reaction was stirred for a further 20 mins. The reaction mixture was diluted with EtOAc and washed with brine. The organic layer was passed through a hydrophobic frit and concentrated in vacuo to give the crude product. LCMS (ES+) 353 (M+H)+, R.T. 1.75 min.

Ethyl 5-(tert-butoxycarbonylamino)-7-chloro-2-methyl-pyrazolo[1,5-a]pyridine-3-carboxylate (420 mg, 1.19 mmol) and hydrogen bromide (48%, 1.8 mL, 15.9 mmol) were refluxed together for 17 h. The reaction mixture was concentrated in vacuo and the residue was loaded onto a 5 g SCX cartridge (preconditioned with MeOH). The residue was eluted with MeOH, then NH₃ (7 M) in MeOH. The ammonia fraction was concentrated in vacuo to give the desired product. LCMS (ES+) 181 (M+H)+, R.T. 1.14 min.

7-Chloro-2-methyl-pyrazolo[1,5-a]pyridin-5-amine (150 mg, 0.826 mmol), 5-chloro-2-pyrazinecarboxylic acid (131 mg, 0.826 mmol), chloro-N,N,N,N-tetramethylformamidinium hexafluorophosphate (348 mg, 1.24 mmol), and 1-methylimidazole (0.20 mL, 2.48 mmol) in MeCN (8 mL) was stirred under nitrogen for 1 h at r.t. The reaction mixture was concentrated in vacuo, diluted with DCM, and washed with aqueous sodium bicarbonate solution. The organic layer was concentrated onto silica and purified by column chromatography, eluting with cyclohexane and EtOAc (0-35% gradient). The appropriate fractions were combined and concentrated in vacuo to give the desired product. LCMS (ES+) 322 (M+H)+, R.T. 1.52 min. ¹H NMR (400 MHz, CDCl₃) δ 9.52 (s, 1H), 9.28 (d, J=1.5 Hz, 1H), 8.60 (d, J=1.3 Hz, 1H), 8.07 (d, J=2.0 Hz, 1H), 7.13 (d, J=2.0 Hz, 1H), 6.42 (s, 1H), 2.55 (s, 3H).

Triethylamine (0.035 mL, 0.251 mmol), 5-chloro-N-(7-chloro-2-methyl-pyrazolo[1,5-a]pyridin-5-yl)pyrazine-2-carboxamide (27 mg, 0.0838 mmol), and N-(azetidin-3-ylmethyl)cyclopropanamine (11 mg, 0.0838 mmol) were combined in MeCN (6 mL) and stirred at 40° C. for 1 h. The reaction was stopped and the mixture concentrated in vacuo. The crude material provided was submitted to achiral SFC for purification. LCMS (ES+) 412 (M+H)+, R.T. 2.86 min (Analytical method AcHSSC18. NMR: ¹H NMR (400 MHz, DMSO) δ 10.55 (s, 1H), 8.71 (d, J=1.4 Hz, 1H), 8.27 (d, J=2.0 Hz, 1H), 7.83 (d, J=1.3 Hz, 1H), 7.63 (d, J=2.1 Hz, 1H), 6.48 (s, 1H), 4.22 (dd, J=8.3, 8.3 Hz, 2H), 3.88-3.79 (m, 2H), 2.89-2.84 (m, 3H), 2.39 (s, 3H), 2.08-2.03 (m, 1H), 0.39-0.34 (m, 2H), 0.22-0.18 (m, 2H).

Example 345: (R)-5-(3-(ethylamino)pyrrolidin-1-yl)-N-(7-methoxy-2-methylimidazo[1,2-a]pyridin-6-yl)pyrazine-2-carboxamide

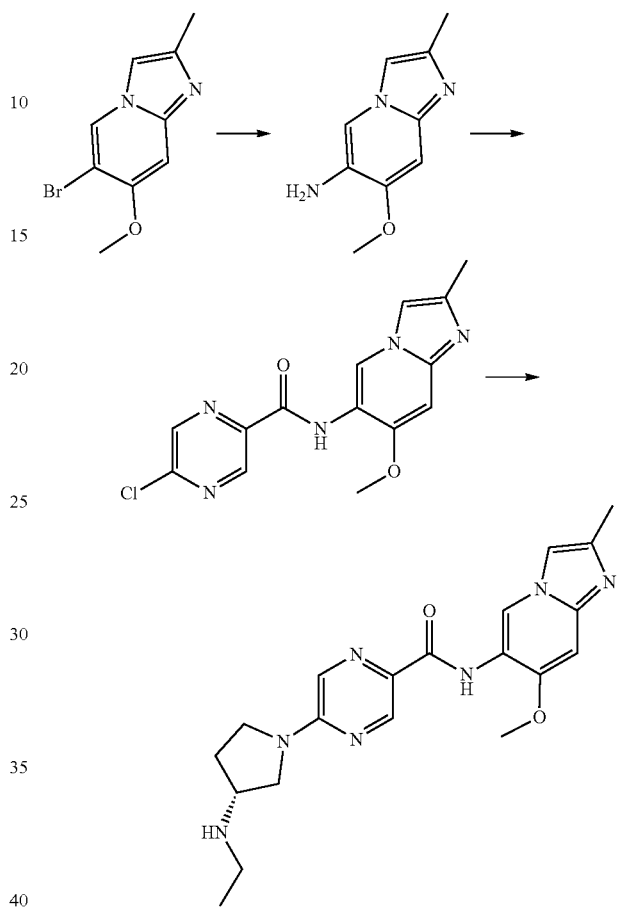

Previously reported 6-bromo-7-methoxy-2-methyl-imidazo[1,2-a]pyridine (1000 mg, 4.15 mmol), copper(I) iodide (158 mg, 0.830 mmol), potassium carbonate (860 mg, 6.22 mmol), L-proline (191 mg, 1.66 mmol), ammonium hydroxide solution, ~12% (12%, 2.1 mL, 6.22 mmol), and dimethyl sulfoxide (10.00 mL) were added to a reaction flask, sealed and heated at 90° C. for 16 h. Additional ammonium hydroxide solution, ~12% (12%, 2.1 mL, 6.22 mmol) was added, and the reaction heated at 90° C. for a further 6 h. The reaction mixture was loaded onto a 70 g SCX cartridge, washed with MeOH, followed by 3.5 N NH₃ in MeOH. LCMS indicated presence of both target material (TM) and starting material (SM) in MeOH phase and no product or SM in 7N NH₃ in MeOH phase. The MeOH phase was concentrated under reduced pressure. Copper(I) iodide (158 mg, 0.830 mmol), potassium carbonate (860 mg, 6.22 mmol), L-proline (191 mg, 1.66 mmol), and ammonium hydroxide solution, ~12% (12%, 2.1 mL, 6.22 mmol) were all added to the mixture of SM and TM in DMSO, and the corresponding mixture was heated to 90° C. for 96 h. After cooling to r.t., the mixture was diluted with DCM, and inorganics filtered off on filter paper. The pH of the filtrate was then acidified to pH 4-5 with aqueous HCl (1 M), and the mixture loaded onto a 20 g SCX, preconditioned with DCM/MeOH=1:1, washed with DCM/MeOH=1:1, to give a fraction which by LCMS didn't contain any target material. The SCX was then flushed with [DCM/MeOH=1:1]: NH₃ in MeOH (7N)=1:1 and fractions were evaporated in vacuo to afford crude 7-methoxy-2-methylimidazo[1,2-a]pyridin-6-amine, which was used as such in next step.

To a solution of previously reported 5-chloropyrazine-2-carbonyl chloride (440 mg, 2.49 mmol) in DCM (5 mL) was added dropwise a solution of 7-methoxy-2-methyl-imidazo[1,2-a]pyridin-6-amine (400 mg, 2.26 mmol) in DCM (5 mL) and triethylamine (0.35 mL, 2.52 mmol). The resulting mixture was stirred under N₂ for 22 h. The mixture was then diluted with cyclohexane, resulting in solid precipitation, which was filtered off and dried, affording 5-chloro-N-(7-methoxy-2-methylimidazo[1,2-a]pyridin-6-yl)pyrazine-2-carboxamide, which was used as such in the next step.

(3R)—N-ethylpyrrolidin-3-amine (29 mg, 0.252 mmol), triethylamine (0.11 mL, 0.755 mmol), and 5-chloro-N-(7-methoxy-2-methyl-imidazo[1,2-a]pyridin-6-yl)pyrazine-2-carboxamide (80 mg, 0.252 mmol) were combined in acetonitrile (2.10 mL) and stirred at 55° C. over the weekend. The mixture was diluted with DCM and loaded onto silica and purified by silica gel chromatography, eluting with EtOAc/EtOH=3:1+NH₃ in MeOH (7 N) 0 to 5%, to afford product material, which was combined with another batch and purified under the same conditions. Another round of achiral SFC purification yielded the title compound. LCMS (ES+) 396.357 (M+H)+, RT 1.86 min (Analytical method AcHSSC18); ¹H NMR (400 MHz, DMSO) δ 9.76 (s, 1H), 9.37 (s, 1H), 8.75 (d, J=1.1 Hz, 1H), 8.06 (d, J=1.1 Hz, 1H), 7.60 (s, 1H), 7.01 (s, 1H), 4.00 (s, 3H), 3.72-3.62 (m, 2H), 3.60-3.54 (m, 1H), 3.45-3.39 (m, 2H), 2.67-2.56 (m, 2H), 2.28 (s, 3H), 2.18-2.09 (m, 1H), 1.94-1.87 (m, 1H), 1.05 (t, J=7.1 Hz, 3H).

Example 346 and Example 347: (R)—N-(8-fluoro-2-methylimidazo[1,2-a]pyridin-6-yl)-5-(3-(morpholin-3-yl)azetidin-1-yl)pyrazine-2-carboxamide and and (S)—N-(8-fluoro-2-methylimidazo[1,2-a]pyridin-6-yl)-5-(3-(morpholin-3-yl)azetidin-1-yl)pyrazine-2-carboxamide

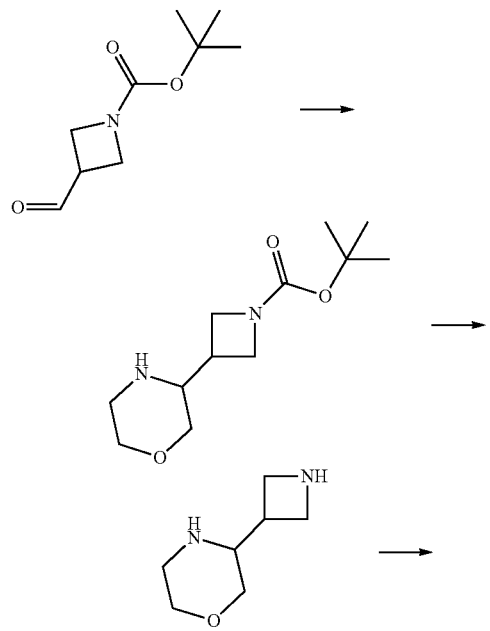

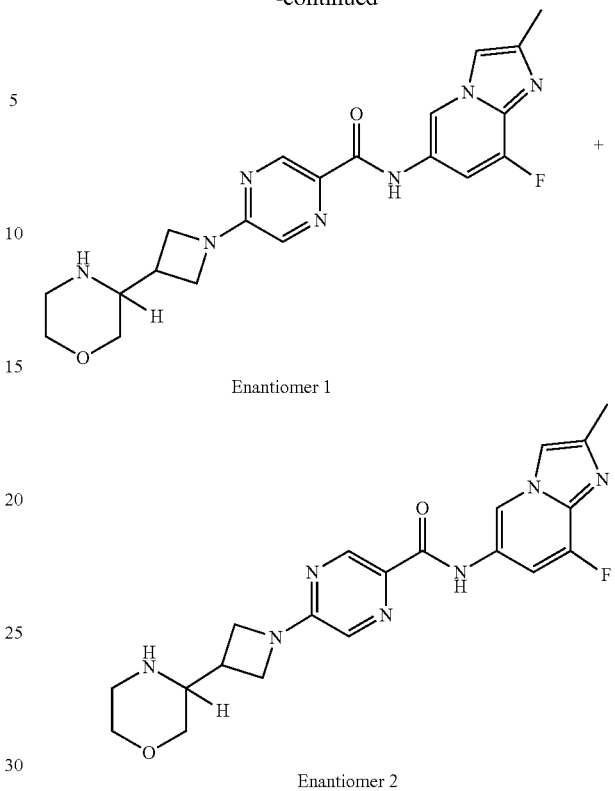

Enantiomer 1

Enantiomer 2 tert-Butyl 3-formylazetidine-1-carboxylate (86 mg, 0.462 mmol) neat in a vial was ran on the Synple automated synthesiser using the extended method (~11 h) and the SnAP morpholine (H001) cartridge containing the solid supported reagents: SnAP M Reagent solid supported (0.5 mmol), 2,6-lutidine solid supported (0.5 mmol), and copper(II) trifluoromethanesulfonate solid supported (0.5 mmol). The sequence was repeated once again, and both were combined to afford tert-butyl 3-(morpholin-3-yl)azetidine-1-carboxylate after evaporation, which was used as such in the next step.

To a solution of tert-butyl 3-morpholin-3-ylazetidine-1-carboxylate (104 mg, 0.429 mmol) in DCM (2 mL), trifluoroacetic acid (2 mL, 26.1 mmol) was added and the mixture stirred at r.t. for 16 h. The mixture was then evaporated to dryness, and the product material was loaded onto SCX (1 g) preconditioned with DCM/MeOH, washed with DCM/MeOH, before being flushed off with MeOH/NH₃. The basic fraction was concentrated in vacuo to afford 3-(azetidin-3-yl)morpholine, which was used as such in the next step.

3-(Azetidin-3-yl)morpholine (45 mg, 0.316 mmol), triethylamine (0.13 mL, 0.949 mmol), and 5-chloro-N-(8-fluoro-2-methyl-imidazo[1,2-a]pyridin-6-yl)pyrazine-2-carboxamide (90%, 107 mg, 0.316 mmol) were combined in acetonitrile (1.5 mL) and stirred at 55° C. for 16 h. The mixture was purified by silica chromatography, eluting with EA/EtOH=3:1+NH₃ in MeOH (7 N) 0 to 4%, to afford product material, that was further purified by chiral SFC for enantiomer separation to give:

Example 346, Enantiomer 1 N-(8-fluoro-2-methylimidazo[1,2-a]pyridin-6-yl)-5-(3-(morpholin-3-yl)azetidin-1-yl)pyrazine-2-carboxamide was recovered and required further purification by achiral SFC to afford the titled compound. LCMS (ES+) 412 (M+H)+, RT 1.76 min (Analytical method AcHSSC18); RT 3.57 min (SFC4, YMC AMYLOSE-C+0.1% DEAISO 45% EtOH SOL2); ¹H NMR (400 MHz, DMSO) δ 10.45 (s, 1H), 9.19 (d, J=1.6 Hz, 1H), 8.72 (d, J=1.3 Hz, 1H), 7.90 (dd, J=0.9, 3.2 Hz, 1H), 7.84 (d, J=1.4 Hz, 1H), 7.56 (dd, J=1.5, 13.1 Hz, 1H), 4.23-4.11 (m, 3H), 4.02 (dd, J=5.8, 9.0 Hz, 1H), 3.73-3.65 (m, 2H), 3.02 (dd, J=10.1, 10.1 Hz, 1H), 2.92-2.85 (m, 1H), 2.80-2.67 (m, 3H), 2.35 (s, 3H). 1H under H₂O peak, 1 exchangeable not seen.

Example 347, Enantiomer 2 N-(8-fluoro-2-methylimidazo[1,2-a]pyridin-6-yl)-5-(3-(morpholin-3-yl)azetidin-1-yl)pyrazine-2-carboxamide. LCMS (ES+) 412.2 (M+H)+, RT 1.75 min (Analytical method AcHSSC18); RT 8.8 min (SFC1, YMC AMYLOSE-C+0.1% DEAISO 45% EtOH SOL2); ¹H NMR (400 MHz, DMSO) δ 10.45 (s, 1H), 9.19 (d, J=1.6 Hz, 1H), 8.72 (d, J=1.3 Hz, 1H), 7.90 (d, J=2.8 Hz, 1H), 7.84 (d, J=1.4 Hz, 1H), 7.56 (dd, J=1.6, 13.1 Hz, 1H), 4.17 (dt, J=8.8, 15.6 Hz, 3H), 4.02 (dd, J=5.8, 9.0 Hz, 1H), 3.75-3.64 (m, 2H), 3.04 (dd, J=10.2, 10.2 Hz, 1H), 2.94-2.90 (m, 1H), 2.82-2.67 (m, 3H), 2.35 (s, 3H). 1H under H₂O peak, 1 exchangeable not seen.

Example 348: (R)-5-(3-(cyclopropylamino)-2-oxopyrrolidin-1-yl)-N-(8-fluoro-2-methylimidazo[1,2-a]pyridin-6-yl)pyrazine-2-carboxamide

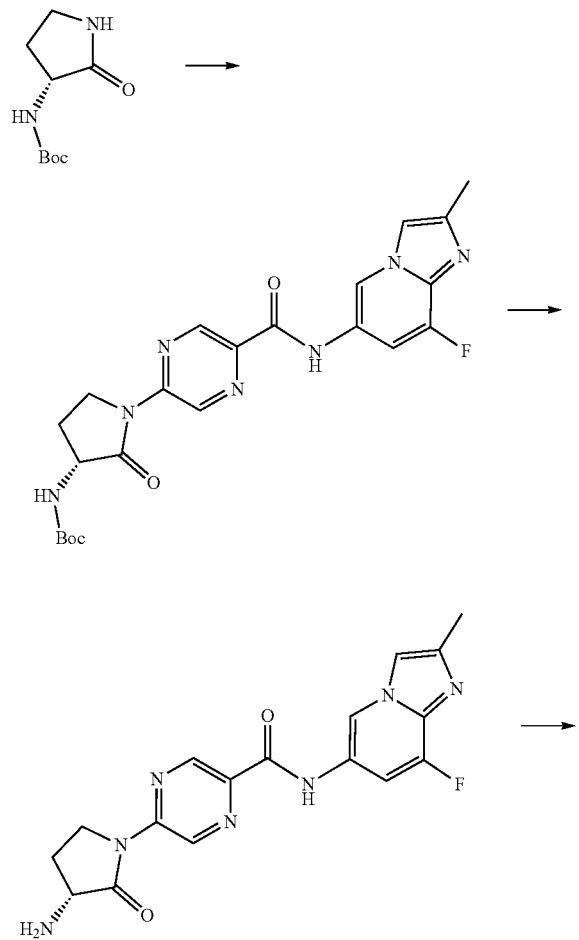

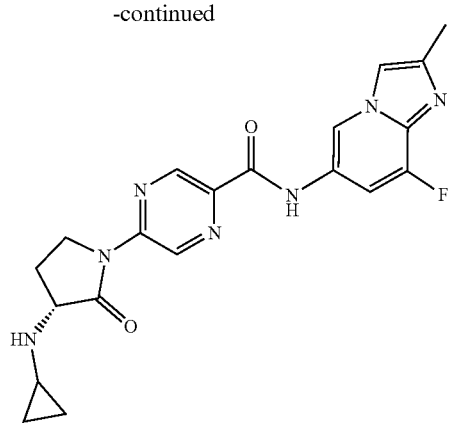

To a solution of 5-chloro-N-(8-fluoro-2-methyl-imidazo[1,2-a]pyridin-6-yl)pyrazine-2-carboxamide (700 mg, 2.29 mmol) and tert-butyl N-[(3R)-2-oxopyrrolidin-3-yl]carbamate (504 mg, 2.52 mmol) in 1,4-dioxane (11.5 mL), was added cesium carbonate (1120 mg, 3.43 mmol) and the mixture was degassed under N₂ sparging for 20 min. Xantphos (132 mg, 0.23 mmol) and tris(dibenzylideneacetone)dipalladium(0) (52 mg, 0.0572 mmol) were added and the mixture heated to 100° C. under inert atmosphere for 24 h. Heating stopped and the reaction mixture was left to cool to r.t. The mixture was purified by silica chromatography, eluting with cyHex/[EtOAc:EtOH=3:1] 1:0 to 6:4 to afford tert-butyl (R)-(1-(5-((8-fluoro-2-methylimidazo[1,2-a]pyridin-6-yl)carbamoyl)pyrazin-2-yl)-2-oxopyrrolidin-3-yl)carbamate. LCMS (ES+) 470 (M+H)+, R.T. 1.37 min. ¹H NMR (400 MHz, DMSO) δ 10.90 (s, 1H), 9.70 (s, 1H), 9.23 (s, 1H), 9.13 (d, J=1.3 Hz, 1H), 7.93 (d, J=2.6 Hz, 1H), 7.61-7.57 (m, 1H), 7.40 (d, J=8.8 Hz, 1H), 4.59-4.50 (m, 1H), 4.15-4.08 (m, 1H), 3.84-3.75 (m, 1H), 2.47-2.39 (m, 1H), 2.36 (s, 3H), 2.13-2.00 (m, 1H), 1.44 (s, 9H).

To a solution of tert-butyl N-[(3R)-1-[5-[(8-fluoro-2-methyl-imidazo[1,2-a]pyridin-6-yl)carbamoyl]pyrazin-2-yl]-2-oxo-pyrrolidin-3-yl]carbamate (150 mg, 0.320 mmol) in DCM (2.13 mL) was added 4 M hydrogen chloride in dioxane (4 M) (0.80 mL, 3.20 mmol), and the solution left stirring at r.t. for 18 h. The mixture was then evaporated to dryness. The product material was then free based using MP-carbonate resin (8 eq 1 g of 3 mmol/g), shaking in DCM/IPA for 16 h, then filtered over celite and the filtrate was evaporated to dryness to yield (R)-5-(3-amino-2-oxopyrrolidin-1-yl)-N-(8-fluoro-2-methylimidazo[1,2-a]pyridin-6-yl)pyrazine-2-carboxamide, which was used as such in the next step. LCMS (ES+) 370 (M+H)+, R.T. 0.99 min.

5-[(3R)-3-amino-2-oxo-pyrrolidin-1-yl]-N-(8-fluoro-2-methyl-imidazo[1,2-a]pyridin-6-yl)pyrazine-2-carboxamide (41 mg, 0.111 mmol), (1-ethoxycyclopropoxy)trimethylsilane (0.022 mL, 0.111 mmol) and MeOH (0.73 mL) were combined, followed by acetic acid (0.0059 mL), before the reaction was heated to 55° C. for 19 h. Sodium cyanoborohydride (7.7 mg, 0.122 mmol) was then added and the reaction was stirred at 55° C. for an additional 4.5 h. The mixture was cooled to r.t., diluted with DCM, washed with NaHCO₃ solution, dried over a phase separator paper, and concentrated in vacuo. The mixture was purified by silica chromatography, eluting with EA/EtOH=1:0 to 92:8, to give the title compound, which was then further purified by achiral SFC. (R)-5-(3-(cyclopropylamino)-2-oxopyrrolidin-1-yl)-N-(8-fluoro-2-methylimidazo[1,2-a]pyridin-6-yl)pyrazine-2-carboxamide. LCMS (ES+) 410 (M+H)+, RT 3.58 min (Analytical method BicarbBEHC18); ¹H NMR (400 MHz, DMSO) δ 10.90 (s, 1H), 9.72 (d, J=1.4 Hz, 1H), 9.24 (d, J=1.6 Hz, 1H), 9.13 (d, J=1.4 Hz, 1H), 8.33-8.19 (m, 1H), 7.94 (d, J=2.8 Hz, 1H), 7.59 (dd, J=1.6, 13.0 Hz, 1H), 4.14-4.09 (m, 1H), 3.86-3.78 (m, 2H), 2.99-2.90 (m, 2H), 2.36 (s, 3H), 2.00-1.92 (m, 1H), 0.47-0.44 (m, 2H), 0.36-0.30 (m, 2H).

Example 349: N-(4-fluoro-2-methylbenzo[d]oxazol-6-yl)-5-(3-((methylamino)methyl)azetidin-1-yl)pyrazine-2-carboxamide

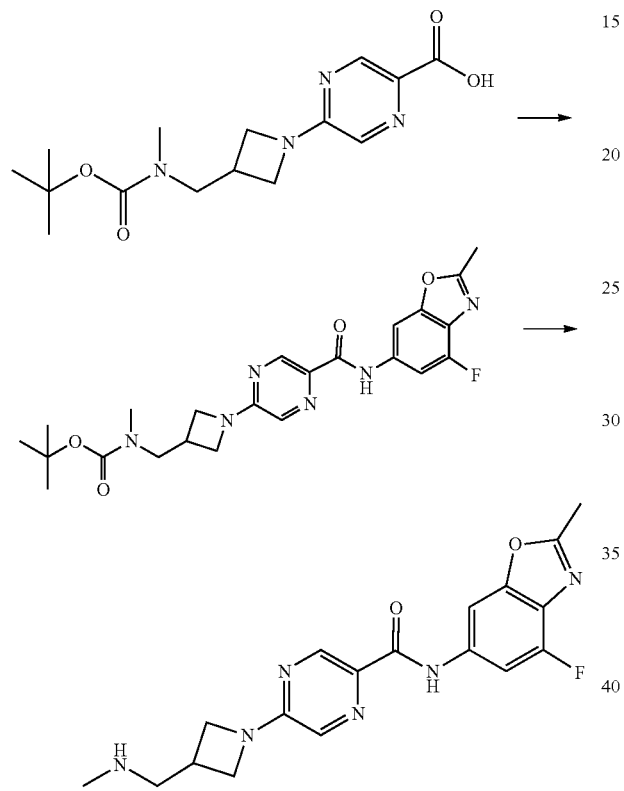

4-Fluoro-2-methyl-1,3-benzoxazol-6-amine (80 mg, 0.481 mmol), 5-[3-[[tert-butoxycarbonyl (methyl)amino]methyl]azetidin-1-yl]pyrazine-2-carboxylic acid (155 mg, 0.481 mmol), and 1-methylimidazole (0.12 mL, 1.44 mmol) were suspended in acetonitrile (5 mL). Chloro-N,N,N,N-tetramethylformamidinium hexafluorophosphate (149 mg, 0.530 mmol) was added and stirred at r.t. for 18 h. The reaction was filtered, and the collected solid washed with CH₃CN and water. The solid was dried in a vacuum oven overnight to give product material. Used in next step without further purification.

tert-Butyl N-[[1-[5-[(4-fluoro-2-methyl-1,3-benzoxazol-6-yl)carbamoyl]pyrazin-2-yl]azetidin-3-yl]methyl]-N-methyl-carbamate (100 mg, 0.213 mmol) was dissolved in DCM (3 mL) and trifluoroacetic acid (1 mL, 13.1 mmol) was added at r.t. The reaction was stirred for 1 h at r.t. The solvent was removed in vacuo to give a residue. The residue was dissolved in DCM (3 mL) and treated with MP-carbonate (to free base the TFA salt) at r.t. overnight. The solid MP-carbonate was removed by filtration and the DCM removed in vacuo to give a residue. The residue was purified by achiral SFC to give the title compound. LCMS (ES+) 371.1 (M+H)+, RT 2.6 min (Analytical method AcHSSC18); ¹H NMR (400 MHz, DMSO) δ 10.63 (s, 1H), 8.77 (d, J=1.3 Hz, 1H), 8.23 (d, J=1.5 Hz, 1H), 7.90-7.85 (m, 2H), 4.28 (dd, J=8.7, 8.7 Hz, 2H), 3.93 (dd, J=5.4, 9.2 Hz, 2H), 3.02-2.93 (m, 1H), 2.82 (d, J=7.1 Hz, 2H), 2.66 (s, 3H), 2.37 (s, 3H) ¹⁹F NMR (400 MHz, DMSO) δ −126.13 (d, J=13.4 Hz, 1F).

Example 350: N-(7-fluoro-2-methyl-2H-indazol-5-yl)-5-(3-((3-fluoroazetidin-1-yl)methyl)azetidin-1-yl)pyrazine-2-carboxamide

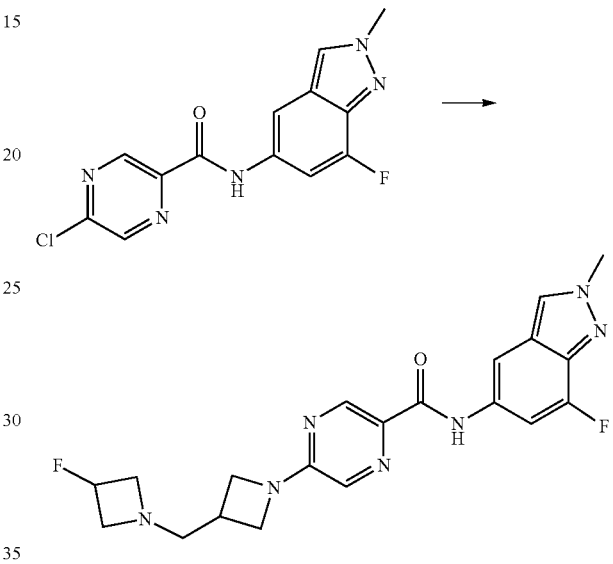

Cesium carbonate (426 mg, 1.31 mmol), 5-chloro-N-(7-fluoro-2-methyl-indazol-5-yl)pyrazine-2-carboxamide (100 mg, 0.327 mmol), and 1-(azetidin-3-ylmethyl)-3-fluoro-azetidine hydrochloride (59 mg, 0.327 mmol) were combined in N,N-dimethylformamide (3 mL) and stirred at 100° C. for 17 h. The reaction was cooled to r.t. and then the reaction mixture was filtered. The filtrate was purified by preparative HPLC to yield the title compound. LCMS (ES+) 414 (M+H)+, RT 2.27 min (Analytical method AcHSSC18); ¹H NMR (400 MHz, DMSO) δ 10.27 (1H, s), 8.72 (1H, d, J=1.4 Hz), 8.43 (1H, d, J=2.9 Hz), 8.16 (1H, d, J=1.6 Hz), 7.86 (1H, d, J=1.4 Hz), 7.57 (1H, dd, J=1.6, 13.6 Hz), 5.26-5.07 (m, 1H), 4.23 (2H, dd, J=8.3, 8.3 Hz), 4.18 (3H, s), 3.84 (2H, dd, J=5.1, 9.0 Hz), 3.64-3.55 (2H, m), 3.22-3.09 (2H, m), 2.86-2.73 (m, 3H); ¹⁹F NMR (400 MHz, DMSO) δ −128.42 (dd, J=3.2, 13.7 Hz, 1F), −177.5--177.8 (m, 1F).

Example 351: (S)-5-(3-((cyclopropylamino)methyl)pyrrolidin-1-yl)-N-(6-methoxy-2-methyl-2H-indazol-5-yl)pyrazine-2-carboxamide

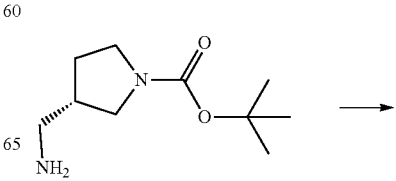

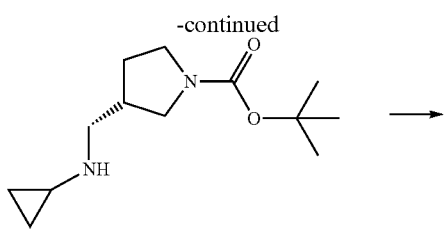

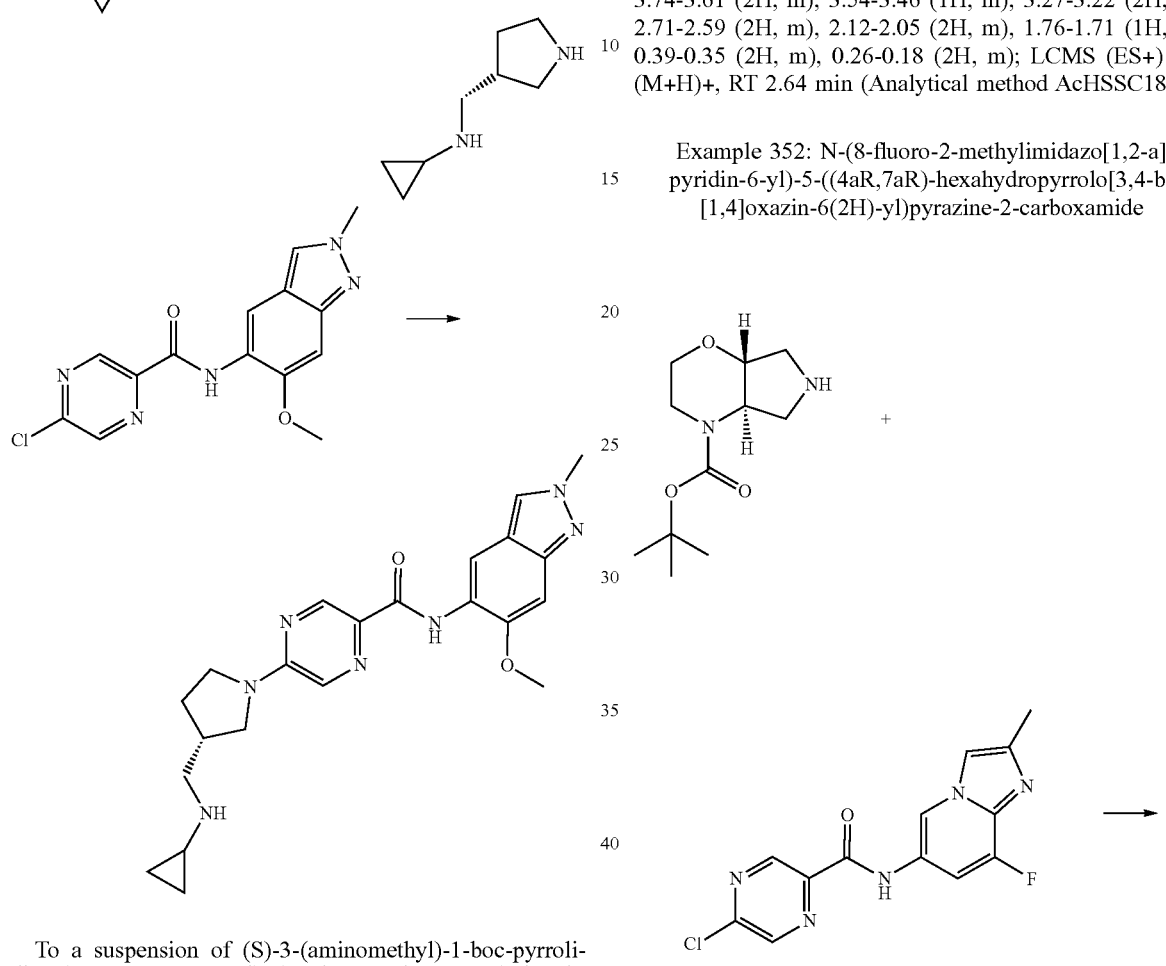

To a suspension of (S)-3-(aminomethyl)-1-boc-pyrrolidine (500 mg, 2.5 mmol), (1-ethoxycyclopropoxy)trimethylsilane (0.5 mL, 2.5 mmol) in methanol (25 mL), was added sodium cyanoborohydride (173 mg, 2.8 mmol) followed by acetic acid (0.2 mL), and the reaction was then heated at 55° C. overnight. The mixture was cooled to r.t., diluted with DCM and washed with 10% aqueous sodium hydroxide solution. The organic phase was dried over magnesium sulfate, filtered, and concentrated under reduced pressure to yield tert-butyl (3S)-3-[(cyclopropylamino)methyl]pyrrolidine-1-carboxylate, which was used crude in the next step.

To a solution of tert-butyl (3S)-3-[(cyclopropylamino) methyl]pyrrolidine-1-carboxylate (450 mg, 1.8 mmol) in methanol (20 mL), was added 4M hydrogen chloride in 1,4-dioxane (2.3 mL, 9.4 mmol) and the reaction stirred at r.t. overnight. The reaction mixture was concentrated under reduced pressure, then 2M aqueous sodium hydroxide solution was added and the product extracted into DCM. The organic phase was dried over a hydrophobic frit and concentrated under reduced pressure to yield N-[[(3R)-pyrrolidin-3-yl]methyl]cyclopropanamine, which was used crude in the next step.

5-Chloro-N-(6-methoxy-2-methyl-indazol-5-yl)pyrazine-2-carboxamide (200 mg, 0.63 mmol), N-[[(3R)-pyrrolidin-3-yl]methyl]cyclopropanamine (134 mg, 0.63 mmol), and cesium carbonate (615 mg, 1.89 mmol) in N,N-dimethylformamide (2 mL) were stirred overnight at 100° C. The reaction mixture was filtered and purified by prep-HPLC to yield the title compound. $^1$H NMR (400 MHz, DMSO) δ 10.03 (1H, s), 8.74-8.73 (1H, m), 8.67 (1H, s), 8.21 (1H, s), 8.03-8.01 (1H, m), 7.09 (1H, s), 4.08 (3H, s), 3.97 (3H, s), 3.74-3.61 (2H, m), 3.54-3.46 (1H, m), 3.27-3.22 (2H, m), 2.71-2.59 (2H, m), 2.12-2.05 (2H, m), 1.76-1.71 (1H, m), 0.39-0.35 (2H, m), 0.26-0.18 (2H, m); LCMS (ES+) 422 (M+H)+, RT 2.64 min (Analytical method AcHSSC18)

Example 352: N-(8-fluoro-2-methylimidazo[1,2-a] pyridin-6-yl)-5-((4aR,7aR)-hexahydropyrrolo[3,4-b] [1,4]oxazin-6(2H)-yl)pyrazine-2-carboxamide

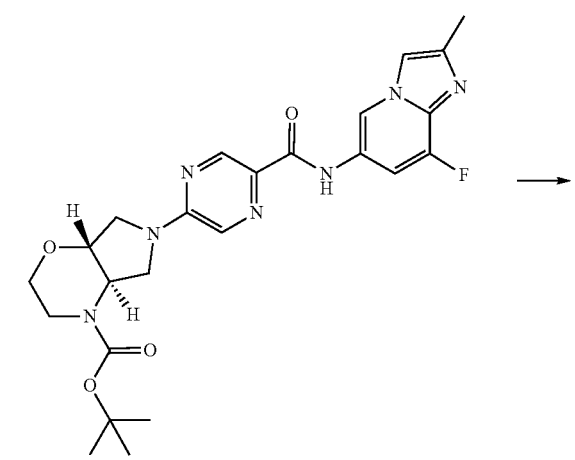

-continued

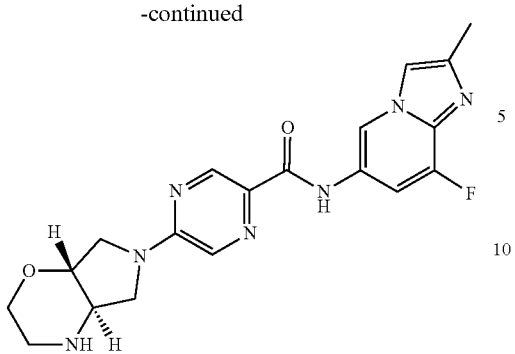

tert-Butyl (4aR,7aR)-3,4a,5,6,7,7a-hexahydro-2H-pyrrolo[3,4-b][1,4]oxazine-4-carboxylate (75 mg, 0.33 mmol), 5-chloro-N-(8-fluoro-2-methyl-imidazo[1,2-a]pyridin-6-yl)pyrazine-2-carboxamide (100 mg, 0.33 mmol), and cesium carbonate (213 mg, 0.65 mmol) in N,N-dimethylformamide (1 mL) was stirred overnight at 100° C. The reaction mixture was filtered, diluted with DMSO, and purified by prep-HPLC. This yielded tert-butyl (4aR,7aR)-6-[5-[(8-fluoro-2-methyl-imidazo[1,2-a]pyridin-6-yl)carbamoyl]pyrazin-2-yl]-2,3,4a,5,7,7a-hexahydropyrrolo[3,4-b][1,4]oxazine-4-carboxylate. LCMS (ES+) 498.

To a solution of tert-butyl (4aR,7aR)-6-[5-[(8-fluoro-2-methyl-imidazo[1,2-a]pyridin-6-yl)carbamoyl]pyrazin-2-yl]-2,3,4a,5,7,7a-hexahydropyrrolo[3,4-b][1,4]oxazine-4-carboxylate (15 mg, 0.03 mmol) in methyl alcohol (0.25 mL), was added 4M hydrogen chloride in 1,4-dioxane (0.075 mL, 0.30 mmol), and the reaction was stirred at room temperature for 3 h. The reaction mixture was loaded onto an SCX cartridge, washed with methanol, and the product eluted with 3.5 N $NH_3$ in methanol. The eluent was concentrated under reduced pressure and lyophilised. This yielded the title compound. 1H NMR (400 MHz, DMSO) δ 10.48 (1H, s), 9.23 (1H, d, J=1.5 Hz), 8.80-8.79 (1H, m), 8.04 (1H, d, J=1.0 Hz), 7.93 (1H, d, J=2.5 Hz), 7.61 (1H, dd, J=1.5, 13.1 Hz), 4.01-3.90 (3H, m), 3.69-3.58 (3H, m), 3.20 (1H, s), 2.91-2.86 (4H, m), 2.39 (3H, s); $^{19}F$ NMR (376 MHz, DMSO) δ −132.1−−132.2 (m, 1F); LCMS (ES+) 398 (M+H)+, RT 1.64 min (Analytical method AcHSSC18)

Example 353 N-(8-fluoro-2-methylimidazo[1,2-a]pyridin-6-yl)-5-(methyl(2,2,6,6-tetramethylpiperidin-4-yl)amino)pyrazine-2-carboxamide

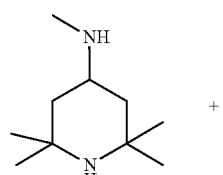

+

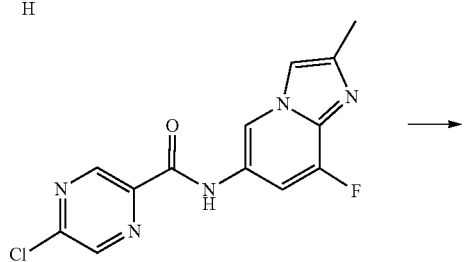

-continued

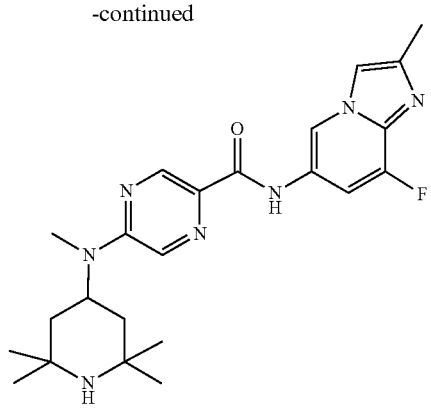

To a solution of 5-chloro-N-(8-fluoro-2-methylimidazo[1,2-a]pyridin-6-yl)pyrazine-2-carboxamide (75 mg, 0.245 mmol) in dioxane (1 mL) was added N,2,2,6,6-pentamethylpiperidin-4-amine (63 mg, 0.368 mmol). Triethylamine (0.037 mL, 0.368 mmol) was added and the reaction was heated in a microwave at 145° C. for 45 minutes. The solvent was removed in vacuo and the residue purified by prep HPLC to give N-(8-fluoro-2-methylimidazo[1,2-a]pyridin-6-yl)-5-(methyl(2,2,6,6-tetramethylpiperidin-4-yl)amino)pyrazine-2-carboxamide. LCMS (ES+) 440 (M+H)+, RT 2.11 min (Analytical method AcHSSC18); $^1H$ NMR (400 MHz, DMSO) δ 10.44 (s, 1H), 9.22 (d, J=1.5 Hz, 1H), 8.77 (d, J=1.1 Hz, 1H), 8.26 (s, 1H), 8.17 (d, J=1.0 Hz, 1H), 7.90 (d, J=2.8 Hz, 1H), 7.56 (dd, J=1.6, 13.1 Hz, 1H), 3.05 (s, 3H), 2.35 (s, 3H), 1.62-1.55 (m, 4H), 1.32 (s, 6H), 1.19 (s, 6H).

Example 354: N-(7-fluoro-2,8-dimethyl-imidazo[1,2-a]pyridin-6-yl)-5-[(3R)-3-(methylamino)pyrrolidin-1-yl]pyrazine-2-carboxamide

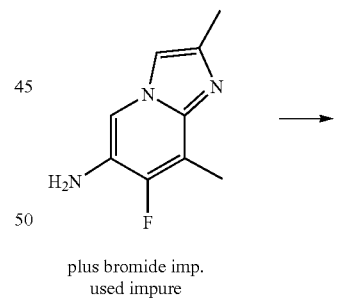

plus bromide imp.
used impure

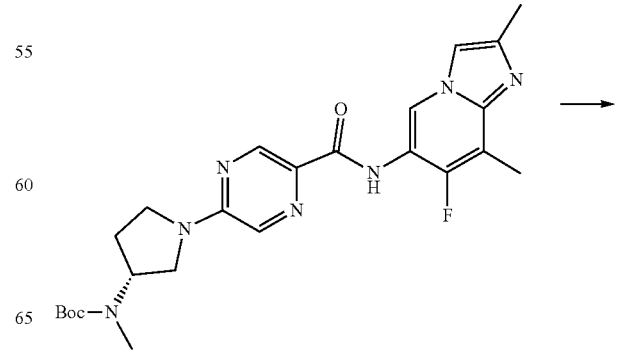

-continued

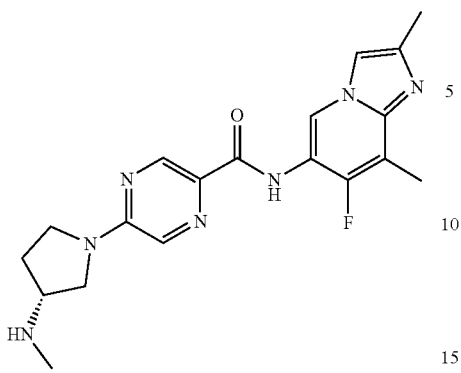

7-Fluoro-2,8-dimethyl-imidazo[1,2-a]pyridin-6-amine hydrochloride (~40 mg, 0.183 mmol, 1.00 eq) (170 mg of crude material used), [5-[(3R)-3-[tert-butoxycarbonyl(methyl)amino]pyrrolidin-1-yl]pyrazine-2-carbonyl]oxylithium (65 mg, 0.198 mmol), HBTU (75 mg, 0.198 mmol), N,N-dimethylformamide (3 mL), and triethylamine (1.1 mL, 7.74 mmol) were combined and stirred at r.t. for 2 h. The reaction mixture was purified by prep HPLC to give tert-butyl N-[(3R)-1-[5-[(7-fluoro-2,8-dimethyl-imidazo[1,2-a]pyridin-6-yl)carbamoyl]pyrazin-2-yl]pyrrolidin-3-yl]-N-methyl-carbamate. LCMS (ES+) 484 (M+H)+.

tert-Butyl N-[(3R)-1-[5-[(7-fluoro-2,8-dimethyl-imidazo[1,2-a]pyridin-6-yl)carbamoyl]pyrazin-2-yl]pyrrolidin-3-yl]-N-methyl-carbamate (5.7 mg, 0.0119 mmol), MeOH (1 mL), and 4 M hydrogen chloride in dioxane (1 mL, 4.00 mmol) were combined and stirred at r.t. for 30 mins. The reaction mixture was concentrated in vacuo. The residue was purified by prep HPLC to give N-(7-fluoro-2,8-dimethyl-imidazo[1,2-a]pyridin-6-yl)-5-[(3R)-3-(methylamino)pyrrolidin-1-yl]pyrazine-2-carboxamide. LCMS (ES+) 384.2 (M+H)+, RT 3.09 min (Analytical method BicarbBEHC18). ¹H NMR (400 MHz, DMSO) δ 9.79 (s, 1H), 8.98 (d, J=7.2 Hz, 1H), 8.73 (d, J=1.3 Hz, 1H), 8.04 (d, J=1.4 Hz, 1H), 7.72 (s, 1H), 3.70-3.57 (m, 3H), 3.42-3.38 (m, 1H), 2.40 (d, J=1.9 Hz, 3H), 2.33 (s, 6H), 2.12-2.08 (m, 1H), 1.92-1.92 (m, 2H).

Example 355: 5-[3-[(cyclopropylamino)methyl]azetidin-1-yl]-N-(7-fluoro-2,8-dimethyl-imidazo[1,2-a]pyridin-6-yl)pyrazine-2-carboxamide

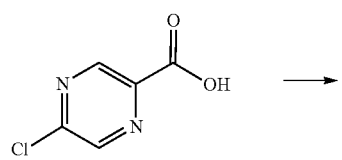

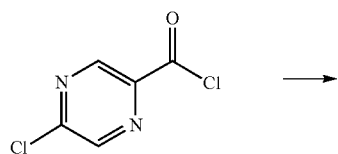

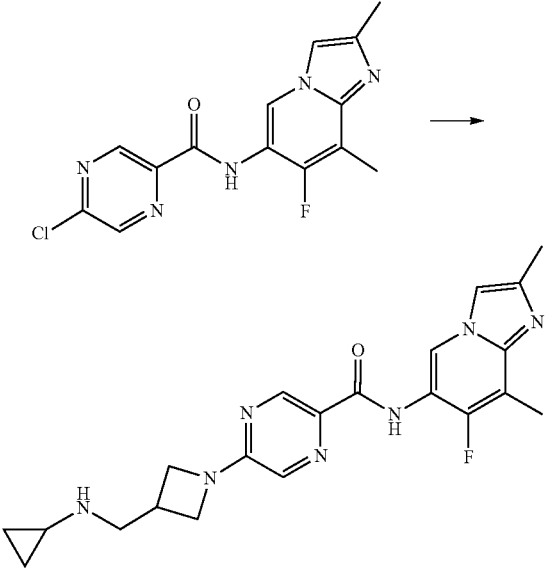

5-Chloro-2-pyrazinecarboxylic acid (87 mg, 0.550 mmol), DCM (5 mL), and oxalyl chloride (0.096 mL, 1.10 mmol) were combined and stirred at r.t. under a nitrogen atmosphere. DMF (1 drop) was added as catalyst to reaction. The reaction mixture was stirred overnight, then concentrated in vacuo to give product material, which was used crude in next step.

A solution of 5-chloropyrazine-2-carbonyl chloride (97 mg, 0.550 mmol) in DCM (15 mL) was added to a mixture of triethylamine (1 mL, 7.17 mmol) and 7-fluoro-2,8-dimethyl-imidazo[1,2-a]pyridin-6-amine hydrochloride/6-bromo-7-fluoro-2,8-dimethyl-imidazo[1,2-a]pyridine (inseparable mixture from previous reaction) (406 mg, estimated to have ~100 mg of 7-fluoro-2,8-dimethyl-imidazo[1,2-a]pyridin-6-amine hydrochloride). The reaction mixture was stirred at r.t. for 1 h. LCMS analysis indicated 5-chloro-N-(7-fluoro-2,8-dimethyl-imidazo[1,2-a]pyridin-6-yl)pyrazine-2-carboxamide and 6-bromo-7-fluoro-2,8-dimethyl-imidazo[1,2-a]pyridine (impurity from starting material) were both present. The reaction mixture was concentrated in vacuo to give product material, which was used crude in next step.

5-Chloro-N-(7-fluoro-2,8-dimethyl-imidazo[1,2-a]pyridin-6-yl)pyrazine-2-carboxamide (crude from previous step), N-(azetidin-3-ylmethyl)cyclopropanamine 2,2,2-trifluoroacetic acid (195 mg, 0.550 mmol), acetonitrile (20 mL), and triethylamine (1 mL, 7.17 mmol) were combined and the reaction mixture was heated to 80° C. overnight, then cooled to r.t., and concentrated in vacuo. The residue was purified by prep HPLC, followed by achiral SFC purification to give 5-[3-[(cyclopropylamino)methyl]azetidin-1-yl]-N-(7-fluoro-2,8-dimethyl-imidazo[1,2-a]pyridin-6-yl)pyrazine-2-carboxamide. LCMS (ES+) 410 (M+H)+, RT 1.9 min (Analytical method AcHSSC18). ¹H NMR (400 MHz, DMSO) δ 9.80 (s, 1H), 8.93 (d, J=7.2 Hz, 1H), 8.68 (d, J=1.3 Hz, 1H), 7.88 (d, J=1.4 Hz, 1H), 7.70 (s, 1H), 4.21 (dd, J=8.3, 8.3 Hz, 2H), 3.85 (dd, J=4.8, 9.2 Hz, 2H), 2.92-2.82 (m, 3H), 2.38 (d, J=1.9 Hz, 4H), 2.31 (s, 3H), 2.08-2.05 (m, 1H), 0.39-0.34 (m, 2H), 0.22-0.18 (m, 2H).

Example 356: N-(8-fluoro-2-methyl-imidazo[1,2-a]pyridin-6-yl)-5-[3-[[(3R)-3-fluoro-3-methyl-pyrrolidin-1-yl]methyl]azetidin-1-yl]pyrazine-2-carboxamide

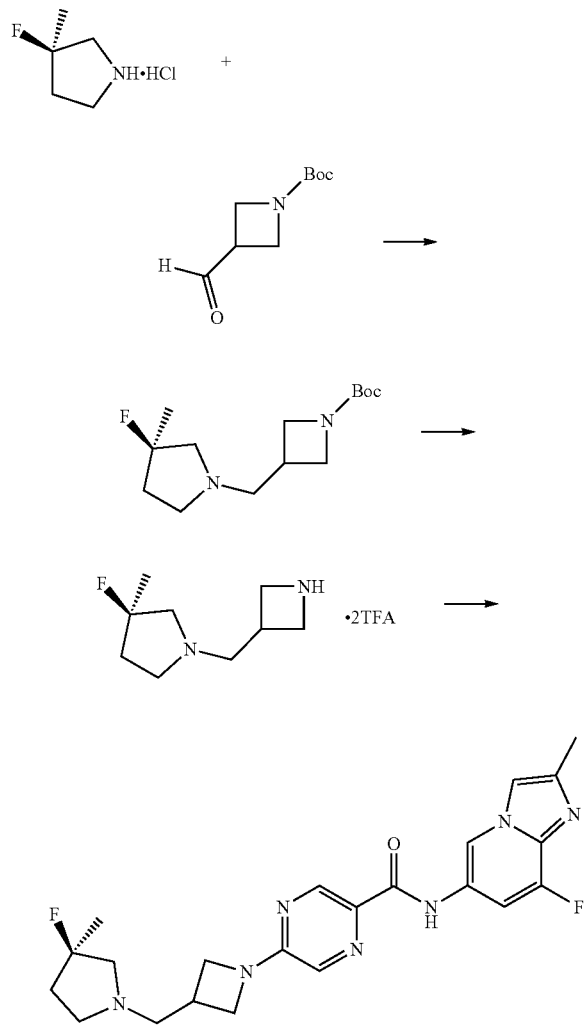

(3R)-3-Fluoro-3-methyl-pyrrolidine hydrochloride (100 mg, 0.716 mmol), tert-butyl 3-formylazetidine-1-carboxylate (120 mg, 0.650 mmol), sodium triacetoxyborohydride (303 mg, 1.43 mmol), and DCM (10 mL) were combined and stirred at r.t. for 24 h. Saturated aqueous sodium hydrogen carbonate solution was added to the reaction mixture and stirred vigorously for 10 mins. The reaction mixture was basified further with ~10% NaOH, extracted with DCM, dried (MgSO$_4$) and the organic phase was concentrated in vacuo to give tert-butyl 3-[[(3R)-3-fluoro-3-methyl-pyrrolidin-1-yl]methyl]azetidine-1-carboxylate, which was used directly in next step.

tert-Butyl 3-[[(3R)-3-fluoro-3-methyl-pyrrolidin-1-yl]methyl]azetidine-1-carboxylate (188 mg) (crude from previous step), DCM (2 mL), and TFA (2 mL) were combined and stirred at r.t. for 3 h. The reaction mixture was concentrated in vacuo to give (3R)-1-(azetidin-3-ylmethyl)-3-fluoro-3-methyl-pyrrolidine 2TFA, which was used directly in next step.

(3R)-1-(Azetidin-3-ylmethyl)-3-fluoro-3-methyl-pyrrolidine 2TFA (260 mg, 0.650 mmol), 5-chloro-N-(8-fluoro-2-methyl-imidazo[1,2-a]pyridin-6-yl)pyrazine-2-carboxamide (152 mg, 0.496 mmol), cesium carbonate (741 mg, 2.28 mmol), and N,N-dimethylformamide (4 mL) were combined in a sealed tube and heated to 100° C. overnight. The reaction mixture was cooled to r.t. and cesium salts were filtered off. The resultant material was purified by prep HPLC to give N-(8-fluoro-2-methyl-imidazo[1,2-a]pyridin-6-yl)-5-[3-[[(3R)-3-fluoro-3-methyl-pyrrolidin-1-yl]methyl]azetidin-1-yl]pyrazine-2-carboxamide. LCMS (ES+) 442 (M+H)+, RT 1.85 min (Analytical method AcHSSC18). $^1$H NMR (400 MHz, DMSO) δ 10.45 (s, 1H), 9.19 (d, J=1.6 Hz, 1H), 8.72 (d, J=1.3 Hz, 1H), 7.90-7.87 (m, 2H), 7.56 (dd, J=1.5, 13.1 Hz, 1H), 4.28 (dd, J=8.6, 8.6 Hz, 2H), 3.87 (dd, J=5.6, 9.0 Hz, 2H), 2.98-2.72 (m, 5H), 2.52 (t, J=1.8 Hz, 1H), 2.57-2.46 (m, 1H), 2.35 (s, 3H), 2.10-1.82 (m, 3H), 1.45 (d, J=21.3 Hz, 3H).

The opposite enantiomer was synthesised using the same chemistry.

| Example | Structure | Analytical data |
|---|---|---|
| Example 357 | 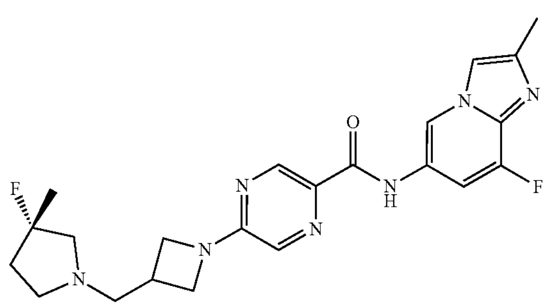 [SMILES: Cc1cn2cc(NC(=O)c3cnc(N4CC(CN5CC[C@](C)(F)C5)C4)cn3)cc(F)c2n1] | LCMS (ES+) 442 (M + H)+, RT 1.86 min (Analytical method AcHSSC18). $^1$H NMR (400 MHz, DMSO) δ 10.45 (s, 1H), 9.19 (d, J = 1.6 Hz, 1H), 8.72 (d, J = 1.3 Hz, 1H), 7.90-7.87 (m, 2H), 7.56 (dd, J = 1.5, 13.1 Hz, 1H), 4.28 (dd, J = 8.6, 8.6 Hz, 2H), 3.87 (dd, J = 5.6, 9.0 Hz, 2H), 2.98-2.72 (m, 5H), 2.52 (t, J = 1.8 Hz, 1H), 2.57-2.46 (m, 1H), 2.35 (s, 3H), 2.10-1.82 (m, 3H), 1.45 (d, J = 21.3 Hz, 3H). |

Example 358: N-(8-fluoro-2-methyl-imidazo[1,2-a]pyridin-6-yl)-5-(1,2,3,6-tetrahydropyridin-4-yl)pyrazine-2-carboxamide

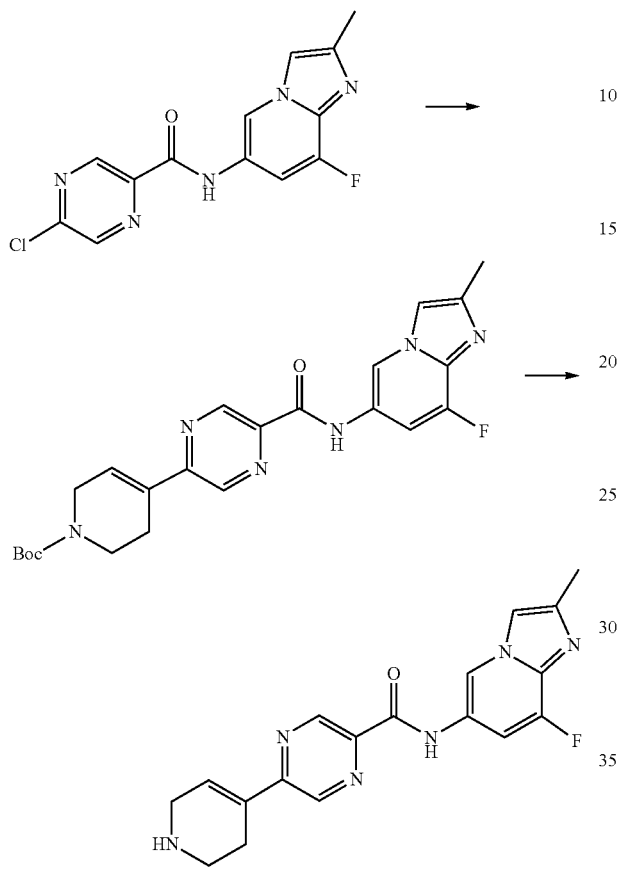

5-Chloro-N-(8-fluoro-2-methyl-imidazo[1,2-a]pyridin-6-yl)pyrazine-2-carboxamide (106 mg, 0.347 mmol), N-Boc-1,2,3,6-tetrahydropyridine-4-boronic acid pinacol ester (107 mg, 0.347 mmol), sodium carbonate (81 mg, 0.763 mmol), bis(triphenylphosphine)palladium(II) dichloride (24 mg, 0.0347 mmol), 1,4-dioxane (10 mL), and water (1 mL) were combined in a sealed tube and heated to 100° C. overnight. The reaction mixture was cooled to r.t. and sodium salts were filtered through a celite plug rinsing with EtOAc. The filtrate was concentrated in vacuo and purified by prep HPLC to give tert-butyl 4-[5-[(8-fluoro-2-methyl-imidazo[1,2-a]pyridin-6-yl)carbamoyl]pyrazin-2-yl]-3,6-dihydro-2H-pyridine-1-carboxylate. LCMS (ES+) 453 (M+H)+.

tert-Butyl 4-[5-[(8-fluoro-2-methyl-imidazo[1,2-a]pyridin-6-yl)carbamoyl]pyrazin-2-yl]-3,6-dihydro-2H-pyridine-1-carboxylate (73 mg, 0.161 mmol), DCM (2 mL), and trifluoroacetic acid (2 mL, 26.1 mmol) were combined and stirred at r.t. for 1 h. The reaction mixture was concentrated in vacuo. The residue was purified by prep HPLC, followed by SFC purification to give N-(8-fluoro-2-methyl-imidazo[1,2-a]pyridin-6-yl)-5-(1,2,3,6-tetrahydropyridin-4-yl)pyrazine-2-carboxamide. LCMS (ES+) 353 (M+H)+, RT 1.72 min (Analytical method AcHSSC18). $^1$H NMR (400 MHz, DMSO) δ 10.92 (s, 1H), 9.23 (dd, J=1.5, 8.2 Hz, 2H), 8.96 (d, J=1.4 Hz, 1H), 7.94 (d, J=2.8 Hz, 1H), 7.58 (dd, J=1.6, 12.9 Hz, 1H), 7.13 (s, 1H), 3.52-3.50 (m, 2H), 2.96 (dd, J=5.6, 5.6 Hz, 2H), 2.36 (s, 3H). One CH$_2$ obscured by DMSO or water peak.

Example 359: 5-[3-[(3-Methoxyazetidin-1-yl)methyl]azetidin-1-yl]-N-(8-methoxy-2-methyl-imidazo[1,2-a]pyrazin-6-yl)pyrazine-2-carboxamide

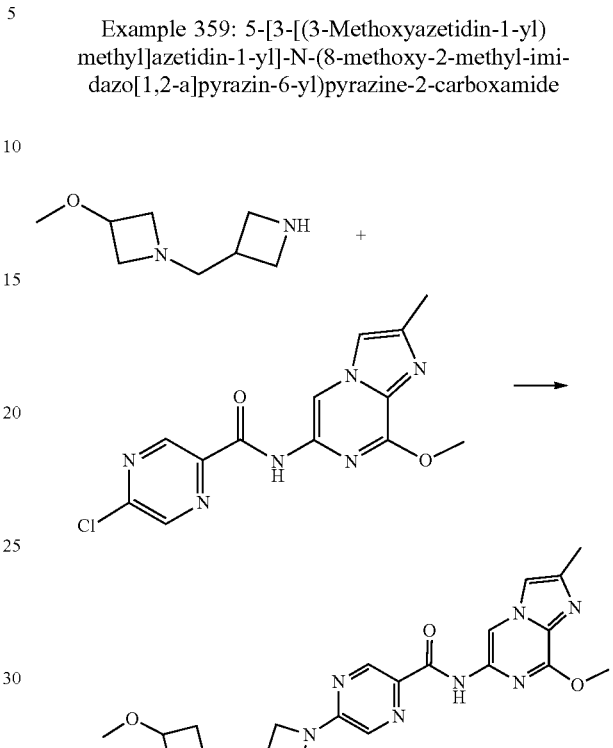

A suspension of 5-chloro-N-(8-methoxy-2-methyl-imidazo[1,2-a]pyrazin-6-yl)pyrazine-2-carboxamide (40 mg, 0.126 mmol), 1-(azetidin-3-ylmethyl)-3-methoxy-azetidine (25 mg, 0.163 mmol), and cesium carbonate (164 mg, 0.502 mmol) in N,N-dimethylformamide (1.50 mL) was heated at 100° C. for 24 hours. The reaction mixture was filtered and the crude material purified by reverse phase HPLC (Xbridge Phenyl 19×150 mm, 10 μm 40-100% MeOH/H$_2$O (10 mM NH$_4$CO$_3$), 20 mL/min, RT) to yield 5-[3-[(3-methoxyazetidin-1-yl)methyl]azetidin-1-yl]-N-(8-methoxy-2-methyl-imidazo[1,2-a]pyrazin-6-yl)pyrazine-2-carboxamide.
LCMS (ES+) 439 [M+H]+, RT 3.34 min (Analytical method BicarbBEHC18). $^1$H NMR (400 MHz, DMSO) δ 9.51 (s, 1H), 8.90 (s, 1H), 8.72 (d, J=1.3 Hz, 1H), 7.95 (s, 1H), 7.90 (d, J=1.4 Hz, 1H), 4.22 (dd, J=8.7, 8.7 Hz, 2H), 4.07 (s, 3H), 4.00-3.93 (m, 1H), 3.84 (dd, J=5.4, 9.0 Hz, 2H), 3.52 (dt, J=1.9, 6.1 Hz, 2H), 3.16 (s, 3H), 2.87-2.77 (m, 3H), 2.69 (d, J=7.5 Hz, 2H), 2.35 (s, 3H).

Example 360: N-(2,8-dimethylimidazo[1,2-a]pyrazin-6-yl)-5-[3-[(3-methoxyazetidin-1-yl)methyl]azetidin-1-yl]pyrazine-2-carboxamide

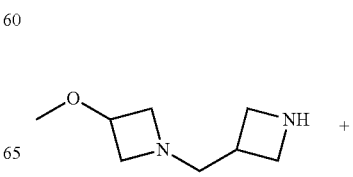

677

-continued

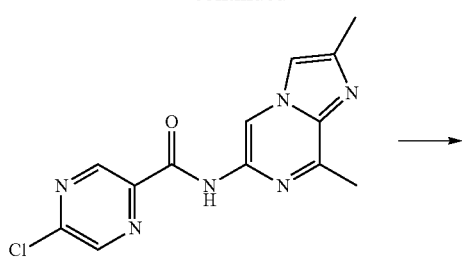 →

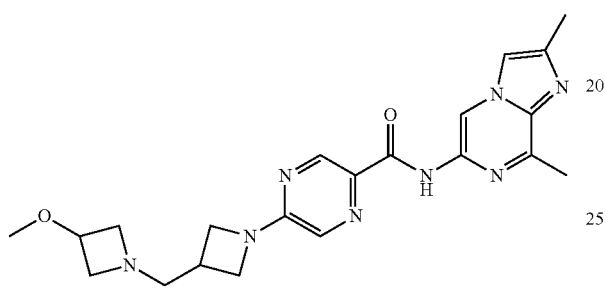

A suspension of 5-chloro-N-(2,8-dimethylimidazo[1,2-a]pyrazin-6-yl)pyrazine-2-carboxamide (150 mg, 0.496 mmol), 1-(azetidin-3-ylmethyl)-3-methoxy-azetidine (101 mg, 0.644 mmol), and cesium carbonate (646 mg, 1.98 mmol) in N,N-dimethylformamide (3 mL) was heated at 100° C. for 24 hours. The reaction mixture was filtered and the crude material purified by reverse phase HPLC (Xbridge Phenyl 19×150 mm, 10 μm 20-80% MeOH/H$_2$O (10 mM NH$_4$CO$_3$), 20 mL/min, RT then Sunfire C18 19×150 mm, 10 μm 5-60% ACN/H$_2$O (10 mM NH$_4$CO$_3$), 20 mL/min, RT) to yield N-(2,8-dimethylimidazo[1,2-a]pyrazin-6-yl)-5-[3-[(3-methoxyazetidin-1-yl)methyl]azetidin-1-yl]pyrazine-2-carboxamide. LCMS (ES+) 423 [M+H]+, RT 3.22 min (Analytical method BicarbBEHC18). $^1$H NMR (400 MHz, DMSO) δ 9.66 (s, 1H), 9.14 (s, 1H), 8.72 (d, J=1.3 Hz, 1H), 8.01 (s, 1H), 7.89 (d, J=1.3 Hz, 1H), 4.23 (dd, J=8.6, 8.6 Hz, 2H), 4.00-3.92 (m, 1H), 3.84 (dd, J=5.4, 9.0 Hz, 2H), 3.54-3.50 (m, 2H), 3.16 (s, 3H), 2.87-2.82 (m, 2H), 2.81-2.74 (m, 1H), 2.71-2.67 (m, 5H), 2.40 (s, 3H).

Example 361: 5-(2,6-Diazabicyclo[3.2.0]heptan-6-yl)-N-(8-methoxy-2-methyl-imidazo[1,2-a]pyrazin-6-yl)pyrazine-2-carboxamide

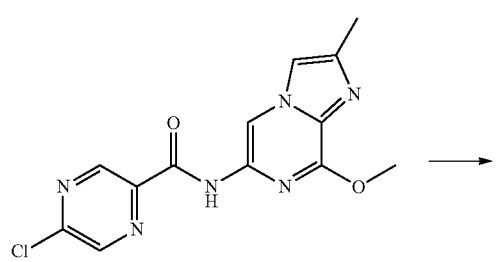 →

678

-continued

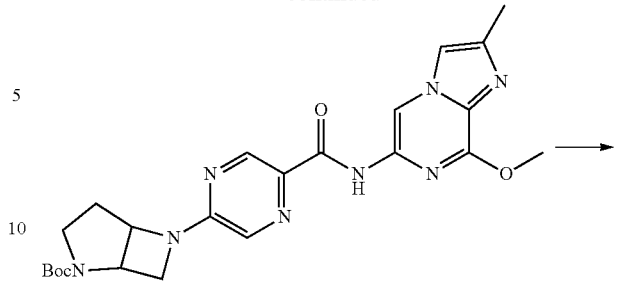 →

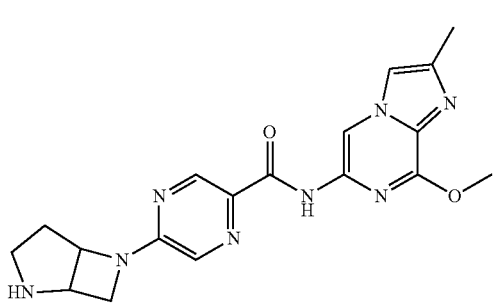

Enantiomer 1 + Enantiomer 2

5-Chloro-N-(8-methoxy-2-methylimidazo[1,2-a]pyrazin-6-yl)pyrazine-2-carboxamide (402 mg, 1.26 mmol), 2-Boc-2,6-diazabicyclo[3.2.0]heptane (250 mg, 1.26 mmol), cesium carbonate (425 mg, 1.39 mmol) and DMF (5 mL) were combined in a sealed tube and heated to 100° C. over the weekend. Reaction mixture was cooled to room temperature, diluted with dichloromethane, and inorganics were filtered off. The filtrate was evaporated to dryness and purified by flash chromatography to give tert-butyl 6-(5-((8-methoxy-2-methylimidazo[1,2-a]pyrazin-6-yl)carbamoyl)pyrazin-2-yl)-2,6-diazabicyclo[3.2.0]heptane-2-carboxylate. LCMS (ES+) 481 [M+H]+.

A solution of tert-butyl 6-[5-[(8-methoxy-2-methyl-imidazo[1,2-a]pyrazin-6-yl)carbamoyl]pyrazin-2-yl]-2,6-diazabicyclo[3.2.0]heptane-2-carboxylate (380 mg, 0.791 mmol) in trifluoroacetic acid (1.2 mL, 15.8 mmol) and dichloromethane (6 mL) was stirred at room temperature for 1.5 hours. The reaction mixture was concentrated under reduced pressure. The crude material was taken in MeOH and passed through an SCX-2 cartridge (10 g), and the compound eluted with 2M NH$_3$ in MeOH. The eluent was concentrated under reduced pressure to yield the crude material. The crude material was purified by reverse phase HPLC (HPLC (Xbridge Phenyl 19×150 mm, 10 μm 20-80% MeOH/H$_2$O (10 mM NH$_4$CO$_3$), 20 mL/min, RT) to yield 5-(2,6-diazabicyclo[3.2.0]heptan-6-yl)-N-(8-methoxy-2-methyl-imidazo[1,2-a]pyrazin-6-yl)pyrazine-2-carboxamide. LCMS (ES+) 381 [M+H]+, RT 2.92 min (Analytical method BicarbBEHC18). $^1$H NMR (400 MHz, DMSO) δ 9.49 (s, 1H), 8.90 (s, 1H), 8.71 (d, J=1.4 Hz, 1H), 7.95 (s, 1H), 7.91 (s, 1H), 5.00 (dd, J=5.1, 5.1 Hz, 1H), 4.30-4.18 (m, 2H), 4.07 (s, 3H), 3.70 (d, J=8.4 Hz, 1H), 3.21 (dd, J=7.2, 11.5 Hz, 1H), 2.99-2.90 (m, 1H), 2.35 (s, 3H), 2.08 (dd, J=4.9, 13.2 Hz, 1H), 1.52-1.41 (m, 1H).

Example 362: 5-(4-((Cyclopropylamino)methyl)-2-methylpyrrolidin-1-yl)-N-(2,8-dimethylimidazo[1,2-a]pyrazin-6-yl)pyrazine-2-carboxamide

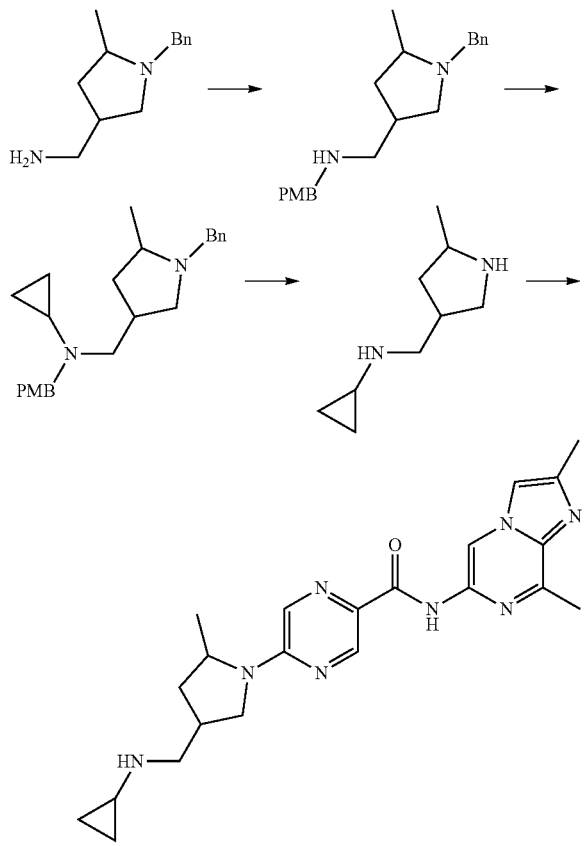

(1-Benzyl-5-methyl-pyrrolidin-3-yl)methanamine (1.00 g, 4.89 mmol), p-anisaldehyde (0.77 mL, 6.36 mmol), and magnesium sulfate (1.77 g, 14.7 mmol) in 2-methyltetrahydrofuran (23.88 mL) were stirred at r.t. and acetic acid (0.60 mL) was added. The reaction was stirred for 2.5 h. Sodium triacetoxyborohydride (1.35 g, 6.36 mmol) was then added portionwise. The reaction was stirred for a further 48 h at r.t. The inorganics were filtered off and washed with 2-methyltetrahydrofuran and DCM. The filtrate was loaded onto an SCX cartridge and eluted with MeOH first, then flushed off with $NH_3$ in MeOH (3.5 M). The ammonia flush was concentrated in vacuo to give product material. A mixture of the desired N-[(1-benzyl-5-methyl-pyrrolidin-3-yl)methyl]-1-(4-methoxyphenyl)methanamine and unwanted bis-PMB protected material was observed by LCMS.

To a solution of N-[(1-benzyl-5-methyl-pyrrolidin-3-yl)methyl]-1-(4-methoxyphenyl)methanamine (1400 mg, 4.31 mmol) in methyl alcohol (14 mL) was added (1-ethoxycyclopropoxy)trimethylsilane (1.7 mL, 8.63 mmol), acetic acid (0.072 mL), and sodium cyanoborohydride (542 mg, 8.63 mmol). The reaction mixture was heated at 50° C. overnight. The reaction mixture was then partitioned between DCM and aqueous $NaHCO_3$ solution, and the aqueous phase was reextracted with DCM (×2). The combined organic phases were dried through a phase separator before being evaporated to dryness to give the crude product.

N-[(1-Benzyl-5-methyl-pyrrolidin-3-yl)methyl]-N-[(4-methoxyphenyl)methyl]cyclopropanamine (1.04 g, 2.84 mmol) was dissolved in ethyl acetate (50 mL). Palladium on carbon (20%, 600 mg) was added, followed by acetic acid (5 mL). The reaction was stirred under $H_2$ (1 atmosphere) for 16 h. The catalyst was removed by filtering through Celite, and the Celite washed further with EtOAc. The crude product was passed through an SCX cartridge, eluting with MeOH to wash out acetic acid and $NH_3$ (7 M) in MeOH to retrieve the product. The solvent was removed in vacuo to give the desired product. LCMS (ES+) 155 (M+H)+, RT 0.33 min.

N-[(5-Methylpyrrolidin-3-yl)methyl]cyclopropanamine (13 mg, 0.0826 mmol), triethylamine (0.092 mL, 0.660 mmol), and 5-chloro-N-(2,8-dimethylimidazo[1,2-a]pyrazin-6-yl)pyrazine-2-carboxamide (25 mg, 0.0826 mmol) were combined in acetonitrile (2 mL) and stirred at 70° C. for 16 h. The reaction mixture was concentrated in vacuo and submitted for reverse phase purification. A slight impurity was detected in the QC. The product was dissolved in DCM and passed through an SCX cartridge, eluting with 1:1 MeOH:DCM and $NH_3$ (7 M) in MeOH. The product was concentrated in vacuo to give the desired product. LCMS (ES+) 421 (M+H)+, RT 2.32 min (Analytical method AcHSSC18). $^1H$ NMR (400 MHz, $CDCl_3$) δ 9.72 (s, 1H), 9.14 (s, 1H), 8.91 (s, 1H), 7.79 (d, J=11.5 Hz, 1H), 7.45 (s, 1H), 4.27-4.18 (m, 1H), 3.95-3.89 (m, 1H), 3.84-3.77 (m, 1H), 2.91-2.78 (m, 5H), 2.48-2.36 (m, 5H), 2.19-2.12 (m, 1H), 1.96-1.83 (m, 1H), 1.54-1.46 (m, 1H), 1.40-1.28 (m, 3H), 0.49-0.46 (m, 2H), 0.35 (dt, J=2.3, 5.7 Hz, 2H).

Example 363: (R)-5-(3-(Methylamino)pyrrolidin-1-yl)-N-(2-methylbenzo[d]oxazol-6-yl)pyrazine-2-carboxamide

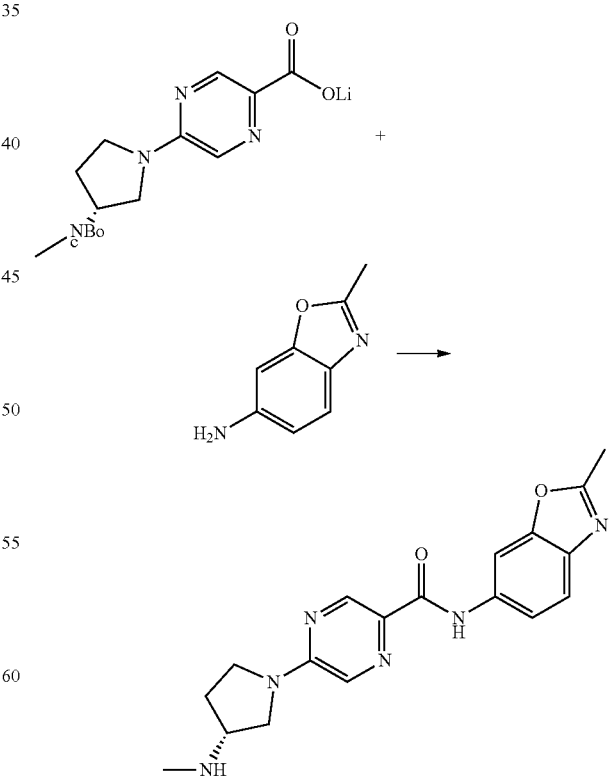

Prepared using Method B, followed by Method E, from lithium (R)-3-(3-(methylamino)pyrrolidin-1-yl)pyrazine-2- carboxylate (179 mg, 0.55 mmol) and 2-methylbenzo[d]oxazol-6-amine (81 mg, 0.55 mmol). LCMS (ES+) 353 (M+H)+, RT 2.42 min (Analytical method AcHSSC18). ¹H NMR (400 MHz, DMSO) δ 10.41 (s, 1H), 8.77 (d, J=1.3 Hz, 1H), 8.33 (d, J=1.9 Hz, 1H), 7.99 (d, J=1.4 Hz, 1H), 7.78 (dd, J=1.9, 8.7 Hz, 1H), 7.60 (d, J=8.7 Hz, 1H), 3.71-3.56 (m, 3H), 3.43-3.28 (m, 2H), 2.61 (s, 3H), 2.34 (s, 3H), 2.18-2.09 (m, 1H), 1.93-1.91 (m, 1H).

Example 364: 5-[3-(Dimethylamino)prop-1-ynyl]-N-(8-fluoro-2-methyl-imidazo[1,2-a]pyridin-6-yl)pyrazine-2-carboxamide

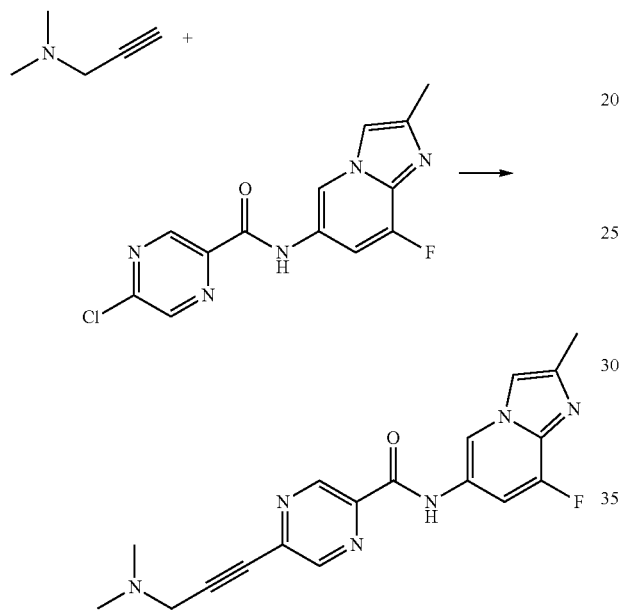

To a degassed solution of 3-dimethylamino-1-propyne (0.11 mL, 0.981 mmol) in N,N-dimethylformamide (3 mL) were successively added triethylamine (0.14 mL, 0.981 mmol), copper(I) iodide (19 mg, 0.0981 mmol), 5-chloro-N-(8-fluoro-2-methyl-imidazo[1,2-a]pyridin-6-yl)pyrazine-2-carboxamide (150 mg, 0.491 mmol), and bis(triphenylphosphine)palladium(II) dichloride (34 mg, 0.0491 mmol) and the reaction stirred for 3 hours at room temperature. The reaction mixture was filtered and concentrated under reduced pressure. The crude material was purified by flash column chromatography (0-20% MeOH in DCM; 25 g column). The product containing fractions were concentrated under reduced pressure and submitted to reverse phase HPLC (Xbridge Phenyl 19×150 mm, 10 um 20-80% MeOH/H₂O (10 mM NH₄CO₃), 20 ml/min, rt) for further purification to yield 5-[3-(dimethylamino)prop-1-ynyl]-N-(8-fluoro-2-methyl-imidazo[1,2-a]pyridin-6-yl)pyrazine-2-carboxamide. LCMS (ES+) 353.2 [M+H]+, RT 1.69 min (Analytical method AcHSSC18). ¹H NMR (400 MHz, DMSO) δ 11.03 (s, 1H), 9.27 (d, J=1.4 Hz, 1H), 9.24 (d, J=1.6 Hz, 1H), 8.90 (d, J=1.4 Hz, 1H), 7.96 (d, J=2.8 Hz, 1H), 7.58 (dd, J=1.6, 12.9 Hz, 1H), 3.64 (s, 2H), 2.36 (s, 3H), 2.31 (s, 6H).

Example 365: 5-(((1-Cyclopropylpiperidin-3-yl)methyl)amino)-N-(8-fluoro-2-methylimidazo[1,2-a]pyridin-6-yl)pyrazine-2-carboxamide

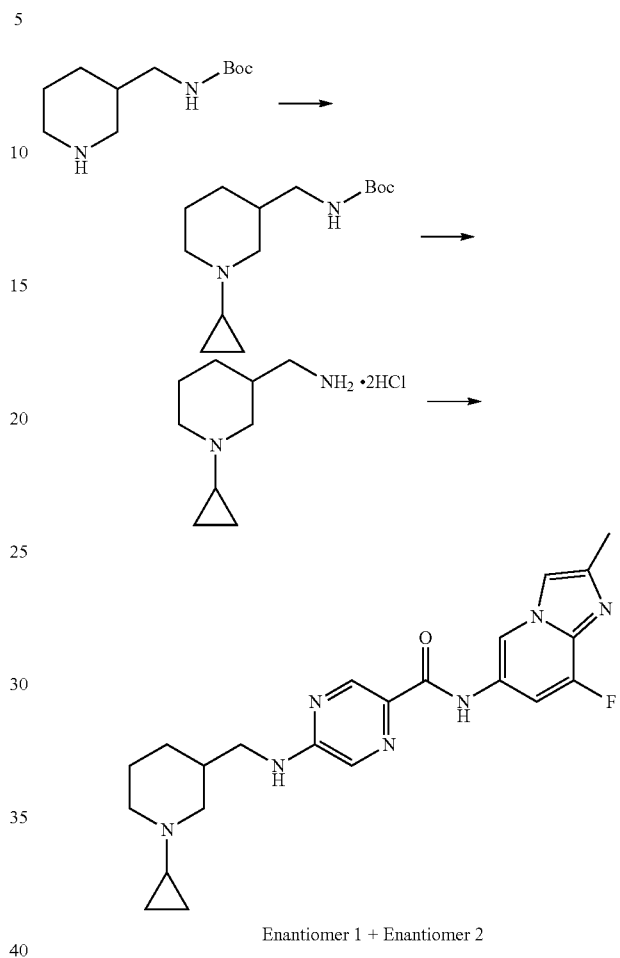

Enantiomer 1 + Enantiomer 2

3-(Boc-aminomethyl)piperidine (514 mg, 2.40 mmol, 1.00 eq), (1-ethoxycyclopropoxy)trimethylsilane (0.48 mL, 2.40 mmol, 1.00 eq), and methyl alcohol (50.00 mL) were combined. Sodium cyanoborohydride (166 mg, 2.64 mmol, 1.10 eq) was added, followed by acetic acid (0.20 mL). The reaction was then hot block heated to 55° C. for 20 hours, then cooled to room temperature. The reaction was then diluted with dichloromethane, washed with 10% NaOH solution, dried (MgSO₄), and concentrated in vacuo to give tert-butyl N-[(1-cyclopropyl-3-piperidyl)methyl]carbamate, which was used directly in the next step.

tert-Butyl N-[(1-cyclopropyl-3-piperidyl)methyl]carbamate (0.61 g, 2.40 mmol, 1.00 eq), methyl alcohol (10.00 mL), and 4 M hydrogen chloride in dioxane (5.0 mL, 20.0 mmol, 8.34 eq) were combined and stirred at room temperature for 23 hours. The mixture was concentrated in vacuo to give (1-cyclopropyl-3-piperidyl)methanamine dihydrochloride, which was used directly in the next step.

5-Chloro-N-(8-fluoro-2-methyl-imidazo[1,2-a]pyridin-6-yl)pyrazine-2-carboxamide (100 mg, 0.327 mmol, 1.00 eq), (1-cyclopropyl-3-piperidyl)methanamine dihydrochloride (100 mg, 0.44 mmol, 1.35 eq), 1,4-dioxane (3 mL), water (0.50 mL), and triethylamine (0.50 mL, 3.59 mmol, 11.0 eq) were combined in a sealed tube and microwave heated to 145° C. for 2 hours. The mixture was concentrated in vacuo, then purified by HPLC to give 5-[(1-cyclopropyl-3-piperidyl)methylamino]-N-(8-fluoro-2-methyl-imidazo[1,2-a]pyridin-6-yl)pyrazine-2-carboxamide. LCMS (ES+) 424 (M+H)+, RT 1.92 min (Analytical method AcHSSC18). ¹H NMR (400 MHz, DMSO) δ 10.37 (s, 1H), 9.19 (d, J=1.6 Hz, 1H), 8.66 (d, J=1.1 Hz, 1H), 8.02 (d, J=1.3 Hz, 1H), 7.95 (dd, J=5.6, 5.6 Hz, 1H), 7.90 (d, J=2.8 Hz, 1H), 7.55 (dd, J=1.6, 13.2 Hz, 1H), 3.31-3.23 (m, 2H), 2.95 (d, J=9.9 Hz, 1H), 2.81 (d, J=10.9 Hz, 1H), 2.35 (s, 3H), 2.19-2.13 (m, 1H), 1.97 (dd, J=10.4, 10.4 Hz, 1H), 1.79-1.54 (m, 4H), 1.43-1.33 (m, 1H), 1.07-0.97 (m, 1H), 0.43-0.38 (m, 2H), 0.29 (d, J=2.4 Hz, 2H).

Example 366: N-(8-Fluoro-2-methylimidazo[1,2-a]pyridin-6-yl)-5-(((3R,4S)-4-fluoropyrrolidin-3-yl)oxy)pyrazine-2-carboxamide

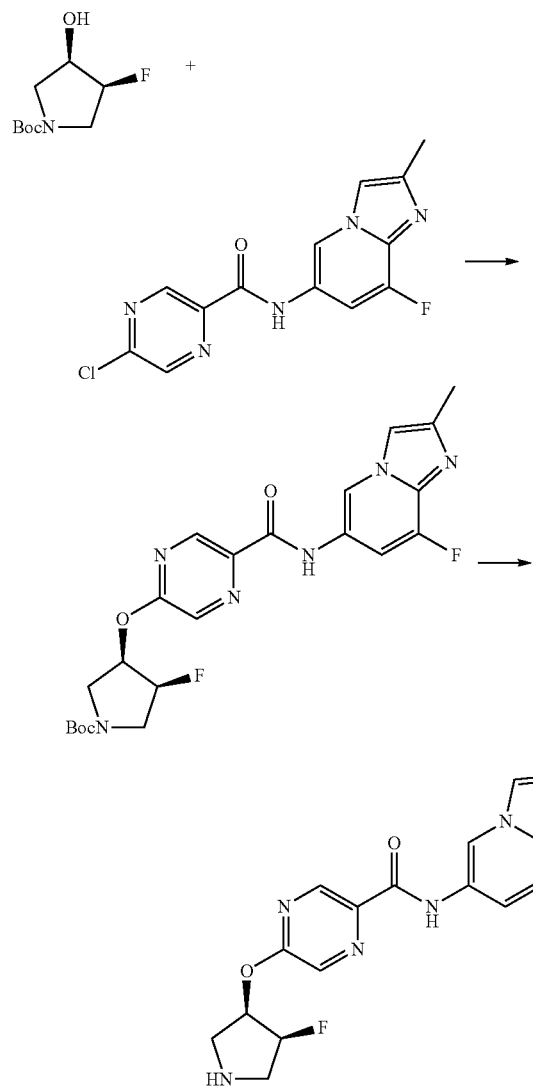

Synthesised using the same method as example 213, from tert-butyl (3S,4R)-3-fluoro-4-hydroxypyrrolidine-1-carboxylate (67 mg, 0.33 mmol) and 5-chloro-N-(8-fluoro-2-methyl-imidazo[1,2-a]pyridin-6-yl)pyrazine-2-carboxamide (100 mg, 0.33 mmol). LCMS (ES+) 375 (M+H)+, RT 1.68 min (Analytical method AcHSSC18) ¹H NMR (400 MHz, DMSO) δ 10.79-10.77 (m, 1H), 9.22 (d, J=1.5 Hz, 1H), 8.92-8.91 (m, 1H), 8.52-8.51 (m, 1H), 7.93 (d, J=2.4 Hz, 1H), 7.57 (dd, J=1.6, 12.9 Hz, 1H), 5.41-5.22 (m, 2H), 3.29-3.23 (m, 1H), 3.05-2.87 (m, 3H), 2.35 (s, 3H).

Example 367: (R)-5-(3-(cyclopropylamino)pyrrolidin-1-yl)-N-(2-(difluoromethyl)-8-fluoroimidazo[1,2-a]pyridin-6-yl)pyrazine-2-carboxamide

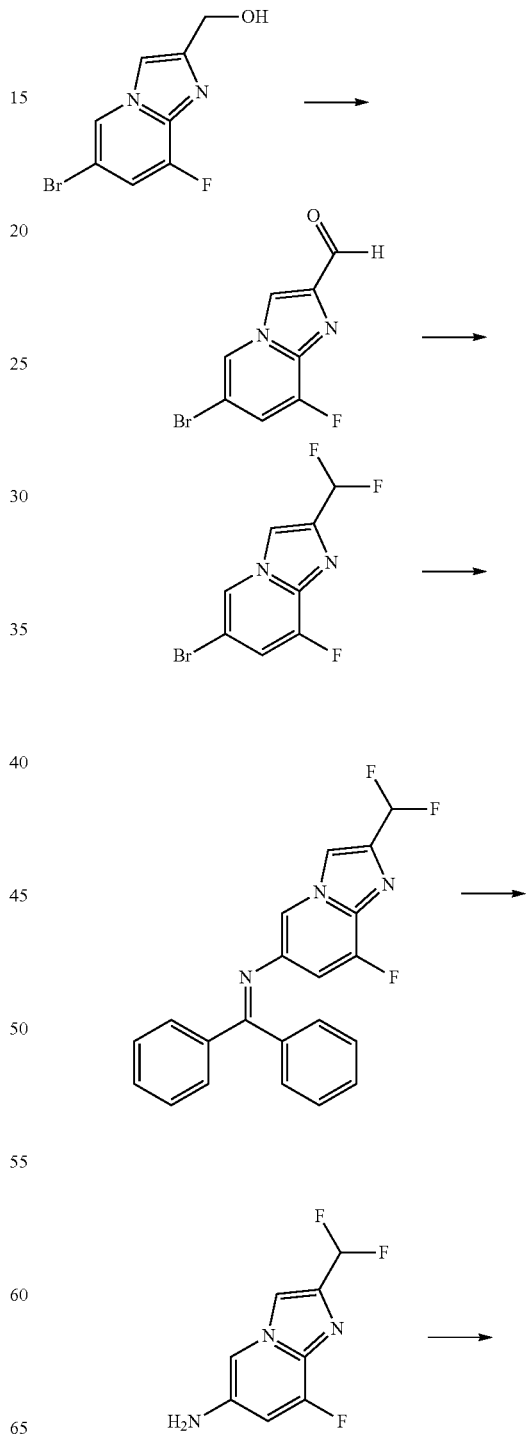

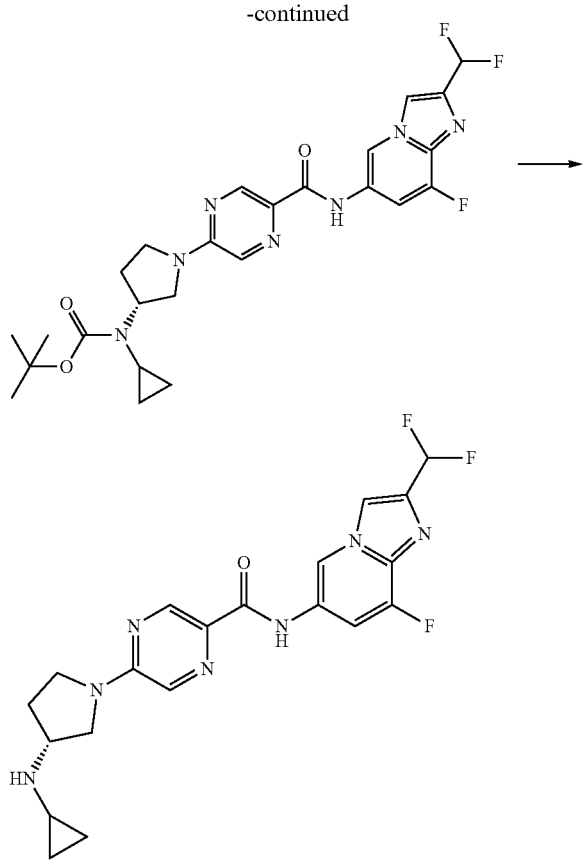

(6-Bromo-8-fluoroimidazo[1,2-a]pyridin-2-yl)methanol (850 mg, 3.47 mmol) was dissolved in DCM (20 mL) and cooled in an ice-bath. Dess-Martin periodinane (2.21 g, 5.20 mmol) was added and the reaction allowed to warm to r.t. over 3 h. The reaction was quenched by sequential addition of saturated sodium hydrogencarbonate and 1M sodium thiosulfate. The aqueous layer was extracted with DCM (×2), and the layers separated using a phase separator. The solvent was removed in vacuo to give a residue, which was purified using silica chromatography, elution gradient 0-100% EtOAc/cyclohexane to give the desired product.

6-Bromo-8-fluoroimidazo[1,2-a]pyridine-2-carbaldehyde (335 mg, 1.38 mmol) was dissolved in DCM (5 mL) and cooled in an ice-bath. DAST (0.46 mL, 3.34 mmol) was added dropwise and the reaction allowed to warm to RT over 18 h. The reaction was cooled in an ice-bath and quenched by addition of saturated sodium hydrogencarbonate. The aqueous layer was extracted with DCM (×2), and the layers were separated using a phase separator. The solvent was removed in vacuo to give a residue, which was purified using silica chromatography, elution gradient 0-100% EtOAc/cyclohexane to give the desired product.

2-(Difluoromethyl)-8-fluoroimidazo[1,2-a]pyridin-6-amine (255 mg, 0.96 mmol) was dissolved in THF (4 mL). Benzophenone imine (174 mg, 0.96 mmol) and cesium carbonate (470 mg, 1.44 mmol) were added and the reaction degassed with nitrogen for 15 minutes. To the mixture was added rac-BINAP (60 mg, 0.096 mmol) and palladium acetate (22 mg, 0.096 mmol), and the mixture was degassed with nitrogen for a further 15 minutes. The reaction tube was sealed and heated at 70° C. for 18 h. The reaction was cooled to RT and the solvent removed in vacuo. The residue was purified by silica chromatography, elution gradient 0-100% EtOAc/cyclohexane to give the desired product.

N-(2-(Difluoromethyl)-8-fluoroimidazo[1,2-a]pyridin-6-yl)-1,1-diphenylmethanimine (215 mg, 0.59 mmol) was dissolved in methanol (2 mL), and 4M HCl in dioxane (4 mL) was added. The reaction was stirred at r.t. for 4 h. The solvent was removed in vacuo to give a residue, which was further purified by SCX chromatography, eluting with methanol and then 10% 7N ammonia in methanol/methanol. The ammonical fractions were combined and the solvent removed in vacuo to give the desired product.

2-(Difluoromethyl)-8-fluoroimidazo[1,2-a]pyridin-6-amine (72 mg, 0.36 mmol) and lithium (R)-5-(3-((tert-butoxycarbonyl)(cyclopropyl)amino)pyrrolidin-1-yl)pyrazine-2-carboxylate (91 mg, 0.36 mmol) were dissolved in DMF (2 mL), and TEA (0.5 mL) and HBTU (149 mg, 0.39 mmol) were added. The reaction was stirred at r.t. for 18 h. The solvent was removed in vacuo and the residue purified by preparative HPLC to give a residue, which was further purified using silica chromatography, elution gradient 0-100% EtOAc/cyclohexane to give the desired product.

tert-Butyl (R)-cyclopropyl(1-(5-((2-(difluoromethyl)-8-fluoroimidazo[1,2-a]pyridin-6-yl)carbamoyl)pyrazin-2-yl)pyrrolidin-3-yl)carbamate (10 mg, 0.02 mmol) was dissolved in DCM (1.7 mL), and TFA (0.3 mL) was added. The reaction was stirred at RT for 3 h and the solvent removed in vacuo to give a residue, which was further purified by SCX chromatography, eluting with methanol and then 10% 7N ammonia in methanol/methanol. The ammonical fractions were combined and the solvent removed in vacuo to give a residue, which was further purified by silica chromatography, elution gradient 0-100% 3:1 EtOAc:ethanol/cyclohexane to give the title compound. LCMS (ES+) 432 (M+H)+, RT 2.64 min (Analytical method AcHSSC18); $^1$H NMR (400 MHz, DMSO) δ 10.54 (s, 1H), 9.39 (d, J=1.5 Hz, 1H), 8.75-8.74 (m, 1H), 8.51-8.49 (m, 1H), 7.97-7.96 (m, 1H), 7.76 (dd, J=1.6, 13.0 Hz, 1H), 7.15 (t, J=54.8 Hz, 1H), 3.73-3.39 (m, 6H), 2.16-2.12 (2H, m), 1.92 (brs, 1H), 0.44-0.37 (2H, m), 0.27-0.19 (2H, m).

Example 368: (R)—N-(7-Fluoro-2-methyl-2H-indazol-5-yl)-5-(3-(methylamino)pyrrolidin-1-yl)pyrazine-2-carboxamide

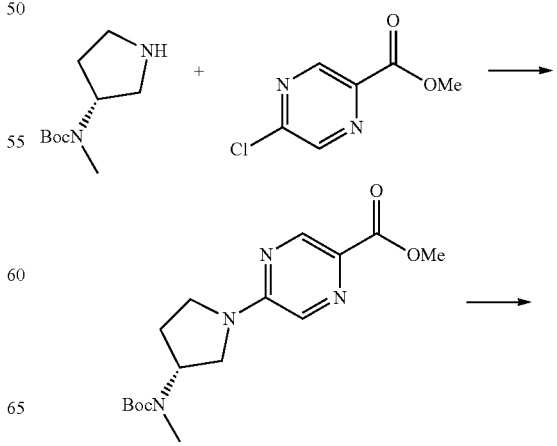

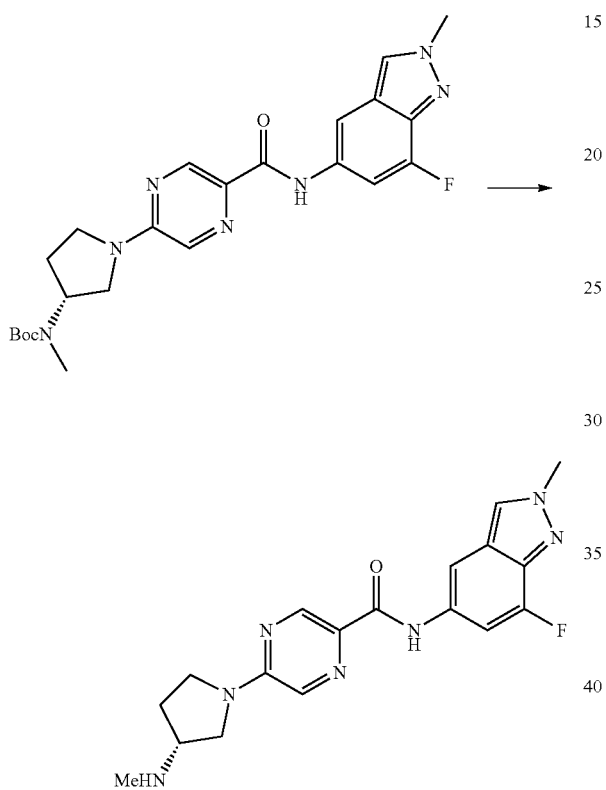

A suspension of methyl 5-chloropyrazine-2-carboxylate (1.00 g, 5.36 mmol), tert-butyl (R)-methyl(pyrrolidin-3-yl)carbamate (1.07 g, 5.36 mmol), and cesium carbonate (5.24 g, 16.1 mmol) in DMF (15 mL) was stirred at 100° C. for 16 h. After cooling to r.t., the mixture was diluted with water and extracted three times with EtOAc. The combined organics were washed with brine, dried using phase separating filter paper and concentrated to give crude methyl (R)-5-(3-((tert-butoxycarbonyl)(methyl)amino)pyrrolidin-1-yl)pyrazine-2-carboxylate, which was used without further purification.

A solution of methyl (R)-5-(3-((tert-butoxycarbonyl)(methyl)amino)pyrrolidin-1-yl)pyrazine-2-carboxylate (1.88 g, 5.36 mmol) in sodium hydroxide (2 M in water, 3.5 mL, 7 mmol) and methanol (150 mL) was stirred at 50° C. for 16 h. The volume was reduced to approximately 50 mL by evaporation. Acidification with 2 M HCl to pH 4 was followed by dilution with water and three extractions with EtOAc. The combined organics were dried using phase separating filter paper and concentrated to give crude (R)-5-(3-((tert-butoxycarbonyl)(methyl)amino)pyrrolidin-1-yl)pyrazine-2-carboxylic acid, which was used without further purification.

A solution of (R)-5-(3-((tert-butoxycarbonyl)(methyl)amino)pyrrolidin-1-yl)pyrazine-2-carboxylic acid (247 mg, 0.734 mmol), 7-fluoro-2-methyl-2H-indazol-5-amine (130 mg, 0.734 mmol), NMI (0.29 mL, 3.7 mmol), and TCFH (247 mg, 0.880 mmol) in acetonitrile (5 mL) was stirred at r.t. for 16 h. The reaction was diluted with water and the precipitated solids were collected by filtration, washing with 2:1 water:acetonitrile. The solid was dried to give crude tert-butyl (R)-(1-(5-((7-fluoro-2-methyl-2H-indazol-5-yl)carbamoyl)pyrazin-2-yl)pyrrolidin-3-yl)(methyl)carbamate, which was used without further purification.

A solution of tert-butyl (R)-(1-(5-((7-fluoro-2-methyl-2H-indazol-5-yl)carbamoyl)pyrazin-2-yl)pyrrolidin-3-yl)(methyl)carbamate (210 mg, 0.424 mmol) in DCM (5 mL) was treated with TFA (2 mL) at r.t. and stirred for 3 h. The solvents were removed by evaporation and the residue dissolved in DCM and applied to an SCX cartridge, eluting with 3 column volumes DCM, then 3 column volumes 2.5 M $NH_3$/MeOH. The ammonia fractions were concentrated to give (R)—N-(7-fluoro-2-methyl-2H-indazol-5-yl)-5-(3-(methylamino)pyrrolidin-1-yl)pyrazine-2-carboxamide. LCMS (ES+) 396 (M+H)+, RT 2.59 min (Analytical method AcHSSC18); $^1$H NMR (400 MHz, DMSO) δ 10.14 (s, 1H), 8.64 (s, 1H), 8.55 (s, 1H), 8.20 (s, 1H), 7.08 (s, 1H), 4.08 (s, 3H), 3.98 (s, 3H), 3.84-3.68 (m, 3H), 3.48 (dd, J=4.3, 11.0 Hz, 1H), 3.24-3.17 (m, 1H), 2.70 (s, 3H), 2.30 (s, 3H), 2.06-1.96 (m, 1H), 1.83-1.74 (m, 1H).

Example 369: 5-((1R,6S)-3-azabicyclo[4.1.0]heptan-6-yl)-N-(8-fluoro-2-methylimidazo[1,2-a]pyridin-6-yl)pyrazine-2-carboxamide, 5-((1S,6R)-3-azabicyclo[4.1.0]heptan-6-yl)-N-(8-fluoro-2-methylimidazo[1,2-a]pyridin-6-yl)pyrazine-2-carboxamide

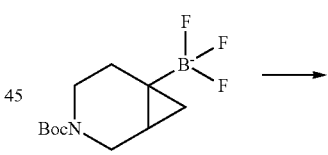

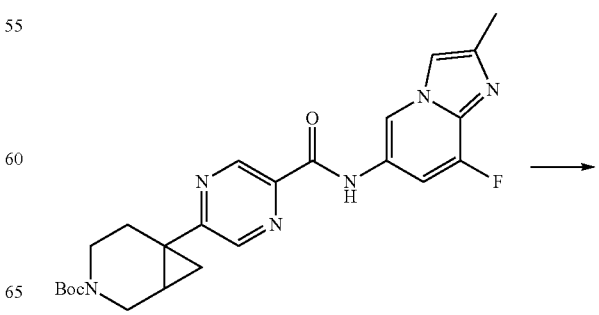

-continued

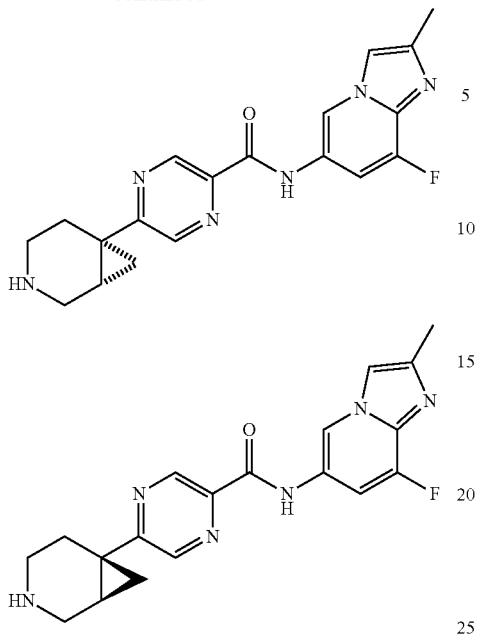

A suspension of potassium (3-(tert-butoxycarbonyl)-3-azabicyclo[4.1.0]heptan-6-yl)trifluoroborate (120 mg, 0.396 mmol), 5-chloro-N-(8-fluoro-2-methylimidazo[1,2-a]pyridin-6-yl)pyrazine-2-carboxamide (101 mg, 0.330 mmol), Pd(dppf)Cl$_2$ (27 mg, 0.033 mmol), and cesium carbonate (215 mg, 0.660 mmol) in toluene (2 mL) and water (0.2 mL) was sparged with N$_2$ and stirred at 110° C. for 16 h. After cooling to r.t., the mixture was filtered through Celite and the filtrate concentrated. Purification by silica chromatography, eluting with 5-60% EtOAc/c-hexane, gave impure tert-butyl 6-(5-((8-fluoro-2-methylimidazo[1,2-a]pyridin-6-yl)carbamoyl)pyrazin-2-yl)-3-azabicyclo[4.1.0]heptane-3-carboxylate, which was used without further purification.

A solution of tert-butyl 6-(5-((8-fluoro-2-methylimidazo[1,2-a]pyridin-6-yl)carbamoyl)pyrazin-2-yl)-3-azabicyclo[4.1.0]heptane-3-carboxylate (108 mg, 0.232 mmol) in TFA (2 mL) and DCM (5 mL) was stirred at RT for 3 h. The mixture was concentrated and the residue was applied to an SCX cartridge, eluting with 3 column volumes MeOH, then 3 column volumes 7 M NH$_3$/MeOH. The ammonia fractions were concentrated and the residue purified by chiral SFC to give one major isomer. LCMS (ES+) 367 (M+H)+, RT 1.76 min (Analytical method AcHSSC18); RT 3.64 min (Analytical method SFC1, YMC CELLULOSE-C+0.1% DEAISO 20% MeOH); $^1$H NMR (400 MHz, DMSO) δ 10.87 (s, 1H), 9.21 (d, J=1.6 Hz, 1H), 9.13 (d, J=1.5 Hz, 1H), 8.69 (d, J=1.4 Hz, 1H), 7.92 (d, J=2.8 Hz, 1H), 7.56 (dd, J=1.6, 13.0 Hz, 1H), 3.15 (dd, J=5.3, 12.6 Hz, 1H), 2.98 (d, J=11.7 Hz, 1H), 2.68-2.52 (m, 3H), 2.34 (s, 3H), 2.02-1.89 (m, 1H), 1.79-1.74 (m, 1H), 1.36 (dd, J=3.8, 9.2 Hz, 1H), 1.27 (dd, J=4.0, 6.5 Hz, 1H).

Example 370: 5-(3-(cyclopropylamino)pyrrolidin-1-yl)-N-(7-(difluoromethyl)-2-methylimidazo[1,2-a]pyridin-6-yl)pyrazine-2-carboxamide

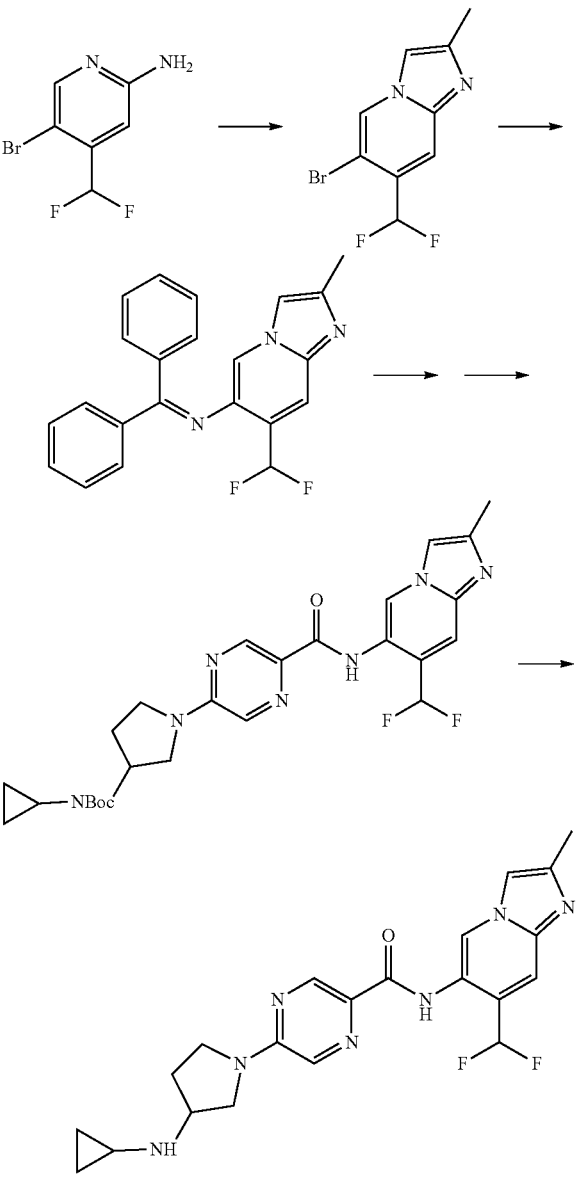

A suspension of 5-bromo-4-(difluoromethyl)pyridin-2-amine (1000 mg, 4.48 mmol), 1-bromo-2,2-dimethoxypropane (0.97 mL, 7.17 mmol), and PPTS (113 mg, 0.448 mmol) in isopropanol (10 mL) was stirred at 65° C. for 16 h. After cooling to RT, the mixture was filtered to collect solids, washing with isopropanol to give crude 6-bromo-7-(difluoromethyl)-2-methylimidazo[1,2-a]pyridine, which was used without further purification.

A suspension of 6-bromo-7-(difluoromethyl)-2-methylimidazo[1,2-a]pyridine (350 mg, 0.34 mmol), benzophenone imine (243 mg, 1.34 mmol), rac-BINAP (83 mg, 0.134 mmol), palladium acetate (30 mg, 0.134 mmol), and cesium carbonate (655 mg, 2.01 mmol) in THF (4 mL) was sparged with N$_2$ and stirred at 100° C. for 16 h. LCMS analysis indicated incomplete reaction; additional rac-BINAP (83 mg, 0.134 mmol) and palladium acetate (30 mg, 0.134 mmol) were added and stirring continued at 100° C. for an additional 16 h. After cooling to RT, the mixture was diluted with brine and extracted with EtOAc (×3). The combined organics were washed with brine, dried with phase separating filter paper, and concentrated. Purification by silica chromatography, eluting with 5-60% EtOAc/c-hexane gave crude N-(7-(difluoromethyl)-2-methylimidazo[1,2-a]pyridin-6-yl)-1,1-diphenylmethanimine, which was used without further purification.

A solution of N-(7-(difluoromethyl)-2-methylimidazo[1,2-a]pyridin-6-yl)-1,1-diphenylmethanimine (245 mg, 0.678 mmol) in methanol (5 mL) was treated with 4 M HCl/MeOH (1.7 mL, 6.78 mmol) and stirred for 16 h at r.t. The mixture was concentrated and the residue applied to an SCX cartridge, eluting with 3 column volumes MeOH, then 3 column volumes 7 M $NH_3$/MeOH. The ammonia fraction was concentrated to give crude 7-(difluoromethyl)-2-methylimidazo[1,2-a]pyridin-6-amine, which was used without further purification.

A solution of lithium 5-(3-((tert-butoxycarbonyl)(ethyl)amino)pyrrolidin-1-yl)pyrazine-2-carboxylate (183 mg, 0.517 mmol), 7-(difluoromethyl)-2-methylimidazo[1,2-a]pyridin-6-amine (102 mg, 0.517 mmol), 1-methylimidazole (0.21 mL, 2.59 mmol), and TCFH (174 mg, 0.621 mmol) in MeCN (2 mL) was stirred at RT for 16 h. The mixture was diluted with water and filtered to collect solids, washing with 2:1 $H_2O$:MeCN to give crude tert-butyl cyclopropyl(1-(5-((7-(difluoromethyl)-2-methylimidazo[1,2-a]pyridin-6-yl)carbamoyl)pyrazin-2-yl)pyrrolidin-3-yl)carbamate, which was used without further purification.

A solution of tert-butyl cyclopropyl(1-(5-((7-(difluoromethyl)-2-methylimidazo[1,2-a]pyridin-6-yl)carbamoyl)pyrazin-2-yl)pyrrolidin-3-yl)carbamate (24 mg, 0.046 mmol) in DCM (5 mL) was treated with TFA (1 mL) at RT and stirred for 16 h. The mixture was concentrated and the residue applied to an SCX cartridge, eluting with 3 column volumes MeOH, then 3 column volumes 7 M $NH_3$/MeOH. The ammonia fraction was concentrated to give 5-(3-(cyclopropylamino)pyrrolidin-1-yl)-N-(7-(difluoromethyl)-2-methylimidazo[1,2-a]pyridin-6-yl)pyrazine-2-carboxamide. LCMS (ES+) 428 (M+H)+, RT 1.79 min (Analytical method AcHSSC18); $^1$H NMR (400 MHz, DMSO) δ 9.95 (s, 1H), 9.11 (s, 1H), 8.72 (s, 1H), 8.01 (s, 1H), 7.88 (s, 1H), 7.75 (s, 1H), 7.17 (t, J=54.6 Hz, 1H), 3.72-3.38 (m, 5H), 2.37 (s, 3H), 2.17-2.06 (m, 2H), 2.00-1.87 (m, 1H), 0.43-0.38 (m, 2H), 0.26-0.23 (m, 2H).

Example 371: (S)-5-(7-amino-5-azaspiro[2.4]heptan-5-yl)-N-(8-fluoro-2-methylimidazo[1,2-a]pyridin-6-yl)pyrazine-2-carboxamide and Example 372: (S)—N-(8-fluoro-2-methylimidazo[1,2-a]pyridin-6-yl)-5-(7-(methylamino)-5-azaspiro[2.4]heptan-5-yl)pyrazine-2-carboxamide

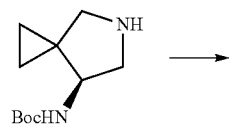

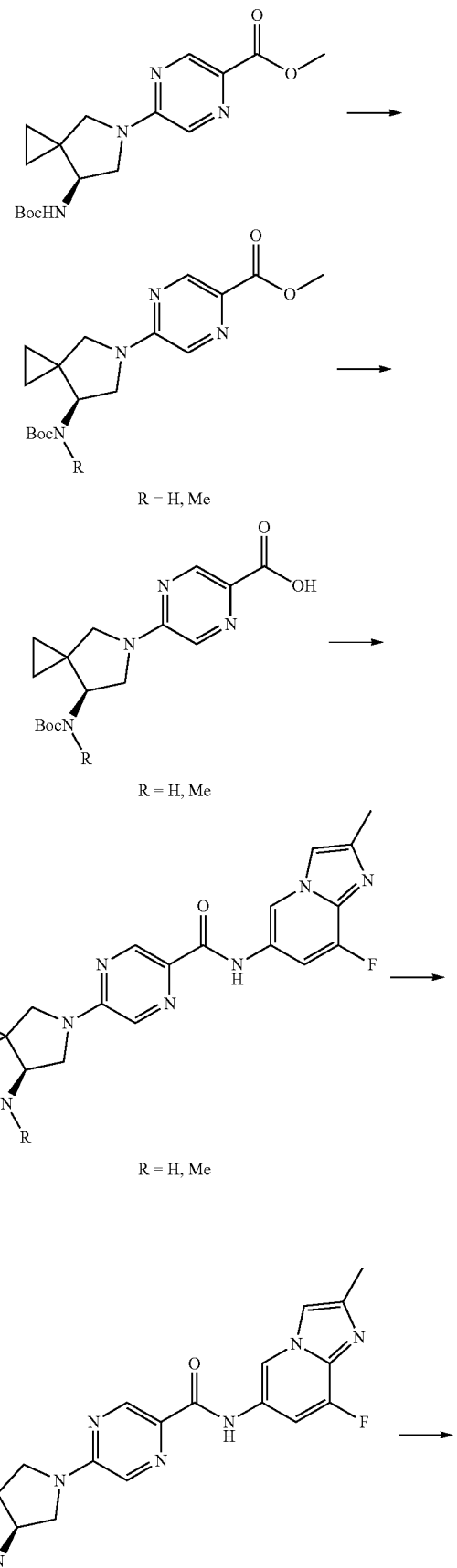

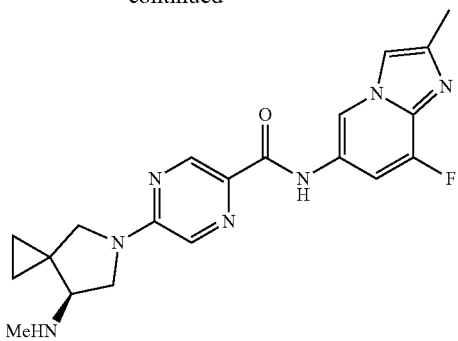

A suspension of tert-butyl (S)-(5-azaspiro[2.4]heptan-7-yl)carbamate (497 mg, 2.34 mmol), methyl 5-chloropyrazine-2-carboxylate (406 mg, 2.35 mmol), and cesium carbonate (849 mg, 2.61 mmol) in DMF (10 mL) was stirred at 100° C. for 16 h. After cooling to r.t., the solids were removed by filtration, washing with EtOAc (10 mL). The filtrate was concentrated to give crude methyl (S)-5-(7-((tert-butoxycarbonyl)amino)-5-azaspiro[2.4]heptan-5-yl)pyrazine-2-carboxylate, which was used without further purification.

A solution of methyl (S)-5-(7-((tert-butoxycarbonyl)amino)-5-azaspiro[2.4]heptan-5-yl)pyrazine-2-carboxylate (796 mg from previous step, 2.3 mmol) in DMF (10 mL) held under $N_2$ at r.t. was treated with NaH (60 wt % in oil, 143 mg, 3.58 mmol). After stirring for 30 min, additional DMF (5 mL) was added to wash the foam that had formed down the sides of the flask. Iodomethane (0.22 mL, 3.53 mmol) was added and the mixture stirred at r.t. for 91 h. At this time, LCMS analysis indicated incomplete methylation and additional NaH (164 mg, 4.1 mmol) was added. 50 min later, additional iodomethane (0.22 mL, 3.53 mmol) was added. Stirring continued at r.t. for 29 h, at which time the reaction was quenched with 1.5 mL sat. aq. $NH_4Cl$, diluted with water (50 mL) and extracted with EtOAc (30 mL) and $Et_2O$ (30 mL). The combined organics were washed with water (30 mL), dried ($Na_2SO_4$), and concentrated to give a mixture of methyl (S)-5-(7-((tert-butoxycarbonyl)amino)-5-azaspiro[2.4]heptan-5-yl)pyrazine-2-carboxylate and methyl (S)-5-(7-((tert-butoxycarbonyl)(methyl)amino)-5-azaspiro[2.4]heptan-5-yl)pyrazine-2-carboxylate, which was used without further purification.

The crude mixture from the previous step was dissolved in MeOH (30 mL) and treated with LiOH (1 M in $H_2O$, 11.5 mL) at r.t. After stirring for 24 h, the mixture was acidified to pH 5 using 2 M HCl. The mixture was extracted with DCM (3×30 mL). The combined organics were dried with a phase separating cartridge and concentrated to give a mixture of (S)-5-(7-((tert-butoxycarbonyl)amino)-5-azaspiro[2.4]heptan-5-yl)pyrazine-2-carboxylic acid and (S)-5-(7-((tert-butoxycarbonyl)(methyl)amino)-5-azaspiro[2.4]heptan-5-yl)pyrazine-2-carboxylic acid, which was used without further purification.

The crude mixture from the previous step was dissolved in MeCN (15 mL) at RT and treated sequentially with 8-fluoro-2-methylimidazo[1,2-a]pyridin-6-amine (345 mg, 1.45 mmol), TCFH (486 mg, 1.73 mmol), and 1-methylimidazole (0.57 mL, 7.15 mmol). After stirring for 23 h, water (30 mL) was added with stirring. The mixture was filtered to collect the formed solids, washing with water (10 mL). The solids were dried at 40° C. under vacuum to give a mixture of tert-butyl (S)-(5-(5-((8-fluoro-2-methylimidazo[1,2-a]pyridin-6-yl)carbamoyl)pyrazin-2-yl)-5-azaspiro[2.4]heptan-7-yl)carbamate and tert-butyl (S)-(5-(5-((8-fluoro-2-methylimidazo[1,2-a]pyridin-6-yl)carbamoyl)pyrazin-2-yl)-5-azaspiro[2.4]heptan-7-yl)(methyl)carbamate, which was used without further purification.

The crude mixture from the previous step was dissolved in DCM (5 mL) and treated at RT with TFA (2 mL). After stirring for 1.5 h, the reaction was quenched with MeOH (10 mL) and concentrated. The residue was applied to an SCX cartridge, eluting with 3 column volumes MeOH, then 3 column volumes 7M $NH_3$/MeOH. The ammonia fraction was concentrated and purified by reverse phase HPLC to give (S)-5-(7-amino-5-azaspiro[2.4]heptan-5-yl)-N-(8-fluoro-2-methylimidazo[1,2-a]pyridin-6-yl)pyrazine-2-carboxamide, and (S)—N-(8-fluoro-2-methylimidazo[1,2-a]pyridin-6-yl)-5-(7-(methylamino)-5-azaspiro[2.4]heptan-5-yl)pyrazine-2-carboxamide.

Data for (S)-5-(7-amino-5-azaspiro[2.4]heptan-5-yl)-N-(8-fluoro-2-methylimidazo[1,2-a]pyridin-6-yl)pyrazine-2-carboxamide: LCMS (ES+) 382 (M+H)+, RT 1.9 min (Analytical method AcHSSC18); $^1H$ NMR (400 MHz, DMSO) δ 10.42 (s, 1H), 9.18 (d, J=1.5 Hz, 1H), 8.73 (d, J=1.2 Hz, 1H), 7.97-7.91 (m, 1H), 7.89-7.87 (m, 1H), 7.56 (dd, J=1.7, 13.1 Hz, 1H), 3.83 (dd, J=5.5, 10.4 Hz, 1H), 3.69 (d, J=10.7 Hz, 1H), 3.46 (d, J=10.8 Hz, 1H), 3.19 (1H, s), 2.33 (s, 3H), 1.75 (s, 2H), 0.88-0.81 (m, 1H), 0.65-0.58 (m, 2H), 0.52-0.45 (m, 1H), 1H obscured by water peak; $^{19}F$ NMR (376 MHz, DMSO) δ −132.2 ppm.

Data for (S)—N-(8-fluoro-2-methylimidazo[1,2-a]pyridin-6-yl)-5-(7-(methylamino)-5-azaspiro[2.4]heptan-5-yl)pyrazine-2-carboxamide: LCMS (ES+) 396 (M+H)+, RT 1.91 min (Analytical method AcHSSC18); $^1H$ NMR (400 MHz, DMSO) δ 10.41 (s, 1H), 9.18 (d, J=1.6 Hz, 1H), 8.73 (d, J=1.3 Hz, 1H), 7.94 (br s, 1H), 7.88 (dd, J=0.8, 3.2 Hz, 1H), 7.56 (dd, J=1.6, 13.0 Hz, 1H), 3.77-3.60 (m, 2H), 2.77 (br s, 1H), 2.33 (d, J=0.7 Hz, 3H), 2.29 (s, 3H), 1.82 (br s, 1H), 0.93-0.87 (m, 1H), 0.67-0.56 (m, 3H), 2H obscured by water peak; $^{19}F$ NMR (376 MHz, DMSO) δ −132.2 ppm.

Example 373: (S)-5-(5-(cyclopropylamino)-2-azaspiro[3.3]heptan-2-yl)-N-(6-methoxy-2-methyl-2H-indazol-5-yl)pyrazine-2-carboxamide

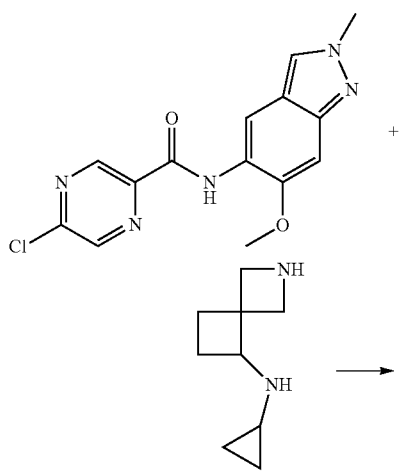

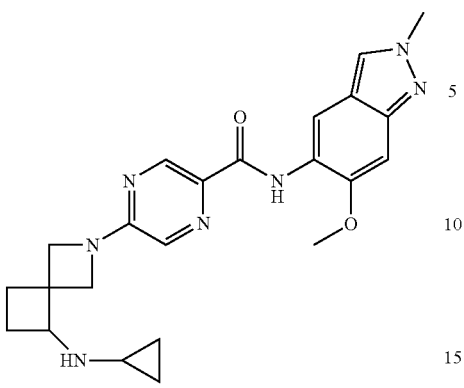

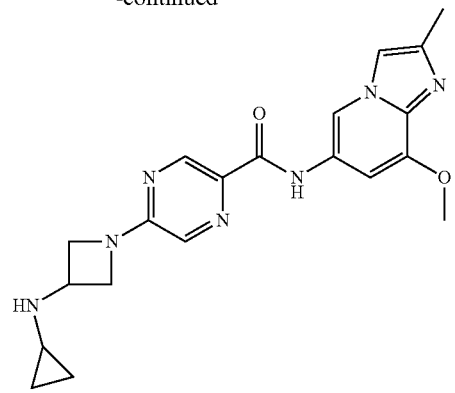

5-Chloro-N-(6-methoxy-2-methyl-indazol-5-yl)pyrazine-2-carboxamide (209 mg, 0.657 mmol, 1.00 eq), cesium carbonate (856 mg, 2.63 mmol, 4.00 eq), and N-cyclopropyl-2-azaspiro[3.3]heptan-7-amine (100 mg, 0.657 mmol, 1.00 eq) were combined in DMF (5 mL) and stirred at 110° C. for 17 h. After cooling to r.t., the mixture was partitioned between EtOAc and water. The aqueous phase was extracted with EtOAc. The combined organic phases were dried over magnesium sulfate, filtered, and concentrated in vacuo. The residue was purified by reverse phase HPLC, then chiral SFC to give both enantiomers of 5-(5-(cyclopropylamino)-2-azaspiro[3.3]heptan-2-yl)-N-(6-methoxy-2-methyl-2H-indazol-5-yl)pyrazine-2-carboxamide. Data for the more active isomer (arbitrarily assigned (S) stereochemistry) are given. LCMS (ES+) 434 (M+H)+, RT 2.67 min (Analytical method AcHSSC18); $^1$H NMR (400 MHz, DMSO) δ 10.02 (s, 1H), 8.70 (d, J=1.3 Hz, 1H), 8.65 (s, 1H), 8.21 (s, 1H), 7.90 (d, J=1.3 Hz, 1H), 7.09 (s, 1H), 4.53 (d, J=9.3 Hz, 1H), 4.08 (s, 3H), 4.08-4.05 (m, 2H), 3.96 (s, 3H), 3.93 (s, 1H), 3.30-3.21 (m, 1H), 2.82 (d, J=8.4 Hz, 1H), 2.11-1.96 (m, 2H), 1.93-1.79 (m, 2H), 1.53-1.44 (m, 1H), 0.37-0.11 (m, 4H).

Example 374: 5-(3-(cyclopropylamino)azetidin-1-yl)-N-(8-methoxy-2-methylimidazo[1,2-a]pyridin-6-yl)pyrazine-2-carboxamide

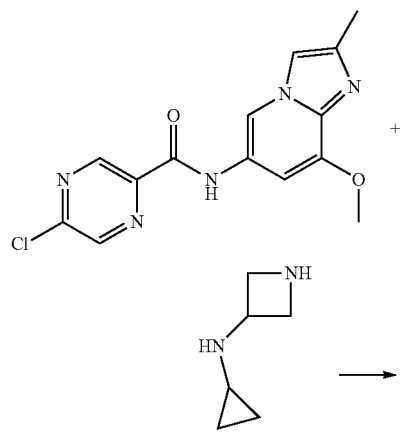

N-Cyclopropylazetidin-3-amine (12 mg, 0.104 mmol, 1.00 eq), triethylamine (0.058 mL, 0.414 mmol, 4.00 eq), and 5-chloro-N-(8-methoxy-2-methyl-imidazo[1,2-a]pyrazin-6-yl)pyrazine-2-carboxamide (33 mg, 0.104 mmol, 1.00 eq) were combined in acetonitrile (2 mL) and stirred at 55° C. for 17 h. The reaction mixture was concentrated, diluted with $CH_2Cl_2$, and washed with brine. The organic layer was concentrated in vacuo and the residue dried under vacuum to give 5-(3-(cyclopropylamino)azetidin-1-yl)-N-(8-methoxy-2-methylimidazo[1,2-a]pyridin-6-yl)pyrazine-2-carboxamide. LCMS (ES+) 395 (M+H)+, RT 1.97 min (Analytical method AcHSSC18); $^1$H NMR (400 MHz, DMSO) δ 9.52 (s, 1H), 8.90 (s, 1H), 8.73 (s, 1H), 7.95 (s, 1H), 7.93 (s, 1H), 4.35 (dd, J=8.0, 8.0 Hz, 2H), 4.07 (s, 3H), 3.96-3.91 (m, 2H), 3.90-3.84 (m, 1H), 2.35 (s, 3H), 2.13-2.08 (m, 1H), 0.42-0.39 (m, 2H), 0.31-0.26 (m, 2H).

Example 375: (R)—N-(2,8-Dimethylimidazo[1,2-a]pyrazin-6-yl)-3-(3-(methylamino)-pyrrolidin-1-yl)-1,2,4-triazine-6-carboxamide

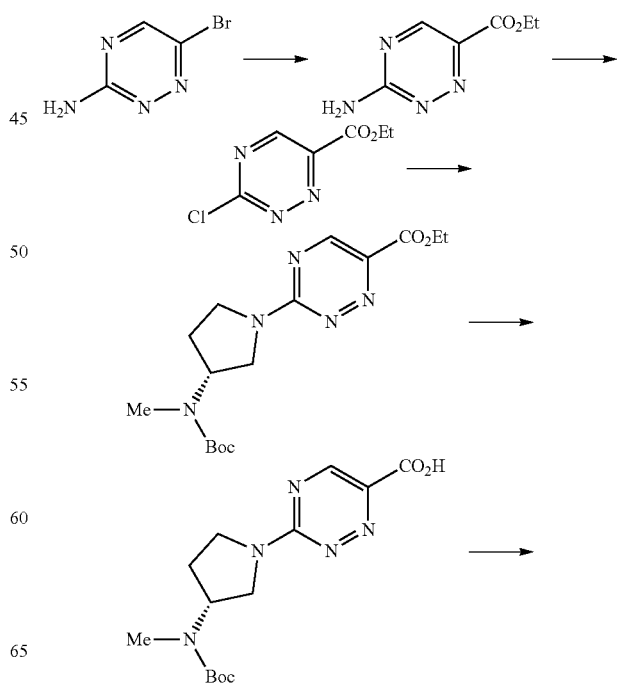

-continued

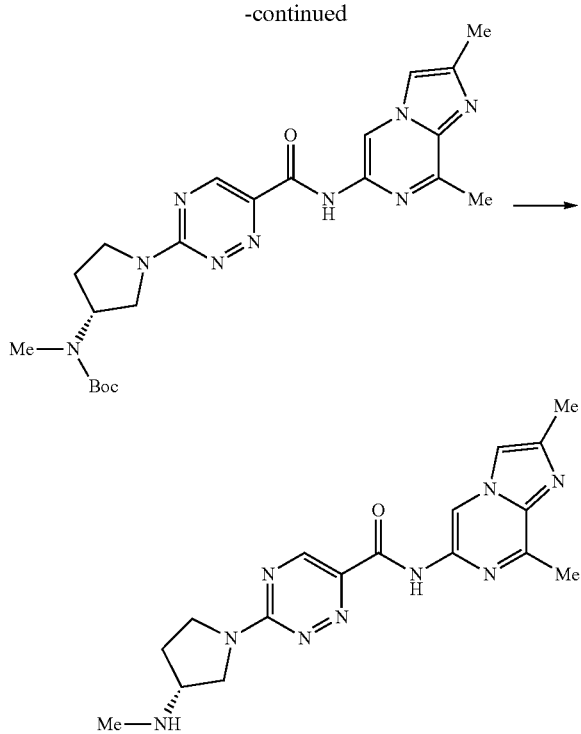

A mixture of 6-bromo-1,2,4-triazin-3-amine (5.00 g, 28.6 mmol) in ethanol (114 mL) was sparged with argon while adding 4,5-bis(diphenylphosphino)-9,9-dimethylxanthene (1.98 g, 3.43 mmol), triethylamine (10.4 mL, 74.3 mmol), and palladium(II) acetate (0.449 g, 2.00 mmol). The mixture was sparged with carbon monoxide for 15 min, and stirred at 80° C. for 32 h under 1 atm of carbon monoxide. After this time, the mixture was cooled to room temperature, filtered through diatomaceous earth, and the filter cake washed with ethyl acetate (3×75 mL). The filtrate was concentrated in vacuo, and the residue obtained was purified by chromatography (silica gel; heptane to 50:50 heptane/ethyl acetate; gradient elution) to afford ethyl 3-amino-1,2,4-triazine-6-carboxylate. $^1$H NMR (500 MHz, DMSO-d$_6$) δ 8.65 (s, 1H), 8.23 (br s, 1H), 7.95 (br s, 1H), 4.34 (q, J=7.0 Hz, 2H), 1.33 (t, J=7.0 Hz, 3H).

tert-Butyl nitrite (1.33 mL, 11.2 mmol) was added to a mixture of ethyl 3-amino-1,2,4-triazine-6-carboxylate (1.25 g, 7.43 mmol) and copper(II) chloride (1.20 g, 8.92 mmol) in acetonitrile (37 mL), and the resulting solution was stirred at 60° C. for 1.5 h. After this time, the reaction mixture was cooled to room temperature and concentrated in vacuo. The residue obtained was purified by chromatography (silica gel; heptane to 50:50 heptane/ethyl acetate; gradient elution) to afford ethyl 3-chloro-1,2,4-triazine-6-carboxylate. $^1$H NMR (500 MHz, DMSO-d$_6$) δ 9.26 (s, 1H), 4.47 (q, J=7.0 Hz, 2H), 1.38 (t, J=7.0 Hz, 3H); MS (ESI) m/z 188 [M+H]+.

Ethyl 3-chloro-1,2,4-triazine-6-carboxylate (0.370 g, 1.97 mmol) was added to a mixture of tert-butyl (R)-methyl (pyrrolidin-3-yl)carbamate (0.593 g, 2.96 mmol) and potassium carbonate (0.818 g, 5.92 mmol) in acetonitrile (20 mL), and the mixture was stirred at 85° C. for 1 h. After this time, the solution was cooled to room temperature, diluted with water (100 mL), and extracted with ethyl acetate (3×85 mL). The combined organic layers were washed with brine (2×80 mL), dried over sodium sulfate, and filtered. The filtrate was concentrated in vacuo, and the residue obtained was purified by chromatography (silica gel; dichloromethane to 95:5 dichloromethane/methanol; gradient elution) to afford ethyl (R)-3-(3-((tert-butoxycarbonyl)(methyl)amino)pyrrolidin-1-yl)-1,2,4-triazine-6-carboxylate. $^1$H NMR (500 MHz, DMSO-d$_6$) δ 8.75 (s, 1H), 4.75 (br s, 1H), 4.36 (q, J=7.0 Hz, 2H), 4.00-3.73 (m, 2H), 3.73-3.41 (m, 2H), 2.77 (d, J=6.0 Hz, 3H), 2.22-2.11 (m, 2H), 1.42 (s, 9H), 1.33 (t, J=7.0 Hz, 3H); MS (ESI) m/z 352 [M+H]+.

Ethyl (R)-3-(3-((tert-butoxycarbonyl)(methyl)amino)pyrrolidin-1-yl)-1,2,4-triazine-6-carboxylate (0.650 g, 1.85 mmol) was dissolved in tetrahydrofuran (9 mL) and methanol (4.5 mL), and 1 M aqueous lithium hydroxide (4.00 mL, 4.00 mmol) was added. The reaction mixture was stirred at room temperature for 16 h. After this time, the solution was cooled to 0° C., the pH was adjusted to 3 with addition of 2 M hydrochloric acid, and the mixture was extracted with dichloromethane (4×60 mL). The combined organic layers were washed with brine (50 mL), dried over sodium sulfate, filtered, and the filtrate was concentrated in vacuo to afford (R)-3-(3-((tert-butoxycarbonyl)(methyl)-amino)pyrrolidin-1-yl)-1,2,4-triazine-6-carboxylic acid. $^1$H NMR (500 MHz, DMSO-d$_6$) δ 13.33 (s, 1H), 8.74 (s, 1H), 4.76 (br s, 1H), 4.02-3.71 (m, 2H), 3.71-3.40 (m, 2H), 2.76 (s, 3H), 2.23-2.09 (m, 2H), 1.42 (s, 9H); MS (ESI) m/z 324 [M+H]+.

(R)-3-(3-((tert-Butoxycarbonyl)(methyl)amino)pyrrolidin-1-yl)-1,2,4-triazine-6-carboxylic acid (0.209 g, 0.647 mmol) and 2,8-dimethylimidazo[1,2-a]pyrazin-6-amine (0.100 g, 0.617 mmol) were dissolved in pyridine (6.1 mL), and 1-ethyl-3-(3-dimethylaminopropyl)carbodiimide hydrochloride (EDC, 0.177 g, 0.925 mmol) was added. The reaction mixture was stirred at room temperature for 16 h. After this time, the solvent was removed in vacuo, and the residue obtained was azeotroped with acetonitrile (2×30 mL) and purified by chromatography (silica gel; dichloromethane to 95:5 dichloromethane/methanol; gradient elution) to afford tert-butyl (R)-(1-(6-((2,8-dimethylimidazo[1,2-a]pyrazin-6-yl)carbamoyl)-1,2,4-triazin-3-yl)pyrrolidin-3-yl)(methyl)-carbamate. $^1$H NMR (500 MHz, DMSO-d$_6$) δ 10.06 (s, 1H), 9.11 (s, 1H), 8.87 (s, 1H), 8.00 (s, 1H), 4.77 (br s, 1H), 4.03-3.75 (m, 2H), 3.75-3.43 (m, 2H), 2.79 (d, J=5.5 Hz, 3H), 2.70 (s, 3H), 2.39 (s, 3H), 2.24-2.12 (m, 2H), 1.43 (s, 9H); MS (ESI) m/z 468 [M+H]+.

Trifluoroacetic acid (1.50 mL, 19.5 mmol) was added to a solution of tert-butyl (R)-(1-(6-((2,8-dimethylimidazo[1,2-a]pyrazin-6-yl)carbamoyl)-1,2,4-triazin-3-yl)pyrrolidin-3-yl)-(methyl)carbamate (0.280 g, 0.599 mmol) in dichloromethane (6 mL), and the solution was stirred at room temperature for 16 h. After this time, the reaction mixture was diluted with dichloromethane (20 mL) and concentrated in vacuo. The residue obtained was azeotroped with toluene (20 mL) and 80:18:2 dichloromethane/methanol/ammonium hydroxide (3×20 mL), and the resulting solid was purified by chromatography (silica gel; dichloromethane to 80:18:2 dichloromethane/methanol/ammonium hydroxide; gradient elution). The product obtained was lyophilized from 1:1 acetonitrile/water (30 mL) to afford (R)—N-(2,8-dimethylimidazo[1,2-a]pyrazin-6-yl)-3-(3-(methylamino)pyrrolidin-1-yl)-1,2,4-triazine-6-carboxamide. mp 215-217° C.; LCMS (ES+) 368 (M+H)+, RT 3.00 min (Analytical method Acidic 1); $^1$H NMR (500 MHz, DMSO-d$_6$) δ 10.06 (s, 1H), 9.13 (s, 1H), 8.85 (d, J=2.0 Hz, 1H), 8.00 (d, J=0.5 Hz, 1H), 3.85-3.76 (m, 2H), 3.69-3.58 (m, 2H), 3.46-3.33 (m, 1H), 2.71 (s, 3H), 2.39 (d, J=0.5 Hz, 3H), 2.31 (d, J=7.0 Hz, 3H), 2.18-1.85 (m, 3H).

Biological Assay Example

Time-Resolved FRET Assay: Q48-Huntingtin and Total-Huntington Detection

Detection of endogenous HTT protein in cell lysates was performed using a protocol adapted from Weiss et al. See Weiss A et al. (2009). Single-step detection of mutant huntingtin in animal and human tissues: a bioassay for Huntington's disease. Anal. Biochem. 395(1): 8-15.

The multiplex assay was performed in human embryonic stem cells (GEN020 hESCs with mutant 48 Q repeat allele) which have been derived by Genea Biocells from human blastocysts of HD donors. Bradley C K et al. (2011). Derivation of Huntington's disease-affected human embryonic stem cell lines, Stem Cells Dev. 2011 March; 20(3): 495-502. Cells were plated into 384-well collagen coated plates (10,000 cells per well) and left to adhere for 24 hours, test compounds were then added for 48 hours (37° C., 5% $CO_2$), cells were then lysed and the lysate was transferred to a black 384-well assay plate.

The assay plate included a combination of HTRF labelled monoclonal antibodies added to recognize discreet areas of the HTT protein, the Tb "donor" antibody (2B7-Tb: 0.2 ng/well) recognizes a sequence at the N-terminus of the protein, an Alexa488 "acceptor 1" antibody (MW1-Alexa488: 30 ng/well) recognizes an area in the polyQ region, whereas a d2 "acceptor 2" antibody (MAB2166-d2: 6 ng/well) recognizes a sequence beyond the polyQ region. These detection reagents were incubated with the cell lysate at room temperature for 4-6 hours before having their fluorescence quantified at 615 nm (donor) and 535 nm and 665 nm (acceptor 1 and 2 respectively). The donor/acceptor ratio between these signals indicated the relative quantities of mHTT and tHTT.

Results for various compounds described herein are provided in the Table below. tHTT activity in this assay is categorized as 10-20 uM (−); 1-10 uM (+); 0.5-1 uM (++); 0.1-0.5 uM (+++); <0.1 uM (++++).

| Example | tHTT EC50 |
|---|---|
| Example 1 | + |
| Example 2 | +++ |
| Example 3 | ++ |
| Example 4 | + |
| Example 5 | + |
| Example 6 | + |
| Example 7 | + |
| Example 8 | + |
| Example 9 | + |
| Example 10 | + |
| Example 11 | +++ |
| Example 12 | ++++ |
| Example 13 | + |
| Example 14 | +++ |
| Example 15 | +++ |
| Example 16 | + |
| Example 17 | + |
| Example 18 | +++ |
| Example 19 | ++ |
| Example 20 | ++ |
| Example 21 | +++ |
| Example 22 | +++ |
| Example 23 | + |
| Example 24 | +++ |
| Example 25 | +++ |
| Example 26 | ++++ |
| Example 27 | ++++ |
| Example 28 | +++ |
| Example 29 | +++ |
| Example 30 | ++ |
| Example 31 | ++ |
| Example 32 | + |
| Example 33 | ++++ |
| Example 34 | +++ |
| Example 35 | ++++ |
| Example 36 | +++ |
| Example 37 | +++ |
| Example 38 | ++ |
| Example 39 | +++ |
| Example 40 | +++ |
| Example 41 | +++ |
| Example 42 | +++ |
| Example 43 | +++ |
| Example 44 | + |
| Example 45 | + |
| Example 46 | ++++ |
| Example 47 | +++ |
| Example 48 | ++ |
| Example 49 | + |
| Example 50 | +++ |
| Example 51 | ++ |
| Example 52 | ++ |
| Example 53 | + |
| Example 54 | ++ |
| Example 55 | ++ |
| Example 56 | +++ |
| Example 57 | +++ |
| Example 58 | +++ |
| Example 59 | ++ |
| Example 60 | +++ |
| Example 61 | +++ |
| Example 62 | ++ |
| Example 63 | +++ |
| Example 64 | + |
| Example 65 | + |
| Example 66 | ++ |
| Example 67 | +++ |
| Example 68 | + |
| Example 69 | + |
| Example 70 | + |
| Example 71 | + |
| Example 72 | + |
| Example 73 | +++ |
| Example 74 | + |
| Example 75 | + |
| Example 76 | +++ |
| Example 77 | ++++ |
| Example 78 | + |
| Example 79 | + |
| Example 80 | +++ |
| Example 81 | +++ |
| Example 82 | ++ |
| Example 83 | ++++ |
| Example 84 | +++ |
| Example 85 | +++ |
| Example 86 | + |
| Example 87 | ++ |
| Example 88 | + |
| Example 89 | + |
| Example 90 | + |
| Example 91 | +++ |
| Example 92 | +++ |
| Example 93 | +++ |
| Example 94 | + |
| Example 95 | + |
| Example 96 | ++ |
| Example 97 | +++ |
| Example 98 | +++ |
| Example 99 | +++ |
| Example 100 | +++ |
| Example 101 | +++ |
| Example 102 | +++ |
| Example 103 | ++ |
| Example 104 | ++++ |
| Example 105 | +++ |
| Example 106 | ++++ |
| Example 107 | ++++ |
| Example 108 | +++ |

-continued

| Example | tHTT EC50 |
|---|---|
| Example 109 | + |
| Example 110 | ++++ |
| Example 111 | +++ |
| Example 112 | +++ |
| Example 113 | +++ |
| Example 114 | ++ |
| Example 115 | ++ |
| Example 116 | + |
| Example 117 | + |
| Example 118 | + |
| Example 119 | + |
| Example 120 | +++ |
| Example 121 | +++ |
| Example 122 | +++ |
| Example 123 | + |
| Example 124 | + |
| Example 125 | ++ |
| Example 126 | + |
| Example 127 | +++ |
| Example 128 | +++ |
| Example 129 | ++ |
| Example 130 | +++ |
| Example 131 | +++ |
| Example 132 | +++ |
| Example 133 | + |
| Example 134 | ++ |
| Example 135 | + |
| Example 136 | +++ |
| Example 137 | +++ |
| Example 138 | ++ |
| Example 139 | + |
| Example 140 | + |
| Example 141 | − |
| Example 142 | ++++ |
| Example 143 | + |
| Example 144 | − |
| Example 148 | +++ |
| Example 149 | ++++ |
| Example 150 | +++ |
| Example 151 | ++++ |
| Example 152 | ++++ |
| Example 153 | ++ |
| Example 154 | +++ |
| Example 155 | ++ |
| Example 156 | ++ |
| Example 157 | ++ |
| Example 158 | +++ |
| Example 159 | +++ |
| Example 160 | ++ |
| Example 161 | +++ |
| Example 162 | +++ |
| Example 163 | +++ |
| Example 164 | +++ |
| Example 165 | ++++ |
| Example 166 | +++ |
| Example 167 | +++ |
| Example 168 | +++ |
| Example 169 | ++ |
| Example 170 | +++ |
| Example 171 | ++++ |
| Example 172 | +++ |
| Example 173 | ++ |
| Example 174 | +++ |
| Example 175 | +++ |
| Example 176 | ++++ |
| Example 177 | +++ |
| Example 178 | ++ |
| Example 179 | ++++ |
| Example 180 | ++++ |
| Example 181 | +++ |
| Example 182 | +++ |
| Example 183 | +++ |
| Example 184 | +++ |
| Example 185 | ++++ |
| Example 186 | ++++ |
| Example 187 | + |
| Example 188 | ++ |

-continued

| Example | tHTT EC50 |
|---|---|
| Example 189 | +++ |
| Example 190 | ++++ |
| Example 191 | +++ |
| Example 192 | +++ |
| Example 193 | +++ |
| Example 194 | ++ |
| Example 195 | +++ |
| Example 196 | +++ |
| Example 197 | +++ |
| Example 198 | +++ |
| Example 199 | +++ |
| Example 200 | +++ |
| Example 201 | +++ |
| Example 202 | +++ |
| Example 203 | ++ |
| Example 204 | +++ |
| Example 205 | ++++ |
| Example 206 | +++ |
| Example 207 | +++ |
| Example 208 | +++ |
| Example 210 | ++++ |
| Example 211 | +++ |
| Example 212 | +++ |
| Example 213 | − |
| Example 214 | +++ |
| Example 215 | ++ |
| Example 216 | +++ |
| Example 217 | +++ |
| Example 218 | ++ |
| Example 219 | +++ |
| Example 220 | ++++ |
| Example 221 | ++++ |
| Example 222 | + |
| Example 223 | ++ |
| Example 224 | +++ |
| Example 225 | ++++ |
| Example 226 | +++ |
| Example 227 | +++ |
| Example 228 | +++ |
| Example 229 | +++ |
| Example 230 | +++ |
| Example 231 | + |
| Example 232 | +++ |
| Example 233 | +++ |
| Example 234 | +++ |
| Example 235 | +++ |
| Example 236 | ++++ |
| Example 237 | +++ |
| Example 238 | +++ |
| Example 239 | ++ |
| Example 240 | +++ |
| Example 241 | ++ |
| Example 242 | ++ |
| Example 243 | +++ |
| Example 244 | ++ |
| Example 245 | +++ |
| Example 246 | +++ |
| Example 247 | +++ |
| Example 248 | ++ |
| Example 249 | +++ |
| Example 250 | ++ |
| Example 251 | +++ |
| Example 252 | ++++ |

| Example | tHTT EC50 |
|---|---|
| Example 253 | +++ |
| Example 254 | ++++ |
| Example 255 | +++ |
| Example 256 | +++ |
| Example 257 | +++ |
| Example 258 | +++ |
| Example 259 | +++ |
| Example 260 | +++ |
| Example 261 | +++ |
| Example 262 | +++ |
| Example 263 | +++ |
| Example 264 | +++ |
| Example 265 | ++++ |
| Example 266 | +++ |
| Example 267 | +++ |
| Example 268 | ++++ |
| Example 269 | +++ |
| Example 270 | +++ |
| Example 271 | ++++ |
| Example 272 | ++++ |
| Example 273 | +++ |
| Example 274 | +++ |
| Example 275 | +++ |
| Example 276 | ++ |
| Example 277 | +++ |
| Example 278 | ++ |
| Example 279 | ++ |
| Example 280 | +++ |
| Example 281 | +++ |
| Example 282 | +++ |
| Example 283 | +++ |
| Example 284 | +++ |
| Example 285 | +++ |
| Example 286 | +++ |
| Example 287 | +++ |
| Example 288 | +++ |
| Example 289 | +++ |
| Example 290 | +++ |
| Example 291 | +++ |
| Example 292 | +++ |
| Example 293 | ++ |
| Example 294 | ++++ |
| Example 295 | +++ |
| Example 296 | ++ |
| Example 297 | +++ |
| Example 298 | ++ |
| Example 299 | +++ |
| Example 300 | ++ |
| Example 301 | ++ |
| Example 302 | ++ |
| Example 303 | +++ |
| Example 304 | +++ |
| Example 305 | +++ |
| Example 306 | +++ |
| Example 307 | +++ |
| Example 308 | +++ |
| Example 309 | +++ |
| Example 310 | +++ |
| Example 311 | +++ |
| Example 312 | ++++ |
| Example 313 | +++ |
| Example 314 | ++++ |
| Example 315 | ++ |
| Example 316 | +++ |
| Example 317 | +++ |
| Example 318 | +++ |
| Example 319 | +++ |
| Example 320 | +++ |
| Example 321 | ++ |
| Example 322 | +++ |
| Example 323 | ++ |
| Example 324 | +++ |
| Example 325 | +++ |
| Example 326 | +++ |
| Example 327 | +++ |
| Example 328 | +++ |
| Example 329 | ++ |
| Example 330 | ++ |
| Example 331 | ++ |
| Example 332 | +++ |
| Example 333 | ++ |
| Example 334 | ++ |
| Example 335 | +++ |
| Example 336 | +++ |
| Example 337 | +++ |
| Example 338 | +++ |
| Example 339 | + |
| Example 340 | +++ |
| Example 341 | ++++ |
| Example 342 | +++ |
| Example 343 | +++ |
| Example 344 | +++ |
| Example 345 | ++++ |
| Example 346 | ++ |
| Example 347 | +++ |
| Example 348 | +++ |
| Example 349 | +++ |
| Example 350 | +++ |
| Example 351 | +++ |
| Example 352 | ++ |
| Example 353 | +++ |
| Example 354 | ++++ |
| Example 355 | ++++ |
| Example 356 | ++++ |
| Example 357 | ++++ |
| Example 358 | +++ |
| Example 359 | +++ |
| Example 360 | +++ |
| Example 361 | +++ |
| Example 362 | + |
| Example 363 | + |
| Example 364 | + |
| Example 365 | + |
| Example 366 | + |
| Example 367 | + |
| Example 368 | + |
| Example 369 | + |
| Example 370 | + |
| Example 371 | ++ |
| Example 372 | ++ |
| Example 373 | + |
| Example 374 | + |
| Example 375 | + |

Some exemplary models for determining reduction of HTT using branaplam and related small molecules are found in International Publication No. WO 2021/084495.

Comparative Biological Activity

Compounds within the scope of International Publication No. WO 2015/197503 were prepared as Comparative Examples 145-147 and the compounds were tested in the assay as described in the Biological Assay Example herein. The results of the assay as compared to compounds of the instant disclosure are as follows:

| Example | tHTT EC50 (µM) | Comparator | tHTT EC50 (µM) |
|---|---|---|---|
| Ex 65 | 1.7 | Comparative Ex 145 | 30 |
| Ex 86 | 3.1 | Comparative Ex 146 | 15.23 |
| Ex 126 | 3.4 | Comparative Ex 147 | 16.8 |

The results indicate that compounds of the instant disclosure exhibit improved HTT lowering activity compared to those of the art. Specifically, the compounds of the instant disclosure including two nitrogen 6-membered aromatic amide are contemplated to exhibit improved activity over compounds including a pyridine amide moiety.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

All publications, patent applications, patents, and other references mentioned herein are expressly incorporated by reference in their entirety, to the same extent as if each were incorporated by reference individually. In case of conflict, the present specification, including definitions, will control.

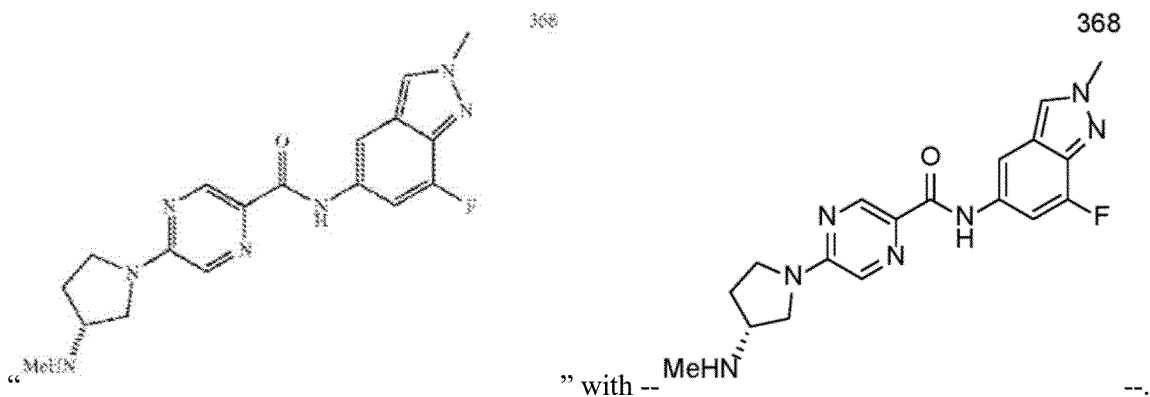

What is claimed is:

1. A compound of Formula I:

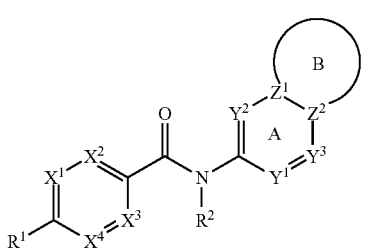

or an isotopically enriched analog, pharmaceutically acceptable salt, tautomer, stereoisomer, or a mixture of stereoisomers thereof, wherein:

$X^1$, $X^2$, $X^3$, and $X^4$ are $CR^4$ or N, wherein at least two but no more than three of $X^1$, $X^2$, $X^3$, and $X^4$ are N;

each $R^4$ is independently hydrogen, halo, hydroxy, $C_{1-6}$alkyl, $C_{1-6}$haloalkyl, or $C_{1-6}$alkoxy;

$Y^1$ is $CR^5$ or N;

$R^5$ is hydrogen, cyano, halo, hydroxy, $C_{1-6}$alkyl, $C_{1-6}$haloalkyl, $C_{1-6}$alkylthio, $C_{1-6}$alkoxy, $C_{1-6}$haloalkoxy, heterocyclyl, —$NH_2$, —$NHR^{17}$, or —$N(R^{17})_2$, and optionally substituted on an available nitrogen atom with $C_{1-6}$alkyl or $C_{1-6}$haloalkyl;

$Y^2$ is absent, $CR^6$ or N;

$R^6$ is hydrogen, cyano, halo, hydroxy, $C_{1-6}$alkyl, $C_{1-6}$haloalkyl, $C_{1-6}$alkylthio, $C_{1-6}$alkoxy, $C_{1-6}$haloalkoxy, heterocyclyl, —$NH_2$, —$NHR^{17}$, or —$N(R^{17})_2$, and optionally substituted on an available nitrogen atom with $C_{1-6}$alkyl or $C_{1-6}$haloalkyl; and $Y^3$ is $CR^3$ or N;

$R^3$ is hydrogen, cyano, halo, hydroxy, $C_{1-6}$alkyl, $C_{1-6}$haloalkyl, $C_{1-6}$alkylthio, $C_{1-6}$alkoxy, $C_{1-6}$haloalkoxy, heterocyclyl, —$NH_2$, —$NHR^{17}$, or —$N(R^{17})_2$, and optionally substituted on an available nitrogen atom with $C_{1-6}$alkyl or $C_{1-6}$haloalkyl;

each $R^{17}$ is independently $C_{1-4}$alkyl, or two $R^{17}$ join, with any intervening atoms, to form a 3- to 6-membered heterocyclyl;

each of $Z^1$ and $Z^2$ is C or N;

Ring A and Ring B together form a 9-membered bicyclic heteroaryl containing 1 to 3 ring nitrogen atoms;

Ring B contains 1 to 3 heteroatoms independently selected from N and O, and is substituted on available carbon atom(s) with 1 to 3 substituents independently selected from halo, hydroxy, $C_{1-6}$alkyl, $C_{1-6}$haloalkyl, $C_{1-6}$alkoxy, and $C_{1-6}$haloalkoxy, or is substituted on an available nitrogen atom with $C_{1-6}$alkyl or $C_{1-6}$haloalkyl;

$R^1$ is -$L^1$-$R^{11}$, wherein $L^1$ is —O—, —S—, —S(O)—, —$S(O)_2$—, —$N(R^{12})$—, —$C_{1-3}$alkylene-, —O—$C_{1-3}$alkylene-, —$N(R^{12})$—$C_{1-3}$alkylene, or absent, and $R^{11}$ is $C_{2-6}$alkynyl, $C_{3-10}$cycloalkyl, heteroaryl, or heterocyclyl, wherein $R^{11}$ is optionally substituted with 1 to 4 $R^{13}$ groups;

$R^{12}$ is hydrogen or $C_{1-6}$alkyl;

each $R^{13}$ is independently selected from halo, cyano, hydroxy, $C_{1-6}$alkyl optionally substituted with $R^{16}$, $C_{1-6}$haloalkyl, $C_{1-6}$hydroxyalkyl, $C_{3-10}$cycloalkyl optionally substituted with $R^{16}$, $C_{3-10}$cycloalkyl-$C_{1-6}$alkyl optionally substituted with $R^{16}$, $C_{6-10}$aryl optionally substituted with $R^{16}$, $C_{6-10}$aryl-$C_{1-6}$alkyl optionally substituted with $R^{16}$, heteroaryl optionally substituted with $R^{16}$, heteroaryl-$C_{1-6}$alkyl optionally substituted with $R^{16}$, heterocyclyl optionally substituted with $R^{16}$, heterocyclyl-$C_{1-6}$alkyl optionally substituted with $R^{16}$, $OR^{14}$, —$NH_2$, —$NHR^{14}$—N$(R^{14})_2$, —$C_{1-6}$alkylene-$NH_2$, —$C_{1-6}$alkylene-$NHR^{14}$, —$C_{1-6}$alkylene-$N(R^{14})_2$, —$C(O)R^{15}$, —$C(O)OR^{15}$, —$C(O)NHR^{15}$, —$C(O)N(C_{1-4}$alkyl)$R^{15}$, —$S(O)_2R^{15}$, —$S(O)R^{15}$, —$NHC(O)R^{15}$, —$N(C_{1-4}$alkyl)$C(O)R^{15}$, —$NHS(O)R^{15}$, —$N(C_{1-4}$alkyl)$S(O)R^{15}$, —$NHS(O)_2R^{15}$, and —$N(C_{1-4}$alkyl)$S(O)_2R^{15}$;

each $R^{14}$ is independently selected from $C_{1-6}$alkyl, $C_{3-10}$cycloalkyl, $C_{6-10}$aryl, heteroaryl, and heterocyclyl; and each $R^{14}$ is optionally substituted with one to six halo, $C_{1-3}$alkyl, $C_{1-3}$alkoxy, $C_{3-10}$cycloalkyl, or —$NHSO_2$-aryl-$N(CH_3)_2$;

each $R^{15}$ is independently hydrogen, —OH, $C_{1-6}$alkyl, $C_{1-6}$haloalkyl, $C_{3-10}$cycloalkyl, $C_{6-10}$aryl, heteroaryl, or heterocyclyl;

each $R^{16}$ is independently halo, cyano, hydroxy, —$NH_2$, —$NHR^{21}$, —$N(R^{21})_2$, $C_{1-6}$alkyl, $C_{1-6}$haloalkyl, $OR^{21}$, or $C_{3-10}$cycloalkyl;

each $R^{21}$ is independently selected from $C_{1-6}$alkyl, $C_{3-10}$cycloalkyl, $C_{6-10}$aryl, heteroaryl, and heterocyclyl, and each $R^{21}$ is optionally substituted with one to six halo or $C_{1-3}$alkoxy; and $R^2$ is hydrogen or $C_{1-6}$alkyl.

2. The compound of claim 1, of Formula Ia:

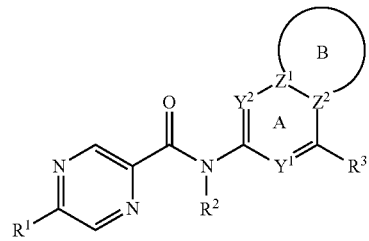

Ia or an isotopically enriched analog, pharmaceutically acceptable salt, tautomer, stereoisomer, or a mixture of stereoisomers thereof.

3. The compound of claim 1, of Formula Ib:

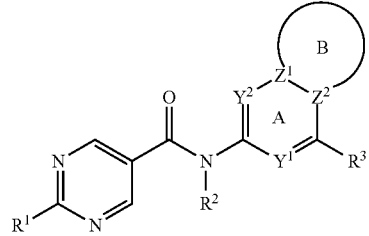

Ib or an isotopically enriched analog, pharmaceutically acceptable salt, tautomer, stereoisomer, or a mixture of stereoisomers thereof.

4. The compound of claim 1, of Formula Ic:

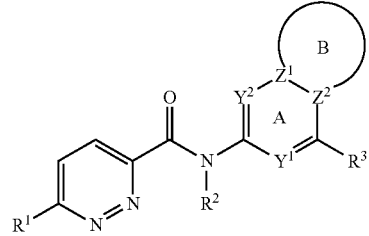

Ic or an isotopically enriched analog, pharmaceutically acceptable salt, tautomer, stereoisomer, or a mixture of stereoisomers thereof.

5. The compound of claim 1, of Formula IIa:

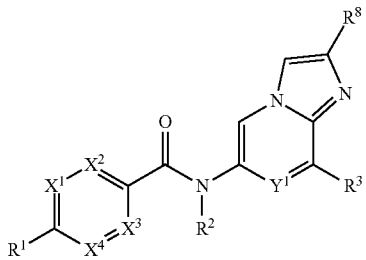

or an isotopically enriched analog, pharmaceutically acceptable salt, tautomer, stereoisomer, or a mixture of stereoisomers thereof, wherein $R^8$ is halo, hydroxy, $C_{1-6}$alkyl, $C_{1-6}$haloalkyl, or $C_{1-6}$alkoxy.

6. The compound of claim 1, of Formula IIb:

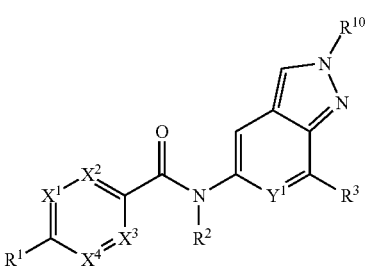

or an isotopically enriched analog, pharmaceutically acceptable salt, tautomer, stereoisomer, or a mixture of stereoisomers thereof, wherein $R^{10}$ is $C_{1-6}$alkyl, or $C_{1-6}$haloalkyl.

7. The compound of claim 1, of Formula IIIa:

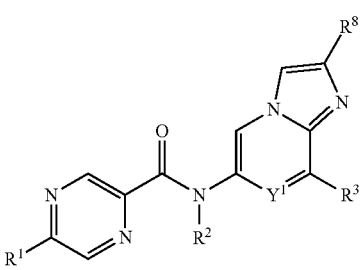

or an isotopically enriched analog, pharmaceutically acceptable salt, tautomer, stereoisomer, or a mixture of stereoisomers thereof, wherein $R^8$ is halo, hydroxy, $C_{1-6}$alkyl, $C_{1-6}$haloalkyl, or $C_{1-6}$alkoxy.

8. The compound of claim 1, of Formula IIIb:

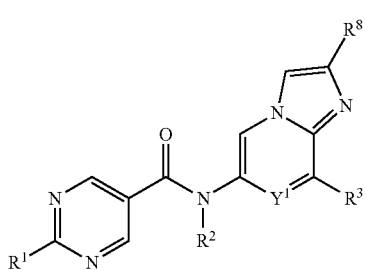

or an isotopically enriched analog, pharmaceutically acceptable salt, tautomer, stereoisomer, or a mixture of stereoisomers thereof, wherein $R^8$ is halo, hydroxy, $C_{1-6}$alkyl, $C_{1-6}$haloalkyl, or $C_{1-6}$alkoxy.

9. The compound of claim 1, of Formula IIIc:

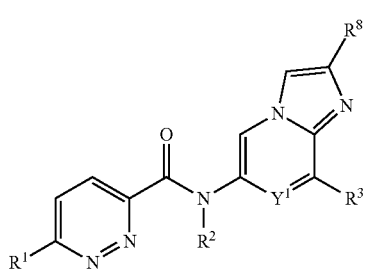

or an isotopically enriched analog, pharmaceutically acceptable salt, tautomer, stereoisomer, or a mixture of stereoisomers thereof, wherein $R^8$ is halo, hydroxy, $C_{1-6}$alkyl, $C_{1-6}$haloalkyl, or $C_{1-6}$alkoxy.

10. The compound of claim 1, wherein $R^{11}$ is heterocyclyl optionally substituted with 1 to 4 groups independently selected from halo, $C_{1-6}$alkyl, $C_{1-6}$haloalkyl, $C_{3-10}$cycloalkyl, heteroaryl, heterocyclyl, heterocyclyl-$C_{1-6}$alkyl, —$NH_2$, —$NHR^{14}$, —$N(R^{14})_2$, —$C_{1-6}$alkylene-$NH_2$, —$C_{1-6}$alkylene-$NHR^{14}$, —$C_{1-6}$alkylene-$N(R^{14})_2$, and —$C(O)OR^{15}$; wherein each $R^{14}$ is independently selected from $C_{1-6}$alkyl, $C_{3-10}$cycloalkyl, and heterocyclyl, and each $R^{14}$ is optionally substituted with one to three halo; and wherein $R^{15}$ is $C_{1-6}$alkyl.

11. The compound of claim 1, wherein $R^{11}$ is

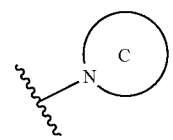

wherein Ring C is a 3- to 10-membered heterocyclyl containing 0, 1 or 2 additional ring nitrogen atoms optionally substituted with 1 to 4 $R^{13}$ groups.

12. The compound of claim 11, wherein Ring C is a 5- to 10-membered bicyclic heterocyclyl containing one additional ring nitrogen atom optionally substituted with 1 to 4 $R^{13}$ groups.

13. The compound of claim 11, wherein Ring C is a 5- to 10-membered spirobicyclic heterocyclyl containing one additional ring nitrogen atom optionally substituted with 1 to 4 $R^{13}$ groups.

14. The compound of claim 11, wherein Ring C is a 5- to 10-membered fused bicyclic heterocyclyl containing one additional ring nitrogen atom optionally substituted with 1 to 4 $R^{13}$ groups.

15. The compound of claim 1, wherein $R^{11}$ is selected from

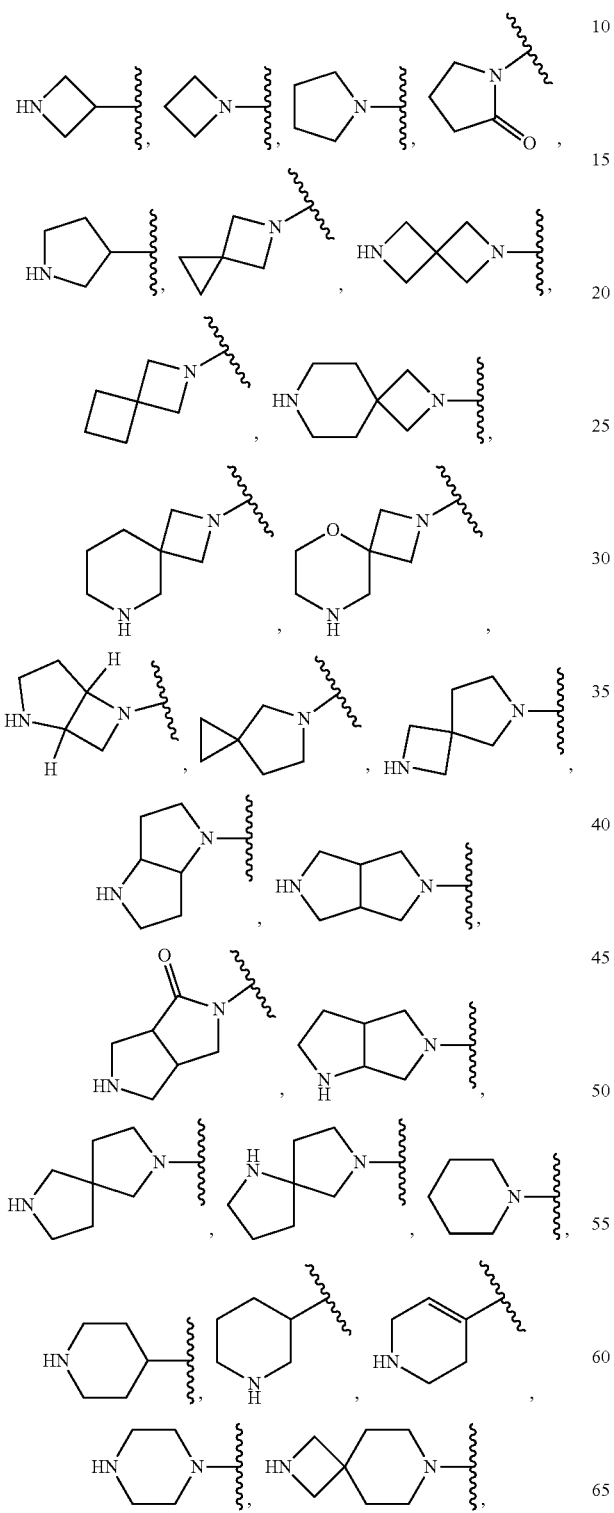

-continued

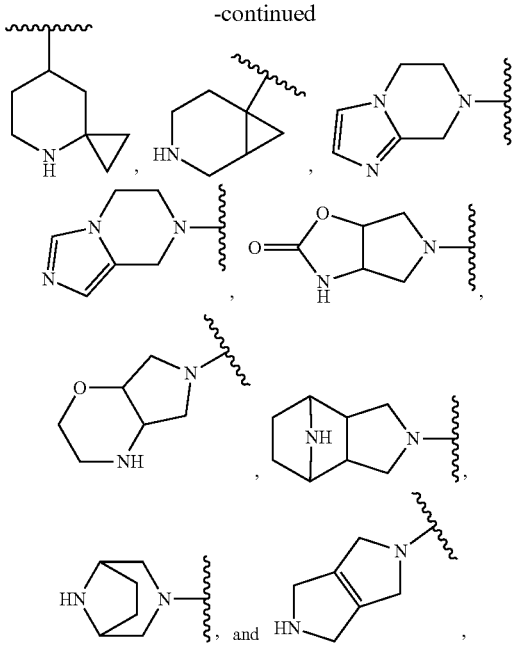

each of which is optionally substituted with 1 to 4 $R^{13}$ groups.

16. The compound of claim 1, wherein $R^{11}$ is optionally substituted with 1 to 4 groups independently selected from fluoro, methyl, ethyl, methoxyethoxy, trifluoromethyl, 2,2-difluoroethylaminomethyl, N-methyl-2,2-difluoroethylaminomethyl, (3,3,3-trifluoroprop-1-ylamino)methyl, cyclopropyl, 1-(cyclopropylamino)-1-cyclopropyl, 1-pyrrolyl, N-morpholinyl, N-pyrrolidinyl, N-pyrrolidinylmethyl, 2-pyrrolidinyl, 1-methyl-2-pyrrolidinyl, 1-methyl-2-piperdinyl, 1-cyclopropyl-2-piperdinyl, cyclopropylamino, N-cyclopropylaminomethyl, (1-methyl-1-cyclopropylamino)methyl, 1-(N-cyclopropylamino)ethyl, N,N-dicyclopropylaminomethyl, N-methoxyethyl-N-cyclopropylaminomethyl, N-cyclopropyl-N-methylamino, N-cyclopropyl-N-methylaminomethyl, amino, aminomethyl, methylamino, ethylamino, isopropylamino, isopropylaminomethyl, N-isopropyl-N-aminomethyl, tert-butylamino, n-butylamino, N-methylaminomethyl, N,N-dimethylaminomethyl, 3,3-difluorocyclobutylamino, tetrahydropyranylamino, oxetanylamino, (3-methoxy-1-azetidinyl)methyl, (3-methoxy-1-pyrrolidinyl)methyl, (3-fluoro-1-pyrrolidinyl)methyl, (3-fluoro-3-methyl-1-pyrrolidinyl)methyl, 4-morpholinylmethyl, and tert-butoxycarbonyl.

17. The compound of claim 1, wherein $R^3$ is halo.

18. The compound of claim 17, wherein $R^3$ is fluoro.

19. The compound of claim 1, wherein $R^3$ is methyl.

20. The compound of claim 1, wherein $R^3$ is methoxy.

21. The compound of claim 1, wherein each $R^4$ is hydrogen.

22. The compound of claim 1, wherein $R^5$ is hydrogen.

23. The compound of claim 1, wherein $R^5$ is $C_{1-6}$alkoxy.

24. The compound of claim 23, wherein $R^5$ is methoxy.

25. The compound of claim 1, wherein Ring B is selected from

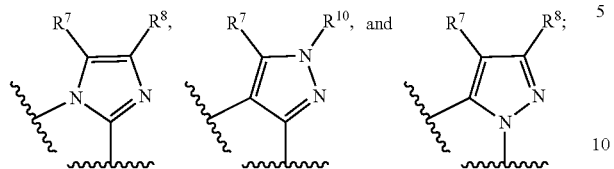

$R^7$ is hydrogen; $R^8$ is $C_{1-6}$alkyl; and $R^{10}$ is $C_{1-6}$alkyl.

26. The compound of claim 25, wherein $R^8$ is methyl.
27. The compound of claim 1, wherein $L^1$ is absent.
28. The compound of claim 1, wherein $Y^1$ is $CR^5$.
29. The compound of claim 1, wherein $Y^1$ is N.
30. The compound of claim 1, wherein $Y^2$ is $CR^6$.
31. The compound of claim 1, wherein $Y^3$ is $CR^3$.
32. The compound of claim 25, wherein Ring B is

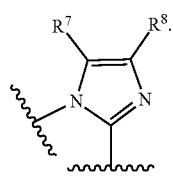

33. The compound of claim 25, wherein Ring B is

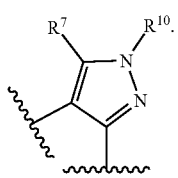

34. A compound of formula:

1

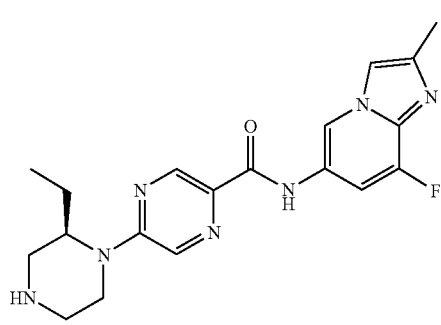

2

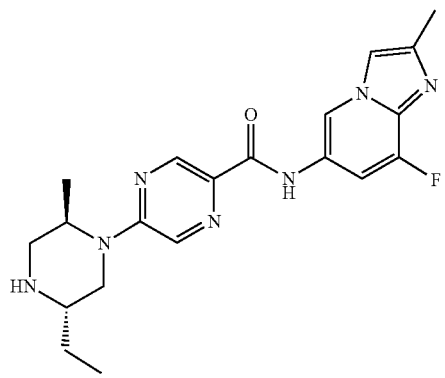

3

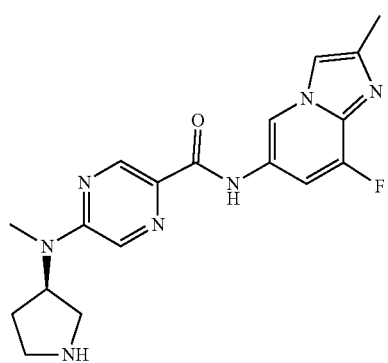

4

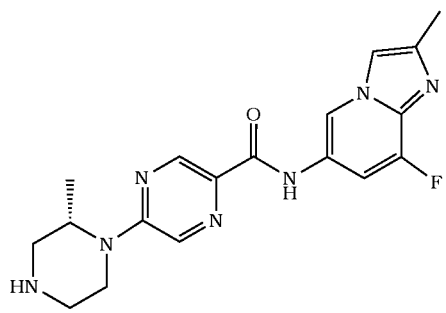

5

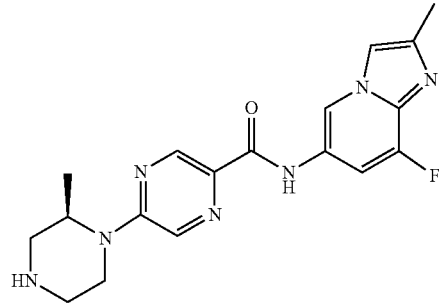

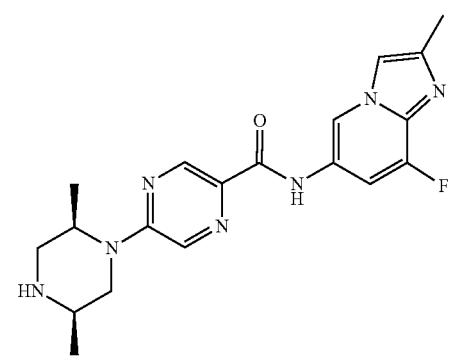
6
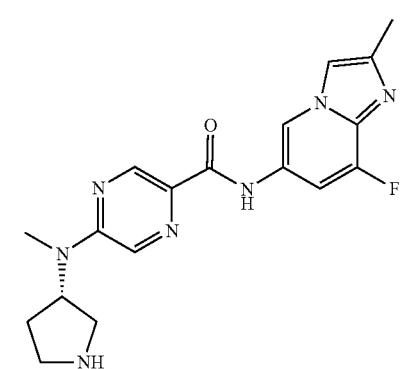
7
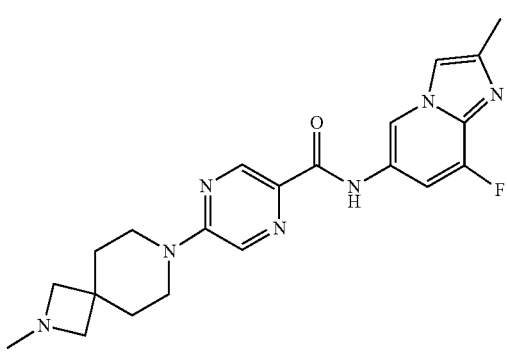
8
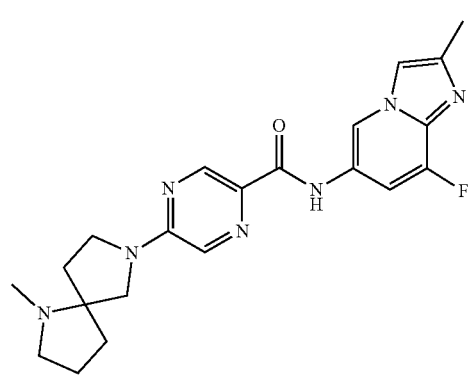
Enantiomer 1 + Enantiomer 2
9
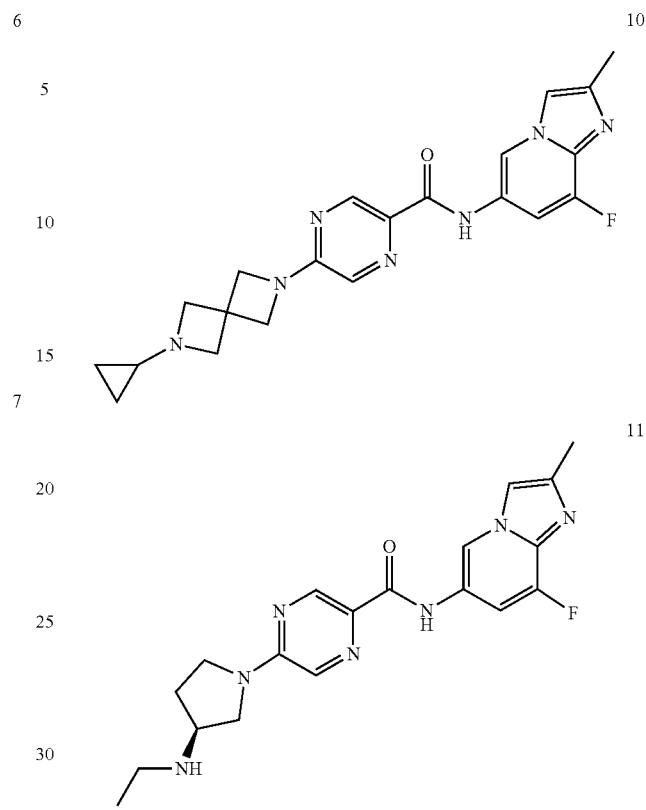
10
11
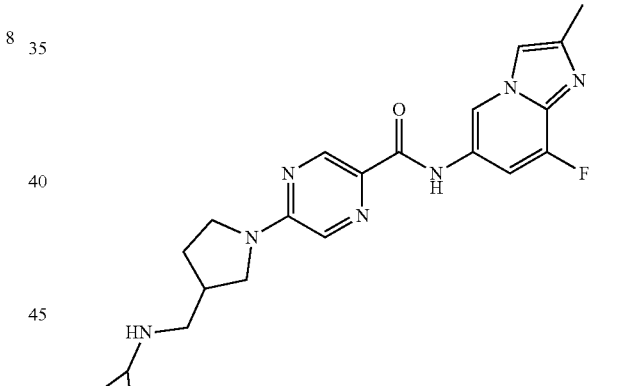
12
Enantiomer 1 + Enantiomer 2
13
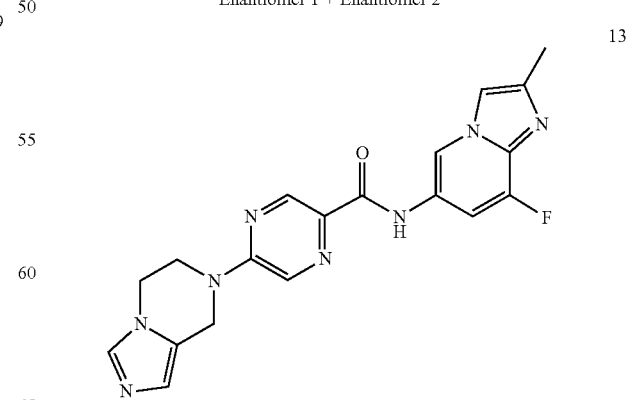

14
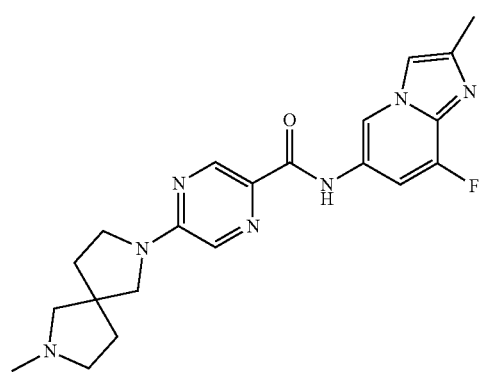
Enantiomer 2
15
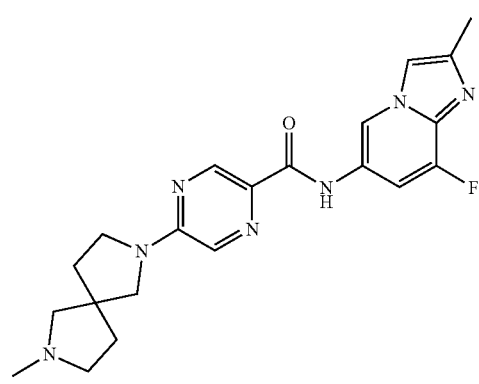
Enantiomer 1
16
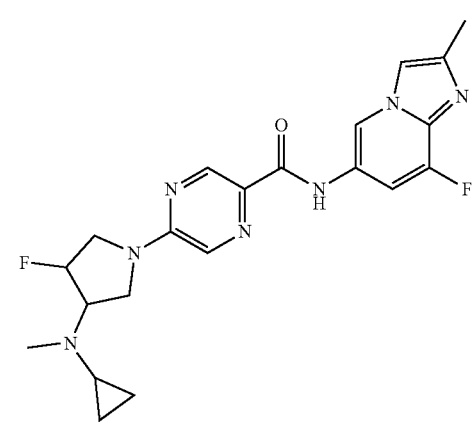
Cis Isomer, Enantiomer 1
17
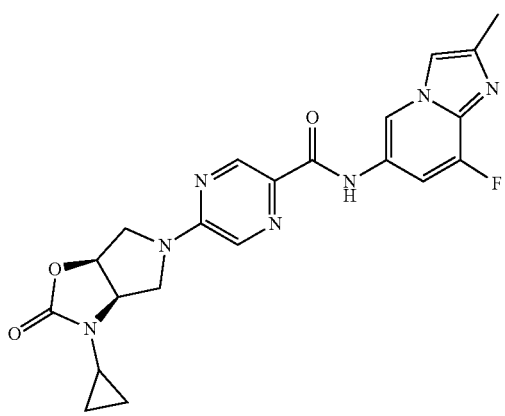
18
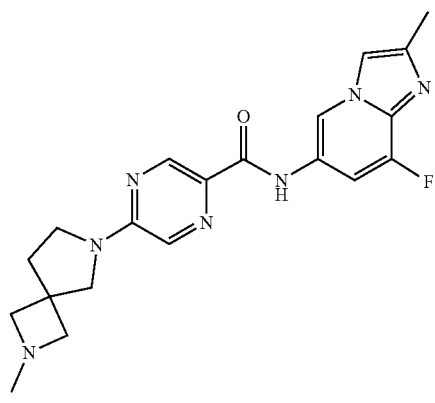
19
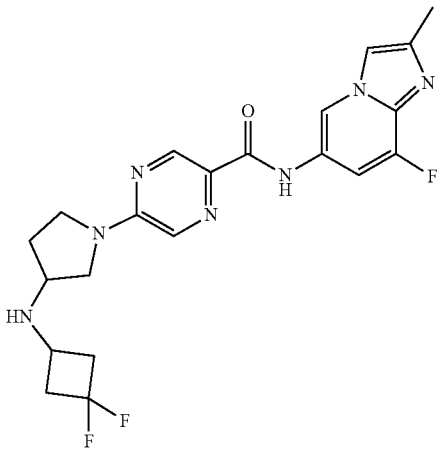
Enantiomer 1

20
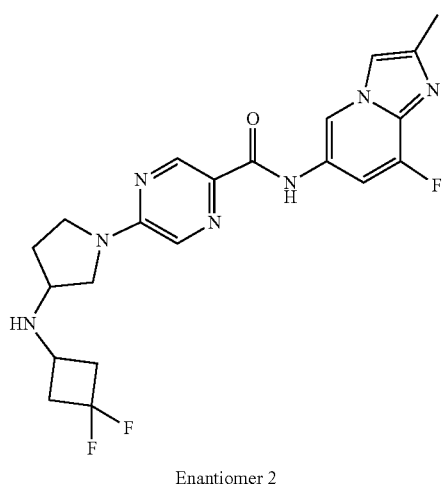
Enantiomer 2
21
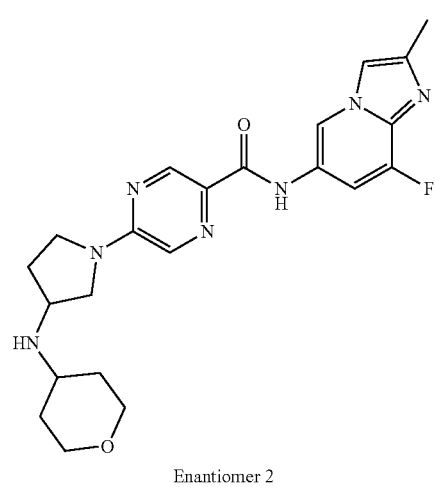
Enantiomer 2
22
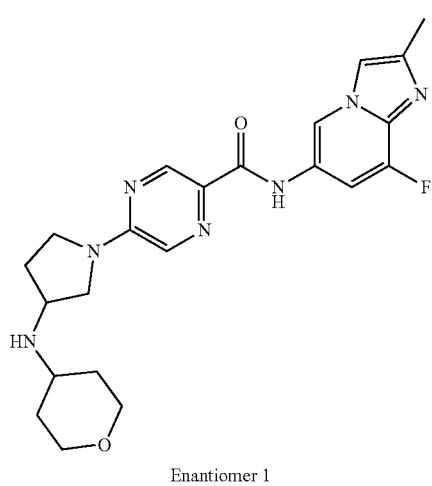
Enantiomer 1
23
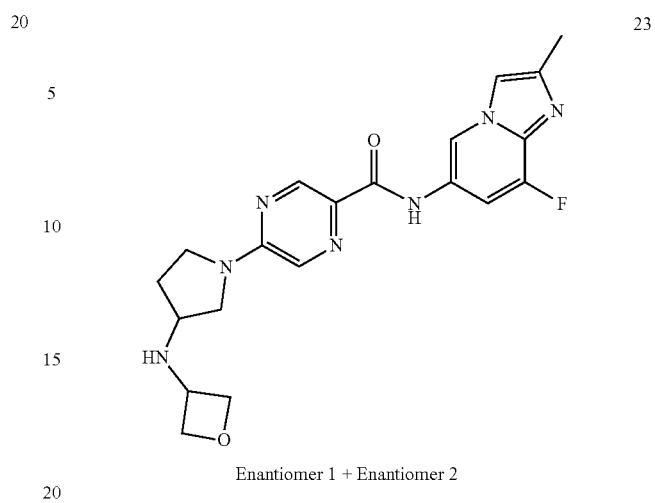
Enantiomer 1 + Enantiomer 2
24
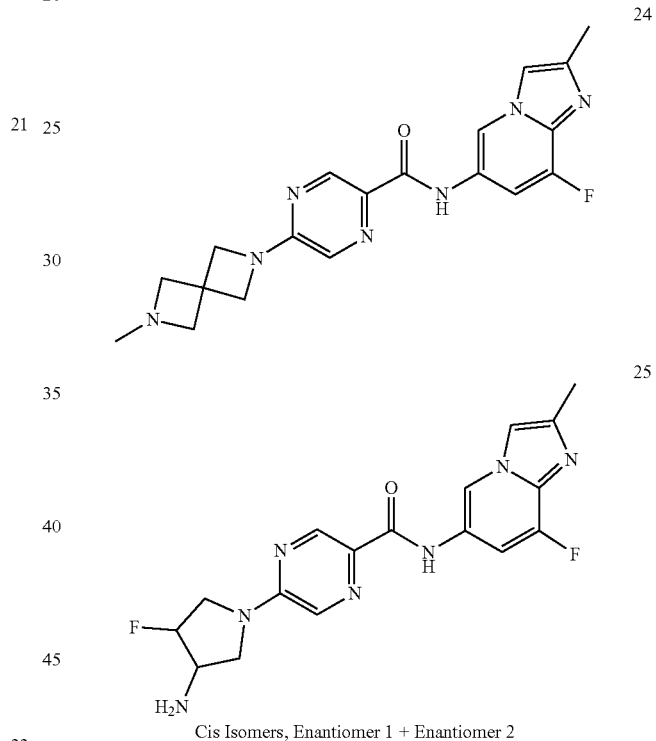
25
Cis Isomers, Enantiomer 1 + Enantiomer 2
26
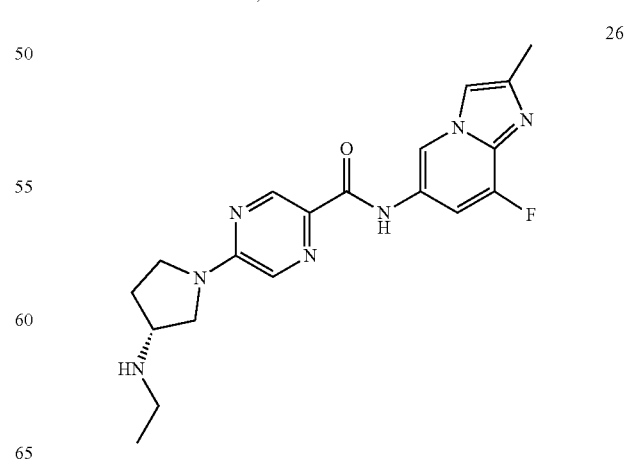

27
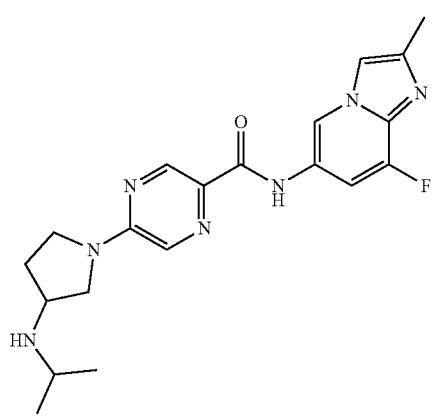
Enantiomer 1
28
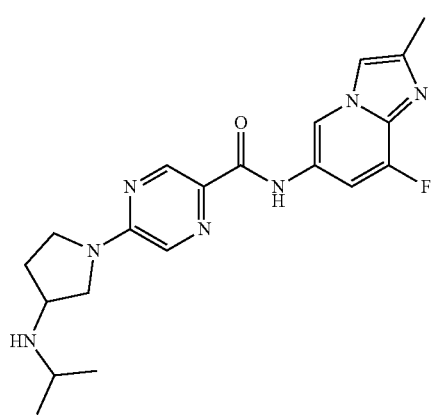
Enantiomer 2
29
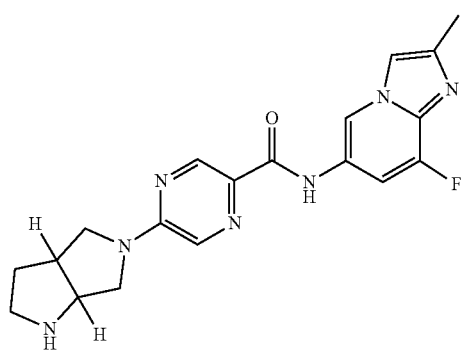
Cis Isomer, Enantiomer 1
30
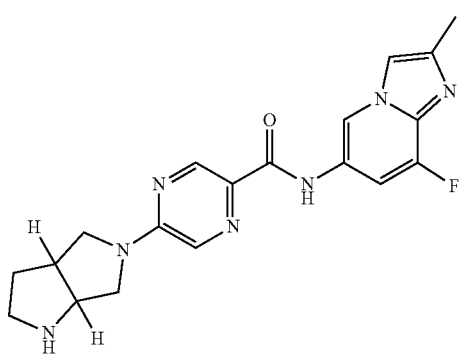
Cis Isomer, Enantiomer 2
31
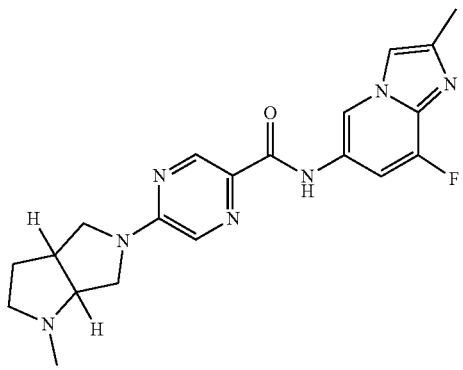
Cis Isomer, Enantiomer 1
32
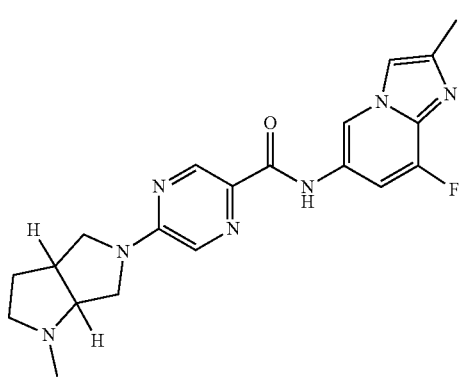
Cis Isomer, Enantiomer 2
33
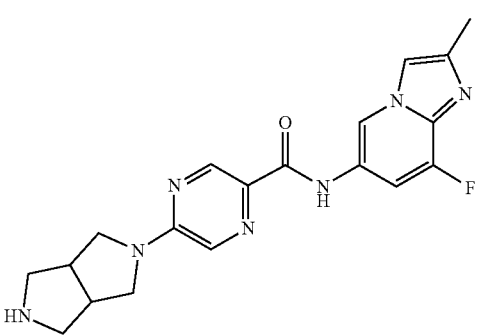

34
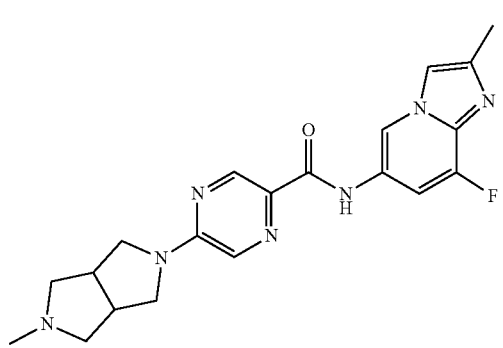
5
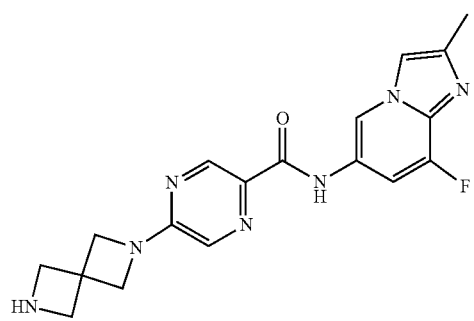
35
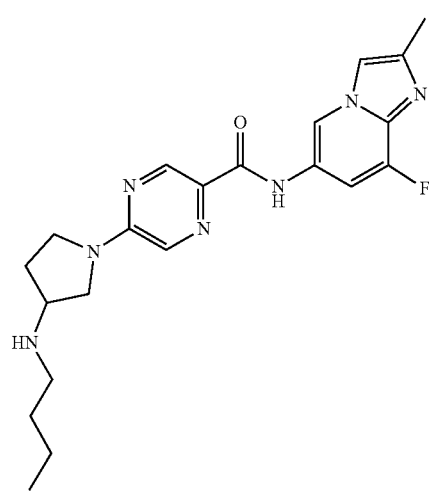
36
Enantiomer 1 + Enantiomer 2
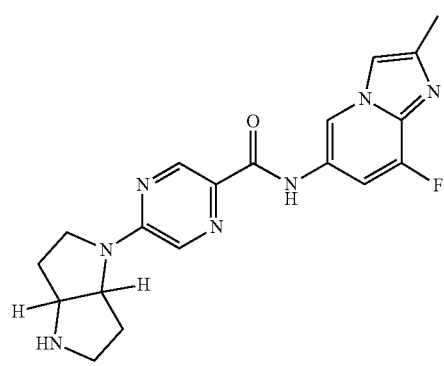
37
Cis Isomer, Enantiomer 2
38
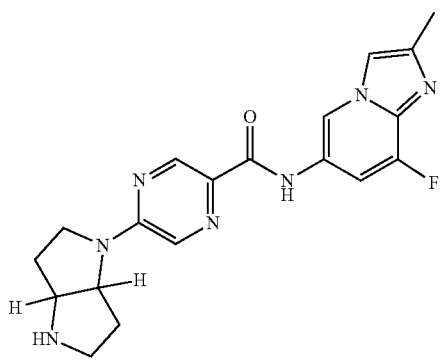
Cis Isomer, Enantiomer 1
39
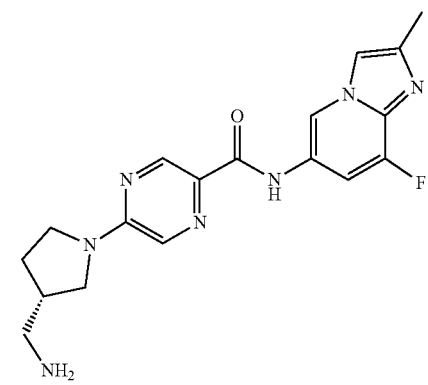
40
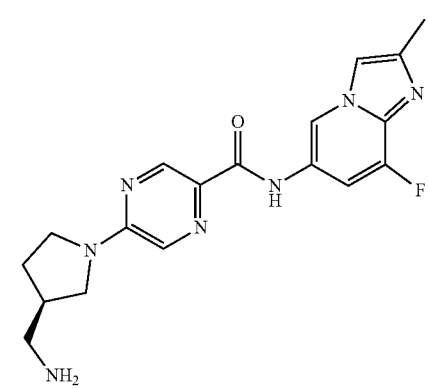
41
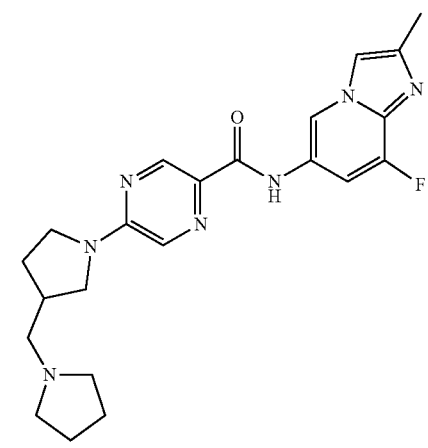
Enantiomer 1 + Enantiomer 2

42
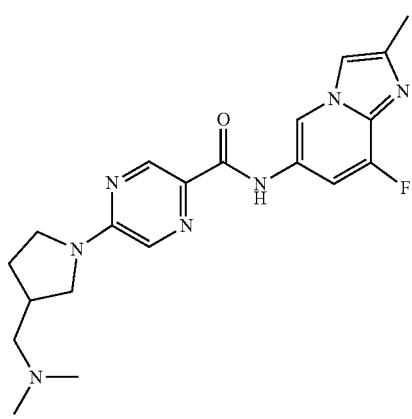
Enantiomer 1 + Enantiomer 2
43
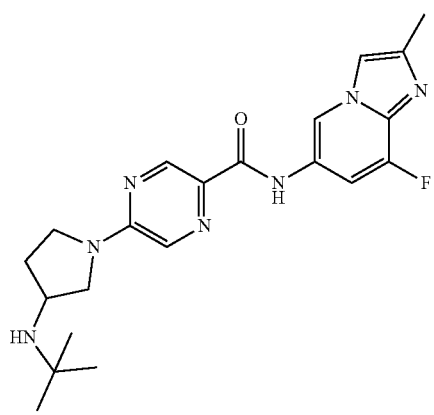
Enantiomer 1 + Enantiomer 2
44
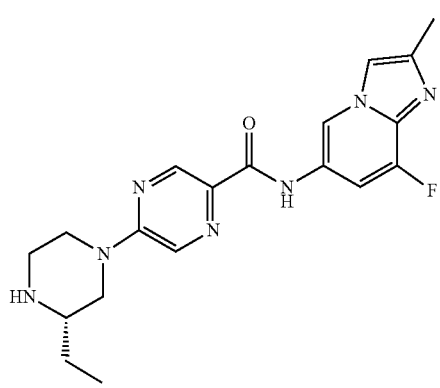
45
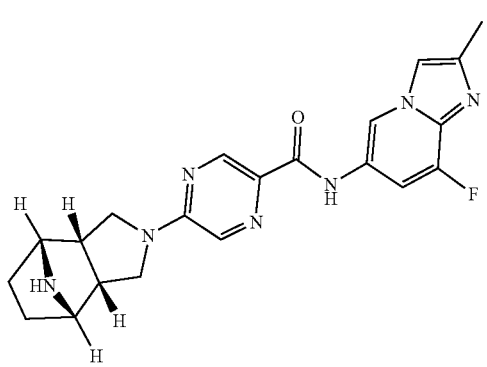
46
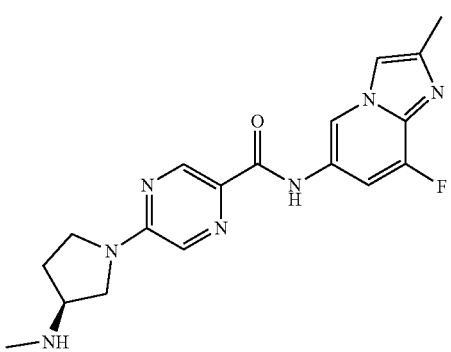
47
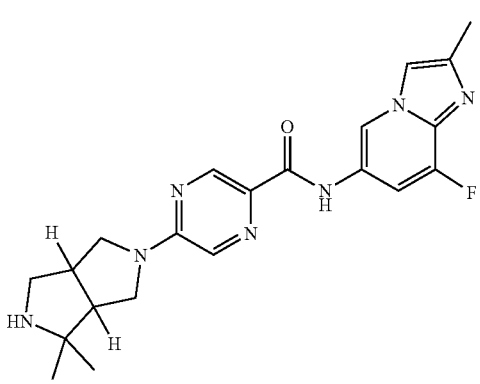
Cis Isomers, Enantiomer 1 + Enantiomer 2
48
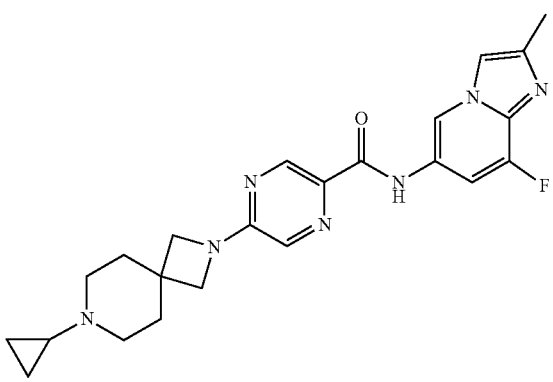
49
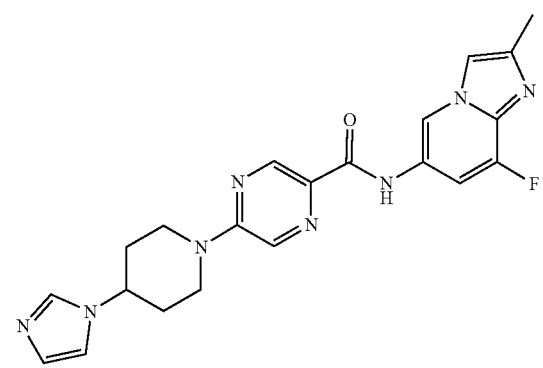

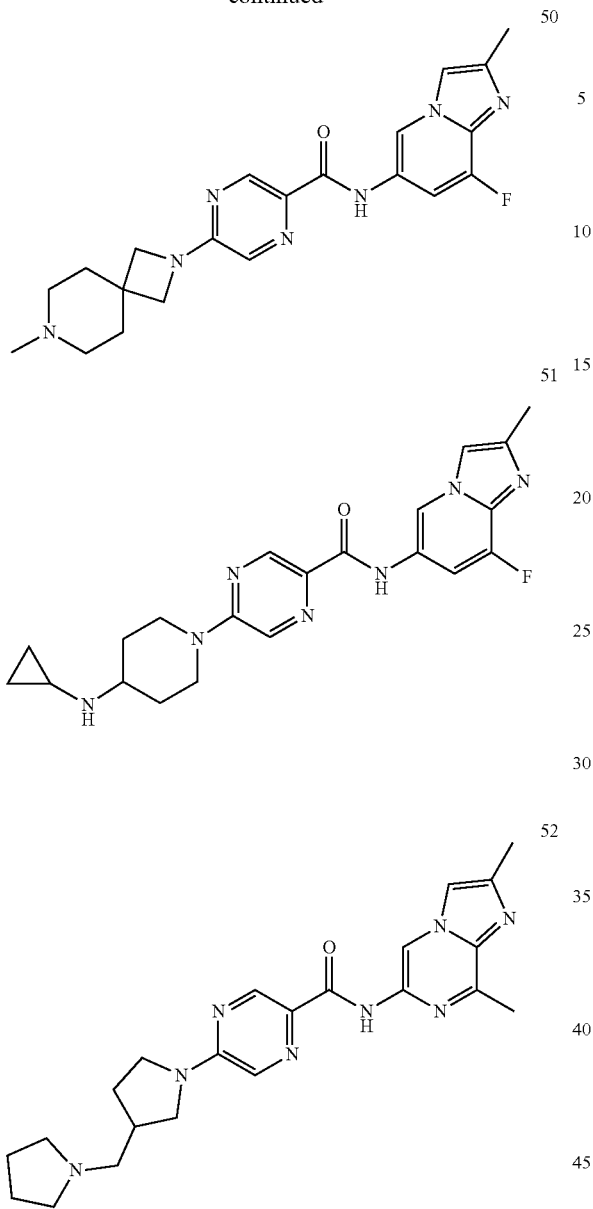
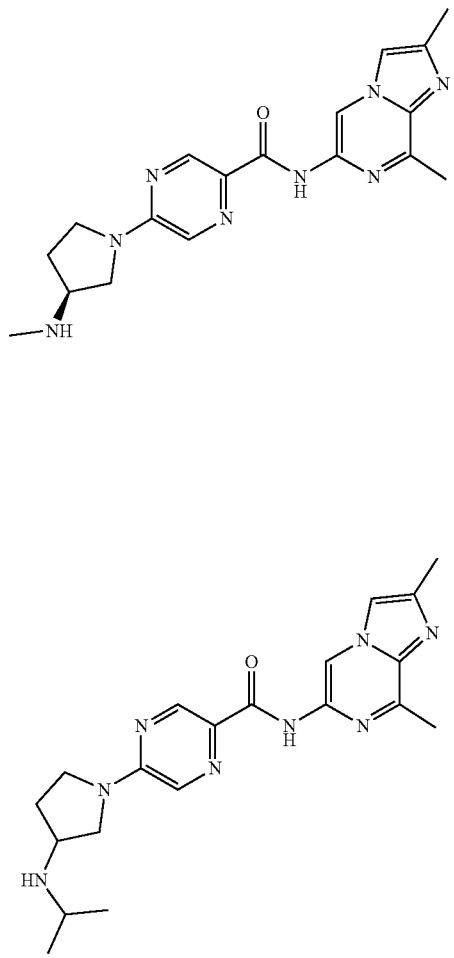
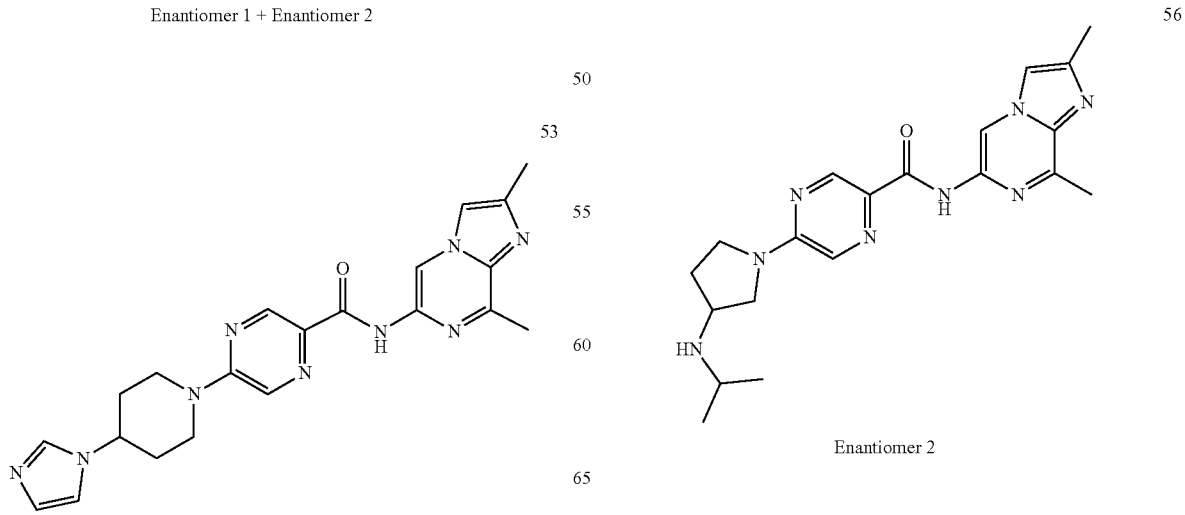

| | |
|---|---|
| 57 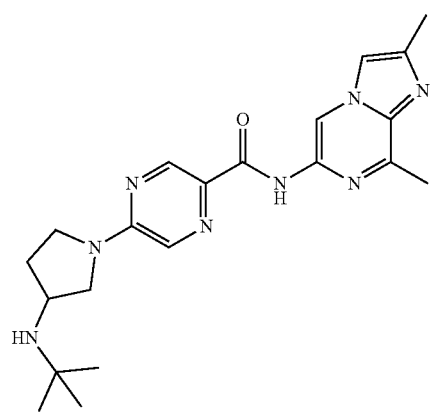<br>Enantiomer 1 + Enantiomer 2 | 61 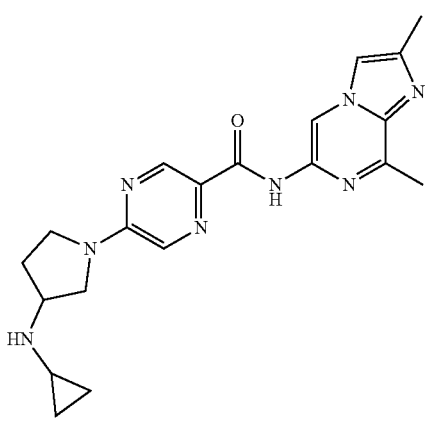<br>Enantiomer 1 |
| 58 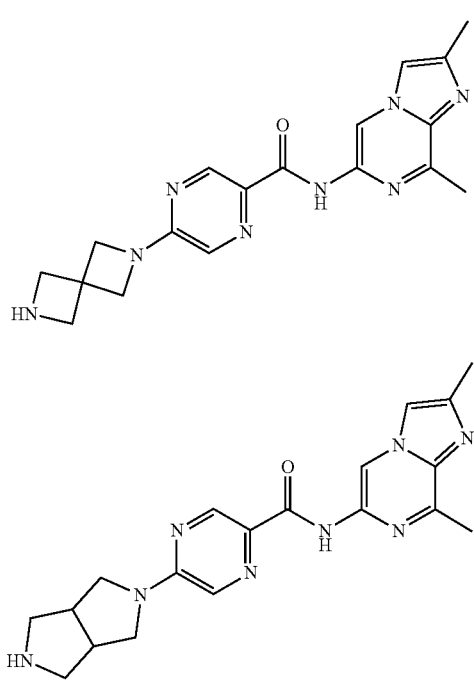<br>59<br>60<br>Enantiomer 2 | 62 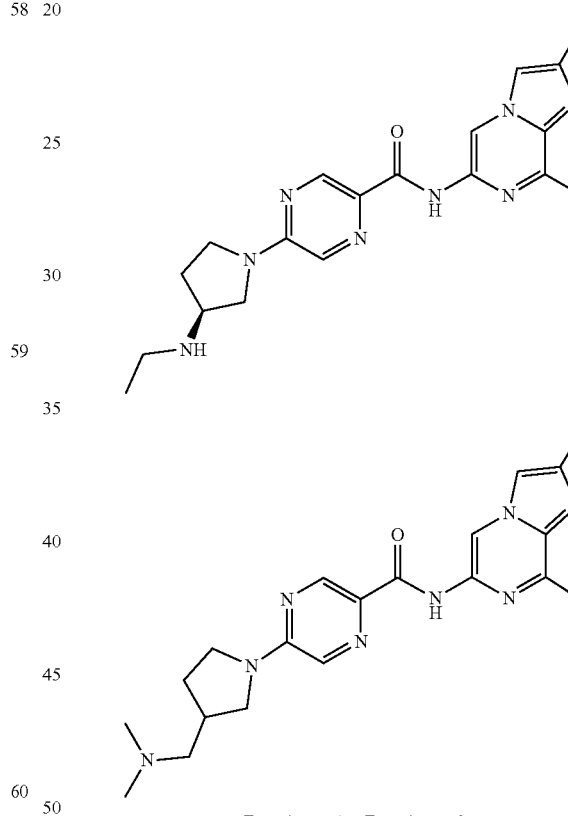<br>63<br>64 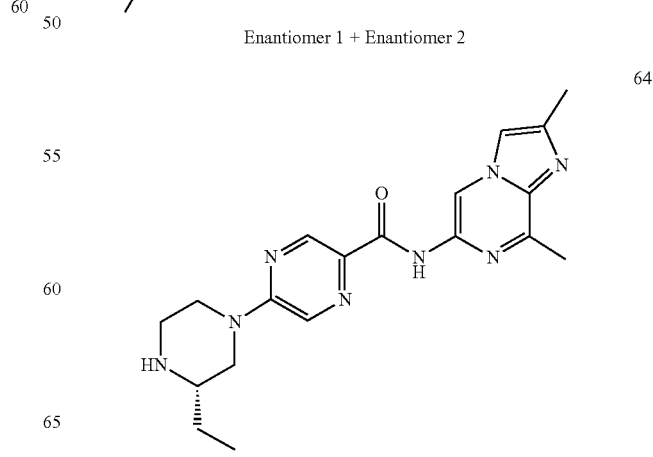 |
(Note: images 2 and 3 combined on left, 5 and 6 on right)

65
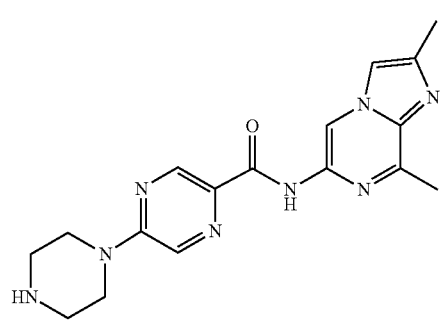
66
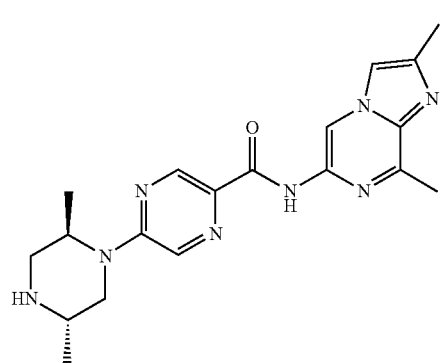
67
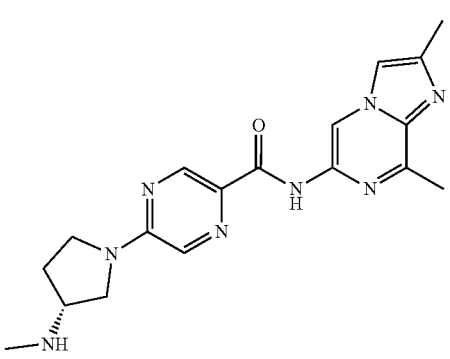
68
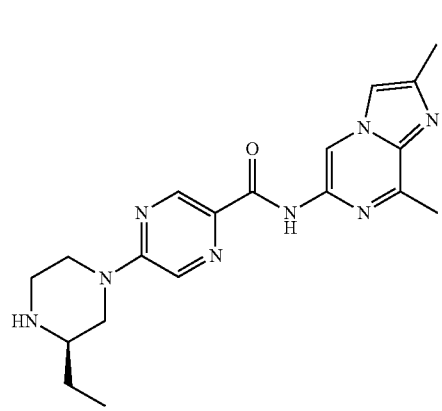
69
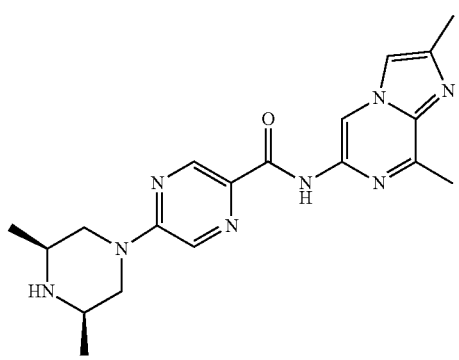
70
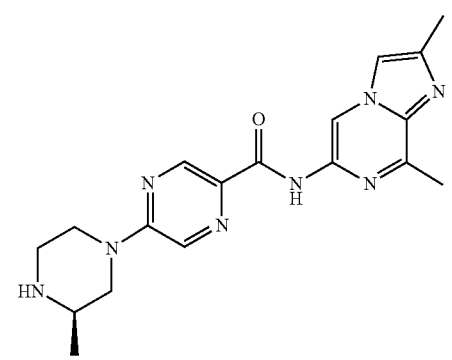
71
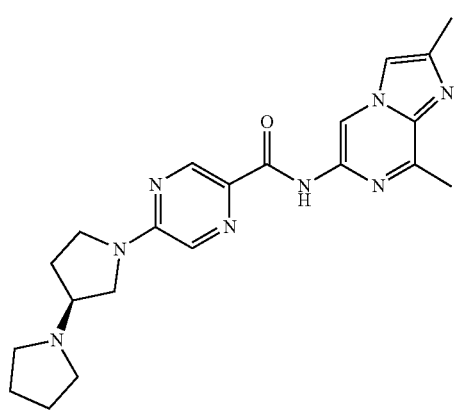
72
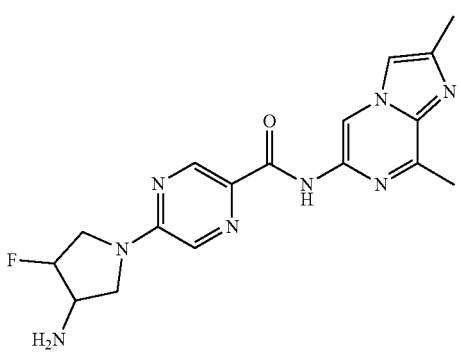
Trans Isomers, Enantiomer 1 + Enantiomer 2

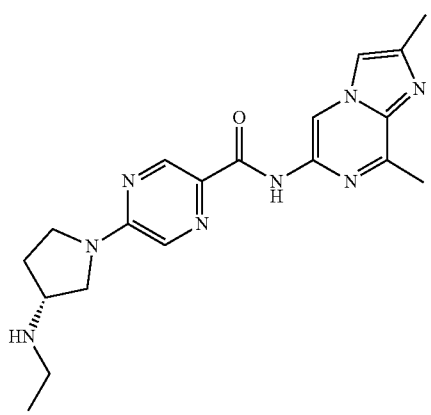
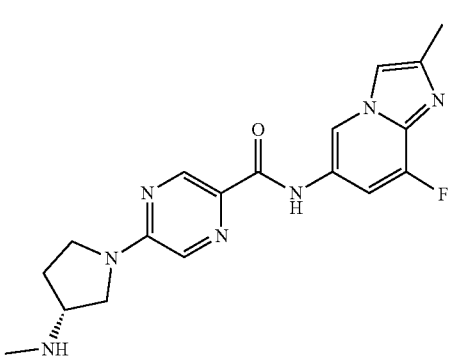
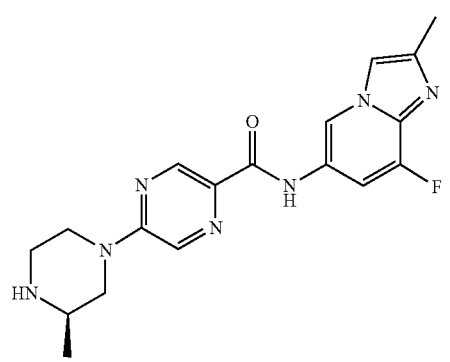
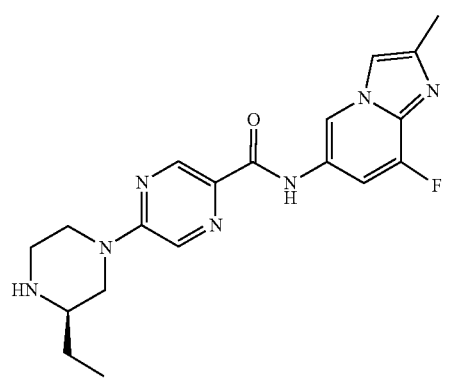
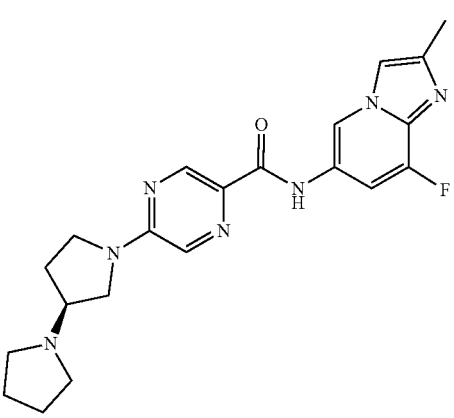

81
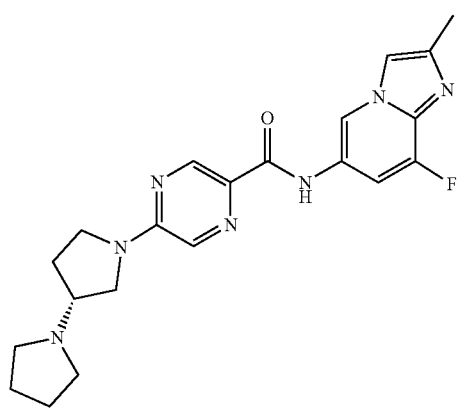
82
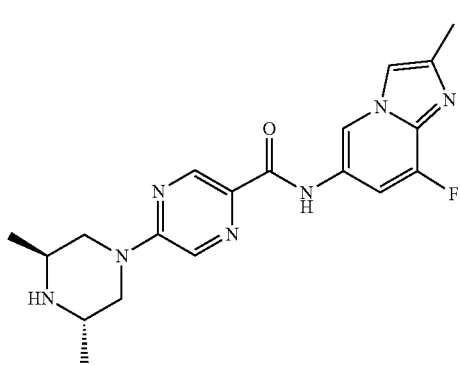
83
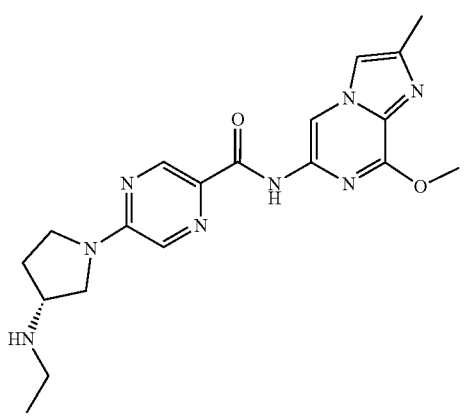
84
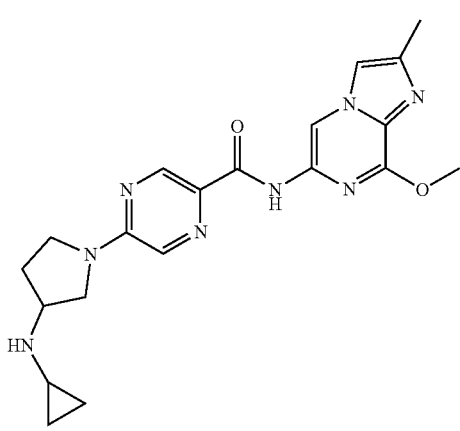
Enantiomer 1
85
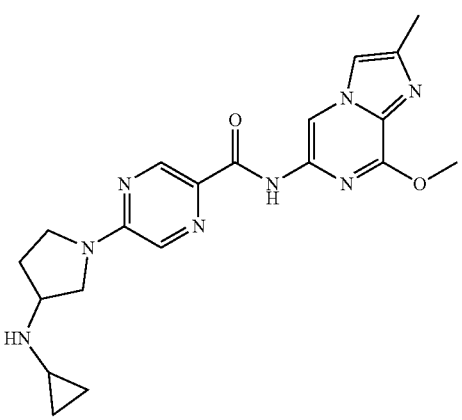
Enantiomer 2
86
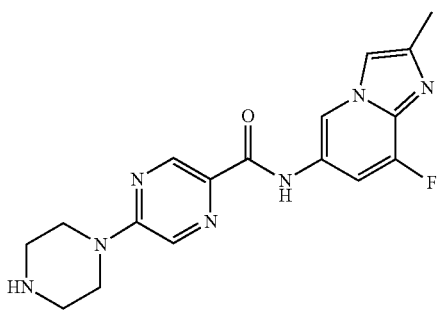
87
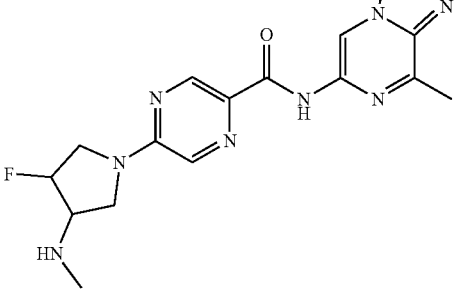
Cis Isomer, Enantiomer 1
88
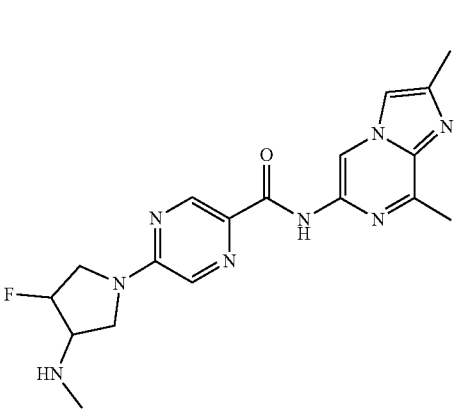
Cis Isomer, Enantiomer 2

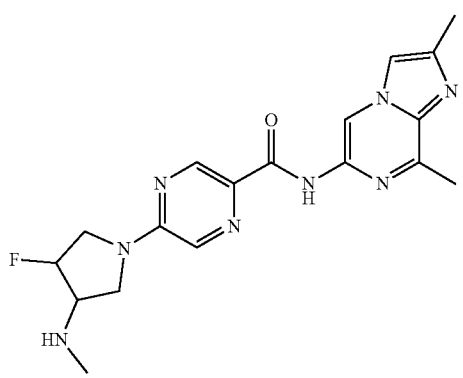
89
Trans Isomers, Enantiomer 1 and Enantiomer 2
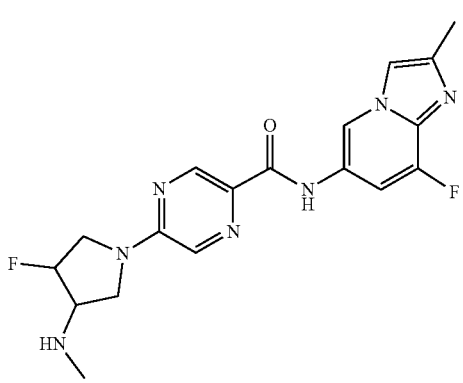
90
Trans Isomers, Enantiomer 1 and Enantiomer 2
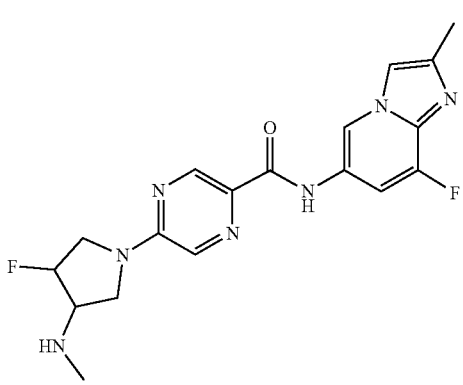
91
Cis Isomer, Enantiomer 1
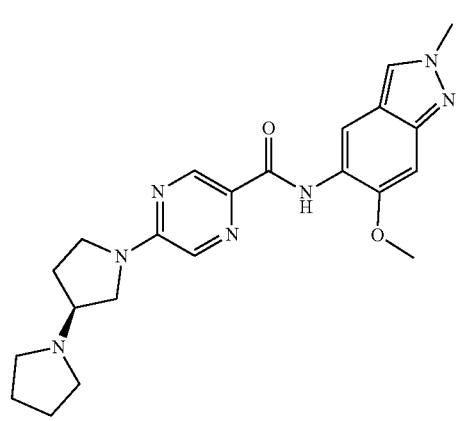
92
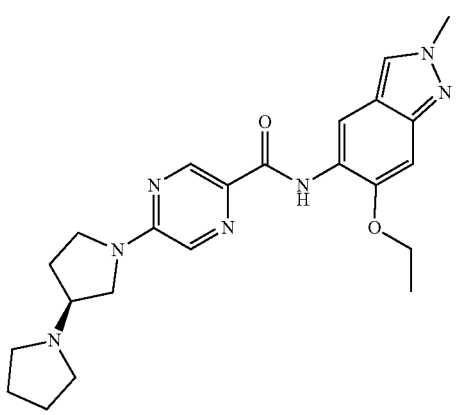
93
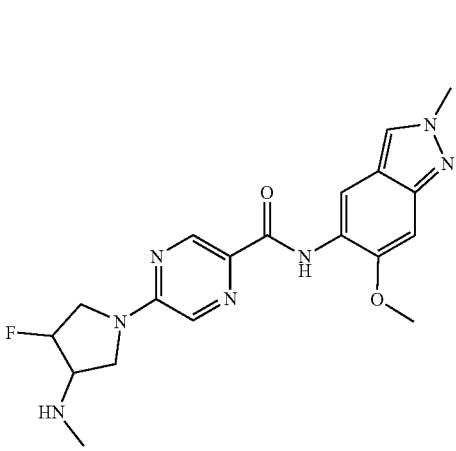
94
Cis Isomers, Enantiomer 1 + Enantiomer 2
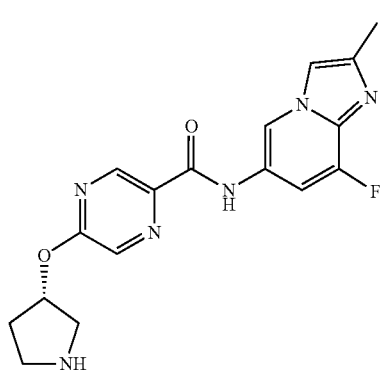
95
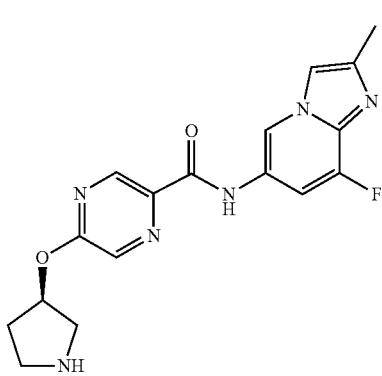
96

| 739 -continued | | 740 -continued | |
|---|---|---|---|
| 97 | 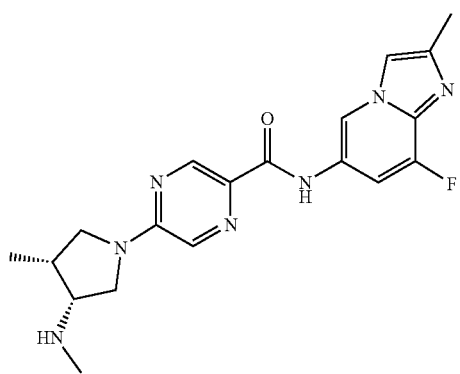 | 101 | 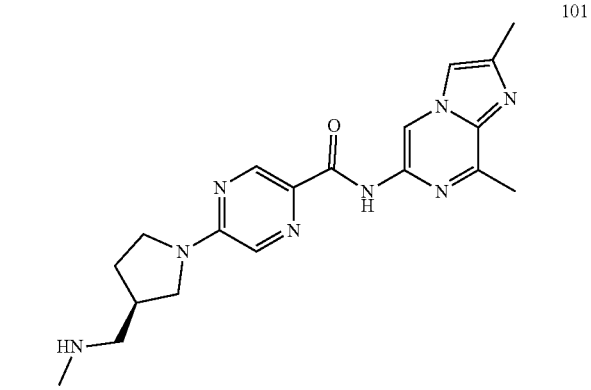 |
| 98 | 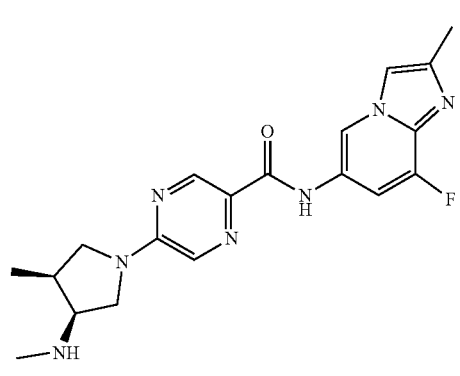 | 102 | 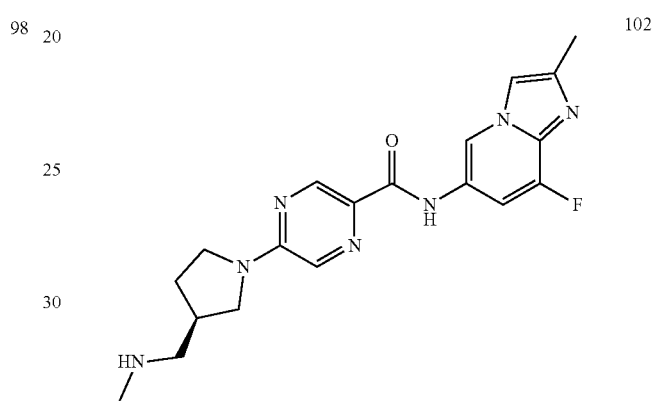 |
| 99 | 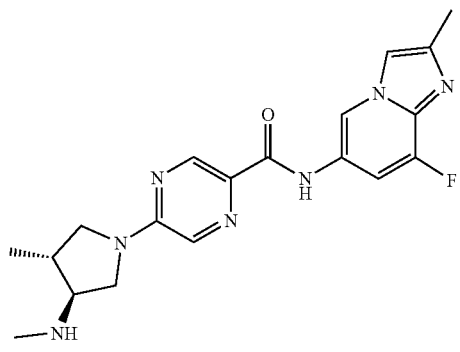 | 103 | 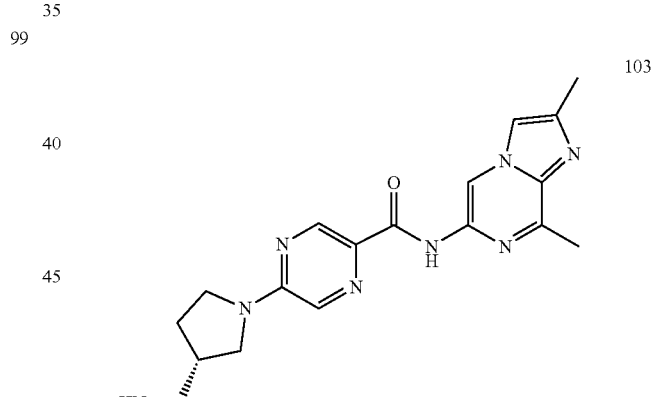 |
| 100 | 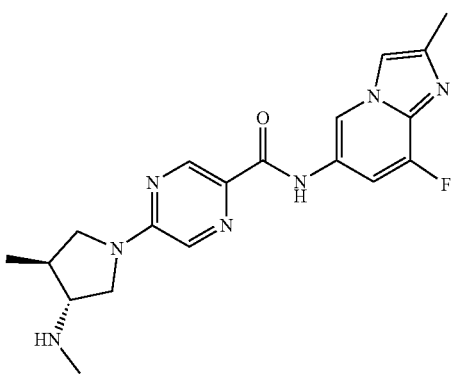 | 104 | 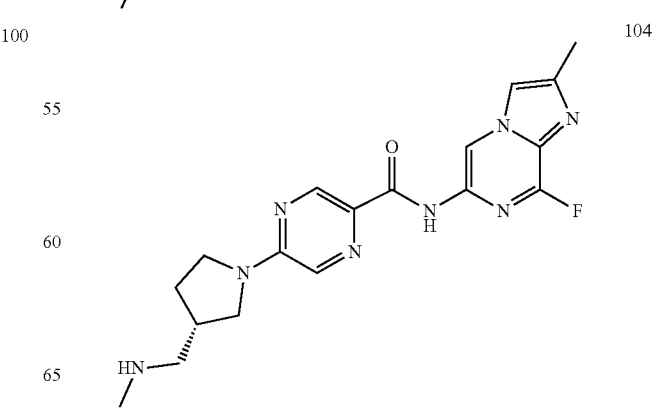 |

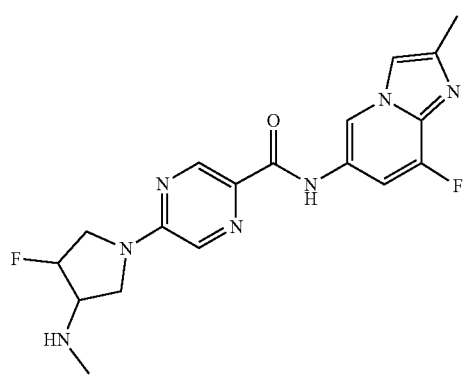
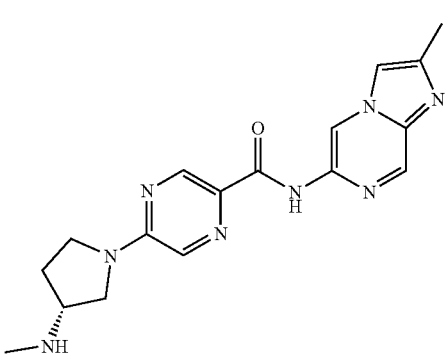

113
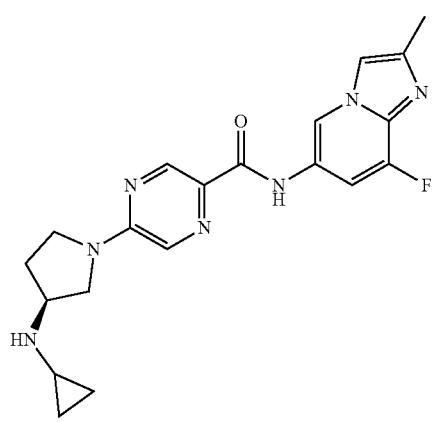
114
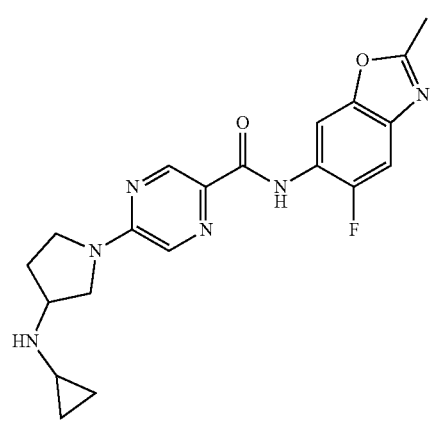
Enantiomer 1 + Enantiomer 2
115
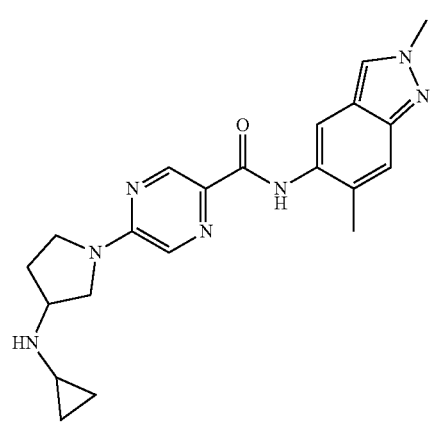
Enantiomer 1 + Enantiomer 2
116
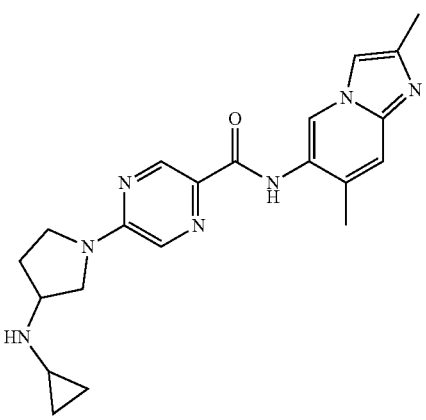
Enantiomer 1 + Enantiomer 2
117
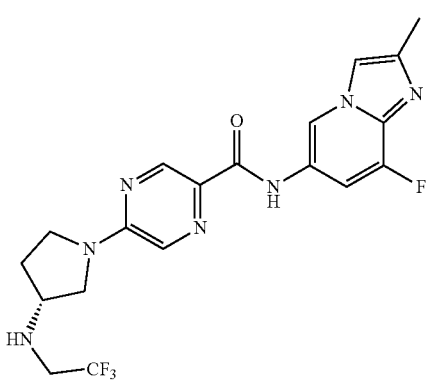
118
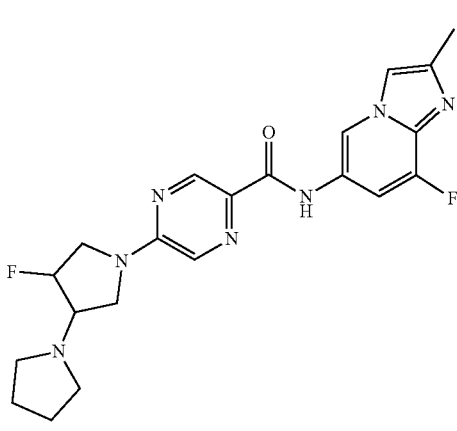
Cis Isomer, Enantiomer 1

119
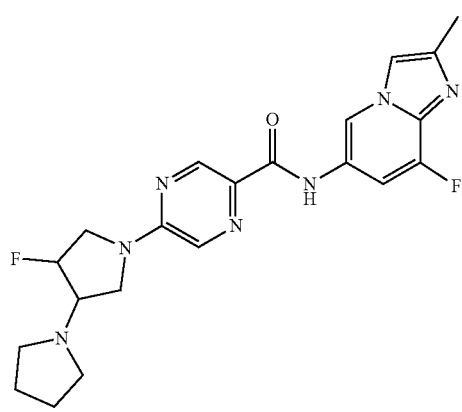
Cis Isomer, Enantiomer 2
120
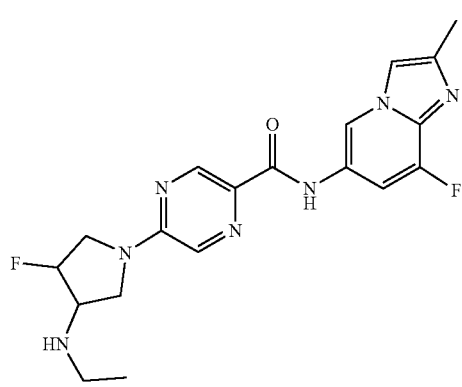
Cis Isomer, Enantiomer 1
121
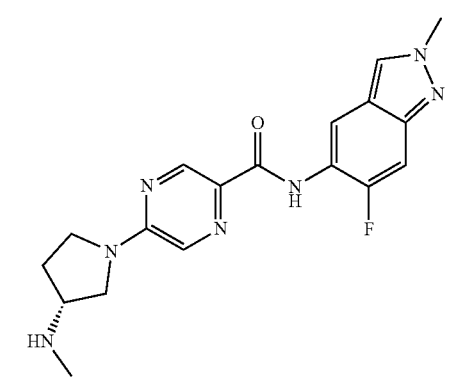
122
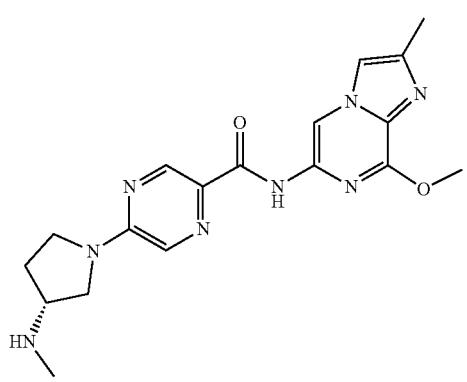
123
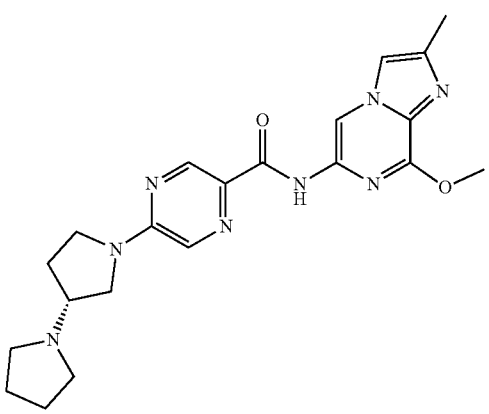
124
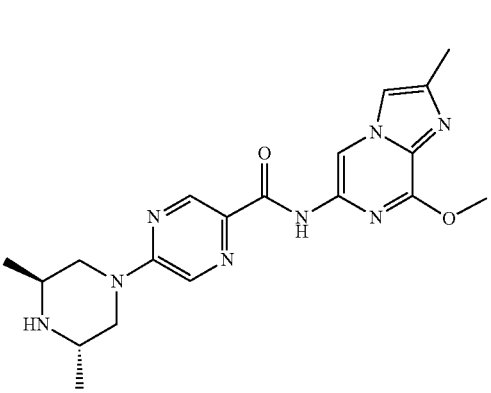
125
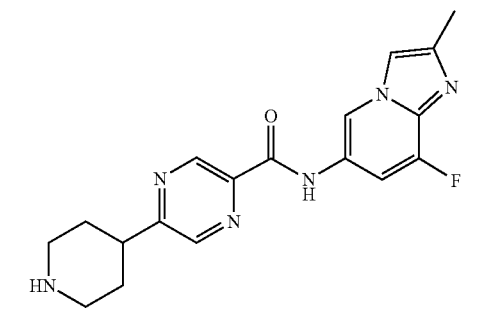
126
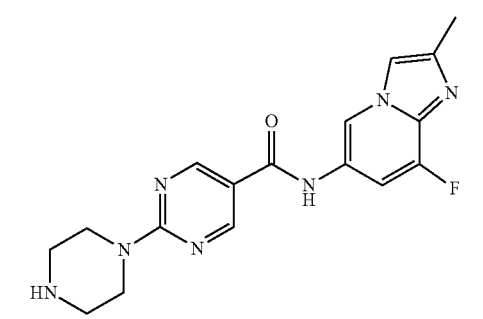

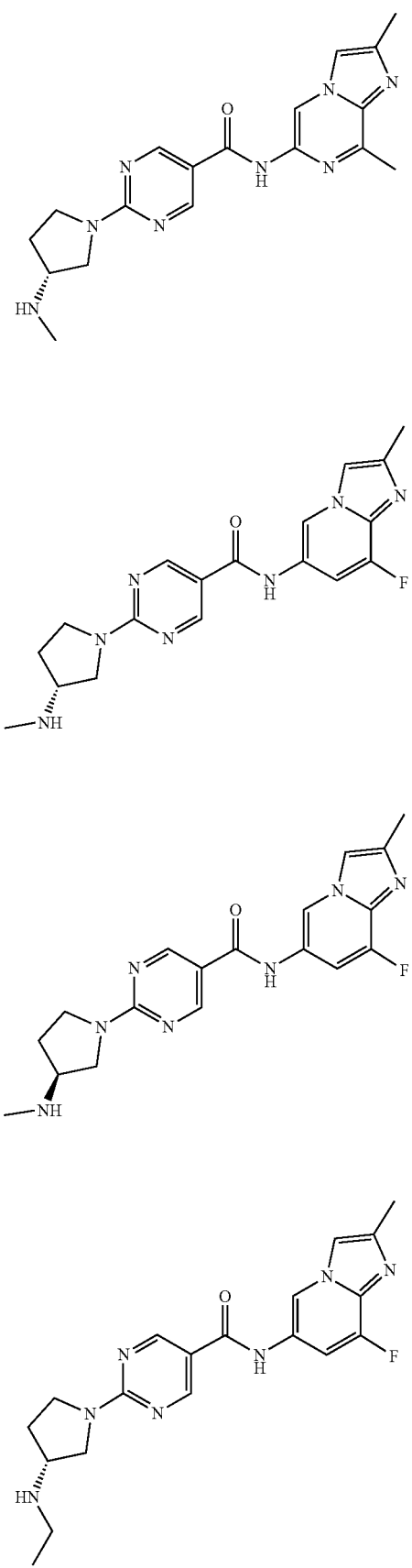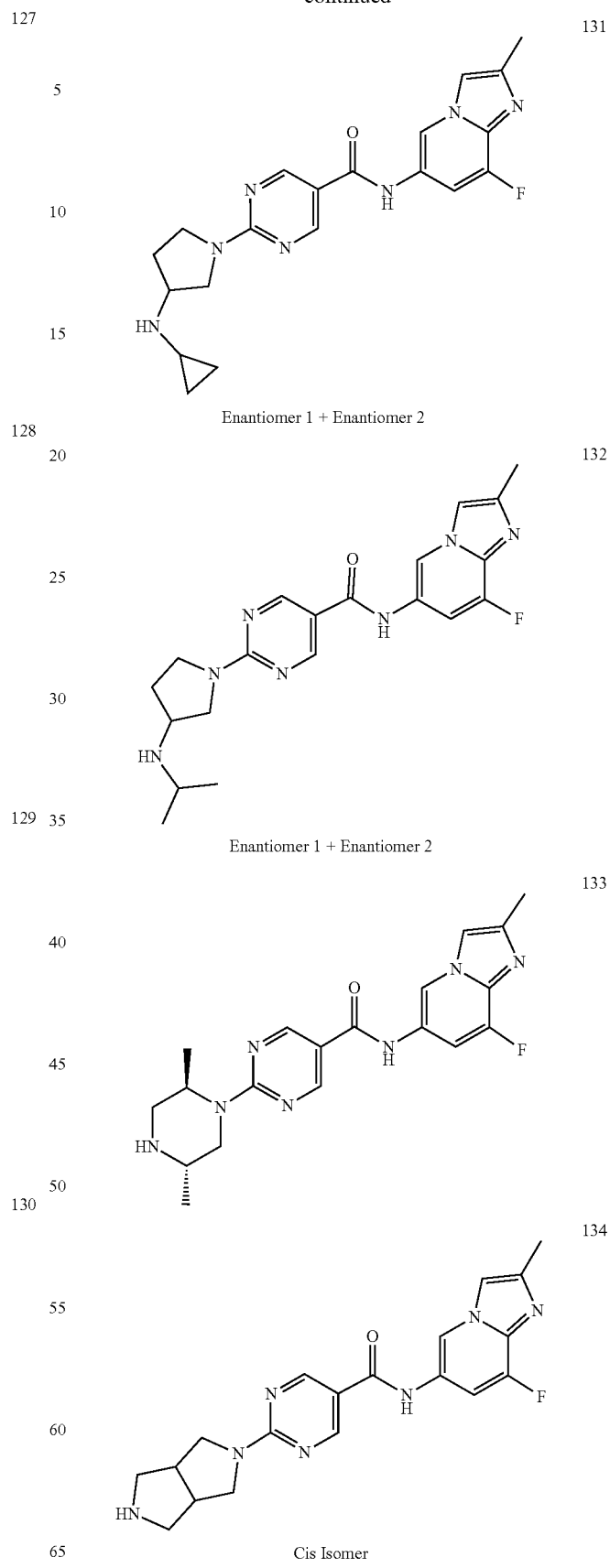

| | |
|---|---|
| 135 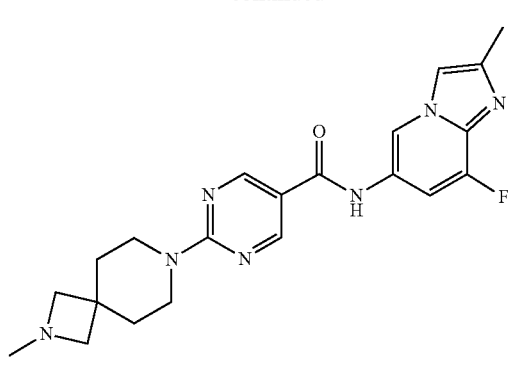 | 139 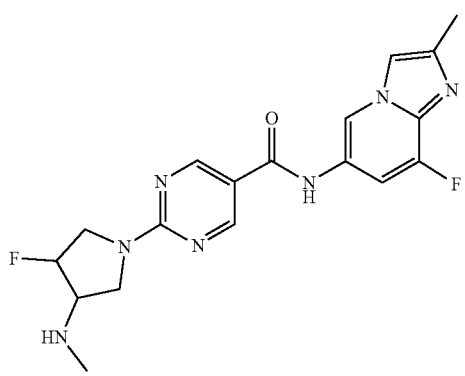<br>Cis Isomer, Enantiomer 1 |
| 136 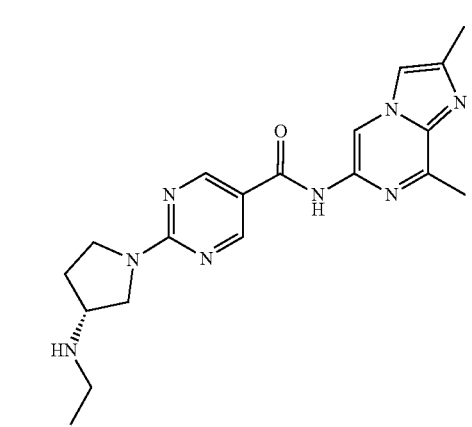 | 140 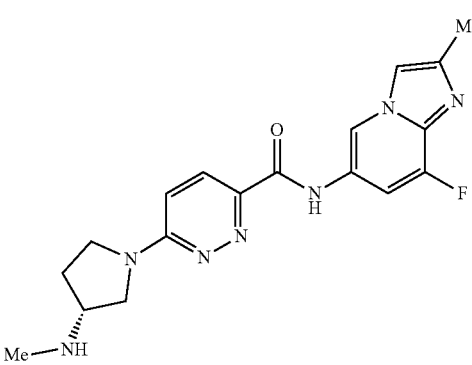 |
| 137 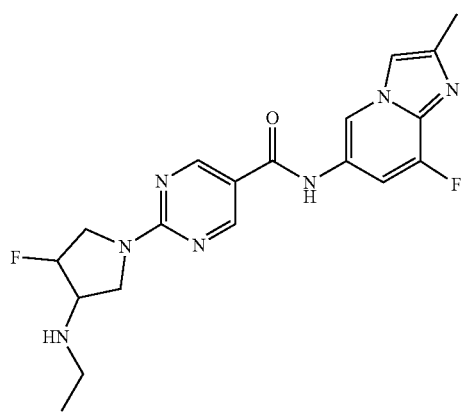<br>Cis Isomer, Enantiomer 1 | 141 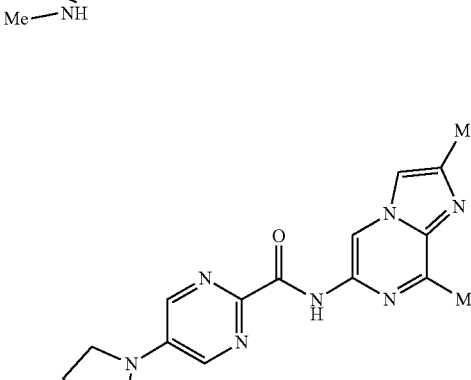 |
| 138 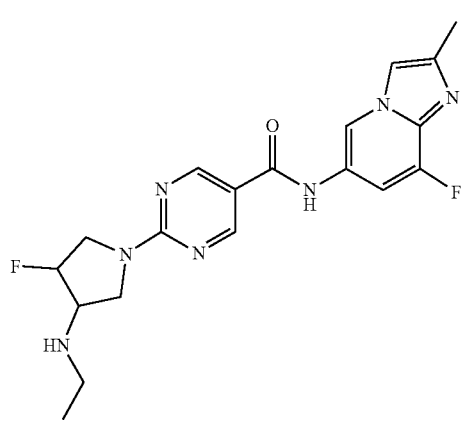<br>Cis Isomer, Enantiomer 2 | 142 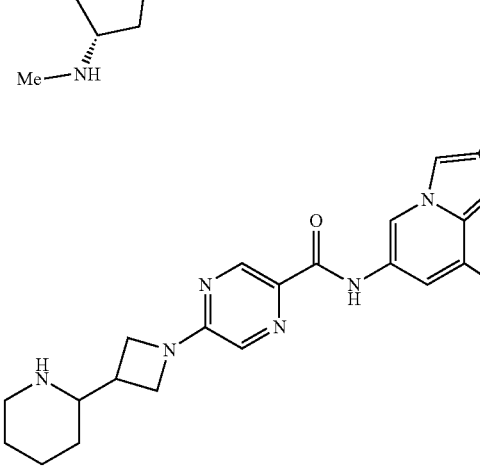<br>Enantiomer 1 |

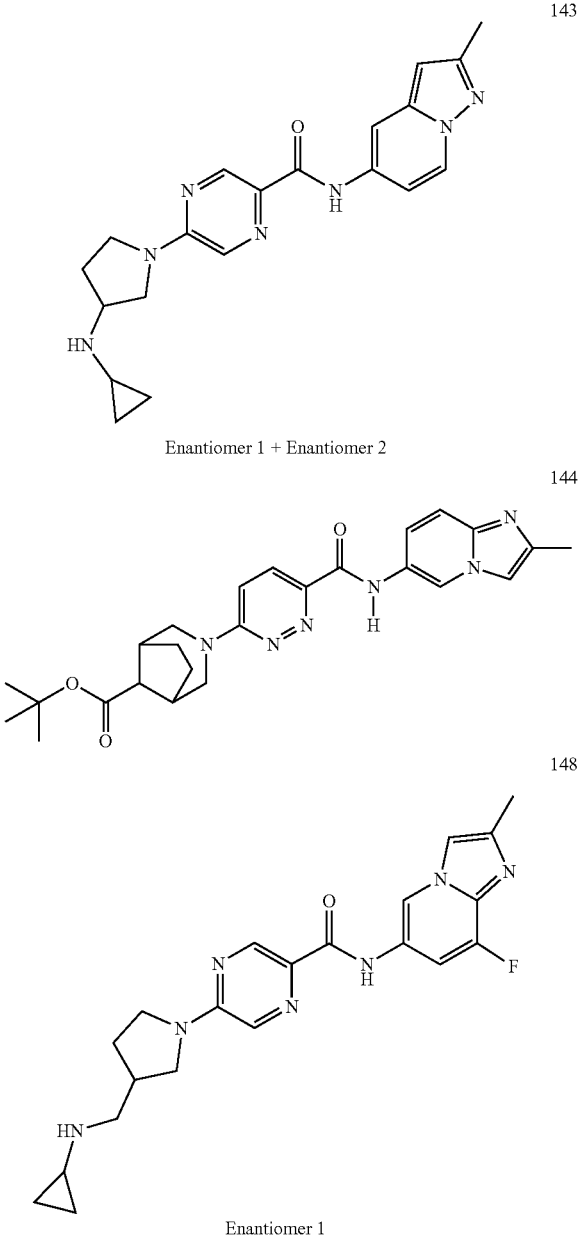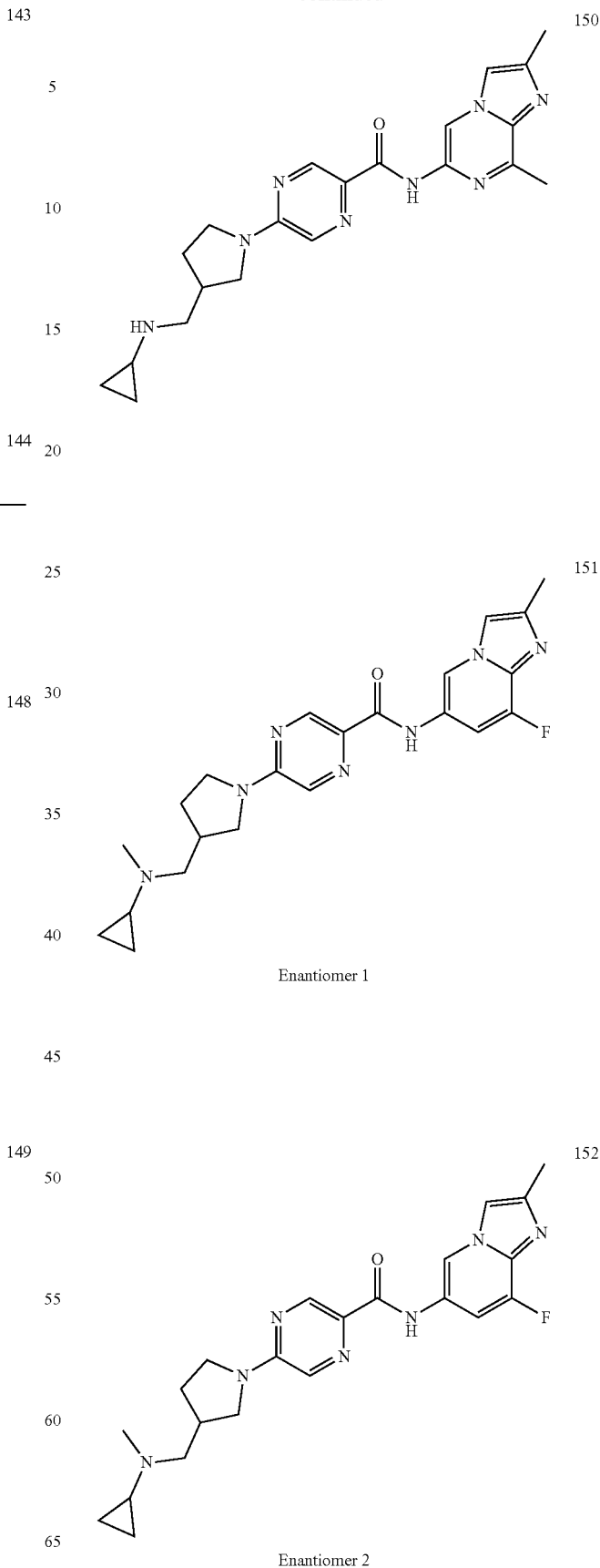

753
-continued
153
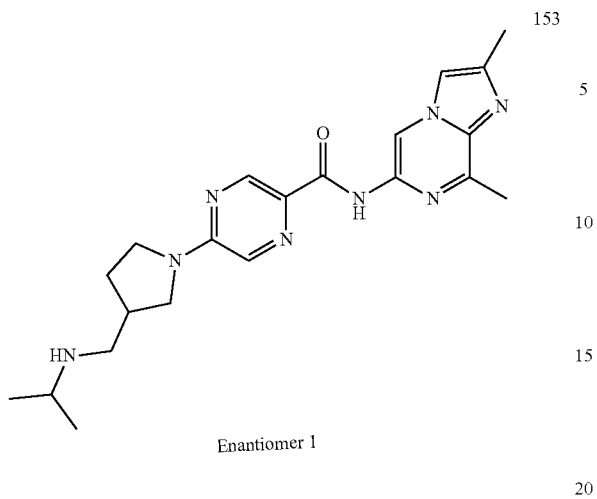
Enantiomer 1
154
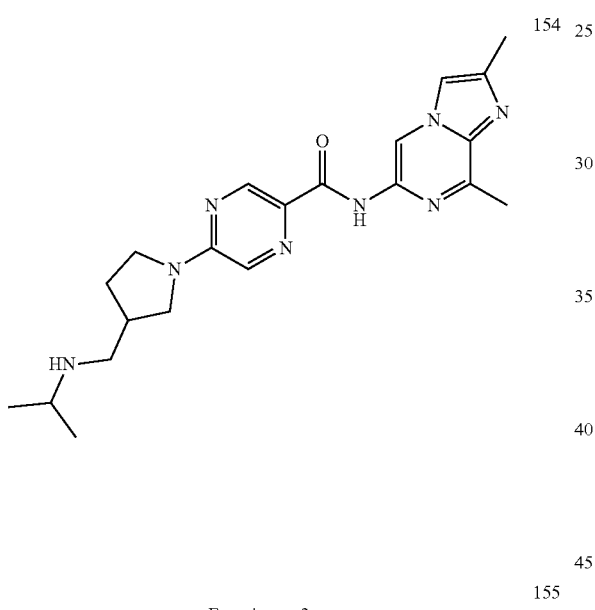
Enantiomer 2
155
Enantiomer 1
754
-continued
156
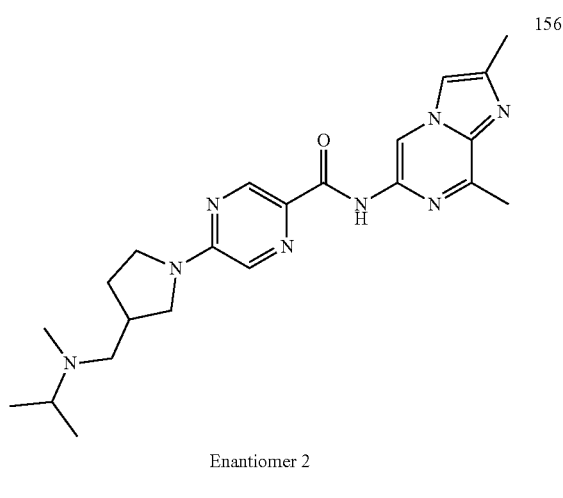
Enantiomer 2
157
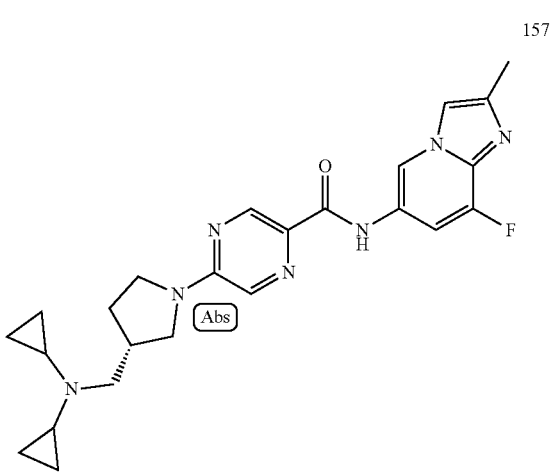
158
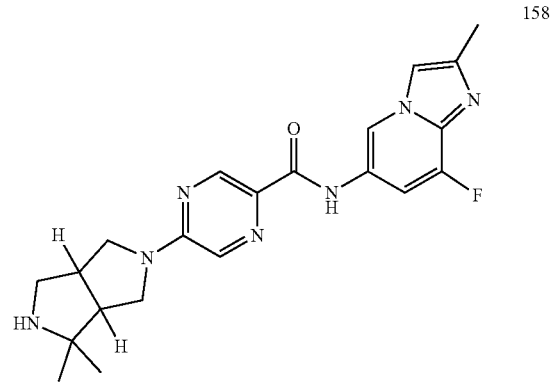

755
-continued
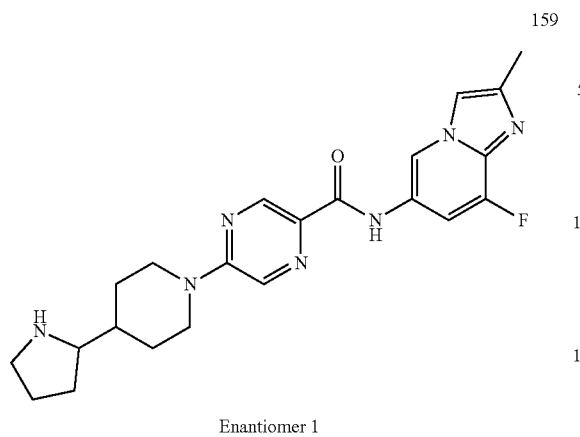
159
Enantiomer 1
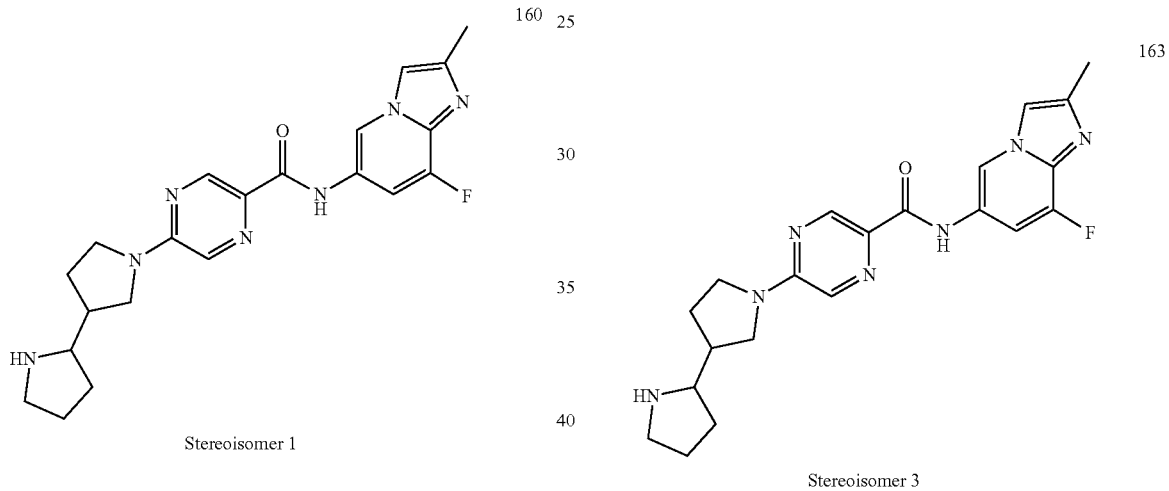
160
Stereoisomer 1
161
Stereoisomer 2
756
-continued
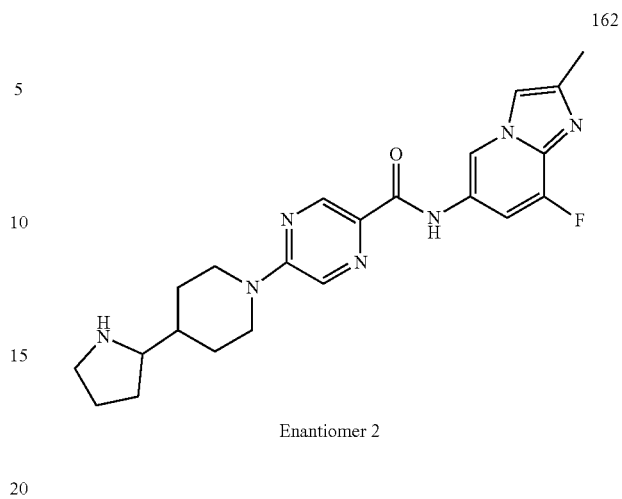
162
Enantiomer 2
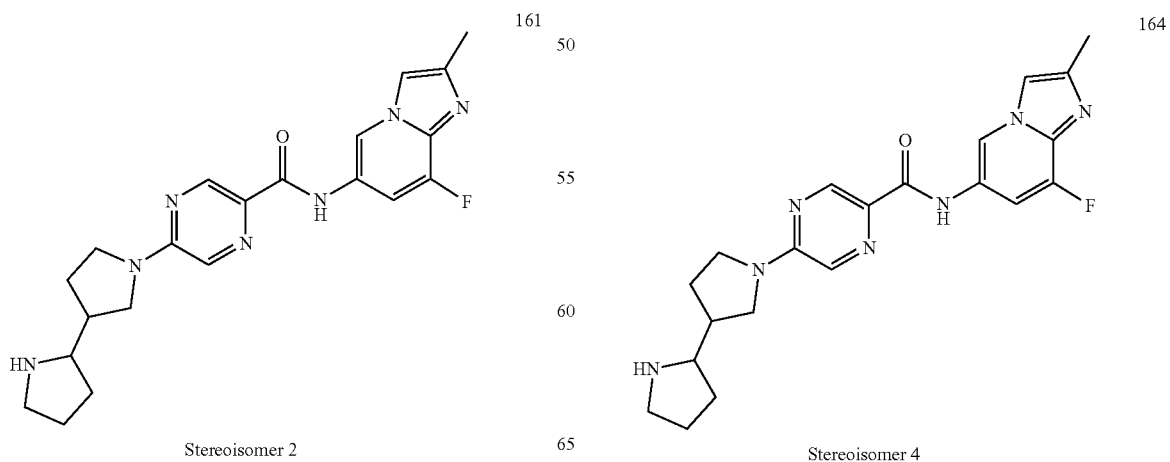
163
Stereoisomer 3
164
Stereoisomer 4

757
-continued
165
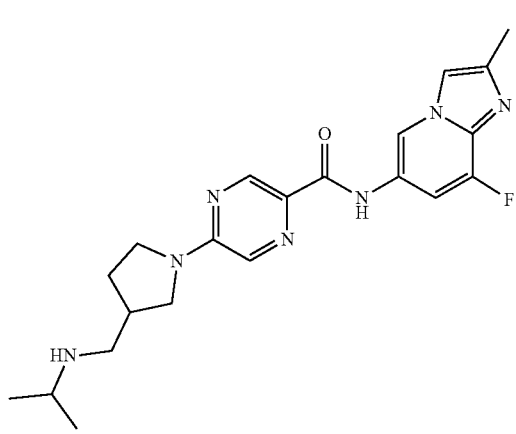
Enantiomer 1
166
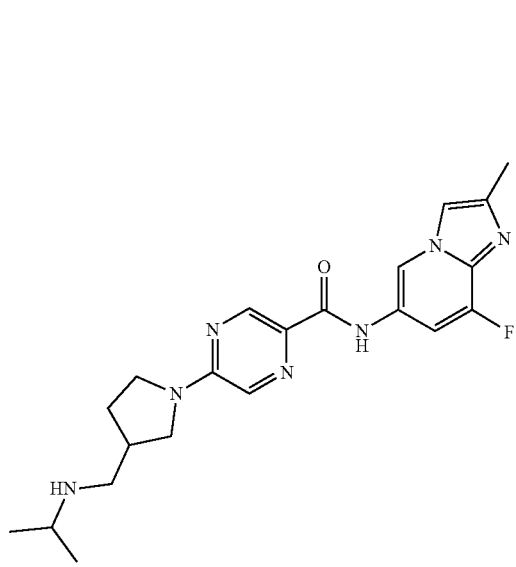
Enantiomer 2
167
Enantiomer 1
758
-continued
168
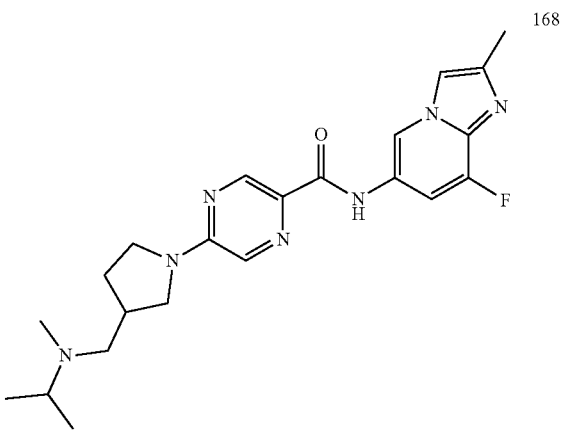
Enantiomer 2
169
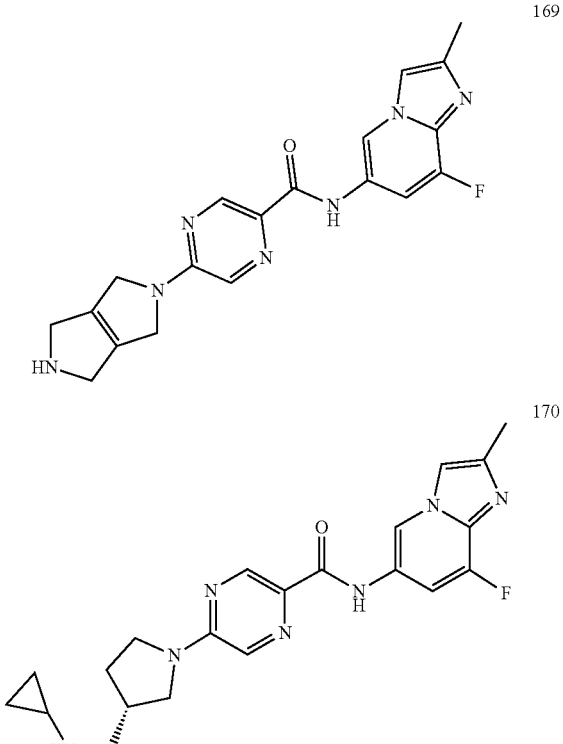
170
171
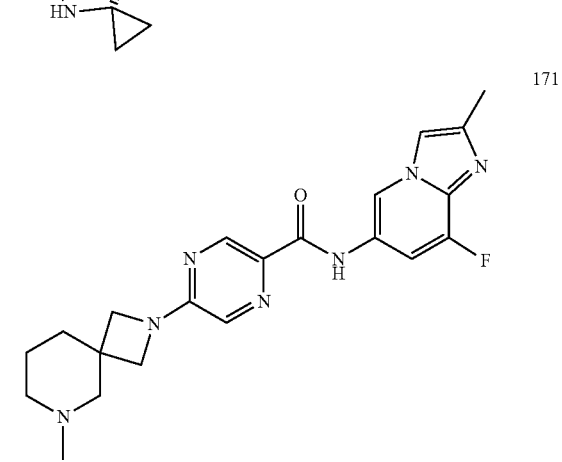

172
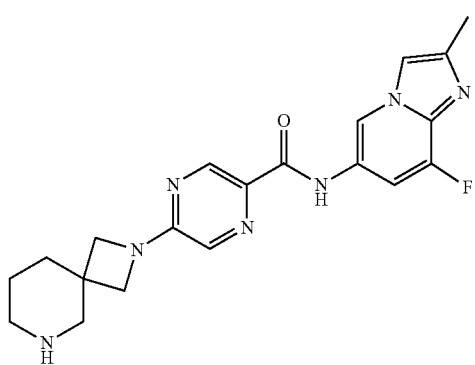
173
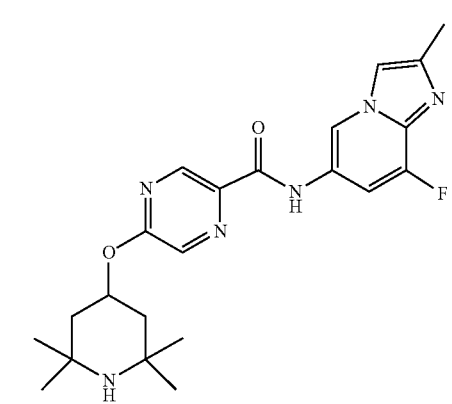
176
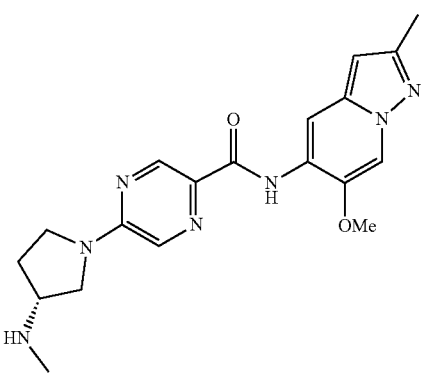
177
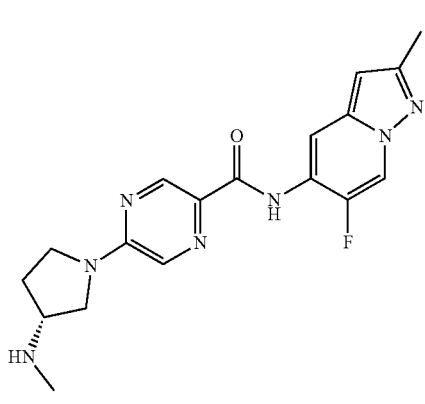
174
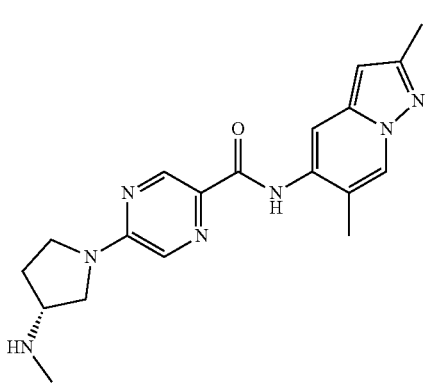
178
175
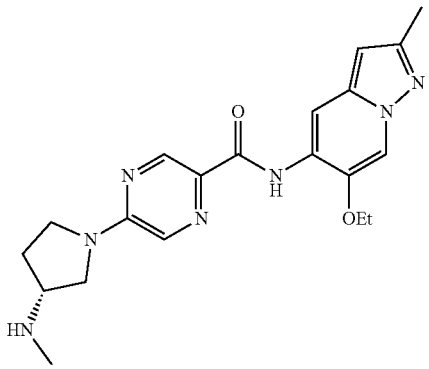
179

180 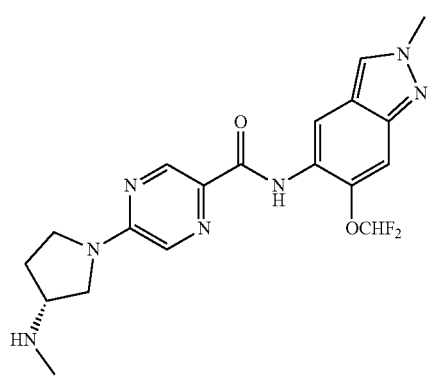
181 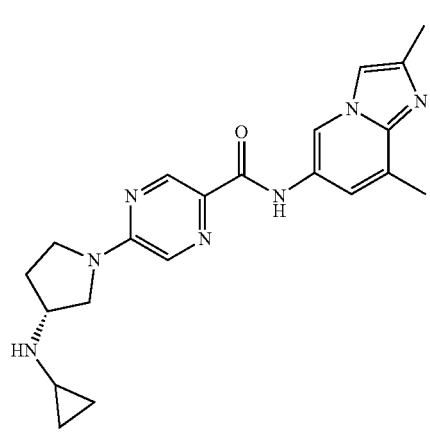
182 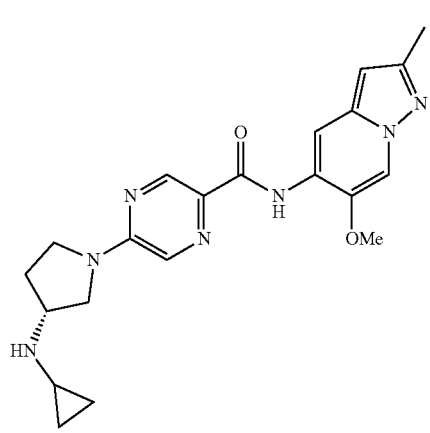
183 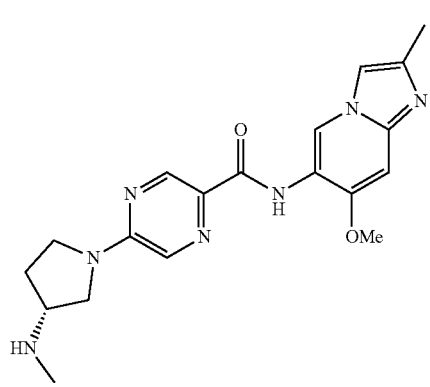
184 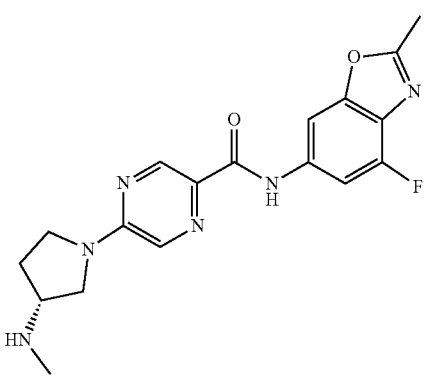
185 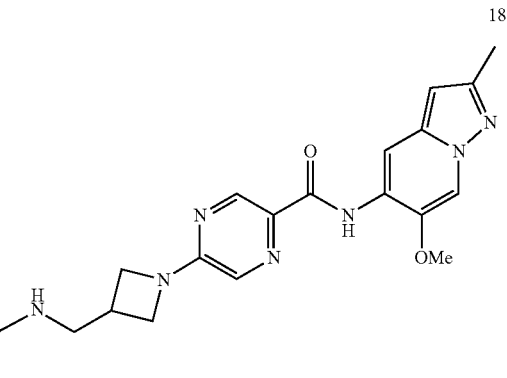
186 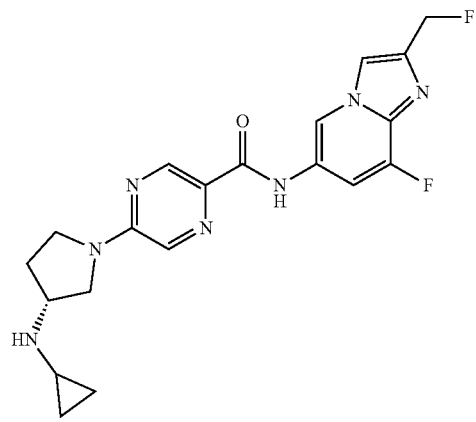
187 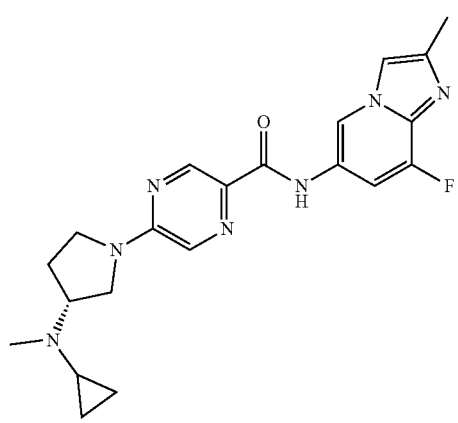

188 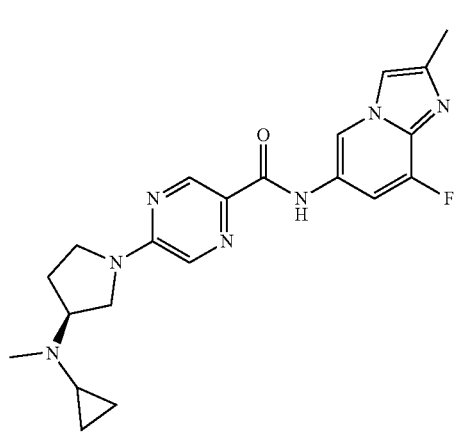
189 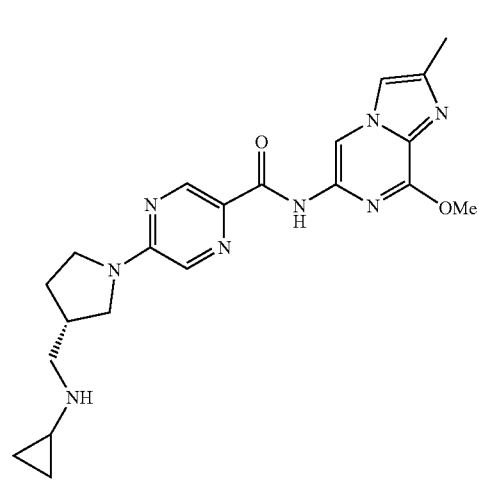
190 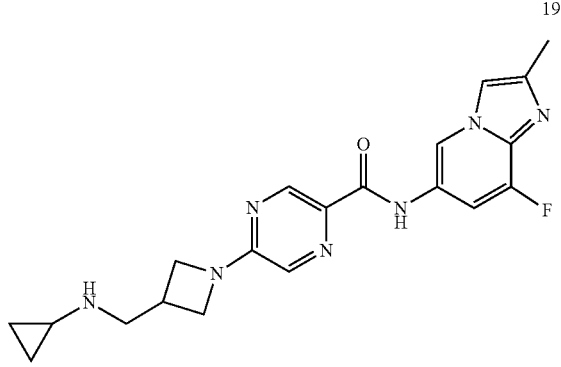
191 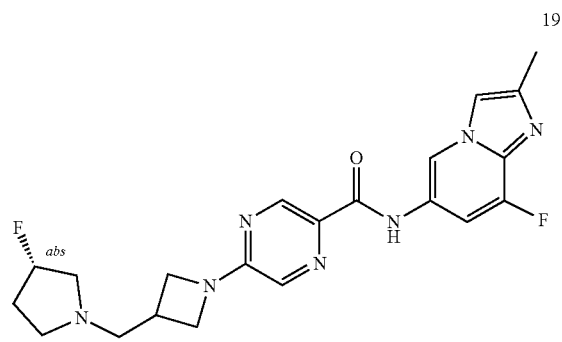
192 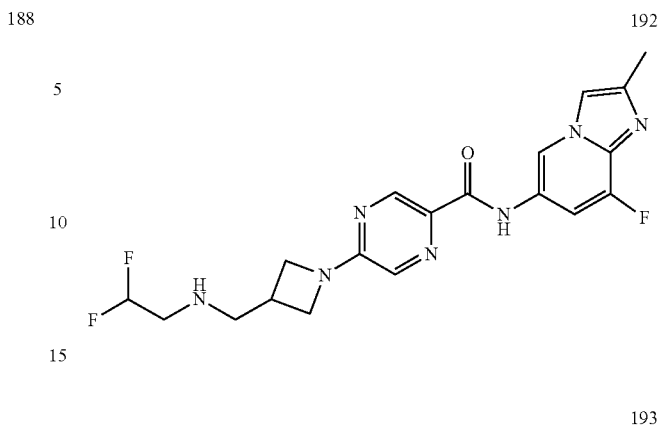
193 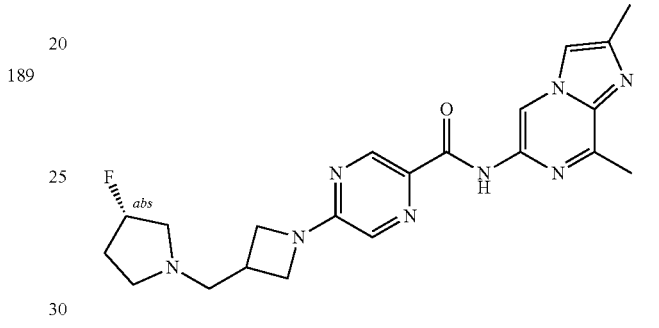
194 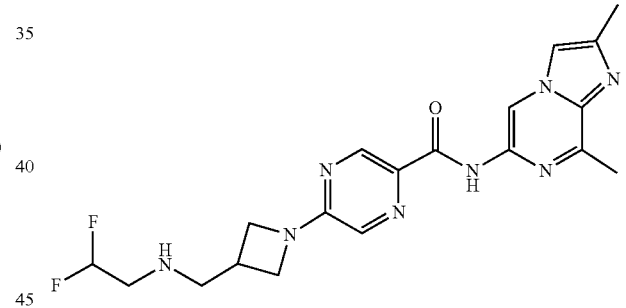
195 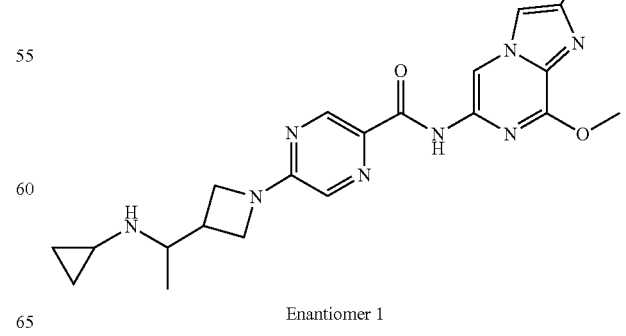
Enantiomer 1

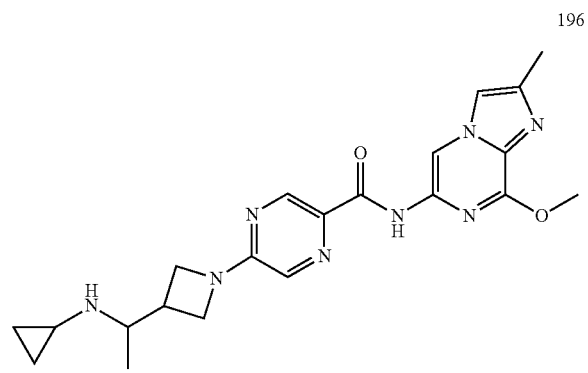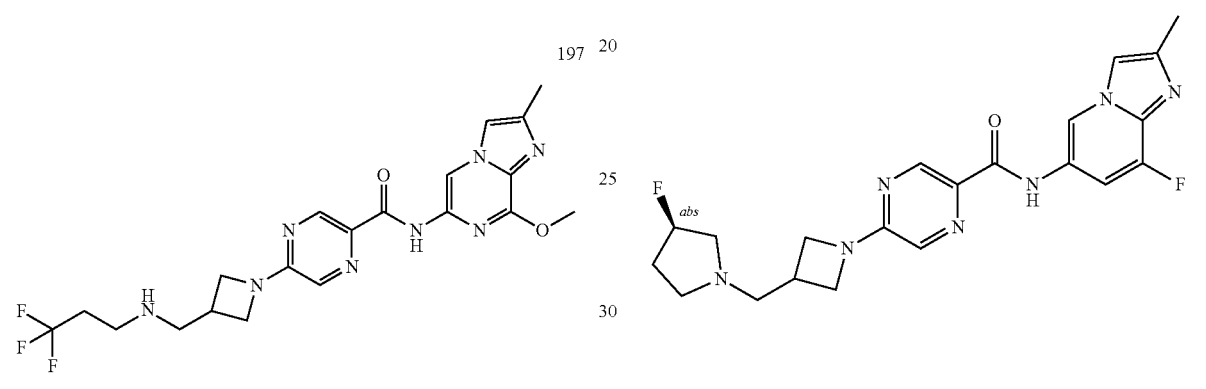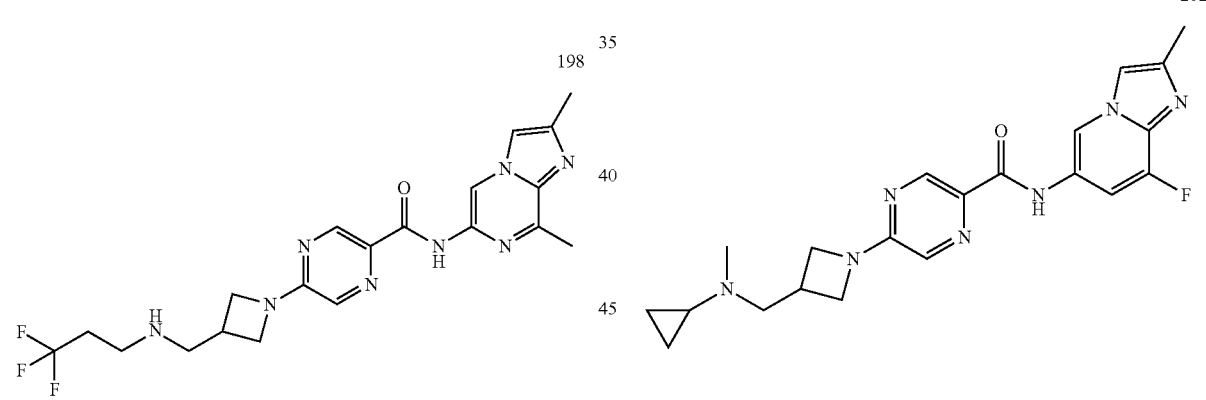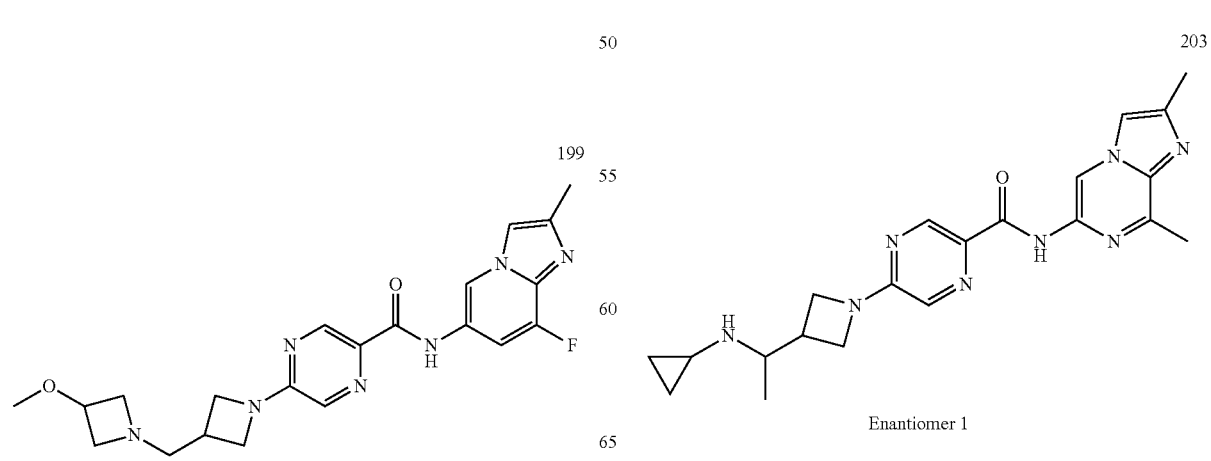

204
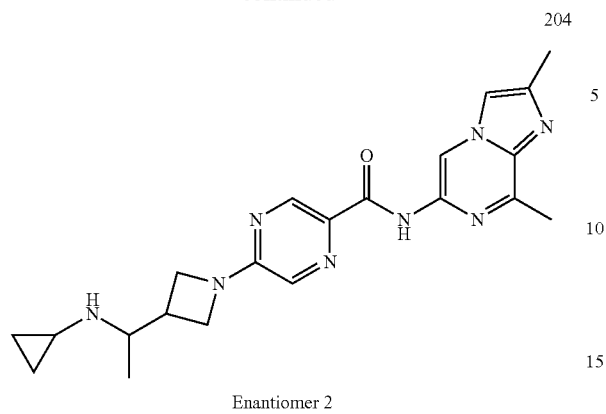
Enantiomer 2
205
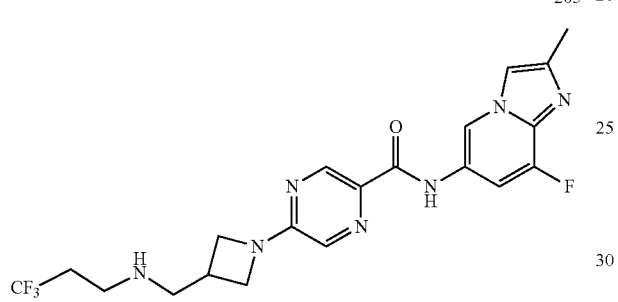
206
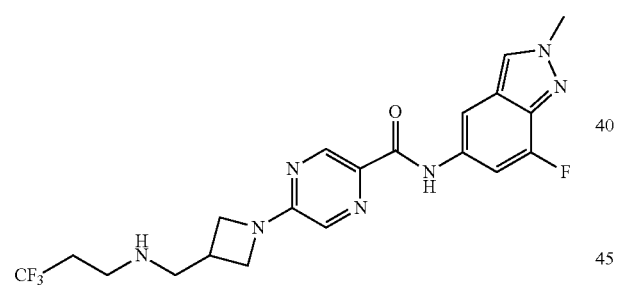
207
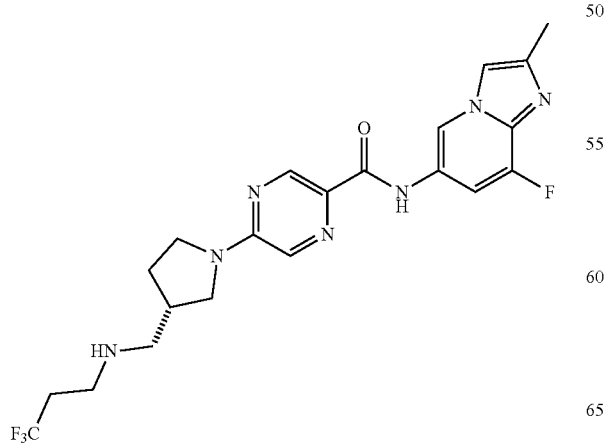
208
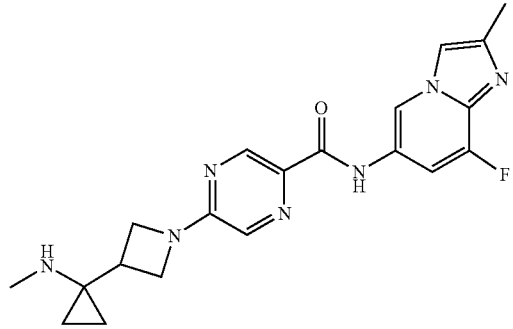
209
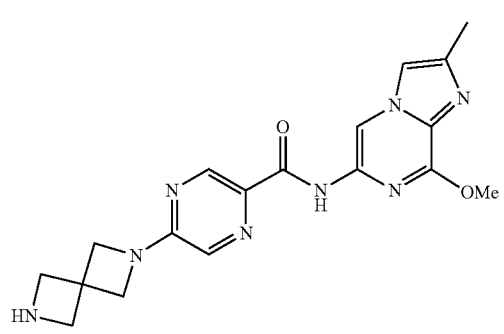
210
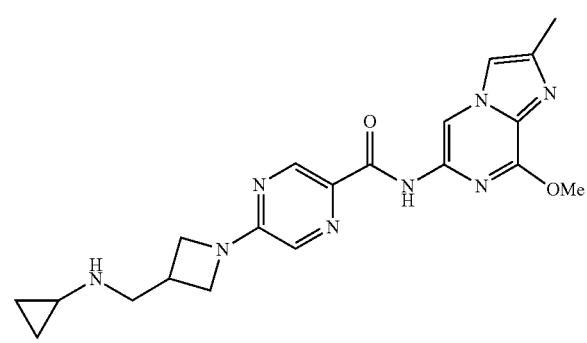
211
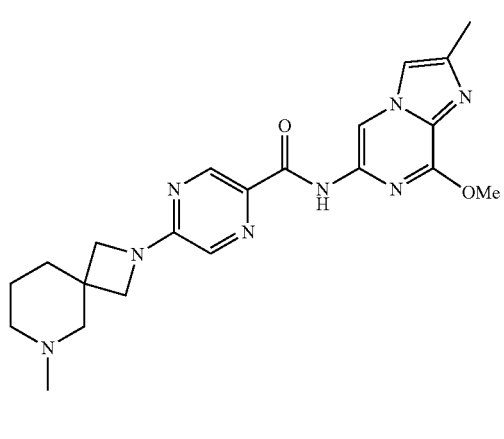

769
-continued
212
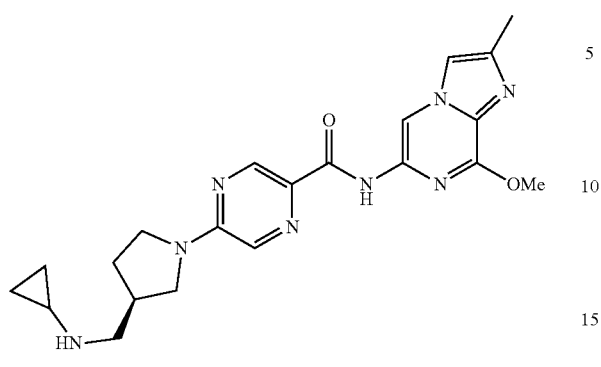
213
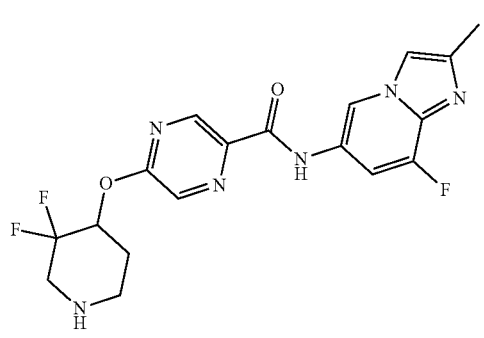
214
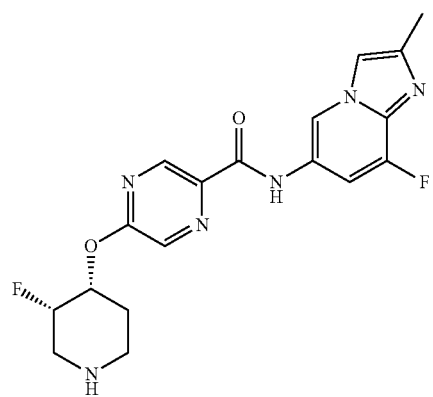
215
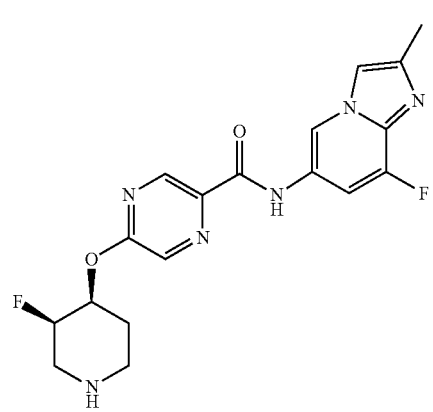
770
-continued
216
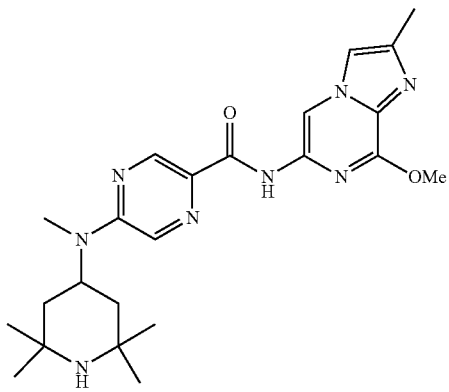
217
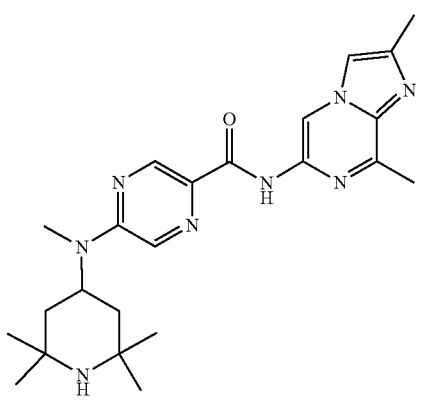
218
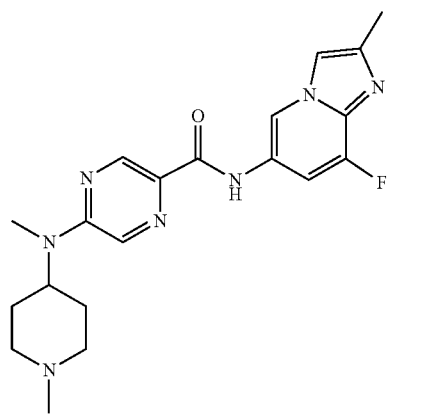
219
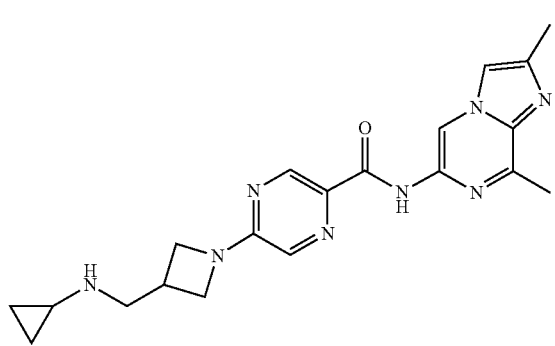

| 771 | 772 |
|---|---|
| 220 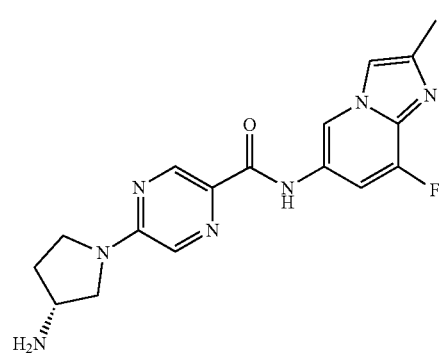 | 224 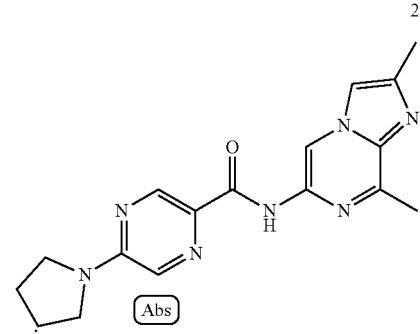 |
| 221 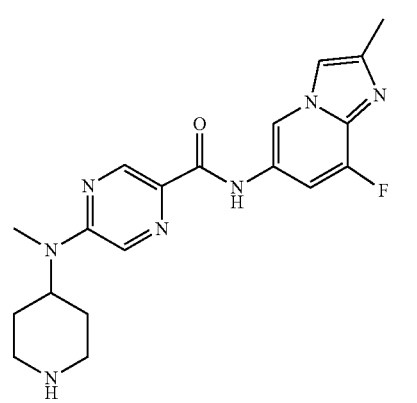 | 225 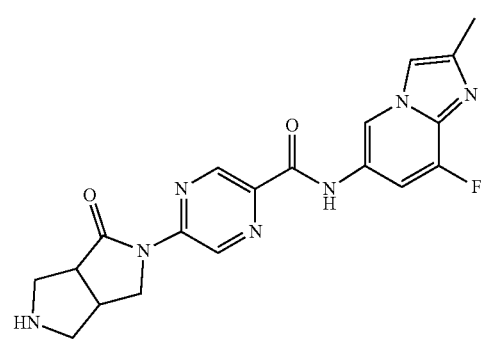 |
| 222 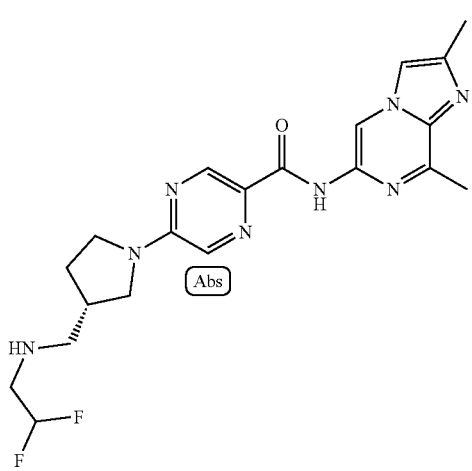 | 226 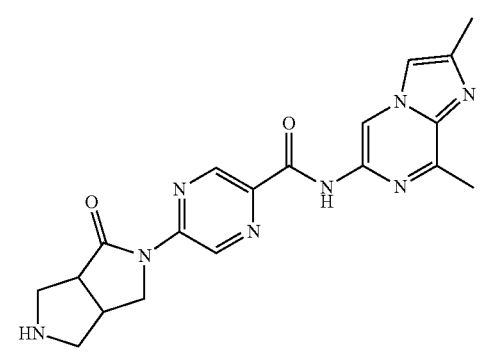 |
| 223 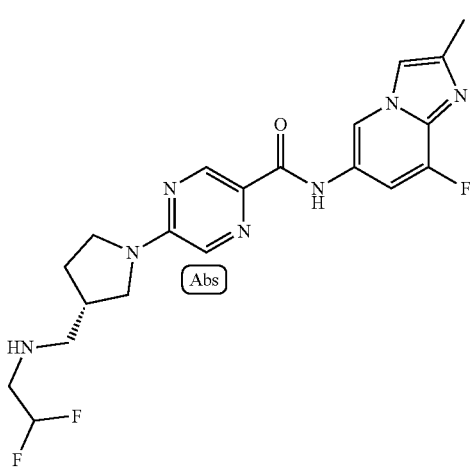 | 227 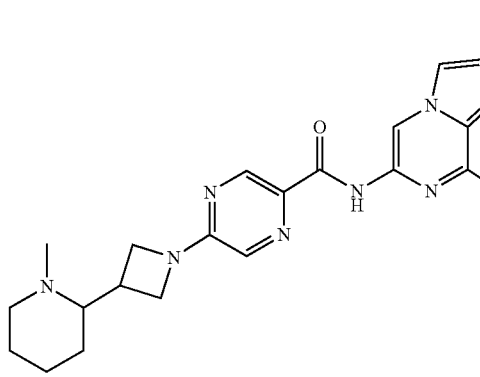<br>Enantiomer 1 |

228
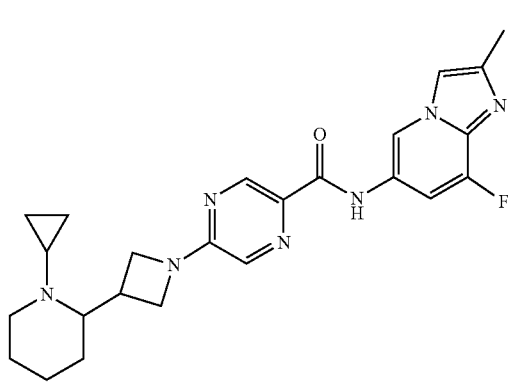
Enantiomer 1
229
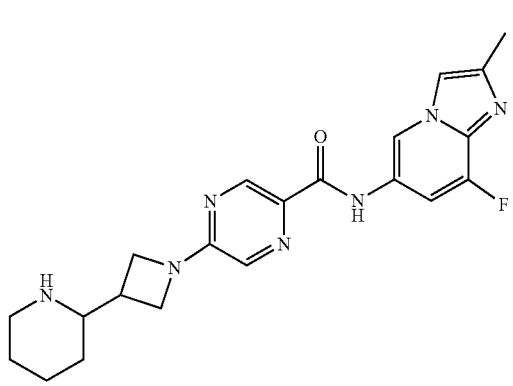
Enantiomer 1
230
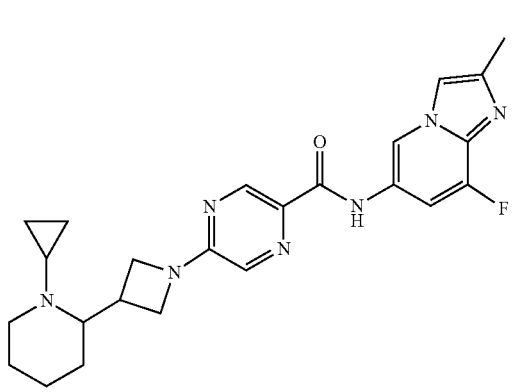
Enantiomer 2
231
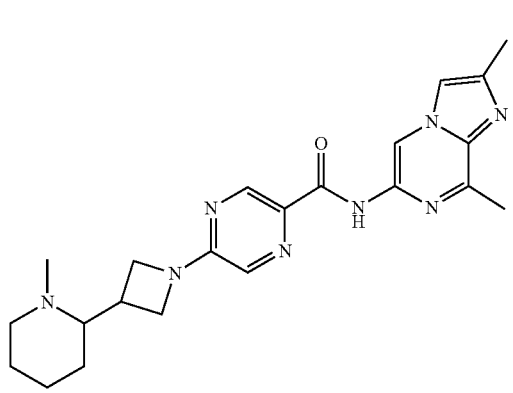
Enantiomer 2
232
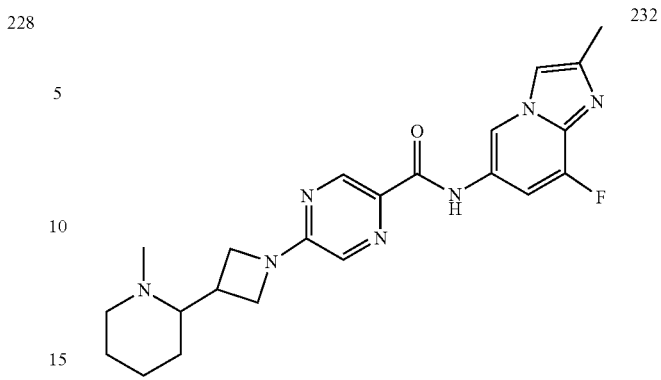
Enantiomer 1
233
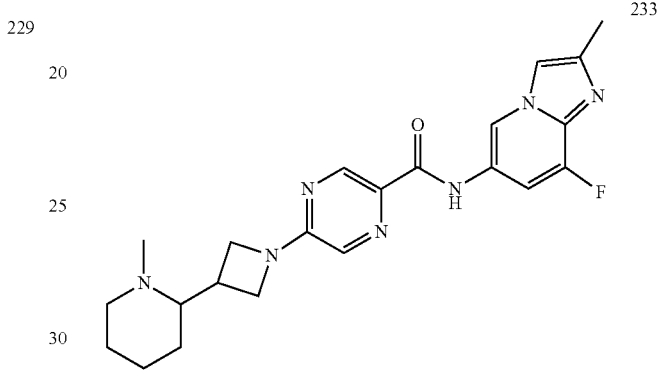
Enantiomer 2
234
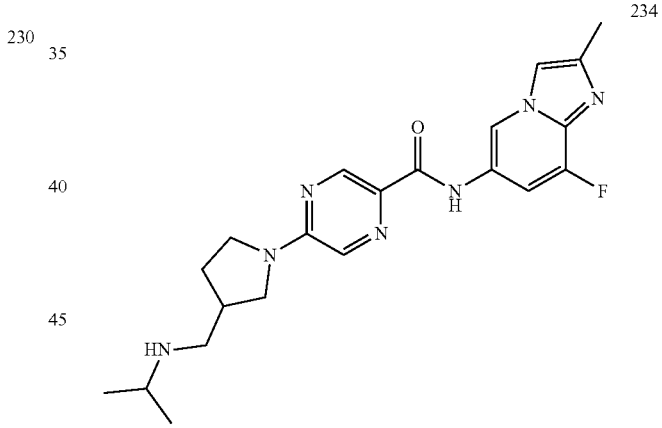
235
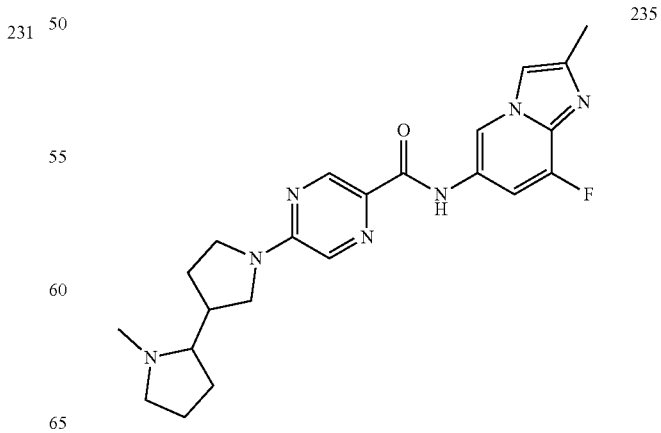
Stereoisomer 1

236
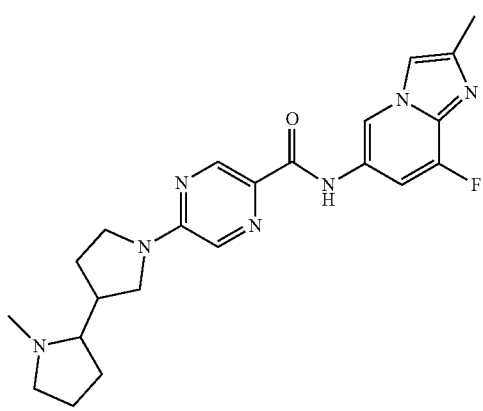
Stereoisomer 2
237
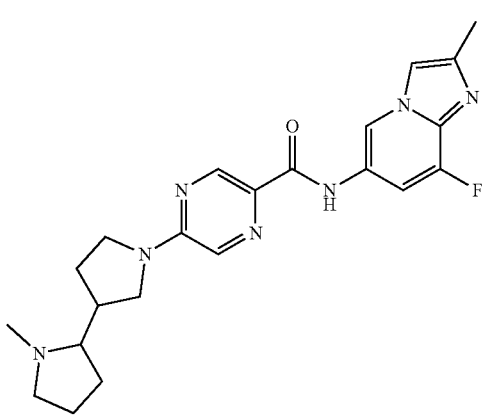
Stereoisomer 3
238
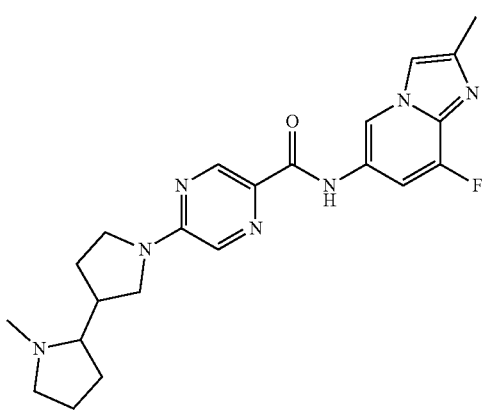
Stereoisomer 4
239
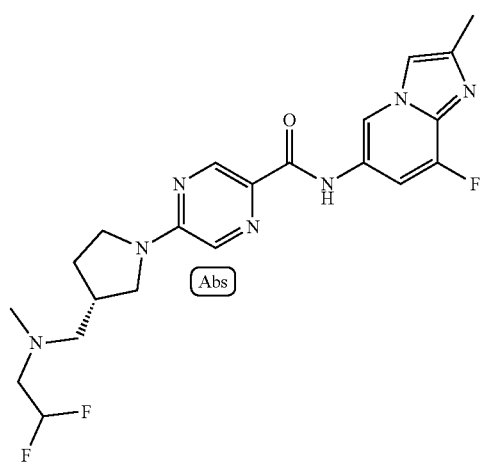
240
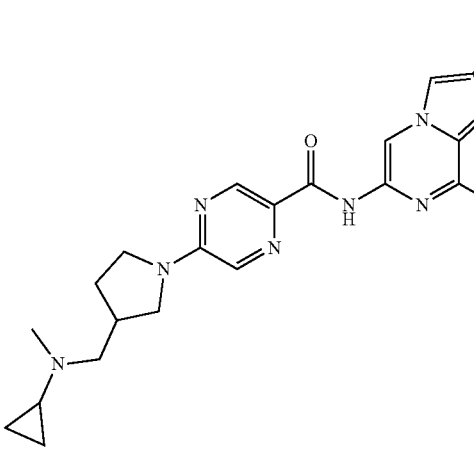
Enantiomer 1
241
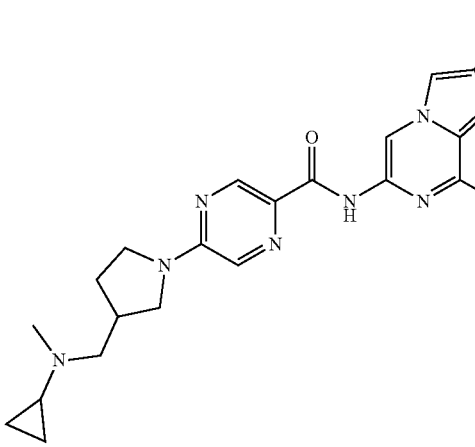
Enantiomer 2

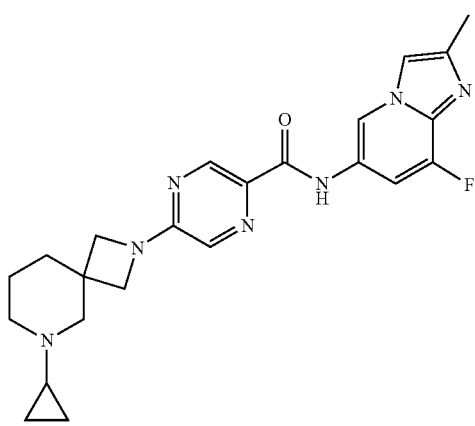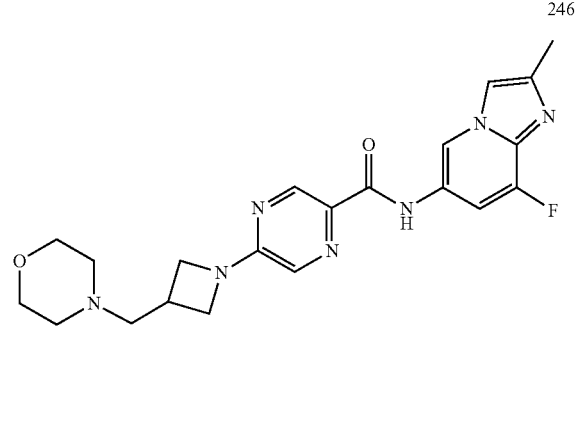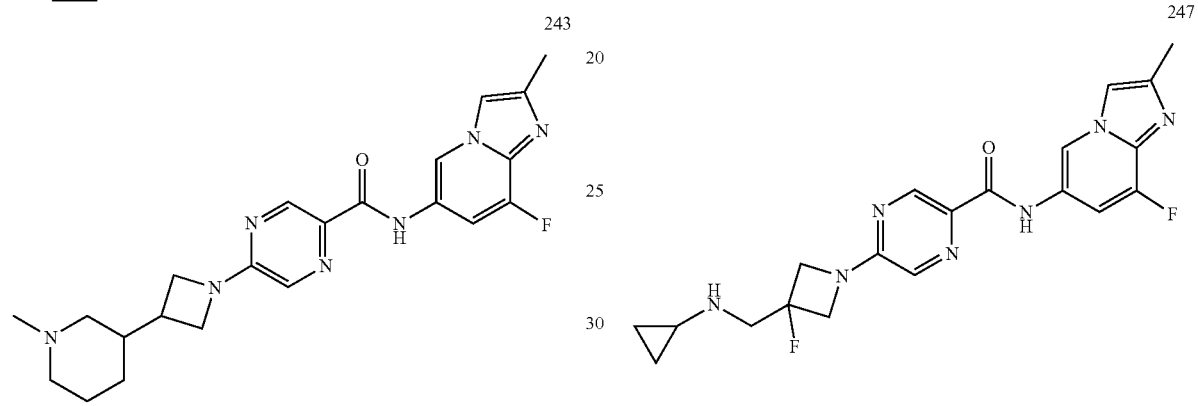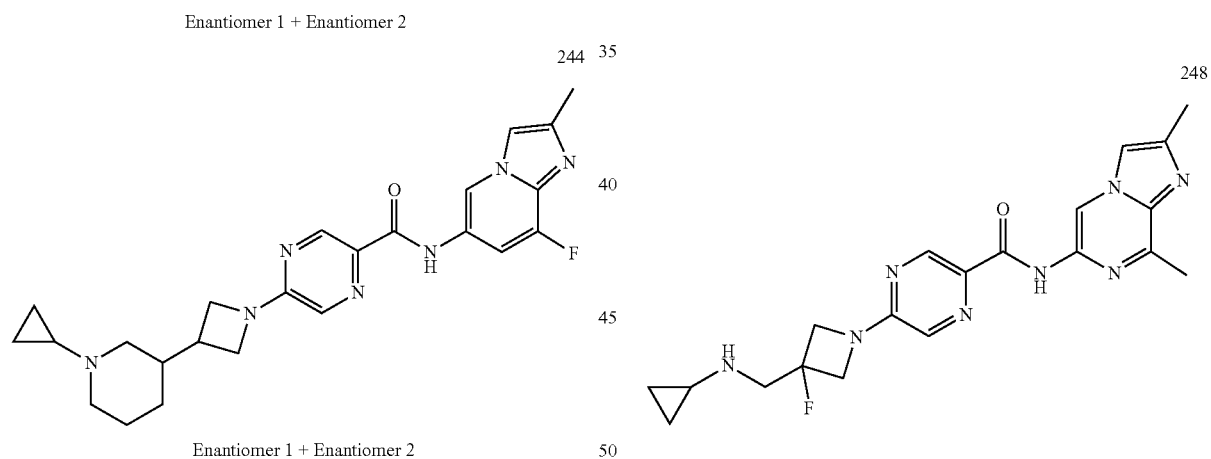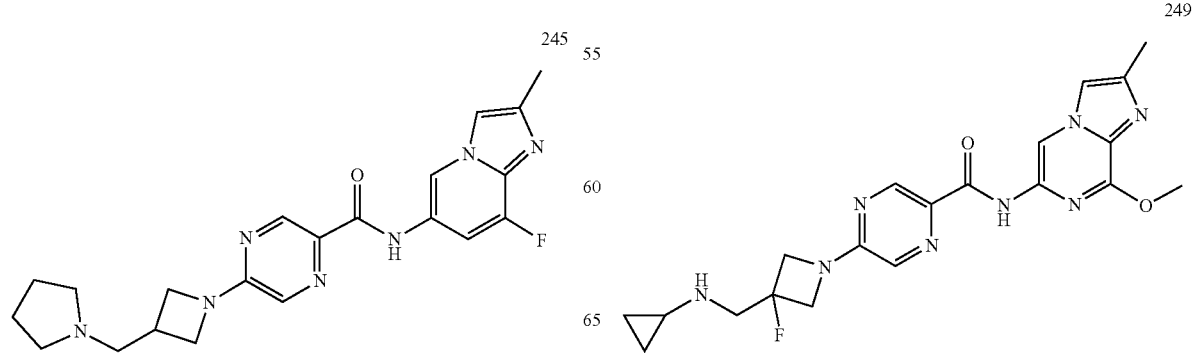

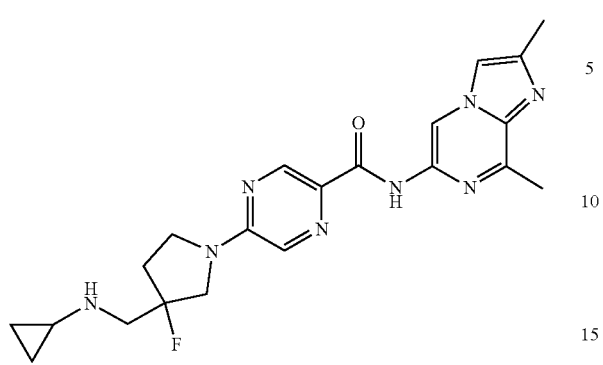
250
Enantiomer 1 + Enantiomer 2
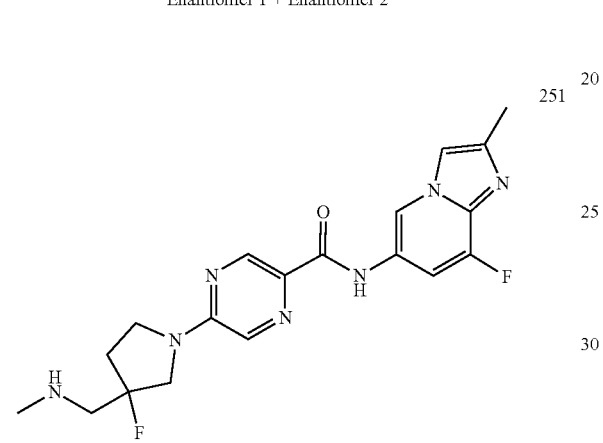
251
Enantiomer 1 + Enantiomer 2
252
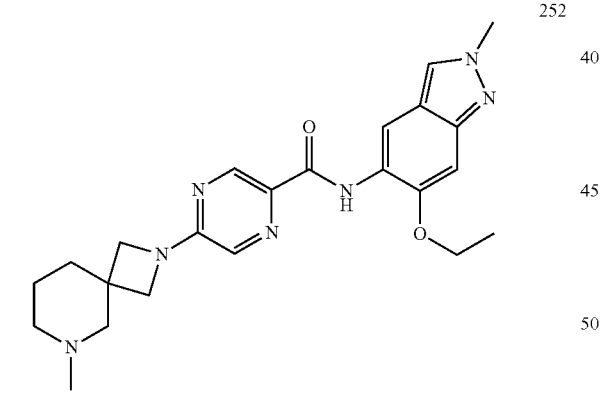
253
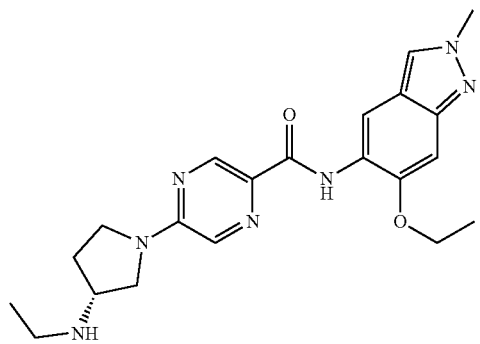
254
255
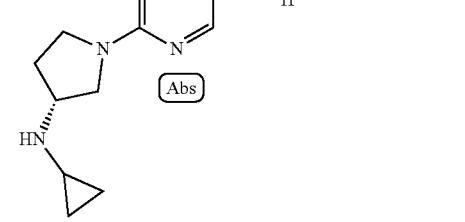
256
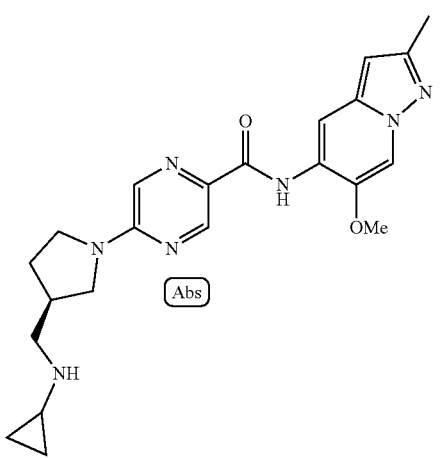
257

781
-continued
258
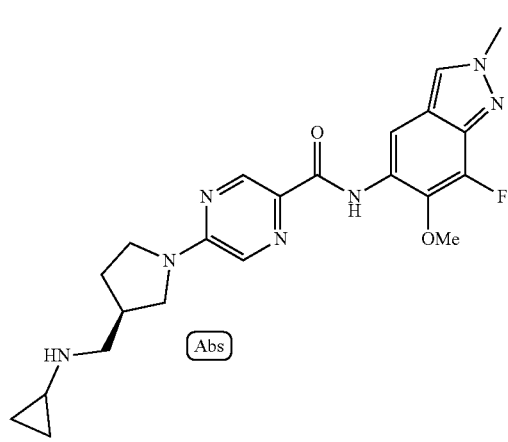
259
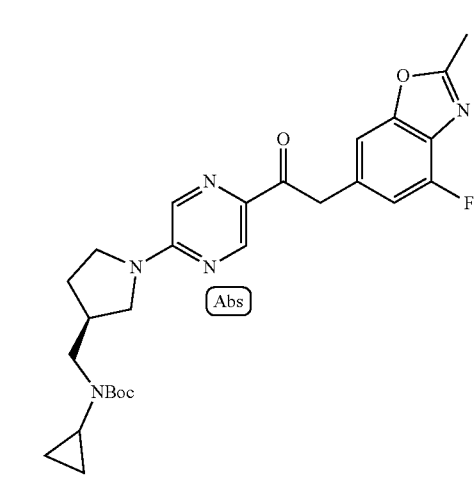
260
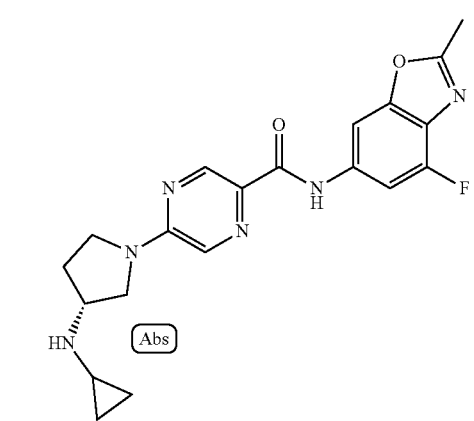
261
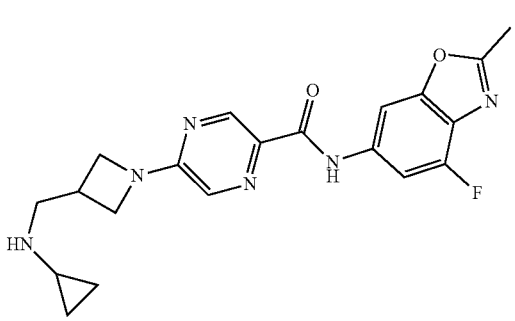
782
-continued
262
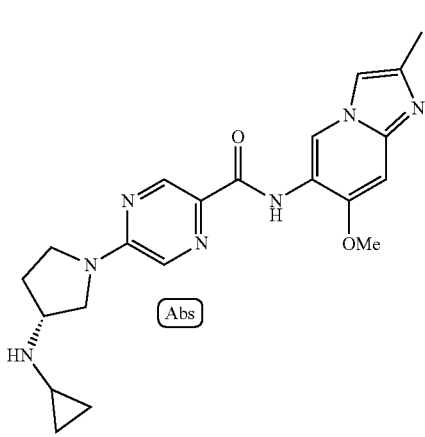
263
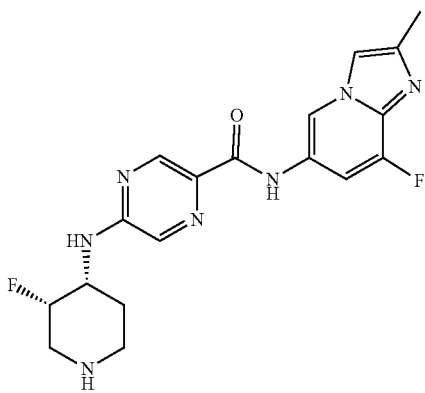
264
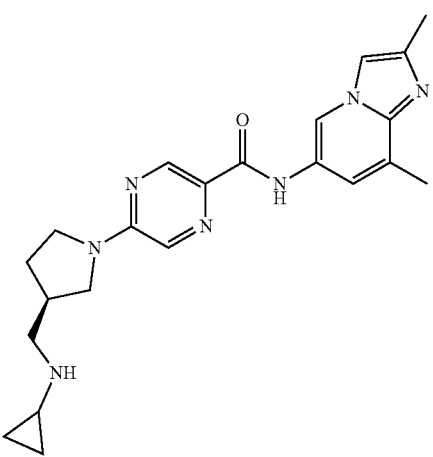
265
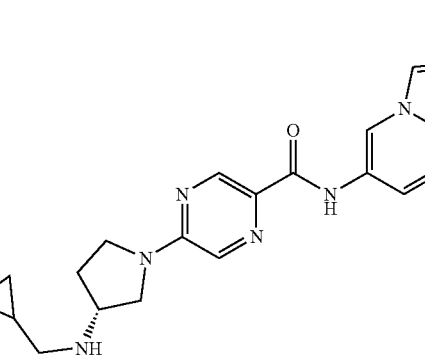

266 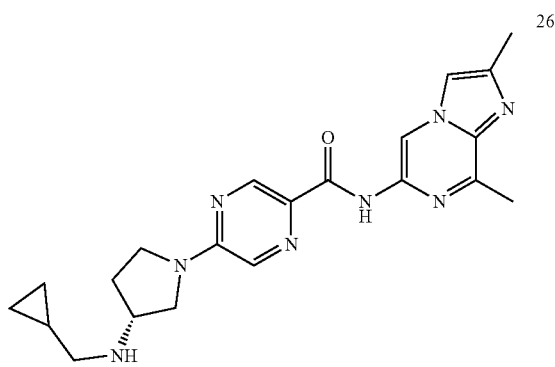
267 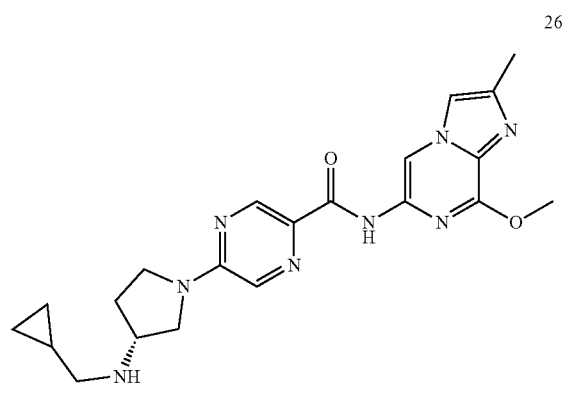
268 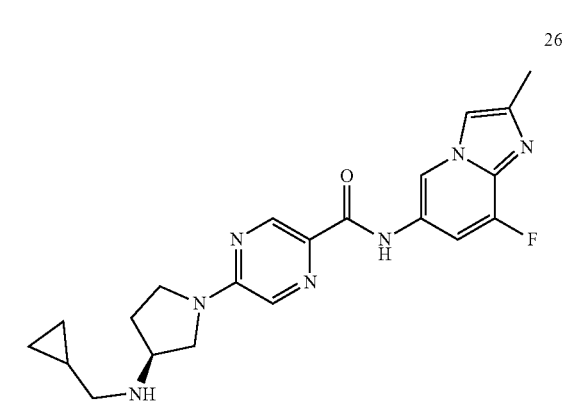
269 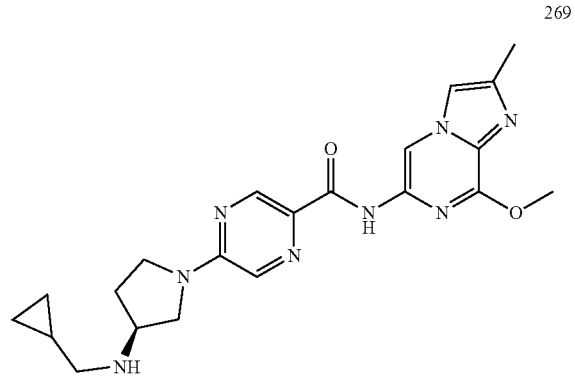
270 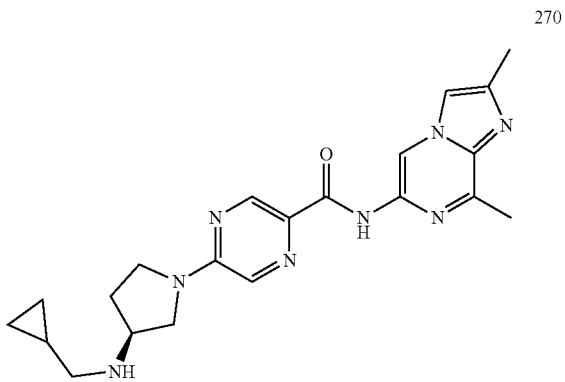
271 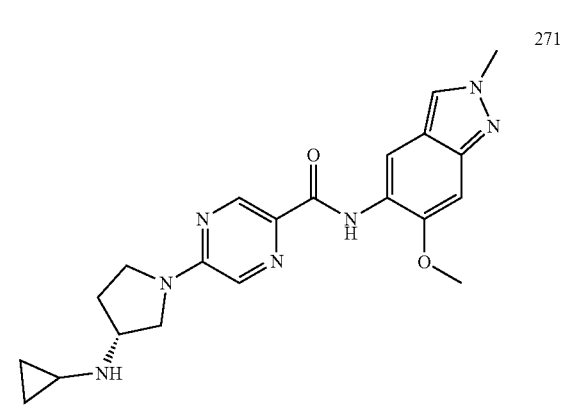
272 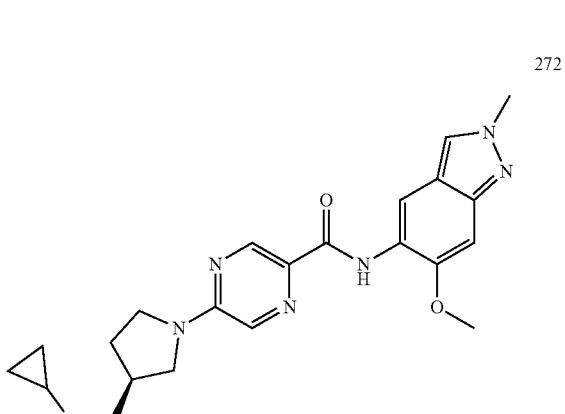
273 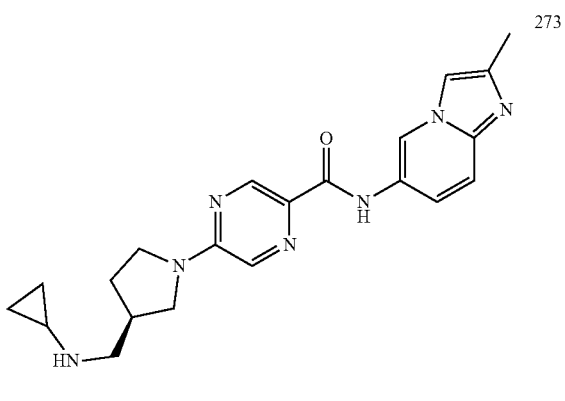

274
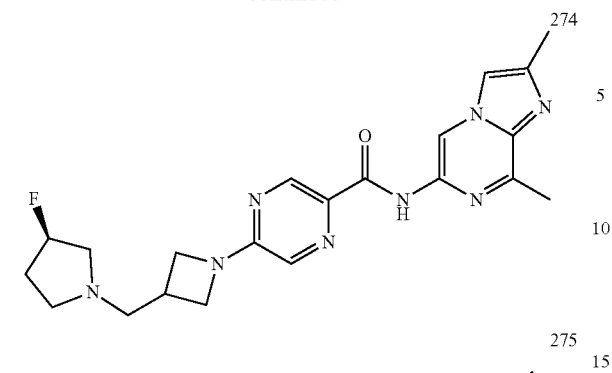
275
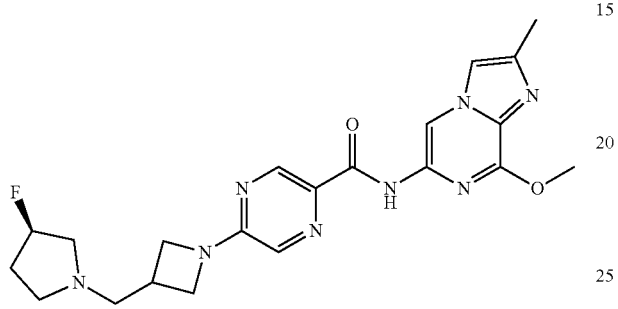
276
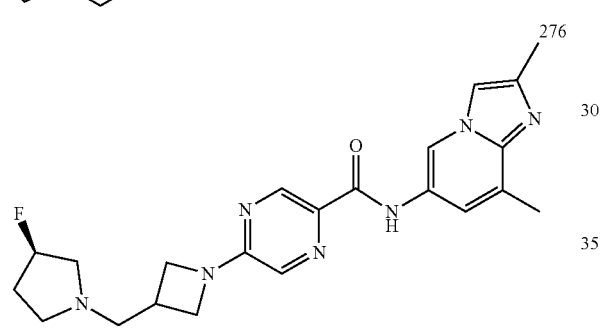
277
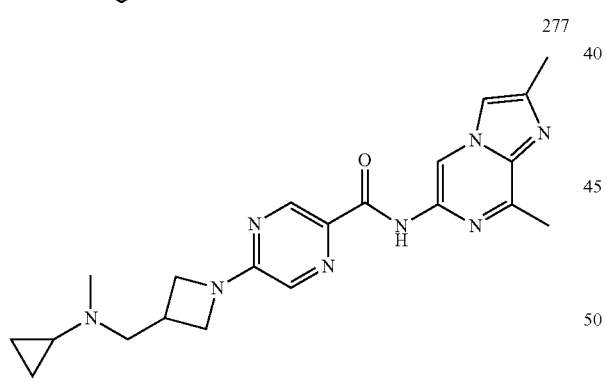
278
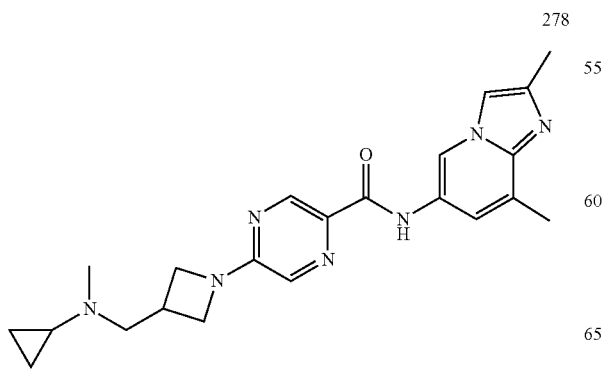
279
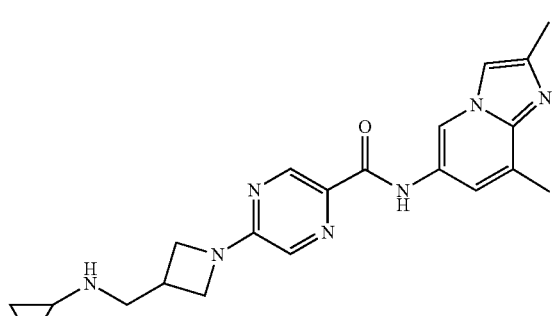
280
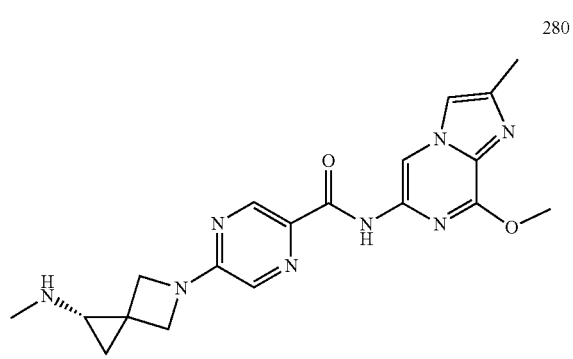
281
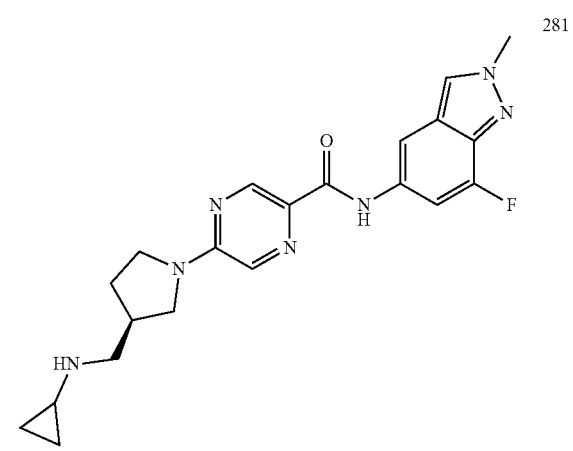
282
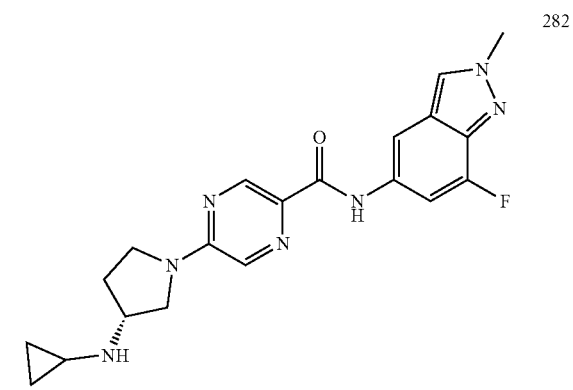

283
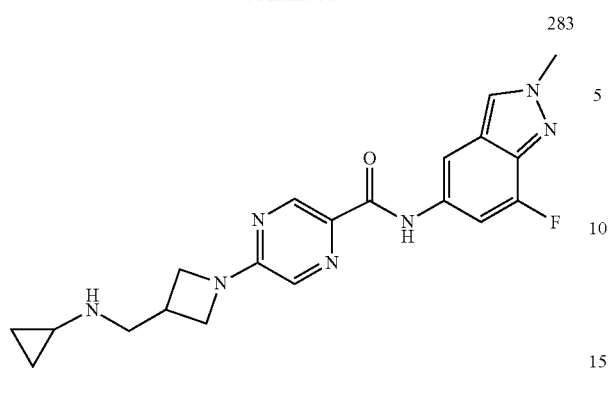
284
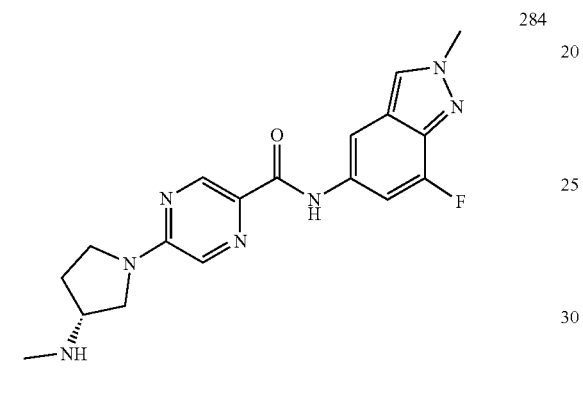
285
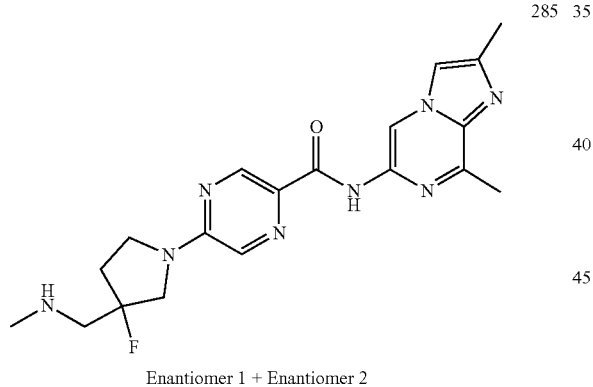
Enantiomer 1 + Enantiomer 2
286
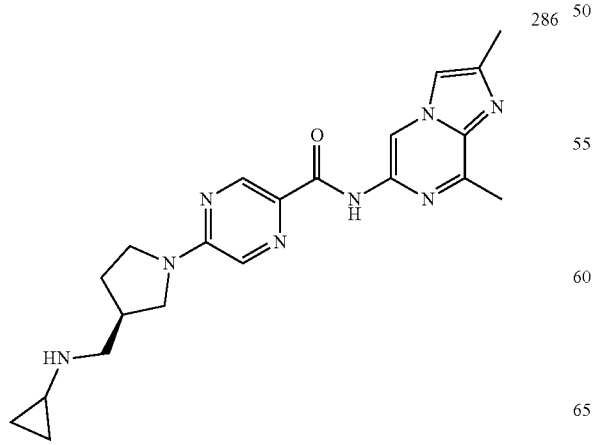
287
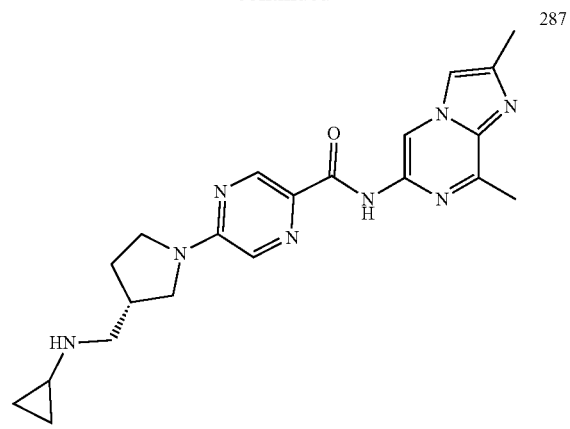
288
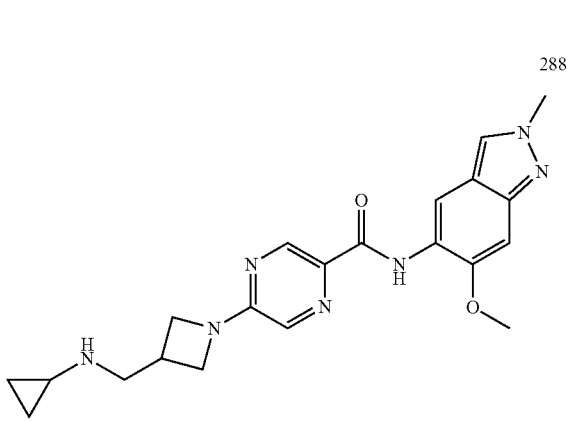
289
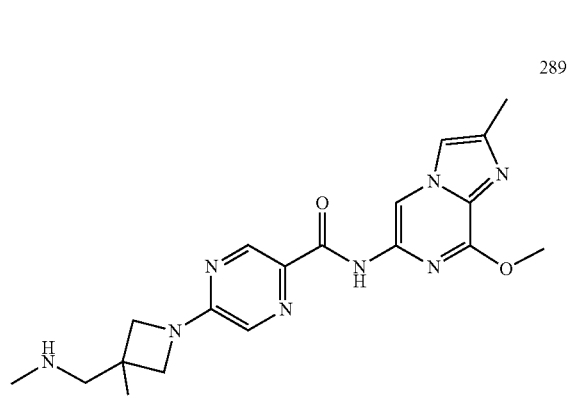
290
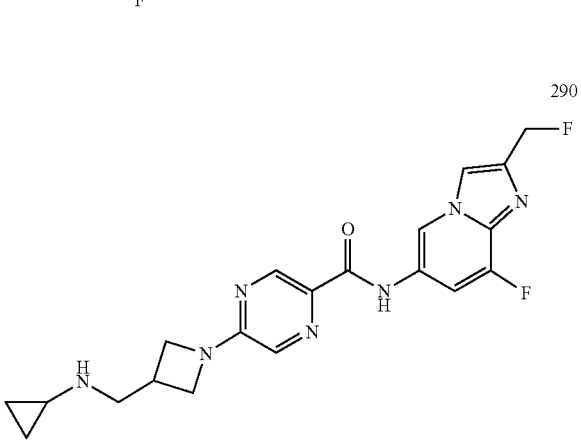

789
-continued
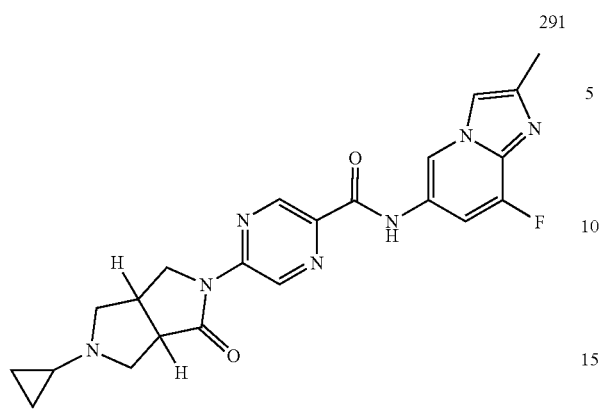
291
Cis Isomer, Enantiomer 1
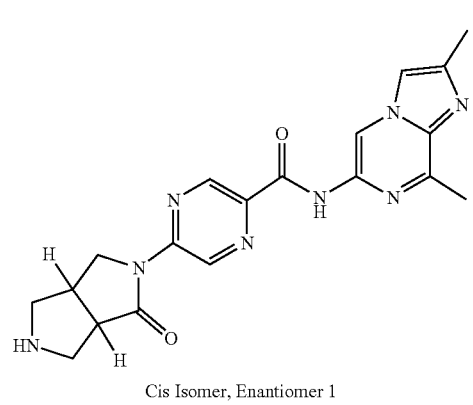
292
Cis Isomer, Enantiomer 1
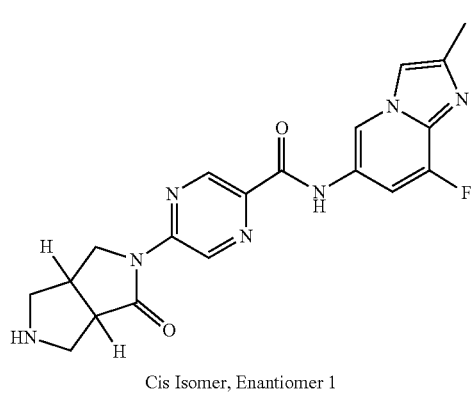
293
Cis Isomer, Enantiomer 1
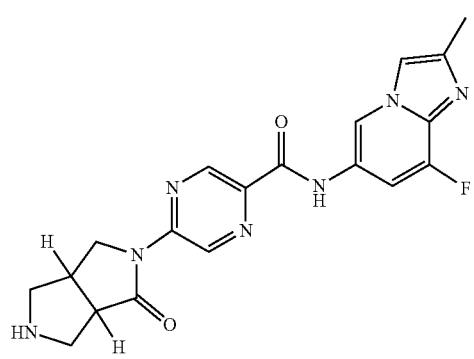
294
Cis Isomer, Enantiomer 2
790
-continued
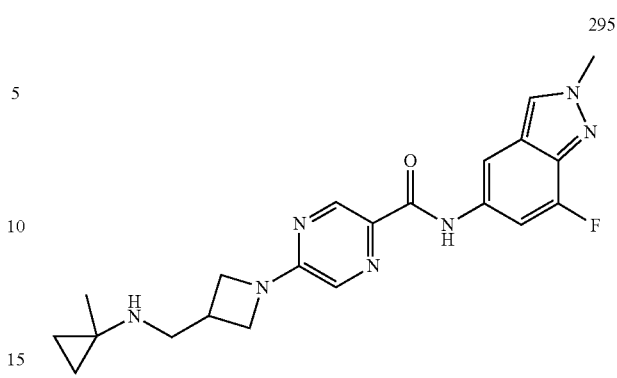
295
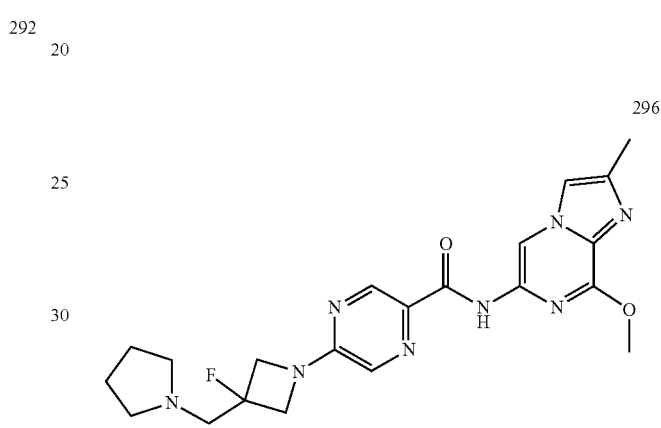
296
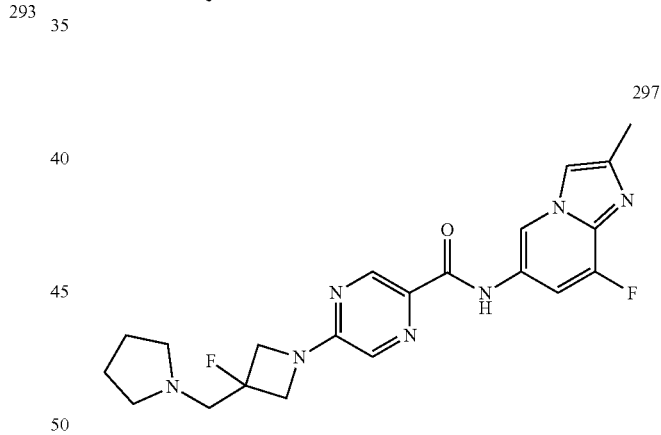
297
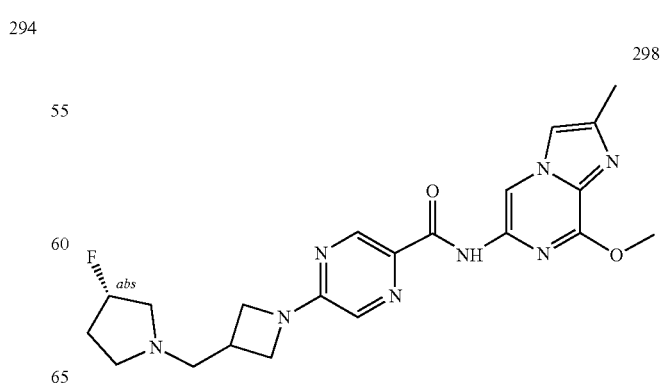
298

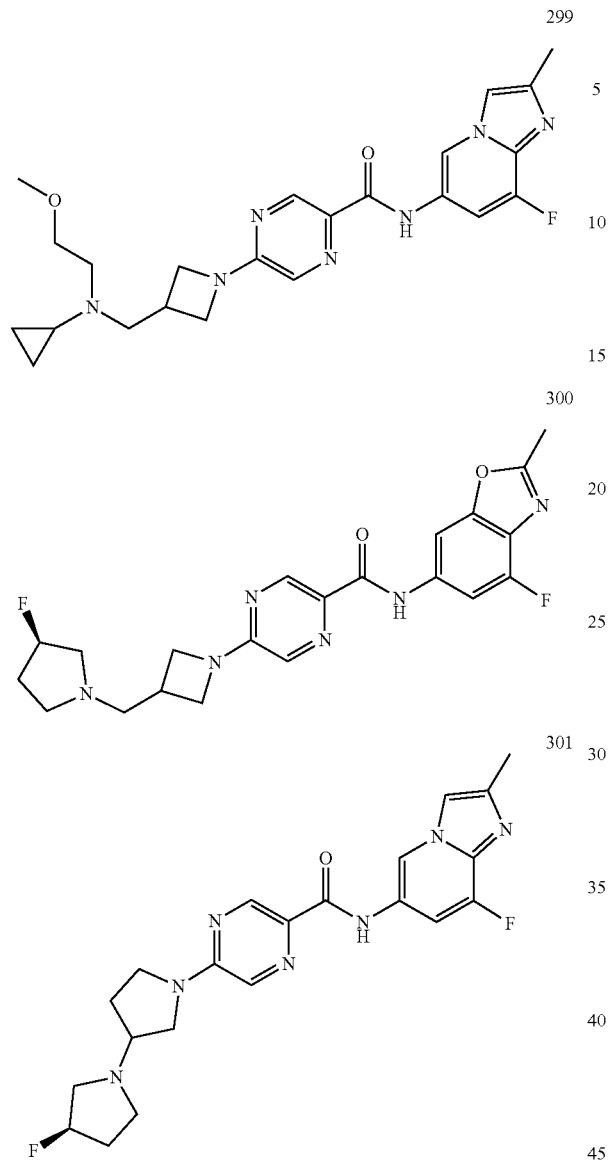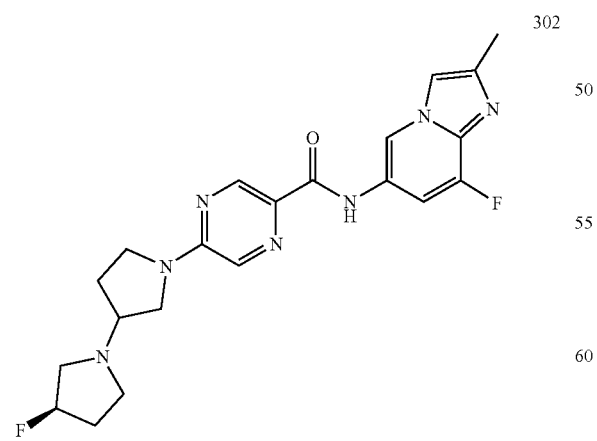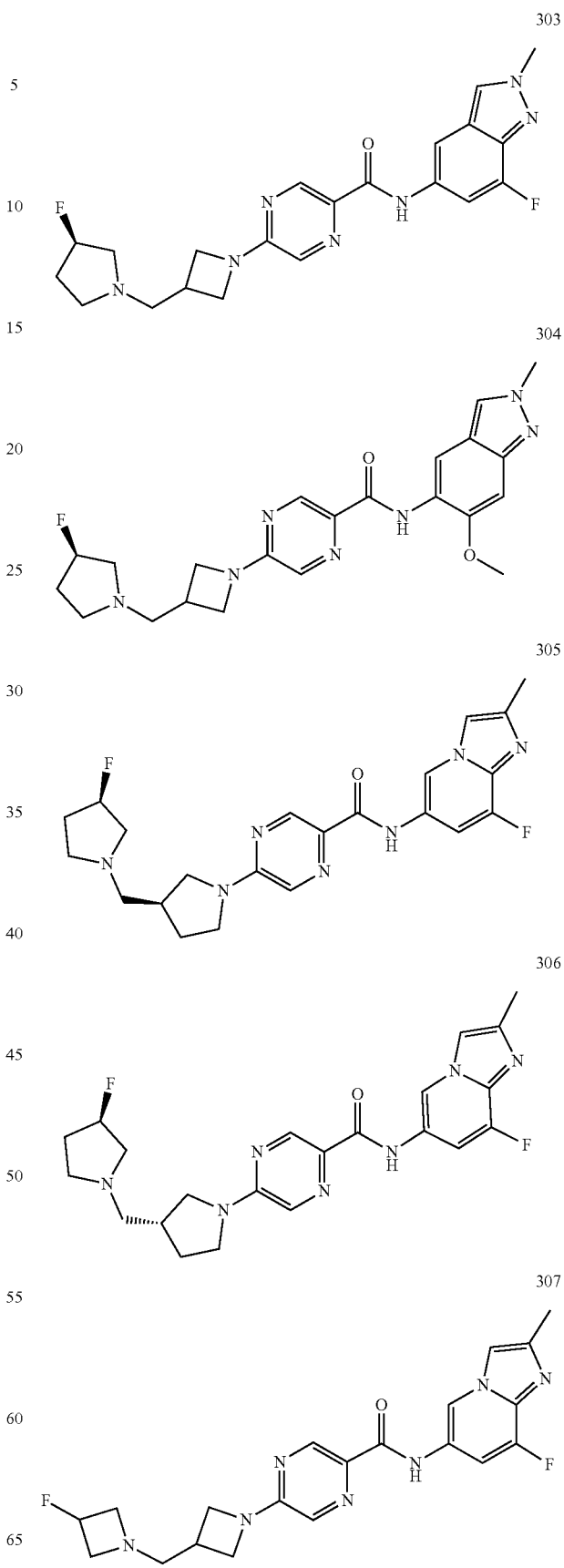

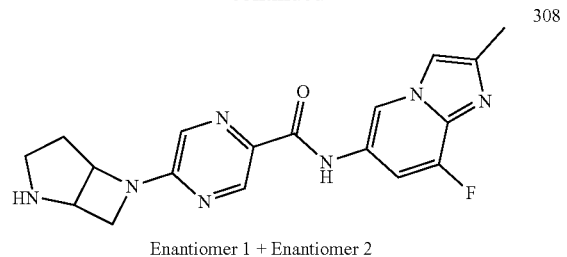
308
Enantiomer 1 + Enantiomer 2
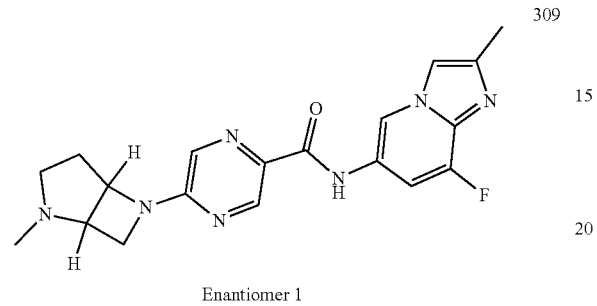
309
Enantiomer 1
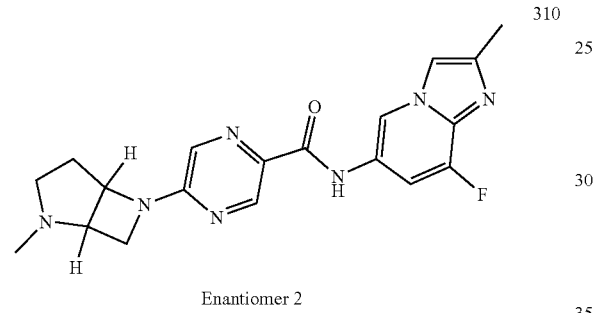
310
Enantiomer 2
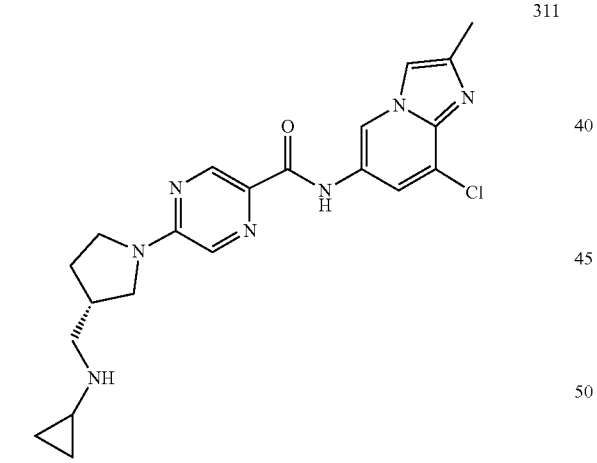
311
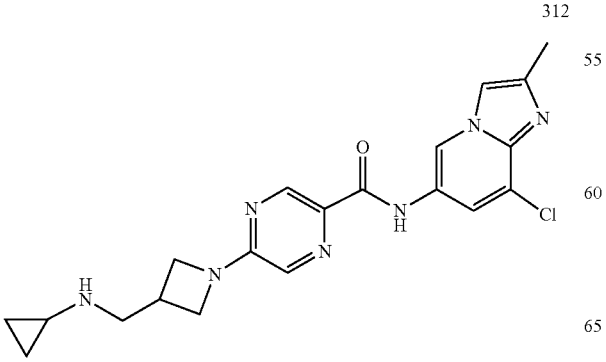
312
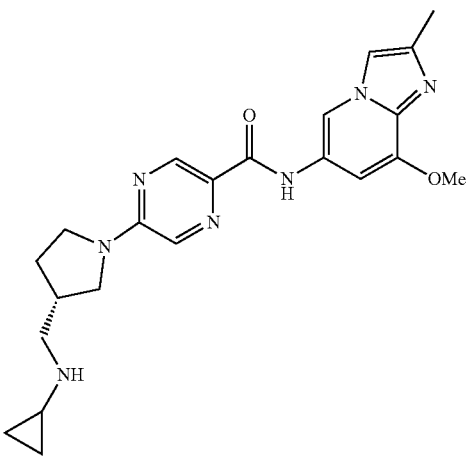
313
314
315
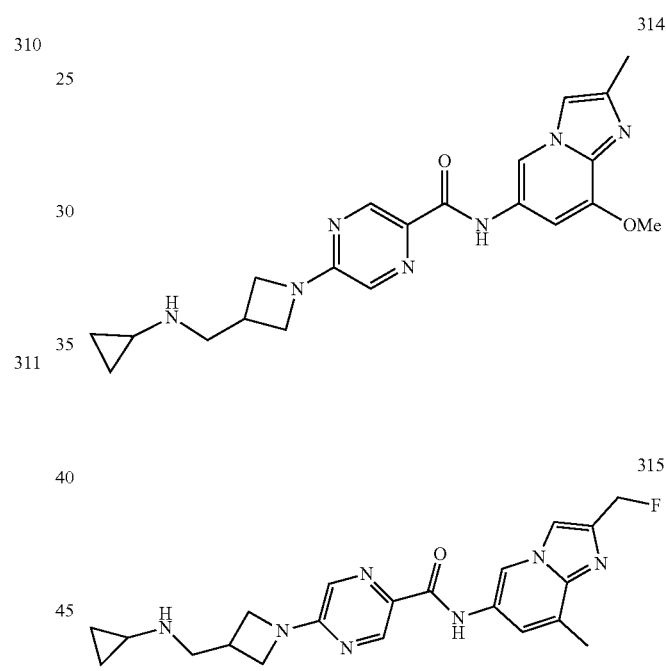
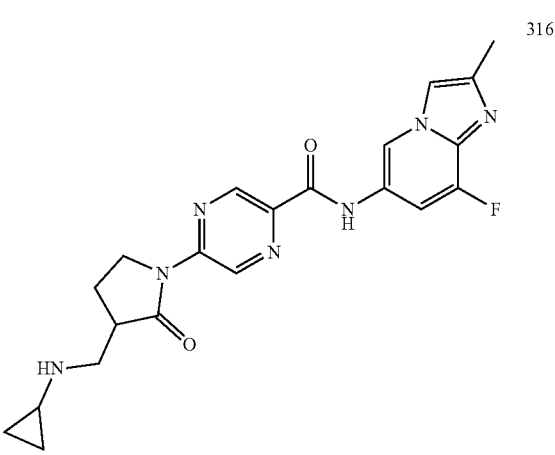
316
Enantiomer 1 + Enantiomer 2

317
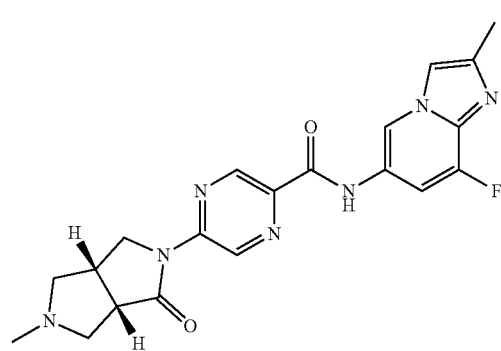
318
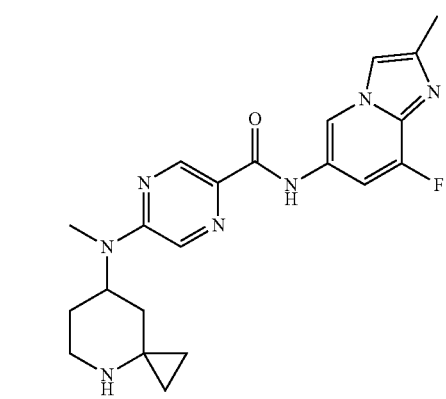
Enantiomer 1
319
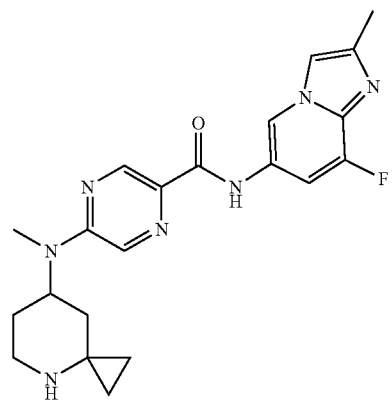
Enantiomer 2
320
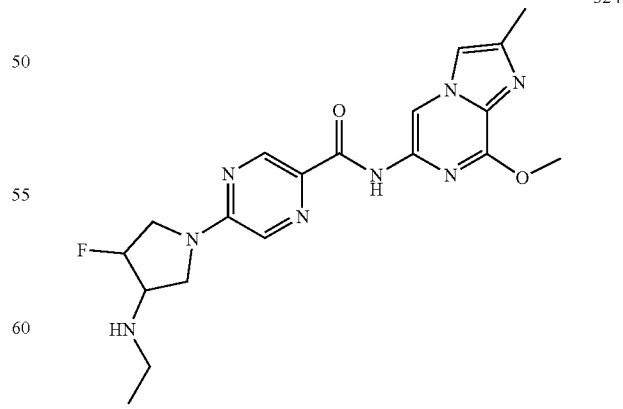
321
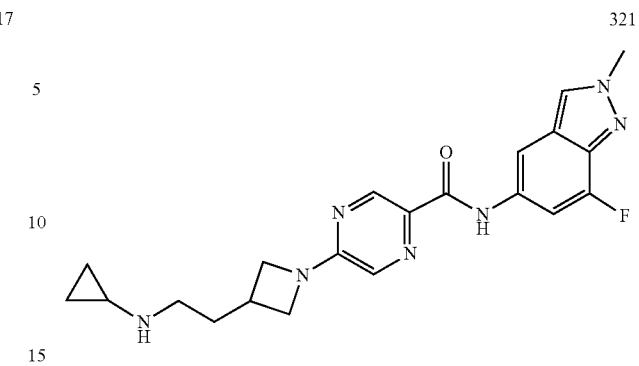
322
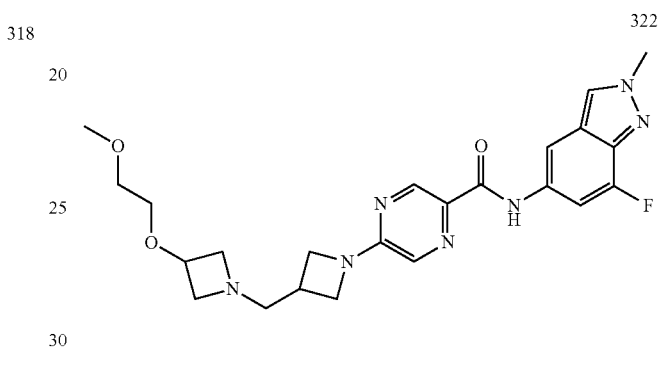
323
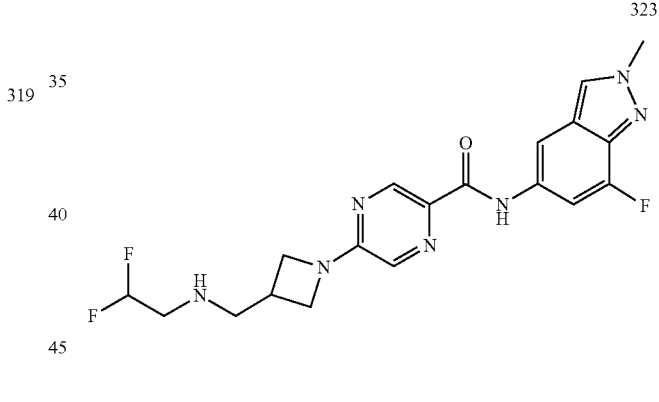
324
Cis Isomer
Enantiomer 1

325
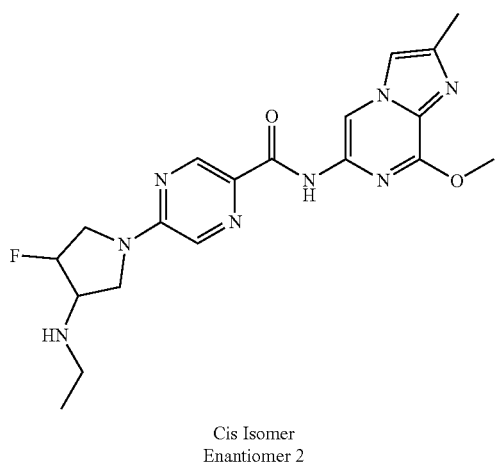
Cis Isomer
Enantiomer 2
326
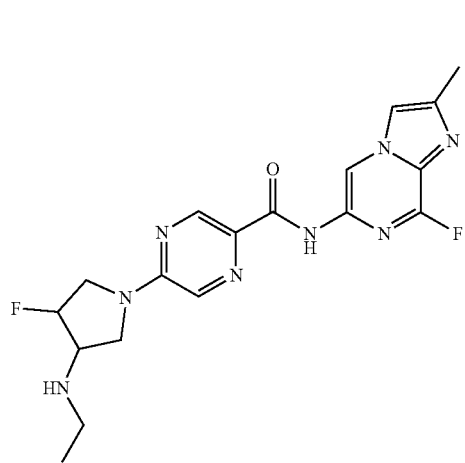
Cis Isomer, Enantiomer 1
327
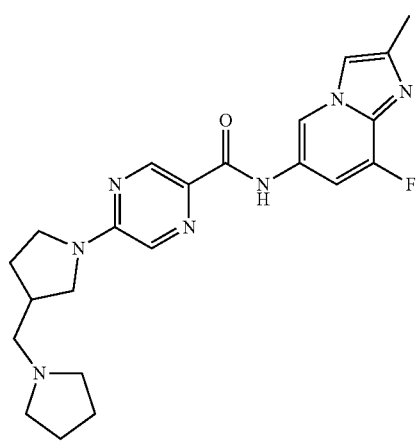
328
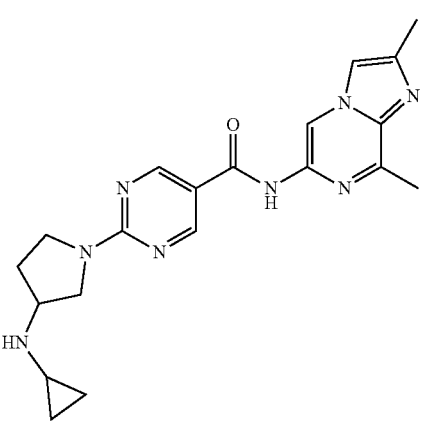
Enantiomer 1
329
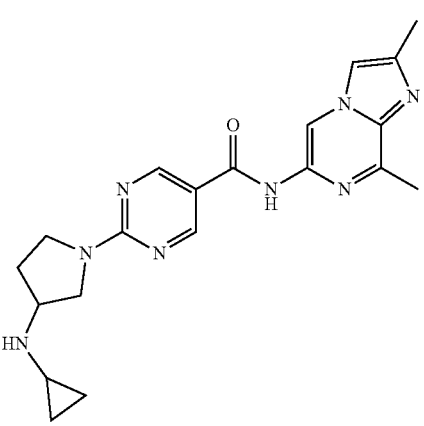
Enantiomer 2
330
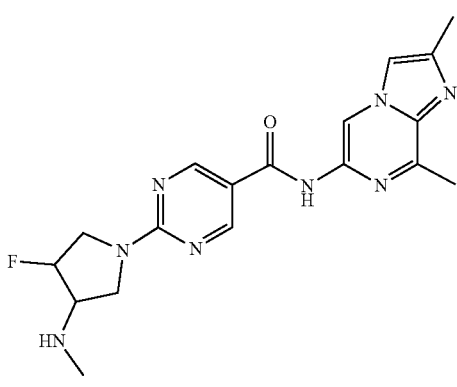
Cis Isomer, Enantiomer 1

-continued
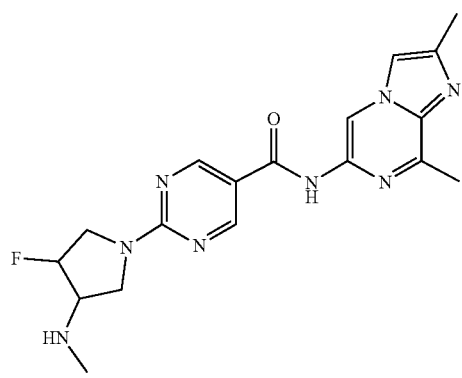
331
Cis Isomer, Enantiomer 2
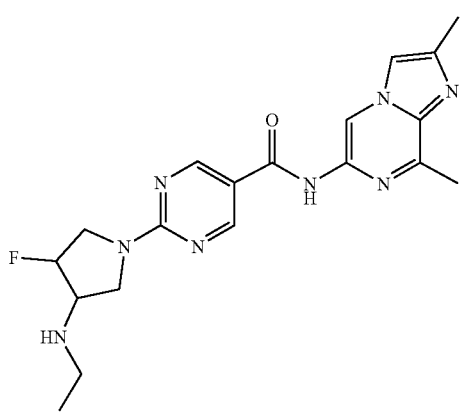
334
Cis Isomer, Enantiomer 2
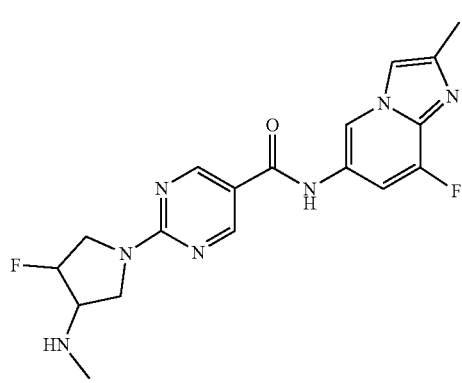
332
Cis Isomer, Enantiomer 1
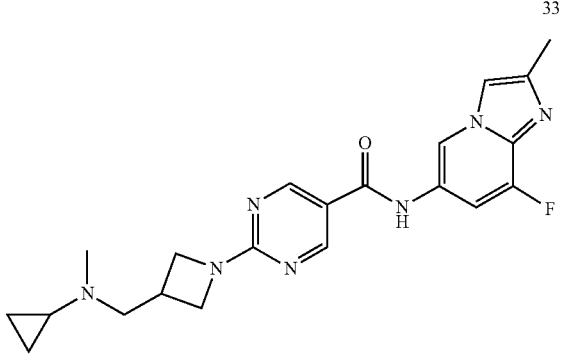
335
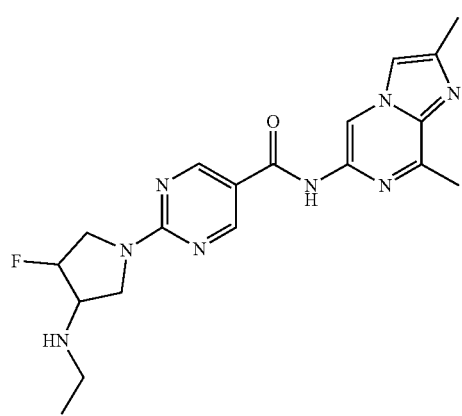
333
Cis Isomer, Enantiomer 1
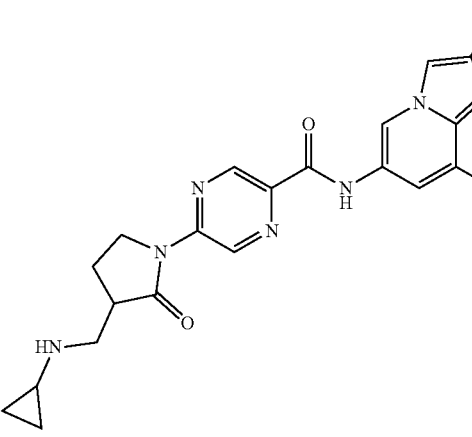
336
Enantiomer 1

801
-continued
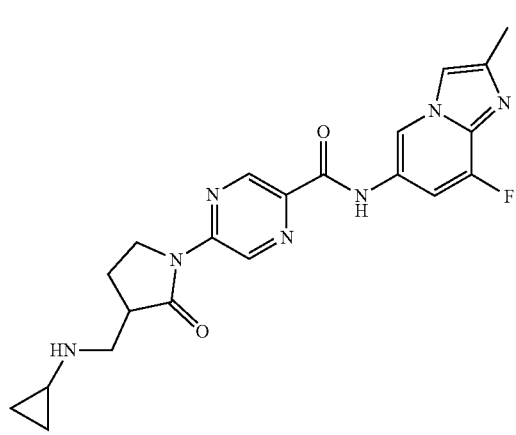
337
Enantiomer 2
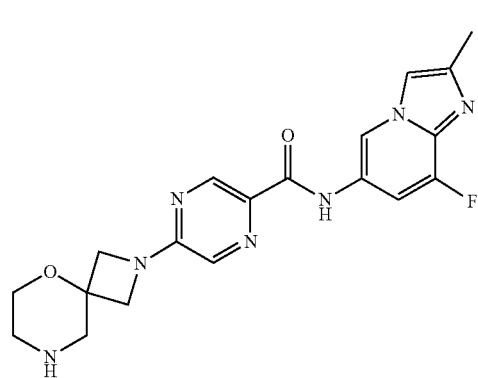
338
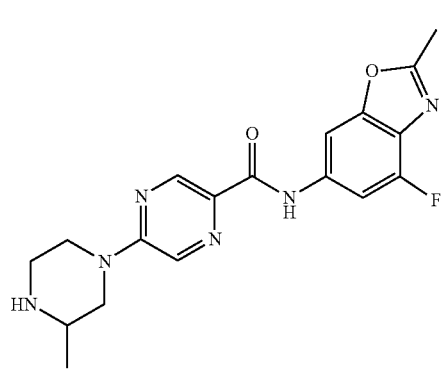
339
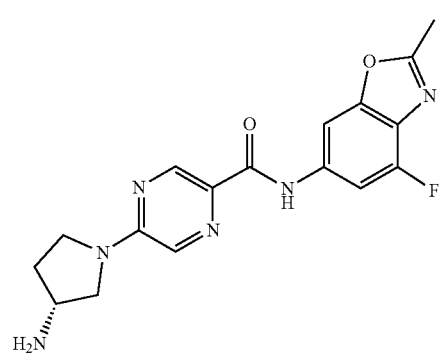
340
802
-continued
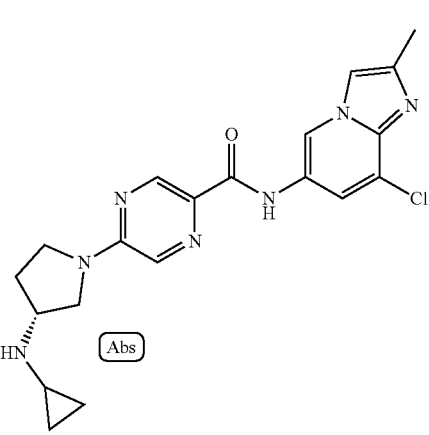
341
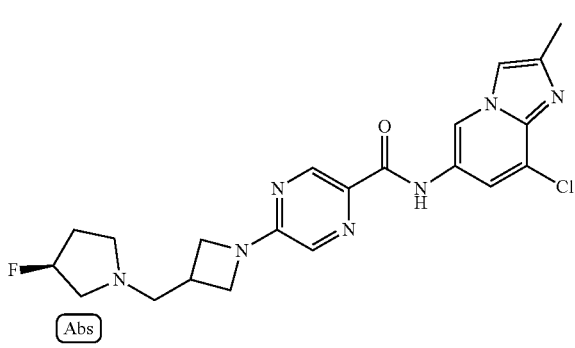
342
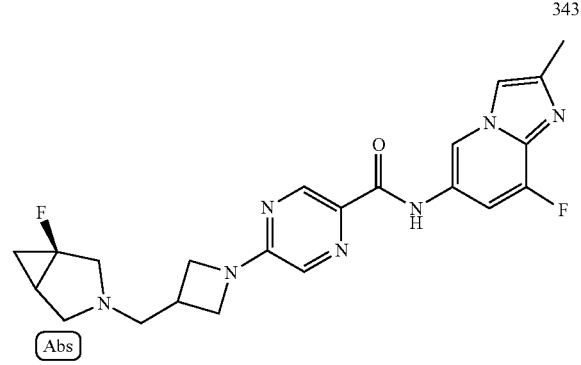
343
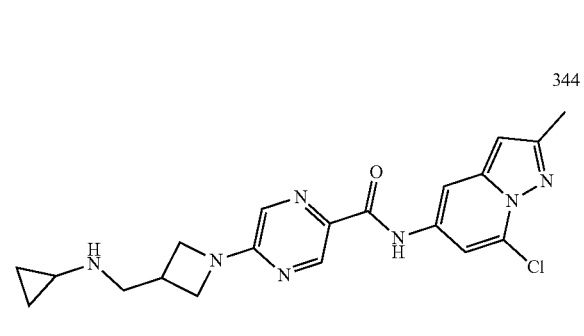
344

345
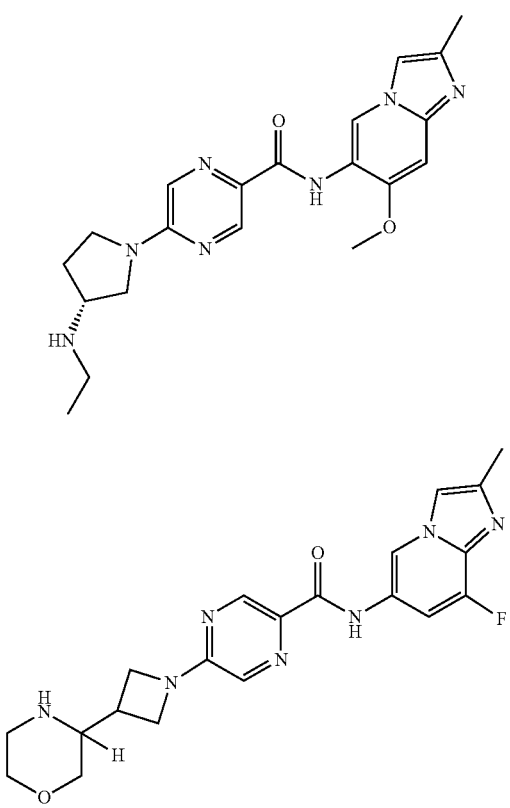
346
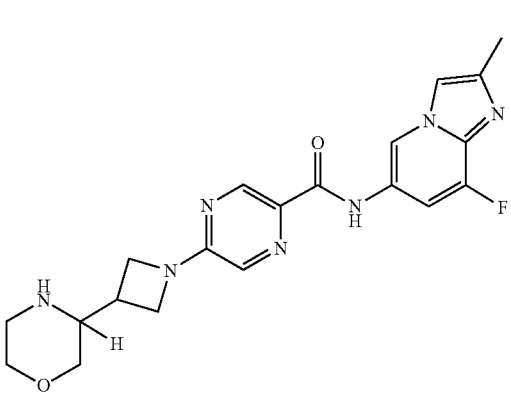
Enantiomer 1
347
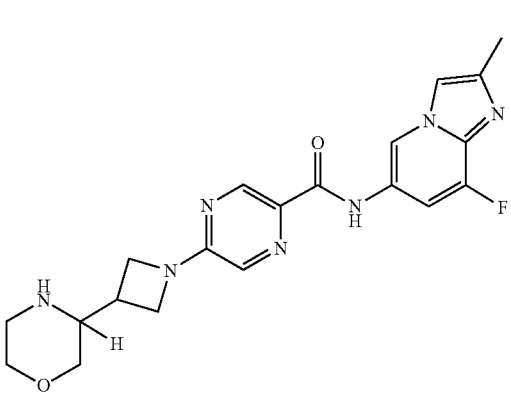
Enantiomer 2
348
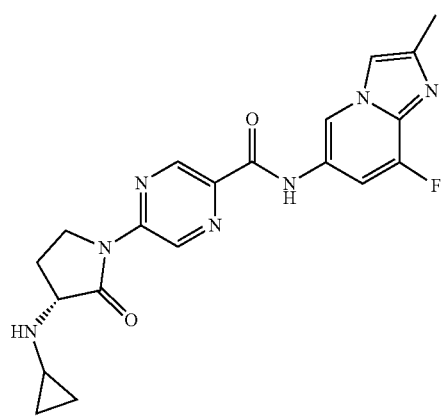
349
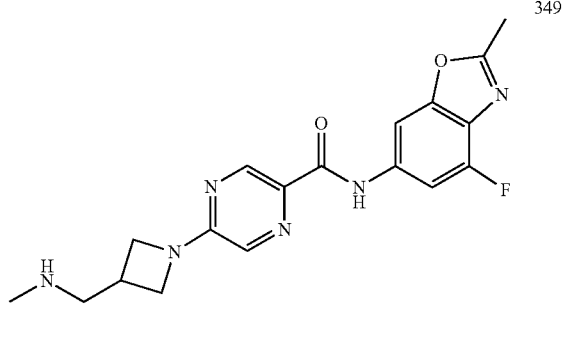
350
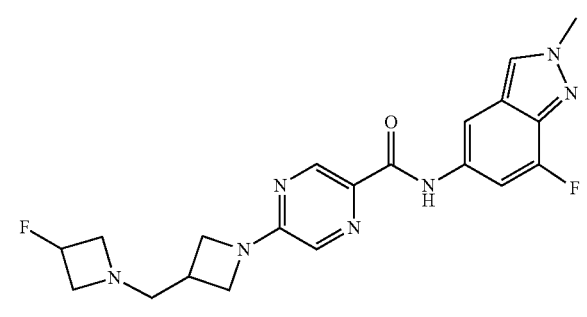
351
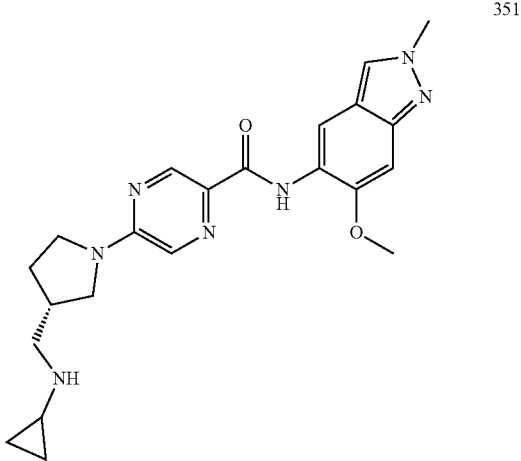
352
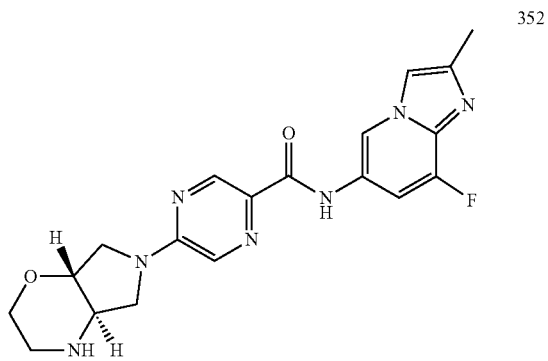

353 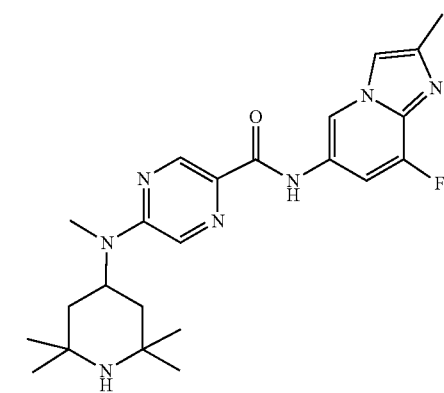
354 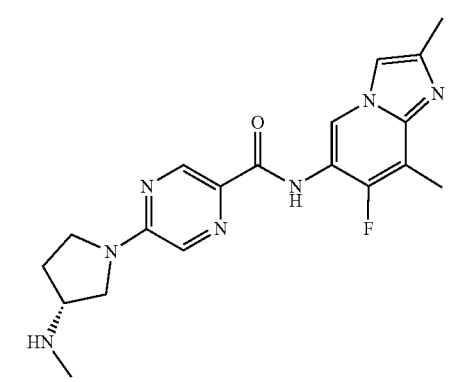
355 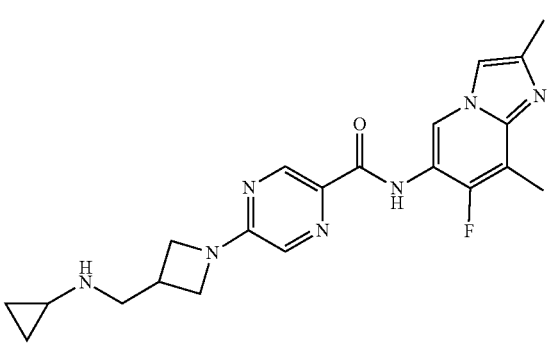
356 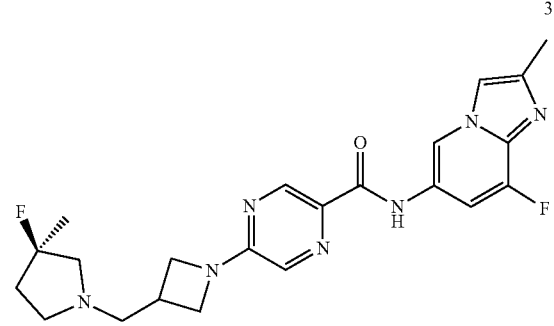
357 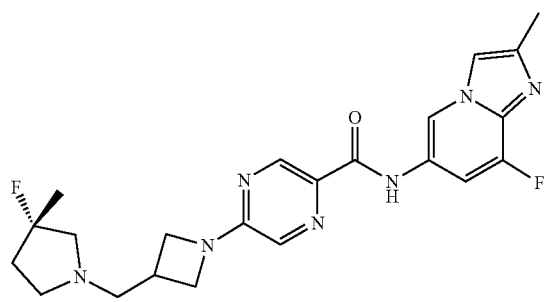
358 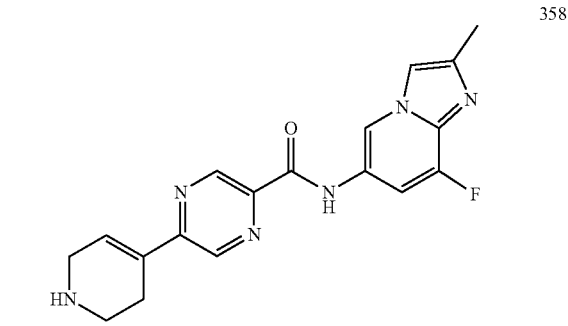
359 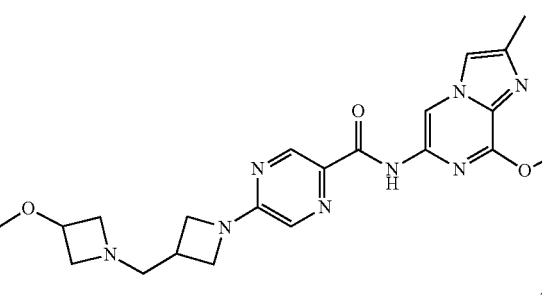
360 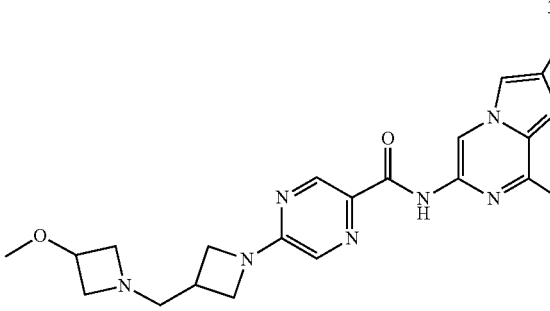
361 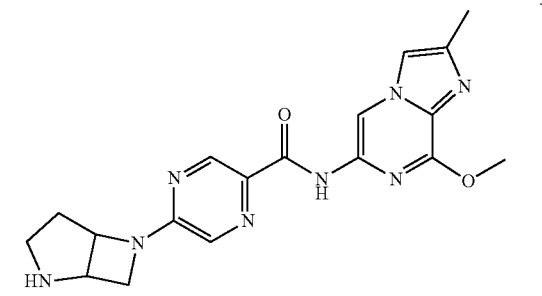
Enantiomer 1 + Enantiomer 2

362
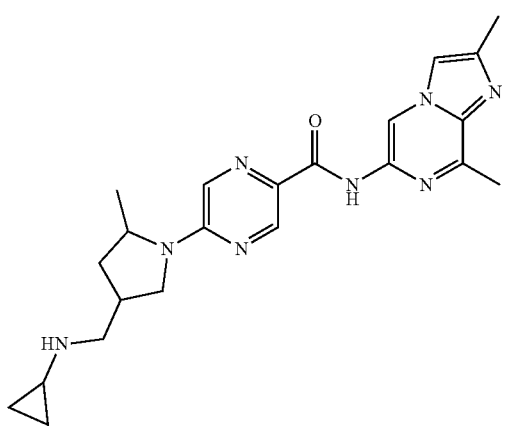
363
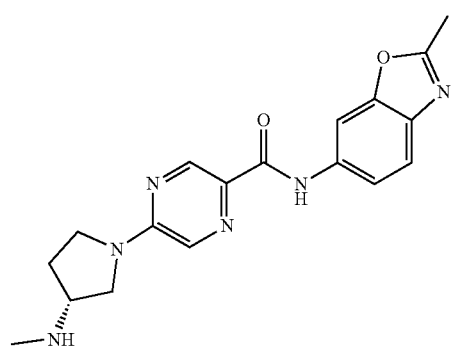
364
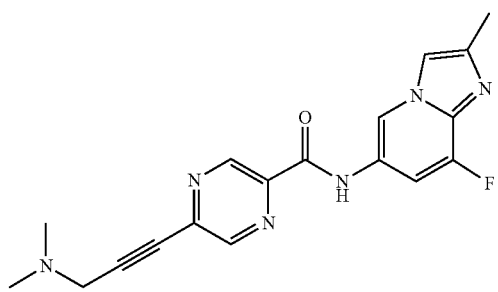
365
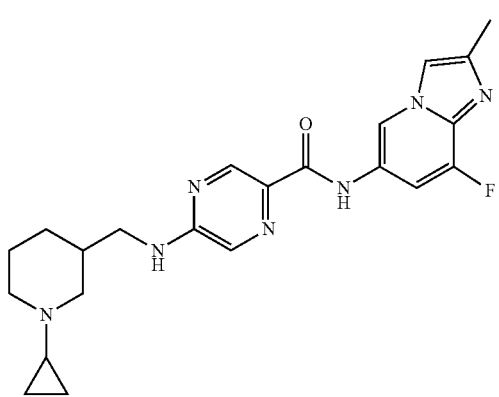
Enantiomer 1 + Enantiomer 2
366
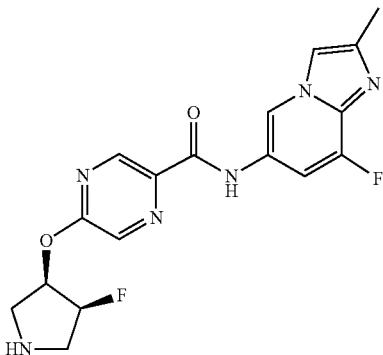
367
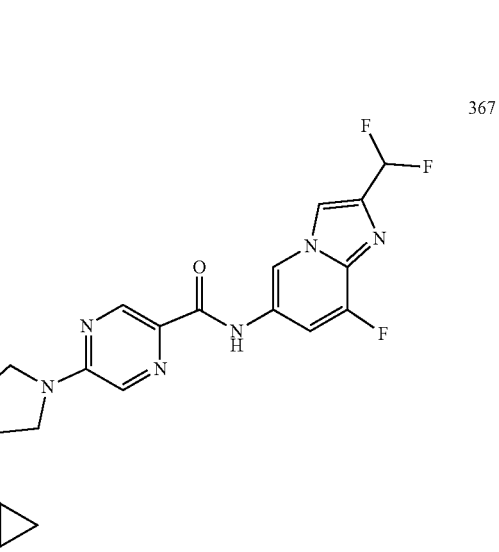
368
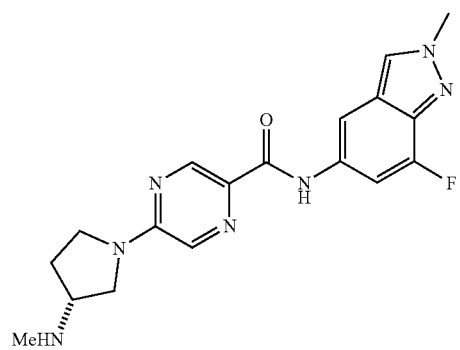

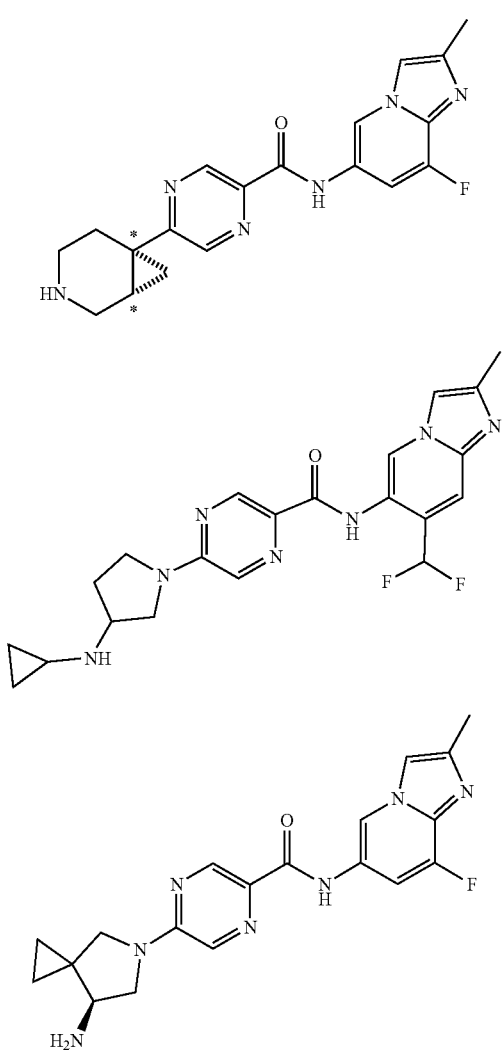

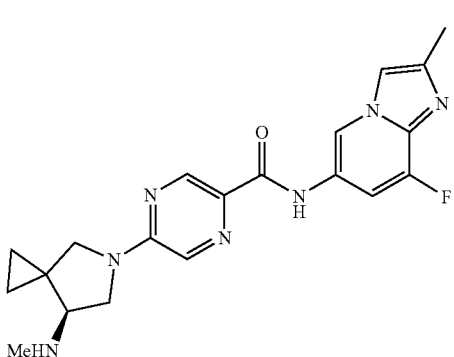

or an isotopically enriched analog, pharmaceutically acceptable salt, tautomer, stereoisomer, or a mixture of stereoisomers thereof.

35. A pharmaceutical composition comprising the compound of claim 1, or an isotopically enriched analog, pharmaceutically acceptable salt, tautomer, stereoisomer, or a mixture of stereoisomers thereof, and a pharmaceutically acceptable excipient.

36. A method for treating Huntington's disease in a patient in need thereof, comprising administering to the patient a therapeutically effective amount of the compound of claim 1, or an isotopically enriched analog, pharmaceutically acceptable salt, tautomer, stereoisomer, or a mixture of stereoisomers thereof.

37. A method for treating Huntington's disease in a patient in need thereof, comprising administering to the patient a therapeutically effective amount of the compound of claim 1, or an isotopically enriched analog, pharmaceutically acceptable salt, tautomer, stereoisomer, or a mixture of stereoisomers thereof, in combination with a second active agent.

\* \* \* \* \*

UNITED STATES PATENT AND TRADEMARK OFFICE
CERTIFICATE OF CORRECTION

PATENT NO. : 11,806,346 B2  
APPLICATION NO. : 17/318693  
DATED : November 7, 2023  
INVENTOR(S) : Dominguez et al.

Page 1 of 4

It is certified that error appears in the above-identified patent and that said Letters Patent is hereby corrected as shown below:

In the Specification

In Column 141, Table 1, Example 207, please replace " 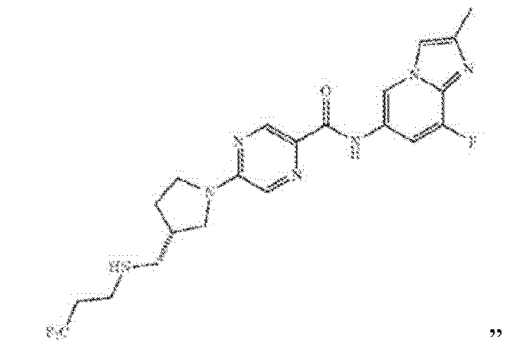 "

with -- 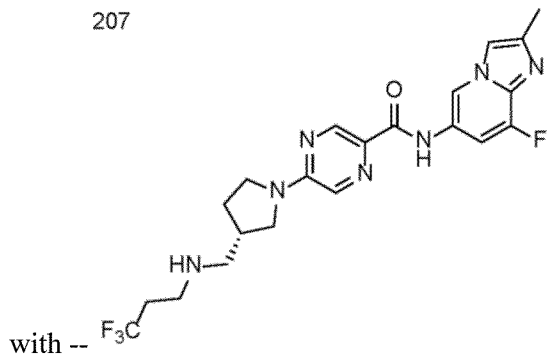 --.

In the Claims

In Claim 1, Column 707, Line 42, please replace "—N(R$^{12}$)—C$_{1-3}$alkylene," with -- —N(R$^{12}$)—C$_{1-3}$alkylene—, --.

Signed and Sealed this  
Twentieth Day of February, 2024

Katherine Kelly Vidal  
*Director of the United States Patent and Trademark Office*

In Claim 34, Column 740, Lines 53-66, please replace " 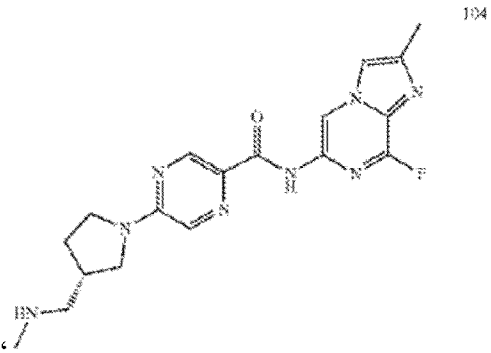 "
with -- 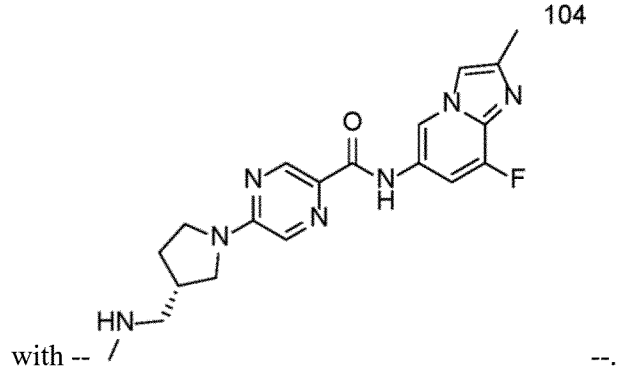 --.
In Claim 34, Column 751, Lines 20-29, please replace " 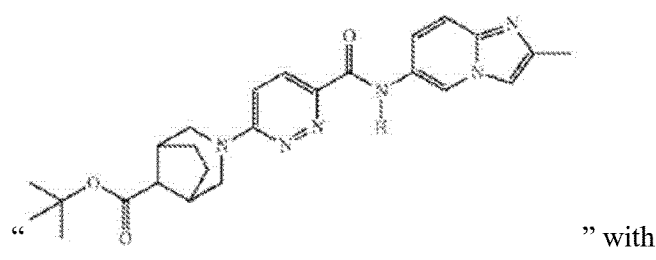 " with
-- 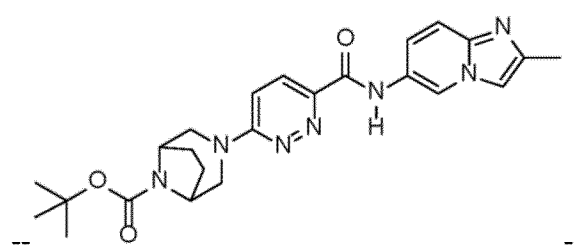 --.

CERTIFICATE OF CORRECTION (continued)
U.S. Pat. No. 11,806,346 B2

In Claim 34, Column 767, Lines 51-66, please replace " 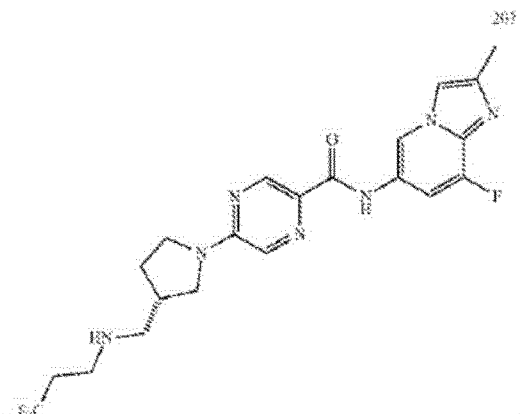 "

with -- 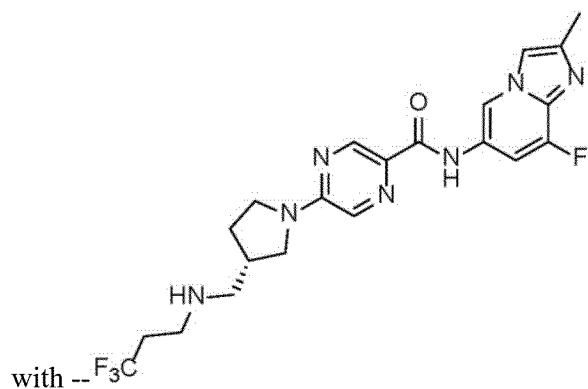 --.

In Claim 34, Column 797, Lines 26-42, please replace " 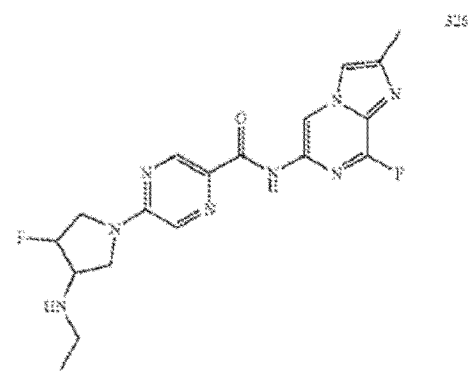 " with

CERTIFICATE OF CORRECTION (continued)
U.S. Pat. No. 11,806,346 B2

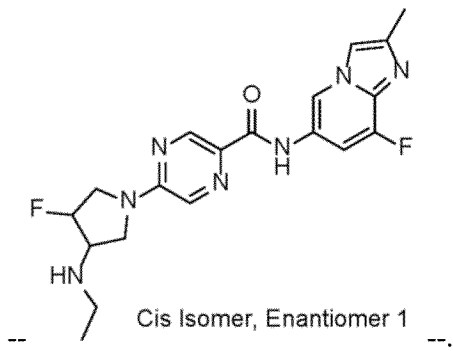

In Claim 34, Column 808, Lines 51-65, please replace